US011964957B2

United States Patent
Ishikawa et al.

(10) Patent No.: US 11,964,957 B2
(45) Date of Patent: Apr. 23, 2024

(54) PYRAZOLE DERIVATIVE AND HARMFUL ORGANISM-CONTROLLING AGENT

(71) Applicant: KUMIAI CHEMICAL INDUSTRY CO., LTD., Tokyo (JP)

(72) Inventors: Ryo Ishikawa, Tokyo (JP); Akira Kinpara, Tokyo (JP); Keiji Toriyabe, Tokyo (JP); Akira Watanabe, Tokyo (JP); Masao Nakatani, Tokyo (JP); Akira Takanezawa, Tokyo (JP); Takeshi Matsuda, Tokyo (JP)

(73) Assignee: KUMIAI CHEMICAL INDUSTRY CO., LTD. (JP)

( * ) Notice: Subject to any disclaimer, the term of this patent is extended or adjusted under 35 U.S.C. 154(b) by 686 days.

(21) Appl. No.: 17/250,107

(22) PCT Filed: May 24, 2019

(86) PCT No.: PCT/JP2019/020656
§ 371 (c)(1),
(2) Date: Nov. 25, 2020

(87) PCT Pub. No.: WO2019/230590
PCT Pub. Date: Dec. 5, 2019

(65) Prior Publication Data
US 2021/0261521 A1    Aug. 26, 2021

(30) Foreign Application Priority Data

May 29, 2018 (JP) .................. 2018-102614
Mar. 13, 2019 (JP) .................. 2019-045383

(51) Int. Cl.
*C07D 401/04* (2006.01)
*A01N 25/04* (2006.01)
*A01N 25/14* (2006.01)
*A01N 25/30* (2006.01)
*A01N 43/56* (2006.01)

(52) U.S. Cl.
CPC ........... *C07D 401/04* (2013.01); *A01N 25/04* (2013.01); *A01N 25/14* (2013.01); *A01N 25/30* (2013.01); *A01N 43/56* (2013.01)

(58) Field of Classification Search
CPC .. C07D 401/04; C07D 413/14; C07D 417/14; C07D 405/14; C07D 401/14; C07D 409/14; A01N 25/04; A01N 25/14; A01N 25/30; A01N 43/56; A01N 43/66; A01N 43/707; A01N 43/76; A01N 43/78; A01N 43/80; A01N 47/04; A01N 47/02; A61P 33/14; A61K 31/4439
See application file for complete search history.

(56) References Cited

FOREIGN PATENT DOCUMENTS

| JP | 2010514710 A | 5/2010 |
|----|--------------|--------|
| JP | 2013082699 A | 5/2013 |
| JP | 2014015447 A | 1/2014 |
| JP | 2014504267 A | 2/2014 |
| RU | 2343151 C2 | 1/2009 |
| WO | 2004067528 A1 | 8/2004 |
| WO | 2012102387 A1 | 8/2012 |
| WO | 2018207847 A1 | 11/2018 |

OTHER PUBLICATIONS

Synthesis of Novel Heterocyclic Pyrazole-3-carboxamides using Nitrilimines. International Journal of ChemTech research. 2013. (Year: 2013).*
Database Registry, Chemical Abstracts Service, Columbus, Ohio, US, Oct. 23, 2016, "1H-Pyrazole-3-carboxylic acid compounds", 5 pgs, XP055871183.
EP19811742.6 Extended European Search Report dated Dec. 20, 2021, 8 pgs.
Jaisankar, et al., Synthesis of Novel Heterocyclic Pyrazole-3-carboxamides using Nitrilimines, International Journal of ChemTech Research, vol. 5, Jan. 1, 2013, pp. 80-84, XP055662607.
PCT/JP2019/020656 International Search Report dated Aug. 13, 2019; 4 pgs.
RU2020142980 Office Action dated Sep. 2, 2022, 24 pgs.

* cited by examiner

*Primary Examiner* — Robert A Wax
*Assistant Examiner* — John Seungjai Kwon
(74) *Attorney, Agent, or Firm* — Bracewell LLP; Brad Y. Chin

(57) ABSTRACT

Embodiments provide a pest control agent that is excellent in safety, controlling effect, residual activity, and so on. According to an embodiment, there is provided a pyrazole derivative represented by general formula [I], or an agriculturally acceptable salt thereof, and a pest control agent containing the same as an active ingredient:

[Chemical formula 1]

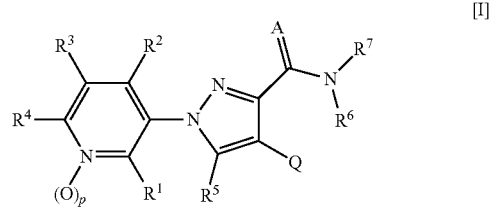

wherein, p represents an integer of 0 or 1, $R^1$, $R^2$, $R^3$, $R^4$, and $R^5$ represent a hydrogen atom, halogen atom, $C_1$-$C_6$ alkyl group, or the like, A represents an oxygen atom or sulfur atom, Q represents a halogen atom, $C_6$-$C_{10}$ aryl group that is unsubstituted or substituted with $(R^8)_m$, or the like, and $R^6$ and $R^7$ represent a hydrogen atom, $C_1$-$C_6$ alkyl group, or the like.

7 Claims, No Drawings

PYRAZOLE DERIVATIVE AND HARMFUL ORGANISM-CONTROLLING AGENT

CROSS REFERENCE TO RELATED APPLICATIONS

This application is related to, and claims priority to, PCT/JP2019/020656, filed on May 24, 2019, entitled (translation), "PYRAZOLE DERIVATIVE AND HARMFUL ORGANISM-CONTROLLING AGENT," which claims the benefit of and priority to Japanese Patent Application Nos. 2019-045383, filed on Mar. 13, 2019, and 2018-102614, filed on May 29, 2018, each of which is hereby incorporated by reference in their entirety into this application.

BACKGROUND OF THE INVENTION

Field of the Invention

The present invention relates to a novel pyrazole derivative or an agriculturally acceptable salt thereof, and a pest control agent containing the derivative as an active ingredient.

Description of the Related Art

Patent Document 1 indicates a pyrazole derivative having a pest control effect, but lacks specific disclosure about a compound having a carboxylic amide at the 3-position of the pyrazole ring.
Non-Patent Document 1 indicates a pyrazole derivative substituted with a phenyl group at the 4-position of the pyrazole ring, but lacks the description about the pest control activity of the pyrazole derivative.
[Patent Document 1] WO 2012/102387 A
[Non-Patent Document 1] International Journal of Chem Tech Research, 2013, Vol. 5, No. 1, pp 80-84

SUMMARY OF THE INVENTION

A pest control agent used for useful crops is requested to be an agent that is applied to soil or foliage, and exhibits sufficient pest controlling effect with a low dose. Also, increased demands for the safety and the influence on environment of chemicals lead to the request for developing a safer pest control agent. Furthermore, in recent years, as a result of long-term use of a pest control agent such as an insecticide or a miticide, pests having acquired the resistance to the pest control agent have emerged, so that it becomes difficult to completely control pests. Also, use of pest control agents having high mammalian toxicity is problematic in terms of the safety and the like for operators.

In light of the aforementioned circumstance, it is an object of the present invention to solve the problems faced by the conventional pest control agents, and to further provide a pest control agent that is excellent in safety, control effect, residual activity, and the like.

In order to develop a pest control agent having desirable characteristics as described above, the present inventors synthesized a variety of pyrazole derivatives, and diligently examined the physiological activity of the pyrazole derivatives. As a result, the present inventors found that a pyrazole derivative represented by the following general formula [I] (hereinafter, referred to as the present compound) shows outstanding effectiveness on various pests, and further continued the research to finally accomplish the present invention.

That is, the present invention has the subject matter having the following features.

(1) A pyrazole derivative represented by general formula [I] or an agriculturally acceptable salt thereof

[Chemical formula 1]

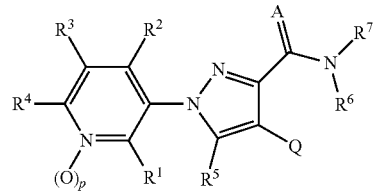

wherein,
p represents an integer of 0 or 1,
$R^1$, $R^2$, $R^3$, $R^4$, and $R^5$ each independently represent a hydrogen atom, halogen atom, $C_1$-$C_6$ alkyl group, hydroxy group, $C_1$-$C_6$ haloalkyl group, $C_1$-$C_6$ alkoxy group, $C_1$-$C_6$ haloalkoxy group, $C_3$-$C_6$ cycloalkyl group, $C_1$-$C_6$ alkylthio group, $C_1$-$C_6$ alkylsulfinyl group, $C_1$-$C_6$ alkylsulfonyl group, amino group, mono($C_1$-$C_6$ alkyl)amino group, di($C_1$-$C_6$ alkyl)amino group, cyano group, or nitro group,
A represents an oxygen atom or sulfur atom,
Q represents a halogen atom, or $C_6$-$C_{10}$ aryl group that is unsubstituted or substituted with $(R^8)_m$, or heteroaryl group that is unsubstituted or substituted with $(R^8)_m$,
$R^6$ and $R^7$ each independently represent a hydrogen atom, $C_1$-$C_6$ alkyl group, $C_3$-$C_6$ cycloalkyl group, $C_3$-$C_6$ cycloalkyl $C_1$-$C_6$ alkyl group, $C_2$-$C_7$ alkynyl group, $C_2$-$C_6$ alkenyl group, hydroxy group, $C_1$-$C_6$ alkoxy group, $C_1$-$C_6$ alkoxy $C_1$-$C_6$ alkyl group, $C_1$-$C_6$ haloalkyl group, 2-tetrahydrofuranyl group, 3-tetrahydrofuranyl group, 2-tetrahydropyranyl group, 4-tetrahydropyranyl group, cyano $C_1$-$C_6$ alkyl group, cyano $C_3$-$C_6$ cycloalkyl group, hydroxy $C_1$-$C_6$ alkyl group, formyl group, amino group, mono($C_1$-$C_6$ alkyl)amino group, di($C_1$-$C_6$ alkyl)amino group, $C_1$-$C_6$ alkylcarbonyl group, $C_1$-$C_6$ alkoxy $C_1$-$C_6$ alkylcarbonyl group, $C_3$-$C_6$ cycloalkylcarbonyl group, $C_3$-$C_6$ cycloalkyl $C_1$-$C_6$ alkylcarbonyl group, $C_1$-$C_6$ alkoxycarbonyl group, carbamoyl group, mono($C_1$-$C_6$ alkyl)aminocarbonyl group, di($C_1$-$C_6$ alkyl)aminocarbonyl group, phenylcarbonyl group that is unsubstituted or substituted with $(R^9)_n$, $C_7$-$C_{13}$ aralkylcarbonyl group that is unsubstituted or substituted with $(R^9)_n$, pyridylcarbonyl group that is unsubstituted or substituted with $(R^9)_n$, pyrazolylcarbonyl group that is unsubstituted or substituted with $(R^9)_n$, pyridine-2-ylmethyl group, pyridine-3-ylmethyl group, ($C_1$-$C_6$ alkyl)thiocarbonyl group, ($C_1$-$C_6$ alkoxy)thiocarbonyl group, thiocarbamoyl group, mono($C_1$-$C_6$ alkyl)aminothiocarbonyl group, di($C_1$-$C_6$ alkyl)aminothiocarbonyl group, $C_1$-$C_6$ alkylsulfonyl group, sulfamoyl group, mono($C_1$-$C_6$ alkyl)aminosulfonyl group, di($C_1$-$C_6$ alkyl)aminosulfonyl group, $R^{10}R^{11}N$—$C_1$-$C_6$ alkyl group, $C_1$-$C_6$ alkoxycarbonyl $C_1$-$C_6$ alkyl group, aminocarbonyl $C_1$-$C_6$ alkyl group, mono($C_1$-$C_6$ alkyl)aminocarbonyl $C_1$-$C_6$ alkyl group, mono($C_3$-$C_6$ cycloalkyl)aminocarbonyl $C_1$-$C_6$ alkyl group, mono($C_1$-$C_6$ haloalkyl)aminocarbonyl $C_1$-$C_6$ alkyl group, di($C_1$-$C_6$ alkyl)aminocarbonyl $C_1$-$C_6$ alkyl group, hydroxyimino group, $C_1$-$C_6$ alkoxyimino group, hydroxyimino $C_1$-$C_6$ alkyl group, or $C_1$-$C_6$ alkoxyimino $C_1$-$C_6$ alkyl group, $R^6$ and $R^7$ may together form =$CR^{12}N(R^{13})R^{14}$ or =$CR^{12}OR^{15}$, and further, $R^6$ and $R^7$ may form together with carbon atoms bound thereto, a 3 to 6-membered carbon ring, or a 3 to 6-membered hetero ring having 1 to 4 hetero atoms selected from an oxygen atom, a sulfur atom, and a nitrogen atom, the hetero ring may be substituted a halogen atom, cyano group, nitro group, $C_1$-$C_6$ alkyl group, $C_1$-$C_6$ alkoxy group, $C_1$-$C_6$ haloalkyl group, or oxo group, $R^8$ represents a hydrogen atom, halogen atom, hydroxy group, thiol group, $C_1$-$C_6$ alkyl group, $C_1$-$C_6$ haloalkyl group, $C_3$-$C_6$ cycloalkyl group, $C_3$-$C_6$ cycloalkyl $C_1$-$C_6$ alkyl group, $C_3$-$C_6$ cycloalkyl $C_2$-$C_6$ alkynyl group, $C_3$-$C_6$ halocycloalkyl group, $C_3$-$C_6$ halocycloalkyl $C_1$-$C_6$ alkyl group, $C_2$-$C_6$ alkenyl group, $C_2$-$C_6$ haloalkenyl group, $C_2$-$C_7$ alkynyl group, $C_2$-$C_6$ haloalkynyl group, $C_1$-$C_6$ alkoxy group, $C_1$-$C_6$ haloalkoxy group, $C_3$-$C_6$ cycloalkoxy group, oxirane-2-yl group, mono(oxirane-2-yl)$C_1$-$C_3$ alkyl group, $C_3$-$C_6$ halocycloalkoxy group, $C_1$-$C_6$ alkylthio group, $C_1$-$C_6$ alkylsulfinyl group, $C_1$-$C_6$ alkylsulfonyl group, $C_3$-$C_6$ cycloalkylthio group, $C_3$-$C_6$ cycloalkylsulfinyl group, $C_3$-$C_6$ cycloalkylsulfonyl group, $C_1$-$C_6$ haloalkylthio group, $C_1$-$C_6$ haloalkylsulfinyl group, $C_1$-$C_6$ haloalkylsulfonyl group, formyl group, $C_1$-$C_6$ alkylcarbonyl group, $C_1$-$C_6$ haloalkylcarbonyl group, $C_1$-$C_6$ alkoxycarbonyl group, aminocarbonyl group, mono($C_1$-$C_6$ alkyl)aminocarbonyl group, di($C_1$-$C_6$ alkyl)aminocarbonyl group, amino $C_1$-$C_6$ alkyl group, mono($C_1$-$C_6$ alkyl)amino $C_1$-$C_6$ alkyl group, di($C_1$-$C_6$ alkyl)amino $C_1$-$C_6$ alkyl group, tri($C_1$-$C_6$ alkyl)silyloxy $C_1$-$C_6$ alkyl group, $C_1$-$C_6$ alkylcarbonyl $C_1$-$C_6$ alkyl group, $C_1$-$C_6$ alkylcarbonyloxy $C_1$-$C_6$ alkyl group, $C_1$-$C_6$ haloalkylcarbonyl $C_1$-$C_6$ alkyl group, $C_1$-$C_6$ alkoxycarbonyl $C_1$-$C_6$ alkyl group, hydroxy $C_1$-$C_6$ alkyl group, $C_1$-$C_6$ alkoxy $C_1$-$C_6$ alkyl group, $C_1$-$C_6$ haloalkoxy $C_1$-$C_6$ alkyl group, $C_1$-$C_6$ alkoxy $C_1$-$C_6$ haloalkyl group, $C_1$-$C_6$ haloalkoxy $C_1$-$C_6$ haloalkyl group, formyloxy group, $C_1$-$C_6$ alkylcarbonyloxy group, $C_1$-$C_6$ haloalkylcarbonyloxy group, aminocarbonyloxy group, mono($C_1$-$C_6$ alkyl)aminocarbonyloxy group, di($C_1$-$C_6$ alkyl)aminocarbonyloxy group, aminocarbonyloxy $C_1$-$C_6$ alkyl group, mono($C_1$-$C_6$ alkyl)aminocarbonyloxy $C_1$-$C_6$ alkyl group, di($C_1$-$C_6$ alkyl)aminocarbonyloxy $C_1$-$C_6$ alkyl group, $C_1$-$C_6$ alkoxycarbonyloxy group, $C_1$-$C_6$ alkoxycarbonyloxy $C_1$-$C_6$ alkyl group, $C_1$-$C_6$ alkylsulfonyloxy group, $C_1$-$C_6$ haloalkylsulfonyloxy group, $C_1$-$C_6$ alkylthio $C_1$-$C_6$ alkyl group, $C_1$-$C_6$ alkylsulfinyl $C_1$-$C_6$ alkyl group, $C_1$-$C_6$ alkylsulfonyl $C_1$-$C_6$ alkyl group, $C_1$-$C_6$ haloalkylthio $C_1$-$C_6$ alkyl group, $C_1$-$C_6$ haloalkylsulfinyl $C_1$-$C_6$ alkyl group, $C_1$-$C_6$ haloalkylsulfonyl $C_1$-$C_6$ alkyl group, $C_3$-$C_6$ cycloalkyl $C_1$-$C_6$ alkoxy group, $C_3$-$C_6$ halocycloalkyl $C_1$-$C_6$ alkoxy group, $C_3$-$C_6$ cycloalkyl $C_1$-$C_6$ alkylthio group, $C_3$-$C_6$ cycloalkyl $C_1$-$C_6$ alkylsulfinyl group, $C_3$-$C_6$ cycloalkyl $C_1$-$C_6$ alkylsulfonyl group, $C_3$-$C_6$ halocycloalkyl $C_1$-$C_6$ alkylthio group, $C_3$-$C_6$ halocycloalkyl $C_1$-$C_6$ alkylsulfinyl group, $C_3$-$C_6$ halocycloalkyl $C_1$-$C_6$ alkylsulfonyl group, phenyl group that is unsubstituted or substituted with $(R^9)_n$, phenoxy group that is unsubstituted or substituted with $(R^9)_n$, benzyl group that is unsubstituted or substituted with $(R^9)_n$, benzyloxy group that is unsubstituted or substituted with $(R^9)_n$, amino group, mono($C_1$-$C_6$ alkyl)amino group, di($C_1$-$C_6$ alkyl)amino group, carboxy group, 1,3-dioxolane-2-yl group, 1,3-dioxane-2-yl group, 1H-imidazole-2-yl group, thiazole-2-yl group, oxazole-2-yl group, (hydroxyimino)methyl group, (methyloxyimino)methyl group, isoxazole-3-yl, 4,5-dihydro-3-isoxazolyl group, cyano group, or nitro group, and further, neighboring two $R^8$s may form, together with a carbon atom bound to each $R^8$, a 4 to 8-membered carbon ring, or a 4 to 8-membered hetero ring having 1 to 4 hetero atoms selected from an oxygen atom, a sulfur atom, and a nitrogen atom, the carbon ring or hetero ring formed at this time may be substituted with one or more chemically acceptable substituents selected from a halogen atom, cyano group, nitro group, $C_1$-$C_6$ alkyl group, $C_1$-$C_6$ haloalkyl group, $C_1$-$C_6$ alkoxy group, $C_1$-$C_6$ haloalkoxy group, or oxo group, $R^9$ represents a halogen atom, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylthio group, $C_1$-$C_6$ alkylsulfinyl group, $C_1$-$C_6$ alkylsulfonyl group, $C_1$-$C_6$ haloalkylthio group, $C_1$-$C_6$ haloalkylsulfinyl group, $C_1$-$C_6$ haloalkylsulfonyl group, amino group, mono($C_1$-$C_6$ alkyl)amino group, di($C_1$-$C_6$ alkyl)amino group, cyano group, or nitro group, $R^{10}$ and $R^{11}$ each independently represent a hydrogen atom, $C_1$-$C_6$ alkyl group, $C_1$-$C_6$ haloalkyl group, or $C_3$-$C_6$ cycloalkyl group, and further, $R^{10}$ and $R^{11}$ may form, together with carbon atoms bound thereto, a 3 to 6-membered ring, $R^{12}$ represents a hydrogen atom, $C_1$-$C_6$ alkyl group, or $C_3$-$C_6$ cycloalkyl group, $R^{13}$ and $R^{14}$ each independently represent a hydrogen atom, $C_1$-$C_6$ alkyl group, $C_1$-$C_6$ haloalkyl group, $C_3$-$C_6$ cycloalkyl group, or $C_1$-$C_6$ alkoxy group, and further, $R^{13}$ and $R^{14}$ may form, together with carbon atoms bound thereto, a 3 to 6-membered carbon ring, or a 3 to 6-membered hetero ring having 1 to 4 hetero atoms selected from an oxygen atom, a sulfur atom, and a nitrogen atom, $R^{15}$ represents a $C_1$-$C_6$ alkyl group, m represents a number of chemically acceptable $R^8$s and is an integer of 0 to 7, $R^8$s may be the same or different from each other when m is 2 or more, n represents a number of chemically acceptable $R^9$s and is an integer of 0 to 5, and $R^9$s may be the same or different from each other when n is 2 or more.

(2) A pyrazole derivative represented by general formula [II] or an agriculturally acceptable salt thereof

[Chemical formula 2]

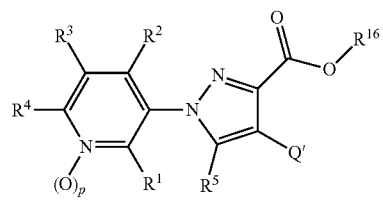

[II]

wherein, p represents an integer of 0 or 1, $R^1$, $R^2$, $R^3$, $R^4$, and $R^5$ each independently represent a hydrogen atom, halogen atom, $C_1$-$C_6$ alkyl group, hydroxy group, $C_1$-$C_6$ haloalkyl group, $C_1$-$C_6$ alkoxy group, $C_1$-$C_6$ haloalkoxy group, $C_3$-$C_6$ cycloalkyl group, $C_1$-$C_6$ alkylthio group, $C_1$-$C_6$ alkylsulfinyl group, $C_1$-$C_6$ alkylsulfonyl group, amino group, mono($C_1$-$C_6$ alkyl)amino group, di($C_1$-$C_6$ alkyl)amino group, cyano group, or nitro group, $R^{16}$ represents a hydrogen atom or $C_1$-$C_6$ alkyl group, Q' represents a halogen atom, $C_1$-$C_6$ alkylsulfonyloxy group, $C_1$-$C_6$ haloalkylsulfonyloxy group, di($C_1$-$C_6$ alkyl)sulfamoyloxy group, phenylsulfonyloxy group that is unsubstituted or substituted with $(R^9)_n$, $C_6$-$C_{10}$ aryl group that is unsubstituted or substituted with $(R^8)_m$, or heteroaryl group that is unsubstituted or substituted with $(R^8)_m$, $R^8$ represents a hydrogen atom, halogen atom, hydroxy group, thiol group, $C_1$-$C_6$ alkyl group, $C_1$-$C_6$ haloalkyl group, $C_3$-$C_6$ cycloalkyl group, $C_3$-$C_6$ cycloalkyl $C_1$-$C_6$ alkyl group, $C_3$-$C_6$ cycloalkyl $C_2$-$C_6$ alkynyl group, $C_3$-$C_6$ halocycloalkyl group, $C_3$-$C_6$ halocycloalkyl $C_1$-$C_6$ alkyl group, $C_2$-$C_6$ alkenyl group, $C_2$-$C_6$ haloalkenyl group, $C_2$-$C_7$ alkynyl group, $C_2$-$C_6$ haloalkynyl group, $C_1$-$C_6$ alkoxy group, $C_1$-$C_6$ haloalkoxy group, $C_3$-$C_6$ cycloalkoxy group, oxirane-2-yl group, mono(oxirane-2-yl)$C_1$-$C_3$ alkyl group, $C_3$-$C_6$ halocycloalkoxy group, $C_1$-$C_6$ alkylthio group, $C_1$-$C_6$ alkylsulfinyl group, $C_1$-$C_6$ alkylsulfonyl group, $C_3$-$C_6$ cycloalkylthio group, $C_3$-$C_6$ cycloalkylsulfinyl group, $C_3$-$C_6$ cycloalkylsulfonyl group, $C_1$-$C_6$ haloalkylthio group, $C_1$-$C_6$ haloalkylsulfinyl group, $C_1$-$C_6$ haloalkylsulfonyl group, formyl group, $C_1$-$C_6$ alkylcarbonyl group, $C_1$-$C_6$ haloalkylcarbonyl group, $C_1$-$C_6$ alkoxycarbonyl group, aminocarbonyl group, mono($C_1$-$C_6$ alkyl)aminocarbonyl group, di($C_1$-$C_6$ alkyl)aminocarbonyl group, amino $C_1$-$C_6$ alkyl group, mono($C_1$-$C_6$ alkyl)amino $C_1$-$C_6$ alkyl group, di($C_1$-$C_6$ alkyl)amino $C_1$-$C_6$ alkyl group, tri($C_1$-$C_6$ alkyl)silyloxy $C_1$-$C_6$ alkyl group, $C_1$-$C_6$ alkylcarbonyl $C_1$-$C_6$ alkyl group, $C_1$-$C_6$ alkylcarbonyloxy $C_1$-$C_6$ alkyl group, $C_1$-$C_6$ haloalkylcarbonyl $C_1$-$C_6$ alkyl group, $C_1$-$C_6$ alkoxycarbonyl $C_1$-$C_6$ alkyl group, hydroxy $C_1$-$C_6$ alkyl group, $C_1$-$C_6$ alkoxy $C_1$-$C_6$ alkyl group, $C_1$-$C_6$ haloalkoxy $C_1$-$C_6$ alkyl group, $C_1$-$C_6$ alkoxy $C_1$-$C_6$ haloalkyl group, $C_1$-$C_6$ haloalkoxy $C_1$-$C_6$ haloalkyl group, formyloxy group, $C_1$-$C_6$ alkylcarbonyloxy group, $C_1$-$C_6$ haloalkylcarbonyloxy group, aminocarbonyloxy group, mono($C_1$-$C_6$ alkyl)aminocarbonyloxy group, di($C_1$-$C_6$ alkyl)aminocarbonyloxy group, aminocarbonyloxy $C_1$-$C_6$ alkyl group, mono($C_1$-$C_6$ alkyl)aminocarbonyloxy $C_1$-$C_6$ alkyl group, di($C_1$-$C_6$ alkyl)aminocarbonyloxy $C_1$-$C_6$ alkyl group, $C_1$-$C_6$ alkoxycarbonyloxy group, $C_1$-$C_6$ alkoxycarbonyloxy $C_1$-$C_6$ alkyl group, $C_1$-$C_6$ alkylsulfonyloxy group, $C_1$-$C_6$ haloalkylsulfonyloxy group, $C_1$-$C_6$ alkylthio $C_1$-$C_6$ alkyl group, $C_1$-$C_6$ alkylsulfinyl $C_1$-$C_6$ alkyl group, $C_1$-$C_6$ alkylsulfonyl $C_1$-$C_6$ alkyl group, $C_1$-$C_6$ haloalkylthio $C_1$-$C_6$ alkyl group, $C_1$-$C_6$ haloalkylsulfinyl $C_1$-$C_6$ alkyl group, $C_1$-$C_6$ haloalkylsulfonyl $C_1$-$C_6$ alkyl group, $C_3$-$C_6$ cycloalkyl $C_1$-$C_6$ alkoxy group, $C_3$-$C_6$ halocycloalkyl $C_1$-$C_6$ alkoxy group, $C_3$-$C_6$ cycloalkyl $C_1$-$C_6$ alkylthio group, $C_3$-$C_6$ cycloalkyl $C_1$-$C_6$ alkylsulfinyl group, $C_3$-$C_6$ cycloalkyl $C_1$-$C_6$ alkylsulfonyl group, $C_3$-$C_6$ halocycloalkyl $C_1$-$C_6$ alkylthio group, $C_3$-$C_6$ halocycloalkyl $C_1$-$C_6$ alkylsulfinyl group, $C_3$-$C_6$ halocycloalkyl $C_1$-$C_6$ alkylsulfonyl group, phenyl group that is unsubstituted or substituted with $(R^9)_n$, phenoxy group that is unsubstituted or substituted with $(R^9)_n$, benzyl group that is unsubstituted or substituted with $(R^9)_n$, benzyloxy group that is unsubstituted or substituted with $(R^9)_n$, amino group, mono($C_1$-$C_6$ alkyl)amino group, di($C_1$-$C_6$ alkyl)amino group, carboxy group, 1,3-dioxolane-2-yl group, 1,3-dioxane-2-yl group, 1H-imidazole-2-yl group, thiazole-2-yl group, oxazole-2-yl group, (hydroxyimino)methyl group, (methyloxyimino)methyl group, isoxazole-3-yl, 4,5-dihydro-3-isoxazolyl group, cyano group, or nitro group, and further, neighboring two $R^8$s may form, together with a carbon atom bound to each $R^8$, a 4 to 8-membered carbon ring, or a 4 to 8-membered hetero ring having 1 to 4 hetero atoms selected from an oxygen atom, a sulfur atom, and a nitrogen atom, the carbon ring or hetero ring formed at this time may be substituted with one or more chemically acceptable substituents selected from a halogen atom, cyano group, nitro group, $C_1$-$C_6$ alkyl group, $C_1$-$C_6$ haloalkyl group, $C_1$-$C_6$ alkoxy group, $C_1$-$C_6$ haloalkoxy group, or oxo group, $R^9$ represents a halogen atom, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylthio group, $C_1$-$C_6$ alkylsulfinyl group, $C_1$-$C_6$ alkylsulfonyl group, $C_1$-$C_6$ haloalkylthio group, $C_1$-$C_6$ haloalkylsulfinyl group, $C_1$-$C_6$ haloalkylsulfonyl group, amino group, mono($C_1$-$C_6$ alkyl)amino group, di($C_1$-$C_6$ alkyl)amino group, cyano group, or nitro group, m represents a number of chemically acceptable $R^8$s and is an integer of 0 to 7, $R^8$s may be the same or different from each other when m is 2 or more, n represents a number of chemically acceptable $R^9$s and is an integer of 0 to 5, and $R^9$s may be the same or different from each other when n is 2 or more.

(3) A agrochemical composition including the pyrazole derivative or an agriculturally acceptable salt thereof according to (1) or (2) as an active ingredient.

(4) The agrochemical composition according to (3), wherein the agrochemical composition further includes a surfactant.

(5) A pest control agent including the pyrazole derivative or an agriculturally acceptable salt thereof according to (1) or (2) as an active ingredient.

(6) The pest control agent according to (5) that is an insecticide.

(7) The pest control agent according to (5) having a control effect on a pest in a dry field or a paddy field where a farming or gardening plant is cultured.

(8) The pest control agent according to (7), wherein the farming or gardening plant is a plant provided with tolerance by a breeding method or a gene recombination technique.

(9) A method for controlling a pest including using an active ingredient amount of the pyrazole derivative or an agriculturally acceptable salt thereof according to (1) or (2).

(10) A method for controlling a pest by letting a agrochemical composition including the pyrazole derivative or an agriculturally acceptable salt thereof according to (1) or (2) as an active ingredient act on a farming or gardening crop or a place where the farming or gardening crop is to be grown or being grown, at once or in batch.

(11) The method for controlling a pest according to (9) or (10), wherein the place where the pest control agent is to be applied is a paddy field, a dry field, a lawn, an orchard, a non-crop land, a greenhouse, a raising seeding facility, or a plant factory.

(12) The method for controlling a pest according to any one of (9) to (11), wherein the pyrazole derivative or an agriculturally acceptable salt thereof is used as an insecticide.

(13) A use method of a pest control agent, using the pest control agent according to any one of (5) to (8) for controlling a pest for a farming or gardening crop.

The pest control agent containing the present compound shows excellent controlling effect on a wide range of pests including Hemiptera pests, Lepidoptera pests, Coleoptera pests, Diptera pests, Hymenoptera pests, Orthoptera pests, Isoptera pests, Thysanoptera pests, Acari pests, and plant parasitic nematoda, and is capable of controlling a pest having acquired drug resistance.

DESCRIPTION OF THE PREFERRED EMBODIMENTS

Symbols and terms used in this specification are described.

In the present invention, "pest control agent" means insecticides, miticides, nematocides, and the like in farming and gardening fields, for animals such as domestic animals and pets, for household use or for prevention of epidemics.

In the present invention, "halogen atom" refers to a fluorine atom, a chlorine atom, a bromine atom, or an iodine atom.

In the present invention, unless otherwise specified, "$C_6$-$C_{10}$ aryl group" refers to an aromatic hydrocarbon group having 6 to 10 carbon atoms, and examples of the $C_6$-$C_{10}$ aryl group include a phenyl, naphthalene-1-yl, or naphthalene-2-yl group.

In the present invention, unless otherwise specified, "heteroaryl group" refers to an aromatic heterocyclic or condensed heterocyclic group, and examples of the heteroaryl group include a pyrrolyl, furanyl, thienyl, pyrazolyl, oxazolyl, isoxazolyl, imidazolyl, 1,2,4-oxadiazolyl, 1,2,3-oxadiazolyl, 1,3,4-oxadiazolyl, 1,2,4-triazolyl, 1,2,3-triazolyl, thiazolyl, isothiazolyl, 1,2,4-thiadiazolyl, 1,2,3-thiadiazolyl, 1,3,4-thiadiazolyl, pyridyl, pyrimidinyl, pyrazinyl, pyridazinyl, 1,3,5-triazinyl, 1,2,4-triazinyl, benzofuranyl, benzothienyl, indolyl, benzoxazolyl, benzoimidazolyl, benzotriazolyl, benzothiazolyl, quinolinyl, quinazolinyl, quinoxalinyl, phthalazinyl, or naphthyridinyl group.

In the present invention, unless otherwise specified, "$C_1$-$C_3$ alkyl group" refers to a linear or branched alkyl group having 1 to 3 carbon atoms, and examples of the $C_1$-$C_3$ alkyl group include a methyl, ethyl, n-propyl, or isopropyl group.

In the present invention, unless otherwise specified, "$C_1$-$C_6$ alkyl group" refers to a linear or branched alkyl group having 1 to 6 carbon atoms, and examples of the $C_1$-$C_6$ alkyl group include, in addition to those exemplified in the "$C_1$-$C_3$ alkyl group", a n-butyl, s-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, or 1-ethyl-2-methylpropyl group.

In the present invention, unless otherwise specified, "$C_1$-$C_6$ haloalkyl group" refers to a linear or branched alkyl group having 1 to 6 carbon atoms, substituted with 1 to 13 same or different halogen atoms, and refers to, for example, a haloalkyl group, and examples of the $C_1$-$C_6$ haloalkyl group include a fluoromethyl, difluoromethyl, trifluoromethyl, chloromethyl, dichloromethyl, trichloromethyl, bromomethyl, dibromomethyl, tribromomethyl, iodomethyl, chlorodifluoromethyl, dichlorofluoromethyl, 1-fluoroethyl, 2-fluoroethyl, 1,1-difluoroethyl, 2,2-difluoroethyl, 2,2,2-trifluoroethyl, 1,1,2,2-tetrafluoroethyl, pentafluoroethyl, 1-chloroethyl, 2-chloroethyl, 1,1-dichloroethyl, 2,2-dichloroethyl, 2,2,2-trichloroethyl, 1,1,2,2-tetrachloroethyl, pentachloroethyl, 1-bromoethyl, 2-bromoethyl, 2,2,2-tribromoethyl, 1-iodoethyl, 2-iodoethyl, 2-chloro-2,2-difluoroethyl, 2,2-dichloro-2-fluoroethyl, 1-fluoropropyl, 2-fluoropropyl, 3-fluoropropyl, 1,1-difluoropropyl, 2,2-difluoropropyl, 3,3-difluoropropyl, 3,3,3-trifluoropropyl, 2,2,3,3,3-pentafluoropropyl, 1,1,2,3,3,3-hexafluoropropyl, heptafluoropropyl, 1-fluoropropane-2-yl, 2-fluoropropane-2-yl, 1,1-difluoropropane-2-yl, 1,2-difluoropropane-2-yl, 1,3-difluoropropane-2-yl, 1,2,3-trifluoropropane-2-yl, 1,1,3,3-tetrafluoropropane-2-yl, 1,1,1,3,3,3-hexafluoropropane-2-yl, heptafluoropropane-2-yl, 1-chloropropyl, 2-chloropropyl, 3-chloropropyl, 1,1-dichloropropyl, 2,2-dichloropropyl, 3,3-dichloropropyl, 3,3,3-trichloropropyl, 2,2,3,3,3-pentachloropropyl, heptachloropropyl, 1-chloropropane-2-yl, 2-chloropropane-2-yl, 1,1-dichloropropane-2-yl, 1,2-dichloropropane-2-yl, 1,3-dichloropropane-2-yl, 1,2,3-trichloropropane-2-yl, 1,1,3,3-tetrachloropropane-2-yl, 1,1,1,3,3,3-hexachloropropane-2-yl, heptachloropropane-2-yl, 1-bromopropyl, 2-bromopropyl, 3-bromopropyl, 1-bromopropane-2-yl, 2-bromopropane-2-yl, 1-iodopropyl, 2-iodopropyl, 3-iodopropyl, 1-iodopropane-2-yl, 2-iodopropane-2-yl, 1-fluorobutyl, 2-fluorobutyl, 3-fluorobutyl, 4-fluorobutyl, 4,4-difluorobutyl, 4,4,4-trifluorobutyl, 3,3,4,4,4-pentafluorobutyl, 2,2,3,3,4,4,4-heptafluorobutyl, nonafluorobutyl, 1,1,1-trifluorobutane-2-yl, 4,4,4-trifluorobutane-2-yl, 3,3,4,4,4-pentafluorobutane-2-yl, nonafluorobutane-2-yl, 1,1,1,3,3,3-hexafluoro-2-(trifluoromethyl)propane-2-yl, 2,2,3,4,4,4-hexafluorobutyl, 1-chlorobutyl, 2-chlorobutyl, 3-chlorobutyl, 4-chlorobutyl, 4,4-dichlorobutyl, 4,4,4-trichlorobutyl, nonachlorobutyl, 1,1,1-trichlorobutane-2-yl, 4,4,4-trichlorobutane-2-yl, nonachlorobutane-2-yl, 1-bromobutyl, 2-bromobutyl, 3-bromobutyl, 4-bromobutyl, 1-iodobutyl, 2-iodobutyl, 3-iodobutyl, 4-iodobutyl, 4-chloro-1,1,2,2,3,3,4,4-octafluorobutyl, 4-bromo-1,1,2,2,3,3,4,4-octafluorobutyl, 1-fluoropentyl, 2-fluoropentyl, 3-fluoropentyl, 4-fluoropentyl, 5-fluoropentyl, 5,5,5-trifluoropentyl, 4,4,5,5,5-pentafluoropentyl, 3,3,4,4,5,5,5-heptafluoropentyl, 2,2,3,3,4,4,5,5-octafluoropentyl, 2,2,3,3,4,4,5,5,5-nonafluoropentyl, undecafluoropentyl, 4,4,4-trifluoro-3-methylbutyl, 1-chloropentyl, 2-chloropentyl, 3-chloropentyl, 4-chloropentyl, 5-chloropentyl, 5,5,5-trichloropentyl, 4,4,5,5,5-pentachloropentyl, 3,3,4,4,5,5,5-heptachloropentyl, 2,2,3,3,4,4,5,5,5-nonachloropentyl, undecachloropentyl, 1-bromopentyl, 2-bromopentyl, 3-bromopentyl, 4-bromopentyl, 5-bromopentyl, 5-iodopentyl, 1-fluorohexyl, 2-fluorohexyl, 3-fluorohexyl, 4-fluorohexyl, 5-fluorohexyl, 6-fluorohexyl, 6,6,6-trifluorohexyl, 5,5,6,6,6-pentafluorohexyl, 4,4,5,5,6,6,6-heptafluorohexyl, 3,3,4,4,5,5,6,6,6-nonafluorohexyl, 2,2,3,3,4,4,5,5,6,6-decafluorohexyl, 2,2,3,3,4,4,5,5,6,6,6-undecafluorohexyl, tridecafluorohexyl, 1-chlorohexyl, 2-chlorohexyl, 3-chlorohexyl, 4-chlorohexyl, 5-chlorohexyl, 6-chlorohexyl, 5-bromohexyl, 6-bromohexyl, 5-iodohexyl, or 6-iodohexyl group.

In the present invention, unless otherwise specified, "$C_1$-$C_6$ alkoxy group" refers to a ($C_1$-$C_6$ alkyl)-O— group in which the alkyl moiety is as defined above, and examples of the $C_1$-$C_6$ alkoxy group include a methoxy, ethoxy, n-propoxy, isopropoxy, n-butoxy, isobutoxy, sec-butoxy, tert-butoxy, n-pentoxy, 1-methylbutoxy, 2-methylbutoxy, 3-methylbutoxy, 1-ethylpropoxy, 1,1-dimethylpropoxy, 1,2-dimethylpropoxy, or n-hexyloxy group.

In the present invention, unless otherwise specified, "$C_1$-$C_6$ haloalkoxy group" refers to a ($C_1$-$C_6$ haloalkyl)-O— group in which the haloalkyl moiety is as defined above, and examples of the $C_1$-$C_6$ haloalkoxy group include difluoromethoxy, dichloromethoxy, trifluoromethoxy, trichloromethoxy, tribromomethoxy, chlorodifluoromethoxy, bromodifluoromethoxy, 2-fluoroethoxy, 1-chloroethoxy, 2-chloroethoxy, 1-bromoethoxy, 2-bromoethoxy, 2,2-difluoroethoxy, 1,2-dichloroethoxy, 2,2-dichloroethoxy, 2,2,2-trifluoroethoxy, 2,2,2-trichloroethoxy, 1,1,2,2-tetrafluoroethoxy, pentafluoroethoxy, 2-bromo-2-chloroethoxy, 2-chloro-1,1,2,2-tetrafluoroethoxy, 1-chloro-1,2,2,2-tetrafluoroethoxy, 1-chloropropoxy, 2-chloropropoxy, 3-chloropropoxy, 2-bromopropoxy, 3-bromopropoxy, 2-bromo-1-methylethoxy, 3-iodopropoxy, 2,3-dichloropropoxy, 2,3-dibromopropoxy, 3,3,3-trifluoropropoxy, 3,3,3-trifluoro-2-propoxy, 3,3,3-trichloropropoxy, 3-bromo-3,3-difluoropropoxy, 2,2-difluoropropoxy, 3,3-dichloro-3-fluoropropoxy, 2,2,3,3-tetrafluoropropoxy, 1-bromo-3,3,3-trifluoropropoxy, 2,2,3,3,3-pentafluoropropoxy, 2,2,2-trifluoro-1-trifluoromethylethoxy, heptafluoropropoxy, heptafluoro-2-propoxy, 1,2,2,2-tetrafluoro-1-trifluoromethylethoxy, 1,1,2,3,3,3-hexafluoropropoxy, 2-chlorobutoxy, 3-chlorobutoxy, 4-chlorobutoxy, 2-chloro-1,1-dimethylethoxy, 4-bromobutoxy, 3-bromo-2-methylpropoxy, 2-bromo-1,1-dimethylethoxy, 2,2-dichloro-1,1-dimethylethoxy, 2-chloro-1-chloromethyl-2-methylethoxy, 4,4,4-trifluorobutoxy, 3,3,3-trifluoro-1-methylpropoxy, 3,3,3-trifluoro-2-methylpropoxy, 2,3,4-trichlorobutoxy, 2,2,2-trichloro-1,1-dimethylethoxy, 4-chloro-4,4-difluorobutoxy, 4,4-dichloro-4-fluorobutoxy, 4-bromo-4,4-difluorobutoxy, 2,4-dibromo-4,4-difluorobutoxy, 3,4-dichloro-3,4,4-trifluorobutoxy, 3,3-dichloro-4,4,4-trifluorobutoxy, 4-bromo-3,3,4,4-tetrafluorobutoxy, 4-bromo-3-chloro-3,4,4-trifluorobutoxy, 2,2,3,3,4,4-hexafluorobutoxy, 2,2,3,4,4,4-hexafluorobutoxy, 2,2,2-trifluoro-1-methyl-1-trifluoromethylethoxy, 3,3,3-trifluoro-2-trifluoromethylpropoxy, 2,2,3,3,4,4,4-heptafluorobutoxy, 3,3,4,4,4-pentafluoro-2-butoxy, 2,3,3,3-tetrafluoro-2-trifluoromethylpropoxy, 1,1,2,2,3,3,4,4-octafluorobutoxy, nonafluorobutoxy, perfluoro-tert-butoxy, 4-chloro-1,1,2,2,3,3,4,4-octafluorobutoxy, 5,5,5-trifluoropentoxy, 4,4,5,5,5-pentafluoropentoxy, 3,3,4,4,5,5,5-heptafluoropentoxy, 3,3,4,4,5,5,5-heptafluoro-2-pentoxy, 2,2,3,3,4,4,5,5,5-nonafluoropentoxy, 2,2,3,3,4,4,5,5-octafluoropentoxy, perfluoropentoxy, 4,4,5,5,5-pentafluoro-2-butoxy, 2,2-bis(trifluoromethyl)propoxy, 2,2,3,3,4,4,5,5,6,6,6-undecafluorohexyloxy, 3,3,4,4,5,5,6,6,6-nonafluorohexyloxy, 4,4,5,5,6,6,6-heptafluorohexyloxy, 2,2,3,3,4,4,5,5,6,6-decafluorohexyloxy, 4,4,4-trifluoro-3,3-bis(trifluoromethyl)butyloxy, or perfluorohexyloxy group.

In the present invention, unless otherwise specified, "$C_3$-$C_6$ cycloalkyl group" refers to a cycloalkyl group having 3 to 6 carbon atoms, and examples of the $C_3$-$C_6$ cycloalkyl group include a cyclopropyl, cyclobutyl, cyclopentyl, or cyclohexyl group.

In the present invention, unless otherwise specified, "$C_3$-$C_6$ halocycloalkyl group" refers to a cycloalkyl group having 3 to 6 carbon atoms, substituted by the same or different 1 to 11 halogen atoms, and examples of the $C_3$-$C_6$ halocycloalkyl group include a 1-fluorocyclopropyl, 2-fluorocyclopropyl, 2,2-difluorocyclopropyl, 2,2,3,3-tetrafluorocyclopropyl, 1-chlorocyclopropyl, 2-chlorocyclopropyl, 2,2-dichlorocyclopropyl, 2,2,3,3-tetrachlorocyclopropyl, 2,2-dibromocyclopropyl, 2,2-diiodocyclopropyl, 1-fluorocyclobutyl, 2-fluorocyclobutyl, 3-fluorocyclobutyl, 3,3-difluorocyclobutyl, heptafluorocyclobutyl, 2-chlorocyclobutyl, 3-chlorocyclobutyl, 3,3-dichlorocyclobutyl, 3,3-dibromocyclobutyl, 3,3-diiodocyclobutyl, 1-fluorocyclopentyl, 2-fluorocyclopentyl, 3-fluorocyclopentyl, 2,2-difluorocyclopentyl, 3,3-difluorocyclopentyl, nonafluorocyclopentyl, 2,2-dichlorocyclopentyl, 3,3-dichlorocyclopentyl, 2,2-dibromocyclopentyl, 3,3-dibromocyclopentyl, 2,2-diiodocyclopentyl, 3,3-diiodocyclopentyl, 1-fluorocyclohexyl, 2-fluorocyclohexyl, 3-fluorocyclohexyl, 4-fluorocyclohexyl, 2,2-difluorocyclohexyl, 3,3-difluorocyclohexyl, 4,4-difluorocyclohexyl, 1-chlorocyclohexyl, 2-chlorocyclohexyl, 3-chlorocyclohexyl, 4-chlorocyclohexyl, 2,2-dichlorocyclohexyl, 3,3-dichlorocyclohexyl, 4,4-dichlorocyclohexyl, 3,3-dibromocyclohexyl, 4,4-dibromocyclohexyl, 3,3-diiodocyclohexyl, or 4,4-diiodocyclohexyl group.

In the present invention, unless otherwise specified, "$C_3$-$C_6$ cycloalkyl $C_1$-$C_6$ alkyl group" refers to a ($C_3$-$C_6$ cycloalkyl)-($C_1$-$C_6$ alkyl)- group in which the cycloalkyl moiety and the alkyl moiety are as defined above, and examples of the $C_3$-$C_6$ cycloalkyl $C_1$-$C_6$ alkyl group include a cyclopropylmethyl, cyclobutylmethyl, cyclopentylmethyl, 2-cyclopropylethyl, 2-cyclobutylethyl, or 2-cyclopentylethyl group.

In the present invention, unless otherwise specified, "$C_3$-$C_6$ halocycloalkyl $C_1$-$C_6$ alkyl group" refers to a ($C_3$-$C_6$ halocycloalkyl)-($C_1$-$C_6$ alkyl)- group in which the halocycloalkyl moiety and the alkyl moiety are as defined above, and examples of the $C_3$-$C_6$ halocycloalkyl $C_1$-$C_6$ alkyl group include a (1-fluorocyclopropyl)methyl, (2-fluorocyclopropyl)methyl, (2,2-difluorocyclopropyl)methyl, (1-chlorocyclopropyl)methyl, (2-chlorocyclopropyl)methyl, or (2,2-dichlorocyclopropyl)methyl group.

In the present invention, "$C_1$-$C_6$ alkoxy $C_1$-$C_6$ alkyl group" refers to a ($C_1$-$C_6$ alkoxy)-($C_1$-$C_6$ alkyl)- group in which the alkoxy moiety is as defined above, and examples of the $C_1$-$C_6$ alkoxy $C_1$-$C_6$ alkyl group include a methoxymethyl, 1-methoxyethyl, 2-methoxyethyl, 2-ethoxyethyl, 3-ethoxypropyl, 3-methoxypropyl, 1-methyl-3-methoxybutyl, or 3-butoxybutyl group.

In the present invention, "$C_1$-$C_6$ alkoxy $C_1$-$C_6$ haloalkyl group" refers to a ($C_1$-$C_6$ alkoxy)-($C_1$-$C_6$ haloalkyl)- group in which the alkoxy moiety is as defined above, and examples of the $C_1$-$C_6$ alkoxy $C_1$-$C_6$ haloalkyl group include a 2-methoxy-1,1,2-trifluoroethyl or 2-ethoxy-1,1,2-trifluoroethyl group.

In the present invention, "$C_1$-$C_6$ haloalkoxy $C_1$-$C_6$ alkyl group" refers to a ($C_1$-$C_6$ haloalkoxy)-($C_1$-$C_6$ alkyl)- group in which the haloalkoxy moiety is as defined above, and examples of the $C_1$-$C_6$ haloalkoxy $C_1$-$C_6$ alkyl group include a 2-(difluoromethoxy)ethyl, 2-(trifluoromethoxy)ethyl, 2-(2,2-difluoroethoxy)ethyl, or 2-(2,2,2-trifluoroethoxy)ethyl group.

In the present invention, "$C_1$-$C_6$ haloalkoxy $C_1$-$C_6$ haloalkyl group" refers to a ($C_1$-$C_6$ haloalkoxy)-($C_1$-$C_6$ haloalkyl)- group in which the haloalkoxy moiety is as defined above, and examples of the $C_1$-$C_6$ haloalkoxy $C_1$-$C_6$ haloalkyl group include a 1,1,2-trifluoro-2-(trifluoromethoxy)ethyl, 1,1,2-trifluoro-2-(pentafluoroethoxy)ethyl, or 1,1,2-trifluoro-2-(heptafluoropropoxy)ethyl group.

In the present invention, unless otherwise specified, "$C_2$-$C_6$ alkenyl group" refers to a linear or branched alkenyl group having 2 to 6 carbon atoms, and examples of the $C_2$-$C_6$ alkenyl group include a vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-prop enyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl, or 2,4-hexadienyl group.

In the present invention, unless otherwise specified, "$C_2$-$C_7$ alkynyl group" refers to a linear or branched alkynyl group having 2 to 7 carbon atoms, and examples of the $C_2$-$C_7$ alkynyl group include an ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(isopropyl)-2-propynyl, 1,1-dimethyl-2-butynyl or 2,2-dimethyl-3-butynyl, 1-heptynyl, 1-(n-butyl)-2-propynyl, 1-(s-butyl)-2-propynyl, 1-isobutyl-2-propynyl, 2-heptynyl, 3-heptynyl, 1-methyl-2-hexynyl, 4-methyl-2-hexynyl, 5-methyl-2-hexynyl, 6-heptynyl, 1,1-diethyl-2-propynyl, 1-methyl-1-propyl-2-propynyl, 1-isopropyl-1-methyl-2-propynyl, 1,1-dimethyl-2-pentynyl, 1,4-dimethyl-2-pentynyl, or 4,4-dimethyl-2-pentynyl group.

In the present invention, unless otherwise specified, "$C_2$-$C_6$ haloalkynyl group" refers to a linear or branched alkynyl group having 2 to 6 carbon atoms, substituted with the same or different 1 to 9 halogen atoms, and examples of the $C_2$-$C_6$ haloalkynyl group include a fluoroethynyl, chloroethynyl, bromoethynyl, iodoethynyl, 3-fluoro-2-propynyl, 3-chloro-2-propynyl, 3-bromo-2-propynyl, 3-iodo-2-propynyl, 4-fluoro-3-butynyl, 4-chloro-3-butynyl, 4-bromo-3-butynyl, 4-iodo-3-butynyl, 4,4-difluoro-2-butynyl, 4,4-dichloro-2-butynyl, 4,4,4-trifluoro-2-butynyl, 4,4,4-trichloro-2-butynyl, 3-fluoro-1-methyl-2-propynyl, 3-chloro-1-methyl-2-propynyl, 5-fluoro-4-pentynyl, 5-chloro-4-pentynyl, 5,5,5-trifluoro-3-pentynyl, 5,5,5-trichloro-3-pentynyl, 4-fluoro-2-methyl-3-butynyl, 4-chloro-2-methyl-3-butynyl, 6-fluoro-5-hexynyl, 6-chloro-5-hexynyl, 6,6,6-trifluoro-4-hexynyl, 6,6,6-trichloro-4-hexynyl, 5-fluoro-3-methyl-4-pentynyl, or 5-chloro-3-methyl-4-pentynyl group.

In the present invention, unless otherwise specified, "$C_2$-$C_6$ haloalkenyl group" refers to a linear or branched alkenyl group having 2 to 6 carbon atoms, substituted with the same or different 1 to 11 halogen atoms, and examples of the $C_2$-$C_6$ haloalkenyl group include a 1-fluorovinyl, 2-fluorovinyl, 1,2-difluorovinyl, 2,2-difluorovinyl, trifluorovinyl, 1-chlorovinyl, 2-chlorovinyl, 1,2-dichlorovinyl, 2,2-dichlorovinyl, trichlorovinyl, 1,2-dibromovinyl, 2,2-dibromovinyl, tribromovinyl, 1,2-diiodovinyl, 2,2-diiodovinyl, triodovinyl, 1-fluoro-2-propenyl, 2-fluoro-2-propenyl, 3-fluoro-2-propenyl, 2,3-difluoro-2-propenyl, 3,3-difluoro-2-propenyl, 3,3-difluoro-1-propenyl, 2,3,3-trifluoro-2-propenyl, 3,3,3-trifluoro-1-propenyl, 2-chloro-3,3,3-trifluoro-1-propenyl, 1,2,3,3,3-pentafluoro-1-propenyl, 1-chloro-2-propenyl, 2-chloro-2-propenyl, 3-chloro-2-propenyl, 2,3-dichloro-2-propenyl, 3,3-dichloro-2-propenyl, 3,3-dichloro-1-propenyl, 2,3,3-trichloro-2-propenyl, 3,3,3-trichloro-1-propenyl, 3-bromo-2-propenyl, 3,3-dibromo-2-propenyl, 3,3-diiodo-2-propenyl, 2,2-difluoro-1-propene-2-yl, 3,3,3-trifluoro-1-propene-2-yl, 3,3,3-trichloro-1-propene-2-yl, 4-fluoro-3-butenyl, 4,4-difluoro-3-butenyl, 4,4-difluoro-3-butene-2-yl, 4,4,4-trifluoro-2-butenyl, 3,4,4-trifluoro-3-butenyl, 2-trifluoromethyl-2-propenyl, 2-trifluoromethyl-3,3-difluoro-2-propenyl, 4,4,4-trifluoro-3-chloro-2-butenyl, 4,4-dichloro-3-butenyl, 4,4,4-trichloro-2-butenyl, 2-trichloromethyl-2-propenyl, 5,5-difluoro-4-pentenyl, 4,5,5-trifluoro-4-pentenyl, 5,5,5-trifluoro-3-pentenyl, 4,4,4-trifluoro-3-methyl-2-butenyl, 4,4,4-trifluoro-3-trifluoromethyl-2-butenyl, 5,5-dichloro-4-pentenyl, 4,4,4-trichloro-3-methyl-2-butenyl, 6,6-difluoro-5-hexenyl, 5,6,6-trifluoro-5-pentenyl, 6,6,6-trifluoro-4-pentenyl, 5,5,5-trifluoro-4-methyl-3-pentenyl, 5,5,5-trifluoro-4-trifluoromethyl-3-pentenyl, 6,6-dichloro-5-hexenyl, or 5,5,5-trichloro-4-methyl-3-pentenyl group.

In the present invention, "$C_1$-$C_6$ alkylthio group" refers to a ($C_1$-$C_6$ alkyl)-S— group in which the alkyl moiety is as defined above, and examples of the $C_1$-$C_6$ alkylthio group include a methylthio, ethylthio, n-propylthio, isopropylthio, n-butylthio, isobutylthio, sec-butylthio, or tert-butylthio group.

In the present invention, "$C_1$-$C_6$ alkylsulfinyl group" refers to a ($C_1$-$C_6$ alkyl)-S(=O)— group in which the alkyl moiety is as defined above, and examples of the $C_1$-$C_6$ alkylsulfinyl group include a methylsulfinyl, ethylsulfinyl, n-propylsulfinyl, isopropylsulfinyl, n-butylsulfinyl, isobutylsulfinyl, sec-butylsulfinyl, or tert-butylsulfinyl group.

In the present invention, "$C_1$-$C_6$ alkylsulfonyl group" refers to a ($C_1$-$C_6$ alkyl)-S(=O)$_2$— group in which the alkyl moiety is as defined above, and examples of the $C_1$-$C_6$ alkylsulfonyl group include a methylsulfonyl, ethylsulfonyl, n-propylsulfonyl, isopropylsulfonyl, n-butylsulfonyl, isobutylsulfonyl, sec-butylsulfonyl, or tert-butylsulfonyl group.

In the present invention, unless otherwise specified, "$C_1$-$C_6$ haloalkylthio group" refers to a ($C_1$-$C_6$ haloalkyl)-S— group in which the haloalkyl moiety is as defined above, and examples of the $C_1$-$C_6$ haloalkylthio group include a fluoromethylthio, difluoromethylthio, trifluoromethylthio, trichloromethylthio, 2,2,2-trifluoroethylthio, pentafluoroethylthio, 2,2,2-trichloroethylthio, 3,3,3-trifluoropropylthio, 1,1,2,3,3,3-hexafluoropropyl, heptafluoropropylthio, 1,1,1,3,3,3-hexafluoropropane-2-ylthio, heptafluoropropane-2-ylthio, or 4,4,4-trifluorobutylthio group.

In the present invention, unless otherwise specified, "$C_1$-$C_6$ haloalkylsulfinyl group" refers to a ($C_1$-$C_6$ haloalkyl)-S(=O)— group in which the haloalkyl moiety is as defined above, and examples of the $C_1$-$C_6$ haloalkylsulfinyl group include a difluoromethylsulfinyl, trifluoromethylsulfinyl, trichloromethylsulfinyl, 2,2,2-trifluoroethylsulfinyl, 2,2,2-trichloroethylsulfinyl, pentafluoroethylsulfinyl, 3,3,3-trifluoropropylsulfinyl, heptafluoropropylsulfinyl, or heptafluoro-2-propylsulfinyl group.

In the present invention, unless otherwise specified, "$C_1$-$C_6$ haloalkylsulfonyl group" refers to a ($C_1$-$C_6$ haloalkyl)-S(=O)$_2$— group in which the haloalkyl moiety is as defined above, and examples of the $C_1$-$C_6$ haloalkylsulfonyl group include a difluoromethylsulfonyl, trifluoromethylsulfonyl, trichloromethylsulfonyl, 2,2,2-trifluoroethylsulfonyl, pentafluoroethylsulfonyl, 3,3,3-trifluoropropylsulfonyl, heptafluoropropylsulfonyl, or heptafluoro-2-propylsulfonyl group.

In the present invention, unless otherwise specified, "$C_1$-$C_6$ alkylthio $C_1$-$C_6$ alkyl group" refers to a ($C_1$-$C_6$ alkyl)-S—($C_1$-$C_6$ alkyl)- group in which the alkyl moiety is as defined above, and examples of the $C_1$-$C_6$ alkylthio $C_1$-$C_6$ alkyl group include a methylthiomethyl, ethylthiomethyl, n-propylthiomethyl, isopropylthiomethyl, 1-(methylthio)

ethyl, 2-(methylthio)ethyl, 2-(ethylthio)ethyl, 1-(n-propylthio)ethyl, 2-(n-propylthio)ethyl, 1-(methylthio)propyl, 2-(methylthio)propyl, 3-(methylthio)propyl, 1-(ethylthio)propyl, 2-(ethylthio)propyl, 3-(ethylthio)propyl, 1-(n-propylthio)propyl, 2-(n-propylthio)propyl, 3-(n-propylthio)propyl, 2-(n-butylthio)ethyl, 2-(isobutylthio)ethyl, sec-butylthioethyl, 2-(tert-butylthio)ethyl, pentylthiomethyl, or hexylthiomethyl group.

In the present invention, unless otherwise specified, "$C_1$-$C_6$ alkylsulfinyl $C_1$-$C_6$ alkyl group" refers to a ($C_1$-$C_6$ alkyl)-S(=O)—($C_1$-$C_6$ alkyl)- group in which the alkyl moiety is as defined above, and examples of the $C_1$-$C_6$ alkylsulfinyl $C_1$-$C_6$ alkyl group include a methylsulfinylmethyl, ethylsulfinylmethyl, n-propylsulfinylmethyl, isopropylsulfinylmethyl, 1-(methylsulfinyl)ethyl, 2-(methylsulfinyl)ethyl, 2-(ethylsulfinyl)ethyl, 1-(n-propylsulfinyl)ethyl, 2-(n-propylsulfinyl)ethyl, 1-(methylsulfinyl)propyl, 2-(methylsulfinyl)propyl, 3-(methylsulfinyl)propyl, 1-(ethylsulfinyl)propyl, 2-(ethylsulfinyl)propyl, 3-(ethylsulfinyl)propyl, 1-(n-propylsulfinyl)propyl, 2-(n-propylsulfinyl)propyl, 3-(n-propylsulfinyl)propyl, 2-(n-butylsulfinyl)ethyl, 2-(isobutylsulfinyl)ethyl, sec-butylsulfinylethyl, 2-(tert-butylsulfinyl)ethyl, pentylsulfinylmethyl, or hexylsulfinylmethyl group.

In the present invention, unless otherwise specified, "$C_1$-$C_6$ alkylsulfonyl $C_1$-$C_6$ alkyl group" refers to a ($C_1$-$C_6$ alkyl)-S(=O)$_2$—($C_1$-$C_6$ alkyl)- group in which the alkyl moiety is as defined above, and examples of the $C_1$-$C_6$ alkylsulfonyl $C_1$-$C_6$ alkyl group include a methylsulfonylmethyl, ethylsulfonylmethyl, n-propylsulfonylmethyl, isopropylsulfonylmethyl, 1-(methylsulfonyl)ethyl, 2-(methylsulfonyl)ethyl, 2-(ethylsulfonyl)ethyl, 1-(n-propylsulfonyl)ethyl, 2-(n-propylsulfonyl)ethyl, 1-(methylsulfonyl)propyl, 2-(methylsulfonyl)propyl, 3-(methylsulfonyl)propyl, 1-(ethylsulfonyl)propyl, 2-(ethylsulfonyl)propyl, 3-(ethylsulfonyl)propyl, 1-(n-propylsulfonyl)propyl, 2-(n-propylsulfonyl)propyl, 3-(n-propylsulfonyl)propyl, 2-(n-butylsulfonyl)ethyl, 2-(isobutylsulfonyl)ethyl, sec-butylsulfonylethyl, 2-(tert-butylsulfonyl)ethyl, pentylsulfonylmethyl, or hexylsulfonylmethyl group.

In the present invention, "$C_1$-$C_6$ haloalkylthio $C_1$-$C_6$ alkyl group" refers to a ($C_1$-$C_6$ haloalkyl)-S—($C_1$-$C_6$ alkyl)- group in which the haloalkylthio moiety and the alkyl moiety are as defined above, and examples of the $C_1$-$C_6$ haloalkylthio $C_1$-$C_6$ alkyl group include a 2-(difluoromethylthio)ethyl, 2-(trifluoromethylthio)ethyl, 2-(2,2-difluoroethylthio)ethyl, 2-(2,2,2-trifluoroethylthio)ethyl, 2-(3,3-difluoropropylthio)ethyl, 2-(3,3,3-trifluoroethylthio)ethyl, 3-(difluoromethylthio)propyl, 3-(trifluoromethylthio)propyl, 3-(2,2-difluoroethylthio)propyl, 3-(2,2,2-trifluoroethylthio)propyl, 3-(3,3-difluoropropylthio)propyl, or 3-(3,3,3-trifluoropropylthio)propyl group.

In the present invention, "$C_1$-$C_6$ haloalkylsulfinyl $C_1$-$C_6$ alkyl group" refers to a ($C_1$-$C_6$ haloalkyl)-S(=O)—($C_1$-$C_6$ alkyl)- group in which the haloalkylsulfinyl moiety and the alkyl moiety are as defined above, and examples of the $C_1$-$C_6$ haloalkylsulfinyl $C_1$-$C_6$ alkyl group include a 2-(difluoromethylsulfinyl)ethyl, 2-(trifluoromethylsulfinyl)ethyl, 2-(2,2-difluoroethylsulfinyl)ethyl, 2-(2,2,2-trifluoroethylsulfinyl)ethyl, 2-(3,3-difluoropropylsulfinyl)ethyl, 2-(3,3,3-trifluoroethylsulfinyl)ethyl, 3-(difluoromethylsulfinyl)propyl, 3-(trifluoromethylsulfinyl)propyl, 3-(2,2-difluoroethylsulfinyl)propyl, 3-(2,2,2-trifluoroethylsulfinyl)propyl, 3-(3,3-difluoropropylsulfinyl)propyl, or 3-(3,3,3-trifluoropropylsulfinyl)propyl group.

In the present invention, "$C_1$-$C_6$ haloalkylsulfonyl $C_1$-$C_6$ alkyl group" refers to a ($C_1$-$C_6$ haloalkyl)-S(=O)$_2$—($C_1$-$C_6$ alkyl)- group in which the haloalkylsulfonyl moiety and the alkyl moiety are as defined above, and examples of the $C_1$-$C_6$ haloalkylsulfonyl $C_1$-$C_6$ alkyl group include a 2-(difluoromethylsulfonyl)ethyl, 2-(trifluoromethylsulfonyl)ethyl, 2-(2,2-difluoroethylsulfonyl)ethyl, 2-(2,2,2-trifluoroethylsulfonyl)ethyl, 2-(3,3-difluoropropylsulfonyl)ethyl, 2-(3,3,3-trifluoroethylsulfonyl)ethyl, 3-(difluoromethylsulfonyl)propyl, 3-(trifluoromethylsulfonyl)propyl, 3-(2,2-difluoroethylsulfonyl)propyl, 3-(2,2,2-trifluoroethylsulfonyl)propyl, 3-(3,3-difluoropropylsulfonyl)propyl, or 3-(3,3,3-trifluoropropylsulfonyl)propyl group.

In the present invention, "mono($C_1$-$C_6$ alkyl)amino group" refers to a ($C_1$-$C_6$ alkyl)-NH— group in which the alkyl moiety is as defined above, and examples of the mono($C_1$-$C_6$ alkyl)amino group include a methylamino, ethylamino, n-propylamino, or isopropyl amino group.

In the present invention, "di($C_1$-$C_6$ alkyl)amino group" refers to a ($C_1$-$C_6$ alkyl)$_2$-N— group in which the alkyl moiety is as defined above, and the two alkyl groups may be different from each other, and examples of the di($C_1$-$C_6$ alkyl)amino group include a dimethylamino, diethylamino, or N-ethyl-N-methylamino group.

In the present invention, "mono($C_1$-$C_6$ alkyl)aminocarbonyl group" refers to a ($C_1$-$C_6$ alkyl)-NH—C(=O)— group in which the alkyl moiety is as defined above, and examples of the mono($C_1$-$C_6$ alkyl)aminocarbonyl group include a methylaminocarbonyl, ethylaminocarbonyl, propylaminocarbonyl, or isopropylaminocarbonyl group.

In the present invention, "di($C_1$-$C_6$ alkyl)aminocarbonyl group" refers to a ($C_1$-$C_6$ alkyl)$_2$-N—C(=O)— group in which the alkyl moiety is as defined above, and the two alkyl groups may be different from each other, and examples of the di($C_1$-$C_6$ alkyl)aminocarbonyl group include a dimethylaminocarbonyl, diethylaminocarbonyl, di(n-propyl)aminocarbonyl, or N-ethyl-N-methylaminocarbonyl group.

In the present invention, "$C_1$-$C_6$ alkylcarbonyl $C_1$-$C_6$ alkyl group" refers to a ($C_1$-$C_6$ alkyl)-C(=O)—($C_1$-$C_6$ alkyl)- group in which the alkyl moiety is as defined above, and examples of the $C_1$-$C_6$ alkylcarbonyl $C_1$-$C_6$ alkyl group include an acetonyl, propionylmethyl, 2-methylpropionylmethyl, pivaloylmethyl, 2-acetylethyl, 2-propionylethyl, 2(2-methylpropionyl)ethyl, 2-pivaloylethyl, 3-acetylpropyl, 3-propionylpropyl, 3(2-methylpropionyl)propyl, or 3-pivaloylpropyl group.

In the present invention, "$C_1$-$C_6$ haloalkylcarbonyl $C_1$-$C_6$ alkyl group" refers to a ($C_1$-$C_6$ haloalkyl)-C(=O)—($C_1$-$C_6$ alkyl)- group in which the haloalkyl moiety and the alkyl moiety are as defined above, and examples of the $C_1$-$C_6$ haloalkylcarbonyl $C_1$-$C_6$ alkyl group include a 3,3,3-trifluoro-2-oxopropyl group.

In the present invention, "$C_1$-$C_6$ alkoxycarbonyl $C_1$-$C_6$ alkyl group" refers to a ($C_1$-$C_6$ alkoxy)-C(=O)—($C_1$-$C_6$ alkyl)- group in which the alkoxy moiety and the alkyl moiety are as defined above, and examples of the $C_1$-$C_6$ alkoxycarbonyl $C_1$-$C_6$ alkyl group include a methoxycarbonylmethyl, ethoxycarbonylmethyl, n-propoxycarbonylmethyl, isopropoxycarbonylmethyl, tert-butoxycarbonylmethyl, 2-(methoxycarbonyl)ethyl, 2-(ethoxycarbonyl)ethyl, or 2-(tert-butoxycarbonyl)ethyl group.

In the present invention, unless otherwise specified, "hydroxy $C_1$-$C_6$ alkyl group" refers to a (hydroxy)-($C_1$-$C_6$ alkyl)- group in which the alkyl moiety is as defined above, and examples of the hydroxy $C_1$-$C_6$ alkyl group include a 2-hydroxyethyl, 2-hydroxypropyl, 3-hydroxypropyl, or 4-hydroxybutyl group.

In the present invention, unless otherwise specified, "cyano $C_1$-$C_6$ alkyl group" refers to a (cyano)-($C_1$-$C_6$ alkyl)- group in which the alkyl moiety is as defined above, and examples of the cyano $C_1$-$C_6$ alkyl group include a cyanomethyl, 1-cyanoethyl, 2-cyanoethyl, 3-cyanopropyl, 2-cyanopropane-2-yl, 1-cyanobutyl, 4-cyanobutyl, 5-cyanopentyl, or 6-cyanohexyl group.

In the present invention, unless otherwise specified, "$C_1$-$C_6$ alkylsulfonyloxy group" refers to a ($C_1$-$C_6$ alkyl)-S(=O)$_2$—O— group in which the alkyl moiety is as defined above, and examples of the $C_1$-$C_6$ alkylsulfonyloxy group include a methylsulfonyloxy, ethylsulfonyloxy, or isopropylsulfonyloxy group.

In the present invention, unless otherwise specified, "$C_1$-$C_6$ haloalkylsulfonyloxy group" refers to a ($C_1$-$C_6$haloalkyl)-S(=O)$_2$—O— group in which the haloalkyl moiety is as defined above, and examples of the $C_1$-$C_6$ haloalkylsulfonyloxy group include a trifluoromethylsulfonyloxy, perfluoroethylsulfonyloxy, perfluoropropylsulfonyloxy, or perfluorobutylsulfonyloxy group.

In the present invention, unless otherwise specified, "$C_1$-$C_6$ alkylcarbonyl group" refers to a ($C_1$-$C_6$ alkyl)-C(=O)— group in which the alkyl moiety is as defined above, and examples of the $C_1$-$C_6$ alkylcarbonyl group include an acetyl or propionyl group.

In the present invention, unless otherwise specified, "$C_1$-$C_6$ haloalkylcarbonyl group" refers to a ($C_1$-$C_6$ haloalkyl)-C(=O)— group in which the haloalkyl moiety is as defined above, and examples of the $C_1$-$C_6$ haloalkylcarbonyl group include a 2,2,2-trifluoroacetyl group or 2,2,2-trichloroacetyl group.

In the present invention, "$C_1$-$C_6$ alkoxycarbonyl group" refers to a ($C_1$-$C_6$ alkoxy)-C(=O)— group in which the alkoxy moiety is as defined above, and examples of the $C_1$-$C_6$ alkoxycarbonyl group include a methoxycarbonyl, ethoxycarbonyl, n-propoxycarbonyl, isopropoxycarbonyl, or tert-butoxycarbonyl group.

In the present invention, unless otherwise specified, "$C_3$-$C_6$ cycloalkoxy group" refers to a ($C_3$-$C_6$ cycloalkyl)-O— group in which the cycloalkyl moiety is as defined above, and examples of the $C_3$-$C_6$ cycloalkoxy group include a cyclopropoxy, cyclobutoxy, cyclopentyloxy, or cyclohexyloxy group.

In the present invention, unless otherwise specified, "$C_3$-$C_6$ halocycloalkoxy group" refers to a ($C_3$-$C_6$ halocycloalkyl)-O— group in which the halocycloalkyl moiety is as defined above, and examples of the $C_3$-$C_6$ halocycloalkoxy group include a 1-fluorocyclopropoxy, 2-fluorocyclopropoxy, 2,2-difluorocyclopropoxy, 2,2,3,3-tetrafluorocyclopropoxy, 1-chlorocyclopropoxy, 2-chlorocyclopropoxy, 2,2-dichlorocyclopropoxy, 2,2,3,3-tetrachlorocyclopropoxy, 1-fluorocyclobutoxy, 2-fluorocyclobutoxy, 3-fluorocyclobutoxy, 3,3-difluorocyclobutoxy, 2-chlorocyclobutoxy, 3-chlorocyclobutoxy, 3,3-dichlorocyclobutoxy, 2-fluorocyclopentyloxy, 3-fluorocyclopentyloxy, 2,2-difluorocyclopentyloxy, 3,3-difluorocyclopentyloxy, 2,2-dichlorocyclopentyloxy, 3,3-dichlorocyclopentyloxy, 1-fluorocyclohexyloxy, 2-fluorocyclohexyloxy, 3-fluorocyclohexyloxy, 4-fluorocyclohexyloxy, 2,2-difluorocyclohexyloxy, 3,3-difluorocyclohexyloxy, 4,4-difluorocyclohexyloxy, 1-chlorocyclohexyloxy, 2-chlorocyclohexyloxy, 3-chlorocyclohexyloxy, 4-chlorocyclohexyloxy, 2,2-dichlorocyclohexyloxy, 3,3-dichlorocyclohexyloxy, or 4,4-dichlorocyclohexyloxy group.

In the present invention, unless otherwise specified, "$C_3$-$C_6$ cycloalkyl $C_1$-$C_6$ alkoxy group" refers to a ($C_3$-$C_6$ cycloalkyl)-($C_1$-$C_6$ alkyl)-O— group in which the cycloalkyl moiety is as defined above, and examples of the $C_3$-$C_6$ cycloalkyl $C_1$-$C_6$ alkoxy group include a cyclopropylmethoxy, cyclobutylmethoxy, cyclopentylmethoxy, 2-cyclopropylethoxy, 2-cyclobutylethoxy, or 2-cyclopentylethoxy group.

In the present invention, unless otherwise specified, "$C_3$-$C_6$ halocycloalkyl $C_1$-$C_6$ alkoxy group" refers to a ($C_3$-$C_6$ halocycloalkyl)-($C_1$-$C_6$ alkyl)-O— group in which the halocycloalkyl moiety is as defined above, and examples of the $C_3$-$C_6$ halocycloalkyl $C_1$-$C_6$ alkoxy group include a (1-fluorocyclopropyl)methoxy, (2-fluorocyclopropyl)methoxy, (2,2-difluorocyclopropyl)methoxy, (2-chlorocyclopropyl)methoxy, or (2,2-dichlorocyclopropyl)methoxy group.

In the present invention, unless otherwise specified, "$C_3$-$C_6$ cycloalkyl $C_1$-$C_6$ alkylthio group" refers to a ($C_3$-$C_6$ cycloalkyl)-($C_1$-$C_6$ alkyl)-S— group in which the cycloalkyl moiety is as defined above, and examples of the $C_3$-$C_6$ cycloalkyl $C_1$-$C_6$ alkylthio group include a (cyclopropylmethyl)thio, (cyclobutylmethyl)thio, (cyclopentylmethyl)thio, (2-cyclopropylethyl)thio, (2-cyclobutylethyl)thio, or (2-cyclopentylethyl)thio group.

In the present invention, unless otherwise specified, "$C_3$-$C_6$ cycloalkyl $C_1$-$C_6$ alkylsulfinyl group" refers to a ($C_3$-$C_6$ cycloalkyl)-($C_1$-$C_6$ alkyl)-S(=O)— group in which the cycloalkyl moiety is as defined above, and examples of the $C_3$-$C_6$ cycloalkyl $C_1$-$C_6$ alkylsulfinyl group include a (cyclopropylmethyl)sulfinyl, (cyclobutylmethyl)sulfinyl, (cyclopentylmethyl)sulfinyl, (2-cyclopropylethyl)sulfinyl, (2-cyclobutylethyl)sulfinyl, or (2-cyclopentylethyl)sulfinyl group.

In the present invention, unless otherwise specified, "$C_3$-$C_6$ cycloalkyl $C_1$-$C_6$ alkylsulfonyl group" refers to a ($C_3$-$C_6$ cycloalkyl)-($C_1$-$C_6$ alkyl)-S(=O)$_2$— group in which the cycloalkyl moiety is as defined above, and examples of the $C_3$-$C_6$ cycloalkyl $C_1$-$C_6$ alkylsulfonyl group include a (cyclopropylmethyl)sulfonyl, (cyclobutylmethyl)sulfonyl, (cyclopentylmethyl)sulfonyl, (2-cyclopropylethyl)sulfonyl, (2-cyclobutylethyl)sulfonyl, or (2-cyclopentylethyl)sulfonyl group.

In the present invention, unless otherwise specified, "$C_3$-$C_6$ halocycloalkyl $C_1$-$C_6$ alkylthio group" refers to a ($C_3$-$C_6$ halocycloalkyl)-($C_1$-$C_6$ alkyl)-S— group in which the halocycloalkyl moiety is as defined above, and examples of the $C_3$-$C_6$ halocycloalkyl $C_1$-$C_6$ alkylthio group include a (1-fluorocyclopropyl)methylthio, (2-fluorocyclopropyl)methylthio, (2,2-difluorocyclopropyl)methylthio, (2-chlorocyclopropyl)methylthio, or (2,2-dichlorocyclopropyl)methylthio group.

In the present invention, unless otherwise specified, "$C_3$-$C_6$ halocycloalkyl $C_1$-$C_6$ alkylsulfinyl group" refers to a ($C_3$-$C_6$ halocycloalkyl)-($C_1$-$C_6$ alkyl)-S(=O)— group in which the halocycloalkyl moiety is as defined above, and examples of the $C_3$-$C_6$ halocycloalkyl $C_1$-$C_6$ alkylsulfinyl group include a (1-fluorocyclopropyl)methylsulfinyl, (2-fluorocyclopropyl)methylsulfinyl, (2,2-difluorocyclopropyl)methylsulfinyl, (2-chlorocyclopropyl)methylsulfinyl, or (2,2-dichlorocyclopropyl)methylsulfinyl group.

In the present invention, unless otherwise specified, "$C_3$-$C_6$ halocycloalkyl $C_1$-$C_6$ alkylsulfonyl group" refers to a ($C_3$-$C_6$ halocycloalkyl)-($C_1$-$C_6$ alkyl)-S(=O)$_2$— group in which the cycloalkyl moiety is as defined above, and examples of the $C_3$-$C_6$ halocycloalkyl $C_1$-$C_6$ alkylsulfonyl group include a (1-fluorocyclopropyl)methylsulfonyl, (2-fluorocyclopropyl)methylsulfonyl, (2,2-difluorocyclopropyl)methylsulfonyl, (2-chlorocyclopropyl)methylsulfonyl, or (2,2-dichlorocyclopropyl)methylsulfonyl group.

In the present invention, unless otherwise specified, "mono(oxirane-2-yl) $C_1$-$C_3$ alkyl group" refers to an (oxirane-2-yl)-($C_1$-$C_3$ alkyl)- group in which the alkyl moiety is as defined above, and examples of the mono(oxirane-2-yl) $C_1$-$C_3$ alkyl group include an oxirane-2-ylmethyl, 2-(oxirane-2-yl)ethyl, or 3-(oxirane-2-yl)propyl group.

In the present invention, unless otherwise specified, "$C_1$-$C_6$ alkylcarbonyloxy group" refers to a ($C_1$-$C_6$ alkyl)-C(=O)—O— group in which the alkyl moiety is as defined above, and examples of the $C_1$-$C_6$ alkylcarbonyloxy group include an acetoxy or propionyloxy group.

In the present invention, unless otherwise specified, "$C_1$-$C_6$ haloalkylcarbonyloxy group" refers to a ($C_1$-$C_6$ haloalkyl)-C(=O)—O— group in which the haloalkyl moiety is as defined above, and examples of the $C_1$-$C_6$ haloalkylcarbonyloxy group include a 2,2,2-trifluoroacetoxy or 2,2,2-trichloroacetoxy group.

In the present invention, unless otherwise specified, "mono($C_1$-$C_6$ alkyl)aminocarbonyloxy group" refers to a ($C_1$-$C_6$ alkyl)-NH—C(=O)—O— group in which the alkyl moiety is as defined above, and examples of the mono($C_1$-$C_6$ alkyl)aminocarbonyloxy group include a (methylcarbamoyl)oxy or (ethylcarbamoyl)oxy group.

In the present invention, unless otherwise specified, "di($C_1$-$C_6$ alkyl)aminocarbonyloxy group" refers to a ($C_1$-$C_6$ alkyl)$_2$-N—C(=O)—O— group in which the alkyl moiety is as defined above, and examples of the di($C_1$-$C_6$ alkyl)aminocarbonyloxy group include a (dimethylcarbamoyl)oxy or (diethylcarbamoyl)oxy group.

In the present invention, unless otherwise specified, "aminocarbonyloxy $C_1$-$C_6$ alkyl group" refers to an (amino)-C(=O)—O—($C_1$-$C_6$ alkyl)- group in which the alkyl moiety is as defined above, and examples of the aminocarbonyloxy $C_1$-$C_6$ alkyl group include a carbamoyloxymethyl or carbamoyloxyethyl group.

In the present invention, unless otherwise specified, "mono($C_1$-$C_6$ alkyl)aminocarbonyloxy $C_1$-$C_6$ alkyl group" refers to a ($C_1$-$C_6$ alkyl)-NH—C(=O)—O—($C_1$-$C_6$ alkyl)- group in which the alkyl moiety is as defined above, and examples of the mono($C_1$-$C_6$ alkyl)aminocarbonyloxy $C_1$-$C_6$ alkyl group include a methylcarbamoyloxymethyl or ethylcarbamoyloxymethyl group.

In the present invention, unless otherwise specified, "di($C_1$-$C_6$ alkyl)aminocarbonyloxy $C_1$-$C_6$ alkyl group" refers to a ($C_1$-$C_6$ alkyl)$_2$-N—C(=O)—O—($C_1$-$C_6$ alkyl)- group in which the alkyl moiety is as defined above, and examples of the di($C_1$-$C_6$ alkyl)aminocarbonyloxy $C_1$-$C_6$ alkyl group include a dimethylcarbamoyloxymethyl or diethylcarbamoyloxymethyl group.

In the present invention, unless otherwise specified, "$C_1$-$C_6$ alkoxycarbonyloxy group" refers to a ($C_1$-$C_6$ alkoxy)-C(=O)—O— group in which the alkoxy moiety is as defined above, and examples of the $C_1$-$C_6$ alkoxycarbonyloxy group include a methoxycarbonyloxy or ethoxycarbonyloxy group.

In the present invention, "$C_1$-$C_6$ alkoxycarbonyloxy $C_1$-$C_6$ alkyl group" refers to a ($C_1$-$C_6$ alkoxy)-C(=O)—O—($C_1$-$C_6$ alkyl)- group in which the alkoxy moiety is as defined above, and examples of the $C_1$-$C_6$ alkoxycarbonyloxy $C_1$-$C_6$ alkyl group include a methoxycarbonyloxymethyl or ethoxycarbonyloxymethyl group.

In the present invention, "$C_3$-$C_6$ cycloalkyl $C_2$-$C_6$ alkynyl group" refers to a ($C_3$-$C_6$ cycloalkyl)-($C_2$-$C_6$ alkynyl)- group in which the cycloalkyl moiety is as defined above, and examples of the $C_3$-$C_6$ cycloalkyl $C_2$-$C_6$ alkynyl group include a cyclopropylethynyl or cyclobutylethynyl group.

In the present invention, "$C_3$-$C_6$ cycloalkylthio group" refers to a ($C_3$-$C_6$ cycloalkyl)-S— group in which the cycloalkyl moiety is as defined above, and examples of the $C_3$-$C_6$ cycloalkylthio group include a cyclopropylthio, cyclobutylthio, or cyclopentylthio group.

In the present invention, "$C_3$-$C_6$ cycloalkylsulfinyl group" refers to a ($C_3$-$C_6$ cycloalkyl)-S(=O)— group in which the cycloalkyl moiety is as defined above, and examples of the $C_3$-$C_6$ cycloalkylsulfinyl group include a cyclopropylsulfinyl, cyclobutylsulfinyl, or cyclopentylsulfinyl group.

In the present invention, "$C_3$-$C_6$ cycloalkylsulfonyl group" refers to a ($C_3$-$C_6$ cycloalkyl)-S(=O)$_2$— group in which the cycloalkyl moiety is as defined above, and examples of the $C_3$-$C_6$ cycloalkylsulfonyl group include a cyclopropylsulfonyl, cyclobutylsulfonyl, or cyclopentylsulfonyl group.

In the present invention, "$C_1$-$C_6$ alkylcarbonyloxy $C_1$-$C_6$ alkyl group" refers to a ($C_1$-$C_6$ alkyl)-C(=O)—O—($C_1$-$C_6$ alkyl)- group in which the alkyl moiety is as defined above, and examples of the $C_1$-$C_6$ alkylcarbonyloxy $C_1$-$C_6$ alkyl group include an acetoxymethyl, 2-acetoxyethyl, or propionylmethyl group.

In the present invention, "di($C_1$-$C_6$ alkyl)sulfamoyloxy group" refers to a ($C_1$-$C_6$ alkyl)$_2$-N—S(=O)$_2$—O— group in which the alkyl moiety is as defined above, and examples of the di($C_1$-$C_6$ alkyl)sulfamoyloxy group include a dimethylsulfamoyloxy or diethylsulfamoyloxy group.

In the present invention, unless otherwise specified, "cyano $C_3$-$C_6$ cycloalkyl group" refers to a (cyano)-($C_3$-$C_6$ cycloalkyl) group in which the cycloalkyl moiety is as defined above, and examples of the cyano $C_3$-$C_6$ cycloalkyl group include a 1-cyanocyclopropyl, 2-cyanocyclopropyl, 1-cyanocyclobutyl, 3-cyanocyclobutyl, or 1-cyanocyclopentyl group.

In the present invention, unless otherwise specified, "$C_1$-$C_6$ alkoxy $C_1$-$C_6$ alkylcarbonyl group" refers to a ($C_1$-$C_6$ alkyl)-O—($C_1$-$C_6$ alkyl)-C(=O)— group in which the alkyl moiety is as defined above, and examples of the $C_1$-$C_6$ alkoxy $C_1$-$C_6$ alkylcarbonyl group include a methoxyacetyl, ethoxyacetyl, propoxyacetyl, isopropoxyacetyl, butoxyacetyl, 2-methoxypropionyl, 3-methoxypropionyl, 2-ethoxypropionyl, 3-ethoxypropionyl, 2-methoxybutanoyl, 4-methoxybutanoyl, 2-methoxypentanoyl, or 5-methoxypentanoyl group.

In the present invention, unless otherwise specified, "$C_3$-$C_6$ cycloalkylcarbonyl group" refers to a ($C_3$-$C_6$ cycloalkyl)-C(=O)— group in which the cycloalkyl moiety is as defined above, and examples of the $C_3$-$C_6$ cycloalkylcarbonyl group include a cyclopropanecarbonyl, cyclobutanecarbonyl, cyclopentanecarbonyl, or cyclohexanecarbonyl group.

In the present invention, "$C_3$-$C_6$ cycloalkyl $C_1$-$C_6$ alkylcarbonyl group" refers to a ($C_3$-$C_6$ cycloalkyl $C_1$-$C_6$ alkyl)-C(=O)— group in which the cycloalkyl alkyl moiety is as defined above, and examples of the $C_3$-$C_6$ cycloalkyl $C_1$-$C_6$ alkylcarbonyl group include a 2-cyclopropylacetyl, 2-cyclobutylacetyl, 2-cyclopentylacetyl, 2-cyclohexylacetyl, 2-cyclopropylpropanoyl, or 2-cyclopropylbutanoyl group.

In the present invention, unless otherwise specified, "$C_7$-$C_{13}$ aralkylcarbonyl group" refers to a ($C_7$-$C_{13}$ aralkyl)-C(=O)— group in which the aralkyl moiety is as defined above, and examples of the $C_7$-$C_{13}$ aralkylcarbonyl group include a phenylethanoyl, 1-phenylpropanoyl, or 2-phenylpropanoyl group.

In the present invention, unless otherwise specified, "($C_1$-$C_6$ alkyl)thiocarbonyl group" refers to a ($C_1$-$C_6$ alkyl)-C(=S)— group in which the alkyl moiety is as defined above, and examples of the ($C_1$-$C_6$ alkyl)thiocarbonyl group include a methylthiocarbonyl, ethylthiocarbonyl, n-propylthiocarbonyl, isopropylthiocarbonyl, n-butylthiocarbonyl, isobutylthiocarbonyl, sec-butylthiocarbonyl, tert-butylthiocarbonyl, or n-pentylthiocarbonyl group.

In the present invention, unless otherwise specified, "($C_1$-$C_6$ alkoxy)thiocarbonyl group" refers to a ($C_1$-$C_6$ alkyl)-O—C(=S)— group in which the alkyl moiety is as defined above, and examples of the ($C_1$-$C_6$ alkoxy)thiocarbonyl group include a methoxythiocarbonyl, ethoxythiocarbonyl, n-propoxythiocarbonyl, isopropoxythiocarbonyl, n-butoxythiocarbonyl, isobutoxythiocarbonyl, sec-butoxythiocarbonyl, tert-butoxythiocarbonyl, n-pentoxythiocarbonyl, 1-methyl butoxythiocarbonyl, 2-methyl butoxythiocarbonyl, 3-methyl butoxythiocarbonyl, 1-ethylpropoxythiocarbonyl, 1,1-dimethylpropoxythiocarbonyl, 1,2-dimethylpropoxythiocarbonyl, or 2,2-dimethylpropoxythiocarbonyl group.

In the present invention, "mono($C_1$-$C_6$ alkyl)aminothiocarbonyl group" refers to a ($C_1$-$C_6$ alkyl)-NH—C(=S)— group in which the alkyl moiety is as defined above, and examples of the mono($C_1$-$C_6$ alkyl)aminothiocarbonyl group include a methylaminothiocarbonyl, ethylaminothiocarbonyl, n-propylaminothiocarbonyl, isopropylaminothiocarbonyl, n-butylaminothiocarbonyl, isobutylaminothiocarbonyl, sec-butylaminothiocarbonyl, tert-butylaminothiocarbonyl, n-pentylaminothiocarbonyl, 1-methylbutylaminothiocarbonyl, 2-methylbutylaminothiocarbonyl, 3-methylbutylaminothiocarbonyl, 1-ethylpropylaminothiocarbonyl, 1,1-dimethylpropylaminothiocarbonyl, 1,2-dimethylpropylaminothiocarbonyl, 2,2-dimethylpropylaminothiocarbonyl, or n-hexylaminothiocarbonyl group.

In the present invention, "di($C_1$-$C_6$ alkyl)aminothiocarbonyl group" refers to a ($C_1$-$C_6$ alkyl)$_2$-N—C(=S)— group in which the alkyl moiety is as defined above, and the two alkyl groups may be different from each other, and examples of the di($C_1$-$C_6$ alkyl)aminothiocarbonyl group include a dimethylaminothiocarbonyl, diethylaminothiocarbonyl, di(n-propyl)aminothiocarbonyl, diisopropylaminothiocarbonyl, dibutylaminothiocarbonyl, N-ethyl-N-methylaminothiocarbonyl, N-methyl-N-propylaminothiocarbonyl, N-isopropyl-N-methylaminothiocarbonyl, N-butyl-N-methylaminothiocarbonyl, N-(s-butyl)-N-methylaminothiocarbonyl, N-isobutyl-N-methylaminothiocarbonyl, N-pentyl-N-methylaminothiocarbonyl, N-ethyl-N-propylaminothiocarbonyl, N-ethyl-N-isopropylaminothiocarbonyl, or N-ethyl-N-butylaminothiocarbonyl group.

In the present invention, "mono($C_1$-$C_6$ alkyl)aminosulfonyl group" refers to a ($C_1$-$C_6$ alkyl)-NH—S(=O)— group in which the alkyl moiety is as defined above, and examples of the mono($C_1$-$C_6$ alkyl)aminosulfonyl group include a methylaminosulfonyl, ethylaminosulfonyl, n-propylaminosulfonyl, isopropylaminosulfonyl, n-butylaminosulfonyl, isobutylaminosulfonyl, sec-butylaminosulfonyl, tert-butylaminosulfonyl, n-pentylaminosulfonyl, 1-methylbutylaminosulfonyl, 2-methylbutylaminosulfonyl, 3-methylbutylaminosulfonyl, 1-ethylpropylaminosulfonyl, 1,1-dimethylpropylaminosulfonyl, 1,2-dimethylpropylaminosulfonyl, 2,2-dimethylpropylaminosulfonyl, or n-hexylaminosulfonyl group.

In the present invention, "di($C_1$-$C_6$ alkyl)aminosulfonyl group" refers to a ($C_1$-$C_6$ alkyl)$_2$-N—S(=O)$_2$— group in which the alkyl moiety is as defined above, and the two alkyl groups may be different from each other, and examples of the di($C_1$-$C_6$ alkyl)aminosulfonyl group include a dimethylaminosulfonyl, diethylaminosulfonyl, di(n-propyl)aminosulfonyl, diisopropylaminosulfonyl, dibutylaminosulfonyl, N-ethyl-N-methylaminosulfonyl, N-methyl-N-propylaminosulfonyl, N-isopropyl-N-methylaminosulfonyl, N-butyl-N-methylaminosulfonyl, N-(s-butyl)-N-methylaminosulfonyl, N-isobutyl-N-methylaminosulfonyl, N-pentyl-N-methylaminosulfonyl, N-ethyl-N-propylaminosulfocarbonyl, N-ethyl-N-isopropylaminosulfocarbonyl, or N-ethyl-N-butylaminosulfonyl group.

In the present invention, "aminocarbonyl $C_1$-$C_6$ alkyl group" refers to a $H_2N$—C(=O)—($C_1$-$C_6$ alkyl)- group in which the alkyl moiety is as defined above, and examples of the aminocarbonyl $C_1$-$C_6$ alkyl group include a carbamoylmethyl, 1-carbamoylethyl, or 2-carbamoylethyl group.

In the present invention, "mono($C_1$-$C_6$ alkyl)aminocarbonyl $C_1$-$C_6$ alkyl group" refers to a ($C_1$-$C_6$ alkyl)-NH—C(=O)—($C_1$-$C_6$ alkyl)- group in which the alkyl moiety is as defined above, and examples of the mono($C_1$-$C_6$ alkyl)aminocarbonyl $C_1$-$C_6$ alkyl group include a N-methylcarbamoylmethyl, N-ethylcarbamoylmethyl, or N-(tert-butyl)carbamoylmethyl group.

In the present invention, "mono($C_1$-$C_6$ haloalkyl)aminocarbonyl $C_1$-$C_6$ alkyl group" refers to a ($C_1$-$C_6$ haloalkyl)-NH—C(=O)—($C_1$-$C_6$ alkyl)- group in which the haloalkyl moiety is as defined above, and examples of the mono($C_1$-$C_6$ haloalkyl)aminocarbonyl $C_1$-$C_6$ alkyl group include a N-(2,2-difluoroethyl)carbamoylmethyl, N-(2,2,2-trifluoroethyl)carbamoylmethyl, 1-{N-(2,2-difluoroethyl)carbamoyl}ethyl, 1-{N-(2,2-trifluoroethyl)carbamoyl}ethyl, 1-{N-(2,2-difluoroethyl)carbamoyl}-1-methylethyl, or 1-{N-(2,2-trifluoroethyl)carbamoyl}-1-methylethyl group.

In the present invention, "mono($C_3$-$C_6$ cycloalkyl)aminocarbonyl $C_1$-$C_6$ alkyl group" refers to a ($C_3$-$C_6$ cycloalkyl)-NH—C(=O)—($C_1$-$C_6$ alkyl)- group in which the cycloalkyl moiety is as defined above, and examples of the mono($C_3$-$C_6$ cycloalkyl)aminocarbonyl $C_1$-$C_6$ alkyl group include a N-cyclopropylcarbamoylmethyl, N-cyclobutylcarbamoylmethyl, N-cyclopentylcarbamoylmethyl, or N-cyclohexylcarbamoylmethyl group.

In the present invention, "di($C_1$-$C_6$ alkyl)aminocarbonyl $C_1$-$C_6$ alkyl group" refers to a ($C_1$-$C_6$ alkyl)$_2$-N—C(=O)—($C_1$-$C_6$ alkyl)- group in which the alkyl moiety is as defined above, and examples of the di($C_1$-$C_6$ alkyl)aminocarbonyl $C_1$-$C_6$ alkyl group include a N,N-dimethylcarbamoylmethyl, N,N-diethylcarbamoylmethyl, N,N-dipropylcarbamoylmethyl, N-ethyl-N-methylcarbamoylmethyl, or N-methyl-N-propylcarbamoylmethyl group.

In the present invention, unless otherwise specified, "$C_1$-$C_6$ alkoxyimino group" refers to a ($C_1$-$C_6$ alkyl)-O—N=C— group in which the alkyl moiety is as defined above, and examples of the $C_1$-$C_6$ alkoxyimino group include a methoxyimino, ethoxyimino, or isopropoxyimino group.

In the present invention, unless otherwise specified, "hydroxyimino $C_1$-$C_6$ alkyl group" refers to a HO—N=($C_1$-$C_6$ alkyl) group in which the alkyl moiety is as defined above, and examples of the hydroxyimino $C_1$-$C_6$ alkyl group include a 1-(hydroxyimino)ethyl, 2-(hydroxyimino)ethyl, 1-(hydroxyimino)propyl, 2-(hydroxyimino)propyl, or 3-(hydroxyimino)propyl group.

In the present invention, unless otherwise specified, "$C_1$-$C_6$ alkoxyimino $C_1$-$C_6$ alkyl group" refers to a ($C_1$-$C_6$ alkyl)-O—N=($C_1$-$C_6$ alkyl) group in which the alkyl moiety is as defined above, and examples of the $C_1$-$C_6$ alkoxyimino $C_1$-$C_6$ alkyl group include a 1-(methoxyimino)ethyl, 2-(methoxyimino)ethyl, 1-(methoxyimino)propyl, 2-(methoxyimino)propyl, 3-(methoxyimino)propyl, 1-(ethoxyimino)ethyl, 2-(ethoxyimino)ethyl, 1-(ethoxyimino)propyl, 2-(ethoxyimino)propyl, 3-(ethoxyimino)propyl, 1-(isopropoxyimino)ethyl, or 2-(isopropoxyimino)ethyl group.

In the present invention, unless otherwise specified, "amino $C_1$-$C_6$ alkyl group" refers to a $H_2N$—($C_1$-$C_6$ alkyl)- group in which the alkyl moiety is as defined above, and examples of the amino $C_1$-$C_6$ alkyl group include an aminomethyl, or 2-aminoethyl group.

In the present invention, unless otherwise specified, "mono($C_1$-$C_6$ alkyl)amino $C_1$-$C_6$ alkyl group" refers to a ($C_1$-$C_6$ alkyl)-NH—($C_1$-$C_6$ alkyl)- group in which the alkyl moiety is as defined above, and examples of the mono($C_1$-$C_6$ alkyl)amino $C_1$-$C_6$ alkyl group include a N-methylaminomethyl, or N-ethylaminomethyl group.

In the present invention, unless otherwise specified, "di ($C_1$-$C_6$ alkyl)amino $C_1$-$C_6$ alkyl group" refers to a ($C_1$-$C_6$ alkyl)$_2$-N—($C_1$-$C_6$ alkyl)- group in which the alkyl moiety is as defined above, and examples of the di($C_1$-$C_6$ alkyl) amino $C_1$-$C_6$ alkyl group include a N,N-dimethylaminomethyl or N,N-diethylaminomethyl group.

In the present invention, unless otherwise specified, "tri ($C_1$-$C_6$ alkyl)silyloxy $C_1$-$C_6$ alkyl group" refers to a ($C_1$-$C_6$ alkyl)$_3$-Si—O—($C_1$-$C_6$ alkyl)- group in which the alkyl moiety is as defined above, and examples of the tri($C_1$-$C_6$ alkyl)silyloxy $C_1$-$C_6$ alkyl group include a trimethylsilyloxymethyl, trimethylsilyloxyethyl, triethylsilyloxymethyl, triethylsilyloxyethyl, triisopropylsilyloxymethyl, triisopropylsilyloxyethyl, tert-butyldimethylsilyloxymethyl, or tert-butyldimethylsilyloxyethyl group.

In the present invention, the wording "agriculturally acceptable salt" or "salt" refers to a salt of a hydroxyl group, a carboxyl group, an amino group or the like when such a group exists in the structure of the present compound represented by general formula [I] or [II], or a nitrogen atom in a pyridine ring, with metal or an organic base, or a salt with a mineral acid or an organic acid, and examples of the metal include alkali metal such as sodium or potassium, and alkali earth metal such as magnesium or calcium, examples of the organic base include triethylamine or diisopropylamine, examples of the mineral acid include phosphoric acid, hydrochloric acid, hydrobromic acid, hydroiodic acid, boric acid, or sulfuric acid, and examples of the organic acid include formic acid, acetic acid, lactic acid, ascorbic acid, succinic acid, fumaric acid, maleic acid, oxalic acid, citric acid, benzoic acid, salicylic acid, tartaric acid, methanesulfonic acid, 4-toluenesulfonic acid, or trifluoromethanesulfonic acid.

Next, representative compound examples of compounds included in the pyrazole derivative of the present invention represented by general formula [I] are shown in Table 1 to Table 194, and representative compound examples of compounds included in the pyrazole derivative of the present invention represented by general formula [II] are shown in Table 195 to Table 314. However, the compounds included in the derivatives of the present invention are not limited to these. The compound numbers in Tables are referred to in the following description.

The compounds included in the pyrazole derivatives of the present invention can have geometrical isomers of E-form and Z-form depending on the kind of the substituent, and the present invention encompasses such E-form, Z-form, or a mixture containing E-form and Z-form in any ratio. The compounds encompassed in the present invention can have optical isomers caused by the existence of one or two or more asymmetric carbon atoms and asymmetric sulfur atoms, and the present invention encompasses any optically active substances, racemic modifications, or diastereomers.

In the present specification, the following signs in tables respectively represent the corresponding groups as shown below.

Me: methyl
Et: ethyl
Pr: n-propyl
i-Pr: isopropyl
Bu: n-butyl
t-Bu: tert-butyl
OMe: methoxy
O(i-Pr): isopropoxy
2-$CF_3$: 2-trifluoromethyl
4-Me,2-$CF_3$: 4-methyl-2-trifluoromethyl
2-$CF_3$-pyridin-3-yl: 2-trifluoromethylpyridine-3-yl
3,6-$Cl_2$-pyridin-2-yl: 3,6-dichloropyridine-2-yl
$CH_2$OTBS: tert-butyldimethylsilyloxymethyl
C(=O)(4-Cl)Ph: 4-chlorobenzoyl

TABLE 1

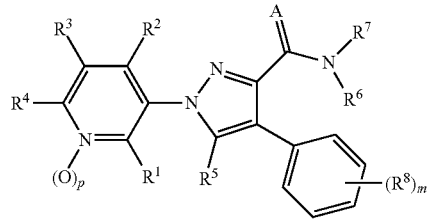

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-0001 | H | H | H | H | H | O | H | H | H | 0 |
| A-0002 | H | H | H | H | H | O | H | H | 2-F | 0 |
| A-0003 | H | H | H | H | H | O | H | H | 3-F | 0 |
| A-0004 | H | H | H | H | H | O | H | H | 4-F | 0 |
| A-0005 | H | H | H | H | H | O | H | H | 2-Cl | 0 |
| A-0006 | H | H | H | H | H | O | H | H | 3-Cl | 0 |
| A-0007 | H | H | H | H | H | O | H | H | 4-Cl | 0 |
| A-0008 | H | H | H | H | H | O | H | H | 2-Br | 0 |
| A0009 | H | H | H | H | H | O | H | H | 3-Br | 0 |
| A-0010 | H | H | H | H | H | O | H | H | 4-Br | 0 |
| A-0011 | H | H | H | H | H | O | H | H | 2-I | 0 |
| A-0012 | H | H | H | H | H | O | H | H | 3-I | 0 |
| A-0013 | H | H | H | H | H | O | H | H | 4-I | 0 |
| A-0014 | H | H | H | H | H | O | H | H | 2-OH | 0 |
| A-0015 | H | H | H | H | H | O | H | H | 3-OH | 0 |
| A-0016 | H | H | H | H | H | O | H | H | 4-OH | 0 |
| A-0017 | H | H | H | H | H | O | H | H | 2-SH | 0 |
| A-0018 | H | H | H | H | H | O | H | H | 3-SH | 0 |
| A-0019 | H | H | H | H | H | O | H | H | 4-SH | 0 |
| A0020 | H | H | H | H | H | O | H | H | 2-Me | 0 |
| A-0021 | H | H | H | H | H | O | H | H | 3-Me | 0 |
| A-0022 | H | H | H | H | H | O | H | H | 4-Me | 0 |
| A-0023 | H | H | H | H | H | O | H | H | 2-Et | 0 |
| A0024 | H | H | H | H | H | O | H | H | 3-Et | 0 |
| A-0025 | H | H | H | H | H | O | H | H | 4-Et | 0 |
| A-0026 | H | H | H | H | H | O | H | H | 2-Pr | 0 |
| A-0027 | H | H | H | H | H | O | H | H | 3-Pr | 0 |
| A-0028 | H | H | H | H | H | O | H | H | 4-Pr | 0 |
| A-0029 | H | H | H | H | H | O | H | H | 2-iPr | 0 |
| A-0030 | H | H | H | H | H | O | H | H | 3-iPr | 0 |
| A-0031 | H | H | H | H | H | O | H | H | 4-iPr | 0 |
| A-0032 | H | H | H | H | H | O | H | H | 2-Bu | 0 |
| A-0033 | H | H | H | H | H | O | H | H | 3-Bu | 0 |
| A-0034 | H | H | H | H | H | O | H | H | 4-Bu | 0 |
| A-0035 | H | H | H | H | H | O | H | H | 2-s-Bu | 0 |
| A-0036 | H | H | H | H | H | O | H | H | 3-s-Bu | 0 |
| A-0037 | H | H | H | H | H | O | H | H | 4-s-Bu | 0 |
| A0038 | H | H | H | H | H | O | H | H | 2-i-Bu | 0 |
| A-0039 | H | H | H | H | H | O | H | H | 3-i-Bu | 0 |
| A-0040 | H | H | H | H | H | O | H | H | 4-i-Bu | 0 |

TABLE 1-continued

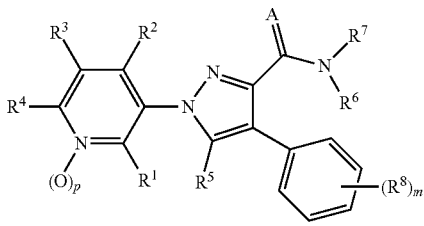

| compound | R¹ | R² | R³ | R⁴ | R⁵ | A | R⁶ | R⁷ | (R⁸)$_m$ | p |
|---|---|---|---|---|---|---|---|---|---|---|
| A-0041 | H | H | H | H | H | O | H | H | 2-t-Bu | 0 |
| A-0042 | H | H | H | H | H | O | H | H | 3-t-Bu | 0 |
| A-0043 | H | H | H | H | H | O | H | H | 4-t-Bu | 0 |
| A0044 | H | H | H | H | H | O | H | H | 2-CF₃ | 0 |
| A-0045 | H | H | H | H | H | O | H | H | 3-CF₃ | 0 |
| A-0046 | H | H | H | H | H | O | H | H | 4-CF₃ | 0 |
| A-0047 | H | H | H | H | H | O | H | H | 2-CHF₂ | 0 |

TABLE 1-continued

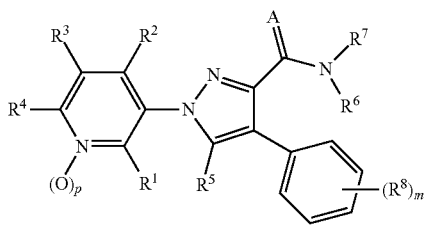

| compound | R¹ | R² | R³ | R⁴ | R⁵ | A | R⁶ | R⁷ | (R⁸)$_m$ | p |
|---|---|---|---|---|---|---|---|---|---|---|
| A0048 | H | H | H | H | H | O | H | H | 3-CHF₂ | 0 |
| A-0049 | H | H | H | H | H | O | H | H | 4-CHF₂ | 0 |
| A0050 | H | H | H | H | H | O | H | H | 2-CH₂F | 0 |
| A-0051 | H | H | H | H | H | O | H | H | 3-CH₂F | 0 |
| A-0052 | H | H | H | H | H | O | H | H | 4-CH₂F | 0 |

TABLE 2

| compound | R¹ | R² | R³ | R⁴ | R⁵ | A | R⁶ | R⁷ | (R⁸)m | p |
|---|---|---|---|---|---|---|---|---|---|---|
| A-0053 | H | H | H | H | H | O | H | H | 2-CF₂Cl | 0 |
| A-0054 | H | H | H | H | H | O | H | H | 3-CF₂Cl | 0 |
| A-0055 | H | H | H | H | H | O | H | H | 4-CF₂Cl | 0 |
| A-0056 | H | H | H | H | H | O | H | H | 2-CF(CF₃)₂ | 0 |
| A-0057 | H | H | H | H | H | O | H | H | 3-CF(CF₃)₂ | 0 |
| A-0058 | H | H | H | H | H | O | H | H | 4-CF(CF₃)₂ | 0 |
| A-0059 | H | H | H | H | H | O | H | H | 2-cyclopropyl | 0 |
| A-0060 | H | H | H | H | H | O | H | H | 3-cyclopropyl | 0 |
| A-0061 | H | H | H | H | H | O | H | H | 4-cyclopropyl | 0 |
| A-0062 | H | H | H | H | H | O | H | H | 2-cyclobutyl | 0 |
| A-0063 | H | H | H | H | H | O | H | H | 3-cyclobutyl | 0 |
| A-0064 | H | H | H | H | H | O | H | H | 4-cyclobutyl | 0 |
| A-0065 | H | H | H | H | H | O | H | H | 2-cyclopentyl | 0 |
| A-0066 | H | H | H | H | H | O | H | H | 3-cyclopentyl | 0 |
| A-0067 | H | H | H | H | H | O | H | H | 4-cyclopentyl | 0 |
| A-0068 | H | H | H | H | H | O | H | H | 2-(cyclopropylmethyl) | 0 |
| A-0069 | H | H | H | H | H | O | H | H | 3-(cyclopropylmethyl) | 0 |
| A-0070 | H | H | H | H | H | O | H | H | 4-(cyclopropylmethyl) | 0 |
| A-0071 | H | H | H | H | H | O | H | H | 2-(cyclobutylmethyl) | 0 |
| A-0072 | H | H | H | H | H | O | H | H | 3-(cyclobutylmethyl) | 0 |
| A-0073 | H | H | H | H | H | O | H | H | 4-(cyclobutylmethyl) | 0 |
| A-0074 | H | H | H | H | H | O | H | H | 2-(cyclopentylmethyl) | 0 |
| A-0075 | H | H | H | H | H | O | H | H | 3-(cyclopentylmethyl) | 0 |
| A-0076 | H | H | H | H | H | O | H | H | 4-(cyclopentylmethyl) | 0 |
| A-0077 | H | H | H | H | H | O | H | H | 2-(cyclopropylethyl) | 0 |
| A-0078 | H | H | H | H | H | O | H | H | 3-(cyclopropylethyl) | 0 |
| A-0079 | H | H | H | H | H | O | H | H | 4-(cyclopropylethyl) | 0 |
| A-0080 | H | H | H | H | H | O | H | H | 2-(2,2-difluorocyclopropyl) | 0 |
| A-0081 | H | H | H | H | H | O | H | H | 3-(2,2-difluorocyclopropyl) | 0 |
| A-0082 | H | H | H | H | H | O | H | H | 4-(2,2-difluorocyclopropyl) | 0 |
| A-0083 | H | H | H | H | H | O | H | H | 2-(2,2-dichlorocyclopropyl) | 0 |
| A-0084 | H | H | H | H | H | O | H | H | 3-(2,2-dichlorocyclopropyl) | 0 |
| A-0085 | H | H | H | H | H | O | H | H | 4-(2,2-dichlorocyclopropyl) | 0 |
| A-0086 | H | H | H | H | H | O | H | H | 2-ethenyl | 0 |
| A-0087 | H | H | H | H | H | O | H | H | 3-ethenyl | 0 |
| A-0088 | H | H | H | H | H | O | H | H | 4-ethenyl | 0 |
| A-0089 | H | H | H | H | H | O | H | H | 2-allyl | 0 |
| A-0090 | H | H | H | H | H | O | H | H | 3-allyl | 0 |
| A-0091 | H | H | H | H | H | O | H | H | 4-allyl | 0 |
| A-0092 | H | H | H | H | H | O | H | H | 2-(prop-1-en-1-yl) | 0 |
| A-0093 | H | H | H | H | H | O | H | H | 3-(prop-1-en-1-yl) | 0 |
| A-0094 | H | H | H | H | H | O | H | H | 4-(prop-1-en-1-yl) | 0 |
| A-0095 | H | H | H | H | H | O | H | H | 2-(trifluoroethenyl) | 0 |
| A-0096 | H | H | H | H | H | O | H | H | 3-(trifluoroethenyl) | 0 |
| A-0097 | H | H | H | H | H | O | H | H | 4-(trifluoroethenyl) | 0 |
| A-0098 | H | H | H | H | H | O | H | H | 2-(2,2-dichloroethenyl) | 0 |
| A-0099 | H | H | H | H | H | O | H | H | 3-(2,2-dichloroethenyl) | 0 |
| A-0100 | H | H | H | H | H | O | H | H | 4-(2,2-dichloroethenyl) | 0 |
| A-0101 | H | H | H | H | H | O | H | H | 2-ethynyl | 0 |
| A-0102 | H | H | H | H | H | O | H | H | 3-ethynyl | 0 |
| A-0103 | H | H | H | H | H | O | H | H | 4-ethynyl | 0 |
| A-0104 | H | H | H | H | H | O | H | H | 2-(1-propyn-1-yl) | 0 |
| A-0105 | H | H | H | H | H | O | H | H | 3-(1-propyn-1-yl) | 0 |

TABLE 2-continued

| compound | R¹ | R² | R³ | R⁴ | R⁵ | A | R⁶ | R⁷ | (R⁸)m | p |
|---|---|---|---|---|---|---|---|---|---|---|
| A-0106 | H | H | H | H | H | O | H | H | 4-(1-propyn-1-yl) | 0 |
| A-0107 | H | H | H | H | H | O | H | H | 2-(2-propyn-1-yl) | 0 |
| A-0108 | H | H | H | H | H | O | H | H | 3-(2-propyn-1-yl) | 0 |
| A-0109 | H | H | H | H | H | O | H | H | 4-(2-propyn-1-yl) | 0 |

TABLE 3

| compound | R¹ | R² | R³ | R⁴ | R⁵ | A | R⁶ | R⁷ | (R⁸)m | p |
|---|---|---|---|---|---|---|---|---|---|---|
| A-0110 | H | H | H | H | H | O | H | H | 2-(2-cyclopropylethynyl) | 0 |
| A-0111 | H | H | H | H | H | O | H | H | 3-(2-cyclopropylethynyl) | 0 |
| A-0112 | H | H | H | H | H | O | H | H | 4-(2-cyclopropylethynyl) | 0 |
| A-0113 | H | H | H | H | H | O | H | H | 2-(2-chloroethynyl) | 0 |
| A-0114 | H | H | H | H | H | O | H | H | 3-(2-chloroethynyl) | 0 |
| A-0115 | H | H | H | H | H | O | H | H | 4-(2-chloroethynyl) | 0 |
| A-0116 | H | H | H | H | H | O | H | H | 2-(2-bromoethynyl) | 0 |
| A-0117 | H | H | H | H | H | O | H | H | 3-(2-bromoethynyl) | 0 |
| A-0118 | H | H | H | H | H | O | H | H | 4-(2-bromoethynyl) | 0 |
| A-0119 | H | H | H | H | H | O | H | H | 2-OMe | 0 |
| A-0120 | H | H | H | H | H | O | H | H | 3-OMe | 0 |
| A-0121 | H | H | H | H | H | O | H | H | 4-OMe | 0 |
| A-0122 | H | H | H | H | H | O | H | H | 2-OEt | 0 |
| A-0123 | H | H | H | H | H | O | H | H | 3-OEt | 0 |
| A-0124 | H | H | H | H | H | O | H | H | 4-OEt | 0 |
| A-0125 | H | H | H | H | H | O | H | H | 2-OPr | 0 |
| A-0126 | H | H | H | H | H | O | H | H | 3-OPr | 0 |
| A-0127 | H | H | H | H | H | O | H | H | 4-OPr | 0 |
| A-0128 | H | H | H | H | H | O | H | H | 2-O(i-Pr) | 0 |
| A-0129 | H | H | H | H | H | O | H | H | 3-O(i-Pr) | 0 |
| A-0130 | H | H | H | H | H | O | H | H | 4-O(i-Pr) | 0 |
| A-0131 | H | H | H | H | H | O | H | H | 2-OBu | 0 |
| A-0132 | H | H | H | H | H | O | H | H | 3-OBu | 0 |
| A-0133 | H | H | H | H | H | O | H | H | 4-OBu | 0 |
| A-0134 | H | H | H | H | H | O | H | H | 2-O(s-Bu) | 0 |
| A-0135 | H | H | H | H | H | O | H | H | 3-O(s-Bu) | 0 |
| A-0136 | H | H | H | H | H | O | H | H | 4-O(s-Bu) | 0 |
| A-0137 | H | H | H | H | H | O | H | H | 2-O(i-Bu) | 0 |
| A-0138 | H | H | H | H | H | O | H | H | 3-O(i-Bu) | 0 |
| A-0139 | H | H | H | H | H | O | H | H | 4-O(i-Bu) | 0 |
| A-0140 | H | H | H | H | H | O | H | H | 2-O(t-Bu) | 0 |
| A-0141 | H | H | H | H | H | O | H | H | 3-O(t-Bu) | 0 |
| A-0142 | H | H | H | H | H | O | H | H | 4-O(t-Bu) | 0 |
| A-0143 | H | H | H | H | H | O | H | H | 2-OCF$_3$ | 0 |
| A-0144 | H | H | H | H | H | O | H | H | 3-OCF$_3$ | 0 |
| A-0145 | H | H | H | H | H | O | H | H | 4-OCF$_3$ | 0 |
| A-0146 | H | H | H | H | H | O | H | H | 2-OCHF$_2$ | 0 |
| A-0147 | H | H | H | H | H | O | H | H | 3-OCHF$_2$ | 0 |
| A-0148 | H | H | H | H | H | O | H | H | 4-OCHF$_2$ | 0 |
| A-0149 | H | H | H | H | H | O | H | H | 2-OCH$_2$CF$_3$ | 0 |
| A-0150 | H | H | H | H | H | O | H | H | 3-OCH$_2$CF$_3$ | 0 |
| A-0151 | H | H | H | H | H | O | H | H | 4-OCH$_2$CF$_3$ | 0 |
| A-0152 | H | H | H | H | H | O | H | H | 2-(cyclopropyloxy) | 0 |
| A-0153 | H | H | H | H | H | O | H | H | 3-(cyclopropyloxy) | 0 |
| A-0154 | H | H | H | H | H | O | H | H | 4-(cyclopropyloxy) | 0 |
| A-0155 | H | H | H | H | H | O | H | H | 2-(cyclobutyloxy) | 0 |
| A-0156 | H | H | H | H | H | O | H | H | 3-(cyclobutyloxy) | 0 |
| A-0157 | H | H | H | H | H | O | H | H | 4-(cyclobutyloxy) | 0 |
| A-0158 | H | H | H | H | H | O | H | H | 2-(cyclopentyloxy) | 0 |
| A-0159 | H | H | H | H | H | O | H | H | 3-(cyclopentyloxy) | 0 |
| A-0160 | H | H | H | H | H | O | H | H | 4-(cyclopentyloxy) | 0 |
| A-0161 | H | H | H | H | H | O | H | H | 2-((2,2-dichlorocyclopropyl)oxy) | 0 |
| A-0162 | H | H | H | H | H | O | H | H | 3-((2,2-dichlorocyclopropyl)oxy) | 0 |
| A-0163 | H | H | H | H | H | O | H | H | 4-((2,2-dichlorocyclopropyl)oxy) | 0 |
| A-0164 | H | H | H | H | H | O | H | H | 2-(cyclopropylmethoxy) | 0 |
| A-0165 | H | H | H | H | H | O | H | H | 3-(cyclopropylmethoxy) | 0 |
| A-0166 | H | H | H | H | H | O | H | H | 4-(cyclopropylmethoxy) | 0 |

TABLE 4

| compound | R¹ | R² | R³ | R⁴ | R⁵ | A | R⁶ | R⁷ | (R⁸)$_m$ | p |
|---|---|---|---|---|---|---|---|---|---|---|
| A-0167 | H | H | H | H | H | O | H | H | 2-((2,2-difluorocyclopropyl)methoxy) | 0 |
| A-0168 | H | H | H | H | H | O | H | H | 3-((2,2-difluorocyclopropyl)methoxy) | 0 |

TABLE 4-continued

| compound | R¹ | R² | R³ | R⁴ | R⁵ | A | R⁶ | R⁷ | (R⁸)ₘ | p |
|---|---|---|---|---|---|---|---|---|---|---|
| A-0169 | H | H | H | H | H | O | H | H | 4-((2,2-difluorocyclopropyl)methoxy) | 0 |
| A-0170 | H | H | H | H | H | O | H | H | 2-(oxiran-2-yl) | 0 |
| A-0171 | H | H | H | H | H | O | H | H | 3-(oxiran-2-yl) | 0 |
| A-0172 | H | H | H | H | H | O | H | H | 4-(oxiran-2-yl) | 0 |
| A-0173 | H | H | H | H | H | O | H | H | 2-(oxiran-2-ylmethyl) | 0 |
| A-0174 | H | H | H | H | H | O | H | H | 3-(oxiran-2-ylmethyl) | 0 |
| A-0175 | H | H | H | H | H | O | H | H | 4-(oxiran-2-ylmethyl) | 0 |
| A-0176 | H | H | H | H | H | O | H | H | 2-SMe | 0 |
| A-0177 | H | H | H | H | H | O | H | H | 3-SMe | 0 |
| A-0178 | H | H | H | H | H | O | H | H | 4-SMe | 0 |
| A-0179 | H | H | H | H | H | O | H | H | 2-SEt | 0 |
| A-0180 | H | H | H | H | H | O | H | H | 3-SEt | 0 |
| A-0181 | H | H | H | H | H | O | H | H | 4-SEt | 0 |
| A-0182 | H | H | H | H | H | O | H | H | 2-S(=O)Me | 0 |
| A-0183 | H | H | H | H | H | O | H | H | 3-S(=O)Me | 0 |
| A-0184 | H | H | H | H | H | O | H | H | 4-S(=O)Me | 0 |
| A-0185 | H | H | H | H | H | O | H | H | 2-S(=O)₂Me | 0 |
| A-0186 | H | H | H | H | H | O | H | H | 3-S(=O)₂Me | 0 |
| A-0187 | H | H | H | H | H | O | H | H | 4-S(=O)₂Me | 0 |
| A-0188 | H | H | H | H | H | O | H | H | 2-SCF₃ | 0 |
| A-0189 | H | H | H | H | H | O | H | H | 3-SCF₃ | 0 |
| A-0190 | H | H | H | H | H | O | H | H | 4-SCF₃ | 0 |
| A-0191 | H | H | H | H | H | O | H | H | 2-S(=O)CF₃ | 0 |
| A-0192 | H | H | H | H | H | O | H | H | 3-S(=O)CF₃ | 0 |
| A-0193 | H | H | H | H | H | O | H | H | 4-S(=O)CF₃ | 0 |
| A-0194 | H | H | H | H | H | O | H | H | 2-S(=O)₂CF₃ | 0 |
| A-0195 | H | H | H | H | H | O | H | H | 3-S(=O)₂CF₃ | 0 |
| A-0196 | H | H | H | H | H | O | H | H | 4-S(=O)₂CF₃ | 0 |
| A-0197 | H | H | H | H | H | O | H | H | 2-SCF(CF₃)₂ | 0 |
| A-0198 | H | H | H | H | H | O | H | H | 3-SCF(CF₃)₂ | 0 |
| A-0199 | H | H | H | H | H | O | H | H | 4-SCF(CF₃)₂ | 0 |
| A-0200 | H | H | H | H | H | O | H | H | 2-(cyclopropylthio) | 0 |
| A-0201 | H | H | H | H | H | O | H | H | 3-(cyclopropylthio) | 0 |
| A-0202 | H | H | H | H | H | O | H | H | 4-(cyclopropylthio) | 0 |
| A-0203 | H | H | H | H | H | O | H | H | 2-(cyclopropylsulfinyl) | 0 |
| A-0204 | H | H | H | H | H | O | H | H | 3-(cyclopropylsulfinyl) | 0 |
| A-0205 | H | H | H | H | H | O | H | H | 4-(cyclopropylsulfinyl) | 0 |
| A-0206 | H | H | H | H | H | O | H | H | 2-(cyclopropylsulfonyl) | 0 |
| A-0207 | H | H | H | H | H | O | H | H | 3-(cyclopropylsulfonyl) | 0 |
| A-0208 | H | H | H | H | H | O | H | H | 4-(cyclopropylsulfonyl) | 0 |
| A-0209 | H | H | H | H | H | O | H | H | 2-((cyclopropylmethyl)thio) | 0 |
| A-0210 | H | H | H | H | H | O | H | H | 3-((cyclopropylmethyl)thio) | 0 |
| A-0211 | H | H | H | H | H | O | H | H | 4-((cyclopropylmethyl)thio) | 0 |
| A-0212 | H | H | H | H | H | O | H | H | 2-((cyclopropylmethyl)sulfinyl) | 0 |
| A-0213 | H | H | H | H | H | O | H | H | 3-((cyclopropylmethyl)sulfinyl) | 0 |
| A-0214 | H | H | H | H | H | O | H | H | 4-((cyclopropylmethyl)sulfinyl) | 0 |
| A-0215 | H | H | H | H | H | O | H | H | 2-((cyclopropylmethyl)sulfonyl) | 0 |
| A-0216 | H | H | H | H | H | O | H | H | 3-((cyclopropylmethyl)sulfonyl) | 0 |
| A-0217 | H | H | H | H | H | O | H | H | 4-((cyclopropylmethyl)sulfonyl) | 0 |
| A-0218 | H | H | H | H | H | O | H | H | 2-(((2,2-difluorocyclopropyl)methyl)thio) | 0 |
| A-0219 | H | H | H | H | H | O | H | H | 3-(((2,2-difluorocyclopropyl)methyl)thio) | 0 |
| A-0220 | H | H | H | H | H | O | H | H | 4-(((2,2-difluorocyclopropyl)methyl)thio) | 0 |
| A-0221 | H | H | H | H | H | O | H | H | 2-(((2,2-difluorocyclopropyl)methyl)sulfinyl) | 0 |
| A-0222 | H | H | H | H | H | O | H | H | 3-(((2,2-difluorocyclopropyl)methyl)sulfinyl) | 0 |
| A-0223 | H | H | H | H | H | O | H | H | 4-(((2,2-difluorocyclopropyl)methyl)sulfinyl) | 0 |

TABLE 5

| compound | R¹ | R² | R³ | R⁴ | R⁵ | A | R⁶ | R⁷ | (R⁸)ₘ | p |
|---|---|---|---|---|---|---|---|---|---|---|
| A-0224 | H | H | H | H | H | O | H | H | 2-(((2,2-difluorocyclopropyl)methyl)sulfonyl) | 0 |
| A-0225 | H | H | H | H | H | O | H | H | 3-(((2,2-difluorocyclopropyl)methyl)sulfonyl) | 0 |
| A-0226 | H | H | H | H | H | O | H | H | 4-(((2,2-difluorocyclopropyl)methyl)sulfonyl) | 0 |
| A-0227 | H | H | H | H | H | O | H | H | 2-C(=O)Me | 0 |
| A-0228 | H | H | H | H | H | O | H | H | 3-C(=O)Me | 0 |
| A-0229 | H | H | H | H | H | O | H | H | 4-C(=O)Me | 0 |
| A-0230 | H | H | H | H | H | O | H | H | 2-C(=O)Et | 0 |
| A-0231 | H | H | H | H | H | O | H | H | 3-C(=O)Et | 0 |
| A-0232 | H | H | H | H | H | O | H | H | 4-C(=O)Et | 0 |
| A-0233 | H | H | H | H | H | O | H | H | 2-C(=O)CF₃ | 0 |
| A-0234 | H | H | H | H | H | O | H | H | 3-C(=O)CF₃ | 0 |
| A-0235 | H | H | H | H | H | O | H | H | 4-C(=O)CF₃ | 0 |
| A-0236 | H | H | H | H | H | O | H | H | 2-C(=O)OMe | 0 |
| A-0237 | H | H | H | H | H | O | H | H | 3-C(=O)OMe | 0 |
| A-0238 | H | H | H | H | H | O | H | H | 4-C(=O)OMe | 0 |

TABLE 5-continued

| compound | R¹ | R² | R³ | R⁴ | R⁵ | A | R⁶ | R⁷ | (R⁸)ₘ | p |
|---|---|---|---|---|---|---|---|---|---|---|
| A-0239 | H | H | H | H | H | O | H | H | 2-C(=O)OET | 0 |
| A-0240 | H | H | H | H | H | O | H | H | 3-C(=O)OET | 0 |
| A-0241 | H | H | H | H | H | O | H | H | 4-C(=O)OET | 0 |
| A-0242 | H | H | H | H | H | O | H | H | 2-C(=O)NH₂ | 0 |
| A-0243 | H | H | H | H | H | O | H | H | 3-C(=O)NH₂ | 0 |
| A-0244 | H | H | H | H | H | O | H | H | 4-C(=O)NH₂ | 0 |
| A-0245 | H | H | H | H | H | O | H | H | 2-C(=O)NHMe | 0 |
| A-0246 | H | H | H | H | H | O | H | H | 3-C(=O)NHMe | 0 |
| A-0247 | H | H | H | H | H | O | H | H | 4-C(=O)NHMe | 0 |
| A-0248 | H | H | H | H | H | O | H | H | 2-C(=O)NMe₂ | 0 |
| A-0249 | H | H | H | H | H | O | H | H | 3-C(=O)NMe₂ | 0 |
| A-0250 | H | H | H | H | H | O | H | H | 4-C(=O)NMe₂ | 0 |
| A-0251 | H | H | H | H | H | O | H | H | 2-CH₂C(=O)CH₃ | 0 |
| A-0252 | H | H | H | H | H | O | H | H | 3-CH₂C(=O)CH₃ | 0 |
| A-0253 | H | H | H | H | H | O | H | H | 4-CH₂C(=O)CH₃ | 0 |
| A-0254 | H | H | H | H | H | O | H | H | 2-CH₂C(=O)CF₃ | 0 |
| A-0255 | H | H | H | H | H | O | H | H | 3-CH₂C(=O)CF₃ | 0 |
| A-0256 | H | H | H | H | H | O | H | H | 4-CH₂C(=O)CF₃ | 0 |
| A-0257 | H | H | H | H | H | O | H | H | 2-CH₂C(=O)OCH₃ | 0 |
| A-0258 | H | H | H | H | H | O | H | H | 3-CH₂C(=O)OCH₃ | 0 |
| A-0259 | H | H | H | H | H | O | H | H | 4-CH₂C(=O)OCH₃ | 0 |
| A-0260 | H | H | H | H | H | O | H | H | 2-CH₂OH | 0 |
| A-0261 | H | H | H | H | H | O | H | H | 3-CH₂OH | 0 |
| A-0262 | H | H | H | H | H | O | H | H | 4-CH₂OH | 0 |
| A-0263 | H | H | H | H | H | O | H | H | 2-CH₂OCH₃ | 0 |
| A-0264 | H | H | H | H | H | O | H | H | 3-CH₂OCH₃ | 0 |
| A-0265 | H | H | H | H | H | O | H | H | 4-CH₂OCH₃ | 0 |
| A-0266 | H | H | H | H | H | O | H | H | 2-CH₂OCH₂CH₃ | 0 |
| A-0267 | H | H | H | H | H | O | H | H | 3-CH₂OCH₂CH₃ | 0 |
| A-0268 | H | H | H | H | H | O | H | H | 4-CH₂OCH₂CH₃ | 0 |
| A-0269 | H | H | H | H | H | O | H | H | 2-CH(CH₃)OCH₃ | 0 |
| A-0270 | H | H | H | H | H | O | H | H | 3-CH(CH₃)OCH₃ | 0 |
| A-0271 | H | H | H | H | H | O | H | H | 4-CH(CH₃)OCH₃ | 0 |
| A-0272 | H | H | H | H | H | O | H | H | 2-CH₂CH₂OCH₃ | 0 |
| A-0273 | H | H | H | H | H | O | H | H | 3-CH₂CH₂OCH₃ | 0 |
| A-0274 | H | H | H | H | H | O | H | H | 4-CH₂CH₂OCH₃ | 0 |
| A-0275 | H | H | H | H | H | O | H | H | 2-CH₂OCF₃ | 0 |
| A-0276 | H | H | H | H | H | O | H | H | 3-CH₂OCF₃ | 0 |
| A-0277 | H | H | H | H | H | O | H | H | 4-CH₂OCF₃ | 0 |
| A-0278 | H | H | H | H | H | O | H | H | 2-CF₂OCH₃ | 0 |
| A-0279 | H | H | H | H | H | O | H | H | 3-CF₂OCH₃ | 0 |
| A-0280 | H | H | H | H | H | O | H | H | 4-CF₂OCH₃ | 0 |

TABLE 6

| compound | R¹ | R² | R³ | R⁴ | R⁵ | A | R⁶ | R⁷ | (R⁸)ₘ | p |
|---|---|---|---|---|---|---|---|---|---|---|
| A-0281 | H | H | H | H | H | O | H | H | 2-CF₂CF₂OCF₃ | 0 |
| A-0282 | H | H | H | H | H | O | H | H | 3-CF₂CF₂OCF₃ | 0 |
| A-0283 | H | H | H | H | H | O | H | H | 4-CF₂CF₂OCF₃ | 0 |
| A-0284 | H | H | H | H | H | O | H | H | 2-OC(=O)CH₃ | 0 |
| A-0285 | H | H | H | H | H | O | H | H | 3-OC(=O)CH₃ | 0 |
| A-0286 | H | H | H | H | H | O | H | H | 4-OC(=O)CH₃ | 0 |
| A-0287 | H | H | H | H | H | O | H | H | 2-OC(=O)CF₃ | 0 |
| A-0288 | H | H | H | H | H | O | H | H | 3-OC(=O)CF₃ | 0 |
| A-0289 | H | H | H | H | H | O | H | H | 4-OC(=O)CF₃ | 0 |
| A-0290 | H | H | H | H | H | O | H | H | 2-OC(=O)NH₂ | 0 |
| A-0291 | H | H | H | H | H | O | H | H | 3-OC(=O)NH₂ | 0 |
| A-0292 | H | H | H | H | H | O | H | H | 4-OC(=O)NH₂ | 0 |
| A-0293 | H | H | H | H | H | O | H | H | 2-OC(=O)NHCH₃ | 0 |
| A-0294 | H | H | H | H | H | O | H | H | 3-OC(=O)NHCH₃ | 0 |
| A-0295 | H | H | H | H | H | O | H | H | 4-OC(=O)NHCH₃ | 0 |
| A-0296 | H | H | H | H | H | O | H | H | 2-OC(=O)N(CH₃)₂ | 0 |
| A-0297 | H | H | H | H | H | O | H | H | 3-OC(=O)N(CH₃)₂ | 0 |
| A-0298 | H | H | H | H | H | O | H | H | 4-OC(=O)N(CH₃)₂ | 0 |
| A-0299 | H | H | H | H | H | O | H | H | 2-CH₂OC(=O)NH₂ | 0 |
| A-0300 | H | H | H | H | H | O | H | H | 3-CH₂OC(=O)NH₂ | 0 |
| A-0301 | H | H | H | H | H | O | H | H | 4-CH₂OC(=O)NH₂ | 0 |
| A-0302 | H | H | H | H | H | O | H | H | 2-CH₂OC(=O)NHCH₃ | 0 |
| A-0303 | H | H | H | H | H | O | H | H | 3-CH₂OC(=O)NHCH₃ | 0 |
| A-0304 | H | H | H | H | H | O | H | H | 4-CH₂OC(=O)NHCH₃ | 0 |
| A-0305 | H | H | H | H | H | O | H | H | 2-CH₂OC(=O)N(CH₃)₂ | 0 |
| A-0306 | H | H | H | H | H | O | H | H | 3-CH₂OC(=O)N(CH₃)₂ | 0 |
| A-0307 | H | H | H | H | H | O | H | H | 4-CH₂OC(=O)N(CH₃)₂ | 0 |
| A-0308 | H | H | H | H | H | O | H | H | 2-OC(=O)OCH₃ | 0 |

TABLE 6-continued

| compound | R¹ | R² | R³ | R⁴ | R⁵ | A | R⁶ | R⁷ | (R⁸)$_m$ | p |
|---|---|---|---|---|---|---|---|---|---|---|
| A-0309 | H | H | H | H | H | O | H | H | 3-OC(=O)OCH$_3$ | 0 |
| A-0310 | H | H | H | H | H | O | H | H | 4-OC(=O)OCH$_3$ | 0 |
| A-0311 | H | H | H | H | H | O | H | H | 2-CH$_2$OC(=O)OCH$_3$ | 0 |
| A-0312 | H | H | H | H | H | O | H | H | 3-CH$_2$OC(=O)OCH$_3$ | 0 |
| A-0313 | H | H | H | H | H | O | H | H | 4-CH$_2$OC(=O)OCH$_3$ | 0 |
| A-0314 | H | H | H | H | H | O | H | H | 2-CH$_2$OC(=O)CH$_3$ | 0 |
| A-0315 | H | H | H | H | H | O | H | H | 3-CH$_2$OC(=O)CH$_3$ | 0 |
| A-0316 | H | H | H | H | H | O | H | H | 4-CH$_2$OC(=O)CH$_3$ | 0 |
| A-0317 | H | H | H | H | H | O | H | H | 2-OS(=O)$_2$CH$_3$ | 0 |
| A-0318 | H | H | H | H | H | O | H | H | 3-OS(=O)$_2$CH$_3$ | 0 |
| A-0319 | H | H | H | H | H | O | H | H | 4-OS(=O)$_2$CH$_3$ | 0 |
| A-0320 | H | H | H | H | H | O | H | H | 2-CH$_2$SCH$_3$ | 0 |
| A-0321 | H | H | H | H | H | O | H | H | 3-CH$_2$SCH$_3$ | 0 |
| A-0322 | H | H | H | H | H | O | H | H | 4-CH$_2$SCH$_3$ | 0 |
| A-0323 | H | H | H | H | H | O | H | H | 2-CH$_2$S(=O)CH$_3$ | 0 |
| A-0324 | H | H | H | H | H | O | H | H | 3-CH$_2$S(=O)CH$_3$ | 0 |
| A-0325 | H | H | H | H | H | O | H | H | 4-CH$_2$S(=O)CH$_3$ | 0 |
| A-0326 | H | H | H | H | H | O | H | H | 2-CH$_2$S(=O)$_2$CH$_3$ | 0 |
| A-0327 | H | H | H | H | H | O | H | H | 3-CH$_2$S(=O)$_2$CH$_3$ | 0 |
| A-0328 | H | H | H | H | H | O | H | H | 4-CH$_2$S(=O)$_2$CH$_3$ | 0 |
| A-0329 | H | H | H | H | H | O | H | H | 2-CH$_2$SCF$_3$ | 0 |
| A-0330 | H | H | H | H | H | O | H | H | 3-CH$_2$SCF$_3$ | 0 |
| A-0331 | H | H | H | H | H | O | H | H | 4-CH$_2$SCF$_3$ | 0 |
| A-0332 | H | H | H | H | H | O | H | H | 2-CH$_2$S(=O)CF$_3$ | 0 |
| A-0333 | H | H | H | H | H | O | H | H | 3-CH$_2$S(=O)CF$_3$ | 0 |
| A-0334 | H | H | H | H | H | O | H | H | 4-CH$_2$S(=O)CF$_3$ | 0 |
| A-0335 | H | H | H | H | H | O | H | H | 2-CH$_2$S(=O)$_2$CF$_3$ | 0 |
| A-0336 | H | H | H | H | H | O | H | H | 3-CH$_2$S(=O)$_2$CF$_3$ | 0 |
| A-0337 | H | H | H | H | H | O | H | H | 4-CH$_2$S(=O)$_2$CF$_3$ | 0 |

TABLE 7

| compound | R¹ | R² | R³ | R⁴ | R⁵ | A | R⁶ | R⁷ | (R⁸)$_m$ | p |
|---|---|---|---|---|---|---|---|---|---|---|
| A-0338 | H | H | H | H | H | O | H | H | 2-phenyl | 0 |
| A-0339 | H | H | H | H | H | O | H | H | 3-phenyl | 0 |
| A-0340 | H | H | H | H | H | O | H | H | 4-phenyl | 0 |
| A-0341 | H | H | H | H | H | O | H | H | 2-(phenyl)oxy | 0 |
| A-0342 | H | H | H | H | H | O | H | H | 3-(phenyl)oxy | 0 |
| A-0343 | H | H | H | H | H | O | H | H | 4-(phenyl)oxy | 0 |
| A-0344 | H | H | H | H | H | O | H | H | 2-benzyl | 0 |
| A-0345 | H | H | H | H | H | O | H | H | 3-benzyl | 0 |
| A-0346 | H | H | H | H | H | O | H | H | 4-benzyl | 0 |
| A-0347 | H | H | H | H | H | O | H | H | 2-(benzyl)oxy | 0 |
| A-0348 | H | H | H | H | H | O | H | H | 3-(benzyl)oxy | 0 |
| A-0349 | H | H | H | H | H | O | H | H | 4-(benzyl)oxy | 0 |
| A-0350 | H | H | H | H | H | O | H | H | 2-((2-fluorobenzyl)oxy) | 0 |
| A-0351 | H | H | H | H | H | O | H | H | 3-((2-fluorobenzyl)oxy) | 0 |
| A-0352 | H | H | H | H | H | O | H | H | 4-((2-fluorobenzyl)oxy) | 0 |
| A-0353 | H | H | H | H | H | O | H | H | 2-((3-fluorobenzyl)oxy) | 0 |
| A-0354 | H | H | H | H | H | O | H | H | 3-((3-fluorobenzyl)oxy) | 0 |
| A-0355 | H | H | H | H | H | O | H | H | 4-((3-fluorobenzyl)oxy) | 0 |
| A-0356 | H | H | H | H | H | O | H | H | 2-((4-fluorobenzyl)oxy) | 0 |
| A-0357 | H | H | H | H | H | O | H | H | 3-((4-fluorobenzyl)oxy) | 0 |
| A-0358 | H | H | H | H | H | O | H | H | 4-((4-fluorobenzyl)oxy) | 0 |
| A-0359 | H | H | H | H | H | O | H | H | 2-((2-chlorobenzyl)oxy) | 0 |
| A-0360 | H | H | H | H | H | O | H | H | 3-((2-chlorobenzyl)oxy) | 0 |
| A-0361 | H | H | H | H | H | O | H | H | 4-((2-chlorobenzyl)oxy) | 0 |
| A-0362 | H | H | H | H | H | O | H | H | 2-((3-chlorobenzyl)oxy) | 0 |
| A-0363 | H | H | H | H | H | O | H | H | 3-((3-chlorobenzyl)oxy) | 0 |
| A-0364 | H | H | H | H | H | O | H | H | 4-((3-chlorobenzyl)oxy) | 0 |
| A-0365 | H | H | H | H | H | O | H | H | 2-((4-chlorobenzyl)oxy) | 0 |
| A-0366 | H | H | H | H | H | O | H | H | 3-((4-chlorobenzyl)oxy) | 0 |
| A-0367 | H | H | H | H | H | O | H | H | 4-((4-chlorobenzyl)oxy) | 0 |
| A-0368 | H | H | H | H | H | O | H | H | 2-((2-methybenzyl)oxy) | 0 |
| A-0369 | H | H | H | H | H | O | H | H | 3-((2-methybenzyl)oxy) | 0 |
| A-0370 | H | H | H | H | H | O | H | H | 4-((2-methybenzyl)oxy) | 0 |
| A-0371 | H | H | H | H | H | O | H | H | 2-((3-methybenzyl)oxy) | 0 |
| A-0372 | H | H | H | H | H | O | H | H | 3-((3-methybenzyl)oxy) | 0 |
| A-0373 | H | H | H | H | H | O | H | H | 4-((3-methybenzyl)oxy) | 0 |
| A-0374 | H | H | H | H | H | O | H | H | 2-((4-methybenzyl)oxy) | 0 |
| A-0375 | H | H | H | H | H | O | H | H | 3-((4-methybenzyl)oxy) | 0 |
| A-0376 | H | H | H | H | H | O | H | H | 4-((4-methybenzyl)oxy) | 0 |
| A-0377 | H | H | H | H | H | O | H | H | 2-((2-trifluoromethyl)benzyl)oxy) | 0 |
| A-0378 | H | H | H | H | H | O | H | H | 3-((2-trifluoromethyl)benzyl)oxy) | 0 |

TABLE 7-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-0379 | H | H | H | H | H | O | H | H | 4-((2-(trifluoromethyl)benzyl)oxy) | 0 |
| A-0380 | H | H | H | H | H | O | H | H | 2-((3-(trifluoromethyl)benzyl)oxy) | 0 |
| A-0381 | H | H | H | H | H | O | H | H | 3-((3-(trifluoromethyl)benzyl)oxy) | 0 |
| A-0382 | H | H | H | H | H | O | H | H | 4-((3-(trifluoromethyl)benzyl)oxy) | 0 |
| A-0383 | H | H | H | H | H | O | H | H | 2-((4-(trifluoromethyl)benzyl)oxy) | 0 |
| A-0384 | H | H | H | H | H | O | H | H | 3-((4-(trifluoromethyl)benzyl)oxy) | 0 |
| A-0385 | H | H | H | H | H | O | H | H | 4-((4-(trifluoromethyl)benzyl)oxy) | 0 |
| A-0386 | H | H | H | H | H | O | H | H | 2-((2-methoxybenzyl)oxy) | 0 |
| A-0387 | H | H | H | H | H | O | H | H | 3-((2-methoxybenzyl)oxy) | 0 |
| A-0388 | H | H | H | H | H | O | H | H | 4-((2-methoxybenzyl)oxy) | 0 |
| A-0389 | H | H | H | H | H | O | H | H | 2-((3-methoxybenzyl)oxy) | 0 |
| A-0390 | H | H | H | H | H | O | H | H | 3-((3-methoxybenzyl)oxy) | 0 |
| A-0391 | H | H | H | H | H | O | H | H | 4-((3-methoxybenzyl)oxy) | 0 |
| A-0392 | H | H | H | H | H | O | H | H | 2-((4-methoxybenzyl)oxy) | 0 |
| A-0393 | H | H | H | H | H | O | H | H | 3-((4-methoxybenzyl)oxy) | 0 |
| A-0394 | H | H | H | H | H | O | H | H | 4-((4-methoxybenzyl)oxy) | 0 |

TABLE 8

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-0395 | H | H | H | H | H | O | H | H | 2-((2-(trifluoromethoxy)benzyl)oxy) | 0 |
| A-0396 | H | H | H | H | H | O | H | H | 3-((2-(trifluoromethoxy)benzyl)oxy) | 0 |
| A-0397 | H | H | H | H | H | O | H | H | 4-((2-(trifluoromethoxy)benzyl)oxy) | 0 |
| A-0398 | H | H | H | H | H | O | H | H | 2-((3-(trifluoromethoxy)benzyl)oxy) | 0 |
| A-0399 | H | H | H | H | H | O | H | H | 3-((3-(trifluoromethoxy)benzyl)oxy) | 0 |
| A-0400 | H | H | H | H | H | O | H | H | 4-((3-(trifluoromethoxy)benzyl)oxy) | 0 |
| A-0401 | H | H | H | H | H | O | H | H | 2-((4-(trifluoromethoxy)benzyl)oxy) | 0 |
| A-0402 | H | H | H | H | H | O | H | H | 3-((4-(trifluoromethoxy)benzyl)oxy) | 0 |
| A-0403 | H | H | H | H | H | O | H | H | 4-((4-(trifluoromethoxy)benzyl)oxy) | 0 |
| A-0404 | H | H | H | H | H | O | H | H | 2-((2-(methylthio)benzyl)oxy) | 0 |
| A-0405 | H | H | H | H | H | O | H | H | 3-((2-(methylthio)benzyl)oxy) | 0 |
| A-0406 | H | H | H | H | H | O | H | H | 4-((2-(methylthio)benzyl)oxy) | 0 |
| A-0407 | H | H | H | H | H | O | H | H | 2-((3-(methylthio)benzyl)oxy) | 0 |
| A-0408 | H | H | H | H | H | O | H | H | 3-((3-(methylthio)benzyl)oxy) | 0 |
| A-0409 | H | H | H | H | H | O | H | H | 4-((3-(methylthio)benzyl)oxy) | 0 |
| A-0410 | H | H | H | H | H | O | H | H | 2-((4-(methylthio)benzyl)oxy) | 0 |
| A-0411 | H | H | H | H | H | O | H | H | 3-((4-(methylthio)benzyl)oxy) | 0 |
| A-0412 | H | H | H | H | H | O | H | H | 4-((4-(methylthio)benzyl)oxy) | 0 |
| A-0413 | H | H | H | H | H | O | H | H | 2-((2-(methylsulfinyl)benzyl)oxy) | 0 |
| A-0414 | H | H | H | H | H | O | H | H | 3-((2-(methylsulfinyl)benzyl)oxy) | 0 |
| A-0415 | H | H | H | H | H | O | H | H | 4-((2-(methylsulfinyl)benzyl)oxy) | 0 |
| A-0416 | H | H | H | H | H | O | H | H | 2-((3-(methylsulfinyl)benzyl)oxy) | 0 |
| A-0417 | H | H | H | H | H | O | H | H | 3-((3-(methylsulfinyl)benzyl)oxy) | 0 |
| A-0418 | H | H | H | H | H | O | H | H | 4-((3-(methylsulfinyl)benzyl)oxy) | 0 |
| A-0419 | H | H | H | H | H | O | H | H | 2-((4-(methylsulfinyl)benzyl)oxy) | 0 |
| A-0420 | H | H | H | H | H | O | H | H | 3-((4-(methylsulfinyl)benzyl)oxy) | 0 |
| A-0421 | H | H | H | H | H | O | H | H | 4-((4-(methylsulfinyl)benzyl)oxy) | 0 |
| A-0422 | H | H | H | H | H | O | H | H | 2-((2-(methylsulfonyl)benzyl)oxy) | 0 |
| A-0423 | H | H | H | H | H | O | H | H | 3-((2-(methylsulfonyl)benzyl)oxy) | 0 |
| A-0424 | H | H | H | H | H | O | H | H | 4-((2-(methylsulfonyl)benzyl)oxy) | 0 |
| A-0425 | H | H | H | H | H | O | H | H | 2-((3-(methylsulfonyl)benzyl)oxy) | 0 |
| A-0426 | H | H | H | H | H | O | H | H | 3-((3-(methylsulfonyl)benzyl)oxy) | 0 |
| A-0427 | H | H | H | H | H | O | H | H | 4-((3-(methylsulfonyl)benzyl)oxy) | 0 |
| A-0428 | H | H | H | H | H | O | H | H | 2-((4-(methylsulfonyl)benzyl)oxy) | 0 |
| A-0429 | H | H | H | H | H | O | H | H | 3-((4-(methylsulfonyl)benzyl)oxy) | 0 |
| A-0430 | H | H | H | H | H | O | H | H | 4-((4-(methylsulfonyl)benzyl)oxy) | 0 |
| A-0431 | H | H | H | H | H | O | H | H | 2-((2-(trifluoromethylthio)benzyl)oxy) | 0 |
| A-0432 | H | H | H | H | H | O | H | H | 3-((2-(trifluoromethylthio)benzyl)oxy) | 0 |
| A-0433 | H | H | H | H | H | O | H | H | 4-((2-(trifluoromethylthio)benzyl)oxy) | 0 |
| A-0434 | H | H | H | H | H | O | H | H | 2-((3-(trifluoromethylthio)benzyl)oxy) | 0 |
| A-0435 | H | H | H | H | H | O | H | H | 3-((3-(trifluoromethylthio)benzyl)oxy) | 0 |
| A-0436 | H | H | H | H | H | O | H | H | 4-((3-(trifluoromethylthio)benzyl)oxy) | 0 |
| A-0437 | H | H | H | H | H | O | H | H | 2-((4-(trifluoromethylthio)benzyl)oxy) | 0 |
| A-0438 | H | H | H | H | H | O | H | H | 3-((4-(trifluoromethylthio)benzyl)oxy) | 0 |
| A-0439 | H | H | H | H | H | O | H | H | 4-((4-(trifluoromethylthio)benzyl)oxy) | 0 |
| A-0440 | H | H | H | H | H | O | H | H | 2-((2-(trifluoromethylsulfinyl)benzyl)oxy) | 0 |
| A-0441 | H | H | H | H | H | O | H | H | 3-((2-(trifluoromethylsulfinyl)benzyl)oxy) | 0 |
| A-0442 | H | H | H | H | H | O | H | H | 4-((2-(trifluoromethylsulfinyl)benzyl)oxy) | 0 |
| A-0443 | H | H | H | H | H | O | H | H | 2-((3-(trifluoromethylsulfinyl)benzyl)oxy) | 0 |
| A-0444 | H | H | H | H | H | O | H | H | 3-((3-(trifluoromethylsulfinyl)benzyl)oxy) | 0 |
| A-0445 | H | H | H | H | H | O | H | H | 4-((3-(trifluoromethylsulfinyl)benzyl)oxy) | 0 |
| A-0446 | H | H | H | H | H | O | H | H | 2-((4-(trifluoromethylsulfinyl)benzyl)oxy) | 0 |
| A-0447 | H | H | H | H | H | O | H | H | 3-((4-(trifluoromethylsulfinyl)benzyl)oxy) | 0 |
| A-0448 | H | H | H | H | H | O | H | H | 4-((4-(trifluoromethylsulfinyl)benzyl)oxy) | 0 |

TABLE 8-continued

| compound | R¹ | R² | R³ | R⁴ | R⁵ | A | R⁶ | R⁷ | (R⁸)ₘ | p |
|---|---|---|---|---|---|---|---|---|---|---|
| A-0449 | H | H | H | H | H | O | H | H | 2-((2-(trifluoromethylsulfonyl)benzyl)oxy) | 0 |
| A-0450 | H | H | H | H | H | O | H | H | 3-((2-(trifluoromethylsulfonyl)benzyl)oxy) | 0 |
| A-0451 | H | H | H | H | H | O | H | H | 4-((2-(trifluoromethylsulfonyl)benzyl)oxy) | 0 |

TABLE 9

| compound | R¹ | R² | R³ | R⁴ | R⁵ | A | R⁶ | R⁷ | (R⁸)ₘ | p |
|---|---|---|---|---|---|---|---|---|---|---|
| A-0452 | H | H | H | H | H | O | H | H | 2-((3-(trifluoromethylsulfonyl)benzyl)oxy) | 0 |
| A-0453 | H | H | H | H | H | O | H | H | 3-((3-(trifluoromethylsulfonyl)benzyl)oxy) | 0 |
| A-0454 | H | H | H | H | H | O | H | H | 4-((3-(trifluoromethylsulfonyl)benzyl)oxy) | 0 |
| A-0455 | H | H | H | H | H | O | H | H | 2-((4-(trifluoromethylsulfonyl)benzyl)oxy) | 0 |
| A-0456 | H | H | H | H | H | O | H | H | 3-((4-(trifluoromethylsulfonyl)benzyl)oxy) | 0 |
| A-0457 | H | H | H | H | H | O | H | H | 4-((4-(trifluoromethylsulfonyl)benzyl)oxy) | 0 |
| A-0458 | H | H | H | H | H | O | H | H | 2-((2-aminobenzyl)oxy) | 0 |
| A-0459 | H | H | H | H | H | O | H | H | 3-((2-aminobenzyl)oxy) | 0 |
| A-0460 | H | H | H | H | H | O | H | H | 4-((2-aminobenzyl)oxy) | 0 |
| A-0461 | H | H | H | H | H | O | H | H | 2-((3-aminobenzyl)oxy) | 0 |
| A-0462 | H | H | H | H | H | O | H | H | 3-((3-aminobenzyl)oxy) | 0 |
| A-0463 | H | H | H | H | H | O | H | H | 4-((3-aminobenzyl)oxy) | 0 |
| A-0464 | H | H | H | H | H | O | H | H | 2-((4-aminobenzyl)oxy) | 0 |
| A-0465 | H | H | H | H | H | O | H | H | 3-((4-aminobenzyl)oxy) | 0 |
| A-0466 | H | H | H | H | H | O | H | H | 4-((4-aminobenzyl)oxy) | 0 |
| A-0467 | H | H | H | H | H | O | H | H | 2-((2-(methylamino)benzyl)oxy) | 0 |
| A-0468 | H | H | H | H | H | O | H | H | 3-((2-(methylamino)benzyl)oxy) | 0 |
| A-0469 | H | H | H | H | H | O | H | H | 4-((2-(methylamino)benzyl)oxy) | 0 |
| A-0470 | H | H | H | H | H | O | H | H | 2-((3-(methylamino)benzyl)oxy) | 0 |
| A-0471 | H | H | H | H | H | O | H | H | 3-((3-(methylamino)benzyl)oxy) | 0 |
| A-0472 | H | H | H | H | H | O | H | H | 4-((3-(methylamino)benzyl)oxy) | 0 |
| A-0473 | H | H | H | H | H | O | H | H | 2-((4-(methylamino)benzyl)oxy) | 0 |
| A-0474 | H | H | H | H | H | O | H | H | 3-((4-(methylamino)benzyl)oxy) | 0 |
| A-0475 | H | H | H | H | H | O | H | H | 4-((4-(methylamino)benzyl)oxy) | 0 |
| A-0476 | H | H | H | H | H | O | H | H | 2-((2-(dimethylamino)benzyl)oxy) | 0 |
| A-0477 | H | H | H | H | H | O | H | H | 3-((2-(dimethylamino)benzyl)oxy) | 0 |
| A-0478 | H | H | H | H | H | O | H | H | 4-((2-(dimethylamino)benzyl)oxy) | 0 |
| A-0479 | H | H | H | H | H | O | H | H | 2-((3-(dimethylamino)benzyl)oxy) | 0 |
| A-0480 | H | H | H | H | H | O | H | H | 3-((3-(dimethylamino)benzyl)oxy) | 0 |
| A-0481 | H | H | H | H | H | O | H | H | 4-((3-(dimethylamino)benzyl)oxy) | 0 |
| A-0482 | H | H | H | H | H | O | H | H | 2-((4-(dimethylamino)benzyl)oxy) | 0 |
| A-0483 | H | H | H | H | H | O | H | H | 3-((4-(dimethylamino)benzyl)oxy) | 0 |
| A-0484 | H | H | H | H | H | O | H | H | 4-((4-(dimethylamino)benzyl)oxy) | 0 |
| A-0485 | H | H | H | H | H | O | H | H | 2-((2-cyanobenzyl)oxy) | 0 |
| A-0486 | H | H | H | H | H | O | H | H | 3-((2-cyanobenzyl)oxy) | 0 |
| A-0487 | H | H | H | H | H | O | H | H | 4-((2-cyanobenzyl)oxy) | 0 |
| A-0488 | H | H | H | H | H | O | H | H | 2-((3-cyanobenzyl)oxy) | 0 |
| A-0489 | H | H | H | H | H | O | H | H | 3-((3-cyanobenzyl)oxy) | 0 |
| A-0490 | H | H | H | H | H | O | H | H | 4-((3-cyanobenzyl)oxy) | 0 |
| A-0491 | H | H | H | H | H | O | H | H | 2-((4-cyanobenzyl)oxy) | 0 |
| A-0492 | H | H | H | H | H | O | H | H | 3-((4-cyanobenzyl)oxy) | 0 |
| A-0493 | H | H | H | H | H | O | H | H | 4-((4-cyanobenzyl)oxy) | 0 |
| A-0494 | H | H | H | H | H | O | H | H | 2-((2-nitrobenzyl)oxy) | 0 |
| A-0495 | H | H | H | H | H | O | H | H | 3-((2-nitrobenzyl)oxy) | 0 |
| A-0496 | H | H | H | H | H | O | H | H | 4-((2-nitrobenzyl)oxy) | 0 |
| A-0497 | H | H | H | H | H | O | H | H | 2-((3-nitrobenzyl)oxy) | 0 |
| A-0498 | H | H | H | H | H | O | H | H | 3-((3-nitrobenzyl)oxy) | 0 |
| A-0499 | H | H | H | H | H | O | H | H | 4-((3-nitrobenzyl)oxy) | 0 |
| A-0500 | H | H | H | H | H | O | H | H | 2-((4-nitrobenzyl)oxy) | 0 |
| A-0501 | H | H | H | H | H | O | H | H | 3-((4-nitrobenzyl)oxy) | 0 |
| A-0502 | H | H | H | H | H | O | H | H | 4-((4-nitrobenzyl)oxy) | 0 |
| A-0503 | H | H | H | H | H | O | H | H | 2-NH₂ | 0 |
| A-0504 | H | H | H | H | H | O | H | H | 3-NH₂ | 0 |
| A-0505 | H | H | H | H | H | O | H | H | 4-NH₂ | 0 |
| A-0506 | H | H | H | H | H | O | H | H | 2-NHMe | 0 |
| A-0507 | H | H | H | H | H | O | H | H | 3-NHMe | 0 |
| A-0508 | H | H | H | H | H | O | H | H | 4-NHMe | 0 |

TABLE 10

| compound | R¹ | R² | R³ | R⁴ | R⁵ | A | R⁶ | R⁷ | (R⁸)ₘ | p |
|---|---|---|---|---|---|---|---|---|---|---|
| A-0509 | H | H | H | H | H | O | H | H | 2-NHEt | 0 |
| A-0510 | H | H | H | H | H | O | H | H | 3-NHEt | 0 |
| A-0511 | H | H | H | H | H | O | H | H | 4-NHEt | 0 |

TABLE 10-continued

| compound | R¹ | R² | R³ | R⁴ | R⁵ | A | R⁶ | R⁷ | (R⁸)$_m$ | p |
|---|---|---|---|---|---|---|---|---|---|---|
| A-0512 | H | H | H | H | H | O | H | H | 2-N(Me)$_2$ | 0 |
| A-0513 | H | H | H | H | H | O | H | H | 3-N(Me)$_2$ | 0 |
| A-0514 | H | H | H | H | H | O | H | H | 4-N(Me)$_2$ | 0 |
| A-0515 | H | H | H | H | H | O | H | H | 2-N(Et)$_2$ | 0 |
| A-0516 | H | H | H | H | H | O | H | H | 3-N(Et)$_2$ | 0 |
| A-0517 | H | H | H | H | H | O | H | H | 4-N(Et)$_2$ | 0 |
| A-0518 | H | H | H | H | H | O | H | H | 2-CHO | 0 |
| A-0519 | H | H | H | H | H | O | H | H | 3-CHO | 0 |
| A-0520 | H | H | H | H | H | O | H | H | 4-CHO | 0 |
| A-0521 | H | H | H | H | H | O | H | H | 2-C(=O)OH | 0 |
| A-0522 | H | H | H | H | H | O | H | H | 3-C(=O)OH | 0 |
| A-0523 | H | H | H | H | H | O | H | H | 4-C(=O)OH | 0 |
| A-0524 | H | H | H | H | H | O | H | H | 2-(1,3-dioxolan-2-yl) | 0 |
| A-0525 | H | H | H | H | H | O | H | H | 3-(1,3-dioxolan-2-yl) | 0 |
| A-0526 | H | H | H | H | H | O | H | H | 4-(1,3-dioxolan-2-yl) | 0 |
| A-0527 | H | H | H | H | H | O | H | H | 2-(1,3-dioxan-2-yl) | 0 |
| A-0528 | H | H | H | H | H | O | H | H | 3-(1,3-dioxan-2-yl) | 0 |
| A-0529 | H | H | H | H | H | O | H | H | 4-(1,3-dioxan-2-yl) | 0 |
| A-0530 | H | H | H | H | H | O | H | H | 2-(1H-imidazol-2-yl) | 0 |
| A-0531 | H | H | H | H | H | O | H | H | 3-(1H-imidazol-2-yl) | 0 |
| A-0532 | H | H | H | H | H | O | H | H | 4-(1H-imidazol-2-yl) | 0 |
| A-0533 | H | H | H | H | H | O | H | H | 2-(thiazol-2-yl) | 0 |
| A-0534 | H | H | H | H | H | O | H | H | 3-(thiazol-2-yl) | 0 |
| A-0535 | H | H | H | H | H | O | H | H | 4-(thiazol-2-yl) | 0 |
| A-0536 | H | H | H | H | H | O | H | H | 2-(oxazol-2-yl) | 0 |
| A-0537 | H | H | H | H | H | O | H | H | 3-(oxazol-2-yl) | 0 |
| A-0538 | H | H | H | H | H | O | H | H | 4-(oxazol-2-yl) | 0 |
| A-0539 | H | H | H | H | H | O | H | H | 2-CH=NOH | 0 |
| A-0540 | H | H | H | H | H | O | H | H | 3-CH=NOH | 0 |
| A-0541 | H | H | H | H | H | O | H | H | 4-CH=NOH | 0 |
| A-0542 | H | H | H | H | H | O | H | H | 2-CH=NOMe | 0 |
| A-0543 | H | H | H | H | H | O | H | H | 3-CH=NOMe | 0 |
| A-0544 | H | H | H | H | H | O | H | H | 4-CH=NOMe | 0 |
| A-0545 | H | H | H | H | H | O | H | H | 2-(4,5-dihydro-3-isoxazolyl) | 0 |
| A-0546 | H | H | H | H | H | O | H | H | 3-(4,5-dihydro-3-isoxazolyl) | 0 |
| A-0547 | H | H | H | H | H | O | H | H | 4-(4,5-dihydro-3-isoxazolyl) | 0 |
| A-0548 | H | H | H | H | H | O | H | H | 2-CN | 0 |
| A-0549 | H | H | H | H | H | O | H | H | 3-CN | 0 |
| A-0550 | H | H | H | H | H | O | H | H | 4-CN | 0 |
| A-0551 | H | H | H | H | H | O | H | H | 2-NO$_2$ | 0 |
| A-0552 | H | H | H | H | H | O | H | H | 3-NO$_2$ | 0 |
| A-0553 | H | H | H | H | H | O | H | H | 4-NO$_2$ | 0 |
| A-0554 | H | H | H | H | H | O | H | H | 2,3-F$_2$ | 0 |
| A-0555 | H | H | H | H | H | O | H | H | 2,4-F$_2$ | 0 |
| A-0556 | H | H | H | H | H | O | H | H | 2,5-F$_2$ | 0 |
| A-0557 | H | H | H | H | H | O | H | H | 2,6-F$_2$ | 0 |
| A-0558 | H | H | H | H | H | O | H | H | 3,4-F$_2$ | 0 |
| A-0559 | H | H | H | H | H | O | H | H | 3,5-F$_2$ | 0 |
| A-0560 | H | H | H | H | H | O | H | H | 2-F,3-Cl | 0 |
| A-0561 | H | H | H | H | H | O | H | H | 2-F,4-Cl | 0 |
| A-0562 | H | H | H | H | H | O | H | H | 2-F,5-Cl | 0 |
| A-0563 | H | H | H | H | H | O | H | H | 2-F,6-Cl | 0 |
| A-0564 | H | H | H | H | H | O | H | H | 3-F,2-Cl | 0 |
| A-0565 | H | H | H | H | H | O | H | H | 3-F,4-Cl | 0 |

TABLE 11

| compound | R¹ | R² | R³ | R⁴ | R⁵ | A | R⁶ | R⁷ | (R⁸)$_m$ | p |
|---|---|---|---|---|---|---|---|---|---|---|
| A-0566 | H | H | H | H | H | O | H | H | 3-F,5-Cl | 0 |
| A-0567 | H | H | H | H | H | O | H | H | 3-F,6-Cl | 0 |
| A-0568 | H | H | H | H | H | O | H | H | 4-F,2-Cl | 0 |
| A-0569 | H | H | H | H | H | O | H | H | 4-F,3-Cl | 0 |
| A-0570 | H | H | H | H | H | O | H | H | 2-F,3-Me | 0 |
| A-0571 | H | H | H | H | H | O | H | H | 2-F,4-Me | 0 |
| A-0572 | H | H | H | H | H | O | H | H | 2-F,5-Me | 0 |
| A-0573 | H | H | H | H | H | O | H | H | 2-F,6-Me | 0 |
| A-0574 | H | H | H | H | H | O | H | H | 3-F,2-Me | 0 |
| A-0575 | H | H | H | H | H | O | H | H | 3-F,4-Me | 0 |
| A-0576 | H | H | H | H | H | O | H | H | 3-F,5-Me | 0 |
| A-0577 | H | H | H | H | H | O | H | H | 3-F,6-Me | 0 |
| A-0578 | H | H | H | H | H | O | H | H | 4-F,2-Me | 0 |
| A-0579 | H | H | H | H | H | O | H | H | 4-F,3-Me | 0 |
| A-0580 | H | H | H | H | H | O | H | H | 2-F,3-CF$_3$ | 0 |
| A-0581 | H | H | H | H | H | O | H | H | 2-F,4-CF$_3$ | 0 |
| A-0582 | H | H | H | H | H | O | H | H | 2-F,5-CF$_3$ | 0 |
| A-0583 | H | H | H | H | H | O | H | H | 2-F,6-CF$_3$ | 0 |
| A-0584 | H | H | H | H | H | O | H | H | 3-F,2-CF$_3$ | 0 |
| A-0585 | H | H | H | H | H | O | H | H | 3-F,4-CF$_3$ | 0 |
| A-0586 | H | H | H | H | H | O | H | H | 3-F,5-CF$_3$ | 0 |
| A-0587 | H | H | H | H | H | O | H | H | 3-F,6-CF$_3$ | 0 |
| A-0588 | H | H | H | H | H | O | H | H | 4-F,2-CF$_3$ | 0 |
| A-0589 | H | H | H | H | H | O | H | H | 4-F,3-CF$_3$ | 0 |
| A-0590 | H | H | H | H | H | O | H | H | 2-F,3-OMe | 0 |
| A-0591 | H | H | H | H | H | O | H | H | 2-F,4-OMe | 0 |
| A-0592 | H | H | H | H | H | O | H | H | 2-F,5-OMe | 0 |
| A-0593 | H | H | H | H | H | O | H | H | 2-F,6-OMe | 0 |
| A-0594 | H | H | H | H | H | O | H | H | 3-F,2-OMe | 0 |
| A-0595 | H | H | H | H | H | O | H | H | 3-F,4-OMe | 0 |
| A-0596 | H | H | H | H | H | O | H | H | 3-F,5-OMe | 0 |
| A-0597 | H | H | H | H | H | O | H | H | 3-F,6-OMe | 0 |

TABLE 11-continued

| compound | R¹ | R² | R³ | R⁴ | R⁵ | A | R⁶ | R⁷ | (R⁸)$_m$ | p |
|---|---|---|---|---|---|---|---|---|---|---|
| A-0598 | H | H | H | H | H | O | H | H | 4-F,2-OMe | 0 |
| A-0599 | H | H | H | H | H | O | H | H | 4-F,3-OMe | 0 |
| A-0600 | H | H | H | H | H | O | H | H | 2,3-Cl$_2$ | 0 |
| A-0601 | H | H | H | H | H | O | H | H | 2,4-Cl$_2$ | 0 |
| A-0602 | H | H | H | H | H | O | H | H | 2,5-Cl$_2$ | 0 |
| A-0603 | H | H | H | H | H | O | H | H | 2,6-Cl$_2$ | 0 |
| A-0604 | H | H | H | H | H | O | H | H | 3,4-Cl$_2$ | 0 |
| A-0605 | H | H | H | H | H | O | H | H | 3,5-Cl$_2$ | 0 |
| A-0606 | H | H | H | H | H | O | H | H | 2-Cl,3-Me | 0 |
| A-0607 | H | H | H | H | H | O | H | H | 2-Cl,4-Me | 0 |
| A-0608 | H | H | H | H | H | O | H | H | 2-Cl,5-Me | 0 |
| A-0609 | H | H | H | H | H | O | H | H | 2-Cl,6-Me | 0 |
| A-0610 | H | H | H | H | H | O | H | H | 3-Cl,2-Me | 0 |
| A-0611 | H | H | H | H | H | O | H | H | 3-Cl,4-Me | 0 |
| A-0612 | H | H | H | H | H | O | H | H | 3-Cl,5-Me | 0 |
| A-0613 | H | H | H | H | H | O | H | H | 3-Cl,6-Me | 0 |
| A-0614 | H | H | H | H | H | O | H | H | 4-Cl,2-Me | 0 |
| A-0615 | H | H | H | H | H | O | H | H | 4-Cl,3-Me | 0 |
| A-0616 | H | H | H | H | H | O | H | H | 2-Cl,3-CF$_3$ | 0 |
| A-0617 | H | H | H | H | H | O | H | H | 2-Cl,4-CF$_3$ | 0 |
| A-0618 | H | H | H | H | H | O | H | H | 2-Cl,5-CF$_3$ | 0 |
| A-0619 | H | H | H | H | H | O | H | H | 2-Cl,6-CF$_3$ | 0 |
| A-0620 | H | H | H | H | H | O | H | H | 3-Cl,2-CF$_3$ | 0 |
| A-0621 | H | H | H | H | H | O | H | H | 3-Cl,4-CF$_3$ | 0 |
| A-0622 | H | H | H | H | H | O | H | H | 3-Cl,5-CF$_3$ | 0 |

TABLE 12

| compound | R¹ | R² | R³ | R⁴ | R⁵ | A | R⁶ | R⁷ | (R⁸)$_m$ | p |
|---|---|---|---|---|---|---|---|---|---|---|
| A-0623 | H | H | H | H | H | O | H | H | 3-Cl,6-CF$_3$ | 0 |
| A-0624 | H | H | H | H | H | O | H | H | 4-Cl,2-CF$_3$ | 0 |
| A-0625 | H | H | H | H | H | O | H | H | 4-Cl,3-CF$_3$ | 0 |
| A-0626 | H | H | H | H | H | O | H | H | 2-Cl,3-OMe | 0 |
| A-0627 | H | H | H | H | H | O | H | H | 2-Cl,4-OMe | 0 |
| A-0628 | H | H | H | H | H | O | H | H | 2-Cl,5-OMe | 0 |
| A-0629 | H | H | H | H | H | O | H | H | 2-Cl,6-OMe | 0 |
| A-0630 | H | H | H | H | H | O | H | H | 3-Cl,2-OMe | 0 |
| A-0631 | H | H | H | H | H | O | H | H | 3-Cl,4-OMe | 0 |
| A-0632 | H | H | H | H | H | O | H | H | 3-Cl,5-OMe | 0 |
| A-0633 | H | H | H | H | H | O | H | H | 3-Cl,6-OMe | 0 |
| A-0634 | H | H | H | H | H | O | H | H | 4-Cl,2-OMe | 0 |
| A-0635 | H | H | H | H | H | O | H | H | 4-Cl,3-OMe | 0 |
| A-0636 | H | H | H | H | H | O | H | H | 2,3-Me$_2$ | 0 |
| A-0637 | H | H | H | H | H | O | H | H | 2,4-Me$_2$ | 0 |
| A-0638 | H | H | H | H | H | O | H | H | 2,5-Me$_2$ | 0 |
| A-0639 | H | H | H | H | H | O | H | H | 2,6-Me$_2$ | 0 |
| A-0640 | H | H | H | H | H | O | H | H | 3,4-Me$_2$ | 0 |
| A-0641 | H | H | H | H | H | O | H | H | 3,5-Me$_2$ | 0 |
| A-0642 | H | H | H | H | H | O | H | H | 2-Me,3-CF$_3$ | 0 |
| A-0643 | H | H | H | H | H | O | H | H | 2-Me,4-CF$_3$ | 0 |
| A-0644 | H | H | H | H | H | O | H | H | 2-Me,5-CF$_3$ | 0 |
| A-0645 | H | H | H | H | H | O | H | H | 2-Me,6-CF$_3$ | 0 |
| A-0646 | H | H | H | H | H | O | H | H | 3-Me,2-CF$_3$ | 0 |
| A-0647 | H | H | H | H | H | O | H | H | 3-Me,4-CF$_3$ | 0 |
| A-0648 | H | H | H | H | H | O | H | H | 3-Me,5-CF$_3$ | 0 |
| A-0649 | H | H | H | H | H | O | H | H | 3-Me,6-CF$_3$ | 0 |
| A-0650 | H | H | H | H | H | O | H | H | 4-Me,2-CF$_3$ | 0 |
| A-0651 | H | H | H | H | H | O | H | H | 4-Me,3-CF$_3$ | 0 |
| A-0652 | H | H | H | H | H | O | H | H | 2-Me,3-OMe | 0 |
| A-0653 | H | H | H | H | H | O | H | H | 2-Me,4-OMe | 0 |
| A-0654 | H | H | H | H | H | O | H | H | 2-Me,5-OMe | 0 |
| A-0655 | H | H | H | H | H | O | H | H | 2-Me,6-OMe | 0 |
| A-0656 | H | H | H | H | H | O | H | H | 3-Me,2-OMe | 0 |
| A-0657 | H | H | H | H | H | O | H | H | 3-Me,4-OMe | 0 |
| A-0658 | H | H | H | H | H | O | H | H | 3-Me,5-OMe | 0 |
| A-0659 | H | H | H | H | H | O | H | H | 3-Me,6-OMe | 0 |
| A-0660 | H | H | H | H | H | O | H | H | 4-Me,2-OMe | 0 |
| A-0661 | H | H | H | H | H | O | H | H | 4-Me,3-OMe | 0 |
| A-0662 | H | H | H | H | H | O | H | H | 2,3-OMe$_2$ | 0 |
| A-0663 | H | H | H | H | H | O | H | H | 2,4-OMe$_2$ | 0 |
| A-0664 | H | H | H | H | H | O | H | H | 2,5-OMe$_2$ | 0 |
| A-0665 | H | H | H | H | H | O | H | H | 2,6-OMe$_2$ | 0 |
| A-0666 | H | H | H | H | H | O | H | H | 3,4-OMe$_2$ | 0 |
| A-0667 | H | H | H | H | H | O | H | H | 3,5-OMe$_2$ | 0 |
| A-0668 | H | H | H | H | H | O | H | H | 2-OMe,3-CF$_3$ | 0 |
| A-0669 | H | H | H | H | H | O | H | H | 2-OMe,4-CF$_3$ | 0 |
| A-0670 | H | H | H | H | H | O | H | H | 2-OMe,5-CF$_3$ | 0 |
| A-0671 | H | H | H | H | H | O | H | H | 2-OMe,6-CF$_3$ | 0 |
| A-0672 | H | H | H | H | H | O | H | H | 3-OMe,2-CF$_3$ | 0 |
| A-0673 | H | H | H | H | H | O | H | H | 3-OMe,4-CF$_3$ | 0 |
| A-0674 | H | H | H | H | H | O | H | H | 3-OMe,5-CF$_3$ | 0 |
| A-0675 | H | H | H | H | H | O | H | H | 3-OMe,6-CF$_3$ | 0 |
| A-0676 | H | H | H | H | H | O | H | H | 4-OMe,2-CF$_3$ | 0 |
| A-0677 | H | H | H | H | H | O | H | H | 4-OMe,3-CF$_3$ | 0 |
| A-0678 | H | H | H | H | H | O | H | H | 2-CHF$_2$,3-F | 0 |
| A-0679 | H | H | H | H | H | O | H | H | 2-CHF$_2$,4-F | 0 |

TABLE 13

| compound | R¹ | R² | R³ | R⁴ | R⁵ | A | R⁶ | R⁷ | (R⁸)$_m$ | p |
|---|---|---|---|---|---|---|---|---|---|---|
| A-0680 | H | H | H | H | H | O | H | H | 2-CHF$_2$,5-F | 0 |
| A-0681 | H | H | H | H | H | O | H | H | 2-CHF$_2$,6-F | 0 |
| A-0682 | H | H | H | H | H | O | H | H | 2-CHF$_2$,3-Me | 0 |
| A-0683 | H | H | H | H | H | O | H | H | 2-CHF$_2$,4-Me | 0 |
| A-0684 | H | H | H | H | H | O | H | H | 2-CHF$_2$,5-Me | 0 |
| A-0685 | H | H | H | H | H | O | H | H | 2-CHF$_2$,6-Me | 0 |
| A-0686 | H | H | H | H | H | O | H | H | 2-cyclopropyl,3-F | 0 |
| A-0687 | H | H | H | H | H | O | H | H | 2-cyclopropyl,4-F | 0 |
| A-0688 | H | H | H | H | H | O | H | H | 2-cyclopropyl,5-F | 0 |
| A-0689 | H | H | H | H | H | O | H | H | 2-cyclopropyl,6-F | 0 |
| A-0690 | H | H | H | H | H | O | H | H | 2-cyclopropyl,3-Me | 0 |
| A-0691 | H | H | H | H | H | O | H | H | 2-cyclopropyl,4-Me | 0 |
| A-0692 | H | H | H | H | H | O | H | H | 2-cyclopropyl,5-Me | 0 |
| A-0693 | H | H | H | H | H | O | H | H | 2-cyclopropyl,6-Me | 0 |
| A-0694 | H | H | H | H | H | O | H | H | 2-ethenyl,3-F | 0 |
| A-0695 | H | H | H | H | H | O | H | H | 2-ethenyl,4-F | 0 |
| A-0696 | H | H | H | H | H | O | H | H | 2-ethenyl,5-F | 0 |
| A-0697 | H | H | H | H | H | O | H | H | 2-ethenyl,6-F | 0 |
| A-0698 | H | H | H | H | H | O | H | H | 2-ethenyl,3-Me | 0 |
| A-0699 | H | H | H | H | H | O | H | H | 2-ethenyl,4-Me | 0 |
| A-0700 | H | H | H | H | H | O | H | H | 2-ethenyl,5-Me | 0 |
| A-0701 | H | H | H | H | H | O | H | H | 2-ethenyl,6-Me | 0 |
| A-0702 | H | H | H | H | H | O | H | H | 2-OET,3-F | 0 |
| A-0703 | H | H | H | H | H | O | H | H | 2-OET,4-F | 0 |
| A-0704 | H | H | H | H | H | O | H | H | 2-OET,5-F | 0 |
| A-0705 | H | H | H | H | H | O | H | H | 2-OET,6-F | 0 |
| A-0706 | H | H | H | H | H | O | H | H | 2-OET,3-Cl | 0 |
| A-0707 | H | H | H | H | H | O | H | H | 2-OET,4-Cl | 0 |
| A-0708 | H | H | H | H | H | O | H | H | 2-OET,5-Cl | 0 |
| A-0709 | H | H | H | H | H | O | H | H | 2-OET,6-Cl | 0 |
| A-0710 | H | H | H | H | H | O | H | H | 2-OET,3-Me | 0 |
| A-0711 | H | H | H | H | H | O | H | H | 2-OET,4-Me | 0 |
| A-0712 | H | H | H | H | H | O | H | H | 2-OET,5-Me | 0 |
| A-0713 | H | H | H | H | H | O | H | H | 2-OET,6-Me | 0 |
| A-0714 | H | H | H | H | H | O | H | H | 2-OPr,3-F | 0 |
| A-0715 | H | H | H | H | H | O | H | H | 2-OPr,4-F | 0 |
| A-0716 | H | H | H | H | H | O | H | H | 2-OPr,5-F | 0 |
| A-0717 | H | H | H | H | H | O | H | H | 2-OPr,6-F | 0 |
| A-0718 | H | H | H | H | H | O | H | H | 2-OPr,3-Me | 0 |
| A-0719 | H | H | H | H | H | O | H | H | 2-OPr,4-Me | 0 |
| A-0720 | H | H | H | H | H | O | H | H | 2-OPr,5-Me | 0 |
| A-0721 | H | H | H | H | H | O | H | H | 2-OPr,6-Me | 0 |
| A-0722 | H | H | H | H | H | O | H | H | 2-O(i-Pr),3-F | 0 |
| A-0723 | H | H | H | H | H | O | H | H | 2-O(i-Pr),4-F | 0 |
| A-0724 | H | H | H | H | H | O | H | H | 2-O(i-Pr),5-F | 0 |
| A-0725 | H | H | H | H | H | O | H | H | 2-O(i-Pr),6-F | 0 |
| A-0726 | H | H | H | H | H | O | H | H | 2-O(i-Pr),3-Me | 0 |
| A-0727 | H | H | H | H | H | O | H | H | 2-O(i-Pr),4-Me | 0 |
| A-0728 | H | H | H | H | H | O | H | H | 2-O(i-Pr),5-Me | 0 |
| A-0729 | H | H | H | H | H | O | H | H | 2-O(i-Pr),6-Me | 0 |
| A-0730 | H | H | H | H | H | O | H | H | 2-OCF$_3$,3-F | 0 |
| A-0731 | H | H | H | H | H | O | H | H | 2-OCF$_3$,4-F | 0 |
| A-0732 | H | H | H | H | H | O | H | H | 2-OCF$_3$,5-F | 0 |

TABLE 13-continued

| compound | R¹ | R² | R³ | R⁴ | R⁵ | A | R⁶ | R⁷ | (R⁸)ₘ | p |
|---|---|---|---|---|---|---|---|---|---|---|
| A-0733 | H | H | H | H | H | O | H | H | 2-OCF₃,6-F | 0 |
| A-0734 | H | H | H | H | H | O | H | H | 2-OCF₃,3-Me | 0 |
| A-0735 | H | H | H | H | H | O | H | H | 2-OCF₃,4-Me | 0 |
| A-0736 | H | H | H | H | H | O | H | H | 2-OCF₃,5-Me | 0 |

TABLE 14

| compound | R¹ | R² | R³ | R⁴ | R⁵ | A | R⁶ | R⁷ | (R⁸)ₘ | p |
|---|---|---|---|---|---|---|---|---|---|---|
| A-0737 | H | H | H | H | H | O | H | H | 2-OCF₃,6-Me | 0 |
| A-0738 | H | H | H | H | H | O | H | H | 2-OCHF₂,3-F | 0 |
| A-0739 | H | H | H | H | H | O | H | H | 2-OCHF₂,4-F | 0 |
| A-0740 | H | H | H | H | H | O | H | H | 2-OCHF₂,5-F | 0 |
| A-0741 | H | H | H | H | H | O | H | H | 2-OCHF₂,6-F | 0 |
| A-0742 | H | H | H | H | H | O | H | H | 2-OCHF₂,3-Me | 0 |
| A-0743 | H | H | H | H | H | O | H | H | 2-OCHF₂,4-Me | 0 |
| A-0744 | H | H | H | H | H | O | H | H | 2-OCHF₂,5-Me | 0 |
| A-0745 | H | H | H | H | H | O | H | H | 2-OCHF₂,6-Me | 0 |
| A-0746 | H | H | H | H | H | O | H | H | 2-(cyclopropyl)oxy),3-F | 0 |
| A-0747 | H | H | H | H | H | O | H | H | 2-(cyclopropyl)oxy),4-F | 0 |
| A-0748 | H | H | H | H | H | O | H | H | 2-(cyclopropyl)oxy),5-F | 0 |
| A-0749 | H | H | H | H | H | O | H | H | 2-(cyclopropyl)oxy),6-F | 0 |
| A-0750 | H | H | H | H | H | O | H | H | 2-(cyclopropyl)oxy),3-Me | 0 |
| A-0751 | H | H | H | H | H | O | H | H | 2-(cyclopropyl)oxy),4-Me | 0 |
| A-0752 | H | H | H | H | H | O | H | H | 2-(cyclopropyl)oxy),5-Me | 0 |
| A-0753 | H | H | H | H | H | O | H | H | 2-(cyclopropyl)oxy),6-Me | 0 |
| A-0754 | H | H | H | H | H | O | H | H | 2-(oxiran-2-yl),3-F | 0 |
| A-0755 | H | H | H | H | H | O | H | H | 2-(oxiran-2-yl),4-F | 0 |
| A-0756 | H | H | H | H | H | O | H | H | 2-(oxiran-2-yl),5-F | 0 |
| A-0757 | H | H | H | H | H | O | H | H | 2-(oxiran-2-yl),6-F | 0 |
| A-0758 | H | H | H | H | H | O | H | H | 2-(oxiran-2-yl),3-Me | 0 |
| A-0759 | H | H | H | H | H | O | H | H | 2-(oxiran-2-yl),4-Me | 0 |
| A-0760 | H | H | H | H | H | O | H | H | 2-(oxiran-2-yl),5-Me | 0 |
| A-0761 | H | H | H | H | H | O | H | H | 2-(oxiran-2-yl),6-Me | 0 |
| A-0762 | H | H | H | H | H | O | H | H | 2-(oxiran-2-ylmethyl),3-F | 0 |
| A-0763 | H | H | H | H | H | O | H | H | 2-(oxiran-2-ylmethyl),4-F | 0 |
| A-0764 | H | H | H | H | H | O | H | H | 2-(oxiran-2-ylmethyl),5-F | 0 |
| A-0765 | H | H | H | H | H | O | H | H | 2-(oxiran-2-ylmethyl),6-F | 0 |
| A-0766 | H | H | H | H | H | O | H | H | 2-(oxiran-2-ylmethyl),3-Me | 0 |
| A-0767 | H | H | H | H | H | O | H | H | 2-(oxiran-2-ylmethyl),4-Me | 0 |
| A-0768 | H | H | H | H | H | O | H | H | 2-(oxiran-2-ylmethyl),5-Me | 0 |
| A-0769 | H | H | H | H | H | O | H | H | 2-(oxiran-2-ylmethyl),6-Me | 0 |
| A-0770 | H | H | H | H | H | O | H | H | 2-SMe,3-F | 0 |
| A-0771 | H | H | H | H | H | O | H | H | 2-SMe,4-F | 0 |
| A-0772 | H | H | H | H | H | O | H | H | 2-SMe,5-F | 0 |
| A-0773 | H | H | H | H | H | O | H | H | 2-SMe,6-F | 0 |
| A-0774 | H | H | H | H | H | O | H | H | 2-SMe,3-Me | 0 |
| A-0775 | H | H | H | H | H | O | H | H | 2-SMe,4-Me | 0 |
| A-0776 | H | H | H | H | H | O | H | H | 2-SMe,5-Me | 0 |
| A-0777 | H | H | H | H | H | O | H | H | 2-SMe,6-Me | 0 |
| A-0778 | H | H | H | H | H | O | H | H | 2-SEt,3-F | 0 |
| A-0779 | H | H | H | H | H | O | H | H | 2-SEt,4-F | 0 |
| A-0780 | H | H | H | H | H | O | H | H | 2-SEt,5-F | 0 |
| A-0781 | H | H | H | H | H | O | H | H | 2-SEt,6-F | 0 |
| A-0782 | H | H | H | H | H | O | H | H | 2-SEt,3-Me | 0 |
| A-0783 | H | H | H | H | H | O | H | H | 2-SEt,4-Me | 0 |
| A-0784 | H | H | H | H | H | O | H | H | 2-SEt,5-Me | 0 |
| A-0785 | H | H | H | H | H | O | H | H | 2-SEt,6-Me | 0 |
| A-0786 | H | H | H | H | H | O | H | H | 2-S(=O)Me,3-F | 0 |
| A-0787 | H | H | H | H | H | O | H | H | 2-S(=O)Me,4-F | 0 |
| A-0788 | H | H | H | H | H | O | H | H | 2-S(=O)Me,5-F | 0 |
| A-0789 | H | H | H | H | H | O | H | H | 2-S(=O)Me,6-F | 0 |
| A-0790 | H | H | H | H | H | O | H | H | 3-S(=O)Me,2-F | 0 |
| A-0791 | H | H | H | H | H | O | H | H | 3-S(=O)Me,4-F | 0 |
| A-0792 | H | H | H | H | H | O | H | H | 3-S(=O)Me,5-F | 0 |
| A-0793 | H | H | H | H | H | O | H | H | 3-S(=O)Me,6-F | 0 |

TABLE 15

| compound | R¹ | R² | R³ | R⁴ | R⁵ | A | R⁶ | R⁷ | (R⁸)ₘ | p |
|---|---|---|---|---|---|---|---|---|---|---|
| A-0794 | H | H | H | H | H | O | H | H | 2-S(=O)Me,3-Me | 0 |
| A-0795 | H | H | H | H | H | O | H | H | 2-S(=O)Me,4-Me | 0 |
| A-0796 | H | H | H | H | H | O | H | H | 2-S(=O)Me,5-Me | 0 |
| A-0797 | H | H | H | H | H | O | H | H | 2-S(=O)Me,6-Me | 0 |

TABLE 15-continued

| compound | R¹ | R² | R³ | R⁴ | R⁵ | A | R⁶ | R⁷ | (R⁸)$_m$ | p |
|---|---|---|---|---|---|---|---|---|---|---|
| A-0798 | H | H | H | H | H | O | H | H | 3-S(=O)Me,2-Me | 0 |
| A-0799 | H | H | H | H | H | O | H | H | 3-S(=O)Me,4-Me | 0 |
| A-0800 | H | H | H | H | H | O | H | H | 3-S(=O)Me,5-Me | 0 |
| A-0801 | H | H | H | H | H | O | H | H | 3-S(=O)Me,6-Me | 0 |
| A-0802 | H | H | H | H | H | O | H | H | 2-S(=O)$_2$Me,3-F | 0 |
| A-0803 | H | H | H | H | H | O | H | H | 2-S(=O)$_2$Me,4-F | 0 |
| A-0804 | H | H | H | H | H | O | H | H | 2-S(=O)$_2$Me,5-F | 0 |
| A-0805 | H | H | H | H | H | O | H | H | 2-S(=O)$_2$Me,6-F | 0 |
| A-0806 | H | H | H | H | H | O | H | H | 2-S(=O)$_2$Me,3-Me | 0 |
| A-0807 | H | H | H | H | H | O | H | H | 2-S(=O)$_2$Me,4-Me | 0 |
| A-0808 | H | H | H | H | H | O | H | H | 2-S(=O)$_2$Me,5-Me | 0 |
| A-0809 | H | H | H | H | H | O | H | H | 2-S(=O)$_2$Me,6-Me | 0 |
| A-0810 | H | H | H | H | H | O | H | H | 2-SCF$_3$,3-F | 0 |
| A-0811 | H | H | H | H | H | O | H | H | 2-SCF$_3$,4-F | 0 |
| A-0812 | H | H | H | H | H | O | H | H | 2-SCF$_3$,5-F | 0 |
| A-0813 | H | H | H | H | H | O | H | H | 2-SCF$_3$,6-F | 0 |
| A-0814 | H | H | H | H | H | O | H | H | 2-SCF$_3$,3-Me | 0 |
| A-0815 | H | H | H | H | H | O | H | H | 2-SCF$_3$,4-Me | 0 |
| A-0816 | H | H | H | H | H | O | H | H | 2-SCF$_3$,5-Me | 0 |
| A-0817 | H | H | H | H | H | O | H | H | 2-SCF$_3$,6-Me | 0 |
| A-0818 | H | H | H | H | H | O | H | H | 2-S(=O)CF$_3$,3-F | 0 |
| A-0819 | H | H | H | H | H | O | H | H | 2-S(=O)CF$_3$,4-F | 0 |
| A-0820 | H | H | H | H | H | O | H | H | 2-S(=O)CF$_3$,5-F | 0 |
| A-0821 | H | H | H | H | H | O | H | H | 2-S(=O)CF$_3$,6-F | 0 |
| A-0822 | H | H | H | H | H | O | H | H | 2-S(=O)CF$_3$,3-Me | 0 |
| A-0823 | H | H | H | H | H | O | H | H | 2-S(=O)CF$_3$,4-Me | 0 |
| A-0824 | H | H | H | H | H | O | H | H | 2-S(=O)CF$_3$,5-Me | 0 |
| A-0825 | H | H | H | H | H | O | H | H | 2-S(=O)CF$_3$,6-Me | 0 |
| A-0826 | H | H | H | H | H | O | H | H | 2-S(=O)$_2$CF$_3$,3-F | 0 |
| A-0827 | H | H | H | H | H | O | H | H | 2-S(=O)$_2$CF$_3$,4-F | 0 |
| A-0828 | H | H | H | H | H | O | H | H | 2-S(=O)$_2$CF$_3$,5-F | 0 |
| A-0829 | H | H | H | H | H | O | H | H | 2-S(=O)$_2$CF$_3$,6-F | 0 |
| A-0830 | H | H | H | H | H | O | H | H | 2-S(=O)$_2$CF$_3$,3-Me | 0 |
| A-0831 | H | H | H | H | H | O | H | H | 2-S(=O)$_2$CF$_3$,4-Me | 0 |
| A-0832 | H | H | H | H | H | O | H | H | 2-S(=O)$_2$CF$_3$,5-Me | 0 |
| A-0833 | H | H | H | H | H | O | H | H | 2-S(=O)$_2$CF$_3$,6-Me | 0 |
| A-0834 | H | H | H | H | H | O | H | H | 2-(cyclopropylthio),3-F | 0 |
| A-0835 | H | H | H | H | H | O | H | H | 2-(cyclopropylthio),4-F | 0 |
| A-0836 | H | H | H | H | H | O | H | H | 2-(cyclopropylthio),5-F | 0 |
| A-0837 | H | H | H | H | H | O | H | H | 2-(cyclopropylthio),6-F | 0 |
| A-0838 | H | H | H | H | H | O | H | H | 2-(cyclopropylthio),3-Me | 0 |
| A-0839 | H | H | H | H | H | O | H | H | 2-(cyclopropylthio),4-Me | 0 |
| A-0840 | H | H | H | H | H | O | H | H | 2-(cyclopropylthio),5-Me | 0 |
| A-0841 | H | H | H | H | H | O | H | H | 2-(cyclopropylthio),6-Me | 0 |
| A-0842 | H | H | H | H | H | O | H | H | 2-C(=O)Me,3-F | 0 |
| A-0843 | H | H | H | H | H | O | H | H | 2-C(=O)Me,4-F | 0 |
| A-0844 | H | H | H | H | H | O | H | H | 2-C(=O)Me,5-F | 0 |
| A-0845 | H | H | H | H | H | O | H | H | 2-C(=O)Me,6-F | 0 |
| A-0846 | H | H | H | H | H | O | H | H | 2-C(=O)Me,3-Me | 0 |
| A-0847 | H | H | H | H | H | O | H | H | 2-C(=O)Me,4-Me | 0 |
| A-0848 | H | H | H | H | H | O | H | H | 2-C(=O)Me,5-Me | 0 |
| A-0849 | H | H | H | H | H | O | H | H | 2-C(=O)Me,6-Me | 0 |
| A-0850 | H | H | H | H | H | O | H | H | 3-C(=O)Me,2-F | 0 |

TABLE 16

| compound | R¹ | R² | R³ | R⁴ | R⁵ | A | R⁶ | R⁷ | (R⁸)$_m$ | p |
|---|---|---|---|---|---|---|---|---|---|---|
| A-0851 | H | H | H | H | H | O | H | H | 3-C(=O)Me,4-F | 0 |
| A-0852 | H | H | H | H | H | O | H | H | 3-C(=O)Me,5-F | 0 |
| A-0853 | H | H | H | H | H | O | H | H | 3-C(=O)Me,6-F | 0 |
| A-0854 | H | H | H | H | H | O | H | H | 3-C(=O)Me,2-Me | 0 |
| A-0855 | H | H | H | H | H | O | H | H | 3-C(=O)Me,4-Me | 0 |
| A-0856 | H | H | H | H | H | O | H | H | 3-C(=O)Me,5-Me | 0 |
| A-0857 | H | H | H | H | H | O | H | H | 3-C(=O)Me,6-Me | 0 |
| A-0858 | H | H | H | H | H | O | H | H | 2-C(=O)OMe,3-F | 0 |
| A-0859 | H | H | H | H | H | O | H | H | 2-C(=O)OMe,4-F | 0 |
| A-0860 | H | H | H | H | H | O | H | H | 2-C(=O)OMe,5-F | 0 |
| A-0861 | H | H | H | H | H | O | H | H | 2-C(=O)OMe,6-F | 0 |
| A-0862 | H | H | H | H | H | O | H | H | 2-C(=O)OMe,3-Me | 0 |
| A-0863 | H | H | H | H | H | O | H | H | 2-C(=O)OMe,4-Me | 0 |
| A-0864 | H | H | H | H | H | O | H | H | 2-C(=O)OMe,4-Me | 0 |
| A-0865 | H | H | H | H | H | O | H | H | 2-C(=O)OMe,6-Me | 0 |
| A-0866 | H | H | H | H | H | O | H | H | 2-C(=O)OET,3-F | 0 |
| A-0867 | H | H | H | H | H | O | H | H | 2-C(=O)OET,4-F | 0 |
| A-0868 | H | H | H | H | H | O | H | H | 2-C(=O)OET,5-F | 0 |
| A-0869 | H | H | H | H | H | O | H | H | 2-C(=O)OET,6-F | 0 |
| A-0870 | H | H | H | H | H | O | H | H | 2-C(=O)OET,3-Me | 0 |
| A-0871 | H | H | H | H | H | O | H | H | 2-C(=O)OET,4-Me | 0 |
| A-0872 | H | H | H | H | H | O | H | H | 2-C(=O)OET,5-Me | 0 |
| A-0873 | H | H | H | H | H | O | H | H | 2-C(=O)OET,6-Me | 0 |
| A-0874 | H | H | H | H | H | O | H | H | 2-C(=O)NH$_2$,3-F | 0 |
| A-0875 | H | H | H | H | H | O | H | H | 2-C(=O)NH$_2$,4-F | 0 |
| A-0876 | H | H | H | H | H | O | H | H | 2-C(=O)NH$_2$,5-F | 0 |
| A-0877 | H | H | H | H | H | O | H | H | 2-C(=O)NH$_2$,6-F | 0 |
| A-0878 | H | H | H | H | H | O | H | H | 2-C(=O)NH$_2$,3-Me | 0 |
| A-0879 | H | H | H | H | H | O | H | H | 2-C(=O)NH$_2$,4-Me | 0 |
| A-0880 | H | H | H | H | H | O | H | H | 2-C(=O)NH$_2$,5-Me | 0 |
| A-0881 | H | H | H | H | H | O | H | H | 2-C(=O)NH$_2$,6-Me | 0 |
| A-0882 | H | H | H | H | H | O | H | H | 2-C(=O)NHMe,3-F | 0 |

TABLE 16-continued

| compound | R¹ | R² | R³ | R⁴ | R⁵ | A | R⁶ | R⁷ | (R⁸)$_m$ | p |
|---|---|---|---|---|---|---|---|---|---|---|
| A-0883 | H | H | H | H | H | O | H | H | 2-C(=O)NHMe,4-F | 0 |
| A-0884 | H | H | H | H | H | O | H | H | 2-C(=O)NHMe,5-F | 0 |
| A-0885 | H | H | H | H | H | O | H | H | 2-C(=O)NHMe,6-F | 0 |
| A-0886 | H | H | H | H | H | O | H | H | 2-C(=O)NHMe,3-Me | 0 |
| A-0887 | H | H | H | H | H | O | H | H | 2-C(=O)NHMe,4-Me | 0 |
| A-0888 | H | H | H | H | H | O | H | H | 2-C(=O)NHMe,5-Me | 0 |
| A-0889 | H | H | H | H | H | O | H | H | 2-C(=O)NHMe,6-Me | 0 |
| A-0890 | H | H | H | H | H | O | H | H | 2-C(=O)NMe₂,3-F | 0 |
| A-0891 | H | H | H | H | H | O | H | H | 2-C(=O)NMe₂,4-F | 0 |
| A-0892 | H | H | H | H | H | O | H | H | 2-C(=O)NMe₂,5-F | 0 |
| A-0893 | H | H | H | H | H | O | H | H | 2-C(=O)NMe₂,6-F | 0 |
| A-0894 | H | H | H | H | H | O | H | H | 2-C(=O)NMe₂,3-Me | 0 |
| A-0895 | H | H | H | H | H | O | H | H | 2-C(=O)NMe₂,4-Me | 0 |
| A-0896 | H | H | H | H | H | O | H | H | 2-C(=O)NMe₂,5-Me | 0 |
| A-0897 | H | H | H | H | H | O | H | H | 2-C(=O)NMe₂,6-Me | 0 |
| A-0898 | H | H | H | H | H | O | H | H | 2-CH₂OH,3-F | 0 |
| A-0899 | H | H | H | H | H | O | H | H | 2-CH₂OH,4-F | 0 |
| A-0900 | H | H | H | H | H | O | H | H | 2-CH₂OH,5-F | 0 |
| A-0901 | H | H | H | H | H | O | H | H | 2-CH₂OH,6-F | 0 |
| A-0902 | H | H | H | H | H | O | H | H | 2-CH₂OH,3-Me | 0 |
| A-0903 | H | H | H | H | H | O | H | H | 2-CH₂OH,4-Me | 0 |
| A-0904 | H | H | H | H | H | O | H | H | 2-CH₂OH,5-Me | 0 |
| A-0905 | H | H | H | H | H | O | H | H | 2-CH₂OH,6-Me | 0 |
| A-0906 | H | H | H | H | H | O | H | H | 2-CH₂OCH₃,3-F | 0 |
| A-0907 | H | H | H | H | H | O | H | H | 2-CH₂OCH₃,4-F | 0 |

TABLE 17

| compound | R¹ | R² | R³ | R⁴ | R⁵ | A | R⁶ | R⁷ | (R⁸)$_m$ | p |
|---|---|---|---|---|---|---|---|---|---|---|
| A-0908 | H | H | H | H | H | O | H | H | 2-CH₂OCH₃,5-F | 0 |
| A-0909 | H | H | H | H | H | O | H | H | 2-CH₂OCH₃,6-F | 0 |
| A-0910 | H | H | H | H | H | O | H | H | 2-CH₂OCH₃,3-Me | 0 |
| A-0911 | H | H | H | H | H | O | H | H | 2-CH₂OCH₃,4-Me | 0 |
| A-0912 | H | H | H | H | H | O | H | H | 2-CH₂OCH₃,5-Me | 0 |
| A-0913 | H | H | H | H | H | O | H | H | 2-CH₂OCH₃,6-Me | 0 |
| A-0914 | H | H | H | H | H | O | H | H | 2-CH₂OCH₂CH₃,3-F | 0 |
| A-0915 | H | H | H | H | H | O | H | H | 2-CH₂OCH₂CH₃,4-F | 0 |
| A-0916 | H | H | H | H | H | O | H | H | 2-CH₂OCH₂CH₃,5-F | 0 |
| A-0917 | H | H | H | H | H | O | H | H | 2-CH₂OCH₂CH₃,6-F | 0 |
| A-0918 | H | H | H | H | H | O | H | H | 2-CH₂OCH₂CH₃,3-Me | 0 |
| A-0919 | H | H | H | H | H | O | H | H | 2-CH₂OCH₂CH₃,4-Me | 0 |
| A-0920 | H | H | H | H | H | O | H | H | 2-CH₂OCH₂CH₃,5-Me | 0 |
| A-0921 | H | H | H | H | H | O | H | H | 2-CH₂OCH₂CH₃,6-Me | 0 |
| A-0922 | H | H | H | H | H | O | H | H | 2-OC(=O)CH₃,3-F | 0 |
| A-0923 | H | H | H | H | H | O | H | H | 2-OC(=O)CH₃,4-F | 0 |
| A-0924 | H | H | H | H | H | O | H | H | 2-OC(=O)CH₃,5-F | 0 |
| A-0925 | H | H | H | H | H | O | H | H | 2-OC(=O)CH₃,6-F | 0 |
| A-0926 | H | H | H | H | H | O | H | H | 2-OC(=O)CH₃,3-Me | 0 |
| A-0927 | H | H | H | H | H | O | H | H | 2-OC(=O)CH₃,4-Me | 0 |
| A-0928 | H | H | H | H | H | O | H | H | 2-OC(=O)CH₃,5-Me | 0 |
| A-0929 | H | H | H | H | H | O | H | H | 2-OC(=O)CH₃,6-Me | 0 |
| A-0930 | H | H | H | H | H | O | H | H | 2-OS(=O)₂CH₃,3-F | 0 |
| A-0931 | H | H | H | H | H | O | H | H | 2-OS(=O)₂CH₃,4-F | 0 |
| A-0932 | H | H | H | H | H | O | H | H | 2-OS(=O)₂CH₃,5-F | 0 |
| A-0933 | H | H | H | H | H | O | H | H | 2-OS(=O)₂CH₃,6-F | 0 |
| A-0934 | H | H | H | H | H | O | H | H | 2-OS(=O)₂CH₃,3-Me | 0 |
| A-0935 | H | H | H | H | H | O | H | H | 2-OS(=O)₂CH₃,4-Me | 0 |
| A-0936 | H | H | H | H | H | O | H | H | 2-OS(=O)₂CH₃,5-Me | 0 |
| A-0937 | H | H | H | H | H | O | H | H | 2-OS(=O)₂CH₃,6-Me | 0 |
| A-0938 | H | H | H | H | H | O | H | H | 2-CH₂SCH₃,3-F | 0 |
| A-0939 | H | H | H | H | H | O | H | H | 2-CH₂SCH₃,4-F | 0 |
| A-0940 | H | H | H | H | H | O | H | H | 2-CH₂SCH₃,5-F | 0 |
| A-0941 | H | H | H | H | H | O | H | H | 2-CH₂SCH₃,6-F | 0 |
| A-0942 | H | H | H | H | H | O | H | H | 2-CH₂SCH₃,3-Me | 0 |
| A-0943 | H | H | H | H | H | O | H | H | 2-CH₂SCH₃,4-Me | 0 |
| A-0944 | H | H | H | H | H | O | H | H | 2-CH₂SCH₃,5-Me | 0 |
| A-0945 | H | H | H | H | H | O | H | H | 2-CH₂SCH₃,6-Me | 0 |
| A-0946 | H | H | H | H | H | O | H | H | 2-CH₂SCF₃,3-F | 0 |
| A-0947 | H | H | H | H | H | O | H | H | 2-CH₂SCF₃,4-F | 0 |
| A-0948 | H | H | H | H | H | O | H | H | 2-CH₂SCF₃,5-F | 0 |
| A-0949 | H | H | H | H | H | O | H | H | 2-CH₂SCF₃,6-F | 0 |
| A-0950 | H | H | H | H | H | O | H | H | 2-CH₂SCF₃,3-Me | 0 |
| A-0951 | H | H | H | H | H | O | H | H | 2-CH₂SCF₃,4-Me | 0 |
| A-0952 | H | H | H | H | H | O | H | H | 2-CH₂SCF₃,5-Me | 0 |
| A-0953 | H | H | H | H | H | O | H | H | 2-CH₂SCF₃,6-Me | 0 |
| A-0954 | H | H | H | H | H | O | H | H | 2-(benzyloxy),3-F | 0 |
| A-0955 | H | H | H | H | H | O | H | H | 2-(benzyloxy),4-F | 0 |
| A-0956 | H | H | H | H | H | O | H | H | 2-(benzyloxy),5-F | 0 |
| A-0957 | H | H | H | H | H | O | H | H | 2-(benzyloxy),6-F | 0 |
| A-0958 | H | H | H | H | H | O | H | H | 2-(benzyloxy),3-Me | 0 |
| A-0959 | H | H | H | H | H | O | H | H | 2-(benzyloxy),4-Me | 0 |
| A-0960 | H | H | H | H | H | O | H | H | 2-(benzyloxy),5-Me | 0 |
| A-0961 | H | H | H | H | H | O | H | H | 2-(benzyloxy),6-Me | 0 |

TABLE 17-continued

| compound | R¹ | R² | R³ | R⁴ | R⁵ | A | R⁶ | R⁷ | (R⁸)ₘ | p |
|---|---|---|---|---|---|---|---|---|---|---|
| A-0962 | H | H | H | H | H | O | H | H | 2-NH₂,3-F | 0 |
| A-0963 | H | H | H | H | H | O | H | H | 2-NH₂,4-F | 0 |
| A-0964 | H | H | H | H | H | O | H | H | 2-NH₂,5-F | 0 |

TABLE 18

| compound | R¹ | R² | R³ | R⁴ | R⁵ | A | R⁶ | R⁷ | (R⁸)ₘ | p |
|---|---|---|---|---|---|---|---|---|---|---|
| A-0965 | H | H | H | H | H | O | H | H | 2-NH₂,6-F | 0 |
| A-0966 | H | H | H | H | H | O | H | H | 2-NH₂,3-Me | 0 |
| A-0967 | H | H | H | H | H | O | H | H | 2-NH₂,4-Me | 0 |
| A-0968 | H | H | H | H | H | O | H | H | 2-NH₂,5-Me | 0 |
| A-0969 | H | H | H | H | H | O | H | H | 2-NH₂,6-Me | 0 |
| A-0970 | H | H | H | H | H | O | H | H | 2-NHMe,3-F | 0 |
| A-0971 | H | H | H | H | H | O | H | H | 2-NHMe,4-F | 0 |
| A-0972 | H | H | H | H | H | O | H | H | 2-NHMe,5-F | 0 |
| A-0973 | H | H | H | H | H | O | H | H | 2-NHMe,6-F | 0 |
| A-0974 | H | H | H | H | H | O | H | H | 2-NHMe,3-Me | 0 |
| A-0975 | H | H | H | H | H | O | H | H | 2-NHMe,4-Me | 0 |
| A-0976 | H | H | H | H | H | O | H | H | 2-NHMe,5-Me | 0 |
| A-0977 | H | H | H | H | H | O | H | H | 2-NHMe,6-Me | 0 |
| A-0978 | H | H | H | H | H | O | H | H | 2-NHEt,3-F | 0 |
| A-0979 | H | H | H | H | H | O | H | H | 2-NHEt,4-F | 0 |
| A-0980 | H | H | H | H | H | O | H | H | 2-NHEt,5-F | 0 |
| A-0981 | H | H | H | H | H | O | H | H | 2-NHEt,6-F | 0 |
| A-0982 | H | H | H | H | H | O | H | H | 2-NHEt,3-Me | 0 |
| A-0983 | H | H | H | H | H | O | H | H | 2-NHEt,4-Me | 0 |
| A-0984 | H | H | H | H | H | O | H | H | 2-NHEt,5-Me | 0 |
| A-0985 | H | H | H | H | H | O | H | H | 2-NHEt,6-Me | 0 |
| A-0986 | H | H | H | H | H | O | H | H | 2-NMe₂,3-F | 0 |
| A-0987 | H | H | H | H | H | O | H | H | 2-NMe₂,4-F | 0 |
| A-0988 | H | H | H | H | H | O | H | H | 2-NMe₂,5-F | 0 |
| A-0989 | H | H | H | H | H | O | H | H | 2-NMe₂,6-F | 0 |
| A-0990 | H | H | H | H | H | O | H | H | 2-NMe₂,3-Me | 0 |
| A-0991 | H | H | H | H | H | O | H | H | 2-NMe₂,4-Me | 0 |
| A-0992 | H | H | H | H | H | O | H | H | 2-NMe₂,5-Me | 0 |
| A-0993 | H | H | H | H | H | O | H | H | 2-NMe₂,6-Me | 0 |
| A-0994 | H | H | H | H | H | O | H | H | 2-NEt₂,3-F | 0 |
| A-0995 | H | H | H | H | H | O | H | H | 2-NEt₂,4-F | 0 |
| A-0996 | H | H | H | H | H | O | H | H | 2-NEt₂,5-F | 0 |
| A-0997 | H | H | H | H | H | O | H | H | 2-NEt₂,6-F | 0 |
| A-0998 | H | H | H | H | H | O | H | H | 2-NEt₂,3-Me | 0 |
| A-0999 | H | H | H | H | H | O | H | H | 2-NEt₂,4-Me | 0 |
| A-1000 | H | H | H | H | H | O | H | H | 2-NEt₂,5-Me | 0 |
| A-1001 | H | H | H | H | H | O | H | H | 2-NEt₂,6-Me | 0 |
| A-1002 | H | H | H | H | H | O | H | H | 2-CHO,3-F | 0 |
| A-1003 | H | H | H | H | H | O | H | H | 2-CHO,4-F | 0 |
| A-1004 | H | H | H | H | H | O | H | H | 2-CHO,5-F | 0 |
| A-1005 | H | H | H | H | H | O | H | H | 2-CHO,6-F | 0 |
| A-1006 | H | H | H | H | H | O | H | H | 2-CHO,3-Me | 0 |
| A-1007 | H | H | H | H | H | O | H | H | 2-CHO,4-Me | 0 |
| A-1008 | H | H | H | H | H | O | H | H | 2-CHO,5-Me | 0 |
| A-1009 | H | H | H | H | H | O | H | H | 2-CHO,6-Me | 0 |
| A-1010 | H | H | H | H | H | O | H | H | 2-C(=O)OH,3-F | 0 |
| A-1011 | H | H | H | H | H | O | H | H | 2-C(=O)OH,4-F | 0 |
| A-1012 | H | H | H | H | H | O | H | H | 2-C(=O)OH,5-F | 0 |
| A-1013 | H | H | H | H | H | O | H | H | 2-C(=O)OH,6-F | 0 |
| A-1014 | H | H | H | H | H | O | H | H | 2-C(=O)OH,3-Me | 0 |
| A-1015 | H | H | H | H | H | O | H | H | 2-C(=O)OH,4-Me | 0 |
| A-1016 | H | H | H | H | H | O | H | H | 2-C(=O)OH,5-Me | 0 |
| A-1017 | H | H | H | H | H | O | H | H | 2-C(=O)OH,6-Me | 0 |
| A-1018 | H | H | H | H | H | O | H | H | 2-(1,3-dioxolan-2-yl),3-F | 0 |
| A-1019 | H | H | H | H | H | O | H | H | 2-(1,3-dioxolan-2-yl),4-F | 0 |
| A-1020 | H | H | H | H | H | O | H | H | 2-(1,3-dioxolan-2-yl),5-F | 0 |
| A-1021 | H | H | H | H | H | O | H | H | 2-(1,3-dioxolan-2-yl),6-F | 0 |

TABLE 19

| compound | R¹ | R² | R³ | R⁴ | R⁵ | A | R⁶ | R⁷ | (R⁸)ₘ | p |
|---|---|---|---|---|---|---|---|---|---|---|
| A-1022 | H | H | H | H | H | O | H | H | 2-(1,3-dioxolan-2-yl),3-Me | 0 |
| A-1023 | H | H | H | H | H | O | H | H | 2-(1,3-dioxolan-2-yl),4-Me | 0 |
| A-1024 | H | H | H | H | H | O | H | H | 2-(1,3-dioxolan-2-yl),5-Me | 0 |

TABLE 19-continued

| compound | R¹ | R² | R³ | R⁴ | R⁵ | A | R⁶ | R⁷ | (R⁸)$_m$ | p |
|---|---|---|---|---|---|---|---|---|---|---|
| A-1025 | H | H | H | H | H | O | H | H | 2-(1,3-dioxolan-2-yl),6-Me | 0 |
| A-1026 | H | H | H | H | H | O | H | H | 2-(1,3-dioxan-2-yl),3-F | 0 |
| A-1027 | H | H | H | H | H | O | H | H | 2-(1,3-dioxan-2-yl),4-F | 0 |
| A-1028 | H | H | H | H | H | O | H | H | 2-(1,3-dioxan-2-yl),5-F | 0 |
| A-1029 | H | H | H | H | H | O | H | H | 2-(1,3-dioxan-2-yl),6-F | 0 |
| A-1030 | H | H | H | H | H | O | H | H | 2-(1,3-dioxan-2-yl),3-Me | 0 |
| A-1031 | H | H | H | H | H | O | H | H | 2-(1,3-dioxan-2-yl),4-Me | 0 |
| A-1032 | H | H | H | H | H | O | H | H | 2-(1,3-dioxan-2-yl),5-Me | 0 |
| A-1033 | H | H | H | H | H | O | H | H | 2-(1,3-dioxan-2-yl),6-Me | 0 |
| A-1034 | H | H | H | H | H | O | H | H | 2-(thiazol-2-yl),3-F | 0 |
| A-1035 | H | H | H | H | H | O | H | H | 2-(thiazol-2-yl),4-F | 0 |
| A-1036 | H | H | H | H | H | O | H | H | 2-(thiazol-2-yl),5-F | 0 |
| A-1037 | H | H | H | H | H | O | H | H | 2-(thiazol-2-yl),6-F | 0 |
| A-1038 | H | H | H | H | H | O | H | H | 2-(thiazol-2-yl),3-Me | 0 |
| A-1039 | H | H | H | H | H | O | H | H | 2-(thiazol-2-yl),4-Me | 0 |
| A-1040 | H | H | H | H | H | O | H | H | 2-(thiazol-2-yl),5-Me | 0 |
| A-1041 | H | H | H | H | H | O | H | H | 2-(thiazol-2-yl),6-Me | 0 |
| A-1042 | H | H | H | H | H | O | H | H | 2-(oxazol-2-yl),3-F | 0 |
| A-1043 | H | H | H | H | H | O | H | H | 2-(oxazol-2-yl),4-F | 0 |
| A-1044 | H | H | H | H | H | O | H | H | 2-(oxazol-2-yl),5-F | 0 |
| A-1045 | H | H | H | H | H | O | H | H | 2-(oxazol-2-yl),6-F | 0 |
| A-1046 | H | H | H | H | H | O | H | H | 2-(oxazol-2-yl),3-Me | 0 |
| A-1047 | H | H | H | H | H | O | H | H | 2-(oxazol-2-yl),4-Me | 0 |
| A-1048 | H | H | H | H | H | O | H | H | 2-(oxazol-2-yl),5-Me | 0 |
| A-1049 | H | H | H | H | H | O | H | H | 2-(oxazol-2-yl),6-Me | 0 |
| A-1050 | H | H | H | H | H | O | H | H | 2-CH=NOH,3-F | 0 |
| A-1051 | H | H | H | H | H | O | H | H | 2-CH=NOH,4-F | 0 |
| A-1052 | H | H | H | H | H | O | H | H | 2-CH=NOH,5-F | 0 |
| A-1053 | H | H | H | H | H | O | H | H | 2-CH=NOH,6-F | 0 |
| A-1054 | H | H | H | H | H | O | H | H | 2-CH=NOH,3-Me | 0 |
| A-1055 | H | H | H | H | H | O | H | H | 2-CH=NOH,4-Me | 0 |
| A-1056 | H | H | H | H | H | O | H | H | 2-CH=NOH,5-Me | 0 |
| A-1057 | H | H | H | H | H | O | H | H | 2-CH=NOH,6-Me | 0 |
| A-1058 | H | H | H | H | H | O | H | H | 2-CH=NOMe,3-F | 0 |
| A-1059 | H | H | H | H | H | O | H | H | 2-CH=NOMe,4-F | 0 |
| A-1060 | H | H | H | H | H | O | H | H | 2-CH=NOMe,5-F | 0 |
| A-1061 | H | H | H | H | H | O | H | H | 2-CH=NOMe,6-F | 0 |
| A-1062 | H | H | H | H | H | O | H | H | 2-CH=NOMe,3-Me | 0 |
| A-1063 | H | H | H | H | H | O | H | H | 2-CH=NOMe,4-Me | 0 |
| A-1064 | H | H | H | H | H | O | H | H | 2-CH=NOMe,5-Me | 0 |
| A-1065 | H | H | H | H | H | O | H | H | 2-CH=NOMe,6-Me | 0 |
| A-1066 | H | H | H | H | H | O | H | H | 2-CN,3-F | 0 |
| A-1067 | H | H | H | H | H | O | H | H | 2-CN,4-F | 0 |
| A-1068 | H | H | H | H | H | O | H | H | 2-CN,5-F | 0 |
| A-1069 | H | H | H | H | H | O | H | H | 2-CN,6-F | 0 |
| A-1070 | H | H | H | H | H | O | H | H | 2-CN,3-Cl | 0 |
| A-1071 | H | H | H | H | H | O | H | H | 2-CN,4-Cl | 0 |
| A-1072 | H | H | H | H | H | O | H | H | 2-CN,5-Cl | 0 |
| A-1073 | H | H | H | H | H | O | H | H | 2-CN,6-Cl | 0 |
| A-1074 | H | H | H | H | H | O | H | H | 2-CN,3-Me | 0 |
| A-1075 | H | H | H | H | H | O | H | H | 2-CN,4-Me | 0 |
| A-1076 | H | H | H | H | H | O | H | H | 2-CN,5-Me | 0 |
| A-1077 | H | H | H | H | H | O | H | H | 2-CN,6-Me | 0 |
| A-1078 | H | H | H | H | H | O | H | H | 2-CN,3-OMe | 0 |

TABLE 20

| compound | R¹ | R² | R³ | R⁴ | R⁵ | A | R⁶ | R⁷ | (R⁸)$_m$ | p |
|---|---|---|---|---|---|---|---|---|---|---|
| A-1079 | H | H | H | H | H | O | H | H | 2-CN,4-OMe | 0 |
| A-1080 | H | H | H | H | H | O | H | H | 2-CN,5-OMe | 0 |
| A-1081 | H | H | H | H | H | O | H | H | 2-CN,6-OMe | 0 |
| A-1082 | H | H | H | H | H | O | H | H | 3-CN,2-F | 0 |
| A-1083 | H | H | H | H | H | O | H | H | 3-CN,4-F | 0 |
| A-1084 | H | H | H | H | H | O | H | H | 3-CN,5-F | 0 |
| A-1085 | H | H | H | H | H | O | H | H | 3-CN,6-F | 0 |
| A-1086 | H | H | H | H | H | O | H | H | 3-CN,2-Cl | 0 |
| A-1087 | H | H | H | H | H | O | H | H | 3-CN,4-Cl | 0 |
| A-1088 | H | H | H | H | H | O | H | H | 3-CN,5-Cl | 0 |
| A-1089 | H | H | H | H | H | O | H | H | 3-CN,6-Cl | 0 |
| A-1090 | H | H | H | H | H | O | H | H | 3-CN,2-Me | 0 |
| A-1091 | H | H | H | H | H | O | H | H | 3-CN,4-Me | 0 |
| A-1092 | H | H | H | H | H | O | H | H | 3-CN,5-Me | 0 |
| A-1093 | H | H | H | H | H | O | H | H | 3-CN,6-Me | 0 |
| A-1094 | H | H | H | H | H | O | H | H | 3-CN,2-OMe | 0 |
| A-1095 | H | H | H | H | H | O | H | H | 3-CN,4-OMe | 0 |
| A-1096 | H | H | H | H | H | O | H | H | 3-CN,5-OMe | 0 |
| A-1097 | H | H | H | H | H | O | H | H | 3-CN,6-OMe | 0 |
| A-1098 | H | H | H | H | H | O | H | H | 4-CN,2-F | 0 |
| A-1099 | H | H | H | H | H | O | H | H | 4-CN,3-F | 0 |
| A-1100 | H | H | H | H | H | O | H | H | 4-CN,2-Cl | 0 |
| A-1101 | H | H | H | H | H | O | H | H | 4-CN,3-Cl | 0 |
| A-1102 | H | H | H | H | H | O | H | H | 4-CN,2-Me | 0 |
| A-1103 | H | H | H | H | H | O | H | H | 4-CN,3-Me | 0 |
| A-1104 | H | H | H | H | H | O | H | H | 4-CN,2-OMe | 0 |
| A-1105 | H | H | H | H | H | O | H | H | 4-CN,3-OMe | 0 |
| A-1106 | H | H | H | H | H | O | H | H | 2-NO$_2$,3-F | 0 |
| A-1107 | H | H | H | H | H | O | H | H | 2-NO$_2$,4-F | 0 |
| A-1108 | H | H | H | H | H | O | H | H | 2-NO$_2$,5-F | 0 |
| A-1109 | H | H | H | H | H | O | H | H | 2-NO$_2$,6-F | 0 |
| A-1110 | H | H | H | H | H | O | H | H | 2-NO$_2$,3-Me | 0 |

TABLE 20-continued

| compound | R¹ | R² | R³ | R⁴ | R⁵ | A | R⁶ | R⁷ | (R⁸)$_m$ | p |
|---|---|---|---|---|---|---|---|---|---|---|
| A-1111 | H | H | H | H | H | O | H | H | 2-NO$_2$,4-Me | 0 |
| A-1112 | H | H | H | H | H | O | H | H | 2-NO$_2$,5-Me | 0 |
| A-1113 | H | H | H | H | H | O | H | H | 2-NO$_2$,6-Me | 0 |
| A-1114 | H | H | H | H | H | O | H | H | 2-Me,3,4-F$_2$ | 0 |
| A-1115 | H | H | H | H | H | O | H | H | 2-Me,3,5-F$_2$ | 0 |
| A-1116 | H | H | H | H | H | O | H | H | 2-Me,3,6-F$_2$ | 0 |
| A-1117 | H | H | H | H | H | O | H | H | 2-Me,4,5-F$_2$ | 0 |
| A-1118 | H | H | H | H | H | O | H | H | 2-OMe,3,4-F$_2$ | 0 |
| A-1119 | H | H | H | H | H | O | H | H | 2-OMe,3,5-F$_2$ | 0 |
| A-1120 | H | H | H | H | H | O | H | H | 2-OMe,3,6-F$_2$ | 0 |
| A-1121 | H | H | H | H | H | O | H | H | 2-OMe,4,5-F$_2$ | 0 |
| A-1122 | H | H | H | H | H | O | H | H | 2-(CH$_2$)$_3$-3 | 0 |
| A-1123 | H | H | H | H | H | O | H | H | 2-(CH$_2$)$_4$-3 | 0 |
| A-1124 | H | H | H | H | H | O | H | H | 2-(OCH$_2$CH$_2$)-3 | 0 |
| A-1125 | H | H | H | H | H | O | H | H | 2-(OCH$_2$CH$_2$)-3 | 0 |
| A-1126 | H | H | H | H | H | O | H | H | 2-(CH$_2$CH$_2$O)-3 | 0 |
| A-1127 | H | H | H | H | H | O | H | H | 2-(CH$_2$CH$_2$CH$_2$O)-3 | 0 |
| A-1128 | H | H | H | H | H | O | H | H | 3-(CH$_2$)$_3$-4 | 0 |
| A-1129 | H | H | H | H | H | O | H | H | 3-(CH$_2$)$_4$-4 | 0 |
| A-1130 | H | H | H | H | H | O | H | H | 3-(OCH$_2$CH$_2$)-4 | 0 |
| A-1131 | H | H | H | H | H | O | H | H | 3-(OCH$_2$CH$_2$CH$_2$)-4 | 0 |
| A-1132 | H | H | H | H | H | O | H | H | 3-(CH$_2$CH$_2$O)-4 | 0 |
| A-1133 | H | H | H | H | H | O | H | H | 3-(CH$_2$CH$_2$CH$_2$O)-4 | 0 |
| A-1134 | H | H | H | H | H | O | H | H | 2-(OCH$_2$O)-3 | 0 |
| A-1135 | H | H | H | H | H | O | H | H | 3-(OCH$_2$O)-4 | 0 |

TABLE 21

| compound | R¹ | R² | R³ | R⁴ | R⁵ | A | R⁶ | R⁷ | (R⁸)$_m$ | p |
|---|---|---|---|---|---|---|---|---|---|---|
| A-1136 | H | H | H | H | H | O | H | H | 2-(OCH$_2$CH$_2$O)-3 | 0 |
| A-1137 | H | H | H | H | H | O | H | H | 3-(OCH$_2$CH$_2$O)-4 | 0 |
| A-1138 | H | H | H | H | H | O | H | H | 2-(OCF$_2$O)-3 | 0 |
| A-1139 | H | H | H | H | H | O | H | H | 3-(OCF$_2$O)-4 | 0 |
| A-1140 | H | H | H | H | H | O | H | H | 2-Me,6-Et | 0 |
| A-1141 | H | H | H | H | H | O | H | H | 2-CH$_2$OTBS | 0 |
| A-1142 | H | H | H | H | H | O | H | H | 2-cyclopropyl,3-OMe | 0 |
| A-1143 | H | H | H | H | H | O | H | H | 2-cyclopropyl,4-OMe | 0 |
| A-1144 | H | H | H | H | H | O | H | H | 2-cyclopropyl,5-OMe | 0 |
| A-1145 | H | H | H | H | H | O | H | H | 2-cyclopropyl,6-OMe | 0 |
| A-1146 | H | H | H | H | H | O | H | H | 2-Me,3-OMe,6-Me | 0 |
| A-1147 | H | H | H | H | H | O | H | H | 2-Me,4-OMe,6-Me | 0 |
| A-1148 | H | H | H | H | H | O | H | H | 2-OMe,3-Me,6-Me | 0 |
| A-1149 | H | H | H | H | H | O | H | H | 2-OMe,5-Me,6-Me | 0 |
| A-1150 | H | H | H | H | H | O | H | H | 2-OMe,3-F,6-Me | 0 |
| A-1151 | H | H | H | H | H | O | H | H | 2-OMe,5-F,6-Me | 0 |
| A-1152 | H | H | H | H | H | O | H | H | 2-OMe,5-Me,6-F | 0 |
| A-1153 | H | H | H | H | H | O | H | H | 2-Cl,3-Me,6-F | 0 |
| A-1154 | H | H | H | H | H | O | H | H | 2-Cl,5-Me,6-F | 0 |
| A-1155 | H | H | H | H | H | O | H | H | 2-Cl,3-OMe,6-F | 0 |
| A-1156 | H | H | H | H | H | O | H | H | 2-Cl,5-OMe,6-F | 0 |
| A-1157 | H | H | H | H | H | O | H | H | 2-Me,5-Et | 0 |
| A-1158 | H | H | H | H | H | O | H | H | 2,6-Et$_2$ | 0 |
| A-1159 | H | H | H | H | H | O | H | H | 2-Et,6-F | 0 |
| A-1160 | H | H | H | H | H | O | H | H | 2-CH$_2$OCH$_3$,6-Cl | 0 |
| A-1161 | H | H | H | H | H | O | H | H | 2-CH$_2$OCH$_2$CH$_3$,6-Cl | 0 |
| A-1162 | H | H | H | H | H | O | H | H | 2-OMe,5-CH=NOMe | 0 |
| A-1163 | H | H | H | H | H | O | H | H | 2-CH$_2$NMe$_2$ | 0 |
| A-1164 | H | H | H | H | H | O | H | H | 2-CH$_2$OCH$_3$,6-CF$_3$ | 0 |
| A-1165 | H | H | H | H | H | O | H | H | 2-CHCl$_2$ | 0 |
| A-1166 | H | H | H | H | H | O | H | H | 2-Me | 0 |
| A-1167 | H | H | H | H | H | O | CH$_3$ | H | H | 0 |
| A-1168 | H | H | H | H | H | O | CH$_3$ | H | 2-F | 0 |
| A-1169 | H | H | H | H | H | O | CH$_3$ | H | 2-Cl | 0 |
| A-1170 | H | H | H | H | H | O | CH$_3$ | H | 2-Br | 0 |
| A-1171 | H | H | H | H | H | O | CH$_3$ | H | 2-OH | 0 |
| A-1172 | H | H | H | H | H | O | CH$_3$ | H | 2-Me | 0 |
| A-1173 | H | H | H | H | H | O | CH$_3$ | H | 2-Et | 0 |
| A-1174 | H | H | H | H | H | O | CH$_3$ | H | 2-Pr | 0 |
| A-1175 | H | H | H | H | H | O | CH$_3$ | H | 2-CF$_3$ | 0 |
| A-1176 | H | H | H | H | H | O | CH$_3$ | H | 2-CHF$_2$ | 0 |
| A-1177 | H | H | H | H | H | O | CH$_3$ | H | 2-CH$_2$F | 0 |
| A-1178 | H | H | H | H | H | O | CH$_3$ | H | 2-CF$_2$Cl | 0 |
| A-1179 | H | H | H | H | H | O | CH$_3$ | H | 2-cyclopropyl | 0 |
| A-1180 | H | H | H | H | H | O | CH$_3$ | H | 2-cyclobutyl | 0 |
| A-1181 | H | H | H | H | H | O | CH$_3$ | H | 2-cyclopentyl | 0 |
| A-1182 | H | H | H | H | H | O | CH$_3$ | H | 2-ethenyl | 0 |
| A-1183 | H | H | H | H | H | O | CH$_3$ | H | 2-allyl | 0 |
| A-1184 | H | H | H | H | H | O | CH$_3$ | H | 2-(prop-1-en-1-yl) | 0 |
| A-1185 | H | H | H | H | H | O | CH$_3$ | H | 2-(trifluoroethenyl) | 0 |
| A-1186 | H | H | H | H | H | O | CH$_3$ | H | 2-OMe | 0 |
| A-1187 | H | H | H | H | H | O | CH$_3$ | H | 2-OEt | 0 |
| A-1188 | H | H | H | H | H | O | CH$_3$ | H | 2-OPr | 0 |
| A-1189 | H | H | H | H | H | O | CH$_3$ | H | 2-O(i-Pr) | 0 |
| A-1190 | H | H | H | H | H | O | CH$_3$ | H | 2-OCF$_3$ | 0 |
| A-1191 | H | H | H | H | H | O | CH$_3$ | H | 2-OCHF$_2$ | 0 |
| A-1192 | H | H | H | H | H | O | CH$_3$ | H | 2-(cyclopropyloxy) | 0 |

TABLE 22

| compound | R¹ | R² | R³ | R⁴ | R⁵ | A | R⁶ | R⁷ | (R⁸)ₘ | p |
|---|---|---|---|---|---|---|---|---|---|---|
| A-1193 | H | H | H | H | H | O | CH₃ | H | 2-(cyclobutyloxy) | 0 |
| A-1194 | H | H | H | H | H | O | CH₃ | H | 2-(cyclopentyloxy) | 0 |
| A-1195 | H | H | H | H | H | O | CH₃ | H | 2-((2,2-dichlorocyclopropyl)oxy) | 0 |
| A-1196 | H | H | H | H | H | O | CH₃ | H | 2-(oxiran-2-yl) | 0 |
| A-1197 | H | H | H | H | H | O | CH₃ | H | 2-SMe | 0 |
| A-1198 | H | H | H | H | H | O | CH₃ | H | 3-SMe | 0 |
| A-1199 | H | H | H | H | H | O | CH₃ | H | 2-S(=O)Me | 0 |
| A-1200 | H | H | H | H | H | O | CH₃ | H | 3-S(=O)Me | 0 |
| A-1201 | H | H | H | H | H | O | CH₃ | H | 2-S(=O)₂Me | 0 |
| A-1202 | H | H | H | H | H | O | CH₃ | H | 3-S(=O)₂Me | 0 |
| A-1203 | H | H | H | H | H | O | CH₃ | H | 2-SCF₃ | 0 |
| A-1204 | H | H | H | H | H | O | CH₃ | H | 3-SCF₃ | 0 |
| A-1205 | H | H | H | H | H | O | CH₃ | H | 3-S(O)CF₃ | 0 |
| A-1206 | H | H | H | H | H | O | CH₃ | H | 3-SCF(CF₃)₂ | 0 |
| A-1207 | H | H | H | H | H | O | CH₃ | H | 2-(cyclopropylthio) | 0 |
| A-1208 | H | H | H | H | H | O | CH₃ | H | 2-(cyclopropylsulfinyl) | 0 |
| A-1209 | H | H | H | H | H | O | CH₃ | H | 2-(cyclopropylsulfonyl) | 0 |
| A-1210 | H | H | H | H | H | O | CH₃ | H | 2-C(=O)Me | 0 |
| A-1211 | H | H | H | H | H | O | CH₃ | H | 2-CH₂C(=O)CH₃ | 0 |
| A-1212 | H | H | H | H | H | O | CH₃ | H | 2-CH₂C(=O)CF₃ | 0 |
| A-1213 | H | H | H | H | H | O | CH₃ | H | 2-CH₂OH | 0 |
| A-1214 | H | H | H | H | H | O | CH₃ | H | 2-CH₂OCH₃ | 0 |
| A-1215 | H | H | H | H | H | O | CH₃ | H | 2-CH₂OCH₂CH₃ | 0 |
| A-1216 | H | H | H | H | H | O | CH₃ | H | 2-CH₂SCH₃ | 0 |
| A-1217 | H | H | H | H | H | O | CH₃ | H | 2-CH₂S(=O)CH₃ | 0 |
| A-1218 | H | H | H | H | H | O | CH₃ | H | 2-CH₂S(=O)₂CH₃ | 0 |
| A-1219 | H | H | H | H | H | O | CH₃ | H | 2-(benzyloxy) | 0 |
| A-1220 | H | H | H | H | H | O | CH₃ | H | 2-NH₂ | 0 |
| A-1221 | H | H | H | H | H | O | CH₃ | H | 2-NHMe | 0 |
| A-1222 | H | H | H | H | H | O | CH₃ | H | 2-N(Me)₂ | 0 |
| A-1223 | H | H | H | H | H | O | CH₃ | H | 2-(1,3-dioxolan-2-yl) | 0 |
| A-1224 | H | H | H | H | H | O | CH₃ | H | 2-(1,3-dioxan-2-yl) | 0 |
| A-1225 | H | H | H | H | H | O | CH₃ | H | 2-(1H-imidazol-2-yl) | 0 |
| A-1226 | H | H | H | H | H | O | CH₃ | H | 2-(thiazol-2-yl) | 0 |
| A-1227 | H | H | H | H | H | O | CH₃ | H | 2-(oxazol-2-yl) | 0 |
| A-1228 | H | H | H | H | H | O | CH₃ | H | 2-CH=NOH | 0 |
| A-1229 | H | H | H | H | H | O | CH₃ | H | 2-CH=NOMe | 0 |
| A-1230 | H | H | H | H | H | O | CH₃ | H | 2-(4,5-dihydro-3-isoxazolyl) | 0 |
| A-1231 | H | H | H | H | H | O | CH₃ | H | 2-CN | 0 |
| A-1232 | H | H | H | H | H | O | CH₃ | H | 2-NO2 | 0 |
| A-1233 | H | H | H | H | H | O | CH₃ | H | 2-F,6-Cl | 0 |
| A-1234 | H | H | H | H | H | O | CH₃ | H | 2-F,6-Me | 0 |
| A-1235 | H | H | H | H | H | O | CH₃ | H | 3-F,6-Me | 0 |
| A-1236 | H | H | H | H | H | O | CH₃ | H | 4-F,2-Me | 0 |
| A-1237 | H | H | H | H | H | O | CH₃ | H | 2-F,6-OMe | 0 |
| A-1238 | H | H | H | H | H | O | CH₃ | H | 3-F,6-OMe | 0 |
| A-1239 | H | H | H | H | H | O | CH₃ | H | 2,6-Cl₂ | 0 |
| A-1240 | H | H | H | H | H | O | CH₃ | H | 2-Cl,6-Me | 0 |
| A-1241 | H | H | H | H | H | O | CH₃ | H | 3-Cl,6-Me | 0 |
| A-1242 | H | H | H | H | H | O | CH₃ | H | 4-Cl,2-Me | 0 |
| A-1243 | H | H | H | H | H | O | CH₃ | H | 2-Cl,5-CF₃ | 0 |
| A-1244 | H | H | H | H | H | O | CH₃ | H | 2-Cl,6-CF₃ | 0 |
| A-1245 | H | H | H | H | H | O | CH₃ | H | 2-Cl,6-OMe | 0 |
| A-1246 | H | H | H | H | H | O | CH₃ | H | 3-Cl,6-OMe | 0 |
| A-1247 | H | H | H | H | H | O | CH₃ | H | 4-Cl,2-OMe | 0 |
| A-1248 | H | H | H | H | H | O | CH₃ | H | 2,4-Me₂ | 0 |
| A-1249 | H | H | H | H | H | O | CH₃ | H | 2,5-Me₂ | 0 |

TABLE 23

| compound | R¹ | R² | R³ | R⁴ | R⁵ | A | R⁶ | R⁷ | (R⁸)ₘ | p |
|---|---|---|---|---|---|---|---|---|---|---|
| A-1250 | H | H | H | H | H | O | CH₃ | H | 2,6-Me2 | 0 |
| A-1251 | H | H | H | H | H | O | CH₃ | H | 2-Me,4-CF₃ | 0 |
| A-1252 | H | H | H | H | H | O | CH₃ | H | 2-Me,5-CF₃ | 0 |
| A-1253 | H | H | H | H | H | O | CH₃ | H | 2-Me,6-CF₃ | 0 |
| A-1254 | H | H | H | H | H | O | CH₃ | H | 2-Me,4-OMe | 0 |
| A-1255 | H | H | H | H | H | O | CH₃ | H | 2-Me,5-OMe | 0 |
| A-1256 | H | H | H | H | H | O | CH₃ | H | 2-Me,6-OMe | 0 |
| A-1257 | H | H | H | H | H | O | CH₃ | H | 3-Me,6-OMe | 0 |
| A-1258 | H | H | H | H | H | O | CH₃ | H | 4-Me,2-OMe | 0 |
| A-1259 | H | H | H | H | H | O | CH₃ | H | 2,5-OMe₂ | 0 |
| A-1260 | H | H | H | H | H | O | CH₃ | H | 2,6-OMe₂ | 0 |
| A-1261 | H | H | H | H | H | O | CH₃ | H | 2-OMe,6-CF₃ | 0 |
| A-1262 | H | H | H | H | H | O | CH₃ | H | 2-CHF₂,5-F | 0 |

TABLE 23-continued

| compound | R¹ | R² | R³ | R⁴ | R⁵ | A | R⁶ | R⁷ | (R⁸)$_m$ | p |
|---|---|---|---|---|---|---|---|---|---|---|
| A-1263 | H | H | H | H | H | O | CH₃ | H | 2-CHF₂,6-F | 0 |
| A-1264 | H | H | H | H | H | O | CH₃ | H | 2-CHF₂,5-Me | 0 |
| A-1265 | H | H | H | H | H | O | CH₃ | H | 2-CHF₂,6-Me | 0 |
| A-1266 | H | H | H | H | H | O | CH₃ | H | 2-cyclopropyl,5-F | 0 |
| A-1267 | H | H | H | H | H | O | CH₃ | H | 2-cyclopropyl,6-F | 0 |
| A-1268 | H | H | H | H | H | O | CH₃ | H | 2-cyclopropyl,5-Me | 0 |
| A-1269 | H | H | H | H | H | O | CH₃ | H | 2-cyclopropyl,6-Me | 0 |
| A-1270 | H | H | H | H | H | O | CH₃ | H | 2-ethenyl,6-F | 0 |
| A-1271 | H | H | H | H | H | O | CH₃ | H | 2-ethenyl,6-Me | 0 |
| A-1272 | H | H | H | H | H | O | CH₃ | H | 2-OEt,5-F | 0 |
| A-1273 | H | H | H | H | H | O | CH₃ | H | 2-OEt,6-F | 0 |
| A-1274 | H | H | H | H | H | O | CH₃ | H | 2-OEt,5-Cl | 0 |
| A-1275 | H | H | H | H | H | O | CH₃ | H | 2-OEt,6-Cl | 0 |
| A-1276 | H | H | H | H | H | O | CH₃ | H | 2-OEt,5-Me | 0 |
| A-1277 | H | H | H | H | H | O | CH₃ | H | 2-OEt,6-Me | 0 |
| A-1278 | H | H | H | H | H | O | CH₃ | H | 2-OCHF₂,5-F | 0 |
| A-1279 | H | H | H | H | H | O | CH₃ | H | 2-OCHF₂,6-F | 0 |
| A-1280 | H | H | H | H | H | O | CH₃ | H | 2-OCHF₂,5-Me | 0 |
| A-1281 | H | H | H | H | H | O | CH₃ | H | 2-OCHF₂,6-Me | 0 |
| A-1282 | H | H | H | H | H | O | CH₃ | H | 2-(cyclopyloxy),5-F | 0 |
| A-1283 | H | H | H | H | H | O | CH₃ | H | 2-(cyclopyloxy),6-F | 0 |
| A-1284 | H | H | H | H | H | O | CH₃ | H | 2-(cyclopyloxy),5-Me | 0 |
| A-1285 | H | H | H | H | H | O | CH₃ | H | 2-(cyclopyloxy),6-Me | 0 |
| A-1286 | H | H | H | H | H | O | CH₃ | H | 2-SMe,5-F | 0 |
| A-1287 | H | H | H | H | H | O | CH₃ | H | 2-SMe,6-F | 0 |
| A-1288 | H | H | H | H | H | O | CH₃ | H | 2-SMe,5-Me | 0 |
| A-1289 | H | H | H | H | H | O | CH₃ | H | 2-SMe,6-Me | 0 |
| A-1290 | H | H | H | H | H | O | CH₃ | H | 2-S(=O)Me,5-F | 0 |
| A-1291 | H | H | H | H | H | O | CH₃ | H | 2-S(=O)Me,6-F | 0 |
| A-1292 | H | H | H | H | H | O | CH₃ | H | 2-S(=O)Me,5-Me | 0 |
| A-1293 | H | H | H | H | H | O | CH₃ | H | 2-S(=O)Me,6-Me | 0 |
| A-1294 | H | H | H | H | H | O | CH₃ | H | 2-S(=O)₂Me,5-F | 0 |
| A-1295 | H | H | H | H | H | O | CH₃ | H | 2-S(=O)₂Me,6-F | 0 |
| A-1296 | H | H | H | H | H | O | CH₃ | H | 2-S(=O)₂Me,5-Me | 0 |
| A-1297 | H | H | H | H | H | O | CH₃ | H | 2-S(=O)₂Me,6-Me | 0 |
| A-1298 | H | H | H | H | H | O | CH₃ | H | 2-SCF₃,5-F | 0 |
| A-1299 | H | H | H | H | H | O | CH₃ | H | 2-SCF₃,6-F | 0 |
| A-1300 | H | H | H | H | H | O | CH₃ | H | 2-SCF₃,5-Me | 0 |
| A-1301 | H | H | H | H | H | O | CH₃ | H | 2-SCF₃,6-Me | 0 |
| A-1302 | H | H | H | H | H | O | CH₃ | H | 2-S(=O)CF₃,5-F | 0 |
| A-1303 | H | H | H | H | H | O | CH₃ | H | 2-S(=O)CF₃,6-F | 0 |
| A-1304 | H | H | H | H | H | O | CH₃ | H | 2-S(=O)CF₃,5-Me | 0 |
| A-1305 | H | H | H | H | H | O | CH₃ | H | 2-S(=O)CF₃,6-Me | 0 |
| A-1306 | H | H | H | H | H | O | CH₃ | H | 2-S(=O)₂CF₃,5-F | 0 |

TABLE 24

| compound | R¹ | R² | R³ | R⁴ | R⁵ | A | R⁶ | R⁷ | (R⁸)$_m$ | p |
|---|---|---|---|---|---|---|---|---|---|---|
| A-1307 | H | H | H | H | H | O | CH₃ | H | 2-S(=O)₂CF₃,6-F | 0 |
| A-1308 | H | H | H | H | H | O | CH₃ | H | 2-S(=O)₂CF₃,5-Me | 0 |
| A-1309 | H | H | H | H | H | O | CH₃ | H | 2-S(=O)₂CF₃,6-Me | 0 |
| A-1310 | H | H | H | H | H | O | CH₃ | H | 2-(cyclopropylthio),5-F | 0 |
| A-1311 | H | H | H | H | H | O | CH₃ | H | 2-(cyclopropylthio),6-F | 0 |
| A-1312 | H | H | H | H | H | O | CH₃ | H | 2-(cyclopropylthio),5-Me | 0 |
| A-1313 | H | H | H | H | H | O | CH₃ | H | 2-(cyclopropylthio),6-Me | 0 |
| A-1314 | H | H | H | H | H | O | CH₃ | H | 2-C(=O)Me,5-F | 0 |
| A-1315 | H | H | H | H | H | O | CH₃ | H | 2-C(=O)Me,6-F | 0 |
| A-1316 | H | H | H | H | H | O | CH₃ | H | 2-C(=O)Me,5-Me | 0 |
| A-1317 | H | H | H | H | H | O | CH₃ | H | 2-C(=O)Me,6-Me | 0 |
| A-1318 | H | H | H | H | H | O | CH₃ | H | 2-CH₂OH,5-F | 0 |
| A-1319 | H | H | H | H | H | O | CH₃ | H | 2-CH₂OH,6-F | 0 |
| A-1320 | H | H | H | H | H | O | CH₃ | H | 2-CH₂OH,5-Me | 0 |
| A-1321 | H | H | H | H | H | O | CH₃ | H | 2-CH₂OH,6-Me | 0 |
| A-1322 | H | H | H | H | H | O | CH₃ | H | 2-CH₂OCH₃,4-F | 0 |
| A-1323 | H | H | H | H | H | O | CH₃ | H | 2-CH₂OCH₃,5-F | 0 |
| A-1324 | H | H | H | H | H | O | CH₃ | H | 2-CH₂OCH₃,6-F | 0 |
| A-1325 | H | H | H | H | H | O | CH₃ | H | 2-CH₂OCH₃,4-Me | 0 |
| A-1326 | H | H | H | H | H | O | CH₃ | H | 2-CH₂OCH₃,5-Me | 0 |
| A-1327 | H | H | H | H | H | O | CH₃ | H | 2-CH₂OCH₃,6-Me | 0 |
| A-1328 | H | H | H | H | H | O | CH₃ | H | 2-OC(=O)CH₃,5-F | 0 |
| A-1329 | H | H | H | H | H | O | CH₃ | H | 2-OC(=O)CH₃,6-F | 0 |
| A-1330 | H | H | H | H | H | O | CH₃ | H | 2-OC(=O)CH₃,5-Me | 0 |
| A-1331 | H | H | H | H | H | O | CH₃ | H | 2-OC(=O)CH₃,6-Me | 0 |
| A-1332 | H | H | H | H | H | O | CH₃ | H | 2-OS(=O)₂CH₃,5-F | 0 |

TABLE 24-continued

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-1333 | H | H | H | H | H | O | $CH_3$ | H | 2-OS(=O)$_2$CH$_3$,6-F | 0 |
| A-1334 | H | H | H | H | H | O | $CH_3$ | H | 2-OS(=O)$_2$CH$_3$,5-Me | 0 |
| A-1335 | H | H | H | H | H | O | $CH_3$ | H | 2-OS(=O)$_2$CH$_3$,6-Me | 0 |
| A-1336 | H | H | H | H | H | O | $CH_3$ | H | 2-CH$_2$SCH$_3$,5-F | 0 |
| A-1337 | H | H | H | H | H | O | $CH_3$ | H | 2-CH$_2$SCH$_3$,6-F | 0 |
| A-1338 | H | H | H | H | H | O | $CH_3$ | H | 2-CH$_2$SCH$_3$,5-Me | 0 |
| A-1339 | H | H | H | H | H | O | $CH_3$ | H | 2-CH$_2$SCH3,6-Me | 0 |
| A-1340 | H | H | H | H | H | O | $CH_3$ | H | 2-NMe$_2$,5-F | 0 |
| A-1341 | H | H | H | H | H | O | $CH_3$ | H | 2-NMe$_2$,6-F | 0 |
| A-1342 | H | H | H | H | H | O | $CH_3$ | H | 2-NMe$_2$,5-Me | 0 |
| A-1343 | H | H | H | H | H | O | $CH_3$ | H | 2-NMe$_2$,6-Me | 0 |
| A-1344 | H | H | H | H | H | O | $CH_3$ | H | 2-CN,4-F | 0 |
| A-1345 | H | H | H | H | H | O | $CH_3$ | H | 2-CN,5-F | 0 |
| A-1346 | H | H | H | H | H | O | $CH_3$ | H | 2-CN,6-F | 0 |
| A-1347 | H | H | H | H | H | O | $CH_3$ | H | 2-CN,6-Me | 0 |
| A-1348 | H | H | H | H | H | O | $CH_3$ | H | 2-CN,5-OMe | 0 |
| A-1349 | H | H | H | H | H | O | $CH_3$ | H | 2-CN,6-OMe | 0 |
| A-1350 | H | H | H | H | H | O | $CH_3$ | H | 3-CN,6-Me | 0 |
| A-1351 | H | H | H | H | H | O | $CH_3$ | H | 3-CN,6-OMe | 0 |
| A-1352 | H | H | H | H | H | O | $CH_3$ | H | 4-CN,2-Me | 0 |
| A-1353 | H | H | H | H | H | O | $CH_3$ | H | 4-CN,2-OMe | 0 |
| A-1354 | H | H | H | H | H | O | $CH_3$ | H | 2-NO$_2$,4-F | 0 |
| A-1355 | H | H | H | H | H | O | $CH_3$ | H | 2-NO$_2$,5-F | 0 |
| A-1356 | H | H | H | H | H | O | $CH_3$ | H | 2-NO$_2$,6-F | 0 |
| A-1357 | H | H | H | H | H | O | $CH_3$ | H | 2-NO$_2$,4-Me | 0 |
| A-1358 | H | H | H | H | H | O | $CH_3$ | H | 2-NO$_2$,5-Me | 0 |
| A-1359 | H | H | H | H | H | O | $CH_3$ | H | 2-NO$_2$,6-Me | 0 |
| A-1360 | H | H | H | H | H | O | $CH_3$ | H | 2-Me,4,5-F$_2$ | 0 |
| A-1361 | H | H | H | H | H | O | $CH_3$ | H | 2-Me,6-Et | 0 |
| A-1362 | H | H | H | H | H | O | $CH_3$ | H | 2-cyclopropyl,6-OMe | 0 |
| A-1363 | H | H | H | H | H | O | $CH_3$ | H | 2-Me,5-Et | 0 |

TABLE 25

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-1364 | H | H | H | H | H | O | $CH_3$ | H | 2,6-Et2 | 0 |
| A-1365 | H | H | H | H | H | O | $CH_3$ | H | 2-Et,6-F | 0 |
| A-1366 | H | H | H | H | H | O | $CH_3$ | H | 2-CH$_2$OCH$_3$,6-Cl | 0 |
| A-1367 | H | H | H | H | H | O | $CH_3$ | H | 2-CH$_2$OCH$_2$CH$_3$,6+-Cl | 0 |
| A-1368 | H | H | H | H | H | O | $CH_3$ | H | 2-CH$_2$NMe$_2$ | 0 |
| A-1369 | H | H | H | H | H | O | $CH_2CH_3$ | H | H | 0 |
| A-1370 | H | H | H | H | H | O | $CH_2CH_3$ | H | 2-F | 0 |
| A-1371 | H | H | H | H | H | O | $CH_2CH_3$ | H | 2-Cl | 0 |
| A-1372 | H | H | H | H | H | O | $CH_2CH_3$ | H | 2-Br | 0 |
| A-1373 | H | H | H | H | H | O | $CH_2CH_3$ | H | 2-OH | 0 |
| A-1374 | H | H | H | H | H | O | $CH_2CH_3$ | H | 2-Me | 0 |
| A-1375 | H | H | H | H | H | O | $CH_2CH_3$ | H | 2-Et | 0 |
| A-1376 | H | H | H | H | H | O | $CH_2CH_3$ | H | 2-Pr | 0 |
| A-1377 | H | H | H | H | H | O | $CH_2CH_3$ | H | 2-CF$_3$ | 0 |
| A-1378 | H | H | H | H | H | O | $CH_2CH_3$ | H | 2-CHF$_2$ | 0 |
| A-1379 | H | H | H | H | H | O | $CH_2CH_3$ | H | 2-CH$_2$F | 0 |
| A-1380 | H | H | H | H | H | O | $CH_2CH_3$ | H | 2-CF$_2$Cl | 0 |
| A-1381 | H | H | H | H | H | O | $CH_2CH_3$ | H | 2-cyclopropyl | 0 |
| A-1382 | H | H | H | H | H | O | $CH_2CH_3$ | H | 2-cyclobutyl | 0 |
| A-1383 | H | H | H | H | H | O | $CH_2CH_3$ | H | 2-cyclopentyl | 0 |
| A-1384 | H | H | H | H | H | O | $CH_2CH_3$ | H | 2-ethenyl | 0 |
| A-1385 | H | H | H | H | H | O | $CH_2CH_3$ | H | 2-allyl | 0 |
| A-1386 | H | H | H | H | H | O | $CH_2CH_3$ | H | 2-(prop-1-en-1-y) | 0 |
| A-1387 | H | H | H | H | H | O | $CH_2CH_3$ | H | 2-(trifluoroethenyl) | 0 |
| A-1388 | H | H | H | H | H | O | $CH_2CH_3$ | H | 2-OMe | 0 |
| A-1389 | H | H | H | H | H | O | $CH_2CH_3$ | H | 2-OEt | 0 |
| A-1390 | H | H | H | H | H | O | $CH_2CH_3$ | H | 2-OPr | 0 |
| A-1391 | H | H | H | H | H | O | $CH_2CH_3$ | H | 2-O(i-Pr) | 0 |
| A-1392 | H | H | H | H | H | O | $CH_2CH_3$ | H | 2-OCF$_3$ | 0 |
| A-1393 | H | H | H | H | H | O | $CH_2CH_3$ | H | 2-OCHF$_2$ | 0 |
| A-1394 | H | H | H | H | H | O | $CH_2CH_3$ | H | 2-(cyclopropyloxy) | 0 |
| A-1395 | H | H | H | H | H | O | $CH_2CH_3$ | H | 2-(cyclobutyloxy) | 0 |
| A-1396 | H | H | H | H | H | O | $CH_2CH_3$ | H | 2-(cyclopentyloxy) | 0 |
| A-1397 | H | H | H | H | H | O | $CH_2CH_3$ | H | 2-((2,2-dichl;orocyclopropyl)oxy) | 0 |
| A-1398 | H | H | H | H | H | O | $CH_2CH_3$ | H | 2-(oxiran-2-yl) | 0 |
| A-1399 | H | H | H | H | H | O | $CH_2CH_3$ | H | 2-SMe | 0 |
| A-1400 | H | H | H | H | H | O | $CH_2CH_3$ | H | 3-SMe | 0 |
| A-1401 | H | H | H | H | H | O | $CH_2CH_3$ | H | 2-S(=O)Me | 0 |
| A-1402 | H | H | H | H | H | O | $CH_2CH_3$ | H | 3-S(=O)Me | 0 |

TABLE 25-continued

| compound | R¹ | R² | R³ | R⁴ | R⁵ | A | R⁶ | R⁷ | (R⁸)ₘ | p |
|---|---|---|---|---|---|---|---|---|---|---|
| A-1403 | H | H | H | H | H | O | CH₂CH₃ | H | 2-S(=O)₂Me | 0 |
| A-1404 | H | H | H | H | H | O | CH₂CH₃ | H | 3-S(=O)₂Me | 0 |
| A-1405 | H | H | H | H | H | O | CH₂CH₃ | H | 2-SCF₃ | 0 |
| A-1406 | H | H | H | H | H | O | CH₂CH₃ | H | 3-SCF₃ | 0 |
| A-1407 | H | H | H | H | H | O | CH₂CH₃ | H | 3-S(=O)CF₃ | 0 |
| A-1408 | H | H | H | H | H | O | CH₂CH₃ | H | 3-SCF(CF₃)₂ | 0 |
| A-1409 | H | H | H | H | H | O | CH₂CH₃ | H | 2-(cyclopropylthio) | 0 |
| A-1410 | H | H | H | H | H | O | CH₂CH₃ | H | 2-(cyclopropylsulfinyl) | 0 |
| A-1411 | H | H | H | H | H | O | CH₂CH₃ | H | 2-(cyclopropylsulfonyl) | 0 |
| A-1412 | H | H | H | H | H | O | CH₂CH₃ | H | 2-C(=O)Me | 0 |
| A-1413 | H | H | H | H | H | O | CH₂CH₃ | H | 2-CH₂C(=O)CH₃ | 0 |
| A-1414 | H | H | H | H | H | O | CH₂CH₃ | H | 2-CH₂C(=O)CF₃ | 0 |
| A-1415 | H | H | H | H | H | O | CH₂CH₃ | H | 2-CH₂OH | 0 |
| A-1416 | H | H | H | H | H | O | CH₂CH₃ | H | 2-CH₂OCH₃ | 0 |
| A-1417 | H | H | H | H | H | O | CH₂CH₃ | H | 2-CH₂OCH₂CH₃ | 0 |
| A-1418 | H | H | H | H | H | O | CH₂CH₃ | H | 2-CH₂SCH₃ | 0 |
| A-1419 | H | H | H | H | H | O | CH₂CH₃ | H | 2-CH₂S(=O)CH₃ | 0 |
| A-1420 | H | H | H | H | H | O | CH₂CH₃ | H | 2-CH₂S(=O)₂CH₃ | 0 |

TABLE 26

| compound | R¹ | R² | R³ | R⁴ | R⁵ | A | R⁶ | R⁷ | (R⁸)ₘ | p |
|---|---|---|---|---|---|---|---|---|---|---|
| A-1421 | H | H | H | H | H | O | CH₂CH₃ | H | 2-(benzyloxy) | 0 |
| A-1422 | H | H | H | H | H | O | CH₂CH₃ | H | 2-NH₂ | 0 |
| A-1423 | H | H | H | H | H | O | CH₂CH₃ | H | 2-NHMe | 0 |
| A-1424 | H | H | H | H | H | O | CH₂CH₃ | H | 2-N(Me)₂ | 0 |
| A-1425 | H | H | H | H | H | O | CH₂CH₃ | H | 2-(1,3-dioxolan-2-yl) | 0 |
| A-1426 | H | H | H | H | H | O | CH₂CH₃ | H | 2-(1,3-dioxan-2-yl) | 0 |
| A-1427 | H | H | H | H | H | O | CH₂CH₃ | H | 2-(1H-imidazol-2-yl) | 0 |
| A-1428 | H | H | H | H | H | O | CH₂CH₃ | H | 2-(thiazol-2-yl) | 0 |
| A-1429 | H | H | H | H | H | O | CH₂CH₃ | H | 2-(oxazol-2-y) | 0 |
| A-1430 | H | H | H | H | H | O | CH₂CH₃ | H | 2-CH=NOH | 0 |
| A-1431 | H | H | H | H | H | O | CH₂CH₃ | H | 2-CH=NOMe | 0 |
| A-1432 | H | H | H | H | H | O | CH₂CH₃ | H | 2-(4,5-dihydro-3-isoxazolyl) | 0 |
| A-1433 | H | H | H | H | H | O | CH₂CH₃ | H | 2-CN | 0 |
| A-1434 | H | H | H | H | H | O | CH₂CH₃ | H | 2-NO₂ | 0 |
| A-1435 | H | H | H | H | H | O | CH₂CH₃ | H | 2-F,6-Cl | 0 |
| A-1436 | H | H | H | H | H | O | CH₂CH₃ | H | 2-F,6-Me | 0 |
| A-1437 | H | H | H | H | H | O | CH₂CH₃ | H | 3-F,6-Me | 0 |
| A-1438 | H | H | H | H | H | O | CH₂CH₃ | H | 4-F,2-Me | 0 |
| A-1439 | H | H | H | H | H | O | CH₂CH₃ | H | 2-F,6-OMe | 0 |
| A-1440 | H | H | H | H | H | O | CH₂CH₃ | H | 3-F,6-OMe | 0 |
| A-1441 | H | H | H | H | H | O | CH₂CH₃ | H | 2,6-Cl₂ | 0 |
| A-1442 | H | H | H | H | H | O | CH₂CH₃ | H | 2-Cl,6-Me | 0 |
| A-1443 | H | H | H | H | H | O | CH₂CH₃ | H | 3-Cl,6-Me | 0 |
| A-1444 | H | H | H | H | H | O | CH₂CH₃ | H | 4-Cl,2-Me | 0 |
| A-1445 | H | H | H | H | H | O | CH₂CH₃ | H | 2-Cl,5-CF₃ | 0 |
| A-1446 | H | H | H | H | H | O | CH₂CH₃ | H | 2-Cl,6-CF₃ | 0 |
| A-1447 | H | H | H | H | H | O | CH₂CH₃ | H | 2-Cl,6-OMe | 0 |
| A-1448 | H | H | H | H | H | O | CH₂CH₃ | H | 3-Cl,6-OMe | 0 |
| A-1449 | H | H | H | H | H | O | CH₂CH₃ | H | 4-Cl,2-OMe | 0 |
| A-1450 | H | H | H | H | H | O | CH₂CH₃ | H | 2,4-Me₂ | 0 |
| A-1451 | H | H | H | H | H | O | CH₂CH₃ | H | 2,5-Me₂ | 0 |
| A-1452 | H | H | H | H | H | O | CH₂CH₃ | H | 2,6-Me₂ | 0 |
| A-1453 | H | H | H | H | H | O | CH₂CH₃ | H | 2-Me,4-CF₃ | 0 |
| A-1454 | H | H | H | H | H | O | CH₂CH₃ | H | 2-Me,5-CF₃ | 0 |
| A-1455 | H | H | H | H | H | O | CH₂CH₃ | H | 2-Me,6-CF₃ | 0 |
| A-1456 | H | H | H | H | H | O | CH₂CH₃ | H | 2-Me,4-OMe | 0 |
| A-1457 | H | H | H | H | H | O | CH₂CH₃ | H | 2-Me,5-OMe | 0 |
| A-1458 | H | H | H | H | H | O | CH₂CH₃ | H | 2-Me,6-OMe | 0 |
| A-1459 | H | H | H | H | H | O | CH₂CH₃ | H | 3-Me,6-OMe | 0 |
| A-1460 | H | H | H | H | H | O | CH₂CH₃ | H | 4-Me,2-OMe | 0 |
| A-1461 | H | H | H | H | H | O | CH₂CH₃ | H | 2,5-OMe₂ | 0 |
| A-1462 | H | H | H | H | H | O | CH₂CH₃ | H | 2,6-OMe₂ | 0 |
| A-1463 | H | H | H | H | H | O | CH₂CH₃ | H | 2-OMe,6-CF₃ | 0 |
| A-1464 | H | H | H | H | H | O | CH₂CH₃ | H | 2-CHF₂,5-F | 0 |
| A-1465 | H | H | H | H | H | O | CH₂CH₃ | H | 2-CHF₂,6-F | 0 |
| A-1466 | H | H | H | H | H | O | CH₂CH₃ | H | 2-CHF₂,5-Me | 0 |
| A-1467 | H | H | H | H | H | O | CH₂CH₃ | H | 2-CHF₂,6-Me | 0 |
| A-1468 | H | H | H | H | H | O | CH₂CH₃ | H | 2-cyclopropyl,5-F | 0 |
| A-1469 | H | H | H | H | H | O | CH₂CH₃ | H | 2-cyclopropyl,6-F | 0 |
| A-1470 | H | H | H | H | H | O | CH₂CH₃ | H | 2-cyclopropyl,5-Me | 0 |
| A-1471 | H | H | H | H | H | O | CH₂CH₃ | H | 2-cyclopropyl,6-Me | 0 |
| A-1472 | H | H | H | H | H | O | CH₂CH₃ | H | 2-ethenyl,6-F | 0 |

TABLE 26-continued

| compound | R¹ | R² | R³ | R⁴ | R⁵ | A | R⁶ | R⁷ | (R⁸)ₘ | p |
|---|---|---|---|---|---|---|---|---|---|---|
| A-1473 | H | H | H | H | H | O | CH₂CH₃ | H | 2-ethenyl,6-Me | 0 |
| A-1474 | H | H | H | H | H | O | CH₂CH₃ | H | 2-OEt,5-F | 0 |
| A-1475 | H | H | H | H | H | O | CH₂CH₃ | H | 2-OEt,6-F | 0 |
| A-1476 | H | H | H | H | H | O | CH₂CH₃ | H | 2-OEt,5-Cl | 0 |
| A-1477 | H | H | H | H | H | O | CH₂CH₃ | H | 2-OEt,6-Cl | 0 |

TABLE 27

| compound | R¹ | R² | R³ | R⁴ | R⁵ | A | R⁶ | R⁷ | (R⁸)ₘ | p |
|---|---|---|---|---|---|---|---|---|---|---|
| A-1478 | H | H | H | H | H | O | CH₂CH₃ | H | 2-OEt,5-Me | 0 |
| A-1479 | H | H | H | H | H | O | CH₂CH₃ | H | 2-OEt,6-Me | 0 |
| A-1480 | H | H | H | H | H | O | CH₂CH₃ | H | 2-OCHF₂,5-F | 0 |
| A-1481 | H | H | H | H | H | O | CH₂CH₃ | H | 2-OCHF₂,6-F | 0 |
| A-1482 | H | H | H | H | H | O | CH₂CH₃ | H | 2-OCHF₂,5-Me | 0 |
| A-1483 | H | H | H | H | H | O | CH₂CH₃ | H | 2-OCHF₂,6-Me | 0 |
| A-1484 | H | H | H | H | H | O | CH₂CH₃ | H | 2-(cyclopropyloxy),5-F | 0 |
| A-1485 | H | H | H | H | H | O | CH₂CH₃ | H | 2-(cyclopropyloxy),6-F | 0 |
| A-1486 | H | H | H | H | H | O | CH₂CH₃ | H | 2-(cyclopropyloxy),5-Me | 0 |
| A-1487 | H | H | H | H | H | O | CH₂CH₃ | H | 2-(cyclopropyloxy),6-Me | 0 |
| A-1488 | H | H | H | H | H | O | CH₂CH₃ | H | 2-SMe,5-F | 0 |
| A-1489 | H | H | H | H | H | O | CH₂CH₃ | H | 2-SMe,6-F | 0 |
| A-1490 | H | H | H | H | H | O | CH₂CH₃ | H | 2-SMe,5-Me | 0 |
| A-1491 | H | H | H | H | H | O | CH₂CH₃ | H | 2-SMe,6-Me | 0 |
| A-1492 | H | H | H | H | H | O | CH₂CH₃ | H | 2-S(=O)Me,5-F | 0 |
| A-1493 | H | H | H | H | H | O | CH₂CH₃ | H | 2-S(=O)Me,6-F | 0 |
| A-1494 | H | H | H | H | H | O | CH₂CH₃ | H | 2-S(=O)Me,5-Me | 0 |
| A-1495 | H | H | H | H | H | O | CH₂CH₃ | H | 2-S(=O)Me,6-Me | 0 |
| A-1496 | H | H | H | H | H | O | CH₂CH₃ | H | 2-S(=O)₂Me,5-F | 0 |
| A-1497 | H | H | H | H | H | O | CH₂CH₃ | H | 2-S(=O)₂Me,6-F | 0 |
| A-1498 | H | H | H | H | H | O | CH₂CH₃ | H | 2-S(=O)₂Me,5-Me | 0 |
| A-1499 | H | H | H | H | H | O | CH₂CH₃ | H | 2-S(=O)₂Me,6-Me | 0 |
| A-1500 | H | H | H | H | H | O | CH₂CH₃ | H | 2-SCF₃,5-F | 0 |
| A-1501 | H | H | H | H | H | O | CH₂CH₃ | H | 2-SCF₃,6-F | 0 |
| A-1502 | H | H | H | H | H | O | CH₂CH₃ | H | 2-SCF₃,5-Me | 0 |
| A-1503 | H | H | H | H | H | O | CH₂CH₃ | H | 2-SCF₃,6-Me | 0 |
| A-1504 | H | H | H | H | H | O | CH₂CH₃ | H | 2-S(=O)CF₃,5-F | 0 |
| A-1505 | H | H | H | H | H | O | CH₂CH₃ | H | 2-S(=O)CF₃,6-F | 0 |
| A-1506 | H | H | H | H | H | O | CH₂CH₃ | H | 2-S(=O)CF₃,5-Me | 0 |
| A-1507 | H | H | H | H | H | O | CH₂CH₃ | H | 2-S(=O)CF₃,6-Me | 0 |
| A-1508 | H | H | H | H | H | O | CH₂CH₃ | H | 2-S(=O)₂CF₃,5-F | 0 |
| A-1509 | H | H | H | H | H | O | CH₂CH₃ | H | 2-S(=O)₂CF₃,6-F | 0 |
| A-1510 | H | H | H | H | H | O | CH₂CH₃ | H | 2-S(=O)₂CF₃,5-Me | 0 |
| A-1511 | H | H | H | H | H | O | CH₂CH₃ | H | 2-S(=O)₂CF₃,6-Me | 0 |
| A-1512 | H | H | H | H | H | O | CH₂CH₃ | H | 2-(cyclopropylthio),5-F | 0 |
| A-1513 | H | H | H | H | H | O | CH₂CH₃ | H | 2-(cyclopropylthio),6-F | 0 |
| A-1514 | H | H | H | H | H | O | CH₂CH₃ | H | 2-(cyclopropylthio),5-Me | 0 |
| A-1515 | H | H | H | H | H | O | CH₂CH₃ | H | 2-(cyclopropylthio),6-Me | 0 |
| A-1516 | H | H | H | H | H | O | CH₂CH₃ | H | 2-C(=O)Me,5-F | 0 |
| A-1517 | H | H | H | H | H | O | CH₂CH₃ | H | 2-C(=O)Me,6-F | 0 |
| A-1518 | H | H | H | H | H | O | CH₂CH₃ | H | 2-C(=O)Me,5-Me | 0 |
| A-1519 | H | H | H | H | H | O | CH₂CH₃ | H | 2-C(=O)Me,6-Me | 0 |
| A-1520 | H | H | H | H | H | O | CH₂CH₃ | H | 2-CH₂OH,5-F | 0 |
| A-1521 | H | H | H | H | H | O | CH₂CH₃ | H | 2-CH₂OH,6-F | 0 |
| A-1522 | H | H | H | H | H | O | CH₂CH₃ | H | 2-CH₂OH,5-Me | 0 |
| A-1523 | H | H | H | H | H | O | CH₂CH₃ | H | 2-CH₂OH,6-Me | 0 |
| A-1524 | H | H | H | H | H | O | CH₂CH₃ | H | 2-CH₂OCH₃,4-F | 0 |
| A-1525 | H | H | H | H | H | O | CH₂CH₃ | H | 2-CH₂OCH₃,5-F | 0 |
| A-1526 | H | H | H | H | H | O | CH₂CH₃ | H | 2-CH₂OCH₃,6-F | 0 |
| A-1527 | H | H | H | H | H | O | CH₂CH₃ | H | 2-CH₂OCH₃,4-Me | 0 |
| A-1528 | H | H | H | H | H | O | CH₂CH₃ | H | 2-CH₂OCH₃,5-Me | 0 |
| A-1529 | H | H | H | H | H | O | CH₂CH₃ | H | 2-CH₂OCH₃,6-Me | 0 |
| A-1530 | H | H | H | H | H | O | CH₂CH₃ | H | 2-OC(=O)CH₃,5-F | 0 |
| A-1531 | H | H | H | H | H | O | CH₂CH₃ | H | 2-OC(=O)CH₃,6-F | 0 |
| A-1532 | H | H | H | H | H | O | CH₂CH₃ | H | 2-OC(=O)CH₃,5-Me | 0 |
| A-1533 | H | H | H | H | H | O | CH₂CH₃ | H | 2-OC(=O)CH₃,6-Me | 0 |
| A-1534 | H | H | H | H | H | O | CH₂CH₃ | H | 2-OS(=O)₂CH₃,5-F | 0 |

TABLE 28

| compound | R¹ | R² | R³ | R⁴ | R⁵ | A | R⁶ | R⁷ | (R⁸)$_m$ | p |
|---|---|---|---|---|---|---|---|---|---|---|
| A-1535 | H | H | H | H | H | O | CH₂CH₃ | H | 2-OS(=O)₂CH₃,6-F | 0 |
| A-1536 | H | H | H | H | H | O | CH₂CH₃ | H | 2-OS(=O)₂CH₃,5-Me | 0 |
| A-1537 | H | H | H | H | H | O | CH₂CH₃ | H | 2-OS(=O)₂CH₃,6-Me | 0 |
| A-1538 | H | H | H | H | H | O | CH₂CH₃ | H | 2-CH₂SCH₃,5-F | 0 |
| A-1539 | H | H | H | H | H | O | CH₂CH₃ | H | 2-CH₂SCH₃,6-F | 0 |
| A-1540 | H | H | H | H | H | O | CH₂CH₃ | H | 2-CH₂SCH₃,5-Me | 0 |
| A-1541 | H | H | H | H | H | O | CH₂CH₃ | H | 2-CH₂SCH₃,6-Me | 0 |
| A-1542 | H | H | H | H | H | O | CH₂CH₃ | H | 2-NMe₂,5-F | 0 |
| A-1543 | H | H | H | H | H | O | CH₂CH₃ | H | 2-NMe₂,6-F | 0 |
| A-1544 | H | H | H | H | H | O | CH₂CH₃ | H | 2-NMe₂,5-Me | 0 |
| A-1545 | H | H | H | H | H | O | CH₂CH₃ | H | 2-NMe₂,6-Me | 0 |
| A-1546 | H | H | H | H | H | O | CH₂CH₃ | H | 2-CN,4-F | 0 |
| A-1547 | H | H | H | H | H | O | CH₂CH₃ | H | 2-CN,5-F | 0 |
| A-1548 | H | H | H | H | H | O | CH₂CH₃ | H | 2-CN,6-F | 0 |
| A-1549 | H | H | H | H | H | O | CH₂CH₃ | H | 2-CN,6-Me | 0 |
| A-1550 | H | H | H | H | H | O | CH₂CH₃ | H | 2-CN,5-OMe | 0 |
| A-1551 | H | H | H | H | H | O | CH₂CH₃ | H | 2-CN,6-OMe | 0 |
| A-1552 | H | H | H | H | H | O | CH₂CH₃ | H | 3-CN,6-Me | 0 |
| A-1553 | H | H | H | H | H | O | CH₂CH₃ | H | 3-CN,6-OMe | 0 |
| A-1554 | H | H | H | H | H | O | CH₂CH₃ | H | 4-CN,2-Me | 0 |
| A-1555 | H | H | H | H | H | O | CH₂CH₃ | H | 4-CN,2-OMe | 0 |
| A-1556 | H | H | H | H | H | O | CH₂CH₃ | H | 2-NO₂,4-F | 0 |
| A-1557 | H | H | H | H | H | O | CH₂CH₃ | H | 2-NO₂,5-F | 0 |
| A-1558 | H | H | H | H | H | O | CH₂CH₃ | H | 2-NO₂,6-F | 0 |
| A-1559 | H | H | H | H | H | O | CH₂CH₃ | H | 2-NO₂,4-Me | 0 |
| A-1560 | H | H | H | H | H | O | CH₂CH₃ | H | 2-NO₂,5-Me | 0 |
| A-1561 | H | H | H | H | H | O | CH₂CH₃ | H | 2-NO₂,6-Me | 0 |
| A-1562 | H | H | H | H | H | O | CH₂CH₃ | H | 2-Me,4,5-F₂ | 0 |
| A-1563 | H | H | H | H | H | O | CH₂CH₃ | H | 2-Me,6-Et | 0 |
| A-1564 | H | H | H | H | H | O | CH₂CH₃ | H | 2-cyclopropyl,6-OMe | 0 |
| A-1565 | H | H | H | H | H | O | CH₂CH₃ | H | 2-Me,5-Et | 0 |
| A-1566 | H | H | H | H | H | O | CH₂CH₃ | H | 2,6-Et₂ | 0 |
| A-1567 | H | H | H | H | H | O | CH₂CH₃ | H | 2-Et,6-F | 0 |
| A-1568 | H | H | H | H | H | O | CH₂CH₃ | H | 2-CH₂OCH₃,6-Cl | 0 |
| A-1569 | H | H | H | H | H | O | CH₂CH₃ | H | 2-CH₂OCH₂CH₃,6-Cl | 0 |
| A-1570 | H | H | H | H | H | O | CH₂CH₃ | H | 2-CH₂NMe₂ | 0 |
| A-1571 | H | H | H | H | H | O | CH₂CH₂CH₃ | H | H | 0 |
| A-1572 | H | H | H | H | H | O | CH₂CH₂CH₃ | H | 2-F | 0 |
| A-1573 | H | H | H | H | H | O | CH₂CH₂CH₃ | H | 2-Cl | 0 |
| A-1574 | H | H | H | H | H | O | CH₂CH₂CH₃ | H | 2-Br | 0 |
| A-1575 | H | H | H | H | H | O | CH₂CH₂CH₃ | H | 2-OH | 0 |
| A-1576 | H | H | H | H | H | O | CH₂CH₂CH₃ | H | 2-Me | 0 |
| A-1577 | H | H | H | H | H | O | CH₂CH₂CH₃ | H | 2-Et | 0 |
| A-1578 | H | H | H | H | H | O | CH₂CH₂CH₃ | H | 2-Pr | 0 |
| A-1579 | H | H | H | H | H | O | CH₂CH₂CH₃ | H | 2-CF₃ | 0 |
| A-1580 | H | H | H | H | H | O | CH₂CH₂CH₃ | H | 2-CHF₂ | 0 |
| A-1581 | H | H | H | H | H | O | CH₂CH₂CH₃ | H | 2-CH₂F | 0 |
| A-1582 | H | H | H | H | H | O | CH₂CH₂CH₃ | H | 2-CF₂Cl | 0 |
| A-1583 | H | H | H | H | H | O | CH₂CH₂CH₃ | H | 2-cyclopropyl | 0 |
| A-1584 | H | H | H | H | H | O | CH₂CH₂CH₃ | H | 2-cyclobutyl | 0 |
| A-1585 | H | H | H | H | H | O | CH₂CH₂CH₃ | H | 2-cyclopentyl | 0 |
| A-1586 | H | H | H | H | H | O | CH₂CH₂CH₃ | H | 2-ethenyl | 0 |
| A-1587 | H | H | H | H | H | O | CH₂CH₂CH₃ | H | 2-allyl | 0 |
| A-1588 | H | H | H | H | H | O | CH₂CH₂CH₃ | H | 2-(prop-1-en-1-yl) | 0 |
| A-1589 | H | H | H | H | H | O | CH₂CH₂CH₃ | H | 2-(trifluoroethenyl) | 0 |
| A-1590 | H | H | H | H | H | O | CH₂CH₂CH₃ | H | 2-OMe | 0 |
| A-1591 | H | H | H | H | H | O | CH₂CH₂CH₃ | H | 2-OEt | 0 |

TABLE 29

| compound | R¹ | R² | R³ | R⁴ | R⁵ | A | R⁶ | R⁷ | (R⁸)$_m$ | p |
|---|---|---|---|---|---|---|---|---|---|---|
| A-1592 | H | H | H | H | H | O | CH₂CH₂CH₃ | H | 2-OPr | 0 |
| A-1593 | H | H | H | H | H | O | CH₂CH₂CH₃ | H | 2-O(i-Pr) | 0 |
| A-1594 | H | H | H | H | H | O | CH₂CH₂CH₃ | H | 2-OCF₃ | 0 |
| A-1595 | H | H | H | H | H | O | CH₂CH₂CH₃ | H | 2-OCHF₂ | 0 |
| A-1596 | H | H | H | H | H | O | CH₂CH₂CH₃ | H | 2-(cyclopropyloxy) | 0 |
| A-1597 | H | H | H | H | H | O | CH₂CH₂CH₃ | H | 2-(cyclobutyloxy) | 0 |
| A-1598 | H | H | H | H | H | O | CH₂CH₂CH₃ | H | 2-(cyclopentyloxy) | 0 |
| A-1599 | H | H | H | H | H | O | CH₂CH₂CH₃ | H | 2-((2,2-dichlorocyclopropyl)oxy) | 0 |
| A-1600 | H | H | H | H | H | O | CH₂CH₂CH₃ | H | 2-(oxiran-2-yl) | 0 |
| A-1601 | H | H | H | H | H | O | CH₂CH₂CH₃ | H | 2-SMe | 0 |
| A-1602 | H | H | H | H | H | O | CH₂CH₂CH₃ | H | 3-SMe | 0 |
| A-1603 | H | H | H | H | H | O | CH₂CH₂CH₃ | H | 2-S(=O)Me | 0 |
| A-1604 | H | H | H | H | H | O | CH₂CH₂CH₃ | H | 3-S(=O)Me | 0 |

TABLE 29-continued

| compound | R¹ | R² | R³ | R⁴ | R⁵ | A | R⁶ | R⁷ | (R⁸)ₘ | p |
|---|---|---|---|---|---|---|---|---|---|---|
| A-1605 | H | H | H | H | H | O | CH₂CH₂CH₃ | H | 2-S(=O)₂Me | 0 |
| A-1606 | H | H | H | H | H | O | CH₂CH₂CH₃ | H | 3-S(=O)₂Me | 0 |
| A-1607 | H | H | H | H | H | O | CH₂CH₂CH₃ | H | 2-SCF₃ | 0 |
| A-1608 | H | H | H | H | H | O | CH₂CH₂CH₃ | H | 3-SCF₃ | 0 |
| A-1609 | H | H | H | H | H | O | CH₂CH₂CH₃ | H | 3-S(=O)CF₃ | 0 |
| A-1610 | H | H | H | H | H | O | CH₂CH₂CH₃ | H | 3-SCF(CF₃)₂ | 0 |
| A-1611 | H | H | H | H | H | O | CH₂CH₂CH₃ | H | 2-(cyclopropylthio) | 0 |
| A-1612 | H | H | H | H | H | O | CH₂CH₂CH₃ | H | 2-(cyclopropylsulfinyl) | 0 |
| A-1613 | H | H | H | H | H | O | CH₂CH₂CH₃ | H | 2-(cyclopropylsulfonyl) | 0 |
| A-1614 | H | H | H | H | H | O | CH₂CH₂CH₃ | H | 2-C(=O)Me | 0 |
| A-1615 | H | H | H | H | H | O | CH₂CH₂CH₃ | H | 2-CH₂C(=O)CH₃ | 0 |
| A-1616 | H | H | H | H | H | O | CH₂CH₂CH₃ | H | 2-CH₂C(=O)CF₃ | 0 |
| A-1617 | H | H | H | H | H | O | CH₂CH₂CH₃ | H | 2-CH₂OH | 0 |
| A-1618 | H | H | H | H | H | O | CH₂CH₂CH₃ | H | 2-CH₂OCH₃ | 0 |
| A-1619 | H | H | H | H | H | O | CH₂CH₂CH₃ | H | 2-CH₂OCH₂CH₃ | 0 |
| A-1620 | H | H | H | H | H | O | CH₂CH₂CH₃ | H | 2-CH₂SCH₃ | 0 |
| A-1621 | H | H | H | H | H | O | CH₂CH₂CH₃ | H | 2-CH₂S(=O)CH₃ | 0 |
| A-1622 | H | H | H | H | H | O | CH₂CH₂CH₃ | H | 2-CH₂S(=O)₂CH₃ | 0 |
| A-1623 | H | H | H | H | H | O | CH₂CH₂CH₃ | H | 2-(benzyloxy) | 0 |
| A-1624 | H | H | H | H | H | O | CH₂CH₂CH₃ | H | 2-NH₂ | 0 |
| A-1625 | H | H | H | H | H | O | CH₂CH₂CH₃ | H | 2-NHMe | 0 |
| A-1626 | H | H | H | H | H | O | CH₂CH₂CH₃ | H | 2-N(Me)₂ | 0 |
| A-1627 | H | H | H | H | H | O | CH₂CH₂CH₃ | H | 2-(1,3-dioxolan-2-yl) | 0 |
| A-1628 | H | H | H | H | H | O | CH₂CH₂CH₃ | H | 2-(1,3-dioxan-2-yl) | 0 |
| A-1629 | H | H | H | H | H | O | CH₂CH₂CH₃ | H | 2-(1H-imidazol-2-yl) | 0 |
| A-1630 | H | H | H | H | H | O | CH₂CH₂CH₃ | H | 2-(thiazol-2-yl) | 0 |
| A-1631 | H | H | H | H | H | O | CH₂CH₂CH₃ | H | 2-(oxazol-2-yl) | 0 |
| A-1632 | H | H | H | H | H | O | CH₂CH₂CH₃ | H | 2-CH=NOH | 0 |
| A-1633 | H | H | H | H | H | O | CH₂CH₂CH₃ | H | 2-CH=NOMe | 0 |
| A-1634 | H | H | H | H | H | O | CH₂CH₂CH₃ | H | 2-(4,5-dihydro-3-isoxazolyl) | 0 |
| A-1635 | H | H | H | H | H | O | CH₂CH₂CH₃ | H | 2-CN | 0 |
| A-1636 | H | H | H | H | H | O | CH₂CH₂CH₃ | H | 2-NO₂ | 0 |
| A-1637 | H | H | H | H | H | O | CH₂CH₂CH₃ | H | 2-F,6-Cl | 0 |
| A-1638 | H | H | H | H | H | O | CH₂CH₂CH₃ | H | 2-F,6-Me | 0 |
| A-1639 | H | H | H | H | H | O | CH₂CH₂CH₃ | H | 3-F,6-Me | 0 |
| A-1640 | H | H | H | H | H | O | CH₂CH₂CH₃ | H | 4-F,2-Me | 0 |
| A-1641 | H | H | H | H | H | O | CH₂CH₂CH₃ | H | 2-F,6-OMe | 0 |
| A-1642 | H | H | H | H | H | O | CH₂CH₂CH₃ | H | 3-F,6-OMe | 0 |
| A-1643 | H | H | H | H | H | O | CH₂CH₂CH₃ | H | 2,6-Cl₂ | 0 |
| A-1644 | H | H | H | H | H | O | CH₂CH₂CH₃ | H | 2-Cl,6-Me | 0 |
| A-1645 | H | H | H | H | H | O | CH₂CH₂CH₃ | H | 3-Cl,6-Me | 0 |
| A-1646 | H | H | H | H | H | O | CH₂CH₂CH₃ | H | 4-Cl,2-Me | 0 |
| A-1647 | H | H | H | H | H | O | CH₂CH₂CH₃ | H | 2-Cl,5-CF₃ | 0 |
| A-1648 | H | H | H | H | H | O | CH₂CH₂CH₃ | H | 2-Cl,6-CF₃ | 0 |

TABLE 30

| compound | R¹ | R² | R³ | R⁴ | R⁵ | A | R⁶ | R⁷ | (R⁸)ₘ | p |
|---|---|---|---|---|---|---|---|---|---|---|
| A-1649 | H | H | H | H | H | O | CH₂CH₂CH₃ | H | 2-Cl,6-OMe | 0 |
| A-1650 | H | H | H | H | H | O | CH₂CH₂CH₃ | H | 3-Cl,6-OMe | 0 |
| A-1651 | H | H | H | H | H | O | CH₂CH₂CH₃ | H | 4-Cl,2-OMe | 0 |
| A-1652 | H | H | H | H | H | O | CH₂CH₂CH₃ | H | 2,4-Me₂ | 0 |
| A-1653 | H | H | H | H | H | O | CH₂CH₂CH₃ | H | 2,5-Me₂ | 0 |
| A-1654 | H | H | H | H | H | O | CH₂CH₂CH₃ | H | 2,6-Me₂ | 0 |
| A-1655 | H | H | H | H | H | O | CH₂CH₂CH₃ | H | 2-Me,4-CF₃ | 0 |
| A-1656 | H | H | H | H | H | O | CH₂CH₂CH₃ | H | 2-Me,5-CF₃ | 0 |
| A-1657 | H | H | H | H | H | O | CH₂CH₂CH₃ | H | 2-Me,6-CF₃ | 0 |
| A-1658 | H | H | H | H | H | O | CH₂CH₂CH₃ | H | 2-Me,4-OMe | 0 |
| A-1659 | H | H | H | H | H | O | CH₂CH₂CH₃ | H | 2-Me,5-OMe | 0 |
| A-1660 | H | H | H | H | H | O | CH₂CH₂CH₃ | H | 2-Me,6-OMe | 0 |
| A-1661 | H | H | H | H | H | O | CH₂CH₂CH₃ | H | 3-Me,6-OMe | 0 |
| A-1662 | H | H | H | H | H | O | CH₂CH₂CH₃ | H | 4-Me,2-OMe | 0 |
| A-1663 | H | H | H | H | H | O | CH₂CH₂CH₃ | H | 2,5-OMe₂ | 0 |
| A-1664 | H | H | H | H | H | O | CH₂CH₂CH₃ | H | 2,6-OMe₂ | 0 |
| A-1665 | H | H | H | H | H | O | CH₂CH₂CH₃ | H | 2-OMe,6-CF₃ | 0 |
| A-1666 | H | H | H | H | H | O | CH₂CH₂CH₃ | H | 2-CHF₂,5-F | 0 |
| A-1667 | H | H | H | H | H | O | CH₂CH₂CH₃ | H | 2-CHF₂,6-F | 0 |
| A-1668 | H | H | H | H | H | O | CH₂CH₂CH₃ | H | 2-CHF₂,5-Me | 0 |
| A-1669 | H | H | H | H | H | O | CH₂CH₂CH₃ | H | 2-CHF₂,6-Me | 0 |
| A-1670 | H | H | H | H | H | O | CH₂CH₂CH₃ | H | 2-cyclopropyl,5-F | 0 |
| A-1671 | H | H | H | H | H | O | CH₂CH₂CH₃ | H | 2-cyclopropyl,6-F | 0 |
| A-1672 | H | H | H | H | H | O | CH₂CH₂CH₃ | H | 2-cyclopropyl,5-Me | 0 |
| A-1673 | H | H | H | H | H | O | CH₂CH₂CH₃ | H | 2-cyclopropyl,6-Me | 0 |
| A-1674 | H | H | H | H | H | O | CH₂CH₂CH₃ | H | 2-ethenyl,6-F | 0 |

TABLE 30-continued

| compound | R¹ | R² | R³ | R⁴ | R⁵ | A | R⁶ | R⁷ | (R⁸)ₘ | p |
|---|---|---|---|---|---|---|---|---|---|---|
| A-1675 | H | H | H | H | H | O | CH₂CH₂CH₃ | H | 2-ethenyl,6-Me | 0 |
| A-1676 | H | H | H | H | H | O | CH₂CH₂CH₃ | H | 2-OEt,5-F | 0 |
| A-1677 | H | H | H | H | H | O | CH₂CH₂CH₃ | H | 2-OEt,6-F | 0 |
| A-1678 | H | H | H | H | H | O | CH₂CH₂CH₃ | H | 2-OEt,5-Cl | 0 |
| A-1679 | H | H | H | H | H | O | CH₂CH₂CH₃ | H | 2-OEt,6-Cl | 0 |
| A-1680 | H | H | H | H | H | O | CH₂CH₂CH₃ | H | 2-OEt,5-Me | 0 |
| A-1681 | H | H | H | H | H | O | CH₂CH₂CH₃ | H | 2-OEt,6-Me | 0 |
| A-1682 | H | H | H | H | H | O | CH₂CH₂CH₃ | H | 2-OCHF₂,5-F | 0 |
| A-1683 | H | H | H | H | H | O | CH₂CH₂CH₃ | H | 2-OCHF₂,6-F | 0 |
| A-1684 | H | H | H | H | H | O | CH₂CH₂CH₃ | H | 2-OCHF₂,5-Me | 0 |
| A-1685 | H | H | H | H | H | O | CH₂CH₂CH₃ | H | 2-OCHF₂,6-Me | 0 |
| A-1686 | H | H | H | H | H | O | CH₂CH₂CH₃ | H | 2-(cyclopropyloxy),5-F | 0 |
| A-1687 | H | H | H | H | H | O | CH₂CH₂CH₃ | H | 2-(cyclopropyloxy),6-F | 0 |
| A-1688 | H | H | H | H | H | O | CH₂CH₂CH₃ | H | 2-(cyclopropyloxy),5-Me | 0 |
| A-1689 | H | H | H | H | H | O | CH₂CH₂CH₃ | H | 2-(cyclopropyloxy),6-Me | 0 |
| A-1690 | H | H | H | H | H | O | CH₂CH₂CH₃ | H | 2-SMe,5-F | 0 |
| A-1691 | H | H | H | H | H | O | CH₂CH₂CH₃ | H | 2-SMe,6-F | 0 |
| A-1692 | H | H | H | H | H | O | CH₂CH₂CH₃ | H | 2-SMe,5-Me | 0 |
| A-1693 | H | H | H | H | H | O | CH₂CH₂CH₃ | H | 2-SMe,6-Me | 0 |
| A-1694 | H | H | H | H | H | O | CH₂CH₂CH₃ | H | 2-S(=O)Me,5-F | 0 |
| A-1695 | H | H | H | H | H | O | CH₂CH₂CH₃ | H | 2-S(=O)Me,6-F | 0 |
| A-1696 | H | H | H | H | H | O | CH₂CH₂CH₃ | H | 2-S(=O)Me,5-Me | 0 |
| A-1697 | H | H | H | H | H | O | CH₂CH₂CH₃ | H | 2-S(=O)Me,6-Me | 0 |
| A-1698 | H | H | H | H | H | O | CH₂CH₂CH₃ | H | 2-S(=O)₂Me,5-F | 0 |
| A-1699 | H | H | H | H | H | O | CH₂CH₂CH₃ | H | 2-S(=O)₂Me,6-F | 0 |
| A-1700 | H | H | H | H | H | O | CH₂CH₂CH₃ | H | 2-S(=O)₂Me,5-Me | 0 |
| A-1701 | H | H | H | H | H | O | CH₂CH₂CH₃ | H | 2-S(=O)₂Me,6-Me | 0 |
| A-1702 | H | H | H | H | H | O | CH₂CH₂CH₃ | H | 2-SCF₃,5-F | 0 |
| A-1703 | H | H | H | H | H | O | CH₂CH₂CH₃ | H | 2-SCF₃,6-F | 0 |
| A-1704 | H | H | H | H | H | O | CH₂CH₂CH₃ | H | 2-SCF₃,5-Me | 0 |
| A-1705 | H | H | H | H | H | O | CH₂CH₂CH₃ | H | 2-SCF₃,6-Me | 0 |

TABLE 31

| compound | R¹ | R² | R³ | R⁴ | R⁵ | A | R⁶ | R⁷ | (R⁸)ₘ | p |
|---|---|---|---|---|---|---|---|---|---|---|
| A-1706 | H | H | H | H | H | O | CH₂CH₂CH₃ | H | 2-S(=O)CF₃,5-F | 0 |
| A-1707 | H | H | H | H | H | O | CH₂CH₂CH₃ | H | 2-S(=O)CF₃,6-F | 0 |
| A-1708 | H | H | H | H | H | O | CH₂CH₂CH₃ | H | 2-S(=O)CF₃,5-Me | 0 |
| A-1709 | H | H | H | H | H | O | CH₂CH₂CH₃ | H | 2-S(=O)CF₃,6-Me | 0 |
| A-1710 | H | H | H | H | H | O | CH₂CH₂CH₃ | H | 2-S(=O)₂CF₃,5-F | 0 |
| A-1711 | H | H | H | H | H | O | CH₂CH₂CH₃ | H | 2-S(=O)₂CF₃,6-F | 0 |
| A-1712 | H | H | H | H | H | O | CH₂CH₂CH₃ | H | 2-S(=O)₂CF₃,5-Me | 0 |
| A-1713 | H | H | H | H | H | O | CH₂CH₂CH₃ | H | 2-S(=O)₂CF₃,6-Me | 0 |
| A-1714 | H | H | H | H | H | O | CH₂CH₂CH₃ | H | 2-(cyclopropylthio),5-F | 0 |
| A-1715 | H | H | H | H | H | O | CH₂CH₂CH₃ | H | 2-(cyclopropylthio),6-F | 0 |
| A-1716 | H | H | H | H | H | O | CH₂CH₂CH₃ | H | 2-(cyclopropylthio),5-Me | 0 |
| A-1717 | H | H | H | H | H | O | CH₂CH₂CH₃ | H | 2-(cyclopropylthio),6-Me | 0 |
| A-1718 | H | H | H | H | H | O | CH₂CH₂CH₃ | H | 2-C(=O)Me,5-F | 0 |
| A-1719 | H | H | H | H | H | O | CH₂CH₂CH₃ | H | 2-C(=O)Me,6-F | 0 |
| A-1720 | H | H | H | H | H | O | CH₂CH₂CH₃ | H | 2-C(=O)Me,5-Me | 0 |
| A-1721 | H | H | H | H | H | O | CH₂CH₂CH₃ | H | 2-C(=O)Me,6-Me | 0 |
| A-1722 | H | H | H | H | H | O | CH₂CH₂CH₃ | H | 2-CH₂OH,5-F | 0 |
| A-1723 | H | H | H | H | H | O | CH₂CH₂CH₃ | H | 2-CH₂OH,6-F | 0 |
| A-1724 | H | H | H | H | H | O | CH₂CH₂CH₃ | H | 2-CH₂OH,5-Me | 0 |
| A-1725 | H | H | H | H | H | O | CH₂CH₂CH₃ | H | 2-CH₂OH,6-Me | 0 |
| A-1726 | H | H | H | H | H | O | CH₂CH₂CH₃ | H | 2-CH₂OCH₃,4-F | 0 |
| A-1727 | H | H | H | H | H | O | CH₂CH₂CH₃ | H | 2-CH₂OCH₃,5-F | 0 |
| A-1728 | H | H | H | H | H | O | CH₂CH₂CH₃ | H | 2-CH₂OCH₃,6-F | 0 |
| A-1729 | H | H | H | H | H | O | CH₂CH₂CH₃ | H | 2-CH₂OCH₃,4-Me | 0 |
| A-1730 | H | H | H | H | H | O | CH₂CH₂CH₃ | H | 2-CH₂OCH₃,5-Me | 0 |
| A-1731 | H | H | H | H | H | O | CH₂CH₂CH₃ | H | 2-CH₂OCH₃,6-Me | 0 |
| A-1732 | H | H | H | H | H | O | CH₂CH₂CH₃ | H | 2-OC(=O)CH₃,5-F | 0 |
| A-1733 | H | H | H | H | H | O | CH₂CH₂CH₃ | H | 2-OC(=O)CH₃,6-F | 0 |
| A-1734 | H | H | H | H | H | O | CH₂CH₂CH₃ | H | 2-OC(=O)CH₃,5-Me | 0 |
| A-1735 | H | H | H | H | H | O | CH₂CH₂CH₃ | H | 2-OC(=O)CH₃,6-Me | 0 |
| A-1736 | H | H | H | H | H | O | CH₂CH₂CH₃ | H | 2-OS(=O)₂CH₃,5-F | 0 |
| A-1737 | H | H | H | H | H | O | CH₂CH₂CH₃ | H | 2-OS(=O)₂CH₃,6-F | 0 |
| A-1738 | H | H | H | H | H | O | CH₂CH₂CH₃ | H | 2-OS(=O)₂CH₃,5-Me | 0 |
| A-1739 | H | H | H | H | H | O | CH₂CH₂CH₃ | H | 2-OS(=O)₂CH₃,6-Me | 0 |
| A-1740 | H | H | H | H | H | O | CH₂CH₂CH₃ | H | 2-CH₂SCH₃,5-F | 0 |
| A-1741 | H | H | H | H | H | O | CH₂CH₂CH₃ | H | 2-CH₂SCH₃,6-F | 0 |
| A-1742 | H | H | H | H | H | O | CH₂CH₂CH₃ | H | 2-CH₂SCH₃,5-Me | 0 |
| A-1743 | H | H | H | H | H | O | CH₂CH₂CH₃ | H | 2-CH₂SCH₃,6-Me | 0 |
| A-1744 | H | H | H | H | H | O | CH₂CH₂CH₃ | H | 2-NMe₂,5-F | 0 |

TABLE 31-continued

| compound | R¹ | R² | R³ | R⁴ | R⁵ | A | R⁶ | R⁷ | (R⁸)ₘ | p |
|---|---|---|---|---|---|---|---|---|---|---|
| A-1745 | H | H | H | H | H | O | CH₂CH₂CH₃ | H | 2-NMe₂,6-F | 0 |
| A-1746 | H | H | H | H | H | O | CH₂CH₂CH₃ | H | 2-NMe₂,5-Me | 0 |
| A-1747 | H | H | H | H | H | O | CH₂CH₂CH₃ | H | 2-NMe₂,6-Me | 0 |
| A-1748 | H | H | H | H | H | O | CH₂CH₂CH₃ | H | 2-CN,4-F | 0 |
| A-1749 | H | H | H | H | H | O | CH₂CH₂CH₃ | H | 2-CN,5-F | 0 |
| A-1750 | H | H | H | H | H | O | CH₂CH₂CH₃ | H | 2-CN,6-F | 0 |
| A-1751 | H | H | H | H | H | O | CH₂CH₂CH₃ | H | 2-CN,6-Me | 0 |
| A-1752 | H | H | H | H | H | O | CH₂CH₂CH₃ | H | 2-CN,5-OMe | 0 |
| A-1753 | H | H | H | H | H | O | CH₂CH₂CH₃ | H | 2-CN,6-OMe | 0 |
| A-1754 | H | H | H | H | H | O | CH₂CH₂CH₃ | H | 3-CN,6-Me | 0 |
| A-1755 | H | H | H | H | H | O | CH₂CH₂CH₃ | H | 3-CN,6-OMe | 0 |
| A-1756 | H | H | H | H | H | O | CH₂CH₂CH₃ | H | 4-CN,2-Me | 0 |
| A-1757 | H | H | H | H | H | O | CH₂CH₂CH₃ | H | 4-CN,2-OMe | 0 |
| A-1758 | H | H | H | H | H | O | CH₂CH₂CH₃ | H | 2-NO₂,4-F | 0 |
| A-1759 | H | H | H | H | H | O | CH₂CH₂CH₃ | H | 2-NO₂,5-F | 0 |
| A-1760 | H | H | H | H | H | O | CH₂CH₂CH₃ | H | 2-NO₂,6-F | 0 |
| A-1761 | H | H | H | H | H | O | CH₂CH₂CH₃ | H | 2-NO₂,4-Me | 0 |
| A-1762 | H | H | H | H | H | O | CH₂CH₂CH₃ | H | 2-NO₂,5-Me | 0 |

TABLE 32

| compound | R¹ | R² | R³ | R⁴ | R⁵ | A | R⁶ | R⁷ | (R⁸)ₘ | p |
|---|---|---|---|---|---|---|---|---|---|---|
| A-1763 | H | H | H | H | H | O | CH₂CH₂CH₃ | H | 2-NO₂,6-Me | 0 |
| A-1764 | H | H | H | H | H | O | CH₂CH₂CH₃ | H | 2-Me,4,5-F₂ | 0 |
| A-1765 | H | H | H | H | H | O | CH₂CH₂CH₃ | H | 2-Me,6-Et | 0 |
| A-1766 | H | H | H | H | H | O | CH₂CH₂CH₃ | H | 2-cyclopropyl,6-OMe | 0 |
| A-1767 | H | H | H | H | H | O | CH₂CH₂CH₃ | H | 2-Me,5-Et | 0 |
| A-1768 | H | H | H | H | H | O | CH₂CH₂CH₃ | H | 2,6-Et₂ | 0 |
| A-1769 | H | H | H | H | H | O | CH₂CH₂CH₃ | H | 2-Et,6-F | 0 |
| A-1770 | H | H | H | H | H | O | CH₂CH₂CH₃ | H | 2-CH₂OCH₃,6-Cl | 0 |
| A-1771 | H | H | H | H | H | O | CH₂CH₂CH₃ | H | 2-CH₂OCH₂CH₃,6-Cl | 0 |
| A-1772 | H | H | H | H | H | O | CH₂CH₂CH₃ | H | 2-CH₂NMe₂ | 0 |
| A-1773 | H | H | H | H | H | O | cyclopropyl | H | H | 0 |
| A-1774 | H | H | H | H | H | O | cyclopropyl | H | 2-F | 0 |
| A-1775 | H | H | H | H | H | O | cyclopropyl | H | 2-Cl | 0 |
| A-1776 | H | H | H | H | H | O | cyclopropyl | H | 2-Br | 0 |
| A-1777 | H | H | H | H | H | O | cyclopropyl | H | 2-OH | 0 |
| A-1778 | H | H | H | H | H | O | cyclopropyl | H | 2-Me | 0 |
| A-1779 | H | H | H | H | H | O | cyclopropyl | H | 2-Et | 0 |
| A-1780 | H | H | H | H | H | O | cyclopropyl | H | 2-Pr | 0 |
| A-1781 | H | H | H | H | H | O | cyclopropyl | H | 2-CF₃ | 0 |
| A-1782 | H | H | H | H | H | O | cyclopropyl | H | 2-CHF₂ | 0 |
| A-1783 | H | H | H | H | H | O | cyclopropyl | H | 2-CH₂F | 0 |
| A-1784 | H | H | H | H | H | O | cyclopropyl | H | 2-CF₂Cl | 0 |
| A-1785 | H | H | H | H | H | O | cyclopropyl | H | 2-cyclopropyl | 0 |
| A-1786 | H | H | H | H | H | O | cyclopropyl | H | 2-cyclobutyl | 0 |
| A-1787 | H | H | H | H | H | O | cyclopropyl | H | 2-cyclopentyl | 0 |
| A-1788 | H | H | H | H | H | O | cyclopropyl | H | 2-ethenyl | 0 |
| A-1789 | H | H | H | H | H | O | cyclopropyl | H | 2-allyl | 0 |
| A-1790 | H | H | H | H | H | O | cyclopropyl | H | 2-(prop-1-en-1-yl) | 0 |
| A-1791 | H | H | H | H | H | O | cyclopropyl | H | 2-(trifluoroethenyl) | 0 |
| A-1792 | H | H | H | H | H | O | cyclopropyl | H | 2-OMe | 0 |
| A-1793 | H | H | H | H | H | O | cyclopropyl | H | 2-OEt | 0 |
| A-1794 | H | H | H | H | H | O | cyclopropyl | H | 2-OPr | 0 |
| A-1795 | H | H | H | H | H | O | cyclopropyl | H | 2-O(i-Pr) | 0 |
| A-1796 | H | H | H | H | H | O | cyclopropyl | H | 2-OCF₃ | 0 |
| A-1797 | H | H | H | H | H | O | cyclopropyl | H | 2-OCHF₂ | 0 |
| A-1798 | H | H | H | H | H | O | cyclopropyl | H | 2-(cyclopropyloxy) | 0 |
| A-1799 | H | H | H | H | H | O | cyclopropyl | H | 2-(cyclobutyloxy) | 0 |
| A-1800 | H | H | H | H | H | O | cyclopropyl | H | 2-(cyclopentyloxy) | 0 |
| A-1801 | H | H | H | H | H | O | cyclopropyl | H | 2-((2,2-dichlorocyclopropyl)oxy) | 0 |
| A-1802 | H | H | H | H | H | O | cyclopropyl | H | 2-(oxiran-2-yl) | 0 |
| A-1803 | H | H | H | H | H | O | cyclopropyl | H | 2-SMe | 0 |
| A-1804 | H | H | H | H | H | O | cyclopropyl | H | 3-SMe | 0 |
| A-1805 | H | H | H | H | H | O | cyclopropyl | H | 2-S(=O)Me | 0 |
| A-1806 | H | H | H | H | H | O | cyclopropyl | H | 3-S(=O)Me | 0 |
| A-1807 | H | H | H | H | H | O | cyclopropyl | H | 2-S(=O)₂Me | 0 |
| A-1808 | H | H | H | H | H | O | cyclopropyl | H | 3-S(=O)₂Me | 0 |
| A-1809 | H | H | H | H | H | O | cyclopropyl | H | 2-SCF₃ | 0 |
| A-1810 | H | H | H | H | H | O | cyclopropyl | H | 3-SCF₃ | 0 |
| A-1811 | H | H | H | H | H | O | cyclopropyl | H | 3-S(=O)CF₃ | 0 |
| A-1812 | H | H | H | H | H | O | cyclopropyl | H | 3-SCF(CF₃)₂ | 0 |
| A-1813 | H | H | H | H | H | O | cyclopropyl | H | 2-(cyclopropylthio) | 0 |
| A-1814 | H | H | H | H | H | O | cyclopropyl | H | 2-(cyclopropylsulfinyl) | 0 |

TABLE 32-continued

| compound | R¹ | R² | R³ | R⁴ | R⁵ | A | R⁶ | R⁷ | (R⁸)$_m$ | p |
|---|---|---|---|---|---|---|---|---|---|---|
| A-1815 | H | H | H | H | H | O | cyclopropyl | H | 2-(cyclopropylsulfonyl) | 0 |
| A-1816 | H | H | H | H | H | O | cyclopropyl | H | 2-C(=O)Me | 0 |
| A-1817 | H | H | H | H | H | O | cyclopropyl | H | 2-CH$_2$C(=O)CH$_3$ | 0 |
| A-1818 | H | H | H | H | H | O | cyclopropyl | H | 2-CH$_2$C(=O)CF$_3$ | 0 |
| A-1819 | H | H | H | H | H | O | cyclopropyl | H | 2-CH$_2$OH | 0 |

TABLE 33

| compound | R¹ | R² | R³ | R⁴ | R⁵ | A | R⁶ | R⁷ | (R⁸)$_m$ | p |
|---|---|---|---|---|---|---|---|---|---|---|
| A-1820 | H | H | H | H | H | O | cyclopropyl | H | 2-CH$_2$OCH$_3$ | 0 |
| A-1821 | H | H | H | H | H | O | cyclopropyl | H | 2-CH$_2$OCH$_2$CH$_3$ | 0 |
| A-1822 | H | H | H | H | H | O | cyclopropyl | H | 2-CH$_2$SCH$_3$ | 0 |
| A-1823 | H | H | H | H | H | O | cyclopropyl | H | 2-CH$_2$S(=O)CH$_3$ | 0 |
| A-1824 | H | H | H | H | H | O | cyclopropyl | H | 2-CH$_2$S(=O)$_2$CH$_3$ | 0 |
| A-1825 | H | H | H | H | H | O | cyclopropyl | H | 2-(benzyloxy) | 0 |
| A-1826 | H | H | H | H | H | O | cyclopropyl | H | 2-NH$_2$ | 0 |
| A-1827 | H | H | H | H | H | O | cyclopropyl | H | 2-NHMe | 0 |
| A-1828 | H | H | H | H | H | O | cyclopropyl | H | 2-N(Me)$_2$ | 0 |
| A-1829 | H | H | H | H | H | O | cyclopropyl | H | 2-(1,3-dioxolan-2-yl) | 0 |
| A-1830 | H | H | H | H | H | O | cyclopropyl | H | 2-(1,3-dioxan-2-yl) | 0 |
| A-1831 | H | H | H | H | H | O | cyclopropyl | H | 2-(1-imidazol-2-y-l) | 0 |
| A-1832 | H | H | H | H | H | O | cyclopropyl | H | 2-(thiazol-2-yl) | 0 |
| A-1833 | H | H | H | H | H | O | cyclopropyl | H | 2-(oxazol2-yl) | 0 |
| A-1834 | H | H | H | H | H | O | cyclopropyl | H | 2-CH=NOH | 0 |
| A-1835 | H | H | H | H | H | O | cyclopropyl | H | 2-CH=NOMe | 0 |
| A-1836 | H | H | H | H | H | O | cyclopropyl | H | 2-(4,5-dihydro-3-isoxazolyl) | 0 |
| A-1837 | H | H | H | H | H | O | cyclopropyl | H | 2-CN | 0 |
| A-1838 | H | H | H | H | H | O | cyclopropyl | H | 2-NO$_2$ | 0 |
| A-1839 | H | H | H | H | H | O | cyclopropyl | H | 2,6-Cl | 0 |
| A-1840 | H | H | H | H | H | O | cyclopropyl | H | 2-F,6-Me | 0 |
| A-1841 | H | H | H | H | H | O | cyclopropyl | H | 3-F,6-Me | 0 |
| A-1842 | H | H | H | H | H | O | cyclopropyl | H | 4-F,2-Me | 0 |
| A-1843 | H | H | H | H | H | O | cyclopropyl | H | 2-F,6-OMe | 0 |
| A-1844 | H | H | H | H | H | O | cyclopropyl | H | 3-F,6-OMe | 0 |
| A-1845 | H | H | H | H | H | O | cyclopropyl | H | 2,6-Cl$_2$ | 0 |
| A-1846 | H | H | H | H | H | O | cyclopropyl | H | 2-Cl,6-Me | 0 |
| A-1847 | H | H | H | H | H | O | cyclopropyl | H | 3-Cl,6-Me | 0 |
| A-1848 | H | H | H | H | H | O | cyclopropyl | H | 4-Cl,2-Me | 0 |
| A-1849 | H | H | H | H | H | O | cyclopropyl | H | 2-Cl,5-CF$_3$ | 0 |
| A-1850 | H | H | H | H | H | O | cyclopropyl | H | 2-Cl,6-CF$_3$ | 0 |
| A-1851 | H | H | H | H | H | O | cyclopropyl | H | 2-Cl,6-OMe | 0 |
| A-1852 | H | H | H | H | H | O | cyclopropyl | H | 3-Cl,6-OMe | 0 |
| A-1853 | H | H | H | H | H | O | cyclopropyl | H | 4-Cl,2-OMe | 0 |
| A-1854 | H | H | H | H | H | O | cyclopropyl | H | 2,4-Me$_2$ | 0 |
| A-1855 | H | H | H | H | H | O | cyclopropyl | H | 2,5-Me$_2$ | 0 |
| A-1856 | H | H | H | H | H | O | cyclopropyl | H | 2,6-Me$_2$ | 0 |
| A-1857 | H | H | H | H | H | O | cyclopropyl | H | 2-Me,4-CF$_3$ | 0 |
| A-1858 | H | H | H | H | H | O | cyclopropyl | H | 2-Me,5-CF$_3$ | 0 |
| A-1859 | H | H | H | H | H | O | cyclopropyl | H | 2-Me,6-CF$_3$ | 0 |
| A-1860 | H | H | H | H | H | O | cyclopropyl | H | 2-Me,4-OMe | 0 |
| A-1861 | H | H | H | H | H | O | cyclopropyl | H | 2-Me,5-OMe | 0 |
| A-1862 | H | H | H | H | H | O | cyclopropyl | H | 2-Me,6-OMe | 0 |
| A-1863 | H | H | H | H | H | O | cyclopropyl | H | 3-Me,6-OMe | 0 |
| A-1864 | H | H | H | H | H | O | cyclopropyl | H | 4-Me,2-OMe | 0 |
| A-1865 | H | H | H | H | H | O | cyclopropyl | H | 2,5-OMe$_2$ | 0 |
| A-1866 | H | H | H | H | H | O | cyclopropyl | H | 2,6-OMe$_2$ | 0 |
| A-1867 | H | H | H | H | H | O | cyclopropyl | H | 2-OMe,6-CF$_3$ | 0 |
| A-1868 | H | H | H | H | H | O | cyclopropyl | H | 2-CHF$_2$,5-F | 0 |
| A-1869 | H | H | H | H | H | O | cyclopropyl | H | 2-CHF$_2$,6-F | 0 |
| A-1870 | H | H | H | H | H | O | cyclopropyl | H | 2-CHF$_2$,5-Me | 0 |
| A-1871 | H | H | H | H | H | O | cyclopropyl | H | 2-CHF$_2$,6-Me | 0 |
| A-1872 | H | H | H | H | H | O | cyclopropyl | H | 2-cyclopropyl,5-F | 0 |
| A-1873 | H | H | H | H | H | O | cyclopropyl | H | 2-cyclopropyl,6-F | 0 |
| A-1874 | H | H | H | H | H | O | cyclopropyl | H | 2-cyclopropyl,5-Me | 0 |
| A-1875 | H | H | H | H | H | O | cyclopropyl | H | 2-cyclopropyl,6-Me | 0 |
| A-1876 | H | H | H | H | H | O | cyclopropyl | H | 2-ethenyl,6-F | 0 |

TABLE 34

| compound | R¹ | R² | R³ | R⁴ | R⁵ | A | R⁶ | R⁷ | (R⁸)ₘ | p |
|---|---|---|---|---|---|---|---|---|---|---|
| A-1877 | H | H | H | H | H | O | cyclopropyl | H | 2-ethenyl,6-Me | 0 |
| A-1878 | H | H | H | H | H | O | cyclopropyl | H | 2-OEt,5-F | 0 |
| A-1879 | H | H | H | H | H | O | cyclopropyl | H | 2-OEt,6-F | 0 |
| A-1880 | H | H | H | H | H | O | cyclopropyl | H | 2-OEt,5-Cl | 0 |
| A-1881 | H | H | H | H | H | O | cyclopropyl | H | 2-OEt,6-Cl | 0 |
| A-1882 | H | H | H | H | H | O | cyclopropyl | H | 2-OEt,5-Me | 0 |
| A-1883 | H | H | H | H | H | O | cyclopropyl | H | 2-OEt,6-Me | 0 |
| A-1884 | H | H | H | H | H | O | cyclopropyl | H | 2-OCHF$_2$,5-F | 0 |
| A-1885 | H | H | H | H | H | O | cyclopropyl | H | 2-OCHF$_2$,6-F | 0 |
| A-1886 | H | H | H | H | H | O | cyclopropyl | H | 2-OCHF$_2$,5-Me | 0 |
| A-1887 | H | H | H | H | H | O | cyclopropyl | H | 2-OCHF$_2$,6-Me | 0 |
| A-1888 | H | H | H | H | H | O | cyclopropyl | H | 2-(cyclopropyloxy),5-F | 0 |
| A-1889 | H | H | H | H | H | O | cyclopropyl | H | 2-(cyclopropyloxy),6-F | 0 |
| A-1890 | H | H | H | H | H | O | cyclopropyl | H | 2-(cyclopropyloxy),5-Me | 0 |
| A-1891 | H | H | H | H | H | O | cyclopropyl | H | 2-(cyclopropyloxy),6-Me | 0 |
| A-1892 | H | H | H | H | H | O | cyclopropyl | H | 2-SMe,5-F | 0 |
| A-1893 | H | H | H | H | H | O | cyclopropyl | H | 2-SMe,6-F | 0 |
| A-1894 | H | H | H | H | H | O | cyclopropyl | H | 2-SMe,5-Me | 0 |
| A-1895 | H | H | H | H | H | O | cyclopropyl | H | 2-SMe,6-Me | 0 |
| A-1896 | H | H | H | H | H | O | cyclopropyl | H | 2-S(=O)Me,5-F | 0 |
| A-1897 | H | H | H | H | H | O | cyclopropyl | H | 2-S(=O)Me,6-F | 0 |
| A-1898 | H | H | H | H | H | O | cyclopropyl | H | 2-S(=O)Me,5-Me | 0 |
| A-1899 | H | H | H | H | H | O | cyclopropyl | H | 2-S(=O)Me,6-Me | 0 |
| A-1900 | H | H | H | H | H | O | cyclopropyl | H | 2-S(=O)$_2$Me,5-F | 0 |
| A-1901 | H | H | H | H | H | O | cyclopropyl | H | 2-S(=O)$_2$Me,6-F | 0 |
| A-1902 | H | H | H | H | H | O | cyclopropyl | H | 2-S(=O)$_2$Me,5-Me | 0 |
| A-1903 | H | H | H | H | H | O | cyclopropyl | H | 2-S(=O)$_2$Me,6-Me | 0 |
| A-1904 | H | H | H | H | H | O | cyclopropyl | H | 2-SCF$_3$,5-F | 0 |
| A-1905 | H | H | H | H | H | O | cyclopropyl | H | 2-SCF$_3$,6-F | 0 |
| A-1906 | H | H | H | H | H | O | cyclopropyl | H | 2-SCF$_3$,5-Me | 0 |
| A-1907 | H | H | H | H | H | O | cyclopropyl | H | 2-SCF$_3$,6-Me | 0 |
| A-1908 | H | H | H | H | H | O | cyclopropyl | H | 2-S(=O)CF$_3$,5-F | 0 |
| A-1909 | H | H | H | H | H | O | cyclopropyl | H | 2-S(=O)CF$_3$,6-F | 0 |
| A-1910 | H | H | H | H | H | O | cyclopropyl | H | 2-S(=O)CF$_3$,5-Me | 0 |
| A-1911 | H | H | H | H | H | O | cyclopropyl | H | 2-S(=O)CF$_3$,6-Me | 0 |
| A-1912 | H | H | H | H | H | O | cyclopropyl | H | 2-S(=O)$_2$CF$_3$,5-F | 0 |
| A-1913 | H | H | H | H | H | O | cyclopropyl | H | 2-S(=O)$_2$CF$_3$,6-F | 0 |
| A-1914 | H | H | H | H | H | O | cyclopropyl | H | 2-S(=O)$_2$CF$_3$,5-Me | 0 |
| A-1915 | H | H | H | H | H | O | cyclopropyl | H | 2-S(=O)$_2$CF$_3$,6-Me | 0 |
| A-1916 | H | H | H | H | H | O | cyclopropyl | H | 2-(cyclopropylthio),5-F | 0 |
| A-1917 | H | H | H | H | H | O | cyclopropyl | H | 2-(cyclopropylthio),6-F | 0 |
| A-1918 | H | H | H | H | H | O | cyclopropyl | H | 2-(cyclopropylthio),5-Me | 0 |
| A-1919 | H | H | H | H | H | O | cyclopropyl | H | 2-(cyclopropylthio),6-Me | 0 |
| A-1920 | H | H | H | H | H | O | cyclopropyl | H | 2-C(=O)Me,5-F | 0 |
| A-1921 | H | H | H | H | H | O | cyclopropyl | H | 2-C(=O)Me,6-F | 0 |
| A-1922 | H | H | H | H | H | O | cyclopropyl | H | 2-C(=O)Me,5-Me | 0 |
| A-1923 | H | H | H | H | H | O | cyclopropyl | H | 2-C(=O)Me,6-Me | 0 |
| A-1924 | H | H | H | H | H | O | cyclopropyl | H | 2-CH$_2$OH,5-F | 0 |
| A-1925 | H | H | H | H | H | O | cyclopropyl | H | 2-CH$_2$OH,6-F | 0 |
| A-1926 | H | H | H | H | H | O | cyclopropyl | H | 2-CH$_2$OH,5-Me | 0 |
| A-1927 | H | H | H | H | H | O | cyclopropyl | H | 2-CH$_2$OH,6-Me | 0 |
| A-1928 | H | H | H | H | H | O | cyclopropyl | H | 2-CH$_2$OCH$_3$,4-F | 0 |
| A-1929 | H | H | H | H | H | O | cyclopropyl | H | 2-CH$_2$OCH$_3$,5-F | 0 |
| A-1930 | H | H | H | H | H | O | cyclopropyl | H | 2-CH$_2$OCH$_3$,6-F | 0 |
| A-1931 | H | H | H | H | H | O | cyclopropyl | H | 2-CH$_2$OCH$_3$,4-Me | 0 |
| A-1932 | H | H | H | H | H | O | cyclopropyl | H | 2-CH$_2$OCH$_3$,5-Me | 0 |
| A-1933 | H | H | H | H | H | O | cyclopropyl | H | 2-CH$_2$OCH$_3$,6-Me | 0 |

TABLE 35

| compound | R¹ | R² | R³ | R⁴ | R⁵ | A | R⁶ | R⁷ | (R⁸)ₘ | p |
|---|---|---|---|---|---|---|---|---|---|---|
| A-1934 | H | H | H | H | H | O | cyclopropyl | H | 2-OC(=O)CH$_3$,5-F | 0 |
| A-1935 | H | H | H | H | H | O | cyclopropyl | H | 2-OC(=O)CH$_3$,6-F | 0 |
| A-1936 | H | H | H | H | H | O | cyclopropyl | H | 2-OC(=O)CH$_3$,5-Me | 0 |
| A-1937 | H | H | H | H | H | O | cyclopropyl | H | 2-OC(=O)CH$_3$,6-Me | 0 |
| A-1938 | H | H | H | H | H | O | cyclopropyl | H | 2-OS(=O)$_2$CH$_3$,5-F | 0 |
| A-1939 | H | H | H | H | H | O | cyclopropyl | H | 2-OS(=O)$_2$CH$_3$,6-F | 0 |
| A-1940 | H | H | H | H | H | O | cyclopropyl | H | 2-OS(=O)$_2$CH$_3$,5-Me | 0 |
| A-1941 | H | H | H | H | H | O | cyclopropyl | H | 2-OS(=O)$_2$CH$_3$,6-Me | 0 |
| A-1942 | H | H | H | H | H | O | cyclopropyl | H | 2-CH$_2$SCH$_3$,5-F | 0 |
| A-1943 | H | H | H | H | H | O | cyclopropyl | H | 2-CH$_2$SCH$_3$,6-F | 0 |
| A-1944 | H | H | H | H | H | O | cyclopropyl | H | 2-CH$_2$SCH$_3$,5-Me | 0 |
| A-1945 | H | H | H | H | H | O | cyclopropyl | H | 2-CH$_2$SCH$_3$,6-Me | 0 |
| A-1946 | H | H | H | H | H | O | cyclopropyl | H | 2-NMe$_2$,5-F | 0 |

TABLE 35-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-1947 | H | H | H | H | H | O | cyclopropyl | H | 2-NMe$_2$,6-F | 0 |
| A-1948 | H | H | H | H | H | O | cyclopropyl | H | 2-NMe$_2$,5-Me | 0 |
| A-1949 | H | H | H | H | H | O | cyclopropyl | H | 2-NMe$_2$,6-Me | 0 |
| A-1950 | H | H | H | H | H | O | cyclopropyl | H | 2-CN,4-F | 0 |
| A-1951 | H | H | H | H | H | O | cyclopropyl | H | 2-CN,5-F | 0 |
| A-1952 | H | H | H | H | H | O | cyclopropyl | H | 2-CN,6-F | 0 |
| A-1953 | H | H | H | H | H | O | cyclopropyl | H | 2-CN,6-Me | 0 |
| A-1954 | H | H | H | H | H | O | cyclopropyl | H | 2-CN,5-OMe | 0 |
| A-1955 | H | H | H | H | H | O | cyclopropyl | H | 2-CN,6-OMe | 0 |
| A-1956 | H | H | H | H | H | O | cyclopropyl | H | 3-CN,6-Me | 0 |
| A-1957 | H | H | H | H | H | O | cyclopropyl | H | 3-CN,6-OMe | 0 |
| A-1958 | H | H | H | H | H | O | cyclopropyl | H | 4-CN,2-Me | 0 |
| A-1959 | H | H | H | H | H | O | cyclopropyl | H | 4-CN,2-OMe | 0 |
| A-1960 | H | H | H | H | H | O | cyclopropyl | H | 2-NO$_2$,4-F | 0 |
| A-1961 | H | H | H | H | H | O | cyclopropyl | H | 2-NO$_2$,5-F | 0 |
| A-1962 | H | H | H | H | H | O | cyclopropyl | H | 2-NO$_2$,6-F | 0 |
| A-1963 | H | H | H | H | H | O | cyclopropyl | H | 2-NO$_2$,4-Me | 0 |
| A-1964 | H | H | H | H | H | O | cyclopropyl | H | 2-NO$_2$,5-Me | 0 |
| A-1965 | H | H | H | H | H | O | cyclopropyl | H | 2-NO$_2$,6-Me | 0 |
| A-1966 | H | H | H | H | H | O | cyclopropyl | H | 2-Me,4,5-F$_2$ | 0 |
| A-1967 | H | H | H | H | H | O | cyclopropyl | H | 2-Me,6-Et | 0 |
| A-1968 | H | H | H | H | H | O | cyclopropyl | H | 2-cyclopropyl,6-OMe | 0 |
| A-1969 | H | H | H | H | H | O | cyclopropyl | H | 2-Me,5-Et | 0 |
| A-1970 | H | H | H | H | H | O | cyclopropyl | H | 2,6-Et$_2$ | 0 |
| A-1971 | H | H | H | H | H | O | cyclopropyl | H | 2-Et,6-F | 0 |
| A-1972 | H | H | H | H | H | O | cyclopropyl | H | 2-CH$_2$OCH$_3$,6-Cl | 0 |
| A-1973 | H | H | H | H | H | O | cyclopropyl | H | 2-CH$_2$OCH$_2$CH$_3$,6-Cl | 0 |
| A-1974 | H | H | H | H | H | O | cyclopropyl | H | 2-CH$_2$NMe$_2$ | 0 |
| A-1975 | H | H | H | H | H | O | cyclohexyl | H | H | 0 |
| A-1976 | H | H | H | H | H | O | cyclohexyl | H | 2-F | 0 |
| A-1977 | H | H | H | H | H | O | cyclohexyl | H | 2-Cl | 0 |
| A-1978 | H | H | H | H | H | O | cyclohexyl | H | 2-Br | 0 |
| A-1979 | H | H | H | H | H | O | cyclohexyl | H | 2-OH | 0 |
| A-1980 | H | H | H | H | H | O | cyclohexyl | H | 2-Me | 0 |
| A-1981 | H | H | H | H | H | O | cyclohexyl | H | 2-Et | 0 |
| A-1982 | H | H | H | H | H | O | cyclohexyl | H | 2-Pr | 0 |
| A-1983 | H | H | H | H | H | O | cyclohexyl | H | 2-CF$_3$ | 0 |
| A-1984 | H | H | H | H | H | O | cyclohexyl | H | 2-CHF$_2$ | 0 |
| A-1985 | H | H | H | H | H | O | cyclohexyl | H | 2-CH$_2$F | 0 |
| A-1986 | H | H | H | H | H | O | cyclohexyl | H | 2-CF$_2$Cl | 0 |
| A-1987 | H | H | H | H | H | O | cyclohexyl | H | 2-cyclopropyl | 0 |
| A-1988 | H | H | H | H | H | O | cyclohexyl | H | 2-cyclobutyl | 0 |
| A-1989 | H | H | H | H | H | O | cyclohexyl | H | 2-cyclopentyl | 0 |
| A-1990 | H | H | H | H | H | O | cyclohexyl | H | 2-ethenyl | 0 |

TABLE 36

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-1991 | H | H | H | H | H | O | cyclohexyl | H | 2-allyl | 0 |
| A-1992 | H | H | H | H | H | O | cyclohexyl | H | 2-(prop-1-en-1-yl) | 0 |
| A-1993 | H | H | H | H | H | O | cyclohexyl | H | 2-(trifluoroethenyl) | 0 |
| A-1994 | H | H | H | H | H | O | cyclohexyl | H | 2-OMe | 0 |
| A-1995 | H | H | H | H | H | O | cyclohexyl | H | 2-OEt | 0 |
| A-1996 | H | H | H | H | H | O | cyclohexyl | H | 2-OPr | 0 |
| A-1997 | H | H | H | H | H | O | cyclohexyl | H | 2-O(i-Pr) | 0 |
| A-1998 | H | H | H | H | H | O | cyclohexyl | H | 2-OCF$_3$ | 0 |
| A-1999 | H | H | H | H | H | O | cyclohexyl | H | 2-OCHF$_2$ | 0 |
| A-2000 | H | H | H | H | H | O | cyclohexyl | H | 2-(cyclopropyloxy) | 0 |
| A-2001 | H | H | H | H | H | O | cyclohexyl | H | 2-(cyclobutyloxy) | 0 |
| A-2002 | H | H | H | H | H | O | cyclohexyl | H | 2-(cyclopentyloxy) | 0 |
| A-2003 | H | H | H | H | H | O | cyclohexyl | H | 2-((2,2-dichlorocyclopropyl)oxy) | 0 |
| A-2004 | H | H | H | H | H | O | cyclohexyl | H | 2-(oxiran-2-yl) | 0 |
| A-2005 | H | H | H | H | H | O | cyclohexyl | H | 2-SMe | 0 |
| A-2006 | H | H | H | H | H | O | cyclohexyl | H | 3-SMe | 0 |
| A-2007 | H | H | H | H | H | O | cyclohexyl | H | 2-S(=O)Me | 0 |
| A-2008 | H | H | H | H | H | O | cyclohexyl | H | 3-S(=O)Me | 0 |
| A-2009 | H | H | H | H | H | O | cyclohexyl | H | 2-S(=O)$_2$Me | 0 |
| A-2010 | H | H | H | H | H | O | cyclohexyl | H | 3-S(=O)$_2$Me | 0 |
| A-2011 | H | H | H | H | H | O | cyclohexyl | H | 2-SCF$_3$ | 0 |
| A-2012 | H | H | H | H | H | O | cyclohexyl | H | 3-SCF$_3$ | 0 |
| A-2013 | H | H | H | H | H | O | cyclohexyl | H | 3-S(=O)CF$_3$ | 0 |
| A-2014 | H | H | H | H | H | O | cyclohexyl | H | 3-SCF(CF$_3$)$_2$ | 0 |
| A-2015 | H | H | H | H | H | O | cyclohexyl | H | 2-(cyclopropylthio) | 0 |
| A-2016 | H | H | H | H | H | O | cyclohexyl | H | 2-(cyclopropylsulfinyl) | 0 |

TABLE 36-continued

| compound | R¹ | R² | R³ | R⁴ | R⁵ | A | R⁶ | R⁷ | (R⁸)ₘ | p |
|---|---|---|---|---|---|---|---|---|---|---|
| A-2017 | H | H | H | H | H | O | cyclohexyl | H | 2-(cyclopropylsulfonyl) | 0 |
| A-2018 | H | H | H | H | H | O | cyclohexyl | H | 2-C(=O)Me | 0 |
| A-2019 | H | H | H | H | H | O | cyclohexyl | H | 2-CH₂C(=O)CH₃ | 0 |
| A-2020 | H | H | H | H | H | O | cyclohexyl | H | 2-CH₂C(=O)CF₃ | 0 |
| A-2021 | H | H | H | H | H | O | cyclohexyl | H | 2-CH₂OH | 0 |
| A-2022 | H | H | H | H | H | O | cyclohexyl | H | 2-CH₂OCH₃ | 0 |
| A-2023 | H | H | H | H | H | O | cyclohexyl | H | 2-CH₂OCH₂CH₃ | 0 |
| A-2024 | H | H | H | H | H | O | cyclohexyl | H | 2-CH₂SCH₃ | 0 |
| A-2025 | H | H | H | H | H | O | cyclohexyl | H | 2-CH₂S(=O)CH₃ | 0 |
| A-2026 | H | H | H | H | H | O | cyclohexyl | H | 2-CH₂S(=O)₂CH₃ | 0 |
| A-2027 | H | H | H | H | H | O | cyclohexyl | H | 2-(benzyloxy) | 0 |
| A-2028 | H | H | H | H | H | O | cyclohexyl | H | 2-NH₂ | 0 |
| A-2029 | H | H | H | H | H | O | cyclohexyl | H | 2-NHMe | 0 |
| A-2030 | H | H | H | H | H | O | cyclohexyl | H | 2-N(Me)₂ | 0 |
| A-2031 | H | H | H | H | H | O | cyclohexyl | H | 2-(1,3-dioxolan-2-yl) | 0 |
| A-2032 | H | H | H | H | H | O | cyclohexyl | H | 2-(1,3-dioxan-2-yl) | 0 |
| A-2033 | H | H | H | H | H | O | cyclohexyl | H | 2-(1H-imidazol-2-yl) | 0 |
| A-2034 | H | H | H | H | H | O | cyclohexyl | H | 2-(thiazol-2-yl) | 0 |
| A-2035 | H | H | H | H | H | O | cyclohexyl | H | 2-(oxazol-2-yl) | 0 |
| A-2036 | H | H | H | H | H | O | cyclohexyl | H | 2-CH=NOH | 0 |
| A-2037 | H | H | H | H | H | O | cyclohexyl | H | 2-CH=NOMe | 0 |
| A-2038 | H | H | H | H | H | O | cyclohexyl | H | 2-(4,5-dihydro-3-isoxazolyl) | 0 |
| A-2039 | H | H | H | H | H | O | cyclohexyl | H | 2-CN | 0 |
| A-2040 | H | H | H | H | H | O | cyclohexyl | H | 2-NO₂ | 0 |
| A-2041 | H | H | H | H | H | O | cyclohexyl | H | 2-F,6-Cl | 0 |
| A-2042 | H | H | H | H | H | O | cyclohexyl | H | 2-F,6-Me | 0 |
| A-2043 | H | H | H | H | H | O | cyclohexyl | H | 3-F,6-Me | 0 |
| A-2044 | H | H | H | H | H | O | cyclohexyl | H | 4-F,2-Me | 0 |
| A-2045 | H | H | H | H | H | O | cyclohexyl | H | 2-F,6-OMe | 0 |
| A-2046 | H | H | H | H | H | O | cyclohexyl | H | 3-F,6-OMe | 0 |
| A-2047 | H | H | H | H | H | O | cyclohexyl | H | 2,6-Cl₂ | 0 |

TABLE 37

| compound | R¹ | R² | R³ | R⁴ | R⁵ | A | R⁶ | R⁷ | (R⁸)ₘ | p |
|---|---|---|---|---|---|---|---|---|---|---|
| A-2048 | H | H | H | H | H | O | cyclohexyl | H | 2-Cl,6-Me | 0 |
| A-2049 | H | H | H | H | H | O | cyclohexyl | H | 3-Cl,6-Me | 0 |
| A-2050 | H | H | H | H | H | O | cyclohexyl | H | 4-Cl,2-Me | 0 |
| A-2051 | H | H | H | H | H | O | cyclohexyl | H | 2-Cl,5-CF₃ | 0 |
| A-2052 | H | H | H | H | H | O | cyclohexyl | H | 2-Cl,6-CF₃ | 0 |
| A-2053 | H | H | H | H | H | O | cyclohexyl | H | 2-Cl,6-OMe | 0 |
| A-2054 | H | H | H | H | H | O | cyclohexyl | H | 3-Cl,6-OMe | 0 |
| A-2055 | H | H | H | H | H | O | cyclohexyl | H | 4-Cl,2-OMe | 0 |
| A-2056 | H | H | H | H | H | O | cyclohexyl | H | 2,4-Me₂ | 0 |
| A-2057 | H | H | H | H | H | O | cyclohexyl | H | 2,5-Me₂ | 0 |
| A-2058 | H | H | H | H | H | O | cyclohexyl | H | 2,6-Me₂ | 0 |
| A-2059 | H | H | H | H | H | O | cyclohexyl | H | 2-Me,4-CF₃ | 0 |
| A-2060 | H | H | H | H | H | O | cyclohexyl | H | 2-Me,5-CF₃ | 0 |
| A-2061 | H | H | H | H | H | O | cyclohexyl | H | 2-Me,6-CF₃ | 0 |
| A-2062 | H | H | H | H | H | O | cyclohexyl | H | 2-Me,4-OMe | 0 |
| A-2063 | H | H | H | H | H | O | cyclohexyl | H | 2-Me,5-OMe | 0 |
| A-2064 | H | H | H | H | H | O | cyclohexyl | H | 2-Me,6-OMe | 0 |
| A-2065 | H | H | H | H | H | O | cyclohexyl | H | 3-Me,6-OMe | 0 |
| A-2066 | H | H | H | H | H | O | cyclohexyl | H | 4-Me,2-OMe | 0 |
| A-2067 | H | H | H | H | H | O | cyclohexyl | H | 2,5-OMe₂ | 0 |
| A-2068 | H | H | H | H | H | O | cyclohexyl | H | 2,6-OMe₂ | 0 |
| A-2069 | H | H | H | H | H | O | cyclohexyl | H | 2-OMe,6-CF₃ | 0 |
| A-2070 | H | H | H | H | H | O | cyclohexyl | H | 2-CHF₂,5-F | 0 |
| A-2071 | H | H | H | H | H | O | cyclohexyl | H | 2-CHF₂,6-F | 0 |
| A-2072 | H | H | H | H | H | O | cyclohexyl | H | 2-CHF₂,5-Me | 0 |
| A-2073 | H | H | H | H | H | O | cyclohexyl | H | 2-CHF₂,6-Me | 0 |
| A-2074 | H | H | H | H | H | O | cyclohexyl | H | 2-cyclopropyl,5-F | 0 |
| A-2075 | H | H | H | H | H | O | cyclohexyl | H | 2-cyclopropyl,6-F | 0 |
| A-2076 | H | H | H | H | H | O | cyclohexyl | H | 2-cyclopropyl,5-Me | 0 |
| A-2077 | H | H | H | H | H | O | cyclohexyl | H | 2-cyclopropyl,6-Me | 0 |
| A-2078 | H | H | H | H | H | O | cyclohexyl | H | 2-ethenyl,6-F | 0 |
| A-2079 | H | H | H | H | H | O | cyclohexyl | H | 2-ethenyl,6-Me | 0 |
| A-2080 | H | H | H | H | H | O | cyclohexyl | H | 2-OEt,5-F | 0 |
| A-2081 | H | H | H | H | H | O | cyclohexyl | H | 2-OEt,6-F | 0 |
| A-2082 | H | H | H | H | H | O | cyclohexyl | H | 2-OEt,5-Cl | 0 |
| A-2083 | H | H | H | H | H | O | cyclohexyl | H | 2-OEt,6-Cl | 0 |
| A-2084 | H | H | H | H | H | O | cyclohexyl | H | 2-OEt,5-Me | 0 |
| A-2085 | H | H | H | H | H | O | cyclohexyl | H | 2-OEt,6-Me | 0 |
| A-2086 | H | H | H | H | H | O | cyclohexyl | H | 2-OCHF₂,5-F | 0 |

TABLE 37-continued

| compound | R¹ | R² | R³ | R⁴ | R⁵ | A | R⁶ | R⁷ | (R⁸)$_m$ | p |
|---|---|---|---|---|---|---|---|---|---|---|
| A-2087 | H | H | H | H | H | O | cyclohexyl | H | 2-OCHF$_2$,6-F | 0 |
| A-2088 | H | H | H | H | H | O | cyclohexyl | H | 2-OCHF$_2$,5-Me | 0 |
| A-2089 | H | H | H | H | H | O | cyclohexyl | H | 2-OCHF$_2$,6-Me | 0 |
| A-2090 | H | H | H | H | H | O | cyclohexyl | H | 2-(cyclopropyloxy),5-F | 0 |
| A-2091 | H | H | H | H | H | O | cyclohexyl | H | 2-(cyclopropyloxy),6-F | 0 |
| A-2092 | H | H | H | H | H | O | cyclohexyl | H | 2-(cyclopropyloxy),5-Me | 0 |
| A-2093 | H | H | H | H | H | O | cyclohexyl | H | 2-(cyclopropyloxy),6-Me | 0 |
| A-2094 | H | H | H | H | H | O | cyclohexyl | H | 2-SMe,5-F | 0 |
| A-2095 | H | H | H | H | H | O | cyclohexyl | H | 2-SMe,6-F | 0 |
| A-2096 | H | H | H | H | H | O | cyclohexyl | H | 2-SMe,5-Me | 0 |
| A-2097 | H | H | H | H | H | O | cyclohexyl | H | 2-SMe,6-Me | 0 |
| A-2098 | H | H | H | H | H | O | cyclohexyl | H | 2-S(=O)Me,5-F | 0 |
| A-2099 | H | H | H | H | H | O | cyclohexyl | H | 2-S(=O)Me,6-F | 0 |
| A-2100 | H | H | H | H | H | O | cyclohexyl | H | 2-S(=O)Me,5-Me | 0 |
| A-2101 | H | H | H | H | H | O | cyclohexyl | H | 2-S(=O)Me,6-Me | 0 |
| A-2102 | H | H | H | H | H | O | cyclohexyl | H | 2-S(=O)$_2$Me,5-F | 0 |
| A-2103 | H | H | H | H | H | O | cyclohexyl | H | 2-S(=O)$_2$Me,6-F | 0 |
| A-2104 | H | H | H | H | H | O | cyclohexyl | H | 2-S(=O)$_2$Me,5-Me | 0 |

TABLE 38

| compound | R¹ | R² | R³ | R⁴ | R⁵ | A | R⁶ | R⁷ | (R⁸)$_m$ | p |
|---|---|---|---|---|---|---|---|---|---|---|
| A-2105 | H | H | H | H | H | O | cyclohexyl | H | 2-S(=O)$_2$Me,6-Me | 0 |
| A-2106 | H | H | H | H | H | O | cyclohexyl | H | 2-SCF$_3$,5-F | 0 |
| A-2107 | H | H | H | H | H | O | cyclohexyl | H | 2-SCF$_3$,6-F | 0 |
| A-2108 | H | H | H | H | H | O | cyclohexyl | H | 2-SCF$_3$,5-Me | 0 |
| A-2109 | H | H | H | H | H | O | cyclohexyl | H | 2-SCF$_3$,6-Me | 0 |
| A-2110 | H | H | H | H | H | O | cyclohexyl | H | 2-S(=O)CF$_3$,5-F | 0 |
| A-2111 | H | H | H | H | H | O | cyclohexyl | H | 2-S(=O)CF$_3$,6-F | 0 |
| A-2112 | H | H | H | H | H | O | cyclohexyl | H | 2-S(=O)CF$_3$,5-Me | 0 |
| A-2113 | H | H | H | H | H | O | cyclohexyl | H | 2-S(=O)CF$_3$,6-Me | 0 |
| A-2114 | H | H | H | H | H | O | cyclohexyl | H | 2-S(=O)$_2$CF$_3$,5-F | 0 |
| A-2115 | H | H | H | H | H | O | cyclohexyl | H | 2-S(=O)$_2$CF$_3$,6-F | 0 |
| A-2116 | H | H | H | H | H | O | cyclohexyl | H | 2-S(=O)$_2$CF$_3$,5-Me | 0 |
| A-2117 | H | H | H | H | H | O | cyclohexyl | H | 2-S(=O)$_2$CF$_3$,6-Me | 0 |
| A-2118 | H | H | H | H | H | O | cyclohexyl | H | 2-(cyclopropylthio),5-F | 0 |
| A-2119 | H | H | H | H | H | O | cyclohexyl | H | 2-(cyclopropylthio),6-F | 0 |
| A-2120 | H | H | H | H | H | O | cyclohexyl | H | 2-(cyclopropylthio),5-Me | 0 |
| A-2121 | H | H | H | H | H | O | cyclohexyl | H | 2-(cyclopropylthio),6-Me | 0 |
| A-2122 | H | H | H | H | H | O | cyclohexyl | H | 2-C(=O)Me,5-F | 0 |
| A-2123 | H | H | H | H | H | O | cyclohexyl | H | 2-C(=O)Me,6-F | 0 |
| A-2124 | H | H | H | H | H | O | cyclohexyl | H | 2-C(=O)Me,5-Me | 0 |
| A-2125 | H | H | H | H | H | O | cyclohexyl | H | 2-C(=O)Me,6-Me | 0 |
| A-2126 | H | H | H | H | H | O | cyclohexyl | H | 2-CH$_2$OH,5-F | 0 |
| A-2127 | H | H | H | H | H | O | cyclohexyl | H | 2-CH$_2$OH,6-F | 0 |
| A-2128 | H | H | H | H | H | O | cyclohexyl | H | 2-CH$_2$OH,5-Me | 0 |
| A-2129 | H | H | H | H | H | O | cyclohexyl | H | 2-CH$_2$OH,6-Me | 0 |
| A-2130 | H | H | H | H | H | O | cyclohexyl | H | 2-CH$_2$OCH$_3$,4-F | 0 |
| A-2131 | H | H | H | H | H | O | cyclohexyl | H | 2-CH$_2$OCH$_3$,5-F | 0 |
| A-2132 | H | H | H | H | H | O | cyclohexyl | H | 2-CH$_2$OCH$_3$,6-F | 0 |
| A-2133 | H | H | H | H | H | O | cyclohexyl | H | 2-CH$_2$OCH$_3$,4-Me | 0 |
| A-2134 | H | H | H | H | H | O | cyclohexyl | H | 2-CH$_2$OCH$_3$,5-Me | 0 |
| A-2135 | H | H | H | H | H | O | cyclohexyl | H | 2-CH$_2$OCH$_3$,6-Me | 0 |
| A-2136 | H | H | H | H | H | O | cyclohexyl | H | 2-OC(=O)CH$_3$,5-F | 0 |
| A-2137 | H | H | H | H | H | O | cyclohexyl | H | 2-OC(=O)CH$_3$,6-F | 0 |
| A-2138 | H | H | H | H | H | O | cyclohexyl | H | 2-OC(=O)CH$_3$,5-Me | 0 |
| A-2139 | H | H | H | H | H | O | cyclohexyl | H | 2-OC(=O)CH$_3$,6-Me | 0 |
| A-2140 | H | H | H | H | H | O | cyclohexyl | H | 2-OS(=O)$_2$CH$_3$,5-F | 0 |
| A-2141 | H | H | H | H | H | O | cyclohexyl | H | 2-OS(=O)$_2$CH$_3$,6-F | 0 |
| A-2142 | H | H | H | H | H | O | cyclohexyl | H | 2-OS(=O)$_2$CH$_3$,5-Me | 0 |
| A-2143 | H | H | H | H | H | O | cyclohexyl | H | 2-OS(=O)$_2$CH$_3$,6-Me | 0 |
| A-2144 | H | H | H | H | H | O | cyclohexyl | H | 2-CH$_2$SCH$_3$,5-F | 0 |
| A-2145 | H | H | H | H | H | O | cyclohexyl | H | 2-CH$_2$SCH$_3$,6-F | 0 |
| A-2146 | H | H | H | H | H | O | cyclohexyl | H | 2-CH$_2$SCH$_3$,5-Me | 0 |
| A-2147 | H | H | H | H | H | O | cyclohexyl | H | 2-CH$_2$SCH$_3$,6-Me | 0 |
| A-2148 | H | H | H | H | H | O | cyclohexyl | H | 2-NMe$_2$,5-F | 0 |
| A-2149 | H | H | H | H | H | O | cyclohexyl | H | 2-NMe$_2$,6-F | 0 |
| A-2150 | H | H | H | H | H | O | cyclohexyl | H | 2-NMe$_2$,5-Me | 0 |
| A-2151 | H | H | H | H | H | O | cyclohexyl | H | 2-NMe$_2$,6-Me | 0 |
| A-2152 | H | H | H | H | H | O | cyclohexyl | H | 2-CN,4-F | 0 |
| A-2153 | H | H | H | H | H | O | cyclohexyl | H | 2-CN,5-F | 0 |
| A-2154 | H | H | H | H | H | O | cyclohexyl | H | 2-CN,6-F | 0 |
| A-2155 | H | H | H | H | H | O | cyclohexyl | H | 2-CN,6-Me | 0 |
| A-2156 | H | H | H | H | H | O | cyclohexyl | H | 2-CN,5-OMe | 0 |

TABLE 38-continued

| compound | R¹ | R² | R³ | R⁴ | R⁵ | A | R⁶ | R⁷ | (R⁸)ₘ | p |
|---|---|---|---|---|---|---|---|---|---|---|
| A-2157 | H | H | H | H | H | O | cyclohexyl | H | 2-CN,6-OMe | 0 |
| A-2158 | H | H | H | H | H | O | cyclohexyl | H | 3-CN,6-Me | 0 |
| A-2159 | H | H | H | H | H | O | cyclohexyl | H | 3-CN,6-OMe | 0 |
| A-2160 | H | H | H | H | H | O | cyclohexyl | H | 4-CN,2-Me | 0 |
| A-2161 | H | H | H | H | H | O | cyclohexyl | H | 4-CN,2-OMe | 0 |

TABLE 39

| compound | R¹ | R² | R³ | R⁴ | R⁵ | A | R⁶ | R⁷ | (R⁸)ₘ | p |
|---|---|---|---|---|---|---|---|---|---|---|
| A-2162 | H | H | H | H | H | O | cyclohexyl | H | 2-NO$_2$,4-F | 0 |
| A-2163 | H | H | H | H | H | O | cyclohexyl | H | 2-NO$_2$,5-F | 0 |
| A-2164 | H | H | H | H | H | O | cyclohexyl | H | 2-NO$_2$,6-F | 0 |
| A-2165 | H | H | H | H | H | O | cyclohexyl | H | 2-NO$_2$,4-Me | 0 |
| A-2166 | H | H | H | H | H | O | cyclohexyl | H | 2-NO$_2$,5-Me | 0 |
| A-2167 | H | H | H | H | H | O | cyclohexyl | H | 2-NO$_2$,6-Me | 0 |
| A-2168 | H | H | H | H | H | O | cyclohexyl | H | 2-Me,4,5-F$_2$ | 0 |
| A-2169 | H | H | H | H | H | O | cyclohexyl | H | 2-Me,6-Et | 0 |
| A-2170 | H | H | H | H | H | O | cyclohexyl | H | 2-cyclopropyl,6-OMe | 0 |
| A-2171 | H | H | H | H | H | O | cyclohexyl | H | 2-Me,5-Et | 0 |
| A-2172 | H | H | H | H | H | O | cyclohexyl | H | 2,6-Et$_2$ | 0 |
| A-2173 | H | H | H | H | H | O | cyclohexyl | H | 2-Et,6-F | 0 |
| A-2174 | H | H | H | H | H | O | cyclohexyl | H | 2-CH$_2$OCH$_3$,6-Cl | 0 |
| A-2175 | H | H | H | H | H | O | cyclohexyl | H | 2-CH$_2$OCH$_2$CH$_3$,6-Cl | 0 |
| A-2176 | H | H | H | H | H | O | cyclohexyl | H | 2-CH$_2$NMe$_2$ | 0 |
| A-2177 | H | H | H | H | H | O | allyl | H | H | 0 |
| A-2178 | H | H | H | H | H | O | allyl | H | 2-F | 0 |
| A-2179 | H | H | H | H | H | O | allyl | H | 2-C | 0 |
| A-2180 | H | H | H | H | H | O | allyl | H | 2-Br | 0 |
| A-2181 | H | H | H | H | H | O | allyl | H | 2-OH | 0 |
| A-2182 | H | H | H | H | H | O | allyl | H | 2-Me | 0 |
| A-2183 | H | H | H | H | H | O | allyl | H | 2-Et | 0 |
| A-2184 | H | H | H | H | H | O | allyl | H | 2-Pr | 0 |
| A-2185 | H | H | H | H | H | O | allyl | H | 2-CF$_3$ | 0 |
| A-2186 | H | H | H | H | H | O | allyl | H | 2-CHF$_2$ | 0 |
| A-2187 | H | H | H | H | H | O | allyl | H | 2-CH$_2$F | 0 |
| A-2188 | H | H | H | H | H | O | allyl | H | 2-CF$_2$Cl | 0 |
| A-2189 | H | H | H | H | H | O | allyl | H | 2-cyclopropyl | 0 |
| A-2190 | H | H | H | H | H | O | allyl | H | 2-cyclobutyl | 0 |
| A-2191 | H | H | H | H | H | O | allyl | H | 2-cyclopentyl | 0 |
| A-2192 | H | H | H | H | H | O | allyl | H | 2-ethenyl | 0 |
| A-2193 | H | H | H | H | H | O | allyl | H | 2-allyl | 0 |
| A-2194 | H | H | H | H | H | O | allyl | H | 2-(prop-1-en-1-yl) | 0 |
| A-2195 | H | H | H | H | H | O | allyl | H | 2-(trifluorothenyl) | 0 |
| A-2196 | H | H | H | H | H | O | allyl | H | 2-OMe | 0 |
| A-2197 | H | H | H | H | H | O | allyl | H | 2-OEt | 0 |
| A-2198 | H | H | H | H | H | O | allyl | H | 2-OPr | 0 |
| A-2199 | H | H | H | H | H | O | allyl | H | 2-O(i-Pr) | 0 |
| A-2200 | H | H | H | H | H | O | allyl | H | 2-OCF$_3$ | 0 |
| A-2201 | H | H | H | H | H | O | allyl | H | 2-OCHF$_2$ | 0 |
| A-2202 | H | H | H | H | H | O | allyl | H | 2-(cyclopropyloxy) | 0 |
| A-2203 | H | H | H | H | H | O | allyl | H | 2-(cyclobutyloxy) | 0 |
| A-2204 | H | H | H | H | H | O | allyl | H | 2-(cyclopentyloxy) | 0 |
| A-2205 | H | H | H | H | H | O | allyl | H | 2-((2,2-dichlorocyclopropyl)oxy) | 0 |
| A-2206 | H | H | H | H | H | O | allyl | H | 2-(oxiran-2-yl) | 0 |
| A-2207 | H | H | H | H | H | O | allyl | H | 2-SMe | 0 |
| A-2208 | H | H | H | H | H | O | allyl | H | 3-SMe | 0 |
| A-2209 | H | H | H | H | H | O | allyl | H | 2-S(=O)Me | 0 |
| A-2210 | H | H | H | H | H | O | allyl | H | 3-S(=O)Me | 0 |
| A-2211 | H | H | H | H | H | O | allyl | H | 2-S(=O)$_2$Me | 0 |
| A-2212 | H | H | H | H | H | O | allyl | H | 3-S(=O)$_2$Me | 0 |
| A-2213 | H | H | H | H | H | O | allyl | H | 2-SCF$_3$ | 0 |
| A-2214 | H | H | H | H | H | O | allyl | H | 3-SCF$_3$ | 0 |
| A-2215 | H | H | H | H | H | O | allyl | H | 3-S(=O)CF$_3$ | 0 |
| A-2216 | H | H | H | H | H | O | allyl | H | 3-SCF(CF$_3$)$_2$ | 0 |
| A-2217 | H | H | H | H | H | O | allyl | H | 2-(cyclopropylthio) | 0 |
| A-2218 | H | H | H | H | H | O | allyl | H | 2-(cyclopropylsulfinyl) | 0 |

TABLE 40

| compound | R¹ | R² | R³ | R⁴ | R⁵ | A | R⁶ | R⁷ | (R⁸)$_m$ | p |
|---|---|---|---|---|---|---|---|---|---|---|
| A-2219 | H | H | H | H | H | O | allyl | H | 2-(cyclopropylsulfonyl) | 0 |
| A-2220 | H | H | H | H | H | O | allyl | H | 2-C(=O)Me | 0 |
| A-2221 | H | H | H | H | H | O | allyl | H | 2-CH$_2$C(=O)CH$_3$ | 0 |
| A-2222 | H | H | H | H | H | O | allyl | H | 2-CH$_2$C(=O)CF$_3$ | 0 |
| A-2223 | H | H | H | H | H | O | allyl | H | 2-CH$_2$OH | 0 |
| A-2224 | H | H | H | H | H | O | allyl | H | 2-CH$_2$OCH$_3$ | 0 |
| A-2225 | H | H | H | H | H | O | allyl | H | 2-CH$_2$OCH$_2$CH$_3$ | 0 |
| A-2226 | H | H | H | H | H | O | allyl | H | 2-CH$_2$SCH$_3$ | 0 |
| A-2227 | H | H | H | H | H | O | allyl | H | 2-CH$_2$S(=O)CH$_3$ | 0 |
| A-2228 | H | H | H | H | H | O | allyl | H | 2-CH$_2$S(=O)$_2$CH$_3$ | 0 |
| A-2229 | H | H | H | H | H | O | allyl | H | 2-(benzyloxy) | 0 |
| A-2230 | H | H | H | H | H | O | allyl | H | 2-NH$_2$ | 0 |
| A-2231 | H | H | H | H | H | O | allyl | H | 2-NHMe | 0 |
| A-2232 | H | H | H | H | H | O | allyl | H | 2-N(Me)$_2$ | 0 |
| A-2233 | H | H | H | H | H | O | allyl | H | 2-(1,3-ioxolan-2-yl) | 0 |
| A-2234 | H | H | H | H | H | O | allyl | H | 2-(1,3-dioxan-2-yl) | 0 |
| A-2235 | H | H | H | H | H | O | allyl | H | 2-(1H-imidazol-2-yl) | 0 |
| A-2236 | H | H | H | H | H | O | allyl | H | 2-(thizol-2-yl) | 0 |
| A-2237 | H | H | H | H | H | O | allyl | H | 2-(oxazol-2-yl) | 0 |
| A-2238 | H | H | H | H | H | O | allyl | H | 2-CH=NOH | 0 |
| A-2239 | H | H | H | H | H | O | allyl | H | 2-CH=NOMe | 0 |
| A-2240 | H | H | H | H | H | O | allyl | H | 2-(4,5-dihydro-3-isoxazolyl) | 0 |
| A-2241 | H | H | H | H | H | O | allyl | H | 2-CN | 0 |
| A-2242 | H | H | H | H | H | O | allyl | H | 2-NO$_2$ | 0 |
| A-2243 | H | H | H | H | H | O | allyl | H | 2-F,6-Cl | 0 |
| A-2244 | H | H | H | H | H | O | allyl | H | 2-F,6-Me | 0 |
| A-2245 | H | H | H | H | H | O | allyl | H | 3-F,6-Me | 0 |
| A-2246 | H | H | H | H | H | O | allyl | H | 4-F,2-Me | 0 |
| A-2247 | H | H | H | H | H | O | allyl | H | 2-F,6-OMe | 0 |
| A-2248 | H | H | H | H | H | O | allyl | H | 3-F,6-OMe | 0 |
| A-2249 | H | H | H | H | H | O | allyl | H | 2,6-Cl | 0 |
| A-2250 | H | H | H | H | H | O | allyl | H | 2-Cl,6-Me | 0 |
| A-2251 | H | H | H | H | H | O | allyl | H | 3-Cl,6-Me | 0 |
| A-2252 | H | H | H | H | H | O | allyl | H | 4-Cl,2-Me | 0 |
| A-2253 | H | H | H | H | H | O | allyl | H | 2-Cl,5-CF$_3$ | 0 |
| A-2254 | H | H | H | H | H | O | allyl | H | 2-Cl,6-CF$_3$ | 0 |
| A-2255 | H | H | H | H | H | O | allyl | H | 2-Cl,6-OMe | 0 |
| A-2256 | H | H | H | H | H | O | allyl | H | 3-Cl,6-OMe | 0 |
| A-2257 | H | H | H | H | H | O | allyl | H | 4-Cl,2-OMe | 0 |
| A-2258 | H | H | H | H | H | O | allyl | H | 2,4-Me$_2$ | 0 |
| A-2259 | H | H | H | H | H | O | allyl | H | 2,5-Me$_2$ | 0 |
| A-2260 | H | H | H | H | H | O | allyl | H | 2,6-Me$_2$ | 0 |
| A-2261 | H | H | H | H | H | O | allyl | H | 2-Me,4-CF$_3$ | 0 |
| A-2262 | H | H | H | H | H | O | allyl | H | 2-Me,5-CF$_3$ | 0 |
| A-2263 | H | H | H | H | H | O | allyl | H | 2-Me,6-CF$_3$ | 0 |
| A-2264 | H | H | H | H | H | O | allyl | H | 2-Me,4-OMe | 0 |
| A-2265 | H | H | H | H | H | O | allyl | H | 2-Me,5-OMe | 0 |
| A-2266 | H | H | H | H | H | O | allyl | H | 2-Me,6-OMe | 0 |
| A-2267 | H | H | H | H | H | O | allyl | H | 3-Me,6-OMe | 0 |
| A-2268 | H | H | H | H | H | O | allyl | H | 4-Me,2-OMe | 0 |
| A-2269 | H | H | H | H | H | O | allyl | H | 2,5-OMe$_2$ | 0 |
| A-2270 | H | H | H | H | H | O | allyl | H | 2,6-OMe$_2$ | 0 |
| A-2271 | H | H | H | H | H | O | allyl | H | 2-OMe,6-CF$_3$ | 0 |
| A-2272 | H | H | H | H | H | O | allyl | H | 2-CHF$_2$,5-F | 0 |
| A-2273 | H | H | H | H | H | O | allyl | H | 2-CHF$_2$,6-F | 0 |
| A-2274 | H | H | H | H | H | O | allyl | H | 2-CHF$_2$,5-Me | 0 |
| A-2275 | H | H | H | H | H | O | allyl | H | 2-CHF$_2$,6-Me | 0 |

TABLE 41

| compound | R¹ | R² | R³ | R⁴ | R⁵ | A | R⁶ | R⁷ | (R⁸)$_m$ | p |
|---|---|---|---|---|---|---|---|---|---|---|
| A-2276 | H | H | H | H | H | O | allyl | H | 2-cyclopropyl,5-F | 0 |
| A-2277 | H | H | H | H | H | O | allyl | H | 2-cyclopropyl,6-F | 0 |
| A-2278 | H | H | H | H | H | O | allyl | H | 2-cyclopropyl,5-Me | 0 |
| A-2279 | H | H | H | H | H | O | allyl | H | 2-cyclopropyl,6-Me | 0 |
| A-2280 | H | H | H | H | H | O | allyl | H | 2-ethenyl,6-F | 0 |
| A-2281 | H | H | H | H | H | O | allyl | H | 2-ethenyl,6-Me | 0 |
| A-2282 | H | H | H | H | H | O | allyl | H | 2-OEt,5-F | 0 |
| A-2283 | H | H | H | H | H | O | allyl | H | 2-OEt,6-F | 0 |
| A-2284 | H | H | H | H | H | O | allyl | H | 2-OEt,5-Cl | 0 |
| A-2285 | H | H | H | H | H | O | allyl | H | 2-OEt,6-Cl | 0 |
| A-2286 | H | H | H | H | H | O | allyl | H | 2-OEt,5-Me | 0 |
| A-2287 | H | H | H | H | H | O | allyl | H | 2-OEt,6-Me | 0 |
| A-2288 | H | H | H | H | H | O | allyl | H | 2-OCHF$_2$,5-F | 0 |

TABLE 41-continued

| compound | R¹ | R² | R³ | R⁴ | R⁵ | A | R⁶ | R⁷ | (R⁸)ₘ | p |
|---|---|---|---|---|---|---|---|---|---|---|
| A-2289 | H | H | H | H | H | O | allyl | H | 2-OCHF$_2$,6-F | 0 |
| A-2290 | H | H | H | H | H | O | allyl | H | 2-OCHF$_2$,5-Me | 0 |
| A-2291 | H | H | H | H | H | O | allyl | H | 2-OCHF$_2$,6-Me | 0 |
| A-2292 | H | H | H | H | H | O | allyl | H | 2-(cyclopropyloxy),5-F | 0 |
| A-2293 | H | H | H | H | H | O | allyl | H | 2-(cyclopropyloxy),6-F | 0 |
| A-2294 | H | H | H | H | H | O | allyl | H | 2-(cyclopropyloxy),5-Me | 0 |
| A-2295 | H | H | H | H | H | O | allyl | H | 2-(cyclopropyloxy),6-Me | 0 |
| A-2296 | H | H | H | H | H | O | allyl | H | 2-SMe,5-F | 0 |
| A-2297 | H | H | H | H | H | O | allyl | H | 2-SMe,6-F | 0 |
| A-2298 | H | H | H | H | H | O | allyl | H | 2-SMe,5-Me | 0 |
| A-2299 | H | H | H | H | H | O | allyl | H | 2-SMe,6-Me | 0 |
| A-2300 | H | H | H | H | H | O | allyl | H | 2-S(=O)Me,5-F | 0 |
| A-2301 | H | H | H | H | H | O | allyl | H | 2-S(=O)Me,6-F | 0 |
| A-2302 | H | H | H | H | H | O | allyl | H | 2-S(=O)Me,5-Me | 0 |
| A-2303 | H | H | H | H | H | O | allyl | H | 2-S(=O)Me,6-Me | 0 |
| A-2304 | H | H | H | H | H | O | allyl | H | 2-S(=O)$_2$Me,5-F | 0 |
| A-2305 | H | H | H | H | H | O | allyl | H | 2-S(=O)$_2$Me,6-F | 0 |
| A-2306 | H | H | H | H | H | O | allyl | H | 2-S(=O)$_2$Me,5-Me | 0 |
| A-2307 | H | H | H | H | H | O | allyl | H | 2-S(=O)$_2$Me,6-Me | 0 |
| A-2308 | H | H | H | H | H | O | allyl | H | 2-SCF$_3$,5-F | 0 |
| A-2309 | H | H | H | H | H | O | allyl | H | 2-SCF$_3$,6-F | 0 |
| A-2310 | H | H | H | H | H | O | allyl | H | 2-SCF$_3$,5-Me | 0 |
| A-2311 | H | H | H | H | H | O | allyl | H | 2-SCF$_3$,6-Me | 0 |
| A-2312 | H | H | H | H | H | O | allyl | H | 2-S(=O)CF$_3$,5-F | 0 |
| A-2313 | H | H | H | H | H | O | allyl | H | 2-S(=O)CF$_3$,6-F | 0 |
| A-2314 | H | H | H | H | H | O | allyl | H | 2-S(=O)CF$_3$,5-Me | 0 |
| A-2315 | H | H | H | H | H | O | allyl | H | 2-S(=O)CF$_3$,6-Me | 0 |
| A-2316 | H | H | H | H | H | O | allyl | H | 2-S(=O)$_2$CF$_3$,5-F | 0 |
| A-2317 | H | H | H | H | H | O | allyl | H | 2-S(=O)$_2$CF$_3$,6-F | 0 |
| A-2318 | H | H | H | H | H | O | allyl | H | 2-S(=O)$_2$CF$_3$,5-Me | 0 |
| A-2319 | H | H | H | H | H | O | allyl | H | 2-S(=O)$_2$CF$_3$,6-Me | 0 |
| A-2320 | H | H | H | H | H | O | allyl | H | 2-(cyclopropylthio),5-F | 0 |
| A-2321 | H | H | H | H | H | O | allyl | H | 2-(cyclopropylthio),6-F | 0 |
| A-2322 | H | H | H | H | H | O | allyl | H | 2-(cyclopropylthio),5-Me | 0 |
| A-2323 | H | H | H | H | H | O | allyl | H | 2-(cyclopropylthio),6-Me | 0 |
| A-2324 | H | H | H | H | H | O | allyl | H | 2-C(=O)Me,5-F | 0 |
| A-2325 | H | H | H | H | H | O | allyl | H | 2-C(=O)Me,6-F | 0 |
| A-2326 | H | H | H | H | H | O | allyl | H | 2-C(=O)Me,5-Me | 0 |
| A-2327 | H | H | H | H | H | O | allyl | H | 2-C(=O)Me,6-Me | 0 |
| A-2328 | H | H | H | H | H | O | allyl | H | 2-CH$_2$OH,5-F | 0 |
| A-2329 | H | H | H | H | H | O | allyl | H | 2-CH$_2$OH,6-F | 0 |
| A-2330 | H | H | H | H | H | O | allyl | H | 2-CH$_2$OH,5-Me | 0 |
| A-2331 | H | H | H | H | H | O | allyl | H | 2-CH$_2$OH,6-Me | 0 |
| A-2332 | H | H | H | H | H | O | allyl | H | 2-CH$_2$OCH$_3$,4-F | 0 |

TABLE 42

| compound | R¹ | R² | R³ | R⁴ | R⁵ | A | R⁶ | R⁷ | (R⁸)ₘ | p |
|---|---|---|---|---|---|---|---|---|---|---|
| A-2333 | H | H | H | H | H | O | allyl | H | 2-CH$_2$OCH$_3$,5-F | 0 |
| A-2334 | H | H | H | H | H | O | allyl | H | 2-CH$_2$OCH$_3$,6-F | 0 |
| A-2335 | H | H | H | H | H | O | allyl | H | 2-CH$_2$OCH$_3$,4-Me | 0 |
| A-2336 | H | H | H | H | H | O | allyl | H | 2-CH$_2$OCH$_3$,5-Me | 0 |
| A-2337 | H | H | H | H | H | O | allyl | H | 2-CH$_2$OCH$_3$,6-Me | 0 |
| A-2338 | H | H | H | H | H | O | allyl | H | 2-OC(=O)CH$_3$,5-F | 0 |
| A-2339 | H | H | H | H | H | O | allyl | H | 2-OC(=O)CH$_3$,6-F | 0 |
| A-2340 | H | H | H | H | H | O | allyl | H | 2-OC(=O)CH$_3$,5-Me | 0 |
| A-2341 | H | H | H | H | H | O | allyl | H | 2-OC(=O)CH$_3$,6-Me | 0 |
| A-2342 | H | H | H | H | H | O | allyl | H | 2-OS(=O)$_2$CH$_3$,5-F | 0 |
| A-2343 | H | H | H | H | H | O | allyl | H | 2-OS(=O)$_2$CH$_3$,6-F | 0 |
| A-2344 | H | H | H | H | H | O | allyl | H | 2-OS(=O)$_2$CH$_3$,5-Me | 0 |
| A-2345 | H | H | H | H | H | O | allyl | H | 2-OS(=O)$_2$CH$_3$,6-Me | 0 |
| A-2346 | H | H | H | H | H | O | allyl | H | 2-CH$_2$SCH$_3$,5-F | 0 |
| A-2347 | H | H | H | H | H | O | allyl | H | 2-CH$_2$SCH$_3$,6-F | 0 |
| A-2348 | H | H | H | H | H | O | allyl | H | 2-CH$_2$SCH$_3$,5-Me | 0 |
| A-2349 | H | H | H | H | H | O | allyl | H | 2-CH$_2$SCH$_3$,6-Me | 0 |
| A-2350 | H | H | H | H | H | O | allyl | H | 2-NMe$_2$,5-F | 0 |
| A-2351 | H | H | H | H | H | O | allyl | H | 2-NMe$_2$,6-F | 0 |
| A-2352 | H | H | H | H | H | O | allyl | H | 2-NMe$_2$,5-Me | 0 |
| A-2353 | H | H | H | H | H | O | allyl | H | 2-NMe$_2$,6-Me | 0 |
| A-2354 | H | H | H | H | H | O | allyl | H | 2-CN,4-F | 0 |
| A-2355 | H | H | H | H | H | O | allyl | H | 2-CN,5-F | 0 |
| A-2356 | H | H | H | H | H | O | allyl | H | 2-CN,6-F | 0 |
| A-2357 | H | H | H | H | H | O | allyl | H | 2-CN,6-Me | 0 |
| A-2358 | H | H | H | H | H | O | allyl | H | 2-CN,5-OMe | 0 |

TABLE 42-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-2359 | H | H | H | H | H | O | allyl | H | 2-CN,6-OMe | 0 |
| A-2360 | H | H | H | H | H | O | allyl | H | 3-CN,6-Me | 0 |
| A-2361 | H | H | H | H | H | O | allyl | H | 3-CN,6-OMe | 0 |
| A-2362 | H | H | H | H | H | O | allyl | H | 4-CN,2-Me | 0 |
| A-2363 | H | H | H | H | H | O | allyl | H | 4-CN,2-OMe | 0 |
| A-2364 | H | H | H | H | H | O | allyl | H | 2-NO$_2$,4-F | 0 |
| A-2365 | H | H | H | H | H | O | allyl | H | 2-NO$_2$,5-F | 0 |
| A-2366 | H | H | H | H | H | O | allyl | H | 2-NO$_2$,6-F | 0 |
| A-2367 | H | H | H | H | H | O | allyl | H | 2-NO$_2$,4-Me | 0 |
| A-2368 | H | H | H | H | H | O | allyl | H | 2-NO$_2$,5-Me | 0 |
| A-2369 | H | H | H | H | H | O | allyl | H | 2-NO$_2$,6-Me | 0 |
| A-2370 | H | H | H | H | H | O | allyl | H | 2-Me,4,5-F$_2$ | 0 |
| A-2371 | H | H | H | H | H | O | allyl | H | 2-Me,6-Et | 0 |
| A-2372 | H | H | H | H | H | O | allyl | H | 2-cyclopropyl,6-OMe | 0 |
| A-2373 | H | H | H | H | H | O | allyl | H | 2-Me,5-Et | 0 |
| A-2374 | H | H | H | H | H | O | allyl | H | 2,6-Et$_2$ | 0 |
| A-2375 | H | H | H | H | H | O | allyl | H | 2-Et,6-F | 0 |
| A-2376 | H | H | H | H | H | O | allyl | H | 2-CH$_2$OCH$_3$,6-Cl | 0 |
| A-2377 | H | H | H | H | H | O | allyl | H | 2-CH$_2$OCH$_2$CH$_3$,6-Cl | 0 |
| A-2378 | H | H | H | H | H | O | allyl | H | 2-CH$_2$NMe$_2$ | 0 |
| A-2379 | H | H | H | H | H | O | 1-cyclohexylethyl | H | H | 0 |
| A-2380 | H | H | H | H | H | O | 1-cyclohexylethyl | H | 2-F | 0 |
| A-2381 | H | H | H | H | H | O | 1-cyclohexylethyl | H | 2-Cl | 0 |
| A-2382 | H | H | H | H | H | O | 1-cyclohexylethyl | H | 2-Br | 0 |
| A-2383 | H | H | H | H | H | O | 1-cyclohexylethyl | H | 2-OH | 0 |
| A-2384 | H | H | H | H | H | O | 1-cyclohexylethyl | H | 2-Me | 0 |
| A-2385 | H | H | H | H | H | O | 1-cyclohexylethyl | H | 2-Et | 0 |
| A-2386 | H | H | H | H | H | O | 1-cyclohexylethyl | H | 2-Pr | 0 |
| A-2387 | H | H | H | H | H | O | 1-cyclohexylethyl | H | 2-CF$_3$ | 0 |
| A-2388 | H | H | H | H | H | O | 1-cyclohexylethyl | H | 2-CHF$_2$ | 0 |
| A-2389 | H | H | H | H | H | O | 1-cyclohexylethyl | H | 2-CH$_2$F | 0 |

TABLE 43

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-2390 | H | H | H | H | H | O | 1-cyclohexylethyl | H | 2-CF$_2$Cl | 0 |
| A-2391 | H | H | H | H | H | O | 1-cyclohexylethyl | H | 2-cyclopropyl | 0 |
| A-2392 | H | H | H | H | H | O | 1-cyclohexylethyl | H | 2-cyclobutyl | 0 |
| A-2393 | H | H | H | H | H | O | 1-cyclohexylethyl | H | 2-cyclopentyl | 0 |
| A-2394 | H | H | H | H | H | O | 1-cyclohexylethyl | H | 2-ethenyl | 0 |
| A-2395 | H | H | H | H | H | O | 1-cyclohexylethyl | H | 2-allyl | 0 |
| A-2396 | H | H | H | H | H | O | 1-cyclohexylethyl | H | 2-(prop-1-en-1-yl) | 0 |
| A-2397 | H | H | H | H | H | O | 1-cyclohexylethyl | H | 2-(trifluoroethenyl) | 0 |
| A-2398 | H | H | H | H | H | O | 1-cyclohexylethyl | H | 2-OMe | 0 |
| A-2399 | H | H | H | H | H | O | 1-cyclohexylethyl | H | 2-OEt | 0 |
| A-2400 | H | H | H | H | H | O | 1-cyclohexylethyl | H | 2-OPr | 0 |
| A-2401 | H | H | H | H | H | O | 1-cyclohexylethyl | H | 2-O(i-Pr) | 0 |
| A-2402 | H | H | H | H | H | O | 1-cyclohexylethyl | H | 2-OCF$_3$ | 0 |
| A-2403 | H | H | H | H | H | O | 1-cyclohexylethyl | H | 2-OCHF$_2$ | 0 |
| A-2404 | H | H | H | H | H | O | 1-cyclohexylethyl | H | 2-(cyclopropyloxy) | 0 |
| A-2405 | H | H | H | H | H | O | 1-cyclohexylethyl | H | 2-(cyclobutyloxy) | 0 |
| A-2406 | H | H | H | H | H | O | 1-cyclohexylethyl | H | 2-(cyclopentyloxy) | 0 |
| A-2407 | H | H | H | H | H | O | 1-cyclohexylethyl | H | 2-((2,2-dichlorocyclopropyl)oxy) | 0 |
| A-2408 | H | H | H | H | H | O | 1-cyclohexylethyl | H | 2-(oxiran-2-yl) | 0 |
| A-2409 | H | H | H | H | H | O | 1-cyclohexylethyl | H | 2-SMe | 0 |
| A-2410 | H | H | H | H | H | O | 1-cyclohexylethyl | H | 3-SMe | 0 |
| A-2411 | H | H | H | H | H | O | 1-cyclohexylethyl | H | 2-S(=O)Me | 0 |
| A-2412 | H | H | H | H | H | O | 1-cyclohexylethyl | H | 3-S(=O)Me | 0 |
| A-2413 | H | H | H | H | H | O | 1-cyclohexylethyl | H | 2-S(=O)$_2$Me | 0 |
| A-2414 | H | H | H | H | H | O | 1-cyclohexylethyl | H | 3-S(=O)$_2$Me | 0 |
| A-2415 | H | H | H | H | H | O | 1-cyclohexylethyl | H | 2-SCF$_3$ | 0 |
| A-2416 | H | H | H | H | H | O | 1-cyclohexylethyl | H | 3-SCF$_3$ | 0 |
| A-2417 | H | H | H | H | H | O | 1-cyclohexylethyl | H | 3-S(=O)CF$_3$ | 0 |
| A-2418 | H | H | H | H | H | O | 1-cyclohexylethyl | H | 3-SCF(CF$_3$)$_2$ | 0 |
| A-2419 | H | H | H | H | H | O | 1-cyclohexylethyl | H | 2-(cyclopropylthio) | 0 |
| A-2420 | H | H | H | H | H | O | 1-cyclohexylethyl | H | 2-(cyclopropylsulfinyl) | 0 |
| A-2421 | H | H | H | H | H | O | 1-cyclohexylethyl | H | 2-(cyclopropylsulfonyl) | 0 |
| A-2422 | H | H | H | H | H | O | 1-cyclohexylethyl | H | 2-C(=O)Me | 0 |
| A-2423 | H | H | H | H | H | O | 1-cyclohexylethyl | H | 2-CH$_2$C(=O)CH$_3$ | 0 |
| A-2424 | H | H | H | H | H | O | 1-cyclohexylethyl | H | 2-CH$_2$C(=O)CF$_3$ | 0 |
| A-2425 | H | H | H | H | H | O | 1-cyclohexylethyl | H | 2-CH$_2$OH | 0 |
| A-2426 | H | H | H | H | H | O | 1-cyclohexylethyl | H | 2-CH$_2$OCH$_3$ | 0 |
| A-2427 | H | H | H | H | H | O | 1-cyclohexylethyl | H | 2-CH$_2$OCH$_2$CH$_3$ | 0 |
| A-2428 | H | H | H | H | H | O | 1-cyclohexylethyl | H | 2-CH$_2$SCH$_3$ | 0 |

TABLE 43-continued

| compound | R¹ | R² | R³ | R⁴ | R⁵ | A | R⁶ | R⁷ | (R⁸)ₘ | p |
|---|---|---|---|---|---|---|---|---|---|---|
| A-2429 | H | H | H | H | H | O | 1-cyclohexylethyl | H | 2-CH₂S(=O)CH₃ | 0 |
| A-2430 | H | H | H | H | H | O | 1-cyclohexylethyl | H | 2-CH₂S(=O)₂CH₃ | 0 |
| A-2431 | H | H | H | H | H | O | 1-cyclohexylethyl | H | 2-(benzyloxy) | 0 |
| A-2432 | H | H | H | H | H | O | 1-cyclohexylethyl | H | 2-NH₂ | 0 |
| A-2433 | H | H | H | H | H | O | 1-cyclohexylethyl | H | 2-NHMe | 0 |
| A-2434 | H | H | H | H | H | O | 1-cyclohexylethyl | H | 2-N(Me)₂ | 0 |
| A-2435 | H | H | H | H | H | O | 1-cyclohexylethyl | H | 2-(1,3-dioxolan-2-yl) | 0 |
| A-2436 | H | H | H | H | H | O | 1-cyclohexylethyl | H | 2-(1,3-dioxan-2-yl) | 0 |
| A-2437 | H | H | H | H | H | O | 1-cyclohexylethyl | H | 2-(1H-imidazol-2-yl) | 0 |
| A-2438 | H | H | H | H | H | O | 1-cyclohexylethyl | H | 2-(thiazol-2-yl) | 0 |
| A-2439 | H | H | H | H | H | O | 1-cyclohexylethyl | H | 2-(oxazol-2-yl) | 0 |
| A-2440 | H | H | H | H | H | O | 1-cyclohexylethyl | H | 2-CH=NOH | 0 |
| A-2441 | H | H | H | H | H | O | 1-cyclohexylethyl | H | 2-CH=NOMe | 0 |
| A-2442 | H | H | H | H | H | O | 1-cyclohexylethyl | H | 2-(4,5-dihydro-3-isoxazolyl) | 0 |
| A-2443 | H | H | H | H | H | O | 1-cyclohexylethyl | H | 2-CN | 0 |
| A-2444 | H | H | H | H | H | O | 1-cyclohexylethyl | H | 2-NO₂ | 0 |
| A-2445 | H | H | H | H | H | O | 1-cyclohexylethyl | H | 2-F,6-Cl | 0 |
| A-2446 | H | H | H | H | H | O | 1-cyclohexylethyl | H | 2-F,6-Me | 0 |

TABLE 44

| compound | R¹ | R² | R³ | R⁴ | R⁵ | A | R⁶ | R⁷ | (R⁸)ₘ | p |
|---|---|---|---|---|---|---|---|---|---|---|
| A-2447 | H | H | H | H | H | O | 1-cyclohexylethyl | H | 3-F,6-Me | 0 |
| A-2448 | H | H | H | H | H | O | 1-cyclohexylethyl | H | 4-F,2-Me | 0 |
| A-2449 | H | H | H | H | H | O | 1-cyclohexylethyl | H | 2-F,6-OMe | 0 |
| A-2450 | H | H | H | H | H | O | 1-cyclohexylethyl | H | 3-F,6-OMe | 0 |
| A-2451 | H | H | H | H | H | O | 1-cyclohexylethyl | H | 2,6-Cl₂ | 0 |
| A-2452 | H | H | H | H | H | O | 1-cyclohexylethyl | H | 2-Cl,6-Me | 0 |
| A-2453 | H | H | H | H | H | O | 1-cyclohexylethyl | H | 3-Cl,6-Me | 0 |
| A-2454 | H | H | H | H | H | O | 1-cyclohexylethyl | H | 4-Cl,2-Me | 0 |
| A-2455 | H | H | H | H | H | O | 1-cyclohexylethyl | H | 2-Cl,5-CF₃ | 0 |
| A-2456 | H | H | H | H | H | O | 1-cyclohexylethyl | H | 2-Cl,6-CF₃ | 0 |
| A-2457 | H | H | H | H | H | O | 1-cyclohexylethyl | H | 2-Cl,6-OMe | 0 |
| A-2458 | H | H | H | H | H | O | 1-cyclohexylethyl | H | 3-Cl,6-OMe | 0 |
| A-2459 | H | H | H | H | H | O | 1-cyclohexylethyl | H | 4-Cl,2-OMe | 0 |
| A-2460 | H | H | H | H | H | O | 1-cyclohexylethyl | H | 2,4-Me₂ | 0 |
| A-2461 | H | H | H | H | H | O | 1-cyclohexylethyl | H | 2,5-Me₂ | 0 |
| A-2462 | H | H | H | H | H | O | 1-cyclohexylethyl | H | 2,6-Me₂ | 0 |
| A-2463 | H | H | H | H | H | O | 1-cyclohexylethyl | H | 2-Me,4-CF₃ | 0 |
| A-2464 | H | H | H | H | H | O | 1-cyclohexylethyl | H | 2-Me,5-CF₃ | 0 |
| A-2465 | H | H | H | H | H | O | 1-cyclohexylethyl | H | 2-Me,6-CF₃ | 0 |
| A-2466 | H | H | H | H | H | O | 1-cyclohexylethyl | H | 2-Me,4-OMe | 0 |
| A-2467 | H | H | H | H | H | O | 1-cyclohexylethyl | H | 2-Me,5-OMe | 0 |
| A-2468 | H | H | H | H | H | O | 1-cyclohexylethyl | H | 2-Me,6-OMe | 0 |
| A-2469 | H | H | H | H | H | O | 1-cyclohexylethyl | H | 3-Me,6-OMe | 0 |
| A-2470 | H | H | H | H | H | O | 1-cyclohexylethyl | H | 4-Me,2-OMe | 0 |
| A-2471 | H | H | H | H | H | O | 1-cyclohexylethyl | H | 2,5-OMe₂ | 0 |
| A-2472 | H | H | H | H | H | O | 1-cyclohexylethyl | H | 2,6-OMe₂ | 0 |
| A-2473 | H | H | H | H | H | O | 1-cyclohexylethyl | H | 2-OMe,6-CF₃ | 0 |
| A-2474 | H | H | H | H | H | O | 1-cyclohexylethyl | H | 2-CHF₂,5-F | 0 |
| A-2475 | H | H | H | H | H | O | 1-cyclohexylethyl | H | 2-CHF₂,6-F | 0 |
| A-2476 | H | H | H | H | H | O | 1-cyclohexylethyl | H | 2-CHF₂,5-Me | 0 |
| A-2477 | H | H | H | H | H | O | 1-cyclohexylethyl | H | 2-CHF₂,6-Me | 0 |
| A-2478 | H | H | H | H | H | O | 1-cyclohexylethyl | H | 2-cyclopropyl,5-F | 0 |
| A-2479 | H | H | H | H | H | O | 1-cyclohexylethyl | H | 2-cyclopropyl,6-F | 0 |
| A-2480 | H | H | H | H | H | O | 1-cyclohexylethyl | H | 2-cyclopropyl,5-Me | 0 |
| A-2481 | H | H | H | H | H | O | 1-cyclohexylethyl | H | 2-cyclopropyl,6-Me | 0 |
| A-2482 | H | H | H | H | H | O | 1-cyclohexylethyl | H | 2-ethenyl,6-F | 0 |
| A-2483 | H | H | H | H | H | O | 1-cyclohexylethyl | H | 2-ethenyl,6-Me | 0 |
| A-2484 | H | H | H | H | H | O | 1-cyclohexylethyl | H | 2-OEt,5-F | 0 |
| A-2485 | H | H | H | H | H | O | 1-cyclohexylethyl | H | 2-OEt,6-F | 0 |
| A-2486 | H | H | H | H | H | O | 1-cyclohexylethyl | H | 2-OEt,5-Cl | 0 |
| A-2487 | H | H | H | H | H | O | 1-cyclohexylethyl | H | 2-OEt,6-Cl | 0 |
| A-2488 | H | H | H | H | H | O | 1-cyclohexylethyl | H | 2-OEt,5-Me | 0 |
| A-2489 | H | H | H | H | H | O | 1-cyclohexylethyl | H | 2-OEt,6-Me | 0 |
| A-2490 | H | H | H | H | H | O | 1-cyclohexylethyl | H | 2-OCHF₂,5-F | 0 |
| A-2491 | H | H | H | H | H | O | 1-cyclohexylethyl | H | 2-OCHF₂,6-F | 0 |
| A-2492 | H | H | H | H | H | O | 1-cyclohexylethyl | H | 2-OCHF₂,5-Me | 0 |
| A-2493 | H | H | H | H | H | O | 1-cyclohexylethyl | H | 2-OCHF₂,6-Me | 0 |
| A-2494 | H | H | H | H | H | O | 1-cyclohexylethyl | H | 2-(cyclopropyloxy),5-F | 0 |
| A-2495 | H | H | H | H | H | O | 1-cyclohexylethyl | H | 2-(cyclopropyloxy),6-F | 0 |
| A-2496 | H | H | H | H | H | O | 1-cyclohexylethyl | H | 2-(cyclopropyloxy),5-Me | 0 |
| A-2497 | H | H | H | H | H | O | 1-cyclohexylethyl | H | 2-(cyclopropyloxy),6-Me | 0 |
| A-2498 | H | H | H | H | H | O | 1-cyclohexylethyl | H | 2-SMe,5-F | 0 |

TABLE 44-continued

| compound | R¹ | R² | R³ | R⁴ | R⁵ | A | R⁶ | R⁷ | (R⁸)ₘ | p |
|---|---|---|---|---|---|---|---|---|---|---|
| A-2499 | H | H | H | H | H | O | 1-cyclohexylethyl | H | 2-SMe,6-F | 0 |
| A-2500 | H | H | H | H | H | O | 1-cyclohexylethyl | H | 2-SMe,5-Me | 0 |
| A-2501 | H | H | H | H | H | O | 1-cyclohexylethyl | H | 2-SMe,6-Me | 0 |
| A-2502 | H | H | H | H | H | O | 1-cyclohexylethyl | H | 2-S(=O)Me,5-F | 0 |
| A-2503 | H | H | H | H | H | O | 1-cyclohexylethyl | H | 2-S(=O)Me,6-F | 0 |

TABLE 45

| compound | R¹ | R² | R³ | R⁴ | R⁵ | A | R⁶ | R⁷ | (R⁸)ₘ | p |
|---|---|---|---|---|---|---|---|---|---|---|
| A-2504 | H | H | H | H | H | O | 1-cyclohexylethyl | H | 2-S(=O)Me,5-Me | 0 |
| A-2505 | H | H | H | H | H | O | 1-cyclohexylethyl | H | 2-S(=O)Me,6-Me | 0 |
| A-2506 | H | H | H | H | H | O | 1-cyclohexylethyl | H | 2-S(=O)₂Me,5-F | 0 |
| A-2507 | H | H | H | H | H | O | 1-cyclohexylethyl | H | 2-S(=O)₂Me,6-F | 0 |
| A-2508 | H | H | H | H | H | O | 1-cyclohexylethyl | H | 2-S(=O)₂Me,5-Me | 0 |
| A-2509 | H | H | H | H | H | O | 1-cyclohexylethyl | H | 2-S(=O)₂Me,6-Me | 0 |
| A-2510 | H | H | H | H | H | O | 1-cyclohexylethyl | H | 2-SCF₃,5-F | 0 |
| A-2511 | H | H | H | H | H | O | 1-cyclohexylethyl | H | 2-SCF₃,6-F | 0 |
| A-2512 | H | H | H | H | H | O | 1-cyclohexylethyl | H | 2-SCF₃,5-Me | 0 |
| A-2513 | H | H | H | H | H | O | 1-cyclohexylethyl | H | 2-SCF₃,6-Me | 0 |
| A-2514 | H | H | H | H | H | O | 1-cyclohexylethyl | H | 2-S(=O)CF₃,5-F | 0 |
| A-2515 | H | H | H | H | H | O | 1-cyclohexylethyl | H | 2-S(=O)CF₃,6-F | 0 |
| A-2516 | H | H | H | H | H | O | 1-cyclohexylethyl | H | 2-S(=O)CF₃,5-Me | 0 |
| A-2517 | H | H | H | H | H | O | 1-cyclohexylethyl | H | 2-S(=O)CF₃,6-Me | 0 |
| A-2518 | H | H | H | H | H | O | 1-cyclohexylethyl | H | 2-S(=O)₂CF₃,5-F | 0 |
| A-2519 | H | H | H | H | H | O | 1-cyclohexylethyl | H | 2-S(=O)₂CF₃,6-F | 0 |
| A-2520 | H | H | H | H | H | O | 1-cyclohexylethyl | H | 2-S(=O)₂CF₃,5-Me | 0 |
| A-2521 | H | H | H | H | H | O | 1-cyclohexylethyl | H | 2-S(=O)₂CF₃,6-Me | 0 |
| A-2522 | H | H | H | H | H | O | 1-cyclohexylethyl | H | 2-(cyclopropylthio),5-F | 0 |
| A-2523 | H | H | H | H | H | O | 1-cyclohexylethyl | H | 2-(cyclopropylthio),6-F | 0 |
| A-2524 | H | H | H | H | H | O | 1-cyclohexylethyl | H | 2-(cyclopropylthio),5-Me | 0 |
| A-2525 | H | H | H | H | H | O | 1-cyclohexylethyl | H | 2-(cyclopropylthio),6-Me | 0 |
| A-2526 | H | H | H | H | H | O | 1-cyclohexylethyl | H | 2-C(=O)Me,5-F | 0 |
| A-2527 | H | H | H | H | H | O | 1-cyclohexylethyl | H | 2-C(=O)Me,6-F | 0 |
| A-2528 | H | H | H | H | H | O | 1-cyclohexylethyl | H | 2-C(=O)Me,5-Me | 0 |
| A-2529 | H | H | H | H | H | O | 1-cyclohexylethyl | H | 2-C(=O)Me,6-Me | 0 |
| A-2530 | H | H | H | H | H | O | 1-cyclohexylethyl | H | 2-CH₂OH,5-F | 0 |
| A-2531 | H | H | H | H | H | O | 1-cyclohexylethyl | H | 2-CH₂OH,6-F | 0 |
| A-2532 | H | H | H | H | H | O | 1-cyclohexylethyl | H | 2-CH₂OH,5-Me | 0 |
| A-2533 | H | H | H | H | H | O | 1-cyclohexylethyl | H | 2-CH₂OH,6-Me | 0 |
| A-2534 | H | H | H | H | H | O | 1-cyclohexylethyl | H | 2-CH₂OCH₃,4-F | 0 |
| A-2535 | H | H | H | H | H | O | 1-cyclohexylethyl | H | 2-CH₂OCH₃,5-F | 0 |
| A-2536 | H | H | H | H | H | O | 1-cyclohexylethyl | H | 2-CH₂OCH₃,6-F | 0 |
| A-2537 | H | H | H | H | H | O | 1-cyclohexylethyl | H | 2-CH₂OCH₃,4-Me | 0 |
| A-2538 | H | H | H | H | H | O | 1-cyclohexylethyl | H | 2-CH₂OCH₃,5-Me | 0 |
| A-2539 | H | H | H | H | H | O | 1-cyclohexylethyl | H | 2-CH₂OCH₃,6-Me | 0 |
| A-2540 | H | H | H | H | H | O | 1-cyclohexylethyl | H | 2-OC(=O)CH₃,5-F | 0 |
| A-2541 | H | H | H | H | H | O | 1-cyclohexylethyl | H | 2-OC(=O)CH₃,6-F | 0 |
| A-2542 | H | H | H | H | H | O | 1-cyclohexylethyl | H | 2-OC(=O)CH₃,5-Me | 0 |
| A-2543 | H | H | H | H | H | O | 1-cyclohexylethyl | H | 2-OC(=O)CH₃,6-Me | 0 |
| A-2544 | H | H | H | H | H | O | 1-cyclohexylethyl | H | 2-OS(=O)₂CH₃,5-F | 0 |
| A-2545 | H | H | H | H | H | O | 1-cyclohexylethyl | H | 2-OS(=O)₂CH₃,6-F | 0 |
| A-2546 | H | H | H | H | H | O | 1-cyclohexylethyl | H | 2-OS(=O)₂CH₃,5-Me | 0 |
| A-2547 | H | H | H | H | H | O | 1-cyclohexylethyl | H | 2-OS(=O)₂CH₃,6-Me | 0 |
| A-2548 | H | H | H | H | H | O | 1-cyclohexylethyl | H | 2-CH₂SCH₃,5-F | 0 |
| A-2549 | H | H | H | H | H | O | 1-cyclohexylethyl | H | 2-CH₂SCH₃,6-F | 0 |
| A-2550 | H | H | H | H | H | O | 1-cyclohexylethyl | H | 2-CH₂SCH₃,5-Me | 0 |
| A-2551 | H | H | H | H | H | O | 1-cyclohexylethyl | H | 2-CH₂SCH₃,6-Me | 0 |
| A-2552 | H | H | H | H | H | O | 1-cyclohexylethyl | H | 2-NMe₂,5-F | 0 |
| A-2553 | H | H | H | H | H | O | 1-cyclohexylethyl | H | 2-NMe₂,6-F | 0 |
| A-2554 | H | H | H | H | H | O | 1-cyclohexylethyl | H | 2-NMe₂,5-Me | 0 |
| A-2555 | H | H | H | H | H | O | 1-cyclohexylethyl | H | 2-NMe₂,6-Me | 0 |
| A-2556 | H | H | H | H | H | O | 1-cyclohexylethyl | H | 2-CN,4-F | 0 |
| A-2557 | H | H | H | H | H | O | 1-cyclohexylethyl | H | 2-CN,5-F | 0 |
| A-2558 | H | H | H | H | H | O | 1-cyclohexylethyl | H | 2-CN,6-F | 0 |
| A-2559 | H | H | H | H | H | O | 1-cyclohexylethyl | H | 2-CN,6-Me | 0 |
| A-2560 | H | H | H | H | H | O | 1-cyclohexylethyl | H | 2-CN,5-OMe | 0 |

TABLE 46

| compound | R¹ | R² | R³ | R⁴ | R⁵ | A | R⁶ | R⁷ | (R⁸)$_m$ | p |
|---|---|---|---|---|---|---|---|---|---|---|
| A-2561 | H | H | H | H | H | O | 1-cyclohexylethyl | H | 2-CN,6-Me | 0 |
| A-2562 | H | H | H | H | H | O | 1-cyclohexylethyl | H | 3-CN,6-Me | 0 |
| A-2563 | H | H | H | H | H | O | 1-cyclohexylethyl | H | 3-CN,6-OMe | 0 |
| A-2564 | H | H | H | H | H | O | 1-cyclohexylethyl | H | 4-CN,2-Me | 0 |
| A-2565 | H | H | H | H | H | O | 1-cyclohexylethyl | H | 4-CN,2-OMe | 0 |
| A-2566 | H | H | H | H | H | O | 1-cyclohexylethyl | H | 2-NO$_2$,4-F | 0 |
| A-2567 | H | H | H | H | H | O | 1-cyclohexylethyl | H | 2-NO$_2$,5-F | 0 |
| A-2568 | H | H | H | H | H | O | 1-cyclohexylethyl | H | 2-NO$_2$,6-F | 0 |
| A-2569 | H | H | H | H | H | O | 1-cyclohexylethyl | H | 2-NO$_2$,4-Me | 0 |
| A-2570 | H | H | H | H | H | O | 1-cyclohexylethyl | H | 2-NO$_2$,5-Me | 0 |
| A-2571 | H | H | H | H | H | O | 1-cyclohexylethyl | H | 2-NO$_2$,6-Me | 0 |
| A-2572 | H | H | H | H | H | O | 1-cyclohexylethyl | H | 2-Me,4,5-F$_2$ | 0 |
| A-2573 | H | H | H | H | H | O | 1-cyclohexylethyl | H | 2-Me,6-Et | 0 |
| A-2574 | H | H | H | H | H | O | 1-cyclohexylethyl | H | 2-cyclopropyl,6-OMe | 0 |
| A-2575 | H | H | H | H | H | O | 1-cyclohexylethyl | H | 2-Me,5-Et | 0 |
| A-2576 | H | H | H | H | H | O | 1-cyclohexylethyl | H | 2,6-Et$_2$ | 0 |
| A-2577 | H | H | H | H | H | O | 1-cyclohexylethyl | H | 2-Et,6-F | 0 |
| A-2578 | H | H | H | H | H | O | 1-cyclohexylethyl | H | 2-CH$_2$OCH$_3$,6-Cl | 0 |
| A-2579 | H | H | H | H | H | O | 1-cyclohexylethyl | H | 2-CH$_2$OCH$_2$CH$_3$,6-Cl | 0 |
| A-2580 | H | H | H | H | H | O | 1-cyclohexylethyl | H | 2-CH$_2$NMe$_2$ | 0 |
| A-2581 | H | H | H | H | H | O | CH$_2$C≡CH | H | H | 0 |
| A-2582 | H | H | H | H | H | O | CH$_2$C≡CH | H | 2-F | 0 |
| A-2583 | H | H | H | H | H | O | CH$_2$C≡CH | H | 2-Cl | 0 |
| A-2584 | H | H | H | H | H | O | CH$_2$C≡CH | H | 2-Br | 0 |
| A-2585 | H | H | H | H | H | O | CH$_2$C≡CH | H | 2-OH | 0 |
| A-2586 | H | H | H | H | H | O | CH$_2$C≡CH | H | 2-Me | 0 |
| A-2587 | H | H | H | H | H | O | CH$_2$C≡CH | H | 2-Et | 0 |
| A-2588 | H | H | H | H | H | O | CH$_2$C≡CH | H | 2-Pr | 0 |
| A-2589 | H | H | H | H | H | O | CH$_2$C≡CH | H | 2-CF$_3$ | 0 |
| A-2590 | H | H | H | H | H | O | CH$_2$C≡CH | H | 2-CHF$_2$ | 0 |
| A-2591 | H | H | H | H | H | O | CH$_2$C≡CH | H | 2-CH$_2$F | 0 |
| A-2592 | H | H | H | H | H | O | CH$_2$C≡CH | H | 2-CF$_2$Cl | 0 |
| A-2593 | H | H | H | H | H | O | CH$_2$C≡CH | H | 2-cyclopropyl | 0 |
| A-2594 | H | H | H | H | H | O | CH$_2$C≡CH | H | 2-cyclobutyl | 0 |
| A-2595 | H | H | H | H | H | O | CH$_2$C≡CH | H | 2-cyclopentyl | 0 |
| A-2596 | H | H | H | H | H | O | CH$_2$C≡CH | H | 2-ethenyl | 0 |
| A-2597 | H | H | H | H | H | O | CH$_2$C≡CH | H | 2-allyl | 0 |
| A-2598 | H | H | H | H | H | O | CH$_2$C≡CH | H | 2-(prop-1-en-1-yl) | 0 |
| A-2599 | H | H | H | H | H | O | CH$_2$C≡CH | H | 2-(trifluoroethenyl) | 0 |
| A-2600 | H | H | H | H | H | O | CH$_2$C≡CH | H | 2-OMe | 0 |
| A-2601 | H | H | H | H | H | O | CH$_2$C≡CH | H | 2-OEt | 0 |
| A-2602 | H | H | H | H | H | O | CH$_2$C≡CH | H | 2-OPr | 0 |
| A-2603 | H | H | H | H | H | O | CH$_2$C≡CH | H | 2-O(i-Pr) | 0 |
| A-2604 | H | H | H | H | H | O | CH$_2$C≡CH | H | 2-OCF$_3$ | 0 |
| A-2605 | H | H | H | H | H | O | CH$_2$C≡CH | H | 2-OCHF$_2$ | 0 |
| A-2606 | H | H | H | H | H | O | CH$_2$C≡CH | H | 2-(cyclopropyloxy) | 0 |
| A-2607 | H | H | H | H | H | O | CH$_2$C≡CH | H | 2-(cyclobutyloxy) | 0 |
| A-2608 | H | H | H | H | H | O | CH$_2$C≡CH | H | 2-(cyclopentyloxy) | 0 |
| A-2609 | H | H | H | H | H | O | CH$_2$C≡CH | H | 2-((2,2-dichlorocyclopropyl)oxy) | 0 |
| A-2610 | H | H | H | H | H | O | CH$_2$C≡CH | H | 2-(oxiran-2-yl) | 0 |
| A-2611 | H | H | H | H | H | O | CH$_2$C≡CH | H | 2-SMe | 0 |
| A-2612 | H | H | H | H | H | O | CH$_2$C≡CH | H | 3-SMe | 0 |
| A-2613 | H | H | H | H | H | O | CH$_2$C≡CH | H | 2-S(=O)Me | 0 |
| A-2614 | H | H | H | H | H | O | CH$_2$C≡CH | H | 3-S(=O)Me | 0 |
| A-2615 | H | H | H | H | H | O | CH$_2$C≡CH | H | 2-S(=O)$_2$Me | 0 |
| A-2616 | H | H | H | H | H | O | CH$_2$C≡CH | H | 3-S(=O)$_2$Me | 0 |
| A-2617 | H | H | H | H | H | O | CH$_2$C≡CH | H | 2-SCF$_3$ | 0 |

TABLE 47

| compound | R¹ | R² | R³ | R⁴ | R⁵ | A | R⁶ | R⁷ | (R⁸)$_m$ | p |
|---|---|---|---|---|---|---|---|---|---|---|
| A-2618 | H | H | H | H | H | O | CH$_2$C≡CH | H | 3-SCF$_3$ | 0 |
| A-2619 | H | H | H | H | H | O | CH$_2$C≡CH | H | 3-S(=O)CF$_3$ | 0 |
| A-2620 | H | H | H | H | H | O | CH$_2$C≡CH | H | 3-SCF(CF$_3$)$_2$ | 0 |
| A-2621 | H | H | H | H | H | O | CH$_2$C≡CH | H | 2-(cyclopropylthio) | 0 |
| A-2622 | H | H | H | H | H | O | CH$_2$C≡CH | H | 2-(cyclopropylsulfinyl) | 0 |
| A-2623 | H | H | H | H | H | O | CH$_2$C≡CH | H | 2-(cyclopropylsulfonyl) | 0 |
| A-2624 | H | H | H | H | H | O | CH$_2$C≡CH | H | 2-C(=O)Me | 0 |
| A-2625 | H | H | H | H | H | O | CH$_2$C≡CH | H | 2-CH$_2$C(=O)CH$_3$ | 0 |
| A-2626 | H | H | H | H | H | O | CH$_2$C≡CH | H | 2-CH$_2$C(=O)CF$_3$ | 0 |
| A-2627 | H | H | H | H | H | O | CH$_2$C≡CH | H | 2-CH$_2$OH | 0 |
| A-2628 | H | H | H | H | H | O | CH$_2$C≡CH | H | 2-CH$_2$OCH$_3$ | 0 |
| A-2629 | H | H | H | H | H | O | CH$_2$C≡CH | H | 2-CH$_2$OCH$_2$CH$_3$ | 0 |
| A-2630 | H | H | H | H | H | O | CH$_2$C≡CH | H | 2-CH$_2$SCH$_3$ | 0 |

TABLE 47-continued

| compound | R¹ | R² | R³ | R⁴ | R⁵ | A | R⁶ | R⁷ | (R⁸)$_m$ | p |
|---|---|---|---|---|---|---|---|---|---|---|
| A-2631 | H | H | H | H | H | O | CH$_2$C≡CH | H | 2-CH$_2$S(=O)CH$_3$ | 0 |
| A-2632 | H | H | H | H | H | O | CH$_2$C≡CH | H | 2-CH$_2$S(=O)$_2$CH$_3$ | 0 |
| A-2633 | H | H | H | H | H | O | CH$_2$C≡CH | H | 2-(benzyloxy) | 0 |
| A-2634 | H | H | H | H | H | O | CH$_2$C≡CH | H | 2-NH$_2$ | 0 |
| A-2635 | H | H | H | H | H | O | CH$_2$C≡CH | H | 2-NHMe | 0 |
| A-2636 | H | H | H | H | H | O | CH$_2$C≡CH | H | 2-N(Me)$_2$ | 0 |
| A-2637 | H | H | H | H | H | O | CH$_2$C≡CH | H | 2-(1,3-dioxolan-2-yl) | 0 |
| A-2638 | H | H | H | H | H | O | CH$_2$C≡CH | H | 2-(1,3-dioxan-2-yl) | 0 |
| A-2639 | H | H | H | H | H | O | CH$_2$C≡CH | H | 2-(1H-imidazol-2-yl) | 0 |
| A-2640 | H | H | H | H | H | O | CH$_2$C≡CH | H | 2-(thiazol-2-yl) | 0 |
| A-2641 | H | H | H | H | H | O | CH$_2$C≡CH | H | 2-(oxazol-2-yl) | 0 |
| A-2642 | H | H | H | H | H | O | CH$_2$C≡CH | H | 2-CH=NOH | 0 |
| A-2643 | H | H | H | H | H | O | CH$_2$C≡CH | H | 2-CH=NOMe | 0 |
| A-2644 | H | H | H | H | H | O | CH$_2$C≡CH | H | 2-(4,5-dihydro-3-isoxazolyl) | 0 |
| A-2645 | H | H | H | H | H | O | CH$_2$C≡CH | H | 2-CN | 0 |
| A-2646 | H | H | H | H | H | O | CH$_2$C≡CH | H | 2-NO$_2$ | 0 |
| A-2647 | H | H | H | H | H | O | CH$_2$C≡CH | H | 2-F,6-Cl | 0 |
| A-2648 | H | H | H | H | H | O | CH$_2$C≡CH | H | 2-F,6-Me | 0 |
| A-2649 | H | H | H | H | H | O | CH$_2$C≡CH | H | 3-F,6-Me | 0 |
| A-2650 | H | H | H | H | H | O | CH$_2$C≡CH | H | 4-F,2-Me | 0 |
| A-2651 | H | H | H | H | H | O | CH$_2$C≡CH | H | 2-F,6-OMe | 0 |
| A-2652 | H | H | H | H | H | O | CH$_2$C≡CH | H | 3-F,6-OMe | 0 |
| A-2653 | H | H | H | H | H | O | CH$_2$C≡CH | H | 2,6-Cl$_2$ | 0 |
| A-2654 | H | H | H | H | H | O | CH$_2$C≡CH | H | 2-Cl,6-Me | 0 |
| A-2655 | H | H | H | H | H | O | CH$_2$C≡CH | H | 3-Cl,6-Me | 0 |
| A-2656 | H | H | H | H | H | O | CH$_2$C≡CH | H | 4-Cl,2-Me | 0 |
| A-2657 | H | H | H | H | H | O | CH$_2$C≡CH | H | 2-Cl,5-CF$_3$ | 0 |
| A-2658 | H | H | H | H | H | O | CH$_2$C≡CH | H | 2-Cl,6-CF$_3$ | 0 |
| A-2659 | H | H | H | H | H | O | CH$_2$C≡CH | H | 2-Cl,6-OMe | 0 |
| A-2660 | H | H | H | H | H | O | CH$_2$C≡CH | H | 3-Cl,6-OMe | 0 |
| A-2661 | H | H | H | H | H | O | CH$_2$C≡CH | H | 4-Cl,2-OMe | 0 |
| A-2662 | H | H | H | H | H | O | CH$_2$C≡CH | H | 2,4-Me$_2$ | 0 |
| A-2663 | H | H | H | H | H | O | CH$_2$C≡CH | H | 2,5-Me$_2$ | 0 |
| A-2664 | H | H | H | H | H | O | CH$_2$C≡CH | H | 2,6-Me$_2$ | 0 |
| A-2665 | H | H | H | H | H | O | CH$_2$C≡CH | H | 2-Me,4-CF$_3$ | 0 |
| A-2666 | H | H | H | H | H | O | CH$_2$C≡CH | H | 2-Me,5-CF$_3$ | 0 |
| A-2667 | H | H | H | H | H | O | CH$_2$C≡CH | H | 2-Me,6-CF$_3$ | 0 |
| A-2668 | H | H | H | H | H | O | CH$_2$C≡CH | H | 2-Me,4-OMe | 0 |
| A-2669 | H | H | H | H | H | O | CH$_2$C≡CH | H | 2-Me,5-OMe | 0 |
| A-2670 | H | H | H | H | H | O | CH$_2$C≡CH | H | 2-Me,6-OMe | 0 |
| A-2671 | H | H | H | H | H | O | CH$_2$C≡CH | H | 3-Me,6-OMe | 0 |
| A-2672 | H | H | H | H | H | O | CH$_2$C≡CH | H | 4-Me,2-OMe | 0 |
| A-2673 | H | H | H | H | H | O | CH$_2$C≡CH | H | 2,5-OMe$_2$ | 0 |
| A-2674 | H | H | H | H | H | O | CH$_2$C≡CH | H | 2,6-OMe$_2$ | 0 |

TABLE 48

| compound | R¹ | R² | R³ | R⁴ | R⁵ | A | R⁶ | R⁷ | (R⁸)$_m$ | p |
|---|---|---|---|---|---|---|---|---|---|---|
| A-2675 | H | H | H | H | H | O | CH$_2$C≡CH | H | 2-OMe,6-CF$_3$ | 0 |
| A-2676 | H | H | H | H | H | O | CH$_2$C≡CH | H | 2-CHF$_2$,5-F | 0 |
| A-2677 | H | H | H | H | H | O | CH$_2$C≡CH | H | 2-CHF$_2$,6-F | 0 |
| A-2678 | H | H | H | H | H | O | CH$_2$C≡CH | H | 2-CHF$_2$,5-Me | 0 |
| A-2679 | H | H | H | H | H | O | CH$_2$C≡CH | H | 2-CHF$_2$,6-Me | 0 |
| A-2680 | H | H | H | H | H | O | CH$_2$C≡CH | H | 2-cyclopropyl,5-F | 0 |
| A-2681 | H | H | H | H | H | O | CH$_2$C≡CH | H | 2-cyclopropyl,6-F | 0 |
| A-2682 | H | H | H | H | H | O | CH$_2$C≡CH | H | 2-cyclopropyl,5-Me | 0 |
| A-2683 | H | H | H | H | H | O | CH$_2$C≡CH | H | 2-cyclopropyl,6-Me | 0 |
| A-2684 | H | H | H | H | H | O | CH$_2$C≡CH | H | 2-ethenyl,6-F | 0 |
| A-2685 | H | H | H | H | H | O | CH$_2$C≡CH | H | 2-ethenyl,6-Me | 0 |
| A-2686 | H | H | H | H | H | O | CH$_2$C≡CH | H | 2-OEt,5-F | 0 |
| A-2687 | H | H | H | H | H | O | CH$_2$C≡CH | H | 2-OEt,6-F | 0 |
| A-2688 | H | H | H | H | H | O | CH$_2$C≡CH | H | 2-OEt,5-Cl | 0 |
| A-2689 | H | H | H | H | H | O | CH$_2$C≡CH | H | 2-OEt,6-Cl | 0 |
| A-2690 | H | H | H | H | H | O | CH$_2$C≡CH | H | 2-OEt,5-Me | 0 |
| A-2691 | H | H | H | H | H | O | CH$_2$C≡CH | H | 2-OEt,6-Me | 0 |
| A-2692 | H | H | H | H | H | O | CH$_2$C≡CH | H | 2-OCHF$_2$,5-F | 0 |
| A-2693 | H | H | H | H | H | O | CH$_2$C≡CH | H | 2-OCHF$_2$,6-F | 0 |
| A-2694 | H | H | H | H | H | O | CH$_2$C≡CH | H | 2-OCHF$_2$,5-Me | 0 |
| A-2695 | H | H | H | H | H | O | CH$_2$C≡CH | H | 2-OCHF$_2$,6-Me | 0 |
| A-2696 | H | H | H | H | H | O | CH$_2$C≡CH | H | 2-(cyclopropyloxy),5-F | 0 |
| A-2697 | H | H | H | H | H | O | CH$_2$C≡CH | H | 2-(cyclopropyloxy),6-F | 0 |
| A-2698 | H | H | H | H | H | O | CH$_2$C≡CH | H | 2-(cyclopropyloxy),5-Me | 0 |
| A-2699 | H | H | H | H | H | O | CH$_2$C≡CH | H | 2-(cyclopropyloxy),6-Me | 0 |
| A-2700 | H | H | H | H | H | O | CH$_2$C≡CH | H | 2-SMe,5-F | 0 |

TABLE 48-continued

| compound | R¹ | R² | R³ | R⁴ | R⁵ | A | R⁶ | R⁷ | (R⁸)ₘ | p |
|---|---|---|---|---|---|---|---|---|---|---|
| A-2701 | H | H | H | H | H | O | CH₂C≡CH | H | 2-SMe,6-F | 0 |
| A-2702 | H | H | H | H | H | O | CH₂C≡CH | H | 2-SMe,5-Me | 0 |
| A-2703 | H | H | H | H | H | O | CH₂C≡CH | H | 2-SMe,6-Me | 0 |
| A-2704 | H | H | H | H | H | O | CH₂C≡CH | H | 2-S(=O)Me,5-F | 0 |
| A-2705 | H | H | H | H | H | O | CH₂C≡CH | H | 2-S(=O)Me,6-F | 0 |
| A-2706 | H | H | H | H | H | O | CH₂C≡CH | H | 2-S(=O)Me,5-Me | 0 |
| A-2707 | H | H | H | H | H | O | CH₂C≡CH | H | 2-S(=O)Me,6-Me | 0 |
| A-2708 | H | H | H | H | H | O | CH₂C≡CH | H | 2-S(=O)₂Me,5-F | 0 |
| A-2709 | H | H | H | H | H | O | CH₂C≡CH | H | 2-S(=O)₂Me,6-F | 0 |
| A-2710 | H | H | H | H | H | O | CH₂C≡CH | H | 2-S(=O)₂Me,5-Me | 0 |
| A-2711 | H | H | H | H | H | O | CH₂C≡CH | H | 2-S(=O)₂Me,6-Me | 0 |
| A-2712 | H | H | H | H | H | O | CH₂C≡CH | H | 2-SCF₃,5-F | 0 |
| A-2713 | H | H | H | H | H | O | CH₂C≡CH | H | 2-SCF₃,6-F | 0 |
| A-2714 | H | H | H | H | H | O | CH₂C≡CH | H | 2-SCF₃,5-Me | 0 |
| A-2715 | H | H | H | H | H | O | CH₂C≡CH | H | 2-SCF₃,6-Me | 0 |
| A-2716 | H | H | H | H | H | O | CH₂C≡CH | H | 2-S(=O)CF₃,5-F | 0 |
| A-2717 | H | H | H | H | H | O | CH₂C≡CH | H | 2-S(=O)CF₃,6-F | 0 |
| A-2718 | H | H | H | H | H | O | CH₂C≡CH | H | 2-S(=O)CF₃,5-Me | 0 |
| A-2719 | H | H | H | H | H | O | CH₂C≡CH | H | 2-S(=O)CF₃,6-Me | 0 |
| A-2720 | H | H | H | H | H | O | CH₂C≡CH | H | 2-S(=O)₂CF₃,5-F | 0 |
| A-2721 | H | H | H | H | H | O | CH₂C≡CH | H | 2-S(=O)₂CF₃,6-F | 0 |
| A-2722 | H | H | H | H | H | O | CH₂C≡CH | H | 2-S(=O)₂CF₃,5-Me | 0 |
| A-2723 | H | H | H | H | H | O | CH₂C≡CH | H | 2-S(=O)₂CF₃,6-Me | 0 |
| A-2724 | H | H | H | H | H | O | CH₂C≡CH | H | 2-(cyclopropylthio),5-F | 0 |
| A-2725 | H | H | H | H | H | O | CH₂C≡CH | H | 2-(cyclopropylthio),6-F | 0 |
| A-2726 | H | H | H | H | H | O | CH₂C≡CH | H | 2-(cyclopropylthio),5-Me | 0 |
| A-2727 | H | H | H | H | H | O | CH₂C≡CH | H | 2-(cyclopropylthio),6-Me | 0 |
| A-2728 | H | H | H | H | H | O | CH₂C≡CH | H | 2-C(=O)Me,5-F | 0 |
| A-2729 | H | H | H | H | H | O | CH₂C≡CH | H | 2-C(=O)Me,6-F | 0 |
| A-2730 | H | H | H | H | H | O | CH₂C≡CH | H | 2-C(=O)Me,5-Me | 0 |
| A-2731 | H | H | H | H | H | O | CH₂C≡CH | H | 2-C(=O)Me,6-Me | 0 |

TABLE 49

| compound | R¹ | R² | R³ | R⁴ | R⁵ | A | R⁶ | R⁷ | (R⁸)ₘ | p |
|---|---|---|---|---|---|---|---|---|---|---|
| A-2732 | H | H | H | H | H | O | CH₂C≡CH | H | 2-CH₂OH,5-F | 0 |
| A-2733 | H | H | H | H | H | O | CH₂C≡CH | H | 2-CH₂OH,6-F | 0 |
| A-2734 | H | H | H | H | H | O | CH₂C≡CH | H | 2-CH₂OH,5-Me | 0 |
| A-2735 | H | H | H | H | H | O | CH₂C≡CH | H | 2-CH₂OH,6-Me | 0 |
| A-2736 | H | H | H | H | H | O | CH₂C≡CH | H | 2-CH₂OCH₃,4-F | 0 |
| A-2737 | H | H | H | H | H | O | CH₂C≡CH | H | 2-CH₂OCH₃,5-F | 0 |
| A-2738 | H | H | H | H | H | O | CH₂C≡CH | H | 2-CH₂OCH₃,6-F | 0 |
| A-2739 | H | H | H | H | H | O | CH₂C≡CH | H | 2-CH₂OCH₃,4-Me | 0 |
| A-2740 | H | H | H | H | H | O | CH₂C≡CH | H | 2-CH₂OCH₃,5-Me | 0 |
| A-2741 | H | H | H | H | H | O | CH₂C≡CH | H | 2-CH₂OCH₃,6-Me | 0 |
| A-2742 | H | H | H | H | H | O | CH₂C≡CH | H | 2-OC(=O)CH₃,5-F | 0 |
| A-2743 | H | H | H | H | H | O | CH₂C≡CH | H | 2-OC(=O)CH₃,6-F | 0 |
| A-2744 | H | H | H | H | H | O | CH₂C≡CH | H | 2-OC(=O)CH₃,5-Me | 0 |
| A-2745 | H | H | H | H | H | O | CH₂C≡CH | H | 2-OC(=O)CH₃,6-Me | 0 |
| A-2746 | H | H | H | H | H | O | CH₂C≡CH | H | 2-OS(=O)₂CH₃,5-F | 0 |
| A-2747 | H | H | H | H | H | O | CH₂C≡CH | H | 2-OS(=O)₂CH₃,6-F | 0 |
| A-2748 | H | H | H | H | H | O | CH₂C≡CH | H | 2-OS(=O)₂CH₃,5-Me | 0 |
| A-2749 | H | H | H | H | H | O | CH₂C≡CH | H | 2-OS(=O)₂CH₃,6-Me | 0 |
| A-2750 | H | H | H | H | H | O | CH₂C≡CH | H | 2-CH₂SCH₃,5-F | 0 |
| A-2751 | H | H | H | H | H | O | CH₂C≡CH | H | 2-CH₂SCH₃,6-F | 0 |
| A-2752 | H | H | H | H | H | O | CH₂C≡CH | H | 2-CH₂SCH₃,5-Me | 0 |
| A-2753 | H | H | H | H | H | O | CH₂C≡CH | H | 2-CH₂SCH₃,6-Me | 0 |
| A-2754 | H | H | H | H | H | O | CH₂C≡CH | H | 2-NMe₂,5-F | 0 |
| A-2755 | H | H | H | H | H | O | CH₂C≡CH | H | 2-NMe₂,6-F | 0 |
| A-2756 | H | H | H | H | H | O | CH₂C≡CH | H | 2-NMe₂,5-Me | 0 |
| A-2757 | H | H | H | H | H | O | CH₂C≡CH | H | 2-NMe₂,6-Me | 0 |
| A-2758 | H | H | H | H | H | O | CH₂C≡CH | H | 2-CN,4-F | 0 |
| A-2759 | H | H | H | H | H | O | CH₂C≡CH | H | 2-CN,5-F | 0 |
| A-2760 | H | H | H | H | H | O | CH₂C≡CH | H | 2-CN,6-F | 0 |
| A-2761 | H | H | H | H | H | O | CH₂C≡CH | H | 2-CN,6-Me | 0 |
| A-2762 | H | H | H | H | H | O | CH₂C≡CH | H | 2-CN,5-OMe | 0 |
| A-2763 | H | H | H | H | H | O | CH₂C≡CH | H | 2-CN,6-OMe | 0 |
| A-2764 | H | H | H | H | H | O | CH₂C≡CH | H | 3-CN,6-Me | 0 |
| A-2765 | H | H | H | H | H | O | CH₂C≡CH | H | 3-CN,6-OMe | 0 |
| A-2766 | H | H | H | H | H | O | CH₂C≡CH | H | 4-CN,2-Me | 0 |
| A-2767 | H | H | H | H | H | O | CH₂C≡CH | H | 4-CN,2-OMe | 0 |
| A-2768 | H | H | H | H | H | O | CH₂C≡CH | H | 2-NO₂,4-F | 0 |
| A-2769 | H | H | H | H | H | O | CH₂C≡CH | H | 2-NO₂,5-F | 0 |
| A-2770 | H | H | H | H | H | O | CH₂C≡CH | H | 2-NO₂,6-F | 0 |

TABLE 49-continued

| compound | R¹ | R² | R³ | R⁴ | R⁵ | A | R⁶ | R⁷ | (R⁸)ₘ | p |
|---|---|---|---|---|---|---|---|---|---|---|
| A-2771 | H | H | H | H | H | O | CH₂C≡CH | H | 2-NO₂,4-Me | 0 |
| A-2772 | H | H | H | H | H | O | CH₂C≡CH | H | 2-NO₂,5-Me | 0 |
| A-2773 | H | H | H | H | H | O | CH₂C≡CH | H | 2-NO₂,6-Me | 0 |
| A-2774 | H | H | H | H | H | O | CH₂C≡CH | H | 2-Me,4,5-F₂ | 0 |
| A-2775 | H | H | H | H | H | O | CH₂C≡CH | H | 2-Me,6-Et | 0 |
| A-2776 | H | H | H | H | H | O | CH₂C≡CH | H | 2-cyclopropyl,6-OMe | 0 |
| A-2777 | H | H | H | H | H | O | CH₂C≡CH | H | 2-Me,5-Et | 0 |
| A-2778 | H | H | H | H | H | O | CH₂C≡CH | H | 2,6-Et₂ | 0 |
| A-2779 | H | H | H | H | H | O | CH₂C≡CH | H | 2-Et,6-F | 0 |
| A-2780 | H | H | H | H | H | O | CH₂C≡CH | H | 2-CH₂OCH₃,6-Cl | 0 |
| A-2781 | H | H | H | H | H | O | CH₂C≡CH | H | 2-CH₂OCH₂CH₃,6-Cl | 0 |
| A-2782 | H | H | H | H | H | O | CH₂C≡CH | H | 2-CH₂NMe₂ | 0 |
| A-2783 | H | H | H | H | H | O | OH | H | H | 0 |
| A-2784 | H | H | H | H | H | O | OH | H | 2-F | 0 |
| A-2785 | H | H | H | H | H | O | OH | H | 2-Cl | 0 |
| A-2786 | H | H | H | H | H | O | OH | H | 2-Br | 0 |
| A-2787 | H | H | H | H | H | O | OH | H | 2-OH | 0 |
| A-2788 | H | H | H | H | H | O | OH | H | 2-Me | 0 |

TABLE 50

| compound | R¹ | R² | R³ | R⁴ | R⁵ | A | R⁶ | R⁷ | (R⁸)ₘ | p |
|---|---|---|---|---|---|---|---|---|---|---|
| A-2789 | H | H | H | H | H | O | OH | H | 2-Et | 0 |
| A-2790 | H | H | H | H | H | O | OH | H | 2-Pr | 0 |
| A-2791 | H | H | H | H | H | O | OH | H | 2-CF₃ | 0 |
| A-2792 | H | H | H | H | H | O | OH | H | 2-CHF₂ | 0 |
| A-2793 | H | H | H | H | H | O | OH | H | 2-CH₂F | 0 |
| A-2794 | H | H | H | H | H | O | OH | H | 2-CF₂Cl | 0 |
| A-2795 | H | H | H | H | H | O | OH | H | 2-cyclopropyl | 0 |
| A-2796 | H | H | H | H | H | O | OH | H | 2-cyclobutyl | 0 |
| A-2797 | H | H | H | H | H | O | OH | H | 2-cyclopentyl | 0 |
| A-2798 | H | H | H | H | H | O | OH | H | 2-ethenyl | 0 |
| A-2799 | H | H | H | H | H | O | OH | H | 2-allyl | 0 |
| A-2800 | H | H | H | H | H | O | OH | H | 2-(prop-1-en-1-yl) | 0 |
| A-2801 | H | H | H | H | H | O | OH | H | 2-(trifluoroethenyl) | 0 |
| A-2802 | H | H | H | H | H | O | OH | H | 2-OMe | 0 |
| A-2803 | H | H | H | H | H | O | OH | H | 2-OEt | 0 |
| A-2804 | H | H | H | H | H | O | OH | H | 2-OPr | 0 |
| A-2805 | H | H | H | H | H | O | OH | H | 2-O(i-Pr) | 0 |
| A-2806 | H | H | H | H | H | O | OH | H | 2-OCF₃ | 0 |
| A-2807 | H | H | H | H | H | O | OH | H | 2-OCHF₂ | 0 |
| A-2808 | H | H | H | H | H | O | OH | H | 2-(cyclopropyloxy) | 0 |
| A-2809 | H | H | H | H | H | O | OH | H | 2-(cyclobutyloxy) | 0 |
| A-2810 | H | H | H | H | H | O | OH | H | 2-(cyclopentyloxy) | 0 |
| A-2811 | H | H | H | H | H | O | OH | H | 2-((2,2-dichlorocyclopropyl)oxy) | 0 |
| A-2812 | H | H | H | H | H | O | OH | H | 2-(oxiran-2-yl) | 0 |
| A-2813 | H | H | H | H | H | O | OH | H | 2-SMe | 0 |
| A-2814 | H | H | H | H | H | O | OH | H | 3-SMe | 0 |
| A-2815 | H | H | H | H | H | O | OH | H | 2-S(=O)Me | 0 |
| A-2816 | H | H | H | H | H | O | OH | H | 3-S(=O)Me | 0 |
| A-2817 | H | H | H | H | H | O | OH | H | 2-S(=O)₂Me | 0 |
| A-2818 | H | H | H | H | H | O | OH | H | 3-S(=O)₂Me | 0 |
| A-2819 | H | H | H | H | H | O | OH | H | 2-SCF₃ | 0 |
| A-2820 | H | H | H | H | H | O | OH | H | 3-SCF₃ | 0 |
| A-2821 | H | H | H | H | H | O | OH | H | 3-S(=O)CF₃ | 0 |
| A-2822 | H | H | H | H | H | O | OH | H | 3-SCF(CF₃)₂ | 0 |
| A-2823 | H | H | H | H | H | O | OH | H | 2-(cyclopropylthio) | 0 |
| A-2824 | H | H | H | H | H | O | OH | H | 2-(cyclopropylsulfinyl) | 0 |
| A-2825 | H | H | H | H | H | O | OH | H | 2-(cyclopropylsulfonyl) | 0 |
| A-2826 | H | H | H | H | H | O | OH | H | 2-C(=O)Me | 0 |
| A-2827 | H | H | H | H | H | O | OH | H | 2-CH₂C(=O)CH₃ | 0 |
| A-2828 | H | H | H | H | H | O | OH | H | 2-CH₂C(=O)CF₃ | 0 |
| A-2829 | H | H | H | H | H | O | OH | H | 2-CH₂OH | 0 |
| A-2830 | H | H | H | H | H | O | OH | H | 2-CH₂OCH₃ | 0 |
| A-2831 | H | H | H | H | H | O | OH | H | 2-CH₂OCH₂CH₃ | 0 |
| A-2832 | H | H | H | H | H | O | OH | H | 2-CH₂SCH₃ | 0 |
| A-2833 | H | H | H | H | H | O | OH | H | 2-CH₂S(=O)CH₃ | 0 |
| A-2834 | H | H | H | H | H | O | OH | H | 2-CH₂S(=O)₂CH₃ | 0 |
| A-2835 | H | H | H | H | H | O | OH | H | 2-(benzyloxy) | 0 |
| A-2836 | H | H | H | H | H | O | OH | H | 2-NH₂ | 0 |
| A-2837 | H | H | H | H | H | O | OH | H | 2-NHMe | 0 |
| A-2838 | H | H | H | H | H | O | OH | H | 2-N(Me)₂ | 0 |
| A-2839 | H | H | H | H | H | O | OH | H | 2-(1,3-dioxolan-2-yl) | 0 |
| A-2840 | H | H | H | H | H | O | OH | H | 2-(1,3-dioxan-2-yl) | 0 |

TABLE 50-continued

| compound | R¹ | R² | R³ | R⁴ | R⁵ | A | R⁶ | R⁷ | (R⁸)$_m$ | p |
|---|---|---|---|---|---|---|---|---|---|---|
| A-2841 | H | H | H | H | H | O | OH | H | 2-(1H-imidazol-2-yl) | 0 |
| A-2842 | H | H | H | H | H | O | OH | H | 2-(thiazol-2-yl) | 0 |
| A-2843 | H | H | H | H | H | O | OH | H | 2-(oxazol-2-yl) | 0 |
| A-2844 | H | H | H | H | H | O | OH | H | 2-CH=NOH | 0 |
| A-2845 | H | H | H | H | H | O | OH | H | 2-CH=NOMe | 0 |

TABLE 51

| compound | R¹ | R² | R³ | R⁴ | R⁵ | A | R⁶ | R⁷ | (R⁸)$_m$ | p |
|---|---|---|---|---|---|---|---|---|---|---|
| A-2846 | H | H | H | H | H | O | OH | H | 2-(4,5-dihydro-3-isoxazolyl) | 0 |
| A-2847 | H | H | H | H | H | O | OH | H | 2-CN | 0 |
| A-2848 | H | H | H | H | H | O | OH | H | 2-NO₂ | 0 |
| A-2849 | H | H | H | H | H | O | OH | H | 2-F,6-Cl | 0 |
| A-2850 | H | H | H | H | H | O | OH | H | 2-F,6-Me | 0 |
| A-2851 | H | H | H | H | H | O | OH | H | 3-F,6-Me | 0 |
| A-2852 | H | H | H | H | H | O | OH | H | 4-F,2-Me | 0 |
| A-2853 | H | H | H | H | H | O | OH | H | 2-F,6-OMe | 0 |
| A-2854 | H | H | H | H | H | O | OH | H | 3-F,6-OMe | 0 |
| A-2855 | H | H | H | H | H | O | OH | H | 2,6-Cl₂ | 0 |
| A-2856 | H | H | H | H | H | O | OH | H | 2-Cl,6-Me | 0 |
| A-2857 | H | H | H | H | H | O | OH | H | 3-Cl,6-Me | 0 |
| A-2858 | H | H | H | H | H | O | OH | H | 4-Cl,2-Me | 0 |
| A-2859 | H | H | H | H | H | O | OH | H | 2-Cl,5-CF₃ | 0 |
| A-2860 | H | H | H | H | H | O | OH | H | 2-Cl,6-CF₃ | 0 |
| A-2861 | H | H | H | H | H | O | OH | H | 2-Cl,6-OMe | 0 |
| A-2862 | H | H | H | H | H | O | OH | H | 3-Cl,6-OMe | 0 |
| A-2863 | H | H | H | H | H | O | OH | H | 4-Cl,2-OMe | 0 |
| A-2864 | H | H | H | H | H | O | OH | H | 2,4-Me₂ | 0 |
| A-2865 | H | H | H | H | H | O | OH | H | 2,5-Me₂ | 0 |
| A-2866 | H | H | H | H | H | O | OH | H | 2,6-Me₂ | 0 |
| A-2867 | H | H | H | H | H | O | OH | H | 2-Me,4-CF₃ | 0 |
| A-2868 | H | H | H | H | H | O | OH | H | 2-Me,5-CF₃ | 0 |
| A-2869 | H | H | H | H | H | O | OH | H | 2-Me,6-CF₃ | 0 |
| A-2870 | H | H | H | H | H | O | OH | H | 2-Me,4-OMe | 0 |
| A-2871 | H | H | H | H | H | O | OH | H | 2-Me,5-OMe | 0 |
| A-2872 | H | H | H | H | H | O | OH | H | 2-Me,6-OMe | 0 |
| A-2873 | H | H | H | H | H | O | OH | H | 3-Me,6-OMe | 0 |
| A-2874 | H | H | H | H | H | O | OH | H | 4-Me,2-OMe | 0 |
| A-2875 | H | H | H | H | H | O | OH | H | 2,5-OMe₂ | 0 |
| A-2876 | H | H | H | H | H | O | OH | H | 2,6-OMe₂ | 0 |
| A-2877 | H | H | H | H | H | O | OH | H | 2-OMe,6-CF₃ | 0 |
| A-2878 | H | H | H | H | H | O | OH | H | 2-CHF₂,5-F | 0 |
| A-2879 | H | H | H | H | H | O | OH | H | 2-CHF₂,6-F | 0 |
| A-2880 | H | H | H | H | H | O | OH | H | 2-CHF₂,5-Me | 0 |
| A-2881 | H | H | H | H | H | O | OH | H | 2-CHF₂,6-Me | 0 |
| A-2882 | H | H | H | H | H | O | OH | H | 2-cyclopropyl,5-F | 0 |
| A-2883 | H | H | H | H | H | O | OH | H | 2-cyclopropyl,6-F | 0 |
| A-2884 | H | H | H | H | H | O | OH | H | 2-cyclopropyl,5-Me | 0 |
| A-2885 | H | H | H | H | H | O | OH | H | 2-cyclopropyl,6-Me | 0 |
| A-2886 | H | H | H | H | H | O | OH | H | 2-ethenyl,6-F | 0 |
| A-2887 | H | H | H | H | H | O | OH | H | 2-ethenyl,6-Me | 0 |
| A-2888 | H | H | H | H | H | O | OH | H | 2-OEt,5-F | 0 |
| A-2889 | H | H | H | H | H | O | OH | H | 2-OEt,6-F | 0 |
| A-2890 | H | H | H | H | H | O | OH | H | 2-OEt,5-Cl | 0 |
| A-2891 | H | H | H | H | H | O | OH | H | 2-OEt,6-Cl | 0 |
| A-2892 | H | H | H | H | H | O | OH | H | 2-OEt,5-Me | 0 |
| A-2893 | H | H | H | H | H | O | OH | H | 2-OEt,6-Me | 0 |
| A-2894 | H | H | H | H | H | O | OH | H | 2-OCHF₂,5-F | 0 |
| A-2895 | H | H | H | H | H | O | OH | H | 2-OCHF₂,6-F | 0 |
| A-2896 | H | H | H | H | H | O | OH | H | 2-OCHF₂,5-Me | 0 |
| A-2897 | H | H | H | H | H | O | OH | H | 2-OCHF₂,6-Me | 0 |
| A-2898 | H | H | H | H | H | O | OH | H | 2-(cyclopropyloxy),5-F | 0 |
| A-2899 | H | H | H | H | H | O | OH | H | 2-(cyclopropyloxy),6-F | 0 |
| A-2900 | H | H | H | H | H | O | OH | H | 2-(cyclopropyloxy),5-Me | 0 |
| A-2901 | H | H | H | H | H | O | OH | H | 2-(cyclopropyloxy),6-Me | 0 |
| A-2902 | H | H | H | H | H | O | OH | H | 2-SMe,5-F | 0 |

TABLE 52

| compound | R¹ | R² | R³ | R⁴ | R⁵ | A | R⁶ | R⁷ | $(R^8)_m$ | p |
|---|---|---|---|---|---|---|---|---|---|---|
| A-2903 | H | H | H | H | H | O | OH | H | 2-SMe,6-F | 0 |
| A-2904 | H | H | H | H | H | O | OH | H | 2-SMe,5-Me | 0 |
| A-2905 | H | H | H | H | H | O | OH | H | 2-SMe,6-Me | 0 |
| A-2906 | H | H | H | H | H | O | OH | H | 2-S(=O)Me,5-F | 0 |
| A-2907 | H | H | H | H | H | O | OH | H | 2-S(=O)Me,6-F | 0 |
| A-2908 | H | H | H | H | H | O | OH | H | 2-S(=O)Me,5-Me | 0 |
| A-2909 | H | H | H | H | H | O | OH | H | 2-S(=O)Me,6-Me | 0 |
| A-2910 | H | H | H | H | H | O | OH | H | 2-S(=O)₂Me,5-F | 0 |
| A-2911 | H | H | H | H | H | O | OH | H | 2-S(=O)₂Me,6-F | 0 |
| A-2912 | H | H | H | H | H | O | OH | H | 2-S(=O)₂Me,5-Me | 0 |
| A-2913 | H | H | H | H | H | O | OH | H | 2-S(=O)₂Me,6-Me | 0 |
| A-2914 | H | H | H | H | H | O | OH | H | 2-SCF₃,5-F | 0 |
| A-2915 | H | H | H | H | H | O | OH | H | 2-SCF₃,6-F | 0 |
| A-2916 | H | H | H | H | H | O | OH | H | 2-SCF₃,5-Me | 0 |
| A-2917 | H | H | H | H | H | O | OH | H | 2-SCF₃,6-Me | 0 |
| A-2918 | H | H | H | H | H | O | OH | H | 2-S(=O)CF₃,5-F | 0 |
| A-2919 | H | H | H | H | H | O | OH | H | 2-S(=O)CF₃,6-F | 0 |
| A-2920 | H | H | H | H | H | O | OH | H | 2-S(=O)CF₃,5-Me | 0 |
| A-2921 | H | H | H | H | H | O | OH | H | 2-S(=O)CF₃,6-Me | 0 |
| A-2922 | H | H | H | H | H | O | OH | H | 2-S(=O)₂CF₃,5-F | 0 |
| A-2923 | H | H | H | H | H | O | OH | H | 2-S(=O)₂CF₃,6-F | 0 |
| A-2924 | H | H | H | H | H | O | OH | H | 2-S(=O)₂CF₃,5-Me | 0 |
| A-2925 | H | H | H | H | H | O | OH | H | 2-S(=O)₂CF₃,6-Me | 0 |
| A-2926 | H | H | H | H | H | O | OH | H | 2-(cyclopropylthio),5-F | 0 |
| A-2927 | H | H | H | H | H | O | OH | H | 2-(cyclopropylthio),6-F | 0 |
| A-2928 | H | H | H | H | H | O | OH | H | 2-(cyclopropylthio),5-Me | 0 |
| A-2929 | H | H | H | H | H | O | OH | H | 2-(cyclopropylthio),6-Me | 0 |
| A-2930 | H | H | H | H | H | O | OH | H | 2-C(=O)Me,5-F | 0 |
| A-2931 | H | H | H | H | H | O | OH | H | 2-C(=O)Me,6-F | 0 |
| A-2932 | H | H | H | H | H | O | OH | H | 2-C(=O)Me,5-Me | 0 |
| A-2933 | H | H | H | H | H | O | OH | H | 2-C(=O)Me,6-Me | 0 |
| A-2934 | H | H | H | H | H | O | OH | H | 2-CH₂OH,5-F | 0 |
| A-2935 | H | H | H | H | H | O | OH | H | 2-CH₂OH,6-F | 0 |
| A-2936 | H | H | H | H | H | O | OH | H | 2-CH₂OH,5-Me | 0 |
| A-2937 | H | H | H | H | H | O | OH | H | 2-CH₂OH,6-Me | 0 |
| A-2938 | H | H | H | H | H | O | OH | H | 2-CH₂OCH₃,4-F | 0 |
| A-2939 | H | H | H | H | H | O | OH | H | 2-CH₂OCH₃,5-F | 0 |
| A-2940 | H | H | H | H | H | O | OH | H | 2-CH₂OCH₃,6-F | 0 |
| A-2941 | H | H | H | H | H | O | OH | H | 2-CH₂OCH₃,4-Me | 0 |
| A-2942 | H | H | H | H | H | O | OH | H | 2-CH₂OCH₃,5-Me | 0 |
| A-2943 | H | H | H | H | H | O | OH | H | 2-CH₂OCH₃,6-Me | 0 |
| A-2944 | H | H | H | H | H | O | OH | H | 2-OC(=O)CH₃,5-F | 0 |
| A-2945 | H | H | H | H | H | O | OH | H | 2-OC(=O)CH₃,6-F | 0 |
| A-2946 | H | H | H | H | H | O | OH | H | 2-OC(=O)CH₃,5-Me | 0 |
| A-2947 | H | H | H | H | H | O | OH | H | 2-OC(=O)CH₃,6-Me | 0 |
| A-2948 | H | H | H | H | H | O | OH | H | 2-OS(=O)₂CH₃,5-F | 0 |
| A-2949 | H | H | H | H | H | O | OH | H | 2-OS(=O)₂CH₃,6-F | 0 |
| A-2950 | H | H | H | H | H | O | OH | H | 2-OS(=O)₂CH₃,5-Me | 0 |
| A-2951 | H | H | H | H | H | O | OH | H | 2-OS(=O)₂CH₃,6-Me | 0 |
| A-2952 | H | H | H | H | H | O | OH | H | 2-CH₂SCH₃,5-F | 0 |
| A-2953 | H | H | H | H | H | O | OH | H | 2-CH₂SCH₃,6-F | 0 |
| A-2954 | H | H | H | H | H | O | OH | H | 2-CH₂SCH₃,5-Me | 0 |
| A-2955 | H | H | H | H | H | O | OH | H | 2-CH₂SCH₃,6-Me | 0 |
| A-2956 | H | H | H | H | H | O | OH | H | 2-NMe₂,5-F | 0 |
| A-2957 | H | H | H | H | H | O | OH | H | 2-NMe₂,6-F | 0 |
| A-2958 | H | H | H | H | H | O | OH | H | 2-NMe₂,5-Me | 0 |
| A-2959 | H | H | H | H | H | O | OH | H | 2-NMe₂,6-Me | 0 |

TABLE 53

| compound | R¹ | R² | R³ | R⁴ | R⁵ | A | R⁶ | R⁷ | $(R^8)_m$ | p |
|---|---|---|---|---|---|---|---|---|---|---|
| A-2960 | H | H | H | H | H | O | OH | H | 2-CN,4-F | 0 |
| A-2961 | H | H | H | H | H | O | OH | H | 2-CN,5-F | 0 |
| A-2962 | H | H | H | H | H | O | OH | H | 2-CN,6-F | 0 |
| A-2963 | H | H | H | H | H | O | OH | H | 2-CN,6-Me | 0 |
| A-2964 | H | H | H | H | H | O | OH | H | 2-CN,5-OMe | 0 |
| A-2965 | H | H | H | H | H | O | OH | H | 2-CN,6-OMe | 0 |
| A-2966 | H | H | H | H | H | O | OH | H | 3-CN,6-Me | 0 |
| A-2967 | H | H | H | H | H | O | OH | H | 3-CN,6-OMe | 0 |
| A-2968 | H | H | H | H | H | O | OH | H | 4-CN,2-Me | 0 |
| A-2969 | H | H | H | H | H | O | OH | H | 4-CN,2-OMe | 0 |
| A-2970 | H | H | H | H | H | O | OH | H | 2-NO₂,4-F | 0 |
| A-2971 | H | H | H | H | H | O | OH | H | 2-NO₂,5-F | 0 |
| A-2972 | H | H | H | H | H | O | OH | H | 2-NO₂,6-F | 0 |

TABLE 53-continued

| compound | R¹ | R² | R³ | R⁴ | R⁵ | A | R⁶ | R⁷ | (R⁸)$_m$ | p |
|---|---|---|---|---|---|---|---|---|---|---|
| A-2973 | H | H | H | H | H | O | OH | H | 2-NO$_2$,4-Me | 0 |
| A-2974 | H | H | H | H | H | O | OH | H | 2-NO$_2$,5-Me | 0 |
| A-2975 | H | H | H | H | H | O | OH | H | 2-NO$_2$,6-Me | 0 |
| A-2976 | H | H | H | H | H | O | OH | H | 2-Me,4,5-F$_2$ | 0 |
| A-2977 | H | H | H | H | H | O | OH | H | 2-Me,6-Et | 0 |
| A-2978 | H | H | H | H | H | O | OH | H | 2-cyclopropyl,6-OMe | 0 |
| A-2979 | H | H | H | H | H | O | OH | H | 2-Me,5-Et | 0 |
| A-2980 | H | H | H | H | H | O | OH | H | 2,6-Et$_2$ | 0 |
| A-2981 | H | H | H | H | H | O | OH | H | 2-Et,6-F | 0 |
| A-2982 | H | H | H | H | H | O | OH | H | 2-CH$_2$OCH$_3$,6-Cl | 0 |
| A-2983 | H | H | H | H | H | O | OH | H | 2-CH$_2$OCH$_2$CH$_3$,6-Cl | 0 |
| A-2984 | H | H | H | H | H | O | OH | H | 2-CH$_2$NMe$_2$ | 0 |
| A-2985 | H | H | H | H | H | O | OCH$_2$CH$_3$ | H | H | 0 |
| A-2986 | H | H | H | H | H | O | OCH$_2$CH$_3$ | H | 2-F | 0 |
| A-2987 | H | H | H | H | H | O | OCH$_2$CH$_3$ | H | 2-Cl | 0 |
| A-2988 | H | H | H | H | H | O | OCH$_2$CH$_3$ | H | 2-Br | 0 |
| A-2989 | H | H | H | H | H | O | OCH$_2$CH$_3$ | H | 2-OH | 0 |
| A-2990 | H | H | H | H | H | O | OCH$_2$CH$_3$ | H | 2-Me | 0 |
| A-2991 | H | H | H | H | H | O | OCH$_2$CH$_3$ | H | 2-Et | 0 |
| A-2992 | H | H | H | H | H | O | OCH$_2$CH$_3$ | H | 2-Pr | 0 |
| A-2993 | H | H | H | H | H | O | OCH$_2$CH$_3$ | H | 2-CF$_3$ | 0 |
| A-2994 | H | H | H | H | H | O | OCH$_2$CH$_3$ | H | 2-CHF$_2$ | 0 |
| A-2995 | H | H | H | H | H | O | OCH$_2$CH$_3$ | H | 2-CH$_2$F | 0 |
| A-2996 | H | H | H | H | H | O | OCH$_2$CH$_3$ | H | 2-CF$_2$Cl | 0 |
| A-2997 | H | H | H | H | H | O | OCH$_2$CH$_3$ | H | 2-cyclopropyl | 0 |
| A-2998 | H | H | H | H | H | O | OCH$_2$CH$_3$ | H | 2-cyclobutyl | 0 |
| A-2999 | H | H | H | H | H | O | OCH$_2$CH$_3$ | H | 2-cyclopentyl | 0 |
| A-3000 | H | H | H | H | H | O | OCH$_2$CH$_3$ | H | 2-ethenyl | 0 |
| A-3001 | H | H | H | H | H | O | OCH$_2$CH$_3$ | H | 2-allyl | 0 |
| A-3002 | H | H | H | H | H | O | OCH$_2$CH$_3$ | H | 2-(prop-1-en-1-yl) | 0 |
| A-3003 | H | H | H | H | H | O | OCH$_2$CH$_3$ | H | 2-(trifluoroethenyl) | 0 |
| A-3004 | H | H | H | H | H | O | OCH$_2$CH$_3$ | H | 2-OMe | 0 |
| A-3005 | H | H | H | H | H | O | OCH$_2$CH$_3$ | H | 2-OEt | 0 |
| A-3006 | H | H | H | H | H | O | OCH$_2$CH$_3$ | H | 2-OPr | 0 |
| A-3007 | H | H | H | H | H | O | OCH$_2$CH$_3$ | H | 2-O(i-Pr) | 0 |
| A-3008 | H | H | H | H | H | O | OCH$_2$CH$_3$ | H | 2-OCF$_3$ | 0 |
| A-3009 | H | H | H | H | H | O | OCH$_2$CH$_3$ | H | 2-OCHF$_2$ | 0 |
| A-3010 | H | H | H | H | H | O | OCH$_2$CH$_3$ | H | 2-(cyclopropyloxy) | 0 |
| A-3011 | H | H | H | H | H | O | OCH$_2$CH$_3$ | H | 2-(cyclobutyloxy) | 0 |
| A-3012 | H | H | H | H | H | O | OCH$_2$CH$_3$ | H | 2-(cyclopentyloxy) | 0 |
| A-3013 | H | H | H | H | H | O | OCH$_2$CH$_3$ | H | 2-((2,2-dichlorocyclopropyl)oxy) | 0 |
| A-3014 | H | H | H | H | H | O | OCH$_2$CH$_3$ | H | 2-(oxiran-2-yl) | 0 |
| A-3015 | H | H | H | H | H | O | OCH$_2$CH$_3$ | H | 2-SMe | 0 |
| A-3016 | H | H | H | H | H | O | OCH$_2$CH$_3$ | H | 3-SMe | 0 |

TABLE 54

| compound | R¹ | R² | R³ | R⁴ | R⁵ | A | R⁶ | R⁷ | (R⁸)$_m$ | p |
|---|---|---|---|---|---|---|---|---|---|---|
| A-3017 | H | H | H | H | H | O | OCH$_2$CH$_3$ | H | 2-S(=O)Me | 0 |
| A-3018 | H | H | H | H | H | O | OCH$_2$CH$_3$ | H | 3-S(=O)Me | 0 |
| A-3019 | H | H | H | H | H | O | OCH$_2$CH$_3$ | H | 2-S(=O)$_2$Me | 0 |
| A-3020 | H | H | H | H | H | O | OCH$_2$CH$_3$ | H | 3-S(=O)$_2$Me | 0 |
| A-3021 | H | H | H | H | H | O | OCH$_2$CH$_3$ | H | 2-SCF$_3$ | 0 |
| A-3022 | H | H | H | H | H | O | OCH$_2$CH$_3$ | H | 3-SCF$_3$ | 0 |
| A-3023 | H | H | H | H | H | O | OCH$_2$CH$_3$ | H | 3-S(=O)CF$_3$ | 0 |
| A-3024 | H | H | H | H | H | O | OCH$_2$CH$_3$ | H | 3-SCF(CF$_3$)$_2$ | 0 |
| A-3025 | H | H | H | H | H | O | OCH$_2$CH$_3$ | H | 2-(cyclopropylthio) | 0 |
| A-3026 | H | H | H | H | H | O | OCH$_2$CH$_3$ | H | 2-(cyclopropylsulfinyl) | 0 |
| A-3027 | H | H | H | H | H | O | OCH$_2$CH$_3$ | H | 2-(cyclopropylsulfonyl) | 0 |
| A-3028 | H | H | H | H | H | O | OCH$_2$CH$_3$ | H | 2-C(=O)Me | 0 |
| A-3029 | H | H | H | H | H | O | OCH$_2$CH$_3$ | H | 2-CH$_2$C(=O)CH$_3$ | 0 |
| A-3030 | H | H | H | H | H | O | OCH$_2$CH$_3$ | H | 2-CH$_2$C(=O)CF$_3$ | 0 |
| A-3031 | H | H | H | H | H | O | OCH$_2$CH$_3$ | H | 2-CH$_2$OH | 0 |
| A-3032 | H | H | H | H | H | O | OCH$_2$CH$_3$ | H | 2-CH$_2$OCH$_3$ | 0 |
| A-3033 | H | H | H | H | H | O | OCH$_2$CH$_3$ | H | 2-CH$_2$OCH$_2$CH$_3$ | 0 |
| A-3034 | H | H | H | H | H | O | OCH$_2$CH$_3$ | H | 2-CH$_2$SCH$_3$ | 0 |
| A-3035 | H | H | H | H | H | O | OCH$_2$CH$_3$ | H | 2-CH$_2$S(=O)CH$_3$ | 0 |
| A-3036 | H | H | H | H | H | O | OCH$_2$CH$_3$ | H | 2-CH$_2$S(=O)$_2$CH$_3$ | 0 |
| A-3037 | H | H | H | H | H | O | OCH$_2$CH$_3$ | H | 2-(benzyloxy) | 0 |
| A-3038 | H | H | H | H | H | O | OCH$_2$CH$_3$ | H | 2-NH$_2$ | 0 |
| A-3039 | H | H | H | H | H | O | OCH$_2$CH$_3$ | H | 2-NHMe | 0 |
| A-3040 | H | H | H | H | H | O | OCH$_2$CH$_3$ | H | 2-N(Me)$_2$ | 0 |
| A-3041 | H | H | H | H | H | O | OCH$_2$CH$_3$ | H | 2-(1,3-dioxolan-2-yl) | 0 |
| A-3042 | H | H | H | H | H | O | OCH$_2$CH$_3$ | H | 2-(1,3-dioxan-2-yl) | 0 |

TABLE 54-continued

| compound | R¹ | R² | R³ | R⁴ | R⁵ | A | R⁶ | R⁷ | (R⁸)$_m$ | p |
|---|---|---|---|---|---|---|---|---|---|---|
| A-3043 | H | H | H | H | H | O | OCH$_2$CH$_3$ | H | 2-(1H-imidazol-2-yl) | 0 |
| A-3044 | H | H | H | H | H | O | OCH$_2$CH$_3$ | H | 2-(thiazol-2-yl) | 0 |
| A-3045 | H | H | H | H | H | O | OCH$_2$CH$_3$ | H | 2-(oxazol-2-yl) | 0 |
| A-3046 | H | H | H | H | H | O | OCH$_2$CH$_3$ | H | 2-CH=NOH | 0 |
| A-3047 | H | H | H | H | H | O | OCH$_2$CH$_3$ | H | 2-CH=NOMe | 0 |
| A-3048 | H | H | H | H | H | O | OCH$_2$CH$_3$ | H | 2-(4,5-dihydro-3-isoxazolyl) | 0 |
| A-3049 | H | H | H | H | H | O | OCH$_2$CH$_3$ | H | 2-CN | 0 |
| A-3050 | H | H | H | H | H | O | OCH$_2$CH$_3$ | H | 2-NO$_2$ | 0 |
| A-3051 | H | H | H | H | H | O | OCH$_2$CH$_3$ | H | 2-F,6-Cl | 0 |
| A-3052 | H | H | H | H | H | O | OCH$_2$CH$_3$ | H | 2-F,6-Me | 0 |
| A-3053 | H | H | H | H | H | O | OCH$_2$CH$_3$ | H | 3-F,6-Me | 0 |
| A-3054 | H | H | H | H | H | O | OCH$_2$CH$_3$ | H | 4-F,2-Me | 0 |
| A-3055 | H | H | H | H | H | O | OCH$_2$CH$_3$ | H | 2-F,6-OMe | 0 |
| A-3056 | H | H | H | H | H | O | OCH$_2$CH$_3$ | H | 3-F,6-OMe | 0 |
| A-3057 | H | H | H | H | H | O | OCH$_2$CH$_3$ | H | 2,6-Cl$_2$ | 0 |
| A-3058 | H | H | H | H | H | O | OCH$_2$CH$_3$ | H | 2-Cl,6-Me | 0 |
| A-3059 | H | H | H | H | H | O | OCH$_2$CH$_3$ | H | 3-Cl,6-Me | 0 |
| A-3060 | H | H | H | H | H | O | OCH$_2$CH$_3$ | H | 4-Cl,2-Me | 0 |
| A-3061 | H | H | H | H | H | O | OCH$_2$CH$_3$ | H | 2-Cl,5-CF$_3$ | 0 |
| A-3062 | H | H | H | H | H | O | OCH$_2$CH$_3$ | H | 2-Cl,6-CF$_3$ | 0 |
| A-3063 | H | H | H | H | H | O | OCH$_2$CH$_3$ | H | 2-Cl,6-OMe | 0 |
| A-3064 | H | H | H | H | H | O | OCH$_2$CH$_3$ | H | 3-Cl,6-OMe | 0 |
| A-3065 | H | H | H | H | H | O | OCH$_2$CH$_3$ | H | 4-Cl,2-OMe | 0 |
| A-3066 | H | H | H | H | H | O | OCH$_2$CH$_3$ | H | 2,4-Me$_2$ | 0 |
| A-3067 | H | H | H | H | H | O | OCH$_2$CH$_3$ | H | 2,5-Me$_2$ | 0 |
| A-3068 | H | H | H | H | H | O | OCH$_2$CH$_3$ | H | 2,6-Me$_2$ | 0 |
| A-3069 | H | H | H | H | H | O | OCH$_2$CH$_3$ | H | 2-Me,4-CF$_3$ | 0 |
| A-3070 | H | H | H | H | H | O | OCH$_2$CH$_3$ | H | 2-Me,5-CF$_3$ | 0 |
| A-3071 | H | H | H | H | H | O | OCH$_2$CH$_3$ | H | 2-Me,6-CF$_3$ | 0 |
| A-3072 | H | H | H | H | H | O | OCH$_2$CH$_3$ | H | 2-Me,4-OMe | 0 |
| A-3073 | H | H | H | H | H | O | OCH$_2$CH$_3$ | H | 2-Me,5-OMe | 0 |

TABLE 55

| compound | R¹ | R² | R³ | R⁴ | R⁵ | A | R⁶ | R⁷ | (R⁸)$_m$ | p |
|---|---|---|---|---|---|---|---|---|---|---|
| A-3074 | H | H | H | H | H | O | OCH$_2$CH$_3$ | H | 2-Me,6-OMe | 0 |
| A-3075 | H | H | H | H | H | O | OCH$_2$CH$_3$ | H | 3-Me,6-OMe | 0 |
| A-3076 | H | H | H | H | H | O | OCH$_2$CH$_3$ | H | 4-Me,2-OMe | 0 |
| A-3077 | H | H | H | H | H | O | OCH$_2$CH$_3$ | H | 2,5-OMe$_2$ | 0 |
| A-3078 | H | H | H | H | H | O | OCH$_2$CH$_3$ | H | 2,6-OMe$_2$ | 0 |
| A-3079 | H | H | H | H | H | O | OCH$_2$CH$_3$ | H | 2-OMe,6-CF$_3$ | 0 |
| A-3080 | H | H | H | H | H | O | OCH$_2$CH$_3$ | H | 2-CHF$_2$,5-F | 0 |
| A-3081 | H | H | H | H | H | O | OCH$_2$CH$_3$ | H | 2-CHF$_2$,6-F | 0 |
| A-3082 | H | H | H | H | H | O | OCH$_2$CH$_3$ | H | 2-CHF$_2$,5-Me | 0 |
| A-3083 | H | H | H | H | H | O | OCH$_2$CH$_3$ | H | 2-CHF$_2$,6-Me | 0 |
| A-3084 | H | H | H | H | H | O | OCH$_2$CH$_3$ | H | 2-cyclopropyl,5-F | 0 |
| A-3085 | H | H | H | H | H | O | OCH$_2$CH$_3$ | H | 2-cyclopropyl,6-F | 0 |
| A-3086 | H | H | H | H | H | O | OCH$_2$CH$_3$ | H | 2-cyclopropyl,5-Me | 0 |
| A-3087 | H | H | H | H | H | O | OCH$_2$CH$_3$ | H | 2-cyclopropyl,6-Me | 0 |
| A-3088 | H | H | H | H | H | O | OCH$_2$CH$_3$ | H | 2-ethenyl,6-F | 0 |
| A-3089 | H | H | H | H | H | O | OCH$_2$CH$_3$ | H | 2-ethenyl,6-Me | 0 |
| A-3090 | H | H | H | H | H | O | OCH$_2$CH$_3$ | H | 2-OEt,5-F | 0 |
| A-3091 | H | H | H | H | H | O | OCH$_2$CH$_3$ | H | 2-OEt,6-F | 0 |
| A-3092 | H | H | H | H | H | O | OCH$_2$CH$_3$ | H | 2-OEt,5-Cl | 0 |
| A-3093 | H | H | H | H | H | O | OCH$_2$CH$_3$ | H | 2-OEt,6-Cl | 0 |
| A-3094 | H | H | H | H | H | O | OCH$_2$CH$_3$ | H | 2-OEt,5-Me | 0 |
| A-3095 | H | H | H | H | H | O | OCH$_2$CH$_3$ | H | 2-OEt,6-Me | 0 |
| A-3096 | H | H | H | H | H | O | OCH$_2$CH$_3$ | H | 2-OCHF$_2$,5-F | 0 |
| A-3097 | H | H | H | H | H | O | OCH$_2$CH$_3$ | H | 2-OCHF$_2$,6-F | 0 |
| A-3098 | H | H | H | H | H | O | OCH$_2$CH$_3$ | H | 2-OCHF$_2$,5-Me | 0 |
| A-3099 | H | H | H | H | H | O | OCH$_2$CH$_3$ | H | 2-OCHF$_2$,6-Me | 0 |
| A-3100 | H | H | H | H | H | O | OCH$_2$CH$_3$ | H | 2-(cyclopropyloxy),5-F | 0 |
| A-3101 | H | H | H | H | H | O | OCH$_2$CH$_3$ | H | 2-(cyclopropyloxy),6-F | 0 |
| A-3102 | H | H | H | H | H | O | OCH$_2$CH$_3$ | H | 2-(cyclopropyloxy),5-Me | 0 |
| A-3103 | H | H | H | H | H | O | OCH$_2$CH$_3$ | H | 2-(cyclopropyloxy),6-Me | 0 |
| A-3104 | H | H | H | H | H | O | OCH$_2$CH$_3$ | H | 2-SMe,5-F | 0 |
| A-3105 | H | H | H | H | H | O | OCH$_2$CH$_3$ | H | 2-SMe,6-F | 0 |
| A-3106 | H | H | H | H | H | O | OCH$_2$CH$_3$ | H | 2-SMe,5-Me | 0 |
| A-3107 | H | H | H | H | H | O | OCH$_2$CH$_3$ | H | 2-SMe,6-Me | 0 |
| A-3108 | H | H | H | H | H | O | OCH$_2$CH$_3$ | H | 2-S(=O)Me,5-F | 0 |
| A-3109 | H | H | H | H | H | O | OCH$_2$CH$_3$ | H | 2-S(=O)Me,6-F | 0 |
| A-3110 | H | H | H | H | H | O | OCH$_2$CH$_3$ | H | 2-S(=O)Me,5-Me | 0 |
| A-3111 | H | H | H | H | H | O | OCH$_2$CH$_3$ | H | 2-S(=O)Me,6-Me | 0 |
| A-3112 | H | H | H | H | H | O | OCH$_2$CH$_3$ | H | 2-S(=O)$_2$Me,5-F | 0 |

TABLE 55-continued

| compound | R¹ | R² | R³ | R⁴ | R⁵ | A | R⁶ | R⁷ | (R⁸)ₘ | p |
|---|---|---|---|---|---|---|---|---|---|---|
| A-3113 | H | H | H | H | H | O | OCH$_2$CH$_3$ | H | 2-S(=O)$_2$Me,6-F | 0 |
| A-3114 | H | H | H | H | H | O | OCH$_2$CH$_3$ | H | 2-S(=O)$_2$Me,5-Me | 0 |
| A-3115 | H | H | H | H | H | O | OCH$_2$CH$_3$ | H | 2-S(=O)$_2$Me,6-Me | 0 |
| A-3116 | H | H | H | H | H | O | OCH$_2$CH$_3$ | H | 2-SCF$_3$,5-F | 0 |
| A-3117 | H | H | H | H | H | O | OCH$_2$CH$_3$ | H | 2-SCF$_3$,6-F | 0 |
| A-3118 | H | H | H | H | H | O | OCH$_2$CH$_3$ | H | 2-SCF$_3$,5-Me | 0 |
| A-3119 | H | H | H | H | H | O | OCH$_2$CH$_3$ | H | 2-SCF$_3$,6-Me | 0 |
| A-3120 | H | H | H | H | H | O | OCH$_2$CH$_3$ | H | 2-S(=O)CF$_3$,5-F | 0 |
| A-3121 | H | H | H | H | H | O | OCH$_2$CH$_3$ | H | 2-S(=O)CF$_3$,6-F | 0 |
| A-3122 | H | H | H | H | H | O | OCH$_2$CH$_3$ | H | 2-S(=O)CF$_3$,5-Me | 0 |
| A-3123 | H | H | H | H | H | O | OCH$_2$CH$_3$ | H | 2-S(=O)CF$_3$,6-Me | 0 |
| A-3124 | H | H | H | H | H | O | OCH$_2$CH$_3$ | H | 2-S(=O)$_2$CF$_3$,5-F | 0 |
| A-3125 | H | H | H | H | H | O | OCH$_2$CH$_3$ | H | 2-S(=O)$_2$CF$_3$,6-F | 0 |
| A-3126 | H | H | H | H | H | O | OCH$_2$CH$_3$ | H | 2-S(=O)$_2$CF$_3$,5-Me | 0 |
| A-3127 | H | H | H | H | H | O | OCH$_2$CH$_3$ | H | 2-S(=O)$_2$CF$_3$,6-Me | 0 |
| A-3128 | H | H | H | H | H | O | OCH$_2$CH$_3$ | H | 2-(cyclopropylthio),5-F | 0 |
| A-3129 | H | H | H | H | H | O | OCH$_2$CH$_3$ | H | 2-(cyclopropylthio),6-F | 0 |
| A-3130 | H | H | H | H | H | O | OCH$_2$CH$_3$ | H | 2-(cyclopropylthio),5-Me | 0 |

TABLE 56

| compound | R¹ | R² | R³ | R⁴ | R⁵ | A | R⁶ | R⁷ | (R⁸)ₘ | p |
|---|---|---|---|---|---|---|---|---|---|---|
| A-3131 | H | H | H | H | H | O | OCH$_2$CH$_3$ | H | 2-(cyclopropylthio),6-Me | 0 |
| A-3132 | H | H | H | H | H | O | OCH$_2$CH$_3$ | H | 2-C(=O)Me,5-F | 0 |
| A-3133 | H | H | H | H | H | O | OCH$_2$CH$_3$ | H | 2-C(=O)Me,6-F | 0 |
| A-3134 | H | H | H | H | H | O | OCH$_2$CH$_3$ | H | 2-C(=O)Me,5-Me | 0 |
| A-3135 | H | H | H | H | H | O | OCH$_2$CH$_3$ | H | 2-C(=O)Me,6-Me | 0 |
| A-3136 | H | H | H | H | H | O | OCH$_2$CH$_3$ | H | 2-CH$_2$OH,5-F | 0 |
| A-3137 | H | H | H | H | H | O | OCH$_2$CH$_3$ | H | 2-CH$_2$OH,6-F | 0 |
| A-3138 | H | H | H | H | H | O | OCH$_2$CH$_3$ | H | 2-CH$_2$OH,5-Me | 0 |
| A-3139 | H | H | H | H | H | O | OCH$_2$CH$_3$ | H | 2-CH$_2$OH,6-Me | 0 |
| A-3140 | H | H | H | H | H | O | OCH$_2$CH$_3$ | H | 2-CH$_2$OCH$_3$,4-F | 0 |
| A-3141 | H | H | H | H | H | O | OCH$_2$CH$_3$ | H | 2-CH$_2$OCH$_3$,5-F | 0 |
| A-3142 | H | H | H | H | H | O | OCH$_2$CH$_3$ | H | 2-CH$_2$OCH$_3$,6-F | 0 |
| A-3143 | H | H | H | H | H | O | OCH$_2$CH$_3$ | H | 2-CH$_2$OCH$_3$,4-Me | 0 |
| A-3144 | H | H | H | H | H | O | OCH$_2$CH$_3$ | H | 2-CH$_2$OCH$_3$,5-Me | 0 |
| A-3145 | H | H | H | H | H | O | OCH$_2$CH$_3$ | H | 2-CH$_2$OCH$_3$,6-Me | 0 |
| A-3146 | H | H | H | H | H | O | OCH$_2$CH$_3$ | H | 2-OC(=O)CH$_3$,5-F | 0 |
| A-3147 | H | H | H | H | H | O | OCH$_2$CH$_3$ | H | 2-OC(=O)CH$_3$,6-F | 0 |
| A-3148 | H | H | H | H | H | O | OCH$_2$CH$_3$ | H | 2-OC(=O)CH$_3$,5-Me | 0 |
| A-3149 | H | H | H | H | H | O | OCH$_2$CH$_3$ | H | 2-OC(=O)CH$_3$,6-Me | 0 |
| A-3150 | H | H | H | H | H | O | OCH$_2$CH$_3$ | H | 2-OS(=O)$_2$-CH$_3$,5-F | 0 |
| A-3151 | H | H | H | H | H | O | OCH$_2$CH$_3$ | H | 2-OS(=O)$_2$-CH$_3$,6-F | 0 |
| A-3152 | H | H | H | H | H | O | OCH$_2$CH$_3$ | H | 2-OS(=O)$_2$CH$_3$,5-Me | 0 |
| A-3153 | H | H | H | H | H | O | OCH$_2$CH$_3$ | H | 2-OS(=O)$_2$CH$_3$,6-Me | 0 |
| A-3154 | H | H | H | H | H | O | OCH$_2$CH$_3$ | H | 2-CH$_2$SCH$_3$,5-F | 0 |
| A-3155 | H | H | H | H | H | O | OCH$_2$CH$_3$ | H | 2-CH$_2$SCH$_3$,6-F | 0 |
| A-3156 | H | H | H | H | H | O | OCH$_2$CH$_3$ | H | 2-CH$_2$SCH$_3$,5-Me | 0 |
| A-3157 | H | H | H | H | H | O | OCH$_2$CH$_3$ | H | 2-CH$_2$SCH$_3$,6-Me | 0 |
| A-3158 | H | H | H | H | H | O | OCH$_2$CH$_3$ | H | 2-NMe$_2$,5-F | 0 |
| A-3159 | H | H | H | H | H | O | OCH$_2$CH$_3$ | H | 2-NMe$_2$,6-F | 0 |
| A-3160 | H | H | H | H | H | O | OCH$_2$CH$_3$ | H | 2-NMe$_2$,5-Me | 0 |
| A-3161 | H | H | H | H | H | O | OCH$_2$CH$_3$ | H | 2-NMe$_2$,6-Me | 0 |
| A-3162 | H | H | H | H | H | O | OCH$_2$CH$_3$ | H | 2-CN,4-F | 0 |
| A-3163 | H | H | H | H | H | O | OCH$_2$CH$_3$ | H | 2-CN,5-F | 0 |
| A-3164 | H | H | H | H | H | O | OCH$_2$CH$_3$ | H | 2-CN,6-F | 0 |
| A-3165 | H | H | H | H | H | O | OCH$_2$CH$_3$ | H | 2-CN,6-Me | 0 |
| A-3166 | H | H | H | H | H | O | OCH$_2$CH$_3$ | H | 2-CN,5-OMe | 0 |
| A-3167 | H | H | H | H | H | O | OCH$_2$CH$_3$ | H | 2-CN,6-OMe | 0 |
| A-3168 | H | H | H | H | H | O | OCH$_2$CH$_3$ | H | 3-CN,6-Me | 0 |
| A-3169 | H | H | H | H | H | O | OCH$_2$CH$_3$ | H | 3-CN,6-OMe | 0 |
| A-3170 | H | H | H | H | H | O | OCH$_2$CH$_3$ | H | 4-CN,2-Me | 0 |
| A-3171 | H | H | H | H | H | O | OCH$_2$CH$_3$ | H | 4-CN,2-OMe | 0 |
| A-3172 | H | H | H | H | H | O | OCH$_2$CH$_3$ | H | 2-NO$_2$,4-F | 0 |
| A-3173 | H | H | H | H | H | O | OCH$_2$CH$_3$ | H | 2-NO$_2$,5-F | 0 |
| A-3174 | H | H | H | H | H | O | OCH$_2$CH$_3$ | H | 2-NO$_2$,6-F | 0 |
| A-3175 | H | H | H | H | H | O | OCH$_2$CH$_3$ | H | 2-NO$_2$,4-Me | 0 |
| A-3176 | H | H | H | H | H | O | OCH$_2$CH$_3$ | H | 2-NO$_2$,5-Me | 0 |
| A-3177 | H | H | H | H | H | O | OCH$_2$CH$_3$ | H | 2-NO$_2$,6-Me | 0 |
| A-3178 | H | H | H | H | H | O | OCH$_2$CH$_3$ | H | 2-Me,4,5-F$_2$ | 0 |
| A-3179 | H | H | H | H | H | O | OCH$_2$CH$_3$ | H | 2-Me,6-Et | 0 |
| A-3180 | H | H | H | H | H | O | OCH$_2$CH$_3$ | H | 2-cyclopropyl,6-OMe | 0 |
| A-3181 | H | H | H | H | H | O | OCH$_2$CH$_3$ | H | 2-Me,5-Et | 0 |
| A-3182 | H | H | H | H | H | O | OCH$_2$CH$_3$ | H | 2,6-Et$_2$ | 0 |

TABLE 56-continued

| compound | R¹ | R² | R³ | R⁴ | R⁵ | A | R⁶ | R⁷ | (R⁸)ₘ | p |
|---|---|---|---|---|---|---|---|---|---|---|
| A-3183 | H | H | H | H | H | O | OCH₂CH₃ | H | 2-Et,6-F | 0 |
| A-3184 | H | H | H | H | H | O | OCH₂CH₃ | H | 2-CH₂OCH₃,6-Cl | 0 |
| A-3185 | H | H | H | H | H | O | OCH₂CH₃ | H | 2-CH₂OCH₂CH₃,6-Cl | 0 |
| A-3186 | H | H | H | H | H | O | OCH₂CH₃ | H | 2-CH₂NMe₂ | 0 |
| A-3187 | H | H | H | H | H | O | CH₂CF₃ | H | H | 0 |

TABLE 57

| compound | R¹ | R² | R³ | R⁴ | R⁵ | A | R⁶ | R⁷ | (R⁸)ₘ | p |
|---|---|---|---|---|---|---|---|---|---|---|
| A-3188 | H | H | H | H | H | O | CH₂CF₃ | H | 2-F | 0 |
| A-3189 | H | H | H | H | H | O | CH₂CF₃ | H | 2-Cl | 0 |
| A-3190 | H | H | H | H | H | O | CH₂CF₃ | H | 2-Br | 0 |
| A-3191 | H | H | H | H | H | O | CH₂CF₃ | H | 2-OH | 0 |
| A-3192 | H | H | H | H | H | O | CH₂CF₃ | H | 2-Me | 0 |
| A-3193 | H | H | H | H | H | O | CH₂CF₃ | H | 2-Et | 0 |
| A-3194 | H | H | H | H | H | O | CH₂CF₃ | H | 2-Pr | 0 |
| A-3195 | H | H | H | H | H | O | CH₂CF₃ | H | 2-CF₃ | 0 |
| A-3196 | H | H | H | H | H | O | CH₂CF₃ | H | 2-CHF₂ | 0 |
| A-3197 | H | H | H | H | H | O | CH₂CF₃ | H | 2-CH₂F | 0 |
| A-3198 | H | H | H | H | H | O | CH₂CF₃ | H | 2-CF₂Cl | 0 |
| A-3199 | H | H | H | H | H | O | CH₂CF₃ | H | 2-cyclopropyl | 0 |
| A-3200 | H | H | H | H | H | O | CH₂CF₃ | H | 2-cyclobutyl | 0 |
| A-3201 | H | H | H | H | H | O | CH₂CF₃ | H | 2-cyclopentyl | 0 |
| A-3202 | H | H | H | H | H | O | CH₂CF₃ | H | 2-ethenyl | 0 |
| A-3203 | H | H | H | H | H | O | CH₂CF₃ | H | 2-allyl | 0 |
| A-3204 | H | H | H | H | H | O | CH₂CF₃ | H | 2-(prop-1-en-1-yl) | 0 |
| A-3205 | H | H | H | H | H | O | CH₂CF₃ | H | 2-(trifluoroethenyl) | 0 |
| A-3206 | H | H | H | H | H | O | CH₂CF₃ | H | 2-OMe | 0 |
| A-3207 | H | H | H | H | H | O | CH₂CF₃ | H | 2-OEt | 0 |
| A-3208 | H | H | H | H | H | O | CH₂CF₃ | H | 2-OPr | 0 |
| A-3209 | H | H | H | H | H | O | CH₂CF₃ | H | 2-O(i-Pr) | 0 |
| A-3210 | H | H | H | H | H | O | CH₂CF₃ | H | 2-OCF₃ | 0 |
| A-3211 | H | H | H | H | H | O | CH₂CF₃ | H | 2-OCHF₂ | 0 |
| A-3212 | H | H | H | H | H | O | CH₂CF₃ | H | 2-(cyclopropyloxy) | 0 |
| A-3213 | H | H | H | H | H | O | CH₂CF₃ | H | 2-(cyclobutyloxy) | 0 |
| A-3214 | H | H | H | H | H | O | CH₂CF₃ | H | 2-(cyclopentyloxy) | 0 |
| A-3215 | H | H | H | H | H | O | CH₂CF₃ | H | 2-((2,2-dichlorocyclopropyl)oxy) | 0 |
| A-3216 | H | H | H | H | H | O | CH₂CF₃ | H | 2-(oxiran-2-yl) | 0 |
| A-3217 | H | H | H | H | H | O | CH₂CF₃ | H | 2-SMe | 0 |
| A-3218 | H | H | H | H | H | O | CH₂CF₃ | H | 3-SMe | 0 |
| A-3219 | H | H | H | H | H | O | CH₂CF₃ | H | 2-S(=O)Me | 0 |
| A-3220 | H | H | H | H | H | O | CH₂CF₃ | H | 3-S(=O)Me | 0 |
| A-3221 | H | H | H | H | H | O | CH₂CF₃ | H | 2-S(=O)₂Me | 0 |
| A-3222 | H | H | H | H | H | O | CH₂CF₃ | H | 3-S(=O)₂Me | 0 |
| A-3223 | H | H | H | H | H | O | CH₂CF₃ | H | 2-SCF₃ | 0 |
| A-3224 | H | H | H | H | H | O | CH₂CF₃ | H | 3-SCF₃ | 0 |
| A-3225 | H | H | H | H | H | O | CH₂CF₃ | H | 3-S(=O)CF₃ | 0 |
| A-3226 | H | H | H | H | H | O | CH₂CF₃ | H | 3-SCF(CF₃)₂ | 0 |
| A-3227 | H | H | H | H | H | O | CH₂CF₃ | H | 2-(cyclopropylthio) | 0 |
| A-3228 | H | H | H | H | H | O | CH₂CF₃ | H | 2-(cyclopropylsulfinyl) | 0 |
| A-3229 | H | H | H | H | H | O | CH₂CF₃ | H | 2-(cyclopropylsulfonyl) | 0 |
| A-3230 | H | H | H | H | H | O | CH₂CF₃ | H | 2-C(=O)Me | 0 |
| A-3231 | H | H | H | H | H | O | CH₂CF₃ | H | 2-CH₂C(=O)CH₃ | 0 |
| A-3232 | H | H | H | H | H | O | CH₂CF₃ | H | 2-CH₂C(=O)CF₃ | 0 |
| A-3233 | H | H | H | H | H | O | CH₂CF₃ | H | 2-CH₂OH | 0 |
| A-3234 | H | H | H | H | H | O | CH₂CF₃ | H | 2-CH₂OCH₃ | 0 |
| A-3235 | H | H | H | H | H | O | CH₂CF₃ | H | 2-CH₂OCH₂CH₃ | 0 |
| A-3236 | H | H | H | H | H | O | CH₂CF₃ | H | 2-CH₂SCH₃ | 0 |
| A-3237 | H | H | H | H | H | O | CH₂CF₃ | H | 2-CH₂S(=O)CH₃ | 0 |
| A-3238 | H | H | H | H | H | O | CH₂CF₃ | H | 2-CH₂S(=O)₂CH₃ | 0 |
| A-3239 | H | H | H | H | H | O | CH₂CF₃ | H | 2-(benzyloxy) | 0 |
| A-3240 | H | H | H | H | H | O | CH₂CF₃ | H | 2-NH₂ | 0 |
| A-3241 | H | H | H | H | H | O | CH₂CF₃ | H | 2-NHMe | 0 |
| A-3242 | H | H | H | H | H | O | CH₂CF₃ | H | 2-N(Me)₂ | 0 |
| A-3243 | H | H | H | H | H | O | CH₂CF₃ | H | 2-(1,3-dioxolan-2-yl) | 0 |
| A-3244 | H | H | H | H | H | O | CH₂CF₃ | H | 2-(1,3-dioxan-2-yl) | 0 |

TABLE 58

| compound | R¹ | R² | R³ | R⁴ | R⁵ | A | R⁶ | R⁷ | (R⁸)$_m$ | p |
|---|---|---|---|---|---|---|---|---|---|---|
| A-3245 | H | H | H | H | H | O | CH$_2$CF$_3$ | H | 2-(1H-imidazol-2-yl) | 0 |
| A-3246 | H | H | H | H | H | O | CH$_2$CF$_3$ | H | 2-(thiazol-2-yl) | 0 |
| A-3247 | H | H | H | H | H | O | CH$_2$CF$_3$ | H | 2-(oxazol-2-yl) | 0 |
| A-3248 | H | H | H | H | H | O | CH$_2$CF$_3$ | H | 2-CH=NOH | 0 |
| A-3249 | H | H | H | H | H | O | CH$_2$CF$_3$ | H | 2-CH=NOMe | 0 |
| A-3250 | H | H | H | H | H | O | CH$_2$CF$_3$ | H | 2-(4,5-dihydro-3-isoxazolyl) | 0 |
| A-3251 | H | H | H | H | H | O | CH$_2$CF$_3$ | H | 2-CN | 0 |
| A-3252 | H | H | H | H | H | O | CH$_2$CF$_3$ | H | 2-NO$_2$ | 0 |
| A-3253 | H | H | H | H | H | O | CH$_2$CF$_3$ | H | 2-F,6-Cl | 0 |
| A-3254 | H | H | H | H | H | O | CH$_2$CF$_3$ | H | 2-F,6-Me | 0 |
| A-3255 | H | H | H | H | H | O | CH$_2$CF$_3$ | H | 3-F,6-Me | 0 |
| A-3256 | H | H | H | H | H | O | CH$_2$CF$_3$ | H | 4-F,2-Me | 0 |
| A-3257 | H | H | H | H | H | O | CH$_2$CF$_3$ | H | 2-F,6-OMe | 0 |
| A-3258 | H | H | H | H | H | O | CH$_2$CF$_3$ | H | 3-F,6-OMe | 0 |
| A-3259 | H | H | H | H | H | O | CH$_2$CF$_3$ | H | 2,6-Cl$_2$ | 0 |
| A-3260 | H | H | H | H | H | O | CH$_2$CF$_3$ | H | 2-Cl,6-Me | 0 |
| A-3261 | H | H | H | H | H | O | CH$_2$CF$_3$ | H | 3-Cl,6-Me | 0 |
| A-3262 | H | H | H | H | H | O | CH$_2$CF$_3$ | H | 4-Cl,2-Me | 0 |
| A-3263 | H | H | H | H | H | O | CH$_2$CF$_3$ | H | 2-Cl,5-CF$_3$ | 0 |
| A-3264 | H | H | H | H | H | O | CH$_2$CF$_3$ | H | 2-Cl,6-CF$_3$ | 0 |
| A-3265 | H | H | H | H | H | O | CH$_2$CF$_3$ | H | 2-Cl,6-OMe | 0 |
| A-3266 | H | H | H | H | H | O | CH$_2$CF$_3$ | H | 3-Cl,6-OMe | 0 |
| A-3267 | H | H | H | H | H | O | CH$_2$CF$_3$ | H | 4-Cl,2-OMe | 0 |
| A-3268 | H | H | H | H | H | O | CH$_2$CF$_3$ | H | 2,4-Me$_2$ | 0 |
| A-3269 | H | H | H | H | H | O | CH$_2$CF$_3$ | H | 2,5-Me$_2$ | 0 |
| A-3270 | H | H | H | H | H | O | CH$_2$CF$_3$ | H | 2,6-Me$_2$ | 0 |
| A-3271 | H | H | H | H | H | O | CH$_2$CF$_3$ | H | 2-Me,4-CF$_3$ | 0 |
| A-3272 | H | H | H | H | H | O | CH$_2$CF$_3$ | H | 2-Me,5-CF$_3$ | 0 |
| A-3273 | H | H | H | H | H | O | CH$_2$CF$_3$ | H | 2-Me,6-CF$_3$ | 0 |
| A-3274 | H | H | H | H | H | O | CH$_2$CF$_3$ | H | 2-Me,4-OMe | 0 |
| A-3275 | H | H | H | H | H | O | CH$_2$CF$_3$ | H | 2-Me,5-OMe | 0 |
| A-3276 | H | H | H | H | H | O | CH$_2$CF$_3$ | H | 2-Me,6-OMe | 0 |
| A-3277 | H | H | H | H | H | O | CH$_2$CF$_3$ | H | 3-Me,6-OMe | 0 |
| A-3278 | H | H | H | H | H | O | CH$_2$CF$_3$ | H | 4-Me,2-OMe | 0 |
| A-3279 | H | H | H | H | H | O | CH$_2$CF$_3$ | H | 2,5-OMe$_2$ | 0 |
| A-3280 | H | H | H | H | H | O | CH$_2$CF$_3$ | H | 2,6-OMe$_2$ | 0 |
| A-3281 | H | H | H | H | H | O | CH$_2$CF$_3$ | H | 2-OMe,6-CF$_3$ | 0 |
| A-3282 | H | H | H | H | H | O | CH$_2$CF$_3$ | H | 2-CHF$_2$,5-F | 0 |
| A-3283 | H | H | H | H | H | O | CH$_2$CF$_3$ | H | 2-CHF$_2$,6-F | 0 |
| A-3284 | H | H | H | H | H | O | CH$_2$CF$_3$ | H | 2-CHF$_2$,5-Me | 0 |
| A-3285 | H | H | H | H | H | O | CH$_2$CF$_3$ | H | 2-CHF$_2$,6-Me | 0 |
| A-3286 | H | H | H | H | H | O | CH$_2$CF$_3$ | H | 2-cyclopropyl,5-F | 0 |
| A-3287 | H | H | H | H | H | O | CH$_2$CF$_3$ | H | 2-cyclopropyl,6-F | 0 |
| A-3288 | H | H | H | H | H | O | CH$_2$CF$_3$ | H | 2-cyclopropyl,5-Me | 0 |
| A-3289 | H | H | H | H | H | O | CH$_2$CF$_3$ | H | 2-cyclopropyl,6-Me | 0 |
| A-3290 | H | H | H | H | H | O | CH$_2$CF$_3$ | H | 2-ethenyl,6-F | 0 |
| A-3291 | H | H | H | H | H | O | CH$_2$CF$_3$ | H | 2-ethenyl,6-Me | 0 |
| A-3292 | H | H | H | H | H | O | CH$_2$CF$_3$ | H | 2-OEt,5-F | 0 |
| A-3293 | H | H | H | H | H | O | CH$_2$CF$_3$ | H | 2-OEt,6-F | 0 |
| A-3294 | H | H | H | H | H | O | CH$_2$CF$_3$ | H | 2-OEt,5-Cl | 0 |
| A-3295 | H | H | H | H | H | O | CH$_2$CF$_3$ | H | 2-OEt,6-Cl | 0 |
| A-3296 | H | H | H | H | H | O | CH$_2$CF$_3$ | H | 2-OEt,5-Me | 0 |
| A-3297 | H | H | H | H | H | O | CH$_2$CF$_3$ | H | 2-OEt,6-Me | 0 |
| A-3298 | H | H | H | H | H | O | CH$_2$CF$_3$ | H | 2-OCHF$_2$,5-F | 0 |
| A-3299 | H | H | H | H | H | O | CH$_2$CF$_3$ | H | 2-OCHF$_2$,6-F | 0 |
| A-3300 | H | H | H | H | H | O | CH$_2$CF$_3$ | H | 2-OCHF$_2$,5-Me | 0 |
| A-3301 | H | H | H | H | H | O | CH$_2$CF$_3$ | H | 2-OCHF$_2$,6-Me | 0 |

TABLE 59

| compound | R¹ | R² | R³ | R⁴ | R⁵ | A | R⁶ | R⁷ | (R⁸)$_m$ | p |
|---|---|---|---|---|---|---|---|---|---|---|
| A-3302 | H | H | H | H | H | O | CH$_2$CF$_3$ | H | 2-(cyclopropyloxy),5-F | 0 |
| A-3303 | H | H | H | H | H | O | CH$_2$CF$_3$ | H | 2-(cyclopropyloxy),6-F | 0 |
| A-3304 | H | H | H | H | H | O | CH$_2$CF$_3$ | H | 2-(cyclopropyloxy),5-Me | 0 |
| A-3305 | H | H | H | H | H | O | CH$_2$CF$_3$ | H | 2-(cyclopropyloxy),6-Me | 0 |
| A-3306 | H | H | H | H | H | O | CH$_2$CF$_3$ | H | 2-SMe,5-F | 0 |
| A-3307 | H | H | H | H | H | O | CH$_2$CF$_3$ | H | 2-SMe,6-F | 0 |
| A-3308 | H | H | H | H | H | O | CH$_2$CF$_3$ | H | 2-SMe,5-Me | 0 |
| A-3309 | H | H | H | H | H | O | CH$_2$CF$_3$ | H | 2-SMe,6-Me | 0 |
| A-3310 | H | H | H | H | H | O | CH$_2$CF$_3$ | H | 2-S(=O)Me,5-F | 0 |
| A-3311 | H | H | H | H | H | O | CH$_2$CF$_3$ | H | 2-S(=O)Me,6-F | 0 |
| A-3312 | H | H | H | H | H | O | CH$_2$CF$_3$ | H | 2-S(=O)Me,5-Me | 0 |
| A-3313 | H | H | H | H | H | O | CH$_2$CF$_3$ | H | 2-S(=O)Me,6-Me | 0 |
| A-3314 | H | H | H | H | H | O | CH$_2$CF$_3$ | H | 2-S(=O)$_2$Me,5-F | 0 |

TABLE 59-continued

| compound | R¹ | R² | R³ | R⁴ | R⁵ | A | R⁶ | R⁷ | (R⁸)ₘ | p |
|---|---|---|---|---|---|---|---|---|---|---|
| A-3315 | H | H | H | H | H | O | CH₂CF₃ | H | 2-S(=O)₂Me,6-F | 0 |
| A-3316 | H | H | H | H | H | O | CH₂CF₃ | H | 2-S(=O)₂Me,5-Me | 0 |
| A-3317 | H | H | H | H | H | O | CH₂CF₃ | H | 2-S(=O)₂Me,6-Me | 0 |
| A-3318 | H | H | H | H | H | O | CH₂CF₃ | H | 2-SCF₃,5-F | 0 |
| A-3319 | H | H | H | H | H | O | CH₂CF₃ | H | 2-SCF₃,6-F | 0 |
| A-3320 | H | H | H | H | H | O | CH₂CF₃ | H | 2-SCF₃,5-Me | 0 |
| A-3321 | H | H | H | H | H | O | CH₂CF₃ | H | 2-SCF₃,6-Me | 0 |
| A-3322 | H | H | H | H | H | O | CH₂CF₃ | H | 2-S(=O)CF₃,5-F | 0 |
| A-3323 | H | H | H | H | H | O | CH₂CF₃ | H | 2-S(=O)CF₃,6-F | 0 |
| A-3324 | H | H | H | H | H | O | CH2CF₃ | H | 2-S(=O)CF₃,5-Me | 0 |
| A-3325 | H | H | H | H | H | O | CH₂CF₃ | H | 2-S(=O)CF₃,6-Me | 0 |
| A-3326 | H | H | H | H | H | O | CH₂CF₃ | H | 2-S(=O)₂CF₃,5-F | 0 |
| A-3327 | H | H | H | H | H | O | CH₂CF₃ | H | 2-S(=O)₂CF₃,6-F | 0 |
| A-3328 | H | H | H | H | H | O | CH₂CF₃ | H | 2-S(=O)₂CF₃,5-Me | 0 |
| A-3329 | H | H | H | H | H | O | CH₂CF₃ | H | 2-S(=O)₂CF₃,6-Me | 0 |
| A-3330 | H | H | H | H | H | O | CH₂CF₃ | H | 2-(cyclopropylthio),5-F | 0 |
| A-3331 | H | H | H | H | H | O | CH₂CF₃ | H | 2-(cyclopropylthio),6-F | 0 |
| A-3332 | H | H | H | H | H | O | CH₂CF₃ | H | 2-(cyclopropylthio),5-Me | 0 |
| A-3333 | H | H | H | H | H | O | CH₂CF₃ | H | 2-(cyclopropylthio),6-Me | 0 |
| A-3334 | H | H | H | H | H | O | CH₂CF₃ | H | 2-C(=O)Me,5-F | 0 |
| A-3335 | H | H | H | H | H | O | CH₂CF₃ | H | 2-C(=O)Me,6-F | 0 |
| A-3336 | H | H | H | H | H | O | CH₂CF₃ | H | 2-C(=O)Me,5-Me | 0 |
| A-3337 | H | H | H | H | H | O | CH₂CF₃ | H | 2-C(=O)Me,6-Me | 0 |
| A-3338 | H | H | H | H | H | O | CH₂CF₃ | H | 2-CH₂OH,5-F | 0 |
| A-3339 | H | H | H | H | H | O | CH₂CF₃ | H | 2-CH₂OH,6-F | 0 |
| A-3340 | H | H | H | H | H | O | CH₂CF₃ | H | 2-CH₂OH,5-Me | 0 |
| A-3341 | H | H | H | H | H | O | CH₂CF₃ | H | 2-CH₂OH,6-Me | 0 |
| A-3342 | H | H | H | H | H | O | CH₂CF₃ | H | 2-CH₂OCH₃,4-F | 0 |
| A-3343 | H | H | H | H | H | O | CH₂CF₃ | H | 2-CH₂OCH₃,5-F | 0 |
| A-3344 | H | H | H | H | H | O | CH₂CF₃ | H | 2-CH₂OCH₃,6-F | 0 |
| A-3345 | H | H | H | H | H | O | CH₂CF₃ | H | 2-CH₂OCH₃,4-Me | 0 |
| A-3346 | H | H | H | H | H | O | CH₂CF₃ | H | 2-CH₂OCH₃,5-Me | 0 |
| A-3347 | H | H | H | H | H | O | CH₂CF₃ | H | 2-CH₂OCH₃,6-Me | 0 |
| A-3348 | H | H | H | H | H | O | CH₂CF₃ | H | 2-OC(=O)CH₃,5-F | 0 |
| A-3349 | H | H | H | H | H | O | CH₂CF₃ | H | 2-OC(=O)CH₃,6-F | 0 |
| A-3350 | H | H | H | H | H | O | CH₂CF₃ | H | 2-OC(=O)CH₃,5-Me | 0 |
| A-3351 | H | H | H | H | H | O | CH₂CF₃ | H | 2-OC(=O)CH₃,6-Me | 0 |
| A-3352 | H | H | H | H | H | O | CH₂CF₃ | H | 2-OS(=O)₂CH₃,5-F | 0 |
| A-3353 | H | H | H | H | H | O | CH₂CF₃ | H | 2-OS(=O)₂CH₃,6-F | 0 |
| A-3354 | H | H | H | H | H | O | CH₂CF₃ | H | 2-OS(=O)₂CH₃,5-Me | 0 |
| A-3355 | H | H | H | H | H | O | CH₂CF₃ | H | 2-OS(=O)₂CH₃,6-Me | 0 |
| A-3356 | H | H | H | H | H | O | CH₂CF₃ | H | 2-CH₂SCH₃,5-F | 0 |
| A-3357 | H | H | H | H | H | O | CH₂CF₃ | H | 2-CH₂SCH₃,6-F | 0 |
| A-3358 | H | H | H | H | H | O | CH₂CF₃ | H | 2-CH₂SCH₃,5-Me | 0 |

TABLE 60

| compound | R¹ | R² | R³ | R⁴ | R⁵ | A | R⁶ | R⁷ | (R⁸)ₘ | p |
|---|---|---|---|---|---|---|---|---|---|---|
| A-3359 | H | H | H | H | H | O | CH₂CF₃ | H | 2-CH₂SCH₃,6-Me | 0 |
| A-3360 | H | H | H | H | H | O | CH₂CF₃ | H | 2-NMe₂,5-F | 0 |
| A-3361 | H | H | H | H | H | O | CH₂CF₃ | H | 2-NMe₂,6-F | 0 |
| A-3362 | H | H | H | H | H | O | CH₂CF₃ | H | 2-NMe₂,5-Me | 0 |
| A-3363 | H | H | H | H | H | O | CH₂CF₃ | H | 2-NMe₂,6-Me | 0 |
| A-3364 | H | H | H | H | H | O | CH₂CF₃ | H | 2-CN,4-F | 0 |
| A-3365 | H | H | H | H | H | O | CH₂CF₃ | H | 2-CN,5-F | 0 |
| A-3366 | H | H | H | H | H | O | CH₂CF₃ | H | 2-CN,6-F | 0 |
| A-3367 | H | H | H | H | H | O | CH₂CF₃ | H | 2-CN,6-Me | 0 |
| A-3368 | H | H | H | H | H | O | CH₂CF₃ | H | 2-CN,5-OMe | 0 |
| A-3369 | H | H | H | H | H | O | CH₂CF₃ | H | 2-CN,6-OMe | 0 |
| A-3370 | H | H | H | H | H | O | CH₂CF₃ | H | 3-CN,6-Me | 0 |
| A-3371 | H | H | H | H | H | O | CH₂CF₃ | H | 3-CN,6-OMe | 0 |
| A-3372 | H | H | H | H | H | O | CH₂CF₃ | H | 4-CN,2-Me | 0 |
| A-3373 | H | H | H | H | H | O | CH₂CF₃ | H | 4-CN,2-OMe | 0 |
| A-3374 | H | H | H | H | H | O | CH₂CF₃ | H | 2-NO₂,4-F | 0 |
| A-3375 | H | H | H | H | H | O | CH₂CF₃ | H | 2-NO₂,5-F | 0 |
| A-3376 | H | H | H | H | H | O | CH₂CF₃ | H | 2-NO₂,6-F | 0 |
| A-3377 | H | H | H | H | H | O | CH₂CF₃ | H | 2-NO₂,4-Me | 0 |
| A-3378 | H | H | H | H | H | O | CH₂CF₃ | H | 2-NO₂,5-Me | 0 |
| A-3379 | H | H | H | H | H | O | CH₂CF₃ | H | 2-NO₂,6-Me | 0 |
| A-3380 | H | H | H | H | H | O | CH₂CF₃ | H | 2-Me,4,5-F₂ | 0 |
| A-3381 | H | H | H | H | H | O | CH₂CF₃ | H | 2-Me,6-Et | 0 |
| A-3382 | H | H | H | H | H | O | CH₂CF₃ | H | 2-cyclopropyl,6-OMe | 0 |
| A-3383 | H | H | H | H | H | O | CH₂CF₃ | H | 2-Me,5-Et | 0 |
| A-3384 | H | H | H | H | H | O | CH₂CF₃ | H | 2,6-Et₂ | 0 |

TABLE 60-continued

| compound | R¹ | R² | R³ | R⁴ | R⁵ | A | R⁶ | R⁷ | (R⁸)$_m$ | p |
|---|---|---|---|---|---|---|---|---|---|---|
| A-3385 | H | H | H | H | H | O | CH$_2$CF$_3$ | H | 2-Et,6-F | 0 |
| A-3386 | H | H | H | H | H | O | CH$_2$CF$_3$ | H | 2-CH$_2$OCH$_3$,6-Cl | 0 |
| A-3387 | H | H | H | H | H | O | CH$_2$CF$_3$ | H | 2-CH$_2$OCH$_2$CH$_3$,6-Cl | 0 |
| A-3388 | H | H | H | H | H | O | CH$_2$CF$_3$ | H | 2-CH$_2$NMe$_2$ | 0 |
| A-3389 | H | H | H | H | H | O | tetrahydrofuran-3-yl | H | H | 0 |
| A-3390 | H | H | H | H | H | O | tetrahydrofuran-3-yl | H | 2-F | 0 |
| A-3391 | H | H | H | H | H | O | tetrahydrofuran-3-yl | H | 2-Cl | 0 |
| A-3392 | H | H | H | H | H | O | tetrahydrofuran-3-yl | H | 2-Br | 0 |
| A-3393 | H | H | H | H | H | O | tetrahydrofuran-3-yl | H | 2-OH | 0 |
| A-3394 | H | H | H | H | H | O | tetrahydrofuran-3-yl | H | 2-Me | 0 |
| A-3395 | H | H | H | H | H | O | tetrahydrofuran-3-yl | H | 2-Et | 0 |
| A-3396 | H | H | H | H | H | O | tetrahydrofuran-3-yl | H | 2-Pr | 0 |
| A-3397 | H | H | H | H | H | O | tetrahydrofuran-3-yl | H | 2-CF$_3$ | 0 |
| A-3398 | H | H | H | H | H | O | tetrahydrofuran-3-yl | H | 2-CHF$_2$ | 0 |
| A-3399 | H | H | H | H | H | O | tetrahydrofuran-3-yl | H | 2-CH$_2$F | 0 |
| A-3400 | H | H | H | H | H | O | tetrahydrofuran-3-yl | H | 2-CF$_2$Cl | 0 |
| A-3401 | H | H | H | H | H | O | tetrahydrofuran-3-yl | H | 2-cyclopropyl | 0 |
| A-3402 | H | H | H | H | H | O | tetrahydrofuran-3-yl | H | 2-cyclobutyl | 0 |
| A-3403 | H | H | H | H | H | O | tetrahydrofuran-3-yl | H | 2-cyclopentyl | 0 |
| A-3404 | H | H | H | H | H | O | tetrahydrofuran-3-yl | H | 2-ethenyl | 0 |
| A-3405 | H | H | H | H | H | O | tetrahydrofuran-3-yl | H | 2-allyl | 0 |
| A-3406 | H | H | H | H | H | O | tetrahydrofuran-3-yl | H | 2-(prop-1-en-1-yl) | 0 |
| A-3407 | H | H | H | H | H | O | tetrahydrofuran-3-yl | H | 2-(trifluoroethenyl) | 0 |
| A-3408 | H | H | H | H | H | O | tetrahydrofuran-3-yl | H | 2-OMe | 0 |
| A-3409 | H | H | H | H | H | O | tetrahydrofuran-3-yl | H | 2-OEt | 0 |
| A-3410 | H | H | H | H | H | O | tetrahydrofuran-3-yl | H | 2-OPr | 0 |
| A-3411 | H | H | H | H | H | O | tetrahydrofuran-3-yl | H | 2-O(i-Pr) | 0 |
| A-3412 | H | H | H | H | H | O | tetrahydrofuran-3-yl | H | 2-OCF$_3$ | 0 |
| A-3413 | H | H | H | H | H | O | tetrahydrofuran-3-yl | H | 2-OCHF$_2$ | 0 |
| A-3414 | H | H | H | H | H | O | tetrahydrofuran-3-yl | H | 2-(cyclopropyloxy) | 0 |
| A-3415 | H | H | H | H | H | O | tetrahydrofuran-3-yl | H | 2-(cyclobutyloxy) | 0 |

TABLE 61

| compound | R¹ | R² | R³ | R⁴ | R⁵ | A | R⁶ | R⁷ | (R⁸)$_m$ | p |
|---|---|---|---|---|---|---|---|---|---|---|
| A-3416 | H | H | H | H | H | O | tetrahydrofuran-3-yl | H | 2-(cyclopentyloxy) | 0 |
| A-3417 | H | H | H | H | H | O | tetrahydrofuran-3-yl | H | 2-((2,2-dichlorocyclopropyl)oxy) | 0 |
| A-3418 | H | H | H | H | H | O | tetrahydrofuran-3-yl | H | 2-(oxiran-2-yl) | 0 |
| A-3419 | H | H | H | H | H | O | tetrahydrofuran-3-yl | H | 2-SMe | 0 |
| A-3420 | H | H | H | H | H | O | tetrahydrofuran-3-yl | H | 3-SMe | 0 |
| A-3421 | H | H | H | H | H | O | tetrahydrofuran-3-yl | H | 2-S(=O)Me | 0 |
| A-3422 | H | H | H | H | H | O | tetrahydrofuran-3-yl | H | 3-S(=O)Me | 0 |
| A-3423 | H | H | H | H | H | O | tetrahydrofuran-3-yl | H | 2-S(=O)$_2$Me | 0 |
| A-3424 | H | H | H | H | H | O | tetrahydrofuran-3-yl | H | 3-S(=O)$_2$Me | 0 |
| A-3425 | H | H | H | H | H | O | tetrahydrofuran-3-yl | H | 2-SCF$_3$ | 0 |
| A-3426 | H | H | H | H | H | O | tetrahydrofuran-3-yl | H | 3-SCF$_3$ | 0 |
| A-3427 | H | H | H | H | H | O | tetrahydrofuran-3-yl | H | 3-S(=O)CF$_3$ | 0 |
| A-3428 | H | H | H | H | H | O | tetrahydrofuran-3-yl | H | 3-SCF(CF$_3$)$_2$ | 0 |
| A-3429 | H | H | H | H | H | O | tetrahydrofuran-3-yl | H | 2-(cyclopropylthio) | 0 |
| A-3430 | H | H | H | H | H | O | tetrahydrofuran-3-yl | H | 2-(cyclopropylsulfinyl) | 0 |
| A-3431 | H | H | H | H | H | O | tetrahydrofuran-3-yl | H | 2-(cyclopropylsulfonyl) | 0 |
| A-3432 | H | H | H | H | H | O | tetrahydrofuran-3-yl | H | 2-C(=O)Me | 0 |
| A-3433 | H | H | H | H | H | O | tetrahydrofuran-3-yl | H | 2-CH$_2$C(=O)CH$_3$ | 0 |
| A-3434 | H | H | H | H | H | O | tetrahydrofuran-3-yl | H | 2-CH$_2$C(=O)CF$_3$ | 0 |
| A-3435 | H | H | H | H | H | O | tetrahydrofuran-3-yl | H | 2-CH$_2$OH | 0 |
| A-3436 | H | H | H | H | H | O | tetrahydrofuran-3-yl | H | 2-CH$_2$OCH$_3$ | 0 |
| A-3437 | H | H | H | H | H | O | tetrahydrofuran-3-yl | H | 2-CH$_2$OCH$_2$CH$_3$ | 0 |
| A-3438 | H | H | H | H | H | O | tetrahydrofuran-3-yl | H | 2-CH$_2$SCH$_3$ | 0 |
| A-3439 | H | H | H | H | H | O | tetrahydrofuran-3-yl | H | 2-CH$_2$S(=O)CH$_3$ | 0 |
| A-3440 | H | H | H | H | H | O | tetrahydrofuran-3-yl | H | 2-CH$_2$S(=O)$_2$CH$_3$ | 0 |
| A-3441 | H | H | H | H | H | O | tetrahydrofuran-3-yl | H | 2-(benzyloxy) | 0 |
| A-3442 | H | H | H | H | H | O | tetrahydrofuran-3-yl | H | 2-NH$_2$ | 0 |
| A-3443 | H | H | H | H | H | O | tetrahydrofuran-3-yl | H | 2-NHMe | 0 |
| A-3444 | H | H | H | H | H | O | tetrahydrofuran-3-yl | H | 2-N(Me)$_2$ | 0 |
| A-3445 | H | H | H | H | H | O | tetrahydrofuran-3-yl | H | 2-(1,3-dioxolan-2-yl) | 0 |
| A-3446 | H | H | H | H | H | O | tetrahydrofuran-3-yl | H | 2-(1,3-dioxan-2-yl) | 0 |
| A-3447 | H | H | H | H | H | O | tetrahydrofuran-3-yl | H | 2-(1H-imidazol-2-yl) | 0 |
| A-3448 | H | H | H | H | H | O | tetrahydrofuran-3-yl | H | 2-(thiazol-2-yl) | 0 |
| A-3449 | H | H | H | H | H | O | tetrahydrofuran-3-yl | H | 2-(oxazol-2-yl) | 0 |
| A-3450 | H | H | H | H | H | O | tetrahydrofuran-3-yl | H | 2-CH=NOH | 0 |
| A-3451 | H | H | H | H | H | O | tetrahydrofuran-3-yl | H | 2-CH=NOMe | 0 |
| A-3452 | H | H | H | H | H | O | tetrahydrofuran-3-yl | H | 2-(4,5-dihydro-3-isoxazolyl) | 0 |
| A-3453 | H | H | H | H | H | O | tetrahydrofuran-3-yl | H | 2-CN | 0 |
| A-3454 | H | H | H | H | H | O | tetrahydrofuran-3-yl | H | 2-NO$_2$ | 0 |

TABLE 61-continued

| compound | R¹ | R² | R³ | R⁴ | R⁵ | A | R⁶ | R⁷ | (R⁸)ₘ | p |
|---|---|---|---|---|---|---|---|---|---|---|
| A-3455 | H | H | H | H | H | O | tetrahydrofuran-3-yl | H | 2-F,6-Cl | 0 |
| A-3456 | H | H | H | H | H | O | tetrahydrofuran-3-yl | H | 2-F,6-Me | 0 |
| A-3457 | H | H | H | H | H | O | tetrahydrofuran-3-yl | H | 3-F,6-Me | 0 |
| A-3458 | H | H | H | H | H | O | tetrahydrofuran-3-yl | H | 4-F,2-Me | 0 |
| A-3459 | H | H | H | H | H | O | tetrahydrofuran-3-yl | H | 2-F,6-OMe | 0 |
| A-3460 | H | H | H | H | H | O | tetrahydrofuran-3-yl | H | 3-F,6-OMe | 0 |
| A-3461 | H | H | H | H | H | O | tetrahydrofuran-3-yl | H | 2,6-Cl₂ | 0 |
| A-3462 | H | H | H | H | H | O | tetrahydrofuran-3-yl | H | 2-Cl,6-Me | 0 |
| A-3463 | H | H | H | H | H | O | tetrahydrofuran-3-yl | H | 3-Cl,6-Me | 0 |
| A-3464 | H | H | H | H | H | O | tetrahydrofuran-3-yl | H | 4-Cl,2-Me | 0 |
| A-3465 | H | H | H | H | H | O | tetrahydrofuran-3-yl | H | 2-Cl,5-CF₃ | 0 |
| A-3466 | H | H | H | H | H | O | tetrahydrofuran-3-yl | H | 2-Cl,6-CF₃ | 0 |
| A-3467 | H | H | H | H | H | O | tetrahydrofuran-3-yl | H | 2-Cl,6-OMe | 0 |
| A-3468 | H | H | H | H | H | O | tetrahydrofuran-3-yl | H | 3-Cl,6-OMe | 0 |
| A-3469 | H | H | H | H | H | O | tetrahydrofuran-3-yl | H | 4-Cl,2-OMe | 0 |
| A-3470 | H | H | H | H | H | O | tetrahydrofuran-3-yl | H | 2,4-Me₂ | 0 |
| A-3471 | H | H | H | H | H | O | tetrahydrofuran-3-yl | H | 2,5-Me₂ | 0 |
| A-3472 | H | H | H | H | H | O | tetrahydrofuran-3-yl | H | 2,6-Me₂ | 0 |

TABLE 62

| compound | R¹ | R² | R³ | R⁴ | R⁵ | A | R⁶ | R⁷ | (R⁸)ₘ | p |
|---|---|---|---|---|---|---|---|---|---|---|
| A-3473 | H | H | H | H | H | O | tetrahydrofuran-3-yl | H | 2-Me,4-CF₃ | 0 |
| A-3474 | H | H | H | H | H | O | tetrahydrofuran-3-yl | H | 2-Me,5-CF₃ | 0 |
| A-3475 | H | H | H | H | H | O | tetrahydrofuran-3-yl | H | 2-Me,6-CF₃ | 0 |
| A-3476 | H | H | H | H | H | O | tetrahydrofuran-3-yl | H | 2-Me,4-OMe | 0 |
| A-3477 | H | H | H | H | H | O | tetrahydrofuran-3-yl | H | 2-Me,5-OMe | 0 |
| A-3478 | H | H | H | H | H | O | tetrahydrofuran-3-yl | H | 2-Me,6-OMe | 0 |
| A-3479 | H | H | H | H | H | O | tetrahydrofuran-3-yl | H | 3-Me,6-OMe | 0 |
| A-3480 | H | H | H | H | H | O | tetrahydrofuran-3-yl | H | 4-Me,2-OMe | 0 |
| A-3481 | H | H | H | H | H | O | tetrahydrofuran-3-yl | H | 2,5-OMe₂ | 0 |
| A-3482 | H | H | H | H | H | O | tetrahydrofuran-3-yl | H | 2,6-OMe₂ | 0 |
| A-3483 | H | H | H | H | H | O | tetrahydrofuran-3-yl | H | 2-OMe,6-CF₃ | 0 |
| A-3484 | H | H | H | H | H | O | tetrahydrofuran-3-yl | H | 2-CHF₂,5-F | 0 |
| A-3485 | H | H | H | H | H | O | tetrahydrofuran-3-yl | H | 2-CHF₂,6-F | 0 |
| A-3486 | H | H | H | H | H | O | tetrahydrofuran-3-yl | H | 2-CHF₂,5-Me | 0 |
| A-3487 | H | H | H | H | H | O | tetrahydrofuran-3-yl | H | 2-CHF₂,6-Me | 0 |
| A-3488 | H | H | H | H | H | O | tetrahydrofuran-3-yl | H | 2-cyclopropyl,5-F | 0 |
| A-3489 | H | H | H | H | H | O | tetrahydrofuran-3-yl | H | 2-cyclopropyl,6-F | 0 |
| A-3490 | H | H | H | H | H | O | tetrahydrofuran-3-yl | H | 2-cyclopropyl,5-Me | 0 |
| A-3491 | H | H | H | H | H | O | tetrahydrofuran-3-yl | H | 2-cyclopropyl,6-Me | 0 |
| A-3492 | H | H | H | H | H | O | tetrahydrofuran-3-yl | H | 2-ethenyl,6-F | 0 |
| A-3493 | H | H | H | H | H | O | tetrahydrofuran-3-yl | H | 2-ethenyl,6-Me | 0 |
| A-3494 | H | H | H | H | H | O | tetrahydrofuran-3-yl | H | 2-OEt,5-F | 0 |
| A-3495 | H | H | H | H | H | O | tetrahydrofuran-3-yl | H | 2-OEt,6-F | 0 |
| A-3496 | H | H | H | H | H | O | tetrahydrofuran-3-yl | H | 2-OEt,5-Cl | 0 |
| A-3497 | H | H | H | H | H | O | tetrahydrofuran-3-yl | H | 2-OEt,6-Cl | 0 |
| A-3498 | H | H | H | H | H | O | tetrahydrofuran-3-yl | H | 2-OEt,5-Me | 0 |
| A-3499 | H | H | H | H | H | O | tetrahydrofuran-3-yl | H | 2-OEt,6-Me | 0 |
| A-3500 | H | H | H | H | H | O | tetrahydrofuran-3-yl | H | 2-OCHF₂,5-F | 0 |
| A-3501 | H | H | H | H | H | O | tetrahydrofuran-3-yl | H | 2-OCHF₂,6-F | 0 |
| A-3502 | H | H | H | H | H | O | tetrahydrofuran-3-yl | H | 2-OCHF₂,5-Me | 0 |
| A-3503 | H | H | H | H | H | O | tetrahydrofuran-3-yl | H | 2-OCHF₂,6-Me | 0 |
| A-3504 | H | H | H | H | H | O | tetrahydrofuran-3-yl | H | 2-(cyclopropyloxy),5-F | 0 |
| A-3505 | H | H | H | H | H | O | tetrahydrofuran-3-yl | H | 2-(cyclopropyloxy),6-F | 0 |
| A-3506 | H | H | H | H | H | O | tetrahydrofuran-3-yl | H | 2-(cyclopropyloxy),5-Me | 0 |
| A-3507 | H | H | H | H | H | O | tetrahydrofuran-3-yl | H | 2-(cyclopropyloxy),6-Me | 0 |
| A-3508 | H | H | H | H | H | O | tetrahydrofuran-3-yl | H | 2-SMe,5-F | 0 |
| A-3509 | H | H | H | H | H | O | tetrahydrofuran-3-yl | H | 2-SMe,6-F | 0 |
| A-3510 | H | H | H | H | H | O | tetrahydrofuran-3-yl | H | 2-SMe,5-Me | 0 |
| A-3511 | H | H | H | H | H | O | tetrahydrofuran-3-yl | H | 2-SMe,6-Me | 0 |
| A-3512 | H | H | H | H | H | O | tetrahydrofuran-3-yl | H | 2-S(=O)Me,5-F | 0 |
| A-3513 | H | H | H | H | H | O | tetrahydrofuran-3-yl | H | 2-S(=O)Me,6-F | 0 |
| A-3514 | H | H | H | H | H | O | tetrahydrofuran-3-yl | H | 2-S(=O)Me,5-Me | 0 |
| A-3515 | H | H | H | H | H | O | tetrahydrofuran-3-yl | H | 2-S(=O)Me,6-Me | 0 |
| A-3516 | H | H | H | H | H | O | tetrahydrofuran-3-yl | H | 2-S(=O)₂Me,5-F | 0 |
| A-3517 | H | H | H | H | H | O | tetrahydrofuran-3-yl | H | 2-S(=O)₂Me,6-F | 0 |
| A-3518 | H | H | H | H | H | O | tetrahydrofuran-3-yl | H | 2-S(=O)₂Me,5-Me | 0 |
| A-3519 | H | H | H | H | H | O | tetrahydrofuran-3-yl | H | 2-S(=O)₂Me,6-Me | 0 |
| A-3520 | H | H | H | H | H | O | tetrahydrofuran-3-yl | H | 2-SCF₃,5-F | 0 |
| A-3521 | H | H | H | H | H | O | tetrahydrofuran-3-yl | H | 2-SCF₃,6-F | 0 |
| A-3522 | H | H | H | H | H | O | tetrahydrofuran-3-yl | H | 2-SCF₃,5-Me | 0 |
| A-3523 | H | H | H | H | H | O | tetrahydrofuran-3-yl | H | 2-SCF₃,6-Me | 0 |
| A-3524 | H | H | H | H | H | O | tetrahydrofuran-3-yl | H | 2-S(=O)CF₃,5-F | 0 |

TABLE 62-continued

| compound | R¹ | R² | R³ | R⁴ | R⁵ | A | R⁶ | R⁷ | (R⁸)ₘ | p |
|---|---|---|---|---|---|---|---|---|---|---|
| A-3525 | H | H | H | H | H | O | tetrahydrofuran-3-yl | H | 2-S(=O)CF₃,6-F | 0 |
| A-3526 | H | H | H | H | H | O | tetrahydrofuran-3-yl | H | 2-S(=O)CF₃,5-Me | 0 |
| A-3527 | H | H | H | H | H | O | tetrahydrofuran-3-yl | H | 2-S(=O)CF₃,6-Me | 0 |
| A-3528 | H | H | H | H | H | O | tetrahydrofuran-3-yl | H | 2-S(=O)₂CF₃,5-F | 0 |
| A-3529 | H | H | H | H | H | O | tetrahydrofuran-3-yl | H | 2-S(=O)₂CF₃,6-F | 0 |

TABLE 63

| compound | R¹ | R² | R³ | R⁴ | R⁵ | A | R⁶ | R⁷ | (R⁸)ₘ | p |
|---|---|---|---|---|---|---|---|---|---|---|
| A-3530 | H | H | H | H | H | O | tetrahydrofuran-3-yl | H | 2-S(=O)₂CF₃,5-Me | 0 |
| A-3531 | H | H | H | H | H | O | tetrahydrofuran-3-yl | H | 2-S(=O)₂CF₃,6-Me | 0 |
| A-3532 | H | H | H | H | H | O | tetrahydrofuran-3-yl | H | 2-(cyclopropylthio),5-F | 0 |
| A-3533 | H | H | H | H | H | O | tetrahydrofuran-3-yl | H | 2-(cyclopropylthio),6-F | 0 |
| A-3534 | H | H | H | H | H | O | tetrahydrofuran-3-yl | H | 2-(cyclopropylthio),5-Me | 0 |
| A-3535 | H | H | H | H | H | O | tetrahydrofuran-3-yl | H | 2-(cyclopropylthio),6-Me | 0 |
| A-3536 | H | H | H | H | H | O | tetrahydrofuran-3-yl | H | 2-C(=O)Me,5-F | 0 |
| A-3537 | H | H | H | H | H | O | tetrahydrofuran-3-yl | H | 2-C(=O)Me,6-F | 0 |
| A-3538 | H | H | H | H | H | O | tetrahydrofuran-3-yl | H | 2-C(=O)Me,5-Me | 0 |
| A-3539 | H | H | H | H | H | O | tetrahydrofuran-3-yl | H | 2-C(=O)Me,6-Me | 0 |
| A-3540 | H | H | H | H | H | O | tetrahydrofuran-3-yl | H | 2-CH₂OH,5-F | 0 |
| A-3541 | H | H | H | H | H | O | tetrahydrofuran-3-yl | H | 2-CH₂OH,6-F | 0 |
| A-3542 | H | H | H | H | H | O | tetrahydrofuran-3-yl | H | 2-CH₂OH,5-Me | 0 |
| A-3543 | H | H | H | H | H | O | tetrahydrofuran-3-yl | H | 2-CH₂OH,6-Me | 0 |
| A-3544 | H | H | H | H | H | O | tetrahydrofuran-3-yl | H | 2-CH₂OCH₃,4-F | 0 |
| A-3545 | H | H | H | H | H | O | tetrahydrofuran-3-yl | H | 2-CH₂OCH₃,5-F | 0 |
| A-3546 | H | H | H | H | H | O | tetrahydrofuran-3-yl | H | 2-CH₂OCH₃,6-F | 0 |
| A-3547 | H | H | H | H | H | O | tetrahydrofuran-3-yl | H | 2-CH₂OCH₃,4-Me | 0 |
| A-3548 | H | H | H | H | H | O | tetrahydrofuran-3-yl | H | 2-CH₂OCH₃,5-Me | 0 |
| A-3549 | H | H | H | H | H | O | tetrahydrofuran-3-yl | H | 2-CH₂OCH₃,6-Me | 0 |
| A-3550 | H | H | H | H | H | O | tetrahydrofuran-3-yl | H | 2-OC(=O)CH₃,5-F | 0 |
| A-3551 | H | H | H | H | H | O | tetrahydrofuran-3-yl | H | 2-OC(=O)CH₃,6-F | 0 |
| A-3552 | H | H | H | H | H | O | tetrahydrofuran-3-yl | H | 2-OC(=O)CH₃,5-Me | 0 |
| A-3553 | H | H | H | H | H | O | tetrahydrofuran-3-yl | H | 2-OC(=O)CH₃,6-Me | 0 |
| A-3554 | H | H | H | H | H | O | tetrahydrofuran-3-yl | H | 2-OS(=O)₂CH₃,5-F | 0 |
| A-3555 | H | H | H | H | H | O | tetrahydrofuran-3-yl | H | 2-OS(=O)₂CH₃,6-F | 0 |
| A-3556 | H | H | H | H | H | O | tetrahydrofuran-3-yl | H | 2-OS(=O)₂CH₃,5-Me | 0 |
| A-3557 | H | H | H | H | H | O | tetrahydrofuran-3-yl | H | 2-OS(=O)₂CH₃,6-Me | 0 |
| A-3558 | H | H | H | H | H | O | tetrahydrofuran-3-yl | H | 2-CH₂SCH₃,5-F | 0 |
| A-3559 | H | H | H | H | H | O | tetrahydrofuran-3-yl | H | 2-CH₂SCH₃,6-F | 0 |
| A-3560 | H | H | H | H | H | O | tetrahydrofuran-3-yl | H | 2-CH₂SCH₃,5-Me | 0 |
| A-3561 | H | H | H | H | H | O | tetrahydrofuran-3-yl | H | 2-CH₂SCH₃,6-Me | 0 |
| A-3562 | H | H | H | H | H | O | tetrahydrofuran-3-yl | H | 2-NMe₂,5-F | 0 |
| A-3563 | H | H | H | H | H | O | tetrahydrofuran-3-yl | H | 2-NMe₂,6-F | 0 |
| A-3564 | H | H | H | H | H | O | tetrahydrofuran-3-yl | H | 2-NMe₂,5-Me | 0 |
| A-3565 | H | H | H | H | H | O | tetrahydrofuran-3-yl | H | 2-NMe₂,6-Me | 0 |
| A-3566 | H | H | H | H | H | O | tetrahydrofuran-3-yl | H | 2-CN,4-F | 0 |
| A-3567 | H | H | H | H | H | O | tetrahydrofuran-3-yl | H | 2-CN,5-F | 0 |
| A-3568 | H | H | H | H | H | O | tetrahydrofuran-3-yl | H | 2-CN,6-F | 0 |
| A-3569 | H | H | H | H | H | O | tetrahydrofuran-3-yl | H | 2-CN,6-Me | 0 |
| A-3570 | H | H | H | H | H | O | tetrahydrofuran-3-yl | H | 2-CN,5-OMe | 0 |
| A-3571 | H | H | H | H | H | O | tetrahydrofuran-3-yl | H | 2-CN,6-OMe | 0 |
| A-3572 | H | H | H | H | H | O | tetrahydrofuran-3-yl | H | 3-CN,6-Me | 0 |
| A-3573 | H | H | H | H | H | O | tetrahydrofuran-3-yl | H | 3-CN,6-OMe | 0 |
| A-3574 | H | H | H | H | H | O | tetrahydrofuran-3-yl | H | 4-CN,2-Me | 0 |
| A-3575 | H | H | H | H | H | O | tetrahydrofuran-3-yl | H | 4-CN,2-OMe | 0 |
| A-3576 | H | H | H | H | H | O | tetrahydrofuran-3-yl | H | 2-NO₂,4-F | 0 |
| A-3577 | H | H | H | H | H | O | tetrahydrofuran-3-yl | H | 2-NO₂,5-F | 0 |
| A-3578 | H | H | H | H | H | O | tetrahydrofuran-3-yl | H | 2-NO₂,6-F | 0 |
| A-3579 | H | H | H | H | H | O | tetrahydrofuran-3-yl | H | 2-NO₂,4-Me | 0 |
| A-3580 | H | H | H | H | H | O | tetrahydrofuran-3-yl | H | 2-NO₂,5-Me | 0 |
| A-3581 | H | H | H | H | H | O | tetrahydrofuran-3-yl | H | 2-NO₂,6-Me | 0 |
| A-3582 | H | H | H | H | H | O | tetrahydrofuran-3-yl | H | 2-Me,4,5-F₂ | 0 |
| A-3583 | H | H | H | H | H | O | tetrahydrofuran-3-yl | H | 2-Me,6-Et | 0 |
| A-3584 | H | H | H | H | H | O | tetrahydrofuran-3-yl | H | 2-cyclopropyl,6-OMe | 0 |
| A-3585 | H | H | H | H | H | O | tetrahydrofuran-3-yl | H | 2-Me,5-Et | 0 |
| A-3586 | H | H | H | H | H | O | tetrahydrofuran-3-yl | H | 2,6-Et₂ | 0 |

TABLE 64

| compound | R¹ | R² | R³ | R⁴ | R⁵ | A | R⁶ | R⁷ | (R⁸)ₘ | p |
|---|---|---|---|---|---|---|---|---|---|---|
| A-3587 | H | H | H | H | H | O | tetrahydrofuran-3-yl | H | 2-Et,6-F | 0 |
| A-3588 | H | H | H | H | H | O | tetrahydrofuran-3-yl | H | 2-CH$_2$OCH$_3$,6-Cl | 0 |
| A-3589 | H | H | H | H | H | O | tetrahydrofuran-3-yl | H | 2-CH$_2$OCH$_2$CH$_3$,6-Cl | 0 |
| A-3590 | H | H | H | H | H | O | tetrahydrofuran-3-yl | H | 2-CH$_2$NMe$_2$ | 0 |
| A-3591 | H | H | H | H | H | O | tetrahydropyran-4-yl | H | H | 0 |
| A-3592 | H | H | H | H | H | O | tetrahydropyran-4-yl | H | 2-F | 0 |
| A-3593 | H | H | H | H | H | O | tetrahydropyran-4-yl | H | 2-Cl | 0 |
| A-3594 | H | H | H | H | H | O | tetrahydropyran-4-yl | H | 2-Br | 0 |
| A-3595 | H | H | H | H | H | O | tetrahydropyran-4-yl | H | 2-OH | 0 |
| A-3596 | H | H | H | H | H | O | tetrahydropyran-4-yl | H | 2-Me | 0 |
| A-3597 | H | H | H | H | H | O | tetrahydropyran-4-yl | H | 2-Et | 0 |
| A-3598 | H | H | H | H | H | O | tetrahydropyran-4-yl | H | 2-Pr | 0 |
| A-3599 | H | H | H | H | H | O | tetrahydropyran-4-yl | H | 2-CF$_3$ | 0 |
| A-3600 | H | H | H | H | H | O | tetrahydropyran-4-yl | H | 2-CHF$_2$ | 0 |
| A-3601 | H | H | H | H | H | O | tetrahydropyran-4-yl | H | 2-CH$_2$F | 0 |
| A-3602 | H | H | H | H | H | O | tetrahydropyran-4-yl | H | 2-CF$_2$Cl | 0 |
| A-3603 | H | H | H | H | H | O | tetrahydropyran-4-yl | H | 2-cyclopropyl | 0 |
| A-3604 | H | H | H | H | H | O | tetrahydropyran-4-yl | H | 2-cyclobutyl | 0 |
| A-3605 | H | H | H | H | H | O | tetrahydropyran-4-yl | H | 2-cyclopentyl | 0 |
| A-3606 | H | H | H | H | H | O | tetrahydropyran-4-yl | H | 2-ethenyl | 0 |
| A-3607 | H | H | H | H | H | O | tetrahydropyran-4-yl | H | 2-allyl | 0 |
| A-3608 | H | H | H | H | H | O | tetrahydropyran-4-yl | H | 2-(prop-1-en-1-y) | 0 |
| A-3609 | H | H | H | H | H | O | tetrahydropyran-4-yl | H | 2-(trifluoroethenyl) | 0 |
| A-3610 | H | H | H | H | H | O | tetrahydropyran-4-yl | H | 2-OMe | 0 |
| A-3611 | H | H | H | H | H | O | tetrahydropyran-4-yl | H | 2-OEt | 0 |
| A-3612 | H | H | H | H | H | O | tetrahydropyran-4-yl | H | 2-OPr | 0 |
| A-3613 | H | H | H | H | H | O | tetrahydropyran-4-yl | H | 2-O(i-Pr) | 0 |
| A-3614 | H | H | H | H | H | O | tetrahydropyran-4-yl | H | 2-OCF$_3$ | 0 |
| A-3615 | H | H | H | H | H | O | tetrahydropyran-4-yl | H | 2-OCHF$_2$ | 0 |
| A-3616 | H | H | H | H | H | O | tetrahydropyran-4-yl | H | 2-(cyclopropyloxy) | 0 |
| A-3617 | H | H | H | H | H | O | tetrahydropyran-4-yl | H | 2-(cyclobutyloxy) | 0 |
| A-3618 | H | H | H | H | H | O | tetrahydropyran-4-yl | H | 2-(cyclopentyloxy) | 0 |
| A-3619 | H | H | H | H | H | O | tetrahydropyran-4-yl | H | 2-((2,2-dichlorocyclopropyl)oxy) | 0 |
| A-3620 | H | H | H | H | H | O | tetrahydropyran-4-yl | H | 2-(oxiran-2-yl) | 0 |
| A-3621 | H | H | H | H | H | O | tetrahydropyran-4-yl | H | 2-SMe | 0 |
| A-3622 | H | H | H | H | H | O | tetrahydropyran-4-yl | H | 3-SMe | 0 |
| A-3623 | H | H | H | H | H | O | tetrahydropyran-4-yl | H | 2-S(=O)Me | 0 |
| A-3624 | H | H | H | H | H | O | tetrahydropyran-4-yl | H | 3-S(=O)Me | 0 |
| A-3625 | H | H | H | H | H | O | tetrahydropyran-4-yl | H | 2-S(=O)$_2$Me | 0 |
| A-3626 | H | H | H | H | H | O | tetrahydropyran-4-yl | H | 3-S(=O)$_2$Me | 0 |
| A-3627 | H | H | H | H | H | O | tetrahydropyran-4-yl | H | 2-SCF$_3$ | 0 |
| A-3628 | H | H | H | H | H | O | tetrahydropyran-4-yl | H | 3-SCF$_3$ | 0 |
| A-3629 | H | H | H | H | H | O | tetrahydropyran-4-yl | H | 3-S(=O)CF$_3$ | 0 |
| A-3630 | H | H | H | H | H | O | tetrahydropyran-4-yl | H | 3-SCF(CF$_3$)$_2$ | 0 |
| A-3631 | H | H | H | H | H | O | tetrahydropyran-4-yl | H | 2-(cyclopropylthio) | 0 |
| A-3632 | H | H | H | H | H | O | tetrahydropyran-4-yl | H | 2-(cyclopropylsulfinyl) | 0 |
| A-3633 | H | H | H | H | H | O | tetrahydropyran-4-yl | H | 2-(cyclopropylsulfonyl) | 0 |
| A-3634 | H | H | H | H | H | O | tetrahydropyran-4-yl | H | 2-C(=O)Me | 0 |
| A-3635 | H | H | H | H | H | O | tetrahydropyran-4-yl | H | 2-CH$_2$C(=O)CH$_3$ | 0 |
| A-3636 | H | H | H | H | H | O | tetrahydropyran-4-yl | H | 2-CH$_2$C(=O)CF$_3$ | 0 |
| A-3637 | H | H | H | H | H | O | tetrahydropyran-4-yl | H | 2-CH$_2$OH | 0 |
| A-3638 | H | H | H | H | H | O | tetrahydropyran-4-yl | H | 2-CH$_2$OCH$_3$ | 0 |
| A-3639 | H | H | H | H | H | O | tetrahydropyran-4-yl | H | 2-CH$_2$OCH$_2$CH$_3$ | 0 |
| A-3640 | H | H | H | H | H | O | tetrahydropyran-4-yl | H | 2-CH$_2$SCH$_3$ | 0 |
| A-3641 | H | H | H | H | H | O | tetrahydropyran-4-yl | H | 2-CH$_2$S(=O)CH$_3$ | 0 |
| A-3642 | H | H | H | H | H | O | tetrahydropyran-4-yl | H | 2-CH$_2$S(=O)$_2$CH$_3$ | 0 |
| A-3643 | H | H | H | H | H | O | tetrahydropyran-4-yl | H | 2-(benzyloxy) | 0 |

TABLE 65

| compound | R¹ | R² | R³ | R⁴ | R⁵ | A | R⁶ | R⁷ | (R⁸)ₘ | p |
|---|---|---|---|---|---|---|---|---|---|---|
| A-3644 | H | H | H | H | H | O | tetrahydropyran-4-yl | H | 2-NH$_2$ | 0 |
| A-3645 | H | H | H | H | H | O | tetrahydropyran-4-yl | H | 2-NHMe | 0 |
| A-3646 | H | H | H | H | H | O | tetrahydropyran-4-yl | H | 2-N(Me)$_2$ | 0 |
| A-3647 | H | H | H | H | H | O | tetrahydropyran-4-yl | H | 2-(1,3-dioxolan-2-yl) | 0 |
| A-3648 | H | H | H | H | H | O | tetrahydropyran-4-yl | H | 2-(1,3-dioxan-2-yl) | 0 |
| A-3649 | H | H | H | H | H | O | tetrahydropyran-4-yl | H | 2-(1H-imidazol-2-yl) | 0 |
| A-3650 | H | H | H | H | H | O | tetrahydropyran-4-yl | H | 2-(thiazol-2-yl) | 0 |
| A-3651 | H | H | H | H | H | O | tetrahydropyran-4-yl | H | 2-(oxazol-2-yl) | 0 |
| A-3652 | H | H | H | H | H | O | tetrahydropyran-4-yl | H | 2-CH=NOH | 0 |
| A-3653 | H | H | H | H | H | O | tetrahydropyran-4-yl | H | 2-CH=NOMe | 0 |
| A-3654 | H | H | H | H | H | O | tetrahydropyran-4-yl | H | 2-(4,5-dihydro-3-isoxazolyl) | 0 |
| A-3655 | H | H | H | H | H | O | tetrahydropyran-4-yl | H | 2-CN | 0 |
| A-3656 | H | H | H | H | H | O | tetrahydropyran-4-yl | H | 2-NO$_2$ | 0 |

TABLE 65-continued

| compound | R¹ | R² | R³ | R⁴ | R⁵ | A | R⁶ | R⁷ | (R⁸)$_m$ | p |
|---|---|---|---|---|---|---|---|---|---|---|
| A-3657 | H | H | H | H | H | O | tetrahydropyran-4-yl | H | 2-F,6-Cl | 0 |
| A-3658 | H | H | H | H | H | O | tetrahydropyran-4-yl | H | 2-F,6-Me | 0 |
| A-3659 | H | H | H | H | H | O | tetrahydropyran-4-yl | H | 3-F,6-Me | 0 |
| A-3660 | H | H | H | H | H | O | tetrahydropyran-4-yl | H | 4-F,2-Me | 0 |
| A-3661 | H | H | H | H | H | O | tetrahydropyran-4-yl | H | 2-F,6-OMe | 0 |
| A-3662 | H | H | H | H | H | O | tetrahydropyran-4-yl | H | 3-F,6-OMe | 0 |
| A-3663 | H | H | H | H | H | O | tetrahydropyran-4-yl | H | 2,6-Cl$_2$ | 0 |
| A-3664 | H | H | H | H | H | O | tetrahydropyran-4-yl | H | 2-Cl,6-Me | 0 |
| A-3665 | H | H | H | H | H | O | tetrahydropyran-4-yl | H | 3-Cl,6-Me | 0 |
| A-3666 | H | H | H | H | H | O | tetrahydropyran-4-yl | H | 4-Cl,2-Me | 0 |
| A-3667 | H | H | H | H | H | O | tetrahydropyran-4-yl | H | 2-Cl,5-CF$_3$ | 0 |
| A-3668 | H | H | H | H | H | O | tetrahydropyran-4-yl | H | 2-Cl,6-CF$_3$ | 0 |
| A-3669 | H | H | H | H | H | O | tetrahydropyran-4-yl | H | 2-Cl,6-OMe | 0 |
| A-3670 | H | H | H | H | H | O | tetrahydropyran-4-yl | H | 3-Cl,6-OMe | 0 |
| A-3671 | H | H | H | H | H | O | tetrahydropyran-4-yl | H | 4-Cl,2-OMe | 0 |
| A-3672 | H | H | H | H | H | O | tetrahydropyran-4-yl | H | 2,4-Me$_2$ | 0 |
| A-3673 | H | H | H | H | H | O | tetrahydropyran-4-yl | H | 2,5-Me$_2$ | 0 |
| A-3674 | H | H | H | H | H | O | tetrahydropyran-4-yl | H | 2,6-Me$_2$ | 0 |
| A-3675 | H | H | H | H | H | O | tetrahydropyran-4-yl | H | 2-Me,4-CF$_3$ | 0 |
| A-3676 | H | H | H | H | H | O | tetrahydropyran-4-yl | H | 2-Me,5-CF$_3$ | 0 |
| A-3677 | H | H | H | H | H | O | tetrahydropyran-4-yl | H | 2-Me,6-CF$_3$ | 0 |
| A-3678 | H | H | H | H | H | O | tetrahydropyran-4-yl | H | 2-Me,4-OMe | 0 |
| A-3679 | H | H | H | H | H | O | tetrahydropyran-4-yl | H | 2-Me,5-OMe | 0 |
| A-3680 | H | H | H | H | H | O | tetrahydropyran-4-yl | H | 2-Me,6-OMe | 0 |
| A-3681 | H | H | H | H | H | O | tetrahydropyran-4-yl | H | 3-Me,6-OMe | 0 |
| A-3682 | H | H | H | H | H | O | tetrahydropyran-4-yl | H | 4-Me,2-OMe | 0 |
| A-3683 | H | H | H | H | H | O | tetrahydropyran-4-yl | H | 2,5-OMe$_2$ | 0 |
| A-3684 | H | H | H | H | H | O | tetrahydropyran-4-yl | H | 2,6-OMe$_2$ | 0 |
| A-3685 | H | H | H | H | H | O | tetrahydropyran-4-yl | H | 2-OMe,6-CF$_3$ | 0 |
| A-3686 | H | H | H | H | H | O | tetrahydropyran-4-yl | H | 2-CHF$_2$,5-F | 0 |
| A-3687 | H | H | H | H | H | O | tetrahydropyran-4-yl | H | 2-CHF$_2$,6-F | 0 |
| A-3688 | H | H | H | H | H | O | tetrahydropyran-4-yl | H | 2-CHF$_2$,5-Me | 0 |
| A-3689 | H | H | H | H | H | O | tetrahydropyran-4-yl | H | 2-CHF$_2$,6-Me | 0 |
| A-3690 | H | H | H | H | H | O | tetrahydropyran-4-yl | H | 2-cyclopropyl,5-F | 0 |
| A-3691 | H | H | H | H | H | O | tetrahydropyran-4-yl | H | 2-cyclopropyl,6-F | 0 |
| A-3692 | H | H | H | H | H | O | tetrahydropyran-4-yl | H | 2-cyclopropyl,5-Me | 0 |
| A-3693 | H | H | H | H | H | O | tetrahydropyran-4-yl | H | 2-cyclopropyl,6-Me | 0 |
| A-3694 | H | H | H | H | H | O | tetrahydropyran-4-yl | H | 2-ethenyl,6-F | 0 |
| A-3695 | H | H | H | H | H | O | tetrahydropyran-4-yl | H | 2-ethenyl,6-Me | 0 |
| A-3696 | H | H | H | H | H | O | tetrahydropyran-4-yl | H | 2-OEt,5-F | 0 |
| A-3697 | H | H | H | H | H | O | tetrahydropyran-4-yl | H | 2-OEt,6-F | 0 |
| A-3698 | H | H | H | H | H | O | tetrahydropyran-4-yl | H | 2-OEt,5-Cl | 0 |
| A-3699 | H | H | H | H | H | O | tetrahydropyran-4-yl | H | 2-OEt,6-Cl | 0 |
| A-3700 | H | H | H | H | H | O | tetrahydropyran-4-yl | H | 2-OEt,5-Me | 0 |

TABLE 66

| compound | R¹ | R² | R³ | R⁴ | R⁵ | A | R⁶ | R⁷ | (R⁸)$_m$ | p |
|---|---|---|---|---|---|---|---|---|---|---|
| A-3701 | H | H | H | H | H | O | tetrahydropyran-4-yl | H | 2-OEt,6-Me | 0 |
| A-3702 | H | H | H | H | H | O | tetrahydropyran-4-yl | H | 2-OCHF$_2$,5-F | 0 |
| A-3703 | H | H | H | H | H | O | tetrahydropyran-4-yl | H | 2-OCHF$_2$,6-F | 0 |
| A-3704 | H | H | H | H | H | O | tetrahydropyran-4-yl | H | 2-OCHF$_2$,5-Me | 0 |
| A-3705 | H | H | H | H | H | O | tetrahydropyran-4-yl | H | 2-OCHF$_2$,6-Me | 0 |
| A-3706 | H | H | H | H | H | O | tetrahydropyran-4-yl | H | 2-(cyclopropyloxy),5-F | 0 |
| A-3707 | H | H | H | H | H | O | tetrahydropyran-4-yl | H | 2-(cyclopropyloxy),6-F | 0 |
| A-3708 | H | H | H | H | H | O | tetrahydropyran-4-yl | H | 2-(cyclopropyloxy),5-Me | 0 |
| A-3709 | H | H | H | H | H | O | tetrahydropyran-4-yl | H | 2-(cyclopropyloxy),6-Me | 0 |
| A-3710 | H | H | H | H | H | O | tetrahydropyran-4-yl | H | 2-SMe,5-F | 0 |
| A-3711 | H | H | H | H | H | O | tetrahydropyran-4-yl | H | 2-SMe,6-F | 0 |
| A-3712 | H | H | H | H | H | O | tetrahydropyran-4-yl | H | 2-SMe,5-Me | 0 |
| A-3713 | H | H | H | H | H | O | tetrahydropyran-4-yl | H | 2-SMe,6-Me | 0 |
| A-3714 | H | H | H | H | H | O | tetrahydropyran-4-yl | H | 2-S(=O)Me,5-F | 0 |
| A-3715 | H | H | H | H | H | O | tetrahydropyran-4-yl | H | 2-S(=O)Me,6-F | 0 |
| A-3716 | H | H | H | H | H | O | tetrahydropyran-4-yl | H | 2-S(=O)Me,5-Me | 0 |
| A-3717 | H | H | H | H | H | O | tetrahydropyran-4-yl | H | 2-S(=O)Me,6-Me | 0 |
| A-3718 | H | H | H | H | H | O | tetrahydropyran-4-yl | H | 2-S(=O)$_2$Me,5-F | 0 |
| A-3719 | H | H | H | H | H | O | tetrahydropyran-4-yl | H | 2-S(=O)$_2$Me,6-F | 0 |
| A-3720 | H | H | H | H | H | O | tetrahydropyran-4-yl | H | 2-S(=O)$_2$Me,5-Me | 0 |
| A-3721 | H | H | H | H | H | O | tetrahydropyran-4-yl | H | 2-S(=O)$_2$Me,6-Me | 0 |
| A-3722 | H | H | H | H | H | O | tetrahydropyran-4-yl | H | 2-SCF$_3$,5-F | 0 |
| A-3723 | H | H | H | H | H | O | tetrahydropyran-4-yl | H | 2-SCF$_3$,6-F | 0 |
| A-3724 | H | H | H | H | H | O | tetrahydropyran-4-yl | H | 2-SCF$_3$,5-Me | 0 |
| A-3725 | H | H | H | H | H | O | tetrahydropyran-4-yl | H | 2-SCF$_3$,6-Me | 0 |
| A-3726 | H | H | H | H | H | O | tetrahydropyran-4-yl | H | 2-S(=O)CF$_3$,5-F | 0 |

TABLE 66-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-3727 | H | H | H | H | H | O | tetrahydropyran-4-yl | H | 2-S(=O)CF$_3$,6-F | 0 |
| A-3728 | H | H | H | H | H | O | tetrahydropyran-4-yl | H | 2-S(=O)CF$_3$,5-Me | 0 |
| A-3729 | H | H | H | H | H | O | tetrahydropyran-4-yl | H | 2-S(=O)CF$_3$,6-Me | 0 |
| A-3730 | H | H | H | H | H | O | tetrahydropyran-4-yl | H | 2-S(=O)$_2$CF$_3$,5-F | 0 |
| A-3731 | H | H | H | H | H | O | tetrahydropyran-4-yl | H | 2-S(=O)$_2$CF$_3$,6-F | 0 |
| A-3732 | H | H | H | H | H | O | tetrahydropyran-4-yl | H | 2-S(=O)$_2$CF$_3$,5-Me | 0 |
| A-3733 | H | H | H | H | H | O | tetrahydropyran-4-yl | H | 2-S(=O)$_2$CF$_3$,6-Me | 0 |
| A-3734 | H | H | H | H | H | O | tetrahydropyran-4-yl | H | 2-(cyclopropylthio),5-F | 0 |
| A-3735 | H | H | H | H | H | O | tetrahydropyran-4-yl | H | 2-(cyclopropylthio),6-F | 0 |
| A-3736 | H | H | H | H | H | O | tetrahydropyran-4-yl | H | 2-(cyclopropylthio),5-Me | 0 |
| A-3737 | H | H | H | H | H | O | tetrahydropyran-4-yl | H | 2-(cyclopropylthio),6-Me | 0 |
| A-3738 | H | H | H | H | H | O | tetrahydropyran-4-yl | H | 2-C(=O)Me,5-F | 0 |
| A-3739 | H | H | H | H | H | O | tetrahydropyran-4-yl | H | 2-C(=O)Me,6-F | 0 |
| A-3740 | H | H | H | H | H | O | tetrahydropyran-4-yl | H | 2-C(=O)Me,5-Me | 0 |
| A-3741 | H | H | H | H | H | O | tetrahydropyran-4-yl | H | 2-C(=O)Me,6-Me | 0 |
| A-3742 | H | H | H | H | H | O | tetrahydropyran-4-yl | H | 2-CH$_2$OH,5-F | 0 |
| A-3743 | H | H | H | H | H | O | tetrahydropyran-4-yl | H | 2-CH$_2$OH,6-F | 0 |
| A-3744 | H | H | H | H | H | O | tetrahydropyran-4-yl | H | 2-CH$_2$OH,5-Me | 0 |
| A-3745 | H | H | H | H | H | O | tetrahydropyran-4-yl | H | 2-CH$_2$OH,6-Me | 0 |
| A-3746 | H | H | H | H | H | O | tetrahydropyran-4-yl | H | 2-CH$_2$OCH$_3$,4-F | 0 |
| A-3747 | H | H | H | H | H | O | tetrahydropyran-4-yl | H | 2-CH$_2$OCH$_3$,5-F | 0 |
| A-3748 | H | H | H | H | H | O | tetrahydropyran-4-yl | H | 2-CH$_2$OCH$_3$,6-F | 0 |
| A-3749 | H | H | H | H | H | O | tetrahydropyran-4-yl | H | 2-CH$_2$OCH$_3$,4-Me | 0 |
| A-3750 | H | H | H | H | H | O | tetrahydropyran-4-yl | H | 2-CH$_2$OCH$_3$,5-Me | 0 |
| A-3751 | H | H | H | H | H | O | tetrahydropyran-4-yl | H | 2-CH$_2$OCH$_3$,6-Me | 0 |
| A-3752 | H | H | H | H | H | O | tetrahydropyran-4-yl | H | 2-OC(=O)CH$_3$,5-F | 0 |
| A-3753 | H | H | H | H | H | O | tetrahydropyran-4-yl | H | 2-OC(=O)CH$_3$,6-F | 0 |
| A-3754 | H | H | H | H | H | O | tetrahydropyran-4-yl | H | 2-OC(=O)CH$_3$,5-Me | 0 |
| A-3755 | H | H | H | H | H | O | tetrahydropyran-4-yl | H | 2-OC(=O)CH$_3$,6-Me | 0 |
| A-3756 | H | H | H | H | H | O | tetrahydropyran-4-yl | H | 2-OS(=O)$_2$CH$_3$,5-F | 0 |
| A-3757 | H | H | H | H | H | O | tetrahydropyran-4-yl | H | 2-OS(=O)$_2$CH$_3$,6-F | 0 |

TABLE 67

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-3758 | H | H | H | H | H | O | tetrahydropyran-4-yl | H | 2-OS(=O)$_2$CH$_3$,5-Me | 0 |
| A-3759 | H | H | H | H | H | O | tetrahydropyran-4-yl | H | 2-OS(=O)$_2$CH$_3$,6-Me | 0 |
| A-3760 | H | H | H | H | H | O | tetrahydropyran-4-yl | H | 2-CH$_2$SCH$_3$,5-F | 0 |
| A-3761 | H | H | H | H | H | O | tetrahydropyran-4-yl | H | 2-CH$_2$SCH$_3$,6-F | 0 |
| A-3762 | H | H | H | H | H | O | tetrahydropyran-4-yl | H | 2-CH$_2$SCH$_3$,5-Me | 0 |
| A-3763 | H | H | H | H | H | O | tetrahydropyran-4-yl | H | 2-CH$_2$SCH$_3$,6-Me | 0 |
| A-3764 | H | H | H | H | H | O | tetrahydropyran-4-yl | H | 2-NMe$_2$,5-F | 0 |
| A-3765 | H | H | H | H | H | O | tetrahydropyran-4-yl | H | 2-NMe$_2$,6-F | 0 |
| A-3766 | H | H | H | H | H | O | tetrahydropyran-4-yl | H | 2-NMe$_2$,5-Me | 0 |
| A-3767 | H | H | H | H | H | O | tetrahydropyran-4-yl | H | 2-NMe$_2$,6-Me | 0 |
| A-3768 | H | H | H | H | H | O | tetrahydropyran-4-yl | H | 2-CN,4-F | 0 |
| A-3769 | H | H | H | H | H | O | tetrahydropyran-4-yl | H | 2-CN,5-F | 0 |
| A-3770 | H | H | H | H | H | O | tetrahydropyran-4-yl | H | 2-CN,6-F | 0 |
| A-3771 | H | H | H | H | H | O | tetrahydropyran-4-yl | H | 2-CN,6-Me | 0 |
| A-3772 | H | H | H | H | H | O | tetrahydropyran-4-yl | H | 2-CN,5-OMe | 0 |
| A-3773 | H | H | H | H | H | O | tetrahydropyran-4-yl | H | 2-CN,6-OMe | 0 |
| A-3774 | H | H | H | H | H | O | tetrahydropyran-4-yl | H | 3-CN,6-Me | 0 |
| A-3775 | H | H | H | H | H | O | tetrahydropyran-4-yl | H | 3-CN,6-OMe | 0 |
| A-3776 | H | H | H | H | H | O | tetrahydropyran-4-yl | H | 4-CN,2-Me | 0 |
| A-3777 | H | H | H | H | H | O | tetrahydropyran-4-yl | H | 4-CN,2-OMe | 0 |
| A-3778 | H | H | H | H | H | O | tetrahydropyran-4-yl | H | 2-NO$_2$,4-F | 0 |
| A-3779 | H | H | H | H | H | O | tetrahydropyran-4-yl | H | 2-NO$_2$,5-F | 0 |
| A-3780 | H | H | H | H | H | O | tetrahydropyran-4-yl | H | 2-NO$_2$,6-F | 0 |
| A-3781 | H | H | H | H | H | O | tetrahydropyran-4-yl | H | 2-NO$_2$,4-Me | 0 |
| A-3782 | H | H | H | H | H | O | tetrahydropyran-4-yl | H | 2-NO$_2$,5-Me | 0 |
| A-3783 | H | H | H | H | H | O | tetrahydropyran-4-yl | H | 2-NO$_2$,6-Me | 0 |
| A-3784 | H | H | H | H | H | O | tetrahydropyran-4-yl | H | 2-Me,4,5-F$_2$ | 0 |
| A-3785 | H | H | H | H | H | O | tetrahydropyran-4-yl | H | 2-Me,6-Et | 0 |
| A-3786 | H | H | H | H | H | O | tetrahydropyran-4-yl | H | 2-cyclopropyl,6-OMe | 0 |
| A-3787 | H | H | H | H | H | O | tetrahydropyran-4-yl | H | 2-Me,5-Et | 0 |
| A-3788 | H | H | H | H | H | O | tetrahydropyran-4-yl | H | 2,6-Et$_2$ | 0 |
| A-3789 | H | H | H | H | H | O | tetrahydropyran-4-yl | H | 2-Et,6-F | 0 |
| A-3790 | H | H | H | H | H | O | tetrahydropyran-4-yl | H | 2-CH$_2$OCH$_3$,6-Cl | 0 |
| A-3791 | H | H | H | H | H | O | tetrahydropyran-4-yl | H | 2-CH$_2$OCH$_2$CH$_3$,6-Cl | 0 |
| A-3792 | H | H | H | H | H | O | tetrahydropyran-4-yl | H | 2-CH$_2$NMe$_2$ | 0 |
| A-3793 | H | H | H | H | H | O | CH$_2$CN | H | H | 0 |
| A-3794 | H | H | H | H | H | O | CH$_2$CN | H | 2-F | 0 |
| A-3795 | H | H | H | H | H | O | CH$_2$CN | H | 2-Cl | 0 |
| A-3796 | H | H | H | H | H | O | CH$_2$CN | H | 2-Br | 0 |

TABLE 67-continued

| compound | R¹ | R² | R³ | R⁴ | R⁵ | A | R⁶ | R⁷ | (R⁸)$_m$ | p |
|---|---|---|---|---|---|---|---|---|---|---|
| A-3797 | H | H | H | H | H | O | CH₂CN | H | 2-OH | 0 |
| A-3798 | H | H | H | H | H | O | CH₂CN | H | 2-Me | 0 |
| A-3799 | H | H | H | H | H | O | CH₂CN | H | 2-Et | 0 |
| A-3800 | H | H | H | H | H | O | CH₂CN | H | 2-Pr | 0 |
| A-3801 | H | H | H | H | H | O | CH₂CN | H | 2-CF₃ | 0 |
| A-3802 | H | H | H | H | H | O | CH₂CN | H | 2-CHF₂ | 0 |
| A-3803 | H | H | H | H | H | O | CH₂CN | H | 2-CH₂F | 0 |
| A-3804 | H | H | H | H | H | O | CH₂CN | H | 2-CF₂Cl | 0 |
| A-3805 | H | H | H | H | H | O | CH₂CN | H | 2-cyclopropyl | 0 |
| A-3806 | H | H | H | H | H | O | CH₂CN | H | 2-cyclobutyl | 0 |
| A-3807 | H | H | H | H | H | O | CH₂CN | H | 2-cyclopentyl | 0 |
| A-3808 | H | H | H | H | H | O | CH₂CN | H | 2-ethenyl | 0 |
| A-3809 | H | H | H | H | H | O | CH₂CN | H | 2-allyl | 0 |
| A-3810 | H | H | H | H | H | O | CH₂CN | H | 2-(prop-1-en-1-yl) | 0 |
| A-3811 | H | H | H | H | H | O | CH₂CN | H | 2-(trifluoroethenyl) | 0 |
| A-3812 | H | H | H | H | H | O | CH₂CN | H | 2-OMe | 0 |
| A-3813 | H | H | H | H | H | O | CH₂CN | H | 2-OEt | 0 |
| A-3814 | H | H | H | H | H | O | CH₂CN | H | 2-OPr | 0 |

TABLE 68

| compound | R¹ | R² | R³ | R⁴ | R⁵ | A | R⁶ | R⁷ | (R⁸)$_m$ | p |
|---|---|---|---|---|---|---|---|---|---|---|
| A-3815 | H | H | H | H | H | O | CH₂CN | H | 2-O(i-Pr) | 0 |
| A-3816 | H | H | H | H | H | O | CH₂CN | H | 2-OCF₃ | 0 |
| A-3817 | H | H | H | H | H | O | CH₂CN | H | 2-OCHF₂ | 0 |
| A-3818 | H | H | H | H | H | O | CH₂CN | H | 2-(cyclopropyloxy) | 0 |
| A-3819 | H | H | H | H | H | O | CH₂CN | H | 2-(cyclobutyloxy) | 0 |
| A-3820 | H | H | H | H | H | O | CH₂CN | H | 2-(cyclopentyloxy) | 0 |
| A-3821 | H | H | H | H | H | O | CH₂CN | H | 2-((2,2-dichlorocyclopropyl)oxy) | 0 |
| A-3822 | H | H | H | H | H | O | CH₂CN | H | 2-(oxiran-2-yl) | 0 |
| A-3823 | H | H | H | H | H | O | CH₂CN | H | 2-SMe | 0 |
| A-3824 | H | H | H | H | H | O | CH₂CN | H | 3-SMe | 0 |
| A-3825 | H | H | H | H | H | O | CH₂CN | H | 2-S(=O)Me | 0 |
| A-3826 | H | H | H | H | H | O | CH₂CN | H | 3-S(=O)Me | 0 |
| A-3827 | H | H | H | H | H | O | CH₂CN | H | 2-S(=O)₂Me | 0 |
| A-3828 | H | H | H | H | H | O | CH₂CN | H | 3-S(=O)₂Me | 0 |
| A-3829 | H | H | H | H | H | O | CH₂CN | H | 2-SCF₃ | 0 |
| A-3830 | H | H | H | H | H | O | CH₂CN | H | 3-SCF₃ | 0 |
| A-3831 | H | H | H | H | H | O | CH₂CN | H | 3-S(=O)CF₃ | 0 |
| A-3832 | H | H | H | H | H | O | CH₂CN | H | 3-SCF(CF₃)₂ | 0 |
| A-3833 | H | H | H | H | H | O | CH₂CN | H | 2-(cyclopropylthio) | 0 |
| A-3834 | H | H | H | H | H | O | CH₂CN | H | 2-(cyclopropylsulfinyl) | 0 |
| A-3835 | H | H | H | H | H | O | CH₂CN | H | 2-(cyclopropylsulfonyl) | 0 |
| A-3836 | H | H | H | H | H | O | CH₂CN | H | 2-C(=O)Me | 0 |
| A-3837 | H | H | H | H | H | O | CH₂CN | H | 2-CH₂C(=O)CH₃ | 0 |
| A-3838 | H | H | H | H | H | O | CH₂CN | H | 2-CH₂C(=O)CF₃ | 0 |
| A-3839 | H | H | H | H | H | O | CH₂CN | H | 2-CH₂OH | 0 |
| A-3840 | H | H | H | H | H | O | CH₂CN | H | 2-CH₂OCH₃ | 0 |
| A-3841 | H | H | H | H | H | O | CH₂CN | H | 2-CH₂OCH₂CH₃ | 0 |
| A-3842 | H | H | H | H | H | O | CH₂CN | H | 2-CH₂SCH₃ | 0 |
| A-3843 | H | H | H | H | H | O | CH₂CN | H | 2-CH₂S(=O)CH₃ | 0 |
| A-3844 | H | H | H | H | H | O | CH₂CN | H | 2-CH₂S(=O)₂CH₃ | 0 |
| A-3845 | H | H | H | H | H | O | CH₂CN | H | 2-(benzyloxy) | 0 |
| A-3846 | H | H | H | H | H | O | CH₂CN | H | 2-NH₂ | 0 |
| A-3847 | H | H | H | H | H | O | CH₂CN | H | 2-NHMe | 0 |
| A-3848 | H | H | H | H | H | O | CH₂CN | H | 2-N(Me)₂ | 0 |
| A-3849 | H | H | H | H | H | O | CH₂CN | H | 2-(1,3-dioxolan-2-yl) | 0 |
| A-3850 | H | H | H | H | H | O | CH₂CN | H | 2-(1,3-dioxan-2-yl) | 0 |
| A-3851 | H | H | H | H | H | O | CH₂CN | H | 2-(1H-imidazol-2-yl) | 0 |
| A-3852 | H | H | H | H | H | O | CH₂CN | H | 2-(thiazol-2-yl) | 0 |
| A-3853 | H | H | H | H | H | O | CH₂CN | H | 2-(oxazol-2-yl) | 0 |
| A-3854 | H | H | H | H | H | O | CH₂CN | H | 2-CH=NOH | 0 |
| A-3855 | H | H | H | H | H | O | CH₂CN | H | 2-CH=NOMe | 0 |
| A-3856 | H | H | H | H | H | O | CH₂CN | H | 2-(4,5-dihydro-3-isoxazolyl) | 0 |
| A-3857 | H | H | H | H | H | O | CH₂CN | H | 2-CN | 0 |
| A-3858 | H | H | H | H | H | O | CH₂CN | H | 2-NO₂ | 0 |
| A-3859 | H | H | H | H | H | O | CH₂CN | H | 2-F,6-Cl | 0 |
| A-3860 | H | H | H | H | H | O | CH₂CN | H | 2-F,6-Me | 0 |
| A-3861 | H | H | H | H | H | O | CH₂CN | H | 3-F,6-Me | 0 |
| A-3862 | H | H | H | H | H | O | CH₂CN | H | 4-F,2-Me | 0 |
| A-3863 | H | H | H | H | H | O | CH₂CN | H | 2-F,6-OMe | 0 |
| A-3864 | H | H | H | H | H | O | CH₂CN | H | 3-F,6-OMe | 0 |
| A-3865 | H | H | H | H | H | O | CH₂CN | H | 2,6-Cl₂ | 0 |
| A-3866 | H | H | H | H | H | O | CH₂CN | H | 2-Cl,6-Me | 0 |

TABLE 68-continued

| compound | R¹ | R² | R³ | R⁴ | R⁵ | A | R⁶ | R⁷ | (R⁸)ₘ | p |
|---|---|---|---|---|---|---|---|---|---|---|
| A-3867 | H | H | H | H | H | O | CH₂CN | H | 3-Cl,6-Me | 0 |
| A-3868 | H | H | H | H | H | O | CH₂CN | H | 4-Cl,2-Me | 0 |
| A-3869 | H | H | H | H | H | O | CH₂CN | H | 2-Cl,5-CF₃ | 0 |
| A-3870 | H | H | H | H | H | O | CH₂CN | H | 2-Cl,6-CF₃ | 0 |
| A-3871 | H | H | H | H | H | O | CH₂CN | H | 2-Cl,6-OMe | 0 |

TABLE 69

| compound | R¹ | R² | R³ | R⁴ | R⁵ | A | R⁶ | R⁷ | (R⁸)ₘ | p |
|---|---|---|---|---|---|---|---|---|---|---|
| A-3872 | H | H | H | H | H | O | CH₂CN | H | 3-Cl,6-OMe | 0 |
| A-3873 | H | H | H | H | H | O | CH₂CN | H | 4-Cl,2-OMe | 0 |
| A-3874 | H | H | H | H | H | O | CH₂CN | H | 2,4-Me₂ | 0 |
| A-3875 | H | H | H | H | H | O | CH₂CN | H | 2,5-Me₂ | 0 |
| A-3876 | H | H | H | H | H | O | CH₂CN | H | 2,6-Me₂ | 0 |
| A-3877 | H | H | H | H | H | O | CH₂CN | H | 2-Me,4-CF₃ | 0 |
| A-3878 | H | H | H | H | H | O | CH₂CN | H | 2-Me,5-CF₃ | 0 |
| A-3879 | H | H | H | H | H | O | CH₂CN | H | 2-Me,6-CF₃ | 0 |
| A-3880 | H | H | H | H | H | O | CH₂CN | H | 2-Me,4-OMe | 0 |
| A-3881 | H | H | H | H | H | O | CH₂CN | H | 2-Me,5-OMe | 0 |
| A-3882 | H | H | H | H | H | O | CH₂CN | H | 2-Me,6-OMe | 0 |
| A-3883 | H | H | H | H | H | O | CH₂CN | H | 3-Me,6-OMe | 0 |
| A-3884 | H | H | H | H | H | O | CH₂CN | H | 4-Me,2-OMe | 0 |
| A-3885 | H | H | H | H | H | O | CH₂CN | H | 2,5-OMe₂ | 0 |
| A-3886 | H | H | H | H | H | O | CH₂CN | H | 2,6-OMe₂ | 0 |
| A-3887 | H | H | H | H | H | O | CH₂CN | H | 2-OMe,6-CF₃ | 0 |
| A-3888 | H | H | H | H | H | O | CH₂CN | H | 2-CHF₂,5-F | 0 |
| A-3889 | H | H | H | H | H | O | CH₂CN | H | 2-CHF₂,6-F | 0 |
| A-3890 | H | H | H | H | H | O | CH₂CN | H | 2-CHF₂,5-Me | 0 |
| A-3891 | H | H | H | H | H | O | CH₂CN | H | 2-CHF₂,6-Me | 0 |
| A-3892 | H | H | H | H | H | O | CH₂CN | H | 2-cyclopropyl,5-F | 0 |
| A-3893 | H | H | H | H | H | O | CH₂CN | H | 2-cyclopropyl,6-F | 0 |
| A-3894 | H | H | H | H | H | O | CH₂CN | H | 2-cyclopropyl,5-Me | 0 |
| A-3895 | H | H | H | H | H | O | CH₂CN | H | 2-cyclopropyl,6-Me | 0 |
| A-3896 | H | H | H | H | H | O | CH₂CN | H | 2-ethenyl,6-F | 0 |
| A-3897 | H | H | H | H | H | O | CH₂CN | H | 2-ethenyl,6-Me | 0 |
| A-3898 | H | H | H | H | H | O | CH₂CN | H | 2-OEt,5-F | 0 |
| A-3899 | H | H | H | H | H | O | CH₂CN | H | 2-OEt,6-F | 0 |
| A-3900 | H | H | H | H | H | O | CH₂CN | H | 2-OEt,5-Cl | 0 |
| A-3901 | H | H | H | H | H | O | CH₂CN | H | 2-OEt,6-Cl | 0 |
| A-3902 | H | H | H | H | H | O | CH₂CN | H | 2-OEt,5-Me | 0 |
| A-3903 | H | H | H | H | H | O | CH₂CN | H | 2-OEt,6-Me | 0 |
| A-3904 | H | H | H | H | H | O | CH₂CN | H | 2-OCHF₂,5-F | 0 |
| A-3905 | H | H | H | H | H | O | CH₂CN | H | 2-OCHF₂,6-F | 0 |
| A-3906 | H | H | H | H | H | O | CH₂CN | H | 2-OCHF₂,5-Me | 0 |
| A-3907 | H | H | H | H | H | O | CH₂CN | H | 2-OCHF₂,6-Me | 0 |
| A-3908 | H | H | H | H | H | O | CH₂CN | H | 2-(cyclopropyloxy),5-F | 0 |
| A-3909 | H | H | H | H | H | O | CH₂CN | H | 2-(cyclopropyloxy),6-F | 0 |
| A-3910 | H | H | H | H | H | O | CH₂CN | H | 2-(cyclopropyloxy),5-Me | 0 |
| A-3911 | H | H | H | H | H | O | CH₂CN | H | 2-(cyclopropyloxy),6-Me | 0 |
| A-3912 | H | H | H | H | H | O | CH₂CN | H | 2-SMe,5-F | 0 |
| A-3913 | H | H | H | H | H | O | CH₂CN | H | 2-SMe,6-F | 0 |
| A-3914 | H | H | H | H | H | O | CH₂CN | H | 2-SMe,5-Me | 0 |
| A-3915 | H | H | H | H | H | O | CH₂CN | H | 2-SMe,6-Me | 0 |
| A-3916 | H | H | H | H | H | O | CH₂CN | H | 2-S(=O)Me,5-F | 0 |
| A-3917 | H | H | H | H | H | O | CH₂CN | H | 2-S(=O)Me,6-F | 0 |
| A-3918 | H | H | H | H | H | O | CH₂CN | H | 2-S(=O)Me,5-Me | 0 |
| A-3919 | H | H | H | H | H | O | CH₂CN | H | 2-S(=O)Me,6-Me | 0 |
| A-3920 | H | H | H | H | H | O | CH₂CN | H | 2-S(=O)₂Me,5-F | 0 |
| A-3921 | H | H | H | H | H | O | CH₂CN | H | 2-S(=O)₂Me,6-F | 0 |
| A-3922 | H | H | H | H | H | O | CH₂CN | H | 2-S(=O)₂Me,5-Me | 0 |
| A-3923 | H | H | H | H | H | O | CH₂CN | H | 2-S(=O)₂Me,6-Me | 0 |
| A-3924 | H | H | H | H | H | O | CH₂CN | H | 2-SCF₃,5-F | 0 |
| A-3925 | H | H | H | H | H | O | CH₂CN | H | 2-SCF₃,6-F | 0 |
| A-3926 | H | H | H | H | H | O | CH₂CN | H | 2-SCF₃,5-Me | 0 |
| A-3927 | H | H | H | H | H | O | CH₂CN | H | 2-SCF₃,6-Me | 0 |
| A-3928 | H | H | H | H | H | O | CH₂CN | H | 2-S(=O)CF₃,5-F | 0 |

TABLE 70

| compound | R¹ | R² | R³ | R⁴ | R⁵ | A | R⁶ | R⁷ | $(R^8)_m$ | p |
|---|---|---|---|---|---|---|---|---|---|---|
| A-3929 | H | H | H | H | H | O | CH₂CN | H | 2-S(=O)CF₃,6-F | 0 |
| A-3930 | H | H | H | H | H | O | CH₂CN | H | 2-S(=O)CF₃,5-Me | 0 |
| A-3931 | H | H | H | H | H | O | CH₂CN | H | 2-S(=O)CF₃,6-Me | 0 |
| A-3932 | H | H | H | H | H | O | CH₂CN | H | 2-S(=O)₂CF₃,5-F | 0 |
| A-3933 | H | H | H | H | H | O | CH₂CN | H | 2-S(=O)₂CF₃,6-F | 0 |
| A-3934 | H | H | H | H | H | O | CH₂CN | H | 2-S(=O)₂CF₃,5-Me | 0 |
| A-3935 | H | H | H | H | H | O | CH₂CN | H | 2-S(=O)₂CF₃,6-Me | 0 |
| A-3936 | H | H | H | H | H | O | CH₂CN | H | 2-(cyclopropylthio),5-F | 0 |
| A-3937 | H | H | H | H | H | O | CH₂CN | H | 2-(cyclopropylthio),6-F | 0 |
| A-3938 | H | H | H | H | H | O | CH₂CN | H | 2-(cyclopropylthio),5-Me | 0 |
| A-3939 | H | H | H | H | H | O | CH₂CN | H | 2-(cyclopropylthio),6-Me | 0 |
| A-3940 | H | H | H | H | H | O | CH₂CN | H | 2-C(=O)Me,5-F | 0 |
| A-3941 | H | H | H | H | H | O | CH₂CN | H | 2-C(=O)Me,6-F | 0 |
| A-3942 | H | H | H | H | H | O | CH₂CN | H | 2-C(=O)Me,5-Me | 0 |
| A-3943 | H | H | H | H | H | O | CH₂CN | H | 2-C(=O)Me,6-Me | 0 |
| A-3944 | H | H | H | H | H | O | CH₂CN | H | 2-CH₂OH,5-F | 0 |
| A-3945 | H | H | H | H | H | O | CH₂CN | H | 2-CH₂OH,6-F | 0 |
| A-3946 | H | H | H | H | H | O | CH₂CN | H | 2-CH₂OH,5-Me | 0 |
| A-3947 | H | H | H | H | H | O | CH₂CN | H | 2-CH₂OH,6-Me | 0 |
| A-3948 | H | H | H | H | H | O | CH₂CN | H | 2-CH₂OCH₃,4-F | 0 |
| A-3949 | H | H | H | H | H | O | CH₂CN | H | 2-CH₂OCH₃,5-F | 0 |
| A-3950 | H | H | H | H | H | O | CH₂CN | H | 2-CH₂OCH₃,6-F | 0 |
| A-3951 | H | H | H | H | H | O | CH₂CN | H | 2-CH₂OCH₃,4-Me | 0 |
| A-3952 | H | H | H | H | H | O | CH₂CN | H | 2-CH₂OCH₃,5-Me | 0 |
| A-3953 | H | H | H | H | H | O | CH₂CN | H | 2-CH₂OCH₃,6-Me | 0 |
| A-3954 | H | H | H | H | H | O | CH₂CN | H | 2-OC(=O)CH₃,5-F | 0 |
| A-3955 | H | H | H | H | H | O | CH₂CN | H | 2-OC(=O)CH₃,6-F | 0 |
| A-3956 | H | H | H | H | H | O | CH₂CN | H | 2-OC(=O)CH₃,5-Me | 0 |
| A-3957 | H | H | H | H | H | O | CH₂CN | H | 2-OC(=O)CH₃,6-Me | 0 |
| A-3958 | H | H | H | H | H | O | CH₂CN | H | 2-OS(=O)₂CH₃,5-F | 0 |
| A-3959 | H | H | H | H | H | O | CH₂CN | H | 2-OS(=O)₂CH₃,6-F | 0 |
| A-3960 | H | H | H | H | H | O | CH₂CN | H | 2-OS(=O)₂CH₃,5-Me | 0 |
| A-3961 | H | H | H | H | H | O | CH₂CN | H | 2-OS(=O)₂CH₃,6-Me | 0 |
| A-3962 | H | H | H | H | H | O | CH₂CN | H | 2-CH₂SCH₃,5-F | 0 |
| A-3963 | H | H | H | H | H | O | CH₂CN | H | 2-CH₂SCH₃,6-F | 0 |
| A-3964 | H | H | H | H | H | O | CH₂CN | H | 2-CH₂SCH₃,5-Me | 0 |
| A-3965 | H | H | H | H | H | O | CH₂CN | H | 2-CH₂SCH₃,6-Me | 0 |
| A-3966 | H | H | H | H | H | O | CH₂CN | H | 2-NMe₂,5-F | 0 |
| A-3967 | H | H | H | H | H | O | CH₂CN | H | 2-NMe₂,6-F | 0 |
| A-3968 | H | H | H | H | H | O | CH₂CN | H | 2-NMe₂,5-Me | 0 |
| A-3969 | H | H | H | H | H | O | CH₂CN | H | 2-NMe₂,6-Me | 0 |
| A-3970 | H | H | H | H | H | O | CH₂CN | H | 2-CN,4-F | 0 |
| A-3971 | H | H | H | H | H | O | CH₂CN | H | 2-CN,5-F | 0 |
| A-3972 | H | H | H | H | H | O | CH₂CN | H | 2-CN,6-F | 0 |
| A-3973 | H | H | H | H | H | O | CH₂CN | H | 2-CN,6-Me | 0 |
| A-3974 | H | H | H | H | H | O | CH₂CN | H | 2-CN,5-OMe | 0 |
| A-3975 | H | H | H | H | H | O | CH₂CN | H | 2-CN,6-OMe | 0 |
| A-3976 | H | H | H | H | H | O | CH₂CN | H | 3-CN,6-Me | 0 |
| A-3977 | H | H | H | H | H | O | CH₂CN | H | 3-CN,6-OMe | 0 |
| A-3978 | H | H | H | H | H | O | CH₂CN | H | 4-CN,2-Me | 0 |
| A-3979 | H | H | H | H | H | O | CH₂CN | H | 4-CN,2-OMe | 0 |
| A-3980 | H | H | H | H | H | O | CH₂CN | H | 2-NO₂,4-F | 0 |
| A-3981 | H | H | H | H | H | O | CH₂CN | H | 2-NO₂,5-F | 0 |
| A-3982 | H | H | H | H | H | O | CH₂CN | H | 2-NO₂,6-F | 0 |
| A-3983 | H | H | H | H | H | O | CH₂CN | H | 2-NO₂,4-Me | 0 |
| A-3984 | H | H | H | H | H | O | CH₂CN | H | 2-NO₂,5-Me | 0 |
| A-3985 | H | H | H | H | H | O | CH₂CN | H | 2-NO₂,6-Me | 0 |

TABLE 71

| compound | R¹ | R² | R³ | R⁴ | R⁵ | A | R⁶ | R⁷ | $(R^8)_m$ | p |
|---|---|---|---|---|---|---|---|---|---|---|
| A-3986 | H | H | H | H | H | O | CH₂CN | H | 2-Me,4,5-F₂ | 0 |
| A-3987 | H | H | H | H | H | O | CH₂CN | H | 2-Me,6-Et | 0 |
| A-3988 | H | H | H | H | H | O | CH₂CN | H | 2-cyclopropyl,6-OMe | 0 |
| A-3989 | H | H | H | H | H | O | CH₂CN | H | 2-Me,5-Et | 0 |
| A-3990 | H | H | H | H | H | O | CH₂CN | H | 2,6-Et₂ | 0 |
| A-3991 | H | H | H | H | H | O | CH₂CN | H | 2-Et,6F | 0 |
| A-3992 | H | H | H | H | H | O | CH₂CN | H | 2-CH₂OCH₃,6-Cl | 0 |
| A-3993 | H | H | H | H | H | O | CH₂CN | H | 2-CH₂OCH₂CH₃,6-Cl | 0 |
| A-3994 | H | H | H | H | H | O | CH₂CN | H | 2-CH₂NMe₂ | 0 |
| A-3995 | H | H | H | H | H | O | 1-CN-cyclopropyl | H | H | 0 |
| A-3996 | H | H | H | H | H | O | 1-CN-cyclopropyl | H | 2-F | 0 |
| A-3997 | H | H | H | H | H | O | 1-CN-cyclopropyl | H | 2-Cl | 0 |
| A-3998 | H | H | H | H | H | O | 1-CN-cyclopropyl | H | 2-Br | 0 |

TABLE 71-continued

| compound | R¹ | R² | R³ | R⁴ | R⁵ | A | R⁶ | R⁷ | (R⁸)ₘ | p |
|---|---|---|---|---|---|---|---|---|---|---|
| A-3999 | H | H | H | H | H | O | 1-CN-cyclopropyl | H | 2-OH | 0 |
| A-4000 | H | H | H | H | H | O | 1-CN-cyclopropyl | H | 2-Me | 0 |
| A-4001 | H | H | H | H | H | O | 1-CN-cyclopropyl | H | 2-Et | 0 |
| A-4002 | H | H | H | H | H | O | 1-CN-cyclopropyl | H | 2-Pr | 0 |
| A-4003 | H | H | H | H | H | O | 1-CN-cyclopropyl | H | 2-CF₃ | 0 |
| A-4004 | H | H | H | H | H | O | 1-CN-cyclopropyl | H | 2-CHF₂ | 0 |
| A-4005 | H | H | H | H | H | O | 1-CN-cyclopropyl | H | 2-CH₂F | 0 |
| A-4006 | H | H | H | H | H | O | 1-CN-cyclopropyl | H | 2-CF₂Cl | 0 |
| A-4007 | H | H | H | H | H | O | 1-CN-cyclopropyl | H | 2-cyclopropyl | 0 |
| A-4008 | H | H | H | H | H | O | 1-CN-cyclopropyl | H | 2-cyclobutyl | 0 |
| A-4009 | H | H | H | H | H | O | 1-CN-cyclopropyl | H | 2-cyclopentyl | 0 |
| A-4010 | H | H | H | H | H | O | 1-CN-cyclopropyl | H | 2-ethenyl | 0 |
| A-4011 | H | H | H | H | H | O | 1-CN-cyclopropyl | H | 2-allyl | 0 |
| A-4012 | H | H | H | H | H | O | 1-CN-cyclopropyl | H | 2-(prop-1-en-1-yl) | 0 |
| A-4013 | H | H | H | H | H | O | 1-CN-cyclopropyl | H | 2-(trifluoroethenyl) | 0 |
| A-4014 | H | H | H | H | H | O | 1-CN-cyclopropyl | H | 2-OMe | 0 |
| A-4015 | H | H | H | H | H | O | 1-CN-cyclopropyl | H | 2-OEt | 0 |
| A-4016 | H | H | H | H | H | O | 1-CN-cyclopropyl | H | 2-OPr | 0 |
| A-4017 | H | H | H | H | H | O | 1-CN-cyclopropyl | H | 2-O(i-Pr) | 0 |
| A-4018 | H | H | H | H | H | O | 1-CN-cyclopropyl | H | 2-OCF₃ | 0 |
| A-4019 | H | H | H | H | H | O | 1-CN-cyclopropyl | H | 2-OCHF₂ | 0 |
| A-4020 | H | H | H | H | H | O | 1-CN-cyclopropyl | H | 2-(cyclopropyloxy) | 0 |
| A-4021 | H | H | H | H | H | O | 1-CN-cyclopropyl | H | 2-(cyclobutyloxy) | 0 |
| A-4022 | H | H | H | H | H | O | 1-CN-cyclopropyl | H | 2-(cyclopentyloxy) | 0 |
| A-4023 | H | H | H | H | H | O | 1-CN-cyclopropyl | H | 2-((2,2-dichbrocyclopropyl)oxy) | 0 |
| A-4024 | H | H | H | H | H | O | 1-CN-cyclopropyl | H | 2-(oxiran-2-yl) | 0 |
| A-4025 | H | H | H | H | H | O | 1-CN-cyclopropyl | H | 2-SMe | 0 |
| A-4026 | H | H | H | H | H | O | 1-CN-cyclopropyl | H | 3-SMe | 0 |
| A-4027 | H | H | H | H | H | O | 1-CN-cyclopropyl | H | 2-S(=O)Me | 0 |
| A-4028 | H | H | H | H | H | O | 1-CN-cyclopropyl | H | 3-S(=O)Me | 0 |
| A-4029 | H | H | H | H | H | O | 1-CN-cyclopropyl | H | 2-S(=O)₂Me | 0 |
| A-4030 | H | H | H | H | H | O | 1-CN-cyclopropyl | H | 3-S(=O)₂Me | 0 |
| A-4031 | H | H | H | H | H | O | 1-CN-cyclopropyl | H | 2-SCF₃ | 0 |
| A-4032 | H | H | H | H | H | O | 1-CN-cyclopropyl | H | 3-SCF₃ | 0 |
| A-4033 | H | H | H | H | H | O | 1-CN-cyclopropyl | H | 3-S(=O)CF₃ | 0 |
| A-4034 | H | H | H | H | H | O | 1-CN-cyclopropyl | H | 3-SCF(CF₃)₂ | 0 |
| A-4035 | H | H | H | H | H | O | 1-CN-cyclopropyl | H | 2-(cyclopropylthio) | 0 |
| A-4036 | H | H | H | H | H | O | 1-CN-cyclopropyl | H | 2-(cyclopropylsulfinyl) | 0 |
| A-4037 | H | H | H | H | H | O | 1-CN-cyclopropyl | H | 2-(cyclopropylsulfonyl) | 0 |
| A-4038 | H | H | H | H | H | O | 1-CN-cyclopropyl | H | 2-C(=O)Me | 0 |
| A-4039 | H | H | H | H | H | O | 1-CN-cyclopropyl | H | 2-CH₂C(=O)CH₃ | 0 |
| A-4040 | H | H | H | H | H | O | 1-CN-cyclopropyl | H | 2-CH₂C(=O)CF₃ | 0 |
| A-4041 | H | H | H | H | H | O | 1-CN-cyclopropyl | H | 2-CH₂OH | 0 |
| A-4042 | H | H | H | H | H | O | 1-CN-cyclopropyl | H | 2-CH₂OCH₃ | 0 |

TABLE 72

| compound | R¹ | R² | R³ | R⁴ | R⁵ | A | R⁶ | R⁷ | (R⁸)ₘ | p |
|---|---|---|---|---|---|---|---|---|---|---|
| A-4043 | H | H | H | H | H | O | 1-CN-cyclopropyl | H | 2-CH₂OCH₂CH₃ | 0 |
| A-4044 | H | H | H | H | H | O | 1-CN-cyclopropyl | H | 2-CH₂SCH | 0 |
| A-4045 | H | H | H | H | H | O | 1-CN-cyclopropyl | H | 2-CH₂S(=O)CH₃ | 0 |
| A-4046 | H | H | H | H | H | O | 1-CN-cyclopropyl | H | 2-CH₂S(=O)₂CH₃ | 0 |
| A-4047 | H | H | H | H | H | O | 1-CN-cyclopropyl | H | 2-(benzylboxy) | 0 |
| A-4048 | H | H | H | H | H | O | 1-CN-cyclopropyl | H | 2-NH₂ | 0 |
| A-4049 | H | H | H | H | H | O | 1-CN-cyclopropyl | H | 2-NHMe | 0 |
| A-4050 | H | H | H | H | H | O | 1-CN-cyclopropyl | H | 2-N(Me)₂ | 0 |
| A-4051 | H | H | H | H | H | O | 1-CN-cyclopropyl | H | 2-(1,3-dioxolan-2-yl) | 0 |
| A-4052 | H | H | H | H | H | O | 1-CN-cyclopropyl | H | 2-(1,3-dioxan-2-yl) | 0 |
| A-4053 | H | H | H | H | H | O | 1-CN-cyclopropyl | H | 2-(1H-imidazo-2-yl) | 0 |
| A-4054 | H | H | H | H | H | O | 1-CN-cyclopropyl | H | 2-(thiazol-2-yl) | 0 |
| A-4055 | H | H | H | H | H | O | 1-CN-cyclopropyl | H | 2-(oxazol-2-yl) | 0 |
| A-4056 | H | H | H | H | H | O | 1-CN-cyclopropyl | H | 2-CH=NOH | 0 |
| A-4057 | H | H | H | H | H | O | 1-CN-cyclopropyl | H | 2-CH=NOMe | 0 |
| A-4058 | H | H | H | H | H | O | 1-CN-cyclopropyl | H | 2-(4,5-dihydro-3-isoxazolyl) | 0 |
| A-4059 | H | H | H | H | H | O | 1-CN-cyclopropyl | H | 2-CN | 0 |
| A-4060 | H | H | H | H | H | O | 1-CN-cyclopropyl | H | 2-NO₂ | 0 |
| A-4061 | H | H | H | H | H | O | 1-CN-cyclopropyl | H | 2-F,6-Cl | 0 |
| A-4062 | H | H | H | H | H | O | 1-CN-cyclopropyl | H | 2-F,6-Me | 0 |
| A-4063 | H | H | H | H | H | O | 1-CN-cyclopropyl | H | 3-F,6-Me | 0 |
| A-4064 | H | H | H | H | H | O | 1-CN-cyclopropyl | H | 4-F,2-Me | 0 |
| A-4065 | H | H | H | H | H | O | 1-CN-cyclopropyl | H | 2-F,6-OMe | 0 |
| A-4066 | H | H | H | H | H | O | 1-CN-cyclopropyl | H | 3-F,6-OMe | 0 |
| A-4067 | H | H | H | H | H | O | 1-CN-cyclopropyl | H | 2,6-Cl₂ | 0 |
| A-4068 | H | H | H | H | H | O | 1-CN-cyclopropyl | H | 2-Cl,6-Me | 0 |

TABLE 72-continued

| compound | R¹ | R² | R³ | R⁴ | R⁵ | A | R⁶ | R⁷ | (R⁸)$_m$ | p |
|---|---|---|---|---|---|---|---|---|---|---|
| A-4069 | H | H | H | H | H | O | 1-CN-cyclopropyl | H | 3-Cl,6-Me | 0 |
| A-4070 | H | H | H | H | H | O | 1-CN-cyclopropyl | H | 4-Cl,2-Me | 0 |
| A-4071 | H | H | H | H | H | O | 1-CN-cyclopropyl | H | 2-Cl,5-CF₃ | 0 |
| A-4072 | H | H | H | H | H | O | 1-CN-cyclopropyl | H | 2-Cl,6-CF₃ | 0 |
| A-4073 | H | H | H | H | H | O | 1-CN-cyclopropyl | H | 2-Cl,6-OMe | 0 |
| A-4074 | H | H | H | H | H | O | 1-CN-cyclopropyl | H | 3-Cl,6-OMe | 0 |
| A-4075 | H | H | H | H | H | O | 1-CN-cyclopropyl | H | 4-Cl,2-OMe | 0 |
| A-4076 | H | H | H | H | H | O | 1-CN-cyclopropyl | H | 2,4-Me₂ | 0 |
| A-4077 | H | H | H | H | H | O | 1-CN-cyclopropyl | H | 2,5-Me₂ | 0 |
| A-4078 | H | H | H | H | H | O | 1-CN-cyclopropyl | H | 2,6-Me₂ | 0 |
| A-4079 | H | H | H | H | H | O | 1-CN-cyclopropyl | H | 2-Me,4-CF₃ | 0 |
| A-4080 | H | H | H | H | H | O | 1-CN-cyclopropyl | H | 2-Me,5-CF₃ | 0 |
| A-4081 | H | H | H | H | H | O | 1-CN-cyclopropyl | H | 2-Me,6-CF₃ | 0 |
| A-4082 | H | H | H | H | H | O | 1-CN-cyclopropyl | H | 2-Me,4-OMe | 0 |
| A-4083 | H | H | H | H | H | O | 1-CN-cyclopropyl | H | 2-Me,5-OMe | 0 |
| A-4084 | H | H | H | H | H | O | 1-CN-cyclopropyl | H | 2-Me,6-OMe | 0 |
| A-4085 | H | H | H | H | H | O | 1-CN-cyclopropyl | H | 3-Me,6-OMe | 0 |
| A-4086 | H | H | H | H | H | O | 1-CN-cyclopropyl | H | 4-Me,2-OMe | 0 |
| A-4087 | H | H | H | H | H | O | 1-CN-cyclopropyl | H | 2,5-OMe₂ | 0 |
| A-4088 | H | H | H | H | H | O | 1-CN-cyclopropyl | H | 2,6-OMe₂ | 0 |
| A-4089 | H | H | H | H | H | O | 1-CN-cyclopropyl | H | 2-OMe,6-CF₃ | 0 |
| A-4090 | H | H | H | H | H | O | 1-CN-cyclopropyl | H | 2-CHF₂,5-F | 0 |
| A-4091 | H | H | H | H | H | O | 1-CN-cyclopropyl | H | 2-CHF₂,6-F | 0 |
| A-4092 | H | H | H | H | H | O | 1-CN-cyclopropyl | H | 2-CHF₂,5-Me | 0 |
| A-4093 | H | H | H | H | H | O | 1-CN-cyclopropyl | H | 2-CHF₂,6-Me | 0 |
| A-4094 | H | H | H | H | H | O | 1-CN-cyclopropyl | H | 2-cyclopropyl,5-F | 0 |
| A-4095 | H | H | H | H | H | O | 1-CN-cyclopropyl | H | 2-cyclopropyl,6-F | 0 |
| A-4096 | H | H | H | H | H | O | 1-CN-cyclopropyl | H | 2-cyclopropyl,5-Me | 0 |
| A-4097 | H | H | H | H | H | O | 1-CN-cyclopropyl | H | 2-cyclopropyl,6-Me | 0 |
| A-4098 | H | H | H | H | H | O | 1-CN-cyclopropyl | H | 2-ethenyl,6-F | 0 |
| A-4099 | H | H | H | H | H | O | 1-CN-cyclopropyl | H | 2-ethenyl,6-Me | 0 |

TABLE 73

| compound | R¹ | R² | R³ | R⁴ | R⁵ | A | R⁶ | R⁷ | (R⁸)$_m$ | p |
|---|---|---|---|---|---|---|---|---|---|---|
| A-4100 | H | H | H | H | H | O | 1-CN-cyclopropyl | H | 2-OEt,5-F | 0 |
| A-4101 | H | H | H | H | H | O | 1-CN-cyclopropyl | H | 2-OEt,6-F | 0 |
| A-4102 | H | H | H | H | H | O | 1-CN-cyclopropyl | H | 2-OEt,5-Cl | 0 |
| A-4103 | H | H | H | H | H | O | 1-CN-cyclopropyl | H | 2-OEt,6-Cl | 0 |
| A-4104 | H | H | H | H | H | O | 1-CN-cyclopropyl | H | 2-OEt,5-Me | 0 |
| A-4105 | H | H | H | H | H | O | 1-CN-cyclopropyl | H | 2-OEt,6-Me | 0 |
| A-4106 | H | H | H | H | H | O | 1-CN-cyclopropyl | H | 2-OCHF₂,5-F | 0 |
| A-4107 | H | H | H | H | H | O | 1-CN-cyclopropyl | H | 2-OCHF₂,6-F | 0 |
| A-4108 | H | H | H | H | H | O | 1-CN-cyclopropyl | H | 2-OCHF₂,5-Me | 0 |
| A-4109 | H | H | H | H | H | O | 1-CN-cyclopropyl | H | 2-OCHF₂,6-Me | 0 |
| A-4110 | H | H | H | H | H | O | 1-CN-cyclopropyl | H | 2-(cyclopropyloxy),5-F | 0 |
| A-4111 | H | H | H | H | H | O | 1-CN-cyclopropyl | H | 2-(cyclopropyloxy),6-F | 0 |
| A-4112 | H | H | H | H | H | O | 1-CN-cyclopropyl | H | 2-(cyclopropyloxy),5-Me | 0 |
| A-4113 | H | H | H | H | H | O | 1-CN-cyclopropyl | H | 2-(cyclopropyloxy),6-Me | 0 |
| A-4114 | H | H | H | H | H | O | 1-CN-cyclopropyl | H | 2-SMe,5-F | 0 |
| A-4115 | H | H | H | H | H | O | 1-CN-cyclopropyl | H | 2-SMe,6-F | 0 |
| A-4116 | H | H | H | H | H | O | 1-CN-cyclopropyl | H | 2-SMe,5-Me | 0 |
| A-4117 | H | H | H | H | H | O | 1-CN-cyclopropyl | H | 2-SMe,6-Me | 0 |
| A-4118 | H | H | H | H | H | O | 1-CN-cyclopropyl | H | 2-S(=O)Me,5-F | 0 |
| A-4119 | H | H | H | H | H | O | 1-CN-cyclopropyl | H | 2-S(=O)Me,6-F | 0 |
| A-4120 | H | H | H | H | H | O | 1-CN-cyclopropyl | H | 2-S(=O)Me,5-Me | 0 |
| A-4121 | H | H | H | H | H | O | 1-CN-cyclopropyl | H | 2-S(=O)Me,6-Me | 0 |
| A-4122 | H | H | H | H | H | O | 1-CN-cyclopropyl | H | 2-S(=O)₂Me,5-F | 0 |
| A-4123 | H | H | H | H | H | O | 1-CN-cyclopropyl | H | 2-S(=O)₂Me,6-F | 0 |
| A-4124 | H | H | H | H | H | O | 1-CN-cyclopropyl | H | 2-S(=O)₂Me,5-Me | 0 |
| A-4125 | H | H | H | H | H | O | 1-CN-cyclopropyl | H | 2-S(=O)₂Me,6-Me | 0 |
| A-4126 | H | H | H | H | H | O | 1-CN-cyclopropyl | H | 2-SCF₃,5-F | 0 |
| A-4127 | H | H | H | H | H | O | 1-CN-cyclopropyl | H | 2-SCF₃,6-F | 0 |
| A-4128 | H | H | H | H | H | O | 1-CN-cyclopropyl | H | 2-SCF₃,5-Me | 0 |
| A-4129 | H | H | H | H | H | O | 1-CN-cyclopropyl | H | 2-SCF₃,6-Me | 0 |
| A-4130 | H | H | H | H | H | O | 1-CN-cyclopropyl | H | 2-S(=O)CF₃,5-F | 0 |
| A-4131 | H | H | H | H | H | O | 1-CN-cyclopropyl | H | 2-S(=O)CF₃,6-F | 0 |
| A-4132 | H | H | H | H | H | O | 1-CN-cyclopropyl | H | 2-S(=O)CF₃,5-Me | 0 |
| A-4133 | H | H | H | H | H | O | 1-CN-cyclopropyl | H | 2-S(=O)CF₃,6-Me | 0 |
| A-4134 | H | H | H | H | H | O | 1-CN-cyclopropyl | H | 2-S(=O)₂CF₃,5-F | 0 |
| A-4135 | H | H | H | H | H | O | 1-CN-cyclopropyl | H | 2-S(=O)₂CF₃,6-F | 0 |
| A-4136 | H | H | H | H | H | O | 1-CN-cyclopropyl | H | 2-S(=O)₂CF₃,5-Me | 0 |
| A-4137 | H | H | H | H | H | O | 1-CN-cyclopropyl | H | 2-S(=O)₂CF₃,6-Me | 0 |
| A-4138 | H | H | H | H | H | O | 1-CN-cyclopropyl | H | 2-(cyclopropylthio),5-F | 0 |

TABLE 73-continued

| compound | R¹ | R² | R³ | R⁴ | R⁵ | A | R⁶ | R⁷ | (R⁸)ₘ | p |
|---|---|---|---|---|---|---|---|---|---|---|
| A-4139 | H | H | H | H | H | O | 1-CN-cyclopropyl | H | 2-(cyclopropylthio),6-F | 0 |
| A-4140 | H | H | H | H | H | O | 1-CN-cyclopropyl | H | 2-(cyclopropylthio),5-Me | 0 |
| A-4141 | H | H | H | H | H | O | 1-CN-cyclopropyl | H | 2-(cyclopropylthio),6-Me | 0 |
| A-4142 | H | H | H | H | H | O | 1-CN-cyclopropyl | H | 2-C(=O)Me,5-F | 0 |
| A-4143 | H | H | H | H | H | O | 1-CN-cyclopropyl | H | 2-C(=O)Me,6-F | 0 |
| A-4144 | H | H | H | H | H | O | 1-CN-cyclopropyl | H | 2-C(=O)Me,5-Me | 0 |
| A-4145 | H | H | H | H | H | O | 1-CN-cyclopropyl | H | 2-C(=O)Me,6-Me | 0 |
| A-4146 | H | H | H | H | H | O | 1-CN-cyclopropyl | H | 2-CH₂OH,5-F | 0 |
| A-4147 | H | H | H | H | H | O | 1-CN-cyclopropyl | H | 2-CH₂OH,6-F | 0 |
| A-4148 | H | H | H | H | H | O | 1-CN-cyclopropyl | H | 2-CH₂OH,5-Me | 0 |
| A-4149 | H | H | H | H | H | O | 1-CN-cyclopropyl | H | 2-CH₂OH,6-Me | 0 |
| A-4150 | H | H | H | H | H | O | 1-CN-cyclopropyl | H | 2-CH₂OCH₃,4-F | 0 |
| A-4151 | H | H | H | H | H | O | 1-CN-cyclopropyl | H | 2-CH₂OCH₃,5-F | 0 |
| A-4152 | H | H | H | H | H | O | 1-CN-cyclopropyl | H | 2-CH₂OCH₃,6-F | 0 |
| A-4153 | H | H | H | H | H | O | 1-CN-cyclopropyl | H | 2-CH₂OCH₃,4-Me | 0 |
| A-4154 | H | H | H | H | H | O | 1-CN-cyclopropyl | H | 2-CH₂OCH₃,5-Me | 0 |
| A-4155 | H | H | H | H | H | O | 1-CN-cyclopropyl | H | 2-CH₂OCH₃,6-Me | 0 |
| A-4156 | H | H | H | H | H | O | 1-CN-cyclopropyl | H | 2-OC(=O)CH₃,5-F | 0 |

TABLE 74

| compound | R¹ | R² | R³ | R⁴ | R⁵ | A | R⁶ | R⁷ | (R⁸)ₘ | p |
|---|---|---|---|---|---|---|---|---|---|---|
| A-4157 | H | H | H | H | H | O | 1-CN-cyclopropyl | H | 2-OC(=O)CH₃,6-F | 0 |
| A-4158 | H | H | H | H | H | O | 1-CN-cyclopropyl | H | 2-OC(=O)CH₃,5-Me | 0 |
| A-4159 | H | H | H | H | H | O | 1-CN-cyclopropyl | H | 2-OC(=O)CH₃,6-Me | 0 |
| A-4160 | H | H | H | H | H | O | 1-CN-cyclopropyl | H | 2-OS(=O)₂CH₃,5-F | 0 |
| A-4161 | H | H | H | H | H | O | 1-CN-cyclopropyl | H | 2-OS(=O)₂CH₃,6-F | 0 |
| A-4162 | H | H | H | H | H | O | 1-CN-cyclopropyl | H | 2-OS(=O)₂CH₃,5-Me | 0 |
| A-4163 | H | H | H | H | H | O | 1-CN-cyclopropyl | H | 2-OS(=O)₂CH₃,6-Me | 0 |
| A-4164 | H | H | H | H | H | O | 1-CN-cyclopropyl | H | 2-CH₂SCH₃,5-F | 0 |
| A-4165 | H | H | H | H | H | O | 1-CN-cyclopropyl | H | 2-CH₂SCH₃,6-F | 0 |
| A-4166 | H | H | H | H | H | O | 1-CN-cyclopropyl | H | 2-CH₂SCH₃,5-Me | 0 |
| A-4167 | H | H | H | H | H | O | 1-CN-cyclopropyl | H | 2-CH₂SCH₃,6-Me | 0 |
| A-4168 | H | H | H | H | H | O | 1-CN-cyclopropyl | H | 2-NMe₂,5-F | 0 |
| A-4169 | H | H | H | H | H | O | 1-CN-cyclopropyl | H | 2-NMe₂,6-F | 0 |
| A-4170 | H | H | H | H | H | O | 1-CN-cyclopropyl | H | 2-NMe₂,5-Me | 0 |
| A-4171 | H | H | H | H | H | O | 1-CN-cyclopropyl | H | 2-NMe₂,6-Me | 0 |
| A-4172 | H | H | H | H | H | O | 1-CN-cyclopropyl | H | 2-CN,4-F | 0 |
| A-4173 | H | H | H | H | H | O | 1-CN-cyclopropyl | H | 2-CN,5-F | 0 |
| A-4174 | H | H | H | H | H | O | 1-CN-cyclopropyl | H | 2-CN,6-F | 0 |
| A-4175 | H | H | H | H | H | O | 1-CN-cyclopropyl | H | 2-CN,6-Me | 0 |
| A-4176 | H | H | H | H | H | O | 1-CN-cyclopropyl | H | 2-CN,5-OMe | 0 |
| A-4177 | H | H | H | H | H | O | 1-CN-cyclopropyl | H | 2-CN,6-OMe | 0 |
| A-4178 | H | H | H | H | H | O | 1-CN-cyclopropyl | H | 3-CN,6-Me | 0 |
| A-4179 | H | H | H | H | H | O | 1-CN-cyclopropyl | H | 3-CN,6-OMe | 0 |
| A-4180 | H | H | H | H | H | O | 1-CN-cyclopropyl | H | 4-CN,2-Me | 0 |
| A-4181 | H | H | H | H | H | O | 1-CN-cyclopropyl | H | 4-CN,2-OMe | 0 |
| A-4182 | H | H | H | H | H | O | 1-CN-cyclopropyl | H | 2-NO₂,4-F | 0 |
| A-4183 | H | H | H | H | H | O | 1-CN-cyclopropyl | H | 2-NO₂,5-F | 0 |
| A-4184 | H | H | H | H | H | O | 1-CN-cyclopropyl | H | 2-NO₂,6-F | 0 |
| A-4185 | H | H | H | H | H | O | 1-CN-cyclopropyl | H | 2-NO₂,4-Me | 0 |
| A-4186 | H | H | H | H | H | O | 1-CN-cyclopropyl | H | 2-NO₂,5-Me | 0 |
| A-4187 | H | H | H | H | H | O | 1-CN-cyclopropyl | H | 2-NO₂,6-Me | 0 |
| A-4188 | H | H | H | H | H | O | 1-CN-cyclopropyl | H | 2-Me,4,5-F₂ | 0 |
| A-4189 | H | H | H | H | H | O | 1-CN-cyclopropyl | H | 2-Me,6-Et | 0 |
| A-4190 | H | H | H | H | H | O | 1-CN-cyclopropyl | H | 2-cyclopropyl,6-OMe | 0 |
| A-4191 | H | H | H | H | H | O | 1-CN-cyclopropyl | H | 2-Me,5-Et | 0 |
| A-4192 | H | H | H | H | H | O | 1-CN-cyclopropyl | H | 2,6-Et₂ | 0 |
| A-4193 | H | H | H | H | H | O | 1-CN-cyclopropyl | H | 2-Et,6-F | 0 |
| A-4194 | H | H | H | H | H | O | 1-CN-cyclopropyl | H | 2-CH₂OCH₃,6-Cl | 0 |
| A-4195 | H | H | H | H | H | O | 1-CN-cyclopropyl | H | 2-CH₂OCH₂CH₃,6-Cl | 0 |
| A-4196 | H | H | H | H | H | O | 1-CN-cyclopropyl | H | 2-CH₂NMe₂ | 0 |
| A-4197 | H | H | H | H | H | O | CH₂OH | H | H | 0 |
| A-4198 | H | H | H | H | H | O | CH₂OH | H | 2-F | 0 |
| A-4199 | H | H | H | H | H | O | CH₂OH | H | 2-Cl | 0 |
| A-4200 | H | H | H | H | H | O | CH₂OH | H | 2-Br | 0 |
| A-4201 | H | H | H | H | H | O | CH₂OH | H | 2-OH | 0 |
| A-4202 | H | H | H | H | H | O | CH₂OH | H | 2-Me | 0 |
| A-4203 | H | H | H | H | H | O | CH₂OH | H | 2-Et | 0 |
| A-4204 | H | H | H | H | H | O | CH₂OH | H | 2-Pr | 0 |
| A-4205 | H | H | H | H | H | O | CH₂OH | H | 2-CF₃ | 0 |
| A-4206 | H | H | H | H | H | O | CH₂OH | H | 2-CHF₂ | 0 |
| A-4207 | H | H | H | H | H | O | CH₂OH | H | 2-CH₂F | 0 |
| A-4208 | H | H | H | H | H | O | CH₂OH | H | 2-CF₂Cl | 0 |

TABLE 74-continued

| compound | R¹ | R² | R³ | R⁴ | R⁵ | A | R⁶ | R⁷ | (R⁸)ₘ | p |
|---|---|---|---|---|---|---|---|---|---|---|
| A-4209 | H | H | H | H | H | O | CH₂OH | H | 2-cyclopropyl | 0 |
| A-4210 | H | H | H | H | H | O | CH₂OH | H | 2-cyclobutyl | 0 |
| A-4211 | H | H | H | H | H | O | CH₂OH | H | 2-cyclopentyl | 0 |
| A-4212 | H | H | H | H | H | O | CH₂OH | H | 2-ethenyl | 0 |
| A-4213 | H | H | H | H | H | O | CH₂OH | H | 2-allyl | 0 |

TABLE 75

| compound | R¹ | R² | R³ | R⁴ | R⁵ | A | R⁶ | R⁷ | (R⁸)ₘ | p |
|---|---|---|---|---|---|---|---|---|---|---|
| A-4214 | H | H | H | H | H | O | CH₂OH | H | 2-(prop-1-en-1-yl) | 0 |
| A-4215 | H | H | H | H | H | O | CH₂OH | H | 2-(trifluoroephenyl) | 0 |
| A-4216 | H | H | H | H | H | O | CH₂OH | H | 2-OMe | 0 |
| A-4217 | H | H | H | H | H | O | CH₂OH | H | 2-OEt | 0 |
| A-4218 | H | H | H | H | H | O | CH₂OH | H | 2-OPr | 0 |
| A-4219 | H | H | H | H | H | O | CH₂OH | H | 2-O(i-Pr) | 0 |
| A-4220 | H | H | H | H | H | O | CH₂OH | H | 2-OCF₃ | 0 |
| A-4221 | H | H | H | H | H | O | CH₂OH | H | 2-OCHF₂ | 0 |
| A-4222 | H | H | H | H | H | O | CH₂OH | H | 2-(cyclopropyloxy) | 0 |
| A-4223 | H | H | H | H | H | O | CH₂OH | H | 2-(cyclobutyloxy) | 0 |
| A-4224 | H | H | H | H | H | O | CH₂OH | H | 2-(cyclopentyloxy) | 0 |
| A-4225 | H | H | H | H | H | O | CH₂OH | H | 2-((2,2-dichlorocyclopropyl)oxy) | 0 |
| A-4226 | H | H | H | H | H | O | CH₂OH | H | 2-(oxiran-2-yl) | 0 |
| A-4227 | H | H | H | H | H | O | CH₂OH | H | 2-SMe | 0 |
| A-4228 | H | H | H | H | H | O | CH₂OH | H | 3-SMe | 0 |
| A-4229 | H | H | H | H | H | O | CH₂OH | H | 2-S(=O)Me | 0 |
| A-4230 | H | H | H | H | H | O | CH₂OH | H | 3-S(=O)Me | 0 |
| A-4231 | H | H | H | H | H | O | CH₂OH | H | 2-S(=O)₂Me | 0 |
| A-4232 | H | H | H | H | H | O | CH₂OH | H | 3-S(=O)₂Me | 0 |
| A-4233 | H | H | H | H | H | O | CH₂OH | H | 2-SCF₃ | 0 |
| A-4234 | H | H | H | H | H | O | CH₂OH | H | 3-SCF₃ | 0 |
| A-4235 | H | H | H | H | H | O | CH₂OH | H | 3-S(=O)CF₃ | 0 |
| A-4236 | H | H | H | H | H | O | CH₂OH | H | 3-SCF(CF₃)₂ | 0 |
| A-4237 | H | H | H | H | H | O | CH₂OH | H | 2-(cyclopropylthio) | 0 |
| A-4238 | H | H | H | H | H | O | CH₂OH | H | 2-(cyclopropylsulfinyl) | 0 |
| A-4239 | H | H | H | H | H | O | CH₂OH | H | 2-(cyclopropylsulfonyl) | 0 |
| A-4240 | H | H | H | H | H | O | CH₂OH | H | 2-C(=O)Me | 0 |
| A-4241 | H | H | H | H | H | O | CH₂OH | H | 2-CH₂C(=O)CH₃ | 0 |
| A-4242 | H | H | H | H | H | O | CH₂OH | H | 2-CH₂C(=O)CF₃ | 0 |
| A-4243 | H | H | H | H | H | O | CH₂OH | H | 2-CH₂OH | 0 |
| A-4244 | H | H | H | H | H | O | CH₂OH | H | 2-CH₂OCH₃ | 0 |
| A-4245 | H | H | H | H | H | O | CH₂OH | H | 2-CH₂OCH₂CH₃ | 0 |
| A-4246 | H | H | H | H | H | O | CH₂OH | H | 2-CH₂SCH₃ | 0 |
| A-4247 | H | H | H | H | H | O | CH₂OH | H | 2-CH₂S(=O)CH₃ | 0 |
| A-4248 | H | H | H | H | H | O | CH₂OH | H | 2-CH₂S(=O)₂CH₃ | 0 |
| A-4249 | H | H | H | H | H | O | CH₂OH | H | 2-(benzyloxy) | 0 |
| A-4250 | H | H | H | H | H | O | CH₂OH | H | 2-NH₂ | 0 |
| A-4251 | H | H | H | H | H | O | CH₂OH | H | 2-NHMe | 0 |
| A-4252 | H | H | H | H | H | O | CH₂OH | H | 2-N(Me)₂ | 0 |
| A-4253 | H | H | H | H | H | O | CH₂OH | H | 2-(1,3-dioxolan-2-yl) | 0 |
| A-4254 | H | H | H | H | H | O | CH₂OH | H | 2-(1,3-dioxan-2-yl) | 0 |
| A-4255 | H | H | H | H | H | O | CH₂OH | H | 2-(1H-imidazol-2-yl) | 0 |
| A-4256 | H | H | H | H | H | O | CH₂OH | H | 2-(thiazol-2-yl) | 0 |
| A-4257 | H | H | H | H | H | O | CH₂OH | H | 2-(oxazol-2-yl) | 0 |
| A-4258 | H | H | H | H | H | O | CH₂OH | H | 2-CH=NOH | 0 |
| A-4259 | H | H | H | H | H | O | CH₂OH | H | 2-CH=NOMe | 0 |
| A-4260 | H | H | H | H | H | O | CH₂OH | H | 2-(4,5-dihydro-3-isoxazolyl) | 0 |
| A-4261 | H | H | H | H | H | O | CH₂OH | H | 2-CN | 0 |
| A-4262 | H | H | H | H | H | O | CH₂OH | H | 2-NO₂ | 0 |
| A-4263 | H | H | H | H | H | O | CH₂OH | H | 2-F,6-Cl | 0 |
| A-4264 | H | H | H | H | H | O | CH₂OH | H | 2-F,6-Me | 0 |
| A-4265 | H | H | H | H | H | O | CH₂OH | H | 3-F,6-Me | 0 |
| A-4266 | H | H | H | H | H | O | CH₂OH | H | 4-F,2-Me | 0 |
| A-4267 | H | H | H | H | H | O | CH₂OH | H | 2-F,6-OMe | 0 |
| A-4268 | H | H | H | H | H | O | CH₂OH | H | 3-F,6-OMe | 0 |
| A-4269 | H | H | H | H | H | O | CH₂OH | H | 2,6-Cl₂ | 0 |
| A-4270 | H | H | H | H | H | O | CH₂OH | H | 2-Cl,6-Me | 0 |

TABLE 76

| compound | R¹ | R² | R³ | R⁴ | R⁵ | A | R⁶ | R⁷ | (R⁸)ₘ | p |
|---|---|---|---|---|---|---|---|---|---|---|
| A-4271 | H | H | H | H | H | O | CH₂OH | H | 3-Cl,6-Me | 0 |
| A-4272 | H | H | H | H | H | O | CH₂OH | H | 4-Cl,2-Me | 0 |
| A-4273 | H | H | H | H | H | O | CH₂OH | H | 2-Cl,5-CF₃ | 0 |
| A-4274 | H | H | H | H | H | O | CH₂OH | H | 2-Cl,6-CF₃ | 0 |
| A-4275 | H | H | H | H | H | O | CH₂OH | H | 2-Cl,6-OMe | 0 |
| A-4276 | H | H | H | H | H | O | CH₂OH | H | 3-Cl,6-OMe | 0 |
| A-4277 | H | H | H | H | H | O | CH₂OH | H | 4-Cl,2-OMe | 0 |
| A-4278 | H | H | H | H | H | O | CH₂OH | H | 2,4-Me₂ | 0 |
| A-4279 | H | H | H | H | H | O | CH₂OH | H | 2,5-Me₂ | 0 |
| A-4280 | H | H | H | H | H | O | CH₂OH | H | 2,6-Me₂ | 0 |
| A-4281 | H | H | H | H | H | O | CH₂OH | H | 2-Me,4-CF₃ | 0 |
| A-4282 | H | H | H | H | H | O | CH₂OH | H | 2-Me,5-CF₃ | 0 |
| A-4283 | H | H | H | H | H | O | CH₂OH | H | 2-Me,6-CF₃ | 0 |
| A-4284 | H | H | H | H | H | O | CH₂OH | H | 2-Me,4-OMe | 0 |
| A-4285 | H | H | H | H | H | O | CH₂OH | H | 2-Me,5-OMe | 0 |
| A-4286 | H | H | H | H | H | O | CH₂OH | H | 2-Me,6-OMe | 0 |
| A-4287 | H | H | H | H | H | O | CH₂OH | H | 3-Me,6-OMe | 0 |
| A-4288 | H | H | H | H | H | O | CH₂OH | H | 4-Me,2-OMe | 0 |
| A-4289 | H | H | H | H | H | O | CH₂OH | H | 2,5-OMe₂ | 0 |
| A-4290 | H | H | H | H | H | O | CH₂OH | H | 2,6-OMe₂ | 0 |
| A-4291 | H | H | H | H | H | O | CH₂OH | H | 2-OMe,6-CF₃ | 0 |
| A-4292 | H | H | H | H | H | O | CH₂OH | H | 2-CHF₂,5-F | 0 |
| A-4293 | H | H | H | H | H | O | CH₂OH | H | 2-CHF₂,6-F | 0 |
| A-4294 | H | H | H | H | H | O | CH₂OH | H | 2-CHF₂,5-Me | 0 |
| A-4295 | H | H | H | H | H | O | CH₂OH | H | 2-CHF₂,6-Me | 0 |
| A-4296 | H | H | H | H | H | O | CH₂OH | H | 2-cyclopropyl,5-F | 0 |
| A-4297 | H | H | H | H | H | O | CH₂OH | H | 2-cyclopropyl,6-F | 0 |
| A-4298 | H | H | H | H | H | O | CH₂OH | H | 2-cyclopropyl,5-Me | 0 |
| A-4299 | H | H | H | H | H | O | CH₂OH | H | 2-cyclopropyl,6-Me | 0 |
| A-4300 | H | H | H | H | H | O | CH₂OH | H | 2-ethenyl,6-F | 0 |
| A-4301 | H | H | H | H | H | O | CH₂OH | H | 2-ethenyl,6-Me | 0 |
| A-4302 | H | H | H | H | H | O | CH₂OH | H | 2-OEt,5-F | 0 |
| A-4303 | H | H | H | H | H | O | CH₂OH | H | 2-OEt,6-F | 0 |
| A-4304 | H | H | H | H | H | O | CH₂OH | H | 2-OEt,5-Cl | 0 |
| A-4305 | H | H | H | H | H | O | CH₂OH | H | 2-OEt,6-Cl | 0 |
| A-4306 | H | H | H | H | H | O | CH₂OH | H | 2-OEt,5-Me | 0 |
| A-4307 | H | H | H | H | H | O | CH₂OH | H | 2-OEt,6-Me | 0 |
| A-4308 | H | H | H | H | H | O | CH₂OH | H | 2-OCHF₂,5-F | 0 |
| A-4309 | H | H | H | H | H | O | CH₂OH | H | 2-OCHF₂,6-F | 0 |
| A-4310 | H | H | H | H | H | O | CH₂OH | H | 2-OCHF₂,5-Me | 0 |
| A-4311 | H | H | H | H | H | O | CH₂OH | H | 2-OCHF₂,6-Me | 0 |
| A-4312 | H | H | H | H | H | O | CH₂OH | H | 2-(cyclopropyloxy),5-F | 0 |
| A-4313 | H | H | H | H | H | O | CH₂OH | H | 2-(cyclopropyloxy),6-F | 0 |
| A-4314 | H | H | H | H | H | O | CH₂OH | H | 2-(cyclopropyloxy),5-Me | 0 |
| A-4315 | H | H | H | H | H | O | CH₂OH | H | 2-(cyclopropyloxy),6-Me | 0 |
| A-4316 | H | H | H | H | H | O | CH₂OH | H | 2-SMe,5-F | 0 |
| A-4317 | H | H | H | H | H | O | CH₂OH | H | 2-SMe,6-F | 0 |
| A-4318 | H | H | H | H | H | O | CH₂OH | H | 2-SMe,5-Me | 0 |
| A-4319 | H | H | H | H | H | O | CH₂OH | H | 2-SMe,6-Me | 0 |
| A-4320 | H | H | H | H | H | O | CH₂OH | H | 2-S(=O)Me,5-F | 0 |
| A-4321 | H | H | H | H | H | O | CH₂OH | H | 2-S(=O)Me,6-F | 0 |
| A-4322 | H | H | H | H | H | O | CH₂OH | H | 2-S(=O)Me,5-Me | 0 |
| A-4323 | H | H | H | H | H | O | CH₂OH | H | 2-S(=O)Me,6-Me | 0 |
| A-4324 | H | H | H | H | H | O | CH₂OH | H | 2-S(=O)₂Me,5-F | 0 |
| A-4325 | H | H | H | H | H | O | CH₂OH | H | 2-S(=O)₂Me,6-F | 0 |
| A-4326 | H | H | H | H | H | O | CH₂OH | H | 2-S(=O)₂Me,5-Me | 0 |
| A-4327 | H | H | H | H | H | O | CH₂OH | H | 2-S(=O)₂Me,6-Me | 0 |

TABLE 77

| compound | R¹ | R² | R³ | R⁴ | R⁵ | A | R⁶ | R⁷ | (R⁸)ₘ | p |
|---|---|---|---|---|---|---|---|---|---|---|
| A-4328 | H | H | H | H | H | O | CH₂OH | H | 2-SCF₃,5-F | 0 |
| A-4329 | H | H | H | H | H | O | CH₂OH | H | 2-SCF₃,6-F | 0 |
| A-4330 | H | H | H | H | H | O | CH₂OH | H | 2-SCF₃,5-Me | 0 |
| A-4331 | H | H | H | H | H | O | CH₂OH | H | 2-SCF₃,6-Me | 0 |
| A-4332 | H | H | H | H | H | O | CH₂OH | H | 2-S(=O)CF₃,5-F | 0 |
| A-4333 | H | H | H | H | H | O | CH₂OH | H | 2-S(=O)CF₃,6-F | 0 |
| A-4334 | H | H | H | H | H | O | CH₂OH | H | 2-S(=O)CF₃,5-Me | 0 |
| A-4335 | H | H | H | H | H | O | CH₂OH | H | 2-S(=O)CF₃,6-Me | 0 |
| A-4336 | H | H | H | H | H | O | CH₂OH | H | 2-S(=O)₂CF₃,5-F | 0 |
| A-4337 | H | H | H | H | H | O | CH₂OH | H | 2-S(=O)₂CF₃,6-F | 0 |
| A-4338 | H | H | H | H | H | O | CH₂OH | H | 2-S(=O)₂CF₃,5-Me | 0 |
| A-4339 | H | H | H | H | H | O | CH₂OH | H | 2-S(=O)₂CF₃,6-Me | 0 |
| A-4340 | H | H | H | H | H | O | CH₂OH | H | 2-(cyclopropylthio),5-F | 0 |

TABLE 77-continued

| compound | R¹ | R² | R³ | R⁴ | R⁵ | A | R⁶ | R⁷ | (R⁸)ₘ | p |
|---|---|---|---|---|---|---|---|---|---|---|
| A-4341 | H | H | H | H | H | O | CH₂OH | H | 2-(cyclopropylthio),6-F | 0 |
| A-4342 | H | H | H | H | H | O | CH₂OH | H | 2-(cyclopropylthio),5-Me | 0 |
| A-4343 | H | H | H | H | H | O | CH₂OH | H | 2-(cyclopropylthio),6-Me | 0 |
| A-4344 | H | H | H | H | H | O | CH₂OH | H | 2-C(=O)Me,5-F | 0 |
| A-4345 | H | H | H | H | H | O | CH₂OH | H | 2-C(=O)Me,6-F | 0 |
| A-4346 | H | H | H | H | H | O | CH₂OH | H | 2-C(=O)Me,5-Me | 0 |
| A-4347 | H | H | H | H | H | O | CH₂OH | H | 2-C(=O)Me,6-Me | 0 |
| A-4348 | H | H | H | H | H | O | CH₂OH | H | 2-CH₂OH,5-F | 0 |
| A-4349 | H | H | H | H | H | O | CH₂OH | H | 2-CH₂OH,6-F | 0 |
| A-4350 | H | H | H | H | H | O | CH₂OH | H | 2-CH₂OH,5-Me | 0 |
| A-4351 | H | H | H | H | H | O | CH₂OH | H | 2-CH₂OH,6-Me | 0 |
| A-4352 | H | H | H | H | H | O | CH₂OH | H | 2-CH₂OCH₃,4-F | 0 |
| A-4353 | H | H | H | H | H | O | CH₂OH | H | 2-CH₂OCH₃,5-F | 0 |
| A-4354 | H | H | H | H | H | O | CH₂OH | H | 2-CH₂OCH₃,6-F | 0 |
| A-4355 | H | H | H | H | H | O | CH₂OH | H | 2-CH₂OCH₃,4-Me | 0 |
| A-4356 | H | H | H | H | H | O | CH₂OH | H | 2-CH₂OCH₃,5-Me | 0 |
| A-4357 | H | H | H | H | H | O | CH₂OH | H | 2-CH₂OCH₃,6-Me | 0 |
| A-4358 | H | H | H | H | H | O | CH₂OH | H | 2-OC(=O)CH₃,5-F | 0 |
| A-4359 | H | H | H | H | H | O | CH₂OH | H | 2-OC(=O)CH₃,6-F | 0 |
| A-4360 | H | H | H | H | H | O | CH₂OH | H | 2-OC(=O)CH₃,5-Me | 0 |
| A-4361 | H | H | H | H | H | O | CH₂OH | H | 2-OC(=O)CH₃,6-Me | 0 |
| A-4362 | H | H | H | H | H | O | CH₂OH | H | 2-OS(=O)₂CH₃,5-F | 0 |
| A-4363 | H | H | H | H | H | O | CH₂OH | H | 2-OS(=O)₂CH₃,6-F | 0 |
| A-4364 | H | H | H | H | H | O | CH₂OH | H | 2-OS(=O)₂CH₃,5-Me | 0 |
| A-4365 | H | H | H | H | H | O | CH₂OH | H | 2-OS(=O)₂CH₃,6-Me | 0 |
| A-4366 | H | H | H | H | H | O | CH₂OH | H | 2-CH₂SCH₃,5-F | 0 |
| A-4367 | H | H | H | H | H | O | CH₂OH | H | 2-CH₂SCH₃,6-F | 0 |
| A-4368 | H | H | H | H | H | O | CH₂OH | H | 2-CH2SCH₃,5-Me | 0 |
| A-4369 | H | H | H | H | H | O | CH₂OH | H | 2-CH₂SCH₃,6-Me | 0 |
| A-4370 | H | H | H | H | H | O | CH₂OH | H | 2-NMe₂,5-F | 0 |
| A-4371 | H | H | H | H | H | O | CH₂OH | H | 2-NMe₂,6-F | 0 |
| A-4372 | H | H | H | H | H | O | CH₂OH | H | 2-NMe₂,5-Me | 0 |
| A-4373 | H | H | H | H | H | O | CH₂OH | H | 2-NMe₂,6-Me | 0 |
| A-4374 | H | H | H | H | H | O | CH₂OH | H | 2-CN,4-F | 0 |
| A-4375 | H | H | H | H | H | O | CH₂OH | H | 2-CN,5-F | 0 |
| A-4376 | H | H | H | H | H | O | CH₂OH | H | 2-CN,6-F | 0 |
| A-4377 | H | H | H | H | H | O | CH₂OH | H | 2-CN,6-Me | 0 |
| A-4378 | H | H | H | H | H | O | CH₂OH | H | 2-CN,5-OMe | 0 |
| A-4379 | H | H | H | H | H | O | CH₂OH | H | 2-CN,6-OMe | 0 |
| A-4380 | H | H | H | H | H | O | CH₂OH | H | 3-CN,6-Me | 0 |
| A-4381 | H | H | H | H | H | O | CH₂OH | H | 3-CN,6-OMe | 0 |
| A-4382 | H | H | H | H | H | O | CH₂OH | H | 4-CN,2-Me | 0 |
| A-4383 | H | H | H | H | H | O | CH₂OH | H | 4-CN,2-OMe | 0 |
| A-4384 | H | H | H | H | H | O | CH₂OH | H | 2-NO₂,4-F | 0 |

TABLE 78

| compound | R¹ | R² | R³ | R⁴ | R⁵ | A | R⁶ | R⁷ | (R⁸)ₘ | p |
|---|---|---|---|---|---|---|---|---|---|---|
| A-4385 | H | H | H | H | H | O | CH₂OH | H | 2-NO₂,5-F | 0 |
| A-4386 | H | H | H | H | H | O | CH₂OH | H | 2-NO₂,6-F | 0 |
| A-4387 | H | H | H | H | H | O | CH₂OH | H | 2-NO₂,4-Me | 0 |
| A-4388 | H | H | H | H | H | O | CH₂OH | H | 2-NO₂,5-Me | 0 |
| A-4389 | H | H | H | H | H | O | CH₂OH | H | 2-NO₂,6-Me | 0 |
| A-4390 | H | H | H | H | H | O | CH₂OH | H | 2-Me,4,5-F2 | 0 |
| A-4391 | H | H | H | H | H | O | CH₂OH | H | 2-Me,6-Et | 0 |
| A-4392 | H | H | H | H | H | O | CH₂OH | H | 2-cyclopropyl,6-OMe | 0 |
| A-4393 | H | H | H | H | H | O | CH₂OH | H | 2-Me,5-Et | 0 |
| A-4394 | H | H | H | H | H | O | CH₂OH | H | 2,6-Et₂ | 0 |
| A-4395 | H | H | H | H | H | O | CH₂OH | H | 2-Et,6-F | 0 |
| A-4396 | H | H | H | H | H | O | CH₂OH | H | 2-CH₂OCH₃,6-Cl | 0 |
| A-4397 | H | H | H | H | H | O | CH₂OH | H | 2-CH₂OCH₂CH₃,6-Cl | 0 |
| A-4398 | H | H | H | H | H | O | CH₂OH | H | 2-CH₂NMe₂ | 0 |
| A-4399 | H | H | H | H | H | O | NH₂ | H | H | 0 |
| A-4400 | H | H | H | H | H | O | NH₂ | H | 2-F | 0 |
| A-4401 | H | H | H | H | H | O | NH₂ | H | 2-Cl | 0 |
| A-4402 | H | H | H | H | H | O | NH₂ | H | 2-Br | 0 |
| A-4403 | H | H | H | H | H | O | NH₂ | H | 2-OH | 0 |
| A-4404 | H | H | H | H | H | O | NH₂ | H | 2-Me | 0 |
| A-4405 | H | H | H | H | H | O | NH₂ | H | 2-Et | 0 |
| A-4406 | H | H | H | H | H | O | NH₂ | H | 2-Pr | 0 |
| A-4407 | H | H | H | H | H | O | NH₂ | H | 2-CF₃ | 0 |
| A-4408 | H | H | H | H | H | O | NH₂ | H | 2-CHF₂ | 0 |
| A-4409 | H | H | H | H | H | O | NH₂ | H | 2-CH₂F | 0 |
| A-4410 | H | H | H | H | H | O | NH₂ | H | 2-CF₂Cl | 0 |

TABLE 78-continued

| compound | R¹ | R² | R³ | R⁴ | R⁵ | A | R⁶ | R⁷ | (R⁸)$_m$ | p |
|---|---|---|---|---|---|---|---|---|---|---|
| A-4411 | H | H | H | H | H | O | NH₂ | H | 2-cyclopropyl | 0 |
| A-4412 | H | H | H | H | H | O | NH₂ | H | 2-cyclobutyl | 0 |
| A-4413 | H | H | H | H | H | O | NH₂ | H | 2-cyclopentyl | 0 |
| A-4414 | H | H | H | H | H | O | NH₂ | H | 2-ethenyl | 0 |
| A-4415 | H | H | H | H | H | O | NH₂ | H | 2-allyl | 0 |
| A-4416 | H | H | H | H | H | O | NH₂ | H | 2-(prop-1-en-1-yl) | 0 |
| A-4417 | H | H | H | H | H | O | NH₂ | H | 2-(trifluoroethenyl) | 0 |
| A-4418 | H | H | H | H | H | O | NH₂ | H | 2-OMe | 0 |
| A-4419 | H | H | H | H | H | O | NH₂ | H | 2-OEt | 0 |
| A-4420 | H | H | H | H | H | O | NH₂ | H | 2-OPr | 0 |
| A-4421 | H | H | H | H | H | O | NH₂ | H | 2-O(i-Pr) | 0 |
| A-4422 | H | H | H | H | H | O | NH₂ | H | 2-OCF₃ | 0 |
| A-4423 | H | H | H | H | H | O | NH₂ | H | 2-OCHF₂ | 0 |
| A-4424 | H | H | H | H | H | O | NH₂ | H | 2-(cyclopropyloxyl) | 0 |
| A-4425 | H | H | H | H | H | O | NH₂ | H | 2-(cycbbutyloxyl) | 0 |
| A-4426 | H | H | H | H | H | O | NH₂ | H | 2-(cyclopentyloxyl) | 0 |
| A-4427 | H | H | H | H | H | O | NH₂ | H | 2-((2,2-dichborocyclopropyl)oxy) | 0 |
| A-4428 | H | H | H | H | H | O | NH₂ | H | 2-(oxiran-2-yl) | 0 |
| A-4429 | H | H | H | H | H | O | NH₂ | H | 2-SMe | 0 |
| A-4430 | H | H | H | H | H | O | NH₂ | H | 3-SMe | 0 |
| A-4431 | H | H | H | H | H | O | NH₂ | H | 2-S(=O)Me | 0 |
| A-4432 | H | H | H | H | H | O | NH₂ | H | 3-S(=O)Me | 0 |
| A-4433 | H | H | H | H | H | O | NH₂ | H | 2-S(=O)₂Me | 0 |
| A-4434 | H | H | H | H | H | O | NH₂ | H | 3-S(=O)₂Me | 0 |
| A-4435 | H | H | H | H | H | O | NH₂ | H | 2-SCF₃ | 0 |
| A-4436 | H | H | H | H | H | O | NH₂ | H | 3-SCF₃ | 0 |
| A-4437 | H | H | H | H | H | O | NH₂ | H | 3-S(=O)CF₃ | 0 |
| A-4438 | H | H | H | H | H | O | NH₂ | H | 3-SCF(CF₃)₂ | 0 |
| A-4439 | H | H | H | H | H | O | NH₂ | H | 2-(cyclopropylthio) | 0 |
| A-4440 | H | H | H | H | H | O | NH₂ | H | 2-(cyclopropylsulfinyl) | 0 |
| A-4441 | H | H | H | H | H | O | NH₂ | H | 2-(cyclopropylsulfonyl) | 0 |

TABLE 79

| compound | R¹ | R² | R³ | R⁴ | R⁵ | A | R⁶ | R⁷ | (R⁸)$_m$ | p |
|---|---|---|---|---|---|---|---|---|---|---|
| A-4442 | H | H | H | H | H | O | NH₂ | H | 2-C(=O)Me | 0 |
| A-4443 | H | H | H | H | H | O | NH₂ | H | 2-CH₂C(=O)CH₃ | 0 |
| A-4444 | H | H | H | H | H | O | NH₂ | H | 2-CH₂C(=O)CF₃ | 0 |
| A-4445 | H | H | H | H | H | O | NH₂ | H | 2-CH₂OH | 0 |
| A-4446 | H | H | H | H | H | O | NH₂ | H | 2-CH₂OCH₃ | 0 |
| A-4447 | H | H | H | H | H | O | NH₂ | H | 2-CH₂OCH₂CH₃ | 0 |
| A-4448 | H | H | H | H | H | O | NH₂ | H | 2-CH₂SCH₃ | 0 |
| A-4449 | H | H | H | H | H | O | NH₂ | H | 2-CH₂S(=O)CH₃ | 0 |
| A-4450 | H | H | H | H | H | O | NH₂ | H | 2-CH₂S(=O)₂CH₃ | 0 |
| A-4451 | H | H | H | H | H | O | NH₂ | H | 2-(benzyloxy) | 0 |
| A-4452 | H | H | H | H | H | O | NH₂ | H | 2-NH₂ | 0 |
| A-4453 | H | H | H | H | H | O | NH₂ | H | 2-NHMe | 0 |
| A-4454 | H | H | H | H | H | O | NH₂ | H | 2-N(Me)₂ | 0 |
| A-4455 | H | H | H | H | H | O | NH₂ | H | 2-(1,3-dioxolan-2-yl) | 0 |
| A-4456 | H | H | H | H | H | O | NH₂ | H | 2-(1,3-dioxan-2-yl) | 0 |
| A-4457 | H | H | H | H | H | O | NH₂ | H | 2-(1H-imidazol-2-yl) | 0 |
| A-4458 | H | H | H | H | H | O | NH₂ | H | 2-(thiazol-2-yl) | 0 |
| A-4459 | H | H | H | H | H | O | NH₂ | H | 2-(oxazol-2-yl) | 0 |
| A-4460 | H | H | H | H | H | O | NH₂ | H | 2-CH=NOH | 0 |
| A-4461 | H | H | H | H | H | O | NH₂ | H | 2-CH=NOMe | 0 |
| A-4462 | H | H | H | H | H | O | NH₂ | H | 2-(4,5-dihydro-3-isoxazolyl) | 0 |
| A-4463 | H | H | H | H | H | O | NH₂ | H | 2-CN | 0 |
| A-4464 | H | H | H | H | H | O | NH₂ | H | 2-NO₂ | 0 |
| A-4465 | H | H | H | H | H | O | NH₂ | H | 2-F,6-Cl | 0 |
| A-4466 | H | H | H | H | H | O | NH₂ | H | 2-F,6-Me | 0 |
| A-4467 | H | H | H | H | H | O | NH₂ | H | 3-F,6-Me | 0 |
| A-4468 | H | H | H | H | H | O | NH₂ | H | 4-F,2-Me | 0 |
| A-4469 | H | H | H | H | H | O | NH₂ | H | 2-F,6-OMe | 0 |
| A-4470 | H | H | H | H | H | O | NH₂ | H | 3-F,6-OMe | 0 |
| A-4471 | H | H | H | H | H | O | NH₂ | H | 2,6-Cl₂ | 0 |
| A-4472 | H | H | H | H | H | O | NH₂ | H | 2-Cl,6-Me | 0 |
| A-4473 | H | H | H | H | H | O | NH₂ | H | 3-Cl,6-Me | 0 |
| A-4474 | H | H | H | H | H | O | NH₂ | H | 4-Cl,2-Me | 0 |
| A-4475 | H | H | H | H | H | O | NH₂ | H | 2-Cl,5-CF₃ | 0 |
| A-4476 | H | H | H | H | H | O | NH₂ | H | 2-Cl,6-CF₃ | 0 |
| A-4477 | H | H | H | H | H | O | NH₂ | H | 2-Cl,6-OMe | 0 |
| A-4478 | H | H | H | H | H | O | NH₂ | H | 3-Cl,6-OMe | 0 |
| A-4479 | H | H | H | H | H | O | NH₂ | H | 4-Cl,2-OMe | 0 |
| A-4480 | H | H | H | H | H | O | NH₂ | H | 2,4-Me₂ | 0 |

TABLE 79-continued

| compound | R¹ | R² | R³ | R⁴ | R⁵ | A | R⁶ | R⁷ | (R⁸)ₘ | p |
|---|---|---|---|---|---|---|---|---|---|---|
| A-4481 | H | H | H | H | H | O | NH₂ | H | 2,5-Me₂ | 0 |
| A-4482 | H | H | H | H | H | O | NH₂ | H | 2,6-Me₂ | 0 |
| A-4483 | H | H | H | H | H | O | NH₂ | H | 2-Me,4-CF₃ | 0 |
| A-4484 | H | H | H | H | H | O | NH₂ | H | 2-Me,5-CF₃ | 0 |
| A-4485 | H | H | H | H | H | O | NH₂ | H | 2-Me,6-CF₃ | 0 |
| A-4486 | H | H | H | H | H | O | NH₂ | H | 2-Me,4-OMe | 0 |
| A-4487 | H | H | H | H | H | O | NH₂ | H | 2-Me,5-OMe | 0 |
| A-4488 | H | H | H | H | H | O | NH₂ | H | 2-Me,6-OMe | 0 |
| A-4489 | H | H | H | H | H | O | NH₂ | H | 3-Me,6-OMe | 0 |
| A-4490 | H | H | H | H | H | O | NH₂ | H | 4-Me,2-OMe | 0 |
| A-4491 | H | H | H | H | H | O | NH₂ | H | 2,5-OMe₂ | 0 |
| A-4492 | H | H | H | H | H | O | NH₂ | H | 2,6-OMe₂ | 0 |
| A-4493 | H | H | H | H | H | O | NH₂ | H | 2-OMe,6-CF₃ | 0 |
| A-4494 | H | H | H | H | H | O | NH₂ | H | 2-CHF₂,5-F | 0 |
| A-4495 | H | H | H | H | H | O | NH₂ | H | 2-CHF₂,6-F | 0 |
| A-4496 | H | H | H | H | H | O | NH₂ | H | 2-CHF₂,5-Me | 0 |
| A-4497 | H | H | H | H | H | O | NH₂ | H | 2-CHF₂,6-Me | 0 |
| A-4498 | H | H | H | H | H | O | NH₂ | H | 2-cyclopropyl,5-F | 0 |

TABLE 80

| compound | R¹ | R² | R³ | R⁴ | R⁵ | A | R⁶ | R⁷ | (R⁸)ₘ | p |
|---|---|---|---|---|---|---|---|---|---|---|
| A-4499 | H | H | H | H | H | O | NH₂ | H | 2-cyclopropyl,6-F | 0 |
| A-4500 | H | H | H | H | H | O | NH₂ | H | 2-cyclopropyl,5-Me | 0 |
| A-4501 | H | H | H | H | H | O | NH₂ | H | 2-cyclopropyl,6-Me | 0 |
| A-4502 | H | H | H | H | H | O | NH₂ | H | 2-ethenyl,6-F | 0 |
| A-4503 | H | H | H | H | H | O | NH₂ | H | 2-ethenyl,6-Me | 0 |
| A-4504 | H | H | H | H | H | O | NH₂ | H | 2-OEt,5-F | 0 |
| A-4505 | H | H | H | H | H | O | NH₂ | H | 2-OEt,6-F | 0 |
| A-4506 | H | H | H | H | H | O | NH₂ | H | 2-OEt,5-Cl | 0 |
| A-4507 | H | H | H | H | H | O | NH₂ | H | 2-OEt,6-Cl | 0 |
| A-4508 | H | H | H | H | H | O | NH₂ | H | 2-OEt,5-Me | 0 |
| A-4509 | H | H | H | H | H | O | NH₂ | H | 2-OEt,6-Me | 0 |
| A-4510 | H | H | H | H | H | O | NH₂ | H | 2-OCHF₂,5-F | 0 |
| A-4511 | H | H | H | H | H | O | NH₂ | H | 2-OCHF₂,6-F | 0 |
| A-4512 | H | H | H | H | H | O | NH₂ | H | 2-OCHF₂,5-Me | 0 |
| A-4513 | H | H | H | H | H | O | NH₂ | H | 2-OCHF₂,6-Me | 0 |
| A-4514 | H | H | H | H | H | O | NH₂ | H | 2-(cyclopropyloxy),5-F | 0 |
| A-4515 | H | H | H | H | H | O | NH₂ | H | 2-(cyclopropyloxy),6-F | 0 |
| A-4516 | H | H | H | H | H | O | NH₂ | H | 2-(cyclopropyloxy),5-Me | 0 |
| A-4517 | H | H | H | H | H | O | NH₂ | H | 2-(cyclopropyloxy),6-Me | 0 |
| A-4518 | H | H | H | H | H | O | NH₂ | H | 2-SMe,5-F | 0 |
| A-4519 | H | H | H | H | H | O | NH₂ | H | 2-SMe,6-F | 0 |
| A-4520 | H | H | H | H | H | O | NH₂ | H | 2-SMe,5-Me | 0 |
| A-4521 | H | H | H | H | H | O | NH₂ | H | 2-SMe,6-Me | 0 |
| A-4522 | H | H | H | H | H | O | NH₂ | H | 2-S(=O)Me,5-F | 0 |
| A-4523 | H | H | H | H | H | O | NH₂ | H | 2-S(=O)Me,6-F | 0 |
| A-4524 | H | H | H | H | H | O | NH₂ | H | 2-S(=O)Me,5-Me | 0 |
| A-4525 | H | H | H | H | H | O | NH₂ | H | 2-S(=O)Me,6-Me | 0 |
| A-4526 | H | H | H | H | H | O | NH₂ | H | 2-S(=O)₂Me,5-F | 0 |
| A-4527 | H | H | H | H | H | O | NH₂ | H | 2-S(=O)₂Me,6-F | 0 |
| A-4528 | H | H | H | H | H | O | NH₂ | H | 2-S(=O)₂Me,5-Me | 0 |
| A-4529 | H | H | H | H | H | O | NH₂ | H | 2-S(=O)₂Me,6-Me | 0 |
| A-4530 | H | H | H | H | H | O | NH₂ | H | 2-SCF₃,5-F | 0 |
| A-4531 | H | H | H | H | H | O | NH₂ | H | 2-SCF₃,6-F | 0 |
| A-4532 | H | H | H | H | H | O | NH₂ | H | 2-SCF₃,5-Me | 0 |
| A-4533 | H | H | H | H | H | O | NH₂ | H | 2-SCF₃,6-Me | 0 |
| A-4534 | H | H | H | H | H | O | NH₂ | H | 2-S(=O)CF₃,5-F | 0 |
| A-4535 | H | H | H | H | H | O | NH₂ | H | 2-S(=O)CF₃,6-F | 0 |
| A-4536 | H | H | H | H | H | O | NH₂ | H | 2-S(=O)CF₃,5-Me | 0 |
| A-4537 | H | H | H | H | H | O | NH₂ | H | 2-S(=O)CF₃,6-Me | 0 |
| A-4538 | H | H | H | H | H | O | NH₂ | H | 2-S(=O)₂CF₃,5-F | 0 |
| A-4539 | H | H | H | H | H | O | NH₂ | H | 2-S(=O)₂CF₃,6-F | 0 |
| A-4540 | H | H | H | H | H | O | NH₂ | H | 2-S(=O)₂CF₃,5-Me | 0 |
| A-4541 | H | H | H | H | H | O | NH₂ | H | 2-S(=O)₂CF₃,6-Me | 0 |
| A-4542 | H | H | H | H | H | O | NH₂ | H | 2-(cyclopropylthio),5-F | 0 |
| A-4543 | H | H | H | H | H | O | NH₂ | H | 2-(cyclopropylthio),6-F | 0 |
| A-4544 | H | H | H | H | H | O | NH₂ | H | 2-(cyclopropylthio),5-Me | 0 |
| A-4545 | H | H | H | H | H | O | NH₂ | H | 2-(cyclopropylthio),6-Me | 0 |
| A-4546 | H | H | H | H | H | O | NH₂ | H | 2-C(=O)Me,5-F | 0 |
| A-4547 | H | H | H | H | H | O | NH₂ | H | 2-C(=O)Me,6-F | 0 |
| A-4548 | H | H | H | H | H | O | NH₂ | H | 2-C(=O)Me,5-Me | 0 |
| A-4549 | H | H | H | H | H | O | NH₂ | H | 2-C(=O)Me,6-Me | 0 |
| A-4550 | H | H | H | H | H | O | NH₂ | H | 2-CH₂OH,5-F | 0 |

TABLE 80-continued

| compound | R¹ | R² | R³ | R⁴ | R⁵ | A | R⁶ | R⁷ | (R⁸)ₘ | p |
|---|---|---|---|---|---|---|---|---|---|---|
| A-4551 | H | H | H | H | H | O | NH₂ | H | 2-CH₂OH,6-F | 0 |
| A-4552 | H | H | H | H | H | O | NH₂ | H | 2-CH₂OH,5-Me | 0 |
| A-4553 | H | H | H | H | H | O | NH₂ | H | 2-CH₂OH,6-Me | 0 |
| A-4554 | H | H | H | H | H | O | NH₂ | H | 2-CH₂OCH₃,4-F | 0 |
| A-4555 | H | H | H | H | H | O | NH₂ | H | 2-CH₂OCH₃,5-F | 0 |

TABLE 81

| compound | R¹ | R² | R³ | R⁴ | R⁵ | A | R⁶ | R⁷ | (R⁸)ₘ | p |
|---|---|---|---|---|---|---|---|---|---|---|
| A-4556 | H | H | H | H | H | O | NH₂ | H | 2-CH₂OCH₃,6-F | 0 |
| A-4557 | H | H | H | H | H | O | NH₂ | H | 2-CH₂OCH₃,4-Me | 0 |
| A-4558 | H | H | H | H | H | O | NH₂ | H | 2-CH₂OCH₃,5-Me | 0 |
| A-4559 | H | H | H | H | H | O | NH₂ | H | 2-CH₂OCH₃,6-Me | 0 |
| A-4560 | H | H | H | H | H | O | NH₂ | H | 2-OC(=O)CH₃,5-F | 0 |
| A-4561 | H | H | H | H | H | O | NH₂ | H | 2-OC(=O)CH₃,6-F | 0 |
| A-4562 | H | H | H | H | H | O | NH₂ | H | 2-OC(=O)CH₃,5-Me | 0 |
| A-4563 | H | H | H | H | H | O | NH₂ | H | 2-OC(=O)CH₃,6-Me | 0 |
| A-4564 | H | H | H | H | H | O | NH₂ | H | 2-OS(=O)₂CH₃,5-F | 0 |
| A-4565 | H | H | H | H | H | O | NH₂ | H | 2-OS(=O)₂CH₃,6-F | 0 |
| A-4566 | H | H | H | H | H | O | NH₂ | H | 2-OS(=O)₂CH₃,5-Me | 0 |
| A-4567 | H | H | H | H | H | O | NH₂ | H | 2-OS(=O)₂CH₃,6-Me | 0 |
| A-4568 | H | H | H | H | H | O | NH₂ | H | 2-CH₂SCH₃,5-F | 0 |
| A-4569 | H | H | H | H | H | O | NH₂ | H | 2-CH₂SCH₃,6-F | 0 |
| A-4570 | H | H | H | H | H | O | NH₂ | H | 2-CH₂SCH₃,5-Me | 0 |
| A-4571 | H | H | H | H | H | O | NH₂ | H | 2-CH₂SCH₃,6-Me | 0 |
| A-4572 | H | H | H | H | H | O | NH₂ | H | 2-NMe₂,5-F | 0 |
| A-4573 | H | H | H | H | H | O | NH₂ | H | 2-NMe₂,6-F | 0 |
| A-4574 | H | H | H | H | H | O | NH₂ | H | 2-NMe₂,5-Me | 0 |
| A-4575 | H | H | H | H | H | O | NH₂ | H | 2-NMe₂,6-Me | 0 |
| A-4576 | H | H | H | H | H | O | NH₂ | H | 2-CN,4-F | 0 |
| A-4577 | H | H | H | H | H | O | NH₂ | H | 2-CN,5-F | 0 |
| A-4578 | H | H | H | H | H | O | NH₂ | H | 2-CN,6-F | 0 |
| A-4579 | H | H | H | H | H | O | NH₂ | H | 2-CN,6-Me | 0 |
| A-4580 | H | H | H | H | H | O | NH₂ | H | 2-CN,5-OMe | 0 |
| A-4581 | H | H | H | H | H | O | NH₂ | H | 2-CN,6-OMe | 0 |
| A-4582 | H | H | H | H | H | O | NH₂ | H | 3-CN,6-Me | 0 |
| A-4583 | H | H | H | H | H | O | NH₂ | H | 3-CN,6-OMe | 0 |
| A-4584 | H | H | H | H | H | O | NH₂ | H | 4-CN,2-Me | 0 |
| A-4585 | H | H | H | H | H | O | NH₂ | H | 4-CN,2-OMe | 0 |
| A-4586 | H | H | H | H | H | O | NH₂ | H | 2-NO₂,4-F | 0 |
| A-4587 | H | H | H | H | H | O | NH₂ | H | 2-NO₂,5-F | 0 |
| A-4588 | H | H | H | H | H | O | NH₂ | H | 2-NO₂,6-F | 0 |
| A-4589 | H | H | H | H | H | O | NH₂ | H | 2-NO₂,4-Me | 0 |
| A-4590 | H | H | H | H | H | O | NH₂ | H | 2-NO₂,5-Me | 0 |
| A-4591 | H | H | H | H | H | O | NH₂ | H | 2-NO₂,6-Me | 0 |
| A-4592 | H | H | H | H | H | O | NH₂ | H | 2-Me,4,5-F₂ | 0 |
| A-4593 | H | H | H | H | H | O | NH₂ | H | 2-Me,6-Et | 0 |
| A-4594 | H | H | H | H | H | O | NH₂ | H | 2-cyclopropyl,6-OMe | 0 |
| A-4595 | H | H | H | H | H | O | NH₂ | H | 2-Me,5-Et | 0 |
| A-4596 | H | H | H | H | H | O | NH₂ | H | 2,6-Et₂ | 0 |
| A-4597 | H | H | H | H | H | O | NH₂ | H | 2-Et,6-F | 0 |
| A-4598 | H | H | H | H | H | O | NH₂ | H | 2-CH₂OCH₃,6-Cl | 0 |
| A-4599 | H | H | H | H | H | O | NH₂ | H | 2-CH₂OCH₂CH₃,6-Cl | 0 |
| A-4600 | H | H | H | H | H | O | NH₂ | H | 2-CH₂NMe₂ | 0 |
| A-4601 | H | H | H | H | H | O | C(=O)CH₃ | H | H | 0 |
| A-4602 | H | H | H | H | H | O | C(=O)CH₃ | H | 2-F | 0 |
| A-4603 | H | H | H | H | H | O | C(=O)CH₃ | H | 2-Cl | 0 |
| A-4604 | H | H | H | H | H | O | C(=O)CH₃ | H | 2-Br | 0 |
| A-4605 | H | H | H | H | H | O | C(=O)CH₃ | H | 2-OH | 0 |
| A-4606 | H | H | H | H | H | O | C(=O)CH₃ | H | 2-Me | 0 |
| A-4607 | H | H | H | H | H | O | C(=O)CH₃ | H | 2-Et | 0 |
| A-4608 | H | H | H | H | H | O | C(=O)CH₃ | H | 2-Pr | 0 |
| A-4609 | H | H | H | H | H | O | C(=O)CH₃ | H | 2-CF₃ | 0 |
| A-4610 | H | H | H | H | H | O | C(=O)CH₃ | H | 2-CHF₂ | 0 |
| A-4611 | H | H | H | H | H | O | C(=O)CH₃ | H | 2-CH₂F | 0 |
| A-4612 | H | H | H | H | H | O | C(=O)CH₃ | H | 2-CF₂Cl | 0 |

TABLE 82

| compound | R¹ | R² | R³ | R⁴ | R⁵ | A | R⁶ | R⁷ | (R⁸)$_m$ | p |
|---|---|---|---|---|---|---|---|---|---|---|
| A-4613 | H | H | H | H | H | O | C(=O)CH₃ | H | 2-cyclopropyl | 0 |
| A-4614 | H | H | H | H | H | O | C(=O)CH₃ | H | 2-cyclobutyl | 0 |
| A-4615 | H | H | H | H | H | O | C(=O)CH₃ | H | 2-cyclopentyl | 0 |
| A-4616 | H | H | H | H | H | O | C(=O)CH₃ | H | 2-ethenyl | 0 |
| A-4617 | H | H | H | H | H | O | C(=O)CH₃ | H | 2-allyl | 0 |
| A-4618 | H | H | H | H | H | O | C(=O)CH₃ | H | 2-(prop-1-en-1-yl) | 0 |
| A-4619 | H | H | H | H | H | O | C(=O)CH₃ | H | 2-(trifluoroethenyl) | 0 |
| A-4620 | H | H | H | H | H | O | C(=O)CH₃ | H | 2-OMe | 0 |
| A-4621 | H | H | H | H | H | O | C(=O)CH₃ | H | 2-OEt | 0 |
| A-4622 | H | H | H | H | H | O | C(=O)CH₃ | H | 2-OPr | 0 |
| A-4623 | H | H | H | H | H | O | C(=O)CH₃ | H | 2-O(i-Pr) | 0 |
| A-4624 | H | H | H | H | H | O | C(=O)CH₃ | H | 2-OCF₃ | 0 |
| A-4625 | H | H | H | H | H | O | C(=O)CH₃ | H | 2-OCHF₂ | 0 |
| A-4626 | H | H | H | H | H | O | C(=O)CH₃ | H | 2-(cyclopropyloxy) | 0 |
| A-4627 | H | H | H | H | H | O | C(=O)CH₃ | H | 2-(cyclobutyloxy) | 0 |
| A-4628 | H | H | H | H | H | O | C(=O)CH₃ | H | 2-(cyclopentyloxy) | 0 |
| A-4629 | H | H | H | H | H | O | C(=O)CH₃ | H | 2-((2,2-dichlorocyclopropyl)oxy) | 0 |
| A-4630 | H | H | H | H | H | O | C(=O)CH₃ | H | 2-(oxiran-2-yl) | 0 |
| A-4631 | H | H | H | H | H | O | C(=O)CH₃ | H | 2-SMe | 0 |
| A-4632 | H | H | H | H | H | O | C(=O)CH₃ | H | 3-SMe | 0 |
| A-4633 | H | H | H | H | H | O | C(=O)CH₃ | H | 2-S(=O)Me | 0 |
| A-4634 | H | H | H | H | H | O | C(=O)CH₃ | H | 3-S(=O)Me | 0 |
| A-4635 | H | H | H | H | H | O | C(=O)CH₃ | H | 2-S(=O)₂Me | 0 |
| A-4636 | H | H | H | H | H | O | C(=O)CH₃ | H | 3-S(=O)₂Me | 0 |
| A-4637 | H | H | H | H | H | O | C(=O)CH₃ | H | 2-SCF₃ | 0 |
| A-4638 | H | H | H | H | H | O | C(=O)CH₃ | H | 3-SCF₃ | 0 |
| A-4639 | H | H | H | H | H | O | C(=O)CH₃ | H | 3-S(=O)CF₃ | 0 |
| A-4640 | H | H | H | H | H | O | C(=O)CH₃ | H | 3-SCF(CF₃)₂ | 0 |
| A-4641 | H | H | H | H | H | O | C(=O)CH₃ | H | 2-(cyclopropylthio) | 0 |
| A-4642 | H | H | H | H | H | O | C(=O)CH₃ | H | 2-(cyclopropylsulfinyl) | 0 |
| A-4643 | H | H | H | H | H | O | C(=O)CH₃ | H | 2-(cyclopropylsulfonyl) | 0 |
| A-4644 | H | H | H | H | H | O | C(=O)CH₃ | H | 2-C(=O)Me | 0 |
| A-4645 | H | H | H | H | H | O | C(=O)CH₃ | H | 2-CH₂C(=O)CH₃ | 0 |
| A-4646 | H | H | H | H | H | O | C(=O)CH₃ | H | 2-CH₂C(=O)CF₃ | 0 |
| A-4647 | H | H | H | H | H | O | C(=O)CH₃ | H | 2-CH₂OH | 0 |
| A-4648 | H | H | H | H | H | O | C(=O)CH₃ | H | 2-CH₂OCH₃ | 0 |
| A-4649 | H | H | H | H | H | O | C(=O)CH₃ | H | 2-CH₂OCH₂CH₃ | 0 |
| A-4650 | H | H | H | H | H | O | C(=O)CH₃ | H | 2-CH₂SCH₃ | 0 |
| A-4651 | H | H | H | H | H | O | C(=O)CH₃ | H | 2-CH₂S(=O)CH₃ | 0 |
| A-4652 | H | H | H | H | H | O | C(=O)CH₃ | H | 2-CH₂S(=O)₂CH₃ | 0 |
| A-4653 | H | H | H | H | H | O | C(=O)CH₃ | H | 2-(benzyloxy) | 0 |
| A-4654 | H | H | H | H | H | O | C(=O)CH₃ | H | 2-NH₂ | 0 |
| A-4655 | H | H | H | H | H | O | C(=O)CH₃ | H | 2-NHMe | 0 |
| A-4656 | H | H | H | H | H | O | C(=O)CH₃ | H | 2-N(Me)₂ | 0 |
| A-4657 | H | H | H | H | H | O | C(=O)CH₃ | H | 2-(1,3-dioxolan-2-yl) | 0 |
| A-4658 | H | H | H | H | H | O | C(=O)CH₃ | H | 2-(1,3-dioxan-2-yl) | 0 |
| A-4659 | H | H | H | H | H | O | C(=O)CH₃ | H | 2-(1H-imidazol-2-yl) | 0 |
| A-4660 | H | H | H | H | H | O | C(=O)CH₃ | H | 2-(thiazol-2-yl) | 0 |
| A-4661 | H | H | H | H | H | O | C(=O)CH₃ | H | 2-(oxazol-2-yl) | 0 |
| A-4662 | H | H | H | H | H | O | C(=O)CH₃ | H | 2-CH=NOH | 0 |
| A-4663 | H | H | H | H | H | O | C(=O)CH₃ | H | 2-CH=NOMe | 0 |
| A-4664 | H | H | H | H | H | O | C(=O)CH₃ | H | 2-(4,5-dihydro-3-isoxazolyl) | 0 |
| A-4665 | H | H | H | H | H | O | C(=O)CH₃ | H | 2-CN | 0 |
| A-4666 | H | H | H | H | H | O | C(=O)CH₃ | H | 2-NO₂ | 0 |
| A-4667 | H | H | H | H | H | O | C(=O)CH₃ | H | 2-F,6-Cl | 0 |
| A-4668 | H | H | H | H | H | O | C(=O)CH₃ | H | 2-F,6-Me | 0 |
| A-4669 | H | H | H | H | H | O | C(=O)CH₃ | H | 3-F,6-Me | 0 |

TABLE 83

| compound | R¹ | R² | R³ | R⁴ | R⁵ | A | R⁶ | R⁷ | (R⁸)$_m$ | p |
|---|---|---|---|---|---|---|---|---|---|---|
| A-4670 | H | H | H | H | H | O | C(=O)CH₃ | H | 4-F,2-Me | 0 |
| A-4671 | H | H | H | H | H | O | C(=O)CH₃ | H | 2-F,6-OMe | 0 |
| A-4672 | H | H | H | H | H | O | C(=O)CH₃ | H | 3-F,6-OMe | 0 |
| A-4673 | H | H | H | H | H | O | C(=O)CH₃ | H | 2,6-Cl₂ | 0 |
| A-4674 | H | H | H | H | H | O | C(=O)CH₃ | H | 2-Cl,6-Me | 0 |
| A-4675 | H | H | H | H | H | O | C(=O)CH₃ | H | 3-Cl,6-Me | 0 |
| A-4676 | H | H | H | H | H | O | C(=O)CH₃ | H | 4-Cl,2-Me | 0 |
| A-4677 | H | H | H | H | H | O | C(=O)CH₃ | H | 2-Cl,5-CF₃ | 0 |
| A-4678 | H | H | H | H | H | O | C(=O)CH₃ | H | 2-Cl,6-CF₃ | 0 |
| A-4679 | H | H | H | H | H | O | C(=O)CH₃ | H | 2-Cl,6-OMe | 0 |
| A-4680 | H | H | H | H | H | O | C(=O)CH₃ | H | 3-Cl,6-OMe | 0 |
| A-4681 | H | H | H | H | H | O | C(=O)CH₃ | H | 4-Cl,2-OMe | 0 |
| A-4682 | H | H | H | H | H | O | C(=O)CH₃ | H | 2,4-Me₂ | 0 |

TABLE 83-continued

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-4683 | H | H | H | H | H | O | C(=O)CH$_3$ | H | 2,5-Me$_2$ | 0 |
| A-4684 | H | H | H | H | H | O | C(=O)CH$_3$ | H | 2,6-Me$_2$ | 0 |
| A-4685 | H | H | H | H | H | O | C(=O)CH$_3$ | H | 2-Me,4-CF$_3$ | 0 |
| A-4686 | H | H | H | H | H | O | C(=O)CH$_3$ | H | 2-Me,5-CF$_3$ | 0 |
| A-4687 | H | H | H | H | H | O | C(=O)CH$_3$ | H | 2-Me,6-CF$_3$ | 0 |
| A-4688 | H | H | H | H | H | O | C(=O)CH$_3$ | H | 2-Me,4-OMe | 0 |
| A-4689 | H | H | H | H | H | O | C(=O)CH$_3$ | H | 2-Me,5-OMe | 0 |
| A-4690 | H | H | H | H | H | O | C(=O)CH$_3$ | H | 2-Me,6-OMe | 0 |
| A-4691 | H | H | H | H | H | O | C(=O)CH$_3$ | H | 3-Me,6-OMe | 0 |
| A-4692 | H | H | H | H | H | O | C(=O)CH$_3$ | H | 4-Me,2-OMe | 0 |
| A-4693 | H | H | H | H | H | O | C(=O)CH$_3$ | H | 2,5-OMe$_2$ | 0 |
| A-4694 | H | H | H | H | H | O | C(=O)CH$_3$ | H | 2,6-OMe$_2$ | 0 |
| A-4695 | H | H | H | H | H | O | C(=O)CH$_3$ | H | 2-OMe,6-CF$_3$ | 0 |
| A-4696 | H | H | H | H | H | O | C(=O)CH$_3$ | H | 2-CHF$_2$,5-F | 0 |
| A-4697 | H | H | H | H | H | O | C(=O)CH$_3$ | H | 2-CHF$_2$,6-F | 0 |
| A-4698 | H | H | H | H | H | O | C(=O)CH$_3$ | H | 2-CHF$_2$,5-Me | 0 |
| A-4699 | H | H | H | H | H | O | C(=O)CH$_3$ | H | 2-CHF$_2$,6-Me | 0 |
| A-4700 | H | H | H | H | H | O | C(=O)CH$_3$ | H | 2-cyclopropyl,5-F | 0 |
| A-4701 | H | H | H | H | H | O | C(=O)CH$_3$ | H | 2-cyclopropyl,6-F | 0 |
| A-4702 | H | H | H | H | H | O | C(=O)CH$_3$ | H | 2-cyclopropyl,5-Me | 0 |
| A-4703 | H | H | H | H | H | O | C(=O)CH$_3$ | H | 2-cyclopropyl,6-Me | 0 |
| A-4704 | H | H | H | H | H | O | C(=O)CH$_3$ | H | 2-ethenyl,6-F | 0 |
| A-4705 | H | H | H | H | H | O | C(=O)CH$_3$ | H | 2-ethenyl,6-Me | 0 |
| A-4706 | H | H | H | H | H | O | C(=O)CH$_3$ | H | 2-OEt,5-F | 0 |
| A-4707 | H | H | H | H | H | O | C(=O)CH$_3$ | H | 2-OEt,6-F | 0 |
| A-4708 | H | H | H | H | H | O | C(=O)CH$_3$ | H | 2-OEt,5-Cl | 0 |
| A-4709 | H | H | H | H | H | O | C(=O)CH$_3$ | H | 2-OEt,6-Cl | 0 |
| A-4710 | H | H | H | H | H | O | C(=O)CH$_3$ | H | 2-OEt,5-Me | 0 |
| A-4711 | H | H | H | H | H | O | C(=O)CH$_3$ | H | 2-OEt,6-Me | 0 |
| A-4712 | H | H | H | H | H | O | C(=O)CH$_3$ | H | 2-OCHF$_2$,5-F | 0 |
| A-4713 | H | H | H | H | H | O | C(=O)CH$_3$ | H | 2-OCHF$_2$,6-F | 0 |
| A-4714 | H | H | H | H | H | O | C(=O)CH$_3$ | H | 2-OCHF$_2$,5-Me | 0 |
| A-4715 | H | H | H | H | H | O | C(=O)CH$_3$ | H | 2-OCHF$_2$,6-Me | 0 |
| A-4716 | H | H | H | H | H | O | C(=O)CH$_3$ | H | 2-(cyclopropyloxy),5-F | 0 |
| A-4717 | H | H | H | H | H | O | C(=O)CH$_3$ | H | 2-(cyclopropyloxy),6-F | 0 |
| A-4718 | H | H | H | H | H | O | C(=O)CH$_3$ | H | 2-(cyclopropyloxy),5-Me | 0 |
| A-4719 | H | H | H | H | H | O | C(=O)CH$_3$ | H | 2-(cyclopropyloxy),6-Me | 0 |
| A-4720 | H | H | H | H | H | O | C(=O)CH$_3$ | H | 2-SMe,5-F | 0 |
| A-4721 | H | H | H | H | H | O | C(=O)CH$_3$ | H | 2-SMe,6-F | 0 |
| A-4722 | H | H | H | H | H | O | C(=O)CH$_3$ | H | 2-SMe,5-Me | 0 |
| A-4723 | H | H | H | H | H | O | C(=O)CH$_3$ | H | 2-SMe,6-Me | 0 |
| A-4724 | H | H | H | H | H | O | C(=O)CH$_3$ | H | 2-S(=O)Me,5-F | 0 |
| A-4725 | H | H | H | H | H | O | C(=O)CH$_3$ | H | 2-S(=O)Me,6-F | 0 |
| A-4726 | H | H | H | H | H | O | C(=O)CH$_3$ | H | 2-S(=O)Me,5-Me | 0 |

TABLE 84

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-4727 | H | H | H | H | H | O | C(=O)CH$_3$ | H | 2-S(=O)Me,6-Me | 0 |
| A-4728 | H | H | H | H | H | O | C(=O)CH$_3$ | H | 2-S(=O)$_2$Me,5-F | 0 |
| A-4729 | H | H | H | H | H | O | C(=O)CH$_3$ | H | 2-S(=O)$_2$Me,6-F | 0 |
| A-4730 | H | H | H | H | H | O | C(=O)CH$_3$ | H | 2-S(=O)$_2$Me,5-Me | 0 |
| A-4731 | H | H | H | H | H | O | C(=O)CH$_3$ | H | 2-S(=O)$_2$Me,6-Me | 0 |
| A-4732 | H | H | H | H | H | O | C(=O)CH$_3$ | H | 2-SCF$_3$,5-F | 0 |
| A-4733 | H | H | H | H | H | O | C(=O)CH$_3$ | H | 2-SCF$_3$,6-F | 0 |
| A-4734 | H | H | H | H | H | O | C(=O)CH$_3$ | H | 2-SCF$_3$,5-Me | 0 |
| A-4735 | H | H | H | H | H | O | C(=O)CH$_3$ | H | 2-SCF$_3$,6-Me | 0 |
| A-4736 | H | H | H | H | H | O | C(=O)CH$_3$ | H | 2-S(=O)CF$_3$,5-F | 0 |
| A-4737 | H | H | H | H | H | O | C(=O)CH$_3$ | H | 2-S(=O)CF$_3$,6-F | 0 |
| A-4738 | H | H | H | H | H | O | C(=O)CH$_3$ | H | 2-S(=O)CF$_3$,5-Me | 0 |
| A-4739 | H | H | H | H | H | O | C(=O)CH$_3$ | H | 2-S(=O)CF$_3$,6-Me | 0 |
| A-4740 | H | H | H | H | H | O | C(=O)CH$_3$ | H | 2-S(=O)$_2$CF$_3$,5-F | 0 |
| A-4741 | H | H | H | H | H | O | C(=O)CH$_3$ | H | 2-S(=O)$_2$CF$_3$,6-F | 0 |
| A-4742 | H | H | H | H | H | O | C(=O)CH$_3$ | H | 2-S(=O)$_2$CF$_3$,5-Me | 0 |
| A-4743 | H | H | H | H | H | O | C(=O)CH$_3$ | H | 2-S(=O)$_2$CF$_3$,6-Me | 0 |
| A-4744 | H | H | H | H | H | O | C(=O)CH$_3$ | H | 2-(cyclopropylthio),5-F | 0 |
| A-4745 | H | H | H | H | H | O | C(=O)CH$_3$ | H | 2-(cyclopropylthio),6-F | 0 |
| A-4746 | H | H | H | H | H | O | C(=O)CH$_3$ | H | 2-(cyclopropylthio),5-Me | 0 |
| A-4747 | H | H | H | H | H | O | C(=O)CH$_3$ | H | 2-(cyclopropylthio),6-Me | 0 |
| A-4748 | H | H | H | H | H | O | C(=O)CH$_3$ | H | 2-C(=O)Me,5-F | 0 |
| A-4749 | H | H | H | H | H | O | C(=O)CH$_3$ | H | 2-C(=O)Me,6-F | 0 |
| A-4750 | H | H | H | H | H | O | C(=O)CH$_3$ | H | 2-C(=O)Me,5-Me | 0 |
| A-4751 | H | H | H | H | H | O | C(=O)CH$_3$ | H | 2-C(=O)Me,6-Me | 0 |
| A-4752 | H | H | H | H | H | O | C(=O)CH$_3$ | H | 2-CH$_2$OH,5-F | 0 |

TABLE 84-continued

| compound | R¹ | R² | R³ | R⁴ | R⁵ | A | R⁶ | R⁷ | (R⁸)$_m$ | p |
|---|---|---|---|---|---|---|---|---|---|---|
| A-4753 | H | H | H | H | H | O | C(=O)CH₃ | H | 2-CH₂OH,6-F | 0 |
| A-4754 | H | H | H | H | H | O | C(=O)CH₃ | H | 2-CH₂OH,5-Me | 0 |
| A-4755 | H | H | H | H | H | O | C(=O)CH₃ | H | 2-CH₂OH,6-Me | 0 |
| A-4756 | H | H | H | H | H | O | C(=O)CH₃ | H | 2-CH₂OCH₃,4-F | 0 |
| A-4757 | H | H | H | H | H | O | C(=O)CH₃ | H | 2-CH₂OCH₃,5-F | 0 |
| A-4758 | H | H | H | H | H | O | C(=O)CH₃ | H | 2-CH₂OCH₃,6-F | 0 |
| A-4759 | H | H | H | H | H | O | C(=O)CH₃ | H | 2-CH₂OCH₃,4-Me | 0 |
| A-4760 | H | H | H | H | H | O | C(=O)CH₃ | H | 2-CH₂OCH₃,5-Me | 0 |
| A-4761 | H | H | H | H | H | O | C(=O)CH₃ | H | 2-CH₂OCH₃,6-Me | 0 |
| A-4762 | H | H | H | H | H | O | C(=O)CH₃ | H | 2-OC(=O)CH₃,5-F | 0 |
| A-4763 | H | H | H | H | H | O | C(=O)CH₃ | H | 2-OC(=O)CH₃,6-F | 0 |
| A-4764 | H | H | H | H | H | O | C(=O)CH₃ | H | 2-OC(=O)CH₃,5-Me | 0 |
| A-4765 | H | H | H | H | H | O | C(=O)CH₃ | H | 2-OC(=O)CH₃,6-Me | 0 |
| A-4766 | H | H | H | H | H | O | C(=O)CH₃ | H | 2-OS(=O)₂CH₃,5-F | 0 |
| A-4767 | H | H | H | H | H | O | C(=O)CH₃ | H | 2-OS(=O)₂CH₃,6-F | 0 |
| A-4768 | H | H | H | H | H | O | C(=O)CH₃ | H | 2-OS(=O)₂CH₃,5-Me | 0 |
| A-4769 | H | H | H | H | H | O | C(=O)CH₃ | H | 2-OS(=O)₂CH₃,6-Me | 0 |
| A-4770 | H | H | H | H | H | O | C(=O)CH₃ | H | 2-CH₂SCH₃,5-F | 0 |
| A-4771 | H | H | H | H | H | O | C(=O)CH₃ | H | 2-CH₂SCH₃,6-F | 0 |
| A-4772 | H | H | H | H | H | O | C(=O)CH₃ | H | 2-CH₂SCH₃,5-Me | 0 |
| A-4773 | H | H | H | H | H | O | C(=O)CH₃ | H | 2-CH₂SCH₃,6-Me | 0 |
| A-4774 | H | H | H | H | H | O | C(=O)CH₃ | H | 2-NMe₂,5-F | 0 |
| A-4775 | H | H | H | H | H | O | C(=O)CH₃ | H | 2-NMe₂,6-F | 0 |
| A-4776 | H | H | H | H | H | O | C(=O)CH₃ | H | 2-NMe₂,5-Me | 0 |
| A-4777 | H | H | H | H | H | O | C(=O)CH₃ | H | 2-NMe₂,6-Me | 0 |
| A-4778 | H | H | H | H | H | O | C(=O)CH₃ | H | 2-CN,4-F | 0 |
| A-4779 | H | H | H | H | H | O | C(=O)CH₃ | H | 2-CN,5-F | 0 |
| A-4780 | H | H | H | H | H | O | C(=O)CH₃ | H | 2-CN,6-F | 0 |
| A-4781 | H | H | H | H | H | O | C(=O)CH₃ | H | 2-CN,6-Me | 0 |
| A-4782 | H | H | H | H | H | O | C(=O)CH₃ | H | 2-CN,5-OMe | 0 |
| A-4783 | H | H | H | H | H | O | C(=O)CH₃ | H | 2-CN,6-OMe | 0 |

TABLE 85

| compound | R¹ | R² | R³ | R⁴ | R⁵ | A | R⁶ | R⁷ | (R⁸)$_m$ | p |
|---|---|---|---|---|---|---|---|---|---|---|
| A-4784 | H | H | H | H | H | O | C(=O)CH₃ | H | 3-CN,6-Me | 0 |
| A-4785 | H | H | H | H | H | O | C(=O)CH₃ | H | 3-CN,6-OMe | 0 |
| A-4786 | H | H | H | H | H | O | C(=O)CH₃ | H | 4-CN,2-Me | 0 |
| A-4787 | H | H | H | H | H | O | C(=O)CH₃ | H | 4-CN,2-OMe | 0 |
| A-4788 | H | H | H | H | H | O | C(=O)CH₃ | H | 2-NO₂,4-F | 0 |
| A-4789 | H | H | H | H | H | O | C(=O)CH₃ | H | 2-NO₂,5-F | 0 |
| A-4790 | H | H | H | H | H | O | C(=O)CH₃ | H | 2-NO₂,6-F | 0 |
| A-4791 | H | H | H | H | H | O | C(=O)CH₃ | H | 2-NO₂,4-Me | 0 |
| A-4792 | H | H | H | H | H | O | C(=O)CH₃ | H | 2-NO₂,5-Me | 0 |
| A-4793 | H | H | H | H | H | O | C(=O)CH₃ | H | 2-NO₂,6-Me | 0 |
| A-4794 | H | H | H | H | H | O | C(=O)CH₃ | H | 2-Me,4,5F₂ | 0 |
| A-4795 | H | H | H | H | H | O | C(=O)CH₃ | H | 2-Me,6-Et | 0 |
| A-4796 | H | H | H | H | H | O | C(=O)CH₃ | H | 2-cyclopropyl,6-OMe | 0 |
| A-4797 | H | H | H | H | H | O | C(=O)CH₃ | H | 2-Me,5-Et | 0 |
| A-4798 | H | H | H | H | H | O | C(=O)CH₃ | H | 2,6-Et2 | 0 |
| A-4799 | H | H | H | H | H | O | C(=O)CH₃ | H | 2-Et,6-F | 0 |
| A-4800 | H | H | H | H | H | O | C(=O)CH₃ | H | 2-CH₂OCH₃,6-Cl | 0 |
| A-4801 | H | H | H | H | H | O | C(=O)CH₃ | H | 2-CH₂OCH₂CH₃,6-Cl | 0 |
| A-4802 | H | H | H | H | H | O | C(=O)CH₃ | H | 2-CH₂NMe₂ | 0 |
| A-4803 | H | H | H | H | H | O | C(=O)CH₂OCH₃ | H | H | 0 |
| A-4804 | H | H | H | H | H | O | C(=O)CH₂OCH₃ | H | 2-F | 0 |
| A-4805 | H | H | H | H | H | O | C(=O)CH₂OCH₃ | H | 2-Cl | 0 |
| A-4806 | H | H | H | H | H | O | C(=O)CH₂OCH₃ | H | 2-Br | 0 |
| A-4807 | H | H | H | H | H | O | C(=O)CH₂OCH₃ | H | 2-OH | 0 |
| A-4808 | H | H | H | H | H | O | C(=O)CH₂OCH₃ | H | 2-Me | 0 |
| A-4809 | H | H | H | H | H | O | C(=O)CH₂OCH₃ | H | 2-Et | 0 |
| A-4810 | H | H | H | H | H | O | C(=O)CH₂OCH₃ | H | 2-Pr | 0 |
| A-4811 | H | H | H | H | H | O | C(=O)CH₂OCH₃ | H | 2-CF₃ | 0 |
| A-4812 | H | H | H | H | H | O | C(=O)CH₂OCH₃ | H | 2-CHF₂ | 0 |
| A-4813 | H | H | H | H | H | O | C(=O)CH₂OCH₃ | H | 2-CH₂F | 0 |
| A-4814 | H | H | H | H | H | O | C(=O)CH₂OCH₃ | H | 2-CF₂Cl | 0 |
| A-4815 | H | H | H | H | H | O | C(=O)CH₂OCH₃ | H | 2-cyclopropyl | 0 |
| A-4816 | H | H | H | H | H | O | C(=O)CH₂OCH₃ | H | 2-cyclobutyl | 0 |
| A-4817 | H | H | H | H | H | O | C(=O)CH₂OCH₃ | H | 2-cyclopentyl | 0 |
| A-4818 | H | H | H | H | H | O | C(=O)CH₂OCH₃ | H | 2-ethenyl | 0 |
| A-4819 | H | H | H | H | H | O | C(=O)CH₂OCH₃ | H | 2-allyl | 0 |
| A-4820 | H | H | H | H | H | O | C(=O)CH₂OCH₃ | H | 2-(prop-1-en-1-yl) | 0 |
| A-4821 | H | H | H | H | H | O | C(=O)CH₂OCH₃ | H | 2-(trifluoroethenyl) | 0 |
| A-4822 | H | H | H | H | H | O | C(=O)CH₂OCH₃ | H | 2-OMe | 0 |

TABLE 85-continued

| compound | R¹ | R² | R³ | R⁴ | R⁵ | A | R⁶ | R⁷ | (R⁸)ₘ | p |
|---|---|---|---|---|---|---|---|---|---|---|
| A-4823 | H | H | H | H | H | O | C(=O)CH₂OCH₃ | H | 2-OEt | 0 |
| A-4824 | H | H | H | H | H | O | C(=O)CH₂OCH₃ | H | 2-OPr | 0 |
| A-4825 | H | H | H | H | H | O | C(=O)CH₂OCH₃ | H | 2-O(i-Pr) | 0 |
| A-4826 | H | H | H | H | H | O | C(=O)CH₂OCH₃ | H | 2-OCF₃ | 0 |
| A-4827 | H | H | H | H | H | O | C(=O)CH₂OCH₃ | H | 2-OCHF₂ | 0 |
| A-4828 | H | H | H | H | H | O | C(=O)CH₂OCH₃ | H | 2-(cyclopropyloxy) | 0 |
| A-4829 | H | H | H | H | H | O | C(=O)CH₂OCH₃ | H | 2-(cyclobutyloxy) | 0 |
| A-4830 | H | H | H | H | H | O | C(=O)CH₂OCH₃ | H | 2-(cyclopentyloxy) | 0 |
| A-4831 | H | H | H | H | H | O | C(=O)CH₂OCH₃ | H | 2-((2,2-dichlorocyclopropyl)oxy) | 0 |
| A-4832 | H | H | H | H | H | O | C(=O)CH₂OCH₃ | H | 2-(oxiran-2-yl) | 0 |
| A-4833 | H | H | H | H | H | O | C(=O)CH₂OCH₃ | H | 2-SMe | 0 |
| A-4834 | H | H | H | H | H | O | C(=O)CH₂OCH₃ | H | 3-SMe | 0 |
| A-4835 | H | H | H | H | H | O | C(=O)CH₂OCH₃ | H | 2-S(=O)Me | 0 |
| A-4836 | H | H | H | H | H | O | C(=O)CH₂OCH₃ | H | 3-S(=O)Me | 0 |
| A-4837 | H | H | H | H | H | O | C(=O)CH₂OCH₃ | H | 2-S(=O)₂Me | 0 |
| A-4838 | H | H | H | H | H | O | C(=O)CH₂OCH₃ | H | 3-S(=O)₂Me | 0 |
| A-4839 | H | H | H | H | H | O | C(=O)CH₂OCH₃ | H | 2-SCF₃ | 0 |
| A-4840 | H | H | H | H | H | O | C(=O)CH₂OCH₃ | H | 3-SCF₃ | 0 |

TABLE 86

| compound | R¹ | R² | R³ | R⁴ | R⁵ | A | R⁶ | R⁷ | (R⁸)ₘ | p |
|---|---|---|---|---|---|---|---|---|---|---|
| A-4841 | H | H | H | H | H | O | C(=O)CH₂OCH₃ | H | 3-S(=O)CF₃ | 0 |
| A-4842 | H | H | H | H | H | O | C(=O)CH₂OCH₃ | H | 3-SCF(CF₃)₂ | 0 |
| A-4843 | H | H | H | H | H | O | C(=O)CH₂OCH₃ | H | 2-(cyclopropylthio) | 0 |
| A-4844 | H | H | H | H | H | O | C(=O)CH₂OCH₃ | H | 2-(cyclopropylsulfinyl) | 0 |
| A-4845 | H | H | H | H | H | O | C(=O)CH₂OCH₃ | H | 2-(cyclopropylsulfonyl) | 0 |
| A-4846 | H | H | H | H | H | O | C(=O)CH₂OCH₃ | H | 2-C(=O)Me | 0 |
| A-4847 | H | H | H | H | H | O | C(=O)CH₂OCH₃ | H | 2-CH₂C(=O)CH₃ | 0 |
| A-4848 | H | H | H | H | H | O | C(=O)CH₂OCH₃ | H | 2-CH₂C(=O)CF₃ | 0 |
| A-4849 | H | H | H | H | H | O | C(=O)CH₂OCH₃ | H | 2-CH₂OH | 0 |
| A-4850 | H | H | H | H | H | O | C(=O)CH₂OCH₃ | H | 2-CH₂OCH₃ | 0 |
| A-4851 | H | H | H | H | H | O | C(=O)CH₂OCH₃ | H | 2-CH₂OCH₂CH₃ | 0 |
| A-4852 | H | H | H | H | H | O | C(=O)CH₂OCH₃ | H | 2-CH₂SCH₃ | 0 |
| A-4853 | H | H | H | H | H | O | C(=O)CH₂OCH₃ | H | 2-CH₂S(=O)CH₃ | 0 |
| A-4854 | H | H | H | H | H | O | C(=O)CH₂OCH₃ | H | 2-CH₂S(=O)₂CH₃ | 0 |
| A-4855 | H | H | H | H | H | O | C(=O)CH₂OCH₃ | H | 2-(benzyloxy) | 0 |
| A-4856 | H | H | H | H | H | O | C(=O)CH₂OCH₃ | H | 2-NH₂ | 0 |
| A-4857 | H | H | H | H | H | O | C(=O)CH₂OCH₃ | H | 2-NHMe | 0 |
| A-4858 | H | H | H | H | H | O | C(=O)CH₂OCH₃ | H | 2-N(Me)₂ | 0 |
| A-4859 | H | H | H | H | H | O | C(=O)CH₂OCH₃ | H | 2-(1,3-dioxolan-2-yl) | 0 |
| A-4860 | H | H | H | H | H | O | C(=O)CH₂OCH₃ | H | 2-(1,3-dioxan-2-yl) | 0 |
| A-4861 | H | H | H | H | H | O | C(=O)CH₂OCH₃ | H | 2-(1H-imidazol-2-yl) | 0 |
| A-4862 | H | H | H | H | H | O | C(=O)CH₂OCH₃ | H | 2-(thiazol-2-yl) | 0 |
| A-4863 | H | H | H | H | H | O | C(=O)CH₂OCH₃ | H | 2-(oxazol-2-yl) | 0 |
| A-4864 | H | H | H | H | H | O | C(=O)CH₂OCH₃ | H | 2-CH=NOH | 0 |
| A-4865 | H | H | H | H | H | O | C(=O)CH₂OCH₃ | H | 2-CH=NOMe | 0 |
| A-4866 | H | H | H | H | H | O | C(=O)CH₂OCH₃ | H | 2-(4,5-dihydro-3-isoxazolyl) | 0 |
| A-4867 | H | H | H | H | H | O | C(=O)CH₂OCH₃ | H | 2-CN | 0 |
| A-4868 | H | H | H | H | H | O | C(=O)CH₂OCH₃ | H | 2-NO₂ | 0 |
| A-4869 | H | H | H | H | H | O | C(=O)CH₂OCH₃ | H | 2F,6-Cl | 0 |
| A-4870 | H | H | H | H | H | O | C(=O)CH₂OCH₃ | H | 2-F,6-Me | 0 |
| A-4871 | H | H | H | H | H | O | C(=O)CH₂OCH₃ | H | 3-F,6-Me | 0 |
| A-4872 | H | H | H | H | H | O | C(=O)CH₂OCH₃ | H | 4-F,2-Me | 0 |
| A-4873 | H | H | H | H | H | O | C(=O)CH₂OCH₃ | H | 2-F,6-OMe | 0 |
| A-4874 | H | H | H | H | H | O | C(=O)CH₂OCH₃ | H | 3-F,6-OMe | 0 |
| A-4875 | H | H | H | H | H | O | C(=O)CH₂OCH₃ | H | 2,6-Cl₂ | 0 |
| A-4876 | H | H | H | H | H | O | C(=O)CH₂OCH₃ | H | 2-Cl,6-Me | 0 |
| A-4877 | H | H | H | H | H | O | C(=O)CH₂OCH₃ | H | 3-Cl,6-Me | 0 |
| A-4878 | H | H | H | H | H | O | C(=O)CH₂OCH₃ | H | 4-Cl,2-Me | 0 |
| A-4879 | H | H | H | H | H | O | C(=O)CH₂OCH₃ | H | 2-Cl,5-CF₃ | 0 |
| A-4880 | H | H | H | H | H | O | C(=O)CH₂OCH₃ | H | 2-Cl,6-CF₃ | 0 |
| A-4881 | H | H | H | H | H | O | C(=O)CH₂OCH₃ | H | 2-Cl,6-OMe | 0 |
| A-4882 | H | H | H | H | H | O | C(=O)CH₂OCH₃ | H | 3-Cl,6-OMe | 0 |
| A-4883 | H | H | H | H | H | O | C(=O)CH₂OCH₃ | H | 4-Cl,2-OMe | 0 |
| A-4884 | H | H | H | H | H | O | C(=O)CH₂OCH₃ | H | 2,4-Me₂ | 0 |
| A-4885 | H | H | H | H | H | O | C(=O)CH₂OCH₃ | H | 2,5-Me₂ | 0 |
| A-4886 | H | H | H | H | H | O | C(=O)CH₂OCH₃ | H | 2,6-Me₂ | 0 |
| A-4887 | H | H | H | H | H | O | C(=O)CH₂OCH₃ | H | 2-Me,4-CF₃ | 0 |
| A-4888 | H | H | H | H | H | O | C(=O)CH₂OCH₃ | H | 2-Me,5-CF₃ | 0 |
| A-4889 | H | H | H | H | H | O | C(=O)CH₂OCH₃ | H | 2-Me,6-CF₃ | 0 |
| A-4890 | H | H | H | H | H | O | C(=O)CH₂OCH₃ | H | 2-Me,4-OMe | 0 |
| A-4891 | H | H | H | H | H | O | C(=O)CH₂OCH₃ | H | 2-Me,5-OMe | 0 |
| A-4892 | H | H | H | H | H | O | C(=O)CH₂OCH₃ | H | 2-Me,6-OMe | 0 |

TABLE 86-continued

| compound | R¹ | R² | R³ | R⁴ | R⁵ | A | R⁶ | R⁷ | (R⁸)$_m$ | p |
|---|---|---|---|---|---|---|---|---|---|---|
| A-4893 | H | H | H | H | H | O | C(=O)CH₂OCH₃ | H | 3-Me,6-OMe | 0 |
| A-4894 | H | H | H | H | H | O | C(=O)CH₂OCH₃ | H | 4-Me,2-OMe | 0 |
| A-4895 | H | H | H | H | H | O | C(=O)CH₂OCH₃ | H | 2,5-OMe₂ | 0 |
| A-4896 | H | H | H | H | H | O | C(=O)CH₂OCH₃ | H | 2,6-OMe₂ | 0 |
| A-4897 | H | H | H | H | H | O | C(=O)CH₂OCH₃ | H | 2-OMe,6-CF₃ | 0 |

TABLE 87

| compound | R¹ | R² | R³ | R⁴ | R⁵ | A | R⁶ | R⁷ | (R⁸)$_m$ | p |
|---|---|---|---|---|---|---|---|---|---|---|
| A-4898 | H | H | H | H | H | O | C(=O)CH₂OCH₃ | H | 2-CHF₂,5-F | 0 |
| A-4899 | H | H | H | H | H | O | C(=O)CH₂OCH₃ | H | 2-CHF₂,6-F | 0 |
| A-4900 | H | H | H | H | H | O | C(=O)CH₂OCH₃ | H | 2-CHF₂,5-Me | 0 |
| A-4901 | H | H | H | H | H | O | C(=O)CH₂OCH₃ | H | 2-CHF₂,6-Me | 0 |
| A-4902 | H | H | H | H | H | O | C(=O)CH₂OCH₃ | H | 2-cyclopropyl,5-F | 0 |
| A-4903 | H | H | H | H | H | O | C(=O)CH₂OCH₃ | H | 2-cyclopropyl,6-F | 0 |
| A-4904 | H | H | H | H | H | O | C(=O)CH₂OCH₃ | H | 2-cyclopropyl,5-Me | 0 |
| A-4905 | H | H | H | H | H | O | C(=O)CH₂OCH₃ | H | 2-cyclopropyl,6-Me | 0 |
| A-4906 | H | H | H | H | H | O | C(=O)CH₂OCH₃ | H | 2-ethenyl,6-F | 0 |
| A-4907 | H | H | H | H | H | O | C(=O)CH₂OCH₃ | H | 2-ethenyl,6-Me | 0 |
| A-4908 | H | H | H | H | H | O | C(=O)CH₂OCH₃ | H | 2-OEt,5-F | 0 |
| A-4909 | H | H | H | H | H | O | C(=O)CH₂OCH₃ | H | 2-OEt,6-F | 0 |
| A-4910 | H | H | H | H | H | O | C(=O)CH₂OCH₃ | H | 2-OEt,5-Cl | 0 |
| A-4911 | H | H | H | H | H | O | C(=O)CH₂OCH₃ | H | 2-OEt,6-Cl | 0 |
| A-4912 | H | H | H | H | H | O | C(=O)CH₂OCH₃ | H | 2-OEt,5-Me | 0 |
| A-4913 | H | H | H | H | H | O | C(=O)CH₂OCH₃ | H | 2-OEt,6-Me | 0 |
| A-4914 | H | H | H | H | H | O | C(=O)CH₂OCH₃ | H | 2-OCHF₂,5-F | 0 |
| A-4915 | H | H | H | H | H | O | C(=O)CH₂OCH₃ | H | 2-OCHF₂,6-F | 0 |
| A-4916 | H | H | H | H | H | O | C(=O)CH₂OCH₃ | H | 2-OCHF₂,5-Me | 0 |
| A-4917 | H | H | H | H | H | O | C(=O)CH₂OCH₃ | H | 2-OCHF₂,6-Me | 0 |
| A-4918 | H | H | H | H | H | O | C(=O)CH₂OCH₃ | H | 2-(cyclopropyloxy),5-F | 0 |
| A-4919 | H | H | H | H | H | O | C(=O)CH₂OCH₃ | H | 2-(cyclopropyloxy),6-F | 0 |
| A-4920 | H | H | H | H | H | O | C(=O)CH₂OCH₃ | H | 2-(cyclopropyloxy),5-Me | 0 |
| A-4921 | H | H | H | H | H | O | C(=O)CH₂OCH₃ | H | 2-(cyclopropyloxy),6-Me | 0 |
| A-4922 | H | H | H | H | H | O | C(=O)CH₂OCH₃ | H | 2-SMe,5-F | 0 |
| A-4923 | H | H | H | H | H | O | C(=O)CH₂OCH₃ | H | 2-SMe,6-F | 0 |
| A-4924 | H | H | H | H | H | O | C(=O)CH₂OCH₃ | H | 2-SMe,5-Me | 0 |
| A-4925 | H | H | H | H | H | O | C(=O)CH₂OCH₃ | H | 2-SMe,6-Me | 0 |
| A-4926 | H | H | H | H | H | O | C(=O)CH₂OCH₃ | H | 2-S(=O)Me,5-F | 0 |
| A-4927 | H | H | H | H | H | O | C(=O)CH₂OCH₃ | H | 2-S(=O)Me,6-F | 0 |
| A-4928 | H | H | H | H | H | O | C(=O)CH₂OCH₃ | H | 2-S(=O)Me,5-Me | 0 |
| A-4929 | H | H | H | H | H | O | C(=O)CH₂OCH₃ | H | 2-S(=O)Me,6-Me | 0 |
| A-4930 | H | H | H | H | H | O | C(=O)CH₂OCH₃ | H | 2-S(=O)₂Me,5-F | 0 |
| A-4931 | H | H | H | H | H | O | C(=O)CH₂OCH₃ | H | 2-S(=O)₂Me,6-F | 0 |
| A-4932 | H | H | H | H | H | O | C(=O)CH₂OCH₃ | H | 2-S(=O)₂Me,5-Me | 0 |
| A-4933 | H | H | H | H | H | O | C(=O)CH₂OCH₃ | H | 2-S(=O)₂Me,6-Me | 0 |
| A-4934 | H | H | H | H | H | O | C(=O)CH₂OCH₃ | H | 2-SCF₃,5-F | 0 |
| A-4935 | H | H | H | H | H | O | C(=O)CH₂OCH₃ | H | 2-SCF₃,6-F | 0 |
| A-4936 | H | H | H | H | H | O | C(=O)CH₂OCH₃ | H | 2-SCF₃,5-Me | 0 |
| A-4937 | H | H | H | H | H | O | C(=O)CH₂OCH₃ | H | 2-SCF₃,6-Me | 0 |
| A-4938 | H | H | H | H | H | O | C(=O)CH₂OCH₃ | H | 2-S(=O)CF₃,5-F | 0 |
| A-4939 | H | H | H | H | H | O | C(=O)CH₂OCH₃ | H | 2-S(=O)CF₃,6-F | 0 |
| A-4940 | H | H | H | H | H | O | C(=O)CH₂OCH₃ | H | 2-S(=O)CF₃,5-Me | 0 |
| A-4941 | H | H | H | H | H | O | C(=O)CH₂OCH₃ | H | 2-S(=O)CF₃,6-Me | 0 |
| A-4942 | H | H | H | H | H | O | C(=O)CH₂OCH₃ | H | 2-S(=O)₂CF₃,5-F | 0 |
| A-4943 | H | H | H | H | H | O | C(=O)CH₂OCH₃ | H | 2-S(=O)₂CF₃,6-F | 0 |
| A-4944 | H | H | H | H | H | O | C(=O)CH₂OCH₃ | H | 2-S(=O)₂CF₃,5-Me | 0 |
| A-4945 | H | H | H | H | H | O | C(=O)CH₂OCH₃ | H | 2-S(=O)₂CF₃,6-Me | 0 |
| A-4946 | H | H | H | H | H | O | C(=O)CH₂OCH₃ | H | 2-(cyclopropylthio),5-F | 0 |
| A-4947 | H | H | H | H | H | O | C(=O)CH₂OCH₃ | H | 2-(cyclopropylthio),6-F | 0 |
| A-4948 | H | H | H | H | H | O | C(=O)CH₂OCH₃ | H | 2-(cyclopropylthio),5-Me | 0 |
| A-4949 | H | H | H | H | H | O | C(=O)CH₂OCH₃ | H | 2-(cyclopropylthio),6-Me | 0 |
| A-4950 | H | H | H | H | H | O | C(=O)CH₂OCH₃ | H | 2-C(=O)Me,5-F | 0 |
| A-4951 | H | H | H | H | H | O | C(=O)CH₂OCH₃ | H | 2-C(=O)Me,6-F | 0 |
| A-4952 | H | H | H | H | H | O | C(=O)CH₂OCH₃ | H | 2-C(=O)Me,5-Me | 0 |
| A-4953 | H | H | H | H | H | O | C(=O)CH₂OCH₃ | H | 2-C(=O)Me,6-Me | 0 |
| A-4954 | H | H | H | H | H | O | C(=O)CH₂OCH₃ | H | 2-CH₂OH,5-F | 0 |

TABLE 88

| compound | R¹ | R² | R³ | R⁴ | R⁵ | A | R⁶ | R⁷ | (R⁸)ₘ | p |
|---|---|---|---|---|---|---|---|---|---|---|
| A-4955 | H | H | H | H | H | O | C(=O)CH₂OCH₃ | H | 2-CH₂OH,6-F | 0 |
| A-4956 | H | H | H | H | H | O | C(=O)CH₂OCH₃ | H | 2-CH₂OH,5-Me | 0 |
| A-4957 | H | H | H | H | H | O | C(=O)CH₂OCH₃ | H | 2-CH₂OH,6-Me | 0 |
| A-4958 | H | H | H | H | H | O | C(=O)CH₂OCH₃ | H | 2-CH₂OCH₃,4-F | 0 |
| A-4959 | H | H | H | H | H | O | C(=O)CH₂OCH₃ | H | 2-CH₂OCH₃,5-F | 0 |
| A-4960 | H | H | H | H | H | O | C(=O)CH₂OCH₃ | H | 2-CH₂OCH₃,6-F | 0 |
| A-4961 | H | H | H | H | H | O | C(=O)CH₂OCH₃ | H | 2-CH₂OCH₃,4-Me | 0 |
| A-4962 | H | H | H | H | H | O | C(=O)CH₂OCH₃ | H | 2-CH₂OCH₃,5-Me | 0 |
| A-4963 | H | H | H | H | H | O | C(=O)CH₂OCH₃ | H | 2-CH₂OCH₃,6-Me | 0 |
| A-4964 | H | H | H | H | H | O | C(=O)CH₂OCH₃ | H | 2-OC(=O)CH₃,5-F | 0 |
| A-4965 | H | H | H | H | H | O | C(=O)CH₂OCH₃ | H | 2-OC(=O)CH₃,6-F | 0 |
| A-4966 | H | H | H | H | H | O | C(=O)CH₂OCH₃ | H | 2-OC(=O)CH₃,5-Me | 0 |
| A-4967 | H | H | H | H | H | O | C(=O)CH₂OCH₃ | H | 2-OC(=O)CH₃,6-Me | 0 |
| A-4968 | H | H | H | H | H | O | C(=O)CH₂OCH₃ | H | 2-OS(=O)₂CH₃,5-F | 0 |
| A-4969 | H | H | H | H | H | O | C(=O)CH₂OCH₃ | H | 2-OS(=O)₂CH₃,6-F | 0 |
| A-4970 | H | H | H | H | H | O | C(=O)CH₂OCH₃ | H | 2-OS(=O)₂CH₃,5-Me | 0 |
| A-4971 | H | H | H | H | H | O | C(=O)CH₂OCH₃ | H | 2-OS(=O)₂CH₃,6-Me | 0 |
| A-4972 | H | H | H | H | H | O | C(=O)CH₂OCH₃ | H | 2-CH₂SCH₃,5-F | 0 |
| A-4973 | H | H | H | H | H | O | C(=O)CH₂OCH₃ | H | 2-CH₂SCH₃,6-F | 0 |
| A-4974 | H | H | H | H | H | O | C(=O)CH₂OCH₃ | H | 2-CH₂SCH₃,5-Me | 0 |
| A-4975 | H | H | H | H | H | O | C(=O)CH₂OCH₃ | H | 2-CH₂SCH₃,6-Me | 0 |
| A-4976 | H | H | H | H | H | O | C(=O)CH₂OCH₃ | H | 2-NMe₂,5-F | 0 |
| A-4977 | H | H | H | H | H | O | C(=O)CH₂OCH₃ | H | 2-NMe₂,6-F | 0 |
| A-4978 | H | H | H | H | H | O | C(=O)CH₂OCH₃ | H | 2-NMe₂,5-Me | 0 |
| A-4979 | H | H | H | H | H | O | C(=O)CH₂OCH₃ | H | 2-NMe₂,6-Me | 0 |
| A-4980 | H | H | H | H | H | O | C(=O)CH₂OCH₃ | H | 2-CN,4-F | 0 |
| A-4981 | H | H | H | H | H | O | C(=O)CH₂OCH₃ | H | 2-CN,5-F | 0 |
| A-4982 | H | H | H | H | H | O | C(=O)CH₂OCH₃ | H | 2-CN,6-F | 0 |
| A-4983 | H | H | H | H | H | O | C(=O)CH₂OCH₃ | H | 2-CN,6-Me | 0 |
| A-4984 | H | H | H | H | H | O | C(=O)CH₂OCH₃ | H | 2-CN,5-OMe | 0 |
| A-4985 | H | H | H | H | H | O | C(=O)CH₂OCH₃ | H | 2-CN,6-OMe | 0 |
| A-4986 | H | H | H | H | H | O | C(=O)CH₂OCH₃ | H | 3-CN,6-Me | 0 |
| A-4987 | H | H | H | H | H | O | C(=O)CH₂OCH₃ | H | 3-CN,6-OMe | 0 |
| A-4988 | H | H | H | H | H | O | C(=O)CH₂OCH₃ | H | 4-CN,2-Me | 0 |
| A-4989 | H | H | H | H | H | O | C(=O)CH₂OCH₃ | H | 4-CN,2-OMe | 0 |
| A-4990 | H | H | H | H | H | O | C(=O)CH₂OCH₃ | H | 2-NO₂,4-F | 0 |
| A-4991 | H | H | H | H | H | O | C(=O)CH₂OCH₃ | H | 2-NO₂,5-F | 0 |
| A-4992 | H | H | H | H | H | O | C(=O)CH₂OCH₃ | H | 2-NO₂,6-F | 0 |
| A-4993 | H | H | H | H | H | O | C(=O)CH₂OCH₃ | H | 2-NO₂,4-Me | 0 |
| A-4994 | H | H | H | H | H | O | C(=O)CH₂OCH₃ | H | 2-NO₂,5-Me | 0 |
| A-4995 | H | H | H | H | H | O | C(=O)CH₂OCH₃ | H | 2-NO₂,6-Me | 0 |
| A-4996 | H | H | H | H | H | O | C(=O)CH₂OCH₃ | H | 2-Me,4,5-F₂ | 0 |
| A-4997 | H | H | H | H | H | O | C(=O)CH₂OCH₃ | H | 2-Me,6-Et | 0 |
| A-4998 | H | H | H | H | H | O | C(=O)CH₂OCH₃ | H | 2-cyclopropyl,6-OMe | 0 |
| A-4999 | H | H | H | H | H | O | C(=O)CH₂OCH₃ | H | 2-Me,5-Et | 0 |
| A-5000 | H | H | H | H | H | O | C(=O)CH₂OCH₃ | H | 2,6-Et₂ | 0 |
| A-5001 | H | H | H | H | H | O | C(=O)CH₂OCH₃ | H | 2-Et,6-F | 0 |
| A-5002 | H | H | H | H | H | O | C(=O)CH₂OCH₃ | H | 2-CH₂OCH₃,6-Cl | 0 |
| A-5003 | H | H | H | H | H | O | C(=O)CH₂OCH₃ | H | 2-CH₂OCH₂CH₃,6-Cl | 0 |
| A-5004 | H | H | H | H | H | O | C(=O)CH₂OCH₃ | H | 2-CH₂NMe₂ | 0 |
| A-5005 | H | H | H | H | H | O | C(=O)cyclopropyl | H | H | 0 |
| A-5006 | H | H | H | H | H | O | C(=O)cyclopropyl | H | 2-F | 0 |
| A-5007 | H | H | H | H | H | O | C(=O)cyclopropyl | H | 2-Cl | 0 |
| A-5008 | H | H | H | H | H | O | C(=O)cyclopropyl | H | 2-Br | 0 |
| A-5009 | H | H | H | H | H | O | C(=O)cyclopropyl | H | 2-OH | 0 |
| A-5010 | H | H | H | H | H | O | C(=O)cyclopropyl | H | 2-Me | 0 |
| A-5011 | H | H | H | H | H | O | C(=O)cyclopropyl | H | 2-Et | 0 |

TABLE 89

| compound | R¹ | R² | R³ | R⁴ | R⁵ | A | R⁶ | R⁷ | (R⁸)ₘ | p |
|---|---|---|---|---|---|---|---|---|---|---|
| A-5012 | H | H | H | H | H | O | C(=O)cyclopropyl | H | 2-Pr | 0 |
| A-5013 | H | H | H | H | H | O | C(=O)cyclopropyl | H | 2-CF₃ | 0 |
| A-5014 | H | H | H | H | H | O | C(=O)cyclopropyl | H | 2-CHF₂ | 0 |
| A-5015 | H | H | H | H | H | O | C(=O)cyclopropyl | H | 2-CH₂F | 0 |
| A-5016 | H | H | H | H | H | O | C(=O)cyclopropyl | H | 2-CF₂Cl | 0 |
| A-5017 | H | H | H | H | H | O | C(=O)cyclopropyl | H | 2-cyclopropyl | 0 |
| A-5018 | H | H | H | H | H | O | C(=O)cyclopropyl | H | 2-cyclobutyl | 0 |
| A-5019 | H | H | H | H | H | O | C(=O)cyclopropyl | H | 2-cyclopentyl | 0 |
| A-5020 | H | H | H | H | H | O | C(=O)cyclopropyl | H | 2-ethenyl | 0 |
| A-5021 | H | H | H | H | H | O | C(=O)cyclopropyl | H | 2-allyl | 0 |
| A-5022 | H | H | H | H | H | O | C(=O)cyclopropyl | H | 2-(prop-1-en-1-yl) | 0 |
| A-5023 | H | H | H | H | H | O | C(=O)cyclopropyl | H | 2-(trifluoroethenyl) | 0 |
| A-5024 | H | H | H | H | H | O | C(=O)cyclopropyl | H | 2-OMe | 0 |

TABLE 89-continued

| compound | R¹ | R² | R³ | R⁴ | R⁵ | A | R⁶ | R⁷ | (R⁸)ₘ | p |
|---|---|---|---|---|---|---|---|---|---|---|
| A-5025 | H | H | H | H | H | O | C(=O)cyclopropyl | H | 2-OEt | 0 |
| A-5026 | H | H | H | H | H | O | C(=O)cyclopropyl | H | 2-OPr | 0 |
| A-5027 | H | H | H | H | H | O | C(=O)cyclopropyl | H | 2-O(i-Pr) | 0 |
| A-5028 | H | H | H | H | H | O | C(=O)cyclopropyl | H | 2-OCF₃ | 0 |
| A-5029 | H | H | H | H | H | O | C(=O)cyclopropyl | H | 2-OCHF₂ | 0 |
| A-5030 | H | H | H | H | H | O | C(=O)cyclopropyl | H | 2-(cyclopropyloxy) | 0 |
| A-5031 | H | H | H | H | H | O | C(=O)cyclopropyl | H | 2-(cyclobutyloxy) | 0 |
| A-5032 | H | H | H | H | H | O | C(=O)cyclopropyl | H | 2-(cyclopentyloxy) | 0 |
| A-5033 | H | H | H | H | H | O | C(=O)cyclopropyl | H | 2-((2,2-dichlorocyclopropyl)oxy) | 0 |
| A-5034 | H | H | H | H | H | O | C(=O)cyclopropyl | H | 2-(oxiran-2-yl) | 0 |
| A-5035 | H | H | H | H | H | O | C(=O)cyclopropyl | H | 2-SMe | 0 |
| A-5036 | H | H | H | H | H | O | C(=O)cyclopropyl | H | 3-SMe | 0 |
| A-5037 | H | H | H | H | H | O | C(=O)cyclopropyl | H | 2-S(=O)Me | 0 |
| A-5038 | H | H | H | H | H | O | C(=O)cyclopropyl | H | 3-S(=O)Me | 0 |
| A-5039 | H | H | H | H | H | O | C(=O)cyclopropyl | H | 2-S(=O)₂Me | 0 |
| A-5040 | H | H | H | H | H | O | C(=O)cyclopropyl | H | 3-S(=O)₂Me | 0 |
| A-5041 | H | H | H | H | H | O | C(=O)cyclopropyl | H | 2-SCF₃ | 0 |
| A-5042 | H | H | H | H | H | O | C(=O)cyclopropyl | H | 3-SCF₃ | 0 |
| A-5043 | H | H | H | H | H | O | C(=O)cyclopropyl | H | 3-S(=O)CF₃ | 0 |
| A-5044 | H | H | H | H | H | O | C(=O)cyclopropyl | H | 3-SCF(CF₃)₂ | 0 |
| A-5045 | H | H | H | H | H | O | C(=O)cyclopropyl | H | 2-(cyclopropylthio) | 0 |
| A-5046 | H | H | H | H | H | O | C(=O)cyclopropyl | H | 2-(cyclopropylsulfinyl) | 0 |
| A-5047 | H | H | H | H | H | O | C(=O)cyclopropyl | H | 2-(cyclopropylsulfonyl) | 0 |
| A-5048 | H | H | H | H | H | O | C(=O)cyclopropyl | H | 2-C(=O)Me | 0 |
| A-5049 | H | H | H | H | H | O | C(=O)cyclopropyl | H | 2-CH₂C(=O)CH₃ | 0 |
| A-5050 | H | H | H | H | H | O | C(=O)cyclopropyl | H | 2-CH₂C(=O)CF₃ | 0 |
| A-5051 | H | H | H | H | H | O | C(=O)cyclopropyl | H | 2-CH₂OH | 0 |
| A 5052 | H | H | H | H | H | O | C(=O)cyclopropyl | H | 2-CH₂OCH₃ | 0 |
| A-5053 | H | H | H | H | H | O | C(=O)cyclopropyl | H | 2-CH₂OCH₂CH₃ | 0 |
| A-5054 | H | H | H | H | H | O | C(=O)cyclopropyl | H | 2-CH₂SCH₃ | 0 |
| A-5055 | H | H | H | H | H | O | C(=O)cyclopropyl | H | 2-CH₂S(=O)CH₃ | 0 |
| A-5056 | H | H | H | H | H | O | C(=O)cyclopropyl | H | 2-CH₂S(=O)2CH₃ | 0 |
| A-5057 | H | H | H | H | H | O | C(=O)cyclopropyl | H | 2-(benzyloxy) | 0 |
| A-5058 | H | H | H | H | H | O | C(=O)cyclopropyl | H | 2-NH₂ | 0 |
| A-5059 | H | H | H | H | H | O | C(=O)cyclopropyl | H | 2-NHMe | 0 |
| A-5060 | H | H | H | H | H | O | C(=O)cyclopropyl | H | 2-N(Me)₂ | 0 |
| A-5061 | H | H | H | H | H | O | C(=O)cyclopropyl | H | 2-(1,3-dioxolan-2-yl) | 0 |
| A-5062 | H | H | H | H | H | O | C(=O)cyclopropyl | H | 2-(1,3-dioxan-2-yl) | 0 |
| A-5063 | H | H | H | H | H | O | C(=O)cyclopropyl | H | 2-(1H-imidazol-2-yl) | 0 |
| A 5064 | H | H | H | H | H | O | C(=O)cyclopropyl | H | 2-(thiazol-2-yl) | 0 |
| A-5065 | H | H | H | H | H | O | C(=O)cyclopropyl | H | 2-(oxazol-2-yl) | 0 |
| A-5066 | H | H | H | H | H | O | C(=O)cyclopropyl | H | 2-CH=NOH | 0 |
| A-5067 | H | H | H | H | H | O | C(=O)cyclopropyl | H | 2-CH=NOMe | 0 |
| A-5068 | H | H | H | H | H | O | C(=O)cyclopropyl | H | 2-(4,5-dihydro-3-isoxazolyl) | 0 |

TABLE 90

| compound | R¹ | R² | R³ | R⁴ | R⁵ | A | R⁶ | R⁷ | (R⁸)ₘ | p |
|---|---|---|---|---|---|---|---|---|---|---|
| A-5069 | H | H | H | H | H | O | C(=O)cyclopropyl | H | 2-CN | 0 |
| A-5070 | H | H | H | H | H | O | C(=O)cyclopropyl | H | 2-NO₂ | 0 |
| A-5071 | H | H | H | H | H | O | C(=O)cyclopropyl | H | 2-F,6-Cl | 0 |
| A-5072 | H | H | H | H | H | O | C(=O)cyclopropyl | H | 2-F,6-Me | 0 |
| A-5073 | H | H | H | H | H | O | C(=O)cyclopropyl | H | 3-F,6-Me | 0 |
| A-5074 | H | H | H | H | H | O | C(=O)cyclopropyl | H | 4-F,2-Me | 0 |
| A-5075 | H | H | H | H | H | O | C(=O)cyclopropyl | H | 2-F,6-OMe | 0 |
| A-5076 | H | H | H | H | H | O | C(=O)cyclopropyl | H | 3-F,6-OMe | 0 |
| A-5077 | H | H | H | H | H | O | C(=O)cyclopropyl | H | 2,6-Cl₂ | 0 |
| A-5078 | H | H | H | H | H | O | C(=O)cyclopropyl | H | 2-Cl,6-Me | 0 |
| A-5079 | H | H | H | H | H | O | C(=O)cyclopropyl | H | 3-Cl,6-Me | 0 |
| A-5080 | H | H | H | H | H | O | C(=O)cyclopropyl | H | 4-Cl,2-Me | 0 |
| A-5081 | H | H | H | H | H | O | C(=O)cyclopropyl | H | 2-Cl,5-CF₃ | 0 |
| A-5082 | H | H | H | H | H | O | C(=O)cyclopropyl | H | 2-Cl,6-CF₃ | 0 |
| A-5083 | H | H | H | H | H | O | C(=O)cyclopropyl | H | 2-Cl,6 OMe | 0 |
| A-5084 | H | H | H | H | H | O | C(=O)cyclopropyl | H | 3-Cl,6-OMe | 0 |
| A-5085 | H | H | H | H | H | O | C(=O)cyclopropyl | H | 4-Cl,2-OMe | 0 |
| A-5086 | H | H | H | H | H | O | C(=O)cyclopropyl | H | 2,4-Me₂ | 0 |
| A-5087 | H | H | H | H | H | O | C(=O)cyclopropyl | H | 2,5-Me₂ | 0 |
| A-5088 | H | H | H | H | H | O | C(=O)cyclopropyl | H | 2,6-Me₂ | 0 |
| A-5089 | H | H | H | H | H | O | C(=O)cyclopropyl | H | 2-Me,4-CF₃ | 0 |
| A-5090 | H | H | H | H | H | O | C(=O)cyclopropyl | H | 2-Me,5-CF₃ | 0 |
| A-5091 | H | H | H | H | H | O | C(=O)cyclopropyl | H | 2-Me,6-CF₃ | 0 |
| A-5092 | H | H | H | H | H | O | C(=O)cyclopropyl | H | 2-Me,4-OMe | 0 |
| A-5093 | H | H | H | H | H | O | C(=O)cyclopropyl | H | 2-Me,5-OMe | 0 |
| A-5094 | H | H | H | H | H | O | C(=O)cyclopropyl | H | 2-Me,6-OMe | 0 |

TABLE 90-continued

| compound | R¹ | R² | R³ | R⁴ | R⁵ | A | R⁶ | R⁷ | (R⁸)$_m$ | p |
|---|---|---|---|---|---|---|---|---|---|---|
| A-5095 | H | H | H | H | H | O | C(=O)cyclopropyl | H | 3-Me,6-OMe | 0 |
| A-5096 | H | H | H | H | H | O | C(=O)cyclopropyl | H | 4-Me,2-OMe | 0 |
| A-5097 | H | H | H | H | H | O | C(=O)cyclopropyl | H | 2,5-OMe$_2$ | 0 |
| A-5098 | H | H | H | H | H | O | C(=O)cyclopropyl | H | 2,6-OMe$_2$ | 0 |
| A-5099 | H | H | H | H | H | O | C(=O)cyclopropyl | H | 2-OMe,6-CF$_3$ | 0 |
| A-5100 | H | H | H | H | H | O | C(=O)cyclopropyl | H | 2-CHF$_2$,5-F | 0 |
| A-5101 | H | H | H | H | H | O | C(=O)cyclopropyl | H | 2-CHF$_2$,6-F | 0 |
| A-5102 | H | H | H | H | H | O | C(=O)cyclopropyl | H | 2-CHF$_2$,5-Me | 0 |
| A-5103 | H | H | H | H | H | O | C(=O)cyclopropyl | H | 2-CHF$_2$,6-Me | 0 |
| A-5104 | H | H | H | H | H | O | C(=O)cyclopropyl | H | 2-cyclopropyl,5-F | 0 |
| A-5105 | H | H | H | H | H | O | C(=O)cyclopropyl | H | 2-cyclopropyl,6-F | 0 |
| A-5106 | H | H | H | H | H | O | C(=O)cyclopropyl | H | 2-cyclopropyl,5-Me | 0 |
| A-5107 | H | H | H | H | H | O | C(=O)cyclopropyl | H | 2-cyclopropyl,6-Me | 0 |
| A-5108 | H | H | H | H | H | O | C(=O)cyclopropyl | H | 2-ethenyl,6-F | 0 |
| A-5109 | H | H | H | H | H | O | C(=O)cyclopropyl | H | 2-ethenyl,6-Me | 0 |
| A-5110 | H | H | H | H | H | O | C(=O)cyclopropyl | H | 2-OEt,5-F | 0 |
| A-5111 | H | H | H | H | H | O | C(=O)cyclopropyl | H | 2-OEt,6-F | 0 |
| A-5112 | H | H | H | H | H | O | C(=O)cyclopropyl | H | 2-OEt,5-Cl | 0 |
| A-5113 | H | H | H | H | H | O | C(=O)cyclopropyl | H | 2-OEt,6-Cl | 0 |
| A-5114 | H | H | H | H | H | O | C(=O)cyclopropyl | H | 2-OEt,5-Me | 0 |
| A-5115 | H | H | H | H | H | O | C(=O)cyclopropyl | H | 2-OEt,6-Me | 0 |
| A-5116 | H | H | H | H | H | O | C(=O)cyclopropyl | H | 2-OCHF$_2$,5-F | 0 |
| A-5117 | H | H | H | H | H | O | C(=O)cyclopropyl | H | 2-OCHF$_2$,6-F | 0 |
| A-5118 | H | H | H | H | H | O | C(=O)cyclopropyl | H | 2-OCHF$_2$,5-Me | 0 |
| A-5119 | H | H | H | H | H | O | C(=O)cyclopropyl | H | 2-OCHF$_2$,6-Me | 0 |
| A-5120 | H | H | H | H | H | O | C(=O)cyclopropyl | H | 2-(cyclopropyloxy),5-F | 0 |
| A-5121 | H | H | H | H | H | O | C(=O)cyclopropyl | H | 2-(cyclopropyloxy),6-F | 0 |
| A-5122 | H | H | H | H | H | O | C(=O)cyclopropyl | H | 2-(cyclopropyloxy),5-Me | 0 |
| A-5123 | H | H | H | H | H | O | C(=O)cyclopropyl | H | 2-(cyclopropyloxy),6-Me | 0 |
| A-5124 | H | H | H | H | H | O | C(=O)cyclopropyl | H | 2-SMe,5-F | 0 |
| A-5125 | H | H | H | H | H | O | C(=O)cyclopropyl | H | 2-SMe,6-F | 0 |

TABLE 91

| compound | R¹ | R² | R³ | R⁴ | R⁵ | A | R⁶ | R⁷ | (R⁸)$_m$ | p |
|---|---|---|---|---|---|---|---|---|---|---|
| A-5126 | H | H | H | H | H | O | C(=O)cyclopropyl | H | 2-SMe,5-Me | 0 |
| A-5127 | H | H | H | H | H | O | C(=O)cyclopropyl | H | 2-SMe,6-Me | 0 |
| A-5128 | H | H | H | H | H | O | C(=O)cyclopropyl | H | 2-S(=O)Me,5-F | 0 |
| A-5129 | H | H | H | H | H | O | C(=O)cyclopropyl | H | 2-S(=O)Me,6-F | 0 |
| A-5130 | H | H | H | H | H | O | C(=O)cyclopropyl | H | 2-S(=O)Me,5-Me | 0 |
| A-5131 | H | H | H | H | H | O | C(=O)cyclopropyl | H | 2-S(=O)Me,6-Me | 0 |
| A-5132 | H | H | H | H | H | O | C(=O)cyclopropyl | H | 2-S(=O)$_2$Me,5-F | 0 |
| A-5133 | H | H | H | H | H | O | C(=O)cyclopropyl | H | 2-S(=O)$_2$Me,6-F | 0 |
| A-5134 | H | H | H | H | H | O | C(=O)cyclopropyl | H | 2-S(=O)$_2$Me,5-Me | 0 |
| A-5135 | H | H | H | H | H | O | C(=O)cyclopropyl | H | 2-S(=O)$_2$Me,6-Me | 0 |
| A-5136 | H | H | H | H | H | O | C(=O)cyclopropyl | H | 2-SCF$_3$,5-F | 0 |
| A-5137 | H | H | H | H | H | O | C(=O)cyclopropyl | H | 2-SCF$_3$,6-F | 0 |
| A-5138 | H | H | H | H | H | O | C(=O)cyclopropyl | H | 2-SCF$_3$,5-Me | 0 |
| A-5139 | H | H | H | H | H | O | C(=O)cyclopropyl | H | 2-SCF$_3$,6-Me | 0 |
| A-5140 | H | H | H | H | H | O | C(=O)cyclopropyl | H | 2-S(=O)CF$_3$,5-F | 0 |
| A-5141 | H | H | H | H | H | O | C(=O)cyclopropyl | H | 2-S(=O)CF$_3$,6-F | 0 |
| A-5142 | H | H | H | H | H | O | C(=O)cyclopropyl | H | 2-S(=O)CF$_3$,5-Me | 0 |
| A-5143 | H | H | H | H | H | O | C(=O)cyclopropyl | H | 2-S(=O)CF$_3$,6-Me | 0 |
| A-5144 | H | H | H | H | H | O | C(=O)cyclopropyl | H | 2-S(=O)$_2$CF$_3$,5-F | 0 |
| A-5145 | H | H | H | H | H | O | C(=O)cyclopropyl | H | 2-S(=O)$_2$CF$_3$,6-F | 0 |
| A-5146 | H | H | H | H | H | O | C(=O)cyclopropyl | H | 2-S(=O)$_2$CF$_3$,5-Me | 0 |
| A-5147 | H | H | H | H | H | O | C(=O)cyclopropyl | H | 2-S(=O)$_2$CF$_3$,6-Me | 0 |
| A-5148 | H | H | H | H | H | O | C(=O)cyclopropyl | H | 2-(cyclopropylthio),5-F | 0 |
| A-5149 | H | H | H | H | H | O | C(=O)cyclopropyl | H | 2-(cyclopropylthio),6-F | 0 |
| A-5150 | H | H | H | H | H | O | C(=O)cyclopropyl | H | 2-(cyclopropylthio),5-Me | 0 |
| A-5151 | H | H | H | H | H | O | C(=O)cyclopropyl | H | 2-(cyclopropylthio),6-Me | 0 |
| A-5152 | H | H | H | H | H | O | C(=O)cyclopropyl | H | 2-C(=O)Me,5-F | 0 |
| A-5153 | H | H | H | H | H | O | C(=O)cyclopropyl | H | 2-C(=O)Me,6-F | 0 |
| A-5154 | H | H | H | H | H | O | C(=O)cyclopropyl | H | 2-C(=O)Me,5-Me | 0 |
| A-5155 | H | H | H | H | H | O | C(=O)cyclopropyl | H | 2-C(=O)Me,6-Me | 0 |
| A-5156 | H | H | H | H | H | O | C(=O)cyclopropyl | H | 2-CH$_2$OH,5-F | 0 |
| A-5157 | H | H | H | H | H | O | C(=O)cyclopropyl | H | 2-CH$_2$OH,6-F | 0 |
| A-5158 | H | H | H | H | H | O | C(=O)cyclopropyl | H | 2-CH$_2$OH,5-Me | 0 |
| A-5159 | H | H | H | H | H | O | C(=O)cyclopropyl | H | 2-CH$_2$OH,6-Me | 0 |
| A-5160 | H | H | H | H | H | O | C(=O)cyclopropyl | H | 2-CH$_2$OCH$_3$,4-F | 0 |
| A-5161 | H | H | H | H | H | O | C(=O)cyclopropyl | H | 2-CH$_2$OCH$_3$,5-F | 0 |
| A-5162 | H | H | H | H | H | O | C(=O)cyclopropyl | H | 2-CH$_2$OCH$_3$,6-F | 0 |
| A-5163 | H | H | H | H | H | O | C(=O)cyclopropyl | H | 2-CH$_2$OCH$_3$,4-Me | 0 |
| A-5164 | H | H | H | H | H | O | C(=O)cyclopropyl | H | 2-CH$_2$OCH$_3$,5-Me | 0 |

TABLE 91-continued

| compound | R¹ | R² | R³ | R⁴ | R⁵ | A | R⁶ | R⁷ | (R⁸)$_m$ | p |
|---|---|---|---|---|---|---|---|---|---|---|
| A-5165 | H | H | H | H | H | O | C(=O)cyclopropyl | H | 2-CH₂OCH₃,6-Me | 0 |
| A-5166 | H | H | H | H | H | O | C(=O)cyclopropyl | H | 2-OC(=O)CH₃,5-F | 0 |
| A-5167 | H | H | H | H | H | O | C(=O)cyclopropyl | H | 2-OC(=O)CH₃,6-F | 0 |
| A-5168 | H | H | H | H | H | O | C(=O)cyclopropyl | H | 2-OC(=O)CH₃,5-Me | 0 |
| A-5169 | H | H | H | H | H | O | C(=O)cyclopropyl | H | 2-OC(=O)CH₃,6-Me | 0 |
| A-5170 | H | H | H | H | H | O | C(=O)cyclopropyl | H | 2-OS(=O)CH₃,5-F | 0 |
| A-5171 | H | H | H | H | H | O | C(=O)cyclopropyl | H | 2-OS(=O)CH₃,6-F | 0 |
| A-5172 | H | H | H | H | H | O | C(=O)cyclopropyl | H | 2-OS(=O)CH₃,5-Me | 0 |
| A-5173 | H | H | H | H | H | O | C(=O)cyclopropyl | H | 2-OS(=O)CH₃,6-Me | 0 |
| A-5174 | H | H | H | H | H | O | C(=O)cyclopropyl | H | 2-CH₂SCH₃,5-F | 0 |
| A-5175 | H | H | H | H | H | O | C(=O)cyclopropyl | H | 2-CH₂SCH₃,6-F | 0 |
| A-5176 | H | H | H | H | H | O | C(=O)cyclopropyl | H | 2-CH₂SCH₃,5-Me | 0 |
| A-5177 | H | H | H | H | H | O | C(=O)cyclopropyl | H | 2-CH₂SCH₃,6-Me | 0 |
| A-5178 | H | H | H | H | H | O | C(=O)cyclopropyl | H | 2-NMe₂,5-F | 0 |
| A-5179 | H | H | H | H | H | O | C(=O)cyclopropyl | H | 2-NMe₂,6-F | 0 |
| A-5180 | H | H | H | H | H | O | C(=O)cyclopropyl | H | 2-NMe₂,5-Me | 0 |
| A-5181 | H | H | H | H | H | O | C(=O)cyclopropyl | H | 2-NMe₂,6-Me | 0 |
| A-5182 | H | H | H | H | H | O | C(=O)cyclopropyl | H | 2-CN,4-F | 0 |

TABLE 92

| compound | R¹ | R² | R³ | R⁴ | R⁵ | A | R⁶ | R⁷ | (R⁸)$_m$ | p |
|---|---|---|---|---|---|---|---|---|---|---|
| A-5183 | H | H | H | H | H | O | C(=O)cyclopropyl | H | 2-CN,5-F | 0 |
| A-5184 | H | H | H | H | H | O | C(=O)cyclopropyl | H | 2-CN,6-F | 0 |
| A-5185 | H | H | H | H | H | O | C(=O)cyclopropyl | H | 2-CN,6-Me | 0 |
| A-5186 | H | H | H | H | H | O | C(=O)cyclopropyl | H | 2-CN,5-OMe | 0 |
| A-5187 | H | H | H | H | H | O | C(=O)cyclopropyl | H | 2-CN,6-OMe | 0 |
| A-5188 | H | H | H | H | H | O | C(=O)cyclopropyl | H | 3-CN,6-Me | 0 |
| A-5189 | H | H | H | H | H | O | C(=O)cyclopropyl | H | 3-CN,6-OMe | 0 |
| A-5190 | H | H | H | H | H | O | C(=O)cyclopropyl | H | 4-CN,2-Me | 0 |
| A-5191 | H | H | H | H | H | O | C(=O)cyclopropyl | H | 4-CN,2-OMe | 0 |
| A-5192 | H | H | H | H | H | O | C(=O)cyclopropyl | H | 2-NO₂,4-F | 0 |
| A-5193 | H | H | H | H | H | O | C(=O)cyclopropyl | H | 2-NO₂,5-F | 0 |
| A-5194 | H | H | H | H | H | O | C(=O)cyclopropyl | H | 2-NO₂,6-F | 0 |
| A-5195 | H | H | H | H | H | O | C(=O)cyclopropyl | H | 2-NO₂,4-Me | 0 |
| A-5196 | H | H | H | H | H | O | C(=O)cyclopropyl | H | 2-NO₂,5-Me | 0 |
| A-5197 | H | H | H | H | H | O | C(=O)cyclopropyl | H | 2-NO₂,6-Me | 0 |
| A-5198 | H | H | H | H | H | O | C(=O)cyclopropyl | H | 2-Me,4,5 F₂ | 0 |
| A-5199 | H | H | H | H | H | O | C(=O)cyclopropyl | H | 2-Me,6-Et | 0 |
| A-5200 | H | H | H | H | H | O | C(=O)cyclopropyl | H | 2-cyclopropyl,6-OMe | 0 |
| A-5201 | H | H | H | H | H | O | C(=O)cyclopropyl | H | 2-Me,5-Et | 0 |
| A-5202 | H | H | H | H | H | O | C(=O)cyclopropyl | H | 2,6-Et₂ | 0 |
| A-5203 | H | H | H | H | H | O | C(=O)cyclopropyl | H | 2-Et,6-F | 0 |
| A-5204 | H | H | H | H | H | O | C(=O)cyclopropyl | H | 2-CH₂OCH₃,6-Cl | 0 |
| A-5205 | H | H | H | H | H | O | C(=O)cyclopropyl | H | 2-CH₂OCH₂CH₃,6-Cl | 0 |
| A-5206 | H | H | H | H | H | O | C(=O)cyclopropyl | H | 2-CH₂NMe₂ | 0 |
| A-5207 | H | H | H | H | H | O | C(=O)OCH₃ | H | H | 0 |
| A-5208 | H | H | H | H | H | O | C(=O)OCH₃ | H | 2-F | 0 |
| A-5209 | H | H | H | H | H | O | C(=O)OCH₃ | H | 2-C | 0 |
| A-5210 | H | H | H | H | H | O | C(=O)OCH₃ | H | 2-Br | 0 |
| A-5211 | H | H | H | H | H | O | C(=O)OCH₃ | H | 2-OH | 0 |
| A-5212 | H | H | H | H | H | O | C(=O)OCH₃ | H | 2-Me | 0 |
| A-5213 | H | H | H | H | H | O | C(=O)OCH₃ | H | 2-Et | 0 |
| A-5214 | H | H | H | H | H | O | C(=O)OCH₃ | H | 2-Pr | 0 |
| A-5215 | H | H | H | H | H | O | C(=O)OCH₃ | H | 2-CF | 0 |
| A-5216 | H | H | H | H | H | O | C(=O)OCH₃ | H | 2-CHF₂ | 0 |
| A-5217 | H | H | H | H | H | O | C(=O)OCH₃ | H | 2-CH₂F | 0 |
| A-5218 | H | H | H | H | H | O | C(=O)OCH₃ | H | 2-CF₂Cl | 0 |
| A-5219 | H | H | H | H | H | O | C(=O)OCH₃ | H | 2-cyclopropyl | 0 |
| A-5220 | H | H | H | H | H | O | C(=O)OCH₃ | H | 2-cyclobutyl | 0 |
| A-5221 | H | H | H | H | H | O | C(=O)OCH₃ | H | 2-cyclopentyl | 0 |
| A-5222 | H | H | H | H | H | O | C(=O)OCH₃ | H | 2-ethenyl | 0 |
| A-5223 | H | H | H | H | H | O | C(=O)OCH₃ | H | 2-allyl | 0 |
| A-5224 | H | H | H | H | H | O | C(=O)OCH₃ | H | 2-(prop-1en-1-yl) | 0 |
| A-5225 | H | H | H | H | H | O | C(=O)OCH₃ | H | 2-(trifluoroethenyl) | 0 |
| A-5226 | H | H | H | H | H | O | C(=O)OCH₃ | H | 2-OMe | 0 |
| A-5227 | H | H | H | H | H | O | C(=O)OCH₃ | H | 2-OEt | 0 |
| A-5228 | H | H | H | H | H | O | C(=O)OCH₃ | H | 2-OPr | 0 |
| A-5229 | H | H | H | H | H | O | C(=O)OCH₃ | H | 2-O(i-Pr) | 0 |
| A 5230 | H | H | H | H | H | O | C(=O)OCH₃ | H | 2-OCF₃ | 0 |
| A-5231 | H | H | H | H | H | O | C(=O)OCH₃ | H | 2-OCHF₂ | 0 |
| A-5232 | H | H | H | H | H | O | C(=O)OCH₃ | H | 2-(cyclopropyloxy) | 0 |
| A-5233 | H | H | H | H | H | O | C(=O)OCH₃ | H | 2-(cyclobutyloxy) | 0 |
| A-5234 | H | H | H | H | H | O | C(=O)OCH₃ | H | 2-(cyclopentyloxy) | 0 |

TABLE 92-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-5235 | H | H | H | H | H | O | C(=O)OCH$_3$ | H | 2-((2,2-dichlorocyclopropyl)oxy) | 0 |
| A-5236 | H | H | H | H | H | O | C(=O)OCH$_3$ | H | 2-(oxiran-2-yl) | 0 |
| A-5237 | H | H | H | H | H | O | C(=O)OCH$_3$ | H | 2-SMe | 0 |
| A-5238 | H | H | H | H | H | O | C(=O)OCH$_3$ | H | 3-SMe | 0 |
| A-5239 | H | H | H | H | H | O | C(=O)OCH$_3$ | H | 2-S(=O)Me | 0 |

TABLE 93

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-5240 | H | H | H | H | H | O | C(=O)OCH$_3$ | H | 3-S(=O)Me | 0 |
| A-5241 | H | H | H | H | H | O | C(=O)OCH$_3$ | H | 2-S(=O)$_2$Me | 0 |
| A-5242 | H | H | H | H | H | O | C(=O)OCH$_3$ | H | 3-S(=O)$_2$Me | 0 |
| A 5243 | H | H | H | H | H | O | C(=O)OCH$_3$ | H | 2-SCF$_3$ | 0 |
| A-5244 | H | H | H | H | H | O | C(=O)OCH$_3$ | H | 3-SCF$_3$ | 0 |
| A-5245 | H | H | H | H | H | O | C(=O)OCH$_3$ | H | 3-S(=O)CF$_3$ | 0 |
| A-5246 | H | H | H | H | H | O | C(=O)OCH$_3$ | H | 3-SCF(CF$_3$)$_2$ | 0 |
| A-5247 | H | H | H | H | H | O | C(=O)OCH$_3$ | H | 2-(cyclopropylthio) | 0 |
| A-5248 | H | H | H | H | H | O | C(=O)OCH$_3$ | H | 2-(cyclopropylsulfinyl) | 0 |
| A-5249 | H | H | H | H | H | O | C(=O)OCH$_3$ | H | 2-(cyclopropylsulfonyl) | 0 |
| A-5250 | H | H | H | H | H | O | C(=O)OCH$_3$ | H | 2-C(=O)Me | 0 |
| A-5251 | H | H | H | H | H | O | C(=O)OCH$_3$ | H | 2-CH$_2$C(=O)CH$_3$ | 0 |
| A-5252 | H | H | H | H | H | O | C(=O)OCH$_3$ | H | 2-CH$_2$C(=O)CF$_3$ | 0 |
| A-5253 | H | H | H | H | H | O | C(=O)OCH$_3$ | H | 2-CH$_2$OH | 0 |
| A-5254 | H | H | H | H | H | O | C(=O)OCH$_3$ | H | 2-CH$_2$OCH$_3$ | 0 |
| A-5255 | H | H | H | H | H | O | C(=O)OCH$_3$ | H | 2-CH$_2$OCH$_2$CH$_3$ | 0 |
| A-5256 | H | H | H | H | H | O | C(=O)OCH$_3$ | H | 2-CH$_2$SCH$_3$ | 0 |
| A-5257 | H | H | H | H | H | O | C(=O)OCH$_3$ | H | 2-CH$_2$S(=O)CH$_3$ | 0 |
| A-5258 | H | H | H | H | H | O | C(=O)OCH$_3$ | H | 2-CH$_2$S(=O)$_2$CH$_3$ | 0 |
| A-5259 | H | H | H | H | H | O | C(=O)OCH$_3$ | H | 2-(benzyloxy) | 0 |
| A-5260 | H | H | H | H | H | O | C(=O)OCH$_3$ | H | 2-NH$_2$ | 0 |
| A-5261 | H | H | H | H | H | O | C(=O)OCH$_3$ | H | 2-NHMe | 0 |
| A-5262 | H | H | H | H | H | O | C(=O)OCH$_3$ | H | 2-N(Me)$_2$ | 0 |
| A-5263 | H | H | H | H | H | O | C(=O)OCH$_3$ | H | 2-(1,3-dioxolan-2-yl) | 0 |
| A-5264 | H | H | H | H | H | O | C(=O)OCH$_3$ | H | 2-(1,3-dioxan-2-yl) | 0 |
| A-5265 | H | H | H | H | H | O | C(=O)OCH$_3$ | H | 2-(1H-imidazol-2-yl) | 0 |
| A-5266 | H | H | H | H | H | O | C(=O)OCH$_3$ | H | 2-(thiazol-2-yl) | 0 |
| A-5267 | H | H | H | H | H | O | C(=O)OCH$_3$ | H | 2-(oxazol-2-yl) | 0 |
| A-5268 | H | H | H | H | H | O | C(=O)OCH$_3$ | H | 2-CH=NOH | 0 |
| A-5269 | H | H | H | H | H | O | C(=O)OCH$_3$ | H | 2-CH=NOMe | 0 |
| A-5270 | H | H | H | H | H | O | C(=O)OCH$_3$ | H | 2-(4,5-dihydro-3-isoxazolyl) | 0 |
| A-5271 | H | H | H | H | H | O | C(=O)OCH$_3$ | H | 2-CN | 0 |
| A-5272 | H | H | H | H | H | O | C(=O)OCH$_3$ | H | 2-NO$_2$ | 0 |
| A-5273 | H | H | H | H | H | O | C(=O)OCH$_3$ | H | 2-F,6-Cl | 0 |
| A-5274 | H | H | H | H | H | O | C(=O)OCH$_3$ | H | 2-F,6-Me | 0 |
| A-5275 | H | H | H | H | H | O | C(=O)OCH$_3$ | H | 3-F,6-Me | 0 |
| A-5276 | H | H | H | H | H | O | C(=O)OCH$_3$ | H | 4-F,2-Me | 0 |
| A-5277 | H | H | H | H | H | O | C(=O)OCH$_3$ | H | 2-F,6-OMe | 0 |
| A-5278 | H | H | H | H | H | O | C(=O)OCH$_3$ | H | 3-F,6-OMe | 0 |
| A-5279 | H | H | H | H | H | O | C(=O)OCH$_3$ | H | 2,6-Cl$_2$ | 0 |
| A-5280 | H | H | H | H | H | O | C(=O)OCH$_3$ | H | 2-Cl,6-Me | 0 |
| A-5281 | H | H | H | H | H | O | C(=O)OCH$_3$ | H | 3-Cl,6-Me | 0 |
| A-5282 | H | H | H | H | H | O | C(=O)OCH$_3$ | H | 4-Cl,2-Me | 0 |
| A-5283 | H | H | H | H | H | O | C(=O)OCH$_3$ | H | 2-Cl,5-CF$_3$ | 0 |
| A-5284 | H | H | H | H | H | O | C(=O)OCH$_3$ | H | 2-Cl,6-CF$_3$ | 0 |
| A-5285 | H | H | H | H | H | O | C(=O)OCH$_3$ | H | 2-Cl,6-OMe | 0 |
| A-5286 | H | H | H | H | H | O | C(=O)OCH$_3$ | H | 3-Cl,6 OMe | 0 |
| A-5287 | H | H | H | H | H | O | C(=O)OCH$_3$ | H | 4-Cl,2-OMe | 0 |
| A-5288 | H | H | H | H | H | O | C(=O)OCH$_3$ | H | 2,4-Me$_2$ | 0 |
| A-5289 | H | H | H | H | H | O | C(=O)OCH$_3$ | H | 2,5-Me$_2$ | 0 |
| A-5290 | H | H | H | H | H | O | C(=O)OCH$_3$ | H | 2,6-Me$_2$ | 0 |
| A-5291 | H | H | H | H | H | O | C(=O)OCH$_3$ | H | 2-Me,4-CF$_3$ | 0 |
| A-5292 | H | H | H | H | H | O | C(=O)OCH$_3$ | H | 2-Me,5-CF$_3$ | 0 |
| A-5293 | H | H | H | H | H | O | C(=O)OCH$_3$ | H | 2-Me,6-CF$_3$ | 0 |
| A-5294 | H | H | H | H | H | O | C(=O)OCH$_3$ | H | 2-Me,4-OMe | 0 |
| A-5295 | H | H | H | H | H | O | C(=O)OCH$_3$ | H | 2-Me,5-OMe | 0 |
| A-5296 | H | H | H | H | H | O | C(=O)OCH$_3$ | H | 2-Me,6-OMe | 0 |

TABLE 94

| compound | R¹ | R² | R³ | R⁴ | R⁵ | A | R⁶ | R⁷ | (R⁸)ₘ | p |
|---|---|---|---|---|---|---|---|---|---|---|
| A-5297 | H | H | H | H | H | O | C(=O)OCH₃ | H | 3-Me,6-OMe | 0 |
| A-5298 | H | H | H | H | H | O | C(=O)OCH₃ | H | 4-Me,2-OMe | 0 |
| A-5299 | H | H | H | H | H | O | C(=O)OCH₃ | H | 2,5-OMe₂ | 0 |
| A-5300 | H | H | H | H | H | O | C(=O)OCH₃ | H | 2,6-OMe₂ | 0 |
| A-5301 | H | H | H | H | H | O | C(=O)OCH₃ | H | 2-OMe,6-CF₃ | 0 |
| A-5302 | H | H | H | H | H | O | C(=O)OCH₃ | H | 2-CHF₂,5-F | 0 |
| A-5303 | H | H | H | H | H | O | C(=O)OCH₃ | H | 2-CHF₂,6-F | 0 |
| A-5304 | H | H | H | H | H | O | C(=O)OCH₃ | H | 2-CHF₂,5-Me | 0 |
| A-5305 | H | H | H | H | H | O | C(=O)OCH₃ | H | 2-CHF₂,6-Me | 0 |
| A-5306 | H | H | H | H | H | O | C(=O)OCH₃ | H | 2-cyclopropyl,5-F | 0 |
| A-5307 | H | H | H | H | H | O | C(=O)OCH₃ | H | 2-cyclopropyl,6-F | 0 |
| A-5308 | H | H | H | H | H | O | C(=O)OCH₃ | H | 2-cyclopropyl,5-Me | 0 |
| A-5309 | H | H | H | H | H | O | C(=O)OCH₃ | H | 2-cyclopropyl,6-Me | 0 |
| A-5310 | H | H | H | H | H | O | C(=O)OCH₃ | H | 2-ethenyl,6-F | 0 |
| A-5311 | H | H | H | H | H | O | C(=O)OCH₃ | H | 2-ethenyl,6-Me | 0 |
| A-5312 | H | H | H | H | H | O | C(=O)OCH₃ | H | 2-OEt,5-F | 0 |
| A-5313 | H | H | H | H | H | O | C(=O)OCH₃ | H | 2-OEt,6-F | 0 |
| A-5314 | H | H | H | H | H | O | C(=O)OCH₃ | H | 2-OEt,5-Cl | 0 |
| A-5315 | H | H | H | H | H | O | C(=O)OCH₃ | H | 2-OEt,6-Cl | 0 |
| A-5316 | H | H | H | H | H | O | C(=O)OCH₃ | H | 2-OEt,5-Me | 0 |
| A-5317 | H | H | H | H | H | O | C(=O)OCH₃ | H | 2-OEt,6-Me | 0 |
| A-5318 | H | H | H | H | H | O | C(=O)OCH₃ | H | 2-OCHF₂,5-F | 0 |
| A-5319 | H | H | H | H | H | O | C(=O)OCH₃ | H | 2-OCHF₂,6-F | 0 |
| A-5320 | H | H | H | H | H | O | C(=O)OCH₃ | H | 2-OCHF₂,5-Me | 0 |
| A-5321 | H | H | H | H | H | O | C(=O)OCH₃ | H | 2-OCHF₂,6-Me | 0 |
| A-5322 | H | H | H | H | H | O | C(=O)OCH₃ | H | 2-(cyclopropyloxy),5-F | 0 |
| A-5323 | H | H | H | H | H | O | C(=O)OCH₃ | H | 2-(cyclopropyloxy),6-F | 0 |
| A-5324 | H | H | H | H | H | O | C(=O)OCH₃ | H | 2-(cyclopropyloxy),5-Me | 0 |
| A-5325 | H | H | H | H | H | O | C(=O)OCH₃ | H | 2-(cyclopropyloxy),6-Me | 0 |
| A-5326 | H | H | H | H | H | O | C(=O)OCH₃ | H | 2-SMe,5-F | 0 |
| A-5327 | H | H | H | H | H | O | C(=O)OCH₃ | H | 2-SMe,6-F | 0 |
| A-5328 | H | H | H | H | H | O | C(=O)OCH₃ | H | 2-SMe,5-Me | 0 |
| A-5329 | H | H | H | H | H | O | C(=O)OCH₃ | H | 2-SMe,6-Me | 0 |
| A-5330 | H | H | H | H | H | O | C(=O)OCH₃ | H | 2-S(=O)Me,5-F | 0 |
| A-5331 | H | H | H | H | H | O | C(=O)OCH₃ | H | 2-S(=O)Me,6-F | 0 |
| A-5332 | H | H | H | H | H | O | C(=O)OCH₃ | H | 2-S(=O)Me,5-Me | 0 |
| A-5333 | H | H | H | H | H | O | C(=O)OCH₃ | H | 2-S(=O)Me,6-Me | 0 |
| A-5334 | H | H | H | H | H | O | C(=O)OCH₃ | H | 2-S(=O)2Me,5-F | 0 |
| A-5335 | H | H | H | H | H | O | C(=O)OCH₃ | H | 2-S(=O)2Me,6-F | 0 |
| A-5336 | H | H | H | H | H | O | C(=O)OCH₃ | H | 2-S=O)2Me,5-Me | 0 |
| A-5337 | H | H | H | H | H | O | C(=O)OCH₃ | H | 2-S(=O)2Me,6-Me | 0 |
| A-5338 | H | H | H | H | H | O | C(=O)OCH₃ | H | 2-SCF₃,5-F | 0 |
| A-5339 | H | H | H | H | H | O | C(=O)OCH₃ | H | 2-SCF₃,6-F | 0 |
| A-5340 | H | H | H | H | H | O | C(=O)OCH₃ | H | 2-SCF₃,5-Me | 0 |
| A-5341 | H | H | H | H | H | O | C(=O)OCH₃ | H | 2-SCF₃,6-Me | 0 |
| A-5342 | H | H | H | H | H | O | C(=O)OCH₃ | H | 2-S(=O)CF₃,5-F | 0 |
| A-5343 | H | H | H | H | H | O | C(=O)OCH₃ | H | 2-S(=O)CF₃,6-F | 0 |
| A-5344 | H | H | H | H | H | O | C(=O)OCH₃ | H | 2-S(=O)CF₃,5-Me | 0 |
| A-5345 | H | H | H | H | H | O | C(=O)OCH₃ | H | 2-S(=O)CF₃,6-Me | 0 |
| A-5346 | H | H | H | H | H | O | C(=O)OCH₃ | H | 2-S(=O)₂CF₃,5-F | 0 |
| A-5347 | H | H | H | H | H | O | C(=O)OCH₃ | H | 2-S(=O)₂CF₃,6-F | 0 |
| A-5348 | H | H | H | H | H | O | C(=O)OCH₃ | H | 2-S(=O)₂CF₃,5-Me | 0 |
| A-5349 | H | H | H | H | H | O | C(=O)OCH₃ | H | 2-S(=O)₂CF₃,6-Me | 0 |
| A-5350 | H | H | H | H | H | O | C(=O)OCH₃ | H | 2-(cyclopropylthio),5-F | 0 |
| A-5351 | H | H | H | H | H | O | C(=O)OCH₃ | H | 2-(cyclopropylthio),6-F | 0 |
| A-5352 | H | H | H | H | H | O | C(=O)OCH₃ | H | 2-(cyclopropylthio),5-Me | 0 |
| A-5353 | H | H | H | H | H | O | C(=O)OCH₃ | H | 2-(cyclopropylthio),6-Me | 0 |

TABLE 95

| compound | R¹ | R² | R³ | R⁴ | R⁵ | A | R⁶ | R⁷ | (R⁸)ₘ | p |
|---|---|---|---|---|---|---|---|---|---|---|
| A-5354 | H | H | H | H | H | O | C(=O)OCH₃ | H | 2-C(=O)Me,5-F | O |
| A-5355 | H | H | H | H | H | O | C(=O)OCH₃ | H | 2-C(=O)Me,6-F | O |
| A-5356 | H | H | H | H | H | O | C(=O)OCH₃ | H | 2-C(=O)Me,5-Me | O |
| A-5357 | H | H | H | H | H | O | C(=O)OCH₃ | H | 2-C(=O)Me,6-Me | O |
| A-5358 | H | H | H | H | H | O | C(=O)OCH₃ | H | 2-CH₂OH,5-F | O |
| A-5359 | H | H | H | H | H | O | C(=O)OCH₃ | H | 2-CH₂OH,6-F | O |
| A-5360 | H | H | H | H | H | O | C(=O)OCH₃ | H | 2-CH₂OH,5-Me | O |
| A-5361 | H | H | H | H | H | O | C(=O)OCH₃ | H | 2-CH₂OH,6-Me | O |
| A-5362 | H | H | H | H | H | O | C(=O)OCH₃ | H | 2-CH₂OCH₃,4-F | O |
| A-5363 | H | H | H | H | H | O | C(=O)OCH₃ | H | 2-CH₂OCH₃,5-F | O |
| A-5364 | H | H | H | H | H | O | C(=O)OCH₃ | H | 2-CH₂OCH₃,6-F | O |
| A-5365 | H | H | H | H | H | O | C(=O)OCH₃ | H | 2-CH₂OCH₃,4-Me | O |
| A-5366 | H | H | H | H | H | O | C(=O)OCH₃ | H | 2-CH₂OCH₃,5-Me | O |

TABLE 95-continued

| compound | R¹ | R² | R³ | R⁴ | R⁵ | A | R⁶ | R⁷ | (R⁸)$_m$ | p |
|---|---|---|---|---|---|---|---|---|---|---|
| A-5367 | H | H | H | H | H | O | C(=O)OCH₃ | H | 2-CH₂OCH₃,6-Me | 0 |
| A-5368 | H | H | H | H | H | O | C(=O)OCH₃ | H | 2-OC(=O)CH₃,5-F | 0 |
| A-5369 | H | H | H | H | H | O | C(=O)OCH₃ | H | 2-OC(=O)CH₃,6-F | 0 |
| A-5370 | H | H | H | H | H | O | C(=O)OCH₃ | H | 2-OC(=O)CH₃,5-Me | 0 |
| A-5371 | H | H | H | H | H | O | C(=O)OCH₃ | H | 2-OC(=O)CH₃,6-Me | 0 |
| A-5372 | H | H | H | H | H | O | C(=O)OCH₃ | H | 2-OS(=O)₂CH₃,5-F | 0 |
| A-5373 | H | H | H | H | H | O | C(=O)OCH₃ | H | 2-OS(=O)₂CH₃,6-F | 0 |
| A-5374 | H | H | H | H | H | O | C(=O)OCH₃ | H | 2-OS(=O)₂CH₃,5-Me | 0 |
| A-5375 | H | H | H | H | H | O | C(=O)OCH₃ | H | 2-OS(=O)₂CH₃,6-Me | 0 |
| A-5376 | H | H | H | H | H | O | C(=O)OCH₃ | H | 2-CH₂SCH₃,5-F | 0 |
| A-5377 | H | H | H | H | H | O | C(=O)OCH₃ | H | 2-CH₂SCH₃,6-F | 0 |
| A-5378 | H | H | H | H | H | O | C(=O)OCH₃ | H | 2-CH₂SCH₃,5-Me | 0 |
| A-5379 | H | H | H | H | H | O | C(=O)OCH₃ | H | 2-CH₂SCH₃,6-Me | 0 |
| A-5380 | H | H | H | H | H | O | C(=O)OCH₃ | H | 2-NMe₂,5-F | 0 |
| A-5381 | H | H | H | H | H | O | C(=O)OCH₃ | H | 2-NMe₂,6-F | 0 |
| A-5382 | H | H | H | H | H | O | C(=O)OCH₃ | H | 2-NMe₂,5-Me | 0 |
| A-5383 | H | H | H | H | H | O | C(=O)OCH₃ | H | 2-NMe₂,6-Me | 0 |
| A-5384 | H | H | H | H | H | O | C(=O)OCH₃ | H | 2-CN,4-F | 0 |
| A-5385 | H | H | H | H | H | O | C(=O)OCH₃ | H | 2-CN,5F | 0 |
| A-5386 | H | H | H | H | H | O | C(=O)OCH₃ | H | 2-CN,6-F | 0 |
| A-5387 | H | H | H | H | H | O | C(=O)OCH₃ | H | 2-CN,6-Me | 0 |
| A-5388 | H | H | H | H | H | O | C(=O)OCH₃ | H | 2-CN,5-OMe | 0 |
| A-5389 | H | H | H | H | H | O | C(=O)OCH₃ | H | 2-CN,6-OMe | 0 |
| A-5390 | H | H | H | H | H | O | C(=O)OCH₃ | H | 3-CN,6-Me | 0 |
| A-5391 | H | H | H | H | H | O | C(=O)OCH₃ | H | 3-CN,6-OMe | 0 |
| A-5392 | H | H | H | H | H | O | C(=O)OCH₃ | H | 4-CN,2-Me | 0 |
| A-5393 | H | H | H | H | H | O | C(=O)OCH₃ | H | 4-CN,2-OMe | 0 |
| A-5394 | H | H | H | H | H | O | C(=O)OCH₃ | H | 2-NO₂,4-F | 0 |
| A-5395 | H | H | H | H | H | O | C(=O)OCH₃ | H | 2-NO₂,5-F | 0 |
| A-5396 | H | H | H | H | H | O | C(=O)OCH₃ | H | 2-NO₂,6-F | 0 |
| A-5397 | H | H | H | H | H | O | C(=O)OCH₃ | H | 2-NO₂,4-Me | 0 |
| A-5398 | H | H | H | H | H | O | C(=O)OCH₃ | H | 2-NO₂,5-Me | 0 |
| A-5399 | H | H | H | H | H | O | C(=O)OCH₃ | H | 2-NO₂,6-Me | 0 |
| A-5400 | H | H | H | H | H | O | C(=O)OCH₃ | H | 2-Me,4,5-F₂ | 0 |
| A-5401 | H | H | H | H | H | O | C(=O)OCH₃ | H | 2-Me,6-Et | 0 |
| A-5402 | H | H | H | H | H | O | C(=O)OCH₃ | H | 2-cyclopropyl,6-OMe | 0 |
| A-5403 | H | H | H | H | H | O | C(=O)OCH₃ | H | 2-Me,5-Et | 0 |
| A-5404 | H | H | H | H | H | O | C(=O)OCH₃ | H | 2,6-Et₂ | 0 |
| A-5405 | H | H | H | H | H | O | C(=O)OCH₃ | H | 2-Et,6-F | 0 |
| A-5406 | H | H | H | H | H | O | C(=O)OCH₃ | H | 2-CH₂OCH₃,6-Cl | 0 |
| A-5407 | H | H | H | H | H | O | C(=O)OCH₃ | H | 2-CH₂OCH₂CH₃,6-Cl | 0 |
| A-5408 | H | H | H | H | H | O | C(=O)OCH₃ | H | 2-CH₂NMe₂ | 0 |
| A-5409 | H | H | H | H | H | O | C(=O)OCH₃ | H | H | 0 |
| A-5410 | H | H | H | H | H | O | C(=O)OCH₃ | H | 2F | 0 |

TABLE 96

| compound | R¹ | R² | R³ | R⁴ | R⁵ | A | R⁶ | R⁷ | (R⁸)$_m$ | p |
|---|---|---|---|---|---|---|---|---|---|---|
| A-5411 | H | H | H | H | H | O | C(=O)OCH₂CH₃ | H | 2-Cl | 0 |
| A-5412 | H | H | H | H | H | O | C(=O)OCH₂CH₃ | H | 2-Br | 0 |
| A-5413 | H | H | H | H | H | O | C(=O)OCH₂CH₃ | H | 2-OH | 0 |
| A-5414 | H | H | H | H | H | O | C(=O)OCH₂CH₃ | H | 2-Me | 0 |
| A-5415 | H | H | H | H | H | O | C(=O)OCH₂CH₃ | H | 2-Et | 0 |
| A-5416 | H | H | H | H | H | O | C(=O)OCH₂CH₃ | H | 2-Pr | 0 |
| A-5417 | H | H | H | H | H | O | C(=O)OCH₂CH₃ | H | 2-CF₃ | 0 |
| A-5418 | H | H | H | H | H | O | C(=O)OCH₂CH₃ | H | 2-CHF₂ | 0 |
| A-5419 | H | H | H | H | H | O | C(=O)OCH₂CH₃ | H | 2-CH₂F | 0 |
| A-5420 | H | H | H | H | H | O | C(=O)OCH₂CH₃ | H | 2-CF₂Cl | 0 |
| A-5421 | H | H | H | H | H | O | C(=O)OCH₂CH₃ | H | 2-cyclopropyl | 0 |
| A-5422 | H | H | H | H | H | O | C(=O)OCH₂CH₃ | H | 2-cyclobutyl | 0 |
| A-5423 | H | H | H | H | H | O | C(=O)OCH₂CH₃ | H | 2-cyclopentyl | 0 |
| A-5424 | H | H | H | H | H | O | C(=O)OCH₂CH₃ | H | 2-ethenyl | 0 |
| A-5425 | H | H | H | H | H | O | C(=O)OCH₂CH₃ | H | 2-allyl | 0 |
| A-5426 | H | H | H | H | H | O | C(=O)OCH₂CH₃ | H | 2-(prop-1-en-1-yl) | 0 |
| A-5427 | H | H | H | H | H | O | C(=O)OCH₂CH₃ | H | 2-(trifluoroethenyl) | 0 |
| A-5428 | H | H | H | H | H | O | C(=O)OCH₂CH₃ | H | 2-OMe | 0 |
| A-5429 | H | H | H | H | H | O | C(=O)OCH₂CH₃ | H | 2-OEt | 0 |
| A-5430 | H | H | H | H | H | O | C(=O)OCH₂CH₃ | H | 2-OPr | 0 |
| A-5431 | H | H | H | H | H | O | C(=O)OCH₂CH₃ | H | 2-O(i-Pr) | 0 |
| A-5432 | H | H | H | H | H | O | C(=O)OCH₂CH₃ | H | 2-OCF₃ | 0 |
| A-5433 | H | H | H | H | H | O | C(=O)OCH₂CH₃ | H | 2-OCHF₂ | 0 |
| A-5434 | H | H | H | H | H | O | C(=O)OCH₂CH₃ | H | 2-(cyclopropyloxy) | 0 |
| A-5435 | H | H | H | H | H | O | C(=O)OCH₂CH₃ | H | 2-(cyclobutyloxy) | 0 |
| A-5436 | H | H | H | H | H | O | C(=O)OCH₂CH₃ | H | 2-(cyclopentyloxy) | 0 |

TABLE 96-continued

| compound | R¹ | R² | R³ | R⁴ | R⁵ | A | R⁶ | R⁷ | (R⁸)ₘ | p |
|---|---|---|---|---|---|---|---|---|---|---|
| A-5437 | H | H | H | H | H | O | C(=O)OCH₂CH₃ | H | 2-((2,2-dichlorocyclopropyl)oxy) | O |
| A-5438 | H | H | H | H | H | O | C(=O)OCH₂CH₃ | H | 2-(oxiran-2-yl) | O |
| A-5439 | H | H | H | H | H | O | C(=O)OCH₂CH₃ | H | 2-SMe | O |
| A-5440 | H | H | H | H | H | O | C(=O)OCH₂CH₃ | H | 3-SMe | O |
| A-5441 | H | H | H | H | H | O | C(=O)OCH₂CH₃ | H | 2-S(=O)Me | O |
| A-5442 | H | H | H | H | H | O | C(=O)OCH₂CH₃ | H | 3-S(=O)Me | O |
| A-5443 | H | H | H | H | H | O | C(=O)OCH₂CH₃ | H | 2-S(=O)₂Me | O |
| A-5444 | H | H | H | H | H | O | C(=O)OCH₂CH₃ | H | 3-S(=O)₂Me | O |
| A-5445 | H | H | H | H | H | O | C(=O)OCH₂CH₃ | H | 2-SCF₃ | O |
| A-5446 | H | H | H | H | H | O | C(=O)OCH₂CH₃ | H | 3-SCF₃ | O |
| A-5447 | H | H | H | H | H | O | C(=O)OCH₂CH₃ | H | 3-S(=O)CF₃ | O |
| A-5448 | H | H | H | H | H | O | C(=O)OCH₂CH₃ | H | 3-SCF(CF₃)₂ | O |
| A-5449 | H | H | H | H | H | O | C(=O)OCH₂CH₃ | H | 2-(cyclopropylthio) | O |
| A-5450 | H | H | H | H | H | O | C(=O)OCH₂CH₃ | H | 2-(cyclopropylsulfinyl) | O |
| A-5451 | H | H | H | H | H | O | C(=O)OCH₂CH₃ | H | 2-(cyclopropylsulfonyl) | O |
| A-5452 | H | H | H | H | H | O | C(=O)OCH₂CH₃ | H | 2-C(=O)Me | O |
| A-5453 | H | H | H | H | H | O | C(=O)OCH₂CH₃ | H | 2-CH₂C(=O)CH₃ | O |
| A-5454 | H | H | H | H | H | O | C(=O)OCH₂CH₃ | H | 2-CH₂C(=O)CF₃ | O |
| A-5455 | H | H | H | H | H | O | C(=O)OCH₂CH₃ | H | 2-CH₂OH | O |
| A-5456 | H | H | H | H | H | O | C(=O)OCH₂CH₃ | H | 2-CH₂OCH₃ | O |
| A-5457 | H | H | H | H | H | O | C(=O)OCH₂CH₃ | H | 2-CH₂OCH₂CH₃ | O |
| A-5458 | H | H | H | H | H | O | C(=O)OCH₂CH₃ | H | 2-CH₂SCH₃ | O |
| A-5459 | H | H | H | H | H | O | C(=O)OCH₂CH₃ | H | 2-CH₂S(=O)CH₃ | O |
| A-5460 | H | H | H | H | H | O | C(=O)OCH₂CH₃ | H | 2-CH₂S(=O)₂CH₃ | O |
| A-5461 | H | H | H | H | H | O | C(=O)OCH₂CH₃ | H | 2-(benzyloxy) | O |
| A-5462 | H | H | H | H | H | O | C(=O)OCH₂CH₃ | H | 2-NH₂ | O |
| A-5463 | H | H | H | H | H | O | C(=O)OCH₂CH₃ | H | 2-NHMe | O |
| A-5464 | H | H | H | H | H | O | C(=O)OCH₂CH₃ | H | 2-N(Me)₂ | O |
| A-5465 | H | H | H | H | H | O | C(=O)OCH₂CH₃ | H | 2-(1,3-dioxolan-2-yl) | O |
| A-5466 | H | H | H | H | H | O | C(=O)OCH₂CH₃ | H | 2-(1,3-dioxan-2-yl) | O |
| A-5467 | H | H | H | H | H | O | C(=O)OCH₂CH₃ | H | 2-(1H-midazo-2-yl) | O |

TABLE 97

| compound | R¹ | R² | R³ | R⁴ | R⁵ | A | R⁶ | R⁷ | (R⁸)ₘ | p |
|---|---|---|---|---|---|---|---|---|---|---|
| A-5468 | H | H | H | H | H | O | C(=O)OCH₂CH₃ | H | 2-(thiazol-2-yl) | O |
| A-5469 | H | H | H | H | H | O | C(=O)OCH₂CH₃ | H | 2-(oxazol-2-yl) | O |
| A-5470 | H | H | H | H | H | O | C(=O)OCH₂CH₃ | H | 2-CH=NOH | O |
| A-5471 | H | H | H | H | H | O | C(=O)OCH₂CH₃ | H | 2-CH=NOMe | O |
| A-5472 | H | H | H | H | H | O | C(=O)OCH₂CH₃ | H | 2-(4,5-dihydro-3-isoxazolyl) | O |
| A-5473 | H | H | H | H | H | O | C(=O)OCH₂CH₃ | H | 2-CN | O |
| A-5474 | H | H | H | H | H | O | C(=O)OCH₂CH₃ | H | 2-NO₂ | O |
| A-5475 | H | H | H | H | H | O | C(=O)OCH₂CH₃ | H | 2-F,6-Cl | O |
| A-5476 | H | H | H | H | H | O | C(=O)OCH₂CH₃ | H | 2-F,6-Me | O |
| A-5477 | H | H | H | H | H | O | C(=O)OCH₂CH₃ | H | 3-F,6-Me | O |
| A-5478 | H | H | H | H | H | O | C(=O)OCH₂CH₃ | H | 4-F,2-Me | O |
| A-5479 | H | H | H | H | H | O | C(=O)OCH₂CH₃ | H | 2-F,6-OMe | O |
| A-5480 | H | H | H | H | H | O | C(=O)OCH₂CH₃ | H | 3-F,6-OMe | O |
| A-5481 | H | H | H | H | H | O | C(=O)OCH₂CH₃ | H | 2,6-Cl₂ | O |
| A-5482 | H | H | H | H | H | O | C(=O)OCH₂CH₃ | H | 2-Cl,6-Me | O |
| A-5483 | H | H | H | H | H | O | C(=O)OCH₂CH₃ | H | 3-Cl,6-Me | O |
| A-5484 | H | H | H | H | H | O | C(=O)OCH₂CH₃ | H | 4-Cl,2-Me | O |
| A-5485 | H | H | H | H | H | O | C(=O)OCH₂CH₃ | H | 2-Cl,5-CF₃ | O |
| A-5486 | H | H | H | H | H | O | C(=O)OCH₂CH₃ | H | 2-Cl,6-CF₃ | O |
| A-5487 | H | H | H | H | H | O | C(=O)OCH₂CH₃ | H | 2-Cl,6-OMe | O |
| A-5488 | H | H | H | H | H | O | C(=O)OCH₂CH₃ | H | 3-Cl,6-OMe | O |
| A-5489 | H | H | H | H | H | O | C(=O)OCH₂CH₃ | H | 4-Cl,2-OMe | O |
| A-5490 | H | H | H | H | H | O | C(=O)OCH₂CH₃ | H | 2,4-Me₂ | O |
| A-5491 | H | H | H | H | H | O | C(=O)OCH₂CH₃ | H | 2,5-Me₂ | O |
| A-5492 | H | H | H | H | H | O | C(=O)OCH₂CH₃ | H | 2,6-Me₂ | O |
| A-5493 | H | H | H | H | H | O | C(=O)OCH₂CH₃ | H | 2-Me,4-CF₃ | O |
| A-5494 | H | H | H | H | H | O | C(=O)OCH₂CH₃ | H | 2-Me,5-CF₃ | O |
| A-5495 | H | H | H | H | H | O | C(=O)OCH₂CH₃ | H | 2-Me,6-CF₃ | O |
| A-5496 | H | H | H | H | H | O | C(=O)OCH₂CH₃ | H | 2-Me,4-OMe | O |
| A-5497 | H | H | H | H | H | O | C(=O)OCH₂CH₃ | H | 2-Me,5-OMe | O |
| A-5498 | H | H | H | H | H | O | C(=O)OCH₂CH₃ | H | 2-Me,6-OMe | O |
| A-5499 | H | H | H | H | H | O | C(=O)OCH₂CH₃ | H | 3-Me,6-OMe | O |
| A-5500 | H | H | H | H | H | O | C(=O)OCH₂CH₃ | H | 4-Me,2-OMe | O |
| A-5501 | H | H | H | H | H | O | C(=O)OCH₂CH₃ | H | 2,5-OMe₂ | O |
| A-5502 | H | H | H | H | H | O | C(=O)OCH₂CH₃ | H | 2,6-OMe₂ | O |
| A-5503 | H | H | H | H | H | O | C(=O)OCH₂CH₃ | H | 2-OMe,6-CF₃ | O |
| A-5504 | H | H | H | H | H | O | C(=O)OCH₂CH₃ | H | 2-CHF₂,5-F | O |
| A-5505 | H | H | H | H | H | O | C(=O)OCH₂CH₃ | H | 2-CHF₂,6-F | O |
| A-5506 | H | H | H | H | H | O | C(=O)OCH₂CH₃ | H | 2-CHF₂,5-Me | O |

TABLE 97-continued

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-5507 | H | H | H | H | H | O | C(=O)OCH$_2$CH$_3$ | H | 2-CHF$_2$,6-Me | 0 |
| A-5508 | H | H | H | H | H | O | C(=O)OCH$_2$CH$_3$ | H | 2-cyclopropyl,5-F | 0 |
| A-5509 | H | H | H | H | H | O | C(=O)OCH$_2$CH$_3$ | H | 2-cyclopropyl,6-F | 0 |
| A-5510 | H | H | H | H | H | O | C(=O)OCH$_2$CH$_3$ | H | 2-cyclopropyl,5-Me | 0 |
| A-5511 | H | H | H | H | H | O | C(=O)OCH$_2$CH$_3$ | H | 2-cyclopropyl,6-Me | 0 |
| A-5512 | H | H | H | H | H | O | C(=O)OCH$_2$CH$_3$ | H | 2-ethenyl,6-F | 0 |
| A-5513 | H | H | H | H | H | O | C(=O)OCH$_2$CH$_3$ | H | 2-ethenyl,6-Me | 0 |
| A-5514 | H | H | H | H | H | O | C(=O)OCH$_2$CH$_3$ | H | 2-OEt,5-F | 0 |
| A-5515 | H | H | H | H | H | O | C(=O)OCH$_2$CH$_3$ | H | 2-OEt,6-F | 0 |
| A-5516 | H | H | H | H | H | O | C(=O)OCH$_2$CH$_3$ | H | 2-OEt,5-Cl | 0 |
| A-5517 | H | H | H | H | H | O | C(=O)OCH$_2$CH$_3$ | H | 2-OEt,6-Cl | 0 |
| A-5518 | H | H | H | H | H | O | C(=O)OCH$_2$CH$_3$ | H | 2-OEt,5-Me | 0 |
| A-5519 | H | H | H | H | H | O | C(=O)OCH$_2$CH$_3$ | H | 2-OEt,6-Me | 0 |
| A-5520 | H | H | H | H | H | O | C(=O)OCH$_2$CH$_3$ | H | 2-OCHF$_2$,5-F | 0 |
| A-5521 | H | H | H | H | H | O | C(=O)OCH$_2$CH$_3$ | H | 2-OCHF$_2$,6-F | 0 |
| A-5522 | H | H | H | H | H | O | C(=O)OCH$_2$CH$_3$ | H | 2-OCHF$_2$,5-Me | 0 |
| A-5523 | H | H | H | H | H | O | C(=O)OCH$_2$CH$_3$ | H | 2-OCHF$_2$,6-Me | 0 |
| A-5524 | H | H | H | H | H | O | C(=O)OCH$_2$CH$_3$ | H | 2-(cyclopropyloxy),5-F | 0 |

TABLE 98

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-5525 | H | H | H | H | H | O | C(=O)OCH$_2$CH$_3$ | H | 2-(cyclopropyloxy),6-F | 0 |
| A-5526 | H | H | H | H | H | O | C(=O)OCH$_2$CH$_3$ | H | 2-(cyclopropyloxy),5-Me | 0 |
| A-5527 | H | H | H | H | H | O | C(=O)OCH$_2$CH$_3$ | H | 2-(cyclopropyloxy),6-Me | 0 |
| A-5528 | H | H | H | H | H | O | C(=O)OCH$_2$CH$_3$ | H | 2-SMe,5-F | 0 |
| A-5529 | H | H | H | H | H | O | C(=O)OCH$_2$CH$_3$ | H | 2-SMe,6-F | 0 |
| A-5530 | H | H | H | H | H | O | C(=O)OCH$_2$CH$_3$ | H | 2-SMe,5-Me | 0 |
| A-5531 | H | H | H | H | H | O | C(=O)OCH$_2$CH$_3$ | H | 2-SMe,6-Me | 0 |
| A-5532 | H | H | H | H | H | O | C(=O)OCH$_2$CH$_3$ | H | 2-S(=O)Me,5-F | 0 |
| A-5533 | H | H | H | H | H | O | C(=O)OCH$_2$CH$_3$ | H | 2-S(=O)Me,6-F | 0 |
| A-5534 | H | H | H | H | H | O | C(=O)OCH$_2$CH$_3$ | H | 2-S(=O)Me,5-Me | 0 |
| A-5535 | H | H | H | H | H | O | C(=O)OCH$_2$CH$_3$ | H | 2-S(=O)Me,6-Me | 0 |
| A-5536 | H | H | H | H | H | O | C(=O)OCH$_2$CH$_3$ | H | 2-S(=O)2Me,5-F | 0 |
| A-5537 | H | H | H | H | H | O | C(=O)OCH$_2$CH$_3$ | H | 2-S(=O)$_2$Me,6-F | 0 |
| A-5538 | H | H | H | H | H | O | C(=O)OCH$_2$CH$_3$ | H | 2-S(=O)$_2$Me,5-Me | 0 |
| A-5539 | H | H | H | H | H | O | C(=O)OCH$_2$CH$_3$ | H | 2-S(=O)$_2$Me,6-Me | 0 |
| A-5540 | H | H | H | H | H | O | C(=O)OCH$_2$CH$_3$ | H | 2-SCF$_3$,5-F | 0 |
| A-5541 | H | H | H | H | H | O | C(=O)OCH$_2$CH$_3$ | H | 2-SCF$_3$,6-F | 0 |
| A-5542 | H | H | H | H | H | O | C(=O)OCH$_2$CH$_3$ | H | 2-SCF$_3$,5-Me | 0 |
| A-5543 | H | H | H | H | H | O | C(=O)OCH$_2$CH$_3$ | H | 2-SCF$_3$,6-Me | 0 |
| A-5544 | H | H | H | H | H | O | C(=O)OCH$_2$CH$_3$ | H | 2-S(=O)CF$_3$,5-F | 0 |
| A-5545 | H | H | H | H | H | O | C(=O)OCH$_2$CH$_3$ | H | 2-S(=O)CF$_3$,6-F | 0 |
| A-5546 | H | H | H | H | H | O | C(=O)OCH$_2$CH$_3$ | H | 2-S(=O)CF$_3$,5-Me | 0 |
| A-5547 | H | H | H | H | H | O | C(=O)OCH$_2$CH$_3$ | H | 2-S(=O)CF$_3$,6-Me | 0 |
| A-5548 | H | H | H | H | H | O | C(=O)OCH$_2$CH$_3$ | H | 2-S(=O)$_2$CF$_3$,5-F | 0 |
| A-5549 | H | H | H | H | H | O | C(=O)OCH$_2$CH$_3$ | H | 2-S(=O)$_2$CF$_3$,6-F | 0 |
| A-5550 | H | H | H | H | H | O | C(=O)OCH$_2$CH$_3$ | H | 2-S(=O)$_2$CF$_3$,5-Me | 0 |
| A-5551 | H | H | H | H | H | O | C(=O)OCH$_2$CH$_3$ | H | 2-S(=O)$_2$CF$_3$,6-Me | 0 |
| A-5552 | H | H | H | H | H | O | C(=O)OCH$_2$CH$_3$ | H | 2-(cyclopropylthio),5-F | 0 |
| A-5553 | H | H | H | H | H | O | C(=O)OCH$_2$CH$_3$ | H | 2-(cyclopropylthio),6-F | 0 |
| A-5554 | H | H | H | H | H | O | C(=O)OCH$_2$CH$_3$ | H | 2-(cyclopropylthio),5-Me | 0 |
| A-5555 | H | H | H | H | H | O | C(=O)OCH$_2$CH$_3$ | H | 2-(cyclopropylthio),6-Me | 0 |
| A-5556 | H | H | H | H | H | O | C(=O)OCH$_2$CH$_3$ | H | 2-C(=O)Me,5-F | 0 |
| A-5557 | H | H | H | H | H | O | C(=O)OCH$_2$CH$_3$ | H | 2-C(=O)Me,6-F | 0 |
| A-5558 | H | H | H | H | H | O | C(=O)OCH$_2$CH$_3$ | H | 2-C(=O)Me,5-Me | 0 |
| A-5559 | H | H | H | H | H | O | C(=O)OCH$_2$CH$_3$ | H | 2-C(=O)Me,6-Me | 0 |
| A-5560 | H | H | H | H | H | O | C(=O)OCH$_2$CH$_3$ | H | 2-CH$_2$OH,5-F | 0 |
| A-5561 | H | H | H | H | H | O | C(=O)OCH$_2$CH$_3$ | H | 2-CH$_2$OH,6-F | 0 |
| A-5562 | H | H | H | H | H | O | C(=O)OCH$_2$CH$_3$ | H | 2-CH$_2$OH,5-Me | 0 |
| A-5563 | H | H | H | H | H | O | C(=O)OCH$_2$CH$_3$ | H | 2-CH$_2$OH,6-Me | 0 |
| A-5564 | H | H | H | H | H | O | C(=O)OCH$_2$CH$_3$ | H | 2-CH$_2$OCH$_3$,4-F | 0 |
| A-5565 | H | H | H | H | H | O | C(=O)OCH$_2$CH$_3$ | H | 2-CH$_2$OCH$_3$,5-F | 0 |
| A-5566 | H | H | H | H | H | O | C(=O)OCH$_2$CH$_3$ | H | 2-CH$_2$OCH$_3$,6-F | 0 |
| A-5567 | H | H | H | H | H | O | C(=O)OCH$_2$CH$_3$ | H | 2-CH$_2$OCH$_3$,4-Me | 0 |
| A-5568 | H | H | H | H | H | O | C(=O)OCH$_2$CH$_3$ | H | 2-CH$_2$OCH$_3$,5-Me | 0 |
| A-5569 | H | H | H | H | H | O | C(=O)OCH$_2$CH$_3$ | H | 2-CH$_2$OCH$_3$,6-Me | 0 |
| A-5570 | H | H | H | H | H | O | C(=O)OCH$_2$CH$_3$ | H | 2-OC(=O)CH$_3$,5-F | 0 |
| A-5571 | H | H | H | H | H | O | C(=O)OCH$_2$CH$_3$ | H | 2-OC(=O)CH$_3$,6-F | 0 |
| A-5572 | H | H | H | H | H | O | C(=O)OCH$_2$CH$_3$ | H | 2-OC(=O)CH$_3$,5-Me | 0 |
| A-5573 | H | H | H | H | H | O | C(=O)OCH$_2$CH$_3$ | H | 2-OC(=O)CH$_3$,6-Me | 0 |
| A-5574 | H | H | H | H | H | O | C(=O)OCH$_2$CH$_3$ | H | 2-OS(=O)$_2$CH$_3$,5-F | 0 |
| A-5575 | H | H | H | H | H | O | C(=O)OCH$_2$CH$_3$ | H | 2-OC(=O)$_2$CH$_3$,6-F | 0 |
| A-5576 | H | H | H | H | H | O | C(=O)OCH$_2$CH$_3$ | H | 2-OS(=O)$_2$CH$_3$,5-Me | 0 |

TABLE 98-continued

| compound | R¹ | R² | R³ | R⁴ | R⁵ | A | R⁶ | R⁷ | (R⁸)ₘ | p |
|---|---|---|---|---|---|---|---|---|---|---|
| A-5577 | H | H | H | H | H | O | C(=O)OCH₂CH₃ | H | 2-OS(=O)₂CH₃,6-Me | O |
| A-5578 | H | H | H | H | H | O | C(=O)OCH₂CH₃ | H | 2-CH₂SCH₃,5-F | O |
| A-5579 | H | H | H | H | H | O | C(=O)OCH₂CH₃ | H | 2-CH₂SCH₃,6-F | O |
| A-5580 | H | H | H | H | H | O | C(=O)OCH₂CH₃ | H | 2-CH₂SCH₃,5-Me | O |
| A-5581 | H | H | H | H | H | O | C(=O)OCH₂CH₃ | H | 2-CH₂SCH₃,6-Me | O |

TABLE 99

| compound | R¹ | R² | R³ | R⁴ | R⁵ | A | R⁶ | R⁷ | (R⁸)ₘ | p |
|---|---|---|---|---|---|---|---|---|---|---|
| A-5582 | H | H | H | H | H | O | C(=O)OCH₂CH₃ | H | 2-NMe₂,5-F | O |
| A-5583 | H | H | H | H | H | O | C(=O)OCH₂CH₃ | H | 2-NMe₂,6-F | O |
| A-5584 | H | H | H | H | H | O | C(=O)OCH₂CH₃ | H | 2-NMe₂,5-Me | O |
| A-5585 | H | H | H | H | H | O | C(=O)OCH₂CH₃ | H | 2-NMe₂,6-Me | O |
| A-5586 | H | H | H | H | H | O | C(=O)OCH₂CH₃ | H | 2-CN,4-F | O |
| A-5587 | H | H | H | H | H | O | C(=O)OCH₂CH₃ | H | 2-CN,5-F | O |
| A-5588 | H | H | H | H | H | O | C(=O)OCH₂CH₃ | H | 2-CN,6-F | O |
| A-5589 | H | H | H | H | H | O | C(=O)OCH₂CH₃ | H | 2-CN,6-Me | O |
| A-5590 | H | H | H | H | H | O | C(=O)OCH₂CH₃ | H | 2-CN,5-OMe | O |
| A-5591 | H | H | H | H | H | O | C(=O)OCH₂CH₃ | H | 2-CN,6-OMe | O |
| A-5592 | H | H | H | H | H | O | C(=O)OCH₂CH₃ | H | 3-CN,6-Me | O |
| A-5593 | H | H | H | H | H | O | C(=O)OCH₂CH₃ | H | 3-CN,6-OMe | O |
| A-5594 | H | H | H | H | H | O | C(=O)OCH₂CH₃ | H | 4-CN,2-Me | O |
| A-5595 | H | H | H | H | H | O | C(=O)OCH₂CH₃ | H | 4-CN,2-OMe | O |
| A-5596 | H | H | H | H | H | O | C(=O)OCH₂CH₃ | H | 2-NO₂,4-F | O |
| A-5597 | H | H | H | H | H | O | C(=O)OCH₂CH₃ | H | 2-NO₂,5-F | O |
| A-5598 | H | H | H | H | H | O | C(=O)OCH₂CH₃ | H | 2-NO₂,6-F | O |
| A-5599 | H | H | H | H | H | O | C(=O)OCH₂CH₃ | H | 2-NO₂,4-Me | O |
| A-5600 | H | H | H | H | H | O | C(=O)OCH₂CH₃ | H | 2-NO₂,5-Me | O |
| A-5601 | H | H | H | H | H | O | C(=O)OCH₂CH₃ | H | 2-NO₂,6-Me | O |
| A-5602 | H | H | H | H | H | O | C(=O)OCH₂CH₃ | H | 2-Me,4,5-F₂ | O |
| A-5603 | H | H | H | H | H | O | C(=O)OCH₂CH₃ | H | 2-Me,6-Et | O |
| A-5604 | H | H | H | H | H | O | C(=O)OCH₂CH₃ | H | 2-cyclopropyl,6-OMe | O |
| A-5605 | H | H | H | H | H | O | C(=O)OCH₂CH₃ | H | 2-Me,5-Et | O |
| A-5606 | H | H | H | H | H | O | C(=O)OCH₂CH₃ | H | 2,6-Et₂ | O |
| A-5607 | H | H | H | H | H | O | C(=O)OCH₂CH₃ | H | 2-Et,6-F | O |
| A-5608 | H | H | H | H | H | O | C(=O)OCH₂CH₃ | H | 2-CH₂OCH₃,6-Cl | O |
| A-5609 | H | H | H | H | H | O | C(=O)OCH₂CH₃ | H | 2-CH₂OCH₂CH₃,6-Cl | O |
| A-5610 | H | H | H | H | H | O | C(=O)OCH₂CH₃ | H | 2-CH₂NMe₂ | O |
| A-5611 | H | H | H | H | H | O | C(=O)OCH₂CH₃ | H | H | O |
| A-5612 | H | H | H | H | H | O | C(=O)OCH₂CH₃ | H | 2-F | O |
| A-5613 | H | H | H | H | H | O | C(=O)OCH₂CH₃ | H | 2-Cl | O |
| A-5614 | H | H | H | H | H | O | C(=O)OCH₂CH₃ | H | 2-Br | O |
| A-5615 | H | H | H | H | H | O | C(=O)OCH₂CH₃ | H | 2-OH | O |
| A-5616 | H | H | H | H | H | O | C(=O)OCH₂CH₃ | H | 2-Me | O |
| A-5617 | H | H | H | H | H | O | C(=O)OCH₂CH₃ | H | 2-Et | O |
| A-5618 | H | H | H | H | H | O | C(=O)OCH₂CH₃ | H | 2-Pr | O |
| A-5619 | H | H | H | H | H | O | C(=O)OCH₂CH₃ | H | 2-CF₃ | O |
| A-5620 | H | H | H | H | H | O | C(=O)OCH₂CH₃ | H | 2-CHF₂ | O |
| A-5621 | H | H | H | H | H | O | C(=O)OCH₂CH₃ | H | 2-CH₂F | O |
| A-5622 | H | H | H | H | H | O | C(=O)OCH₂CH₃ | H | 2-CF₂Cl | O |
| A-5623 | H | H | H | H | H | O | C(=O)OCH₂CH₃ | H | 2-cyclopropyl | O |
| A-5624 | H | H | H | H | H | O | C(=O)OCH₂CH₃ | H | 2-cyclobutyl | O |
| A-5625 | H | H | H | H | H | O | C(=O)OCH₂CH₃ | H | 2-cyclopentyl | O |
| A-5626 | H | H | H | H | H | O | C(=O)OCH₂CH₃ | H | 2-ethenyl | O |
| A-5627 | H | H | H | H | H | O | C(=O)OCH₂CH₃ | H | 2-allyl | O |
| A-5628 | H | H | H | H | H | O | C(=O)OCH₂CH₃ | H | 2-(prop-1-en-1-yl) | O |
| A-5629 | H | H | H | H | H | O | C(=O)OCH₂CH₃ | H | 2-(trifluoroethenyl) | O |
| A-5630 | H | H | H | H | H | O | C(=O)OCH₂CH₃ | H | 2-OMe | O |
| A-5631 | H | H | H | H | H | O | C(=O)OCH₂CH₃ | H | 2-OEt | O |
| A-5632 | H | H | H | H | H | O | C(=O)OCH₂CH₃ | H | 2-OPr | O |
| A-5633 | H | H | H | H | H | O | C(=O)OCH₂CH₃ | H | 2-O(i-Pr) | O |
| A-5634 | H | H | H | H | H | O | C(=O)OCH₂CH₃ | H | 2-OCF₃ | O |
| A-5635 | H | H | H | H | H | O | C(=O)OCH₂CH₃ | H | 2-OCHF₂ | O |
| A-5636 | H | H | H | H | H | O | C(=O)OCH₂CH₃ | H | 2-(cyclopropyloxy) | O |
| A-5637 | H | H | H | H | H | O | C(=O)OCH₂CH₃ | H | 2-(cyclobutyloxy) | O |
| A-5638 | H | H | H | H | H | O | C(=O)OCH₂CH₃ | H | 2-(cyclopentyloxy) | O |

TABLE 100

| compound | R¹ | R² | R³ | R⁴ | R⁵ | A | R⁶ | R⁷ | (R⁸)ₘ | p |
|---|---|---|---|---|---|---|---|---|---|---|
| A-5639 | H | H | H | H | H | O | C(=O)OCH₂CH₃ | H | 2-((2,2-dichbrocyclopropyl)oxy) | 0 |
| A-5640 | H | H | H | H | H | O | C(=O)OCH₂CH₃ | H | 2-(oxiran-2-yl) | 0 |
| A-5641 | H | H | H | H | H | O | C(=O)OCH₂CH₃ | H | 2-SMe | 0 |
| A-5642 | H | H | H | H | H | O | C(=O)OCH₂CH₃ | H | 3-SMe | 0 |
| A-5643 | H | H | H | H | H | O | C(=O)OCH₂CH₃ | H | 2-S(=O)Me | 0 |
| A-5644 | H | H | H | H | H | O | C(=O)OCH₂CH₃ | H | 3-S(=O)Me | 0 |
| A-5645 | H | H | H | H | H | O | C(=O)OCH₂CH₃ | H | 2-S(=O)₂Me | 0 |
| A-5646 | H | H | H | H | H | O | C(=O)OCH₂CH₃ | H | 3-S(=O)₂Me | 0 |
| A-5647 | H | H | H | H | H | O | C(=O)OCH₂CH₃ | H | 2-SCF₃ | 0 |
| A-5648 | H | H | H | H | H | O | C(=O)OCH₂CH₃ | H | 3-SCF₃ | 0 |
| A-5649 | H | H | H | H | H | O | C(=O)OCH₂CH₃ | H | 3-S(=O)CF₃ | 0 |
| A-5650 | H | H | H | H | H | O | C(=O)OCH₂CH₃ | H | 3-SCF(CF₃)₂ | 0 |
| A-5651 | H | H | H | H | H | O | C(=O)OCH₂CH₃ | H | 2-(cyclopropylthio) | 0 |
| A-5652 | H | H | H | H | H | O | C(=O)OCH₂CH₃ | H | 2-(cyclopropylsulfinyl) | 0 |
| A-5653 | H | H | H | H | H | O | C(=O)OCH₂CH₃ | H | 2-(cyclopropylsulfonyl) | 0 |
| A-5654 | H | H | H | H | H | O | C(=O)OCH₂CH₃ | H | 2-C(=O)Me | 0 |
| A-5655 | H | H | H | H | H | O | C(=O)OCH₂CH₃ | H | 2-CH₂C(=O)CH₃ | 0 |
| A-5656 | H | H | H | H | H | O | C(=O)OCH₂CH₃ | H | 2-CH₂C(=O)CF₃ | 0 |
| A-5657 | H | H | H | H | H | O | C(=O)OCH₂CH₃ | H | 2-CH₂OH | 0 |
| A-5658 | H | H | H | H | H | O | C(=O)OCH₂CH₃ | H | 2-CH₂OCH₃ | 0 |
| A-5659 | H | H | H | H | H | O | C(=O)OCH₂CH₃ | H | 2-CH₂OCH₂CH₃ | 0 |
| A-5660 | H | H | H | H | H | O | C(=O)OCH₂CH₃ | H | 2-CH₂SCH₃ | 0 |
| A-5661 | H | H | H | H | H | O | C(=O)OCH₂CH₃ | H | 2-CH₂S(=O)CH₃ | 0 |
| A-5662 | H | H | H | H | H | O | C(=O)OCH₂CH₃ | H | 2-CH₂S(=O)₂CH₃ | 0 |
| A-5663 | H | H | H | H | H | O | C(=O)OCH₂CH₃ | H | 2-(benzyloxy) | 0 |
| A-5664 | H | H | H | H | H | O | C(=O)OCH₂CH₃ | H | 2-NH₂ | 0 |
| A-5665 | H | H | H | H | H | O | C(=O)OCH₂CH₃ | H | 2-NHMe | 0 |
| A-5666 | H | H | H | H | H | O | C(=O)OCH₂CH₃ | H | 2-N(Me)₂ | 0 |
| A-5667 | H | H | H | H | H | O | C(=O)OCH₂CH₃ | H | 2-(1,3-dioxolan-2-yl) | 0 |
| A-5668 | H | H | H | H | H | O | C(=O)OCH₂CH₃ | H | 2-(1,3-dioxan-2-yl) | 0 |
| A-5669 | H | H | H | H | H | O | C(=O)OCH₂CH₃ | H | 2-(1H-midazol-2-yl) | 0 |
| A-5670 | H | H | H | H | H | O | C(=O)OCH₂CH₃ | H | 2-(thiazol-2-yl) | 0 |
| A-5671 | H | H | H | H | H | O | C(=O)OCH₂CH₃ | H | 2-(oxazol-2-yl) | 0 |
| A-5672 | H | H | H | H | H | O | C(=O)OCH₂CH₃ | H | 2-CH=NOH | 0 |
| A-5673 | H | H | H | H | H | O | C(=O)OCH₂CH₃ | H | 2-CH=NOMe | 0 |
| A-5674 | H | H | H | H | H | O | C(=O)OCH₂CH₃ | H | 2-(4,5-dihydro-3-isoxazolyl) | 0 |
| A-5675 | H | H | H | H | H | O | C(=O)OCH₂CH₃ | H | 2-CN | 0 |
| A-5676 | H | H | H | H | H | O | C(=O)OCH₂CH₃ | H | 2-NO₂ | 0 |
| A-5677 | H | H | H | H | H | O | C(=O)OCH₂CH₃ | H | 2-F,6-Cl | 0 |
| A-5678 | H | H | H | H | H | O | C(=O)OCH₂CH₃ | H | 2-F,6-Me | 0 |
| A-5679 | H | H | H | H | H | O | C(=O)OCH₂CH₃ | H | 3-F,6-Me | 0 |
| A-5680 | H | H | H | H | H | O | C(=O)OCH₂CH₃ | H | 4-F,2-Me | 0 |
| A-5681 | H | H | H | H | H | O | C(=O)OCH₂CH₃ | H | 2-F,6-OMe | 0 |
| A-5682 | H | H | H | H | H | O | C(=O)OCH₂CH₃ | H | 3-F,6-OMe | 0 |
| A-5683 | H | H | H | H | H | O | C(=O)OCH₂CH₃ | H | 2,6-Cl₂ | 0 |
| A-5684 | H | H | H | H | H | O | C(=O)OCH₂CH₃ | H | 2-Cl,6-Me | 0 |
| A-5685 | H | H | H | H | H | O | C(=O)OCH₂CH₃ | H | 3-Cl,6-Me | 0 |
| A-5686 | H | H | H | H | H | O | C(=O)OCH₂CH₃ | H | 4-Cl,2-Me | 0 |
| A-5687 | H | H | H | H | H | O | C(=O)OCH₂CH₃ | H | 2-Cl,5-CF₃ | 0 |
| A-5688 | H | H | H | H | H | O | C(=O)OCH₂CH₃ | H | 2-Cl,6-CF₃ | 0 |
| A-5689 | H | H | H | H | H | O | C(=O)OCH₂CH₃ | H | 2-Cl,6-OMe | 0 |
| A-5690 | H | H | H | H | H | O | C(=O)OCH₂CH₃ | H | 3-Cl,6-OMe | p |
| A-5691 | H | H | H | H | H | O | C(=O)OCH₂CH₃ | H | 4-Cl,2-OMe | 0 |
| A-5692 | H | H | H | H | H | O | C(=O)OCH₂CH₃ | H | 2,4-Me₂ | 0 |
| A-5693 | H | H | H | H | H | O | C(=O)OCH₂CH₃ | H | 2,5-Me₂ | 0 |
| A-5694 | H | H | H | H | H | O | C(=O)OCH₂CH₃ | H | 2,6-Me₂ | 0 |
| A-5695 | H | H | H | H | H | O | C(=O)OCH₂CH₃ | H | 2-Me,4-CF₃ | 0 |

TABLE 101

| compound | R¹ | R² | R³ | R⁴ | R⁵ | A | R⁶ | R⁷ | (R⁸)ₘ | p |
|---|---|---|---|---|---|---|---|---|---|---|
| A-5696 | H | H | H | H | H | O | C(=O)N(CH₃)₂ | H | 2-Me,5-CF₃ | 0 |
| A-5697 | H | H | H | H | H | O | C(=O)N(CH₃)₂ | H | 2-Me,6-CF₃ | 0 |
| A-5698 | H | H | H | H | H | O | C(=O)N(CH₃)₂ | H | 2-Me,4-OMe | 0 |
| A-5699 | H | H | H | H | H | O | C(=O)N(CH₃)₂ | H | 2-Me,5-OMe | 0 |
| A-5700 | H | H | H | H | H | O | C(=O)N(CH₃)₂ | H | 2-Me,6-OMe | 0 |
| A-5701 | H | H | H | H | H | O | C(=O)N(CH₃)₂ | H | 3-Me,6-OMe | 0 |
| A-5702 | H | H | H | H | H | O | C(=O)N(CH₃)₂ | H | 4-Me,2-OMe | 0 |
| A-5703 | H | H | H | H | H | O | C(=O)N(CH₃)₂ | H | 2,5-OMe₂ | 0 |
| A-5704 | H | H | H | H | H | O | C(=O)N(CH₃)₂ | H | 2,6-OMe₂ | 0 |
| A-5705 | H | H | H | H | H | O | C(=O)N(CH₃)₂ | H | 2-OMe,6-CF₃ | 0 |
| A-5706 | H | H | H | H | H | O | C(=O)N(CH₃)₂ | H | 2-CHF₂,5-F | 0 |
| A-5707 | H | H | H | H | H | O | C(=O)N(CH₃)₂ | H | 2-CHF₂,6-F | 0 |
| A-5708 | H | H | H | H | H | O | C(=O)N(CH₃)₂ | H | 2-CHF₂,5-Me | 0 |

TABLE 101-continued

| compound | R¹ | R² | R³ | R⁴ | R⁵ | A | R⁶ | R⁷ | (R⁸)ₘ | p |
|---|---|---|---|---|---|---|---|---|---|---|
| A-5709 | H | H | H | H | H | O | C(=O)N(CH₃)₂ | H | 2-CHF₂,6-Me | O |
| A-5710 | H | H | H | H | H | O | C(=O)N(CH₃)₂ | H | 2-cyclopropyl,5-F | O |
| A-5711 | H | H | H | H | H | O | C(=O)N(CH₃)₂ | H | 2-cyclopropyl,6-F | O |
| A-5712 | H | H | H | H | H | O | C(=O)N(CH₃)₂ | H | 2-cyclopropyl,5-Me | O |
| A-5713 | H | H | H | H | H | O | C(=O)N(CH₃)₂ | H | 2-cyclopropyl,6-Me | O |
| A-5714 | H | H | H | H | H | O | C(=O)N(CH₃)₂ | H | 2-ethenyl,6-F | O |
| A-5715 | H | H | H | H | H | O | C(=O)N(CH₃)₂ | H | 2-ethenyl,6-Me | O |
| A-5716 | H | H | H | H | H | O | C(=O)N(CH₃)₂ | H | 2-OEt,5-F | O |
| A-5717 | H | H | H | H | H | O | C(=O)N(CH₃)₂ | H | 2-OEt,6-F | O |
| A-5718 | H | H | H | H | H | O | C(=O)N(CH₃)₂ | H | 2-OEt,5-Cl | O |
| A-5719 | H | H | H | H | H | O | C(=O)N(CH₃)₂ | H | 2-OEt,6-Cl | O |
| A-5720 | H | H | H | H | H | O | C(=O)N(CH₃)₂ | H | 2-OEt,5-Me | O |
| A-5721 | H | H | H | H | H | O | C(=O)N(CH₃)₂ | H | 2-OEt,6-Me | O |
| A-5722 | H | H | H | H | H | O | C(=O)N(CH₃)₂ | H | 2-OCHF₂,5-F | O |
| A-5723 | H | H | H | H | H | O | C(=O)N(CH₃)₂ | H | 2-OCHF₂,6-F | O |
| A-5724 | H | H | H | H | H | O | C(=O)N(CH₃)₂ | H | 2-OCHF₂,5-Me | O |
| A-5725 | H | H | H | H | H | O | C(=O)N(CH₃)₂ | H | 2-OCHF₂,6-Me | O |
| A-5726 | H | H | H | H | H | O | C(=O)N(CH₃)₂ | H | 2-(cyclopropyloxy),5-F | O |
| A-5727 | H | H | H | H | H | O | C(=O)N(CH₃)₂ | H | 2-(cyclopropyloxy),6-F | O |
| A-5728 | H | H | H | H | H | O | C(=O)N(CH₃)₂ | H | 2-(cyclopropyloxy),5-Me | O |
| A-5729 | H | H | H | H | H | O | C(=O)N(CH₃)₂ | H | 2-(cyclopropyloxy),6-Me | O |
| A-5730 | H | H | H | H | H | O | C(=O)N(CH₃)₂ | H | 2-SMe,5-F | O |
| A-5731 | H | H | H | H | H | O | C(=O)N(CH₃)₂ | H | 2-SMe,6-F | O |
| A-5732 | H | H | H | H | H | O | C(=O)N(CH₃)₂ | H | 2-SMe,5-Me | O |
| A-5733 | H | H | H | H | H | O | C(=O)N(CH₃)₂ | H | 2-SMe,6-Me | O |
| A-5734 | H | H | H | H | H | O | C(=O)N(CH₃)₂ | H | 2-S(=O)Me,5-F | O |
| A-5735 | H | H | H | H | H | O | C(=O)N(CH₃)₂ | H | 2-S(=O)Me,6-F | O |
| A-5736 | H | H | H | H | H | O | C(=O)N(CH₃)₂ | H | 2-S(=O)Me,5-Me | O |
| A-5737 | H | H | H | H | H | O | C(=O)N(CH₃)₂ | H | 2-S(=O)Me,6-Me | O |
| A-5738 | H | H | H | H | H | O | C(=O)N(CH₃)₂ | H | 2-S(=O)₂Me,5-F | O |
| A-5739 | H | H | H | H | H | O | C(=O)N(CH₃)₂ | H | 2-S(=O)₂Me,6-F | O |
| A-5740 | H | H | H | H | H | O | C(=O)N(CH₃)₂ | H | 2-S(=O)₂Me,5-Me | O |
| A-5741 | H | H | H | H | H | O | C(=O)N(CH₃)₂ | H | 2-S(=O)₂Me,6-Me | O |
| A-5742 | H | H | H | H | H | O | C(=O)N(CH₃)₂ | H | 2-SCF₃,5-F | O |
| A-5743 | H | H | H | H | H | O | C(=O)N(CH₃)₂ | H | 2-SCF₃,6-F | O |
| A-5744 | H | H | H | H | H | O | C(=O)N(CH₃)₂ | H | 2-SCF₃,5-Me | O |
| A-5745 | H | H | H | H | H | O | C(=O)N(CH₃)₂ | H | 2-SCF₃,6-Me | O |
| A-5746 | H | H | H | H | H | O | C(=O)N(CH₃)₂ | H | 2-S(=O)CF₃,5F | O |
| A-5747 | H | H | H | H | H | O | C(=O)N(CH₃)₂ | H | 2-S(=O)CF₃,6-F | O |
| A-5748 | H | H | H | H | H | O | C(=O)N(CH₃)₂ | H | 2-S(=O)CF₃,5-Me | O |
| A-5749 | H | H | H | H | H | O | C(=O)N(CH₃)₂ | H | 2-S(=O)CF₃,6-Me | O |
| A-5750 | H | H | H | H | H | O | C(=O)N(CH₃)₂ | H | 2-S(=O)₂CF3,5-F | O |
| A-5751 | H | H | H | H | H | O | C(=O)N(CH₃)₂ | H | 2-S(=O)₂CF3,6-F | O |
| A-5752 | H | H | H | H | H | O | C(=O)N(CH₃)₂ | H | 2-S(=O)₂CF₃,5-Me | O |

TABLE 102

| compound | R¹ | R² | R³ | R⁴ | R⁵ | A | R⁶ | R⁷ | (R⁸)ₘ | p |
|---|---|---|---|---|---|---|---|---|---|---|
| A-5753 | H | H | H | H | H | O | C(=O)N(CH₃)₂ | H | 2-S(=O)2CF3,6-Me | O |
| A-5754 | H | H | H | H | H | O | C(=O)N(CH₃)₂ | H | 2-(cyclopropylthio),5-F | O |
| A-5755 | H | H | H | H | H | O | C(=O)N(CH₃)₂ | H | 2-(cyclopropylthio),6-F | O |
| A-5756 | H | H | H | H | H | O | C(=O)N(CH₃)₂ | H | 2-(cyclopropylthio),5-Me | O |
| A-5757 | H | H | H | H | H | O | C(=O)N(CH₃)₂ | H | 2-(cyclopropylthio),6-Me | O |
| A-5758 | H | H | H | H | H | O | C(=O)N(CH₃)₂ | H | 2-C(=O)Me,5-F | O |
| A-5759 | H | H | H | H | H | O | C(=O)N(CH₃)₂ | H | 2-C(=O)Me,6-F | O |
| A-5760 | H | H | H | H | H | O | C(=O)N(CH₃)₂ | H | 2-C(=O)Me,5-Me | O |
| A-5761 | H | H | H | H | H | O | C(=O)N(CH₃)₂ | H | 2-C(=O)Me,6-Me | O |
| A-5762 | H | H | H | H | H | O | C(=O)N(CH₃)₂ | H | 2-CH₂OH,5-F | O |
| A-5763 | H | H | H | H | H | O | C(=O)N(CH₃)₂ | H | 2-CH₂OH,6-F | O |
| A-5764 | H | H | H | H | H | O | C(=O)N(CH₃)₂ | H | 2-CH₂OH,5-Me | O |
| A-5765 | H | H | H | H | H | O | C(=O)N(CH₃)₂ | H | 2-CH₂OH,6-Me | O |
| A-5766 | H | H | H | H | H | O | C(=O)N(CH₃)₂ | H | 2-CH₂OCH₃,4-F | O |
| A-5767 | H | H | H | H | H | O | C(=O)N(CH₃)₂ | H | 2-CH₂OCH₃,5-F | O |
| A-5768 | H | H | H | H | H | O | C(=O)N(CH₃)₂ | H | 2-CH₂OCH₃,6-F | O |
| A-5769 | H | H | H | H | H | O | C(=O)N(CH₃)₂ | H | 2-CH₂OCH₃,4-Me | O |
| A-5770 | H | H | H | H | H | O | C(=O)N(CH₃)₂ | H | 2-CH₂OCH₃,5-Me | O |
| A-5771 | H | H | H | H | H | O | C(=O)N(CH₃)₂ | H | 2-CH₂OCH₃,6-Me | O |
| A-5772 | H | H | H | H | H | O | C(=O)N(CH₃)₂ | H | 2-OC(=O)CH₃,5-F | O |
| A-5773 | H | H | H | H | H | O | C(=O)N(CH₃)₂ | H | 2-OC(=O)CH₃,6-F | O |
| A-5774 | H | H | H | H | H | O | C(=O)N(CH₃)₂ | H | 2-OC(=O)CH₃,5-Me | O |
| A-5775 | H | H | H | H | H | O | C(=O)N(CH₃)₂ | H | 2-OC(=O)CH₃,6-Me | O |
| A-5776 | H | H | H | H | H | O | C(=O)N(CH₃)₂ | H | 2-OS(=O)₂CH₃,5-F | O |
| A-5777 | H | H | H | H | H | O | C(=O)N(CH₃)₂ | H | 2-OS(=O)₂CH₃,6-F | O |
| A-5778 | H | H | H | H | H | O | C(=O)N(CH₃)₂ | H | 2-OS(=O)₂CH₃,5-Me | O |

TABLE 102-continued

| compound | R¹ | R² | R³ | R⁴ | R⁵ | A | R⁶ | R⁷ | (R⁸)ₘ | p |
|---|---|---|---|---|---|---|---|---|---|---|
| A-5779 | H | H | H | H | H | O | C(=O)N(CH₃)₂ | H | 2-OS(=O)₂CH₃,6-Me | 0 |
| A-5780 | H | H | H | H | H | O | C(=O)N(CH₃)₂ | H | 2-CH₂SCH₃,5-F | 0 |
| A-5781 | H | H | H | H | H | O | C(=O)N(CH₃)₂ | H | 2-CH₂SCH₃,6-F | 0 |
| A-5782 | H | H | H | H | H | O | C(=O)N(CH₃)₂ | H | 2-CH₂SCH₃,5-Me | 0 |
| A-5783 | H | H | H | H | H | O | C(=O)N(CH₃)₂ | H | 2-CH₂SCH₃,6-Me | 0 |
| A-5784 | H | H | H | H | H | O | C(=O)N(CH₃)₂ | H | 2-NMe₂,5-F | 0 |
| A-5785 | H | H | H | H | H | O | C(=O)N(CH₃)₂ | H | 2-NMe₂,6-F | 0 |
| A-5786 | H | H | H | H | H | O | C(=O)N(CH₃)₂ | H | 2-NMe₂,5-Me | 0 |
| A-5787 | H | H | H | H | H | O | C(=O)N(CH₃)₂ | H | 2-NMe₂,6-Me | 0 |
| A-5788 | H | H | H | H | H | O | C(=O)N(CH₃)₂ | H | 2-CN,4-F | 0 |
| A-5789 | H | H | H | H | H | O | C(=O)N(CH₃)₂ | H | 2-CN,5-F | 0 |
| A-5790 | H | H | H | H | H | O | C(=O)N(CH₃)₂ | H | 2-CN,6-F | 0 |
| A-5791 | H | H | H | H | H | O | C(=O)N(CH₃)₂ | H | 2-CN,6-Me | 0 |
| A-5792 | H | H | H | H | H | O | C(=O)N(CH₃)₂ | H | 2-CN,5-OMe | 0 |
| A-5793 | H | H | H | H | H | O | C(=O)N(CH₃)₂ | H | 2-CN,6-OMe | 0 |
| A-5794 | H | H | H | H | H | O | C(=O)N(CH₃)₂ | H | 3-CN,6-Me | 0 |
| A-5795 | H | H | H | H | H | O | C(=O)N(CH₃)₂ | H | 3-CN,6-OMe | 0 |
| A-5796 | H | H | H | H | H | O | C(=O)N(CH₃)₂ | H | 4-CN,2-Me | 0 |
| A-5797 | H | H | H | H | H | O | C(=O)N(CH₃)₂ | H | 4-CN,2-OMe | 0 |
| A-5798 | H | H | H | H | H | O | C(=O)N(CH₃)₂ | H | 2-NO₂,4-F | 0 |
| A-5799 | H | H | H | H | H | O | C(=O)N(CH₃)₂ | H | 2-NO₂,5-F | 0 |
| A-5800 | H | H | H | H | H | O | C(=O)N(CH₃)₂ | H | 2-NO₂,6-F | 0 |
| A-5801 | H | H | H | H | H | O | C(=O)N(CH₃)₂ | H | 2-NO₂,4-Me | 0 |
| A-5802 | H | H | H | H | H | O | C(=O)N(CH₃)₂ | H | 2-NO₂,5-Me | 0 |
| A-5803 | H | H | H | H | H | O | C(=O)N(CH₃)₂ | H | 2-NO₂,6-Me | 0 |
| A-5804 | H | H | H | H | H | O | C(=O)N(CH₃)₂ | H | 2-Me,4,5-F₂ | 0 |
| A-5805 | H | H | H | H | H | O | C(=O)N(CH₃)₂ | H | 2-Me,6-Et | 0 |
| A-5806 | H | H | H | H | H | O | C(=O)N(CH₃)₂ | H | 2-cyclopropyl,6-OMe | 0 |
| A-5807 | H | H | H | H | H | O | C(=O)N(CH₃)₂ | H | 2-Me,5-Et | 0 |
| A-5808 | H | H | H | H | H | O | C(=O)N(CH₃)₂ | H | 2,6-Et₂ | 0 |
| A-5809 | H | H | H | H | H | O | C(=O)N(CH₃)₂ | H | 2-Et,6-F | 0 |

TABLE 103

| compound | R¹ | R² | R³ | R⁴ | R⁵ | A | R⁶ | R⁷ | (R⁸)ₘ | p |
|---|---|---|---|---|---|---|---|---|---|---|
| A-5810 | H | H | H | H | H | O | C(=O)N(CH₃)₂ | H | 2-CH₂OCH₃,6-Cl | 0 |
| A-5811 | H | H | H | H | H | O | C(=O)N(CH₃)₂ | H | 2-CH₂OCH₂CH₃,6-Cl | 0 |
| A-5812 | H | H | H | H | H | O | C(=O)N(CH₃)₂ | H | 2-CH₂NMe₂ | 0 |
| A-5813 | H | H | H | H | H | O | C(=O)(4-Cl)Ph | H | H | 0 |
| A-5814 | H | H | H | H | H | O | C(=O)(4-Cl)Ph | H | 2-F | 0 |
| A-5815 | H | H | H | H | H | O | C(=O)(4-Cl)Ph | H | 2-Cl | 0 |
| A-5816 | H | H | H | H | H | O | C(=O)(4-Cl)Ph | H | 2-Br | 0 |
| A-5817 | H | H | H | H | H | O | C(=O)(4-Cl)Ph | H | 2-OH | 0 |
| A-5818 | H | H | H | H | H | O | C(=O)(4-Cl)Ph | H | 2-Me | 0 |
| A-5819 | H | H | H | H | H | O | C(=O)(4-Cl)Ph | H | 2-Et | 0 |
| A-5820 | H | H | H | H | H | O | C(=O)(4-Cl)Ph | H | 2-Pr | 0 |
| A-5821 | H | H | H | H | H | O | C(=O)(4-Cl)Ph | H | 2-CF₃ | 0 |
| A-5822 | H | H | H | H | H | O | C(=O)(4-Cl)Ph | H | 2-CHF₂ | 0 |
| A-5823 | H | H | H | H | H | O | C(=O)(4-Cl)Ph | H | 2-CH₂F | 0 |
| A-5824 | H | H | H | H | H | O | C(=O)(4-Cl)Ph | H | 2-CF₂Cl | 0 |
| A-5825 | H | H | H | H | H | O | C(=O)(4-Cl)Ph | H | 2-cyclopropyl | 0 |
| A-5826 | H | H | H | H | H | O | C(=O)(4-Cl)Ph | H | 2-cyclobutyl | 0 |
| A-5827 | H | H | H | H | H | O | C(=O)(4-Cl)Ph | H | 2-cyclopentyl | 0 |
| A-5828 | H | H | H | H | H | O | C(=O)(4-Cl)Ph | H | 2-ethenyl | 0 |
| A-5829 | H | H | H | H | H | O | C(=O)(4-Cl)Ph | H | 2-allyl | 0 |
| A-5830 | H | H | H | H | H | O | C(=O)(4-Cl)Ph | H | 2-(prop-1-en-1-yl) | 0 |
| A-5831 | H | H | H | H | H | O | C(=O)(4-Cl)Ph | H | 2-(trifluoroethenyl) | 0 |
| A-5832 | H | H | H | H | H | O | C(=O)(4-Cl)Ph | H | 2-OMe | 0 |
| A-5833 | H | H | H | H | H | O | C(=O)(4-Cl)Ph | H | 2-OEt | 0 |
| A-5834 | H | H | H | H | H | O | C(=O)(4-Cl)Ph | H | 2-OPr | 0 |
| A-5835 | H | H | H | H | H | O | C(=O)(4-Cl)Ph | H | 2-O(i-Pr) | 0 |
| A-5836 | H | H | H | H | H | O | C(=O)(4-Cl)Ph | H | 2-OCF₃ | 0 |
| A-5837 | H | H | H | H | H | O | C(=O)(4-Cl)Ph | H | 2-OCHF₂ | 0 |
| A-5838 | H | H | H | H | H | O | C(=O)(4-Cl)Ph | H | 2-(cyclopropyloxy) | 0 |
| A-5839 | H | H | H | H | H | O | C(=O)(4-Cl)Ph | H | 2-(cyclobutyloxy) | 0 |
| A-5840 | H | H | H | H | H | O | C(=O)(4-Cl)Ph | H | 2-(cyclopentyloxy) | 0 |
| A-5841 | H | H | H | H | H | O | C(=O)(4-Cl)Ph | H | 2-((2,2-dichlorocyclopropyl)oxy) | 0 |
| A-5842 | H | H | H | H | H | O | C(=O)(4-Cl)Ph | H | 2-(oxiran-2-yl) | 0 |
| A-5843 | H | H | H | H | H | O | C(=O)(4-Cl)Ph | H | 2-SMe | 0 |
| A-5844 | H | H | H | H | H | O | C(=O)(4-Cl)Ph | H | 3-SMe | 0 |
| A-5845 | H | H | H | H | H | O | C(=O)(4-Cl)Ph | H | 2-S(=O)Me | 0 |
| A-5846 | H | H | H | H | H | O | C(=O)(4-Cl)Ph | H | 3-S(=O)Me | 0 |
| A-5847 | H | H | H | H | H | O | C(=O)(4-Cl)Ph | H | 2-S(=O)₂Me | 0 |
| A-5848 | H | H | H | H | H | O | C(=O)(4-Cl)Ph | H | 3-S(=O)₂Me | 0 |

TABLE 103-continued

| compound | R¹ | R² | R³ | R⁴ | R⁵ | A | R⁶ | R⁷ | (R⁸)ₘ | p |
|---|---|---|---|---|---|---|---|---|---|---|
| A-5849 | H | H | H | H | H | O | C(=O)(4-Cl)Ph | H | 2-SCF₃ | 0 |
| A-5850 | H | H | H | H | H | O | C(=O)(4-Cl)Ph | H | 3-SCF₃ | 0 |
| A-5851 | H | H | H | H | H | O | C(=O)(4-Cl)Ph | H | 3-S(=O)CF₃ | 0 |
| A-5852 | H | H | H | H | H | O | C(=O)(4-Cl)Ph | H | 3-SCF(CF₃)₂ | 0 |
| A-5853 | H | H | H | H | H | O | C(=O)(4-Cl)Ph | H | 2-(cyclopropylthio) | 0 |
| A-5854 | H | H | H | H | H | O | C(=O)(4-Cl)Ph | H | 2-(cyclopropylsulfinyl) | 0 |
| A-5855 | H | H | H | H | H | O | C(=O)(4-Cl)Ph | H | 2-(cyclopropylsulfonyl) | 0 |
| A-5856 | H | H | H | H | H | O | C(=O)(4-Cl)Ph | H | 2-C(=O)Me | 0 |
| A-5857 | H | H | H | H | H | O | C(=O)(4-Cl)Ph | H | 2-CH₂C(=O)CH₃ | 0 |
| A-5858 | H | H | H | H | H | O | C(=O)(4-Cl)Ph | H | 2-CH₂C(=O)CF₃ | 0 |
| A-5859 | H | H | H | H | H | O | C(=O)(4-Cl)Ph | H | 2-CH₂OH | 0 |
| A-5860 | H | H | H | H | H | O | C(=O)(4-Cl)Ph | H | 2-CH₂OCH₃ | 0 |
| A-5861 | H | H | H | H | H | O | C(=O)(4-Cl)Ph | H | 2-CH₂OCH₂CH₃ | 0 |
| A-5862 | H | H | H | H | H | O | C(=O)(4-Cl)Ph | H | 2-CH₂SCH₃ | 0 |
| A-5863 | H | H | H | H | H | O | C(=O)(4-Cl)Ph | H | 2-CH₂S(=O)CH₃ | 0 |
| A-5864 | H | H | H | H | H | O | C(=O)(4-Cl)Ph | H | 2-CH2S(=O)₂CH₃ | 0 |
| A-5865 | H | H | H | H | H | O | C(=O)(4-Cl)Ph | H | 2-(benzyloxy) | 0 |
| A-5866 | H | H | H | H | H | O | C(=O)(4-Cl)Ph | H | 2-NH₂ | 0 |

TABLE 104

| compound | R¹ | R² | R³ | R⁴ | R⁵ | A | R⁶ | R⁷ | (R⁸)ₘ | p |
|---|---|---|---|---|---|---|---|---|---|---|
| A-5867 | H | H | H | H | H | O | C(=O)(4-Cl)Ph | H | 2-NHMe | 0 |
| A-5868 | H | H | H | H | H | O | C(=O)(4-Cl)Ph | H | 2-N(Me)₂ | 0 |
| A-5869 | H | H | H | H | H | O | C(=O)(4-Cl)Ph | H | 2-(1,3-dioxolan-2-yl) | 0 |
| A-5870 | H | H | H | H | H | O | C(=O)(4-Cl)Ph | H | 2-(1,3-dioxan-2-yl) | 0 |
| A-5871 | H | H | H | H | H | O | C(=O)(4-Cl)Ph | H | 2-(1H-imidazo1-2-yl) | 0 |
| A-5872 | H | H | H | H | H | O | C(=O)(4-Cl)Ph | H | 2-(thiazol-2-yl) | 0 |
| A-5873 | H | H | H | H | H | O | C(=O)(4-Cl)Ph | H | 2-(oxazol-2-yl) | 0 |
| A-5874 | H | H | H | H | H | O | C(=O)(4-Cl)Ph | H | 2-CH=NOH | 0 |
| A-5875 | H | H | H | H | H | O | C(=O)(4-Cl)Ph | H | 2-CH=NOMe | 0 |
| A-5876 | H | H | H | H | H | O | C(=O)(4-Cl)Ph | H | 2-(4,5-dihydro-3-isoxazol)yl) | 0 |
| A-5877 | H | H | H | H | H | O | C(=O)(4-Cl)Ph | H | 2-CN | 0 |
| A-5878 | H | H | H | H | H | O | C(=O)(4-Cl)Ph | H | 2-NO₂ | 0 |
| A-5879 | H | H | H | H | H | O | C(=O)(4-Cl)Ph | H | 2-F,6-Cl | 0 |
| A-5880 | H | H | H | H | H | O | C(=O)(4-Cl)Ph | H | 2-F,6-Me | 0 |
| A-5881 | H | H | H | H | H | O | C(=O)(4-Cl)Ph | H | 3-F,6-Me | 0 |
| A-5882 | H | H | H | H | H | O | C(=O)(4-Cl)Ph | H | 4-F,2-Me | 0 |
| A-5883 | H | H | H | H | H | O | C(=O)(4-Cl)Ph | H | 2-F,6-OMe | 0 |
| A-5884 | H | H | H | H | H | O | C(=O)(4-Cl)Ph | H | 3-F,6-OMe | 0 |
| A-5885 | H | H | H | H | H | O | C(=O)(4-Cl)Ph | H | 2,6-Cl₂ | 0 |
| A-5886 | H | H | H | H | H | O | C(=O)(4-Cl)Ph | H | 2-Cl,6-Me | 0 |
| A-5887 | H | H | H | H | H | O | C(=O)(4-Cl)Ph | H | 3-Cl,6-Me | 0 |
| A-5888 | H | H | H | H | H | O | C(=O)(4-Cl)Ph | H | 4-Cl,2-Me | 0 |
| A-5889 | H | H | H | H | H | O | C(=O)(4-Cl)Ph | H | 2-Cl,5-CF₃ | 0 |
| A-5890 | H | H | H | H | H | O | C(=O)(4-Cl)Ph | H | 2-Cl,6-CF₃ | 0 |
| A-5891 | H | H | H | H | H | O | C(=O)(4-Cl)Ph | H | 2-Cl,6-OMe | 0 |
| A-5892 | H | H | H | H | H | O | C(=O)(4-Cl)Ph | H | 3-Cl,6-OMe | 0 |
| A-5893 | H | H | H | H | H | O | C(=O)(4-Cl)Ph | H | 4-Cl,2-OMe | 0 |
| A-5894 | H | H | H | H | H | O | C(=O)(4-Cl)Ph | H | 2,4-Me₂ | 0 |
| A-5895 | H | H | H | H | H | O | C(=O)(4-Cl)Ph | H | 2,5-Me₂ | 0 |
| A-5896 | H | H | H | H | H | O | C(=O)(4-Cl)Ph | H | 2,6-Me₂ | 0 |
| A-5897 | H | H | H | H | H | O | C(=O)(4-Cl)Ph | H | 2-Me,4-CF₃ | 0 |
| A-5898 | H | H | H | H | H | O | C(=O)(4-Cl)Ph | H | 2-Me,5-CF₃ | 0 |
| A-5899 | H | H | H | H | H | O | C(=O)(4-Cl)Ph | H | 2-Me,6-CF₃ | 0 |
| A-5900 | H | H | H | H | H | O | C(=O)(4-Cl)Ph | H | 2-Me,4-OMe | 0 |
| A-5901 | H | H | H | H | H | O | C(=O)(4-Cl)Ph | H | 2-Me,5-OMe | 0 |
| A-5902 | H | H | H | H | H | O | C(=O)(4-Cl)Ph | H | 2-Me,6-OMe | 0 |
| A-5903 | H | H | H | H | H | O | C(=O)(4-Cl)Ph | H | 3-Me,6-OMe | 0 |
| A-5904 | H | H | H | H | H | O | C(=O)(4-Cl)Ph | H | 4-Me,2-OMe | 0 |
| A-5905 | H | H | H | H | H | O | C(=O)(4-Cl)Ph | H | 2,5-OMe₂ | 0 |
| A-5906 | H | H | H | H | H | O | C(=O)(4-Cl)Ph | H | 2,6-OMe₂ | 0 |
| A-5907 | H | H | H | H | H | O | C(=O)(4-Cl)Ph | H | 2-OMe,6-CF₃ | 0 |
| A-5908 | H | H | H | H | H | O | C(=O)(4-Cl)Ph | H | 2-CHF₂,5-F | 0 |
| A-5909 | H | H | H | H | H | O | C(=O)(4-Cl)Ph | H | 2-CHF₂,6-F | 0 |
| A-5910 | H | H | H | H | H | O | C(=O)(4-Cl)Ph | H | 2-CHF₂,5-Me | 0 |
| A-5911 | H | H | H | H | H | O | C(=O)(4-Cl)Ph | H | 2-CHF₂,6-Me | 0 |
| A-5912 | H | H | H | H | H | O | C(=O)(4-Cl)Ph | H | 2-cyclopropyl,5-F | 0 |
| A-5913 | H | H | H | H | H | O | C(=O)(4-Cl)Ph | H | 2-cyclopropyl,6-F | 0 |
| A-5914 | H | H | H | H | H | O | C(=O)(4-Cl)Ph | H | 2-cyclopropyl,5-Me | 0 |
| A-5915 | H | H | H | H | H | O | C(=O)(4-Cl)Ph | H | 2-cyclopropyl,6-Me | 0 |
| A-5916 | H | H | H | H | H | O | C(=O)(4-Cl)Ph | H | 2-ethenyl,6-F | 0 |
| A-5917 | H | H | H | H | H | O | C(=O)(4-Cl)Ph | H | 2-ethenyl,6-Me | 0 |
| A-5918 | H | H | H | H | H | O | C(=O)(4-Cl)Ph | H | 2-OEt,5-F | 0 |

TABLE 104-continued

| compound | R¹ | R² | R³ | R⁴ | R⁵ | A | R⁶ | R⁷ | (R⁸)ₘ | p |
|---|---|---|---|---|---|---|---|---|---|---|
| A-5919 | H | H | H | H | H | O | C(=O)(4-Cl)Ph | H | 2-OEt,6-F | 0 |
| A-5920 | H | H | H | H | H | O | C(=O)(4-Cl)Ph | H | 2-OEt,5-Cl | 0 |
| A-5921 | H | H | H | H | H | O | C(=O)(4-Cl)Ph | H | 2-OEt,6-Cl | 0 |
| A-5922 | H | H | H | H | H | O | C(=O)(4-Cl)Ph | H | 2-OEt,5-Me | 0 |
| A-5923 | H | H | H | H | H | O | C(=O)(4-Cl)Ph | H | 2-OEt,6-Me | 0 |

TABLE 105

| compound | R¹ | R² | R³ | R⁴ | R⁵ | A | R⁶ | R⁷ | (R⁸)ₘ | p |
|---|---|---|---|---|---|---|---|---|---|---|
| A-5924 | H | H | H | H | H | O | C(=O)(4-Cl)Ph | H | 2-OCHF₂,5-F | 0 |
| A-5925 | H | H | H | H | H | O | C(=O)(4-Cl)Ph | H | 2-OCHF₂,6-F | 0 |
| A-5926 | H | H | H | H | H | O | C(=O)(4-Cl)Ph | H | 2-OCHF₂,5-Me | 0 |
| A-5927 | H | H | H | H | H | O | C(=O)(4-Cl)Ph | H | 2-OCHF₂,6-Me | 0 |
| A-5928 | H | H | H | H | H | O | C(=O)(4-Cl)Ph | H | 2-(cyclopropyloxy),5-F | 0 |
| A-5929 | H | H | H | H | H | O | C(=O)(4-Cl)Ph | H | 2-(cyclopropyloxy),6-F | 0 |
| A-5930 | H | H | H | H | H | O | C(=O)(4-Cl)Ph | H | 2-(cyclopropyloxy),5-Me | 0 |
| A-5931 | H | H | H | H | H | O | C(=O)(4-Cl)Ph | H | 2-(cyclopropyloxy),6-Me | 0 |
| A-5932 | H | H | H | H | H | O | C(=O)(4-Cl)Ph | H | 2-SMe,5-F | 0 |
| A-5933 | H | H | H | H | H | O | C(=O)(4-Cl)Ph | H | 2-SMe,6-F | 0 |
| A-5934 | H | H | H | H | H | O | C(=O)(4-Cl)Ph | H | 2-SMe,5-Me | 0 |
| A-5935 | H | H | H | H | H | O | C(=O)(4-Cl)Ph | H | 2-SMe,6-Me | 0 |
| A-5936 | H | H | H | H | H | O | C(=O)(4-Cl)Ph | H | 2-S(=O)Me,5-F | 0 |
| A-5937 | H | H | H | H | H | O | C(=O)(4-Cl)Ph | H | 2-S(=O)Me,6-F | 0 |
| A-5938 | H | H | H | H | H | O | C(=O)(4-Cl)Ph | H | 2-S(=O)Me,5-Me | 0 |
| A-5939 | H | H | H | H | H | O | C(=O)(4-Cl)Ph | H | 2-S(=O)Me,6-Me | 0 |
| A-5940 | H | H | H | H | H | O | C(=O)(4-Cl)Ph | H | 2-S(=O)₂Me,5-F | 0 |
| A-5941 | H | H | H | H | H | O | C(=O)(4-Cl)Ph | H | 2-S(=O)₂Me,6-F | 0 |
| A-5942 | H | H | H | H | H | O | C(=O)(4-Cl)Ph | H | 2-S(=O)₂Me,5-Me | 0 |
| A-5943 | H | H | H | H | H | O | C(=O)(4-Cl)Ph | H | 2-S(=O)₂Me,6-Me | 0 |
| A-5944 | H | H | H | H | H | O | C(=O)(4-Cl)Ph | H | 2-SCF₃,5-F | 0 |
| A-5945 | H | H | H | H | H | O | C(=O)(4-Cl)Ph | H | 2-SCF₃,6-F | 0 |
| A-5946 | H | H | H | H | H | O | C(=O)(4-Cl)Ph | H | 2-SCF₃,5-Me | 0 |
| A-5947 | H | H | H | H | H | O | C(=O)(4-Cl)Ph | H | 2-SCF₃,6-Me | 0 |
| A-5948 | H | H | H | H | H | O | C(=O)(4-Cl)Ph | H | 2-S(=O)CF₃,5-F | 0 |
| A-5949 | H | H | H | H | H | O | C(=O)(4-Cl)Ph | H | 2-S(=O)CF₃,6-F | 0 |
| A-5950 | H | H | H | H | H | O | C(=O)(4-Cl)Ph | H | 2-S(=O)CF₃,5-Me | 0 |
| A-5951 | H | H | H | H | H | O | C(=O)(4-Cl)Ph | H | 2-S(=O)CF3,6-Me | 0 |
| A-5952 | H | H | H | H | H | O | C(=O)(4-Cl)Ph | H | 2-S(=O)₂CF₃,5-F | 0 |
| A-5953 | H | H | H | H | H | O | C(=O)(4-Cl)Ph | H | 2-S(=O)₂CF₃,6-F | 0 |
| A-5954 | H | H | H | H | H | O | C(=O)(4-Cl)Ph | H | 2-S(=O)₂CF₃,5-Me | 0 |
| A-5955 | H | H | H | H | H | O | C(=O)(4-Cl)Ph | H | 2-S(=O)₂CF₃,6-Me | 0 |
| A-5956 | H | H | H | H | H | O | C(=O)(4-Cl)Ph | H | 2-(cyclopropylthio),5-F | 0 |
| A-5957 | H | H | H | H | H | O | C(=O)(4-Cl)Ph | H | 2-(cyclopropylthio),6-F | 0 |
| A-5958 | H | H | H | H | H | O | C(=O)(4-Cl)Ph | H | 2-(cyclopropylthio),5-Me | 0 |
| A-5959 | H | H | H | H | H | O | C(=O)(4-Cl)Ph | H | 2-(cyclopropylthio),6-Me | 0 |
| A-5960 | H | H | H | H | H | O | C(=O)(4-Cl)Ph | H | 2-C(=O)Me,5-F | 0 |
| A-5961 | H | H | H | H | H | O | C(=O)(4-Cl)Ph | H | 2-C(=O)Me,6-F | 0 |
| A-5962 | H | H | H | H | H | O | C(=O)(4-Cl)Ph | H | 2-C(=O)Me,5-Me | 0 |
| A-5963 | H | H | H | H | H | O | C(=O)(4-Cl)Ph | H | 2-C(=O)Me,6-Me | 0 |
| A-5964 | H | H | H | H | H | O | C(=O)(4-Cl)Ph | H | 2-CH₂OH,5-F | 0 |
| A-5965 | H | H | H | H | H | O | C(=O)(4-Cl)Ph | H | 2-CH₂OH,6-F | 0 |
| A-5966 | H | H | H | H | H | O | C(=O)(4-Cl)Ph | H | 2-CH₂OH,5-Me | 0 |
| A-5967 | H | H | H | H | H | O | C(=O)(4-Cl)Ph | H | 2-CH₂OH,6-Me | 0 |
| A-5968 | H | H | H | H | H | O | C(=O)(4-Cl)Ph | H | 2-CH₂OCH₃,4-F | 0 |
| A-5969 | H | H | H | H | H | O | C(=O)(4-Cl)Ph | H | 2-CH₂OCH₃,5-F | 0 |
| A-5970 | H | H | H | H | H | O | C(=O)(4-Cl)Ph | H | 2-CH₂OCH₃,6-F | 0 |
| A-5971 | H | H | H | H | H | O | C(=O)(4-Cl)Ph | H | 2-CH₂OCH₃,4-Me | 0 |
| A-5972 | H | H | H | H | H | O | C(=O)(4-Cl)Ph | H | 2-CH₂OCH₃,5-Me | 0 |
| A-5973 | H | H | H | H | H | O | C(=O)(4-Cl)Ph | H | 2-CH₂OCH₃,6-Me | 0 |
| A-5974 | H | H | H | H | H | O | C(=O)(4-Cl)Ph | H | 2-OC(=O)CH₃,5-F | 0 |
| A-5975 | H | H | H | H | H | O | C(=O)(4-Cl)Ph | H | 2-OC(=O)CH₃,6-F | 0 |
| A-5976 | H | H | H | H | H | O | C(=O)(4-Cl)Ph | H | 2-OC(=O)CH₃,5-Me | 0 |
| A-5977 | H | H | H | H | H | O | C(=O)(4-Cl)Ph | H | 2-OC(=O)CH₃,6-Me | 0 |
| A-5978 | H | H | H | H | H | O | C(=O)(4-Cl)Ph | H | 2-OS(=O)₂CH₃,5-F | 0 |
| A-5979 | H | H | H | H | H | O | C(=O)(4-Cl)Ph | H | 2-OS(=O)₂CH₃,6-F | 0 |
| A-5980 | H | H | H | H | H | O | C(=O)(4-Cl)Ph | H | 2-OS(=O)₂CH₃,5-Me | 0 |

TABLE 106

| compound | R¹ | R² | R³ | R⁴ | R⁵ | A | R⁶ | R⁷ | (R⁸)ₘ | p |
|---|---|---|---|---|---|---|---|---|---|---|
| A-5981 | H | H | H | H | H | O | C(=O)(4-Cl)Ph | H | 2-OS(=O)2CH₃,6-Me | 0 |
| A-5982 | H | H | H | H | H | O | C(=O)(4-Cl)Ph | H | 2-CH₂SCH₃,5-F | 0 |
| A-5983 | H | H | H | H | H | O | C(=O)(4-Cl)Ph | H | 2-CH₂SCH₃,6-F | 0 |
| A-5984 | H | H | H | H | H | O | C(=O)(4-Cl)Ph | H | 2-CH₂SCH | 0 |
| A-5985 | H | H | H | H | H | O | C(=O)(4-Cl)Ph | H | 2-CH₂SCH₃,6-Me | 0 |
| A-5986 | H | H | H | H | H | O | C(=O)(4-Cl)Ph | H | 2-NMe₂,5-F | 0 |
| A-5987 | H | H | H | H | H | O | C(=O)(4-Cl)Ph | H | 2-NMe₂,6-F | 0 |
| A-5988 | H | H | H | H | H | O | C(=O)(4-Cl)Ph | H | 2-NMe₂,5-Me | 0 |
| A-5989 | H | H | H | H | H | O | C(=O)(4-Cl)Ph | H | 2-NMe₂,6-Me | 0 |
| A-5990 | H | H | H | H | H | O | C(=O)(4-Cl)Ph | H | 2-CN,4-F | 0 |
| A-5991 | H | H | H | H | H | O | C(=O)(4-Cl)Ph | H | 2-CN,5-F | 0 |
| A-5992 | H | H | H | H | H | O | C(=O)(4-Cl)Ph | H | 2-CN,6-F | 0 |
| A-5993 | H | H | H | H | H | O | C(=O)(4-Cl)Ph | H | 2-CN,6-Me | 0 |
| A-5994 | H | H | H | H | H | O | C(=O)(4-Cl)Ph | H | 2-CN,5-OMe | 0 |
| A-5995 | H | H | H | H | H | O | C(=O)(4-Cl)Ph | H | 2-CN,6-OMe | 0 |
| A-5996 | H | H | H | H | H | O | C(=O)(4-Cl)Ph | H | 3-CN,6-Me | 0 |
| A-5997 | H | H | H | H | H | O | C(=O)(4-Cl)Ph | H | 3-CN,6-OMe | 0 |
| A-5998 | H | H | H | H | H | O | C(=O)(4-Cl)Ph | H | 4-CN,2-Me | 0 |
| A-5999 | H | H | H | H | H | O | C(=O)(4-Cl)Ph | H | 4-CN,2-OMe | 0 |
| A-6000 | H | H | H | H | H | O | C(=O)(4-Cl)Ph | H | 2-NO₂,4-F | 0 |
| A-6001 | H | H | H | H | H | O | C(=O)(4-Cl)Ph | H | 2-NO₂,5-F | 0 |
| A-6002 | H | H | H | H | H | O | C(=O)(4-Cl)Ph | H | 2-NO₂,6-F | 0 |
| A-6003 | H | H | H | H | H | O | C(=O)(4-Cl)Ph | H | 2-NO₂,4-Me | 0 |
| A-6004 | H | H | H | H | H | O | C(=O)(4-Cl)Ph | H | 2-NO₂,5-Me | 0 |
| A-6005 | H | H | H | H | H | O | C(=O)(4-Cl)Ph | H | 2-NO₂,6-Me | 0 |
| A-6006 | H | H | H | H | H | O | C(=O)(4-Cl)Ph | H | 2-Me,4,5-F₂ | 0 |
| A-6007 | H | H | H | H | H | O | C(=O)(4-Cl)Ph | H | 2-Me,6-Et | 0 |
| A-6008 | H | H | H | H | H | O | C(=O)(4-Cl)Ph | H | 2-cyclopropyl,6-OMe | 0 |
| A-6009 | H | H | H | H | H | O | C(=O)(4-Cl)Ph | H | 2-Me,5-Et | 0 |
| A-6010 | H | H | H | H | H | O | C(=O)(4-Cl)Ph | H | 2,6-Et₂ | 0 |
| A-6011 | H | H | H | H | H | O | C(=O)(4-Cl)Ph | H | 2-Et,6-F | 0 |
| A-6012 | H | H | H | H | H | O | C(=O)(4-Cl)Ph | H | 2-CH₂OCH₃,6-Cl | 0 |
| A-6013 | H | H | H | H | H | O | C(=O)(4-Cl)Ph | H | 2-CH₂OCH₂CH₃,6-Cl | 0 |
| A-6014 | H | H | H | H | H | O | C(=O)(4-Cl)Ph | H | 2-CH₂NMe₂ | 0 |
| A-6015 | H | H | H | H | H | O | C(=S)OCH₃ | H | H | 0 |
| A-6016 | H | H | H | H | H | O | C(=S)OCH₃ | H | 2-F | 0 |
| A-6017 | H | H | H | H | H | O | C(=S)OCH₃ | H | 2-Cl | 0 |
| A-6018 | H | H | H | H | H | O | C(=S)OCH₃ | H | 2-Br | 0 |
| A-6019 | H | H | H | H | H | O | C(=S)OCH₃ | H | 2-OH | 0 |
| A-6020 | H | H | H | H | H | O | C(=S)OCH₃ | H | 2-Me | 0 |
| A-6021 | H | H | H | H | H | O | C(=S)OCH₃ | H | 2-Et | 0 |
| A-6022 | H | H | H | H | H | O | C(=S)OCH₃ | H | 2-Pr | 0 |
| A-6023 | H | H | H | H | H | O | C(=S)OCH₃ | H | 2-CF₃ | 0 |
| A-6024 | H | H | H | H | H | O | C(=S)OCH₃ | H | 2-CHF₂ | 0 |
| A-6025 | H | H | H | H | H | O | C(=S)OCH₃ | H | 2-CH₂F | 0 |
| A-6026 | H | H | H | H | H | O | C(=S)OCH₃ | H | 2-CF₂Cl | 0 |
| A-6027 | H | H | H | H | H | O | C(=S)OCH₃ | H | 2-cyclopropyl | 0 |
| A-6028 | H | H | H | H | H | O | C(=S)OCH₃ | H | 2-cyclobutyl | 0 |
| A-6029 | H | H | H | H | H | O | C(=S)OCH₃ | H | 2-cyclopentyl | 0 |
| A-6030 | H | H | H | H | H | O | C(=S)OCH₃ | H | 2-ethenyl | 0 |
| A-6031 | H | H | H | H | H | O | C(=S)OCH₃ | H | 2-allyl | 0 |
| A-6032 | H | H | H | H | H | O | C(=S)OCH₃ | H | 2-(prop-1-en-1-yl) | 0 |
| A-6033 | H | H | H | H | H | O | C(=S)OCH₃ | H | 2-(trifluoroethenyl) | 0 |
| A-6034 | H | H | H | H | H | O | C(=S)OCH₃ | H | 2-OMe | 0 |
| A-6035 | H | H | H | H | H | O | C(=S)OCH₃ | H | 2-OEt | 0 |
| A-6036 | H | H | H | H | H | O | C(=S)OCH₃ | H | 2-OPr | 0 |
| A-6037 | H | H | H | H | H | O | C(=S)OCH₃ | H | 2-O(i-Pr) | 0 |

TABLE 107

| compound | R¹ | R² | R³ | R⁴ | R⁵ | A | R⁶ | R⁷ | (R⁸)ₘ | p |
|---|---|---|---|---|---|---|---|---|---|---|
| A-6038 | H | H | H | H | H | O | C(=S)OCH₃ | H | 2-OCF₃ | 0 |
| A-6039 | H | H | H | H | H | O | C(=S)OCH₃ | H | 2-OCHF₂ | 0 |
| A-6040 | H | H | H | H | H | O | C(=S)OCH₃ | H | 2-(cyclopropyloxy) | 0 |
| A-6041 | H | H | H | H | H | O | C(=S)OCH₃ | H | 2-(cyclobutyloxy) | 0 |
| A-6042 | H | H | H | H | H | O | C(=S)OCH₃ | H | 2-(cyclopentyloxy) | 0 |
| A-6043 | H | H | H | H | H | O | C(=S)OCH₃ | H | 2-((2,2-dichlorocyclopropyl)oxy) | 0 |
| A-6044 | H | H | H | H | H | O | C(=S)OCH₃ | H | 2-(oxiran-2-yl) | 0 |
| A-6045 | H | H | H | H | H | O | C(=S)OCH₃ | H | 2-SMe | 0 |
| A-6046 | H | H | H | H | H | O | C(=S)OCH₃ | H | 3-SMe | 0 |
| A-6047 | H | H | H | H | H | O | C(=S)OCH₃ | H | 2-S(=O)Me | 0 |
| A-6048 | H | H | H | H | H | O | C(=S)OCH₃ | H | 3-S(=O)Me | 0 |
| A-6049 | H | H | H | H | H | O | C(=S)OCH₃ | H | 2-S(=O)₂Me | 0 |
| A-6050 | H | H | H | H | H | O | C(=S)OCH₃ | H | 3-S(=O)₂Me | 0 |

TABLE 107-continued

| compound | R¹ | R² | R³ | R⁴ | R⁵ | A | R⁶ | R⁷ | (R⁸)$_m$ | p |
|---|---|---|---|---|---|---|---|---|---|---|
| A-6051 | H | H | H | H | H | O | C(=S)OCH₃ | H | 2-SCF₃ | 0 |
| A-6052 | H | H | H | H | H | O | C(=S)OCH₃ | H | 3-SCF₃ | 0 |
| A-6053 | H | H | H | H | H | O | C(=S)OCH₃ | H | 3-S(=O)CF₃ | 0 |
| A-6054 | H | H | H | H | H | O | C(=S)OCH₃ | H | 3-SCF(CF₃)₂ | 0 |
| A-6055 | H | H | H | H | H | O | C(=S)OCH₃ | H | 2-(cyclopropylthio) | 0 |
| A-6056 | H | H | H | H | H | O | C(=S)OCH₃ | H | 2-(cyclopropylsulfinyl) | 0 |
| A-6057 | H | H | H | H | H | O | C(=S)OCH₃ | H | 2-(cyclopropylsulfonyl) | 0 |
| A-6058 | H | H | H | H | H | O | C(=S)OCH₃ | H | 2-C(=O)Me | 0 |
| A-6059 | H | H | H | H | H | O | C(=S)OCH₃ | H | 2-CH₂C(=O)CH₃ | 0 |
| A-6060 | H | H | H | H | H | O | C(=S)OCH₃ | H | 2-CH₂C(=O)CF₃ | 0 |
| A-6061 | H | H | H | H | H | O | C(=S)OCH₃ | H | 2-CH₂OH | 0 |
| A-6062 | H | H | H | H | H | O | C(=S)OCH₃ | H | 2-CH₂OCH₃ | 0 |
| A-6063 | H | H | H | H | H | O | C(=S)OCH₃ | H | 2-CH₂OCH₂CH₃ | 0 |
| A-6064 | H | H | H | H | H | O | C(=S)OCH₃ | H | 2-CH₂SCH₃ | 0 |
| A-6065 | H | H | H | H | H | O | C(=S)OCH₃ | H | 2-CH₂S(=O)CH₃ | 0 |
| A-6066 | H | H | H | H | H | O | C(=S)OCH₃ | H | 2-CH₂S(=O)₂CH₃ | 0 |
| A-6067 | H | H | H | H | H | O | C(=S)OCH₃ | H | 2-(benzyloxy) | 0 |
| A-6068 | H | H | H | H | H | O | C(=S)OCH₃ | H | 2-NH₂ | 0 |
| A-6069 | H | H | H | H | H | O | C(=S)OCH₃ | H | 2-NHMe | 0 |
| A-6070 | H | H | H | H | H | O | C(=S)OCH₃ | H | 2-N(Me)₂ | 0 |
| A-6071 | H | H | H | H | H | O | C(=S)OCH₃ | H | 2-(1,3-dioxolan-2-yl) | 0 |
| A-6072 | H | H | H | H | H | O | C(=S)OCH₃ | H | 2-(1,3-dioxan-2-yl) | 0 |
| A-6073 | H | H | H | H | H | O | C(=S)OCH₃ | H | 2-(1H-imidazol-2-yl) | 0 |
| A-6074 | H | H | H | H | H | O | C(=S)OCH₃ | H | 2-(thiazol-2-yl) | 0 |
| A-6075 | H | H | H | H | H | O | C(=S)OCH₃ | H | 2-(oxazol-2-yl) | 0 |
| A-6076 | H | H | H | H | H | O | C(=S)OCH₃ | H | 2-CH=NOH | 0 |
| A-6077 | H | H | H | H | H | O | C(=S)OCH₃ | H | 2-CH=NOMe | 0 |
| A-6078 | H | H | H | H | H | O | C(=S)OCH₃ | H | 2-(4,5-dihydro-3-isoxazolyl) | 0 |
| A-6079 | H | H | H | H | H | O | C(=S)OCH₃ | H | 2-CN | 0 |
| A-6080 | H | H | H | H | H | O | C(=S)OCH₃ | H | 2-NO₂ | 0 |
| A-6081 | H | H | H | H | H | O | C(=S)OCH₃ | H | 2-F,6-Cl | 0 |
| A-6082 | H | H | H | H | H | O | C(=S)OCH₃ | H | 2-F,6-Me | 0 |
| A-6083 | H | H | H | H | H | O | C(=S)OCH₃ | H | 3-F,6-Me | 0 |
| A-6084 | H | H | H | H | H | O | C(=S)OCH₃ | H | 4-F,2-Me | 0 |
| A-6085 | H | H | H | H | H | O | C(=S)OCH₃ | H | 2-F,6-OMe | 0 |
| A-6086 | H | H | H | H | H | O | C(=S)OCH₃ | H | 3-F,6-OMe | 0 |
| A-6087 | H | H | H | H | H | O | C(=S)OCH₃ | H | 2,6-Cl₂ | 0 |
| A-6088 | H | H | H | H | H | O | C(=S)OCH₃ | H | 2-Cl,6-Me | 0 |
| A-6089 | H | H | H | H | H | O | C(=S)OCH₃ | H | 3-Cl,6-Me | 0 |
| A-6090 | H | H | H | H | H | O | C(=S)OCH₃ | H | 4-Cl,2-Me | 0 |
| A-6091 | H | H | H | H | H | O | C(=S)OCH₃ | H | 2-Cl,5-CF₃ | 0 |
| A-6092 | H | H | H | H | H | O | C(=S)OCH₃ | H | 2-Cl,6-CF₃ | 0 |
| A-6093 | H | H | H | H | H | O | C(=S)OCH₃ | H | 2-Cl,6-OMe | 0 |
| A-6094 | H | H | H | H | H | O | C(=S)OCH₃ | H | 3-Cl,6-OMe | 0 |

TABLE 108

| compound | R¹ | R² | R³ | R⁴ | R⁵ | A | R⁶ | R⁷ | (R⁸)$_m$ | p |
|---|---|---|---|---|---|---|---|---|---|---|
| A-6095 | H | H | H | H | H | O | C(=S)OCH₃ | H | 4-Cl,2-OMe | 0 |
| A-6096 | H | H | H | H | H | O | C(=S)OCH₃ | H | 2,4-Me₂ | 0 |
| A-6097 | H | H | H | H | H | O | C(=S)OCH₃ | H | 2,5-Me₂ | 0 |
| A-6098 | H | H | H | H | H | O | C(=S)OCH₃ | H | 2,6-Me₂ | 0 |
| A-6099 | H | H | H | H | H | O | C(=S)OCH₃ | H | 2-Me,4-CF₃ | 0 |
| A-6100 | H | H | H | H | H | O | C(=S)OCH₃ | H | 2-Me,5-CF₃ | 0 |
| A-6101 | H | H | H | H | H | O | C(=S)OCH₃ | H | 2-Me,6-CF₃ | 0 |
| A-6102 | H | H | H | H | H | O | C(=S)OCH₃ | H | 2-Me,4-OMe | 0 |
| A-6103 | H | H | H | H | H | O | C(=S)OCH₃ | H | 2-Me,5-OMe | 0 |
| A-6104 | H | H | H | H | H | O | C(=S)OCH₃ | H | 2-Me,6-OMe | 0 |
| A-6105 | H | H | H | H | H | O | C(=S)OCH₃ | H | 3-Me,6-OMe | 0 |
| A-6106 | H | H | H | H | H | O | C(=S)OCH₃ | H | 4-Me,2-OMe | 0 |
| A-6107 | H | H | H | H | H | O | C(=S)OCH₃ | H | 2,5-OMe₂ | 0 |
| A-6108 | H | H | H | H | H | O | C(=S)OCH₃ | H | 2,6-OMe₂ | 0 |
| A-6109 | H | H | H | H | H | O | C(=S)OCH₃ | H | 2-OMe,6-CF₃ | 0 |
| A-6110 | H | H | H | H | H | O | C(=S)OCH₃ | H | 2-CHF₂,5-F | 0 |
| A-6111 | H | H | H | H | H | O | C(=S)OCH₃ | H | 2-CHF₂,6-F | 0 |
| A-6112 | H | H | H | H | H | O | C(=S)OCH₃ | H | 2-CHF₂,5-Me | 0 |
| A-6113 | H | H | H | H | H | O | C(=S)OCH₃ | H | 2-CHF₂,6-Me | 0 |
| A-6114 | H | H | H | H | H | O | C(=S)OCH₃ | H | 2-cyclopropyl,5-F | 0 |
| A-6115 | H | H | H | H | H | O | C(=S)OCH₃ | H | 2-cyclopropyl,6-F | 0 |
| A-6116 | H | H | H | H | H | O | C(=S)OCH₃ | H | 2-cyclopropyl,5-Me | 0 |
| A-6117 | H | H | H | H | H | O | C(=S)OCH₃ | H | 2-cyclopropyl,6-Me | 0 |
| A-6118 | H | H | H | H | H | O | C(=S)OCH₃ | H | 2-ethenyl,6-F | 0 |
| A-6119 | H | H | H | H | H | O | C(=S)OCH₃ | H | 2-ethenyl,6-Me | 0 |
| A-6120 | H | H | H | H | H | O | C(=S)OCH₃ | H | 2-OEt,5-F | 0 |

TABLE 108-continued

| compound | R¹ | R² | R³ | R⁴ | R⁵ | A | R⁶ | R⁷ | (R⁸)$_m$ | p |
|---|---|---|---|---|---|---|---|---|---|---|
| A-6121 | H | H | H | H | H | O | C(=S)OCH$_3$ | H | 2-OEt,6-F | 0 |
| A-6122 | H | H | H | H | H | O | C(=S)OCH$_3$ | H | 2-OEt,5-Cl | 0 |
| A-6123 | H | H | H | H | H | O | C(=S)OCH$_3$ | H | 2-OEt,6-Cl | 0 |
| A-6124 | H | H | H | H | H | O | C(=S)OCH$_3$ | H | 2-OEt,5-Me | 0 |
| A-6125 | H | H | H | H | H | O | C(=S)OCH$_3$ | H | 2-OEt,6-Me | 0 |
| A-6126 | H | H | H | H | H | O | C(=S)OCH$_3$ | H | 2-OCHF$_2$,5-F | 0 |
| A-6127 | H | H | H | H | H | O | C(=S)OCH$_3$ | H | 2-OCHF$_2$,6-F | 0 |
| A-6128 | H | H | H | H | H | O | C(=S)OCH$_3$ | H | 2-OCHF$_2$,5-Me | 0 |
| A-6129 | H | H | H | H | H | O | C(=S)OCH$_3$ | H | 2-OCHF$_2$,6-Me | 0 |
| A-6130 | H | H | H | H | H | O | C(=S)OCH$_3$ | H | 2-(cyclopropyloxy),5-F | 0 |
| A-6131 | H | H | H | H | H | O | C(=S)OCH$_3$ | H | 2-(cyclopropyloxy),6-F | 0 |
| A-6132 | H | H | H | H | H | O | C(=S)OCH$_3$ | H | 2-(cyclopropyloxy),5-Me | 0 |
| A-6133 | H | H | H | H | H | O | C(=S)OCH$_3$ | H | 2-(cyclopropyloxy),6-Me | 0 |
| A-6134 | H | H | H | H | H | O | C(=S)OCH$_3$ | H | 2-SMe,5-F | 0 |
| A-6135 | H | H | H | H | H | O | C(=S)OCH$_3$ | H | 2-SMe,6-F | 0 |
| A-6136 | H | H | H | H | H | O | C(=S)OCH$_3$ | H | 2-SMe,5-Me | 0 |
| A-6137 | H | H | H | H | H | O | C(=S)OCH$_3$ | H | 2-SMe,6-Me | 0 |
| A-6138 | H | H | H | H | H | O | C(=S)OCH$_3$ | H | 2-S(=O)Me,5-F | 0 |
| A-6139 | H | H | H | H | H | O | C(=S)OCH$_3$ | H | 2-S(=O)Me,6-F | 0 |
| A-6140 | H | H | H | H | H | O | C(=S)OCH$_3$ | H | 2-S(=O)Me,5-Me | 0 |
| A-6141 | H | H | H | H | H | O | C(=S)OCH$_3$ | H | 2-S(=O)Me,6-Me | 0 |
| A-6142 | H | H | H | H | H | O | C(=S)OCH$_3$ | H | 2-S(=O)$_2$Me,5-F | 0 |
| A-6143 | H | H | H | H | H | O | C(=S)OCH$_3$ | H | 2-S(=O)$_2$Me,6-F | 0 |
| A-6144 | H | H | H | H | H | O | C(=S)OCH$_3$ | H | 2-S(=O)$_2$Me,5-Me | 0 |
| A-6145 | H | H | H | H | H | O | C(=S)OCH$_3$ | H | 2-S(=O)$_2$Me,6-Me | 0 |
| A-6146 | H | H | H | H | H | O | C(=S)OCH$_3$ | H | 2-SCF$_3$,5-F | 0 |
| A-6147 | H | H | H | H | H | O | C(=S)OCH$_3$ | H | 2-SCF$_3$,6-F | 0 |
| A-6148 | H | H | H | H | H | O | C(=S)OCH$_3$ | H | 2-SCF$_3$,5-Me | 0 |
| A-6149 | H | H | H | H | H | O | C(=S)OCH$_3$ | H | 2-SCF$_3$,6-Me | 0 |
| A-6150 | H | H | H | H | H | O | C(=S)OCH$_3$ | H | 2-S(=O)CF$_3$,5-F | 0 |
| A-6151 | H | H | H | H | H | O | C(=S)OCH$_3$ | H | 2-S(=O)CF$_3$,6-F | 0 |

TABLE 109

| compound | R¹ | R² | R³ | R⁴ | R⁵ | A | R⁶ | R⁷ | (R⁸)$_m$ | p |
|---|---|---|---|---|---|---|---|---|---|---|
| A-6152 | H | H | H | H | H | O | C(=S)OCH$_3$ | H | 2-S(=O)CF$_3$,5-Me | 0 |
| A-6153 | H | H | H | H | H | O | C(=S)OCH$_3$ | H | 2-S(=O)CF$_3$,6-Me | 0 |
| A-6154 | H | H | H | H | H | O | C(=S)OCH$_3$ | H | 2-S(=O)$_2$CF$_3$,5-F | 0 |
| A-6155 | H | H | H | H | H | O | C(=S)OCH$_3$ | H | 2-S(=O)$_2$CF$_3$,6-F | 0 |
| A-6156 | H | H | H | H | H | O | C(=S)OCH$_3$ | H | 2-S(=O)$_2$CF$_3$,5-Me | 0 |
| A-6157 | H | H | H | H | H | O | C(=S)OCH$_3$ | H | 2-S(=O)$_2$CF$_3$,6-Me | 0 |
| A-6158 | H | H | H | H | H | O | C(=S)OCH$_3$ | H | 2-(cyclopropylthio),5-F | 0 |
| A-6159 | H | H | H | H | H | O | C(=S)OCH$_3$ | H | 2-(cyclopropylthio),6-F | 0 |
| A-6160 | H | H | H | H | H | O | C(=S)OCH$_3$ | H | 2-(cyclopropylthio),5-Me | 0 |
| A-6161 | H | H | H | H | H | O | C(=S)OCH$_3$ | H | 2-(cyclopropylthio),6-Me | 0 |
| A-6162 | H | H | H | H | H | O | C(=S)OCH$_3$ | H | 2-C(=O)Me,5-F | 0 |
| A-6163 | H | H | H | H | H | O | C(=S)OCH$_3$ | H | 2-C(=O)Me,6-F | 0 |
| A-6164 | H | H | H | H | H | O | C(=S)OCH$_3$ | H | 2-C(=O)Me,5-Me | 0 |
| A-6165 | H | H | H | H | H | O | C(=S)OCH$_3$ | H | 2-C(=O)Me,6-Me | 0 |
| A-6166 | H | H | H | H | H | O | C(=S)OCH$_3$ | H | 2-CH$_2$OH,5-F | 0 |
| A-6167 | H | H | H | H | H | O | C(=S)OCH$_3$ | H | 2-CH$_2$OH,6-F | 0 |
| A-6168 | H | H | H | H | H | O | C(=S)OCH$_3$ | H | 2-CH$_2$OH,5-Me | 0 |
| A-6169 | H | H | H | H | H | O | C(=S)OCH$_3$ | H | 2-CH$_2$OH,6-Me | 0 |
| A-6170 | H | H | H | H | H | O | C(=S)OCH$_3$ | H | 2-CH$_2$OCH$_3$,4-F | 0 |
| A-6171 | H | H | H | H | H | O | C(=S)OCH$_3$ | H | 2-CH$_2$OCH$_3$,5-F | 0 |
| A-6172 | H | H | H | H | H | O | C(=S)OCH$_3$ | H | 2-CH$_2$OCH$_3$,6-F | 0 |
| A-6173 | H | H | H | H | H | O | C(=S)OCH$_3$ | H | 2-CH$_2$OCH$_3$,4-Me | 0 |
| A-6174 | H | H | H | H | H | O | C(=S)OCH$_3$ | H | 2-CH$_2$OCH$_3$,5-Me | 0 |
| A-6175 | H | H | H | H | H | O | C(=S)OCH$_3$ | H | 2-CH$_2$OCH$_3$,6-Me | 0 |
| A-6176 | H | H | H | H | H | O | C(=S)OCH$_3$ | H | 2-OC(=O)CH$_3$,5-F | 0 |
| A-6177 | H | H | H | H | H | O | C(=S)OCH$_3$ | H | 2-OC(=O)CH$_3$,6-F | 0 |
| A-6178 | H | H | H | H | H | O | C(=S)OCH$_3$ | H | 2-OC(=O)CH$_3$,5-Me | 0 |
| A-6179 | H | H | H | H | H | O | C(=S)OCH$_3$ | H | 2-OC(=O)CH$_3$,6-Me | 0 |
| A-6180 | H | H | H | H | H | O | C(=S)OCH$_3$ | H | 2-OS(=O)$_2$CH$_3$,5-F | 0 |
| A-6181 | H | H | H | H | H | O | C(=S)OCH$_3$ | H | 2-OS(=O)$_2$CH$_3$,6-F | 0 |
| A-6182 | H | H | H | H | H | O | C(=S)OCH$_3$ | H | 2-OS(=O)$_2$CH$_3$,5-Me | 0 |
| A-6183 | H | H | H | H | H | O | C(=S)OCH$_3$ | H | 2-OS(=O)$_2$CH$_3$,6-Me | 0 |
| A-6184 | H | H | H | H | H | O | C(=S)OCH$_3$ | H | 2-CH$_2$SCH$_3$,5-F | 0 |
| A-6185 | H | H | H | H | H | O | C(=S)OCH$_3$ | H | 2-CH$_2$SCH$_3$,6-F | 0 |
| A-6186 | H | H | H | H | H | O | C(=S)OCH$_3$ | H | 2-CH$_2$SCH$_3$,5-Me | 0 |
| A-6187 | H | H | H | H | H | O | C(=S)OCH$_3$ | H | 2-CH$_2$SCH$_3$,6-Me | 0 |
| A-6188 | H | H | H | H | H | O | C(=S)OCH$_3$ | H | 2-NMe$_2$,5-F | 0 |
| A-6189 | H | H | H | H | H | O | C(=S)OCH$_3$ | H | 2-NMe$_2$,6-F | 0 |
| A-6190 | H | H | H | H | H | O | C(=S)OCH$_3$ | H | 2-NMe$_2$,5-Me | 0 |

TABLE 109-continued

| compound | R¹ | R² | R³ | R⁴ | R⁵ | A | R⁶ | R⁷ | (R⁸)$_m$ | p |
|---|---|---|---|---|---|---|---|---|---|---|
| A-6191 | H | H | H | H | H | O | C(=S)OCH₃ | H | 2-NMe₂,6-Me | 0 |
| A-6192 | H | H | H | H | H | O | C(=S)OCH₃ | H | 2-CN,4-F | 0 |
| A-6193 | H | H | H | H | H | O | C(=S)OCH₃ | H | 2-CN,5-F | 0 |
| A-6194 | H | H | H | H | H | O | C(=S)OCH₃ | H | 2-CN,6-F | 0 |
| A-6195 | H | H | H | H | H | O | C(=S)OCH₃ | H | 2-CN,6-Me | 0 |
| A-6196 | H | H | H | H | H | O | C(=S)OCH₃ | H | 2-CN,5-OMe | 0 |
| A-6197 | H | H | H | H | H | O | C(=S)OCH₃ | H | 2-CN,6-OMe | 0 |
| A-6198 | H | H | H | H | H | O | C(=S)OCH₃ | H | 3-CN,6-Me | 0 |
| A-6199 | H | H | H | H | H | O | C(=S)OCH₃ | H | 3-CN,6-OMe | 0 |
| A-6200 | H | H | H | H | H | O | C(=S)OCH₃ | H | 4-CN,2-Me | 0 |
| A-6201 | H | H | H | H | H | O | C(=S)OCH₃ | H | 4-CN,2-OMe | 0 |
| A-6202 | H | H | H | H | H | O | C(=S)OCH₃ | H | 2-NO₂,4-F | 0 |
| A-6203 | H | H | H | H | H | O | C(=S)OCH₃ | H | 2-NO₂,5-F | 0 |
| A-6204 | H | H | H | H | H | O | C(=S)OCH₃ | H | 2-NO₂,6-F | 0 |
| A-6205 | H | H | H | H | H | O | C(=S)OCH₃ | H | 2-NO₂,4-Me | 0 |
| A-6206 | H | H | H | H | H | O | C(=S)OCH₃ | H | 2-NO₂,5-Me | 0 |
| A-6207 | H | H | H | H | H | O | C(=S)OCH₃ | H | 2-NO₂,6-Me | 0 |
| A-6208 | H | H | H | H | H | O | C(=S)OCH₃ | H | 2-Me,4,5-F₂ | 0 |

TABLE 110

| compound | R¹ | R² | R³ | R⁴ | R⁵ | A | R⁶ | R⁷ | (R⁸)$_m$ | p |
|---|---|---|---|---|---|---|---|---|---|---|
| A-6209 | H | H | H | H | H | O | C(=S)OCH₃ | H | 2-Me,6-Et | 0 |
| A-6210 | H | H | H | H | H | O | C(=S)OCH₃ | H | 2-cyclopropyl,6-OMe | 0 |
| A-6211 | H | H | H | H | H | O | C(=S)OCH₃ | H | 2-Me,5-Et | 0 |
| A-6212 | H | H | H | H | H | O | C(=S)OCH₃ | H | 2,6-Et₂ | 0 |
| A-6213 | H | H | H | H | H | O | C(=S)OCH₃ | H | 2-Et,6-F | 0 |
| A-6214 | H | H | H | H | H | O | C(=S)OCH₃ | H | 2-CH₂OCH₃,6-Cl | 0 |
| A-6215 | H | H | H | H | H | O | C(=S)OCH₃ | H | 2-CH₂OCH₂CH₃,6-Cl | 0 |
| A-6216 | H | H | H | H | H | O | C(=S)OCH₃ | H | 2-CH₂NMe₂ | 0 |
| A-6217 | H | H | H | H | H | O | C(=S)N(CH₃)₂ | H | H | 0 |
| A-6218 | H | H | H | H | H | O | C(=S)N(CH₃)₂ | H | 2-F | 0 |
| A-6219 | H | H | H | H | H | O | C(=S)N(CH₃)₂ | H | 2-Cl | 0 |
| A-6220 | H | H | H | H | H | O | C(=S)N(CH₃)₂ | H | 2-Br | 0 |
| A-6221 | H | H | H | H | H | O | C(=S)N(CH₃)₂ | H | 2-OH | 0 |
| A-6222 | H | H | H | H | H | O | C(=S)N(CH₃)₂ | H | 2-Me | 0 |
| A-6223 | H | H | H | H | H | O | C(=S)N(CH₃)₂ | H | 2-Et | 0 |
| A-6224 | H | H | H | H | H | O | C(=S)N(CH₃)₂ | H | 2-Pr | 0 |
| A-6225 | H | H | H | H | H | O | C(=S)N(CH₃)₂ | H | 2-CF₃ | 0 |
| A-6226 | H | H | H | H | H | O | C(=S)N(CH₃)₂ | H | 2-CHF₂ | 0 |
| A-6227 | H | H | H | H | H | O | C(=S)N(CH₃)₂ | H | 2-CH₂F | 0 |
| A-6228 | H | H | H | H | H | O | C(=S)N(CH₃)₂ | H | 2-CF₂Cl | 0 |
| A-6229 | H | H | H | H | H | O | C(=S)N(CH₃)₂ | H | 2-cyclopropyl | 0 |
| A-6230 | H | H | H | H | H | O | C(=S)N(CH₃)₂ | H | 2-cyclobutyl | 0 |
| A-6231 | H | H | H | H | H | O | C(=S)N(CH₃)₂ | H | 2-cyclopentyl | 0 |
| A-6232 | H | H | H | H | H | O | C(=S)N(CH₃)₂ | H | 2-ethenyl | 0 |
| A-6233 | H | H | H | H | H | O | C(=S)N(CH₃)₂ | H | 2-allyl | 0 |
| A-6234 | H | H | H | H | H | O | C(=S)N(CH₃)₂ | H | 2-(prop-1-en-1-y) | 0 |
| A-6235 | H | H | H | H | H | O | C(=S)N(CH₃)₂ | H | 2-(trifluoroethenyl) | 0 |
| A-6236 | H | H | H | H | H | O | C(=S)N(CH₃)₂ | H | 2-OMe | 0 |
| A-6237 | H | H | H | H | H | O | C(=S)N(CH₃)₂ | H | 2-OEt | 0 |
| A-6238 | H | H | H | H | H | O | C(=S)N(CH₃)₂ | H | 2-OPr | 0 |
| A-6239 | H | H | H | H | H | O | C(=S)N(CH₃)₂ | H | 2-O(i-Pr) | 0 |
| A-6240 | H | H | H | H | H | O | C(=S)N(CH₃)₂ | H | 2-OCF₃ | 0 |
| A-6241 | H | H | H | H | H | O | C(=S)N(CH₃)₂ | H | 2-OCHF₂ | 0 |
| A-6242 | H | H | H | H | H | O | C(=S)N(CH₃)₂ | H | 2-(cyclopropyloxy) | 0 |
| A-6243 | H | H | H | H | H | O | C(=S)N(CH₃)₂ | H | 2-(cyclobutyloxy) | 0 |
| A-6244 | H | H | H | H | H | O | C(=S)N(CH₃)₂ | H | 2-(cyclopentyloxy) | 0 |
| A-6245 | H | H | H | H | H | O | C(=S)N(CH₃)₂ | H | 2-((2,2-dichlorocyclopropyl)oxy) | 0 |
| A-6246 | H | H | H | H | H | O | C(=S)N(CH₃)₂ | H | 2-(oxiran-2-yl) | 0 |
| A-6247 | H | H | H | H | H | O | C(=S)N(CH₃)₂ | H | 2-SMe | 0 |
| A-6248 | H | H | H | H | H | O | C(=S)N(CH₃)₂ | H | 3-SMe | 0 |
| A-6249 | H | H | H | H | H | O | C(=S)N(CH₃)₂ | H | 2-S(=O)Me | 0 |
| A-6250 | H | H | H | H | H | O | C(=S)N(CH₃)₂ | H | 3-S(=O)Me | 0 |
| A-6251 | H | H | H | H | H | O | C(=S)N(CH₃)₂ | H | 2-S(=O)₂Me | 0 |
| A-6252 | H | H | H | H | H | O | C(=S)N(CH₃)₂ | H | 3-S(=O)₂Me | 0 |
| A-6253 | H | H | H | H | H | O | C(=S)N(CH₃)₂ | H | 2-SCF₃ | 0 |
| A-6254 | H | H | H | H | H | O | C(=S)N(CH₃)₂ | H | 3-SCF₃ | 0 |
| A-6255 | H | H | H | H | H | O | C(=S)N(CH₃)₂ | H | 3-S(=O)CF₃ | 0 |
| A-6256 | H | H | H | H | H | O | C(=S)N(CH₃)₂ | H | 3-SCF(CF₃)₂ | 0 |
| A-6257 | H | H | H | H | H | O | C(=S)N(CH₃)₂ | H | 2-(cyclopropylthio) | 0 |
| A-6258 | H | H | H | H | H | O | C(=S)N(CH₃)₂ | H | 2-(cyclopropylsulfinyl) | 0 |
| A-6259 | H | H | H | H | H | O | C(=S)N(CH₃)₂ | H | 2-(cyclopropylsulfonyl) | 0 |
| A-6260 | H | H | H | H | H | O | C(=S)N(CH₃)₂ | H | 2-C(=O)Me | 0 |

TABLE 110-continued

| compound | R¹ | R² | R³ | R⁴ | R⁵ | A | R⁶ | R⁷ | (R⁸)$_m$ | p |
|---|---|---|---|---|---|---|---|---|---|---|
| A-6261 | H | H | H | H | H | O | C(=S)N(CH$_3$)$_2$ | H | 2-CH$_2$C(=O)CH$_3$ | 0 |
| A-6262 | H | H | H | H | H | O | C(=S)N(CH$_3$)$_2$ | H | 2-CH$_2$C(=O)CF$_3$ | 0 |
| A-6263 | H | H | H | H | H | O | C(=S)N(CH$_3$)$_2$ | H | 2-CH$_2$OH | 0 |
| A-6264 | H | H | H | H | H | O | C(=S)N(CH$_3$)$_2$ | H | 2-CH$_2$OCH$_3$ | 0 |
| A-6265 | H | H | H | H | H | O | C(=S)N(CH$_3$)$_2$ | H | 2-CH$_2$OCH$_2$CH$_3$ | 0 |

TABLE 111

| compound | R¹ | R² | R³ | R⁴ | R⁵ | A | R⁶ | R⁷ | (R⁸)$_m$ | p |
|---|---|---|---|---|---|---|---|---|---|---|
| A-6266 | H | H | H | H | H | O | C(=S)N(CH$_3$)$_2$ | H | 2-CH$_2$SCH$_3$ | 0 |
| A-6267 | H | H | H | H | H | O | C(=S)N(CH$_3$)$_2$ | H | 2-CH$_2$S(=O)CH$_3$ | 0 |
| A-6268 | H | H | H | H | H | O | C(=S)N(CH$_3$)$_2$ | H | 2-CH$_2$S(=O)$_2$CH$_3$ | 0 |
| A-6269 | H | H | H | H | H | O | C(=S)N(CH$_3$)$_2$ | H | 2-(benzyloxy) | 0 |
| A-6270 | H | H | H | H | H | O | C(=S)N(CH$_3$)$_2$ | H | 2-NH$_2$ | 0 |
| A-6271 | H | H | H | H | H | O | C(=S)N(CH$_3$)$_2$ | H | 2-NHMe | 0 |
| A-6272 | H | H | H | H | H | O | C(=S)N(CH$_3$)$_2$ | H | 2-N(Me)$_2$ | 0 |
| A-6273 | H | H | H | H | H | O | C(=S)N(CH$_3$)$_2$ | H | 2-(1,3-dioxolan-2-yl) | 0 |
| A-6274 | H | H | H | H | H | O | C(=S)N(CH$_3$)$_2$ | H | 2-(1,3-dioxan-2-yl) | 0 |
| A-6275 | H | H | H | H | H | O | C(=S)N(CH$_3$)$_2$ | H | 2-(1H-imidazol-2-yl) | 0 |
| A-6276 | H | H | H | H | H | O | C(=S)N(CH$_3$)$_2$ | H | 2-(thiazol-2-yl) | 0 |
| A-6277 | H | H | H | H | H | O | C(=S)N(CH$_3$)$_2$ | H | 2-(oxazol-2-yl) | 0 |
| A-6278 | H | H | H | H | H | O | C(=S)N(CH$_3$)$_2$ | H | 2-CH=NOH | 0 |
| A-6279 | H | H | H | H | H | O | C(=S)N(CH$_3$)$_2$ | H | 2-CH=NOMe | 0 |
| A-6280 | H | H | H | H | H | O | C(=S)N(CH$_3$)$_2$ | H | 2-(4,5-dihydro-3-isoxazolyl) | 0 |
| A-6281 | H | H | H | H | H | O | C(=S)N(CH$_3$)$_2$ | H | 2-CN | 0 |
| A-6282 | H | H | H | H | H | O | C(=S)N(CH$_3$)$_2$ | H | 2-NO$_2$ | 0 |
| A-6283 | H | H | H | H | H | O | C(=S)N(CH$_3$)$_2$ | H | 2-F,6-Cl | 0 |
| A-6284 | H | H | H | H | H | O | C(=S)N(CH$_3$)$_2$ | H | 2-F,6-Me | 0 |
| A-6285 | H | H | H | H | H | O | C(=S)N(CH$_3$)$_2$ | H | 3-F,6-Me | 0 |
| A-6286 | H | H | H | H | H | O | C(=S)N(CH$_3$)$_2$ | H | 4-F,2-Me | 0 |
| A-6287 | H | H | H | H | H | O | C(=S)N(CH$_3$)$_2$ | H | 2-F,6-OMe | 0 |
| A-6288 | H | H | H | H | H | O | C(=S)N(CH$_3$)$_2$ | H | 3-F,6-OMe | 0 |
| A-6289 | H | H | H | H | H | O | C(=S)N(CH$_3$)$_2$ | H | 2,6-Cl$_2$ | 0 |
| A-6290 | H | H | H | H | H | O | C(=S)N(CH$_3$)$_2$ | H | 2-Cl,6-Me | 0 |
| A-6291 | H | H | H | H | H | O | C(=S)N(CH$_3$)$_2$ | H | 3-Cl,6-Me | 0 |
| A-6292 | H | H | H | H | H | O | C(=S)N(CH$_3$)$_2$ | H | 4-Cl,2-Me | 0 |
| A-6293 | H | H | H | H | H | O | C(=S)N(CH$_3$)$_2$ | H | 2-Cl,5-CF$_3$ | 0 |
| A-6294 | H | H | H | H | H | O | C(=S)N(CH$_3$)$_2$ | H | 2-Cl,6-CF$_3$ | 0 |
| A-6295 | H | H | H | H | H | O | C(=S)N(CH$_3$)$_2$ | H | 2-Cl,6-OMe | 0 |
| A-6296 | H | H | H | H | H | O | C(=S)N(CH$_3$)$_2$ | H | 3-Cl,6-OMe | 0 |
| A-6297 | H | H | H | H | H | O | C(=S)N(CH$_3$)$_2$ | H | 4-Cl,2-OMe | 0 |
| A-6298 | H | H | H | H | H | O | C(=S)N(CH$_3$)$_2$ | H | 2,4-Me$_2$ | 0 |
| A-6299 | H | H | H | H | H | O | C(=S)N(CH$_3$)$_2$ | H | 2,5-Me$_2$ | 0 |
| A-6300 | H | H | H | H | H | O | C(=S)N(CH$_3$)$_2$ | H | 2,6-Me$_2$ | 0 |
| A-6301 | H | H | H | H | H | O | C(=S)N(CH$_3$)$_2$ | H | 2-Me,4-CF$_3$ | 0 |
| A-6302 | H | H | H | H | H | O | C(=S)N(CH$_3$)$_2$ | H | 2-Me,5-CF$_3$ | 0 |
| A-6303 | H | H | H | H | H | O | C(=S)N(CH$_3$)$_2$ | H | 2-Me,6-CF$_3$ | 0 |
| A-6304 | H | H | H | H | H | O | C(=S)N(CH$_3$)$_2$ | H | 2-Me,4-OMe | 0 |
| A-6305 | H | H | H | H | H | O | C(=S)N(CH$_3$)$_2$ | H | 2-Me,5-OMe | 0 |
| A-6306 | H | H | H | H | H | O | C(=S)N(CH$_3$)$_2$ | H | 2-Me,6-OMe | 0 |
| A-6307 | H | H | H | H | H | O | C(=S)N(CH$_3$)$_2$ | H | 3-Me,6-OMe | 0 |
| A-6308 | H | H | H | H | H | O | C(=S)N(CH$_3$)$_2$ | H | 4-Me,2-OMe | 0 |
| A-6309 | H | H | H | H | H | O | C(=S)N(CH$_3$)$_2$ | H | 2,5-OMe$_2$ | 0 |
| A-6310 | H | H | H | H | H | O | C(=S)N(CH$_3$)$_2$ | H | 2,6-OMe$_2$ | 0 |
| A-6311 | H | H | H | H | H | O | C(=S)N(CH$_3$)$_2$ | H | 2-OMe,6-CF$_3$ | 0 |
| A-6312 | H | H | H | H | H | O | C(=S)N(CH$_3$)$_2$ | H | 2-CHF$_2$,5-F | 0 |
| A-6313 | H | H | H | H | H | O | C(=S)N(CH$_3$)$_2$ | H | 2-CHF$_2$,6-F | 0 |
| A-6314 | H | H | H | H | H | O | C(=S)N(CH$_3$)$_2$ | H | 2-CHF$_2$,5-Me | 0 |
| A-6315 | H | H | H | H | H | O | C(=S)N(CH$_3$)$_2$ | H | 2-CHF$_2$,6-Me | 0 |
| A-6316 | H | H | H | H | H | O | C(=S)N(CH$_3$)$_2$ | H | 2-cyclopropyl,5-F | 0 |
| A-6317 | H | H | H | H | H | O | C(=S)N(CH$_3$)$_2$ | H | 2-cyclopropyl,6-F | 0 |
| A-6318 | H | H | H | H | H | O | C(=S)N(CH$_3$)$_2$ | H | 2-cyclopropyl,5-Me | 0 |
| A-6319 | H | H | H | H | H | O | C(=S)N(CH$_3$)$_2$ | H | 2-cyclopropyl,6-Me | 0 |
| A-6320 | H | H | H | H | H | O | C(=S)N(CH$_3$)$_2$ | H | 2-ethenyl,6-F | 0 |
| A-6321 | H | H | H | H | H | O | C(=S)N(CH$_3$)$_2$ | H | 2-ethenyl,6-Me | 0 |
| A-6322 | H | H | H | H | H | O | C(=S)N(CH$_3$)$_2$ | H | 2-OEt,5-F | 0 |

TABLE 112

| compound | R¹ | R² | R³ | R⁴ | R⁵ | A | R⁶ | R⁷ | (R⁸)ₘ | p |
|---|---|---|---|---|---|---|---|---|---|---|
| A-6323 | H | H | H | H | H | O | C(=S)N(CH₃)₂ | H | 2-OEt,6-F | 0 |
| A-6324 | H | H | H | H | H | O | C(=S)N(CH₃)₂ | H | 2-OEt,5-Cl | 0 |
| A-6325 | H | H | H | H | H | O | C(=S)N(CH₃)₂ | H | 2-OEt,6-Cl | 0 |
| A-6326 | H | H | H | H | H | O | C(=S)N(CH₃)₂ | H | 2-OEt,5-Me | 0 |
| A-6327 | H | H | H | H | H | O | C(=S)N(CH₃)₂ | H | 2-OEt,6-Me | 0 |
| A-6328 | H | H | H | H | H | O | C(=S)N(CH₃)₂ | H | 2-OCHF₂,5-F | 0 |
| A-6329 | H | H | H | H | H | O | C(=S)N(CH₃)₂ | H | 2-OCHF₂,6-F | 0 |
| A-6330 | H | H | H | H | H | O | C(=S)N(CH₃)₂ | H | 2-OCHF₂,5-Me | 0 |
| A-6331 | H | H | H | H | H | O | C(=S)N(CH₃)₂ | H | 2-OCHF₂,6-Me | 0 |
| A-6332 | H | H | H | H | H | O | C(=S)N(CH₃)₂ | H | 2-(cyclopropyloxy),5-F | 0 |
| A-6333 | H | H | H | H | H | O | C(=S)N(CH₃)₂ | H | 2-(cyclopropyloxy),6-F | 0 |
| A-6334 | H | H | H | H | H | O | C(=S)N(CH₃)₂ | H | 2-(cyclopropyloxy),5-Me | 0 |
| A-6335 | H | H | H | H | H | O | C(=S)N(CH₃)₂ | H | 2-(cyclopropyloxy),6-Me | 0 |
| A-6336 | H | H | H | H | H | O | C(=S)N(CH₃)₂ | H | 2-SMe,5-F | 0 |
| A-6337 | H | H | H | H | H | O | C(=S)N(CH₃)₂ | H | 2-SMe,6-F | 0 |
| A-6338 | H | H | H | H | H | O | C(=S)N(CH₃)₂ | H | 2-SMe,5-Me | 0 |
| A-6339 | H | H | H | H | H | O | C(=S)N(CH₃)₂ | H | 2-SMe,6-Me | 0 |
| A-6340 | H | H | H | H | H | O | C(=S)N(CH₃)₂ | H | 2-S(=O)Me,5-F | 0 |
| A-6341 | H | H | H | H | H | O | C(=S)N(CH₃)₂ | H | 2-S(=O)Me,6-F | 0 |
| A-6342 | H | H | H | H | H | O | C(=S)N(CH₃)₂ | H | 2-S(=O)Me,5-Me | 0 |
| A-6343 | H | H | H | H | H | O | C(=S)N(CH₃)₂ | H | 2-S(=O)Me,6-Me | 0 |
| A-6344 | H | H | H | H | H | O | C(=S)N(CH₃)₂ | H | 2-S(=O)₂Me,5-F | 0 |
| A-6345 | H | H | H | H | H | O | C(=S)N(CH₃)₂ | H | 2-S(=O)₂Me,6-F | 0 |
| A-6346 | H | H | H | H | H | O | C(=S)N(CH₃)₂ | H | 2-S(=O)₂Me,5-Me | 0 |
| A-6347 | H | H | H | H | H | O | C(=S)N(CH₃)₂ | H | 2-S(=O)₂Me,6-Me | 0 |
| A-6348 | H | H | H | H | H | O | C(=S)N(CH₃)₂ | H | 2-SCF₃,5-F | 0 |
| A-6349 | H | H | H | H | H | O | C(=S)N(CH₃)₂ | H | 2-SCF₃,6-F | 0 |
| A-6350 | H | H | H | H | H | O | C(=S)N(CH₃)₂ | H | 2-SCF₃,5-Me | 0 |
| A-6351 | H | H | H | H | H | O | C(=S)N(CH₃)₂ | H | 2-SCF₃,6-Me | 0 |
| A-6352 | H | H | H | H | H | O | C(=S)N(CH₃)₂ | H | 2-S(=O)CF₃,5-F | 0 |
| A-6353 | H | H | H | H | H | O | C(=S)N(CH₃)₂ | H | 2-S(=O)CF₃,6-F | 0 |
| A-6354 | H | H | H | H | H | O | C(=S)N(CH₃)₂ | H | 2-S(=O)CF₃,5-Me | 0 |
| A-6355 | H | H | H | H | H | O | C(=S)N(CH₃)₂ | H | 2-S(=O)CF₃,6-Me | 0 |
| A-6356 | H | H | H | H | H | O | C(=S)N(CH₃)₂ | H | 2-S(=O)₂CF₃,5-F | 0 |
| A-6357 | H | H | H | H | H | O | C(=S)N(CH₃)₂ | H | 2-S(=O)₂CF₃,6-F | 0 |
| A-6358 | H | H | H | H | H | O | C(=S)N(CH₃)₂ | H | 2-S(=O)₂CF₃,5-Me | 0 |
| A-6359 | H | H | H | H | H | O | C(=S)N(CH₃)₂ | H | 2-S(=O)₂CF₃,6-Me | 0 |
| A-6360 | H | H | H | H | H | O | C(=S)N(CH₃)₂ | H | 2-(cyclopropylthio),5-F | 0 |
| A-6361 | H | H | H | H | H | O | C(=S)N(CH₃)₂ | H | 2-(cyclopropylthio),6-F | 0 |
| A-6362 | H | H | H | H | H | O | C(=S)N(CH₃)₂ | H | 2-(cyclopropylthio),5-Me | 0 |
| A-6363 | H | H | H | H | H | O | C(=S)N(CH₃)₂ | H | 2-(cyclopropylthio),6-Me | 0 |
| A-6364 | H | H | H | H | H | O | C(=S)N(CH₃)₂ | H | 2-C(=O)Me,5-F | 0 |
| A-6365 | H | H | H | H | H | O | C(=S)N(CH₃)₂ | H | 2-C(=O)Me,6-F | 0 |
| A-6366 | H | H | H | H | H | O | C(=S)N(CH₃)₂ | H | 2-C(=O)Me,5-Me | 0 |
| A-6367 | H | H | H | H | H | O | C(=S)N(CH₃)₂ | H | 2-C(=O)Me,6-Me | 0 |
| A-6368 | H | H | H | H | H | O | C(=S)N(CH₃)₂ | H | 2-CH₂OH,5-F | 0 |
| A-6369 | H | H | H | H | H | O | C(=S)N(CH₃)₂ | H | 2-CH₂OH,6-F | 0 |
| A-6370 | H | H | H | H | H | O | C(=S)N(CH₃)₂ | H | 2-CH₂OH,5-Me | 0 |
| A-6371 | H | H | H | H | H | O | C(=S)N(CH₃)₂ | H | 2-CH₂OH,6-Me | 0 |
| A-6372 | H | H | H | H | H | O | C(=S)N(CH₃)₂ | H | 2-CH₂OCH₃,4-F | 0 |
| A-6373 | H | H | H | H | H | O | C(=S)N(CH₃)₂ | H | 2-CH₂OCH₃,5-F | 0 |
| A-6374 | H | H | H | H | H | O | C(=S)N(CH₃)₂ | H | 2-CH₂OCH₃,6-F | 0 |
| A-6375 | H | H | H | H | H | O | C(=S)N(CH₃)₂ | H | 2-CH₂OCH₃,4-Me | 0 |
| A-6376 | H | H | H | H | H | O | C(=S)N(CH₃)₂ | H | 2-CH₂OCH₃,5-Me | 0 |
| A-6377 | H | H | H | H | H | O | C(=S)N(CH₃)₂ | H | 2-CH₂OCH₃,6-Me | 0 |
| A-6378 | H | H | H | H | H | O | C(=S)N(CH₃)₂ | H | 2-OC(=O)CH₃,5-F | 0 |
| A-6379 | H | H | H | H | H | O | C(=S)N(CH₃)₂ | H | 2-OC(=O)CH₃,6-F | 0 |

TABLE 113

| compound | R¹ | R² | R³ | R⁴ | R⁵ | A | R⁶ | R⁷ | (R⁸)ₘ | p |
|---|---|---|---|---|---|---|---|---|---|---|
| A-6380 | H | H | H | H | H | O | C(=S)N(CH₃)₂ | H | 2-OC(=O)CH₃,5-Me | 0 |
| A-6381 | H | H | H | H | H | O | C(=S)N(CH₃)₂ | H | 2-OC(=O)CH₃,6-Me | 0 |
| A-6382 | H | H | H | H | H | O | C(=S)N(CH₃)₂ | H | 2-OS(=O)₂CH₃,5-F | 0 |
| A-6383 | H | H | H | H | H | O | C(=S)N(CH₃)₂ | H | 2-OS(=O)₂CH₃,6-F | 0 |
| A-6384 | H | H | H | H | H | O | C(=S)N(CH₃)₂ | H | 2-OS(=O)₂CH₃,5-Me | 0 |
| A-6385 | H | H | H | H | H | O | C(=S)N(CH₃)₂ | H | 2-OS(=O)₂CH₃,6-Me | 0 |
| A-6386 | H | H | H | H | H | O | C(=S)N(CH₃)₂ | H | 2-CH₂SCH₃,5-F | 0 |
| A-6387 | H | H | H | H | H | O | C(=S)N(CH₃)₂ | H | 2-CH₂SCH₃,6-F | 0 |
| A-6388 | H | H | H | H | H | O | C(=S)N(CH₃)₂ | H | 2-CH₂SCH₃,5-Me | 0 |
| A-6389 | H | H | H | H | H | O | C(=S)N(CH₃)₂ | H | 2-CH₂SCH₃,6-Me | 0 |
| A-6390 | H | H | H | H | H | O | C(=S)N(CH₃)₂ | H | 2-NMe₂,5-F | 0 |
| A-6391 | H | H | H | H | H | O | C(=S)N(CH₃)₂ | H | 2-NMe₂,6-F | 0 |
| A-6392 | H | H | H | H | H | O | C(=S)N(CH₃)₂ | H | 2-NMe₂,5-Me | 0 |

TABLE 113-continued

| compound | R¹ | R² | R³ | R⁴ | R⁵ | A | R⁶ | R⁷ | (R⁸)ₘ | p |
|---|---|---|---|---|---|---|---|---|---|---|
| A-6393 | H | H | H | H | H | O | C(=S)N(CH₃)₂ | H | 2-NMe₂,6-Me | 0 |
| A-6394 | H | H | H | H | H | O | C(=S)N(CH₃)₂ | H | 2-CN,4-F | 0 |
| A-6395 | H | H | H | H | H | O | C(=S)N(CH₃)₂ | H | 2-CN,5-F | 0 |
| A-6396 | H | H | H | H | H | O | C(=S)N(CH₃)₂ | H | 2-CN,6-F | 0 |
| A-6397 | H | H | H | H | H | O | C(=S)N(CH₃)₂ | H | 2-CN,6-Me | 0 |
| A-6398 | H | H | H | H | H | O | C(=S)N(CH₃)₂ | H | 2-CN,5-OMe | 0 |
| A-6399 | H | H | H | H | H | O | C(=S)N(CH₃)₂ | H | 2-CN,6-OMe | 0 |
| A-6400 | H | H | H | H | H | O | C(=S)N(CH₃)₂ | H | 3-CN,6-Me | 0 |
| A-6401 | H | H | H | H | H | O | C(=S)N(CH₃)₂ | H | 3-CN,6-OMe | 0 |
| A-6402 | H | H | H | H | H | O | C(=S)N(CH₃)₂ | H | 4-CN,2-Me | 0 |
| A-6403 | H | H | H | H | H | O | C(=S)N(CH₃)₂ | H | 4-CN,2-OMe | 0 |
| A-6404 | H | H | H | H | H | O | C(=S)N(CH₃)₂ | H | 2-NO₂,4-F | 0 |
| A-6405 | H | H | H | H | H | O | C(=S)N(CH₃)₂ | H | 2-NO₂,5-F | 0 |
| A-6406 | H | H | H | H | H | O | C(=S)N(CH₃)₂ | H | 2-NO₂,6-F | 0 |
| A-6407 | H | H | H | H | H | O | C(=S)N(CH₃)₂ | H | 2-NO₂,4-Me | 0 |
| A-6408 | H | H | H | H | H | O | C(=S)N(CH₃)₂ | H | 2-NO₂,5-Me | 0 |
| A-6409 | H | H | H | H | H | O | C(=S)N(CH₃)₂ | H | 2-NO₂,6-Me | 0 |
| A-6410 | H | H | H | H | H | O | C(=S)N(CH₃)₂ | H | 2-Me,4,5-F₂ | 0 |
| A-6411 | H | H | H | H | H | O | C(=S)N(CH₃)₂ | H | 2-Me,6-Et | 0 |
| A-6412 | H | H | H | H | H | O | C(=S)N(CH₃)₂ | H | 2-cyclopropyl,6-OMe | 0 |
| A-6413 | H | H | H | H | H | O | C(=S)N(CH₃)₂ | H | 2-Me,5-Et | 0 |
| A-6414 | H | H | H | H | H | O | C(=S)N(CH₃)₂ | H | 2,6-Et₂ | 0 |
| A-6415 | H | H | H | H | H | O | C(=S)N(CH₃)₂ | H | 2-Et,6-F | 0 |
| A-6416 | H | H | H | H | H | O | C(=S)N(CH₃)₂ | H | 2-CH₂OCH₃,6-Cl | 0 |
| A-6417 | H | H | H | H | H | O | C(=S)N(CH₃)₂ | H | 2-CH₂OCH₂CH₃,6-Cl | 0 |
| A-6418 | H | H | H | H | H | O | C(=S)N(CH₃)₂ | H | 2-CH₂NMe₂ | 0 |
| A-6419 | H | H | H | H | H | O | S(=O)₂CH₃ | H | H | 0 |
| A-6420 | H | H | H | H | H | O | S(=O)₂CH₃ | H | 2-F | 0 |
| A-6421 | H | H | H | H | H | O | S(=O)₂CH₃ | H | 2-Cl | 0 |
| A-6422 | H | H | H | H | H | O | S(=O)₂CH₃ | H | 2-Br | 0 |
| A-6423 | H | H | H | H | H | O | S(=O)₂CH₃ | H | 2-OH | 0 |
| A-6424 | H | H | H | H | H | O | S(=O)₂CH₃ | H | 2-Me | 0 |
| A-6425 | H | H | H | H | H | O | S(=O)₂CH₃ | H | 2-Et | 0 |
| A-6426 | H | H | H | H | H | O | S(=O)₂CH₃ | H | 2-Pr | 0 |
| A-6427 | H | H | H | H | H | O | S(=O)₂CH₃ | H | 2-CF₃ | 0 |
| A-6428 | H | H | H | H | H | O | S(=O)₂CH₃ | H | 2-CHF₂ | 0 |
| A-6429 | H | H | H | H | H | O | S(=O)₂CH₃ | H | 2-CH₂F | 0 |
| A-6430 | H | H | H | H | H | O | S(=O)₂CH₃ | H | 2-CF₂C | 0 |
| A-6431 | H | H | H | H | H | O | S(=O)₂CH₃ | H | 2-cyclopropyl | 0 |
| A-6432 | H | H | H | H | H | O | S(=O)₂CH₃ | H | 2-cyclobutyl | 0 |
| A-6433 | H | H | H | H | H | O | S(=O)₂CH₃ | H | 2-cyclopentyl | 0 |
| A-6434 | H | H | H | H | H | O | S(=O)₂CH₃ | H | 2-ethenyl | 0 |
| A-6435 | H | H | H | H | H | O | S(=O)₂CH₃ | H | 2-allyl | 0 |
| A-6436 | H | H | H | H | H | O | S(=O)₂CH₃ | H | 2-(prop-1-en-1-yl) | 0 |

TABLE 114

| compound | R¹ | R² | R³ | R⁴ | R⁵ | A | R⁶ | R⁷ | (R⁸)ₘ | p |
|---|---|---|---|---|---|---|---|---|---|---|
| A-6437 | H | H | H | H | H | O | S(=O)₂CH₃ | H | 2-(trifluoroethenyl) | 0 |
| A-6438 | H | H | H | H | H | O | S(=O)₂CH₃ | H | 2-OMe | 0 |
| A-6439 | H | H | H | H | H | O | S(=O)₂CH₃ | H | 2-OEt | 0 |
| A-6440 | H | H | H | H | H | O | S(=O)₂CH₃ | H | 2-OPr | 0 |
| A-6441 | H | H | H | H | H | O | S(=O)₂CH₃ | H | 2-O(i-Pr) | 0 |
| A-6442 | H | H | H | H | H | O | S(=O)₂CH₃ | H | 2-OCF₃ | 0 |
| A-6443 | H | H | H | H | H | O | S(=O)₂CH₃ | H | 2-OCHF₂ | 0 |
| A-6444 | H | H | H | H | H | O | S(=O)₂CH₃ | H | 2-(cyclopropyloxy) | 0 |
| A-6445 | H | H | H | H | H | O | S(=O)₂CH₃ | H | 2-(cyclobutyloxy) | 0 |
| A-6446 | H | H | H | H | H | O | S(=O)₂CH₃ | H | 2-(cyclopentyloxy) | 0 |
| A-6447 | H | H | H | H | H | O | S(=O)₂CH₃ | H | 2-((2,2-dichlorocyclopropyl)oxy) | 0 |
| A-6448 | H | H | H | H | H | O | S(=O)₂CH₃ | H | 2-(oxiran-2-yl) | 0 |
| A-6449 | H | H | H | H | H | O | S(=O)₂CH₃ | H | 2-SMe | 0 |
| A-6450 | H | H | H | H | H | O | S(=O)₂CH₃ | H | 3-SMe | 0 |
| A-6451 | H | H | H | H | H | O | S(=O)₂CH₃ | H | 2-S(=O)Me | 0 |
| A-6452 | H | H | H | H | H | O | S(=O)₂CH₃ | H | 3-S(=O)Me | 0 |
| A-6453 | H | H | H | H | H | O | S(=O)₂CH₃ | H | 2-S(=O)₂Me | 0 |
| A-6454 | H | H | H | H | H | O | S(=O)₂CH₃ | H | 3-S(=O)₂Me | 0 |
| A-6455 | H | H | H | H | H | O | S(=O)₂CH₃ | H | 2-SCF₃ | 0 |
| A-6456 | H | H | H | H | H | O | S(=O)₂CH₃ | H | 3-SCF₃ | 0 |
| A-6457 | H | H | H | H | H | O | S(=O)₂CH₃ | H | 3-S(=O)CF₃ | 0 |
| A-6458 | H | H | H | H | H | O | S(=O)₂CH₃ | H | 3-SCF(CF₃)₂ | 0 |
| A-6459 | H | H | H | H | H | O | S(=O)₂CH₃ | H | 2-(cyclopropylthio) | 0 |
| A-6460 | H | H | H | H | H | O | S(=O)₂CH₃ | H | 2-(cyclopropylsulfinyl) | 0 |
| A-6461 | H | H | H | H | H | O | S(=O)₂CH₃ | H | 2-(cyclopropylsulfonyl) | 0 |
| A-6462 | H | H | H | H | H | O | S(=O)₂CH₃ | H | 2-C(=O)Me | 0 |

TABLE 114-continued

| compound | R¹ | R² | R³ | R⁴ | R⁵ | A | R⁶ | R⁷ | (R⁸)ₘ | p |
|---|---|---|---|---|---|---|---|---|---|---|
| A-6463 | H | H | H | H | H | O | S(=O)₂CH₃ | H | 2-CH₂C(=O)CH₃ | 0 |
| A-6464 | H | H | H | H | H | O | S(=O)₂CH₃ | H | 2-CH₂C(=O)CF₃ | 0 |
| A-6465 | H | H | H | H | H | O | S(=O)₂CH₃ | H | 2-CH₂OH | 0 |
| A-6466 | H | H | H | H | H | O | S(=O)₂CH₃ | H | 2-CH₂OCH₃ | 0 |
| A-6467 | H | H | H | H | H | O | S(=O)₂CH₃ | H | 2-CH₂OCH₂CH₃ | 0 |
| A-6468 | H | H | H | H | H | O | S(=O)₂CH₃ | H | 2-CH₂SCH₃ | 0 |
| A-6469 | H | H | H | H | H | O | S(=O)₂CH₃ | H | 2-CH₂S(=O)CH₃ | 0 |
| A-6470 | H | H | H | H | H | O | S(=O)₂CH₃ | H | 2-CH₂S(=O)₂CH₃ | 0 |
| A-6471 | H | H | H | H | H | O | S(=O)₂CH₃ | H | 2-(benzyloxy) | 0 |
| A-6472 | H | H | H | H | H | O | S(=O)₂CH₃ | H | 2-NH₂ | 0 |
| A-6473 | H | H | H | H | H | O | S(=O)₂CH₃ | H | 2-NHMe | 0 |
| A-6474 | H | H | H | H | H | O | S(=O)₂CH₃ | H | 2-N(Me)₂ | 0 |
| A-6475 | H | H | H | H | H | O | S(=O)₂CH₃ | H | 2-(1,3-dioxolan-2-yl) | 0 |
| A-6476 | H | H | H | H | H | O | S(=O)₂CH₃ | H | 2-(1,3-dioxan-2-yl) | 0 |
| A-6477 | H | H | H | H | H | O | S(=O)₂CH₃ | H | 2-(1,3-imidazol-2-yl) | 0 |
| A-6478 | H | H | H | H | H | O | S(=O)₂CH₃ | H | 2-(thiazol-2-yl) | 0 |
| A-6479 | H | H | H | H | H | O | S(=O)₂CH₃ | H | 2-(oxazol-2-yl) | 0 |
| A-6480 | H | H | H | H | H | O | S(=O)₂CH₃ | H | 2-CH=NOH | 0 |
| A-6481 | H | H | H | H | H | O | S(=O)₂CH₃ | H | 2-CH=NOMe | 0 |
| A-6482 | H | H | H | H | H | O | S(=O)₂CH₃ | H | 2-(4,5-dihydro-3-isoxazolyl) | 0 |
| A-6483 | H | H | H | H | H | O | S(=O)₂CH₃ | H | 2-CN | 0 |
| A-6484 | H | H | H | H | H | O | S(=O)₂CH₃ | H | 2-NO₂ | 0 |
| A-6485 | H | H | H | H | H | O | S(=O)₂CH₃ | H | 2-F,6-Cl | 0 |
| A-6486 | H | H | H | H | H | O | S(=O)₂CH₃ | H | 2-F,6-Me | 0 |
| A-6487 | H | H | H | H | H | O | S(=O)₂CH₃ | H | 3-F,6-Me | 0 |
| A-6488 | H | H | H | H | H | O | S(=O)₂CH₃ | H | 4-F,2-Me | 0 |
| A-6489 | H | H | H | H | H | O | S(=O)₂CH₃ | H | 2-F,6-OMe | 0 |
| A-6490 | H | H | H | H | H | O | S(=O)₂CH₃ | H | 3-F,6-OMe | 0 |
| A-6491 | H | H | H | H | H | O | S(=O)₂CH₃ | H | 2,6-Cl₂ | 0 |
| A-6492 | H | H | H | H | H | O | S(=O)₂CH₃ | H | 2-Cl,6-Me | 0 |
| A-6493 | H | H | H | H | H | O | S(=O)₂CH₃ | H | 3-Cl,6-Me | 0 |

TABLE 115

| compound | R¹ | R² | R³ | R⁴ | R⁵ | A | R⁶ | R⁷ | (R⁸)ₘ | p |
|---|---|---|---|---|---|---|---|---|---|---|
| A-6494 | H | H | H | H | H | O | S(=O)₂CH₃ | H | 4-Cl,2-Me | 0 |
| A-6495 | H | H | H | H | H | O | S(=O)₂CH₃ | H | 2-Cl,5-CF₃ | 0 |
| A-6496 | H | H | H | H | H | O | S(=O)₂CH₃ | H | 2-Cl,6-CF₃ | 0 |
| A-6497 | H | H | H | H | H | O | S(=O)₂CH₃ | H | 2-Cl,6-OMe | 0 |
| A-6498 | H | H | H | H | H | O | S(=O)₂CH₃ | H | 3-Cl,6-OMe | 0 |
| A-6499 | H | H | H | H | H | O | S(=O)₂CH₃ | H | 4-Cl,2-OMe | 0 |
| A-6500 | H | H | H | H | H | O | S(=O)₂CH₃ | H | 2,4-Me₂ | 0 |
| A-6501 | H | H | H | H | H | O | S(=O)₂CH₃ | H | 2,5-Me₂ | 0 |
| A-6502 | H | H | H | H | H | O | S(=O)₂CH₃ | H | 2,6-Me₂ | 0 |
| A-6503 | H | H | H | H | H | O | S(=O)₂CH₃ | H | 2-Me,4-CF₃ | 0 |
| A-6504 | H | H | H | H | H | O | S(=O)₂CH₃ | H | 2-Me,5-CF₃ | 0 |
| A-6505 | H | H | H | H | H | O | S(=O)₂CH₃ | H | 2-Me,6-CF₃ | 0 |
| A-6506 | H | H | H | H | H | O | S(=O)₂CH₃ | H | 2-Me,4-OMe | 0 |
| A-6507 | H | H | H | H | H | O | S(=O)₂CH₃ | H | 2-Me,5-OMe | 0 |
| A-6508 | H | H | H | H | H | O | S(=O)₂CH₃ | H | 2-Me,6-OMe | 0 |
| A-6509 | H | H | H | H | H | O | S(=O)₂CH₃ | H | 3-Me,6-OMe | 0 |
| A-6510 | H | H | H | H | H | O | S(=O)₂CH₃ | H | 4-Me,2-OMe | 0 |
| A-6511 | H | H | H | H | H | O | S(=O)₂CH₃ | H | 2,5-OMe₂ | 0 |
| A-6512 | H | H | H | H | H | O | S(=O)₂CH₃ | H | 2,6-OMe₂ | 0 |
| A-6513 | H | H | H | H | H | O | S(=O)₂CH₃ | H | 2-OMe,6-CF₃ | 0 |
| A-6514 | H | H | H | H | H | O | S(=O)₂CH₃ | H | 2-CHF₂,5-F | 0 |
| A-6515 | H | H | H | H | H | O | S(=O)₂CH₃ | H | 2-CHF₂,6-F | 0 |
| A-6516 | H | H | H | H | H | O | S(=O)₂CH₃ | H | 2-CHF₂,5-Me | 0 |
| A-6517 | H | H | H | H | H | O | S(=O)₂CH₃ | H | 2-CHF₂,6-Me | 0 |
| A-6518 | H | H | H | H | H | O | S(=O)₂CH₃ | H | 2-cyclopropyl,5-F | 0 |
| A-6519 | H | H | H | H | H | O | S(=O)₂CH₃ | H | 2-cyclopropyl,6-F | 0 |
| A-6520 | H | H | H | H | H | O | S(=O)₂CH₃ | H | 2-cyclopropyl,5-Me | 0 |
| A-6521 | H | H | H | H | H | O | S(=O)₂CH₃ | H | 2-cyclopropyl,6-Me | 0 |
| A-6522 | H | H | H | H | H | O | S(=O)₂CH₃ | H | 2-ethenyl,6-F | 0 |
| A-6523 | H | H | H | H | H | O | S(=O)₂CH₃ | H | 2-ethenyl,6-Me | 0 |
| A-6524 | H | H | H | H | H | O | S(=O)₂CH₃ | H | 2-OEt,5-F | 0 |
| A-6525 | H | H | H | H | H | O | S(=O)₂CH₃ | H | 2-OEt,6-F | 0 |
| A-6526 | H | H | H | H | H | O | S(=O)₂CH₃ | H | 2-OEt,5-Cl | 0 |
| A-6527 | H | H | H | H | H | O | S(=O)₂CH₃ | H | 2-OEt,6-Cl | 0 |
| A-6528 | H | H | H | H | H | O | S(=O)₂CH₃ | H | 2-OEt,5-Me | 0 |
| A-6529 | H | H | H | H | H | O | S(=O)₂CH₃ | H | 2-OEt,6-Me | 0 |
| A-6530 | H | H | H | H | H | O | S(=O)₂CH₃ | H | 2-OCHF₂,5-F | 0 |
| A-6531 | H | H | H | H | H | O | S(=O)₂CH₃ | H | 2-OCHF₂,6-F | 0 |
| A-6532 | H | H | H | H | H | O | S(=O)₂CH₃ | H | 2-OCHF₂,5-Me | 0 |

TABLE 115-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-6533 | H | H | H | H | H | O | S(=O)$_2$CH$_3$ | H | 2-OCHF$_2$,6-Me | 0 |
| A-6534 | H | H | H | H | H | O | S(=O)$_2$CH$_3$ | H | 2-(cyclopropyloxy),5-F | 0 |
| A-6535 | H | H | H | H | H | O | S(=O)$_2$CH$_3$ | H | 2-(cyclopropyloxy),6-F | 0 |
| A-6536 | H | H | H | H | H | O | S(=O)$_2$CH$_3$ | H | 2-(cyclopropyloxy),5-Me | 0 |
| A-6537 | H | H | H | H | H | O | S(=O)$_2$CH$_3$ | H | 2-(cyclopropyloxy),6-Me | 0 |
| A-6538 | H | H | H | H | H | O | S(=O)$_2$CH$_3$ | H | 2-SMe,5-F | 0 |
| A-6539 | H | H | H | H | H | O | S(=O)$_2$CH$_3$ | H | 2-SMe,6-F | 0 |
| A-6540 | H | H | H | H | H | O | S(=O)$_2$CH$_3$ | H | 2-SMe,5-Me | 0 |
| A-6541 | H | H | H | H | H | O | S(=O)$_2$CH$_3$ | H | 2-SMe,6-Me | 0 |
| A-6542 | H | H | H | H | H | O | S(=O)$_2$CH$_3$ | H | 2-S(=O)Me,5-F | 0 |
| A-6543 | H | H | H | H | H | O | S(=O)$_2$CH$_3$ | H | 2-S(=O)Me,6-F | 0 |
| A-6544 | H | H | H | H | H | O | S(=O)$_2$CH$_3$ | H | 2-S(=O)Me,5-Me | 0 |
| A-6545 | H | H | H | H | H | O | S(=O)$_2$CH$_3$ | H | 2-S(=O)Me,6-Me | 0 |
| A-6546 | H | H | H | H | H | O | S(=O)$_2$CH$_3$ | H | 2-S(=O)$_2$Me,5-F | 0 |
| A-6547 | H | H | H | H | H | O | S(=O)$_2$CH$_3$ | H | 2-S(=O)$_2$Me,6-F | 0 |
| A-6548 | H | H | H | H | H | O | S(=O)$_2$CH$_3$ | H | 2-S(=O)$_2$Me,5-Me | 0 |
| A-6549 | H | H | H | H | H | O | S(=O)$_2$CH$_3$ | H | 2-S(=O)$_2$Me,6-Me | 0 |
| A-6550 | H | H | H | H | H | O | S(=O)$_2$CH$_3$ | H | 2-SCF$_3$,5-F | 0 |

TABLE 116

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-6551 | H | H | H | H | H | O | S(=O)$_2$CH$_3$ | H | 2-SCF$_3$,6-F | 0 |
| A-6552 | H | H | H | H | H | O | S(=O)$_2$CH$_3$ | H | 2-SCF$_3$,5-Me | 0 |
| A-6553 | H | H | H | H | H | O | S(=O)$_2$CH$_3$ | H | 2-SCF$_3$,6-Me | 0 |
| A-6554 | H | H | H | H | H | O | S(=O)$_2$CH$_3$ | H | 2-S(=O)CF$_3$,5-F | 0 |
| A-6555 | H | H | H | H | H | O | S(=O)$_2$CH$_3$ | H | 2-S(=O)CF$_3$,6-F | 0 |
| A-6556 | H | H | H | H | H | O | S(=O)$_2$CH$_3$ | H | 2-S(=O)CF$_3$,5-Me | 0 |
| A-6557 | H | H | H | H | H | O | S(=O)$_2$CH$_3$ | H | 2-S(=O)CF$_3$,6-Me | 0 |
| A-6558 | H | H | H | H | H | O | S(=O)$_2$CH$_3$ | H | 2-S(=O)$_2$CF$_3$,5-F | 0 |
| A-6559 | H | H | H | H | H | O | S(=O)$_2$CH$_3$ | H | 2-S(=O)$_2$CF$_3$,6-F | 0 |
| A-6560 | H | H | H | H | H | O | S(=O)$_2$CH$_3$ | H | 2-S(=O)$_2$CF$_3$,5-Me | 0 |
| A-6561 | H | H | H | H | H | O | S(=O)$_2$CH$_3$ | H | 2-S(=O)$_2$CF$_3$,6-Me | 0 |
| A-6562 | H | H | H | H | H | O | S(=O)$_2$CH$_3$ | H | 2-(cyclopropylthio),5-F | 0 |
| A-6563 | H | H | H | H | H | O | S(=O)$_2$CH$_3$ | H | 2-(cyclopropylthio),6-F | 0 |
| A-6564 | H | H | H | H | H | O | S(=O)$_2$CH$_3$ | H | 2-(cyclopropylthio),5-Me | 0 |
| A-6565 | H | H | H | H | H | O | S(=O)$_2$CH$_3$ | H | 2-(cyclopropylthio),6-Me | 0 |
| A-6566 | H | H | H | H | H | O | S(=O)$_2$CH$_3$ | H | 2-C(=O)Me,5-F | 0 |
| A-6567 | H | H | H | H | H | O | S(=O)$_2$CH$_3$ | H | 2-C(=O)Me,6-F | 0 |
| A-6568 | H | H | H | H | H | O | S(=O)$_2$CH$_3$ | H | 2-C(=O)Me,5-Me | 0 |
| A-6569 | H | H | H | H | H | O | S(=O)$_2$CH$_3$ | H | 2-C(=O)Me,6-Me | 0 |
| A-6570 | H | H | H | H | H | O | S(=O)$_2$CH$_3$ | H | 2-CH$_2$OH,5-F | 0 |
| A-6571 | H | H | H | H | H | O | S(=O)$_2$CH$_3$ | H | 2-CH$_2$OH,6-F | 0 |
| A-6572 | H | H | H | H | H | O | S(=O)$_2$CH$_3$ | H | 2-CH$_2$OH,5-Me | 0 |
| A-6573 | H | H | H | H | H | O | S(=O)$_2$CH$_3$ | H | 2-CH$_2$OH,6-Me | 0 |
| A-6574 | H | H | H | H | H | O | S(=O)$_2$CH$_3$ | H | 2-CH$_2$OCH$_3$,4-F | 0 |
| A-6575 | H | H | H | H | H | O | S(=O)$_2$CH$_3$ | H | 2-CH$_2$OCH$_3$,5-F | 0 |
| A-6576 | H | H | H | H | H | O | S(=O)$_2$CH$_3$ | H | 2-CH$_2$OCH$_3$,6-F | 0 |
| A-6577 | H | H | H | H | H | O | S(=O)$_2$CH$_3$ | H | 2-CH$_2$OCH$_3$,4-Me | 0 |
| A-6578 | H | H | H | H | H | O | S(=O)$_2$CH$_3$ | H | 2-CH$_2$OCH$_3$,5-Me | 0 |
| A-6579 | H | H | H | H | H | O | S(=O)$_2$CH$_3$ | H | 2-CH$_2$OCH$_3$,6-Me | 0 |
| A-6580 | H | H | H | H | H | O | S(=O)$_2$CH$_3$ | H | 2-OC(=O)CH$_3$,5-F | 0 |
| A-6581 | H | H | H | H | H | O | S(=O)$_2$CH$_3$ | H | 2-OC(=O)CH$_3$,6-F | 0 |
| A-6582 | H | H | H | H | H | O | S(=O)$_2$CH$_3$ | H | 2-OC(=O)CH$_3$,5-Me | 0 |
| A-6583 | H | H | H | H | H | O | S(=O)$_2$CH$_3$ | H | 2-OC(=O)CH$_3$,6-Me | 0 |
| A-6584 | H | H | H | H | H | O | S(=O)$_2$CH$_3$ | H | 2-OS(=O)$_2$CH$_3$,5-F | 0 |
| A-6585 | H | H | H | H | H | O | S(=O)$_2$CH$_3$ | H | 2-OS(=O)$_2$CH$_3$,6-F | 0 |
| A-6586 | H | H | H | H | H | O | S(=O)$_2$CH$_3$ | H | 2-OS(=O)$_2$CH$_3$,5-Me | 0 |
| A-6587 | H | H | H | H | H | O | S(=O)$_2$CH$_3$ | H | 2-OS(=O)$_2$CH$_3$,6-Me | 0 |
| A-6588 | H | H | H | H | H | O | S(=O)$_2$CH$_3$ | H | 2-CH$_2$SCH$_3$,5-F | 0 |
| A-6589 | H | H | H | H | H | O | S(=O)$_2$CH$_3$ | H | 2-CH$_2$SCH$_3$,6-F | 0 |
| A-6590 | H | H | H | H | H | O | S(=O)$_2$CH$_3$ | H | 2-CH$_2$SCH$_3$,5-Me | 0 |
| A-6591 | H | H | H | H | H | O | S(=O)$_2$CH$_3$ | H | 2-CH$_2$SCH$_3$,6-Me | 0 |
| A-6592 | H | H | H | H | H | O | S(=O)$_2$CH$_3$ | H | 2-NMe$_2$,5-F | 0 |
| A-6593 | H | H | H | H | H | O | S(=O)$_2$CH$_3$ | H | 2-NMe$_2$,6-F | 0 |
| A-6594 | H | H | H | H | H | O | S(=O)$_2$CH$_3$ | H | 2-NMe$_2$,5-Me | 0 |
| A-6595 | H | H | H | H | H | O | S(=O)$_2$CH$_3$ | H | 2-NMe$_2$,6-Me | 0 |
| A-6596 | H | H | H | H | H | O | S(=O)$_2$CH$_3$ | H | 2-CN,4-F | 0 |
| A-6597 | H | H | H | H | H | O | S(=O)$_2$CH$_3$ | H | 2-CN,5-F | 0 |
| A-6598 | H | H | H | H | H | O | S(=O)$_2$CH$_3$ | H | 2-CN,6-F | 0 |
| A-6599 | H | H | H | H | H | O | S(=O)$_2$CH$_3$ | H | 2-CN,6-Me | 0 |
| A-6600 | H | H | H | H | H | O | S(=O)$_2$CH$_3$ | H | 2-CN,5-OMe | 0 |
| A-6601 | H | H | H | H | H | O | S(=O)$_2$CH$_3$ | H | 2-CN,6-OMe | 0 |
| A-6602 | H | H | H | H | H | O | S(=O)$_2$CH$_3$ | H | 3-CN,6-Me | 0 |

TABLE 116-continued

| compound | R¹ | R² | R³ | R⁴ | R⁵ | A | R⁶ | R⁷ | (R⁸)$_m$ | p |
|---|---|---|---|---|---|---|---|---|---|---|
| A-6603 | H | H | H | H | H | O | S(=O)$_2$CH$_3$ | H | 3-CN,6-OMe | 0 |
| A-6604 | H | H | H | H | H | O | S(=O)$_2$CH$_3$ | H | 4-CN,2-Me | 0 |
| A-6605 | H | H | H | H | H | O | S(=O)$_2$CH$_3$ | H | 4-CN,2-OMe | 0 |
| A-6606 | H | H | H | H | H | O | S(=O)$_2$CH$_3$ | H | 2-NO$_2$,4-F | 0 |
| A-6607 | H | H | H | H | H | O | S(=O)$_2$CH$_3$ | H | 2-NO$_2$,5-F | 0 |

TABLE 117

| compound | R¹ | R² | R³ | R⁴ | R⁵ | A | R⁶ | R⁷ | (R⁸)$_m$ | p |
|---|---|---|---|---|---|---|---|---|---|---|
| A-6608 | H | H | H | H | H | O | S(=O)$_2$CH$_3$ | H | 2NO$_2$,6-F | 0 |
| A-6609 | H | H | H | H | H | O | S(=O)$_2$CH$_3$ | H | 2-NO$_2$,4-Me | 0 |
| A-6610 | H | H | H | H | H | O | S(=O)$_2$CH$_3$ | H | 2-NO$_2$,5-Me | 0 |
| A-6611 | H | H | H | H | H | O | S(=O)$_2$CH$_3$ | H | 2-NO$_2$,6-Me | 0 |
| A-6612 | H | H | H | H | H | O | S(=O)$_2$CH$_3$ | H | 2-Me,4,5-F$_2$ | 0 |
| A-6613 | H | H | H | H | H | O | S(=O)$_2$CH$_3$ | H | 2-Me,6-Et | 0 |
| A-6614 | H | H | H | H | H | O | S(=O)$_2$CH$_3$ | H | 2-cyclopropyl,6-OMe | 0 |
| A-6615 | H | H | H | H | H | O | S(=O)$_2$CH$_3$ | H | 2-Me,5-Et | 0 |
| A-6616 | H | H | H | H | H | O | S(=O)$_2$CH$_3$ | H | 2,6-Et$_2$ | 0 |
| A-6617 | H | H | H | H | H | O | S(=O)$_2$CH$_3$ | H | 2-Et,6-F | 0 |
| A-6618 | H | H | H | H | H | O | S(=O)$_2$CH$_3$ | H | 2-CH$_2$OCH$_3$,6-Cl | 0 |
| A-6619 | H | H | H | H | H | O | S(=O)$_2$CH$_3$ | H | 2-CH$_2$OCH$_2$CH$_3$,6-Cl | 0 |
| A-6620 | H | H | H | H | H | O | S(=O)$_2$CH$_3$ | H | 2-CH$_2$NMe$_2$ | 0 |
| A-6621 | H | H | H | H | H | O | S(=O)$_2$N(CH$_3$)$_2$ | H | H | 0 |
| A-6622 | H | H | H | H | H | O | S(=O)$_2$N(CH$_3$)$_2$ | H | 2-F | 0 |
| A-6623 | H | H | H | H | H | O | S(=O)$_2$N(CH$_3$)$_2$ | H | 2-Cl | 0 |
| A-6624 | H | H | H | H | H | O | S(=O)$_2$N(CH$_3$)$_2$ | H | 2-Br | 0 |
| A-6625 | H | H | H | H | H | O | S(=O)$_2$N(CH$_3$)$_2$ | H | 2-OH | 0 |
| A-6626 | H | H | H | H | H | O | S(=O)$_2$N(CH$_3$)$_2$ | H | 2-Me | 0 |
| A-6627 | H | H | H | H | H | O | S(=O)$_2$N(CH$_3$)$_2$ | H | 2-Et | 0 |
| A-6628 | H | H | H | H | H | O | S(=O)$_2$N(CH$_3$)$_2$ | H | 2-Pr | 0 |
| A-6629 | H | H | H | H | H | O | S(=O)$_2$N(CH$_3$)$_2$ | H | 2-CF$_3$ | 0 |
| A-6630 | H | H | H | H | H | O | S(=O)$_2$N(CH$_3$)$_2$ | H | 2-CHF$_2$ | 0 |
| A-6631 | H | H | H | H | H | O | S(=O)$_2$N(CH$_3$)$_2$ | H | 2-CH$_2$F | 0 |
| A-6632 | H | H | H | H | H | O | S(=O)$_2$N(CH$_3$)$_2$ | H | 2-CF$_2$Cl | 0 |
| A-6633 | H | H | H | H | H | O | S(=O)$_2$N(CH$_3$)$_2$ | H | 2-cyclopropyl | 0 |
| A-6634 | H | H | H | H | H | O | S(=O)$_2$N(CH$_3$)$_2$ | H | 2-cyclobutyl | 0 |
| A-6635 | H | H | H | H | H | O | S(=O)$_2$N(CH$_3$)$_2$ | H | 2-cyclopentyl | 0 |
| A-6636 | H | H | H | H | H | O | S(=O)$_2$N(CH$_3$)$_2$ | H | 2-ethenyl | 0 |
| A-6637 | H | H | H | H | H | O | S(=O)$_2$N(CH$_3$)$_2$ | H | 2-allyl | 0 |
| A-6638 | H | H | H | H | H | O | S(=O)$_2$N(CH$_3$)$_2$ | H | 2-(prop-1-en-1-yl) | 0 |
| A-6639 | H | H | H | H | H | O | S(=O)$_2$N(CH$_3$)$_2$ | H | 2-(trifluoroethenyl) | 0 |
| A-6640 | H | H | H | H | H | O | S(=O)$_2$N(CH$_3$)$_2$ | H | 2-OMe | 0 |
| A-6641 | H | H | H | H | H | O | S(=O)$_2$N(CH$_3$)$_2$ | H | 2-OEt | 0 |
| A-6642 | H | H | H | H | H | O | S(=O)$_2$N(CH$_3$)$_2$ | H | 2-OPr | 0 |
| A-6643 | H | H | H | H | H | O | S(=O)$_2$N(CH$_3$)$_2$ | H | 2-O(i-Pr) | 0 |
| A-6644 | H | H | H | H | H | O | S(=O)$_2$N(CH$_3$)$_2$ | H | 2-OCF$_3$ | 0 |
| A-6645 | H | H | H | H | H | O | S(=O)$_2$N(CH$_3$)$_2$ | H | 2-OCHF$_2$ | 0 |
| A-6646 | H | H | H | H | H | O | S(=O)$_2$N(CH$_3$)$_2$ | H | 2-(cyclopropyloxy) | 0 |
| A-6647 | H | H | H | H | H | O | S(=O)$_2$N(CH$_3$)$_2$ | H | 2-(cyclobutyloxy) | 0 |
| A-6648 | H | H | H | H | H | O | S(=O)$_2$N(CH$_3$)$_2$ | H | 2-(cyclopentyloxy) | 0 |
| A-6649 | H | H | H | H | H | O | S(=O)$_2$N(CH$_3$)$_2$ | H | 2-((2,2-dichlorocyclopropyl)oxy) | 0 |
| A-6650 | H | H | H | H | H | O | S(=O)$_2$N(CH$_3$)$_2$ | H | 2-(oxiran-2-yl) | 0 |
| A-6651 | H | H | H | H | H | O | S(=O)$_2$N(CH$_3$)$_2$ | H | 2-SMe | 0 |
| A-6652 | H | H | H | H | H | O | S(=O)$_2$N(CH$_3$)$_2$ | H | 3-SMe | 0 |
| A-6653 | H | H | H | H | H | O | S(=O)$_2$N(CH$_3$)$_2$ | H | 2-S(=O)Me | 0 |
| A-6654 | H | H | H | H | H | O | S(=O)$_2$N(CH$_3$)$_2$ | H | 3-S(=O)Me | 0 |
| A-6655 | H | H | H | H | H | O | S(=O)$_2$N(CH$_3$)$_2$ | H | 2-S(=O)$_2$Me | 0 |
| A-6656 | H | H | H | H | H | O | S(=O)$_2$N(CH$_3$)$_2$ | H | 3-S(=O)$_2$Me | 0 |
| A-6657 | H | H | H | H | H | O | S(=O)$_2$N(CH$_3$)$_2$ | H | 2-SCF$_3$ | 0 |
| A-6658 | H | H | H | H | H | O | S(=O)$_2$N(CH$_3$)$_2$ | H | 3-SCF$_3$ | 0 |
| A-6659 | H | H | H | H | H | O | S(=O)$_2$N(CH$_3$)$_2$ | H | 3-S(=O)CF$_3$ | 0 |
| A-6660 | H | H | H | H | H | O | S(=O)$_2$N(CH$_3$)$_2$ | H | 3-SCF(CF$_3$)$_2$ | 0 |
| A-6661 | H | H | H | H | H | O | S(=O)$_2$N(CH$_3$)$_2$ | H | 2-(cyclopropylthio) | 0 |
| A-6662 | H | H | H | H | H | O | S(=O)$_2$N(CH$_3$)$_2$ | H | 2-(cyclopropylsulfinyl) | 0 |
| A-6663 | H | H | H | H | H | O | S(=O)$_2$N(CH$_3$)$_2$ | H | 2-(cyclopropylsulfonyl) | 0 |
| A-6664 | H | H | H | H | H | O | S(=O)$_2$N(CH$_3$)$_2$ | H | 2-C(=O)Me | 0 |

TABLE 118

| compound | R¹ | R² | R³ | R⁴ | R⁵ | A | R⁶ | R⁷ | (R⁸)ₘ | p |
|---|---|---|---|---|---|---|---|---|---|---|
| A-6665 | H | H | H | H | H | O | S(=O)₂N(CH₃)₂ | H | 2-CH₂C(=O)CH₃ | 0 |
| A-6666 | H | H | H | H | H | O | S(=O)₂N(CH₃)₂ | H | 2-CH₂C(=O)CF₃ | 0 |
| A-6667 | H | H | H | H | H | O | S(=O)₂N(CH₃)₂ | H | 2-CH₂OH | 0 |
| A-6668 | H | H | H | H | H | O | S(=O)₂N(CH₃)₂ | H | 2-CH₂OCH₃ | 0 |
| A-6669 | H | H | H | H | H | O | S(=O)₂N(CH₃)₂ | H | 2-CH₂OCH₂CH₃ | 0 |
| A-6670 | H | H | H | H | H | O | S(=O)₂N(CH₃)₂ | H | 2-CH₂SCH₃ | 0 |
| A-6671 | H | H | H | H | H | O | S(=O)₂N(CH₃)₂ | H | 2-CH₂S(=O)CH₃ | 0 |
| A-6672 | H | H | H | H | H | O | S(=O)₂N(CH₃)₂ | H | 2-CH₂S(=O)₂CH₃ | 0 |
| A-6673 | H | H | H | H | H | O | S(=O)₂N(CH₃)₂ | H | 2-(benzyboxy) | 0 |
| A-6674 | H | H | H | H | H | O | S(=O)₂N(CH₃)₂ | H | 2-NH₂ | 0 |
| A-6675 | H | H | H | H | H | O | S(=O)₂N(CH₃)₂ | H | 2-NHMe | 0 |
| A-6676 | H | H | H | H | H | O | S(=O)₂N(CH₃)₂ | H | 2-N(Me)₂ | 0 |
| A-6677 | H | H | H | H | H | O | S(=O)₂N(CH₃)₂ | H | 2-(1,3-dioxolan-2-yl) | 0 |
| A-6678 | H | H | H | H | H | O | S(=O)₂N(CH₃)₂ | H | 2-(1,3-dioxan-2-yl) | 0 |
| A-6679 | H | H | H | H | H | O | S(=O)₂N(CH₃)₂ | H | 2-(1H-imidazol-2-yl) | 0 |
| A-6680 | H | H | H | H | H | O | S(=O)₂N(CH₃)₂ | H | 2-(thiazol-2-yl) | 0 |
| A-6681 | H | H | H | H | H | O | S(=O)₂N(CH₃)₂ | H | 2-(oxazol-2-yl) | 0 |
| A-6682 | H | H | H | H | H | O | S(=O)₂N(CH₃)₂ | H | 2-CH=NOH | 0 |
| A-6683 | H | H | H | H | H | O | S(=O)₂N(CH₃)₂ | H | 2-CH=NOMe | 0 |
| A-6684 | H | H | H | H | H | O | S(=O)₂N(CH₃)₂ | H | 2-(4,5-dihydro-3-isoxazolyl) | 0 |
| A-6685 | H | H | H | H | H | O | S(=O)₂N(CH₃)₂ | H | 2-CN | 0 |
| A-6686 | H | H | H | H | H | O | S(=O)₂N(CH₃)₂ | H | 2-NO₂ | 0 |
| A-6687 | H | H | H | H | H | O | S(=O)₂N(CH₃)₂ | H | 2F,6-Cl | 0 |
| A-6688 | H | H | H | H | H | O | S(=O)₂N(CH₃)₂ | H | 2-F,6-Me | 0 |
| A-6689 | H | H | H | H | H | O | S(=O)₂N(CH₃)₂ | H | 3-F,6-Me | 0 |
| A-6690 | H | H | H | H | H | O | S(=O)₂N(CH₃)₂ | H | 4-F,2-Me | 0 |
| A-6691 | H | H | H | H | H | O | S(=O)₂N(CH₃)₂ | H | 2-F,6-OMe | 0 |
| A-6692 | H | H | H | H | H | O | S(=O)₂N(CH₃)₂ | H | 3-F,6-OMe | 0 |
| A-6693 | H | H | H | H | H | O | S(=O)₂N(CH₃)₂ | H | 2,6-Cl₂ | 0 |
| A-6694 | H | H | H | H | H | O | S(=O)₂N(CH₃)₂ | H | 2-Cl,6-Me | 0 |
| A-6695 | H | H | H | H | H | O | S(=O)₂N(CH₃)₂ | H | 3-Cl,6-Me | 0 |
| A-6696 | H | H | H | H | H | O | S(=O)₂N(CH₃)₂ | H | 4-Cl,2-Me | 0 |
| A-6697 | H | H | H | H | H | O | S(=O)₂N(CH₃)₂ | H | 2-Cl,5-CF₃ | 0 |
| A-6698 | H | H | H | H | H | O | S(=O)₂N(CH₃)₂ | H | 2-Cl,6-CF₃ | 0 |
| A-6699 | H | H | H | H | H | O | S(=O)₂N(CH₃)₂ | H | 2-Cl,6-OMe | 0 |
| A-6700 | H | H | H | H | H | O | S(=O)₂N(CH₃)₂ | H | 3-Cl,6-OMe | 0 |
| A-6701 | H | H | H | H | H | O | S(=O)₂N(CH₃)₂ | H | 4-Cl,2-OMe | 0 |
| A-6702 | H | H | H | H | H | O | S(=O)₂N(CH₃)₂ | H | 2,4-Me₂ | 0 |
| A-6703 | H | H | H | H | H | O | S(=O)₂N(CH₃)₂ | H | 2,5-Me₂ | 0 |
| A-6704 | H | H | H | H | H | O | S(=O)₂N(CH₃)₂ | H | 2,6-Me₂ | 0 |
| A-6705 | H | H | H | H | H | O | S(=O)₂N(CH₃)₂ | H | 2-Me,4-CF₃ | 0 |
| A-6706 | H | H | H | H | H | O | S(=O)₂N(CH₃)₂ | H | 2-Me,5-CF₃ | 0 |
| A-6707 | H | H | H | H | H | O | S(=O)₂N(CH₃)₂ | H | 2-Me,6-CF₃ | 0 |
| A-6708 | H | H | H | H | H | O | S(=O)₂N(CH₃)₂ | H | 2-Me,4-OMe | 0 |
| A-6709 | H | H | H | H | H | O | S(=O)₂N(CH₃)₂ | H | 2-Me,5-OMe | 0 |
| A-6710 | H | H | H | H | H | O | S(=O)₂N(CH₃)₂ | H | 2-Me,6-OMe | 0 |
| A-6711 | H | H | H | H | H | O | S(=O)₂N(CH₃)₂ | H | 3-Me,6-OMe | 0 |
| A-6712 | H | H | H | H | H | O | S(=O)₂N(CH₃)₂ | H | 4-Me,2-OMe | 0 |
| A-6713 | H | H | H | H | H | O | S(=O)₂N(CH₃)₂ | H | 2,5-OMe₂ | 0 |
| A-6714 | H | H | H | H | H | O | S(=O)₂N(CH₃)₂ | H | 2,6-OMe₂ | 0 |
| A-6715 | H | H | H | H | H | O | S(=O)₂N(CH₃)₂ | H | 2-OMe,6-CF₃ | 0 |
| A-6716 | H | H | H | H | H | O | S(=O)₂N(CH₃)₂ | H | 2-CHF₂,5-F | 0 |
| A-6717 | H | H | H | H | H | O | S(=O)₂N(CH₃)₂ | H | 2-CHF₂,6-F | 0 |
| A-6718 | H | H | H | H | H | O | S(=O)₂N(CH₃)₂ | H | 2-CHF₂,5-Me | 0 |
| A-6719 | H | H | H | H | H | O | S(=O)₂N(CH₃)₂ | H | 2-CHF₂,6-Me | 0 |
| A-6720 | H | H | H | H | H | O | S(=O)₂N(CH₃)₂ | H | 2-cyclopropyl,5-F | 0 |
| A-6721 | H | H | H | H | H | O | S(=O)₂N(CH₃)₂ | H | 2-cyclopropyl,6-F | 0 |

TABLE 119

| compound | R¹ | R² | R³ | R⁴ | R⁵ | A | R⁶ | R⁷ | (R⁸)ₘ | p |
|---|---|---|---|---|---|---|---|---|---|---|
| A-6722 | H | H | H | H | H | O | S(=O)₂N(CH₃)₂ | H | 2-cyclopropyl,5-Me | 0 |
| A-6723 | H | H | H | H | H | O | S(=O)₂N(CH₃)₂ | H | 2-cyclopropyl,6-Me | 0 |
| A-6724 | H | H | H | H | H | O | S(=O)₂N(CH₃)₂ | H | 2-ethenyl,6-F | 0 |
| A-6725 | H | H | H | H | H | O | S(=O)₂N(CH₃)₂ | H | 2-ethenyl,6-Me | 0 |
| A-6726 | H | H | H | H | H | O | S(=O)₂N(CH₃)₂ | H | 2-OEt,5-F | 0 |
| A-6727 | H | H | H | H | H | O | S(=O)₂N(CH₃)₂ | H | 2-OEt,6-F | 0 |
| A-6728 | H | H | H | H | H | O | S(=O)₂N(CH₃)₂ | H | 2-OEt,5-Cl | 0 |
| A-6729 | H | H | H | H | H | O | S(=O)₂N(CH₃)₂ | H | 2-OEt,6-Cl | 0 |
| A-6730 | H | H | H | H | H | O | S(=O)₂N(CH₃)₂ | H | 2-OEt,5-Me | 0 |
| A-6731 | H | H | H | H | H | O | S(=O)₂N(CH₃)₂ | H | 2-OEt,6-Me | 0 |
| A-6732 | H | H | H | H | H | O | S(=O)₂N(CH₃)₂ | H | 2-OCHF₂,5-F | 0 |
| A-6733 | H | H | H | H | H | O | S(=O)₂N(CH₃)₂ | H | 2-OCHF₂,6-F | 0 |
| A-6734 | H | H | H | H | H | O | S(=O)₂N(CH₃)₂ | H | 2-OCHF₂,5-Me | 0 |

TABLE 119-continued

| compound | R¹ | R² | R³ | R⁴ | R⁵ | A | R⁶ | R⁷ | (R⁸)$_m$ | p |
|---|---|---|---|---|---|---|---|---|---|---|
| A-6735 | H | H | H | H | H | O | S(=O)₂N(CH₃)₂ | H | 2-OCHF₂,6-Me | 0 |
| A-6736 | H | H | H | H | H | O | S(=O)₂N(CH₃)₂ | H | 2-(cyclopropyloxy),5-F | 0 |
| A-6737 | H | H | H | H | H | O | S(=O)₂N(CH₃)₂ | H | 2-(cyclopropyloxy),6-F | 0 |
| A-6738 | H | H | H | H | H | O | S(=O)₂N(CH₃)₂ | H | 2-(cyclopropyloxy),5-Me | 0 |
| A-6739 | H | H | H | H | H | O | S(=O)₂N(CH₃)₂ | H | 2-(cyclopropyloxy),6-Me | 0 |
| A-6740 | H | H | H | H | H | O | S(=O)₂N(CH₃)₂ | H | 2-SMe,5-F | 0 |
| A-6741 | H | H | H | H | H | O | S(=O)₂N(CH₃)₂ | H | 2-SMe,6-F | 0 |
| A-6742 | H | H | H | H | H | O | S(=O)₂N(CH₃)₂ | H | 2-SMe,5-Me | 0 |
| A-6743 | H | H | H | H | H | O | S(=O)₂N(CH₃)₂ | H | 2-SMe,6-Me | 0 |
| A-6744 | H | H | H | H | H | O | S(=O)₂N(CH₃)₂ | H | 2-S(=O)Me,5-F | 0 |
| A-6745 | H | H | H | H | H | O | S(=O)₂N(CH₃)₂ | H | 2-S(=O)Me,6-F | 0 |
| A-6746 | H | H | H | H | H | O | S(=O)₂N(CH₃)₂ | H | 2-S(=O)Me,5-Me | 0 |
| A-6747 | H | H | H | H | H | O | S(=O)₂N(CH₃)₂ | H | 2-S(=O)Me,6-Me | 0 |
| A-6748 | H | H | H | H | H | O | S(=O)₂N(CH₃)₂ | H | 2-S(=O)₂Me,5-F | 0 |
| A-6749 | H | H | H | H | H | O | S(=O)₂N(CH₃)₂ | H | 2-S(=O)₂Me,6-F | 0 |
| A-6750 | H | H | H | H | H | O | S(=O)₂N(CH₃)₂ | H | 2-S(=O)₂Me,5-Me | 0 |
| A-6751 | H | H | H | H | H | O | S(=O)₂N(CH₃)₂ | H | 2-S(=O)₂Me,6-Me | 0 |
| A-6752 | H | H | H | H | H | O | S(=O)₂N(CH₃)₂ | H | 2-SCF₃,5-F | 0 |
| A-6753 | H | H | H | H | H | O | S(=O)₂N(CH₃)₂ | H | 2-SCF₃,6-F | 0 |
| A-6754 | H | H | H | H | H | O | S(=O)₂N(CH₃)₂ | H | 2-SCF₃,5-Me | 0 |
| A-6755 | H | H | H | H | H | O | S(=O)₂N(CH₃)₂ | H | 2-SCF₃,6-Me | 0 |
| A-6756 | H | H | H | H | H | O | S(=O)₂N(CH₃)₂ | H | 2-S(=O)CF₃,5-F | 0 |
| A-6757 | H | H | H | H | H | O | S(=O)₂N(CH₃)₂ | H | 2-S(=O)CF₃,6-F | 0 |
| A-6758 | H | H | H | H | H | O | S(=O)₂N(CH₃)₂ | H | 2-S(=O)CF₃,5-Me | 0 |
| A-6759 | H | H | H | H | H | O | S(=O)₂N(CH₃)₂ | H | 2-S(=O)CF₃,6-Me | 0 |
| A-6760 | H | H | H | H | H | O | S(=O)₂N(CH₃)₂ | H | 2-S(=O)₂CF₃,5-F | 0 |
| A-6761 | H | H | H | H | H | O | S(=O)₂N(CH₃)₂ | H | 2-S(=O)₂CF₃,6-F | 0 |
| A-6762 | H | H | H | H | H | O | S(=O)₂N(CH₃)₂ | H | 2-S(=O)₂CF₃,5-Me | 0 |
| A-6763 | H | H | H | H | H | O | S(=O)₂N(CH₃)₂ | H | 2-S(=O)₂CF₃,6-Me | 0 |
| A-6764 | H | H | H | H | H | O | S(=O)₂N(CH₃)₂ | H | 2-(cyclopropylthio),5-F | 0 |
| A-6765 | H | H | H | H | H | O | S(=O)₂N(CH₃)₂ | H | 2-(cyclopropylthio),6-F | 0 |
| A-6766 | H | H | H | H | H | O | S(=O)₂N(CH₃)₂ | H | 2-(cyclopropylthio),5-Me | 0 |
| A-6767 | H | H | H | H | H | O | S(=O)₂N(CH₃)₂ | H | 2-(cyclopropylthio),6-Me | 0 |
| A-6768 | H | H | H | H | H | O | S(=O)₂N(CH₃)₂ | H | 2-C(=O)Me,5-F | 0 |
| A-6769 | H | H | H | H | H | O | S(=O)₂N(CH₃)₂ | H | 2-C(=O)Me,6-F | 0 |
| A-6770 | H | H | H | H | H | O | S(=O)₂N(CH₃)₂ | H | 2-C(=O)Me,5-Me | 0 |
| A-6771 | H | H | H | H | H | O | S(=O)₂N(CH₃)₂ | H | 2-C(=O)Me,6-Me | 0 |
| A-6772 | H | H | H | H | H | O | S(=O)₂N(CH₃)₂ | H | 2-CH₂OH,5-F | 0 |
| A-6773 | H | H | H | H | H | O | S(=O)₂N(CH₃)₂ | H | 2-CH₂OH,6-F | 0 |
| A-6774 | H | H | H | H | H | O | S(=O)₂N(CH₃)₂ | H | 2-CH₂OH,5-Me | 0 |
| A-6775 | H | H | H | H | H | O | S(=O)₂N(CH₃)₂ | H | 2-CH₂OH,6-Me | 0 |
| A-6776 | H | H | H | H | H | O | S(=O)₂N(CH₃)₂ | H | 2-CH₂OCH₃,4-F | 0 |
| A-6777 | H | H | H | H | H | O | S(=O)₂N(CH₃)₂ | H | 2-CH₂OCH₃,5-F | 0 |
| A-6778 | H | H | H | H | H | O | S(=O)₂N(CH₃)₂ | H | 2-CH₂OCH₃,6-F | 0 |

TABLE 120

| compound | R¹ | R² | R³ | R⁴ | R⁵ | A | R⁶ | R⁷ | (R⁸)$_m$ | p |
|---|---|---|---|---|---|---|---|---|---|---|
| A-6779 | H | H | H | H | H | O | S(=O)₂N(CH₃)₂ | H | 2-CH₂OCH₃,4-Me | 0 |
| A-6780 | H | H | H | H | H | O | S(=O)₂N(CH₃)₂ | H | 2-CH₂OCH₃,5-Me | 0 |
| A-6781 | H | H | H | H | H | O | S(=O)₂N(CH₃)₂ | H | 2-CH₂OCH₃,6-Me | 0 |
| A-6782 | H | H | H | H | H | O | S(=O)₂N(CH₃)₂ | H | 2-OC(=O)CH₃,5-F | 0 |
| A-6783 | H | H | H | H | H | O | S(=O)₂N(CH₃)₂ | H | 2-OC(=O)CH₃,6-F | 0 |
| A-6784 | H | H | H | H | H | O | S(=O)₂N(CH₃)₂ | H | 2-OC(=O)CH₃,5-Me | 0 |
| A-6785 | H | H | H | H | H | O | S(=O)₂N(CH₃)₂ | H | 2-OC(=O)CH₃,6-Me | 0 |
| A-6786 | H | H | H | H | H | O | S(=O)₂N(CH₃)₂ | H | 2-OS(=O)₂CH₃,5-F | 0 |
| A-6787 | H | H | H | H | H | O | S(=O)₂N(CH₃)₂ | H | 2-OS(=O)₂CH₃,6-F | 0 |
| A-6788 | H | H | H | H | H | O | S(=O)₂N(CH₃)₂ | H | 2-OS(=O)₂CH₃,5-Me | 0 |
| A-6789 | H | H | H | H | H | O | S(=O)₂N(CH₃)₂ | H | 2-OS(=O)₂CH₃,6-Me | 0 |
| A-6790 | H | H | H | H | H | O | S(=O)₂N(CH₃)₂ | H | 2-CH₂SCH₃,5-F | 0 |
| A-6791 | H | H | H | H | H | O | S(=O)₂N(CH₃)₂ | H | 2-CH₂SCH₃,6-F | 0 |
| A-6792 | H | H | H | H | H | O | S(=O)₂N(CH₃)₂ | H | 2-CH₂SCH₃,5-Me | 0 |
| A-6793 | H | H | H | H | H | O | S(=O)₂N(CH₃)₂ | H | 2-CH₂SCH₃,6-Me | 0 |
| A-6794 | H | H | H | H | H | O | S(=O)₂N(CH₃)₂ | H | 2-NMe₂,5-F | 0 |
| A-6795 | H | H | H | H | H | O | S(=O)₂N(CH₃)₂ | H | 2-NMe₂,6-F | 0 |
| A-6796 | H | H | H | H | H | O | S(=O)₂N(CH₃)₂ | H | 2-NMe₂,5-Me | 0 |
| A-6797 | H | H | H | H | H | O | S(=O)₂N(CH₃)₂ | H | 2-NMe₂,6-Me | 0 |
| A-6798 | H | H | H | H | H | O | S(=O)₂N(CH₃)₂ | H | 2-CN,4-F | 0 |
| A-6799 | H | H | H | H | H | O | S(=O)₂N(CH₃)₂ | H | 2-CN,5-F | 0 |
| A-6800 | H | H | H | H | H | O | S(=O)₂N(CH₃)₂ | H | 2-CN,6-F | 0 |
| A-6801 | H | H | H | H | H | O | S(=O)₂N(CH₃)₂ | H | 2-CN,6-Me | 0 |
| A-6802 | H | H | H | H | H | O | S(=O)₂N(CH₃)₂ | H | 2-CN,5-OMe | 0 |
| A-6803 | H | H | H | H | H | O | S(=O)₂N(CH₃)₂ | H | 2-CN,6-OMe | 0 |
| A-6804 | H | H | H | H | H | O | S(=O)₂N(CH₃)₂ | H | 3-CN,6-Me | 0 |

TABLE 120-continued

| compound | R¹ | R² | R³ | R⁴ | R⁵ | A | R⁶ | R⁷ | (R⁸)$_m$ | p |
|---|---|---|---|---|---|---|---|---|---|---|
| A-6805 | H | H | H | H | H | O | S(=O)$_2$N(CH$_3$)$_2$ | H | 3-CN,6-OMe | 0 |
| A-6806 | H | H | H | H | H | O | S(=O)$_2$N(CH$_3$)$_2$ | H | 4-CN,2-Me | 0 |
| A-6807 | H | H | H | H | H | O | S(=O)$_2$N(CH$_3$)$_2$ | H | 4-CN,2-OMe | 0 |
| A-6808 | H | H | H | H | H | O | S(=O)$_2$N(CH$_3$)$_2$ | H | 2-NO$_2$,4-F | 0 |
| A-6809 | H | H | H | H | H | O | S(=O)$_2$N(CH$_3$)$_2$ | H | 2-NO$_2$,5-F | 0 |
| A-6810 | H | H | H | H | H | O | S(=O)$_2$N(CH$_3$)$_2$ | H | 2-NO$_2$,6-F | 0 |
| A-6811 | H | H | H | H | H | O | S(=O)$_2$N(CH$_3$)$_2$ | H | 2-NO$_2$,4-Me | 0 |
| A-6812 | H | H | H | H | H | O | S(=O)$_2$N(CH$_3$)$_2$ | H | 2-NO$_2$,5-Me | 0 |
| A-6813 | H | H | H | H | H | O | S(=O)$_2$N(CH$_3$)$_2$ | H | 2-NO$_2$,6-Me | 0 |
| A-6814 | H | H | H | H | H | O | S(=O)$_2$N(CH$_3$)$_2$ | H | 2-Me,4,5-F$_2$ | 0 |
| A-6815 | H | H | H | H | H | O | S(=O)$_2$N(CH$_3$)$_2$ | H | 2-Me,6-Et | 0 |
| A-6816 | H | H | H | H | H | O | S(=O)$_2$N(CH$_3$)$_2$ | H | 2-cyclopropyl,6-OMe | 0 |
| A-6817 | H | H | H | H | H | O | S(=O)$_2$N(CH$_3$)$_2$ | H | 2-Me,5-Et | 0 |
| A-6818 | H | H | H | H | H | O | S(=O)$_2$N(CH$_3$)$_2$ | H | 2,6-Et$_2$ | 0 |
| A-6819 | H | H | H | H | H | O | S(=O)$_2$N(CH$_3$)$_2$ | H | 2-Et,6-F | 0 |
| A-6820 | H | H | H | H | H | O | S(=O)$_2$N(CH$_3$)$_2$ | H | 2-CH$_2$OCH$_3$,6-Cl | 0 |
| A-6821 | H | H | H | H | H | O | S(=O)$_2$N(CH$_3$)$_2$ | H | 2-CH$_2$OCH$_2$CH$_3$,6Cl | 0 |
| A-6822 | H | H | H | H | H | O | S(=O)$_2$N(CH$_3$)$_2$ | H | 2-CH$_2$NMe$_2$ | 0 |
| A-6823 | H | H | H | H | H | O | CH$_2$N(CH$_3$)$_2$ | H | H | 0 |
| A-6824 | H | H | H | H | H | O | CH$_2$N(CH$_3$)$_2$ | H | 2-F | 0 |
| A-6825 | H | H | H | H | H | O | CH$_2$N(CH$_3$)$_2$ | H | 2-Cl | 0 |
| A-6826 | H | H | H | H | H | O | CH$_2$N(CH$_3$)$_2$ | H | 2-Br | 0 |
| A-6827 | H | H | H | H | H | O | CH$_2$N(CH$_3$)$_2$ | H | 2-OH | 0 |
| A-6828 | H | H | H | H | H | O | CH$_2$N(CH$_3$)$_2$ | H | 2-Me | 0 |
| A-6829 | H | H | H | H | H | O | CH$_2$N(CH$_3$)$_2$ | H | 2-Et | 0 |
| A-6830 | H | H | H | H | H | O | CH$_2$N(CH$_3$)$_2$ | H | 2-Pr | 0 |
| A-6831 | H | H | H | H | H | O | CH$_2$N(CH$_3$)$_2$ | H | 2-CF$_3$ | 0 |
| A-6832 | H | H | H | H | H | O | CH$_2$N(CH$_3$)$_2$ | H | 2-CHF$_2$ | 0 |
| A-6833 | H | H | H | H | H | O | CH$_2$N(CH$_3$)$_2$ | H | 2-CH$_2$F | 0 |
| A-6834 | H | H | H | H | H | O | CH$_2$N(CH$_3$)$_2$ | H | 2-CF$_2$Cl | 0 |
| A-6835 | H | H | H | H | H | O | CH$_2$N(CH$_3$)$_2$ | H | 2-cyclopropyl | 0 |

TABLE 121

| compound | R¹ | R² | R³ | R⁴ | R⁵ | A | R⁶ | R⁷ | (R⁸)$_m$ | p |
|---|---|---|---|---|---|---|---|---|---|---|
| A-6836 | H | H | H | H | H | O | CH$_2$N(CH$_3$)$_2$ | H | 2-cyclobutyl | 0 |
| A-6837 | H | H | H | H | H | O | CH$_2$N(CH$_3$)$_2$ | H | 2-cyclopentyl | 0 |
| A-6838 | H | H | H | H | H | O | CH$_2$N(CH$_3$)$_2$ | H | 2-ethenyl | 0 |
| A-6839 | H | H | H | H | H | O | CH$_2$N(CH$_3$)$_2$ | H | 2-allyl | 0 |
| A-6840 | H | H | H | H | H | O | CH$_2$N(CH$_3$)$_2$ | H | 2-(prop-1-en-1-yl) | 0 |
| A-6841 | H | H | H | H | H | O | CH$_2$N(CH$_3$)$_2$ | H | 2-(trifluoroethenyl) | 0 |
| A-6842 | H | H | H | H | H | O | CH$_2$N(CH$_3$)$_2$ | H | 2-OMe | 0 |
| A-6843 | H | H | H | H | H | O | CH$_2$N(CH$_3$)$_2$ | H | 2-OEt | 0 |
| A-6844 | H | H | H | H | H | O | CH$_2$N(CH$_3$)$_2$ | H | 2-OPr | 0 |
| A-6845 | H | H | H | H | H | O | CH$_2$N(CH$_3$)$_2$ | H | 2-O(i-Pr) | 0 |
| A-6846 | H | H | H | H | H | O | CH$_2$N(CH$_3$)$_2$ | H | 2-OCF$_3$ | 0 |
| A-6847 | H | H | H | H | H | O | CH$_2$N(CH$_3$)$_2$ | H | 2-OCHF$_2$ | 0 |
| A-6848 | H | H | H | H | H | O | CH$_2$N(CH$_3$)$_2$ | H | 2-(cyclopropyloxy) | 0 |
| A-6849 | H | H | H | H | H | O | CH$_2$N(CH$_3$)$_2$ | H | 2-(cyclobutyloxy) | 0 |
| A-6850 | H | H | H | H | H | O | CH$_2$N(CH$_3$)$_2$ | H | 2-(cyclopentyloxy) | 0 |
| A-6851 | H | H | H | H | H | O | CH$_2$N(CH$_3$)$_2$ | H | 2-((2,2-dichlorocyclopropyl)oxy) | 0 |
| A-6852 | H | H | H | H | H | O | CH$_2$N(CH$_3$)$_2$ | H | 2-(oxiran-2-yl) | 0 |
| A-6853 | H | H | H | H | H | O | CH$_2$N(CH$_3$)$_2$ | H | 2-SMe | 0 |
| A-6854 | H | H | H | H | H | O | CH$_2$N(CH$_3$)$_2$ | H | 3-SMe | 0 |
| A-6855 | H | H | H | H | H | O | CH$_2$N(CH$_3$)$_2$ | H | 2-S(=O)Me | 0 |
| A-6856 | H | H | H | H | H | O | CH$_2$N(CH$_3$)$_2$ | H | 3-S(=O)Me | 0 |
| A-6857 | H | H | H | H | H | O | CH$_2$N(CH$_3$)$_2$ | H | 2-S(=O)$_2$Me | 0 |
| A-6858 | H | H | H | H | H | O | CH$_2$N(CH$_3$)$_2$ | H | 3-S(=O)$_2$Me | 0 |
| A-6859 | H | H | H | H | H | O | CH$_2$N(CH$_3$)$_2$ | H | 2-SCF$_3$ | 0 |
| A-6860 | H | H | H | H | H | O | CH$_2$N(CH$_3$)$_2$ | H | 3-SCF$_3$ | 0 |
| A-6861 | H | H | H | H | H | O | CH$_2$N(CH$_3$)$_2$ | H | 3-S(=O)CF$_3$ | 0 |
| A-6862 | H | H | H | H | H | O | CH$_2$N(CH$_3$)$_2$ | H | 3-SCF(CF$_3$)$_2$ | 0 |
| A-6863 | H | H | H | H | H | O | CH$_2$N(CH$_3$)$_2$ | H | 2-(cyclopropylthio) | 0 |
| A-6864 | H | H | H | H | H | O | CH$_2$N(CH$_3$)$_2$ | H | 2-(cyclopropylsulfinyl) | 0 |
| A-6865 | H | H | H | H | H | O | CH$_2$N(CH$_3$)$_2$ | H | 2-(cyclopropylsulfonyl) | 0 |
| A-6866 | H | H | H | H | H | O | CH$_2$N(CH$_3$)$_2$ | H | 2-C(=O)Me | 0 |
| A-6867 | H | H | H | H | H | O | CH$_2$N(CH$_3$)$_2$ | H | 2-CH$_2$C(=O)CH$_3$ | 0 |
| A-6868 | H | H | H | H | H | O | CH$_2$N(CH$_3$)$_2$ | H | 2-CH$_2$C(=O)CF$_3$ | 0 |
| A-6869 | H | H | H | H | H | O | CH$_2$N(CH$_3$)$_2$ | H | 2-CH$_2$OH | 0 |
| A-6870 | H | H | H | H | H | O | CH$_2$N(CH$_3$)$_2$ | H | 2-CH$_2$OCH$_3$ | 0 |
| A-6871 | H | H | H | H | H | O | CH$_2$N(CH$_3$)$_2$ | H | 2-CH$_2$OCH$_2$CH$_3$ | 0 |
| A-6872 | H | H | H | H | H | O | CH$_2$N(CH$_3$)$_2$ | H | 2-CH$_2$SCH$_3$ | 0 |
| A-6873 | H | H | H | H | H | O | CH$_2$N(CH$_3$)$_2$ | H | 2-CH$_2$S(=O)CH$_3$ | 0 |
| A-6874 | H | H | H | H | H | O | CH$_2$N(CH$_3$)$_2$ | H | 2-CH$_2$S(=O)$_2$CH$_3$ | 0 |

TABLE 121-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-6875 | H | H | H | H | H | O | CH$_2$N(CH$_3$)$_2$ | H | 2-(benzyloxy) | 0 |
| A-6876 | H | H | H | H | H | O | CH$_2$N(CH$_3$)$_2$ | H | 2-NH$_2$ | 0 |
| A-6877 | H | H | H | H | H | O | CH$_2$N(CH$_3$)$_2$ | H | 2-NHMe | 0 |
| A-6878 | H | H | H | H | H | O | CH$_2$N(CH$_3$)$_2$ | H | 2-N(Me)$_2$ | 0 |
| A-6879 | H | H | H | H | H | O | CH$_2$N(CH$_3$)$_2$ | H | 2-(1,3-dioxolan-2-yl) | 0 |
| A-6880 | H | H | H | H | H | O | CH$_2$N(CH$_3$)$_2$ | H | 2-(1,3-dioxan-2-yl) | 0 |
| A-6881 | H | H | H | H | H | O | CH$_2$N(CH$_3$)$_2$ | H | 2-(1H-imidazol-2-yl) | 0 |
| A-6882 | H | H | H | H | H | O | CH$_2$N(CH$_3$)$_2$ | H | 2-(thiazol-2-yl) | 0 |
| A-6883 | H | H | H | H | H | O | CH$_2$N(CH$_3$)$_2$ | H | 2-(oxazol-2-yl) | 0 |
| A-6884 | H | H | H | H | H | O | CH$_2$N(CH$_3$)$_2$ | H | 2-CH=NOH | 0 |
| A-6885 | H | H | H | H | H | O | CH$_2$N(CH$_3$)$_2$ | H | 2-CH=NOMe | 0 |
| A-6886 | H | H | H | H | H | O | CH$_2$N(CH$_3$)$_2$ | H | 2-(4,5-dihydro-3-isoxazolyl) | 0 |
| A-6887 | H | H | H | H | H | O | CH$_2$N(CH$_3$)$_2$ | H | 2-CN | 0 |
| A-6888 | H | H | H | H | H | O | CH$_2$N(CH$_3$)$_2$ | H | 2-NO$_2$ | 0 |
| A-6889 | H | H | H | H | H | O | CH$_2$N(CH$_3$)$_2$ | H | 2-F,6-Cl | 0 |
| A-6890 | H | H | H | H | H | O | CH$_2$N(CH$_3$)$_2$ | H | 2-F,6-Me | 0 |
| A-6891 | H | H | H | H | H | O | CH$_2$N(CH$_3$)$_2$ | H | 3-F,6-Me | 0 |
| A-6892 | H | H | H | H | H | O | CH$_2$N(CH$_3$)$_2$ | H | 4-F,2-Me | 0 |

TABLE 122

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-6893 | H | H | H | H | H | O | CH$_2$N(CH$_3$)$_2$ | H | 2-F,6-OMe | 0 |
| A-6894 | H | H | H | H | H | O | CH$_2$N(CH$_3$)$_2$ | H | 3-F,6-OMe | 0 |
| A-6895 | H | H | H | H | H | O | CH$_2$N(CH$_3$)$_2$ | H | 2,6-Cl$_2$ | 0 |
| A-6896 | H | H | H | H | H | O | CH$_2$N(CH$_3$)$_2$ | H | 2-Cl,6-Me | 0 |
| A-6897 | H | H | H | H | H | O | CH$_2$N(CH$_3$)$_2$ | H | 3-Cl,6-Me | 0 |
| A-6898 | H | H | H | H | H | O | CH$_2$N(CH$_3$)$_2$ | H | 4-Cl,2-Me | 0 |
| A-6899 | H | H | H | H | H | O | CH$_2$N(CH$_3$)$_2$ | H | 2-Cl,5-CF$_3$ | 0 |
| A-6900 | H | H | H | H | H | O | CH$_2$N(CH$_3$)$_2$ | H | 2-Cl,6-CF$_3$ | 0 |
| A-6901 | H | H | H | H | H | O | CH$_2$N(CH$_3$)$_2$ | H | 2-Cl,6-OMe | 0 |
| A-6902 | H | H | H | H | H | O | CH$_2$N(CH$_3$)$_2$ | H | 3-Cl,6-OMe | 0 |
| A-6903 | H | H | H | H | H | O | CH$_2$N(CH$_3$)$_2$ | H | 4-Cl,2-OMe | 0 |
| A-6904 | H | H | H | H | H | O | CH$_2$N(CH$_3$)$_2$ | H | 2,4-Me$_2$ | 0 |
| A-6905 | H | H | H | H | H | O | CH$_2$N(CH$_3$)$_2$ | H | 2,5-Me$_2$ | 0 |
| A-6906 | H | H | H | H | H | O | CH$_2$N(CH$_3$)$_2$ | H | 2,6-Me$_2$ | 0 |
| A-6907 | H | H | H | H | H | O | CH$_2$N(CH$_3$)$_2$ | H | 2-Me,4-CF$_3$ | 0 |
| A-6908 | H | H | H | H | H | O | CH$_2$N(CH$_3$)$_2$ | H | 2-Me,5-CF$_3$ | 0 |
| A-6909 | H | H | H | H | H | O | CH$_2$N(CH$_3$)$_2$ | H | 2-Me,6-CF$_3$ | 0 |
| A-6910 | H | H | H | H | H | O | CH$_2$N(CH$_3$)$_2$ | H | 2-Me,4-OMe | 0 |
| A-6911 | H | H | H | H | H | O | CH$_2$N(CH$_3$)$_2$ | H | 2-Me,5-OMe | 0 |
| A-6912 | H | H | H | H | H | O | CH$_2$N(CH$_3$)$_2$ | H | 2-Me,6-OMe | 0 |
| A-6913 | H | H | H | H | H | O | CH$_2$N(CH$_3$)$_2$ | H | 3-Me,6-OMe | 0 |
| A-6914 | H | H | H | H | H | O | CH$_2$N(CH$_3$)$_2$ | H | 4-Me,2-OMe | 0 |
| A-6915 | H | H | H | H | H | O | CH$_2$N(CH$_3$)$_2$ | H | 2,5-OMe$_2$ | 0 |
| A-6916 | H | H | H | H | H | O | CH$_2$N(CH$_3$)$_2$ | H | 2,6-OMe$_2$ | 0 |
| A-6917 | H | H | H | H | H | O | CH$_2$N(CH$_3$)$_2$ | H | 2-OMe,6-CF$_3$ | 0 |
| A-6918 | H | H | H | H | H | O | CH$_2$N(CH$_3$)$_2$ | H | 2-CHF$_2$,5-F | 0 |
| A-6919 | H | H | H | H | H | O | CH$_2$N(CH$_3$)$_2$ | H | 2-CHF$_2$,6-F | 0 |
| A-6920 | H | H | H | H | H | O | CH$_2$N(CH$_3$)$_2$ | H | 2-CHF$_2$,5-Me | 0 |
| A-6921 | H | H | H | H | H | O | CH$_2$N(CH$_3$)$_2$ | H | 2-CHF$_2$,6-Me | 0 |
| A-6922 | H | H | H | H | H | O | CH$_2$N(CH$_3$)$_2$ | H | 2-cyclopropyl,5-F | 0 |
| A-6923 | H | H | H | H | H | O | CH$_2$N(CH$_3$)$_2$ | H | 2-cyclopropyl,6-F | 0 |
| A-6924 | H | H | H | H | H | O | CH$_2$N(CH$_3$)$_2$ | H | 2-cyclopropyl,5-Me | 0 |
| A-6925 | H | H | H | H | H | O | CH$_2$N(CH$_3$)$_2$ | H | 2-cyclopropyl,6-Me | 0 |
| A-6926 | H | H | H | H | H | O | CH$_2$N(CH$_3$)$_2$ | H | 2-ethenyl,6-F | 0 |
| A-6927 | H | H | H | H | H | O | CH$_2$N(CH$_3$)$_2$ | H | 2-ethenyl,6-Me | 0 |
| A-6928 | H | H | H | H | H | O | CH$_2$N(CH$_3$)$_2$ | H | 2-OEt,5-F | 0 |
| A-6929 | H | H | H | H | H | O | CH$_2$N(CH$_3$)$_2$ | H | 2-OEt,6-F | 0 |
| A-6930 | H | H | H | H | H | O | CH$_2$N(CH$_3$)$_2$ | H | 2-OEt,5-Cl | 0 |
| A-6931 | H | H | H | H | H | O | CH$_2$N(CH$_3$)$_2$ | H | 2-OEt,6-Cl | 0 |
| A-6932 | H | H | H | H | H | O | CH$_2$N(CH$_3$)$_2$ | H | 2-OEt,5-Me | 0 |
| A-6933 | H | H | H | H | H | O | CH$_2$N(CH$_3$)$_2$ | H | 2-OEt,6-Me | 0 |
| A-6934 | H | H | H | H | H | O | CH$_2$N(CH$_3$)$_2$ | H | 2-OCHF$_2$,5-F | 0 |
| A-6935 | H | H | H | H | H | O | CH$_2$N(CH$_3$)$_2$ | H | 2-OCHF$_2$,6-F | 0 |
| A-6936 | H | H | H | H | H | O | CH$_2$N(CH$_3$)$_2$ | H | 2-OCHF$_2$,5-Me | 0 |
| A-6937 | H | H | H | H | H | O | CH$_2$N(CH$_3$)$_2$ | H | 2-OCHF$_2$,6-Me | 0 |
| A-6938 | H | H | H | H | H | O | CH$_2$N(CH$_3$)$_2$ | H | 2-(cyclopropyloxy),5-F | 0 |
| A-6939 | H | H | H | H | H | O | CH$_2$N(CH$_3$)$_2$ | H | 2-(cyclopropyloxy),6-F | 0 |
| A-6940 | H | H | H | H | H | O | CH$_2$N(CH$_3$)$_2$ | H | 2-(cyclopropyloxy),5-Me | 0 |
| A-6941 | H | H | H | H | H | O | CH$_2$N(CH$_3$)$_2$ | H | 2-(cyclopropyloxy),6-Me | 0 |
| A-6942 | H | H | H | H | H | O | CH$_2$N(CH$_3$)$_2$ | H | 2-SMe,5-F | 0 |
| A-6943 | H | H | H | H | H | O | CH$_2$N(CH$_3$)$_2$ | H | 2-SMe,6-F | 0 |
| A-6944 | H | H | H | H | H | O | CH$_2$N(CH$_3$)$_2$ | H | 2-SMe,5-Me | 0 |

TABLE 122-continued

| compound | R¹ | R² | R³ | R⁴ | R⁵ | A | R⁶ | R⁷ | (R⁸)$_m$ | p |
|---|---|---|---|---|---|---|---|---|---|---|
| A-6945 | H | H | H | H | H | O | CH$_2$N(CH$_3$)$_2$ | H | 2-SMe,6-Me | 0 |
| A-6946 | H | H | H | H | H | O | CH$_2$N(CH$_3$)$_2$ | H | 2-S(=O)Me,5-F | 0 |
| A-6947 | H | H | H | H | H | O | CH$_2$N(CH$_3$)$_2$ | H | 2-S(=O)Me,6-F | 0 |
| A-6948 | H | H | H | H | H | O | CH$_2$N(CH$_3$)$_2$ | H | 2-S(=O)Me,5-Me | 0 |
| A-6949 | H | H | H | H | H | O | CH$_2$N(CH$_3$)$_2$ | H | 2-S(=O)Me,6-Me | 0 |

TABLE 123

| compound | R¹ | R² | R³ | R⁴ | R⁵ | A | R⁶ | R⁷ | (R⁸)$_m$ | p |
|---|---|---|---|---|---|---|---|---|---|---|
| A-6950 | H | H | H | H | H | O | CH$_2$N(CH$_3$)$_2$ | H | 2-S(=O)$_2$Me,5-f | 0 |
| A-6951 | H | H | H | H | H | O | CH$_2$N(CH$_3$)$_2$ | H | 2-S(=O)$_2$Me,6-F | 0 |
| A-6952 | H | H | H | H | H | O | CH$_2$N(CH$_3$)$_2$ | H | 2-S(=O)$_2$Me,5-Me | 0 |
| A-6953 | H | H | H | H | H | O | CH$_2$N(CH$_3$)$_2$ | H | 2-S(=O)$_2$Me,6-Me | 0 |
| A-6954 | H | H | H | H | H | O | CH$_2$N(CH$_3$)$_2$ | H | 2-SCF$_3$,5-F | 0 |
| A-6955 | H | H | H | H | H | O | CH$_2$N(CH$_3$)$_2$ | H | 2-SCF$_3$,6-F | 0 |
| A-6956 | H | H | H | H | H | O | CH$_2$N(CH$_3$)$_2$ | H | 2-SCF$_3$,5-Me | 0 |
| A-6957 | H | H | H | H | H | O | CH$_2$N(CH$_3$)$_2$ | H | 2-SCF$_3$,6-Me | 0 |
| A-6958 | H | H | H | H | H | O | CH$_2$N(CH$_3$)$_2$ | H | 2-S(=O)CF$_3$,5-F | 0 |
| A-6959 | H | H | H | H | H | O | CH$_2$N(CH$_3$)$_2$ | H | 2-S(=O)CF$_3$,6-F | 0 |
| A-6960 | H | H | H | H | H | O | CH$_2$N(CH$_3$)$_2$ | H | 2-S(=O)CF$_3$,5-Me | 0 |
| A-6961 | H | H | H | H | H | O | CH$_2$N(CH$_3$)$_2$ | H | 2-S(=O)CF$_3$,6-Me | 0 |
| A-6962 | H | H | H | H | H | O | CH$_2$N(CH$_3$)$_2$ | H | 2-S(=O)$_2$CF$_3$,5-F | 0 |
| A-6963 | H | H | H | H | H | O | CH$_2$N(CH$_3$)$_2$ | H | 2-S(=O)$_2$CF$_3$,6-F | 0 |
| A-6964 | H | H | H | H | H | O | CH$_2$N(CH$_3$)$_2$ | H | 2-S(=O)$_2$CF$_3$,5-Me | 0 |
| A-6965 | H | H | H | H | H | O | CH$_2$N(CH$_3$)$_2$ | H | 2-S(=O)$_2$CF$_3$,6-Me | 0 |
| A-6966 | H | H | H | H | H | O | CH$_2$N(CH$_3$)$_2$ | H | 2-(cyclopropylthio),5-F | 0 |
| A-6967 | H | H | H | H | H | O | CH$_2$N(CH$_3$)$_2$ | H | 2-(cyclopropylthio),6-F | 0 |
| A-6968 | H | H | H | H | H | O | CH$_2$N(CH$_3$)$_2$ | H | 2-(cyclopropylthio),5-Me | 0 |
| A-6969 | H | H | H | H | H | O | CH$_2$N(CH$_3$)$_2$ | H | 2-(cyclopropylthio),6-Me | 0 |
| A-6970 | H | H | H | H | H | O | CH$_2$N(CH$_3$)$_2$ | H | 2-C(=O)Me,5-F | 0 |
| A-6971 | H | H | H | H | H | O | CH$_2$N(CH$_3$)$_2$ | H | 2-C(=O)Me,6-F | 0 |
| A-6972 | H | H | H | H | H | O | CH$_2$N(CH$_3$)$_2$ | H | 2-C(=O)Me,5-Me | 0 |
| A-6973 | H | H | H | H | H | O | CH$_2$N(CH$_3$)$_2$ | H | 2-C(=O)Me,6-Me | 0 |
| A-6974 | H | H | H | H | H | O | CH$_2$N(CH$_3$)$_2$ | H | 2-CH$_2$OH,5-F | 0 |
| A-6975 | H | H | H | H | H | O | CH$_2$N(CH$_3$)$_2$ | H | 2-CH$_2$OH,6-F | 0 |
| A-6976 | H | H | H | H | H | O | CH$_2$N(CH$_3$)$_2$ | H | 2-CH$_2$OH,5-Me | 0 |
| A-6977 | H | H | H | H | H | O | CH$_2$N(CH$_3$)$_2$ | H | 2-CH$_2$OH,6-Me | 0 |
| A-6978 | H | H | H | H | H | O | CH$_2$N(CH$_3$)$_2$ | H | 2-CH$_2$OCH$_3$,4-F | 0 |
| A-6979 | H | H | H | H | H | O | CH$_2$N(CH$_3$)$_2$ | H | 2-CH$_2$OCH$_3$,5-F | 0 |
| A-6980 | H | H | H | H | H | O | CH$_2$N(CH$_3$)$_2$ | H | 2-CH$_2$OCH$_3$,6-F | 0 |
| A-6981 | H | H | H | H | H | O | CH$_2$N(CH$_3$)$_2$ | H | 2-CH$_2$OCH$_3$,4-Me | 0 |
| A-6982 | H | H | H | H | H | O | CH$_2$N(CH$_3$)$_2$ | H | 2-CH$_2$OCH$_3$,5-Me | 0 |
| A-6983 | H | H | H | H | H | O | CH$_2$N(CH$_3$)$_2$ | H | 2-CH$_2$OCH$_3$,6-Me | 0 |
| A-6984 | H | H | H | H | H | O | CH$_2$N(CH$_3$)$_2$ | H | 2-OC(=O)CH$_3$,5-F | 0 |
| A-6985 | H | H | H | H | H | O | CH$_2$N(CH$_3$)$_2$ | H | 2-OC(=O)CH$_3$,6-F | 0 |
| A-6986 | H | H | H | H | H | O | CH$_2$N(CH$_3$)$_2$ | H | 2-OC(=O)CH$_3$,5-Me | 0 |
| A-6987 | H | H | H | H | H | O | CH$_2$N(CH$_3$)$_2$ | H | 2-OC(=O)CH$_3$,6-Me | 0 |
| A-6988 | H | H | H | H | H | O | CH$_2$N(CH$_3$)$_2$ | H | 2-OS(=O)$_2$CH$_3$,5-F | 0 |
| A-6989 | H | H | H | H | H | O | CH$_2$N(CH$_3$)$_2$ | H | 2-OS(=O)$_2$CH$_3$,6-F | 0 |
| A-6990 | H | H | H | H | H | O | CH$_2$N(CH$_3$)$_2$ | H | 2-OS(=O)$_2$CH$_3$,5-Me | 0 |
| A-6991 | H | H | H | H | H | O | CH$_2$N(CH$_3$)$_2$ | H | 2-OS(=O)$_2$CH$_3$,6-Me | 0 |
| A-6992 | H | H | H | H | H | O | CH$_2$N(CH$_3$)$_2$ | H | 2-CH$_2$SCH$_3$,5-F | 0 |
| A-6993 | H | H | H | H | H | O | CH$_2$N(CH$_3$)$_2$ | H | 2-CH$_2$SCH$_3$,6-F | 0 |
| A-6994 | H | H | H | H | H | O | CH$_2$N(CH$_3$)$_2$ | H | 2-CH$_2$SCH$_3$,5-Me | 0 |
| A-6995 | H | H | H | H | H | O | CH$_2$N(CH$_3$)$_2$ | H | 2-CH$_2$SCH$_3$,6-Me | 0 |
| A-6996 | H | H | H | H | H | O | CH$_2$N(CH$_3$)$_2$ | H | 2-NMe$_2$,5-F | 0 |
| A-6997 | H | H | H | H | H | O | CH$_2$N(CH$_3$)$_2$ | H | 2-NMe$_2$,6-F | 0 |
| A-6998 | H | H | H | H | H | O | CH$_2$N(CH$_3$)$_2$ | H | 2-NMe$_2$,5-Me | 0 |
| A-6999 | H | H | H | H | H | O | CH$_2$N(CH$_3$)$_2$ | H | 2-NMe$_2$,6-Me | 0 |
| A-7000 | H | H | H | H | H | O | CH$_2$N(CH$_3$)$_2$ | H | 2-CN,4-F | 0 |
| A-7001 | H | H | H | H | H | O | CH$_2$N(CH$_3$)$_2$ | H | 2-CN,5-F | 0 |
| A-7002 | H | H | H | H | H | O | CH$_2$N(CH$_3$)$_2$ | H | 2-CN,6-F | 0 |
| A-7003 | H | H | H | H | H | O | CH$_2$N(CH$_3$)$_2$ | H | 2-CN,6-Me | 0 |
| A-7004 | H | H | H | H | H | O | CH$_2$N(CH$_3$)$_2$ | H | 2-CN,5-OMe | 0 |
| A-7005 | H | H | H | H | H | O | CH$_2$N(CH$_3$)$_2$ | H | 2-CN,6-OMe | 0 |
| A-7006 | H | H | H | H | H | O | CH$_2$N(CH$_3$)$_2$ | H | 3-CN,6-Me | 0 |

TABLE 124

| compound | R¹ | R² | R³ | R⁴ | R⁵ | A | R⁶ | R⁷ | (R⁸)ₘ | p |
|---|---|---|---|---|---|---|---|---|---|---|
| A-7007 | H | H | H | H | H | O | CH₂N(CH₃)₂ | H | 3-CN,6-OMe | 0 |
| A-7008 | H | H | H | H | H | O | CH₂N(CH₃)₂ | H | 4-CN,2-Me | 0 |
| A-7009 | H | H | H | H | H | O | CH₂N(CH₃)₂ | H | 4-CN,2-OMe | 0 |
| A-7010 | H | H | H | H | H | O | CH₂N(CH₃)₂ | H | 2-NO₂,4-F | 0 |
| A-7011 | H | H | H | H | H | O | CH₂N(CH₃)₂ | H | 2-NO₂,5-F | 0 |
| A-7012 | H | H | H | H | H | O | CH₂N(CH₃)₂ | H | 2-NO₂,6-F | 0 |
| A-7013 | H | H | H | H | H | O | CH₂N(CH₃)₂ | H | 2-NO₂,4-Me | 0 |
| A-7014 | H | H | H | H | H | O | CH₂N(CH₃)₂ | H | 2-NO₂,5-Me | 0 |
| A-7015 | H | H | H | H | H | O | CH₂N(CH₃)₂ | H | 2-NO₂,6-Me | 0 |
| A-7016 | H | H | H | H | H | O | CH₂N(CH₃)₂ | H | 2-Me,4,5-F₂ | 0 |
| A-7017 | H | H | H | H | H | O | CH₂N(CH₃)₂ | H | 2-Me,6-Et | 0 |
| A-7018 | H | H | H | H | H | O | CH₂N(CH₃)₂ | H | 2-cyclopropyl,6-OMe | 0 |
| A-7019 | H | H | H | H | H | O | CH₂N(CH₃)₂ | H | 2-Me,5-Et | 0 |
| A-7020 | H | H | H | H | H | O | CH₂N(CH₃)₂ | H | 2,6-Et₂ | 0 |
| A-7021 | H | H | H | H | H | O | CH₂N(CH₃)₂ | H | 2-Et,6-F | 0 |
| A-7022 | H | H | H | H | H | O | CH₂N(CH₃)₂ | H | 2-CH₂OCH₃,6-Cl | 0 |
| A-7023 | H | H | H | H | H | O | CH₂N(CH₃)₂ | H | 2-CH₂OCH₂CH₃,6-Cl | 0 |
| A-7024 | H | H | H | H | H | O | CH₂N(CH₃)₂ | H | 2-CH₂NMe₂ | 0 |
| A-7025 | H | H | H | H | H | O | CH₂C(=O)OCH₃ | H | H | 0 |
| A-7026 | H | H | H | H | H | O | CH₂C(=O)OCH₃ | H | 2-F | 0 |
| A-7027 | H | H | H | H | H | O | CH₂C(=O)OCH₃ | H | 2-Cl | 0 |
| A-7028 | H | H | H | H | H | O | CH₂C(=O)OCH₃ | H | 2-Br | 0 |
| A-7029 | H | H | H | H | H | O | CH₂C(=O)OCH₃ | H | 2-OH | 0 |
| A-7030 | H | H | H | H | H | O | CH₂C(=O)OCH₃ | H | 2-Me | 0 |
| A-7031 | H | H | H | H | H | O | CH₂C(=O)OCH₃ | H | 2-Et | 0 |
| A-7032 | H | H | H | H | H | O | CH₂C(=O)OCH₃ | H | 2-Pr | 0 |
| A-7033 | H | H | H | H | H | O | CH₂C(=O)OCH₃ | H | 2-CF₃ | 0 |
| A-7034 | H | H | H | H | H | O | CH₂C(=O)OCH₃ | H | 2-CHF₂ | 0 |
| A-7035 | H | H | H | H | H | O | CH₂C(=O)OCH₃ | H | 2-CH₂F | 0 |
| A-7036 | H | H | H | H | H | O | CH₂C(=O)OCH₃ | H | 2-CF₂Cl | 0 |
| A-7037 | H | H | H | H | H | O | CH₂C(=O)OCH₃ | H | 2-cyclopropyl | 0 |
| A-7038 | H | H | H | H | H | O | CH₂C(=O)OCH₃ | H | 2-cyclobutyl | 0 |
| A-7039 | H | H | H | H | H | O | CH₂C(=O)OCH₃ | H | 2-cyclopentyl | 0 |
| A-7040 | H | H | H | H | H | O | CH₂C(=O)OCH₃ | H | 2-ethenyl | 0 |
| A-7041 | H | H | H | H | H | O | CH₂C(=O)OCH₃ | H | 2-allyl | 0 |
| A-7042 | H | H | H | H | H | O | CH₂C(=O)OCH₃ | H | 2-(prop-1-en-1-yl) | 0 |
| A-7043 | H | H | H | H | H | O | CH₂C(=O)OCH₃ | H | 2-(trifluoroethenyl) | 0 |
| A-7044 | H | H | H | H | H | O | CH₂C(=O)OCH₃ | H | 2-OMe | 0 |
| A-7045 | H | H | H | H | H | O | CH₂C(=O)OCH₃ | H | 2-OEt | 0 |
| A-7046 | H | H | H | H | H | O | CH₂C(=O)OCH₃ | H | 2-OPr | 0 |
| A-7047 | H | H | H | H | H | O | CH₂C(=O)OCH₃ | H | 2-O(i-Pr) | 0 |
| A-7048 | H | H | H | H | H | O | CH₂C(=O)OCH₃ | H | 2-OCF₃ | 0 |
| A-7049 | H | H | H | H | H | O | CH₂C(=O)OCH₃ | H | 2-OCHF₂ | 0 |
| A-7050 | H | H | H | H | H | O | CH₂C(=O)OCH₃ | H | 2-(cyclopropyloxy) | 0 |
| A-7051 | H | H | H | H | H | O | CH₂C(=O)OCH₃ | H | 2-(cycbbutyloxy) | 0 |
| A-7052 | H | H | H | H | H | O | CH₂C(=O)OCH₃ | H | 2-(cyclopentyloxy) | 0 |
| A-7053 | H | H | H | H | H | O | CH₂C(=O)OCH₃ | H | 2-((2,2-dichlorocyclopropyl)oxy) | 0 |
| A-7054 | H | H | H | H | H | O | CH₂C(=O)OCH₃ | H | 2-(oxiran-2-yl) | 0 |
| A-7055 | H | H | H | H | H | O | CH₂C(=O)OCH₃ | H | 2-SMe | 0 |
| A-7056 | H | H | H | H | H | O | CH₂C(=O)OCH₃ | H | 3-SMe | 0 |
| A-7057 | H | H | H | H | H | O | CH₂C(=O)OCH₃ | H | 2-S(=O)Me | 0 |
| A-7058 | H | H | H | H | H | O | CH₂C(=O)OCH₃ | H | 3-S(=O)Me | 0 |
| A-7059 | H | H | H | H | H | O | CH₂C(=O)OCH₃ | H | 2-S(=O)₂Me | 0 |
| A-7060 | H | H | H | H | H | O | CH₂C(=O)OCH₃ | H | 3-S(=O)₂Me | 0 |
| A-7061 | H | H | H | H | H | O | CH₂C(=O)OCH₃ | H | 2-SCF₃ | 0 |
| A-7062 | H | H | H | H | H | O | CH₂C(=O)OCH₃ | H | 3-SCF₃ | 0 |
| A-7063 | H | H | H | H | H | O | CH₂C(=O)OCH₃ | H | 3-S(=O)CF₃ | 0 |

TABLE 125

| compound | R¹ | R² | R³ | R⁴ | R⁵ | A | R⁶ | R⁷ | (R⁸)ₘ | p |
|---|---|---|---|---|---|---|---|---|---|---|
| A-7064 | H | H | H | H | H | 0 | CH₂C(=O)OCH₃ | H | 3-SCF(CF₃)₂ | 0 |
| A-7065 | H | H | H | H | H | 0 | CH₂C(=O)OCH₃ | H | 2-(cyclopropylthio) | 0 |
| A-7066 | H | H | H | H | H | 0 | CH₂C(=O)OCH₃ | H | 2-(cyclopropylsulfinyl) | 0 |
| A-7067 | H | H | H | H | H | 0 | CH₂C(=O)OCH₃ | H | 2-(cyclopropylsulfonyl) | 0 |
| A-7068 | H | H | H | H | H | 0 | CH₂C(=O)OCH₃ | H | 2-C(=O)Me | 0 |
| A-7069 | H | H | H | H | H | 0 | CH₂C(=O)OCH₃ | H | 2-CH₂C(=O)CH₃ | 0 |
| A-7070 | H | H | H | H | H | 0 | CH₂C(=O)OCH₃ | H | 2-CH₂C(=O)CF₃ | 0 |
| A-7071 | H | H | H | H | H | 0 | CH₂C(=O)OCH₃ | H | 2-CH₂O | 0 |
| A-7072 | H | H | H | H | H | 0 | CH₂C(=O)OCH₃ | H | 2-CH₂OCH₃ | 0 |
| A-7073 | H | H | H | H | H | 0 | CH₂C(=O)OCH₃ | H | 2-CH₂OCH₂CH₃ | 0 |
| A-7074 | H | H | H | H | H | 0 | CH₂C(=O)OCH₃ | H | 2-CH₂SCH₃ | 0 |
| A-7075 | H | H | H | H | H | 0 | CH₂C(=O)OCH₃ | H | 2-CH₂S(=O)CH₃ | 0 |
| A-7076 | H | H | H | H | H | 0 | CH₂C(=O)OCH₃ | H | 2-CH₂S(=O)₂CH₃ | 0 |

TABLE 125-continued

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-7077 | H | H | H | H | H | 0 | $CH_2C(=O)OCH_3$ | H | 2-(benzyloxy) | 0 |
| A-7078 | H | H | H | H | H | 0 | $CH_2C(=O)OCH_3$ | H | 2-$NH_2$ | 0 |
| A-7079 | H | H | H | H | H | 0 | $CH_2C(=O)OCH_3$ | H | 2-NHMe | 0 |
| A-7080 | H | H | H | H | H | 0 | $CH_2C(=O)OCH_3$ | H | 2-N(Me)$_2$ | 0 |
| A-7081 | H | H | H | H | H | 0 | $CH_2C(=O)OCH_3$ | H | 2-(1,3-dioxolan-2-yl) | 0 |
| A-7082 | H | H | H | H | H | 0 | $CH_2C(=O)OCH_3$ | H | 2-(1,3-dioxan-2-yl) | 0 |
| A-7083 | H | H | H | H | H | 0 | $CH_2C(=O)OCH_3$ | H | 2-(1H-imidazol-2-yl) | 0 |
| A-7084 | H | H | H | H | H | 0 | $CH_2C(=O)OCH_3$ | H | 2-(thiazol-2-yl) | 0 |
| A-7085 | H | H | H | H | H | 0 | $CH_2C(=O)OCH_3$ | H | 2-(oxazol-2-yl) | 0 |
| A-7086 | H | H | H | H | H | 0 | $CH_2C(=O)OCH_3$ | H | 2-CH=NOH | 0 |
| A-7087 | H | H | H | H | H | 0 | $CH_2C(=O)OCH_3$ | H | 2-CH=NOMe | 0 |
| A-7088 | H | H | H | H | H | 0 | $CH_2C(=O)OCH_3$ | H | 2-(4,5-dihydro-3-isoxazolyl) | 0 |
| A-7089 | H | H | H | H | H | 0 | $CH_2C(=O)OCH_3$ | H | 2-CN | 0 |
| A-7090 | H | H | H | H | H | 0 | $CH_2C(=O)OCH_3$ | H | 2-$NO_2$ | 0 |
| A-7091 | H | H | H | H | H | 0 | $CH_2C(=O)OCH_3$ | H | 2-F,6-Cl | 0 |
| A-7092 | H | H | H | H | H | 0 | $CH_2C(=O)OCH_3$ | H | 2-F,6-Me | 0 |
| A-7093 | H | H | H | H | H | 0 | $CH_2C(=O)OCH_3$ | H | 3-F,6-Me | 0 |
| A-7094 | H | H | H | H | H | 0 | $CH_2C(=O)OCH_3$ | H | 4-F,2-Me | 0 |
| A-7095 | H | H | H | H | H | 0 | $CH_2C(=O)OCH_3$ | H | 2-F,6-OMe | 0 |
| A-7096 | H | H | H | H | H | 0 | $CH_2C(=O)OCH_3$ | H | 3-F,6-OMe | 0 |
| A-7097 | H | H | H | H | H | 0 | $CH_2C(=O)OCH_3$ | H | 2,6-Cl$_2$ | 0 |
| A-7098 | H | H | H | H | H | 0 | $CH_2C(=O)OCH_3$ | H | 2-Cl,6-Me | 0 |
| A-7099 | H | H | H | H | H | 0 | $CH_2C(=O)OCH_3$ | H | 3-Cl,6-Me | 0 |
| A-7100 | H | H | H | H | H | 0 | $CH_2C(=O)OCH_3$ | H | 4-Cl,2-Me | 0 |
| A-7101 | H | H | H | H | H | 0 | $CH_2C(=O)OCH_3$ | H | 2-Cl,5-$CF_3$ | 0 |
| A-7102 | H | H | H | H | H | 0 | $CH_2C(=O)OCH_3$ | H | 2-Cl,6-$CF_3$ | 0 |
| A-7103 | H | H | H | H | H | 0 | $CH_2C(=O)OCH_3$ | H | 2-Cl,6-OMe | 0 |
| A-7104 | H | H | H | H | H | 0 | $CH_2C(=O)OCH_3$ | H | 3-Cl,6-OMe | 0 |
| A-7105 | H | H | H | H | H | 0 | $CH_2C(=O)OCH_3$ | H | 4-Cl,2-OMe | 0 |
| A-7106 | H | H | H | H | H | 0 | $CH_2C(=O)OCH_3$ | H | 2,4-Me$_2$ | 0 |
| A-7107 | H | H | H | H | H | 0 | $CH_2C(=O)OCH_3$ | H | 2,5-Me$_2$ | 0 |
| A-7108 | H | H | H | H | H | 0 | $CH_2C(=O)OCH_3$ | H | 2,6-Me$_2$ | 0 |
| A-7109 | H | H | H | H | H | 0 | $CH_2C(=O)OCH_3$ | H | 2-Me,4-$CF_3$ | 0 |
| A-7110 | H | H | H | H | H | 0 | $CH_2C(=O)OCH_3$ | H | 2-Me,5-$CF_3$ | 0 |
| A-7111 | H | H | H | H | H | 0 | $CH_2C(=O)OCH_3$ | H | 2-Me,6-$CF_3$ | 0 |
| A-7112 | H | H | H | H | H | 0 | $CH_2C(=O)OCH_3$ | H | 2-Me,4-OMe | 0 |
| A-7113 | H | H | H | H | H | 0 | $CH_2C(=O)OCH_3$ | H | 2-Me,5-OMe | 0 |
| A-7114 | H | H | H | H | H | 0 | $CH_2C(=O)OCH_3$ | H | 2-Me,6-OMe | 0 |
| A-7115 | H | H | H | H | H | 0 | $CH_2C(=O)OCH_3$ | H | 3-Me,6-OMe | 0 |
| A-7116 | H | H | H | H | H | 0 | $CH_2C(=O)OCH_3$ | H | 4-Me,2-OMe | 0 |
| A-7117 | H | H | H | H | H | 0 | $CH_2C(=O)OCH_3$ | H | 2,5-OMe$_2$ | 0 |
| A-7118 | H | H | H | H | H | 0 | $CH_2C(=O)OCH_3$ | H | 2,6-OMe$_2$ | 0 |
| A-7119 | H | H | H | H | H | 0 | $CH_2C(=O)OCH_3$ | H | 2-OMe,6-$CF_3$ | 0 |
| A-7120 | H | H | H | H | H | 0 | $CH_2C(=O)OCH_3$ | H | 2-$CHF_2$,5-F | 0 |

TABLE 126

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-7121 | H | H | H | H | H | 0 | $CH_2C(=O)OCH_3$ | H | 2-$CHF_2$,6-F | 0 |
| A-7122 | H | H | H | H | H | 0 | $CH_2C(=O)OCH_3$ | H | 2-$CHF_2$,5-Me | 0 |
| A-7123 | H | H | H | H | H | 0 | $CH_2C(=O)OCH_3$ | H | 2-$CHF_2$,6-Me | 0 |
| A-7124 | H | H | H | H | H | 0 | $CH_2C(=O)OCH_3$ | H | 2-cyclopropyl,5-F | 0 |
| A-7125 | H | H | H | H | H | 0 | $CH_2C(=O)OCH_3$ | H | 2-cyclopropyl,6-F | 0 |
| A-7126 | H | H | H | H | H | 0 | $CH_2C(=O)OCH_3$ | H | 2-cyclopropyl,5-Me | 0 |
| A-7127 | H | H | H | H | H | 0 | $CH_2C(=O)OCH_3$ | H | 2-cyclopropyl,6-Me | 0 |
| A-7128 | H | H | H | H | H | 0 | $CH_2C(=O)OCH_3$ | H | 2-ethenyl,6-F | 0 |
| A-7129 | H | H | H | H | H | 0 | $CH_2C(=O)OCH_3$ | H | 2-ethenyl,6-Me | 0 |
| A-7130 | H | H | H | H | H | 0 | $CH_2C(=O)OCH_3$ | H | 2-OEt,5-F | 0 |
| A-7131 | H | H | H | H | H | 0 | $CH_2C(=O)OCH_3$ | H | 2-OEt,6-F | 0 |
| A-7132 | H | H | H | H | H | 0 | $CH_2C(=O)OCH_3$ | H | 2-OEt,5-Cl | 0 |
| A-7133 | H | H | H | H | H | 0 | $CH_2C(=O)OCH_3$ | H | 2-OEt,6-Cl | 0 |
| A-7134 | H | H | H | H | H | 0 | $CH_2C(=O)OCH_3$ | H | 2-OEt,5-Me | 0 |
| A-7135 | H | H | H | H | H | 0 | $CH_2C(=O)OCH_3$ | H | 2-OEt,6-Me | 0 |
| A-7136 | H | H | H | H | H | 0 | $CH_2C(=O)OCH_3$ | H | 2-$OCHF_2$,5-F | 0 |
| A-7137 | H | H | H | H | H | 0 | $CH_2C(=O)OCH_3$ | H | 2-$OCHF_2$,6-F | 0 |
| A-7138 | H | H | H | H | H | 0 | $CH_2C(=O)OCH_3$ | H | 2-$OCHF_2$,5-Me | 0 |
| A-7139 | H | H | H | H | H | 0 | $CH_2C(=O)OCH_3$ | H | 2-$OCHF_2$,6-Me | 0 |
| A-7140 | H | H | H | H | H | 0 | $CH_2C(=O)OCH_3$ | H | 2-(cyclopropyloxy),5-F | 0 |
| A-7141 | H | H | H | H | H | 0 | $CH_2C(=O)OCH_3$ | H | 2-(cyclopropyloxy),6-F | 0 |
| A-7142 | H | H | H | H | H | 0 | $CH_2C(=O)OCH_3$ | H | 2-(cyclopropyloxy),5-Me | 0 |
| A-7143 | H | H | H | H | H | 0 | $CH_2C(=O)OCH_3$ | H | 2-(cyclopropyloxy),6-Me | 0 |
| A-7144 | H | H | H | H | H | 0 | $CH_2C(=O)OCH_3$ | H | 2-SMe,5-F | 0 |
| A-7145 | H | H | H | H | H | 0 | $CH_2C(=O)OCH_3$ | H | 2-SMe,6-F | 0 |
| A-7146 | H | H | H | H | H | 0 | $CH_2C(=O)OCH_3$ | H | 2-SMe,5-Me | 0 |

TABLE 126-continued

| compound | R¹ | R² | R³ | R⁴ | R⁵ | A | R⁶ | R⁷ | (R⁸)ₘ | p |
|---|---|---|---|---|---|---|---|---|---|---|
| A-7147 | H | H | H | H | H | O | CH₂C(=O)OCH₃ | H | 2-SMe,6-Me | 0 |
| A-7148 | H | H | H | H | H | O | CH₂C(=O)OCH₃ | H | 2-S(=O)Me,5-F | 0 |
| A-7149 | H | H | H | H | H | O | CH₂C(=O)OCH₃ | H | 2-S(=O)Me,6-F | 0 |
| A-7150 | H | H | H | H | H | O | CH₂C(=O)OCH₃ | H | 2-S(=O)Me,5-Me | 0 |
| A-7151 | H | H | H | H | H | O | CH₂C(=O)OCH₃ | H | 2-S(=O)Me,6-Me | 0 |
| A-7152 | H | H | H | H | H | O | CH₂C(=O)OCH₃ | H | 2-S(=O)₂Me,5-F | 0 |
| A-7153 | H | H | H | H | H | O | CH₂C(=O)OCH₃ | H | 2-S(=O)₂Me,6-F | 0 |
| A-7154 | H | H | H | H | H | O | CH₂C(=O)OCH₃ | H | 2-S(=O)₂Me,5-Me | 0 |
| A-7155 | H | H | H | H | H | O | CH₂C(=O)OCH₃ | H | 2-S(=O)₂Me,6-Me | 0 |
| A-7156 | H | H | H | H | H | O | CH₂C(=O)OCH₃ | H | 2-SCF₃,5-F | 0 |
| A-7157 | H | H | H | H | H | O | CH₂C(=O)OCH₃ | H | 2-SCF₃,6-F | 0 |
| A-7158 | H | H | H | H | H | O | CH₂C(=O)OCH₃ | H | 2-SCF₃,5-Me | 0 |
| A-7159 | H | H | H | H | H | O | CH₂C(=O)OCH₃ | H | 2-SCF₃,6-Me | 0 |
| A-7160 | H | H | H | H | H | O | CH₂C(=O)OCH₃ | H | 2-S(=O)CF₃,5-F | 0 |
| A-7161 | H | H | H | H | H | O | CH₂C(=O)OCH₃ | H | 2-S(=O)CF₃,6-F | 0 |
| A-7162 | H | H | H | H | H | O | CH₂C(=O)OCH₃ | H | 2-S(=O)CF₃,5-Me | 0 |
| A-7163 | H | H | H | H | H | O | CH₂C(=O)OCH₃ | H | 2-S(=O)CF₃,6-Me | 0 |
| A-7164 | H | H | H | H | H | O | CH₂C(=O)OCH₃ | H | 2-S(=O)₂CF₃,5-F | 0 |
| A-7165 | H | H | H | H | H | O | CH₂C(=O)OCH₃ | H | 2-S(=O)₂CF₃,6-F | 0 |
| A-7166 | H | H | H | H | H | O | CH₂C(=O)OCH₃ | H | 2-S(=O)₂CF₃,5-Me | 0 |
| A-7167 | H | H | H | H | H | O | CH₂C(=O)OCH₃ | H | 2-S(=O)₂CF₃,6-Me | 0 |
| A-7168 | H | H | H | H | H | O | CH₂C(=O)OCH₃ | H | 2-(cyclopropylthio),5-F | 0 |
| A-7169 | H | H | H | H | H | O | CH₂C(=O)OCH₃ | H | 2-(cyclopropylthio),6-F | 0 |
| A-7170 | H | H | H | H | H | O | CH₂C(=O)OCH₃ | H | 2-(cyclopropylthio),5-Me | 0 |
| A-7171 | H | H | H | H | H | O | CH₂C(=O)OCH₃ | H | 2-(cyclopropylthio),6-Me | 0 |
| A-7172 | H | H | H | H | H | O | CH₂C(=O)OCH₃ | H | 2-C(=O)Me,5-F | 0 |
| A-7173 | H | H | H | H | H | O | CH₂C(=O)OCH₃ | H | 2-C(=O)Me,6-F | 0 |
| A-7174 | H | H | H | H | H | O | CH₂C(=O)OCH₃ | H | 2-C(=O)Me,5-Me | 0 |
| A-7175 | H | H | H | H | H | O | CH₂C(=O)OCH₃ | H | 2-C(=O)Me,6-Me | 0 |
| A-7176 | H | H | H | H | H | O | CH₂C(=O)OCH₃ | H | 2-CH₂OH,5-F | 0 |
| A-7177 | H | H | H | H | H | O | CH₂C(=O)OCH₃ | H | 2-CH₂OH,6-F | 0 |

TABLE 127

| compound | R¹ | R² | R³ | R⁴ | R⁵ | A | R⁶ | R⁷ | (R⁸)ₘ | p |
|---|---|---|---|---|---|---|---|---|---|---|
| A-7178 | H | H | H | H | H | O | CH₂C(=O)OCH₃ | H | 2-CH₂OH,5-Me | 0 |
| A-7179 | H | H | H | H | H | O | CH₂C(=O)OCH₃ | H | 2-CH₂OH,6-Me | 0 |
| A-7180 | H | H | H | H | H | O | CH₂C(=O)OCH₃ | H | 2-CH₂OCH₃,4-F | 0 |
| A-7181 | H | H | H | H | H | O | CH₂C(=O)OCH₃ | H | 2-CH₂OCH₃,5-F | 0 |
| A-7182 | H | H | H | H | H | O | CH₂C(=O)OCH₃ | H | 2-CH₂OCH₃,6-F | 0 |
| A-7183 | H | H | H | H | H | O | CH₂C(=O)OCH₃ | H | 2-CH₂OCH₃,4-Me | 0 |
| A-7184 | H | H | H | H | H | O | CH₂C(=O)OCH₃ | H | 2-CH₂OCH₃,5-Me | 0 |
| A-7185 | H | H | H | H | H | O | CH₂C(=O)OCH₃ | H | 2-CH₂OCH₃,6-Me | 0 |
| A-7186 | H | H | H | H | H | O | CH₂C(=O)OCH₃ | H | 2-OC(=O)CH₃,5-F | 0 |
| A-7187 | H | H | H | H | H | O | CH₂C(=O)OCH₃ | H | 2-OC(=O)CH₃,6-F | 0 |
| A-7188 | H | H | H | H | H | O | CH₂C(=O)OCH₃ | H | 2-OC(=O)CH₃,5-Me | 0 |
| A-7189 | H | H | H | H | H | O | CH₂C(=O)OCH₃ | H | 2-OC(=O)CH₃,6-Me | 0 |
| A-7190 | H | H | H | H | H | O | CH₂C(=O)OCH₃ | H | 2-OS(=O)₂CH₃,5-F | 0 |
| A-7191 | H | H | H | H | H | O | CH₂C(=O)OCH₃ | H | 2-OS(=O)₂CH₃,6-F | 0 |
| A-7192 | H | H | H | H | H | O | CH₂C(=O)OCH₃ | H | 2-OS(=O)₂CH₃,5-Me | 0 |
| A-7193 | H | H | H | H | H | O | CH₂C(=O)OCH₃ | H | 2-OS(=O)₂CH₃,6-Me | 0 |
| A-7194 | H | H | H | H | H | O | CH₂C(=O)OCH₃ | H | 2-CH₂SCH₃,5-F | 0 |
| A-7195 | H | H | H | H | H | O | CH₂C(=O)OCH₃ | H | 2-CH₂SCH₃,6-F | 0 |
| A-7196 | H | H | H | H | H | O | CH₂C(=O)OCH₃ | H | 2-CH₂SCH₃,5-Me | 0 |
| A-7197 | H | H | H | H | H | O | CH₂C(=O)OCH₃ | H | 2-CH₂SCH₃,6-Me | 0 |
| A-7198 | H | H | H | H | H | O | CH₂C(=O)OCH₃ | H | 2-NMe₂,5-F | 0 |
| A-7199 | H | H | H | H | H | O | CH₂C(=O)OCH₃ | H | 2-NMe₂,6-F | 0 |
| A-7200 | H | H | H | H | H | O | CH₂C(=O)OCH₃ | H | 2-NMe₂,5-Me | 0 |
| A-7201 | H | H | H | H | H | O | CH₂C(=O)OCH₃ | H | 2-NMe₂,6-Me | 0 |
| A-7202 | H | H | H | H | H | O | CH₂C(=O)OCH₃ | H | 2-CN,4-F | 0 |
| A-7203 | H | H | H | H | H | O | CH₂C(=O)OCH₃ | H | 2-CN,5-F | 0 |
| A-7204 | H | H | H | H | H | O | CH₂C(=O)OCH₃ | H | 2-CN,6-F | 0 |
| A-7205 | H | H | H | H | H | O | CH₂C(=O)OCH₃ | H | 2-CN,6-Me | 0 |
| A-7206 | H | H | H | H | H | O | CH₂C(=O)OCH₃ | H | 2-CN,5-OMe | 0 |
| A-7207 | H | H | H | H | H | O | CH₂C(=O)OCH₃ | H | 2-CN,6-OMe | 0 |
| A-7208 | H | H | H | H | H | O | CH₂C(=O)OCH₃ | H | 3-CN,6-Me | 0 |
| A-7209 | H | H | H | H | H | O | CH₂C(=O)OCH₃ | H | 3-CN,6-OMe | 0 |
| A-7210 | H | H | H | H | H | O | CH₂C(=O)OCH₃ | H | 4-CN,2-Me | 0 |
| A-7211 | H | H | H | H | H | O | CH₂C(=O)OCH₃ | H | 4-CN,2-OMe | 0 |
| A-7212 | H | H | H | H | H | O | CH₂C(=O)OCH₃ | H | 2-NO₂,4-F | 0 |
| A-7213 | H | H | H | H | H | O | CH₂C(=O)OCH₃ | H | 2-NO₂,5-F | 0 |
| A-7214 | H | H | H | H | H | O | CH₂C(=O)OCH₃ | H | 2-NO₂,6-F | 0 |
| A-7215 | H | H | H | H | H | O | CH₂C(=O)OCH₃ | H | 2-NO₂,4-Me | 0 |
| A-7216 | H | H | H | H | H | O | CH₂C(=O)OCH₃ | H | 2-NO₂,5-Me | 0 |

TABLE 127-continued

| compound | R¹ | R² | R³ | R⁴ | R⁵ | A | R⁶ | R⁷ | (R⁸)$_m$ | p |
|---|---|---|---|---|---|---|---|---|---|---|
| A-7217 | H | H | H | H | H | O | CH$_2$C(=O)OCH$_3$ | H | 2-NO$_2$,6-Me | 0 |
| A-7218 | H | H | H | H | H | O | CH$_2$C(=O)OCH$_3$ | H | 2-Me,4,5-F$_2$ | 0 |
| A-7219 | H | H | H | H | H | O | CH$_2$C(=O)OCH$_3$ | H | 2-Me,6-Et | 0 |
| A-7220 | H | H | H | H | H | O | CH$_2$C(=O)OCH$_3$ | H | 2-cyclopropyl,6-OMe | 0 |
| A-7221 | H | H | H | H | H | O | CH$_2$C(=O)OCH$_3$ | H | 2-Me,5-Et | 0 |
| A-7222 | H | H | H | H | H | O | CH$_2$C(=O)OCH$_3$ | H | 2,6-Et$_2$ | 0 |
| A-7223 | H | H | H | H | H | O | CH$_2$C(=O)OCH$_3$ | H | 2-Et,6-F | 0 |
| A-7224 | H | H | H | H | H | O | CH$_2$C(=O)OCH$_3$ | H | 2-CH$_2$OCH$_3$,6-Cl | 0 |
| A-7225 | H | H | H | H | H | O | CH$_2$C(=O)OCH$_3$ | H | 2-CH$_2$OCH$_2$CH$_3$,6-Cl | 0 |
| A-7226 | H | H | H | H | H | O | CH$_2$C(=O)OCH$_3$ | H | 2-CH$_2$NMe$_2$ | 0 |
| A-7227 | H | H | H | H | H | O | CH$_2$C(=O)NH$_2$ | H | H | 0 |
| A-7228 | H | H | H | H | H | O | CH$_2$C(=O)NH$_2$ | H | 2-F | 0 |
| A-7229 | H | H | H | H | H | O | CH$_2$C(=O)NH$_2$ | H | 2-Cl | 0 |
| A-7230 | H | H | H | H | H | O | CH$_2$C(=O)NH$_2$ | H | 2-Br | 0 |
| A-7231 | H | H | H | H | H | O | CH$_2$C(=O)NH$_2$ | H | 2-OH | 0 |
| A-7232 | H | H | H | H | H | O | CH$_2$C(=O)NH$_2$ | H | 2-Me | 0 |
| A-7233 | H | H | H | H | H | O | CH$_2$C(=O)NH$_2$ | H | 2-Et | 0 |
| A-7234 | H | H | H | H | H | O | CH$_2$C(=O)NH$_2$ | H | 2-Pr | 0 |

TABLE 128

| compound | R¹ | R² | R³ | R⁴ | R⁵ | A | R⁶ | R⁷ | (R⁸)$_m$ | p |
|---|---|---|---|---|---|---|---|---|---|---|
| A-7235 | H | H | H | H | H | O | CH$_2$C(=O)NH$_2$ | H | 2-CF$_3$ | 0 |
| A-7236 | H | H | H | H | H | O | CH$_2$C(=O)NH$_2$ | H | 2-CHF$_2$ | 0 |
| A-7237 | H | H | H | H | H | O | CH$_2$C(=O)NH$_2$ | H | 2-CH$_2$F | 0 |
| A-7238 | H | H | H | H | H | O | CH$_2$C(=O)NH$_2$ | H | 2-CF$_2$Cl | 0 |
| A-7239 | H | H | H | H | H | O | CH$_2$C(=O)NH$_2$ | H | 2-cyclopropyl | 0 |
| A-7240 | H | H | H | H | H | O | CH$_2$C(=O)NH$_2$ | H | 2-cyclobutyl | 0 |
| A-7241 | H | H | H | H | H | O | CH$_2$C(=O)NH$_2$ | H | 2-cyclopentyl | 0 |
| A-7242 | H | H | H | H | H | O | CH$_2$C(=O)NH$_2$ | H | 2-ethenyl | 0 |
| A-7243 | H | H | H | H | H | O | CH$_2$C(=O)NH$_2$ | H | 2-allyl | 0 |
| A-7244 | H | H | H | H | H | O | CH$_2$C(=O)NH$_2$ | H | 2-(prop-1-en-1-yl) | 0 |
| A-7245 | H | H | H | H | H | O | CH$_2$C(=O)NH$_2$ | H | 2-(trifluoroethenyl) | 0 |
| A-7246 | H | H | H | H | H | O | CH$_2$C(=O)NH$_2$ | H | 2-OMe | 0 |
| A-7247 | H | H | H | H | H | O | CH$_2$C(=O)NH$_2$ | H | 2-OEt | 0 |
| A-7248 | H | H | H | H | H | O | CH$_2$C(=O)NH$_2$ | H | 2-OPr | 0 |
| A-7249 | H | H | H | H | H | O | CH$_2$C(=O)NH$_2$ | H | 2-O(i-Pr) | 0 |
| A-7250 | H | H | H | H | H | O | CH$_2$C(=O)NH$_2$ | H | 2-OCF$_3$ | 0 |
| A-7251 | H | H | H | H | H | O | CH$_2$C(=O)NH$_2$ | H | 2-OCHF$_2$ | 0 |
| A-7252 | H | H | H | H | H | O | CH$_2$C(=O)NH$_2$ | H | 2-(cyclopropyloxy) | 0 |
| A-7253 | H | H | H | H | H | O | CH$_2$C(=O)NH$_2$ | H | 2-(cyclobutyloxy) | 0 |
| A-7254 | H | H | H | H | H | O | CH$_2$C(=O)NH$_2$ | H | 2-(cyclopentyloxy) | 0 |
| A-7255 | H | H | H | H | H | O | CH$_2$C(=O)NH$_2$ | H | 2-((2,2-dichlorocyclopropyl)oxy) | 0 |
| A-7256 | H | H | H | H | H | O | CH$_2$C(=O)NH$_2$ | H | 2-(oxiran-2-yl) | 0 |
| A-7257 | H | H | H | H | H | O | CH$_2$C(=O)NH$_2$ | H | 2-SMe | 0 |
| A-7258 | H | H | H | H | H | O | CH$_2$C(=O)NH$_2$ | H | 3-SMe | 0 |
| A-7259 | H | H | H | H | H | O | CH$_2$C(=O)NH$_2$ | H | 2-S(=O)Me | 0 |
| A-7260 | H | H | H | H | H | O | CH$_2$C(=O)NH$_2$ | H | 3-S(=O)Me | 0 |
| A-7261 | H | H | H | H | H | O | CH$_2$C(=O)NH$_2$ | H | 2-S(=O)$_2$Me | 0 |
| A-7262 | H | H | H | H | H | O | CH$_2$C(=O)NH$_2$ | H | 3-S(=O)$_2$Me | 0 |
| A-7263 | H | H | H | H | H | O | CH$_2$C(=O)NH$_2$ | H | 2-SCF$_3$ | 0 |
| A-7264 | H | H | H | H | H | O | CH$_2$C(=O)NH$_2$ | H | 3-SCF$_3$ | 0 |
| A-7265 | H | H | H | H | H | O | CH$_2$C(=O)NH$_2$ | H | 3-S(=O)CF$_3$ | 0 |
| A-7266 | H | H | H | H | H | O | CH$_2$C(=O)NH$_2$ | H | 3-SCF(CF$_3$)$_2$ | 0 |
| A-7267 | H | H | H | H | H | O | CH$_2$C(=O)NH$_2$ | H | 2-(cyclopropylthio) | 0 |
| A-7268 | H | H | H | H | H | O | CH$_2$C(=O)NH$_2$ | H | 2-(cyclopropylsulfinyl) | 0 |
| A-7269 | H | H | H | H | H | O | CH$_2$C(=O)NH$_2$ | H | 2-(cyclopropylsulfonyl) | 0 |
| A-7270 | H | H | H | H | H | O | CH$_2$C(=O)NH$_2$ | H | 2-C(=O)Me | 0 |
| A-7271 | H | H | H | H | H | O | CH$_2$C(=O)NH$_2$ | H | 2-CH$_2$C(=O)CH$_3$ | 0 |
| A-7272 | H | H | H | H | H | O | CH$_2$C(=O)NH$_2$ | H | 2-CH$_2$C(=O)CF$_3$ | 0 |
| A-7273 | H | H | H | H | H | O | CH$_2$C(=O)NH$_2$ | H | 2-CH$_2$OH | 0 |
| A-7274 | H | H | H | H | H | O | CH$_2$C(=O)NH$_2$ | H | 2-CH$_2$OCH$_3$ | 0 |
| A-7275 | H | H | H | H | H | O | CH$_2$C(=O)NH$_2$ | H | 2-CH$_2$OCH$_2$CH$_3$ | 0 |
| A-7276 | H | H | H | H | H | O | CH$_2$C(=O)NH$_2$ | H | 2-CH$_2$SCH$_3$ | 0 |
| A-7277 | H | H | H | H | H | O | CH$_2$C(=O)NH$_2$ | H | 2-CH$_2$S(=O)CH$_3$ | 0 |
| A-7278 | H | H | H | H | H | O | CH$_2$C(=O)NH$_2$ | H | 2-CH$_2$S(=O)$_2$CH$_3$ | 0 |
| A-7279 | H | H | H | H | H | O | CH$_2$C(=O)NH$_2$ | H | 2-(benzyloxy) | 0 |
| A-7280 | H | H | H | H | H | O | CH$_2$C(=O)NH$_2$ | H | 2-NH$_2$ | 0 |
| A-7281 | H | H | H | H | H | O | CH$_2$C(=O)NH$_2$ | H | 2-NHMe | 0 |
| A-7282 | H | H | H | H | H | O | CH$_2$C(=O)NH$_2$ | H | 2-N(Me)$_2$ | 0 |
| A-7283 | H | H | H | H | H | O | CH$_2$C(=O)NH$_2$ | H | 2-(1,3-dioxolan-2-yl) | 0 |
| A-7284 | H | H | H | H | H | O | CH$_2$C(=O)NH$_2$ | H | 2-(1,3-dioxan-2-yl) | 0 |
| A-7285 | H | H | H | H | H | O | CH$_2$C(=O)NH$_2$ | H | 2-(1H-imidazol-2-yl) | 0 |
| A-7286 | H | H | H | H | H | O | CH$_2$C(=O)NH$_2$ | H | 2-(thiazol-2-yl) | 0 |

TABLE 128-continued

| compound | R¹ | R² | R³ | R⁴ | R⁵ | A | R⁶ | R⁷ | (R⁸)ₘ | p |
|---|---|---|---|---|---|---|---|---|---|---|
| A-7287 | H | H | H | H | H | O | CH₂C(=O)NH₂ | H | 2-(oxazol-2-yl) | 0 |
| A-7288 | H | H | H | H | H | O | CH₂C(=O)NH₂ | H | 2-CH=NOH | 0 |
| A-7289 | H | H | H | H | H | O | CH₂C(=O)NH₂ | H | 2-CH=NOMe | 0 |
| A-7290 | H | H | H | H | H | O | CH₂C(=O)NH₂ | H | 2-(4,5-dihydro-3-isoxazolyl) | 0 |
| A-7291 | H | H | H | H | H | O | CH₂C(=O)NH₂ | H | 2-CN | 0 |

TABLE 129

| compound | R¹ | R² | R³ | R⁴ | R⁵ | A | R⁶ | R⁷ | (R⁸)ₘ | p |
|---|---|---|---|---|---|---|---|---|---|---|
| A-7292 | H | H | H | H | H | O | CH₂C(=O)NH₂ | H | 2-NO₂ | 0 |
| A-7293 | H | H | H | H | H | O | CH₂C(=O)NH₂ | H | 2-F,6-Cl | 0 |
| A-7294 | H | H | H | H | H | O | CH₂C(=O)NH₂ | H | 2-F,6-Me | 0 |
| A-7295 | H | H | H | H | H | O | CH₂C(=O)NH₂ | H | 3-F,6-Me | 0 |
| A-7296 | H | H | H | H | H | O | CH₂C(=O)NH₂ | H | 4-F,2-Me | 0 |
| A-7297 | H | H | H | H | H | O | CH₂C(=O)NH₂ | H | 2-F,6-OMe | 0 |
| A-7298 | H | H | H | H | H | O | CH₂C(=O)NH₂ | H | 3-F,6-OMe | 0 |
| A-7299 | H | H | H | H | H | O | CH₂C(=O)NH₂ | H | 2,6-Cl₂ | 0 |
| A-7300 | H | H | H | H | H | O | CH₂C(=O)NH₂ | H | 2-Cl,6-Me | 0 |
| A-7301 | H | H | H | H | H | O | CH₂C(=O)NH₂ | H | 3-Cl,6-Me | 0 |
| A-7302 | H | H | H | H | H | O | CH₂C(=O)NH₂ | H | 4-Cl,2-Me | 0 |
| A-7303 | H | H | H | H | H | O | CH₂C(=O)NH₂ | H | 2-Cl,5-CF₃ | 0 |
| A-7304 | H | H | H | H | H | O | CH₂C(=O)NH₂ | H | 2-Cl,6-CF₃ | 0 |
| A-7305 | H | H | H | H | H | O | CH₂C(=O)NH₂ | H | 2-Cl,6-OMe | 0 |
| A-7306 | H | H | H | H | H | O | CH₂C(=O)NH₂ | H | 3-Cl,6-OMe | 0 |
| A-7307 | H | H | H | H | H | O | CH₂C(=O)NH₂ | H | 4-Cl,2-OMe | 0 |
| A-7308 | H | H | H | H | H | O | CH₂C(=O)NH₂ | H | 2,4-Me₂ | 0 |
| A-7309 | H | H | H | H | H | O | CH₂C(=O)NH₂ | H | 2,5-Me₂ | 0 |
| A-7310 | H | H | H | H | H | O | CH₂C(=O)NH₂ | H | 2,6-Me₂ | 0 |
| A-7311 | H | H | H | H | H | O | CH₂C(=O)NH₂ | H | 2-Me,4-CF₃ | 0 |
| A-7312 | H | H | H | H | H | O | CH₂C(=O)NH₂ | H | 2-Me,5-CF₃ | 0 |
| A-7313 | H | H | H | H | H | O | CH₂C(=O)NH₂ | H | 2-Me,6-CF₃ | 0 |
| A-7314 | H | H | H | H | H | O | CH₂C(=O)NH₂ | H | 2-Me,4-OMe | 0 |
| A-7315 | H | H | H | H | H | O | CH₂C(=O)NH₂ | H | 2-Me,5-OMe | 0 |
| A-7316 | H | H | H | H | H | O | CH₂C(=O)NH₂ | H | 2-Me,6-OMe | 0 |
| A-7317 | H | H | H | H | H | O | CH₂C(=O)NH₂ | H | 3-Me,6-OMe | 0 |
| A-7318 | H | H | H | H | H | O | CH₂C(=O)NH₂ | H | 4-Me,2-OMe | 0 |
| A-7319 | H | H | H | H | H | O | CH₂C(=O)NH₂ | H | 2,5-OMe₂ | 0 |
| A-7320 | H | H | H | H | H | O | CH₂C(=O)NH₂ | H | 2,6-OMe₂ | 0 |
| A-7321 | H | H | H | H | H | O | CH₂C(=O)NH₂ | H | 2-OMe,6-CF₃ | 0 |
| A-7322 | H | H | H | H | H | O | CH₂C(=O)NH₂ | H | 2-CHF₂,5-F | 0 |
| A-7323 | H | H | H | H | H | O | CH₂C(=O)NH₂ | H | 2-CHF₂,6-F | 0 |
| A-7324 | H | H | H | H | H | O | CH₂C(=O)NH₂ | H | 2-CHF₂,5-Me | 0 |
| A-7325 | H | H | H | H | H | O | CH₂C(=O)NH₂ | H | 2-CHF₂,6-Me | 0 |
| A-7326 | H | H | H | H | H | O | CH₂C(=O)NH₂ | H | 2-cyclopropyl,5-F | 0 |
| A-7327 | H | H | H | H | H | O | CH₂C(=O)NH₂ | H | 2-cyclopropyl,6-F | 0 |
| A-7328 | H | H | H | H | H | O | CH₂C(=O)NH₂ | H | 2-cyclopropyl,5-Me | 0 |
| A-7329 | H | H | H | H | H | O | CH₂C(=O)NH₂ | H | 2-cyclopropyl,6-Me | 0 |
| A-7330 | H | H | H | H | H | O | CH₂C(=O)NH₂ | H | 2-ethenyl,6-F | 0 |
| A-7331 | H | H | H | H | H | O | CH₂C(=O)NH₂ | H | 2-ethenyl,6-Me | 0 |
| A-7332 | H | H | H | H | H | O | CH₂C(=O)NH₂ | H | 2-OEt,5-F | 0 |
| A-7333 | H | H | H | H | H | O | CH₂C(=O)NH₂ | H | 2-OEt,6-F | 0 |
| A-7334 | H | H | H | H | H | O | CH₂C(=O)NH₂ | H | 2-OEt,5-Cl | 0 |
| A-7335 | H | H | H | H | H | O | CH₂C(=O)NH₂ | H | 2-OEt,6-Cl | 0 |
| A-7336 | H | H | H | H | H | O | CH₂C(=O)NH₂ | H | 2-OEt,5-Me | 0 |
| A-7337 | H | H | H | H | H | O | CH₂C(=O)NH₂ | H | 2-OEt,6-Me | 0 |
| A-7338 | H | H | H | H | H | O | CH₂C(=O)NH₂ | H | 2-OCHF₂,5-F | 0 |
| A-7339 | H | H | H | H | H | O | CH₂C(=O)NH₂ | H | 2-OCHF₂,6-F | 0 |
| A-7340 | H | H | H | H | H | O | CH₂C(=O)NH₂ | H | 2-OCHF₂,5-Me | 0 |
| A-7341 | H | H | H | H | H | O | CH₂C(=O)NH₂ | H | 2-OCHF₂,6-Me | 0 |
| A-7342 | H | H | H | H | H | O | CH₂C(=O)NH₂ | H | 2-(cyclopropyloxy),5-F | 0 |
| A-7343 | H | H | H | H | H | O | CH₂C(=O)NH₂ | H | 2-(cyclopropyloxy),6-F | 0 |
| A-7344 | H | H | H | H | H | O | CH₂C(=O)NH₂ | H | 2-(cyclopropyloxy),5-Me | 0 |
| A-7345 | H | H | H | H | H | O | CH₂C(=O)NH₂ | H | 2-(cyclopropyloxy),6-Me | 0 |
| A-7346 | H | H | H | H | H | O | CH₂C(=O)NH₂ | H | 2-SMe,5-F | 0 |
| A-7347 | H | H | H | H | H | O | CH₂C(=O)NH₂ | H | 2-SMe,6-F | 0 |
| A-7348 | H | H | H | H | H | O | CH₂C(=O)NH₂ | H | 2-SMe,5-Me | 0 |

TABLE 130

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7349 | H | H | H | H | H | O | CH$_2$C(=O)NH$_2$ | H | 2-SMe,6-Me | 0 |
| A-7350 | H | H | H | H | H | O | CH$_2$C(=O)NH$_2$ | H | 2-S(=O)Me,5-F | 0 |
| A-7351 | H | H | H | H | H | O | CH$_2$C(=O)NH$_2$ | H | 2-S(=O)Me,6-F | 0 |
| A-7352 | H | H | H | H | H | O | CH$_2$C(=O)NH$_2$ | H | 2-S(=O)Me,5-Me | 0 |
| A-7353 | H | H | H | H | H | O | CH$_2$C(=O)NH$_2$ | H | 2-S(=O)Me,6-Me | 0 |
| A-7354 | H | H | H | H | H | O | CH$_2$C(=O)NH$_2$ | H | 2-S(=O)$_2$Me,5-F | 0 |
| A-7355 | H | H | H | H | H | O | CH$_2$C(=O)NH$_2$ | H | 2-S(=O)$_2$Me,6-F | 0 |
| A-7356 | H | H | H | H | H | O | CH$_2$C(=O)NH$_2$ | H | 2-S(=O)$_2$Me,5-Me | 0 |
| A-7357 | H | H | H | H | H | O | CH$_2$C(=O)NH$_2$ | H | 2-S(=O)$_2$Me,6-Me | 0 |
| A-7358 | H | H | H | H | H | O | CH$_2$C(=O)NH$_2$ | H | 2-SCF$_3$,5-F | 0 |
| A-7359 | H | H | H | H | H | O | CH$_2$C(=O)NH$_2$ | H | 2-SCF$_3$,6-F | 0 |
| A-7360 | H | H | H | H | H | O | CH$_2$C(=O)NH$_2$ | H | 2-SCF$_3$,5-Me | 0 |
| A-7361 | H | H | H | H | H | O | CH$_2$C(=O)NH$_2$ | H | 2-SCF$_3$,6-Me | 0 |
| A-7362 | H | H | H | H | H | O | CH$_2$C(=O)NH$_2$ | H | 2-S(=O)CF$_3$,5-F | 0 |
| A-7363 | H | H | H | H | H | O | CH$_2$C(=O)NH$_2$ | H | 2-S(=O)CF$_3$,6-F | 0 |
| A-7364 | H | H | H | H | H | O | CH$_2$C(=O)NH$_2$ | H | 2-S(=O)CF$_3$,5-Me | 0 |
| A-7365 | H | H | H | H | H | O | CH$_2$C(=O)NH$_2$ | H | 2-S(=O)CF$_3$,6-Me | 0 |
| A-7366 | H | H | H | H | H | O | CH$_2$C(=O)NH$_2$ | H | 2-S(=O)$_2$CF$_3$,5-F | 0 |
| A-7367 | H | H | H | H | H | O | CH$_2$C(=O)NH$_2$ | H | 2-S(=O)$_2$CF$_3$,6-F | 0 |
| A-7368 | H | H | H | H | H | O | CH$_2$C(=O)NH$_2$ | H | 2-S(=O)$_2$CF$_3$,5-Me | 0 |
| A-7369 | H | H | H | H | H | O | CH$_2$C(=O)NH$_2$ | H | 2-S(=O)$_2$CF$_3$,6-Me | 0 |
| A-7370 | H | H | H | H | H | O | CH$_2$C(=O)NH$_2$ | H | 2-(cyclopropylthio),5-F | 0 |
| A-7371 | H | H | H | H | H | O | CH$_2$C(=O)NH$_2$ | H | 2-(cyclopropylthio),6-F | 0 |
| A-7372 | H | H | H | H | H | O | CH$_2$C(=O)NH$_2$ | H | 2-(cyclopropylthio),5-Me | 0 |
| A-7373 | H | H | H | H | H | O | CH$_2$C(=O)NH$_2$ | H | 2-(cyclopropylthio),6-Me | 0 |
| A-7374 | H | H | H | H | H | O | CH$_2$C(=O)NH$_2$ | H | 2-C(=O)Me,5-F | 0 |
| A-7375 | H | H | H | H | H | O | CH$_2$C(=O)NH$_2$ | H | 2-C(=O)Me,6-F | 0 |
| A-7376 | H | H | H | H | H | O | CH$_2$C(=O)NH$_2$ | H | 2-C(=O)Me,5-Me | 0 |
| A-7377 | H | H | H | H | H | O | CH$_2$C(=O)NH$_2$ | H | 2-C(=O)Me,6-Me | 0 |
| A-7378 | H | H | H | H | H | O | CH$_2$C(=O)NH$_2$ | H | 2-CH$_2$OH,5-F | 0 |
| A-7379 | H | H | H | H | H | O | CH$_2$C(=O)NH$_2$ | H | 2-CH$_2$OH,6-F | 0 |
| A-7380 | H | H | H | H | H | O | CH$_2$C(=O)NH$_2$ | H | 2-CH$_2$OH,5-Me | 0 |
| A-7381 | H | H | H | H | H | O | CH$_2$C(=O)NH$_2$ | H | 2-CH$_2$OH,6-Me | 0 |
| A-7382 | H | H | H | H | H | O | CH$_2$C(=O)NH$_2$ | H | 2-CH$_2$OCH$_3$,4-F | 0 |
| A-7383 | H | H | H | H | H | O | CH$_2$C(=O)NH$_2$ | H | 2-CH$_2$OCH$_3$,5-F | 0 |
| A-7384 | H | H | H | H | H | O | CH$_2$C(=O)NH$_2$ | H | 2-CH$_2$OCH$_3$,6-F | 0 |
| A-7385 | H | H | H | H | H | O | CH$_2$C(=O)NH$_2$ | H | 2-CH$_2$OCH$_3$,4-Me | 0 |
| A-7386 | H | H | H | H | H | O | CH$_2$C(=O)NH$_2$ | H | 2-CH$_2$OCH$_3$,5-Me | 0 |
| A-7387 | H | H | H | H | H | O | CH$_2$C(=O)NH$_2$ | H | 2-CH$_2$OCH$_3$,6-Me | 0 |
| A-7388 | H | H | H | H | H | O | CH$_2$C(=O)NH$_2$ | H | 2-OC(=O)CH$_3$,5-F | 0 |
| A-7389 | H | H | H | H | H | O | CH$_2$C(=O)NH$_2$ | H | 2-OC(=O)CH$_3$,6-F | 0 |
| A-7390 | H | H | H | H | H | O | CH$_2$C(=O)NH$_2$ | H | 2-OC(=O)CH$_3$,5-Me | 0 |
| A-7391 | H | H | H | H | H | O | CH$_2$C(=O)NH$_2$ | H | 2-OC(=O)CH$_3$,6-Me | 0 |
| A-7392 | H | H | H | H | H | O | CH$_2$C(=O)NH$_2$ | H | 2-OS(=O)$_2$CH$_3$,5-F | 0 |
| A-7393 | H | H | H | H | H | O | CH$_2$C(=O)NH$_2$ | H | 2-OS(=O)$_2$CH$_3$,6-F | 0 |
| A-7394 | H | H | H | H | H | O | CH$_2$C(=O)NH$_2$ | H | 2-OS(=O)$_2$CH$_3$,5-Me | 0 |
| A-7395 | H | H | H | H | H | O | CH$_2$C(=O)NH$_2$ | H | 2-OS(=O)$_2$CH$_3$,6-Me | 0 |
| A-7396 | H | H | H | H | H | O | CH$_2$C(=O)NH$_2$ | H | 2-CH$_2$SCH$_3$,5-F | 0 |
| A-7397 | H | H | H | H | H | O | CH$_2$C(=O)NH$_2$ | H | 2-CH$_2$SCH$_3$,6-F | 0 |
| A-7398 | H | H | H | H | H | O | CH$_2$C(=O)NH$_2$ | H | 2-CH$_2$SCH$_3$,5-Me | 0 |
| A-7399 | H | H | H | H | H | O | CH$_2$C(=O)NH$_2$ | H | 2-CH$_2$SCH$_3$,6-Me | 0 |
| A-7400 | H | H | H | H | H | O | CH$_2$C(=O)NH$_2$ | H | 2-NMe$_2$,5-F | 0 |
| A-7401 | H | H | H | H | H | O | CH$_2$C(=O)NH$_2$ | H | 2-NMe$_2$,6-F | 0 |
| A-7402 | H | H | H | H | H | O | CH$_2$C(=O)NH$_2$ | H | 2-NMe$_2$,5-Me | 0 |
| A-7403 | H | H | H | H | H | O | CH$_2$C(=O)NH$_2$ | H | 2-NMe$_2$,6-Me | 0 |
| A-7404 | H | H | H | H | H | O | CH$_2$C(=O)NH$_2$ | H | 2-CN,4-F | 0 |
| A-7405 | H | H | H | H | H | O | CH$_2$C(=O)NH$_2$ | H | 2-CN,5-F | 0 |

TABLE 131

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7406 | H | H | H | H | H | O | CH$_2$C(=O)NH$_2$ | H | 2-CN,6-F | 0 |
| A-7407 | H | H | H | H | H | O | CH$_2$C(=O)NH$_2$ | H | 2-CN,6-Me | 0 |
| A-7408 | H | H | H | H | H | O | CH$_2$C(=O)NH$_2$ | H | 2-CN,5-OMe | 0 |
| A-7409 | H | H | H | H | H | O | CH$_2$C(=O)NH$_2$ | H | 2-CN,6-OMe | 0 |
| A-7410 | H | H | H | H | H | O | CH$_2$C(=O)NH$_2$ | H | 3-CN,6-Me | 0 |
| A-7411 | H | H | H | H | H | O | CH$_2$C(=O)NH$_2$ | H | 3-CN,6-OMe | 0 |
| A-7412 | H | H | H | H | H | O | CH$_2$C(=O)NH$_2$ | H | 4-CN,2-Me | 0 |
| A-7413 | H | H | H | H | H | O | CH$_2$C(=O)NH$_2$ | H | 4-CN,2-OMe | 0 |
| A-7414 | H | H | H | H | H | O | CH$_2$C(=O)NH$_2$ | H | 2-NO$_2$,4-F | 0 |
| A-7415 | H | H | H | H | H | O | CH$_2$C(=O)NH$_2$ | H | 2-NO$_2$,5-F | 0 |
| A-7416 | H | H | H | H | H | O | CH$_2$C(=O)NH$_2$ | H | 2-NO$_2$,6-F | 0 |
| A-7417 | H | H | H | H | H | O | CH$_2$C(=O)NH$_2$ | H | 2-NO$_2$,4-Me | 0 |
| A-7418 | H | H | H | H | H | O | CH$_2$C(=O)NH$_2$ | H | 2-NO$_2$,5-Me | 0 |

TABLE 131-continued

| compound | R¹ | R² | R³ | R⁴ | R⁵ | A | R⁶ | R⁷ | (R⁸)ₘ | p |
|---|---|---|---|---|---|---|---|---|---|---|
| A-7419 | H | H | H | H | H | O | CH$_2$C(=O)NH$_2$ | H | 2-NO$_2$,6-Me | 0 |
| A-7420 | H | H | H | H | H | O | CH$_2$C(=O)NH$_2$ | H | 2-Me,4,5-F$_2$ | 0 |
| A-7421 | H | H | H | H | H | O | CH$_2$C(=O)NH$_2$ | H | 2-Me,6-Et | 0 |
| A-7422 | H | H | H | H | H | O | CH$_2$C(=O)NH$_2$ | H | 2-cyclopropyl,6-OMe | 0 |
| A-7423 | H | H | H | H | H | O | CH$_2$C(=O)NH$_2$ | H | 2-Me,5-Et | 0 |
| A-7424 | H | H | H | H | H | O | CH$_2$C(=O)NH$_2$ | H | 2,6-Et$_2$ | 0 |
| A-7425 | H | H | H | H | H | O | CH$_2$C(=O)NH$_2$ | H | 2-Et,6-F | 0 |
| A-7426 | H | H | H | H | H | O | CH$_2$C(=O)NH$_2$ | H | 2-CH$_2$OCH$_3$,6-Cl | 0 |
| A-7427 | H | H | H | H | H | O | CH$_2$C(=O)NH$_2$ | H | 2-CH$_2$OCH$_2$CH$_3$,6-Cl | 0 |
| A-7428 | H | H | H | H | H | O | CH$_2$C(=O)NH$_2$ | H | 2-CH$_2$NMe$_2$ | 0 |
| A-7429 | H | H | H | H | H | O | CH=NOH | H | H | 0 |
| A-7430 | H | H | H | H | H | O | CH=NOH | H | 2-F | 0 |
| A-7431 | H | H | H | H | H | O | CH=NOH | H | 2-Cl | 0 |
| A-7432 | H | H | H | H | H | O | CH=NOH | H | 2-Br | 0 |
| A-7433 | H | H | H | H | H | O | CH=NOH | H | 2-OH | 0 |
| A-7434 | H | H | H | H | H | O | CH=NOH | H | 2-Me | 0 |
| A-7435 | H | H | H | H | H | O | CH=NOH | H | 2-Et | 0 |
| A-7436 | H | H | H | H | H | O | CH=NOH | H | 2-Pr | 0 |
| A-7437 | H | H | H | H | H | O | CH=NOH | H | 2-CF$_3$ | 0 |
| A-7438 | H | H | H | H | H | O | CH=NOH | H | 2-CHF$_2$ | 0 |
| A-7439 | H | H | H | H | H | O | CH=NOH | H | 2-CH$_2$F | 0 |
| A-7440 | H | H | H | H | H | O | CH=NOH | H | 2-CF$_2$Cl | 0 |
| A-7441 | H | H | H | H | H | O | CH=NOH | H | 2-cyclopropyl | 0 |
| A-7442 | H | H | H | H | H | O | CH=NOH | H | 2-cyclobutyl | 0 |
| A-7443 | H | H | H | H | H | O | CH=NOH | H | 2-cyclopentyl | 0 |
| A-7444 | H | H | H | H | H | O | CH=NOH | H | 2-ethenyl | 0 |
| A-7445 | H | H | H | H | H | O | CH=NOH | H | 2-allyl | 0 |
| A-7446 | H | H | H | H | H | O | CH=NOH | H | 2-(prop-1-en-1-yl) | 0 |
| A-7447 | H | H | H | H | H | O | CH=NOH | H | 2-(trifluoroethenyl) | 0 |
| A-7448 | H | H | H | H | H | O | CH=NOH | H | 2-OMe | 0 |
| A-7449 | H | H | H | H | H | O | CH=NOH | H | 2-OEt | 0 |
| A-7450 | H | H | H | H | H | O | CH=NOH | H | 2-OPr | 0 |
| A-7451 | H | H | H | H | H | O | CH=NOH | H | 2-O(i-Pr) | 0 |
| A-7452 | H | H | H | H | H | O | CH=NOH | H | 2-OCF$_3$ | 0 |
| A-7453 | H | H | H | H | H | O | CH=NOH | H | 2-OCHF$_2$ | 0 |
| A-7454 | H | H | H | H | H | O | CH=NOH | H | 2-(cyclopropyloxy) | 0 |
| A-7455 | H | H | H | H | H | O | CH=NOH | H | 2-(cyclobutyloxy) | 0 |
| A-7456 | H | H | H | H | H | O | CH=NOH | H | 2-(cyclopentyloxy) | 0 |
| A-7457 | H | H | H | H | H | O | CH=NOH | H | 2-((2,2-dichlorocyclopropyl)oxy) | 0 |
| A-7458 | H | H | H | H | H | O | CH=NOH | H | 2-(oxiran-2-yl) | 0 |
| A-7459 | H | H | H | H | H | O | CH=NOH | H | 2-SMe | 0 |
| A-7460 | H | H | H | H | H | O | CH=NOH | H | 3-SMe | 0 |
| A-7461 | H | H | H | H | H | O | CH=NOH | H | 2-S(=O)Me | 0 |
| A-7462 | H | H | H | H | H | O | CH=NOH | H | 3-S(=O)Me | 0 |

TABLE 132

| compound | R¹ | R² | R³ | R⁴ | R⁵ | A | R⁶ | R⁷ | (R⁸)ₘ | p |
|---|---|---|---|---|---|---|---|---|---|---|
| A-7463 | H | H | H | H | H | O | CH=NOH | H | 2-S(=O)$_2$Me | 0 |
| A-7464 | H | H | H | H | H | O | CH=NOH | H | 3-S(=O)$_2$Me | 0 |
| A-7465 | H | H | H | H | H | O | CH=NOH | H | 2-SCF$_3$ | 0 |
| A-7466 | H | H | H | H | H | O | CH=NOH | H | 3-SCF$_3$ | 0 |
| A-7467 | H | H | H | H | H | O | CH=NOH | H | 3-S(=O)CF$_3$ | 0 |
| A-7468 | H | H | H | H | H | O | CH=NOH | H | 3-SCF(CF$_3$)$_2$ | 0 |
| A-7469 | H | H | H | H | H | O | CH=NOH | H | 2-(cyclopropylthio) | 0 |
| A-7470 | H | H | H | H | H | O | CH=NOH | H | 2-(cyclopropylsulfinyl) | 0 |
| A-7471 | H | H | H | H | H | O | CH=NOH | H | 2-(cyclopropylsulfonyl) | 0 |
| A-7472 | H | H | H | H | H | O | CH=NOH | H | 2-C(=O)Me | 0 |
| A-7473 | H | H | H | H | H | O | CH=NOH | H | 2-CH$_2$C(=O)CH$_3$ | 0 |
| A-7474 | H | H | H | H | H | O | CH=NOH | H | 2-CH$_2$C(=O)CF$_3$ | 0 |
| A-7475 | H | H | H | H | H | O | CH=NOH | H | 2-CH$_2$OH | 0 |
| A-7476 | H | H | H | H | H | O | CH=NOH | H | 2-CH$_2$OCH$_3$ | 0 |
| A-7477 | H | H | H | H | H | O | CH=NOH | H | 2-CH$_2$OCH$_2$CH$_3$ | 0 |
| A-7478 | H | H | H | H | H | O | CH=NOH | H | 2-CH$_2$SCH$_3$ | 0 |
| A-7479 | H | H | H | H | H | O | CH=NOH | H | 2-CH$_2$S(=O)CH$_3$ | 0 |
| A-7480 | H | H | H | H | H | O | CH=NOH | H | 2-CH$_2$S(=O)$_2$CH$_3$ | 0 |
| A-7481 | H | H | H | H | H | O | CH=NOH | H | 2-(benzyloxy) | 0 |
| A-7482 | H | H | H | H | H | O | CH=NOH | H | 2-NH$_2$ | 0 |
| A-7483 | H | H | H | H | H | O | CH=NOH | H | 2-NHMe | 0 |
| A-7484 | H | H | H | H | H | O | CH=NOH | H | 2-N(Me)$_2$ | 0 |
| A-7485 | H | H | H | H | H | O | CH=NOH | H | 2-(1,3-dioxolan-2-yl) | 0 |
| A-7486 | H | H | H | H | H | O | CH=NOH | H | 2-(1,3-dioxan-2-yl) | 0 |
| A-7487 | H | H | H | H | H | O | CH=NOH | H | 2-(1H-imidazol-2-yl) | 0 |
| A-7488 | H | H | H | H | H | O | CH=NOH | H | 2-(thiazol-2-yl) | 0 |

TABLE 132-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7489 | H | H | H | H | H | O | CH=NOH | H | 2-(oxazol-2-yl) | 0 |
| A-7490 | H | H | H | H | H | O | CH=NOH | H | 2-CH=NOH | 0 |
| A-7491 | H | H | H | H | H | O | CH=NOH | H | 2-CH=NOMe | 0 |
| A-7492 | H | H | H | H | H | O | CH=NOH | H | 2-(4,5-dihydro-3-isoxazolyl) | 0 |
| A-7493 | H | H | H | H | H | O | CH=NOH | H | 2-CN | 0 |
| A-7494 | H | H | H | H | H | O | CH=NOH | H | 2-NO$_2$ | 0 |
| A-7495 | H | H | H | H | H | O | CH=NOH | H | 2-F,6-Cl | 0 |
| A-7496 | H | H | H | H | H | O | CH=NOH | H | 2-F,6-Me | 0 |
| A-7497 | H | H | H | H | H | O | CH=NOH | H | 3-F,6-Me | 0 |
| A-7498 | H | H | H | H | H | O | CH=NOH | H | 4-F,2-Me | 0 |
| A-7499 | H | H | H | H | H | O | CH=NOH | H | 2-F,6-OMe | 0 |
| A-7500 | H | H | H | H | H | O | CH=NOH | H | 3-F,6-OMe | 0 |
| A-7501 | H | H | H | H | H | O | CH=NOH | H | 2,6-Cl$_2$ | 0 |
| A-7502 | H | H | H | H | H | O | CH=NOH | H | 2-Cl,6-Me | 0 |
| A-7503 | H | H | H | H | H | O | CH=NOH | H | 3-Cl,6-Me | 0 |
| A-7504 | H | H | H | H | H | O | CH=NOH | H | 4-Cl,2-Me | 0 |
| A-7505 | H | H | H | H | H | O | CH=NOH | H | 2-Cl,5-CF$_3$ | 0 |
| A-7506 | H | H | H | H | H | O | CH=NOH | H | 2-Cl,6-CF$_3$ | 0 |
| A-7507 | H | H | H | H | H | O | CH=NOH | H | 2-Cl,6-OMe | 0 |
| A-7508 | H | H | H | H | H | O | CH=NOH | H | 3-Cl,6-OMe | 0 |
| A-7509 | H | H | H | H | H | O | CH=NOH | H | 4-Cl,2-OMe | 0 |
| A-7510 | H | H | H | H | H | O | CH=NOH | H | 2,4-Me$_2$ | 0 |
| A-7511 | H | H | H | H | H | O | CH=NOH | H | 2,5-Me$_2$ | 0 |
| A-7512 | H | H | H | H | H | O | CH=NOH | H | 2,6-Me$_2$ | 0 |
| A-7513 | H | H | H | H | H | O | CH=NOH | H | 2-Me,4-CF$_3$ | 0 |
| A-7514 | H | H | H | H | H | O | CH=NOH | H | 2-Me,5-CF$_3$ | 0 |
| A-7515 | H | H | H | H | H | O | CH=NOH | H | 2-Me,6-CF$_3$ | 0 |
| A-7516 | H | H | H | H | H | O | CH=NOH | H | 2-Me,4-OMe | 0 |
| A-7517 | H | H | H | H | H | O | CH=NOH | H | 2-Me,5-OMe | 0 |
| A-7518 | H | H | H | H | H | O | CH=NOH | H | 2-Me,6-OMe | 0 |
| A-7519 | H | H | H | H | H | O | CH=NOH | H | 3-Me,6-OMe | 0 |

TABLE 133

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7520 | H | H | H | H | H | O | CH=NOH | H | 4-Me,2-OMe | 0 |
| A-7521 | H | H | H | H | H | O | CH=NOH | H | 2,5-OMe$_2$ | 0 |
| A-7522 | H | H | H | H | H | O | CH=NOH | H | 2,6-OMe$_2$ | 0 |
| A-7523 | H | H | H | H | H | O | CH=NOH | H | 2-OMe,6-CF$_3$ | 0 |
| A-7524 | H | H | H | H | H | O | CH=NOH | H | 2-CHF$_2$,5-F | 0 |
| A-7525 | H | H | H | H | H | O | CH=NOH | H | 2-CHF$_2$,6-F | 0 |
| A-7526 | H | H | H | H | H | O | CH=NOH | H | 2-CHF$_2$,5-Me | 0 |
| A-7527 | H | H | H | H | H | O | CH=NOH | H | 2-CHF$_2$,6-Me | 0 |
| A-7528 | H | H | H | H | H | O | CH=NOH | H | 2-cyclopropyl,5-F | 0 |
| A-7529 | H | H | H | H | H | O | CH=NOH | H | 2-cyclopropyl,6-F | 0 |
| A-7530 | H | H | H | H | H | O | CH=NOH | H | 2-cyclopropyl,5-Me | 0 |
| A-7531 | H | H | H | H | H | O | CH=NOH | H | 2-cyclopropyl,6-Me | 0 |
| A-7532 | H | H | H | H | H | O | CH=NOH | H | 2-ethenyl,6-F | 0 |
| A-7533 | H | H | H | H | H | O | CH=NOH | H | 2-ethenyl,6-Me | 0 |
| A-7534 | H | H | H | H | H | O | CH=NOH | H | 2-OEt,5-F | 0 |
| A-7535 | H | H | H | H | H | O | CH=NOH | H | 2-OEt,6-F | 0 |
| A-7536 | H | H | H | H | H | O | CH=NOH | H | 2-OEt,5-Cl | 0 |
| A-7537 | H | H | H | H | H | O | CH=NOH | H | 2-OEt,6-Cl | 0 |
| A-7538 | H | H | H | H | H | O | CH=NOH | H | 2-OEt,5-Me | 0 |
| A-7539 | H | H | H | H | H | O | CH=NOH | H | 2-OEt,6-Me | 0 |
| A-7540 | H | H | H | H | H | O | CH=NOH | H | 2-OCHF$_2$,5-F | 0 |
| A-7541 | H | H | H | H | H | O | CH=NOH | H | 2-OCHF$_2$,6-F | 0 |
| A-7542 | H | H | H | H | H | O | CH=NOH | H | 2-OCHF$_2$,5-Me | 0 |
| A-7543 | H | H | H | H | H | O | CH=NOH | H | 2-OCHF$_2$,6-Me | 0 |
| A-7544 | H | H | H | H | H | O | CH=NOH | H | 2-(cyclopropyloxy),5-F | 0 |
| A-7545 | H | H | H | H | H | O | CH=NOH | H | 2-(cyclopropyloxy),6-F | 0 |
| A-7546 | H | H | H | H | H | O | CH=NOH | H | 2-(cyclopropyloxy),5-Me | 0 |
| A-7547 | H | H | H | H | H | O | CH=NOH | H | 2-(cyclopropyloxy),6-Me | 0 |
| A-7548 | H | H | H | H | H | O | CH=NOH | H | 2-SMe,5-F | 0 |
| A-7549 | H | H | H | H | H | O | CH=NOH | H | 2-SMe,6-F | 0 |
| A-7550 | H | H | H | H | H | O | CH=NOH | H | 2-SMe,5-Me | 0 |
| A-7551 | H | H | H | H | H | O | CH=NOH | H | 2-SMe,6-Me | 0 |
| A-7552 | H | H | H | H | H | O | CH=NOH | H | 2-S(=O)Me,5-F | 0 |
| A-7553 | H | H | H | H | H | O | CH=NOH | H | 2-S(=O)Me,6-F | 0 |
| A-7554 | H | H | H | H | H | O | CH=NOH | H | 2-S(=O)Me,5-Me | 0 |
| A-7555 | H | H | H | H | H | O | CH=NOH | H | 2-S(=O)Me,6-Me | 0 |
| A-7556 | H | H | H | H | H | O | CH=NOH | H | 2-S(=O)$_2$Me,5-F | 0 |
| A-7557 | H | H | H | H | H | O | CH=NOH | H | 2-S(=O)$_2$Me,6-F | 0 |
| A-7558 | H | H | H | H | H | O | CH=NOH | H | 2-S(=O)$_2$Me,5-Me | 0 |

TABLE 133-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7559 | H | H | H | H | H | O | CH=NOH | H | 2-S(=O)$_2$Me,6-Me | 0 |
| A-7560 | H | H | H | H | H | O | CH=NOH | H | 2-SCF$_3$,5-F | 0 |
| A-7561 | H | H | H | H | H | O | CH=NOH | H | 2-SCF$_3$,6-F | 0 |
| A-7562 | H | H | H | H | H | O | CH=NOH | H | 2-SCF$_3$,5-Me | 0 |
| A-7563 | H | H | H | H | H | O | CH=NOH | H | 2-SCF$_3$,6-Me | 0 |
| A-7564 | H | H | H | H | H | O | CH=NOH | H | 2-S(=O)CF$_3$,5-F | 0 |
| A-7565 | H | H | H | H | H | O | CH=NOH | H | 2-S(=O)CF$_3$,6-F | 0 |
| A-7566 | H | H | H | H | H | O | CH=NOH | H | 2-S(=O)CF$_3$,5-Me | 0 |
| A-7567 | H | H | H | H | H | O | CH=NOH | H | 2-S(=O)CF$_3$,6-Me | 0 |
| A-7568 | H | H | H | H | H | O | CH=NOH | H | 2-S(=O)$_2$CF$_3$,5-F | 0 |
| A-7569 | H | H | H | H | H | O | CH=NOH | H | 2-S(=O)$_2$CF$_3$,6-F | 0 |
| A-7570 | H | H | H | H | H | O | CH=NOH | H | 2-S(=O)$_2$CF$_3$,5-Me | 0 |
| A-7571 | H | H | H | H | H | O | CH=NOH | H | 2-S(=O)$_2$CF$_3$,6-Me | 0 |
| A-7572 | H | H | H | H | H | O | CH=NOH | H | 2-(cyclopropylthio),5-F | 0 |
| A-7573 | H | H | H | H | H | O | CH=NOH | H | 2-(cyclopropylthio),6-F | 0 |
| A-7574 | H | H | H | H | H | O | CH=NOH | H | 2-(cyclopropylthio),5-Me | 0 |
| A-7575 | H | H | H | H | H | O | CH=NOH | H | 2-(cyclopropylthio),6-Me | 0 |
| A-7576 | H | H | H | H | H | O | CH=NOH | H | 2-C(=O)Me,5-F | 0 |

TABLE 134

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7577 | H | H | H | H | H | O | CH=NOH | H | 2-C(=O)Me,6-F | 0 |
| A-7578 | H | H | H | H | H | O | CH=NOH | H | 2-C(=O)Me,5-Me | 0 |
| A-7579 | H | H | H | H | H | O | CH=NOH | H | 2-C(=O)Me,6-Me | 0 |
| A-7580 | H | H | H | H | H | O | CH=NOH | H | 2-CH$_2$OH,5-F | 0 |
| A-7581 | H | H | H | H | H | O | CH=NOH | H | 2-CH$_2$OH,6-F | 0 |
| A-7582 | H | H | H | H | H | O | CH=NOH | H | 2-CH$_2$OH,5-Me | 0 |
| A-7583 | H | H | H | H | H | O | CH=NOH | H | 2-CH$_2$OH,6-Me | 0 |
| A-7584 | H | H | H | H | H | O | CH=NOH | H | 2-CH$_2$OCH$_3$,4-F | 0 |
| A-7585 | H | H | H | H | H | O | CH=NOH | H | 2-CH$_2$OCH$_3$,5-F | 0 |
| A-7586 | H | H | H | H | H | O | CH=NOH | H | 2-CH$_2$OCH$_3$,6-F | 0 |
| A-7587 | H | H | H | H | H | O | CH=NOH | H | 2-CH$_2$OCH$_3$,4-Me | 0 |
| A-7588 | H | H | H | H | H | O | CH=NOH | H | 2-CH$_2$OCH$_3$,5-Me | 0 |
| A-7589 | H | H | H | H | H | O | CH=NOH | H | 2-CH$_2$OCH$_3$,6-Me | 0 |
| A-7590 | H | H | H | H | H | O | CH=NOH | H | 2-OC(=O)CH$_3$,5-F | 0 |
| A-7591 | H | H | H | H | H | O | CH=NOH | H | 2-OC(=O)CH$_3$,6-F | 0 |
| A-7592 | H | H | H | H | H | O | CH=NOH | H | 2-OC(=O)CH$_3$,5-Me | 0 |
| A-7593 | H | H | H | H | H | O | CH=NOH | H | 2-OC(=O)CH$_3$,6-Me | 0 |
| A-7594 | H | H | H | H | H | O | CH=NOH | H | 2-OS(=O)$_2$CH$_3$,5-F | 0 |
| A-7595 | H | H | H | H | H | O | CH=NOH | H | 2-OS(=O)$_2$CH$_3$,6-F | 0 |
| A-7596 | H | H | H | H | H | O | CH=NOH | H | 2-OS(=O)$_2$CH$_3$,5-Me | 0 |
| A-7597 | H | H | H | H | H | O | CH=NOH | H | 2-OS(=O)$_2$CH$_3$,6-Me | 0 |
| A-7598 | H | H | H | H | H | O | CH=NOH | H | 2-CH$_2$SCH$_3$,5-F | 0 |
| A-7599 | H | H | H | H | H | O | CH=NOH | H | 2-CH$_2$SCH$_3$,6-F | 0 |
| A-7600 | H | H | H | H | H | O | CH=NOH | H | 2-CH$_2$SCH$_3$,5-Me | 0 |
| A-7601 | H | H | H | H | H | O | CH=NOH | H | 2-CH$_2$SCH$_3$,6-Me | 0 |
| A-7602 | H | H | H | H | H | O | CH=NOH | H | 2-NMe$_2$,5-F | 0 |
| A-7603 | H | H | H | H | H | O | CH=NOH | H | 2-NMe$_2$,6-F | 0 |
| A-7604 | H | H | H | H | H | O | CH=NOH | H | 2-NMe$_2$,5-Me | 0 |
| A-7605 | H | H | H | H | H | O | CH=NOH | H | 2-NMe$_2$,6-Me | 0 |
| A-7606 | H | H | H | H | H | O | CH=NOH | H | 2-CN,4-F | 0 |
| A-7607 | H | H | H | H | H | O | CH=NOH | H | 2-CN,5-F | 0 |
| A-7608 | H | H | H | H | H | O | CH=NOH | H | 2-CN,6-F | 0 |
| A-7609 | H | H | H | H | H | O | CH=NOH | H | 2-CN,6-Me | 0 |
| A-7610 | H | H | H | H | H | O | CH=NOH | H | 2-CN,5-OMe | 0 |
| A-7611 | H | H | H | H | H | O | CH=NOH | H | 2-CN,6-OMe | 0 |
| A-7612 | H | H | H | H | H | O | CH=NOH | H | 3-CN,6-Me | 0 |
| A-7613 | H | H | H | H | H | O | CH=NOH | H | 3-CN,6-OMe | 0 |
| A-7614 | H | H | H | H | H | O | CH=NOH | H | 4-CN,2-Me | 0 |
| A-7615 | H | H | H | H | H | O | CH=NOH | H | 4-CN,2-OMe | 0 |
| A-7616 | H | H | H | H | H | O | CH=NOH | H | 2-NO$_2$,4-F | 0 |
| A-7617 | H | H | H | H | H | O | CH=NOH | H | 2-NO$_2$,5-F | 0 |
| A-7618 | H | H | H | H | H | O | CH=NOH | H | 2-NO$_2$,6-F | 0 |
| A-7619 | H | H | H | H | H | O | CH=NOH | H | 2-NO$_2$,4-Me | 0 |
| A-7620 | H | H | H | H | H | O | CH=NOH | H | 2-NO$_2$,5-Me | 0 |
| A-7621 | H | H | H | H | H | O | CH=NOH | H | 2-NO$_2$,6-Me | 0 |
| A-7622 | H | H | H | H | H | O | CH=NOH | H | 2-Me,4,5-F$_2$ | 0 |
| A-7623 | H | H | H | H | H | O | CH=NOH | H | 2-Me,6-Et | 0 |
| A-7624 | H | H | H | H | H | O | CH=NOH | H | 2-cyclopropyl,6-OMe | 0 |
| A-7625 | H | H | H | H | H | O | CH=NOH | H | 2-Me,5-Et | 0 |
| A-7626 | H | H | H | H | H | O | CH=NOH | H | 2,6-Et$_2$ | 0 |
| A-7627 | H | H | H | H | H | O | CH=NOH | H | 2-Et,6-F | 0 |
| A-7628 | H | H | H | H | H | O | CH=NOH | H | 2-CH$_2$OCH$_3$,6-Cl | 0 |

TABLE 134-continued

| compound | R¹ | R² | R³ | R⁴ | R⁵ | A | R⁶ | R⁷ | (R⁸)$_m$ | p |
|---|---|---|---|---|---|---|---|---|---|---|
| A-7629 | H | H | H | H | H | O | CH=NOH | H | 2-CH$_2$OCH$_2$CH$_3$,6-Cl | 0 |
| A-7630 | H | H | H | H | H | O | CH=NOH | H | 2-CH$_2$NMe$_2$ | 0 |
| A-7631 | H | H | H | H | H | O | CH=NOCH$_2$CH$_3$ | H | H | 0 |
| A-7632 | H | H | H | H | H | O | CH=NOCH$_2$CH$_3$ | H | 2-F | 0 |
| A-7633 | H | H | H | H | H | O | CH=NOCH$_2$CH$_3$ | H | 2-Cl | 0 |

TABLE 135

| compound | R¹ | R² | R³ | R⁴ | R⁵ | A | R⁶ | R⁷ | (R⁸)$_m$ | p |
|---|---|---|---|---|---|---|---|---|---|---|
| A-7634 | H | H | H | H | H | O | CH=NOCH$_2$CH$_3$ | H | 2-Br | 0 |
| A-7635 | H | H | H | H | H | O | CH=NOCH$_2$CH$_3$ | H | 2-OH | 0 |
| A-7636 | H | H | H | H | H | O | CH=NOCH$_2$CH$_3$ | H | 2-Me | 0 |
| A-7637 | H | H | H | H | H | O | CH=NOCH$_2$CH$_3$ | H | 2-Et | 0 |
| A-7638 | H | H | H | H | H | O | CH=NOCH$_2$CH$_3$ | H | 2-Pr | 0 |
| A-7639 | H | H | H | H | H | O | CH=NOCH$_2$CH$_3$ | H | 2-CF$_3$ | 0 |
| A-7640 | H | H | H | H | H | O | CH=NOCH$_2$CH$_3$ | H | 2-CHF$_2$ | 0 |
| A-7641 | H | H | H | H | H | O | CH=NOCH$_2$CH$_3$ | H | 2-CH$_2$F | 0 |
| A-7642 | H | H | H | H | H | O | CH=NOCH$_2$CH$_3$ | H | 2-CF$_2$Cl | 0 |
| A-7643 | H | H | H | H | H | O | CH=NOCH$_2$CH$_3$ | H | 2-cyclopropyl | 0 |
| A-7644 | H | H | H | H | H | O | CH=NOCH$_2$CH$_3$ | H | 2-cyclobutyl | 0 |
| A-7645 | H | H | H | H | H | O | CH=NOCH$_2$CH$_3$ | H | 2-cyclopentyl | 0 |
| A-7646 | H | H | H | H | H | O | CH=NOCH$_2$CH$_3$ | H | 2-ethenyl | 0 |
| A-7647 | H | H | H | H | H | O | CH=NOCH$_2$CH$_3$ | H | 2-allyl | 0 |
| A-7648 | H | H | H | H | H | O | CH=NOCH$_2$CH$_3$ | H | 2-(prop-1-en-1-yl) | 0 |
| A-7649 | H | H | H | H | H | O | CH=NOCH$_2$CH$_3$ | H | 2-(trifluoroethenyl) | 0 |
| A-7650 | H | H | H | H | H | O | CH=NOCH$_2$CH$_3$ | H | 2-OMe | 0 |
| A-7651 | H | H | H | H | H | O | CH=NOCH$_2$CH$_3$ | H | 2-OEt | 0 |
| A-7652 | H | H | H | H | H | O | CH=NOCH$_2$CH$_3$ | H | 2-OPr | 0 |
| A-7653 | H | H | H | H | H | O | CH=NOCH$_2$CH$_3$ | H | 2-O(i-Pr) | 0 |
| A-7654 | H | H | H | H | H | O | CH=NOCH$_2$CH$_3$ | H | 2-OCF$_3$ | 0 |
| A-7655 | H | H | H | H | H | O | CH=NOCH$_2$CH$_3$ | H | 2-OCHF$_2$ | 0 |
| A-7656 | H | H | H | H | H | O | CH=NOCH$_2$CH$_3$ | H | 2-(cyclopropyloxy) | 0 |
| A-7657 | H | H | H | H | H | O | CH=NOCH$_2$CH$_3$ | H | 2-(cyclobutyloxy) | 0 |
| A-7658 | H | H | H | H | H | O | CH=NOCH$_2$CH$_3$ | H | 2-(cyclopentyloxy) | 0 |
| A-7659 | H | H | H | H | H | O | CH=NOCH$_2$CH$_3$ | H | 2-((2,2-dichlrocyclopropyl)oxy) | 0 |
| A-7660 | H | H | H | H | H | O | CH=NOCH$_2$CH$_3$ | H | 2-(oxiran-2-yl) | 0 |
| A-7661 | H | H | H | H | H | O | CH=NOCH$_2$CH$_3$ | H | 2-SMe | 0 |
| A-7662 | H | H | H | H | H | O | CH=NOCH$_2$CH$_3$ | H | 3-SMe | 0 |
| A-7663 | H | H | H | H | H | O | CH=NOCH$_2$CH$_3$ | H | 2-S(=O)Me | 0 |
| A-7664 | H | H | H | H | H | O | CH=NOCH$_2$CH$_3$ | H | 3-S(=O)Me | 0 |
| A-7665 | H | H | H | H | H | O | CH=NOCH$_2$CH$_3$ | H | 2-S(=O)$_2$Me | 0 |
| A-7666 | H | H | H | H | H | O | CH=NOCH$_2$CH$_3$ | H | 3-S(=O)$_2$Me | 0 |
| A-7667 | H | H | H | H | H | O | CH=NOCH$_2$CH$_3$ | H | 2-SCF$_3$ | 0 |
| A-7668 | H | H | H | H | H | O | CH=NOCH$_2$CH$_3$ | H | 3-SCF$_3$ | 0 |
| A-7669 | H | H | H | H | H | O | CH=NOCH$_2$CH$_3$ | H | 3-S(=O)CF$_3$ | 0 |
| A-7670 | H | H | H | H | H | O | CH=NOCH$_2$CH$_3$ | H | 3-SCF(CF$_3$)$_2$ | 0 |
| A-7671 | H | H | H | H | H | O | CH=NOCH$_2$CH$_3$ | H | 2-(cyclopropylthio) | 0 |
| A-7672 | H | H | H | H | H | O | CH=NOCH$_2$CH$_3$ | H | 2-(cyclopropylsulfinyl) | 0 |
| A-7673 | H | H | H | H | H | O | CH=NOCH$_2$CH$_3$ | H | 2-(cyclopropylsulfonyl) | 0 |
| A-7674 | H | H | H | H | H | O | CH=NOCH$_2$CH$_3$ | H | 2-C(=O)Me | 0 |
| A-7675 | H | H | H | H | H | O | CH=NOCH$_2$CH$_3$ | H | 2-CH$_2$C(=O)CH$_3$ | 0 |
| A-7676 | H | H | H | H | H | O | CH=NOCH$_2$CH$_3$ | H | 2-CH$_2$C(=O)CF$_3$ | 0 |
| A-7677 | H | H | H | H | H | O | CH=NOCH$_2$CH$_3$ | H | 2-CH$_2$OH | 0 |
| A-7678 | H | H | H | H | H | O | CH=NOCH$_2$CH$_3$ | H | 2-CH$_2$OCH$_3$ | 0 |
| A-7679 | H | H | H | H | H | O | CH=NOCH$_2$CH$_3$ | H | 2-CH$_2$SCH$_3$ | 0 |
| A-7680 | H | H | H | H | H | O | CH=NOCH$_2$CH$_3$ | H | 2-CH$_2$SCH$_3$ | 0 |
| A-7681 | H | H | H | H | H | O | CH=NOCH$_2$CH$_3$ | H | 2-CH$_2$S(=O)CH$_3$ | 0 |
| A-7682 | H | H | H | H | H | O | CH=NOCH$_2$CH$_3$ | H | 2-CH$_2$S(=O)$_2$CH$_3$ | 0 |
| A-7683 | H | H | H | H | H | O | CH=NOCH$_2$CH$_3$ | H | 2-(benzyloxy) | 0 |
| A-7684 | H | H | H | H | H | O | CH=NOCH$_2$CH$_3$ | H | 2-NH$_2$ | 0 |
| A-7685 | H | H | H | H | H | O | CH=NOCH$_2$CH$_3$ | H | 2-NHMe | 0 |
| A-7686 | H | H | H | H | H | O | CH=NOCH$_2$CH$_3$ | H | 2-N(Me)$_2$ | 0 |
| A-7687 | H | H | H | H | H | O | CH=NOCH$_2$CH$_3$ | H | 2-(1,3-dioxolan-2-yl) | 0 |
| A-7688 | H | H | H | H | H | O | CH=NOCH$_2$CH$_3$ | H | 2-(1,3-dioxan-2-yl) | 0 |
| A-7689 | H | H | H | H | H | O | CH=NOCH$_2$CH$_3$ | H | 2-(1H-imidazol-2-yl) | 0 |
| A-7690 | H | H | H | H | H | O | CH=NOCH$_2$CH$_3$ | H | 2-(thiazol-2-yl) | 0 |

TABLE 136

| compound | R¹ | R² | R³ | R⁴ | R⁵ | A | R⁶ | R⁷ | (R⁸)$_m$ | p |
|---|---|---|---|---|---|---|---|---|---|---|
| A-7691 | H | H | H | H | H | O | CH=NOCH$_2$CH$_3$ | H | 2-(oxazol-2-yl) | 0 |
| A-7692 | H | H | H | H | H | O | CH=NOCH$_2$CH$_3$ | H | 2-CH=NOH | 0 |
| A-7693 | H | H | H | H | H | O | CH=NOCH$_2$CH$_3$ | H | 2-CH=NOMe | 0 |
| A-7694 | H | H | H | H | H | O | CH=NOCH$_2$CH$_3$ | H | 2-(4,5-dihydro-3-isoxazolyl) | 0 |
| A-7695 | H | H | H | H | H | O | CH=NOCH$_2$CH$_3$ | H | 2-CN | 0 |
| A-7696 | H | H | H | H | H | O | CH=NOCH$_2$CH$_3$ | H | 2-NO$_2$ | 0 |
| A-7697 | H | H | H | H | H | O | CH=NOCH$_2$CH$_3$ | H | 2-F,6-Cl | 0 |
| A-7698 | H | H | H | H | H | O | CH=NOCH$_2$CH$_3$ | H | 2-F,6-Me | 0 |
| A-7699 | H | H | H | H | H | O | CH=NOCH$_2$CH$_3$ | H | 3-F,6-Me | 0 |
| A-7700 | H | H | H | H | H | O | CH=NOCH$_2$CH$_3$ | H | 4-F,2-Me | 0 |
| A-7701 | H | H | H | H | H | O | CH=NOCH$_2$CH$_3$ | H | 2-F,6-OMe | 0 |
| A-7702 | H | H | H | H | H | O | CH=NOCH$_2$CH$_3$ | H | 3-F,6-OMe | 0 |
| A-7703 | H | H | H | H | H | O | CH=NOCH$_2$CH$_3$ | H | 2,6-Cl$_2$ | 0 |
| A-7704 | H | H | H | H | H | O | CH=NOCH$_2$CH$_3$ | H | 2-Cl,6-Me | 0 |
| A-7705 | H | H | H | H | H | O | CH=NOCH$_2$CH$_3$ | H | 3-Cl,6-Me | 0 |
| A-7706 | H | H | H | H | H | O | CH=NOCH$_2$CH$_3$ | H | 4-Cl,2-Me | 0 |
| A-7707 | H | H | H | H | H | O | CH=NOCH$_2$CH$_3$ | H | 2-Cl,5-CF$_3$ | 0 |
| A-7708 | H | H | H | H | H | O | CH=NOCH$_2$CH$_3$ | H | 2-Cl,6-CF$_3$ | 0 |
| A-7709 | H | H | H | H | H | O | CH=NOCH$_2$CH$_3$ | H | 2-Cl,6-OMe | 0 |
| A-7710 | H | H | H | H | H | O | CH=NOCH$_2$CH$_3$ | H | 3-Cl,6-OMe | 0 |
| A-7711 | H | H | H | H | H | O | CH=NOCH$_2$CH$_3$ | H | 4-Cl,2-OMe | 0 |
| A-7712 | H | H | H | H | H | O | CH=NOCH$_2$CH$_3$ | H | 2,4-Me$_2$ | 0 |
| A-7713 | H | H | H | H | H | O | CH=NOCH$_2$CH$_3$ | H | 2,5-Me$_2$ | 0 |
| A-7714 | H | H | H | H | H | O | CH=NOCH$_2$CH$_3$ | H | 2,6-Me$_2$ | 0 |
| A-7715 | H | H | H | H | H | O | CH=NOCH$_2$CH$_3$ | H | 2-Me,4-CF$_3$ | 0 |
| A-7716 | H | H | H | H | H | O | CH=NOCH$_2$CH$_3$ | H | 2-Me,5-CF$_3$ | 0 |
| A-7717 | H | H | H | H | H | O | CH=NOCH$_2$CH$_3$ | H | 2-Me,6-CF$_3$ | 0 |
| A-7718 | H | H | H | H | H | O | CH=NOCH$_2$CH$_3$ | H | 2-Me,4-OMe | 0 |
| A-7719 | H | H | H | H | H | O | CH=NOCH$_2$CH$_3$ | H | 2-Me,5-OMe | 0 |
| A-7720 | H | H | H | H | H | O | CH=NOCH$_2$CH$_3$ | H | 2-Me,6-OMe | 0 |
| A-7721 | H | H | H | H | H | O | CH=NOCH$_2$CH$_3$ | H | 3-Me,6-OMe | 0 |
| A-7722 | H | H | H | H | H | O | CH=NOCH$_2$CH$_3$ | H | 4-Me,2-OMe | 0 |
| A-7723 | H | H | H | H | H | O | CH=NOCH$_2$CH$_3$ | H | 2,5-OMe$_2$ | 0 |
| A-7724 | H | H | H | H | H | O | CH=NOCH$_2$CH$_3$ | H | 2,6-OMe$_2$ | 0 |
| A-7725 | H | H | H | H | H | O | CH=NOCH$_2$CH$_3$ | H | 2-OMe,6-CF$_3$ | 0 |
| A-7726 | H | H | H | H | H | O | CH=NOCH$_2$CH$_3$ | H | 2-CHF$_2$,5-F | 0 |
| A-7727 | H | H | H | H | H | O | CH=NOCH$_2$CH$_3$ | H | 2-CHF$_2$,6-F | 0 |
| A-7728 | H | H | H | H | H | O | CH=NOCH$_2$CH$_3$ | H | 2-CHF$_2$,5-Me | 0 |
| A-7729 | H | H | H | H | H | O | CH=NOCH$_2$CH$_3$ | H | 2-CHF$_2$,6-Me | 0 |
| A-7730 | H | H | H | H | H | O | CH=NOCH$_2$CH$_3$ | H | 2-cyclopropyl,5-F | 0 |
| A-7731 | H | H | H | H | H | O | CH=NOCH$_2$CH$_3$ | H | 2-cyclopropyl,6-F | 0 |
| A-7732 | H | H | H | H | H | O | CH=NOCH$_2$CH$_3$ | H | 2-cyclopropyl,5-Me | 0 |
| A-7733 | H | H | H | H | H | O | CH=NOCH$_2$CH$_3$ | H | 2-cyclopropyl,6-Me | 0 |
| A-7734 | H | H | H | H | H | O | CH=NOCH$_2$CH$_3$ | H | 2-ethenyl,6-F | 0 |
| A-7735 | H | H | H | H | H | O | CH=NOCH$_2$CH$_3$ | H | 2-ethenyl,6-Me | 0 |
| A-7736 | H | H | H | H | H | O | CH=NOCH$_2$CH$_3$ | H | 2-OEt,5-F | 0 |
| A-7737 | H | H | H | H | H | O | CH=NOCH$_2$CH$_3$ | H | 2-OEt,6-F | 0 |
| A-7738 | H | H | H | H | H | O | CH=NOCH$_2$CH$_3$ | H | 2-OEt,5-Cl | 0 |
| A-7739 | H | H | H | H | H | O | CH=NOCH$_2$CH$_3$ | H | 2-OEt,6-Cl | 0 |
| A-7740 | H | H | H | H | H | O | CH=NOCH$_2$CH$_3$ | H | 2-OEt,5-Me | 0 |
| A-7741 | H | H | H | H | H | O | CH=NOCH$_2$CH$_3$ | H | 2-OEt,6-Me | 0 |
| A-7742 | H | H | H | H | H | O | CH=NOCH$_2$CH$_3$ | H | 2-OCHF$_2$,5-F | 0 |
| A-7743 | H | H | H | H | H | O | CH=NOCH$_2$CH$_3$ | H | 2-OCHF$_2$,6-F | 0 |
| A-7744 | H | H | H | H | H | O | CH=NOCH$_2$CH$_3$ | H | 2-OCHF$_2$,5-Me | 0 |
| A-7745 | H | H | H | H | H | O | CH=NOCH$_2$CH$_3$ | H | 2-OCHF$_2$,6-Me | 0 |
| A-7746 | H | H | H | H | H | O | CH=NOCH$_2$CH$_3$ | H | 2-(cyclopropyloxy),5-F | 0 |
| A-7747 | H | H | H | H | H | O | CH=NOCH$_2$CH$_3$ | H | 2-(cyclopropyloxy),6-F | 0 |

TABLE 137

| compound | R¹ | R² | R³ | R⁴ | R⁵ | A | R⁶ | R⁷ | (R⁸)$_m$ | p |
|---|---|---|---|---|---|---|---|---|---|---|
| A-7748 | H | H | H | H | H | O | CH=NOCH$_2$CH$_3$ | H | 2-(cyclopropyloxy),5-Me | 0 |
| A-7749 | H | H | H | H | H | O | CH=NOCH$_2$CH$_3$ | H | 2-(cyclopropyloxy),6-Me | 0 |
| A-7750 | H | H | H | H | H | O | CH=NOCH$_2$CH$_3$ | H | 2-SMe,5-F | 0 |
| A-7751 | H | H | H | H | H | O | CH=NOCH$_2$CH$_3$ | H | 2-SMe,6-F | 0 |
| A-7752 | H | H | H | H | H | O | CH=NOCH$_2$CH$_3$ | H | 2-SMe,5-Me | 0 |
| A-7753 | H | H | H | H | H | O | CH=NOCH$_2$CH$_3$ | H | 2-SMe,6-Me | 0 |
| A-7754 | H | H | H | H | H | O | CH=NOCH$_2$CH$_3$ | H | 2-S(=O)Me,5-F | 0 |
| A-7755 | H | H | H | H | H | O | CH=NOCH$_2$CH$_3$ | H | 2-S(=O)Me,6-F | 0 |
| A-7756 | H | H | H | H | H | O | CH=NOCH$_2$CH$_3$ | H | 2-S(=O)Me,5-Me | 0 |
| A-7757 | H | H | H | H | H | O | CH=NOCH$_2$CH$_3$ | H | 2-S(=O)Me,6-Me | 0 |
| A-7758 | H | H | H | H | H | O | CH=NOCH$_2$CH$_3$ | H | 2-S(=O)$_2$Me,5-F | 0 |
| A-7759 | H | H | H | H | H | O | CH=NOCH$_2$CH$_3$ | H | 2-S(=O)$_2$Me,6-F | 0 |
| A-7760 | H | H | H | H | H | O | CH=NOCH$_2$CH$_3$ | H | 2-S(=O)$_2$Me,5-Me | 0 |

TABLE 137-continued

| compound | R¹ | R² | R³ | R⁴ | R⁵ | A | R⁶ | R⁷ | $(R^8)_m$ | p |
|---|---|---|---|---|---|---|---|---|---|---|
| A-7761 | H | H | H | H | H | O | CH=NOCH$_2$CH$_3$ | H | 2-S(=O)$_2$Me,6-Me | 0 |
| A-7762 | H | H | H | H | H | O | CH=NOCH$_2$CH$_3$ | H | 2-SCF$_3$,5-F | 0 |
| A-7763 | H | H | H | H | H | O | CH=NOCH$_2$CH$_3$ | H | 2-SCF$_3$,6-F | 0 |
| A-7764 | H | H | H | H | H | O | CH=NOCH$_2$CH$_3$ | H | 2-SCF$_3$,5-Me | 0 |
| A-7765 | H | H | H | H | H | O | CH=NOCH$_2$CH$_3$ | H | 2-SCF$_3$,6-Me | 0 |
| A-7766 | H | H | H | H | H | O | CH=NOCH$_2$CH$_3$ | H | 2-S(=O)CF$_3$,5-F | 0 |
| A-7767 | H | H | H | H | H | O | CH=NOCH$_2$CH$_3$ | H | 2-S(=O)CF$_3$,6-F | 0 |
| A-7768 | H | H | H | H | H | O | CH=NOCH$_2$CH$_3$ | H | 2-S(=O)CF$_3$,5-Me | 0 |
| A-7769 | H | H | H | H | H | O | CH=NOCH$_2$CH$_3$ | H | 2-S(=O)CF$_3$,6-Me | 0 |
| A-7770 | H | H | H | H | H | O | CH=NOCH$_2$CH$_3$ | H | 2-S(=O)$_2$CF$_3$,5-F | 0 |
| A-7771 | H | H | H | H | H | O | CH=NOCH$_2$CH$_3$ | H | 2-S(=O)$_2$CF$_3$,6-F | 0 |
| A-7772 | H | H | H | H | H | O | CH=NOCH$_2$CH$_3$ | H | 2-S(=O)$_2$CF$_3$,5-Me | 0 |
| A-7773 | H | H | H | H | H | O | CH=NOCH$_2$CH$_3$ | H | 2-S(=O)$_2$CF$_3$,6-Me | 0 |
| A-7774 | H | H | H | H | H | O | CH=NOCH$_2$CH$_3$ | H | 2-(cyclopropylthio),5-F | 0 |
| A-7775 | H | H | H | H | H | O | CH=NOCH$_2$CH$_3$ | H | 2-(cyclopropylthio),6-F | 0 |
| A-7776 | H | H | H | H | H | O | CH=NOCH$_2$CH$_3$ | H | 2-(cyclopropylthio),5-Me | 0 |
| A-7777 | H | H | H | H | H | O | CH=NOCH$_2$CH$_3$ | H | 2-(cyclopropylthio),6-Me | 0 |
| A-7778 | H | H | H | H | H | O | CH=NOCH$_2$CH$_3$ | H | 2-C(=O)Me,5-F | 0 |
| A-7779 | H | H | H | H | H | O | CH=NOCH$_2$CH$_3$ | H | 2-C(=O)Me,6-F | 0 |
| A-7780 | H | H | H | H | H | O | CH=NOCH$_2$CH$_3$ | H | 2-C(=O)Me,5-Me | 0 |
| A-7781 | H | H | H | H | H | O | CH=NOCH$_2$CH$_3$ | H | 2-C(=O)Me,6-Me | 0 |
| A-7782 | H | H | H | H | H | O | CH=NOCH$_2$CH$_3$ | H | 2-CH$_2$OH,5-F | 0 |
| A-7783 | H | H | H | H | H | O | CH=NOCH$_2$CH$_3$ | H | 2-CH$_2$OH,6-F | 0 |
| A-7784 | H | H | H | H | H | O | CH=NOCH$_2$CH$_3$ | H | 2-CH$_2$OH,5-Me | 0 |
| A-7785 | H | H | H | H | H | O | CH=NOCH$_2$CH$_3$ | H | 2-CH$_2$OH,6-Me | 0 |
| A-7786 | H | H | H | H | H | O | CH=NOCH$_2$CH$_3$ | H | 2-CH$_2$OCH$_3$,4-F | 0 |
| A-7787 | H | H | H | H | H | O | CH=NOCH$_2$CH$_3$ | H | 2-CH$_2$OCH$_3$,5-F | 0 |
| A-7788 | H | H | H | H | H | O | CH=NOCH$_2$CH$_3$ | H | 2-CH$_2$OCH$_3$,6-F | 0 |
| A-7789 | H | H | H | H | H | O | CH=NOCH$_2$CH$_3$ | H | 2-CH$_2$OCH$_3$,4-Me | 0 |
| A-7790 | H | H | H | H | H | O | CH=NOCH$_2$CH$_3$ | H | 2-CH$_2$OCH$_3$,5-Me | 0 |
| A-7791 | H | H | H | H | H | O | CH=NOCH$_2$CH$_3$ | H | 2-CH$_2$OCH$_3$,6-Me | 0 |
| A-7792 | H | H | H | H | H | O | CH=NOCH$_2$CH$_3$ | H | 2-OC(=O)CH$_3$,5-F | 0 |
| A-7793 | H | H | H | H | H | O | CH=NOCH$_2$CH$_3$ | H | 2-OC(=O)CH$_3$,6-F | 0 |
| A-7794 | H | H | H | H | H | O | CH=NOCH$_2$CH$_3$ | H | 2-OC(=O)CH$_3$,5-Me | 0 |
| A-7795 | H | H | H | H | H | O | CH=NOCH$_2$CH$_3$ | H | 2-OC(=O)CH$_3$,6-Me | 0 |
| A-7796 | H | H | H | H | H | O | CH=NOCH$_2$CH$_3$ | H | 2-OS(=O)$_2$CH$_3$,5-F | 0 |
| A-7797 | H | H | H | H | H | O | CH=NOCH$_2$CH$_3$ | H | 2-OS(=O)$_2$CH$_3$,6-F | 0 |
| A-7798 | H | H | H | H | H | O | CH=NOCH$_2$CH$_3$ | H | 2-OS(=O)$_2$CH$_3$,5-Me | 0 |
| A-7799 | H | H | H | H | H | O | CH=NOCH$_2$CH$_3$ | H | 2-OS(=O)$_2$CH$_3$,6-Me | 0 |
| A-7800 | H | H | H | H | H | O | CH=NOCH$_2$CH$_3$ | H | 2-CH$_2$SCH$_3$,5-F | 0 |
| A-7801 | H | H | H | H | H | O | CH=NOCH$_2$CH$_3$ | H | 2-CH$_2$SCH$_3$,6-F | 0 |
| A-7802 | H | H | H | H | H | O | CH=NOCH$_2$CH$_3$ | H | 2-CH$_2$SCH$_3$,5-Me | 0 |
| A-7803 | H | H | H | H | H | O | CH=NOCH$_2$CH$_3$ | H | 2-CH$_2$SCH$_3$,6-Me | 0 |
| A-7804 | H | H | H | H | H | O | CH=NOCH$_2$CH$_3$ | H | 2-NMe$_2$,5-F | 0 |

TABLE 138

| compound | R¹ | R² | R³ | R⁴ | R⁵ | A | R⁶ | R⁷ | $(R^8)_m$ | p |
|---|---|---|---|---|---|---|---|---|---|---|
| A-7805 | H | H | H | H | H | O | CH=NOCH$_2$CH$_3$ | H | 2-NMe$_2$,6-F | 0 |
| A-7806 | H | H | H | H | H | O | CH=NOCH$_2$CH$_3$ | H | 2-NMe$_2$,5-Me | 0 |
| A-7807 | H | H | H | H | H | O | CH=NOCH$_2$CH$_3$ | H | 2-NMe$_2$,6-Me | 0 |
| A-7808 | H | H | H | H | H | O | CH=NOCH$_2$CH$_3$ | H | 2-CN,4-F | 0 |
| A-7809 | H | H | H | H | H | O | CH=NOCH$_2$CH$_3$ | H | 2-CN,5-F | 0 |
| A-7810 | H | H | H | H | H | O | CH=NOCH$_2$CH$_3$ | H | 2-CN,6-F | 0 |
| A-7811 | H | H | H | H | H | O | CH=NOCH$_2$CH$_3$ | H | 2-CN,6-Me | 0 |
| A-7812 | H | H | H | H | H | O | CH=NOCH$_2$CH$_3$ | H | 2-CN,5-OMe | 0 |
| A-7813 | H | H | H | H | H | O | CH=NOCH$_2$CH$_3$ | H | 2-CN,6-OMe | 0 |
| A-7814 | H | H | H | H | H | O | CH=NOCH$_2$CH$_3$ | H | 3-CN,6-Me | 0 |
| A-7815 | H | H | H | H | H | O | CH=NOCH$_2$CH$_3$ | H | 3-CN,6-OMe | 0 |
| A-7816 | H | H | H | H | H | O | CH=NOCH$_2$CH$_3$ | H | 4-CN,2-Me | 0 |
| A-7817 | H | H | H | H | H | O | CH=NOCH$_2$CH$_3$ | H | 4-CN,2-OMe | 0 |
| A-7818 | H | H | H | H | H | O | CH=NOCH$_2$CH$_3$ | H | 2-NO$_2$,4-F | 0 |
| A-7819 | H | H | H | H | H | O | CH=NOCH$_2$CH$_3$ | H | 2-NO$_2$,5-F | 0 |
| A-7820 | H | H | H | H | H | O | CH=NOCH$_2$CH$_3$ | H | 2-NO$_2$,6-F | 0 |
| A-7821 | H | H | H | H | H | O | CH=NOCH$_2$CH$_3$ | H | 2-NO$_2$,4-Me | 0 |
| A-7822 | H | H | H | H | H | O | CH=NOCH$_2$CH$_3$ | H | 2-NO$_2$,5-Me | 0 |
| A-7823 | H | H | H | H | H | O | CH=NOCH$_2$CH$_3$ | H | 2-NO$_2$,6-Me | 0 |
| A-7824 | H | H | H | H | H | O | CH=NOCH$_2$CH$_3$ | H | 2-Me,4,5-F$_2$ | 0 |
| A-7825 | H | H | H | H | H | O | CH=NOCH$_2$CH$_3$ | H | 2-Me,6-Et | 0 |
| A-7826 | H | H | H | H | H | O | CH=NOCH$_2$CH$_3$ | H | 2-cyclopropyl,6-OMe | 0 |
| A-7827 | H | H | H | H | H | O | CH=NOCH$_2$CH$_3$ | H | 2-Me,5-Et | 0 |
| A-7828 | H | H | H | H | H | O | CH=NOCH$_2$CH$_3$ | H | 2,6-Et$_2$ | 0 |
| A-7829 | H | H | H | H | H | O | CH=NOCH$_2$CH$_3$ | H | 2-Et,6-F | 0 |
| A-7830 | H | H | H | H | H | O | CH=NOCH$_2$CH$_3$ | H | 2-CH$_2$OCH$_3$,6-Cl | 0 |

TABLE 138-continued

| compound | R¹ | R² | R³ | R⁴ | R⁵ | A | R⁶ | R⁷ | (R⁸)$_m$ | p |
|---|---|---|---|---|---|---|---|---|---|---|
| A-7831 | H | H | H | H | H | O | CH=NOCH₂CH₃ | H | 2-CH₂OCH₂CH₃,6-Cl | 0 |
| A-7832 | H | H | H | H | H | O | CH=NOCH₂CH₃ | H | 2-CH₂NMe₂ | 0 |
| A-7833 | H | H | H | H | H | O | =CHN(CH₃)₂ | | H | 0 |
| A-7834 | H | H | H | H | H | O | =CHN(CH₃)₂ | | 2-F | 0 |
| A-7835 | H | H | H | H | H | O | =CHN(CH₃)₂ | | 2-Cl | 0 |
| A-7836 | H | H | H | H | H | O | =CHN(CH₃)₂ | | 2-Br | 0 |
| A-7837 | H | H | H | H | H | O | =CHN(CH₃)₂ | | 2-OH | 0 |
| A-7838 | H | H | H | H | H | O | =CHN(CH₃)₂ | | 2-Me | 0 |
| A-7839 | H | H | H | H | H | O | =CHN(CH₃)₂ | | 2-Et | 0 |
| A-7840 | H | H | H | H | H | O | =CHN(CH₃)₂ | | 2-Pr | 0 |
| A-7841 | H | H | H | H | H | O | =CHN(CH₃)₂ | | 2-CF₃ | 0 |
| A-7842 | H | H | H | H | H | O | =CHN(CH₃)₂ | | 2-CHF₂ | 0 |
| A-7843 | H | H | H | H | H | O | =CHN(CH₃)₂ | | 2-CH₂F | 0 |
| A-7844 | H | H | H | H | H | O | =CHN(CH₃)₂ | | 2-CF₂Cl | 0 |
| A-7845 | H | H | H | H | H | O | =CHN(CH₃)₂ | | 2-cyclopropyl | 0 |
| A-7846 | H | H | H | H | H | O | =CHN(CH₃)₂ | | 2-cyclobutyl | 0 |
| A-7847 | H | H | H | H | H | O | =CHN(CH₃)₂ | | 2-cyclopentyl | 0 |
| A-7848 | H | H | H | H | H | O | =CHN(CH₃)₂ | | 2-ethenyl | 0 |
| A-7849 | H | H | H | H | H | O | =CHN(CH₃)₂ | | 2-allyl | 0 |
| A-7850 | H | H | H | H | H | O | =CHN(CH₃)₂ | | 2-(prop-1-en-1-yl) | 0 |
| A-7851 | H | H | H | H | H | O | =CHN(CH₃)₂ | | 2-(trifluoroethenyl) | 0 |
| A-7852 | H | H | H | H | H | O | =CHN(CH₃)₂ | | 2-OMe | 0 |
| A-7853 | H | H | H | H | H | O | =CHN(CH₃)₂ | | 2-OEt | 0 |
| A-7854 | H | H | H | H | H | O | =CHN(CH₃)₂ | | 2-OPr | 0 |
| A-7855 | H | H | H | H | H | O | =CHN(CH₃)₂ | | 2-O(i-Pr) | 0 |
| A-7856 | H | H | H | H | H | O | =CHN(CH₃)₂ | | 2-OCF₃ | 0 |
| A-7857 | H | H | H | H | H | O | =CHN(CH₃)₂ | | 2-OCHF₂ | 0 |
| A-7858 | H | H | H | H | H | O | =CHN(CH₃)₂ | | 2-(cyclopropyloxy) | 0 |
| A-7859 | H | H | H | H | H | O | =CHN(CH₃)₂ | | 2-(cyclobutyloxy) | 0 |
| A-7860 | H | H | H | H | H | O | =CHN(CH₃)₂ | | 2-(cyclopentyloxy) | 0 |
| A-7861 | H | H | H | H | H | O | =CHN(CH₃)₂ | | 2-((2,2-dichlorocyclopropyl)oxy) | 0 |

TABLE 139

| compound | R¹ | R² | R³ | R⁴ | R⁵ | A | R⁶ | R⁷ | (R⁸)$_m$ | p |
|---|---|---|---|---|---|---|---|---|---|---|
| A-7862 | H | H | H | H | H | O | =CHN(CH₃)₂ | | 2-(oxiran-2-yl) | 0 |
| A-7863 | H | H | H | H | H | O | =CHN(CH₃)₂ | | 2-SMe | 0 |
| A-7864 | H | H | H | H | H | O | =CHN(CH₃)₂ | | 3-SMe | 0 |
| A-7865 | H | H | H | H | H | O | =CHN(CH₃)₂ | | 2-S(=O)Me | 0 |
| A-7866 | H | H | H | H | H | O | =CHN(CH₃)₂ | | 3-S(=O)Me | 0 |
| A-7867 | H | H | H | H | H | O | =CHN(CH₃)₂ | | 2-S(=O)₂Me | 0 |
| A-7868 | H | H | H | H | H | O | =CHN(CH₃)₂ | | 3-S(=O)₂Me | 0 |
| A-7869 | H | H | H | H | H | O | =CHN(CH₃)₂ | | 2-SCF₃ | 0 |
| A-7870 | H | H | H | H | H | O | =CHN(CH₃)₂ | | 3-SCF₃ | 0 |
| A-7871 | H | H | H | H | H | O | =CHN(CH₃)₂ | | 3-S(=O)CF₃ | 0 |
| A-7872 | H | H | H | H | H | O | =CHN(CH₃)₂ | | 3-SCF(CF₃)₂ | 0 |
| A-7873 | H | H | H | H | H | O | =CHN(CH₃)₂ | | 2-(cyclopropylthio) | 0 |
| A-7874 | H | H | H | H | H | O | =CHN(CH₃)₂ | | 2-(cyclopropylsulfinyl) | 0 |
| A-7875 | H | H | H | H | H | O | =CHN(CH₃)₂ | | 2-(cyclopropylsulfonyl) | 0 |
| A-7876 | H | H | H | H | H | O | =CHN(CH₃)₂ | | 2-C(=O)Me | 0 |
| A-7877 | H | H | H | H | H | O | =CHN(CH₃)₂ | | 2-CH₂C(=O)CH₃ | 0 |
| A-7878 | H | H | H | H | H | O | =CHN(CH₃)₂ | | 2-CH₂C(=O)CF₃ | 0 |
| A-7879 | H | H | H | H | H | O | =CHN(CH₃)₂ | | 2-CH₂OH | 0 |
| A-7880 | H | H | H | H | H | O | =CHN(CH₃)₂ | | 2-CH₂OCH₃ | 0 |
| A-7881 | H | H | H | H | H | O | =CHN(CH₃)₂ | | 2-CH₂OCH₂CH₃ | 0 |
| A-7882 | H | H | H | H | H | O | =CHN(CH₃)₂ | | 2-CH₂SCH₃ | 0 |
| A-7883 | H | H | H | H | H | O | =CHN(CH₃)₂ | | 2-CH₂S(=O)CH₃ | 0 |
| A-7884 | H | H | H | H | H | O | =CHN(CH₃)₂ | | 2-CH₂S(=O)₂CH₃ | 0 |
| A-7885 | H | H | H | H | H | O | =CHN(CH₃)₂ | | 2-(benzyloxy) | 0 |
| A-7886 | H | H | H | H | H | O | =CHN(CH₃)₂ | | 2-NH₂ | 0 |
| A-7887 | H | H | H | H | H | O | =CHN(CH₃)₂ | | 2-NHMe | 0 |
| A-7888 | H | H | H | H | H | O | =CHN(CH₃)₂ | | 2-N(Me)₂ | 0 |
| A-7889 | H | H | H | H | H | O | =CHN(CH₃)₂ | | 2-(1,3-dioxolan-2-yl) | 0 |
| A-7890 | H | H | H | H | H | O | =CHN(CH₃)₂ | | 2-(1,3-dioxan-2-yl) | 0 |
| A-7891 | H | H | H | H | H | O | =CHN(CH₃)₂ | | 2-(1H-imidazol-2-yl) | 0 |
| A-7892 | H | H | H | H | H | H | =CHN(CH₃)₂ | | 2-(thiazol-2-yl) | 0 |
| A-7893 | H | H | H | H | H | H | =CHN(CH₃)₂ | | 2-(oxazol-2-yl) | 0 |
| A-7894 | H | H | H | H | H | H | =CHN(CH₃)₂ | | 2-CH=NOH | 0 |
| A-7895 | H | H | H | H | H | H | =CHN(CH₃)₂ | | 2-CH=NOMe | 0 |
| A-7896 | H | H | H | H | H | H | =CHN(CH₃)₂ | | 2-(4,5-dihydro-3-isoxazolyl) | 0 |
| A-7897 | H | H | H | H | H | H | =CHN(CH₃)₂ | | 2-CN | 0 |
| A-7898 | H | H | H | H | H | H | =CHN(CH₃)₂ | | 2-NO₂ | 0 |
| A-7899 | H | H | H | H | H | H | =CHN(CH₃)₂ | | 2-F,6-Cl | 0 |
| A-7900 | H | H | H | H | H | H | =CHN(CH₃)₂ | | 2-F,6-Me | 0 |

TABLE 139-continued

| compound | R¹ | R² | R³ | R⁴ | R⁵ | A | R⁶ | R⁷ | $(R^8)_m$ | p |
|---|---|---|---|---|---|---|---|---|---|---|
| A-7901 | H | H | H | H | H | H | | =CHN(CH₃)₂ | 3-F,6-Me | 0 |
| A-7902 | H | H | H | H | H | H | | =CHN(CH₃)₂ | 4-F,2-Me | 0 |
| A-7903 | H | H | H | H | H | H | | =CHN(CH₃)₂ | 2-F,6-OMe | 0 |
| A-7904 | H | H | H | H | H | H | | =CHN(CH₃)₂ | 3-F,6-OMe | 0 |
| A-7905 | H | H | H | H | H | H | | =CHN(CH₃)₂ | 2,6-Cl₂ | 0 |
| A-7906 | H | H | H | H | H | H | | =CHN(CH₃)₂ | 2-Cl,6-Me | 0 |
| A-7907 | H | H | H | H | H | H | | =CHN(CH₃)₂ | 3-Cl,6-Me | 0 |
| A-7908 | H | H | H | H | H | H | | =CHN(CH₃)₂ | 4-Cl,2-Me | 0 |
| A-7909 | H | H | H | H | H | H | | =CHN(CH₃)₂ | 2-Cl,5-CF₃ | 0 |
| A-7910 | H | H | H | H | H | H | | =CHN(CH₃)₂ | 2-Cl,6-CF₃ | 0 |
| A-7911 | H | H | H | H | H | H | | =CHN(CH₃)₂ | 2-Cl,6-OMe | 0 |
| A-7912 | H | H | H | H | H | H | | =CHN(CH₃)₂ | 3-Cl,6-OMe | 0 |
| A-7913 | H | H | H | H | H | H | | =CHN(CH₃)₂ | 4-Cl,2-OMe | 0 |
| A-7914 | H | H | H | H | H | H | | =CHN(CH₃)₂ | 2,4-Me₂ | 0 |
| A-7915 | H | H | H | H | H | H | | =CHN(CH₃)₂ | 2,5-Me₂ | 0 |
| A-7916 | H | H | H | H | H | H | | =CHN(CH₃)₂ | 2,6-Me₂ | 0 |
| A-7917 | H | H | H | H | H | H | | =CHN(CH₃)₂ | 2-Me,4-CF₃ | 0 |
| A-7918 | H | H | H | H | H | H | | =CHN(CH₃)₂ | 2-Me,5-CF₃ | 0 |

TABLE 140

| compound | R¹ | R² | R³ | R⁴ | R⁵ | A | R⁶ | R⁷ | $(R^8)_m$ | p |
|---|---|---|---|---|---|---|---|---|---|---|
| A-7919 | H | H | H | H | H | O | | =CHN(CH₃)₂ | 2-Me, 6-CF₃ | O |
| A-7920 | H | H | H | H | H | O | | =CHN(CH₃)₂ | 2-Me, 4-OMe | O |
| A-7921 | H | H | H | H | H | O | | =CHN(CH₃)₂ | 2-Me, 5-Me | O |
| A-7922 | H | H | H | H | H | O | | =CHN(CH₃)₂ | 2-Me, 6-Me | O |
| A-7923 | H | H | H | H | H | O | | =CHN(CH₃)₂ | 3-Me, 6-OMe | O |
| A-7924 | H | H | H | H | H | O | | =CHN(CH₃)₂ | 4-Me, 2-OMe | O |
| A-7925 | H | H | H | H | H | O | | =CHN(CH₃)₂ | 2,5-OMe₂ | O |
| A-7926 | H | H | H | H | H | O | | =CHN(CH₃)₂ | 2,6-OMe₂ | O |
| A-7927 | H | H | H | H | H | O | | =CHN(CH₃)₂ | 2-OMe, 6-CF₃ | O |
| A-7928 | H | H | H | H | H | O | | =CHN(CH₃)₂ | 2-CHF₂, 5-F | O |
| A-7929 | H | H | H | H | H | O | | =CHN(CH₃)₂ | 2-CHF₂, 6-F | O |
| A-7930 | H | H | H | H | H | O | | =CHN(CH₃)₂ | 2-CHF₂, 5-Me | O |
| A-7931 | H | H | H | H | H | O | | =CHN(CH₃)₂ | 2-CHF₂, 6-Me | O |
| A-7932 | H | H | H | H | H | O | | =CHN(CH₃)₂ | 2-cyclopropyl, 5-F | O |
| A-7933 | H | H | H | H | H | O | | =CHN(CH₃)₂ | 2-cyclopropyl, 6-+F | O |
| A-7934 | H | H | H | H | H | O | | =CHN(CH₃)₂ | 2-cyclopropyl, 5-Me | O |
| A-7935 | H | H | H | H | H | O | | =CHN(CH₃)₂ | 2-cyclopropyl, 6-Me | O |
| A-7936 | H | H | H | H | H | O | | =CHN(CH₃)₂ | 2-ethenyl, 6-F | O |
| A-7937 | H | H | H | H | H | O | | =CHN(CH₃)₂ | 2-ethenyl, 6-Me | O |
| A-7938 | H | H | H | H | H | O | | =CHN(CH₃)₂ | 2-OEt, 5-F | O |
| A-7939 | H | H | H | H | H | O | | =CHN(CH₃)₂ | 2-OEt, 6-F | O |
| A-7940 | H | H | H | H | H | O | | =CHN(CH₃)₂ | 2-OEt, 5-Cl | O |
| A-7941 | H | H | H | H | H | O | | =CHN(CH₃)₂ | 2-OEt, 6-Cl | O |
| A-7942 | H | H | H | H | H | O | | =CHN(CH₃)₂ | 2-OEt, 5-Me | O |
| A-7943 | H | H | H | H | H | O | | =CHN(CH₃)₂ | 2-OEt, 6-Me | O |
| A-7944 | H | H | H | H | H | O | | =CHN(CH₃)₂ | 2-OCHF₂, 5-F | O |
| A-7945 | H | H | H | H | H | O | | =CHN(CH₃)₂ | 2-OCHF₂, 6-F | O |
| A-7946 | H | H | H | H | H | O | | =CHN(CH₃)₂ | 2-OCHF₂, 5-Me | O |
| A-7947 | H | H | H | H | H | O | | =CHN(CH₃)₂ | 2-OCHF₂, 6-Me | O |
| A-7948 | H | H | H | H | H | O | | =CHN(CH₃)₂ | 2-(cyclopropyloxy), 5-F | O |
| A-7949 | H | H | H | H | H | O | | =CHN(CH₃)₂ | 2-(cyclopropyloxy), 6-F | O |
| A-7950 | H | H | H | H | H | O | | =CHN(CH₃)₂ | 2-(cyclopropyloxy), 5-Me | O |
| A-7951 | H | H | H | H | H | O | | =CHN(CH₃)₂ | 2-(cyclopropyloxy), 6-Me | O |
| A-7952 | H | H | H | H | H | O | | =CHN(CH₃)₂ | 2-SMe, 5-F | O |
| A-7953 | H | H | H | H | H | O | | =CHN(CH₃)₂ | 2-SMe, 6-F | O |
| A-7954 | H | H | H | H | H | O | | =CHN(CH₃)₂ | 2-SMe, 5-Me | O |
| A-7955 | H | H | H | H | H | O | | =CHN(CH₃)₂ | 2-SMe, 6-Me | O |
| A-7956 | H | H | H | H | H | O | | =CHN(CH₃)₂ | 2-S(=O)Me, 5-F | O |
| A-7957 | H | H | H | H | H | O | | =CHN(CH₃)₂ | 2-S(=O)Me, 6-F | O |
| A-7958 | H | H | H | H | H | O | | =CHN(CH₃)₂ | 2-S(=O)Me, 5-Me | O |
| A-7959 | H | H | H | H | H | O | | =CHN(CH₃)₂ | 2-S(=O)Me, 6-Me | O |
| A-7960 | H | H | H | H | H | O | | =CHN(CH₃)₂ | 2-S(=O)₂Me, 5-F | O |
| A-7961 | H | H | H | H | H | O | | =CHN(CH₃)₂ | 2-S(=O)₂Me, 6-F | O |
| A-7962 | H | H | H | H | H | O | | =CHN(CH₃)₂ | 2-S(=O)₂Me, 5-Me | O |
| A-7963 | H | H | H | H | H | O | | =CHN(CH₃)₂ | 2-S(=O)₂Me, 6-Me | O |
| A-7964 | H | H | H | H | H | O | | =CHN(CH₃)₂ | 2-SCF₃, 5-F | O |
| A-7965 | H | H | H | H | H | O | | =CHN(CH₃)₂ | 2-SCF₃, 6-F | O |
| A-7966 | H | H | H | H | H | O | | =CHN(CH₃)₂ | 2-SCF₃, 5-Me | O |
| A-7967 | H | H | H | H | H | O | | =CHN(CH₃)₂ | 2-SCF₃, 6-Me | O |
| A-7968 | H | H | H | H | H | O | | =CHN(CH₃)₂ | 2-S(=O)CF₃, 5-F | O |
| A-7969 | H | H | H | H | H | O | | =CHN(CH₃)₂ | 2-S(=O)CF₃, 6-F | O |
| A-7970 | H | H | H | H | H | O | | =CHN(CH₃)₂ | 2-S(=O)CF₃, 5-Me | O |

TABLE 140-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7971 | H | H | H | H | H | O | =CHN(CH$_3$)$_2$ | 2-S(=O)CF$_3$, | 6-Me | 0 |
| A-7972 | H | H | H | H | H | O | =CHN(CH$_3$)$_2$ | 2-S(=O)$_2$CF$_3$, | 5-F | 0 |
| A-7973 | H | H | H | H | H | O | =CHN(CH$_3$)$_2$ | 2-S(=O)$_2$CF$_3$, | 6-F | 0 |
| A-7974 | H | H | H | H | H | O | =CHN(CH$_3$)$_2$ | 2-S(=O)$_2$CF$_3$, | 5-Me | 0 |
| A-7975 | H | H | H | H | H | O | =CHN(CH$_3$)$_2$ | 2-S(=O)$_2$CF$_3$, | 6-Me | 0 |

TABLE 141

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-7976 | H | H | H | H | H | O | =CHN(CH$_3$)$_2$ | 2-(cyclopropylthio), | 5-F | 0 |
| A-7977 | H | H | H | H | H | O | =CHN(CH$_3$)$_2$ | 2-(cyclopropylthio), | 6-F | 0 |
| A-7978 | H | H | H | H | H | O | =CHN(CH$_3$)$_2$ | 2-(cyclopropylthio), | 5-Me | 0 |
| A-7979 | H | H | H | H | H | O | =CHN(CH$_3$)$_2$ | 2-(cyclopropylthio), | 6-Me | 0 |
| A-7980 | H | H | H | H | H | O | =CHN(CH$_3$)$_2$ | 2-C(=O)Me, | 5-F | 0 |
| A-7981 | H | H | H | H | H | O | =CHN(CH$_3$)$_2$ | 2-C(=O)Me, | 6-F | 0 |
| A-7982 | H | H | H | H | H | O | =CHN(CH$_3$)$_2$ | 2-C(=O)Me, | 5-Me | 0 |
| A-7983 | H | H | H | H | H | O | =CHN(CH$_3$)$_2$ | 2-C(=O)Me, | 6-Me | 0 |
| A-7984 | H | H | H | H | H | O | =CHN(CH$_3$)$_2$ | 2-CH$_2$OH, | 5-F | 0 |
| A-7985 | H | H | H | H | H | O | =CHN(CH$_3$)$_2$ | 2-CH$_2$OH, | 6-F | 0 |
| A-7986 | H | H | H | H | H | O | =CHN(CH$_3$)$_2$ | 2-CH$_2$OH, | 5-Me | 0 |
| A-7987 | H | H | H | H | H | O | =CHN(CH$_3$)$_2$ | 2-CH$_2$OH, | 6-Me | 0 |
| A-7988 | H | H | H | H | H | O | =CHN(CH$_3$)$_2$ | 2-CH$_2$OCH$_3$, | 4-F | 0 |
| A-7989 | H | H | H | H | H | O | =CHN(CH$_3$)$_2$ | 2-CH$_2$OCH$_3$, | 5-F | 0 |
| A-7990 | H | H | H | H | H | O | =CHN(CH$_3$)$_2$ | 2-CH$_2$OCH$_3$, | 6-F | 0 |
| A-7991 | H | H | H | H | H | O | =CHN(CH$_3$)$_2$ | 2-CH$_2$OCH$_3$, | 4-Me | 0 |
| A-7992 | H | H | H | H | H | O | =CHN(CH$_3$)$_2$ | 2-CH$_2$OCH$_3$, | 5-Me | 0 |
| A-7993 | H | H | H | H | H | O | =CHN(CH$_3$)$_2$ | 2-CH$_2$OCH$_3$, | 6-Me | 0 |
| A-7994 | H | H | H | H | H | O | =CHN(CH$_3$)$_2$ | 2-OC(=O)CH$_3$, | 5-F | 0 |
| A-7995 | H | H | H | H | H | O | =CHN(CH$_3$)$_2$ | 2-OC(=O)CH$_3$, | 6-F | 0 |
| A-7996 | H | H | H | H | H | O | =CHN(CH$_3$)$_2$ | 2-OC(=O)CH$_3$, | 5-Me | 0 |
| A-7997 | H | H | H | H | H | O | =CHN(CH$_3$)$_2$ | 2-OC(=O)CH$_3$, | 6-Me | 0 |
| A-7998 | H | H | H | H | H | O | =CHN(CH$_3$)$_2$ | 2-OS(=O)$_2$CH$_3$, | 5-F | 0 |
| A-7999 | H | H | H | H | H | O | =CHN(CH$_3$)$_2$ | 2-OS(=O)$_2$CH$_3$, | 6-F | 0 |
| A-8000 | H | H | H | H | H | O | =CHN(CH$_3$)$_2$ | 2-OS(=O)$_2$CH$_3$, | 5-Me | 0 |
| A-8001 | H | H | H | H | H | O | =CHN(CH$_3$)$_2$ | 2-OS(=O)$_2$CH$_3$, | 6-Me | 0 |
| A-8002 | H | H | H | H | H | O | =CHN(CH$_3$)$_2$ | 2-CH$_2$SCH$_3$, | 5-F | 0 |
| A-8003 | H | H | H | H | H | O | =CHN(CH$_3$)$_2$ | 2-CH$_2$SCH$_3$, | 6-F | 0 |
| A-8004 | H | H | H | H | H | O | =CHN(CH$_3$)$_2$ | 2-CH$_2$SCH$_3$, | 5-Me | 0 |
| A-8005 | H | H | H | H | H | O | =CHN(CH$_3$)$_2$ | 2-CH$_2$SCH$_3$, | 6-Me | 0 |
| A-8006 | H | H | H | H | H | O | =CHN(CH$_3$)$_2$ | 2-NMe$_2$, | 5-F | 0 |
| A-8007 | H | H | H | H | H | O | =CHN(CH$_3$)$_2$ | 2-NMe$_2$, | 6-F | 0 |
| A-8008 | H | H | H | H | H | O | =CHN(CH$_3$)$_2$ | 2-NMe$_2$, | 5-Me | 0 |
| A-8009 | H | H | H | H | H | O | =CHN(CH$_3$)$_2$ | 2-NMe$_2$, | 6-Me | 0 |
| A-8010 | H | H | H | H | H | O | =CHN(CH$_3$)$_2$ | 2-CN, | 4-F | 0 |
| A-8011 | H | H | H | H | H | O | =CHN(CH$_3$)$_2$ | 2-CN, | 5-F | 0 |
| A-8012 | H | H | H | H | H | O | =CHN(CH$_3$)$_2$ | 2-CN, | 6-F | 0 |
| A-8013 | H | H | H | H | H | O | =CHN(CH$_3$)$_2$ | 2-CN, | 6-Me | 0 |
| A-8014 | H | H | H | H | H | O | =CHN(CH$_3$)$_2$ | 2-CN, | 5-OMe | 0 |
| A-8015 | H | H | H | H | H | O | =CHN(CH$_3$)$_2$ | 2-CN, | 6-OMe | 0 |
| A-8016 | H | H | H | H | H | O | =CHN(CH$_3$)$_2$ | 3-CN, | 6-Me | 0 |
| A-8017 | H | H | H | H | H | O | =CHN(CH$_3$)$_2$ | 3-CN, | 6-OMe | 0 |
| A-8018 | H | H | H | H | H | O | =CHN(CH$_3$)$_2$ | 4-CN, | 2-Me | 0 |
| A-8019 | H | H | H | H | H | O | =CHN(CH$_3$)$_2$ | 4-CN, | 2-OMe | 0 |
| A-8020 | H | H | H | H | H | O | =CHN(CH$_3$)$_2$ | 2-NO$_2$, | 4-F | 0 |
| A-8021 | H | H | H | H | H | O | =CHN(CH$_3$)$_2$ | 2-NO$_2$, | 5-F | 0 |
| A-8022 | H | H | H | H | H | O | =CHN(CH$_3$)$_2$ | 2-NO$_2$, | 6-F | 0 |
| A-8023 | H | H | H | H | H | O | =CHN(CH$_3$)$_2$ | 2-NO$_2$, | 4-Me | 0 |
| A-8024 | H | H | H | H | H | O | =CHN(CH$_3$)$_2$ | 2-NO$_2$, | 5-Me | 0 |
| A-8025 | H | H | H | H | H | O | =CHN(CH$_3$)$_2$ | 2-NO$_2$, | 6-Me | 0 |
| A-8026 | H | H | H | H | H | O | =CHN(CH$_3$)$_2$ | 2-Me, | 4,5-F$_2$ | 0 |
| A-8027 | H | H | H | H | H | O | =CHN(CH$_3$)$_2$ | 2-Me, | 6-Et | 0 |
| A-8028 | H | H | H | H | H | O | =CHN(CH$_3$)$_2$ | 2-cyclopropyl, | 6-OMe | 0 |
| A-8029 | H | H | H | H | H | O | =CHN(CH$_3$)$_2$ | 2-Me, | 5-Et | 0 |
| A-8030 | H | H | H | H | H | O | =CHN(CH$_3$)$_2$ | 2,6-Et$_2$ | | 0 |
| A-8031 | H | H | H | H | H | O | =CHN(CH$_3$)$_2$ | 2-Et, | 6-F | 0 |
| A-8032 | H | H | H | H | H | O | =CHN(CH$_3$)$_2$ | 2-CH$_2$OCH$_3$, | 6-Cl | 0 |

TABLE 142

| compound | R¹ | R² | R³ | R⁴ | R⁵ | A | R⁶ | R⁷ | $(R^8)_m$ | p |
|---|---|---|---|---|---|---|---|---|---|---|
| A-8033 | H | H | H | H | H | O | =CHN(CH₃)₂ | 2-CH₂OCH₂CH₃, 6-Cl | | O |
| A-8034 | H | H | H | H | H | O | =CHN(CH₃)₂ | 2-CH₂NMe₂ | | O |
| A-8035 | H | H | H | H | H | O | CH₃ | CH₃ | H | O |
| A-8036 | H | H | H | H | H | O | CH₃ | CH₃ | 2-F | O |
| A-8037 | H | H | H | H | H | O | CH₃ | CH₃ | 2-Cl | O |
| A-8038 | H | H | H | H | H | O | CH₃ | CH₃ | 2-Br | O |
| A-8039 | H | H | H | H | H | O | CH₃ | CH₃ | 2-OH | O |
| A-8040 | H | H | H | H | H | O | CH₃ | CH₃ | 2-Me | O |
| A-8041 | H | H | H | H | H | O | CH₃ | CH₃ | 2-Et | O |
| A-8042 | H | H | H | H | H | O | CH₃ | CH₃ | 2-Pr | O |
| A-8043 | H | H | H | H | H | O | CH₃ | CH₃ | 2-CF₃ | O |
| A-8044 | H | H | H | H | H | O | CH₃ | CH₃ | 2-CHF₂ | O |
| A-8045 | H | H | H | H | H | O | CH₃ | CH₃ | 2-CH₂F | O |
| A-8046 | H | H | H | H | H | O | CH₃ | CH₃ | 2-CF₂Cl | O |
| A-8047 | H | H | H | H | H | O | CH₃ | CH₃ | 2-cyclopropyl | O |
| A-8048 | H | H | H | H | H | O | CH₃ | CH₃ | 2-cyclobutyl | O |
| A-8049 | H | H | H | H | H | O | CH₃ | CH₃ | 2-cyclopentyl | O |
| A-8050 | H | H | H | H | H | O | CH₃ | CH₃ | 2-ethenyl | O |
| A-8051 | H | H | H | H | H | O | CH₃ | CH₃ | 2-allyl | O |
| A-8052 | H | H | H | H | H | O | CH₃ | CH₃ | 2-(prop-1-en-1-yl) | O |
| A-8053 | H | H | H | H | H | O | CH₃ | CH₃ | 2-(trifluoroethenyl) | O |
| A-8054 | H | H | H | H | H | O | CH₃ | CH₃ | 2-OMe | O |
| A-8055 | H | H | H | H | H | O | CH₃ | CH₃ | 2-OEt | O |
| A-8056 | H | H | H | H | H | O | CH₃ | CH₃ | 2-OPr | O |
| A-8057 | H | H | H | H | H | O | CH₃ | CH₃ | 2-O(i-Pr) | O |
| A-8058 | H | H | H | H | H | O | CH₃ | CH₃ | 2-OCF₃ | O |
| A-8059 | H | H | H | H | H | O | CH₃ | CH₃ | 2-OCHF₂ | O |
| A-8060 | H | H | H | H | H | O | CH₃ | CH₃ | 2-(cyclopropyloxy) | O |
| A-8061 | H | H | H | H | H | O | CH₃ | CH₃ | 2-(cyclobutyloxy) | O |
| A-8062 | H | H | H | H | H | O | CH₃ | CH₃ | 2-(cyclopentyloxy) | O |
| A-8063 | H | H | H | H | H | O | CH₃ | CH₃ | 2-((2,2-dichlorocyclopropyl)oxy) | O |
| A-8064 | H | H | H | H | H | O | CH₃ | CH₃ | 2-(oxiran-2-yl) | O |
| A-8065 | H | H | H | H | H | O | CH₃ | CH₃ | 2-SMe | O |
| A-8066 | H | H | H | H | H | O | CH₃ | CH₃ | 3-SMe | O |
| A-8067 | H | H | H | H | H | O | CH₃ | CH₃ | 2-S(=O)Me | O |
| A-8068 | H | H | H | H | H | O | CH₃ | CH₃ | 3-S(=O)Me | O |
| A-8069 | H | H | H | H | H | O | CH₃ | CH₃ | 2-S(=O)₂Me | O |
| A-8070 | H | H | H | H | H | O | CH₃ | CH₃ | 3-S(=O)₂Me | O |
| A-8071 | H | H | H | H | H | O | CH₃ | CH₃ | 2-SCF₃ | O |
| A-8072 | H | H | H | H | H | O | CH₃ | CH₃ | 3-SCF₃ | O |
| A-8073 | H | H | H | H | H | O | CH₃ | CH₃ | 3-S(=O)CF₃ | O |
| A-8074 | H | H | H | H | H | O | CH₃ | CH₃ | 3-SCF(CF₃)₂ | O |
| A-8075 | H | H | H | H | H | O | CH₃ | CH₃ | 2-(cyclopropylthio) | O |
| A-8076 | H | H | H | H | H | O | CH₃ | CH₃ | 2-(cyclopropylsulfinyl) | O |
| A-8077 | H | H | H | H | H | O | CH₃ | CH₃ | 2-(cyclopropylsulfonyl) | O |
| A-8078 | H | H | H | H | H | O | CH₃ | CH₃ | 2-C(=O)Me | O |
| A-8079 | H | H | H | H | H | O | CH₃ | CH₃ | 2-CH₂C(=O)CH₃ | O |
| A-8080 | H | H | H | H | H | O | CH₃ | CH₃ | 2-CH₂C(=O)CF₃ | O |
| A-8081 | H | H | H | H | H | O | CH₃ | CH₃ | 2-CH₂OH | O |
| A-8082 | H | H | H | H | H | O | CH₃ | CH₃ | 2-CH₂OCH₃ | O |
| A-8083 | H | H | H | H | H | O | CH₃ | CH₃ | 2-CH₂OCH₂CH₃ | O |
| A-8084 | H | H | H | H | H | O | CH₃ | CH₃ | 2-CH₂SCH₃ | O |
| A-8085 | H | H | H | H | H | O | CH₃ | CH₃ | 2-CH₂S(=O)CH₃ | O |
| A-8086 | H | H | H | H | H | O | CH₃ | CH₃ | 2-CH₂S(=O)₂CH₃ | O |
| A-8087 | H | H | H | H | H | O | CH₃ | CH₃ | 2-(benzyloxy) | O |
| A-8088 | H | H | H | H | H | O | CH₃ | CH₃ | 2-NH₂ | O |
| A-8089 | H | H | H | H | H | O | CH₃ | CH₃ | 2-NHMe | O |

TABLE 143

| compound | R¹ | R² | R³ | R⁴ | R⁵ | A | R⁶ | R⁷ | $(R^8)_m$ | p |
|---|---|---|---|---|---|---|---|---|---|---|
| A-8090 | H | H | H | H | H | O | CH₃ | CH₃ | 2-N(Me)₂ | O |
| A-8091 | H | H | H | H | H | O | CH₃ | CH₃ | 2-(1,3-dioxolan-2-yl) | O |
| A-8092 | H | H | H | H | H | O | CH₃ | CH₃ | 2-(1,3-dioxan-2-yl) | O |
| A-8093 | H | H | H | H | H | O | CH₃ | CH₃ | 2-(1H-midazol-2-yl) | O |
| A-8094 | H | H | H | H | H | O | CH₃ | CH₃ | 2-(thiazol-2-yl) | O |
| A-8095 | H | H | H | H | H | O | CH₃ | CH₃ | 2-(oxazol-2-yl) | O |
| A-8096 | H | H | H | H | H | O | CH₃ | CH₃ | 2-CH=NOH | O |
| A-8097 | H | H | H | H | H | O | CH₃ | CH₃ | 2-CH=NOMe | O |
| A-8098 | H | H | H | H | H | O | CH₃ | CH₃ | 2-(4,5-dihydro-3-isoxazolyl) | O |
| A-8099 | H | H | H | H | H | O | CH₃ | CH₃ | 2-CN | O |
| A-8100 | H | H | H | H | H | O | CH₃ | CH₃ | 2-NO₂ | O |
| A-8101 | H | H | H | H | H | O | CH₃ | CH₃ | 2-F, 6-Cl | O |
| A-8102 | H | H | H | H | H | O | CH₃ | CH₃ | 2-F, 6-Me | O |

TABLE 143-continued

| compound | R¹ | R² | R³ | R⁴ | R⁵ | A | R⁶ | R⁷ | (R⁸)$_m$ | p |
|---|---|---|---|---|---|---|---|---|---|---|
| A-8103 | H | H | H | H | H | O | CH₃ | CH₃ | 3-F, 6-Me | 0 |
| A-8104 | H | H | H | H | H | O | CH₃ | CH₃ | 4-F, 2-Me | 0 |
| A-8105 | H | H | H | H | H | O | CH₃ | CH₃ | 2-F, 6-OMe | 0 |
| A-8106 | H | H | H | H | H | O | CH₃ | CH₃ | 3-F, 6-OMe | 0 |
| A-8107 | H | H | H | H | H | O | CH₃ | CH₃ | 2,6-Cl₂ | 0 |
| A-8108 | H | H | H | H | H | O | CH₃ | CH₃ | 2-Cl, 6-Me | 0 |
| A-8109 | H | H | H | H | H | O | CH₃ | CH₃ | 3-Cl, 6-Me | 0 |
| A-8110 | H | H | H | H | H | O | CH₃ | CH₃ | 4-Cl, 2-Me | 0 |
| A-8111 | H | H | H | H | H | O | CH₃ | CH₃ | 2-Cl, 5-CF₃ | 0 |
| A-8112 | H | H | H | H | H | O | CH₃ | CH₃ | 2-Cl, 6-CF₃ | 0 |
| A-8113 | H | H | H | H | H | O | CH₃ | CH₃ | 2-Cl, 6-OMe | 0 |
| A-8114 | H | H | H | H | H | O | CH₃ | CH₃ | 3-Cl, 6-OMe | 0 |
| A-8115 | H | H | H | H | H | O | CH₃ | CH₃ | 4-Cl, 2-OMe | 0 |
| A-8116 | H | H | H | H | H | O | CH₃ | CH₃ | 2,4-Me₂ | 0 |
| A-8117 | H | H | H | H | H | O | CH₃ | CH₃ | 2,5-Me₂ | 0 |
| A-8118 | H | H | H | H | H | O | CH₃ | CH₃ | 2,6-Me₂ | 0 |
| A-8119 | H | H | H | H | H | O | CH₃ | CH₃ | 2-Me, 4-CF₃ | 0 |
| A-8120 | H | H | H | H | H | O | CH₃ | CH₃ | 2-Me, 5-CF₃ | 0 |
| A-8121 | H | H | H | H | H | O | CH₃ | CH₃ | 2-Me, 6-CF₃ | 0 |
| A-8122 | H | H | H | H | H | O | CH₃ | CH₃ | 2-Me, 4-OMe | 0 |
| A-8123 | H | H | H | H | H | O | CH₃ | CH₃ | 2-Me, 5-OMe | 0 |
| A-8124 | H | H | H | H | H | O | CH₃ | CH₃ | 2-Me, 6-OMe | 0 |
| A-8125 | H | H | H | H | H | O | CH₃ | CH₃ | 3-Me, 6-OMe | 0 |
| A-8126 | H | H | H | H | H | O | CH₃ | CH₃ | 4-Me, 2-OMe | 0 |
| A-8127 | H | H | H | H | H | O | CH₃ | CH₃ | 2,5-OMe₂ | 0 |
| A-8128 | H | H | H | H | H | O | CH₃ | CH₃ | 2,6-OMe₂ | 0 |
| A-8129 | H | H | H | H | H | O | CH₃ | CH₃ | 2-OMe, 6-CF₃ | 0 |
| A-8130 | H | H | H | H | H | O | CH₃ | CH₃ | 2-CHF₂, 5-F | 0 |
| A-8131 | H | H | H | H | H | O | CH₃ | CH₃ | 2-CHF₂, 6-F | 0 |
| A-8132 | H | H | H | H | H | O | CH₃ | CH₃ | 2-CHF₂, 5-Me | 0 |
| A-8133 | H | H | H | H | H | O | CH₃ | CH₃ | 2-CHF₂, 6-Me | 0 |
| A-8134 | H | H | H | H | H | O | CH₃ | CH₃ | 2-cyclopropyl, 5-F | 0 |
| A-8135 | H | H | H | H | H | O | CH₃ | CH₃ | 2-cyclopropyl, 6-F | 0 |
| A-8136 | H | H | H | H | H | O | CH₃ | CH₃ | 2-cyclopropyl, 5-Me | 0 |
| A-8137 | H | H | H | H | H | O | CH₃ | CH₃ | 2-cyclopropyl, 6-Me | 0 |
| A-8138 | H | H | H | H | H | O | CH₃ | CH₃ | 2-ethenyl, 6 F | 0 |
| A-8139 | H | H | H | H | H | O | CH₃ | CH₃ | 2-ethenyl, 6-Me | 0 |
| A-8140 | H | H | H | H | H | O | CH₃ | CH₃ | 2-OEt, 5-F | 0 |
| A-8141 | H | H | H | H | H | O | CH₃ | CH₃ | 2-OEt, 6-F | 0 |
| A-8142 | H | H | H | H | H | O | CH₃ | CH₃ | 2-OEt, 5-Cl | 0 |
| A-8143 | H | H | H | H | H | O | CH₃ | CH₃ | 2-OEt, 6-Cl | 0 |
| A-8144 | H | H | H | H | H | O | CH₃ | CH₃ | 2-OEt, 5-Me | 0 |
| A-8145 | H | H | H | H | H | O | CH₃ | CH₃ | 2-OEt, 6-Me | 0 |
| A-8146 | H | H | H | H | H | O | CH₃ | CH₃ | 2-OCHF₂, 5-F | 0 |

TABLE 144

| compound | R¹ | R² | R³ | R⁴ | R⁵ | A | R⁶ | R⁷ | (R⁸)$_m$ | p |
|---|---|---|---|---|---|---|---|---|---|---|
| A-8147 | H | H | H | H | H | O | CH₃ | CH₃ | 2-OCHF₂, 6-F | 0 |
| A-8148 | H | H | H | H | H | O | CH₃ | CH₃ | 2-OCHF₂, 5-Me | 0 |
| A-8149 | H | H | H | H | H | O | CH₃ | CH₃ | 2-OCHF₂, 6-Me | 0 |
| A-8150 | H | H | H | H | H | O | CH₃ | CH₃ | 2-(cyclopropyloxy), 5-F | 0 |
| A-8151 | H | H | H | H | H | O | CH₃ | CH₃ | 2-(cyclopropyloxy), 6-F | 0 |
| A-8152 | H | H | H | H | H | O | CH₃ | CH₃ | 2-(cyclopropyloxy), 5-Me | 0 |
| A-8153 | H | H | H | H | H | O | CH₃ | CH₃ | 2-(cyclopropyloxy), 6-Me | 0 |
| A-8154 | H | H | H | H | H | O | CH₃ | CH₃ | 2-SMe, 5-F | 0 |
| A-8155 | H | H | H | H | H | O | CH₃ | CH₃ | 2-SMe, 6-F | 0 |
| A-8156 | H | H | H | H | H | O | CH₃ | CH₃ | 2-SMe, 5-Me | 0 |
| A-8157 | H | H | H | H | H | O | CH₃ | CH₃ | 2-SMe, 6-Me | 0 |
| A-8158 | H | H | H | H | H | O | CH₃ | CH₃ | 2-S(=O)Me, 5-F | 0 |
| A-8159 | H | H | H | H | H | O | CH₃ | CH₃ | 2-S(=O)Me, 6-F | 0 |
| A-8160 | H | H | H | H | H | O | CH₃ | CH₃ | 2-S(=O)Me, 5-Me | 0 |
| A-8161 | H | H | H | H | H | O | CH₃ | CH₃ | 2-S(=O)Me, 6-Me | 0 |
| A-8162 | H | H | H | H | H | O | CH₃ | CH₃ | 2-S(=O)₂Me, 5-F | 0 |
| A-8163 | H | H | H | H | H | O | CH₃ | CH₃ | 2-S(=O)₂Me, 6-F | 0 |
| A-8164 | H | H | H | H | H | O | CH₃ | CH₃ | 2-S(=O)₂Me, 5-Me | 0 |
| A-8165 | H | H | H | H | H | O | CH₃ | CH₃ | 2-S(=O)₂Me, 6-Me | 0 |
| A-8166 | H | H | H | H | H | O | CH₃ | CH₃ | 2-SCF₃, 5-F | 0 |
| A-8167 | H | H | H | H | H | O | CH₃ | CH₃ | 2-SCF₃, 6-F | 0 |
| A 8168 | H | H | H | H | H | O | CH₃ | CH₃ | 2-SCF₃, 5-Me | 0 |
| A-8169 | H | H | H | H | H | O | CH₃ | CH₃ | 2-SCF₃, 6-Me | 0 |
| A-8170 | H | H | H | H | H | O | CH₃ | CH₃ | 2-S(=O)CF₃, 5-F | 0 |
| A-8171 | H | H | H | H | H | O | CH₃ | CH₃ | 2-S(=O)CF₃, 6-F | 0 |
| A-8172 | H | H | H | H | H | O | CH₃ | CH₃ | 2-S(=O)CF₃, 5-Me | 0 |

TABLE 144-continued

| compound | R¹ | R² | R³ | R⁴ | R⁵ | A | R⁶ | R⁷ | (R⁸)ₘ | p |
|---|---|---|---|---|---|---|---|---|---|---|
| A-8173 | H | H | H | H | H | O | CH₃ | CH₃ | 2-S(=O)CF₃, 6-Me | O |
| A-8174 | H | H | H | H | H | O | CH₃ | CH₃ | 2-S(=O)₂CF₃, 5-F | O |
| A-8175 | H | H | H | H | H | O | CH₃ | CH₃ | 2-S(=O)₂CF₃, 6-F | O |
| A-8176 | H | H | H | H | H | O | CH₃ | CH₃ | 2-S(=O)₂CF₃, 5-Me | O |
| A-8177 | H | H | H | H | H | O | CH₃ | CH₃ | 2-S(=O)₂CF₃, 6-Me | O |
| A-8178 | H | H | H | H | H | O | CH₃ | CH₃ | 2-(cyclopropylthio), 5-F | O |
| A-8179 | H | H | H | H | H | O | CH₃ | CH₃ | 2-(cyclopropylthio), 6-F | O |
| A 8180 | H | H | H | H | H | O | CH₃ | CH₃ | 2-(cyclopropylthio), 5-Me | O |
| A-8181 | H | H | H | H | H | O | CH₃ | CH₃ | 2-(cyclopropylthio), 6-Me | O |
| A-8182 | H | H | H | H | H | O | CH₃ | CH₃ | 2-C(=O)Me, 5-F | O |
| A-8183 | H | H | H | H | H | O | CH₃ | CH₃ | 2-C(=O)Me, 6-F | O |
| A-8184 | H | H | H | H | H | O | CH₃ | CH₃ | 2-C(=O)Me, 5-Me | O |
| A-8185 | H | H | H | H | H | O | CH₃ | CH₃ | 2-C(=O)Me, 6-Me | O |
| A-8186 | H | H | H | H | H | O | CH₃ | CH₃ | 2-CH₂OH, 5-F | O |
| A-8187 | H | H | H | H | H | O | CH₃ | CH₃ | 2-CH₂OH, 6-F | O |
| A-8188 | H | H | H | H | H | O | CH₃ | CH₃ | 2-CH₂OH, 5-Me | O |
| A-8189 | H | H | H | H | H | O | CH₃ | CH₃ | 2-CH₂OH, 6-Me | O |
| A-8190 | H | H | H | H | H | O | CH₃ | CH₃ | 2-CH₂OCH₃, 4-F | O |
| A-8191 | H | H | H | H | H | O | CH₃ | CH₃ | 2-CH₂OCH₃, 5-F | O |
| A-8192 | H | H | H | H | H | O | CH₃ | CH₃ | 2-CH₂OCH₃, 6-F | O |
| A-8193 | H | H | H | H | H | O | CH₃ | CH₃ | 2-CH₂OCH₃, 4-Me | O |
| A-8194 | H | H | H | H | H | O | CH₃ | CH₃ | 2-CH₂OCH₃, 5-Me | O |
| A-8195 | H | H | H | H | H | O | CH₃ | CH₃ | 2-CH₂OCH₃, 6-Me | O |
| A-8196 | H | H | H | H | H | O | CH₃ | CH₃ | 2-OC(=O)CH₃, 5-F | O |
| A-8197 | H | H | H | H | H | O | CH₃ | CH₃ | 2-OC(=O)CH₃, 6-F | O |
| A-8198 | H | H | H | H | H | O | CH₃ | CH₃ | 2-OC(=O)CH₃, 5-Me | O |
| A-8199 | H | H | H | H | H | O | CH₃ | CH₃ | 2-OC(=O)CH₃, 6-Me | O |
| A-8200 | H | H | H | H | H | O | CH₃ | CH₃ | 2-OS(=O)₂CH₃, 5-F | O |
| A-8201 | H | H | H | H | H | O | CH₃ | CH₃ | 2-OS(=O)₂CH₃, 6-F | O |
| A-8202 | H | H | H | H | H | O | CH₃ | CH₃ | 2-OS(=O)₂CH₃, 5-Me | O |
| A-8203 | H | H | H | H | H | O | CH₃ | CH₃ | 2-OS(=O)2CH₃, 6-Me | O |

TABLE 145

| compound | R¹ | R² | R³ | R⁴ | R⁵ | A | R⁶ | R⁷ | (R⁸)ₘ | p |
|---|---|---|---|---|---|---|---|---|---|---|
| A-8204 | H | H | H | H | H | O | CH₃ | CH₃ | 2-CH₂SCH₃, 5-F | O |
| A-8205 | H | H | H | H | H | O | CH₃ | CH₃ | 2-CH₂SCH₃, 6-F | O |
| A-8206 | H | H | H | H | H | O | CH₃ | CH₃ | 2-CH₂SCH₃, 5-Me | O |
| A-8207 | H | H | H | H | H | O | CH₃ | CH₃ | 2-CH₂SCH₃, 6-Me | O |
| A-8208 | H | H | H | H | H | O | CH₃ | CH₃ | 2-NMe₂, 5-F | O |
| A-8209 | H | H | H | H | H | O | CH₃ | CH₃ | 2-NMe₂, 6-F | O |
| A-8210 | H | H | H | H | H | O | CH₃ | CH₃ | 2-NMe₂, 5-Me | O |
| A-8211 | H | H | H | H | H | O | CH₃ | CH₃ | 2-NMe₂, 6-Me | O |
| A-8212 | H | H | H | H | H | O | CH₃ | CH₃ | 2-CN, 4-F | O |
| A-8213 | H | H | H | H | H | O | CH₃ | CH₃ | 2-CN, 5-F | O |
| A 8214 | H | H | H | H | H | O | CH₃ | CH₃ | 2-CN, 6-F | O |
| A-8215 | H | H | H | H | H | O | CH₃ | CH₃ | 2-CN,6-Me | O |
| A-8216 | H | H | H | H | H | O | CH₃ | CH₃ | 2-CN, 5-OMe | O |
| A-8217 | H | H | H | H | H | O | CH₃ | CH₃ | 2-CN, 6-OMe | O |
| A-8218 | H | H | H | H | H | O | CH₃ | CH₃ | 3-CN, 6-Me | O |
| A-8219 | H | H | H | H | H | O | CH₃ | CH₃ | 3-CN, 6-OMe | O |
| A-8220 | H | H | H | H | H | O | CH₃ | CH₃ | 4-CN, 2-Me | O |
| A-8221 | H | H | H | H | H | O | CH₃ | CH₃ | 4-CN, 2-OMe | O |
| A-8222 | H | H | H | H | H | O | CH₃ | CH₃ | 2-NO₂, 4-F | O |
| A-8223 | H | H | H | H | H | O | CH₃ | CH₃ | 2-NO₂, 5-F | O |
| A-8224 | H | H | H | H | H | O | CH₃ | CH₃ | 2-NO₂, 6-F | O |
| A-8225 | H | H | H | H | H | O | CH₃ | CH₃ | 2-NO₂, 4-Me | O |
| A-8226 | H | H | H | H | H | O | CH₃ | CH₃ | 2-NO₂, 5-Me | O |
| A-8227 | H | H | H | H | H | O | CH₃ | CH₃ | 2-NO₂, 6-Me | O |
| A-8228 | H | H | H | H | H | O | CH₃ | CH₃ | 2-Me, 4,5-F₂ | O |
| A-8229 | H | H | H | H | H | O | CH₃ | CH₃ | 2-Me, 6-Et | O |
| A-8230 | H | H | H | H | H | O | CH₃ | CH₃ | 2-cyclopropyl, 6-OMe | O |
| A-8231 | H | H | H | H | H | O | CH₃ | CH₃ | 2-Me, 5-Et | O |
| A-8232 | H | H | H | H | H | O | CH₃ | CH₃ | 2,6-Et₂ | O |
| A-8233 | H | H | H | H | H | O | CH₃ | CH₃ | 2-Et, 6-F | O |
| A-8234 | H | H | H | H | H | O | CH₃ | CH₃ | 2-CH₂OCH₃, 6-Cl | O |
| A-8235 | H | H | H | H | H | O | CH₃ | CH₃ | 2-CH₂OCH₂CH₃, 6-Cl | O |
| A-8236 | H | H | H | H | H | O | CH₃ | CH₃ | 2-CH₂NMe₂ | O |
| A-8237 | H | H | H | H | H | O | CH₂CN | CH₂CN | H | O |
| A-8238 | H | H | H | H | H | O | CH₂CN | CH₂CN | 2-F | O |
| A-8239 | H | H | H | H | H | O | CH₂CN | CH₂CN | 2-Cl | O |
| A-8240 | H | H | H | H | H | O | CH₂CN | CH₂CN | 2-Br | O |
| A-8241 | H | H | H | H | H | O | CH₂CN | CH₂CN | 2-OH | O |
| A-8242 | H | H | H | H | H | O | CH₂CN | CH₂CN | 2-Me | O |

TABLE 145-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-8243 | H | H | H | H | H | O | CH$_2$CN | CH$_2$CN | 2-Et | 0 |
| A-8244 | H | H | H | H | H | O | CH$_2$CN | CH$_2$CN | 2-Pr | 0 |
| A-8245 | H | H | H | H | H | O | CH$_2$CN | CH$_2$CN | 2-CF$_3$ | 0 |
| A-8246 | H | H | H | H | H | O | CH$_2$CN | CH$_2$CN | 2-CHF$_2$ | 0 |
| A-8247 | H | H | H | H | H | O | CH$_2$CN | CH$_2$CN | 2-CH$_2$F | 0 |
| A-8248 | H | H | H | H | H | O | CH$_2$CN | CH$_2$CN | 2-CF$_2$Cl | 0 |
| A-8249 | H | H | H | H | H | O | CH$_2$CN | CH$_2$CN | 2-cyclopropyl | 0 |
| A-8250 | H | H | H | H | H | O | CH$_2$CN | CH$_2$CN | 2 -cyclobutyl | 0 |
| A-8251 | H | H | H | H | H | O | CH$_2$CN | CH$_2$CN | 2-cyclopentyl | 0 |
| A-8252 | H | H | H | H | H | O | CH$_2$CN | CH$_2$CN | 2-ethenyl | 0 |
| A-8253 | H | H | H | H | H | O | CH$_2$CN | CH$_2$CN | 2-allyl | 0 |
| A-8254 | H | H | H | H | H | O | CH$_2$CN | CH$_2$CN | 2-(prop-1-en-1-yl) | 0 |
| A-8255 | H | H | H | H | H | O | CH$_2$CN | CH$_2$CN | 2-(trifluoroethenyl) | 0 |
| A-8256 | H | H | H | H | H | O | CH$_2$CN | CH$_2$CN | 2-OMe | 0 |
| A-8257 | H | H | H | H | H | O | CH$_2$CN | CH$_2$CN | 2-OEt | 0 |
| A-8258 | H | H | H | H | H | O | CH$_2$CN | CH$_2$CN | 2-OPr | 0 |
| A-8259 | H | H | H | H | H | O | CH$_2$CN | CH$_2$CN | 2-O(i-Pr) | 0 |
| A-8260 | H | H | H | H | H | O | CH$_2$CN | CH$_2$CN | 2-OCF$_3$ | 0 |

TABLE 146

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-8261 | H | H | H | H | H | O | CH$_2$CN | CH$_2$CN | 2-OCHF$_2$ | 0 |
| A-8262 | H | H | H | H | H | O | CH$_2$CN | CH$_2$CN | 2-(cyclopropyboxy) | 0 |
| A-8263 | H | H | H | H | H | O | CH$_2$CN | CH$_2$CN | 2-(cyclobutyloxy) | 0 |
| A-8264 | H | H | H | H | H | O | CH$_2$CN | CH$_2$CN | 2-(cyclopentyloxy) | 0 |
| A-8265 | H | H | H | H | H | O | CH$_2$CN | CH$_2$CN | 2-((2,2-dichlorocyclopropyl)oxy) | 0 |
| A 8266 | H | H | H | H | H | O | CH$_2$CN | CH$_2$CN | 2-(oxiran-2-yl) | 0 |
| A-8267 | H | H | H | H | H | O | CH$_2$CN | CH$_2$CN | 2-SMe | 0 |
| A-8268 | H | H | H | H | H | O | CH$_2$CN | CH$_2$CN | 3-SMe | 0 |
| A-8269 | H | H | H | H | H | O | CH$_2$CN | CH$_2$CN | 2-S(=O)Me | 0 |
| A-8270 | H | H | H | H | H | O | CH$_2$CN | CH$_2$CN | 3-S(=O)Me | 0 |
| A-8271 | H | H | H | H | H | O | CH$_2$CN | CH$_2$CN | 2-S(=O)$_2$Me | 0 |
| A-8272 | H | H | H | H | H | O | CH$_2$CN | CH$_2$CN | 3-S(=O)$_2$Me | 0 |
| A-8273 | H | H | H | H | H | O | CH$_2$CN | CH$_2$CN | 2-SCF$_3$ | 0 |
| A-8274 | H | H | H | H | H | O | CH$_2$CN | CH$_2$CN | 3-SCF$_3$ | 0 |
| A-8275 | H | H | H | H | H | O | CH$_2$CN | CH$_2$CN | 2-S(=O)CF$_3$ | 0 |
| A-8276 | H | H | H | H | H | O | CH$_2$CN | CH$_2$CN | 3-SCF(CF$_3$)$_2$ | 0 |
| A-8277 | H | H | H | H | H | O | CH$_2$CN | CH$_2$CN | 2-(cyclopropylthio) | 0 |
| A-8278 | H | H | H | H | H | O | CH$_2$CN | CH$_2$CN | 2-(cyclopropylsulfinyl) | 0 |
| A-8279 | H | H | H | H | H | O | CH$_2$CN | CH$_2$CN | 2-(cyclopropylsulfonyl) | 0 |
| A-8280 | H | H | H | H | H | O | CH$_2$CN | CH$_2$CN | 2-C(=O)Me | 0 |
| A-8281 | H | H | H | H | H | O | CH$_2$CN | CH$_2$CN | 2-CH$_2$C(=O)CH$_3$ | 0 |
| A-8282 | H | H | H | H | H | O | CH$_2$CN | CH$_2$CN | 2-CH$_2$C(=O)CF$_3$ | 0 |
| A-8283 | H | H | H | H | H | O | CH$_2$CN | CH$_2$CN | 2-CH$_2$OH | 0 |
| A-8284 | H | H | H | H | H | O | CH$_2$CN | CH$_2$CN | 2-CH$_2$OCH$_3$ | 0 |
| A-8285 | H | H | H | H | H | O | CH$_2$CN | CH$_2$CN | 2-CH$_2$OCH$_2$CH$_3$ | 0 |
| A-8286 | H | H | H | H | H | O | CH$_2$CN | CH$_2$CN | 2-CH$_2$SCH$_3$ | 0 |
| A-8287 | H | H | H | H | H | O | CH$_2$CN | CH$_2$CN | 2-CH$_2$S(=O)CH$_3$ | 0 |
| A-8288 | H | H | H | H | H | O | CH$_2$CN | CH$_2$CN | 2-CH$_2$S(=O)$_2$CH$_3$ | 0 |
| A-8289 | H | H | H | H | H | O | CH$_2$CN | CH$_2$CN | 2-(benzyloxy) | 0 |
| A-8290 | H | H | H | H | H | O | CH$_2$CN | CH$_2$CN | 2-NH$_2$ | 0 |
| A-8291 | H | H | H | H | H | O | CH$_2$CN | CH$_2$CN | 2-NHMe | 0 |
| A-8292 | H | H | H | H | H | O | CH$_2$CN | CH$_2$CN | 2-N(Me)$_2$ | 0 |
| A-8293 | H | H | H | H | H | O | CH$_2$CN | CH$_2$CN | 2-(1,3-dioxolan-2-yl) | 0 |
| A-8294 | H | H | H | H | H | O | CH$_2$CN | CH$_2$CN | 2-(1,3-dioxan-2-yl) | 0 |
| A-8295 | H | H | H | H | H | O | CH$_2$CN | CH$_2$CN | 2-(1H-midazol-2-yl) | 0 |
| A-8296 | H | H | H | H | H | O | CH$_2$CN | CH$_2$CN | 2-(thiazol-2-yl) | 0 |
| A-8297 | H | H | H | H | H | O | CH$_2$CN | CH$_2$CN | 2-(oxazol-2-yl) | 0 |
| A-8298 | H | H | H | H | H | O | CH$_2$CN | CH$_2$CN | 2-CH=NOH | 0 |
| A-8299 | H | H | H | H | H | O | CH$_2$CN | CH$_2$CN | 2-CH=NOMe | 0 |
| A-8300 | H | H | H | H | H | O | CH$_2$CN | CH$_2$CN | 2-(4,5-dihydro-3-isoxazolyl) | 0 |
| A-8301 | H | H | H | H | H | O | CH$_2$CN | CH$_2$CN | 2-CN | 0 |
| A-8302 | H | H | H | H | H | O | CH$_2$CN | CH$_2$CN | 2-NO$_2$ | 0 |
| A-8303 | H | H | H | H | H | O | CH$_2$CN | CH$_2$CN | 2-F, 6-Cl | 0 |
| A-8304 | H | H | H | H | H | O | CH$_2$CN | CH$_2$CN | 2-F, 6-Me | 0 |
| A-8305 | H | H | H | H | H | O | CH$_2$CN | CH$_2$CN | 3-F, 6-Me | 0 |
| A-8306 | H | H | H | H | H | O | CH$_2$CN | CH$_2$CN | 4-F, 2-Me | 0 |
| A-8307 | H | H | H | H | H | O | CH$_2$CN | CH$_2$CN | 2-F, 6-OMe | 0 |
| A-8308 | H | H | H | H | H | O | CH$_2$CN | CH$_2$CN | 3-F, 6-OMe | 0 |
| A-8309 | H | H | H | H | H | O | CH$_2$CN | CH$_2$CN | 2,6-Cl$_2$ | 0 |
| A-8310 | H | H | H | H | H | O | CH$_2$CN | CH$_2$CN | 2-Cl, 6-Me | 0 |
| A-8311 | H | H | H | H | H | O | CH$_2$CN | CH$_2$CN | 3-Cl, 6-Me | 0 |
| A-8312 | H | H | H | H | H | O | CH$_2$CN | CH$_2$CN | 4-Cl, 2-Me | 0 |

TABLE 146-continued

| compound | R¹ | R² | R³ | R⁴ | R⁵ | A | R⁶ | R⁷ | (R⁸)ₘ | p |
|---|---|---|---|---|---|---|---|---|---|---|
| A-8313 | H | H | H | H | H | O | CH₂CN | CH₂CN | 2-Cl, 5-CF₃ | O |
| A-8314 | H | H | H | H | H | O | CH₂CN | CH₂CN | 2-Cl, 6-CF₃ | O |
| A-8315 | H | H | H | H | H | O | CH₂CN | CH₂CN | 2-Cl, 6-OMe | O |
| A-8316 | H | H | H | H | H | O | CH₂CN | CH₂CN | 3-Cl, 6-OMe | O |
| A-8317 | H | H | H | H | H | O | CH₂CN | CH₂CN | 4-Cl, 2-OMe | O |

TABLE 147

| compound | R¹ | R² | R³ | R⁴ | R⁵ | A | R⁶ | R⁷ | (R⁸)ₘ | p |
|---|---|---|---|---|---|---|---|---|---|---|
| A-8318 | H | H | H | H | H | O | CH₂CN | CH₂CN | 2,4-Me₂ | O |
| A-8319 | H | H | H | H | H | O | CH₂CN | CH₂CN | 2,5-Me₂ | O |
| A-8320 | H | H | H | H | H | O | CH₂CN | CH₂CN | 2,6-Me₂ | O |
| A-8321 | H | H | H | H | H | O | CH₂CN | CH₂CN | 2-Me, 4-CF₃ | O |
| A-8322 | H | H | H | H | H | O | CH₂CN | CH₂CN | 2-Me, 5 CF₃ | O |
| A-8323 | H | H | H | H | H | O | CH₂CN | CH₂CN | 2-Me, 6-CF₃ | O |
| A-8324 | H | H | H | H | H | O | CH₂CN | CH₂CN | 2-Me, 4-OMe | O |
| A-8325 | H | H | H | H | H | O | CH₂CN | CH₂CN | 2-Me, 5-OMe | O |
| A-8326 | H | H | H | H | H | O | CH₂CN | CH₂CN | 2-Me, 6-OMe | O |
| A-8327 | H | H | H | H | H | O | CH₂CN | CH₂CN | 3-Me, 6-OMe | O |
| A-8328 | H | H | H | H | H | O | CH₂CN | CH₂CN | 4-Me, 2-OMe | O |
| A-8329 | H | H | H | H | H | O | CH₂CN | CH₂CN | 2,5-OMe₂ | O |
| A-8330 | H | H | H | H | H | O | CH₂CN | CH₂CN | 2,6-OMe₂ | O |
| A-8331 | H | H | H | H | H | O | CH₂CN | CH₂CN | 2-OMe, 6-CF₃ | O |
| A-8332 | H | H | H | H | H | O | CH₂CN | CH₂CN | 2-CHF₂, 5-F | O |
| A-8333 | H | H | H | H | H | O | CH₂CN | CH₂CN | 2-CHF₂, 6-F | O |
| A-8334 | H | H | H | H | H | O | CH₂CN | CH₂CN | 2-CHF₂, 5-Me | O |
| A-8335 | H | H | H | H | H | O | CH₂CN | CH₂CN | 2-CHF₂, 6-Me | O |
| A-8336 | H | H | H | H | H | O | CH₂CN | CH₂CN | 2-cyclopropyl, 5-F | O |
| A-8337 | H | H | H | H | H | O | CH₂CN | CH₂CN | 2-cyclopropyl, 6-F | O |
| A-8338 | H | H | H | H | H | O | CH₂CN | CH₂CN | 2-cyclopropyl, 5-Me | O |
| A-8339 | H | H | H | H | H | O | CH₂CN | CH₂CN | 2-cyclopropyl, 6-Me | O |
| A-8340 | H | H | H | H | H | O | CH₂CN | CH₂CN | 2-ethenyl, 6-F | O |
| A-8341 | H | H | H | H | H | O | CH₂CN | CH₂CN | 2-ethenyl, 6-Me | O |
| A-8342 | H | H | H | H | H | O | CH₂CN | CH₂CN | 2-OEt, 5-F | O |
| A-8343 | H | H | H | H | H | O | CH₂CN | CH₂CN | 2-OEt, 6-F | O |
| A-8344 | H | H | H | H | H | O | CH₂CN | CH₂CN | 2-OEt, 5-Cl | O |
| A-8345 | H | H | H | H | H | O | CH₂CN | CH₂CN | 2-OEt, 6-Cl | O |
| A-8346 | H | H | H | H | H | O | CH₂CN | CH₂CN | 2-OEt, 5-Me | O |
| A-8347 | H | H | H | H | H | O | CH₂CN | CH₂CN | 2-OEt, 6-Me | O |
| A-8348 | H | H | H | H | H | O | CH₂CN | CH₂CN | 2-OCHF₂, 5-F | O |
| A-8349 | H | H | H | H | H | O | CH₂CN | CH₂CN | 2-OCHF₂, 6-F | O |
| A-8350 | H | H | H | H | H | O | CH₂CN | CH₂CN | 2-OCHF₂, 5-Me | O |
| A-8351 | H | H | H | H | H | O | CH₂CN | CH₂CN | 2-OCHF₂, 6-Me | O |
| A-8352 | H | H | H | H | H | O | CH₂CN | CH₂CN | 2-(cyclopropyloxy), 5-F | O |
| A-8353 | H | H | H | H | H | O | CH₂CN | CH₂CN | 2-(cyclopropyloxy), 6-F | O |
| A-8354 | H | H | H | H | H | O | CH₂CN | CH₂CN | 2-(cyclopropyloxy), 5-Me | O |
| A-8355 | H | H | H | H | H | O | CH₂CN | CH₂CN | 2-(cyclopropyloxy), 6-Me | O |
| A-8356 | H | H | H | H | H | O | CH₂CN | CH₂CN | 2-SMe, 5-F | O |
| A-8357 | H | H | H | H | H | O | CH₂CN | CH₂CN | 2-SMe, 6-F | O |
| A-8358 | H | H | H | H | H | O | CH₂CN | CH₂CN | 2-SMe, 5-Me | O |
| A-8359 | H | H | H | H | H | O | CH₂CN | CH₂CN | 2-SMe, 6-Me | O |
| A-8360 | H | H | H | H | H | O | CH₂CN | CH₂CN | 2-S(=O)Me, 5-F | O |
| A-8361 | H | H | H | H | H | O | CH₂CN | CH₂CN | 2-S(=O)Me, 6-F | O |
| A-8362 | H | H | H | H | H | O | CH₂CN | CH₂CN | 2-S(=O)Me, 5-Me | O |
| A-8363 | H | H | H | H | H | O | CH₂CN | CH₂CN | 2-S(=O)Me, 6-Me | O |
| A-8364 | H | H | H | H | H | O | CH₂CN | CH₂CN | 2-S(=O)₂Me, 5-F | O |
| A-8365 | H | H | H | H | H | O | CH₂CN | CH₂CN | 2-S(=O)₂Me, 6-F | O |
| A-8366 | H | H | H | H | H | O | CH₂CN | CH₂CN | 2-S(=O)₂Me, 5-Me | O |
| A-8367 | H | H | H | H | H | O | CH₂CN | CH₂CN | 2-S(=O)₂Me, 6-Me | O |
| A-8368 | H | H | H | H | H | O | CH₂CN | CH₂CN | 2-SCF₃, 5-F | O |
| A-8369 | H | H | H | H | H | O | CH₂CN | CH₂CN | 2-SCF₃, 6-F | O |
| A-8370 | H | H | H | H | H | O | CH₂CN | CH₂CN | 2-SCF₃, 5-Me | O |
| A-8371 | H | H | H | H | H | O | CH₂CN | CH₂CN | 2-SCF₃, 6-Me | O |
| A-8372 | H | H | H | H | H | O | CH₂CN | CH₂CN | 2-S(=O)CF₃, 5-F | O |
| A-8373 | H | H | H | H | H | O | CH₂CN | CH₂CN | 2-S(=O)CF₃, 6-F | O |
| A-8374 | H | H | H | H | H | O | CH₂CN | CH₂CN | 2-S(=O)CF₃, 5-Me | O |

TABLE 148

| compound | R¹ | R² | R³ | R⁴ | R⁵ | A | R⁶ | R⁷ | (R⁸)ₘ | p |
|---|---|---|---|---|---|---|---|---|---|---|
| A-8375 | H | H | H | H | H | O | CH₂CN | CH₂CN | 2-S(=O)CF₃, 6-Me | 0 |
| A-8376 | H | H | H | H | H | O | CH₂CN | CH₂CN | 2-S(=O)₂CF₃, 5-F | 0 |
| A-8377 | H | H | H | H | H | O | CH₂CN | CH₂CN | 2-S(=O)₂CF₃, 6-F | 0 |
| A-8378 | H | H | H | H | H | O | CH₂CN | CH₂CN | 2-S(=O)₂CF₃, 5-Me | 0 |
| A-8379 | H | H | H | H | H | O | CH₂CN | CH₂CN | 2-S(=O)₂CF₃, 6-Me | 0 |
| A-8380 | H | H | H | H | H | O | CH₂CN | CH₂CN | 2-(cyclopropylthio), 5-F | 0 |
| A-8381 | H | H | H | H | H | O | CH₂CN | CH₂CN | 2-(cyclopropylthio), 6-F | 0 |
| A-8382 | H | H | H | H | H | O | CH₂CN | CH₂CN | 2-(cyclopropylthio), 5-Me | 0 |
| A-8383 | H | H | H | H | H | O | CH₂CN | CH₂CN | 2-(cyclopropylthio), 6-Me | 0 |
| A-8384 | H | H | H | H | H | O | CH₂CN | CH₂CN | 2-C(=O)Me, 5-F | 0 |
| A-8385 | H | H | H | H | H | O | CH₂CN | CH₂CN | 2-C(=O)Me, 6-F | 0 |
| A-8386 | H | H | H | H | H | O | CH₂CN | CH₂CN | 2-C(=O)Me, 5-Me | 0 |
| A-8387 | H | H | H | H | H | O | CH₂CN | CH₂CN | 2-C(=O)Me, 6-Me | 0 |
| A-8388 | H | H | H | H | H | O | CH₂CN | CH₂CN | 2-CH₂OH, 5-F | 0 |
| A-8389 | H | H | H | H | H | O | CH₂CN | CH₂CN | 2-CH₂OH, 6-F | 0 |
| A-8390 | H | H | H | H | H | O | CH₂CN | CH₂CN | 2-CH₂OH, 5-Me | 0 |
| A-8391 | H | H | H | H | H | O | CH₂CN | CH₂CN | 2-CH₂OH, 6-Me | 0 |
| A-8392 | H | H | H | H | H | O | CH₂CN | CH₂CN | 2-CH₂OCH₃, 4-F | 0 |
| A-8393 | H | H | H | H | H | O | CH₂CN | CH₂CN | 2-CH₂OCH₃, 5-F | 0 |
| A-8394 | H | H | H | H | H | O | CH₂CN | CH₂CN | 2-CH₂OCH₃, 6-F | 0 |
| A-8395 | H | H | H | H | H | O | CH₂CN | CH₂CN | 2-CH₂OCH₃, 4-Me | 0 |
| A-8396 | H | H | H | H | H | O | CH₂CN | CH₂CN | 2-CH₂OCH₃, 5-Me | 0 |
| A-8397 | H | H | H | H | H | O | CH₂CN | CH₂CN | 2-CH₂OCH₃, 6-Me | 0 |
| A-8398 | H | H | H | H | H | O | CH₂CN | CH₂CN | 2-OC(=O)CH₃, 5-F | 0 |
| A-8399 | H | H | H | H | H | O | CH₂CN | CH₂CN | 2-OC(=O)CH₃, 6-F | 0 |
| A-8400 | H | H | H | H | H | O | CH₂CN | CH₂CN | 2-OC(=O)CH₃, 5 Me | 0 |
| A-8401 | H | H | H | H | H | O | CH₂CN | CH₂CN | 2-OC(=O)CH₃, 6-Me | 0 |
| A-8402 | H | H | H | H | H | O | CH₂CN | CH₂CN | 2-OS(=O)₂CH₃, 5-F | 0 |
| A-8403 | H | H | H | H | H | O | CH₂CN | CH₂CN | 2-OS(=O)₂CH₃, 6-F | 0 |
| A-8404 | H | H | H | H | H | O | CH₂CN | CH₂CN | 2-OS(=O)₂CH₃, 5-Me | 0 |
| A-8405 | H | H | H | H | H | O | CH₂CN | CH₂CN | 2-OS(=O)₂CH₃, 6-Me | 0 |
| A-8406 | H | H | H | H | H | O | CH₂CN | CH₂CN | 2-CH₂SCH₃, 5-F | 0 |
| A-8407 | H | H | H | H | H | O | CH₂CN | CH₂CN | 2-CH₂SCH₃, 6-F | 0 |
| A-8408 | H | H | H | H | H | O | CH₂CN | CH₂CN | 2-CH₂SCH₃, 5-Me | 0 |
| A-8409 | H | H | H | H | H | O | CH₂CN | CH₂CN | 2-CH₂SCH₃, 6-Me | 0 |
| A-8410 | H | H | H | H | H | O | CH₂CN | CH₂CN | 2-NMe₂, 5-F | 0 |
| A-8411 | H | H | H | H | H | O | CH₂CN | CH₂CN | 2-NMe₂, 6-F | 0 |
| A-8412 | H | H | H | H | H | O | CH₂CN | CH₂CN | 2-NMe₂, 5-Me | 0 |
| A-8413 | H | H | H | H | H | O | CH₂CN | CH₂CN | 2-NMe₂, 6-Me | 0 |
| A-8414 | H | H | H | H | H | O | CH₂CN | CH₂CN | 2-CN, 4-F | 0 |
| A-8415 | H | H | H | H | H | O | CH₂CN | CH₂CN | 2-CN, 5-F | 0 |
| A-8416 | H | H | H | H | H | O | CH₂CN | CH₂CN | 2-CN, 6-F | 0 |
| A-8417 | H | H | H | H | H | O | CH₂CN | CH₂CN | 2-CN, 6-Me | 0 |
| A-8418 | H | H | H | H | H | O | CH₂CN | CH₂CN | 2-CN, 5-OMe | 0 |
| A-8419 | H | H | H | H | H | O | CH₂CN | CH₂CN | 2-CN, 6-OMe | 0 |
| A-8420 | H | H | H | H | H | O | CH₂CN | CH₂CN | 3-CN, 6-Me | 0 |
| A-8421 | H | H | H | H | H | O | CH₂CN | CH₂CN | 3-CN, 6-OMe | 0 |
| A-8422 | H | H | H | H | H | O | CH₂CN | CH₂CN | 4-CN, 2-Me | 0 |
| A-8423 | H | H | H | H | H | O | CH₂CN | CH₂CN | 4-CN, 2-OMe | 0 |
| A-8424 | H | H | H | H | H | O | CH₂CN | CH₂CN | 2-NO₂, 4-F | 0 |
| A-8425 | H | H | H | H | H | O | CH₂CN | CH₂CN | 2-NO₂, 5-F | 0 |
| A-8426 | H | H | H | H | H | O | CH₂CN | CH₂CN | 2-NO₂, 6-F | 0 |
| A-8427 | H | H | H | H | H | O | CH₂CN | CH₂CN | 2-NO₂, 4-Me | 0 |
| A-8428 | H | H | H | H | H | O | CH₂CN | CH₂CN | 2-NO₂, 5-Me | 0 |
| A-8429 | H | H | H | H | H | O | CH₂CN | CH₂CN | 2-NO₂, 6-Me | 0 |
| A-8430 | H | H | H | H | H | O | CH₂CN | CH₂CN | 2-Me, 4,5-F₂ | 0 |
| A-8431 | H | H | H | H | H | O | CH₂CN | CH₂CN | 2-Me, 6-Et | 0 |

TABLE 149

| compound | R¹ | R² | R³ | R⁴ | R⁵ | A | R⁶ | R⁷ | (R⁸)ₘ | p |
|---|---|---|---|---|---|---|---|---|---|---|
| A-8432 | H | H | H | H | H | O | CH₂CN | CH₂CN | 2-cyclopropyl, 6-OMe | 0 |
| A-8433 | H | H | H | H | H | O | CH₂CN | CH₂CN | 2-Me, 5-Et | 0 |
| A-8434 | H | H | H | H | H | O | CH₂CN | CH₂CN | 2,6-Et₂ | 0 |
| A-8435 | H | H | H | H | H | O | CH₂CN | CH₂CN | 2-Et, 6-F | 0 |
| A-8436 | H | H | H | H | H | O | CH₂CN | CH₂CN | 2-CH₂OCH₃, 6-Cl | 0 |
| A-8437 | H | H | H | H | H | O | CH₂CN | CH₂CN | 2-CH₂OCH₂CH₃, 6-Cl | 0 |
| A-8438 | H | H | H | H | H | O | CH₂CN | CH₂CN | 2-CH₂NMe₂ | 0 |
| A-8439 | H | H | H | H | H | O | —CH₂CH₂—O—CH₂CH₂— | | H | 0 |
| A-8440 | H | H | H | H | H | O | —CH₂CH₂—O—CH₂CH₂— | | 2-F | 0 |
| A-8441 | H | H | H | H | H | O | —CH₂CH₂—O—CH₂CH₂— | | 2-Cl | 0 |
| A-8442 | H | H | H | H | H | O | —CH₂CH₂—O—CH₂CH₂— | | 2-Br | 0 |
| A-8443 | H | H | H | H | H | O | —CH₂CH₂—O—CH₂CH₂— | | 2-OH | 0 |
| A-8444 | H | H | H | H | H | O | —CH₂CH₂—O—CH₂CH₂— | | 2-Me | 0 |

TABLE 149-continued

| compound | R¹ | R² | R³ | R⁴ | R⁵ | A | R⁶ | R⁷ | (R⁸)$_m$ | p |
|---|---|---|---|---|---|---|---|---|---|---|
| A-8445 | H | H | H | H | H | O | —CH$_2$CH$_2$—O—CH$_2$CH$_2$— | | 2-Et | 0 |
| A-8446 | H | H | H | H | H | O | —CH$_2$CH$_2$—O—CH$_2$CH$_2$— | | 2-Pr | 0 |
| A-8447 | H | H | H | H | H | O | —CH$_2$CH$_2$—O—CH$_2$CH$_2$— | | 2-CF$_3$ | 0 |
| A-8448 | H | H | H | H | H | O | —CH$_2$CH$_2$—O—CH$_2$CH$_2$— | | 2-CHF$_2$ | 0 |
| A-8449 | H | H | H | H | H | O | —CH$_2$CH$_2$—O—CH$_2$CH$_2$— | | 2-CH$_2$F | 0 |
| A-8450 | H | H | H | H | H | O | —CH$_2$CH$_2$—O—CH$_2$CH$_2$— | | 2-CF$_2$Cl | 0 |
| A-8451 | H | H | H | H | H | O | —CH$_2$CH$_2$—O—CH$_2$CH$_2$— | | 2-cyclopropyl | 0 |
| A-8452 | H | H | H | H | H | O | —CH$_2$CH$_2$—O—CH$_2$CH$_2$— | | 2-cyclobutyl | 0 |
| A-8453 | H | H | H | H | H | O | —CH$_2$CH$_2$—O—CH$_2$CH$_2$— | | 2-cyclopentyl | 0 |
| A-8454 | H | H | H | H | H | O | —CH$_2$CH$_2$—O—CH$_2$CH$_2$— | | 2-ethenyl | 0 |
| A-8455 | H | H | H | H | H | O | —CH$_2$CH$_2$—O—CH$_2$CH$_2$— | | 2-allyl | 0 |
| A-8456 | H | H | H | H | H | O | —CH$_2$CH$_2$—O—CH$_2$CH$_2$— | | 2-(prop-1-en-1-yl) | 0 |
| A-8457 | H | H | H | H | H | O | —CH$_2$CH$_2$—O—CH$_2$CH$_2$— | | 2-(trifluoroethenyl) | 0 |
| A-8458 | H | H | H | H | H | O | —CH$_2$CH$_2$—O—CH$_2$CH$_2$— | | 2-OMe | 0 |
| A-8459 | H | H | H | H | H | O | —CH$_2$CH$_2$—O—CH$_2$CH$_2$— | | 2-OEt | 0 |
| A-8460 | H | H | H | H | H | O | —CH$_2$CH$_2$—O—CH$_2$CH$_2$— | | 2-OPr | 0 |
| A-8461 | H | H | H | H | H | O | —CH$_2$CH$_2$—O—CH$_2$CH$_2$— | | 2-O(i-Pr) | 0 |
| A-8462 | H | H | H | H | H | O | —CH$_2$CH$_2$—O—CH$_2$CH$_2$— | | 2-OCF$_3$ | 0 |
| A-8463 | H | H | H | H | H | O | —CH$_2$CH$_2$—O—CH$_2$CH$_2$— | | 2-OCHF$_2$ | 0 |
| A-8464 | H | H | H | H | H | O | —CH$_2$CH$_2$—O—CH$_2$CH$_2$— | | 2-(cyclopropyloxy) | 0 |
| A-8465 | H | H | H | H | H | O | —CH$_2$CH$_2$—O—CH$_2$CH$_2$— | | 2-(cyclobutyloxy) | 0 |
| A-8466 | H | H | H | H | H | O | —CH$_2$CH$_2$—O—CH$_2$CH$_2$— | | 2-(cyclopentyloxy) | 0 |
| A-8467 | H | H | H | H | H | O | —CH$_2$CH$_2$—O—CH$_2$CH$_2$— | | 2-((2,2-dichlorocyclopropyl)oxy) | 0 |
| A-8468 | H | H | H | H | H | O | —CH$_2$CH$_2$—O—CH$_2$CH$_2$— | | 2-(oxiran-2-yl) | 0 |
| A-8469 | H | H | H | H | H | O | —CH$_2$CH$_2$—O—CH$_2$CH$_2$— | | 2-SMe | 0 |
| A-8470 | H | H | H | H | H | O | —CH$_2$CH$_2$—O—CH$_2$CH$_2$— | | 3-SMe | 0 |
| A-8471 | H | H | H | H | H | O | —CH$_2$CH$_2$—O—CH$_2$CH$_2$— | | 2-S(=O)Me | 0 |
| A-8472 | H | H | H | H | H | O | —CH$_2$CH$_2$—O—CH$_2$CH$_2$— | | 3-S(=O)Me | 0 |
| A-8473 | H | H | H | H | H | O | —CH$_2$CH$_2$—O—CH$_2$CH$_2$— | | 2-S(=O)$_2$Me | 0 |
| A-8474 | H | H | H | H | H | O | —CH$_2$CH$_2$—O—CH$_2$CH$_2$— | | 3-S(=O)$_2$Me | 0 |
| A-8475 | H | H | H | H | H | O | —CH$_2$CH$_2$—O—CH$_2$CH$_2$— | | 2-SCF$_3$ | 0 |
| A-8476 | H | H | H | H | H | O | —CH$_2$CH$_2$—O—CH$_2$CH$_2$— | | 3-SCF$_3$ | 0 |
| A-8477 | H | H | H | H | H | O | —CH$_2$CH$_2$—O—CH$_2$CH$_2$— | | 3-S(=O)CF$_3$ | 0 |
| A-8478 | H | H | H | H | H | O | —CH$_2$CH$_2$—O—CH$_2$CH$_2$— | | 3-SCF(CF$_3$)$_2$ | 0 |
| A-8479 | H | H | H | H | H | O | —CH$_2$CH$_2$—O—CH$_2$CH$_2$— | | 2-(cyclopropylthio) | 0 |
| A-8480 | H | H | H | H | H | O | —CH$_2$CH$_2$—O—CH$_2$CH$_2$— | | 2-(cyclopropylsulfinyl) | 0 |
| A-8481 | H | H | H | H | H | O | —CH$_2$CH$_2$—O—CH$_2$CH$_2$— | | 2-(cyclopropylsulfonyl) | 0 |
| A-8482 | H | H | H | H | H | O | —CH$_2$CH$_2$—O—CH$_2$CH$_2$— | | 2-C(=O)Me | 0 |
| A-8483 | H | H | H | H | H | O | —CH$_2$CH$_2$—O—CH$_2$CH$_2$— | | 2-CH$_2$C(=O)CH$_3$ | 0 |
| A-8484 | H | H | H | H | H | O | —CH$_2$CH$_2$—O—CH$_2$CH$_2$— | | 2-CH$_2$C(=O)CF$_3$ | 0 |
| A-8485 | H | H | H | H | H | O | —CH$_2$CH$_2$—O—CH$_2$CH$_2$— | | 2-CH$_2$OH | 0 |
| A-8486 | H | H | H | H | H | O | —CH$_2$CH$_2$—O—CH$_2$CH$_2$— | | 2-CH$_2$OCH$_3$ | 0 |
| A-8487 | H | H | H | H | H | O | —CH$_2$CH$_2$—O—CH$_2$CH$_2$— | | 2-CH$_2$OCH$_2$CH$_3$ | 0 |
| A-8488 | H | H | H | H | H | O | —CH$_2$CH$_2$—O—CH$_2$CH$_2$— | | 2-CH$_2$SCH$_3$ | 0 |

TABLE 150

| compound | R¹ | R² | R³ | R⁴ | R⁵ | A | R⁶ | R⁷ | (R⁸)$_m$ | p |
|---|---|---|---|---|---|---|---|---|---|---|
| A-8489 | H | H | H | H | H | O | —CH$_2$CH$_2$—O—CH$_2$CH$_2$— | | 2-CH$_2$S(=O)CH$_3$ | 0 |
| A-8490 | H | H | H | H | H | O | —CH$_2$CH$_2$—O—CH$_2$CH$_2$— | | 2-CH$_2$S(=O)$_2$CH$_3$ | 0 |
| A-8491 | H | H | H | H | H | O | —CH$_2$CH$_2$—O—CH$_2$CH$_2$— | | 2-(benzyloxy) | 0 |
| A-8492 | H | H | H | H | H | O | —CH$_2$CH$_2$—O—CH$_2$CH$_2$— | | 2-NH$_2$ | 0 |
| A-8493 | H | H | H | H | H | O | —CH$_2$CH$_2$—O—CH$_2$CH$_2$— | | 2-NHMe | 0 |
| A-8494 | H | H | H | H | H | O | —CH$_2$CH$_2$—O—CH$_2$CH$_2$— | | 2-N(Me)$_2$ | 0 |
| A-8495 | H | H | H | H | H | O | —CH$_2$CH$_2$—O—CH$_2$CH$_2$— | | 2-(1,3-dioxolan-2-yl) | 0 |
| A-8496 | H | H | H | H | H | O | —CH$_2$CH$_2$—O—CH$_2$CH$_2$— | | 2-(1,3-dioxan-2-yl) | 0 |
| A-8497 | H | H | H | H | H | O | —CH$_2$CH$_2$—O—CH$_2$CH$_2$— | | 2-(1,3-imidazol-2-yl) | 0 |
| A-8498 | H | H | H | H | H | O | —CH$_2$CH$_2$—O—CH$_2$CH$_2$— | | 2-(thiazol-2-yl) | 0 |
| A-8499 | H | H | H | H | H | O | —CH$_2$CH$_2$—O—CH$_2$CH$_2$— | | 2-(oxazol-2-yl) | 0 |
| A-8500 | H | H | H | H | H | O | —CH$_2$CH$_2$—O—CH$_2$CH$_2$— | | 2-CH=NOH | 0 |
| A-8501 | H | H | H | H | H | O | —CH$_2$CH$_2$—O—CH$_2$CH$_2$— | | 2-CH=NOMe | 0 |
| A-8502 | H | H | H | H | H | O | —CH$_2$CH$_2$—O—CH$_2$CH$_2$— | | 2-(4,5-dihydro-3-isoxazolyl) | 0 |
| A-8503 | H | H | H | H | H | O | —CH$_2$CH$_2$—O—CH$_2$CH$_2$— | | 2-CN | 0 |
| A-8504 | H | H | H | H | H | O | —CH$_2$CH$_2$—O—CH$_2$CH$_2$— | | 2-NO$_2$ | 0 |
| A-8505 | H | H | H | H | H | O | —CH$_2$CH$_2$—O—CH$_2$CH$_2$— | | 2-F,6-Cl | 0 |
| A-8506 | H | H | H | H | H | O | —CH$_2$CH$_2$—O—CH$_2$CH$_2$— | | 2,6-Me | 0 |
| A-8507 | H | H | H | H | H | O | —CH$_2$CH$_2$—O—CH$_2$CH$_2$— | | 3-F,6-Me | 0 |
| A-8508 | H | H | H | H | H | O | —CH$_2$CH$_2$—O—CH$_2$CH$_2$— | | 4-F,2-Me | 0 |
| A-8509 | H | H | H | H | H | O | —CH$_2$CH$_2$—O—CH$_2$CH$_2$— | | 2-F,6-OMe | 0 |
| A-8510 | H | H | H | H | H | O | —CH$_2$CH$_2$—O—CH$_2$CH$_2$— | | 3-F,6-OMe | 0 |
| A-8511 | H | H | H | H | H | O | —CH$_2$CH$_2$—O—CH$_2$CH$_2$— | | 2,6-Cl$_2$ | 0 |
| A-8512 | H | H | H | H | H | O | —CH$_2$CH$_2$—O—CH$_2$CH$_2$— | | 2-Cl,6-Me | 0 |
| A-8513 | H | H | H | H | H | O | —CH$_2$CH$_2$—O—CH$_2$CH$_2$— | | 3-Cl,6-Me | 0 |
| A-8514 | H | H | H | H | H | O | —CH$_2$CH$_2$—O—CH$_2$CH$_2$— | | 4-Cl,2-Me | 0 |

TABLE 150-continued

| compound | R¹ | R² | R³ | R⁴ | R⁵ | A | R⁶ | R⁷ | (R⁸)$_m$ | p |
|---|---|---|---|---|---|---|---|---|---|---|
| A-8515 | H | H | H | H | H | O | —CH$_2$CH$_2$—O—CH$_2$CH$_2$— | | 2-Cl,5-CF$_3$ | 0 |
| A-8516 | H | H | H | H | H | O | —CH$_2$CH$_2$—O—CH$_2$CH$_2$— | | 2-Cl,6-CF$_3$ | 0 |
| A-8517 | H | H | H | H | H | O | —CH$_2$CH$_2$—O—CH$_2$CH$_2$— | | 2-Cl,6-OMe | 0 |
| A-8518 | H | H | H | H | H | O | —CH$_2$CH$_2$—O—CH$_2$CH$_2$— | | 3-Cl,6-OMe | 0 |
| A-8519 | H | H | H | H | H | O | —CH$_2$CH$_2$—O—CH$_2$CH$_2$— | | 4-Cl,2-OMe | 0 |
| A-8520 | H | H | H | H | H | O | —CH$_2$CH$_2$—O—CH$_2$CH$_2$— | | 2,4-Me$_2$ | 0 |
| A-8521 | H | H | H | H | H | O | —CH$_2$CH$_2$—O—CH$_2$CH$_2$— | | 2,5-Me$_2$ | 0 |
| A-8522 | H | H | H | H | H | O | —CH$_2$CH$_2$—O—CH$_2$CH$_2$— | | 2,6-Me$_2$ | 0 |
| A-8523 | H | H | H | H | H | O | —CH$_2$CH$_2$—O—CH$_2$CH$_2$— | | 2-Me,4-CF$_3$ | 0 |
| A-8524 | H | H | H | H | H | O | —CH$_2$CH$_2$—O—CH$_2$CH$_2$— | | 2-Me,5-CF$_3$ | 0 |
| A-8525 | H | H | H | H | H | O | —CH$_2$CH$_2$—O—CH$_2$CH$_2$— | | 2-Me,6-CF$_3$ | 0 |
| A-8526 | H | H | H | H | H | O | —CH$_2$CH$_2$—O—CH$_2$CH$_2$— | | 2-Me,4-OMe | 0 |
| A-8527 | H | H | H | H | H | O | —CH$_2$CH$_2$—O—CH$_2$CH$_2$— | | 2-Me,5-OMe | 0 |
| A-8528 | H | H | H | H | H | O | —CH$_2$CH$_2$—O—CH$_2$CH$_2$— | | 2-Me,6-OMe | 0 |
| A-8529 | H | H | H | H | H | O | —CH$_2$CH$_2$—O—CH$_2$CH$_2$— | | 3-Me,6-OMe | 0 |
| A-8530 | H | H | H | H | H | O | —CH$_2$CH$_2$—O—CH$_2$CH$_2$— | | 4-Me,2-OMe | 0 |
| A-8531 | H | H | H | H | H | O | —CH$_2$CH$_2$—O—CH$_2$CH$_2$— | | 2,5-OMe$_2$ | 0 |
| A-8532 | H | H | H | H | H | O | —CH$_2$CH$_2$—O—CH$_2$CH$_2$— | | 2,6-OMe$_2$ | 0 |
| A-8533 | H | H | H | H | H | O | —CH$_2$CH$_2$—O—CH$_2$CH$_2$— | | 2-OMe,6-CF$_3$ | 0 |
| A-8534 | H | H | H | H | H | O | —CH$_2$CH$_2$—O—CH$_2$CH$_2$— | | 2-CHF$_2$,5-F | 0 |
| A-8535 | H | H | H | H | H | O | —CH$_2$CH$_2$—O—CH$_2$CH$_2$— | | 2-CHF$_2$,6-F | 0 |
| A-8536 | H | H | H | H | H | O | —CH$_2$CH$_2$—O—CH$_2$CH$_2$— | | 2-CHF$_2$,5-Me | 0 |
| A-8537 | H | H | H | H | H | O | —CH$_2$CH$_2$—O—CH$_2$CH$_2$— | | 2-CHF$_2$,6-Me | 0 |
| A-8538 | H | H | H | H | H | O | —CH$_2$CH$_2$—O—CH$_2$CH$_2$— | | 2-cyclopropyl,5-F | 0 |
| A-8539 | H | H | H | H | H | O | —CH$_2$CH$_2$—O—CH$_2$CH$_2$— | | 2-cyclopropyl,6-F | 0 |
| A-8540 | H | H | H | H | H | O | —CH$_2$CH$_2$—O—CH$_2$CH$_2$— | | 2-cyclopropyl,5-Me | 0 |
| A-8541 | H | H | H | H | H | O | —CH$_2$CH$_2$—O—CH$_2$CH$_2$— | | 2-cyclopropyl,6-Me | 0 |
| A-8542 | H | H | H | H | H | O | —CH$_2$CH$_2$—O—CH$_2$CH$_2$— | | 2-ethenyl,6-F | 0 |
| A-8543 | H | H | H | H | H | O | —CH$_2$CH$_2$—O—CH$_2$CH$_2$— | | 2-ethenyl,6-Me | 0 |
| A-8544 | H | H | H | H | H | O | —CH$_2$CH$_2$—O—CH$_2$CH$_2$— | | 2-OEt,5-F | 0 |
| A-8545 | H | H | H | H | H | O | —CH$_2$CH$_2$—O—CH$_2$CH$_2$— | | 2-OEt,6-F | 0 |

TABLE 151

| compound | R¹ | R² | R³ | R⁴ | R⁵ | A | R⁶ | R⁷ | (R⁸)$_m$ | p |
|---|---|---|---|---|---|---|---|---|---|---|
| A-8546 | H | H | H | H | H | O | —CH$_2$CH$_2$—O—CH$_2$CH$_2$— | | 2-OEt, 5-Cl | 0 |
| A-8547 | H | H | H | H | H | O | —CH$_2$CH$_2$—O—CH$_2$CH$_2$— | | 2-OEt, 6-Cl | 0 |
| A-8548 | H | H | H | H | H | O | —CH$_2$CH$_2$—O—CH$_2$CH$_2$— | | 2-OEt, 5-Me | 0 |
| A-8549 | H | H | H | H | H | O | —CH$_2$CH$_2$—O—CH$_2$CH$_2$— | | 2-OEt, 6-Me | 0 |
| A-8550 | H | H | H | H | H | O | —CH$_2$CH$_2$—O—CH$_2$CH$_2$— | | 2-OCHF$_2$, 5-F | 0 |
| A-8551 | H | H | H | H | H | O | —CH$_2$CH$_2$—O—CH$_2$CH$_2$— | | 2-OCHF$_2$, 6-F | 0 |
| A-8552 | H | H | H | H | H | O | —CH$_2$CH$_2$—O—CH$_2$CH$_2$— | | 2-OCHF$_2$, 5-Me | 0 |
| A-8553 | H | H | H | H | H | O | —CH$_2$CH$_2$—O—CH$_2$CH$_2$— | | 2-OCHF$_2$, 6-Me | 0 |
| A-8554 | H | H | H | H | H | O | —CH$_2$CH$_2$—O—CH$_2$CH$_2$— | | 2-(cyclopropyloxy), 5-F | 0 |
| A-8555 | H | H | H | H | H | O | —CH$_2$CH$_2$—O—CH$_2$CH$_2$— | | 2-(cyclopropyloxy), 6-F | 0 |
| A-8556 | H | H | H | H | H | O | —CH$_2$CH$_2$—O—CH$_2$CH$_2$— | | 2-(cyclopropyloxy), 5-Me | 0 |
| A-8557 | H | H | H | H | H | O | —CH$_2$CH$_2$—O—CH$_2$CH$_2$— | | 2-(cyclopropyloxy), 6-Me | 0 |
| A-8558 | H | H | H | H | H | O | —CH$_2$CH$_2$—O—CH$_2$CH$_2$— | | 2-SMe, 5-F | 0 |
| A-8559 | H | H | H | H | H | O | —CH$_2$CH$_2$—O—CH$_2$CH$_2$— | | 2-SMe, 6-F | 0 |
| A-8560 | H | H | H | H | H | O | —CH$_2$CH$_2$—O—CH$_2$CH$_2$— | | 2-SMe, 5-Me | 0 |
| A-8561 | H | H | H | H | H | O | —CH$_2$CH$_2$—O—CH$_2$CH$_2$— | | 2-SMe, 6-Me | 0 |
| A-8562 | H | H | H | H | H | O | —CH$_2$CH$_2$—O—CH$_2$CH$_2$— | | 2-S(=O)Me, 5-F | 0 |
| A-8563 | H | H | H | H | H | O | —CH$_2$CH$_2$—O—CH$_2$CH$_2$— | | 2-S(=O)Me, 6-F | 0 |
| A-8564 | H | H | H | H | H | O | —CH$_2$CH$_2$—O—CH$_2$CH$_2$— | | 2-S(=O)Me, 5-Me | 0 |
| A-8565 | H | H | H | H | H | O | —CH$_2$CH$_2$—O—CH$_2$CH$_2$— | | 2-S(=O)Me, 6-Me | 0 |
| A-8566 | H | H | H | H | H | O | —CH$_2$CH$_2$—O—CH$_2$CH$_2$— | | 2-S(=O)$_2$Me, 5-F | 0 |
| A-8567 | H | H | H | H | H | O | —CH$_2$CH$_2$—O—CH$_2$CH$_2$— | | 2-S(=O)$_2$Me, 6-F | 0 |
| A-8568 | H | H | H | H | H | O | —CH$_2$CH$_2$—O—CH$_2$CH$_2$— | | 2-S(=O)$_2$Me, 5-Me | 0 |
| A-8569 | H | H | H | H | H | O | —CH$_2$CH$_2$—O—CH$_2$CH$_2$— | | 2-S(=O)$_2$Me, 6-Me | 0 |
| A-8570 | H | H | H | H | H | O | —CH$_2$CH$_2$—O—CH$_2$CH$_2$— | | 2-SCF$_3$, 5-F | 0 |
| A-8571 | H | H | H | H | H | O | —CH$_2$CH$_2$—O—CH$_2$CH$_2$— | | 2-SCF$_3$, 6-F | 0 |
| A-8572 | H | H | H | H | H | O | —CH$_2$CH$_2$—O—CH$_2$CH$_2$— | | 2-SCF$_3$, 5-Me | 0 |
| A-8573 | H | H | H | H | H | O | —CH$_2$CH$_2$—O—CH$_2$CH$_2$— | | 2-SCF$_3$, 6-Me | 0 |
| A-8574 | H | H | H | H | H | O | —CH$_2$CH$_2$—O—CH$_2$CH$_2$— | | 2-S(=O)CF$_3$, 5-F | 0 |
| A-8575 | H | H | H | H | H | O | —CH$_2$CH$_2$—O—CH$_2$CH$_2$— | | 2-S(=O)CF$_3$, 6-F | 0 |
| A-8576 | H | H | H | H | H | O | —CH$_2$CH$_2$—O—CH$_2$CH$_2$— | | 2-S(=O)CF$_3$, 5-Me | 0 |
| A-8577 | H | H | H | H | H | O | —CH$_2$CH$_2$—O—CH$_2$CH$_2$— | | 2-S(=O)CF$_3$, 6-Me | 0 |
| A-8578 | H | H | H | H | H | O | —CH$_2$CH$_2$—O—CH$_2$CH$_2$— | | 2-S(=O)2CF$_3$, 5-F | 0 |
| A-8579 | H | H | H | H | H | O | —CH$_2$CH$_2$—O—CH$_2$CH$_2$— | | 2-S(=O)2CF$_3$, 6-F | 0 |
| A-8580 | H | H | H | H | H | O | —CH$_2$CH$_2$—O—CH$_2$CH$_2$— | | 2-S(=O)$_2$CF$_3$, 5-Me | 0 |
| A-8581 | H | H | H | H | H | O | —CH$_2$CH$_2$—O—CH$_2$CH$_2$— | | 2-S(=O)$_2$CF$_3$, 6-Me | 0 |
| A-8582 | H | H | H | H | H | O | —CH$_2$CH$_2$—O—CH$_2$CH$_2$— | | 2-(cyclopropylthio), 5-F | 0 |
| A-8583 | H | H | H | H | H | O | —CH$_2$CH$_2$—O—CH$_2$CH$_2$— | | 2-(cyclopropylthio), 6-F | 0 |
| A-8584 | H | H | H | H | H | O | —CH$_2$CH$_2$—O—CH$_2$CH$_2$— | | 2-(cyclopropylthio), 5-Me | 0 |

TABLE 151-continued

| compound | R¹ | R² | R³ | R⁴ | R⁵ | A | R⁶ | R⁷ | (R⁸)$_m$ | p |
|---|---|---|---|---|---|---|---|---|---|---|
| A-8585 | H | H | H | H | H | O | —CH$_2$CH$_2$—O—CH$_2$CH$_2$— | 2-(cyclopropylthio), 6-Me | O |
| A-8586 | H | H | H | H | H | O | —CH$_2$CH$_2$—O—CH$_2$CH$_2$— | 2-C(=O)Me, 5-F | O |
| A-8587 | H | H | H | H | H | O | —CH$_2$CH$_2$—O—CH$_2$CH$_2$— | 2-C(=O)Me, 6-F | O |
| A-8588 | H | H | H | H | H | O | —CH$_2$CH$_2$—O—CH$_2$CH$_2$— | 2-C(=O)Me, 5-Me | O |
| A-8589 | H | H | H | H | H | O | —CH$_2$CH$_2$—O—CH$_2$CH$_2$— | 2-C(=O)Me, 6-Me | O |
| A-8590 | H | H | H | H | H | O | —CH$_2$CH$_2$—O—CH$_2$CH$_2$— | 2-CH$_2$OH, 5-F | O |
| A-8591 | H | H | H | H | H | O | —CH$_2$CH$_2$—O—CH$_2$CH$_2$— | 2-CH$_2$OH, 6-F | O |
| A-8592 | H | H | H | H | H | O | —CH$_2$CH$_2$—O—CH$_2$CH$_2$— | 2-CH$_2$OH, 5-Me | O |
| A-8593 | H | H | H | H | H | O | —CH$_2$CH$_2$—O—CH$_2$CH$_2$— | 2-CH$_2$OH, 6-Me | O |
| A-8594 | H | H | H | H | H | O | —CH$_2$CH$_2$—O—CH$_2$CH$_2$— | 2-CH$_2$OCH$_3$, 4-F | O |
| A-8595 | H | H | H | H | H | O | —CH$_2$CH$_2$—O—CH$_2$CH$_2$— | 2-CH$_2$OCH$_3$, 5-F | O |
| A-8596 | H | H | H | H | H | O | —CH$_2$CH$_2$—O—CH$_2$CH$_2$— | 2-CH$_2$OCH$_3$, 6-F | O |
| A-8597 | H | H | H | H | H | O | —CH$_2$CH$_2$—O—CH$_2$CH$_2$— | 2-CH$_2$OCH$_3$, 4-Me | O |
| A-8598 | H | H | H | H | H | O | —CH$_2$CH$_2$—O—CH$_2$CH$_2$— | 2-CH$_2$OCH$_3$, 5-Me | O |
| A-8599 | H | H | H | H | H | O | —CH$_2$CH$_2$—O—CH$_2$CH$_2$— | 2-CH$_2$OCH$_3$, 6-Me | O |
| A-8600 | H | H | H | H | H | O | —CH$_2$CH$_2$—O—CH$_2$CH$_2$— | 2-OC(=O)CH$_3$, 5-F | O |
| A-8601 | H | H | H | H | H | O | —CH$_2$CH$_2$—O—CH$_2$CH$_2$— | 2-OC(=O)CH$_3$, 6-F | O |
| A-8602 | H | H | H | H | H | O | —CH$_2$CH$_2$—O—CH$_2$CH$_2$— | 2-OC(=O)CH$_3$, 5-Me | O |

TABLE 152

| compound | R¹ | R² | R³ | R⁴ | R⁵ | A | R⁶ | R⁷ | (R⁸) | p |
|---|---|---|---|---|---|---|---|---|---|---|
| A-8603 | H | H | H | H | H | O | —CH$_2$CH$_2$—O—CH$_2$CH$_2$— | 2-OC(=O)CH$_3$, 6-Me | O |
| A-8604 | H | H | H | H | H | O | —CH$_2$CH$_2$—O—CH$_2$CH$_2$— | 2-OS(=O)$_2$CH$_3$, 5-F | O |
| A-8605 | H | H | H | H | H | O | —CH$_2$CH$_2$—O—CH$_2$CH$_2$— | 2-OS(=O)$_2$CH$_3$, 6-F | O |
| A-8606 | H | H | H | H | H | O | —CH$_2$CH$_2$—O—CH$_2$CH$_2$— | 2-OS(=O)$_2$CH$_3$, 5-Me | O |
| A-8607 | H | H | H | H | H | O | —CH$_2$CH$_2$—O—CH$_2$CH$_2$— | 2-OS(=O)$_2$CH$_3$, 6-Me | O |
| A-8608 | H | H | H | H | H | O | —CH$_2$CH$_2$—O—CH$_2$CH$_2$— | 2-CH2SCH$_3$, 5-F | O |
| A-8609 | H | H | H | H | H | O | —CH$_2$CH$_2$—O—CH$_2$CH$_2$— | 2-CH2SCH$_3$, 6-F | O |
| A-8610 | H | H | H | H | H | O | —CH$_2$CH$_2$—O—CH$_2$CH$_2$— | 2-CH2SCH$_3$, 5-Me | O |
| A-8611 | H | H | H | H | H | O | —CH$_2$CH$_2$—O—CH$_2$CH$_2$— | 2-CH2SCH$_3$, 6-F | O |
| A-8612 | H | H | H | H | H | O | —CH$_2$CH$_2$—O—CH$_2$CH$_2$— | 2-NMe$_2$, 5-F | O |
| A-8613 | H | H | H | H | H | O | —CH$_2$CH$_2$—O—CH$_2$CH$_2$— | 2-NMe$_2$, 6-F | O |
| A-8614 | H | H | H | H | H | O | —CH$_2$CH$_2$—O—CH$_2$CH$_2$— | 2-NMe$_2$, 5-Me | O |
| A-8615 | H | H | H | H | H | O | —CH$_2$CH$_2$—O—CH$_2$CH$_2$— | 2-NMe$_2$, 6-Me | O |
| A-8616 | H | H | H | H | H | O | —CH$_2$CH$_2$—O—CH$_2$CH$_2$— | 2-CN, 4-F | O |
| A-8617 | H | H | H | H | H | O | —CH$_2$CH$_2$—O—CH$_2$CH$_2$— | 2-CN, 5-F | O |
| A-8618 | H | H | H | H | H | O | —CH$_2$CH$_2$—O—CH$_2$CH$_2$— | 2-CN, 6-F | O |
| A-8619 | H | H | H | H | H | O | —CH$_2$CH$_2$—O—CH$_2$CH$_2$— | 2-CN, 6-Me | O |
| A-8620 | H | H | H | H | H | O | —CH$_2$CH$_2$—O—CH$_2$CH$_2$— | 2-CN, 5-OMe | O |
| A-8621 | H | H | H | H | H | O | —CH$_2$CH$_2$—O—CH$_2$CH$_2$— | 2-CN, 6-OMe | O |
| A-8622 | H | H | H | H | H | O | —CH$_2$CH$_2$—O—CH$_2$CH$_2$— | 3-CN, 6-Me | O |
| A-8623 | H | H | H | H | H | O | —CH$_2$CH$_2$—O—CH$_2$CH$_2$— | 3-CN, 6-OMe | O |
| A-8624 | H | H | H | H | H | O | —CH$_2$CH$_2$—O—CH$_2$CH$_2$— | 4-CN, 2-Me | O |
| A-8625 | H | H | H | H | H | O | —CH$_2$CH$_2$—O—CH$_2$CH$_2$— | 4-CN, 2-OMe | O |
| A-8626 | H | H | H | H | H | O | —CH$_2$CH$_2$—O—CH$_2$CH$_2$— | 2-NO$_2$, 4-F | O |
| A-8627 | H | H | H | H | H | O | —CH$_2$CH$_2$—O—CH$_2$CH$_2$— | 2-NO$_2$, 5-F | O |
| A-8628 | H | H | H | H | H | O | —CH$_2$CH$_2$—O—CH$_2$CH$_2$— | 2-NO$_2$, 6-F | O |
| A-8629 | H | H | H | H | H | O | —CH$_2$CH$_2$—O—CH$_2$CH$_2$— | 2-NO$_2$, 4-Me | O |
| A-8630 | H | H | H | H | H | O | —CH$_2$CH$_2$—O—CH$_2$CH$_2$— | 2-NO$_2$, 5-Me | O |
| A-8631 | H | H | H | H | H | O | —CH$_2$CH$_2$—O—CH$_2$CH$_2$— | 2-NO$_2$, 6-Me | O |
| A-8632 | H | H | H | H | H | O | —CH$_2$CH$_2$—O—CH$_2$CH$_2$— | 2-Me, 4,5-F$_2$ | O |
| A-8633 | H | H | H | H | H | O | —CH$_2$CH$_2$—O—CH$_2$CH$_2$— | 2-Me, 6-Et | O |
| A-8634 | H | H | H | H | H | O | —CH$_2$CH$_2$—O—CH$_2$CH$_2$— | 2-cyclopropyl, 6-OMe | O |
| A-8635 | H | H | H | H | H | O | —CH$_2$CH$_2$—O—CH$_2$CH$_2$— | 2-Me ,5-Et | O |
| A-8636 | H | H | H | H | H | O | —CH$_2$CH$_2$—O—CH$_2$CH$_2$— | 2,6-Et$_2$ | O |
| A-8637 | H | H | H | H | H | O | —CH$_2$CH$_2$—O—CH$_2$CH$_2$— | 2-Et, 6-F | O |
| A-8638 | H | H | H | H | H | O | —CH$_2$CH$_2$—O—CH$_2$CH$_2$— | 2-CH$_2$OCH$_3$, 6-Cl | O |
| A-8639 | H | H | H | H | H | O | —CH$_2$CH$_2$—O—CH$_2$CH$_2$— | 2-CH$_2$OCH$_2$CH$_3$, 6-Cl | O |
| A-8640 | H | H | H | H | H | O | —CH$_2$CH$_2$—O—CH$_2$CH$_2$— | 2-CH$_2$NMe$_2$ | O |
| A-8641 | H | H | H | H | H | S | H | H | H | O |
| A-8642 | H | H | H | H | H | S | H | H | 2-F | O |
| A-8643 | H | H | H | H | H | S | H | H | 2-Cl | O |
| A-8644 | H | H | H | H | H | S | H | H | 2-Br | O |
| A-8645 | H | H | H | H | H | S | H | H | 2-OH | O |
| A-8646 | H | H | H | H | H | S | H | H | 2-Me | O |
| A-8647 | H | H | H | H | H | S | H | H | 2-Et | O |
| A-8648 | H | H | H | H | H | S | H | H | 2-Pr | O |
| A-8649 | H | H | H | H | H | S | H | H | 2-CF$_3$ | O |
| A-8650 | H | H | H | H | H | S | H | H | 2-CHF$_2$ | O |
| A-8651 | H | H | H | H | H | S | H | H | 2-CH$_2$F | O |
| A-8652 | H | H | H | H | H | S | H | H | 2-CF$_2$Cl | O |
| A-8653 | H | H | H | H | H | S | H | H | 2-cyclopropyl | O |
| A-8654 | H | H | H | H | H | S | H | H | 2-cyclobutyl | O |

TABLE 152-continued

| compound | R¹ | R² | R³ | R⁴ | R⁵ | A | R⁶ | R⁷ | (R⁸) | p |
|---|---|---|---|---|---|---|---|---|---|---|
| A-8655 | H | H | H | H | H | S | H | H | 2-cyclopentyl | 0 |
| A-8656 | H | H | H | H | H | S | H | H | 2-ethenyl | 0 |
| A-8657 | H | H | H | H | H | S | H | H H | 2-allyl | 0 |
| A-8658 | H | H | H | H | H | S | H | H | 2-(prop-1-en-1-yl) | 0 |
| A-8659 | H | H | H | H | H | S | H | H | 2-(trifluoroethenyl) | 0 |

TABLE 153

| compound | R¹ | R² | R³ | R⁴ | R⁵ | A | R⁶ | R⁷ | (R⁸)$_m$ | p |
|---|---|---|---|---|---|---|---|---|---|---|
| A-8660 | H | H | H | H | H | S | H | H | 2-OMe | 0 |
| A-8661 | H | H | H | H | H | S | H | H | 2-OEt | 0 |
| A-8662 | H | H | H | H | H | S | H | H | 2-OPr | 0 |
| A-8663 | H | H | H | H | H | S | H | H | 2-O(i-Pr) | 0 |
| A-8664 | H | H | H | H | H | S | H | H | 2-OCF₃ | 0 |
| A-8665 | H | H | H | H | H | S | H | H | 2-OCHF₂ | 0 |
| A-8666 | H | H | H | H | H | S | H | H | 2-(cyclopropyloxy) | 0 |
| A-8667 | H | H | H | H | H | S | H | H | 2-(cyclobutyloxy) | 0 |
| A-8668 | H | H | H | H | H | S | H | H | 2-(cyclopentyloxy) | 0 |
| A-8669 | H | H | H | H | H | S | H | H | 2-((2,2-dichlorocyclopropyl)oxy) | 0 |
| A-8670 | H | H | H | H | H | S | H | H | 2-(oxiran-2-yl) | 0 |
| A-8671 | H | H | H | H | H | S | H | H | 2-SMe | 0 |
| A-8672 | H | H | H | H | H | S | H | H | 3-SMe | 0 |
| A-8673 | H | H | H | H | H | S | H | H | 2-S(=O)Me | 0 |
| A-8674 | H | H | H | H | H | S | H | H | 3-S(=O)Me | 0 |
| A-8675 | H | H | H | H | H | S | H | H | 2-S(=O)₂Me | 0 |
| A-8676 | H | H | H | H | H | S | H | H | 3-S(=O)₂Me | 0 |
| A-8677 | H | H | H | H | H | S | H | H | 2-SCF₃ | 0 |
| A-8678 | H | H | H | H | H | S | H | H | 3-SCF₃ | 0 |
| A-8679 | H | H | H | H | H | S | H | H | 3-S(=O)CF₃ | 0 |
| A-8680 | H | H | H | H | H | S | H | H | 3-SCF(CF₃)₂ | 0 |
| A-8681 | H | H | H | H | H | S | H | H | 2-(cyclopropylthio) | 0 |
| A-8682 | H | H | H | H | H | S | H | H | 2-(cyclopropylsulfinyl) | 0 |
| A-8683 | H | H | H | H | H | S | H | H | 2-(cyclopropylsulfonyl) | 0 |
| A-8684 | H | H | H | H | H | S | H | H | 2-C(=O)Me | 0 |
| A-8685 | H | H | H | H | H | S | H | H | 2-CH₂C(=O)CH₃ | 0 |
| A-8686 | H | H | H | H | H | S | H | H | 2-CH₂C(=O)CF₃ | 0 |
| A-8687 | H | H | H | H | H | S | H | H | 2-CH₂OH | 0 |
| A-8688 | H | H | H | H | H | S | H | H | 2-CH₂OCH₃ | 0 |
| A-8689 | H | H | H | H | H | S | H | H | 2-CH₂OCH₂CH₃ | 0 |
| A-8690 | H | H | H | H | H | S | H | H | 2-CH₂SCH₃ | 0 |
| A-8691 | H | H | H | H | H | S | H | H | 2-CH₂S(=O)CH₃ | 0 |
| A-8692 | H | H | H | H | H | S | H | H | 2-CH₂S(=O)₂CH₃ | 0 |
| A-8693 | H | H | H | H | H | S | H | H | 2-(benzyloxy) | 0 |
| A-8694 | H | H | H | H | H | S | H | H | 2-NH₂ | 0 |
| A-8695 | H | H | H | H | H | S | H | H | 2-NHMe | 0 |
| A-8696 | H | H | H | H | H | S | H | H | 2-N(Me)₂ | 0 |
| A-8697 | H | H | H | H | H | S | H | H | 2-(1,3-dioxolan-2-yl) | 0 |
| A-8698 | H | H | H | H | H | S | H | H | 2-(1,3-dioxan-2-yl) | 0 |
| A-8699 | H | H | H | H | H | S | H | H | 2-(1H-imidazol-2-yl) | 0 |
| A-8700 | H | H | H | H | H | S | H | H | 2-(thiazol-2-yl) | 0 |
| A-8701 | H | H | H | H | H | S | H | H | 2-(oxazol-2-yl) | 0 |
| A-8702 | H | H | H | H | H | S | H | H | 2-CH=NOH | 0 |
| A-8703 | H | H | H | H | H | S | H | H | 2-CH=NOMe | 0 |
| A-8704 | H | H | H | H | H | S | H | H | 2-(4,5-dihydro-3-isoxazolyl) | 0 |
| A-8705 | H | H | H | H | H | S | H | H | 2-CN | 0 |
| A-8706 | H | H | H | H | H | S | H | H | 2-NO₂ | 0 |
| A-8707 | H | H | H | H | H | S | H | H | 2-F,6-Cl | 0 |
| A-8708 | H | H | H | H | H | S | H | H | 2-F,6-Me | 0 |
| A-8709 | H | H | H | H | H | S | H | H | 3-F,6-Me | 0 |
| A-8710 | H | H | H | H | H | S | H | H | 4-F,2-Me | 0 |
| A-8711 | H | H | H | H | H | S | H | H | 2-F,6-OMe | 0 |
| A-8712 | H | H | H | H | H | S | H | H | 2-F,6-OMe | 0 |
| A-8713 | H | H | H | H | H | S | H | H | 2,6-Cl₂ | 0 |
| A-8714 | H | H | H | H | H | S | H | H | 2-Cl,6-Me | 0 |
| A-8715 | H | H | H | H | H | S | H | H | 3-Cl,6-Me | 0 |
| A-8716 | H | H | H | H | H | S | H | H | 4-Cl,2-Me | 0 |

TABLE 154

| compound | R¹ | R² | R³ | R⁴ | R⁵ | A | R⁶ | R⁷ | (R⁸)ₘ | p |
|---|---|---|---|---|---|---|---|---|---|---|
| A-8717 | H | H | H | H | H | S | H | H | 2-Cl,5-CF$_3$ | 0 |
| A-8718 | H | H | H | H | H | S | H | H | 2-Cl,6-CF$_3$ | 0 |
| A-8719 | H | H | H | H | H | S | H | H | 2-Cl,6-OMe | 0 |
| A-8720 | H | H | H | H | H | S | H | H | 3-Cl,6-OMe | 0 |
| A-8721 | H | H | H | H | H | S | H | H | 4-Cl,2-OMe | 0 |
| A-8722 | H | H | H | H | H | S | H | H | 2,4-Me$_2$ | 0 |
| A-8723 | H | H | H | H | H | S | H | H | 2,5-Me$_2$ | 0 |
| A-8724 | H | H | H | H | H | S | H | H | 2,6-Me$_2$ | 0 |
| A-8725 | H | H | H | H | H | S | H | H | 2-Me,4-CF$_3$ | 0 |
| A-8726 | H | H | H | H | H | S | H | H | 2-Me,5CF$_3$ | 0 |
| A-8727 | H | H | H | H | H | S | H | H | 2-Me, | 0 |
| A-8728 | H | H | H | H | H | S | H | H | 2-Me,4-OMe | 0 |
| A-8729 | H | H | H | H | H | S | H | H | 2-Me,5-OMe | 0 |
| A-8730 | H | H | H | H | H | S | H | H | 2-Me,6-OMe | 0 |
| A-8731 | H | H | H | H | H | S | H | H | 3-Me,6-OMe | 0 |
| A-8732 | H | H | H | H | H | S | H | H | 4-Me,2-OMe | 0 |
| A-8733 | H | H | H | H | H | S | H | H | 2,5-OMe$_2$ | 0 |
| A-8734 | H | H | H | H | H | S | H | H | 2,6-OMe$_2$ | 0 |
| A-8735 | H | H | H | H | H | S | H | H | 2-OMe,6-CF$_3$ | 0 |
| A-8736 | H | H | H | H | H | S | H | H | 2-CHF$_2$,5-F | 0 |
| A-8737 | H | H | H | H | H | S | H | H | 2-CHF$_2$,6-F | 0 |
| A-8738 | H | H | H | H | H | S | H | H | 2-CHF$_2$,5-Me | 0 |
| A-8739 | H | H | H | H | H | S | H | H | 2-CHF$_2$,6-Me | 0 |
| A-8740 | H | H | H | H | H | S | H | H | 2-cyclopropyl,5-F | 0 |
| A-8741 | H | H | H | H | H | S | H | H | 2-cyclopropyl,6-F | 0 |
| A-8742 | H | H | H | H | H | S | H | H | 2-cyclopropyl,5-Me | 0 |
| A-8743 | H | H | H | H | H | S | H | H | 2-cyclopropyl,6-Me | 0 |
| A-8744 | H | H | H | H | H | S | H | H | 2-ethenyl,6-F | 0 |
| A-8745 | H | H | H | H | H | S | H | H | 2-ethenyl,6-Me | 0 |
| A-8746 | H | H | H | H | H | S | H | H | 2-OEt,5-F | 0 |
| A-8747 | H | H | H | H | H | S | H | H | 2-OEt,6-F | 0 |
| A-8748 | H | H | H | H | H | S | H | H | 2-OEt,5-Cl | 0 |
| A-8749 | H | H | H | H | H | S | H | H | 2-OEt,6-Cl | 0 |
| A-8750 | H | H | H | H | H | S | H | H | 2-OEt,5-Me | 0 |
| A-8751 | H | H | H | H | H | S | H | H | 2-OEt,6-Me | 0 |
| A-8752 | H | H | H | H | H | S | H | H | 2-OCHF$_2$,5-F | 0 |
| A-8753 | H | H | H | H | H | S | H | H | 2-OCHF$_2$,6-F | 0 |
| A-8754 | H | H | H | H | H | S | H | H | 2-OCHF$_2$,5-Me | 0 |
| A-8755 | H | H | H | H | H | S | H | H | 2-OCHF$_2$,6-Me | 0 |
| A-8756 | H | H | H | H | H | S | H | H | 2-(cyclopropyloxy),5-F | 0 |
| A-8757 | H | H | H | H | H | S | H | H | 2-(cyclopropyloxy),6-F | 0 |
| A-8758 | H | H | H | H | H | S | H | H | 2-(cyclopropyloxy),5-Me | 0 |
| A-8759 | H | H | H | H | H | S | H | H | 2-(cyclopropyloxy),6-Me | 0 |
| A-8760 | H | H | H | H | H | S | H | H | 2-SMe,5-F | 0 |
| A-8761 | H | H | H | H | H | S | H | H | 2-SMe,6-F | 0 |
| A-8762 | H | H | H | H | H | S | H | H | 2-SMe,5-Me | 0 |
| A-8763 | H | H | H | H | H | S | H | H | 2-SMe,6-Me | 0 |
| A-8764 | H | H | H | H | H | S | H | H | 2-S(=O)Me,5-F | 0 |
| A-8765 | H | H | H | H | H | S | H | H | 2-S(=O)Me,6-F | 0 |
| A-8766 | H | H | H | H | H | S | H | H | 2-S(=O)Me,5-Me | 0 |
| A-8767 | H | H | H | H | H | S | H | H | 2-S(=O)Me,6-Me | 0 |
| A-8768 | H | H | H | H | H | S | H | H | 2-S(=O)$_2$Me,5-F | 0 |
| A-8769 | H | H | H | H | H | S | H | H | 2-S(=O)$_2$Me,6-F | 0 |
| A-8770 | H | H | H | H | H | S | H | H | 2-S(=O)$_2$Me,5-Me | 0 |
| A-8771 | H | H | H | H | H | S | H | H | 2-S(=O)$_2$Me,6-Me | 0 |
| A-8772 | H | H | H | H | H | S | H | H | 2-SCF$_3$,5-F | 0 |
| A-8773 | H | H | H | H | H | S | H | H | 2-SCF$_3$,6-F | 0 |

TABLE 155

| compound | R¹ | R² | R³ | R⁴ | R⁵ | A | R⁶ | R⁷ | (R⁸)ₘ | p |
|---|---|---|---|---|---|---|---|---|---|---|
| A-8774 | H | H | H | H | H | S | H | H | 2-SCF$_3$,5-Me | 0 |
| A-8775 | H | H | H | H | H | S | H | H | 2-SCF$_3$,6-Me | 0 |
| A-8776 | H | H | H | H | H | S | H | H | 2-S(=O)CF$_3$,5-F | 0 |
| A-8777 | H | H | H | H | H | S | H | H | 2-S(=O)CF$_3$,6-F | 0 |
| A-8778 | H | H | H | H | H | S | H | H | 2-S(=O)CF$_3$,5-Me | 0 |
| A-8779 | H | H | H | H | H | S | H | H | 2-S(=O)CF$_3$,6-Me | 0 |
| A-8780 | H | H | H | H | H | S | H | H | 2-S(=O)$_2$CF$_3$,5-F | 0 |
| A-8781 | H | H | H | H | H | S | H | H | 2-S(=O)$_2$CF$_3$,6-F | 0 |
| A-8782 | H | H | H | H | H | S | H | H | 2-S(=O)$_2$CF$_3$,5-Me | 0 |
| A-8783 | H | H | H | H | H | S | H | H | 2-S(=O)$_2$CF$_3$,6-Me | 0 |
| A-8784 | H | H | H | H | H | S | H | H | 2-(cyclopropylthio),5-F | 0 |
| A-8785 | H | H | H | H | H | S | H | H | 2-(cyclopropylthio),6-F | 0 |
| A-8786 | H | H | H | H | H | S | H | H | 2-(cyclopropylthio),5-Me | 0 |

TABLE 155-continued

| compound | R¹ | R² | R³ | R⁴ | R⁵ | A | R⁶ | R⁷ | (R⁸)ₘ | p |
|---|---|---|---|---|---|---|---|---|---|---|
| A-8787 | H | H | H | H | H | S | H | H | 2-(cyclopropylthio),6-Me | 0 |
| A-8788 | H | H | H | H | H | S | H | H | 2-C(=O)Me,5-F | 0 |
| A-8789 | H | H | H | H | H | S | H | H | 2-C(=O)Me,6-F | 0 |
| A-8790 | H | H | H | H | H | S | H | H | 2-C(=O)Me,5-Me | 0 |
| A-8791 | H | H | H | H | H | S | H | H | 2-C(=O)Me,6-Me | 0 |
| A-8792 | H | H | H | H | H | S | H | H | 2-CH₂OH,5-F | 0 |
| A-8793 | H | H | H | H | H | S | H | H | 2-CH₂OH,6-F | 0 |
| A-8794 | H | H | H | H | H | S | H | H | 2-CH₂OH,5-Me | 0 |
| A-8795 | H | H | H | H | H | S | H | H | 2-CH₂OH,6-Me | 0 |
| A-8796 | H | H | H | H | H | S | H | H | 2-CH₂OCH₃,4-F | 0 |
| A-8797 | H | H | H | H | H | S | H | H | 2-CH₂OCH₃,5-F | 0 |
| A-8798 | H | H | H | H | H | S | H | H | 2-CH₂OCH₃,6-F | 0 |
| A-8799 | H | H | H | H | H | S | H | H | 2-CH₂OCH₃,4-Me | 0 |
| A-8800 | H | H | H | H | H | S | H | H | 2-CH₂OCH₃,5-Me | 0 |
| A-8801 | H | H | H | H | H | S | H | H | 2-CH₂OCH₃,6-Me | 0 |
| A-8802 | H | H | H | H | H | S | H | H | 2-OC(=O)CH₃,5-F | 0 |
| A-8803 | H | H | H | H | H | S | H | H | 2-OC(=O)CH₃,6-F | 0 |
| A-8804 | H | H | H | H | H | S | H | H | 2-OC(=O)CH₃,5-Me | 0 |
| A-8805 | H | H | H | H | H | S | H | H | 2-OC(=O)CH₃,6-Me | 0 |
| A-8806 | H | H | H | H | H | S | H | H | 2-OS(=O)₂CH₃,5-F | 0 |
| A-8807 | H | H | H | H | H | S | H | H | 2-OS(=O)₂CH₃,6-F | 0 |
| A-8808 | H | H | H | H | H | S | H | H | 2-OS(=O)₂CH₃,5-Me | 0 |
| A-8809 | H | H | H | H | H | S | H | H | 2-OS(=O)₂CH₃,6-Me | 0 |
| A-8810 | H | H | H | H | H | S | H | H | 2-CH₂SCH₃,5-F | 0 |
| A-8811 | H | H | H | H | H | S | H | H | 2-CH₂SCH₃,6-F | 0 |
| A-8812 | H | H | H | H | H | S | H | H | 2-CH₂SCH₃,5-Me | 0 |
| A-8813 | H | H | H | H | H | S | H | H | 2-CH₂SCH₃,6-Me | 0 |
| A-8814 | H | H | H | H | H | S | H | H | 2-NMe₂,5-F | 0 |
| A-8815 | H | H | H | H | H | S | H | H | 2-NMe₂,6-F | 0 |
| A-8816 | H | H | H | H | H | S | H | H | 2-NMe₂,5-Me | 0 |
| A-8817 | H | H | H | H | H | S | H | H | 2-NMe₂,6-Me | 0 |
| A-8818 | H | H | H | H | H | S | H | H | 2-CN,4-F | 0 |
| A-8819 | H | H | H | H | H | S | H | H | 2-CN,5-F | 0 |
| A-8820 | H | H | H | H | H | S | H | H | 2-CN,6-F | 0 |
| A-8821 | H | H | H | H | H | S | H | H | 2-CN,6-Me | 0 |
| A-8822 | H | H | H | H | H | S | H | H | 2-CN,5-OMe | 0 |
| A-8823 | H | H | H | H | H | S | H | H | 2-CN,6-OMe | 0 |
| A-8824 | H | H | H | H | H | S | H | H | 3-CN,6-Me | 0 |
| A-8825 | H | H | H | H | H | S | H | H | 3-CN,6-OMe | 0 |
| A-8826 | H | H | H | H | H | S | H | H | 4-CN,2-Me | 0 |
| A-8827 | H | H | H | H | H | S | H | H | 4-CN,2-OMe | 0 |
| A-8828 | H | H | H | H | H | S | H | H | 2-NO₂,4-F | 0 |
| A-8829 | H | H | H | H | H | S | H | H | 2-NO₂,5-F | 0 |
| A-8830 | H | H | H | H | H | S | H | H | 2-NO₂,6-F | 0 |

TABLE 156

| compound | R¹ | R² | R³ | R⁴ | R⁵ | A | R⁶ | R⁷ | (R⁸)ₘ | p |
|---|---|---|---|---|---|---|---|---|---|---|
| A-8831 | H | H | H | H | H | S | H | H | 2-NO₂,4-Me | 0 |
| A-8832 | H | H | H | H | H | S | H | H | 2-NO₂,5-Me | 0 |
| A-8833 | H | H | H | H | H | S | H | H | 2-NO₂,6-Me | 0 |
| A-8834 | H | H | H | H | H | S | H | H | 2-Me,4,5-F₂ | 0 |
| A-8835 | H | H | H | H | H | S | H | H | 2-Me,6-Et | 0 |
| A-8836 | H | H | H | H | H | S | H | H | 2-cyclopropyl,6-OMe | 0 |
| A-8837 | H | H | H | H | H | S | H | H | 2-Me,5-Et | 0 |
| A-8838 | H | H | H | H | H | S | H | H | 2,6-Et₂ | 0 |
| A-8839 | H | H | H | H | H | S | H | H | 2-Et,6-F | 0 |
| A-8840 | H | H | H | H | H | S | H | H | 2-CH₂OCH₃,6-Cl | 0 |
| A-8841 | H | H | H | H | H | S | H | H | 2-CH₂OCH₂CH₃,6-Cl | 0 |
| A-8842 | H | H | H | H | H | S | H | H | 2-CH₂NMe₂ | 0 |
| A-8843 | H | H | H | H | H | O | H | H | H | 1 |
| A-8844 | H | H | H | H | H | O | H | H | 2-F | 1 |
| A-8845 | H | H | H | H | H | O | H | H | 3-F | 1 |
| A-8846 | H | H | H | H | H | O | H | H | 4-F | 1 |
| A-8847 | H | H | H | H | H | O | H | H | 2-Cl | 1 |
| A-8848 | H | H | H | H | H | O | H | H | 3-Cl | 1 |
| A-8849 | H | H | H | H | H | O | H | H | 4-Cl | 1 |
| A-8850 | H | H | H | H | H | O | H | H | 2-Br | 1 |
| A-8851 | H | H | H | H | H | O | H | H | 3-Br | 1 |
| A-8852 | H | H | H | H | H | O | H | H | 4-Br | 1 |
| A-8853 | H | H | H | H | H | O | H | H | 2-I | 1 |
| A-8854 | H | H | H | H | H | O | H | H | 3-I | 1 |
| A-8855 | H | H | H | H | H | O | H | H | 4-I | 1 |
| A-8856 | H | H | H | H | H | O | H | H | 2-OH | 1 |
| A-8857 | H | H | H | H | H | O | H | H | 3-OH | 1 |
| A-8858 | H | H | H | H | H | O | H | H | 4-OH | 1 |
| A-8859 | H | H | H | H | H | O | H | H | 2-SH | 1 |
| A-8860 | H | H | H | H | H | O | H | H | 3-SH | 1 |
| A-8861 | H | H | H | H | H | O | H | H | 4-SH | 1 |
| A-8862 | H | H | H | H | H | O | H | H | 2-Me | 1 |
| A-8863 | H | H | H | H | H | O | H | H | 3-Me | 1 |
| A-8864 | H | H | H | H | H | O | H | H | 4-Me | 1 |
| A-8865 | H | H | H | H | H | O | H | H | 2-Et | 1 |
| A-8866 | H | H | H | H | H | O | H | H | 3-Et | 1 |
| A-8867 | H | H | H | H | H | O | H | H | 4-Et | 1 |
| A-8868 | H | H | H | H | H | O | H | H | 2-Pr | 1 |
| A-8869 | H | H | H | H | H | O | H | H | 3-Pr | 1 |
| A-8870 | H | H | H | H | H | O | H | H | 4-Pr | 1 |
| A-8871 | H | H | H | H | H | O | H | H | 2-i-Pr | 1 |
| A-8872 | H | H | H | H | H | O | H | H | 3-i-Pr | 1 |
| A-8873 | H | H | H | H | H | O | H | H | 4-i-Pr | 1 |
| A-8874 | H | H | H | H | H | O | H | H | 2-Bu | 1 |
| A-8875 | H | H | H | H | H | O | H | H | 3-Bu | 1 |
| A-8876 | H | H | H | H | H | O | H | H | 4-Bu | 1 |
| A-8877 | H | H | H | H | H | O | H | H | 2-s-Bu | 1 |
| A-8878 | H | H | H | H | H | O | H | H | 3-s-Bu | 1 |
| A-8879 | H | H | H | H | H | O | H | H | 4-s-Bu | 1 |
| A-8880 | H | H | H | H | H | O | H | H | 2-i-Bu | 1 |

TABLE 156-continued

| compound | R¹ | R² | R³ | R⁴ | R⁵ | A | R⁶ | R⁷ | (R⁸)ₘ | p |
|---|---|---|---|---|---|---|---|---|---|---|
| A-8881 | H | H | H | H | H | O | H | H | 3-i-Bu | 1 |
| A-8882 | H | H | H | H | H | O | H | H | 4-i-Bu | 1 |
| A-8883 | H | H | H | H | H | O | H | H | 2-t-Bu | 1 |
| A-8884 | H | H | H | H | H | O | H | H | 3-t-Bu | 1 |
| A-8885 | H | H | H | H | H | O | H | H | 4-t-Bu | 1 |
| A-8886 | H | H | H | H | H | O | H | H | 2-CF₃ | 1 |
| A-8887 | H | H | H | H | H | O | H | H | 3-CF₃ | 1 |

TABLE 157

| compound | R¹ | R² | R³ | R⁴ | R⁵ | A | R⁶ | R⁷ | (R⁸)ₘ | p |
|---|---|---|---|---|---|---|---|---|---|---|
| A-8888 | H | H | H | H | H | O | H | H | 4-CF₃ | 1 |
| A-8889 | H | H | H | H | H | O | H | H | 2-CHF₂ | 1 |
| A-8890 | H | H | H | H | H | O | H | H | 3CHF₂ | 1 |
| A-8891 | H | H | H | H | H | O | H | H | 4-CHF₂ | 1 |
| A-8892 | H | H | H | H | H | O | H | H | 2-CH₂F | 1 |
| A-8893 | H | H | H | H | H | O | H | H | 3-CH₂F | 1 |
| A-8894 | H | H | H | H | H | O | H | H | 4-CH₂F | 1 |
| A-8895 | H | H | H | H | H | O | H | H | 2-CF₂Cl | 1 |
| A-8896 | H | H | H | H | H | O | H | H | 3-CF₂Cl | 1 |
| A-8897 | H | H | H | H | H | O | H | H | 4-CF₂Cl | 1 |
| A-8898 | H | H | H | H | H | O | H | H | 2-CF(CF₃)₂ | 1 |
| A-8899 | H | H | H | H | H | O | H | H | 3-CF(CF₃)₂ | 1 |
| A-8900 | H | H | H | H | H | O | H | H | 4-CF(CF₃)₂ | 1 |
| A-8901 | H | H | H | H | H | O | H | H | 2-cyclopropyl | 1 |
| A-8902 | H | H | H | H | H | O | H | H | 3-cyclopropyl | 1 |
| A-8903 | H | H | H | H | H | O | H | H | 4-cyclopropyl | 1 |
| A-8904 | H | H | H | H | H | O | H | H | 2-cyclobutyl | 1 |
| A-8905 | H | H | H | H | H | O | H | H | 3-cyclobutyl | 1 |
| A-8906 | H | H | H | H | H | O | H | H | 4-cyclobutyl | 1 |
| A-8907 | H | H | H | H | H | O | H | H | 2-cyclopentyl | 1 |
| A-8908 | H | H | H | H | H | O | H | H | 3-cyclopentyl | 1 |
| A-8909 | H | H | H | H | H | O | H | H | 4-cyclopentyl | 1 |
| A-8910 | H | H | H | H | H | O | H | H | 2-(cyclopropylmethyl) | 1 |
| A-8911 | H | H | H | H | H | O | H | H | 3-(cyclopropylmethyl) | 1 |
| A-8912 | H | H | H | H | H | O | H | H | 4-(cyclopropylmethyl) | 1 |
| A-8913 | H | H | H | H | H | O | H | H | 2-(cyclobutylmethyl) | 1 |
| A-8914 | H | H | H | H | H | O | H | H | 3-(cyclobutylmethyl) | 1 |
| A-8915 | H | H | H | H | H | O | H | H | 4-(cyclobutylmethyl) | 1 |
| A-8916 | H | H | H | H | H | O | H | H | 2-(cyclopentylmethyl) | 1 |
| A-8917 | H | H | H | H | H | O | H | H | 3-(cyclopentylmethyl) | 1 |
| A-8918 | H | H | H | H | H | O | H | H | 4-(cyclopentylmethyl) | 1 |
| A-8919 | H | H | H | H | H | O | H | H | 2-(cyclopropylethyl) | 1 |
| A-8920 | H | H | H | H | H | O | H | H | 3-(cyclopropylethyl) | 1 |
| A-8921 | H | H | H | H | H | O | H | H | 4-(cyclopropylethyl) | 1 |
| A-8922 | H | H | H | H | H | O | H | H | 2-(2,2-difluorocyclopropyl) | 1 |
| A-8923 | H | H | H | H | H | O | H | H | 3-(2,2-difluorocyclopropyl) | 1 |
| A-8924 | H | H | H | H | H | O | H | H | 4-(2,2-difluorocyclopropyl) | 1 |
| A-8925 | H | H | H | H | H | O | H | H | 2-(2,2-dichlorocyclopropyl) | 1 |
| A-8926 | H | H | H | H | H | O | H | H | 3-(2,2-dichlorocyclopropyl) | 1 |
| A-8927 | H | H | H | H | H | O | H | H | 4-(2,2-dichlorocyclopropyl) | 1 |
| A-8928 | H | H | H | H | H | O | H | H | 2-ethenyl | 1 |
| A-8929 | H | H | H | H | H | O | H | H | 3-ethenyl | 1 |
| A-8930 | H | H | H | H | H | O | H | H | 4-ethenyl | 1 |
| A-8931 | H | H | H | H | H | O | H | H | 2-allyl | 1 |
| A-8932 | H | H | H | H | H | O | H | H | 3-allyl | 1 |
| A-8933 | H | H | H | H | H | O | H | H | 4-allyl | 1 |
| A-8934 | H | H | H | H | H | O | H | H | 2-(prop-1-en-1-yl) | 1 |
| A-8935 | H | H | H | H | H | O | H | H | 3-(prop-1-en-1-yl) | 1 |
| A-8936 | H | H | H | H | H | O | H | H | 4-(prop-1-en-1-yl) | 1 |
| A-8937 | H | H | H | H | H | O | H | H | 2-(trifluoroethenyl) | 1 |
| A-8938 | H | H | H | H | H | O | H | H | 3-(trifluoroethenyl) | 1 |
| A-8939 | H | H | H | H | H | O | H | H | 4-(trifluoroethenyl) | 1 |
| A-8940 | H | H | H | H | H | O | H | H | 2-(2,2-dichloroethenyl) | 1 |
| A-8941 | H | H | H | H | H | O | H | H | 3-(2,2-dichloroethenyl) | 1 |
| A-8942 | H | H | H | H | H | O | H | H | 4-(2,2-dichloroethenyl) | 1 |
| A-8943 | H | H | H | H | H | O | H | H | 2-ethynyl | 1 |
| A-8944 | H | H | H | H | H | O | H | H | 3-ethynyl | 1 |

TABLE 158

| compound | R¹ | R² | R³ | R⁴ | R⁵ | A | R⁶ | R⁷ | (R⁸)ₘ | p |
|---|---|---|---|---|---|---|---|---|---|---|
| A-8945 | H | H | H | H | H | O | H | H | 4-ethynyl | 1 |
| A-8946 | H | H | H | H | H | O | H | H | 2-(1-propyn-1-yl) | 1 |

TABLE 158-continued

| compound | R¹ | R² | R³ | R⁴ | R⁵ | A | R⁶ | R⁷ | (R⁸)$_m$ | p |
|---|---|---|---|---|---|---|---|---|---|---|
| A-8947 | H | H | H | H | H | O | H | H | 3-(1-propyn-1-yl) | 1 |
| A-8948 | H | H | H | H | H | O | H | H | 4-(1-propyn-1-yl) | 1 |
| A-8949 | H | H | H | H | H | O | H | H | 2-(2-propyn-1-yl) | 1 |
| A-8950 | H | H | H | H | H | O | H | H | 3-(2-propyn-1-yl) | 1 |
| A-8951 | H | H | H | H | H | O | H | H | 4-(2-propyn-1-yl) | 1 |
| A-8952 | H | H | H | H | H | O | H | H | 2-(2-cyclopropylethynyl) | 1 |
| A-8953 | H | H | H | H | H | O | H | H | 3-(2-cyclopropylethynyl) | 1 |
| A-8954 | H | H | H | H | H | O | H | H | 4-(2-cyclopropylethynyl) | 1 |
| A-8955 | H | H | H | H | H | O | H | H | 2-(2-chloroethynyl) | 1 |
| A-8956 | H | H | H | H | H | O | H | H | 3-(2-chloroethynyl) | 1 |
| A-8957 | H | H | H | H | H | O | H | H | 4-(2-chloroethynyl) | 1 |
| A-8958 | H | H | H | H | H | O | H | H | 2-(2-bromoethynyl) | 1 |
| A-8959 | H | H | H | H | H | O | H | H | 3-(2-bromoethynyl) | 1 |
| A-8960 | H | H | H | H | H | O | H | H | 4-(2-bromoethynyl) | 1 |
| A-8961 | H | H | H | H | H | O | H | H | 2-OMe | 1 |
| A-8962 | H | H | H | H | H | O | H | H | 3-OMe | 1 |
| A-8963 | H | H | H | H | H | O | H | H | 4-OMe | 1 |
| A-8964 | H | H | H | H | H | O | H | H | 2-OEt | 1 |
| A-8965 | H | H | H | H | H | O | H | H | 3-OEt | 1 |
| A-8966 | H | H | H | H | H | O | H | H | 4-OEt | 1 |
| A-8967 | H | H | H | H | H | O | H | H | 2-OPr | 1 |
| A-8968 | H | H | H | H | H | O | H | H | 3-OPr | 1 |
| A-8969 | H | H | H | H | H | O | H | H | 4-OPr | 1 |
| A-8970 | H | H | H | H | H | O | H | H | 2-O(i-Pr) | 1 |
| A-8971 | H | H | H | H | H | O | H | H | 3-O(i-Pr) | 1 |
| A-8972 | H | H | H | H | H | O | H | H | 4-O(i-Pr) | 1 |
| A-8973 | H | H | H | H | H | O | H | H | 2-OBu | 1 |
| A-8974 | H | H | H | H | H | O | H | H | 3-OBu | 1 |
| A-8975 | H | H | H | H | H | O | H | H | 4-OBu | 1 |
| A-8976 | H | H | H | H | H | O | H | H | 2-O(s-Bu) | 1 |
| A-8977 | H | H | H | H | H | O | H | H | 3-O(s-Bu) | 1 |
| A-8978 | H | H | H | H | H | O | H | H | 4-O(s-Bu) | 1 |
| A-8979 | H | H | H | H | H | O | H | H | 2-O(i-Bu) | 1 |
| A-8980 | H | H | H | H | H | O | H | H | 3-O(i-Bu) | 1 |
| A-8981 | H | H | H | H | H | O | H | H | 4-O(i-Bu) | 1 |
| A-8982 | H | H | H | H | H | O | H | H | 2-O(t-Bu) | 1 |
| A-8983 | H | H | H | H | H | O | H | H | 3-O(t-Bu) | 1 |
| A-8984 | H | H | H | H | H | O | H | H | 4-O(t-Bu) | 1 |
| A-8985 | H | H | H | H | H | O | H | H | 2-OCF₃ | 1 |
| A-8986 | H | H | H | H | H | O | H | H | 3-OCF₃ | 1 |
| A-8987 | H | H | H | H | H | O | H | H | 4-OCF₃ | 1 |
| A-8988 | H | H | H | H | H | O | H | H | 2-OCHF₂ | 1 |
| A-8989 | H | H | H | H | H | O | H | H | 3-OCHF₂ | 1 |
| A-8990 | H | H | H | H | H | O | H | H | 4-OCHF₂ | 1 |
| A-8991 | H | H | H | H | H | O | H | H | 2-OCH₂CF₃ | 1 |
| A-8992 | H | H | H | H | H | O | H | H | 3-OCH₂CF₃ | 1 |
| A-8993 | H | H | H | H | H | O | H | H | 4-OCH₂CF₃ | 1 |
| A-8994 | H | H | H | H | H | O | H | H | 2-(cyclopropyloxy) | 1 |
| A-8995 | H | H | H | H | H | O | H | H | 3-(cyclopropyloxy) | 1 |
| A-8996 | H | H | H | H | H | O | H | H | 4-(cyclopropyloxy) | 1 |
| A-8997 | H | H | H | H | H | O | H | H | 2-(cyclobutyloxy) | 1 |
| A-8998 | H | H | H | H | H | O | H | H | 3-(cyclobutyloxy) | 1 |
| A-8999 | H | H | H | H | H | O | H | H | 4-(cyclobutyloxy) | 1 |
| A-9000 | H | H | H | H | H | O | H | H | 2-(cyclopentyloxy) | 1 |
| A-9001 | H | H | H | H | H | O | H | H | 3-(cyclopentyloxy) | 1 |

TABLE 159

| compound | R¹ | R² | R³ | R⁴ | R⁵ | A | R⁶ | R⁷ | (R⁸)$_m$ | p |
|---|---|---|---|---|---|---|---|---|---|---|
| A-9002 | H | H | H | H | H | O | H | H | 4-(cyclopentyloxy) | 1 |
| A-9003 | H | H | H | H | H | O | H | H | 2-((2,2-dichlorocyclopropyl)oxy) | 1 |
| A-9004 | H | H | H | H | H | O | H | H | 3-((2,2-dichlorocyclopropyl)oxy) | 1 |
| A-9005 | H | H | H | H | H | O | H | H | 4-((2,2-dichlorocyclopropyl)oxy) | 1 |
| A-9006 | H | H | H | H | H | O | H | H | 2-(cyclopropylmethoxy) | 1 |
| A-9007 | H | H | H | H | H | O | H | H | 3-(cyclopropylmethoxy) | 1 |
| A-9008 | H | H | H | H | H | O | H | H | 4-(cyclopropylmethoxy) | 1 |
| A-9009 | H | H | H | H | H | O | H | H | 2-((2,2-difluorocyclopropyl)methoxy) | 1 |
| A-9010 | H | H | H | H | H | O | H | H | 3-((2,2-difluorocyclopropyl)methoxy) | 1 |
| A-9011 | H | H | H | H | H | O | H | H | 4-((2,2-difluorocyclopropyl)methoxy) | 1 |
| A-9012 | H | H | H | H | H | O | H | H | 2-(oxiran-2-yl) | 1 |
| A-9013 | H | H | H | H | H | O | H | H | 3-(oxiran-2-yl) | 1 |
| A-9014 | H | H | H | H | H | O | H | H | 4-(oxiran-2-yl) | 1 |
| A-9015 | H | H | H | H | H | O | H | H | 2-(oxiran-2-ylmethyl) | 1 |
| A-9016 | H | H | H | H | H | O | H | H | 3-(oxiran-2-ylmethyl) | 1 |

TABLE 159-continued

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-9017 | H | H | H | H | H | O | H | H | 4-(oxiran-2-ylmethyl) | 1 |
| A-9018 | H | H | H | H | H | O | H | H | 2-SMe | 1 |
| A-9019 | H | H | H | H | H | O | H | H | 3-SMe | 1 |
| A-9020 | H | H | H | H | H | O | H | H | 4-SMe | 1 |
| A-9021 | H | H | H | H | H | O | H | H | 2-SEt | 1 |
| A-9022 | H | H | H | H | H | O | H | H | 3-SEt | 1 |
| A-9023 | H | H | H | H | H | O | H | H | 4-SEt | 1 |
| A-9024 | H | H | H | H | H | O | H | H | 2-S(=O)Me | 1 |
| A-9025 | H | H | H | H | H | O | H | H | 3-S(=O)Me | 1 |
| A-9026 | H | H | H | H | H | O | H | H | 4-S(=O)Me | 1 |
| A-9027 | H | H | H | H | H | O | H | H | 2-S(=O)$_2$Me | 1 |
| A-9028 | H | H | H | H | H | O | H | H | 3-S(=O)$_2$Me | 1 |
| A-9029 | H | H | H | H | H | O | H | H | 4-S(=O)$_2$Me | 1 |
| A-9030 | H | H | H | H | H | O | H | H | 2-SCF$_3$ | 1 |
| A-9031 | H | H | H | H | H | O | H | H | 3-SCF$_3$ | 1 |
| A-9032 | H | H | H | H | H | O | H | H | 4-SCF$_3$ | 1 |
| A-9033 | H | H | H | H | H | O | H | H | 2-S(=O)CF$_3$ | 1 |
| A-9034 | H | H | H | H | H | O | H | H | 3-S(=O)CF$_3$ | 1 |
| A-9035 | H | H | H | H | H | O | H | H | 4-S(=O)CF$_3$ | 1 |
| A-9036 | H | H | H | H | H | O | H | H | 2-S(=O)$_2$CF$_3$ | 1 |
| A-9037 | H | H | H | H | H | O | H | H | 3-S(=O)$_2$CF$_3$ | 1 |
| A-9038 | H | H | H | H | H | O | H | H | 4-S(=O)$_2$CF$_3$ | 1 |
| A-9039 | H | H | H | H | H | O | H | H | 2-SCF(CF$_3$)$_2$ | 1 |
| A-9040 | H | H | H | H | H | O | H | H | 3-SCF(CF$_3$)$_2$ | 1 |
| A-9041 | H | H | H | H | H | O | H | H | 4-SCF(CF$_3$)$_2$ | 1 |
| A-9042 | H | H | H | H | H | O | H | H | 2-(cyclopropylthio) | 1 |
| A-9043 | H | H | H | H | H | O | H | H | 3-(cyclopropylthio) | 1 |
| A-9044 | H | H | H | H | H | O | H | H | 4-(cyclopropylthio) | 1 |
| A-9045 | H | H | H | H | H | O | H | H | 2-(cyclopropylsulfinyl) | 1 |
| A-9046 | H | H | H | H | H | O | H | H | 3-(cyclopropylsulfinyl) | 1 |
| A-9047 | H | H | H | H | H | O | H | H | 4-(cyclopropylsulfinyl) | 1 |
| A-9048 | H | H | H | H | H | O | H | H | 2-(cyclopropylsulfonyl) | 1 |
| A-9049 | H | H | H | H | H | O | H | H | 3-(cyclopropylsulfonyl) | 1 |
| A-9050 | H | H | H | H | H | O | H | H | 4-(cyclopropylsulfonyl) | 1 |
| A-9051 | H | H | H | H | H | O | H | H | 2-((cyclopropylmethyl)thio) | 1 |
| A-9052 | H | H | H | H | H | O | H | H | 3-((cyclopropylmethyl)thio) | 1 |
| A-9053 | H | H | H | H | H | O | H | H | 4-((cyclopropylmethyl)thio) | 1 |
| A-9054 | H | H | H | H | H | O | H | H | 2-((cyclopropylmethyl)sulfinyl) | 1 |
| A-9055 | H | H | H | H | H | O | H | H | 3-((cyclopropylmethyl)sulfinyl) | 1 |
| A-9056 | H | H | H | H | H | O | H | H | 4-((cyclopropylmethyl)sulfinyl) | 1 |
| A-9057 | H | H | H | H | H | O | H | H | 2-((cyclopropylmethyl)sulfonyl) | 1 |
| A-9058 | H | H | H | H | H | O | H | H | 3-((cyclopropylmethyl)sulfonyl) | 1 |

TABLE 160

| compound | R$^1$ | R$^2$ | R$^3$ | R$^4$ | R$^5$ | A | R$^6$ | R$^7$ | (R$^8$)$_m$ | p |
|---|---|---|---|---|---|---|---|---|---|---|
| A-9059 | H | H | H | H | H | O | H | H | 4-((cyclopropymethyl)sulfonyl) | 1 |
| A-9060 | H | H | H | H | H | O | H | H | 2-(((2,2-difluorocyclopropyl)methyl)thio) | 1 |
| A-9061 | H | H | H | H | H | O | H | H | 3-(((2,2-difluorocyclopropyl)methyl)thio) | 1 |
| A-9062 | H | H | H | H | H | O | H | H | 4-(((2,2-difluorocyclopropyl)methyl)thio) | 1 |
| A-9063 | H | H | H | H | H | O | H | H | 2-(((2,2-difluorocyclopropyl)methyl)sulfinyl) | 1 |
| A-9064 | H | H | H | H | H | O | H | H | 3-(((2,2-difluorocyclopropyl)methyl)sulfinyl) | 1 |
| A-9065 | H | H | H | H | H | O | H | H | 4-(((2,2-difluorocyclopropyl)methyl)sulfinyl) | 1 |
| A-9066 | H | H | H | H | H | O | H | H | 2-(((2,2-difluorocyclopropyl)methyl)sulfonyl) | 1 |
| A-9067 | H | H | H | H | H | O | H | H | 3-(((2,2-difluorocyclopropyl)methyl)sulfonyl) | 1 |
| A-9068 | H | H | H | H | H | O | H | H | 4-(((2,2-difluorocyclopropyl)methyl)sulfonyl) | 1 |
| A-9069 | H | H | H | H | H | O | H | H | 2-C(=O)Me | 1 |
| A-9070 | H | H | H | H | H | O | H | H | 3-C(=O)Me | 1 |
| A-9071 | H | H | H | H | H | O | H | H | 4-C(=O)Me | 1 |
| A-9072 | H | H | H | H | H | O | H | H | 2-C(=O)Et | 1 |
| A-9073 | H | H | H | H | H | O | H | H | 3-C(=O)Et | 1 |
| A-9074 | H | H | H | H | H | O | H | H | 4-C(=O)Et | 1 |
| A-9075 | H | H | H | H | H | O | H | H | 2-C(=O)CF$_3$ | 1 |
| A-9076 | H | H | H | H | H | O | H | H | 3-C(=O)CF$_3$ | 1 |
| A-9077 | H | H | H | H | H | O | H | H | 4-C(=O)CF$_3$ | 1 |
| A-9078 | H | H | H | H | H | O | H | H | 2-C(=O) | 1 |
| A-9079 | H | H | H | H | H | O | H | H | 3-C(=O)OMe | 1 |
| A-9080 | H | H | H | H | H | O | H | H | 4-C(=O)OMe | 1 |
| A-9081 | H | H | H | H | H | O | H | H | 2-C(=O)OEt | 1 |
| A-9082 | H | H | H | H | H | O | H | H | 3-C(=O)OEt | 1 |
| A-9083 | H | H | H | H | H | O | H | H | 4-C(=O)OEt | 1 |
| A-9084 | H | H | H | H | H | O | H | H | 2-C(=O)NH$_2$ | 1 |
| A-9085 | H | H | H | H | H | O | H | H | 3-C(=O)NH$_2$ | 1 |
| A-9086 | H | H | H | H | H | O | H | H | 4-C(=O)NH$_2$ | 1 |

TABLE 160-continued

| compound | R¹ | R² | R³ | R⁴ | R⁵ | A | R⁶ | R⁷ | (R⁸)ₘ | p |
|---|---|---|---|---|---|---|---|---|---|---|
| A-9087 | H | H | H | H | H | O | H | H | 2-C(=O)NHMe | 1 |
| A-9088 | H | H | H | H | H | O | H | H | 3-C(=O)NHMe | 1 |
| A-9089 | H | H | H | H | H | O | H | H | 4-C(=O)NHMe | 1 |
| A-9090 | H | H | H | H | H | O | H | H | 2-C(=O)NMe₂ | 1 |
| A-9091 | H | H | H | H | H | O | H | H | 3-C(=O)NMe₂ | 1 |
| A-9092 | H | H | H | H | H | O | H | H | 4-C(=O)NMe₂ | 1 |
| A-9093 | H | H | H | H | H | O | H | H | 2-CH₂C(=O)CH₃ | 1 |
| A-9094 | H | H | H | H | H | O | H | H | 3-CH₂C(=O)CH₃ | 1 |
| A-9095 | H | H | H | H | H | O | H | H | 4-CH₂C(=O)CH₃ | 1 |
| A-9096 | H | H | H | H | H | O | H | H | 2-CH₂C(=O)CF₃ | 1 |
| A-9097 | H | H | H | H | H | O | H | H | 3-CH₂C(=O)CF₃ | 1 |
| A-9098 | H | H | H | H | H | O | H | H | 4-CH₂C(=O)CF₃ | 1 |
| A-9099 | H | H | H | H | H | O | H | H | 2-CH₂C(=O)OCH₃ | 1 |
| A-9100 | H | H | H | H | H | O | H | H | 3-CH₂C(=O)OCH₃ | 1 |
| A-9101 | H | H | H | H | H | O | H | H | 4-CH₂C(=O)OCH₃ | 1 |
| A-9102 | H | H | H | H | H | O | H | H | 2-CH₂OH | 1 |
| A-9103 | H | H | H | H | H | O | H | H | 3-CH₂OH | 1 |
| A-9104 | H | H | H | H | H | O | H | H | 4-CH₂OH | 1 |
| A-9105 | H | H | H | H | H | O | H | H | 2-CH₂OCH₃ | 1 |
| A-9106 | H | H | H | H | H | O | H | H | 3-CH₂OCH₃ | 1 |
| A-9107 | H | H | H | H | H | O | H | H | 4-CH₂OCH₃ | 1 |
| A-9108 | H | H | H | H | H | O | H | H | 2-CH₂OCH₂CH₃ | 1 |
| A-9109 | H | H | H | H | H | O | H | H | 3-CH₂OCH₂CH₃ | 1 |
| A-9110 | H | H | H | H | H | O | H | H | 4-CH₂OCH₂CH₃ | 1 |
| A-9111 | H | H | H | H | H | O | H | H | 2-CH(CH₃)OCH₃ | 1 |
| A-9112 | H | H | H | H | H | O | H | H | 3-CH(CH₃)OCH₃ | 1 |
| A-9113 | H | H | H | H | H | O | H | H | 4-CH(CH₃)OCH₃ | 1 |
| A-9114 | H | H | H | H | H | O | H | H | 2-CH₂CH₂OCH₃ | 1 |
| A-9115 | H | H | H | H | H | O | H | H | 3-CH₂CH₂OCH₃ | 1 |

TABLE 161

| compound | R¹ | R² | R³ | R⁴ | R⁵ | A | R⁶ | R⁷ | (R⁸)ₘ | p |
|---|---|---|---|---|---|---|---|---|---|---|
| A-9116 | H | H | H | H | H | O | H | H | 4-CH₂CH₂OCH₃ | 1 |
| A-9117 | H | H | H | H | H | O | H | H | 2-CH₂OCF₃ | 1 |
| A-9118 | H | H | H | H | H | O | H | H | 3-CH₂OCF₃ | 1 |
| A-9119 | H | H | H | H | H | O | H | H | 4-CH₂OCF₃ | 1 |
| A-9120 | H | H | H | H | H | O | H | H | 2-CF₂OCH₃ | 1 |
| A-9121 | H | H | H | H | H | O | H | H | 3-CF₂OCH₃ | 1 |
| A-9122 | H | H | H | H | H | O | H | H | 4-CF₂OCH₃ | 1 |
| A-9123 | H | H | H | H | H | O | H | H | 2-CF₂CF₂OCF₃ | 1 |
| A-9124 | H | H | H | H | H | O | H | H | 3-CF₂CF₂OCF₃ | 1 |
| A-9125 | H | H | H | H | H | O | H | H | 4-CF₂CF₂OCF₃ | 1 |
| A-9126 | H | H | H | H | H | O | H | H | 2-OC(=O)CH₃ | 1 |
| A-9127 | H | H | H | H | H | O | H | H | 3-OC(=O)CH₃ | 1 |
| A-9128 | H | H | H | H | H | O | H | H | 4-OC(=O)CH₃ | 1 |
| A-9129 | H | H | H | H | H | O | H | H | 2-OC(=O)CF₃ | 1 |
| A-9130 | H | H | H | H | H | O | H | H | 3-OC(=O)CF₃ | 1 |
| A-9131 | H | H | H | H | H | O | H | H | 4-OC(=O)CF₃ | 1 |
| A-9132 | H | H | H | H | H | O | H | H | 2-OC(=O)NH₂ | 1 |
| A-9133 | H | H | H | H | H | O | H | H | 3-OC(=O)NH₂ | 1 |
| A-9134 | H | H | H | H | H | O | H | H | 4-OC(=O)NH₂ | 1 |
| A-9135 | H | H | H | H | H | O | H | H | 2-OC(=O)NHCH₃ | 1 |
| A-9136 | H | H | H | H | H | O | H | H | 3-OC(=O)NHCH₃ | 1 |
| A-9137 | H | H | H | H | H | O | H | H | 4-OC(=O)NHCH₃ | 1 |
| A-9138 | H | H | H | H | H | O | H | H | 2-OC(=O)N(CH₃)₂ | 1 |
| A-9139 | H | H | H | H | H | O | H | H | 3-OC(=O)N(CH₃)₂ | 1 |
| A-9140 | H | H | H | H | H | O | H | H | 4-OC(=O)N(CH₃)₂ | 1 |
| A-9141 | H | H | H | H | H | O | H | H | 2-CH₂OC(=O)NH₂ | 1 |
| A-9142 | H | H | H | H | H | O | H | H | 3-CH₂OC(=O)NH₂ | 1 |
| A-9143 | H | H | H | H | H | O | H | H | 4-CH₂OC(=O)NH₂ | 1 |
| A-9144 | H | H | H | H | H | O | H | H | 2-CH₂OC(=O)NHCH₃ | 1 |
| A-9145 | H | H | H | H | H | O | H | H | 3-CH₂OC(=O)NHCH₃ | 1 |
| A-9146 | H | H | H | H | H | O | H | H | 4-CH₂OC(=O)NHCH₃ | 1 |
| A-9147 | H | H | H | H | H | O | H | H | 2-CH₂OC(=O)N(CH₃)₂ | 1 |
| A-9148 | H | H | H | H | H | O | H | H | 3-CH₂OC(=O)N(CH₃)₂ | 1 |
| A-9149 | H | H | H | H | H | O | H | H | 4-CH₂OC(=O)N(CH₃)₂ | 1 |
| A-9150 | H | H | H | H | H | O | H | H | 2-OC(=O)OCH₃ | 1 |
| A-9151 | H | H | H | H | H | O | H | H | 3-OC(=O)OCH₃ | 1 |
| A-9152 | H | H | H | H | H | O | H | H | 4-OC(=O)OCH₃ | 1 |
| A-9153 | H | H | H | H | H | O | H | H | 2-CH₂OC(=O)OCH₃ | 1 |
| A-9154 | H | H | H | H | H | O | H | H | 3-CH₂OC(=O)OCH₃ | 1 |
| A-9155 | H | H | H | H | H | O | H | H | 4-CH₂OC(=O)OCH₃ | 1 |
| A-9156 | H | H | H | H | H | O | H | H | 2-CH₂OC(=O)CH₃ | 1 |

TABLE 161-continued

| compound | R¹ | R² | R³ | R⁴ | R⁵ | A | R⁶ | R⁷ | (R⁸)ₘ | p |
|---|---|---|---|---|---|---|---|---|---|---|
| A-9157 | H | H | H | H | H | O | H | H | 3-CH$_2$OC(=O)CH$_3$ | 1 |
| A-9158 | H | H | H | H | H | O | H | H | 4-CH$_2$OC(=O)CH$_3$ | 1 |
| A-9159 | H | H | H | H | H | O | H | H | 2-OS(=O)$_2$CH$_3$ | 1 |
| A-9160 | H | H | H | H | H | O | H | H | 3-OS(=O)$_2$CH$_3$ | 1 |
| A-9161 | H | H | H | H | H | O | H | H | 4-OS(=O)$_2$CH$_3$ | 1 |
| A-9162 | H | H | H | H | H | O | H | H | 2-CH$_2$SCH$_3$ | 1 |
| A-9163 | H | H | H | H | H | O | H | H | 3-CH$_2$SCH$_3$ | 1 |
| A-9164 | H | H | H | H | H | O | H | H | 4-CH$_2$SCH$_3$ | 1 |
| A-9165 | H | H | H | H | H | O | H | H | 2-CH$_2$S(=O)CH$_3$ | 1 |
| A-9166 | H | H | H | H | H | O | H | H | 3-CH$_2$S(=O)CH$_3$ | 1 |
| A-9167 | H | H | H | H | H | O | H | H | 4-CH$_2$S(=O)CH$_3$ | 1 |
| A-9168 | H | H | H | H | H | O | H | H | 2-CH$_2$S(=O)$_2$CH$_3$ | 1 |
| A-9169 | H | H | H | H | H | O | H | H | 3-CH$_2$S(=O)$_2$CH$_3$ | 1 |
| A-9170 | H | H | H | H | H | O | H | H | 4-CH$_2$S(=O)$_2$CH$_3$ | 1 |
| A-9171 | H | H | H | H | H | O | H | H | 2-CH$_2$SCF$_3$ | 1 |
| A-9172 | H | H | H | H | H | O | H | H | 3-CH$_2$SCF$_3$ | 1 |

TABLE 162

| compound | R¹ | R² | R³ | R⁴ | R⁵ | A | R⁶ | R⁷ | (R⁸)ₘ | p |
|---|---|---|---|---|---|---|---|---|---|---|
| A-9173 | H | H | H | H | H | O | H | H | 4-CH$_2$SCF$_3$ | 1 |
| A-9174 | H | H | H | H | H | O | H | H | 2-CH$_2$S(=O)CF$_3$ | 1 |
| A-9175 | H | H | H | H | H | O | H | H | 3-CH$_2$S(=O)CF$_3$ | 1 |
| A-9176 | H | H | H | H | H | O | H | H | 4-CH$_2$S(=O)CF$_3$ | 1 |
| A-9177 | H | H | H | H | H | O | H | H | 2-CH$_2$S(=O)$_2$CF$_3$ | 1 |
| A-9178 | H | H | H | H | H | O | H | H | 3-CH$_2$S(=O)$_2$CF$_3$ | 1 |
| A-9179 | H | H | H | H | H | O | H | H | 4-CH$_2$S(=O)$_2$CF$_3$ | 1 |
| A-9180 | H | H | H | H | H | O | H | H | 2-phenyl | 1 |
| A-9181 | H | H | H | H | H | O | H | H | 3-phenyl | 1 |
| A-9182 | H | H | H | H | H | O | H | H | 4-phenyl | 1 |
| A-9183 | H | H | H | H | H | O | H | H | 2-(phenyloxy) | 1 |
| A-9184 | H | H | H | H | H | O | H | H | 3-(phenyloxy) | 1 |
| A-9185 | H | H | H | H | H | O | H | H | 4-(phenyloxy) | 1 |
| A-9186 | H | H | H | H | H | O | H | H | 2-benzyl | 1 |
| A-9187 | H | H | H | H | H | O | H | H | 3-benzyl | 1 |
| A-9188 | H | H | H | H | H | O | H | H | 4-benzyl | 1 |
| A-9189 | H | H | H | H | H | O | H | H | 2-(benzyloxy) | 1 |
| A-9190 | H | H | H | H | H | O | H | H | 3-(benzyloxy) | 1 |
| A-9191 | H | H | H | H | H | O | H | H | 4-(benzyloxy) | 1 |
| A-9192 | H | H | H | H | H | O | H | H | 2-((2-fluorobenzyl)oxy) | 1 |
| A-9193 | H | H | H | H | H | O | H | H | 3-((2-fluorobenzyl)oxy) | 1 |
| A-9194 | H | H | H | H | H | O | H | H | 4-((2-fluorobenzyl)oxy) | 1 |
| A-9195 | H | H | H | H | H | O | H | H | 2-((3-fluorobenzyl)oxy) | 1 |
| A-9196 | H | H | H | H | H | O | H | H | 3-((3-fluorobenzyl)oxy) | 1 |
| A-9197 | H | H | H | H | H | O | H | H | 4-((3-fluorobenzyl)oxy) | 1 |
| A-9198 | H | H | H | H | H | O | H | H | 2-((4-fluorobenzyl)oxy) | 1 |
| A-9199 | H | H | H | H | H | O | H | H | 3-((4-fluorobenzyl)oxy) | 1 |
| A-9200 | H | H | H | H | H | O | H | H | 4-((4-fluorobenzyl)oxy) | 1 |
| A-9201 | H | H | H | H | H | O | H | H | 2-((2-chlorobenzyl)oxy) | 1 |
| A-9202 | H | H | H | H | H | O | H | H | 3-((2-chlorobenzyl)oxy) | 1 |
| A-9203 | H | H | H | H | H | O | H | H | 4-((2-chlorobenzyl)oxy) | 1 |
| A-9204 | H | H | H | H | H | O | H | H | 2-((3-chlorobenzyl)oxy) | 1 |
| A-9205 | H | H | H | H | H | O | H | H | 3-((3-chlorobenzyl)oxy) | 1 |
| A-9206 | H | H | H | H | H | O | H | H | 4-((3-chlorobenzyl)oxy) | 1 |
| A-9207 | H | H | H | H | H | O | H | H | 2-((4-chlorobenzyl)oxy) | 1 |
| A-9208 | H | H | H | H | H | O | H | H | 3-((4-chlorobenzyl)oxy) | 1 |
| A-9209 | H | H | H | H | H | O | H | H | 4-((4-chlorobenzyl)oxy) | 1 |
| A-9210 | H | H | H | H | H | O | H | H | 2-((2-methybenzyl)oxy) | 1 |
| A-9211 | H | H | H | H | H | O | H | H | 3-((2-methybenzyl)oxy) | 1 |
| A-9212 | H | H | H | H | H | O | H | H | 4-((2-methybenzyl)oxy) | 1 |
| A-9213 | H | H | H | H | H | O | H | H | 2-((3-methybenzyl)oxy) | 1 |
| A-9214 | H | H | H | H | H | O | H | H | 3-((3-methybenzyl)oxy) | 1 |
| A-9215 | H | H | H | H | H | O | H | H | 4-((3-methybenzyl)oxy) | 1 |
| A-9216 | H | H | H | H | H | O | H | H | 2-((4-methybenzyl)oxy) | 1 |
| A-9217 | H | H | H | H | H | O | H | H | 3-((4-methybenzyl)oxy) | 1 |
| A-9218 | H | H | H | H | H | O | H | H | 4-((4-methybenzyl)oxy) | 1 |
| A-9219 | H | H | H | H | H | O | H | H | 2-((2-(trifluoromethyl)benzyl)oxy) | 1 |
| A-9220 | H | H | H | H | H | O | H | H | 3-((2-(trifluoromethyl)benzyl)oxy) | 1 |
| A-9221 | H | H | H | H | H | O | H | H | 4-((2-(trifluoromethyl)benzyl)oxy) | 1 |
| A-9222 | H | H | H | H | H | O | H | H | 2-((3-(trifluoromethyl)benzyl)oxy) | 1 |
| A-9223 | H | H | H | H | H | O | H | H | 3-((3-(trifluoromethyl)benzyl)oxy) | 1 |
| A-9224 | H | H | H | H | H | O | H | H | 4-((3-(trifluoromethyl)benzyl)oxy) | 1 |
| A-9225 | H | H | H | H | H | O | H | H | 2-((4-(trifluoromethyl)benzyl)oxy) | 1 |
| A-9226 | H | H | H | H | H | O | H | H | 3-((4-(trifluoromethyl)benzyl)oxy) | 1 |

TABLE 162-continued

| compound | R¹ | R² | R³ | R⁴ | R⁵ | A | R⁶ | R⁷ | (R⁸)ₘ | p |
|---|---|---|---|---|---|---|---|---|---|---|
| A-9227 | H | H | H | H | H | O | H | H | 4-((4-(trifluoromethyl)benzyl)oxy) | 1 |
| A-9228 | H | H | H | H | H | O | H | H | 2-((2-methoxybenzyl)oxy) | 1 |
| A-9229 | H | H | H | H | H | O | H | H | 3-((2-methoxybenzyl)oxy) | 1 |

TABLE 163

| compound | R¹ | R² | R³ | R⁴ | R⁵ | A | R⁶ | R⁷ | (R⁸)ₘ | p |
|---|---|---|---|---|---|---|---|---|---|---|
| A-9230 | H | H | H | H | H | O | H | H | 4-((2-methoxybenzyl)oxy) | 1 |
| A-9231 | H | H | H | H | H | O | H | H | 2-((3-methoxybenzyl)oxy) | 1 |
| A-9232 | H | H | H | H | H | O | H | H | 3-((3-methoxybenzyl)oxy) | 1 |
| A-9233 | H | H | H | H | H | O | H | H | 4-((3-methoxybenzyl)oxy) | 1 |
| A-9234 | H | H | H | H | H | O | H | H | 2-((4-methoxybenzyl)oxy) | 1 |
| A-9235 | H | H | H | H | H | O | H | H | 3-((4-methoxybenzyl)oxy) | 1 |
| A-9236 | H | H | H | H | H | O | H | H | 4-((4-methoxybenzyl)oxy) | 1 |
| A-9237 | H | H | H | H | H | O | H | H | 2-((2-(trifluoromethoxy)benzyl)oxy) | 1 |
| A-9238 | H | H | H | H | H | O | H | H | 3-((2-(trifluoromethoxy)benzyl)oxy) | 1 |
| A-9239 | H | H | H | H | H | O | H | H | 4-((2-(trifluoromethoxy)benzyl)oxy) | 1 |
| A-9240 | H | H | H | H | H | O | H | H | 2-((3-(trifluoromethoxy)benzyl)oxy) | 1 |
| A-9241 | H | H | H | H | H | O | H | H | 3-((3-(trifluoromethoxy)benzyl)oxy) | 1 |
| A-9242 | H | H | H | H | H | O | H | H | 4-((3-(trifluoromethoxy)benzyl)oxy) | 1 |
| A-9243 | H | H | H | H | H | O | H | H | 2-((4-(trifluoromethoxy)benzyl)oxy) | 1 |
| A-9244 | H | H | H | H | H | O | H | H | 3-((4-(trifluoromethoxy)benzyl)oxy) | 1 |
| A-9245 | H | H | H | H | H | O | H | H | 4-((4-(trifluoromethoxy)benzyl)oxy) | 1 |
| A-9246 | H | H | H | H | H | O | H | H | 2-((2-(methylthio)benzyl)oxy) | 1 |
| A-9247 | H | H | H | H | H | O | H | H | 3-((2-(methylthio)benzyl)oxy) | 1 |
| A-9248 | H | H | H | H | H | O | H | H | 4-((2-(methylthio)benzyl)oxy) | 1 |
| A-9249 | H | H | H | H | H | O | H | H | 2-((3-(methylthio)benzyl)oxy) | 1 |
| A-9250 | H | H | H | H | H | O | H | H | 3-((3-(methylthio)benzyl)oxy) | 1 |
| A-9251 | H | H | H | H | H | O | H | H | 4-((3-(methylthio)benzyl)oxy) | 1 |
| A-9252 | H | H | H | H | H | O | H | H | 2-((4-(methylthio)benzyl)oxy) | 1 |
| A-9253 | H | H | H | H | H | O | H | H | 3-((4-(methylthio)benzyl)oxy) | 1 |
| A-9254 | H | H | H | H | H | O | H | H | 4-((4-(methylthio)benzyl)oxy) | 1 |
| A-9255 | H | H | H | H | H | O | H | H | 2-((2-(methylsulfinyl)benzyl)oxy) | 1 |
| A-9256 | H | H | H | H | H | O | H | H | 3-((2-(methylsulfinyl)benzyl)oxy) | 1 |
| A-9257 | H | H | H | H | H | O | H | H | 4-((2-(methylsulfinyl)benzyl)oxy) | 1 |
| A-9258 | H | H | H | H | H | O | H | H | 2-((3-(methylsulfinyl)benzyl)oxy) | 1 |
| A-9259 | H | H | H | H | H | O | H | H | 3-((3-(methylsulfinyl)benzyl)oxy) | 1 |
| A-9260 | H | H | H | H | H | O | H | H | 4-((3-(methylsulfinyl)benzyl)oxy) | 1 |
| A-9261 | H | H | H | H | H | O | H | H | 2-((4-(methylsulfinyl)benzyl)oxy) | 1 |
| A-9262 | H | H | H | H | H | O | H | H | 3-((4-(methylsulfinyl)benzyl)oxy) | 1 |
| A-9263 | H | H | H | H | H | O | H | H | 4-((4-(methylsulfinyl)benzyl)oxy) | 1 |
| A-9264 | H | H | H | H | H | O | H | H | 2-((2-(methylsulfonyl)benzyl)oxy) | 1 |
| A-9265 | H | H | H | H | H | O | H | H | 3-((2-(methylsulfonyl)benzyl)oxy) | 1 |
| A-9266 | H | H | H | H | H | O | H | H | 4-((2-(methylsulfonyl)benzyl)oxy) | 1 |
| A-9267 | H | H | H | H | H | O | H | H | 2-((3-(methylsulfonyl)benzyl)oxy) | 1 |
| A-9268 | H | H | H | H | H | O | H | H | 3-((3-(methylsulfonyl)benzyl)oxy) | 1 |
| A-9269 | H | H | H | H | H | O | H | H | 4-((3-(methylsulfonyl)benzyl)oxy) | 1 |
| A-9270 | H | H | H | H | H | O | H | H | 2-((4-(methylsulfonyl)benzyl)oxy) | 1 |
| A-9271 | H | H | H | H | H | O | H | H | 3-((4-(methylsulfonyl)benzyl)oxy) | 1 |
| A-9272 | H | H | H | H | H | O | H | H | 4-((4-(methylsulfonyl)benzyl)oxy) | 1 |
| A-9273 | H | H | H | H | H | O | H | H | 2-((2-(trifluoromethylthio)benzyl)oxy) | 1 |
| A-9274 | H | H | H | H | H | O | H | H | 3-((2-(trifluoromethylthio)benzyl)oxy) | 1 |
| A-9275 | H | H | H | H | H | O | H | H | 4-((2-(trifluoromethylthio)benzyl)oxy) | 1 |
| A-9276 | H | H | H | H | H | O | H | H | 2-((3-(trifluoromethylthio)benzyl)oxy) | 1 |
| A-9277 | H | H | H | H | H | O | H | H | 3-((3-(trifluoromethylthio)benzyl)oxy) | 1 |
| A-9278 | H | H | H | H | H | O | H | H | 4-((3-(trifluoromethylthio)benzyl)oxy) | 1 |
| A-9279 | H | H | H | H | H | O | H | H | 2-((4-(trifluoromethylthio)benzyl)oxy) | 1 |
| A-9280 | H | H | H | H | H | O | H | H | 3-((4-(trifluoromethylthio)benzyl)oxy) | 1 |
| A-9281 | H | H | H | H | H | O | H | H | 4-((4-(trifluoromethylthio)benzyl)oxy) | 1 |
| A-9282 | H | H | H | H | H | O | H | H | 2-((2-(trifluoromethylsulfinyl)benzyl)oxy) | 1 |
| A-9283 | H | H | H | H | H | O | H | H | 3-((2-(trifluoromethylsulfinyl)benzyl)oxy) | 1 |
| A-9284 | H | H | H | H | H | O | H | H | 4-((2-(trifluoromethylsulfinyl)benzyl)oxy) | 1 |
| A-9285 | H | H | H | H | H | O | H | H | 2-((3-(trifluoromethylsulfinyl)benzyl)oxy) | 1 |
| A-9286 | H | H | H | H | H | O | H | H | 3-((3-(trifluoromethylsulfinyl)benzyl)oxy) | 1 |

TABLE 164

| compound | R¹ | R² | R³ | R⁴ | R⁵ | A | R⁶ | R⁷ | (R⁸)ₘ | p |
|---|---|---|---|---|---|---|---|---|---|---|
| A-9287 | H | H | H | H | H | O | H | H | 4-((3-(trifluoromethylsulfinyl)benzyl)oxy) | 1 |
| A-9288 | H | H | H | H | H | O | H | H | 2-((4-(trifluoromethylsulfinyl)benzyl)oxy) | 1 |
| A-9289 | H | H | H | H | H | O | H | H | 3-((4-(trifluoromethylsulfinyl)benzyl)oxy) | 1 |

TABLE 164-continued

| compound | R¹ | R² | R³ | R⁴ | R⁵ | A | R⁶ | R⁷ | (R⁸)ₘ | p |
|---|---|---|---|---|---|---|---|---|---|---|
| A-9290 | H | H | H | H | H | O | H | H | 4-((4-(trifluoromethylsulfinyl)benzyl)oxy) | 1 |
| A-9291 | H | H | H | H | H | O | H | H | 2-((2-(trifluoromethylsulfonyl)benzyl)oxy) | 1 |
| A-9292 | H | H | H | H | H | O | H | H | 3-((2-(trifluoromethylsulfonyl)benzyl)oxy) | 1 |
| A-9293 | H | H | H | H | H | O | H | H | 4-((2-(trifluoromethylsulfonyl)benzyl)oxy) | 1 |
| A-9294 | H | H | H | H | H | O | H | H | 2-((3-(trifluoromethylsulfonyl)benzyl)oxy) | 1 |
| A-9295 | H | H | H | H | H | O | H | H | 3-((3-(trifluoromethylsulfonyl)benzyl)oxy) | 1 |
| A-9296 | H | H | H | H | H | O | H | H | 4-((3-(trifluoromethylsulfonyl)benzyl)oxy) | 1 |
| A-9297 | H | H | H | H | H | O | H | H | 2-((4-(trifluoromethylsulfonyl)benzyl)oxy) | 1 |
| A-9298 | H | H | H | H | H | O | H | H | 3-((4-(trifluoromethylsulfonyl)benzyl)oxy) | 1 |
| A-9299 | H | H | H | H | H | O | H | H | 4-((4-(trifluoromethylsulfonyl)benzyl)oxy) | 1 |
| A-9300 | H | H | H | H | H | O | H | H | 2-((2-aminobenzyl)oxy) | 1 |
| A-9301 | H | H | H | H | H | O | H | H | 3-((2-aminobenzyl)oxy) | 1 |
| A-9302 | H | H | H | H | H | O | H | H | 4-((2-aminobenzyl)oxy) | 1 |
| A-9303 | H | H | H | H | H | O | H | H | 2-((3-aminobenzyl)oxy) | 1 |
| A-9304 | H | H | H | H | H | O | H | H | 3-((3-aminobenzyl)oxy) | 1 |
| A-9305 | H | H | H | H | H | O | H | H | 4-((3-aminobenzyl)oxy) | 1 |
| A-9306 | H | H | H | H | H | O | H | H | 2-((4-aminobenzyl)oxy) | 1 |
| A-9307 | H | H | H | H | H | O | H | H | 3-((4-aminobenzyl)oxy) | 1 |
| A-9308 | H | H | H | H | H | O | H | H | 4-((4-aminobenzyl)oxy) | 1 |
| A-9309 | H | H | H | H | H | O | H | H | 2-((2-(methylamino)benzyl)oxy) | 1 |
| A-9310 | H | H | H | H | H | O | H | H | 3-((2-(methylamino)benzyl)oxy) | 1 |
| A-9311 | H | H | H | H | H | O | H | H | 4-((2-(methylamino)benzyl)oxy) | 1 |
| A-9312 | H | H | H | H | H | O | H | H | 2-((3-(methylamino)benzyl)oxy) | 1 |
| A-9313 | H | H | H | H | H | O | H | H | 3-((3-(methylamino)benzyl)oxy) | 1 |
| A-9314 | H | H | H | H | H | O | H | H | 4-((3-(methylamino)benzyl)oxy) | 1 |
| A-9315 | H | H | H | H | H | O | H | H | 2-((4-(methylamino)benzyl)oxy) | 1 |
| A-9316 | H | H | H | H | H | O | H | H | 3-((4-(methylamino)benzyl)oxy) | 1 |
| A-9317 | H | H | H | H | H | O | H | H | 4-((4-(methylamino)benzyl)oxy) | 1 |
| A-9318 | H | H | H | H | H | O | H | H | 2-((2-(dimethylamino)benzyl)oxy) | 1 |
| A-9319 | H | H | H | H | H | O | H | H | 3-((2-(dimethylamino)benzyl)oxy) | 1 |
| A-9320 | H | H | H | H | H | O | H | H | 4-((2-(dimethylamino)benzyl)oxy) | 1 |
| A-9321 | H | H | H | H | H | O | H | H | 2-((3-(dimethylamino)benzyl)oxy) | 1 |
| A-9322 | H | H | H | H | H | O | H | H | 3-((3-(dimethylamino)benzyl)oxy) | 1 |
| A-9323 | H | H | H | H | H | O | H | H | 4-((3-(dimethylamino)benzyl)oxy) | 1 |
| A-9324 | H | H | H | H | H | O | H | H | 2-((4-(dimethylamino)benzyl)oxy) | 1 |
| A-9325 | H | H | H | H | H | O | H | H | 3-((4-(dimethylamino)benzyl)oxy) | 1 |
| A-9326 | H | H | H | H | H | O | H | H | 4-((4-(dimethylamino)benzyl)oxy) | 1 |
| A-9327 | H | H | H | H | H | O | H | H | 2-((2-cyanobenzyl)oxy) | 1 |
| A-9328 | H | H | H | H | H | O | H | H | 3-((2-cyanobenzyl)oxy) | 1 |
| A-9329 | H | H | H | H | H | O | H | H | 4-((2-cyanobenzyl)oxy) | 1 |
| A-9330 | H | H | H | H | H | O | H | H | 2-((3-cyanobenzyl)oxy) | 1 |
| A-9331 | H | H | H | H | H | O | H | H | 3-((3-cyanobenzyl)oxy) | 1 |
| A-9332 | H | H | H | H | H | O | H | H | 4-((3-cyanobenzyl)oxy) | 1 |
| A-9333 | H | H | H | H | H | O | H | H | 2-((4-cyanobenzyl)oxy) | 1 |
| A-9334 | H | H | H | H | H | O | H | H | 3-((4-cyanobenzyl)oxy) | 1 |
| A-9335 | H | H | H | H | H | O | H | H | 4-((4-cyanobenzyl)oxy) | 1 |
| A-9336 | H | H | H | H | H | O | H | H | 2-((2-nitrobenzyl)oxy) | 1 |
| A-9337 | H | H | H | H | H | O | H | H | 3-((2-nitrobenzyl)oxy) | 1 |
| A-9338 | H | H | H | H | H | O | H | H | 4-((2-nitrobenzyl)oxy) | 1 |
| A-9339 | H | H | H | H | H | O | H | H | 2-((3-nitrobenzyl)oxy) | 1 |
| A-9340 | H | H | H | H | H | O | H | H | 3-((3-nitrobenzyl)oxy) | 1 |
| A-9341 | H | H | H | H | H | O | H | H | 4-((3-nitrobenzyl)oxy) | 1 |
| A-9342 | H | H | H | H | H | O | H | H | 2-((4-nitrobenzyl)oxy) | 1 |
| A-9343 | H | H | H | H | H | O | H | H | 3-((4-nitrobenzyl)oxy) | 1 |

TABLE 165

| compound | R¹ | R² | R³ | R⁴ | R⁵ | A | R⁶ | R⁷ | (R⁸)ₘ | p |
|---|---|---|---|---|---|---|---|---|---|---|
| A-9344 | H | H | H | H | H | O | H | H | 4-((4-nitrobenzyl)oxy) | 1 |
| A-9345 | H | H | H | H | H | O | H | H | 2-NH₂ | 1 |
| A-9346 | H | H | H | H | H | O | H | H | 3-NH₂ | 1 |
| A-9347 | H | H | H | H | H | O | H | H | 4-NH₂ | 1 |
| A-9348 | H | H | H | H | H | O | H | H | 2-NHMe | 1 |
| A-9349 | H | H | H | H | H | O | H | H | 3-NHMe | 1 |
| A-9350 | H | H | H | H | H | O | H | H | 4-NHMe | 1 |
| A-9351 | H | H | H | H | H | O | H | H | 2-NHEt | 1 |
| A-9352 | H | H | H | H | H | O | H | H | 3-NHEt | 1 |
| A-9353 | H | H | H | H | H | O | H | H | 4-NHEt | 1 |
| A-9354 | H | H | H | H | H | O | H | H | 2-N(Me)₂ | 1 |
| A-9355 | H | H | H | H | H | O | H | H | 3-N(Me)₂ | 1 |
| A-9356 | H | H | H | H | H | O | H | H | 4-N(Me)₂ | 1 |
| A-9357 | H | H | H | H | H | O | H | H | 2-N(Et)₂ | 1 |
| A-9358 | H | H | H | H | H | O | H | H | 3-N(Et)₂ | 1 |
| A-9359 | H | H | H | H | H | O | H | H | 4-N(Et)₂ | 1 |

TABLE 165-continued

| compound | R¹ | R² | R³ | R⁴ | R⁵ | A | R⁶ | R⁷ | (R⁸)$_m$ | p |
|---|---|---|---|---|---|---|---|---|---|---|
| A-9360 | H | H | H | H | H | O | H | H | 2-CHO | 1 |
| A-9361 | H | H | H | H | H | O | H | H | 3-CHO | 1 |
| A-9362 | H | H | H | H | H | O | H | H | 4-CHO | 1 |
| A-9363 | H | H | H | H | H | O | H | H | 2-C(=O)OH | 1 |
| A-9364 | H | H | H | H | H | O | H | H | 3-C(=O)OH | 1 |
| A-9365 | H | H | H | H | H | O | H | H | 4-C(=O)OH | 1 |
| A-9366 | H | H | H | H | H | O | H | H | 2-(1,3-dioxolan-2-yl) | 1 |
| A-9367 | H | H | H | H | H | O | H | H | 3-(1,3-dioxolan-2-yl) | 1 |
| A-9368 | H | H | H | H | H | O | H | H | 4-(1,3-dioxolan-2-yl) | 1 |
| A-9369 | H | H | H | H | H | O | H | H | 2-(1,3-dioxan-2-y) | 1 |
| A-9370 | H | H | H | H | H | O | H | H | 3-(1,3-dioxan-2-yl) | 1 |
| A-9371 | H | H | H | H | H | O | H | H | 4-(1,3-dioxan-2-yl) | 1 |
| A-9372 | H | H | H | H | H | O | H | H | 2-(1H-imidazol-2-yl) | 1 |
| A-9373 | H | H | H | H | H | O | H | H | 3-(1H-imidazol-2-yl) | 1 |
| A-9374 | H | H | H | H | H | O | H | H | 4-(1H-imidazol-2-yl) | 1 |
| A-9375 | H | H | H | H | H | O | H | H | 2-(thiazol-2-yl) | 1 |
| A-9376 | H | H | H | H | H | O | H | H | 3-(thiazol-2-yl) | 1 |
| A-9377 | H | H | H | H | H | O | H | H | 4-(thiazol-2-yl) | 1 |
| A-9378 | H | H | H | H | H | O | H | H | 2-(oxazol-2-yl) | 1 |
| A-9379 | H | H | H | H | H | O | H | H | 3-(oxazol-2-yl) | 1 |
| A-9380 | H | H | H | H | H | O | H | H | 4-(oxazol-2-yl) | 1 |
| A-9381 | H | H | H | H | H | O | H | H | 2-CH=NOH | 1 |
| A-9382 | H | H | H | H | H | O | H | H | 3-CH=NOH | 1 |
| A-9383 | H | H | H | H | H | O | H | H | 4-CH=NOH | 1 |
| A-9384 | H | H | H | H | H | O | H | H | 2-CH=NOMe | 1 |
| A-9385 | H | H | H | H | H | O | H | H | 3-CH=NOMe | 1 |
| A-9386 | H | H | H | H | H | O | H | H | 4-CH=NOMe | 1 |
| A-9387 | H | H | H | H | H | O | H | H | 2-(4,5-dihydro-3-isoxazolyl) | 1 |
| A-9388 | H | H | H | H | H | O | H | H | 3-(4,5-dihydro-3-isoxazolyl) | 1 |
| A-9389 | H | H | H | H | H | O | H | H | 4-(4,5-dihydro-3-isoxazolyl) | 1 |
| A-9390 | H | H | H | H | H | O | H | H | 2-CN | 1 |
| A-9391 | H | H | H | H | H | O | H | H | 3-CN | 1 |
| A-9392 | H | H | H | H | H | O | H | H | 4-CN | 1 |
| A-9393 | H | H | H | H | H | O | H | H | 2-NO$_2$ | 1 |
| A-9394 | H | H | H | H | H | O | H | H | 3-NO$_2$ | 1 |
| A-9395 | H | H | H | H | H | O | H | H | 4-NO$_2$ | 1 |
| A-9396 | H | H | H | H | H | O | H | H | 2,3-F$_2$ | 1 |
| A-9397 | H | H | H | H | H | O | H | H | 2,4-F$_2$ | 1 |
| A-9398 | H | H | H | H | H | O | H | H | 2,5-F$_2$ | 1 |
| A-9399 | H | H | H | H | H | O | H | H | 2,6-F$_2$ | 1 |
| A-9400 | H | H | H | H | H | O | H | H | 3,4-F$_2$ | 1 |

TABLE 166

| compound | R¹ | R² | R³ | R⁴ | R⁵ | A | R⁶ | R⁷ | (R⁸)$_m$ | p |
|---|---|---|---|---|---|---|---|---|---|---|
| A-9401 | H | H | H | H | H | O | H | H | 3,5-F$_2$ | 1 |
| A-9402 | H | H | H | H | H | O | H | H | 2-F,3-Cl | 1 |
| A-9403 | H | H | H | H | H | O | H | H | 2-F,4-Cl | 1 |
| A-9404 | H | H | H | H | H | O | H | H | 2-F,5-Cl | 1 |
| A-9405 | H | H | H | H | H | O | H | H | 2-F,6-Cl | 1 |
| A-9406 | H | H | H | H | H | O | H | H | 3-F,2-Cl | 1 |
| A-9407 | H | H | H | H | H | O | H | H | 3-F,4-Cl | 1 |
| A-9408 | H | H | H | H | H | O | H | H | 3-F,5-Cl | 1 |
| A-9409 | H | H | H | H | H | O | H | H | 3-F,6-Cl | 1 |
| A-9410 | H | H | H | H | H | O | H | H | 4-F,2-Cl | 1 |
| A-9411 | H | H | H | H | H | O | H | H | 4-F,3-Cl | 1 |
| A-9412 | H | H | H | H | H | O | H | H | 2-F,3-Me | 1 |
| A-9413 | H | H | H | H | H | O | H | H | 2-F,4-Me | 1 |
| A-9414 | H | H | H | H | H | O | H | H | 2-F,5-Me | 1 |
| A-9415 | H | H | H | H | H | O | H | H | 2-F,6-Me | 1 |
| A-9416 | H | H | H | H | H | O | H | H | 3-F,2-Me | 1 |
| A-9417 | H | H | H | H | H | O | H | H | 3-F,4-Me | 1 |
| A-9418 | H | H | H | H | H | O | H | H | 3-F,5-Me | 1 |
| A-9419 | H | H | H | H | H | O | H | H | 3-F,6-Me | 1 |
| A-9420 | H | H | H | H | H | O | H | H | 4-F,2-Me | 1 |
| A-9421 | H | H | H | H | H | O | H | H | 4-F,3-Me | 1 |
| A-9422 | H | H | H | H | H | O | H | H | 2-F,3-CF$_3$ | 1 |
| A-9423 | H | H | H | H | H | O | H | H | 2-F,4-CF$_3$ | 1 |
| A-9424 | H | H | H | H | H | O | H | H | 2-F,5-CF$_3$ | 1 |
| A-9425 | H | H | H | H | H | O | H | H | 2-F,6-CF$_3$ | 1 |
| A-9426 | H | H | H | H | H | O | H | H | 3-F,2-CF$_3$ | 1 |
| A-9427 | H | H | H | H | H | O | H | H | 3-F,4-CF$_3$ | 1 |
| A-9428 | H | H | H | H | H | O | H | H | 3-F,5-CF$_3$ | 1 |
| A-9429 | H | H | H | H | H | O | H | H | 3-F,6-CF$_3$ | 1 |
| A-9430 | H | H | H | H | H | O | H | H | 4-F,2-CF$_3$ | 1 |
| A-9431 | H | H | H | H | H | O | H | H | 4-F,3-CF$_3$ | 1 |
| A-9432 | H | H | H | H | H | O | H | H | 2-F,3-OMe | 1 |
| A-9433 | H | H | H | H | H | O | H | H | 2-F,4-OMe | 1 |
| A-9434 | H | H | H | H | H | O | H | H | 2-F,5-OMe | 1 |
| A-9435 | H | H | H | H | H | O | H | H | 2-F,6-OMe | 1 |
| A-9436 | H | H | H | H | H | O | H | H | 3-F,2-OMe | 1 |
| A-9437 | H | H | H | H | H | O | H | H | 3-F,4-OMe | 1 |
| A-9438 | H | H | H | H | H | O | H | H | 3-F,5-OMe | 1 |
| A-9439 | H | H | H | H | H | O | H | H | 3-F,6-OMe | 1 |
| A-9440 | H | H | H | H | H | O | H | H | 4-F,2-OMe | 1 |
| A-9441 | H | H | H | H | H | O | H | H | 3-F,3-OMe | 1 |
| A-9442 | H | H | H | H | H | O | H | H | 2,3-Cl$_2$ | 1 |
| A-9443 | H | H | H | H | H | O | H | H | 2,4-Cl$_2$ | 1 |
| A-9444 | H | H | H | H | H | O | H | H | 2,5-Cl$_2$ | 1 |
| A-9445 | H | H | H | H | H | O | H | H | 2,6-Cl$_2$ | 1 |
| A-9446 | H | H | H | H | H | O | H | H | 3,4-Cl$_2$ | 1 |
| A-9447 | H | H | H | H | H | O | H | H | 3,5-Cl$_2$ | 1 |
| A-9448 | H | H | H | H | H | O | H | H | 2-Cl,3-Me | 1 |
| A-9449 | H | H | H | H | H | O | H | H | 2-Cl,4-Me | 1 |
| A-9450 | H | H | H | H | H | O | H | H | 2-Cl,5-Me | 1 |
| A-9451 | H | H | H | H | H | O | H | H | 2-Cl,6-Me | 1 |
| A-9452 | H | H | H | H | H | O | H | H | 3-Cl,2-Me | 1 |
| A-9453 | H | H | H | H | H | O | H | H | 3-Cl,4-Me | 1 |
| A-9454 | H | H | H | H | H | O | H | H | 3-Cl,5-Me | 1 |
| A-9455 | H | H | H | H | H | O | H | H | 3-Cl,6-Me | 1 |
| A-9456 | H | H | H | H | H | O | H | H | 4-Cl,2-Me | 1 |
| A-9457 | H | H | H | H | H | O | H | H | 4-Cl,3-Me | 1 |

TABLE 167

| compound | R¹ | R² | R³ | R⁴ | R⁵ | A | R⁶ | R⁷ | (R⁸)ₘ | p |
|---|---|---|---|---|---|---|---|---|---|---|
| A-9458 | H | H | H | H | H | O | H | H | 2-Cl,3-CF₃ | 1 |
| A-9459 | H | H | H | H | H | O | H | H | 2-Cl,4-CF₃ | 1 |
| A-9460 | H | H | H | H | H | O | H | H | 2-Cl,5-CF₃ | 1 |
| A-9461 | H | H | H | H | H | O | H | H | 2-Cl,6-CF₃ | 1 |
| A-9462 | H | H | H | H | H | O | H | H | 3-Cl,2-CF₃ | 1 |
| A-9463 | H | H | H | H | H | O | H | H | 3-Cl,4-CF₃ | 1 |
| A-9464 | H | H | H | H | H | O | H | H | 3-Cl,5-CF₃ | 1 |
| A-9465 | H | H | H | H | H | O | H | H | 3-Cl,6-CF₃ | 1 |
| A-9466 | H | H | H | H | H | O | H | H | 4-Cl,2-CF₃ | 1 |
| A-9467 | H | H | H | H | H | O | H | H | 4-Cl,3-CF₃ | 1 |
| A-9468 | H | H | H | H | H | O | H | H | 2-Cl,3-OMe | 1 |
| A-9469 | H | H | H | H | H | O | H | H | 2-Cl,4-OMe | 1 |
| A-9470 | H | H | H | H | H | O | H | H | 2-Cl,5-OMe | 1 |
| A-9471 | H | H | H | H | H | O | H | H | 2-Cl,6-OMe | 1 |
| A-9472 | H | H | H | H | H | O | H | H | 3-Cl,2-OMe | 1 |
| A-9473 | H | H | H | H | H | O | H | H | 3-Cl,4-OMe | 1 |
| A-9474 | H | H | H | H | H | O | H | H | 3-Cl,5-OMe | 1 |
| A-9475 | H | H | H | H | H | O | H | H | 3-Cl,6-OMe | 1 |
| A-9476 | H | H | H | H | H | O | H | H | 4-Cl,2-OMe | 1 |
| A-9477 | H | H | H | H | H | O | H | H | 4-Cl,3-OMe | 1 |
| A-9478 | H | H | H | H | H | O | H | H | 2,3-Me₂ | 1 |
| A-9479 | H | H | H | H | H | O | H | H | 2,4-Me₂ | 1 |
| A-9480 | H | H | H | H | H | O | H | H | 2,5-Me₂ | 1 |
| A-9481 | H | H | H | H | H | O | H | H | 2,6-Me₂ | 1 |
| A-9482 | H | H | H | H | H | O | H | H | 3,4-Me₂ | 1 |
| A-9483 | H | H | H | H | H | O | H | H | 3,5-Me₂ | 1 |
| A-9484 | H | H | H | H | H | O | H | H | 2-Me,3-CF₃ | 1 |
| A-9485 | H | H | H | H | H | O | H | H | 2-Me,4-CF₃ | 1 |
| A-9486 | H | H | H | H | H | O | H | H | 2-Me,5-CF₃ | 1 |
| A-9487 | H | H | H | H | H | O | H | H | 2-Me,6-CF₃ | 1 |
| A-9488 | H | H | H | H | H | O | H | H | 3-Me,2-CF₃ | 1 |
| A-9489 | H | H | H | H | H | O | H | H | 3-Me,4-CF₃ | 1 |
| A-9490 | H | H | H | H | H | O | H | H | 3-Me,5-CF₃ | 1 |
| A-9491 | H | H | H | H | H | O | H | H | 3-Me,6-CF₃ | 1 |
| A-9492 | H | H | H | H | H | O | H | H | 4-Me,2-CF₃ | 1 |
| A-9493 | H | H | H | H | H | O | H | H | 4-Me,3-CF₃ | 1 |
| A-9494 | H | H | H | H | H | O | H | H | 2-Me,3-OMe | 1 |
| A-9495 | H | H | H | H | H | O | H | H | 2-Me,4-OMe | 1 |
| A-9496 | H | H | H | H | H | O | H | H | 2-Me,5-OMe | 1 |
| A-9497 | H | H | H | H | H | O | H | H | 2-Me,6-OMe | 1 |
| A-9498 | H | H | H | H | H | O | H | H | 3-Me,2-OMe | 1 |
| A-9499 | H | H | H | H | H | O | H | H | 3-Me,4-OMe | 1 |
| A-9500 | H | H | H | H | H | O | H | H | 3-Me,5-OMe | 1 |
| A-9501 | H | H | H | H | H | O | H | H | 3-Me,6-OMe | 1 |
| A-9502 | H | H | H | H | H | O | H | H | 4-Me,2-OMe | 1 |
| A-9503 | H | H | H | H | H | O | H | H | 4-Me,3-OMe | 1 |
| A-9504 | H | H | H | H | H | O | H | H | 2,3-OMe₂ | 1 |
| A-9505 | H | H | H | H | H | O | H | H | 2,4-OMe₂ | 1 |
| A-9506 | H | H | H | H | H | O | H | H | 2,5-OMe₂ | 1 |
| A-9507 | H | H | H | H | H | O | H | H | 2,6-OMe₂ | 1 |
| A-9508 | H | H | H | H | H | O | H | H | 3,4-OMe₂ | 1 |
| A-9509 | H | H | H | H | H | O | H | H | 3,5-OMe₂ | 1 |
| A-9510 | H | H | H | H | H | O | H | H | 2-OMe,3-CF₃ | 1 |
| A-9511 | H | H | H | H | H | O | H | H | 2-OMe,4-CF₃ | 1 |
| A-9512 | H | H | H | H | H | O | H | H | 2-OMe,5-CF₃ | 1 |
| A-9513 | H | H | H | H | H | O | H | H | 2-OMe,6-CF₃ | 1 |
| A-9514 | H | H | H | H | H | O | H | H | 3-OMe,2-CF₃ | 1 |

TABLE 168

| compound | R¹ | R² | R³ | R⁴ | R⁵ | A | R⁶ | R⁷ | (R⁸)ₘ | p |
|---|---|---|---|---|---|---|---|---|---|---|
| A-9515 | H | H | H | H | H | O | H | H | 3-OMe,4-CF₃ | 1 |
| A-9516 | H | H | H | H | H | O | H | H | 3-OMe,5-CF₃ | 1 |
| A-9517 | H | H | H | H | H | O | H | H | 3-OMe,6-CF₃ | 1 |
| A-9518 | H | H | H | H | H | O | H | H | 4-OMe,2-CF₃ | 1 |
| A-9519 | H | H | H | H | H | O | H | H | 4-OMe,3-CF₃ | 1 |
| A-9520 | H | H | H | H | H | O | H | H | 2-CHF₂,3-F | 1 |
| A-9521 | H | H | H | H | H | O | H | H | 2-CHF₂,4-F | 1 |
| A-9522 | H | H | H | H | H | O | H | H | 2-CHF₂,5-F | 1 |
| A-9523 | H | H | H | H | H | O | H | H | 2-CHF₂,6-F | 1 |
| A-9524 | H | H | H | H | H | O | H | H | 2-CHF₂,3-Me | 1 |
| A-9525 | H | H | H | H | H | O | H | H | 2-CHF₂,4-Me | 1 |
| A-9526 | H | H | H | H | H | O | H | H | 2-CHF₂,5-Me | 1 |
| A-9527 | H | H | H | H | H | O | H | H | 2-CHF₂,6-Me | 1 |
| A-9528 | H | H | H | H | H | O | H | H | 2-cyclopropyl,3-F | 1 |
| A-9529 | H | H | H | H | H | O | H | H | 2-cyclopropyl,4-F | 1 |
| A-9530 | H | H | H | H | H | O | H | H | 2-cyclopropyl,5-F | 1 |
| A-9531 | H | H | H | H | H | O | H | H | 2-cyclopropyl,6-F | 1 |
| A-9532 | H | H | H | H | H | O | H | H | 2-cyclopropyl,3-Me | 1 |
| A-9533 | H | H | H | H | H | O | H | H | 2-cyclopropyl,4-Me | 1 |
| A-9534 | H | H | H | H | H | O | H | H | 2-cyclopropyl,5-Me | 1 |
| A-9535 | H | H | H | H | H | O | H | H | 2-cyclopropyl,6-Me | 1 |
| A-9536 | H | H | H | H | H | O | H | H | 2-ethenyl,3-F | 1 |
| A-9537 | H | H | H | H | H | O | H | H | 2-ethenyl,4-F | 1 |
| A-9538 | H | H | H | H | H | O | H | H | 2-ethenyl,5-F | 1 |
| A-9539 | H | H | H | H | H | O | H | H | 2-ethenyl,6-F | 1 |
| A-9540 | H | H | H | H | H | O | H | H | 2-ethenyl,3-Me | 1 |
| A-9541 | H | H | H | H | H | O | H | H | 2-ethenyl,4-Me | 1 |
| A-9542 | H | H | H | H | H | O | H | H | 2-ethenyl,5-Me | 1 |
| A-9543 | H | H | H | H | H | O | H | H | 2-ethenyl,6-Me | 1 |
| A-9544 | H | H | H | H | H | O | H | H | 2-OEt,3-F | 1 |
| A-9545 | H | H | H | H | H | O | H | H | 2-OEt,4-F | 1 |
| A-9546 | H | H | H | H | H | O | H | H | 2-OEt,5-F | 1 |
| A-9547 | H | H | H | H | H | O | H | H | 2-OEt,6-F | 1 |
| A-9548 | H | H | H | H | H | O | H | H | 2-OEt,3-Cl | 1 |
| A-9549 | H | H | H | H | H | O | H | H | 2-OEt,4-Cl | 1 |
| A-9550 | H | H | H | H | H | O | H | H | 2-OEt,5-Cl | 1 |
| A-9551 | H | H | H | H | H | O | H | H | 2-OEt,6-Cl | 1 |
| A-9552 | H | H | H | H | H | O | H | H | 2-OEt,3-Me | 1 |
| A-9553 | H | H | H | H | H | O | H | H | 2-OEt,4-Me | 1 |
| A-9554 | H | H | H | H | H | O | H | H | 2-OEt,5-Me | 1 |
| A-9555 | H | H | H | H | H | O | H | H | 2-OEt,6-Me | 1 |
| A-9556 | H | H | H | H | H | O | H | H | 2-OPr,3-F | 1 |
| A-9557 | H | H | H | H | H | O | H | H | 2-OPr,4-F | 1 |
| A-9558 | H | H | H | H | H | O | H | H | 2-OPr,5-F | 1 |
| A-9559 | H | H | H | H | H | O | H | H | 2-OPr,6-F | 1 |
| A-9560 | H | H | H | H | H | O | H | H | 2-OPr,3-Me | 1 |
| A-9561 | H | H | H | H | H | O | H | H | 2-OPr,4-Me | 1 |
| A-9562 | H | H | H | H | H | O | H | H | 2-OPr,5-Me | 1 |
| A-9563 | H | H | H | H | H | O | H | H | 2-OPr,6-Me | 1 |
| A-9564 | H | H | H | H | H | O | H | H | 2-O(i-Pr),3-F | 1 |
| A-9565 | H | H | H | H | H | O | H | H | 2-O(i-Pr),4-F | 1 |
| A-9566 | H | H | H | H | H | O | H | H | 2-O(i-Pr),5-F | 1 |
| A-9567 | H | H | H | H | H | O | H | H | 2-O(i-Pr),6-F | 1 |
| A-9568 | H | H | H | H | H | O | H | H | 2-O(i-Pr),3-Me | 1 |
| A-9569 | H | H | H | H | H | O | H | H | 2-O(i-Pr),4-Me | 1 |
| A-9570 | H | H | H | H | H | O | H | H | 2-O(i-Pr),5-Me | 1 |
| A-9571 | H | H | H | H | H | O | H | H | 2-O(i-Pr),6-Me | 1 |

TABLE 169

| compound | R¹ | R² | R³ | R⁴ | R⁵ | A | R⁶ | R⁷ | (R⁸)ₘ | p |
|---|---|---|---|---|---|---|---|---|---|---|
| A-9572 | H | H | H | H | H | O | H | H | 2-OCF₃,3-F | 1 |
| A-9573 | H | H | H | H | H | O | H | H | 2-OCF₃,4-F | 1 |
| A-9574 | H | H | H | H | H | O | H | H | 2-OCF₃,5-F | 1 |
| A-9575 | H | H | H | H | H | O | H | H | 2-OCF₃,6-F | 1 |
| A-9576 | H | H | H | H | H | O | H | H | 2-OCF₃,3-Me | 1 |
| A-9577 | H | H | H | H | H | O | H | H | 2-OCF₃,4-Me | 1 |
| A-9578 | H | H | H | H | H | O | H | H | 2-OCF₃,5-Me | 1 |
| A-9579 | H | H | H | H | H | O | H | H | 2-OCF₃,6-Me | 1 |
| A-9580 | H | H | H | H | H | O | H | H | 2-OCHF₂,3-F | 1 |
| A-9581 | H | H | H | H | H | O | H | H | 2-OCHF₂,4-F | 1 |
| A-9582 | H | H | H | H | H | O | H | H | 2-OCHF₂,5-F | 1 |
| A-9583 | H | H | H | H | H | O | H | H | 2-OCHF₂,6-F | 1 |

TABLE 169-continued

| compound | R¹ | R² | R³ | R⁴ | R⁵ | A | R⁶ | R⁷ | (R⁸)ₘ | p |
|---|---|---|---|---|---|---|---|---|---|---|
| A-9584 | H | H | H | H | H | O | H | H | 2-OCHF₂,3-Me | 1 |
| A-9585 | H | H | H | H | H | O | H | H | 2-OCHF₂,4-Me | 1 |
| A-9586 | H | H | H | H | H | O | H | H | 2-OCHF₂,5-Me | 1 |
| A-9587 | H | H | H | H | H | O | H | H | 2-OCHF₂,6-Me | 1 |
| A-9588 | H | H | H | H | H | O | H | H | 2-(cyclopropyloxy),3-F | 1 |
| A-9589 | H | H | H | H | H | O | H | H | 2-(cyclopropyloxy),4-F | 1 |
| A-9590 | H | H | H | H | H | O | H | H | 2-(cyclopropyloxy),5-F | 1 |
| A-9591 | H | H | H | H | H | O | H | H | 2-(cyclopropyloxy),6-F | 1 |
| A-9592 | H | H | H | H | H | O | H | H | 2-(cyclopropyloxy),3-Me | 1 |
| A-9593 | H | H | H | H | H | O | H | H | 2-(cyclopropyloxy),4-Me | 1 |
| A-9594 | H | H | H | H | H | O | H | H | 2-(cyclopropyloxy),5-Me | 1 |
| A-9595 | H | H | H | H | H | O | H | H | 2-(cyclopropyloxy),6-Me | 1 |
| A-9596 | H | H | H | H | H | O | H | H | 2-(oxiran-2-yl),3-F | 1 |
| A-9597 | H | H | H | H | H | O | H | H | 2-(oxiran-2-yl),4-F | 1 |
| A-9598 | H | H | H | H | H | O | H | H | 2-(oxiran-2-yl),5-F | 1 |
| A-9599 | H | H | H | H | H | O | H | H | 2-(oxiran-2-yl),6-F | 1 |
| A-9600 | H | H | H | H | H | O | H | H | 2-(oxiran-2-yl),3-Me | 1 |
| A-9601 | H | H | H | H | H | O | H | H | 2-(oxiran-2-yl),4-Me | 1 |
| A-9602 | H | H | H | H | H | O | H | H | 2-(oxiran-2-yl),5-Me | 1 |
| A-9603 | H | H | H | H | H | O | H | H | 2-(oxiran-2-yl),6-Me | 1 |
| A-9604 | H | H | H | H | H | O | H | H | 2-(oxiran-2-ylmethyl),3-F | 1 |
| A-9605 | H | H | H | H | H | O | H | H | 2-(oxiran-2-ylmethyl),4-F | 1 |
| A-9606 | H | H | H | H | H | O | H | H | 2-(oxiran-2-ylmethyl),5-F | 1 |
| A-9607 | H | H | H | H | H | O | H | H | 2-(oxiran-2-ylmethyl),6-F | 1 |
| A-9608 | H | H | H | H | H | O | H | H | 2-(oxiran-2-ylmethyl),3-Me | 1 |
| A-9609 | H | H | H | H | H | O | H | H | 2-(oxiran-2-ylmethyl),4-Me | 1 |
| A-9610 | H | H | H | H | H | O | H | H | 2-(oxiran-2-ylmethyl),5-Me | 1 |
| A-9611 | H | H | H | H | H | O | H | H | 2-(oxiran-2-ylmethyl),6-Me | 1 |
| A-9612 | H | H | H | H | H | O | H | H | 2-SMe,3-F | 1 |
| A-9613 | H | H | H | H | H | O | H | H | 2-SMe,4-F | 1 |
| A-9614 | H | H | H | H | H | O | H | H | 2-SMe,5-F | 1 |
| A-9615 | H | H | H | H | H | O | H | H | 2-SMe,6-F | 1 |
| A-9616 | H | H | H | H | H | O | H | H | 2-SMe,3-Me | 1 |
| A-9617 | H | H | H | H | H | O | H | H | 2-SMe,4-Me | 1 |
| A-9618 | H | H | H | H | H | O | H | H | 2-SMe,5-Me | 1 |
| A-9619 | H | H | H | H | H | O | H | H | 2-SMe,6-Me | 1 |
| A-9620 | H | H | H | H | H | O | H | H | 2-SEt,3-F | 1 |
| A-9621 | H | H | H | H | H | O | H | H | 2-SEt,4-F | 1 |
| A-9622 | H | H | H | H | H | O | H | H | 2-SEt,5-F | 1 |
| A-9623 | H | H | H | H | H | O | H | H | 2-SEt,6-F | 1 |
| A-9624 | H | H | H | H | H | O | H | H | 2-SEt,3-Me | 1 |
| A-9625 | H | H | H | H | H | O | H | H | 2-SEt,4-Me | 1 |
| A-9626 | H | H | H | H | H | O | H | H | 2-SEt,5-Me | 1 |
| A-9627 | H | H | H | H | H | O | H | H | 2-SEt,6-Me | 1 |
| A-9628 | H | H | H | H | H | O | H | H | 2-S(=O)Me,3-F | 1 |

TABLE 170

| compound | R¹ | R² | R³ | R⁴ | R⁵ | A | R⁶ | R⁷ | (R⁸)ₘ | p |
|---|---|---|---|---|---|---|---|---|---|---|
| A-9629 | H | H | H | H | H | O | H | H | 2-S(=O)Me,4-F | 1 |
| A-9630 | H | H | H | H | H | O | H | H | 2-S(=O)Me,5-F | 1 |
| A-9631 | H | H | H | H | H | O | H | H | 2-S(=O)Me,6-F | 1 |
| A-9632 | H | H | H | H | H | O | H | H | 3-S(=O)Me,2-F | 1 |
| A-9633 | H | H | H | H | H | O | H | H | 3-S(=O)Me,4-F | 1 |
| A-9634 | H | H | H | H | H | O | H | H | 3-S(=O)Me,5-F | 1 |
| A-9635 | H | H | H | H | H | O | H | H | 3-S(=O)Me,6-F | 1 |
| A-9636 | H | H | H | H | H | O | H | H | 2-S(=O)Me,3-Me | 1 |
| A-9637 | H | H | H | H | H | O | H | H | 2-S(=O)Me,4-Me | 1 |
| A-9638 | H | H | H | H | H | O | H | H | 2-S(=O)Me,5-Me | 1 |
| A-9639 | H | H | H | H | H | O | H | H | 2-S(=O)Me,6-Me | 1 |
| A-9640 | H | H | H | H | H | O | H | H | 3-S(=O)Me,2-Me | 1 |
| A-9641 | H | H | H | H | H | O | H | H | 3-S(=O)Me,4-Me | 1 |
| A-9642 | H | H | H | H | H | O | H | H | 3-S(=O)Me,5-Me | 1 |
| A-9643 | H | H | H | H | H | O | H | H | 3-S(=O)Me,6-Me | 1 |
| A-9644 | H | H | H | H | H | O | H | H | 2-S(=O)₂Me,3F | 1 |
| A-9645 | H | H | H | H | H | O | H | H | 2-S(=O)₂Me,4-F | 1 |
| A-9646 | H | H | H | H | H | O | H | H | 2-S(=O)₂Me,5-F | 1 |
| A-9647 | H | H | H | H | H | O | H | H | 2-S(=O)₂Me,6-F | 1 |
| A-9648 | H | H | H | H | H | O | H | H | 2-S(=O)₂Me,3-Me | 1 |
| A-9649 | H | H | H | H | H | O | H | H | 2-S(=O)₂Me,4-Me | 1 |
| A-9650 | H | H | H | H | H | O | H | H | 2-S(=O)₂Me,5-Me | 1 |
| A-9651 | H | H | H | H | H | O | H | H | 2-S(=O)₂Me,6-Me | 1 |
| A-9652 | H | H | H | H | H | O | H | H | 2-SCF₃,3-F | 1 |
| A-9653 | H | H | H | H | H | O | H | H | 2-SCF₃,4-F | 1 |

TABLE 170-continued

| compound | R¹ | R² | R³ | R⁴ | R⁵ | A | R⁶ | R⁷ | (R⁸)ₘ | p |
|---|---|---|---|---|---|---|---|---|---|---|
| A-9654 | H | H | H | H | H | O | H | H | 2-SCF₃,5-F | 1 |
| A-9655 | H | H | H | H | H | O | H | H | 2-SCF₃,6-F | 1 |
| A-9656 | H | H | H | H | H | O | H | H | 2-SCF₃,3-Me | 1 |
| A-9657 | H | H | H | H | H | O | H | H | 2-SCF₃,4-Me | 1 |
| A-9658 | H | H | H | H | H | O | H | H | 2-SCF₃,5-Me | 1 |
| A-9659 | H | H | H | H | H | O | H | H | 2-SCF₃,6-Me | 1 |
| A-9660 | H | H | H | H | H | O | H | H | 2-S(=O)CF₃,3-F | 1 |
| A-9661 | H | H | H | H | H | O | H | H | 2-S(=O)CF₃,4-F | 1 |
| A-9662 | H | H | H | H | H | O | H | H | 2-S(=O)CF₃,5-F | 1 |
| A-9663 | H | H | H | H | H | O | H | H | 2-S(=O)CF₃,6-F | 1 |
| A-9664 | H | H | H | H | H | O | H | H | 2-S(=O)CF₃,3-Me | 1 |
| A-9665 | H | H | H | H | H | O | H | H | 2-S(=O)CF₃,4-Me | 1 |
| A-9666 | H | H | H | H | H | O | H | H | 2-S(=O)CF₃,5-Me | 1 |
| A-9667 | H | H | H | H | H | O | H | H | 2-S(=O)CF₃,6-Me | 1 |
| A-9668 | H | H | H | H | H | O | H | H | 2-S(=O)₂CF₃,3-F | 1 |
| A-9669 | H | H | H | H | H | O | H | H | 2-S(=O)₂CF₃,4-F | 1 |
| A-9670 | H | H | H | H | H | O | H | H | 2-S(=O)₂CF₃,5-F | 1 |
| A-9671 | H | H | H | H | H | O | H | H | 2-S(=O)₂CF₃,6-F | 1 |
| A-9672 | H | H | H | H | H | O | H | H | 2-S(=O)₂CF₃,3-Me | 1 |
| A-9673 | H | H | H | H | H | O | H | H | 2-S(=O)₂CF₃,4-Me | 1 |
| A-9674 | H | H | H | H | H | O | H | H | 2-S(=O)₂CF₃,5-Me | 1 |
| A-9675 | H | H | H | H | H | O | H | H | 2-S(=O)₂CF₃,6-Me | 1 |
| A-9676 | H | H | H | H | H | O | H | H | 2-(cyclopropylthio),3-F | 1 |
| A-9677 | H | H | H | H | H | O | H | H | 2-(cyclopropylthio),4-F | 1 |
| A-9678 | H | H | H | H | H | O | H | H | 2-(cyclopropylthio),5-F | 1 |
| A-9679 | H | H | H | H | H | O | H | H | 2-(cyclopropylthio),6-F | 1 |
| A-9680 | H | H | H | H | H | O | H | H | 2-(cyclopropylthio),3-Me | 1 |
| A-9681 | H | H | H | H | H | O | H | H | 2-(cyclopropylthio),4-Me | 1 |
| A-9682 | H | H | H | H | H | O | H | H | 2-(cyclopropylthio),5-Me | 1 |
| A-9683 | H | H | H | H | H | O | H | H | 2-(cyclopropylthio),6-Me | 1 |
| A-9684 | H | H | H | H | H | O | H | H | 2-C(=O)Me,3-F | 1 |
| A-9685 | H | H | H | H | H | O | H | H | 2-C(=O)Me,4-F | 1 |

TABLE 171

| compound | R¹ | R² | R³ | R⁴ | R⁵ | A | R⁶ | R⁷ | (R⁸)ₘ | p |
|---|---|---|---|---|---|---|---|---|---|---|
| A-9686 | H | H | H | H | H | O | H | H | 2-C(=O)Me,5-F | 1 |
| A-9687 | H | H | H | H | H | O | H | H | 2-C(=O)Me,6-F | 1 |
| A-9688 | H | H | H | H | H | O | H | H | 2-C(=O)Me,3-Me | 1 |
| A-9689 | H | H | H | H | H | O | H | H | 2-C(=O)Me,4-Me | 1 |
| A-9690 | H | H | H | H | H | O | H | H | 2-C(=O)Me,5-Me | 1 |
| A-9691 | H | H | H | H | H | O | H | H | 2-C(=O)Me,6-Me | 1 |
| A-9692 | H | H | H | H | H | O | H | H | 3-C(=O)Me,2-F | 1 |
| A-9693 | H | H | H | H | H | O | H | H | 3-C(=O)Me,4-F | 1 |
| A-9694 | H | H | H | H | H | O | H | H | 3-C(=O)Me,5-F | 1 |
| A-9695 | H | H | H | H | H | O | H | H | 3-C(=O)Me,6-F | 1 |
| A-9696 | H | H | H | H | H | O | H | H | 3-C(=O)Me,2-Me | 1 |
| A-9697 | H | H | H | H | H | O | H | H | 3-C(=O)Me,4-Me | 1 |
| A-9698 | H | H | H | H | H | O | H | H | 3-C(=O)Me,5-Me | 1 |
| A-9699 | H | H | H | H | H | O | H | H | 3-C(=O)Me,6-Me | 1 |
| A-9700 | H | H | H | H | H | O | H | H | 2-C(=O)OMe,3-F | 1 |
| A-9701 | H | H | H | H | H | O | H | H | 2-C(=O)OMe,4-F | 1 |
| A-9702 | H | H | H | H | H | O | H | H | 2-C(=O)OMe,5-F | 1 |
| A-9703 | H | H | H | H | H | O | H | H | 2-C(=O)OMe,6-F | 1 |
| A-9704 | H | H | H | H | H | O | H | H | 2-C(=O)OMe,3-Me | 1 |
| A-9705 | H | H | H | H | H | O | H | H | 2-C(=O)OMe,4-Me | 1 |
| A-9706 | H | H | H | H | H | O | H | H | 2-C(=O)OMe,5-Me | 1 |
| A-9707 | H | H | H | H | H | O | H | H | 2-C(=O)OMe,6-Me | 1 |
| A-9708 | H | H | H | H | H | O | H | H | 2-C(=O)OEt,3-F | 1 |
| A-9709 | H | H | H | H | H | O | H | H | 2-C(=O)OEt,4-F | 1 |
| A-9710 | H | H | H | H | H | O | H | H | 2-C(=O)OEt,5-F | 1 |
| A-9711 | H | H | H | H | H | O | H | H | 2-C(=O)OEt,6-F | 1 |
| A-9712 | H | H | H | H | H | O | H | H | 2-C(=O)OEt,3-Me | 1 |
| A-9713 | H | H | H | H | H | O | H | H | 2-C(=O)OEt,4-Me | 1 |
| A-9714 | H | H | H | H | H | O | H | H | 2-C(=O)OEt,5-Me | 1 |
| A-9715 | H | H | H | H | H | O | H | H | 2-C(=O)OEt,6-Me | 1 |
| A-9716 | H | H | H | H | H | O | H | H | 2-C(=O)NH₂,3-F | 1 |
| A-9717 | H | H | H | H | H | O | H | H | 2-C(=O)NH₂,4-F | 1 |
| A-9718 | H | H | H | H | H | O | H | H | 2-C(=O)NH₂,5-F | 1 |
| A-9719 | H | H | H | H | H | O | H | H | 2-C(=O)NH₂,6-F | 1 |
| A-9720 | H | H | H | H | H | O | H | H | 2-C(=O)NH₂,3-Me | 1 |
| A-9721 | H | H | H | H | H | O | H | H | 2-C(=O)NH₂,4-Me | 1 |
| A-9722 | H | H | H | H | H | O | H | H | 2-C(=O)NH₂,5-Me | 1 |
| A-9723 | H | H | H | H | H | O | H | H | 2-C(=O)NH₂,6-Me | 1 |
| A-9724 | H | H | H | H | H | O | H | H | 2-C(=O)NHMe,3-F | 1 |
| A-9725 | H | H | H | H | H | O | H | H | 2-C(=O)NHMe,4-F | 1 |
| A-9726 | H | H | H | H | H | O | H | H | 2-C(=O)NHMe,5-F | 1 |
| A-9727 | H | H | H | H | H | O | H | H | 2-C(=O)NHMe,6-F | 1 |
| A-9728 | H | H | H | H | H | O | H | H | 2-C(=O)NHMe,3-Me | 1 |
| A-9729 | H | H | H | H | H | O | H | H | 2-C(=O)NHMe,4-Me | 1 |
| A-9730 | H | H | H | H | H | O | H | H | 2-C(=O)NHMe,5-Me | 1 |
| A-9731 | H | H | H | H | H | O | H | H | 2-C(=O)NHMe,6-Me | 1 |
| A-9732 | H | H | H | H | H | O | H | H | 2-C(=O)NMe₂,3-F | 1 |
| A-9733 | H | H | H | H | H | O | H | H | 2-C(=O)NMe₂,4-F | 1 |
| A-9734 | H | H | H | H | H | O | H | H | 2-C(=O)NMe₂,5-F | 1 |
| A-9735 | H | H | H | H | H | O | H | H | 2-C(=O)NMe₂,6-F | 1 |
| A-9736 | H | H | H | H | H | O | H | H | 2-C(=O)NMe₂,3-Me | 1 |
| A-9737 | H | H | H | H | H | O | H | H | 2-C(=O)NMe₂,4-Me | 1 |
| A-9738 | H | H | H | H | H | O | H | H | 2-C(=O)NMe₂,5-Me | 1 |
| A-9739 | H | H | H | H | H | O | H | H | 2-C(=O)NMe₂,6-Me | 1 |
| A-9740 | H | H | H | H | H | O | H | H | 2-CH₂OH,3-F | 1 |
| A-9741 | H | H | H | H | H | O | H | H | 2-CH₂OH,4-F | 1 |
| A-9742 | H | H | H | H | H | O | H | H | 2-CH₂OH,5-F | 1 |

TABLE 172

| compound | R¹ | R² | R³ | R⁴ | R⁵ | A | R⁶ | R⁷ | (R⁸)ₘ | p |
|---|---|---|---|---|---|---|---|---|---|---|
| A-9743 | H | H | H | H | H | O | H | H | 2-CH₂OH,6-F | 1 |
| A-9744 | H | H | H | H | H | O | H | H | 2-CH₂OH,3-Me | 1 |

TABLE 172-continued

| compound | R¹ | R² | R³ | R⁴ | R⁵ | A | R⁶ | R⁷ | (R⁸)$_m$ | p |
|---|---|---|---|---|---|---|---|---|---|---|
| A-9745 | H | H | H | H | H | O | H | H | 2-CH$_2$OH,4-Me | 1 |
| A-9746 | H | H | H | H | H | O | H | H | 2-CH$_2$OH,5-Me | 1 |
| A-9747 | H | H | H | H | H | O | H | H | 2-CH$_2$OH,6-Me | 1 |
| A-9748 | H | H | H | H | H | O | H | H | 2-CH$_2$OCH$_3$,3F | 1 |
| A-9749 | H | H | H | H | H | O | H | H | 2-CH$_2$OCH$_3$,4-F | 1 |
| A-9750 | H | H | H | H | H | O | H | H | 2-CH$_2$OCH$_3$,5-F | 1 |
| A-9751 | H | H | H | H | H | O | H | H | 2-CH$_2$OCH$_3$,6-F | 1 |
| A-9752 | H | H | H | H | H | O | H | H | 2-CH$_2$OCH$_3$,3-Me | 1 |
| A-9753 | H | H | H | H | H | O | H | H | 2-CH$_2$OCH$_3$,4-Me | 1 |
| A-9754 | H | H | H | H | H | O | H | H | 2-CH$_2$OCH$_3$,5-Me | 1 |
| A-9755 | H | H | H | H | H | O | H | H | 2-CH$_2$OCH$_3$,6-Me | 1 |
| A-9756 | H | H | H | H | H | O | H | H | 2-CH$_2$OCH$_2$CH$_3$,3-F | 1 |
| A-9757 | H | H | H | H | H | O | H | H | 2-CH$_2$OCH$_2$CH$_3$,4-F | 1 |
| A-9758 | H | H | H | H | H | O | H | H | 2-CH$_2$OCH$_2$CH$_3$,5-F | 1 |
| A-9759 | H | H | H | H | H | O | H | H | 2-CH$_2$OCH$_2$CH$_3$,6-F | 1 |
| A-9760 | H | H | H | H | H | O | H | H | 2-CH$_2$OCH$_2$CH$_3$,3-Me | 1 |
| A-9761 | H | H | H | H | H | O | H | H | 2-CH$_2$OCH$_2$CH$_3$,4-Me | 1 |
| A-9762 | H | H | H | H | H | O | H | H | 2-CH$_2$OCH$_2$CH$_3$,5-Me | 1 |
| A-9763 | H | H | H | H | H | O | H | H | 2-CH$_2$OCH$_2$CH$_3$,6-Me | 1 |
| A-9764 | H | H | H | H | H | O | H | H | 2-OC(=O)CH$_3$,3-F | 1 |
| A-9765 | H | H | H | H | H | O | H | H | 2-OC(=O)CH$_3$,4-F | 1 |
| A-9766 | H | H | H | H | H | O | H | H | 2-OC(=O)CH$_3$,5-F | 1 |
| A-9767 | H | H | H | H | H | O | H | H | 2-OC(=O)CH$_3$,6-F | 1 |
| A-9768 | H | H | H | H | H | O | H | H | 2-OC(=O)CH$_3$,3-Me | 1 |
| A-9769 | H | H | H | H | H | O | H | H | 2-OC(=O)CH$_3$,4-Me | 1 |
| A-9770 | H | H | H | H | H | O | H | H | 2-OC(=O)CH$_3$,5-Me | 1 |
| A-9771 | H | H | H | H | H | O | H | H | 2-OC(=O)CH$_3$,6-Me | 1 |
| A-9772 | H | H | H | H | H | O | H | H | 2-OS(=O)$_2$CH$_3$,3-F | 1 |
| A-9773 | H | H | H | H | H | O | H | H | 2-OS(=O)$_2$CH$_3$,4-F | 1 |
| A-9774 | H | H | H | H | H | O | H | H | 2-OS(=O)$_2$CH$_3$,5-F | 1 |
| A-9775 | H | H | H | H | H | O | H | H | 2-OS(=O)$_2$CH$_3$,6-F | 1 |
| A-9776 | H | H | H | H | H | O | H | H | 2-OS(=O)$_2$CH$_3$,3-Me | 1 |
| A-9777 | H | H | H | H | H | O | H | H | 2-OS(=O)$_2$CH$_3$,4-Me | 1 |
| A-9778 | H | H | H | H | H | O | H | H | 2-OS(=O)$_2$CH$_3$,5-Me | 1 |
| A-9779 | H | H | H | H | H | O | H | H | 2-OS(=O)$_2$CH$_3$,6-Me | 1 |
| A-9780 | H | H | H | H | H | O | H | H | 2-CH$_2$SCH$_3$,3-F | 1 |
| A-9781 | H | H | H | H | H | O | H | H | 2-CH$_2$SCH$_3$,4-F | 1 |
| A-9782 | H | H | H | H | H | O | H | H | 2-CH$_2$SCH$_3$,5-F | 1 |
| A-9783 | H | H | H | H | H | O | H | H | 2-CH$_2$SCH$_3$,6-F | 1 |
| A-9784 | H | H | H | H | H | O | H | H | 2-CH$_2$SCH$_3$,3-Me | 1 |
| A-9785 | H | H | H | H | H | O | H | H | 2-CH$_2$SCH$_3$,4-Me | 1 |
| A-9786 | H | H | H | H | H | O | H | H | 2-CH$_2$SCH$_3$,5-Me | 1 |
| A-9787 | H | H | H | H | H | O | H | H | 2-CH$_2$SCH$_3$,6-Me | 1 |
| A-9788 | H | H | H | H | H | O | H | H | 2-CH$_2$SCF$_3$,3-F | 1 |
| A-9789 | H | H | H | H | H | O | H | H | 2-CH$_2$SCF$_3$,4-F | 1 |
| A-9790 | H | H | H | H | H | O | H | H | 2-CH$_2$SCF$_3$,5-F | 1 |
| A-9791 | H | H | H | H | H | O | H | H | 2-CH$_2$SCF$_3$,6-F | 1 |
| A-9792 | H | H | H | H | H | O | H | H | 2-CH$_2$SCF$_3$,3-Me | 1 |
| A-9793 | H | H | H | H | H | O | H | H | 2-CH$_2$SCF$_3$,4-Me | 1 |
| A-9794 | H | H | H | H | H | O | H | H | 2-CH$_2$SCF$_3$,5-Me | 1 |
| A-9795 | H | H | H | H | H | O | H | H | 2-CH$_2$SCF$_3$,6-Me | 1 |
| A-9796 | H | H | H | H | H | O | H | H | 2-(benzyloxy),3-F | 1 |
| A-9797 | H | H | H | H | H | O | H | H | 2-(benzyloxy),4-F | 1 |
| A-9798 | H | H | H | H | H | O | H | H | 2-(benzyloxy),5-F | 1 |
| A-9799 | H | H | H | H | H | O | H | H | 2-(benzyloxy),6-F | 1 |

TABLE 173

| compound | R¹ | R² | R³ | R⁴ | R⁵ | A | R⁶ | R⁷ | (R⁸)$_m$ | p |
|---|---|---|---|---|---|---|---|---|---|---|
| A-9800 | H | H | H | H | H | O | H | H | 2-(benzyloxy),3-Me | 1 |
| A-9801 | H | H | H | H | H | O | H | H | 2-(benzyloxy),4-Me | 1 |
| A-9802 | H | H | H | H | H | O | H | H | 2-(benzyloxy),5-Me | 1 |
| A-9803 | H | H | H | H | H | O | H | H | 2-(benzyloxy),6-Me | 1 |
| A-9804 | H | H | H | H | H | O | H | H | 2-NH$_2$,3-F | 1 |
| A-9805 | H | H | H | H | H | O | H | H | 2-NH$_2$,4-F | 1 |
| A-9806 | H | H | H | H | H | O | H | H | 2-NH$_2$,5-F | 1 |
| A-9807 | H | H | H | H | H | O | H | H | 2-NH$_2$,6-F | 1 |
| A-9808 | H | H | H | H | H | O | H | H | 2-NH$_2$,3-Me | 1 |
| A-9809 | H | H | H | H | H | O | H | H | 2-NH$_2$,4-Me | 1 |
| A-9810 | H | H | H | H | H | O | H | H | 2-NH$_2$,5-Me | 1 |
| A-9811 | H | H | H | H | H | O | H | H | 2-NH$_2$,6-Me | 1 |
| A-9812 | H | H | H | H | H | O | H | H | 2-NHMe,3-F | 1 |
| A-9813 | H | H | H | H | H | O | H | H | 2-NHMe,4-F | 1 |
| A-9814 | H | H | H | H | H | O | H | H | 2-NHMe,5-F | 1 |
| A-9815 | H | H | H | H | H | O | H | H | 2-NHMe,6-F | 1 |
| A-9816 | H | H | H | H | H | O | H | H | 2-NHMe,3-Me | 1 |
| A-9817 | H | H | H | H | H | O | H | H | 2-NHMe,4-Me | 1 |
| A-9818 | H | H | H | H | H | O | H | H | 2-NHMe,5-Me | 1 |
| A-9819 | H | H | H | H | H | O | H | H | 2-NHMe,6-Me | 1 |
| A-9820 | H | H | H | H | H | O | H | H | 2-NHEt,3-F | 1 |
| A-9821 | H | H | H | H | H | O | H | H | 2-NHEt,4-F | 1 |
| A-9822 | H | H | H | H | H | O | H | H | 2-NHEt,5-F | 1 |
| A-9823 | H | H | H | H | H | O | H | H | 2-NHEt,6-F | 1 |
| A-9824 | H | H | H | H | H | O | H | H | 2-NHEt,3-Me | 1 |
| A-9825 | H | H | H | H | H | O | H | H | 2-NHEt,4-Me | 1 |
| A-9826 | H | H | H | H | H | O | H | H | 2-NHEt,5-Me | 1 |
| A-9827 | H | H | H | H | H | O | H | H | 2-NHEt,6-Me | 1 |
| A-9828 | H | H | H | H | H | O | H | H | 2-NMe$_2$,3-F | 1 |
| A-9829 | H | H | H | H | H | O | H | H | 2-NMe$_2$,4-F | 1 |

TABLE 173-continued

| compound | R¹ | R² | R³ | R⁴ | R⁵ | A | R⁶ | R⁷ | (R⁸)ₘ | p |
|---|---|---|---|---|---|---|---|---|---|---|
| A-9830 | H | H | H | H | H | O | H | H | 2-NMe₂,5-F | 1 |
| A-9831 | H | H | H | H | H | O | H | H | 2-NMe₂,6-F | 1 |
| A-9832 | H | H | H | H | H | O | H | H | 2-NMe₂,3-Me | 1 |
| A-9833 | H | H | H | H | H | O | H | H | 2-NMe₂,4-Me | 1 |
| A-9834 | H | H | H | H | H | O | H | H | 2-NMe₂,5-Me | 1 |
| A-9835 | H | H | H | H | H | O | H | H | 2-NMe₂,6-Me | 1 |
| A-9836 | H | H | H | H | H | O | H | H | 2-NEt₂,3F | 1 |
| A-9837 | H | H | H | H | H | O | H | H | 2-NEt₂,4-F | 1 |
| A-9838 | H | H | H | H | H | O | H | H | 2-NEt₂,5-F | 1 |
| A-9839 | H | H | H | H | H | O | H | H | 2-NEt₂,6-F | 1 |
| A-9840 | H | H | H | H | H | O | H | H | 2-NEt₂,3Me | 1 |
| A-9841 | H | H | H | H | H | O | H | H | 2-NEt₂,4-Me | 1 |
| A-9842 | H | H | H | H | H | O | H | H | 2-NEt₂,5-Me | 1 |
| A-9843 | H | H | H | H | H | O | H | H | 2-NEt₂,6-Me | 1 |
| A-9844 | H | H | H | H | H | O | H | H | 2-CHO,3-F | 1 |
| A-9845 | H | H | H | H | H | O | H | H | 2-CHO,4-F | 1 |
| A-9846 | H | H | H | H | H | O | H | H | 2-CHO,5-F | 1 |
| A-9847 | H | H | H | H | H | O | H | H | 2-CHO,6-F | 1 |
| A-9848 | H | H | H | H | H | O | H | H | 2-CHO,3-Me | 1 |
| A-9849 | H | H | H | H | H | O | H | H | 2-CHO,4-Me | 1 |
| A-9850 | H | H | H | H | H | O | H | H | 2-CHO,5-Me | 1 |
| A-9851 | H | H | H | H | H | O | H | H | 2-CHO,6-Me | 1 |
| A-9852 | H | H | H | H | H | O | H | H | 2-C(=O)OH,3-F | 1 |
| A-9853 | H | H | H | H | H | O | H | H | 2-C(=O)OH,4-F | 1 |
| A-9854 | H | H | H | H | H | O | H | H | 2-C(=O)OH,5-F | 1 |
| A-9855 | H | H | H | H | H | O | H | H | 2-C(=O)OH,6-F | 1 |
| A-9856 | H | H | H | H | H | O | H | H | 2-C(=O)OH,3-Me | 1 |

TABLE 174

| compound | R¹ | R² | R³ | R⁴ | R⁵ | A | R⁶ | R⁷ | (R⁸)ₘ | p |
|---|---|---|---|---|---|---|---|---|---|---|
| A-9857 | H | H | H | H | H | O | H | H | 2-C(=O)OH,4-Me | 1 |
| A-9858 | H | H | H | H | H | O | H | H | 2-C(=O)OH,5-Me | 1 |
| A-9859 | H | H | H | H | H | O | H | H | 2-C(=O)OH,6-Me | 1 |
| A-9860 | H | H | H | H | H | O | H | H | 2-(1,3-dioxolan-2-yl),3-F | 1 |
| A-9861 | H | H | H | H | H | O | H | H | 2-(1,3-dioxolan-2-yl),4-F | 1 |
| A-9862 | H | H | H | H | H | O | H | H | 2-(1,3-dioxolan-2-yl),5-F | 1 |
| A-9863 | H | H | H | H | H | O | H | H | 2-(1,3-dioxolan-2-yl),6-F | 1 |
| A-9864 | H | H | H | H | H | O | H | H | 2-(1,3-dioxolan-2-yl),3-Me | 1 |
| A-9865 | H | H | H | H | H | O | H | H | 2-(1,3-dioxolan-2-yl),4-Me | 1 |
| A-9866 | H | H | H | H | H | O | H | H | 2-(1,3-dioxolan-2-yl),5-Me | 1 |
| A-9867 | H | H | H | H | H | O | H | H | 2-(1,3-dioxolan-2-yl),6-Me | 1 |
| A-9868 | H | H | H | H | H | O | H | H | 2-(1,3-dioxan-2-yl),3-F | 1 |
| A-9869 | H | H | H | H | H | O | H | H | 2-(1,3-dioxan-2-yl),4-F | 1 |
| A-9870 | H | H | H | H | H | O | H | H | 2-(1,3-dioxan-2-yl),5-F | 1 |
| A-9871 | H | H | H | H | H | O | H | H | 2-(1,3-dioxan-2-yl),6-F | 1 |
| A-9872 | H | H | H | H | H | O | H | H | 2-(1,3-dioxan-2-yl),3-Me | 1 |
| A-9873 | H | H | H | H | H | O | H | H | 2-(1,3-dioxan-2-yl),4-Me | 1 |
| A-9874 | H | H | H | H | H | O | H | H | 2-(1,3-dioxan-2-yl),5-Me | 1 |
| A-9875 | H | H | H | H | H | O | H | H | 2-(1,3-dioxan-2-yl),6-Me | 1 |
| A-9876 | H | H | H | H | H | O | H | H | 2-(thiazol-2-yl),3-F | 1 |
| A-9877 | H | H | H | H | H | O | H | H | 2-(thiazol-2-yl),4-F | 1 |
| A-9878 | H | H | H | H | H | O | H | H | 2-(thiazol-2-yl),5-F | 1 |
| A-9879 | H | H | H | H | H | O | H | H | 2-(thiazol-2-yl),6-F | 1 |
| A-9880 | H | H | H | H | H | O | H | H | 2-(thiazol-2-yl),3-Me | 1 |
| A-9881 | H | H | H | H | H | O | H | H | 2-(thiazol-2-yl),4-Me | 1 |
| A-9882 | H | H | H | H | H | O | H | H | 2-(thiazol-2-yl),5-Me | 1 |
| A-9883 | H | H | H | H | H | O | H | H | 2-(thiazol-2-yl),6-Me | 1 |
| A-9884 | H | H | H | H | H | O | H | H | 2-(oxazol-2-yl),3-F | 1 |
| A-9885 | H | H | H | H | H | O | H | H | 2-(oxazol-2-yl),4-F | 1 |
| A-9886 | H | H | H | H | H | O | H | H | 2-(oxazol-2-yl),5-F | 1 |
| A-9887 | H | H | H | H | H | O | H | H | 2-(oxazol-2-yl),6-F | 1 |
| A-9888 | H | H | H | H | H | O | H | H | 2-(oxazol-2-yl),3-Me | 1 |
| A-9889 | H | H | H | H | H | O | H | H | 2-(oxazol-2-yl),4-Me | 1 |
| A-9890 | H | H | H | H | H | O | H | H | 2-(oxazol-2-yl),5-Me | 1 |
| A-9891 | H | H | H | H | H | O | H | H | 2-(oxazol-2-yl),6-Me | 1 |
| A-9892 | H | H | H | H | H | O | H | H | 2-CH=NOH,3F | 1 |
| A-9893 | H | H | H | H | H | O | H | H | 2-CH=NOH,4-F | 1 |
| A-9894 | H | H | H | H | H | O | H | H | 2-CH=NOH,5-F | 1 |
| A-9895 | H | H | H | H | H | O | H | H | 2-CH=NOH,6-F | 1 |
| A-9896 | H | H | H | H | H | O | H | H | 2-CH=NOH,3-Me | 1 |
| A-9897 | H | H | H | H | H | O | H | H | 2-CH=NOH,4-Me | 1 |
| A-9898 | H | H | H | H | H | O | H | H | 2-CH=NOH,5-Me | 1 |
| A-9899 | H | H | H | H | H | O | H | H | 2-CH=NOH,6-Me | 1 |
| A-9900 | H | H | H | H | H | O | H | H | 2-CH=NOMe,3-F | 1 |
| A-9901 | H | H | H | H | H | O | H | H | 2-CH=NOMe,4-F | 1 |
| A-9902 | H | H | H | H | H | O | H | H | 2-CH=NOMe,5-F | 1 |
| A-9903 | H | H | H | H | H | O | H | H | 2-CH=NOMe,6-F | 1 |
| A-9904 | H | H | H | H | H | O | H | H | 2-CH=NOMe,3-Me | 1 |
| A-9905 | H | H | H | H | H | O | H | H | 2-CH=NOMe,4-Me | 1 |
| A-9906 | H | H | H | H | H | O | H | H | 2-CH=NOMe,5-Me | 1 |
| A-9907 | H | H | H | H | H | O | H | H | 2-CH=NOMe,6-Me | 1 |
| A-9908 | H | H | H | H | H | O | H | H | 2-CN,3-F | 1 |

TABLE 174-continued

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-9909 | H | H | H | H | H | O | H | H | 2-CN,4-F | 1 |
| A-9910 | H | H | H | H | H | O | H | H | 2-CN,5-F | 1 |
| A-9911 | H | H | H | H | H | O | H | H | 2-CN,6-F | 1 |
| A-9912 | H | H | H | H | H | O | H | H | 2-CN,3-Cl | 1 |
| A-9913 | H | H | H | H | H | O | H | H | 2-CN,4-Cl | 1 |

TABLE 175

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-9914 | H | H | H | H | H | O | H | H | 2-CN,5-Cl | 1 |
| A-9915 | H | H | H | H | H | O | H | H | 2-CN,6-Cl | 1 |
| A-9916 | H | H | H | H | H | O | H | H | 2-CN,3-Me | 1 |
| A-9917 | H | H | H | H | H | O | H | H | 2-CN,4-Me | 1 |
| A-9918 | H | H | H | H | H | O | H | H | 2-CN,5-Me | 1 |
| A-9919 | H | H | H | H | H | O | H | H | 2-CN,6-Me | 1 |
| A-9920 | H | H | H | H | H | O | H | H | 2-CN,3-OMe | 1 |
| A-9921 | H | H | H | H | H | O | H | H | 2-CN,4-OMe | 1 |
| A-9922 | H | H | H | H | H | O | H | H | 2-CN,5-OMe | 1 |
| A-9923 | H | H | H | H | H | O | H | H | 2-CN,6-OMe | 1 |
| A-9924 | H | H | H | H | H | O | H | H | 3-CN,2-F | 1 |
| A-9925 | H | H | H | H | H | O | H | H | 3-CN,4-F | 1 |
| A-9926 | H | H | H | H | H | O | H | H | 3-CN,5-F | 1 |
| A-9927 | H | H | H | H | H | O | H | H | 3-CN,6-F | 1 |
| A-9928 | H | H | H | H | H | O | H | H | 3-CN,2-Cl | 1 |
| A-9929 | H | H | H | H | H | O | H | H | 3-CN,4-Cl | 1 |
| A-9930 | H | H | H | H | H | O | H | H | 3-CN,5-Cl | 1 |
| A-9931 | H | H | H | H | H | O | H | H | 3-CN,6-Cl | 1 |
| A-9932 | H | H | H | H | H | O | H | H | 3-CN,2-Me | 1 |
| A-9933 | H | H | H | H | H | O | H | H | 3-CN,4-Me | 1 |
| A-9934 | H | H | H | H | H | O | H | H | 3-CN,5-Me | 1 |
| A-9935 | H | H | H | H | H | O | H | H | 3-CN,6-Me | 1 |
| A-9936 | H | H | H | H | H | O | H | H | 3-CN,2-OMe | 1 |
| A-9937 | H | H | H | H | H | O | H | H | 3-CN,4-OMe | 1 |
| A-9938 | H | H | H | H | H | O | H | H | 3-CN,5-OMe | 1 |
| A-9939 | H | H | H | H | H | O | H | H | 3-CN,6-OMe | 1 |
| A-9940 | H | H | H | H | H | O | H | H | 4-CN,2-F | 1 |
| A-9941 | H | H | H | H | H | O | H | H | 4-CN,3-F | 1 |
| A-9942 | H | H | H | H | H | O | H | H | 4-CN,2-Cl | 1 |
| A-9943 | H | H | H | H | H | O | H | H | 4-CN,3-Cl | 1 |
| A-9944 | H | H | H | H | H | O | H | H | 4-CN,2-Me | 1 |
| A-9945 | H | H | H | H | H | O | H | H | 4-CN,3-Me | 1 |
| A-9946 | H | H | H | H | H | O | H | H | 4-CN,2-OMe | 1 |
| A-9947 | H | H | H | H | H | O | H | H | 4-CN,3-OMe | 1 |
| A-9948 | H | H | H | H | H | O | H | H | 2-$NO_2$,3-F | 1 |
| A-9949 | H | H | H | H | H | O | H | H | 2-$NO_2$,4-F | 1 |
| A-9950 | H | H | H | H | H | O | H | H | 2-$NO_2$,5-F | 1 |
| A-9951 | H | H | H | H | H | O | H | H | 2-$NO_2$,6-F | 1 |
| A-9952 | H | H | H | H | H | O | H | H | 2-$NO_2$,3-Me | 1 |
| A-9953 | H | H | H | H | H | O | H | H | 2-$NO_2$,4-Me | 1 |
| A-9954 | H | H | H | H | H | O | H | H | 2-$NO_2$,5-Me | 1 |
| A-9955 | H | H | H | H | H | O | H | H | 2-$NO_2$,6-Me | 1 |
| A-9956 | H | H | H | H | H | O | H | H | 2-Me,3,4-$F_2$ | 1 |
| A-9957 | H | H | H | H | H | O | H | H | 2-Me,3,5-$F_2$ | 1 |
| A-9958 | H | H | H | H | H | O | H | H | 2-Me,3,6-$F_2$ | 1 |
| A-9959 | H | H | H | H | H | O | H | H | 2-Me,4,5-$F_2$ | 1 |
| A-9960 | H | H | H | H | H | O | H | H | 2-OMe,3,4-$F_2$ | 1 |
| A-9961 | H | H | H | H | H | O | H | H | 2-OMe,3,5-$F_2$ | 1 |
| A-9962 | H | H | H | H | H | O | H | H | 2-OMe,3,6-$F_2$ | 1 |
| A-9963 | H | H | H | H | H | O | H | H | 2-OMe,4,5-$F_2$ | 1 |
| A-9964 | H | H | H | H | H | O | H | H | 2-$(CH_2)_3$-3 | 1 |
| A-9965 | H | H | H | H | H | O | H | H | 2-$(CH_2)_4$-3 | 1 |
| A-9966 | H | H | H | H | H | O | H | H | 2-$(OCH_2CH_2)$-3 | 1 |
| A-9967 | H | H | H | H | H | O | H | H | 2-$(OCH_2CH_2CH_2)$-3 | 1 |
| A-9968 | H | H | H | H | H | O | H | H | 2-$(CH_2CH_2O)$-3 | 1 |
| A-9969 | H | H | H | H | H | O | H | H | 2-$(CH_2CH_2CH_2O)$-3 | 1 |
| A-9970 | H | H | H | H | H | O | H | H | 3-$(CH_2)_3$-4 | 1 |

TABLE 176

| compound | $R^1$ | $R^2$ | $R^3$ | $R^4$ | $R^5$ | A | $R^6$ | $R^7$ | $(R^8)_m$ | p |
|---|---|---|---|---|---|---|---|---|---|---|
| A-9971 | H | H | H | H | H | O | H | H | 3-$(CH_2)_4$-4 | 1 |
| A-9972 | H | H | H | H | H | O | H | H | 3-$(OCH_2CH_2)$-4 | 1 |
| A-9973 | H | H | H | H | H | O | H | H | 3-$(OCH_2CH_2CH_2)$-4 | 1 |
| A-9974 | H | H | H | H | H | O | H | H | 3-$(CH_2CH_2O)$-4 | 1 |
| A-9975 | H | H | H | H | H | O | H | H | 3-$(CH_2CH_2CH_2O)$-4 | 1 |
| A-9976 | H | H | H | H | H | O | H | H | 2-$(OCH_2O)$-3 | 1 |
| A-9977 | H | H | H | H | H | O | H | H | 3-$(OCH_2O)$-4 | 1 |
| A-9978 | H | H | H | H | H | O | H | H | 2-$(OCH_2CH_2O)$-3 | 1 |
| A-9979 | H | H | H | H | H | O | H | H | 3-$(OCH_2CH_2O)$-4 | 1 |
| A-9980 | H | H | H | H | H | O | H | H | 2-$(OCF_2O)$-3 | 1 |
| A-9981 | H | H | H | H | H | O | H | H | 3-$(OCF_2O)$-4 | 1 |
| A-9982 | H | H | H | H | H | O | H | H | 2-Me,6-Et | 1 |
| A-9983 | H | H | H | H | H | O | H | H | 2-Me,4,5-$F_2$ | 1 |
| A-9984 | H | H | H | H | H | O | H | H | 2-cyclopropyl,6-OMe | 1 |
| A-9985 | H | H | H | H | H | O | H | H | 2-Me,5-Et | 1 |
| A-9986 | H | H | H | H | H | O | H | H | 2,6-$Et_2$ | 1 |
| A-9987 | H | H | H | H | H | O | H | H | 2-Et,6-F | 1 |
| A-9988 | H | H | H | H | H | O | H | H | 2-$CH_2OCH_3$,6-Cl | 1 |
| A-9989 | H | H | H | H | H | O | H | H | 2-$CH_2OCH_2CH_3$,6-Cl | 1 |
| A-9990 | H | H | H | H | H | O | H | H | 2-$CH_2NMe_2$ | 1 |
| A-9991 | H | H | H | H | H | O | H | H | 2-$CH_2OCH_3$,6-OMe | 0 |
| A-9992 | H | H | H | H | H | O | H | H | 2-$CH_2OCH_3$,6-OMe | 1 |
| A-9993 | H | H | H | H | H | O | pyridin-2-ylmethyl | H | 2-Me | 0 |
| A-9994 | H | H | H | H | H | O | pyridin-3-ylmethyl | H | 2-Me | 0 |

TABLE 177

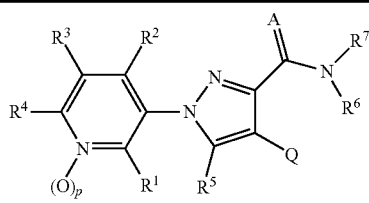

| compound | R¹ | R² | R³ | R⁴ | R⁵ | A | R⁶ | R⁷ | Q | p |
|---|---|---|---|---|---|---|---|---|---|---|
| B-0001 | H | H | H | H | H | O | H | H | Cl | 0 |
| B-0002 | H | H | H | H | H | O | H | H | Br | 0 |
| B-0003 | H | H | H | H | H | O | H | H | I | 0 |
| B-0004 | H | H | H | H | H | O | H | H | naphthalen-1-yl | 0 |
| B-0005 | H | H | H | H | H | O | H | H | 2-F-naphthalen-1-yl | 0 |
| B-0006 | H | H | H | H | H | O | H | H | 2-Me-naphthalen-1-yl | 0 |
| B-0007 | H | H | H | H | H | O | H | H | 2-CF₃-naphthalen-1-yl | 0 |
| B-0008 | H | H | H | H | H | O | H | H | 2-OMe-naphthalen-1-yl | 0 |
| B-0009 | H | H | H | H | H | O | H | H | naphthalen-2-yl | 0 |
| B-0010 | H | H | H | H | H | O | H | H | 1-F-naphthalen-2-yl | 0 |
| B-0011 | H | H | H | H | H | O | H | H | 1-Me-naphthalen-2-y | 0 |
| B-0012 | H | H | H | H | H | O | H | H | 1-CF₃-naphthalen-2-yl | 0 |
| B-0013 | H | H | H | H | H | O | H | H | 1-OMe-naphthalen-2-yl | 0 |
| B-0014 | H | H | H | H | H | O | H | H | 3-F-naphthalen-2-yl | 0 |
| B-0015 | H | H | H | H | H | O | H | H | 3-Me-naphthalen-2-yl | 0 |
| B-0016 | H | H | H | H | H | O | H | H | 3-CF₃-naphthalen-2-yl | 0 |
| B-0017 | H | H | H | H | H | O | H | H | 3-OMe-naphthalen-2-yl | 0 |
| B-0018 | H | H | H | H | H | O | H | H | pyridin-2-yl | 0 |
| B-0019 | H | H | H | H | H | O | H | H | 3-F-pyridin-2-yl | 0 |
| B-0020 | H | H | H | H | H | O | H | H | 4-F-pyridin-2-yl | 0 |
| B-0021 | H | H | H | H | H | O | H | H | 5-F-pyridin-2-yl | 0 |
| B-0022 | H | H | H | H | H | O | H | H | 6-F-pyridin-2-yl | 0 |
| B-0023 | H | H | H | H | H | O | H | H | 3-Cl-pyridin-2-yl | 0 |
| B-0024 | H | H | H | H | H | O | H | H | 4-Cl-pyridin-2-yl | 0 |
| B-0025 | H | H | H | H | H | O | H | H | 5-Cl-pyridin-2-yl | 0 |
| B-0026 | H | H | H | H | H | O | H | H | 6-Cl-pyridin-2-yl | 0 |
| B-0027 | H | H | H | H | H | O | H | H | 3-Me-pyridin-2-yl | 0 |
| B-0028 | H | H | H | H | H | O | H | H | 4-Me-pyridin-2-yl | 0 |
| B-0029 | H | H | H | H | H | O | H | H | 5-Me-pyridin-2-yl | 0 |
| B-0030 | H | H | H | H | H | O | H | H | 6-Me-pyridin-2-yl | 0 |
| B-0031 | H | H | H | H | H | O | H | H | 3-CF₃-pyridin-2-yl | 0 |
| B-0032 | H | H | H | H | H | O | H | H | 4-CF₃-pyridin-2-yl | 0 |
| B-0033 | H | H | H | H | H | O | H | H | 5-CF₃-pyridin-2-yl | 0 |
| B-0034 | H | H | H | H | H | O | H | H | 6-CF₃-pyridin-2-yl | 0 |
| B-0035 | H | H | H | H | H | O | H | H | 3-OMe-pyridin-2-yl | 0 |
| B-0036 | H | H | H | H | H | O | H | H | 4-OMe-pyridin-2-yl | 0 |
| B-0037 | H | H | H | H | H | O | H | H | 5-OMe-pyridin-2-yl | 0 |
| B-0038 | H | H | H | H | H | O | H | H | 6-OMe-pyridin-2-yl | 0 |
| B-0039 | H | H | H | H | H | O | H | H | 3,4-F₂-pyridin-2-yl | 0 |
| B-0040 | H | H | H | H | H | O | H | H | 3,5-F₂-pyridin-2-yl | 0 |
| B-0041 | H | H | H | H | H | O | H | H | 3,6-F₂-pyridin-2-yl | 0 |
| B-0042 | H | H | H | H | H | O | H | H | 3,4-Cl₂-pyridin-2-yl | 0 |
| B-0043 | H | H | H | H | H | O | H | H | 3,5-Cl₂-pyridin-2-yl | 0 |
| B-0044 | H | H | H | H | H | O | H | H | 3,6-Cl₂-pyridin-2-yl | 0 |
| B-0045 | H | H | H | H | H | O | H | H | 3-F-4-Cl-pyridin-2-yl | 0 |
| B-0046 | H | H | H | H | H | O | H | H | 3-F-5-Cl-pyridin-2-yl | 0 |
| B-0047 | H | H | H | H | H | O | H | H | 3-F-6-Cl-pyridin-2-yl | 0 |
| B-0048 | H | H | H | H | H | O | H | H | 3-F-4-Me-pyridin-2-yl | 0 |
| B-0049 | H | H | H | H | H | O | H | H | 3-F-5-Me-pyridin-2-yl | 0 |
| B-0050 | H | H | H | H | H | O | H | H | 3-F-6-Me-pyridin-2-yl | 0 |
| B-0051 | H | H | H | H | H | O | H | H | 3-F-4-OMe-pyridin-2-yl | 0 |
| B-0052 | H | H | H | H | H | O | H | H | 3-F-5-OMe-pyridin-2-yl | 0 |

TABLE 178

| compound | R¹ | R² | R³ | R⁴ | R⁵ | A | R⁶ | R⁷ | Q | p |
|---|---|---|---|---|---|---|---|---|---|---|
| B-0053 | H | H | H | H | H | O | H | H | 3-F-6-OMe-pyridin-2-yl | 0 |
| B-0054 | H | H | H | H | H | O | H | H | 3-Cl-4-F-pyridin-2-yl | 0 |
| B-0055 | H | H | H | H | H | O | H | H | 3-Cl-5-F-pyridin-2-yl | 0 |
| B-0056 | H | H | H | H | H | O | H | H | 3-Cl-6-F-pyridin-2-yl | 0 |
| B-0057 | H | H | H | H | H | O | H | H | 3-Cl-4-Me-pyridin-2-yl | 0 |
| B-0058 | H | H | H | H | H | O | H | H | 3-Cl-5-Me-pyridin-2-yl | 0 |
| B-0059 | H | H | H | H | H | O | H | H | 3-Cl-6-Me-pyridin-2-yl | 0 |
| B-0060 | H | H | H | H | H | O | H | H | 3-Me-4-F-pyridin-2-yl | 0 |

TABLE 178-continued

| compound | R¹ | R² | R³ | R⁴ | R⁵ | A | R⁶ | R⁷ | Q | p |
|---|---|---|---|---|---|---|---|---|---|---|
| B-0061 | H | H | H | H | H | O | H | H | 3-Me-5-F-pyridin-2-yl | 0 |
| B-0062 | H | H | H | H | H | O | H | H | 3-Me-6-F-pyridin-2-yl | 0 |
| B-0063 | H | H | H | H | H | O | H | H | 3-Me-4-Cl-pyridin-2-yl | 0 |
| B-0064 | H | H | H | H | H | O | H | H | 3-Me-5-Cl-pyridin-2-yl | 0 |
| B-0065 | H | H | H | H | H | O | H | H | 3-Me-6-Cl-pyridin-2-yl | 0 |
| B-0066 | H | H | H | H | H | O | H | H | 3,4-(Me)₂-pyridin-2-yl | 0 |
| B-0067 | H | H | H | H | H | O | H | H | 3,5-(Me)₂-pyridin-2-yl | 0 |
| B-0068 | H | H | H | H | H | O | H | H | 3,6-(Me)₂-pyridin-2-yl | 0 |
| B-0069 | H | H | H | H | H | O | H | H | 3-Me-4-OMe-pyridin-2-yl | 0 |
| B-0070 | H | H | H | H | H | O | H | H | 3-Me-5-OMe-pyridin-2-yl | 0 |
| B-0071 | H | H | H | H | H | O | H | H | 3-Me-6-OMe-pyridin-2-yl | 0 |
| B-0072 | H | H | H | H | H | O | H | H | 3-CF₃-4-F-pyridin-2-yl | 0 |
| B-0073 | H | H | H | H | H | O | H | H | 3-CF₃-5-F-pyridin-2-yl | 0 |
| B-0074 | H | H | H | H | H | O | H | H | 3-CF₃-6-F-pyridin-2-yl | 0 |
| B-0075 | H | H | H | H | H | O | H | H | 3-CF₃-4-Me-pyridin-2-yl | 0 |
| B-0076 | H | H | H | H | H | O | H | H | 3-CF₃-5-Me-pyridin-2-yl | 0 |
| B-0077 | H | H | H | H | H | O | H | H | 3-CF₃-6-Me-pyridin-2-yl | 0 |
| B-0078 | H | H | H | H | H | O | H | H | 3-OMe-4-F-pyridin-2-yl | 0 |
| B-0079 | H | H | H | H | H | O | H | H | 3-OMe-5-F-pyridin-2-yl | 0 |
| B-0080 | H | H | H | H | H | O | H | H | 3-OMe-6-F-pyridin-2-yl | 0 |
| B-0081 | H | H | H | H | H | O | H | H | 3-OMe-4-Cl-pyridin-2-yl | 0 |
| B-0082 | H | H | H | H | H | O | H | H | 3-OMe-5-Cl-pyridin-2-yl | 0 |
| B-0083 | H | H | H | H | H | O | H | H | 3-OMe-6-Cl-pyridin-2-yl | 0 |
| B-0084 | H | H | H | H | H | O | H | H | 3-OMe-4-Me-pyridin-2-yl | 0 |
| B-0085 | H | H | H | H | H | O | H | H | 3-OMe-5-Me-pyridin-2-yl | 0 |
| B-0086 | H | H | H | H | H | O | H | H | 3-OMe-6-Me-pyridin-2-yl | 0 |
| B-0087 | H | H | H | H | H | O | H | H | 3,4-(OMe)2-pyridin-2-yl | 0 |
| B-0088 | H | H | H | H | H | O | H | H | 3,5-(OMe)2-pyridin-2-yl | 0 |
| B-0089 | H | H | H | H | H | O | H | H | 3,6-(OMe)2-pyridin-2-yl | 0 |
| B-0090 | H | H | H | H | H | O | H | H | pyridin-3-yl | 0 |
| B-0091 | H | H | H | H | H | O | H | H | 2-F-pyridin-3-yl | 0 |
| B-0092 | H | H | H | H | H | O | H | H | 4-F-pyridin-3-yl | 0 |
| B-0093 | H | H | H | H | H | O | H | H | 5-F-pyridin-3-yl | 0 |
| B-0094 | H | H | H | H | H | O | H | H | 6-F-pyridin-3-yl | 0 |
| B-0095 | H | H | H | H | H | O | H | H | 2-Cl-pyridin-3-yl | 0 |
| B-0096 | H | H | H | H | H | O | H | H | 4-Cl-pyridin-3-yl | 0 |
| B-0097 | H | H | H | H | H | O | H | H | 5-Cl-pyridin-3-yl | 0 |
| B-0098 | H | H | H | H | H | O | H | H | 6-Cl-pyridin-3-yl | 0 |
| B-0099 | H | H | H | H | H | O | H | H | 2-Me-pyridin-3-yl | 0 |
| B-0100 | H | H | H | H | H | O | H | H | 4-Me-pyridin-3-yl | 0 |
| B-0101 | H | H | H | H | H | O | H | H | 5-Me-pyridin-3-yl | 0 |
| B-0102 | H | H | H | H | H | O | H | H | 6-Me-pyridin-3-yl | 0 |
| B-0103 | H | H | H | H | H | O | H | H | 2-CF₃-pyridin-3-yl | 0 |
| B-0104 | H | H | H | H | H | O | H | H | 4-CF₃-pyridin-3-yl | 0 |
| B-0105 | H | H | H | H | H | O | H | H | 5-CF₃-pyridin-3-yl | 0 |
| B-0106 | H | H | H | H | H | O | H | H | 6-CF₃-pyridin-3-yl | 0 |
| B-0107 | H | H | H | H | H | O | H | H | 2-OMe-pyridin-3-yl | 0 |
| B-0108 | H | H | H | H | H | O | H | H | 4-OMe-pyridin-3-yl | 0 |
| B-0109 | H | H | H | H | H | O | H | H | 5-OMe-pyridin-3-yl | 0 |

TABLE 179

| compound | R¹ | R² | R³ | R⁴ | R⁵ | A | R⁶ | R⁷ | Q | p |
|---|---|---|---|---|---|---|---|---|---|---|
| B-0110 | H | H | H | H | H | O | H | H | 6-OMe-pyridin-3-yl | 0 |
| B-0111 | H | H | H | H | H | O | H | H | 2,4-F₂-pyridin-3-yl | 0 |
| B-0112 | H | H | H | H | H | O | H | H | 2,5-F₂-pyridin-3-yl | 0 |
| B-0113 | H | H | H | H | H | O | H | H | 2,6-F₂-pyridin-3-yl | 0 |
| B-0114 | H | H | H | H | H | O | H | H | 4,5-F₂-pyridin-3-yl | 0 |
| B-0115 | H | H | H | H | H | O | H | H | 4,6-F₂-pyridin-3-yl | 0 |
| B-0116 | H | H | H | H | H | O | H | H | 2,4-Cl₂-pyridin-3-yl | 0 |
| B-0117 | H | H | H | H | H | O | H | H | 2,5-Cl₂-pyridin-3-yl | 0 |
| B-0118 | H | H | H | H | H | O | H | H | 2,6-Cl₂-pyridin-3-yl | 0 |
| B-0119 | H | H | H | H | H | O | H | H | 4,5-Cl₂-pyridin-3-yl | 0 |
| B-0120 | H | H | H | H | H | O | H | H | 4,6-Cl₂-pyridin-3-yl | 0 |
| B-0121 | H | H | H | H | H | O | H | H | 2-F-4-Cl-pyridin-3-yl | 0 |
| B-0122 | H | H | H | H | H | O | H | H | 2-F-5-Cl-pyridin-3-yl | 0 |
| B-0123 | H | H | H | H | H | O | H | H | 2-F-6-Cl-pyridin-3-yl | 0 |
| B-0124 | H | H | H | H | H | O | H | H | 4-F-2-Cl-pyridin-3-yl | 0 |
| B-0125 | H | H | H | H | H | O | H | H | 4-F-5-Cl-pyridin-3-yl | 0 |
| B-0126 | H | H | H | H | H | O | H | H | 4-F-6-Cl-pyridin-3-yl | 0 |
| B-0127 | H | H | H | H | H | O | H | H | 2-F-4-Me-pyridin-3-yl | 0 |
| B-0128 | H | H | H | H | H | O | H | H | 2-F-5-Me-pyridin-3-yl | 0 |
| B-0129 | H | H | H | H | H | O | H | H | 2-F-6-Me-pyridin-3-yl | 0 |
| B-0130 | H | H | H | H | H | O | H | H | 4-F-2-Me-pyridin-3-yl | 0 |

TABLE 179-continued

| compound | R¹ | R² | R³ | R⁴ | R⁵ | A | R⁶ | R⁷ | Q | p |
|---|---|---|---|---|---|---|---|---|---|---|
| B-0131 | H | H | H | H | H | O | H | H | 4-F-5-Me-pyridin-3-yl | 0 |
| B-0132 | H | H | H | H | H | O | H | H | 4-F-6-Me-pyridin-3-yl | 0 |
| B-0133 | H | H | H | H | H | O | H | H | 2-F-4-OMe-pyridin-3-yl | 0 |
| B-0134 | H | H | H | H | H | O | H | H | 2-F-5-OMe-pyridin-3-yl | 0 |
| B-0135 | H | H | H | H | H | O | H | H | 2-F-6-OMe-pyridin-3-yl | 0 |
| B-0136 | H | H | H | H | H | O | H | H | 4-F-2-OMe-pyridin-3-yl | 0 |
| B-0137 | H | H | H | H | H | O | H | H | 4-F-5-OMe-pyridin-3-yl | 0 |
| B-0138 | H | H | H | H | H | O | H | H | 4-F-6-OMe-pyridin-3-yl | 0 |
| B-0139 | H | H | H | H | H | O | H | H | 2-Cl-5-F-pyridin-3-yl | 0 |
| B-0140 | H | H | H | H | H | O | H | H | 2-Cl-6-F-pyridin-3-yl | 0 |
| B-0141 | H | H | H | H | H | O | H | H | 4-Cl-5-F-pyridin-3-yl | 0 |
| B-0142 | H | H | H | H | H | O | H | H | 4-Cl-6-F-pyridin-3-yl | 0 |
| B-0143 | H | H | H | H | H | O | H | H | 2-Cl-4-Me-pyridin-3-yl | 0 |
| B-0144 | H | H | H | H | H | O | H | H | 2-Cl-5-Me-pyridin-3-yl | 0 |
| B-0145 | H | H | H | H | H | O | H | H | 2-Cl-6-Me-pyridin-3-yl | 0 |
| B-0146 | H | H | H | H | H | O | H | H | 4-Cl-2-Me-pyridin-3-yl | 0 |
| B-0147 | H | H | H | H | H | O | H | H | 4-Cl-5-Me-pyridin-3-yl | 0 |
| B-0148 | H | H | H | H | H | O | H | H | 4-Cl-6-Me-pyridin-3-yl | 0 |
| B-0149 | H | H | H | H | H | O | H | H | 2-Me-5-F-pyridin-3-yl | 0 |
| B-0150 | H | H | H | H | H | O | H | H | 2-Me-6-F-pyridin-3-yl | 0 |
| B-0151 | H | H | H | H | H | O | H | H | 4-Me-5-F-pyridin-3-yl | 0 |
| B-0152 | H | H | H | H | H | O | H | H | 4-Me-6-F-pyridin-3-yl | 0 |
| B-0153 | H | H | H | H | H | O | H | H | 2-Me-5-Cl-pyridin-3-yl | 0 |
| B-0154 | H | H | H | H | H | O | H | H | 2-Me-6-Cl-pyridin-3-yl | 0 |
| B-0155 | H | H | H | H | H | O | H | H | 4-Me-5-Cl-pyridin-3-yl | 0 |
| B-0156 | H | H | H | H | H | O | H | H | 4-Me-6-Cl-pyridin-3-yl | 0 |
| B-0157 | H | H | H | H | H | O | H | H | 2,4-(Me)₂-pyridin-3-yl | 0 |
| B-0158 | H | H | H | H | H | O | H | H | 2,5-(Me)₂-pyridin-3-yl | 0 |
| B-0159 | H | H | H | H | H | O | H | H | 2,6-(Me)₂-pyridin-3-yl | 0 |
| B-0160 | H | H | H | H | H | O | H | H | 4,5-(Me)₂-pyridin-3-yl | 0 |
| B-0161 | H | H | H | H | H | O | H | H | 4,6-(Me)₂-pyridin-3-yl | 0 |
| B-0162 | H | H | H | H | H | O | H | H | 2-Me-4-OMe-pyridin-3-yl | 0 |
| B-0163 | H | H | H | H | H | O | H | H | 2-Me-5-OMe-pyridin-3-yl | 0 |
| B-0164 | H | H | H | H | H | O | H | H | 2-Me-6-OMe-pyridin-3-yl | 0 |
| B-0165 | H | H | H | H | H | O | H | H | 4-Me-2-OMe-pyridin-3-yl | 0 |
| B-0166 | H | H | H | H | H | O | H | H | 4-Me-5-OMe-pyridin-3-yl | 0 |

TABLE 180

| compound | R¹ | R² | R³ | R⁴ | R⁵ | A | R⁶ | R⁷ | Q | p |
|---|---|---|---|---|---|---|---|---|---|---|
| B-0167 | H | H | H | H | H | O | H | H | 4-Me-6-OMe-pyridin-3-yl | 0 |
| B-0168 | H | H | H | H | H | O | H | H | 2-CF₃-4-F-pyridin-3-yl | 0 |
| B-0169 | H | H | H | H | H | O | H | H | 2-CF₃-5-F-pyridin-3-yl | 0 |
| B-0170 | H | H | H | H | H | O | H | H | 2-CF₃-6-F-pyridin-3-yl | 0 |
| B-0171 | H | H | H | H | H | O | H | H | 4-CF₃-2-F-pyridin-3-yl | 0 |
| B-0172 | H | H | H | H | H | O | H | H | 4-CF₃-5-F-pyridin-3-yl | 0 |
| B-0173 | H | H | H | H | H | O | H | H | 4-CF₃-6-F-pyridin-3-yl | 0 |
| B-0174 | H | H | H | H | H | O | H | H | 2-CF₃-4-Me-pyridin-3-yl | 0 |
| B-0175 | H | H | H | H | H | O | H | H | 2-CF₃-5-Me-pyridin-3-yl | 0 |
| B-0176 | H | H | H | H | H | O | H | H | 2-CF₃-6-Me-pyridin-3-yl | 0 |
| B-0177 | H | H | H | H | H | O | H | H | 4-CF₃-2-Me-pyridin-3-yl | 0 |
| B-0178 | H | H | H | H | H | O | H | H | 4-CF₃-5-Me-pyridin-3-yl | 0 |
| B-0179 | H | H | H | H | H | O | H | H | 4-CF₃-6-Me-pyridin-3-yl | 0 |
| B-0180 | H | H | H | H | H | O | H | H | 2-OMe-5-F-pyridin-3-yl | 0 |
| B-0181 | H | H | H | H | H | O | H | H | 2-OMe-6-F-pyridin-3-yl | 0 |
| B-0182 | H | H | H | H | H | O | H | H | 4-OMe-5-F-pyridin-3-yl | 0 |
| B-0183 | H | H | H | H | H | O | H | H | 4-OMe-6-F-pyridin-3-yl | 0 |
| B-0184 | H | H | H | H | H | O | H | H | 2-OMe-4-Cl-pyridin-3-yl | 0 |
| B-0185 | H | H | H | H | H | O | H | H | 2-OMe-5-Cl-pyridin-3-yl | 0 |
| B-0186 | H | H | H | H | H | O | H | H | 2-OMe-6-Cl-pyridin-3-yl | 0 |
| B-0187 | H | H | H | H | H | O | H | H | 4-OMe-2-Cl-pyridin-3-yl | 0 |
| B-0188 | H | H | H | H | H | O | H | H | 4-OMe-5-Cl-pyridin-3-yl | 0 |
| B-0189 | H | H | H | H | H | O | H | H | 4-OMe-6-Cl-pyridin-3-yl | 0 |
| B-0190 | H | H | H | H | H | O | H | H | 2-OMe-5-Me-pyridin-3-yl | 0 |
| B-0191 | H | H | H | H | H | O | H | H | 2-OMe-6-Me-pyridin-3-yl | 0 |
| B-0192 | H | H | H | H | H | O | H | H | 4-OMe-5-Me-pyridin-3-yl | 0 |
| B-0193 | H | H | H | H | H | O | H | H | 4-OMe-6-Me-pyridin-3-yl | 0 |
| B-0194 | H | H | H | H | H | O | H | H | 2,4-(OMe)₂-pyridin-3-yl | 0 |
| B-0195 | H | H | H | H | H | O | H | H | 2,5-(OMe)₂-pyridin-3-yl | 0 |
| B-0196 | H | H | H | H | H | O | H | H | 2,6-(OMe)₂-pyridin-3-yl | 0 |
| B-0197 | H | H | H | H | H | O | H | H | 4,5-(OMe)₂-pyridin-3-yl | 0 |
| B-0198 | H | H | H | H | H | O | H | H | 4,6-(OMe)₂-pyridin-3-yl | 0 |
| B-0199 | H | H | H | H | H | O | H | H | pyridin-4-yl | 0 |
| B-0200 | H | H | H | H | H | O | H | H | 2-F-pyridin-4-yl | 0 |

TABLE 180-continued

| compound | R¹ | R² | R³ | R⁴ | R⁵ | A | R⁶ | R⁷ | Q | p |
|---|---|---|---|---|---|---|---|---|---|---|
| B-0201 | H | H | H | H | H | O | H | H | 3-F-pyridin-4-yl | 0 |
| B-0202 | H | H | H | H | H | O | H | H | 2-Cl-pyridin-4-yl | 0 |
| B-0203 | H | H | H | H | H | O | H | H | 3-Cl-pyridin-4-yl | 0 |
| B-0204 | H | H | H | H | H | O | H | H | 2-Me-pyridin-4-yl | 0 |
| B-0205 | H | H | H | H | H | O | H | H | 3-Me-pyridin-4-yl | 0 |
| B-0206 | H | H | H | H | H | O | H | H | 2-$CF_3$-pyridin-4-yl | 0 |
| B-0207 | H | H | H | H | H | O | H | H | 3-$CF_3$-pyridin-4-yl | 0 |
| B-0208 | H | H | H | H | H | O | H | H | 2-OMe-pyridin-4-yl | 0 |
| B-0209 | H | H | H | H | H | O | H | H | 3-OMe-pyridin-4-yl | 0 |
| B-0210 | H | H | H | H | H | O | H | H | 2,3-$F_2$-pyridin-4-yl | 0 |
| B-0211 | H | H | H | H | H | O | H | H | 2,5-$F_2$-pyridin-4-yl | 0 |
| B-0212 | H | H | H | H | H | O | H | H | 2,6-$F_2$-pyridin-4-yl | 0 |
| B-0213 | H | H | H | H | H | O | H | H | 3,5-$F_2$-pyridin-4-y | 0 |
| B-0214 | H | H | H | H | H | O | H | H | 2,3-$Cl_2$-pyridin-4-yl | 0 |
| B-0215 | H | H | H | H | H | O | H | H | 2,5-$Cl_2$-pyridin-4-yl | 0 |
| B-0216 | H | H | H | H | H | O | H | H | 2,6-$Cl_2$-pyridin-4-yl | 0 |
| B-0217 | H | H | H | H | H | O | H | H | 3,5-$Cl_2$-pyridin-4-yl | 0 |
| B-0218 | H | H | H | H | H | O | H | H | 3-F-2-Cl-pyridin-4-yl | 0 |
| B-0219 | H | H | H | H | H | O | H | H | 3-F-5-Cl-pyridin-4-yl | 0 |
| B-0220 | H | H | H | H | H | O | H | H | 3-F-6-Cl-pyridin-4-yl | 0 |
| B-0221 | H | H | H | H | H | O | H | H | 3-F-2-Me-pyridin-4-yl | 0 |
| B-0222 | H | H | H | H | H | O | H | H | 3-F-5-Me-pyridin-4-yl | 0 |
| B-0223 | H | H | H | H | H | O | H | H | 3-F-6-Me-pyridin-4-yl | 0 |

TABLE 181

| compound | R¹ | R² | R³ | R⁴ | R⁵ | A | R⁶ | R⁷ | Q | p |
|---|---|---|---|---|---|---|---|---|---|---|
| B-0224 | H | H | H | H | H | O | H | H | 3-F-2-OMe-pyridin-4-yl | 0 |
| B-0225 | H | H | H | H | H | O | H | H | 3-F-5-OMe-pyridin-4-yl | 0 |
| B-0226 | H | H | H | H | H | O | H | H | 3-F-6-OMe-pyridin-4-yl | 0 |
| B-0227 | H | H | H | H | H | O | H | H | 3-Cl-2-F-pyridin-4-yl | 0 |
| B-0228 | H | H | H | H | H | O | H | H | 3-Cl-6-F-pyridin-4-yl | 0 |
| B-0229 | H | H | H | H | H | O | H | H | 3-Cl-2-Me-pyridin-4-yl | 0 |
| B-0230 | H | H | H | H | H | O | H | H | 3-Cl-5-Me-pyridin-4-yl | 0 |
| B-0231 | H | H | H | H | H | O | H | H | 3-Cl-6-Me-pyridin-4-yl | 0 |
| B-0232 | H | H | H | H | H | O | H | H | 3-Me-2-F-pyridin-4-yl | 0 |
| B-0233 | H | H | H | H | H | O | H | H | 3-Me-6-F-pyridin-4-yl | 0 |
| B-0234 | H | H | H | H | H | O | H | H | 3-Me-2-Cl-pyridin-4-y | 0 |
| B-0235 | H | H | H | H | H | O | H | H | 3-Me-6-Cl-pyridin-4-y | 0 |
| B-0236 | H | H | H | H | H | O | H | H | 2,3-$(Me)_2$-pyridin-4-yl | 0 |
| B-0237 | H | H | H | H | H | O | H | H | 3,5-$(Me)_2$-pyridin-4-yl | 0 |
| B-0238 | H | H | H | H | H | O | H | H | 3,6-$(Me)_2$-pyridin-4-yl | 0 |
| B-0239 | H | H | H | H | H | O | H | H | 3-Me-2-OMe-pyridin-4-yl | 0 |
| B-0240 | H | H | H | H | H | O | H | H | 3-Me-5-OMe-pyridin-4-yl | 0 |
| B-0241 | H | H | H | H | H | O | H | H | 3-Me-6-OMe-pyridin-4-yl | 0 |
| B-0242 | H | H | H | H | H | O | H | H | 3-$CF_3$-2-F-pyridin-4-yl | 0 |
| B-0243 | H | H | H | H | H | O | H | H | 3-$CF_3$-5-F-pyridin-4-yl | 0 |
| B-0244 | H | H | H | H | H | O | H | H | 3-$CF_3$-6-F-pyridin-4-yl | 0 |
| B-0245 | H | H | H | H | H | O | H | H | 3-$CF_3$-2-Me-pyridin-4-yl | 0 |
| B-0246 | H | H | H | H | H | O | H | H | 3-$CF_3$-5-Me-pyridin-4-yl | 0 |
| B-0247 | H | H | H | H | H | O | H | H | 3-$CF_3$-6-Me-pyridin-4-yl | 0 |
| B-0248 | H | H | H | H | H | O | H | H | 3-OMe-2-F-pyridin-4-yl | 0 |
| B-0249 | H | H | H | H | H | O | H | H | 3-OMe-6-F-pyridin-4-yl | 0 |
| B-0250 | H | H | H | H | H | O | H | H | 3-OMe-2-Cl-pyridin-4-yl | 0 |
| B-0251 | H | H | H | H | H | O | H | H | 3-OMe-5-Cl-pyridin-4-yl | 0 |
| B-0252 | H | H | H | H | H | O | H | H | 3-OMe-6-Cl-pyridin-4-yl | 0 |
| B-0253 | H | H | H | H | H | O | H | H | 3-OMe-2-Me-pyridin-4-yl | 0 |
| B-0254 | H | H | H | H | H | O | H | H | 3-OMe-6-Me-pyridin-4-yl | 0 |
| B-0255 | H | H | H | H | H | O | H | H | 2,3-$(OMe)_2$-pyridin-4-yl | 0 |
| B-0256 | H | H | H | H | H | O | H | H | 3,5-$(OMe)_2$-pyridin-4-yl | 0 |
| B-0257 | H | H | H | H | H | O | H | H | 3,6-$(OMe)_2$-pyridin-4-yl | 0 |
| B-0258 | H | H | H | H | H | O | H | H | pyrimidin-2-yl | 0 |
| B-0259 | H | H | H | H | H | O | H | H | pyrimidin-4-yl | 0 |
| B-0260 | H | H | H | H | H | O | H | H | 5-F-pyrmidin-4-yl | 0 |
| B-0261 | H | H | H | H | H | O | H | H | 5-Me-pyrimidin-4-yl | 0 |
| B-0262 | H | H | H | H | H | O | H | H | 5-$CF_3$-pyrimidin-4-yl | 0 |
| B-0263 | H | H | H | H | H | O | H | H | 5-OMe-pyrimidin-4-yl | 0 |
| B-0264 | H | H | H | H | H | O | H | H | pyrimidin-5-yl | 0 |
| B-0265 | H | H | H | H | H | O | H | H | 4-F-pyrimidin-5-y | 0 |
| B-0266 | H | H | H | H | H | O | H | H | 4-Cl-pyrimidin-5-yl | 0 |
| B-0267 | H | H | H | H | H | O | H | H | 4-Me-pyrimidin-5-yl | 0 |
| B-0268 | H | H | H | H | H | O | H | H | 4-$CF_3$-pyrimidin-5-yl | 0 |
| B-0269 | H | H | H | H | H | O | H | H | 4-OMe-pyrimidin-5-yl | 0 |
| B-0270 | H | H | H | H | H | O | H | H | pyridazin-3-yl | 0 |

TABLE 181-continued

| compound | R¹ | R² | R³ | R⁴ | R⁵ | A | R⁶ | R⁷ | Q | p |
|---|---|---|---|---|---|---|---|---|---|---|
| B-0271 | H | H | H | H | H | O | H | H | 4-F-pyridazin-3-yl | 0 |
| B-0272 | H | H | H | H | H | O | H | H | 4-Cl-pyridazin-3-yl | 0 |
| B-0273 | H | H | H | H | H | O | H | H | 4-Me-pyridazin-3-yl | 0 |
| B-0274 | H | H | H | H | H | O | H | H | 4-CF₃-pyridazin-3-yl | 0 |
| B-0275 | H | H | H | H | H | O | H | H | 4-OMe-pyridazin-3-yl | 0 |
| B-0276 | H | H | H | H | H | O | H | H | pyridazin-4-yl | 0 |
| B-0277 | H | H | H | H | H | O | H | H | 3-F-pyridazin-4-yl | 0 |
| B-0278 | H | H | H | H | H | O | H | H | 3-Cl-pyridazin-4-yl | 0 |
| B-0279 | H | H | H | H | H | O | H | H | 3-Me-pyridazin-4-yl | 0 |
| B-0280 | H | H | H | H | H | O | H | H | 3-CF₃-pyridazin-4-yl | 0 |

TABLE 182

| compound | R¹ | R² | R³ | R⁴ | R⁵ | A | R⁶ | R⁷ | Q | p |
|---|---|---|---|---|---|---|---|---|---|---|
| B-0281 | H | H | H | H | H | O | H | H | 3-OMe-pyridazin-4-yl | 0 |
| B-0282 | H | H | H | H | H | O | H | H | 5-F-pyridazin-4-yl | 0 |
| B-0283 | H | H | H | H | H | O | H | H | 5-Cl-pyridazin-4-yl | 0 |
| B-0284 | H | H | H | H | H | O | H | H | 5-Me-pyridazin-4-yl | 0 |
| B-0285 | H | H | H | H | H | O | H | H | 5-CF₃-pyridazin-4-yl | 0 |
| B-0286 | H | H | H | H | H | O | H | H | 5-OMe-pyridazin-4-yl | 0 |
| B-0287 | H | H | H | H | H | O | H | H | thiophen-2-yl | 0 |
| B-0288 | H | H | H | H | H | O | H | H | 3-F-thiophen-2-yl | 0 |
| B-0289 | H | H | H | H | H | O | H | H | 3-Cl-thiophen-2-yl | 0 |
| B-0290 | H | H | H | H | H | O | H | H | 3-Me-thiophen-2-yl | 0 |
| B-0291 | H | H | H | H | H | O | H | H | 3-CF₃-thiophen-2-yl | 0 |
| B-0292 | H | H | H | H | H | O | H | H | 3-OMe-thiophen-2-yl | 0 |
| B-0293 | H | H | H | H | H | O | H | H | thiophen-3-yl | 0 |
| B-0294 | H | H | H | H | H | O | H | H | 2-F-thiophen-3-yl | 0 |
| B-0295 | H | H | H | H | H | O | H | H | 2-Cl-thiophen-3-yl | 0 |
| B-0296 | H | H | H | H | H | O | H | H | 2-Me-thiophen-3-yl | 0 |
| B-0297 | H | H | H | H | H | O | H | H | 2-CF₃-thiophen-3-yl | 0 |
| B-0298 | H | H | H | H | H | O | H | H | 2-OMe-thiophen-3-yl | 0 |
| B-0299 | H | H | H | H | H | O | H | H | 4-F-thiophen-3-yl | 0 |
| B-0300 | H | H | H | H | H | O | H | H | 4-Cl-thiophen-3-yl | 0 |
| B-0301 | H | H | H | H | H | O | H | H | 4-Me-thiophen-3-yl | 0 |
| B-0302 | H | H | H | H | H | O | H | H | 4-CF₃-thiophen-3-yl | 0 |
| B-0303 | H | H | H | H | H | O | H | H | 4-OMe-thiophen-3-yl | 0 |
| B-0304 | H | H | H | H | H | O | H | H | thiazol-2-yl | 0 |
| B-0305 | H | H | H | H | H | O | H | H | thiazol-4-yl | 0 |
| B-0306 | H | H | H | H | H | O | H | H | 5-F-thiazol-4-yl | 0 |
| B-0307 | H | H | H | H | H | O | H | H | 5-Me-thiazol-4-yl | 0 |
| B-0308 | H | H | H | H | H | O | H | H | 5-CF₃-thiazol-4-yl | 0 |
| B-0309 | H | H | H | H | H | O | H | H | 5-OMe-thiazol-4-yl | 0 |
| B-0310 | H | H | H | H | H | O | H | H | thiazol-5-yl | 0 |
| B-0311 | H | H | H | H | H | O | H | H | 4-F-thiazol-5-yl | 0 |
| B-0312 | H | H | H | H | H | O | H | H | 4-Me-thiazol-5-yl | 0 |
| B-0313 | H | H | H | H | H | O | H | H | 4-CF₃-thiazol-5-yl | 0 |
| B-0314 | H | H | H | H | H | O | H | H | 4-OMe-thiazol-5-yl | 0 |
| B-0315 | H | H | H | H | H | O | H | H | 1H-pyrrol-1-yl | 0 |
| B-0316 | H | H | H | H | H | O | H | H | 2-F-1H-pyrrol-1-yl | 0 |
| B-0317 | H | H | H | H | H | O | H | H | 2-Me-1H-pyrrol-1-yl | 0 |
| B-0318 | H | H | H | H | H | O | H | H | 2-CF₃-1H-pyrrol-1-yl | 0 |
| B-0319 | H | H | H | H | H | O | H | H | 2-OMe-1H-pyrrol-1-yl | 0 |
| B-0320 | H | H | H | H | H | O | H | H | 1H-pyrrol-2-yl | 0 |
| B-0321 | H | H | H | H | H | O | H | H | 1-Me-1H-pyrrol-2-yl | 0 |
| B-0322 | H | H | H | H | H | O | H | H | 3-F-1H-pyrrol-2-yl | 0 |
| B-0323 | H | H | H | H | H | O | H | H | 3-Me-1H-pyrrol-2-yl | 0 |
| B-0324 | H | H | H | H | H | O | H | H | 3-CF₃-1H-pyrrol-2-yl | 0 |
| B-0325 | H | H | H | H | H | O | H | H | 3-OMe-1H-pyrrol-2-yl | 0 |
| B-0326 | H | H | H | H | H | O | H | H | 1-Me-3-F-1H-pyrrol-2-yl | 0 |
| B-0327 | H | H | H | H | H | O | H | H | 1,3-(Me)₂-1H-pyrrol-2-yl | 0 |
| B-0328 | H | H | H | H | H | O | H | H | 1-Me-3-CF₃-1H-pyrrol-2-yl | 0 |
| B-0329 | H | H | H | H | H | O | H | H | 1-Me-3-OMe-1H-pyrrol-2-yl | 0 |
| B-0330 | H | H | H | H | H | O | H | H | 1H-pyrrol-3-yl | 0 |
| B-0331 | H | H | H | H | H | O | H | H | 1-Me-1H-pyrrol-3-yl | 0 |
| B-0332 | H | H | H | H | H | O | H | H | 2-F-1H-pyrrol-3-yl | 0 |
| B-0333 | H | H | H | H | H | O | H | H | 2-Me-1H-pyrrol-3-yl | 0 |
| B-0334 | H | H | H | H | H | O | H | H | 2-CF₃-1H-pyrrol-1-3-yl | 0 |
| B-0335 | H | H | H | H | H | O | H | H | 2-OMe-1H-pyrrol-1-3-yl | 0 |
| B-0336 | H | H | H | H | H | O | H | H | 1-Me-2-F-1H-pyrrol-3-yl | 0 |
| B-0337 | H | H | H | H | H | O | H | H | 1,2-(Me)₂-1H-pyrrol-3-yl | 0 |

TABLE 183

| compound | R¹ | R² | R³ | R⁴ | R⁵ | A | R⁶ | R⁷ | Q | p |
|---|---|---|---|---|---|---|---|---|---|---|
| B-0338 | H | H | H | H | H | O | H | H | 1-Me-2-CF₃-1H-pyrrol-3-yl | 0 |
| B-0339 | H | H | H | H | H | O | H | H | 1-Me-2-OMe-1H-pyrrol-3-yl | 0 |
| B-0340 | H | H | H | H | H | O | H | H | 4-F-1H-pyrrol-3-yl | 0 |
| B-0341 | H | H | H | H | H | O | H | H | 4-Me-1H-pyrrol-3-yl | 0 |
| B-0342 | H | H | H | H | H | O | H | H | 4-CF₃-1H-pyrrol-3-yl | 0 |
| B-0343 | H | H | H | H | H | O | H | H | 4-OMe-1H-pyrrol-3-yl | 0 |
| B-0344 | H | H | H | H | H | O | H | H | 1-Me-4-F-1H-pyrrol-3-yl | 0 |
| B-0345 | H | H | H | H | H | O | H | H | 1,4-(Me)₂-1H-pyrrol-3-yl | 0 |
| B-0346 | H | H | H | H | H | O | H | H | 1-Me-4-CF₃-1H-pyrrol-3-yl | 0 |
| B-0347 | H | H | H | H | H | O | H | H | 1-Me-4-OMe-1H-pyrrol-3-yl | 0 |
| B-0348 | H | H | H | H | H | O | H | H | 1H-pyrazol-1-yl | 0 |
| B-0349 | H | H | H | H | H | O | H | H | 5F-1H-pyrazol-1-yl | 0 |
| B-0350 | H | H | H | H | H | O | H | H | 5-Cl-1H-pyrazol-1-yl | 0 |
| B-0351 | H | H | H | H | H | O | H | H | 5-Me-1H-pyrazol-1-yl | 0 |
| B-0352 | H | H | H | H | H | O | H | H | 5-CF₃-1H-pyrazol-1-yl | 0 |
| B-0353 | H | H | H | H | H | O | H | H | 5-OMe-1H-pyrazol-1-yl | 0 |
| B-0354 | H | H | H | H | H | O | H | H | 1H-pyrazol-3-yl | 0 |
| B-0355 | H | H | H | H | H | O | H | H | 1-Me-1H-pyrazol-3-yl | 0 |
| B-0356 | H | H | H | H | H | O | H | H | 4-1H-pyrazol-3-yl | 0 |
| B-0357 | H | H | H | H | H | O | H | H | 4-Cl-1H-pyrazol-3-yl | 0 |
| B-0358 | H | H | H | H | H | O | H | H | 4-Me-1H-pyrazol-3-yl | 0 |
| B-0359 | H | H | H | H | H | O | H | H | 4-CF₃-1H-pyrazol-3-yl | 0 |
| B-0360 | H | H | H | H | H | O | H | H | 4-OMe-1H-pyrazol-3-yl | 0 |
| B-0361 | H | H | H | H | H | O | H | H | 1-Me-4F-1H-pyrazol-3-yl | 0 |
| B-0362 | H | H | H | H | H | O | H | H | 1-Me-4-Cl-1H-pyrazol-3-yl | 0 |
| B-0363 | H | H | H | H | H | O | H | H | 1,4-(Me)₂-1H-pyrazol-3-yl | 0 |
| B-0364 | H | H | H | H | H | O | H | H | 1-Me-4-CF₃-1H-pyrazol-3-yl | 0 |
| B-0365 | H | H | H | H | H | O | H | H | 1-Me-4-OMe-1H-pyrazol-3-yl | 0 |
| B-0366 | H | H | H | H | H | O | H | H | 1H-pyrazol-4-yl | 0 |
| B-0367 | H | H | H | H | H | O | H | H | 1-Me-1H-pyrazol-4-yl | 0 |
| B-0368 | H | H | H | H | H | O | H | H | 3-F-1H-pyrazol-4-yl | 0 |
| B-0369 | H | H | H | H | H | O | H | H | 3-Cl-1H-pyrazol-4-yl | 0 |
| B-0370 | H | H | H | H | H | O | H | H | 3-Me-1H-pyrazol-4-yl | 0 |
| B-0371 | H | H | H | H | H | O | H | H | 3-CF₃-1H-pyrazol-4-yl | 0 |
| B-0372 | H | H | H | H | H | O | H | H | 3-OMe-1H-pyrazol-4-yl | 0 |
| B-0373 | H | H | H | H | H | O | H | H | 1-Me-3-F-1H-pyrazol-4-yl | 0 |
| B-0374 | H | H | H | H | H | O | H | H | 1-Me-3-Cl-1H-pyrazol-4-yl | 0 |
| B-0375 | H | H | H | H | H | O | H | H | 1,3-(Me)₂-1H-pyrazol-4-yl | 0 |
| B-0376 | H | H | H | H | H | O | H | H | 1-Me-3-CF₃-1H-pyrazol-4-yl | 0 |
| B-0377 | H | H | H | H | H | O | H | H | 1-Me-3-OMe-1H-pyrazol-4-yl | 0 |
| B-0378 | H | H | H | H | H | O | H | H | 5-F-1H-pyrazol-4-yl | 0 |
| B-0379 | H | H | H | H | H | O | H | H | 5-Cl-1H-pyrazol-4-yl | 0 |
| B-0380 | H | H | H | H | H | O | H | H | 5-Me-1H-pyrazol-4-yl | 0 |
| B-0381 | H | H | H | H | H | O | H | H | 5-CF₃-1H-pyrazol-4-yl | 0 |
| B-0382 | H | H | H | H | H | O | H | H | 5-OMe-1H-pyrazol-4-yl | 0 |
| B-0383 | H | H | H | H | H | O | H | H | 1-Me-5-F-1H-pyrazol-4-yl | 0 |
| B-0384 | H | H | H | H | H | O | H | H | 1-Me-5-Cl-1H-pyrazol-4-yl | 0 |
| B-0385 | H | H | H | H | H | O | H | H | 1,5-(Me)₂-1H-pyrazol-4-yl | 0 |
| B-0386 | H | H | H | H | H | O | H | H | 1-Me-5-CF₃-1H-pyrazol-4-yl | 0 |
| B-0387 | H | H | H | H | H | O | H | H | 1-Me-5-OMe-1H-pyrazol-4-yl | 0 |
| B-0388 | H | H | H | H | H | O | H | H | 1H-pyrazol-5-yl | 0 |
| B-0389 | H | H | H | H | H | O | H | H | 1-Me-1H-pyrazol-5-yl | 0 |
| B-0390 | H | H | H | H | H | O | H | H | 4-F-1H-pyrazol-5-yl | 0 |
| B-0391 | H | H | H | H | H | O | H | H | 4-Cl-1H-pyrazol-5-yl | 0 |
| B-0392 | H | H | H | H | H | O | H | H | 4-Me-1H-pyrazol-5-yl | 0 |
| B-0393 | H | H | H | H | H | O | H | H | 4-CF₃-1H-pyrazol-5-yl | 0 |
| B-0394 | H | H | H | H | H | O | H | H | 4-OMe-1H-pyrazol-5-yl | 0 |

TABLE 184

| compound | R¹ | R² | R³ | R⁴ | R⁵ | A | R⁶ | R⁷ | Q | p |
|---|---|---|---|---|---|---|---|---|---|---|
| B-0395 | H | H | H | H | H | O | H | H | 1-Me-4-F-1H-pyrazol-5-yl | 0 |
| B-0396 | H | H | H | H | H | O | H | H | 1-Me-4-Cl-1H-pyrazol-5-yl | 0 |
| B-0397 | H | H | H | H | H | O | H | H | 1,4-(Me)₂-1H-pyrazol-5-yl | 0 |
| B-0398 | H | H | H | H | H | O | H | H | 1-Me-4-CF₃-1H-pyrazol-5-yl | 0 |
| B-0399 | H | H | H | H | H | O | H | H | 1-Me-4-OMe-1H-pyrazol-5-yl | 0 |
| B-0400 | H | H | H | H | H | O | H | H | furan-2-yl | 0 |
| B-0401 | H | H | H | H | H | O | H | H | 3-F-furan-2-yl | 0 |
| B-0402 | H | H | H | H | H | O | H | H | 3-Me-furan-2-yl | 0 |
| B-0403 | H | H | H | H | H | O | H | H | 3-CF₃-furan-2-yl | 0 |
| B-0404 | H | H | H | H | H | O | H | H | 3-OMe-furan-2-yl | 0 |
| B-0405 | H | H | H | H | H | O | H | H | furan-3-yl | 0 |
| B-0406 | H | H | H | H | H | O | H | H | 2-F-furan-3-yl | 0 |
| B-0407 | H | H | H | H | H | O | H | H | 2-Me-furan-3-yl | 0 |

TABLE 184-continued

| compound | R¹ | R² | R³ | R⁴ | R⁵ | A | R⁶ | R⁷ | Q | p |
|---|---|---|---|---|---|---|---|---|---|---|
| B-0408 | H | H | H | H | H | O | H | H | 2-CF₃-furan-3-yl | 0 |
| B-0409 | H | H | H | H | H | O | H | H | 2-OMe-furan-3-yl | 0 |
| B-0410 | H | H | H | H | H | O | H | H | 4-F-furan-3-yl | 0 |
| B-0411 | H | H | H | H | H | O | H | H | 4-Me-furan-3-yl | 0 |
| B-0412 | H | H | H | H | H | O | H | H | 4-CF₃-furan-3-yl | 0 |
| B-0413 | H | H | H | H | H | O | H | H | 4-OMe-furan-3-yl | 0 |
| B-0414 | H | H | H | H | H | O | H | H | isoxazol-3-yl | 0 |
| B-0415 | H | H | H | H | H | O | H | H | 4-F-isoxazol-3-yl | 0 |
| B-0416 | H | H | H | H | H | O | H | H | 4-Me-isoxazol-3-yl | 0 |
| B-0417 | H | H | H | H | H | O | H | H | 4-CF₃-isoxazol-3-yl | 0 |
| B-0418 | H | H | H | H | H | O | H | H | 4-OMe-isoxazol-3-yl | 0 |
| B-0419 | H | H | H | H | H | O | H | H | isoxazol-4-yl | 0 |
| B-0420 | H | H | H | H | H | O | H | H | 5-F-isoxazol-4-yl | 0 |
| B-0421 | H | H | H | H | H | O | H | H | 5-Me-isoxazol-4-yl | 0 |
| B-0422 | H | H | H | H | H | O | H | H | 5-CF₃-isoxazol-4-y | 0 |
| B-0423 | H | H | H | H | H | O | H | H | 5-OMe-isoxazol-4-yl | 0 |
| B-0424 | H | H | H | H | H | O | H | H | isoxazol-5-yl | 0 |
| B-0425 | H | H | H | H | H | O | H | H | 4-F-isoxazol-5-yl | 0 |
| B-0426 | H | H | H | H | H | O | H | H | 4-Me-isoxazol-15-yl | 0 |
| B-0427 | H | H | H | H | H | O | H | H | 4-CF₃-isoxazol-5-yl | 0 |
| B-0428 | H | H | H | H | H | O | H | H | 4-OMe-isoxazol-5-yl | 0 |
| B-0429 | H | H | H | H | H | O | H | H | 1H-1,2,3-triazol-1-yl | 0 |
| B-0430 | H | H | H | H | H | O | H | H | 5-F-1H-1,2,3-triazol-1-yl | 0 |
| B-0431 | H | H | H | H | H | O | H | H | 5-Me-1H-1,2,3-triazol-1-yl | 0 |
| B-0432 | H | H | H | H | H | O | H | H | 5-CF₃-1H-1,2,3-triazol-1-yl | 0 |
| B-0433 | H | H | H | H | H | O | H | H | 5-OMe-1H-1,2,3-triazol-1-yl | 0 |
| B-0434 | H | H | H | H | H | O | H | H | 1H-1,2,3-triazol-4-yl | 0 |
| B-0435 | H | H | H | H | H | O | H | H | 5-F-1H-1,2,3-triazol-4-yl | 0 |
| B-0436 | H | H | H | H | H | O | H | H | 5-Me-1H-1,2,3-triazol-4-yl | 0 |
| B-0437 | H | H | H | H | H | O | H | H | 5-CF₃-1H-1,2,3-triazol-4-yl | 0 |
| B-0438 | H | H | H | H | H | O | H | H | 5-OMe-1H-1,2,3-triazol-4-yl | 0 |
| B-0439 | H | H | H | H | H | O | H | H | 1H-1,2,3-triazol-5-yl | 0 |
| B-0440 | H | H | H | H | H | O | H | H | 4-F-1H-1,2,3-triazol-5-yl | 0 |
| B-0441 | H | H | H | H | H | O | H | H | 4-Me-1H-1,2,3-triazol-5-yl | 0 |
| B-0442 | H | H | H | H | H | O | H | H | 4-CF₃-1H-1,2,3-triazol-5-yl | 0 |
| B-0443 | H | H | H | H | H | O | H | H | 4-OMe-1H-1,2,3-triazol-5-yl | 0 |
| B-0444 | H | H | H | H | H | O | H | H | 1H-1,2,4-triazol-1-yl | 0 |
| B-0445 | H | H | H | H | H | O | H | H | 5-Me-1H-1,2,4-triazol-1-yl | 0 |
| B-0446 | H | H | H | H | H | O | H | H | 5-F-1H-1,2,4-triazol-1-yl | 0 |
| B-0447 | H | H | H | H | H | O | H | H | 5-CF₃-1H-1,2,4-triazol-1-yl | 0 |
| B-0448 | H | H | H | H | H | O | H | H | 5-OMe-1H-1,2,4-triazol-1-yl | 0 |
| B-0449 | H | H | H | H | H | O | H | H | 1H-1,2,4-triazol-3-yl | 0 |
| B-0450 | H | H | H | H | H | O | H | H | 1-Me-1H-1,2,4-triazol-3-yl | 0 |
| B-0451 | H | H | H | H | H | O | H | H | 1H-1,2,4-triazol-5-yl | 0 |

TABLE 185

| compound | R¹ | R² | R³ | R⁴ | R⁵ | A | R⁶ | R⁷ | Q | p |
|---|---|---|---|---|---|---|---|---|---|---|
| B-0452 | H | H | H | H | H | O | H | H | 1-Me-1H-1,2,4-triazol-5-yl | 0 |
| B-0453 | H | H | H | H | H | O | H | H | 3,5-(Me)₂-isoxazol-4-yl | 0 |
| B-0454 | H | H | H | H | H | O | H | H | 3,5-(Et)₂-isoxazol-4-yl | 0 |
| B-0455 | H | H | H | H | H | O | H | H | 1,3,5-(Me)₃-1H-pyrazol-4-yl | 0 |
| B-0456 | H | H | H | H | H | O | H | H | quinolin-4-yl | 0 |
| B-0457 | H | H | H | H | H | O | H | H | isoquinolin-4-yl | 0 |
| B-0458 | H | H | H | H | H | O | H | H | 3,6-(OMe)₂-pyridazin-4-yl | 0 |
| B-0459 | H | H | H | H | H | O | H | H | 2,4-(OMe)₂-pyrimidin-5-yl | 0 |

TABLE 186

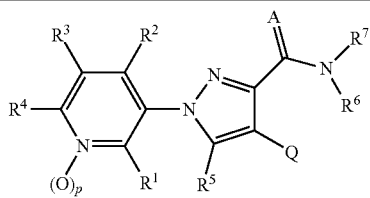

| compound | R¹ | R² | R³ | R⁴ | R⁵ | A | R⁶ | R⁷ | Q | p |
|---|---|---|---|---|---|---|---|---|---|---|
| B-5001 | H | H | H | H | H | O | H | H | Cl | 1 |
| B-5002 | H | H | H | H | H | O | H | H | Br | 1 |
| B-5003 | H | H | H | H | H | O | H | H | I | 1 |

TABLE 186-continued

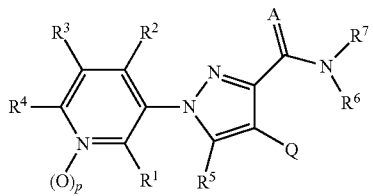

| compound | R¹ | R² | R³ | R⁴ | R⁵ | A | R⁶ | R⁷ | Q | p |
|---|---|---|---|---|---|---|---|---|---|---|
| B-5004 | H | H | H | H | H | O | H | H | naphthalen-1-yl | 1 |
| B-5005 | H | H | H | H | H | O | H | H | 2-F-naphthalen-1-yl | 1 |
| B-5006 | H | H | H | H | H | O | H | H | 2-Me-naphthalen-1-yl | 1 |
| B-5007 | H | H | H | H | H | O | H | H | 2-$CF_3$-naphthalen-1-yl | 1 |
| B-5008 | H | H | H | H | H | O | H | H | 2-OMe-naphthalen-1-yl | 1 |
| B-5009 | H | H | H | H | H | O | H | H | naphthalen-2-yl | 1 |
| B-5010 | H | H | H | H | H | O | H | H | 1-F-naphthalen-2-yl | 1 |
| B-5011 | H | H | H | H | H | O | H | H | 1-Me-naphthalen-2-y | 1 |
| B-5012 | H | H | H | H | H | O | H | H | 1-$CF_3$-naphthalen-2-yl | 1 |
| B-5013 | H | H | H | H | H | O | H | H | 1-OMe-naphthalen-2-yl | 1 |
| B-5014 | H | H | H | H | H | O | H | H | 3-F-naphthalen-2-yl | 1 |
| B-5015 | H | H | H | H | H | O | H | H | 3-Me-naphthalen-2-yl | 1 |
| B-5016 | H | H | H | H | H | O | H | H | 3-$CF_3$-naphthalen-2-yl | 1 |
| B-5017 | H | H | H | H | H | O | H | H | 3-OMe-naphthalen-2-yl | 1 |
| B-5018 | H | H | H | H | H | O | H | H | pyridin-2-yl | 1 |
| B-5019 | H | H | H | H | H | O | H | H | 3-F-pyridin-2-yl | 1 |
| B-5020 | H | H | H | H | H | O | H | H | 4-F-pyridin-2-yl | 1 |
| B-5021 | H | H | H | H | H | O | H | H | 5-F-pyridin-2-yl | 1 |
| B-5022 | H | H | H | H | H | O | H | H | 6-F-pyridin-2-yl | 1 |
| B-5023 | H | H | H | H | H | O | H | H | 3-Cl-pyridin-2-yl | 1 |
| B-5024 | H | H | H | H | H | O | H | H | 4-Cl-pyridin-2-yl | 1 |
| B-5025 | H | H | H | H | H | O | H | H | 5-Cl-pyridin-2-yl | 1 |
| B-5026 | H | H | H | H | H | O | H | H | 6-Cl-pyridin-2-yl | 1 |
| B-5027 | H | H | H | H | H | O | H | H | 3-Me-pyridin-2-yl | 1 |
| B-5028 | H | H | H | H | H | O | H | H | 4-Me-pyridin-2-yl | 1 |
| B-5029 | H | H | H | H | H | O | H | H | 5-Me-pyridin-2-yl | 1 |
| B-5030 | H | H | H | H | H | O | H | H | 6-Me-pyridin-2-yl | 1 |
| B-5031 | H | H | H | H | H | O | H | H | 3-$CF_3$-pyridin-2-yl | 1 |
| B-5032 | H | H | H | H | H | O | H | H | 4-$CF_3$-pyridin-2-yl | 1 |
| B-5033 | H | H | H | H | H | O | H | H | 5-$CF_3$-pyridin-2-yl | 1 |
| B-5034 | H | H | H | H | H | O | H | H | 6-$CF_3$-pyridin-2-yl | 1 |
| B-5035 | H | H | H | H | H | O | H | H | 3-OMe-pyridin-2-yl | 1 |
| B-5036 | H | H | H | H | H | O | H | H | 4-OMe-pyridin-2-yl | 1 |
| B-5037 | H | H | H | H | H | O | H | H | 5-OMe-pyridin-2-yl | 1 |
| B-5038 | H | H | H | H | H | O | H | H | 6-OMe-pyridin-2-yl | 1 |
| B-5039 | H | H | H | H | H | O | H | H | 3,4-$F_2$-pyridin-2-yl | 1 |
| B-5040 | H | H | H | H | H | O | H | H | 3,5-$F_2$-pyridin-2-yl | 1 |
| B-5041 | H | H | H | H | H | O | H | H | 3,6-$F_2$-pyridin-2-yl | 1 |
| B-5042 | H | H | H | H | H | O | H | H | 3,4-$Cl_2$-pyridin-2-yl | 1 |
| B-5043 | H | H | H | H | H | O | H | H | 3,5-$Cl_2$-pyridin-2-yl | 1 |
| B-5044 | H | H | H | H | H | O | H | H | 3,6-$Cl_2$-pyridin-2-yl | 1 |
| B-5045 | H | H | H | H | H | O | H | H | 3-F-4-Cl-pyridin-2-yl | 1 |
| B-5046 | H | H | H | H | H | O | H | H | 3-F-5-Cl-pyridin-2-yl | 1 |
| B-5047 | H | H | H | H | H | O | H | H | 3-F-6-Cl-pyridin-2-yl | 1 |
| B-5048 | H | H | H | H | H | O | H | H | 3-F-4-Me-pyridin-2-yl | 1 |
| B-5049 | H | H | H | H | H | O | H | H | 3-F-5-Me-pyridin-2-yl | 1 |
| B-5050 | H | H | H | H | H | O | H | H | 3-F-6-Me-pyridin-2-yl | 1 |
| B-5051 | H | H | H | H | H | O | H | H | 3-F-4-OMe-pyridin-2-yl | 1 |
| B-5052 | H | H | H | H | H | O | H | H | 3-F-5-OMe-pyridin-2-yl | 1 |

TABLE 187

| compound | R¹ | R² | R³ | R⁴ | R⁵ | A | R⁶ | R⁷ | Q | p |
|---|---|---|---|---|---|---|---|---|---|---|
| B-5053 | H | H | H | H | H | O | H | H | 3-F-6-OMe-pyridin-2-yl | 1 |
| B-5054 | H | H | H | H | H | O | H | H | 3-Cl-4-F-pyridin-2-yl | 1 |
| B-5055 | H | H | H | H | H | O | H | H | 3-Cl-5-F-pyridin-2-yl | 1 |
| B-5056 | H | H | H | H | H | O | H | H | 3-Cl-6-F-pyridin-2-yl | 1 |
| B-5057 | H | H | H | H | H | O | H | H | 3-Cl-4-Me-pyridin-2-yl | 1 |
| B-5058 | H | H | H | H | H | O | H | H | 3-Cl-5-Me-pyridin-2-yl | 1 |
| B-5059 | H | H | H | H | H | O | H | H | 3-Cl-6-Me-pyridin-2-yl | 1 |
| B-5060 | H | H | H | H | H | O | H | H | 3-Me-4-F-pyridin-2-yl | 1 |
| B-5061 | H | H | H | H | H | O | H | H | 3-Me-5-F-pyridin-2-yl | 1 |
| B-5062 | H | H | H | H | H | O | H | H | 3-Me-6-F-pyridin-2-yl | 1 |
| B-5063 | H | H | H | H | H | O | H | H | 3-Me-4-Cl-pyridin-2-yl | 1 |

TABLE 187-continued

| compound | R¹ | R² | R³ | R⁴ | R⁵ | A | R⁶ | R⁷ | Q | p |
|---|---|---|---|---|---|---|---|---|---|---|
| B-5064 | H | H | H | H | H | O | H | H | 3-Me-5-Cl-pyridin-2-yl | 1 |
| B-5065 | H | H | H | H | H | O | H | H | 3-Me-6-Cl-pyridin-2-yl | 1 |
| B-5066 | H | H | H | H | H | O | H | H | 3,4-(Me)$_2$-pyridin-2-yl | 1 |
| B-5067 | H | H | H | H | H | O | H | H | 3,5-(Me)$_2$-pyridin-2-y | 1 |
| B-5068 | H | H | H | H | H | O | H | H | 3,6-(Me)$_2$-pyridin-2-yl | 1 |
| B-5069 | H | H | H | H | H | O | H | H | 3-Me-4-OMe-pyridin-2-yl | 1 |
| B-5070 | H | H | H | H | H | O | H | H | 3-Me-5-OMe-pyridin-2-y | 1 |
| B-5071 | H | H | H | H | H | O | H | H | 3-Me-6-OMe-pyridin-2-yl | 1 |
| B-5072 | H | H | H | H | H | O | H | H | 3-CF$_3$-4-F-pyridin-2-yl | 1 |
| B-5073 | H | H | H | H | H | O | H | H | 3-CF$_3$-5-F-pyridin-2-yl | 1 |
| B-5074 | H | H | H | H | H | O | H | H | 3-CF$_3$-6-F-pyridin-2-yl | 1 |
| B-5075 | H | H | H | H | H | O | H | H | 3-CF$_3$-4-Me-pyridin-2-yl | 1 |
| B-5076 | H | H | H | H | H | O | H | H | 3-CF$_3$-5-Me-pyridin-2-yl | 1 |
| B-5077 | H | H | H | H | H | O | H | H | 3-CF$_3$-6-Me-pyridin-2-yl | 1 |
| B-5078 | H | H | H | H | H | O | H | H | 3-OMe-4-F-pyridin-2-yl | 1 |
| B-5079 | H | H | H | H | H | O | H | H | 3-OMe-5-F-pyridin-2-yl | 1 |
| B-5080 | H | H | H | H | H | O | H | H | 3-OMe-6-F-pyridin-2-yl | 1 |
| B-5081 | H | H | H | H | H | O | H | H | 3-OMe-4-Cl-pyridin-2-yl | 1 |
| B-5082 | H | H | H | H | H | O | H | H | 3-OMe-5-Cl-pyridin-2-yl | 1 |
| B-5083 | H | H | H | H | H | O | H | H | 3-OMe-6-Cl-pyridin-2-yl | 1 |
| B-5084 | H | H | H | H | H | O | H | H | 3-OMe-4-Me-pyridin-2-yl | 1 |
| B-5085 | H | H | H | H | H | O | H | H | 3-OMe-5-Me-pyridin-2-yl | 1 |
| B-5086 | H | H | H | H | H | O | H | H | 3-OMe-6-Me-pyridin-2-yl | 1 |
| B-5087 | H | H | H | H | H | O | H | H | 3,4-(OMe)$_2$-pyridin-2-yl | 1 |
| B-5088 | H | H | H | H | H | O | H | H | 3,5-(OMe)$_2$-pyridin-2-yl | 1 |
| B-5089 | H | H | H | H | H | O | H | H | 3,6-(OMe)$_2$-pyridin-2-yl | 1 |
| B-5090 | H | H | H | H | H | O | H | H | pyridin-3-yl | 1 |
| B-5091 | H | H | H | H | H | O | H | H | 2-F-pyridin-3-yl | 1 |
| B-5092 | H | H | H | H | H | O | H | H | 4-F-pyridin-3-yl | 1 |
| B-5093 | H | H | H | H | H | O | H | H | 5-F-pyridin-3-yl | 1 |
| B-5094 | H | H | H | H | H | O | H | H | 6-F-pyridin-3-yl | 1 |
| B-5095 | H | H | H | H | H | O | H | H | 2-Cl-pyridin-3-yl | 1 |
| B-5096 | H | H | H | H | H | O | H | H | 4-Cl-pyridin-3-yl | 1 |
| B-5097 | H | H | H | H | H | O | H | H | 5-Cl-pyridin-3-yl | 1 |
| B-5098 | H | H | H | H | H | O | H | H | 6-Cl-pyridin-3-yl | 1 |
| B-5099 | H | H | H | H | H | O | H | H | 2-Me-pyridin-3-yl | 1 |
| B-5100 | H | H | H | H | H | O | H | H | 4-Me-pyridin-3-yl | 1 |
| B-5101 | H | H | H | H | H | O | H | H | 5-Me-pyridin-3-yl | 1 |
| B-5102 | H | H | H | H | H | O | H | H | 6-Me-pyridin-3-yl | 1 |
| B-5103 | H | H | H | H | H | O | H | H | 2-CF$_3$-pyridin-3-yl | 1 |
| B-5104 | H | H | H | H | H | O | H | H | 4-CF$_3$-pyridin-3-yl | 1 |
| B-5105 | H | H | H | H | H | O | H | H | 5-CF$_3$-pyridin-3-yl | 1 |
| B-5106 | H | H | H | H | H | O | H | H | 6-CF$_3$-pyridin-3-yl | 1 |
| B-5107 | H | H | H | H | H | O | H | H | 2-OMe-pyridin-3-yl | 1 |
| B-5108 | H | H | H | H | H | O | H | H | 4-OMe-pyridin-3-yl | 1 |
| B-5109 | H | H | H | H | H | O | H | H | 5-OMe-pyridin-3-yl | 1 |

TABLE 188

| compound | R¹ | R² | R³ | R⁴ | R⁵ | A | R⁶ | R⁷ | Q | p |
|---|---|---|---|---|---|---|---|---|---|---|
| B-5110 | H | H | H | H | H | O | H | H | 6-OMe-pyridin-3-yl | 1 |
| B-5111 | H | H | H | H | H | O | H | H | 2,4-F$_2$-pyridin-3-yl | 1 |
| B-5112 | H | H | H | H | H | O | H | H | 2,5-F$_2$-pyridin-3-yl | 1 |
| B-5113 | H | H | H | H | H | O | H | H | 2,6-F$_2$-pyridin-3-yl | 1 |
| B-5114 | H | H | H | H | H | O | H | H | 4,5-F$_2$-pyridin-3-yl | 1 |
| B-5115 | H | H | H | H | H | O | H | H | 4,6-F$_2$-pyridin-3-yl | 1 |
| B-5116 | H | H | H | H | H | O | H | H | 2,4-Cl$_2$-pyridin-3-yl | 1 |
| B-5117 | H | H | H | H | H | O | H | H | 2,5-Cl$_2$-pyridin-3-yl | 1 |
| B-5118 | H | H | H | H | H | O | H | H | 2,6-Cl$_2$-pyridin-3-yl | 1 |
| B-5119 | H | H | H | H | H | O | H | H | 4,5-Cl$_2$-pyridin-3-yl | 1 |
| B-5120 | H | H | H | H | H | O | H | H | 4,6-Cl$_2$-pyridin-3-yl | 1 |
| B-5121 | H | H | H | H | H | O | H | H | 2-F-4-Cl-pyridin-3-yl | 1 |
| B-5122 | H | H | H | H | H | O | H | H | 2-F-5-Cl-pyridin-3-yl | 1 |
| B-5123 | H | H | H | H | H | O | H | H | 2-F-6-Cl-pyridin-3-yl | 1 |
| B-5124 | H | H | H | H | H | O | H | H | 4-F-2-Cl-pyridin-3-yl | 1 |
| B-5125 | H | H | H | H | H | O | H | H | 4-F-5-Cl-pyridin-3-yl | 1 |
| B-5126 | H | H | H | H | H | O | H | H | 4-F-6-Cl-pyridin-3-yl | 1 |
| B-5127 | H | H | H | H | H | O | H | H | 2-F-4-Me-pyridin-3-yl | 1 |
| B-5128 | H | H | H | H | H | O | H | H | 2-F-5-Me-pyridin-3-yl | 1 |
| B-5129 | H | H | H | H | H | O | H | H | 2-F-6-Me-pyridin-3-yl | 1 |
| B-5130 | H | H | H | H | H | O | H | H | 4-F-2-Me-pyridin-3-yl | 1 |
| B-5131 | H | H | H | H | H | O | H | H | 4-F-5-Me-pyridin-3-yl | 1 |
| B-5132 | H | H | H | H | H | O | H | H | 4-F-6-Me-pyridin-3-yl | 1 |
| B-5133 | H | H | H | H | H | O | H | H | 2-4-OMe-pyridin-3-yl | 1 |

TABLE 188-continued

| compound | R¹ | R² | R³ | R⁴ | R⁵ | A | R⁶ | R⁷ | Q | p |
|---|---|---|---|---|---|---|---|---|---|---|
| B-5134 | H | H | H | H | H | O | H | H | 2-F-5-OMe-pyridin-3-yl | 1 |
| B-5135 | H | H | H | H | H | O | H | H | 2-F-6-OMe-pyridin-3-yl | 1 |
| B-5136 | H | H | H | H | H | O | H | H | 4-F-2-OMe-pyridin-3-yl | 1 |
| B-5137 | H | H | H | H | H | O | H | H | 4-F-5-OMe-pyridin-3-yl | 1 |
| B-5138 | H | H | H | H | H | O | H | H | 4-F-6-OMe-pyridin-3-yl | 1 |
| B-5139 | H | H | H | H | H | O | H | H | 2-Cl-5-F-pyridin-3-yl | 1 |
| B-5140 | H | H | H | H | H | O | H | H | 2-Cl-6-F-pyridin-3-yl | 1 |
| B-5141 | H | H | H | H | H | O | H | H | 4-Cl-5-F-pyridin-3-yl | 1 |
| B-5142 | H | H | H | H | H | O | H | H | 4-Cl-6-F-pyridin-3-yl | 1 |
| B-5143 | H | H | H | H | H | O | H | H | 2-Cl-4-Me-pyridin-3-yl | 1 |
| B-5144 | H | H | H | H | H | O | H | H | 2-Cl-5-Me-pyridin-3-yl | 1 |
| B-5145 | H | H | H | H | H | O | H | H | 2-Cl-6-Me-pyridin-3-yl | 1 |
| B-5146 | H | H | H | H | H | O | H | H | 4-Cl-2-Me-pyridin-3-yl | 1 |
| B-5147 | H | H | H | H | H | O | H | H | 4-Cl-5-Me-pyridin-3-yl | 1 |
| B-5148 | H | H | H | H | H | O | H | H | 4-Cl-6-Me-pyridin-3-yl | 1 |
| B-5149 | H | H | H | H | H | O | H | H | 2-Me-5-F-pyridin-3-yl | 1 |
| B-5150 | H | H | H | H | H | O | H | H | 2-Me-6-F-pyridin-3-yl | 1 |
| B-5151 | H | H | H | H | H | O | H | H | 4-Me-5-F-pyridin-3-yl | 1 |
| B-5152 | H | H | H | H | H | O | H | H | 4-Me-6-F-pyridin-3-yl | 1 |
| B-5153 | H | H | H | H | H | O | H | H | 2-Me-5-Cl-pyridin-3-yl | 1 |
| B-5154 | H | H | H | H | H | O | H | H | 2-Me-6-Cl-pyridin-3-yl | 1 |
| B-5155 | H | H | H | H | H | O | H | H | 4-Me-5-Cl-pyridin-3-yl | 1 |
| B-5156 | H | H | H | H | H | O | H | H | 4-Me-6-Cl-pyridin-3-yl | 1 |
| B-5157 | H | H | H | H | H | O | H | H | 2,4-(Me)₂-pyridin-3-yl | 1 |
| B-5158 | H | H | H | H | H | O | H | H | 2,5-(Me)₂-pyridin-3-yl | 1 |
| B-5159 | H | H | H | H | H | O | H | H | 2,6-(Me)₂-pyridin-3-yl | 1 |
| B-5160 | H | H | H | H | H | O | H | H | 4,5-(Me)₂-pyridin-3-yl | 1 |
| B-5161 | H | H | H | H | H | O | H | H | 4,6-(Me)₂-pyridin-3-yl | 1 |
| B-5162 | H | H | H | H | H | O | H | H | 2-Me-4-OMe-pyridin-3-yl | 1 |
| B-5163 | H | H | H | H | H | O | H | H | 2-Me-5-OMe-pyridin-3-yl | 1 |
| B-5164 | H | H | H | H | H | O | H | H | 2-Me-6-OMe-pyridin-3-yl | 1 |
| B-5165 | H | H | H | H | H | O | H | H | 4-Me-2-OMe-pyridin-3-yl | 1 |
| B-5166 | H | H | H | H | H | O | H | H | 4-Me-5-OMe-pyridin-3-yl | 1 |

TABLE 189

| compound | R¹ | R² | R³ | R⁴ | R⁵ | A | R⁶ | R⁷ | Q | p |
|---|---|---|---|---|---|---|---|---|---|---|
| B-5167 | H | H | H | H | H | O | H | H | 4-Me-6-OMe-pyridin-3-yl | 1 |
| B-5168 | H | H | H | H | H | O | H | H | 2-CF₃-4-F-pyridin-3-yl | 1 |
| B-5169 | H | H | H | H | H | O | H | H | 2-CF₃-5-F-pyridin-3-yl | 1 |
| B-5170 | H | H | H | H | H | O | H | H | 2-CF₃-6-F-pyridin-3-yl | 1 |
| B-5171 | H | H | H | H | H | O | H | H | 4-CF₃-2-F-pyridin-3-yl | 1 |
| B-5172 | H | H | H | H | H | O | H | H | 4-CF₃-5-F-pyridin-3-yl | 1 |
| B-5173 | H | H | H | H | H | O | H | H | 4-CF₃-6-F-pyridin-3-yl | 1 |
| B-5174 | H | H | H | H | H | O | H | H | 2-CF₃-4-Me-pyridin-3-yl | 1 |
| B-5175 | H | H | H | H | H | O | H | H | 2-CF₃-5-Me-pyridin-3-yl | 1 |
| B-5176 | H | H | H | H | H | O | H | H | 2-CF₃-6-Me-pyridin-3-yl | 1 |
| B-5177 | H | H | H | H | H | O | H | H | 4-CF₃-2-Me-pyridin-3-yl | 1 |
| B-5178 | H | H | H | H | H | O | H | H | 4-CF₃-5-Me-pyridin-3-yl | 1 |
| B-5179 | H | H | H | H | H | O | H | H | 4-CF₃-6-Me-pyridin-3-yl | 1 |
| B-5180 | H | H | H | H | H | O | H | H | 2-OMe-5-F-pyridin-3-yl | 1 |
| B-5181 | H | H | H | H | H | O | H | H | 2-OMe-6-F-pyridin-3-yl | 1 |
| B-5182 | H | H | H | H | H | O | H | H | 4-OMe-5-F-pyridin-3-yl | 1 |
| B-5183 | H | H | H | H | H | O | H | H | 4-OMe-6-F-pyridin-3-yl | 1 |
| B-5184 | H | H | H | H | H | O | H | H | 2-OMe-4-Cl-pyridin-3-yl | 1 |
| B-5185 | H | H | H | H | H | O | H | H | 2-OMe-5-Cl-pyridin-3-yl | 1 |
| B-5186 | H | H | H | H | H | O | H | H | 2-OMe-6-Cl-pyridin-3-yl | 1 |
| B-5187 | H | H | H | H | H | O | H | H | 4-OMe-2-Cl-pyridin-3-yl | 1 |
| B-5188 | H | H | H | H | H | O | H | H | 4-OMe-5-Cl-pyridin-3-yl | 1 |
| B-5189 | H | H | H | H | H | O | H | H | 4-OMe-6-Cl-pyridin-3-yl | 1 |
| B-5190 | H | H | H | H | H | O | H | H | 2-OMe-5-Me-pyridin-3-yl | 1 |
| B-5191 | H | H | H | H | H | O | H | H | 2-OMe-6-Me-pyridin-3-yl | 1 |
| B-5192 | H | H | H | H | H | O | H | H | 4-OMe-5-Me-pyridin-3-yl | 1 |
| B-5193 | H | H | H | H | H | O | H | H | 4-OMe-6-Me-pyridin-3-yl | 1 |
| B-5194 | H | H | H | H | H | O | H | H | 2,4-(OMe)₂-pyridin-3-yl | 1 |
| B-5195 | H | H | H | H | H | O | H | H | 2,5-(OMe)₂-pyridin-3-yl | 1 |
| B-5196 | H | H | H | H | H | O | H | H | 2,6-(OMe)₂-pyridin-3-yl | 1 |
| B-5197 | H | H | H | H | H | O | H | H | 4,5-(OMe)₂-pyridin-3-yl | 1 |
| B-5198 | H | H | H | H | H | O | H | H | 4,6-(OMe)₂-pyridin-3-yl | 1 |
| B-5199 | H | H | H | H | H | O | H | H | pyridin-4-yl | 1 |
| B-5200 | H | H | H | H | H | O | H | H | 2-F-pyridin-4-yl | 1 |
| B-5201 | H | H | H | H | H | O | H | H | 3-F-pyridin-4-yl | 1 |
| B-5202 | H | H | H | H | H | O | H | H | 2-Cl-pyridin-4-yl | 1 |
| B-5203 | H | H | H | H | H | O | H | H | 3-Cl-pyridin-4-yl | 1 |

TABLE 189-continued

| compound | R¹ | R² | R³ | R⁴ | R⁵ | A | R⁶ | R⁷ | Q | p |
|---|---|---|---|---|---|---|---|---|---|---|
| B-5204 | H | H | H | H | H | O | H | H | 2-Me-pyridin-4-yl | 1 |
| B-5205 | H | H | H | H | H | O | H | H | 3-Me-pyridin-4-yl | 1 |
| B-5206 | H | H | H | H | H | O | H | H | 2-CF₃-pyridin-4-yl | 1 |
| B-5207 | H | H | H | H | H | O | H | H | 3-CF₃-pyridin-4-yl | 1 |
| B-5208 | H | H | H | H | H | O | H | H | 2-OMe-pyridin-4-yl | 1 |
| B-5209 | H | H | H | H | H | O | H | H | 3-OMe-pyridin-4-yl | 1 |
| B-5210 | H | H | H | H | H | O | H | H | 2,3-F₂-pyridin-4-yl | 1 |
| B-5211 | H | H | H | H | H | O | H | H | 2,5-F₂-pyridin-4-yl | 1 |
| B-5212 | H | H | H | H | H | O | H | H | 2,6-F₂-pyridin-4-yl | 1 |
| B-5213 | H | H | H | H | H | O | H | H | 3,5-F₂-pyridin-4-yl | 1 |
| B-5214 | H | H | H | H | H | O | H | H | 2,3-Cl₂-pyridin-4-yl | 1 |
| B-5215 | H | H | H | H | H | O | H | H | 2,5-Cl₂-pyridin-4-yl | 1 |
| B-5216 | H | H | H | H | H | O | H | H | 2,6-Cl₂-pyridin-4-yl | 1 |
| B-5217 | H | H | H | H | H | O | H | H | 3,5-Cl₂-pyridin-4-yl | 1 |
| B-5218 | H | H | H | H | H | O | H | H | 3-F-2-Cl-pyridin-4-yl | 1 |
| B-5219 | H | H | H | H | H | O | H | H | 3-F-5-Cl-pyridin-4-yl | 1 |
| B-5220 | H | H | H | H | H | O | H | H | 3-F-6-Cl-pyridin-4-yl | 1 |
| B-5221 | H | H | H | H | H | O | H | H | 3-F-2-Me-pyridin-4-yl | 1 |
| B-5222 | H | H | H | H | H | O | H | H | 3-F-5-Me-pyridin-4-yl | 1 |
| B-5223 | H | H | H | H | H | O | H | H | 3-F-6-Me-pyridin-4-yl | 1 |

TABLE 190

| compound | R¹ | R² | R³ | R⁴ | R⁵ | A | R⁶ | R⁷ | Q | p |
|---|---|---|---|---|---|---|---|---|---|---|
| B-5224 | H | H | H | H | H | O | H | H | 3-F-2-OMe-pyridin-4-yl | 1 |
| B-5225 | H | H | H | H | H | O | H | H | 3-F-5-OMe-pyridin-4-yl | 1 |
| B-5226 | H | H | H | H | H | O | H | H | 3-F-6-OMe-pyridin-4-yl | 1 |
| B-5227 | H | H | H | H | H | O | H | H | 3-Cl-2-F-pyridin-4-yl | 1 |
| B-5228 | H | H | H | H | H | O | H | H | 3-Cl-6-F-pyridin-4-yl | 1 |
| B-5229 | H | H | H | H | H | O | H | H | 3-Cl-2-Me-pyridin-4-yl | 1 |
| B-5230 | H | H | H | H | H | O | H | H | 3-Cl-5-Me-pyridin-4-yl | 1 |
| B-5231 | H | H | H | H | H | O | H | H | 3-Cl-6-Me-pyridin-4-yl | 1 |
| B-5232 | H | H | H | H | H | O | H | H | 3-Me-2-F-pyridin-4-yl | 1 |
| B-5233 | H | H | H | H | H | O | H | H | 3-Me-6-F-pyridin-4-yl | 1 |
| B-5234 | H | H | H | H | H | O | H | H | 3-Me-2-Cl-pyridin-4-yl | 1 |
| B-5235 | H | H | H | H | H | O | H | H | 3-Me-6-Cl-pyridin-4-yl | 1 |
| B-5236 | H | H | H | H | H | O | H | H | 2,3-(Me)₂-pyridin-4-yl | 1 |
| B-5237 | H | H | H | H | H | O | H | H | 3,5-(Me)₂-pyridin-4-yl | 1 |
| B-5238 | H | H | H | H | H | O | H | H | 3,6-(Me)₂-pyridin-4-yl | 1 |
| B-5239 | H | H | H | H | H | O | H | H | 3-Me-2-OMe-pyridin-4-yl | 1 |
| B-5240 | H | H | H | H | H | O | H | H | 3-Me-5-OMe-pyridin-4-yl | 1 |
| B-5241 | H | H | H | H | H | O | H | H | 3-Me-6-OMe-pyridin-4-yl | 1 |
| B-5242 | H | H | H | H | H | O | H | H | 3-CF₃-2-F-pyridin-4-yl | 1 |
| B-5243 | H | H | H | H | H | O | H | H | 3-CF₃-5-F-pyridin-4-yl | 1 |
| B-5244 | H | H | H | H | H | O | H | H | 3-CF₃-6-F-pyridin-4-yl | 1 |
| B-5245 | H | H | H | H | H | O | H | H | 3-CF₃-2-Me-pyridin-4-yl | 1 |
| B-5246 | H | H | H | H | H | O | H | H | 3-CF₃-5-Me-pyridin-4-yl | 1 |
| B-5247 | H | H | H | H | H | O | H | H | 3-CF₃-6-Me-pyridin-4-yl | 1 |
| B-5248 | H | H | H | H | H | O | H | H | 3-OMe-2-F-pyridin-4-yl | 1 |
| B-5249 | H | H | H | H | H | O | H | H | 3-OMe-6-F-pyridin-4-yl | 1 |
| B-5250 | H | H | H | H | H | O | H | H | 3-OMe-2-Cl-pyridin-4-yl | 1 |
| B-5251 | H | H | H | H | H | O | H | H | 3-OMe-5-Cl-pyridin-4-yl | 1 |
| B-5252 | H | H | H | H | H | O | H | H | 3-OMe-6-Cl-pyridin-4-yl | 1 |
| B-5253 | H | H | H | H | H | O | H | H | 3-OMe-2-Me-pyridin-4-yl | 1 |
| B-5254 | H | H | H | H | H | O | H | H | 3-OMe-6-Me-pyridin-4-yl | 1 |
| B-5255 | H | H | H | H | H | O | H | H | 2,3-(OMe)₂-pyridin-4-yl | 1 |
| B-5256 | H | H | H | H | H | O | H | H | 3,5-(OMe)₂-pyridin-4-yl | 1 |
| B-5257 | H | H | H | H | H | O | H | H | 3,6-(OMe)₂-pyridin-4-yl | 1 |
| B-5258 | H | H | H | H | H | O | H | H | pyrmidin-2-yl | 1 |
| B-5259 | H | H | H | H | H | O | H | H | pyrimidin-4-yl | 1 |
| B-5260 | H | H | H | H | H | O | H | H | 5-F-pyrimidin-4-yl | 1 |
| B-5261 | H | H | H | H | H | O | H | H | 5-Me-pyrimidin-4-yl | 1 |
| B-5262 | H | H | H | H | H | O | H | H | 5-CF₃-pyrimidin-4-yl | 1 |
| B-5263 | H | H | H | H | H | O | H | H | 5-OMe-pyrimidin-4-yl | 1 |
| B-5264 | H | H | H | H | H | O | H | H | pyrimidin-5-yl | 1 |
| B-5265 | H | H | H | H | H | O | H | H | 4-F-pyrimidin-5-yl | 1 |
| B-5266 | H | H | H | H | H | O | H | H | 4-Cl-pyrmidin-5-yl | 1 |
| B-5267 | H | H | H | H | H | O | H | H | 4-Me-pyrmidin-5-yl | 1 |
| B-5268 | H | H | H | H | H | O | H | H | 4-CF₃-pyrimidin-5-yl | 1 |
| B-5269 | H | H | H | H | H | O | H | H | 4-OMe-pyrimidin-5-yl | 1 |
| B-5270 | H | H | H | H | H | O | H | H | pyridazin-3-yl | 1 |
| B-5271 | H | H | H | H | H | O | H | H | 4-F-pyridazin-3-yl | 1 |
| B-5272 | H | H | H | H | H | O | H | H | 4-Cl-pyridazin-3-yl | 1 |
| B-5273 | H | H | H | H | H | O | H | H | 4-Me-pyridazin-3-yl | 1 |

TABLE 190-continued

| compound | R¹ | R² | R³ | R⁴ | R⁵ | A | R⁶ | R⁷ | Q | p |
|---|---|---|---|---|---|---|---|---|---|---|
| B-5274 | H | H | H | H | H | O | H | H | 4-CF₃-pyridazin-3-yl | 1 |
| B-5275 | H | H | H | H | H | O | H | H | 4-OMe-pyridazin-3-yl | 1 |
| B-5276 | H | H | H | H | H | O | H | H | pyridazin-4-yl | 1 |
| B-5277 | H | H | H | H | H | O | H | H | 3-F-pyridazin-4-yl | 1 |
| B-5278 | H | H | H | H | H | O | H | H | 3-Cl-pyridazin-4-yl | 1 |
| B-5279 | H | H | H | H | H | O | H | H | 3-Me-pyridazin-4-yl | 1 |
| B-5280 | H | H | H | H | H | O | H | H | 3-CF₃-pyridazin-4-yl | 1 |

TABLE 191

| compound | R¹ | R² | R³ | R⁴ | R⁵ | A | R⁶ | R⁷ | Q | p |
|---|---|---|---|---|---|---|---|---|---|---|
| B-5281 | H | H | H | H | H | O | H | H | 3-OMe-pyridazin-4-yl | 1 |
| B-5282 | H | H | H | H | H | O | H | H | 5-F-pyridazin-4-yl | 1 |
| B-5283 | H | H | H | H | H | O | H | H | 5-Cl-pyridazin-4-yl | 1 |
| B-5284 | H | H | H | H | H | O | H | H | 5-Me-pyridazin-4-y | 1 |
| B-5285 | H | H | H | H | H | O | H | H | 5-CF₃-pyridazin-4-yl | 1 |
| B-5286 | H | H | H | H | H | O | H | H | 5-OMe-pyridazin-4-yl | 1 |
| B-5287 | H | H | H | H | H | O | H | H | thiophen-2-yl | 1 |
| B-5288 | H | H | H | H | H | O | H | H | 3-F-thiopen-2-yl | 1 |
| B-5289 | H | H | H | H | H | O | H | H | 3-Cl-thiophen-2-yl | 1 |
| B-5290 | H | H | H | H | H | O | H | H | 3-Me-thiophen-2-yl | 1 |
| B-5291 | H | H | H | H | H | O | H | H | 3-CF₃-thiophen-2-y | 1 |
| B-5292 | H | H | H | H | H | O | H | H | 3-OMe-thiophen-2-yl | 1 |
| B-5293 | H | H | H | H | H | O | H | H | thiophen-3-yl | 1 |
| B-5294 | H | H | H | H | H | O | H | H | 2-F-thiophen-3-yl | 1 |
| B-5295 | H | H | H | H | H | O | H | H | 2-Cl-thiophen-3-yl | 1 |
| B-5296 | H | H | H | H | H | O | H | H | 2-Me-thiophen-3-yl | 1 |
| B-5297 | H | H | H | H | H | O | H | H | 2-CF₃-thiophen-3-yl | 1 |
| B-5298 | H | H | H | H | H | O | H | H | 2-OMe-thiophen-3-y | 1 |
| B-5299 | H | H | H | H | H | O | H | H | 4-F-thiophen-3-yl | 1 |
| B-5300 | H | H | H | H | H | O | H | H | 4-Cl-thiophen-3-yl | 1 |
| B-5301 | H | H | H | H | H | O | H | H | 4-Me-thiophen-3-yl | 1 |
| B-5302 | H | H | H | H | H | O | H | H | 4-CF₃-thiophen-3-yl | 1 |
| B-5303 | H | H | H | H | H | O | H | H | 4-OMe-thiophen-3-yl | 1 |
| B-5304 | H | H | H | H | H | O | H | H | thiazol-2-yl | 1 |
| B-5305 | H | H | H | H | H | O | H | H | thiazol-4-yl | 1 |
| B-5306 | H | H | H | H | H | O | H | H | 5-F-thiazol-4-yl | 1 |
| B-5307 | H | H | H | H | H | O | H | H | 5-Me-thiazol4-yl | 1 |
| B-5308 | H | H | H | H | H | O | H | H | 5-CF₃-thiazol-4-yl | 1 |
| B-5309 | H | H | H | H | H | O | H | H | 5-OMe-thiazol-4-yl | 1 |
| B-5310 | H | H | H | H | H | O | H | H | thiazol-5-yl | 1 |
| B-5311 | H | H | H | H | H | O | H | H | 4-F-thiazol-5-y | 1 |
| B-5312 | H | H | H | H | H | O | H | H | 4-Me-thiazol-5-yl | 1 |
| B-5313 | H | H | H | H | H | O | H | H | 4-CF₃-thiazol-5-yl | 1 |
| B-5314 | H | H | H | H | H | O | H | H | 4-OMe-thiazol-5-yl | 1 |
| B-5315 | H | H | H | H | H | O | H | H | 1H-pyrrol-1-yl | 1 |
| B-5316 | H | H | H | H | H | O | H | H | 2-F-1H-pyrrol-1-yl | 1 |
| B-5317 | H | H | H | H | H | O | H | H | 2-Me-1H-pyrrol-1-yl | 1 |
| B-5318 | H | H | H | H | H | O | H | H | 2-CF₃-1H-pyrrol-1-yl | 1 |
| B-5319 | H | H | H | H | H | O | H | H | 2-OMe-1H-pyrrol-1-yl | 1 |
| B-5320 | H | H | H | H | H | O | H | H | 1H-pyrrol-2-yl | 1 |
| B-5321 | H | H | H | H | H | O | H | H | 1-Me-1H-pyrrol-2-yl | 1 |
| B-5322 | H | H | H | H | H | O | H | H | 3-F-1H-pyrrol-2-yl | 1 |
| B-5323 | H | H | H | H | H | O | H | H | 3-Me-1H-pyrrol-2-yl | 1 |
| B-5324 | H | H | H | H | H | O | H | H | 3-CF₃-1H-pyrrol-2-yl | 1 |
| B-5325 | H | H | H | H | H | O | H | H | 3-OMe-1H-pyrrol-2-yl | 1 |
| B-5326 | H | H | H | H | H | O | H | H | 1-Me-3-F-1H-pyrrol-2-yl | 1 |
| B-5327 | H | H | H | H | H | O | H | H | 1,3-(Me)₂-1H-pyrrol-2-yl | 1 |
| B-5328 | H | H | H | H | H | O | H | H | 1-Me-3-CF₃-1H-pyrrol-2-yl | 1 |
| B-5329 | H | H | H | H | H | O | H | H | 1-Me-3-OMe-1H-pyrrol-2-yl | 1 |
| B-5330 | H | H | H | H | H | O | H | H | 1H-pyrrol-3-yl | 1 |
| B-5331 | H | H | H | H | H | O | H | H | 1-Me-1H-pyrrol-3-yl | 1 |
| B-5332 | H | H | H | H | H | O | H | H | 2-F-1H-pyrrol-3-yl | 1 |
| B-5333 | H | H | H | H | H | O | H | H | 2-Me-1H-pyrrol-3-yl | 1 |
| B-5334 | H | H | H | H | H | O | H | H | 2-CF₃-1H-pyrrol-3-yl | 1 |
| B-5335 | H | H | H | H | H | O | H | H | 2-OMe-1H-pyrrol-3-yl | 1 |
| B-5336 | H | H | H | H | H | O | H | H | 1-Me-2-F-1H-pyrrol-3-yl | 1 |
| B-5337 | H | H | H | H | H | O | H | H | 1,2-(Me)₂-1H-pyrrol-3-yl | 1 |

TABLE 192

| compound | R¹ | R² | R³ | R⁴ | R⁵ | A | R⁶ | R⁷ | Q | p |
|---|---|---|---|---|---|---|---|---|---|---|
| B-5338 | H | H | H | H | H | O | H | H | 1-Me-2-CF₃-1H-pyrrol-3-yl | 1 |
| B-5339 | H | H | H | H | H | O | H | H | 1-Me-2-OMe-1H-pyrrol-3-yl | 1 |
| B-5340 | H | H | H | H | H | O | H | H | 4-F-1H-pyrrol-3-yl | 1 |
| B-5341 | H | H | H | H | H | O | H | H | 4-Me-1H-pyrrol-3-yl | 1 |
| B-5342 | H | H | H | H | H | O | H | H | 4-CF₃-1H-pyrrol-3-yl | 1 |
| B-5343 | H | H | H | H | H | O | H | H | 4-OMe-1H-pyrrol-3-yl | 1 |
| B-5344 | H | H | H | H | H | O | H | H | 1-Me-4-F-1H-pyrrol-3-yl | 1 |
| B-5345 | H | H | H | H | H | O | H | H | 1,4-(Me)₂-1H-pyrrol-3-yl | 1 |
| B-5346 | H | H | H | H | H | O | H | H | 1-Me-4-CF₃-1H-pyrrol-3-yl | 1 |
| B-5347 | H | H | H | H | H | O | H | H | 1-Me-4-OMe-1H-pyrrol-3-yl | 1 |
| B-5348 | H | H | H | H | H | O | H | H | 1H-pyrazol-1-yl | 1 |
| B-5349 | H | H | H | H | H | O | H | H | 5-F-1H-pyrazol-1-yl | 1 |
| B-5350 | H | H | H | H | H | O | H | H | 5-Cl-1H-pyrazol-1-yl | 1 |
| B-5351 | H | H | H | H | H | O | H | H | 5-Me-1H-pyrazol-1-yl | 1 |
| B-5352 | H | H | H | H | H | O | H | H | 5-CF₃-1H-pyrazol-1-yl | 1 |
| B-5353 | H | H | H | H | H | O | H | H | 5-OMe-1H-pyrazol-1-yl | 1 |
| B-5354 | H | H | H | H | H | O | H | H | 1H-pyrazol-3-yl | 1 |
| B-5355 | H | H | H | H | H | O | H | H | 1-Me-1H-pyrazol-3-yl | 1 |
| B-5356 | H | H | H | H | H | O | H | H | 4F-1H-pyrazol-3-yl | 1 |
| B-5357 | H | H | H | H | H | O | H | H | 4-Cl-1H-pyrazol-3-yl | 1 |
| B-5358 | H | H | H | H | H | O | H | H | 4-Me-1H-pyrazol-3-yl | 1 |
| B-5359 | H | H | H | H | H | O | H | H | 4-CF₃-1H-pyrazol-3-yl | 1 |
| B-5360 | H | H | H | H | H | O | H | H | 4-OMe-1H-pyrazol-3-yl | 1 |
| B-5361 | H | H | H | H | H | O | H | H | 1-Me-4-F-1H-pyrazol-3-yl | 1 |
| B-5362 | H | H | H | H | H | O | H | H | 1-Me-4-Cl-1H-pyrazol-3-yl | 1 |
| B-5363 | H | H | H | H | H | O | H | H | 1,4-(Me)₂-1H-pyrazol-3-yl | 1 |
| B-5364 | H | H | H | H | H | O | H | H | 1-Me-4-CF₃-1H-pyrazol-3-yl | 1 |
| B-5365 | H | H | H | H | H | O | H | H | 1-Me-4-OMe-1H-pyrazol-3-yl | 1 |
| B-5366 | H | H | H | H | H | O | H | H | 1H-pyrazol4-yl | 1 |
| B-5367 | H | H | H | H | H | O | H | H | 1-Me-1H-pyrazol-4-yl | 1 |
| B-5368 | H | H | H | H | H | O | H | H | 3-F-1H-pyrazol-4-yl | 1 |
| B-5369 | H | H | H | H | H | O | H | H | 3-Cl-1H-pyrazol-4-yl | 1 |
| B-5370 | H | H | H | H | H | O | H | H | 3-Me-1H-pyrazol-4-yl | 1 |
| B-5371 | H | H | H | H | H | O | H | H | 3-CF₃-1H-pyrazol-4-yl | 1 |
| B-5372 | H | H | H | H | H | O | H | H | 3-OMe-1H-pyrazol-4-yl | 1 |
| B-5373 | H | H | H | H | H | O | H | H | 1-Me-3-F-1H-pyrazol-4-yl | 1 |
| B-5374 | H | H | H | H | H | O | H | H | 1-Me-3-Cl-1H-pyrazol-4-yl | 1 |
| B-5375 | H | H | H | H | H | O | H | H | 1,3-(Me)₂-1H-pyrazol-4-yl | 1 |
| B-5376 | H | H | H | H | H | O | H | H | 1-Me-3-CF₃-1H-pyrazol-4-yl | 1 |
| B-5377 | H | H | H | H | H | O | H | H | 1-Me-3-OMe-1H-pyrazol-4-yl | 1 |
| B-5378 | H | H | H | H | H | O | H | H | 5-F-1H-pyrazol-4-yl | 1 |
| B-5379 | H | H | H | H | H | O | H | H | 5-Cl-1H-pyrazol-4-yl | 1 |
| B-5380 | H | H | H | H | H | O | H | H | 5-Me-1H-pyrazol-4-yl | 1 |
| B-5381 | H | H | H | H | H | O | H | H | 5-CF₃-1H-pyrazol-4-yl | 1 |
| B-5382 | H | H | H | H | H | O | H | H | 5-OMe-1H-pyrazol-4-yl | 1 |
| B-5383 | H | H | H | H | H | O | H | H | 1-Me-5F-1H-pyrazol-4-yl | 1 |
| B-5384 | H | H | H | H | H | O | H | H | 1-Me-5-Cl-1H-pyrazol-4-yl | 1 |
| B-5385 | H | H | H | H | H | O | H | H | 1,5-(Me)₂-1H-pyrazol-4-yl | 1 |
| B-5386 | H | H | H | H | H | O | H | H | 1-Me-5-CF₃-1H-pyrazol-4-yl | 1 |
| B-5387 | H | H | H | H | H | O | H | H | 1-Me-5-OMe-1H-pyrazol-4-yl | 1 |
| B-5388 | H | H | H | H | H | O | H | H | 1H-pyrazol-5-yl | 1 |
| B-5389 | H | H | H | H | H | O | H | H | 1-Me-1H-pyrazol-5-yl | 1 |
| B-5390 | H | H | H | H | H | O | H | H | 4-F-1H-pyrazol-5-yl | 1 |
| B-5391 | H | H | H | H | H | O | H | H | 4-Cl-H-pyrazol-5-yl | 1 |
| B-5392 | H | H | H | H | H | O | H | H | 4-Me-1H-pyrazol-5-yl | 1 |
| B-5393 | H | H | H | H | H | O | H | H | 4-CF₃-1H-pyrazol-5-yl | 1 |
| B-5394 | H | H | H | H | H | O | H | H | 4-OMe-1H-pyrazol-5-yl | 1 |

TABLE 193

| compound | R¹ | R² | R³ | R⁴ | R⁵ | A | R⁶ | R⁷ | Q | p |
|---|---|---|---|---|---|---|---|---|---|---|
| B-5395 | H | H | H | H | H | O | H | H | 1-Me-4F-1H-pyrazol-5-yl | 1 |
| B-5396 | H | H | H | H | H | O | H | H | 1-Me-4-Cl-1H-pyrazol-5-yl | 1 |
| B-5397 | H | H | H | H | H | O | H | H | 1,4-(Me)₂-1H-pyrazol-5-yl | 1 |
| B-5398 | H | H | H | H | H | O | H | H | 1-Me-4-CF₃-1H-pyrazol-5-yl | 1 |
| B-5399 | H | H | H | H | H | O | H | H | 1-Me-4-OMe-1H-pyrazol-5-yl | 1 |
| B-5400 | H | H | H | H | H | O | H | H | furan-2-yl | 1 |
| B-5401 | H | H | H | H | H | O | H | H | 3-F-furan-2-yl | 1 |
| B-5402 | H | H | H | H | H | O | H | H | 3-Me-furan-2-yl | 1 |
| B-5403 | H | H | H | H | H | O | H | H | 3-CF₃-furan-2-yl | 1 |
| B-5404 | H | H | H | H | H | O | H | H | 3-OMe-furan-2-yl | 1 |
| B-5405 | H | H | H | H | H | O | H | H | furan-3-yl | 1 |
| B-5406 | H | H | H | H | H | O | H | H | 2-F-furan-3-yl | 1 |
| B-5407 | H | H | H | H | H | O | H | H | 2-Me-furan-3-yl | 1 |

TABLE 193-continued

| compound | R¹ | R² | R³ | R⁴ | R⁵ | A | R⁶ | R⁷ | Q | p |
|---|---|---|---|---|---|---|---|---|---|---|
| B-5408 | H | H | H | H | H | O | H | H | 2-CF₃-furan-3-yl | 1 |
| B-5409 | H | H | H | H | H | O | H | H | 2-OMe-furan-3-yl | 1 |
| B-5410 | H | H | H | H | H | O | H | H | 4-F-furan-3-yl | 1 |
| B-5411 | H | H | H | H | H | O | H | H | 4-Me-furan-3-yl | 1 |
| B-5412 | H | H | H | H | H | O | H | H | 4-CF₃-furan-3-yl | 1 |
| B-5413 | H | H | H | H | H | O | H | H | 4-OMe-furan-3-yl | 1 |
| B-5414 | H | H | H | H | H | O | H | H | isoxazol-3-yl | 1 |
| B-5415 | H | H | H | H | H | O | H | H | 4-F-isoxazol-3-yl | 1 |
| B-5416 | H | H | H | H | H | O | H | H | 4-Me-isoxazol-3-yl | 1 |
| B-5417 | H | H | H | H | H | O | H | H | 4-CF₃-isoxazol-3-yl | 1 |
| B-5418 | H | H | H | H | H | O | H | H | 4-OMe-isoxazol-3-yl | 1 |
| B-5419 | H | H | H | H | H | O | H | H | isoxazol-4-yl | 1 |
| B-5420 | H | H | H | H | H | O | H | H | 5-F-isoxazol-4-yl | 1 |
| B-5421 | H | H | H | H | H | O | H | H | 5-Me-isoxazol-4-yl | 1 |
| B-5422 | H | H | H | H | H | O | H | H | 5-CF₃-isoxazol-4-yl | 1 |
| B-5423 | H | H | H | H | H | O | H | H | 5-OMe-isoxazol-4-yl | 1 |
| B-5424 | H | H | H | H | H | O | H | H | isoxazol-5-yl | 1 |
| B-5425 | H | H | H | H | H | O | H | H | 4-F-isoxazol-5-yl | 1 |
| B-5426 | H | H | H | H | H | O | H | H | 4-Me-isoxazol-5-yl | 1 |
| B-5427 | H | H | H | H | H | O | H | H | 4-CF₃-isoxazol-5-yl | 1 |
| B-5428 | H | H | H | H | H | O | H | H | 4-OMe-isoxazol-5-yl | 1 |
| B-5429 | H | H | H | H | H | O | H | H | 1H-1,2,3-triazol-1-yl | 1 |
| B-5430 | H | H | H | H | H | O | H | H | 5-F-1H-1,2,3-triazol-1-yl | 1 |
| B-5431 | H | H | H | H | H | O | H | H | 5-Me-1H-1,2,3-triazol-1-yl | 1 |
| B-5432 | H | H | H | H | H | O | H | H | 5-CF₃-1H-1,2,3-triazol-1-yl | 1 |
| B-5433 | H | H | H | H | H | O | H | H | 5-OMe-1H-1,2,3-triazol-1-yl | 1 |
| B-5434 | H | H | H | H | H | O | H | H | 1H-1,2,3-triazol-4-yl | 1 |
| B-5435 | H | H | H | H | H | O | H | H | 5-F-1H-1,2,3-triazol-4-yl | 1 |
| B-5436 | H | H | H | H | H | O | H | H | 5-Me-1H-1,2,3-triazol-4-yl | 1 |
| B-5437 | H | H | H | H | H | O | H | H | 5-CF₃-1H-1,2,3-triazol-4-y | 1 |
| B-5438 | H | H | H | H | H | O | H | H | 5-OMe-1H-1,2,3-triazol-4-yl | 1 |
| B-5439 | H | H | H | H | H | O | H | H | 1H-1,2,3-triazol-5-yl | 1 |
| B-5440 | H | H | H | H | H | O | H | H | 4-F-1H-1,2,3-triazol-5-yl | 1 |
| B-5441 | H | H | H | H | H | O | H | H | 4-Me-1H-1,2,3-triazol-5-yl | 1 |
| B-5442 | H | H | H | H | H | O | H | H | 4-CF₃-1H-1,2,3-triazol-5-yl | 1 |
| B-5443 | H | H | H | H | H | O | H | H | 4-OMe-1H-1,2,3-triazol-5-yl | 1 |
| B-5444 | H | H | H | H | H | O | H | H | 1H-1,2,4-triazol-1-yl | 1 |
| B-5445 | H | H | H | H | H | O | H | H | 5-Me-1H-1,2,4-triazol-1-yl | 1 |
| B-5446 | H | H | H | H | H | O | H | H | 5-F-1H-1,2,4-triazol-1-yl | 1 |
| B-5447 | H | H | H | H | H | O | H | H | 5-CF₃-1H-1,2,4-triazol-1-yl | 1 |
| B-5448 | H | H | H | H | H | O | H | H | 5-OMe-1H-1,2,4-triazol-1-yl | 1 |
| B-5449 | H | H | H | H | H | O | H | H | 1H-1,2,4-triazol-3-yl | 1 |
| B-5450 | H | H | H | H | H | O | H | H | 1-Me-1H-1,2,4-triazol-3-yl | 1 |
| B-5451 | H | H | H | H | H | O | H | H | 1H-1,2,4-triazol-5-yl | 1 |

TABLE 194

| compound | R¹ | R² | R³ | R⁴ | R⁵ | A | R⁶ | R⁷ | Q | p |
|---|---|---|---|---|---|---|---|---|---|---|
| B-5452 | H | H | H | H | H | O | H | H | 1-Me-1H-1,2,4-triazol-5-yl | 1 |
| B-5453 | H | H | H | H | H | O | H | H | 3,5-(Me)₂-isoxazol-4-yl | 1 |
| B-5454 | H | H | H | H | H | O | H | H | 3,5-(Me)₂-isoxazol-4-yl | 1 |
| B-5455 | H | H | H | H | H | O | H | H | 1,3,5-(Me)₃-1H-pyrazol-4-yl | 1 |
| B-5456 | H | H | H | H | H | O | H | H | quinolin-4-yl | 1 |
| B-5457 | H | H | H | H | H | O | H | H | isoquinolin-4-yl | 1 |
| B-5458 | H | H | H | H | H | O | H | H | 3,6-(OMe)₂-pyridazin-4-yl | 1 |
| B-5459 | H | H | H | H | H | O | H | H | 2,4-(OMe)₂-pyrmidin-5-yl | 1 |

TABLE 195

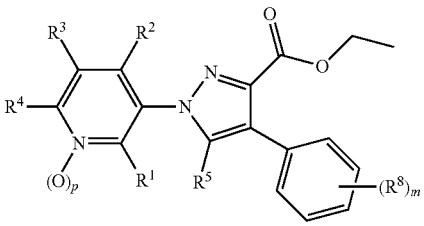

| compound | R¹ | R² | R³ | R⁴ | R⁵ | (R⁸)ₙ | p |
|---|---|---|---|---|---|---|---|
| C-0001 | H | H | H | H | H | H | 0 |
| C-0002 | H | H | H | H | H | 2-F | 0 |
| C-0003 | H | H | H | H | H | 3-F | 0 |
| C-0004 | H | H | H | H | H | 4-F | 0 |
| C-0005 | H | H | H | H | H | 2-Cl | 0 |
| C-0006 | H | H | H | H | H | 3-Cl | 0 |
| C-0007 | H | H | H | H | H | 4-Cl | 0 |
| C-0008 | H | H | H | H | H | 2-Br | 0 |
| C-0009 | H | H | H | H | H | 3-Br | 0 |
| C-0010 | H | H | H | H | H | 4-Br | 0 |
| C-0011 | H | H | H | H | H | 2-I | 0 |
| C-0012 | H | H | H | H | H | 3-I | 0 |
| C-0013 | H | H | H | H | H | 4-I | 0 |
| C-0014 | H | H | H | H | H | 2-OH | 0 |
| C-0015 | H | H | H | H | H | 3-OH | 0 |
| C-0016 | H | H | H | H | H | 4-OH | 0 |
| C-0017 | H | H | H | H | H | 2-SH | 0 |
| C-0018 | H | H | H | H | H | 3-SH | 0 |
| C-0019 | H | H | H | H | H | 4-SH | 0 |
| C-0020 | H | H | H | H | H | 2-Me | 0 |
| C-0021 | H | H | H | H | H | 3-Me | 0 |
| C-0022 | H | H | H | H | H | 4-Me | 0 |
| C-0023 | H | H | H | H | H | 2-Et | 0 |
| C-0024 | H | H | H | H | H | 3-Et | 0 |
| C-0025 | H | H | H | H | H | 4-Et | 0 |
| C-0026 | H | H | H | H | H | 2-Pr | 0 |
| C-0027 | H | H | H | H | H | 3-Pr | 0 |
| C-0028 | H | H | H | H | H | 4-Pr | 0 |
| C-0029 | H | H | H | H | H | 2-i-Pr | 0 |
| C-0030 | H | H | H | H | H | 3-i-Pr | 0 |
| C-0031 | H | H | H | H | H | 4-i-Pr | 0 |
| C-0032 | H | H | H | H | H | 2-Bu | 0 |
| C-0033 | H | H | H | H | H | 3-Bu | 0 |
| C-0034 | H | H | H | H | H | 4-Bu | 0 |
| C-0035 | H | H | H | H | H | 2-s-Bu | 0 |
| C-0036 | H | H | H | H | H | 3-s-Bu | 0 |
| C-0037 | H | H | H | H | H | 4-s-Bu | 0 |
| C-0038 | H | H | H | H | H | 2-i-Bu | 0 |
| C-0039 | H | H | H | H | H | 3-i-Bu | 0 |
| C-0040 | H | H | H | H | H | 4-i-Bu | 0 |
| C-0041 | H | H | H | H | H | 2-t-Bu | 0 |
| C-0042 | H | H | H | H | H | 3-t-Bu | 0 |
| C-0043 | H | H | H | H | H | 4-t-Bu | 0 |
| C-0044 | H | H | H | H | H | 2-CF₃ | 0 |
| C-0045 | H | H | H | H | H | 3-CF₃ | 0 |
| C-0046 | H | H | H | H | H | 4-CF₃ | 0 |
| C-0047 | H | H | H | H | H | 2-CHF₂ | 0 |
| C-0048 | H | H | H | H | H | 3-CHF₂ | 0 |
| C-0049 | H | H | H | H | H | 4-CHF₂ | 0 |
| C-0050 | H | H | H | H | H | 2-CH₂F | 0 |
| C-0051 | H | H | H | H | H | 3-CH₂F | 0 |

TABLE 196

| compound | R¹ | R² | R³ | R⁴ | R⁵ | (R⁸)ₘ | p |
|---|---|---|---|---|---|---|---|
| C-0052 | H | H | H | H | H | 4-CH₂F | 0 |
| C-0053 | H | H | H | H | H | 2-CF₂Cl | 0 |
| C-0054 | H | H | H | H | H | 3-CF₂Cl | 0 |
| C-0055 | H | H | H | H | H | 4-CF₂Cl | 0 |
| C-0056 | H | H | H | H | H | 2-CF(CF₃)₂ | 0 |
| C-0057 | H | H | H | H | H | 3-CF(CF₃)₂ | 0 |
| C-0058 | H | H | H | H | H | 4-CF(CF₃)₂ | 0 |
| C-0059 | H | H | H | H | H | 2-cycloprop | 0 |

TABLE 196-continued

| compound | R¹ | R² | R³ | R⁴ | R⁵ | (R⁸)ₘ | p |
|---|---|---|---|---|---|---|---|
| C-0060 | H | H | H | H | H | 3-cyclopropyl | 0 |
| C-0061 | H | H | H | H | H | 4-cyclopropyl | 0 |
| C-0062 | H | H | H | H | H | 2-cyclobutyl | 0 |
| C-0063 | H | H | H | H | H | 3-cyclobutyl | 0 |
| C-0064 | H | H | H | H | H | 4-cyclobutyl | 0 |
| C-0065 | H | H | H | H | H | 2-cyclopentyl | 0 |
| C-0066 | H | H | H | H | H | 3-cyclopentyl | 0 |
| C-0067 | H | H | H | H | H | 4-cyclopentyl | 0 |
| C-0068 | H | H | H | H | H | 2-(cyclopropylmethyl) | 0 |
| C-0069 | H | H | H | H | H | 3-(cyclopropylmethyl) | 0 |
| C-0070 | H | H | H | H | H | 4-(cyclopropylmethyl) | 0 |
| C-0071 | H | H | H | H | H | 2-(cyclobutylmethyl) | 0 |
| C-0072 | H | H | H | H | H | 3-(cyclobutylmethyl) | 0 |
| C-0073 | H | H | H | H | H | 4-(cyclobutylmethyl) | 0 |
| C-0074 | H | H | H | H | H | 2-(cyclopentylmethyl) | 0 |
| C-0075 | H | H | H | H | H | 3-(cyclopentylmethyl) | 0 |
| C-0076 | H | H | H | H | H | 4-(cyclopentylmethyl) | 0 |
| C-0077 | H | H | H | H | H | 2-(cyclopropylethyl) | 0 |
| C-0078 | H | H | H | H | H | 3-(cyclopropylethyl) | 0 |
| C-0079 | H | H | H | H | H | 4-(cyclopropylethyl) | 0 |
| C-0080 | H | H | H | H | H | 2-(2,2-difluorocyclopropyl) | 0 |
| C-0081 | H | H | H | H | H | 3-(2,2-difluorocyclopropyl) | 0 |
| C-0082 | H | H | H | H | H | 4-(2,2-difluorocyclopropyl) | 0 |
| C-0083 | H | H | H | H | H | 2-(2,2-dichlorocyclopropyl) | 0 |
| C-0084 | H | H | H | H | H | 3-(2,2-dichlorocyclopropyl) | 0 |
| C-0085 | H | H | H | H | H | 4-(2,2-dichlorocyclopropyl) | 0 |
| C-0086 | H | H | H | H | H | 2-ethenyl | 0 |
| C-0087 | H | H | H | H | H | 3-ethenyl | 0 |
| C-0088 | H | H | H | H | H | 4-ethenyl | 0 |
| C-0089 | H | H | H | H | H | 2-allyl | 0 |
| C-0090 | H | H | H | H | H | 3-allyl | 0 |
| C-0091 | H | H | H | H | H | 4-allyl | 0 |
| C-0092 | H | H | H | H | H | 2-(prop-1-en-1-yl) | 0 |
| C-0093 | H | H | H | H | H | 3-(prop-1-en-1-yl) | 0 |
| C-0094 | H | H | H | H | H | 4-(prop-1-en-1-yl) | 0 |
| C-0095 | H | H | H | H | H | 2-(trifluoroethenyl) | 0 |
| C-0096 | H | H | H | H | H | 3-(trifluoroethenyl) | 0 |
| C-0097 | H | H | H | H | H | 4-(trifluoroethenyl) | 0 |
| C-0098 | H | H | H | H | H | 2-(2,2-dichloroethenyl) | 0 |
| C-0099 | H | H | H | H | H | 3-(2,2-dichloroethenyl) | 0 |
| C-0100 | H | H | H | H | H | 4-(2,2-dichloroethenyl) | 0 |
| C-0101 | H | H | H | H | H | 2-ethynyl | 0 |
| C-0102 | H | H | H | H | H | 3-ethynyl | 0 |
| C-0103 | H | H | H | H | H | 4-ethynyl | 0 |
| C-0104 | H | H | H | H | H | 2-(1-propyn-1-yl) | 0 |
| C-0105 | H | H | H | H | H | 3-(1-propyn-1-yl) | 0 |
| C-0106 | H | H | H | H | H | 4-(1-propyn-1-yl) | 0 |
| C-0107 | H | H | H | H | H | 2-(2-propyn-1-yl) | 0 |

TABLE 197

| compound | R¹ | R² | R³ | R⁴ | R⁵ | (R⁸)ₘ | p |
|---|---|---|---|---|---|---|---|
| C-0108 | H | H | H | H | H | 3-(2-propyn-1-yl) | 0 |
| C-0109 | H | H | H | H | H | 4-(2-propyn-1-yl) | 0 |
| C-0110 | H | H | H | H | H | 2-(2-cyclopropylethynyl) | 0 |
| C-0111 | H | H | H | H | H | 3-(2-cyclopropylethynyl) | 0 |
| C-0112 | H | H | H | H | H | 4-(2-cyclopropylethynyl) | 0 |
| C-0113 | H | H | H | H | H | 2-(2-chloroethynyl) | 0 |
| C-0114 | H | H | H | H | H | 3-(2-chloroethynyl) | 0 |
| C-0115 | H | H | H | H | H | 4-(2-chloroethynyl) | 0 |
| C-0116 | H | H | H | H | H | 2-(2-bromoethynyl) | 0 |
| C-0117 | H | H | H | H | H | 3-(2-bromoethynyl) | 0 |
| C-0118 | H | H | H | H | H | 4-(2-bromoethynyl) | 0 |
| C-0119 | H | H | H | H | H | 2-OMe | 0 |
| C-0120 | H | H | H | H | H | 3-OMe | 0 |
| C-0121 | H | H | H | H | H | 4-OMe | 0 |
| C-0122 | H | H | H | H | H | 2-OEt | 0 |
| C-0123 | H | H | H | H | H | 3-OEt | 0 |
| C-0124 | H | H | H | H | H | 4-OEt | 0 |
| C-0125 | H | H | H | H | H | 2-OPr | 0 |
| C-0126 | H | H | H | H | H | 3-OPr | 0 |
| C-0127 | H | H | H | H | H | 4-OPr | 0 |
| C-0128 | H | H | H | H | H | 2-O(i-Pr) | 0 |
| C-0129 | H | H | H | H | H | 3-O(i-Pr) | 0 |

TABLE 197-continued

| compound | R$^1$ | R$^2$ | R$^3$ | R$^4$ | R$^5$ | (R$^8$)$_m$ | p |
|---|---|---|---|---|---|---|---|
| C-0130 | H | H | H | H | H | 4-O(i-Pr) | 0 |
| C-0131 | H | H | H | H | H | 2-OBu | 0 |
| C-0132 | H | H | H | H | H | 3-OBu | 0 |
| C-0133 | H | H | H | H | H | 4-OBu | 0 |
| C-0134 | H | H | H | H | H | 2-O(s-Bu) | 0 |
| C-0135 | H | H | H | H | H | 3-O(s-Bu) | 0 |
| C-0136 | H | H | H | H | H | 4-O(s-Bu) | 0 |
| C-0137 | H | H | H | H | H | 2-O(i-Bu) | 0 |
| C-0138 | H | H | H | H | H | 3-O(i-Bu) | 0 |
| C-0139 | H | H | H | H | H | 4-O(i-Bu) | 0 |
| C-0140 | H | H | H | H | H | 2-O(t-Bu) | 0 |
| C-0141 | H | H | H | H | H | 3-O(t-Bu) | 0 |
| C-0142 | H | H | H | H | H | 4-O(t-Bu) | 0 |
| C-0143 | H | H | H | H | H | 2-OCF$_3$ | 0 |
| C-0144 | H | H | H | H | H | 3-OCF$_3$ | 0 |
| C-0145 | H | H | H | H | H | 4-OCF$_3$ | 0 |
| C-0146 | H | H | H | H | H | 2-OCHF$_2$ | 0 |
| C-0147 | H | H | H | H | H | 3-OCHF$_2$ | 0 |
| C-0148 | H | H | H | H | H | 4-OCHF$_2$ | 0 |
| C-0149 | H | H | H | H | H | 2-OCH$_2$CF$_3$ | 0 |
| C-0150 | H | H | H | H | H | 3-OCH$_2$CF$_3$ | 0 |
| C-0151 | H | H | H | H | H | 4-OCH$_2$CF$_3$ | 0 |
| C-0152 | H | H | H | H | H | 2-(cyclopropyloxy) | 0 |
| C-0153 | H | H | H | H | H | 3-(cyclopropyloxy) | 0 |
| C-0154 | H | H | H | H | H | 4-(cyclopropyloxy) | 0 |
| C-0155 | H | H | H | H | H | 2-(cyclobutyloxy) | 0 |
| C-0156 | H | H | H | H | H | 3-(cyclobutyloxy) | 0 |
| C-0157 | H | H | H | H | H | 4-(cyclobutyloxy) | 0 |
| C-0158 | H | H | H | H | H | 2-(cyclopentyloxy) | 0 |
| C-0159 | H | H | H | H | H | 3-(cyclopentyloxy) | 0 |
| C-0160 | H | H | H | H | H | 4-(cyclopentyloxy) | 0 |
| C-0161 | H | H | H | H | H | 2-((2,2-dichlorocyclopropyl)oxy) | 0 |
| C-0162 | H | H | H | H | H | 3-((2,2-dichlorocyclopropyl)oxy) | 0 |
| C-0163 | H | H | H | H | H | 4-((2,2-dichlorocyclopropyl)oxy) | 0 |

TABLE 198

| compound | R$^1$ | R$^2$ | R$^3$ | R$^4$ | R$^5$ | (R$^8$)$_m$ | p |
|---|---|---|---|---|---|---|---|
| C-0164 | H | H | H | H | H | 2-(cyclopropylmethoxy) | 0 |
| C-0165 | H | H | H | H | H | 3-(cyclopropylmethoxy) | 0 |
| C-0166 | H | H | H | H | H | 4-(cyclopropylmethoxy) | 0 |
| C-0167 | H | H | H | H | H | 2-((2,2-difluorocyclopropyl)methoxy) | 0 |
| C-0168 | H | H | H | H | H | 3-((2,2-difluorocyclopropyl)methoxy) | 0 |
| C-0169 | H | H | H | H | H | 4-((2,2-difluorocyclopropyl)methoxy) | 0 |
| C-0170 | H | H | H | H | H | 2-(oxiran-2-yl) | 0 |
| C-0171 | H | H | H | H | H | 3-(oxiran-2-yl) | 0 |
| C-0172 | H | H | H | H | H | 4-(oxiran-2-yl) | 0 |
| C-0173 | H | H | H | H | H | 2-(oxiran-2-ylmethyl) | 0 |
| C-0174 | H | H | H | H | H | 3-(oxiran-2-ylmethyl) | 0 |
| C-0175 | H | H | H | H | H | 4-(oxiran-2-ylmethyl) | 0 |
| C-0176 | H | H | H | H | H | 2-SMe | 0 |
| C-0177 | H | H | H | H | H | 3-SMe | 0 |
| C-0178 | H | H | H | H | H | 4-SMe | 0 |
| C-0179 | H | H | H | H | H | 2-SEt | 0 |
| C-0180 | H | H | H | H | H | 3-SEt | 0 |
| C-0181 | H | H | H | H | H | 4-SEt | 0 |
| C-0182 | H | H | H | H | H | 2-S(=O)Me | 0 |
| C-0183 | H | H | H | H | H | 3-S(=O)Me | 0 |
| C-0184 | H | H | H | H | H | 4-S(=O)Me | 0 |
| C-0185 | H | H | H | H | H | 2-S(=O)$_2$Me | 0 |
| C-0186 | H | H | H | H | H | 3-S(=O)$_2$Me | 0 |
| C-0187 | H | H | H | H | H | 4-S(=O)$_2$Me | 0 |
| C-0188 | H | H | H | H | H | 2-SCF$_3$ | 0 |
| C-0189 | H | H | H | H | H | 3-SCF$_3$ | 0 |
| C-0190 | H | H | H | H | H | 4-SCF$_3$ | 0 |
| C-0191 | H | H | H | H | H | 2-S(=O)CF$_3$ | 0 |
| C-0192 | H | H | H | H | H | 3-S(=O)CF$_3$ | 0 |
| C-0193 | H | H | H | H | H | 4-S(=O)CF$_3$ | 0 |
| C-0194 | H | H | H | H | H | 2-S(=O)$_2$CF$_3$ | 0 |
| C-0195 | H | H | H | H | H | 3-S(=O)$_2$CF$_3$ | 0 |

TABLE 198-continued

| compound | R$^1$ | R$^2$ | R$^3$ | R$^4$ | R$^5$ | (R$^8$)$_m$ | p |
|---|---|---|---|---|---|---|---|
| C-0196 | H | H | H | H | H | 4-S(=O)$_2$CF$_3$ | 0 |
| C-0197 | H | H | H | H | H | 2-SCF(CF$_3$)$_2$ | 0 |
| C-0198 | H | H | H | H | H | 3-SCF(CF$_3$)$_2$ | 0 |
| C-0199 | H | H | H | H | H | 4-SCF(CF$_3$)$_2$ | 0 |
| C-0200 | H | H | H | H | H | 2-(cyclopropylthio) | 0 |
| C-0201 | H | H | H | H | H | 3-(cyclopropylthio) | 0 |
| C-0202 | H | H | H | H | H | 4-(cyclopropylthio) | 0 |
| C-0203 | H | H | H | H | H | 2-(cyclopropylsulfinyl) | 0 |
| C-0204 | H | H | H | H | H | 3-(cyclopropylsulfinyl) | 0 |
| C-0205 | H | H | H | H | H | 4-(cyclopropylsulfinyl) | 0 |
| C-0206 | H | H | H | H | H | 2-(cyclopropylsulfonyl) | 0 |
| C-0207 | H | H | H | H | H | 3-(cyclopropylsulfonyl) | 0 |
| C-0208 | H | H | H | H | H | 4-(cyclopropylsulfonyl) | 0 |
| C-0209 | H | H | H | H | H | 2-((cyclopropylmethyl)thio) | 0 |
| C-0210 | H | H | H | H | H | 3-((cyclopropylmethyl)thio) | 0 |
| C-0211 | H | H | H | H | H | 4-((cyclopropylmethyl)thio) | 0 |
| C-0212 | H | H | H | H | H | 2-((cyclopropylmethyl)sulfinyl) | 0 |
| C-0213 | H | H | H | H | H | 3-((cyclopropylmethyl)sulfinyl) | 0 |
| C-0214 | H | H | H | H | H | 4-((cyclopropylmethyl)sulfinyl) | 0 |
| C-0215 | H | H | H | H | H | 2-((cyclopropylmethyl)sulfonyl) | 0 |
| C-0216 | H | H | H | H | H | 3-((cyclopropylmethyl)sulfonyl) | 0 |
| C-0217 | H | H | H | H | H | 4-((cyclopropylmethyl)sulfonyl) | 0 |
| C-0218 | H | H | H | H | H | 2-(((2,2-difluorocyclopropyl)methyl)thio) | 0 |
| C-0219 | H | H | H | H | H | 3-(((2,2-difluorocyclopropyl)methyl)thio) | 0 |

TABLE 199

| compound | R$^1$ | R$^2$ | R$^3$ | R$^4$ | R$^5$ | (R$^8$)$_m$ | p |
|---|---|---|---|---|---|---|---|
| C-0220 | H | H | H | H | H | 4-(((2,2-difluorocyclopropyl)methyl)thio) | 0 |
| C-0221 | H | H | H | H | H | 2-(((2,2-difluorocyclopropyl)methyl)sulfinyl) | 0 |
| C-0222 | H | H | H | H | H | 3-(((2,2-difluorocyclopropyl)methyl)sulfinyl) | 0 |
| C-0223 | H | H | H | H | H | 4-(((2,2-difluorocyclopropyl)methyl)sulfinyl) | 0 |
| C-0224 | H | H | H | H | H | 2-(((2,2-difluorocyclopropyl)methyl)sulfonyl) | 0 |
| C-0225 | H | H | H | H | H | 3-(((2,2-difluorocyclopropyl)methyl)sulfonyl) | 0 |
| C-0226 | H | H | H | H | H | 4-(((2,2-difluorocyclopropyl)methyl)sulfonyl) | 0 |
| C-0227 | H | H | H | H | H | 2-C(=O)Me | 0 |
| C-0228 | H | H | H | H | H | 3-C(=O)Me | 0 |
| C-0229 | H | H | H | H | H | 4-C(=O)Me | 0 |
| C-0230 | H | H | H | H | H | 2-C(=O)Et | 0 |
| C-0231 | H | H | H | H | H | 3-C(=O)Et | 0 |
| C-0232 | H | H | H | H | H | 4-C(=O)Et | 0 |
| C-0233 | H | H | H | H | H | 2-C(=O)CF$_3$ | 0 |
| C-0234 | H | H | H | H | H | 3-C(=O)CF$_3$ | 0 |
| C-0235 | H | H | H | H | H | 4-C(=O)CF$_3$ | 0 |
| C-0236 | H | H | H | H | H | 2-C(=O)OMe | 0 |
| C-0237 | H | H | H | H | H | 3-C(=O)OMe | 0 |
| C-0238 | H | H | H | H | H | 4-C(=O)OMe | 0 |
| C-0239 | H | H | H | H | H | 2-C(=O)OEt | 0 |
| C-0240 | H | H | H | H | H | 3-C(=O)OEt | 0 |
| C-0241 | H | H | H | H | H | 4-C(=O)OEt | 0 |
| C-0242 | H | H | H | H | H | 2-C(=O)NH$_2$ | 0 |
| C-0243 | H | H | H | H | H | 3-C(=O)NH$_2$ | 0 |
| C-0244 | H | H | H | H | H | 4-C(=O)NH$_2$ | 0 |
| C-0245 | H | H | H | H | H | 2-C(=O)NHMe | 0 |
| C-0246 | H | H | H | H | H | 3-C(=O)NHMe | 0 |
| C-0247 | H | H | H | H | H | 4-C(=O)NHMe | 0 |
| C-0248 | H | H | H | H | H | 2-C(=O)NMe$_2$ | 0 |
| C-0249 | H | H | H | H | H | 3-C(=O)NMe$_2$ | 0 |
| C-0250 | H | H | H | H | H | 4-C(=O)NMe$_2$ | 0 |
| C-0251 | H | H | H | H | H | 2-CH$_2$C(=O)CH$_3$ | 0 |
| C-0252 | H | H | H | H | H | 3-CH$_2$C(=O)CH$_3$ | 0 |
| C-0253 | H | H | H | H | H | 4-CH$_2$C(=O)CH$_3$ | 0 |
| C-0254 | H | H | H | H | H | 2-CH$_2$C(=O)CF$_3$ | 0 |

TABLE 199-continued

| compound | R¹ | R² | R³ | R⁴ | R⁵ | (R⁸)ₘ | p |
|---|---|---|---|---|---|---|---|
| C-0255 | H | H | H | H | H | 3-CH$_2$C(=O)CF$_3$ | 0 |
| C-0256 | H | H | H | H | H | 4-CH$_2$C(=O)CF$_3$ | 0 |
| C-0257 | H | H | H | H | H | 2-CH$_2$C(=O)OCH$_3$ | 0 |
| C-0258 | H | H | H | H | H | 3-CH$_2$C(=O)OCH$_3$ | 0 |
| C-0259 | H | H | H | H | H | 4-CH$_2$C(=O)OCH$_3$ | 0 |
| C-0260 | H | H | H | H | H | 2-CH$_2$OH | 0 |
| C-0261 | H | H | H | H | H | 3-CH$_2$OH | 0 |
| C-0262 | H | H | H | H | H | 4-CH$_2$OH | 0 |
| C-0263 | H | H | H | H | H | 2-CH$_2$OCH$_3$ | 0 |
| C-0264 | H | H | H | H | H | 3-CH$_2$OCH$_3$ | 0 |
| C-0265 | H | H | H | H | H | 4-CH$_2$OCH$_3$ | 0 |
| C-0266 | H | H | H | H | H | 2-CH$_2$OCH$_2$CH$_3$ | 0 |
| C-0267 | H | H | H | H | H | 3-CH$_2$OCH$_2$CH$_3$ | 0 |
| C-0268 | H | H | H | H | H | 4-CH$_2$OCH$_2$CH$_3$ | 0 |
| C-0269 | H | H | H | H | H | 2-CH(CH$_3$)OCH$_3$ | 0 |
| C-0270 | H | H | H | H | H | 3-CH(CH$_3$)OCH$_3$ | 0 |
| C-0271 | H | H | H | H | H | 4-CH(CH$_3$)OCH$_3$ | 0 |
| C-0272 | H | H | H | H | H | 2-CH$_2$CH$_2$OCH$_3$ | 0 |
| C-0273 | H | H | H | H | H | 3-CH$_2$CH$_2$OCH$_3$ | 0 |
| C-0274 | H | H | H | H | H | 4-CH$_2$CH$_2$OCH$_3$ | 0 |
| C-0275 | H | H | H | H | H | 2-CH$_2$OCF$_3$ | 0 |

TABLE 200

| compound | R¹ | R² | R³ | R⁴ | R⁵ | (R⁸)ₘ | p |
|---|---|---|---|---|---|---|---|
| C-0276 | H | H | H | H | H | 3-CH$_2$OCF$_3$ | 0 |
| C-0277 | H | H | H | H | H | 4-CH$_2$OCF$_3$ | 0 |
| C-0278 | H | H | H | H | H | 2-CF$_2$OCH$_3$ | 0 |
| C-0279 | H | H | H | H | H | 3-CF$_2$OCH$_3$ | 0 |
| C-0280 | H | H | H | H | H | 4-CF$_2$OCH$_3$ | 0 |
| C-0281 | H | H | H | H | H | 2-CF$_2$CF$_2$OCF$_3$ | 0 |
| C-0282 | H | H | H | H | H | 3-CF$_2$CF$_2$OCF$_3$ | 0 |
| C-0283 | H | H | H | H | H | 4-CF$_2$CF$_2$OCF$_3$ | 0 |
| C-0284 | H | H | H | H | H | 2-OC(=O)CH$_3$ | 0 |
| C-0285 | H | H | H | H | H | 3-OC(=O)CH$_3$ | 0 |
| C-0286 | H | H | H | H | H | 4-OC(=O)CH$_3$ | 0 |
| C-0287 | H | H | H | H | H | 2-OC(=O)CF$_3$ | 0 |
| C-0288 | H | H | H | H | H | 3-OC(=O)CF$_3$ | 0 |
| C-0289 | H | H | H | H | H | 4-OC(=O)CF$_3$ | 0 |
| C-0290 | H | H | H | H | H | 2-OC(=O)NH$_2$ | 0 |
| C-0291 | H | H | H | H | H | 3-OC(=O)NH$_2$ | 0 |
| C-0292 | H | H | H | H | H | 4-OC(=O)NH$_2$ | 0 |
| C-0293 | H | H | H | H | H | 2-OC(=O)NHCH$_3$ | 0 |
| C-0294 | H | H | H | H | H | 3-OC(=O)NHCH$_3$ | 0 |
| C-0295 | H | H | H | H | H | 4-OC(=O)NHCH$_3$ | 0 |
| C-0296 | H | H | H | H | H | 2-OC(=O)N(CH$_3$)$_2$ | 0 |
| C-0297 | H | H | H | H | H | 3-OC(=O)N(CH$_3$)$_2$ | 0 |
| C-0298 | H | H | H | H | H | 4-OC(=O)N(CH$_3$)$_2$ | 0 |
| C-0299 | H | H | H | H | H | 2-CH$_2$OC(=O)NH$_2$ | 0 |
| C-0300 | H | H | H | H | H | 3-CH$_2$OC(=O)NH$_2$ | 0 |
| C-0301 | H | H | H | H | H | 4-CH$_2$OC(=O)NH$_2$ | 0 |
| C-0302 | H | H | H | H | H | 2-CH$_2$OC(=O)NHCH$_3$ | 0 |
| C-0303 | H | H | H | H | H | 3-CH$_2$OC(=O)NHCH$_3$ | 0 |
| C-0304 | H | H | H | H | H | 4-CH$_2$OC(=O)NHCH$_3$ | 0 |
| C-0305 | H | H | H | H | H | 2-CH$_2$OC(=O)N(CH$_3$)$_2$ | 0 |
| C-0306 | H | H | H | H | H | 3-CH$_2$OC(=O)N(CH$_3$)$_2$ | 0 |
| C-0307 | H | H | H | H | H | 4-CH$_2$OC(=O)N(CH$_3$)$_2$ | 0 |
| C-0308 | H | H | H | H | H | 2-OC(=O)OCH$_3$ | 0 |
| C-0309 | H | H | H | H | H | 3-OC(=O)OCH$_3$ | 0 |
| C-0310 | H | H | H | H | H | 4-OC(=O)OCH$_3$ | 0 |
| C-0311 | H | H | H | H | H | 2-CH$_2$OC(=O)OCH$_3$ | 0 |
| C-0312 | H | H | H | H | H | 3-CH$_2$OC(=O)OCH$_3$ | 0 |
| C-0313 | H | H | H | H | H | 4-CH$_2$OC(=O)OCH$_3$ | 0 |
| C-0314 | H | H | H | H | H | 2-CH$_2$OC(=O)CH$_3$ | 0 |
| C-0315 | H | H | H | H | H | 3-CH$_2$OC(=O)CH$_3$ | 0 |
| C-0316 | H | H | H | H | H | 4-CH$_2$OC(=O)CH$_3$ | 0 |
| C-0317 | H | H | H | H | H | 2-OS(=O)$_2$CH$_3$ | 0 |
| C-0318 | H | H | H | H | H | 3-OS(=O)$_2$CH$_3$ | 0 |
| C-0319 | H | H | H | H | H | 4-OS(=O)$_2$CH$_3$ | 0 |
| C-0320 | H | H | H | H | H | 2-CH$_2$SCH$_3$ | 0 |
| C-0321 | H | H | H | H | H | 3-CH$_2$SCH$_3$ | 0 |
| C-0322 | H | H | H | H | H | 4-CH$_2$SCH$_3$ | 0 |
| C-0323 | H | H | H | H | H | 2-CH$_2$S(=O)CH$_3$ | 0 |
| C-0324 | H | H | H | H | H | 3-CH$_2$S(=O)CH$_3$ | 0 |
| C-0325 | H | H | H | H | H | 4-CH$_2$S(=O)CH$_3$ | 0 |
| C-0326 | H | H | H | H | H | 2-CH$_2$S(=O)$_2$CH$_3$ | 0 |
| C-0327 | H | H | H | H | H | 3-CH$_2$S(=O)$_2$CH$_3$ | 0 |
| C-0328 | H | H | H | H | H | 4-CH$_2$S(=O)$_2$CH$_3$ | 0 |
| C-0329 | H | H | H | H | H | 2-CH$_2$SCF$_3$ | 0 |
| C-0330 | H | H | H | H | H | 3-CH$_2$SCF$_3$ | 0 |
| C-0331 | H | H | H | H | H | 4-CH$_2$SCF$_3$ | 0 |

TABLE 201

| compound | R¹ | R² | R³ | R⁴ | R⁵ | (R⁸)ₘ | p |
|---|---|---|---|---|---|---|---|
| C-0332 | H | H | H | H | H | 2-CH$_2$S(=O)CF$_3$ | 0 |
| C-0333 | H | H | H | H | H | 3-CH$_2$S(=O)CF$_3$ | 0 |
| C-0334 | H | H | H | H | H | 4-CH$_2$S(=O)CF$_3$ | 0 |
| C-0335 | H | H | H | H | H | 2-CH$_2$S(=O)$_2$CF$_3$ | 0 |
| C-0336 | H | H | H | H | H | 3-CH$_2$S(=O)$_2$CF$_3$ | 0 |
| C-0337 | H | H | H | H | H | 4-CH$_2$S(=O)$_2$CF$_3$ | 0 |
| C-0338 | H | H | H | H | H | 2-phenyl | 0 |
| C-0339 | H | H | H | H | H | 3-phenyl | 0 |
| C-0340 | H | H | H | H | H | 4-phenyl | 0 |
| C-0341 | H | H | H | H | H | 2-(phenyloxy) | 0 |
| C-0342 | H | H | H | H | H | 3-(phenyloxy) | 0 |
| C-0343 | H | H | H | H | H | 4-(phenyloxy) | 0 |
| C-0344 | H | H | H | H | H | 2-benzyl | 0 |
| C-0345 | H | H | H | H | H | 3-benzyl | 0 |
| C-0346 | H | H | H | H | H | 4-benzyl | 0 |
| C-0347 | H | H | H | H | H | 2-(benzyloxy) | 0 |
| C-0348 | H | H | H | H | H | 3-(benzyloxy) | 0 |
| C-0349 | H | H | H | H | H | 4-(benzyloxy) | 0 |
| C-0350 | H | H | H | H | H | 2-((2-fluorobenzyl)oxy) | 0 |
| C-0351 | H | H | H | H | H | 3-((2-fluorobenzyl)oxy) | 0 |
| C-0352 | H | H | H | H | H | 4-((2-fluorobenzyl)oxy) | 0 |
| C-0353 | H | H | H | H | H | 2-((3-fluorobenzyl)oxy) | 0 |
| C-0354 | H | H | H | H | H | 3-((3-fluorobenzyl)oxy) | 0 |
| C-0355 | H | H | H | H | H | 4-((3-fluorobenzyl)oxy) | 0 |
| C-0356 | H | H | H | H | H | 2-((4-fluorobenzyl)oxy) | 0 |
| C-0357 | H | H | H | H | H | 3-((4-fluorobenzyl)oxy) | 0 |
| C-0358 | H | H | H | H | H | 4-((4-fluorobenzyl)oxy) | 0 |
| C-0359 | H | H | H | H | H | 2-((2-chlorobenzyl)oxy) | 0 |
| C-0360 | H | H | H | H | H | 3-((2-chlorobenzyl)oxy) | 0 |
| C-0361 | H | H | H | H | H | 4-((2-chlorobenzyl)oxy) | 0 |
| C-0362 | H | H | H | H | H | 2-((3-chlorobenzyl)oxy) | 0 |
| C-0363 | H | H | H | H | H | 3-((3-chlorobenzyl)oxy) | 0 |
| C-0364 | H | H | H | H | H | 4-((3-chlorobenzyl)oxy) | 0 |
| C-0365 | H | H | H | H | H | 2-((4-chlorobenzyl)oxy) | 0 |
| C-0366 | H | H | H | H | H | 3-((4-chlorobenzyl)oxy) | 0 |
| C-0367 | H | H | H | H | H | 4-((4-chlorobenzyl)oxy) | 0 |
| C-0368 | H | H | H | H | H | 2-((2-methylbenzyl)oxy) | 0 |
| C-0369 | H | H | H | H | H | 3-((2-methylbenzyl)oxy) | 0 |
| C-0370 | H | H | H | H | H | 4-((2-methylbenzyl)oxy) | 0 |
| C-0371 | H | H | H | H | H | 2-((3-methylbenzyl)oxy) | 0 |
| C-0372 | H | H | H | H | H | 3-((3-methylbenzyl)oxy) | 0 |
| C-0373 | H | H | H | H | H | 4-((3-methylbenzyl)oxy) | 0 |
| C-0374 | H | H | H | H | H | 2-((4-methylbenzyl)oxy) | 0 |
| C-0375 | H | H | H | H | H | 3-((4-methylbenzyl)oxy) | 0 |
| C-0376 | H | H | H | H | H | 4-((4-methylbenzyl)oxy) | 0 |
| C-0377 | H | H | H | H | H | 2-((2-(trifluoromethyl)benzyl)oxy) | 0 |
| C-0378 | H | H | H | H | H | 3-((2-(trifluoromethyl)benzyl)oxy) | 0 |
| C-0379 | H | H | H | H | H | 4-((2-(trifluoromethyl)benzyl)oxy) | 0 |
| C-0380 | H | H | H | H | H | 2-((3-(trifluoromethyl)benzyl)oxy) | 0 |
| C-0381 | H | H | H | H | H | 3-((3-(trifluoromethyl)benzyl)oxy) | 0 |
| C-0382 | H | H | H | H | H | 4-((3-(trifluoromethyl)benzyl)oxy) | 0 |
| C-0383 | H | H | H | H | H | 2-((4-(trifluoromethyl)benzyl)oxy) | 0 |
| C-0384 | H | H | H | H | H | 3-((4-(trifluoromethyl)benzyl)oxy) | 0 |
| C-0385 | H | H | H | H | H | 4-((4-(trifluoromethyl)benzyl)oxy) | 0 |
| C-0386 | H | H | H | H | H | 2-((2-methoxybenzyl)oxy) | 0 |
| C-0387 | H | H | H | H | H | 3-((2-methoxybenzyl)oxy) | 0 |

TABLE 202

| compound | R¹ | R² | R³ | R⁴ | R⁵ | (R⁸)ₘ | p |
|---|---|---|---|---|---|---|---|
| C-0388 | H | H | H | H | H | 4-((2-methoxybenzyl)oxy) | 0 |
| C-0389 | H | H | H | H | H | 2-((3-methoxybenzyl)oxy) | 0 |
| C-0390 | H | H | H | H | H | 3-((3-methoxybenzyl)oxy) | 0 |
| C-0391 | H | H | H | H | H | 4-((3-methoxybenzyl)oxy) | 0 |
| C-0392 | H | H | H | H | H | 2-((4-methoxybenzyl)oxy) | 0 |
| C-0393 | H | H | H | H | H | 3-((4-methoxybenzyl)oxy) | 0 |
| C-0394 | H | H | H | H | H | 4-((4-methoxybenzyl)oxy) | 0 |
| C-0395 | H | H | H | H | H | 2-((2-(trifluoromethoxy)benzyl)oxy) | 0 |
| C-0396 | H | H | H | H | H | 3-((2-(trifluoromethoxy)benzyl)oxy) | 0 |
| C-0397 | H | H | H | H | H | 4-((2-(trifluoromethoxy)benzyl)oxy) | 0 |
| C-0398 | H | H | H | H | H | 2-((3-(trifluoromethoxy)benzyl)oxy) | 0 |
| C-0399 | H | H | H | H | H | 3-((3-(trifluoromethoxy)benzyl)oxy) | 0 |
| C-0400 | H | H | H | H | H | 4-((3-(trifluoromethoxy)benzyl)oxy) | 0 |
| C-0401 | H | H | H | H | H | 2-((4-(trifluoromethoxy)benzyl)oxy) | 0 |
| C-0402 | H | H | H | H | H | 3-((4-(trifluoromethoxy)benzyl)oxy) | 0 |
| C-0403 | H | H | H | H | H | 4-((4-(trifluoromethoxy)benzyl)oxy) | 0 |
| C-0404 | H | H | H | H | H | 2-((2-(methylthio)benzyl)oxy) | 0 |
| C-0405 | H | H | H | H | H | 3-((2-(methylthio)benzyl)oxy) | 0 |
| C-0406 | H | H | H | H | H | 4-((2-(methylthio)benzyl)oxy) | 0 |
| C-0407 | H | H | H | H | H | 2-((3-(methylthio)benzyl)oxy) | 0 |
| C-0408 | H | H | H | H | H | 3-((3-(methylthio)benzyl)oxy) | 0 |
| C-0409 | H | H | H | H | H | 4-((3-(methylthio)benzyl)oxy) | 0 |
| C-0410 | H | H | H | H | H | 2-((4-(methylthio)benzyl)oxy) | 0 |
| C-0411 | H | H | H | H | H | 3-((4-(methylthio)benzyl)oxy) | 0 |
| C-0412 | H | H | H | H | H | 4-((4-(methylthio)benzyl)oxy) | 0 |
| C-0413 | H | H | H | H | H | 2-((2-(methylsulfinyl)benzyl)oxy) | 0 |
| C-0414 | H | H | H | H | H | 3-((2-(methylsulfinyl)benzyl)oxy) | 0 |
| C-0415 | H | H | H | H | H | 4-((2-(methylsulfinyl)benzyl)oxy) | 0 |
| C-0416 | H | H | H | H | H | 2-((3-(methylsulfinyl)benzyl)oxy) | 0 |
| C-0417 | H | H | H | H | H | 3-((3-(methylsulfinyl)benzyl)oxy) | 0 |
| C-0418 | H | H | H | H | H | 4-((3-(methylsulfinyl)benzyl)oxy) | 0 |
| C-0419 | H | H | H | H | H | 2-((4-(methylsulfinyl)benzyl)oxy) | 0 |
| C-0420 | H | H | H | H | H | 3-((4-(methylsulfinyl)benzyl)oxy) | 0 |
| C-0421 | H | H | H | H | H | 4-((4-(methylsulfinyl)benzyl)oxy) | 0 |
| C-0422 | H | H | H | H | H | 2-((2-(methylsulfonyl)benzyl)oxy) | 0 |
| C-0423 | H | H | H | H | H | 3-((2-(methylsulfonyl)benzyl)oxy) | 0 |
| C-0424 | H | H | H | H | H | 4-((2-(methylsulfonyl)benzyl)oxy) | 0 |
| C-0425 | H | H | H | H | H | 2-((3-(methylsulfonyl)benzyl)oxy) | 0 |
| C-0426 | H | H | H | H | H | 3-((3-(methylsulfonyl)benzyl)oxy) | 0 |
| C-0427 | H | H | H | H | H | 4-((3-(methylsulfonyl)benzyl)oxy) | 0 |
| C-0428 | H | H | H | H | H | 2-((4-(methylsulfonyl)benzyl)oxy) | 0 |
| C-0429 | H | H | H | H | H | 3-((4-(methylsulfonyl)benzyl)oxy) | 0 |
| C-0430 | H | H | H | H | H | 4-((4-(methylsulfonyl)benzyl)oxy) | 0 |
| C-0431 | H | H | H | H | H | 2-((2-(trifluoromethylthio)benzyl)oxy) | 0 |
| C-0432 | H | H | H | H | H | 3-((2-(trifluoromethylthio)benzyl)oxy) | 0 |
| C-0433 | H | H | H | H | H | 4-((2-(trifluoromethylthio)benzyl)oxy) | 0 |
| C-0434 | H | H | H | H | H | 2-((3-(trifluoromethylthio)benzyl)oxy) | 0 |
| C-0435 | H | H | H | H | H | 3-((3-(trifluoromethylthio)benzyl)oxy) | 0 |
| C-0436 | H | H | H | H | H | 4-((3-(trifluoromethylthio)benzyl)oxy) | 0 |
| C-0437 | H | H | H | H | H | 2-((4-(trifluoromethylthio)benzyl)oxy) | 0 |
| C-0438 | H | H | H | H | H | 3-((4-(trifluoromethylthio)benzyl)oxy) | 0 |
| C-0439 | H | H | H | H | H | 4-((4-(trifluoromethylthio)benzyl)oxy) | 0 |
| C-0440 | H | H | H | H | H | 2-((2-(trifluoromethylsulfinyl)benzyl)oxy) | 0 |
| C-0441 | H | H | H | H | H | 3-((2-(trifluoromethylsulfinyl)benzyl)oxy) | 0 |
| C-0442 | H | H | H | H | H | 4-((2-(trifluoromethylsulfinyl)benzyl)oxy) | 0 |
| C-0443 | H | H | H | H | H | 2-((3-(trifluoromethylsulfinyl)benzyl)oxy) | 0 |

TABLE 203

| compound | R¹ | R² | R³ | R⁴ | R⁵ | (R⁸)ₘ | p |
|---|---|---|---|---|---|---|---|
| C-0444 | H | H | H | H | H | 3-((3-(trifluoromethylsulfinyl)benzyl)oxy) | 0 |
| C-0445 | H | H | H | H | H | 4-((3-(trifluoromethylsulfinyl)benzyl)oxy) | 0 |
| C-0446 | H | H | H | H | H | 2-((4-(trifluoromethylsulfinyl)benzyl)oxy) | 0 |
| C-0447 | H | H | H | H | H | 3-((4-(trifluoromethylsulfinyl)benzyl)oxy) | 0 |
| C-0448 | H | H | H | H | H | 4-((4-(trifluoromethylsulfinyl)benzyl)oxy) | 0 |
| C-0449 | H | H | H | H | H | 2-((2-(trifluoromethylsulfonyl)benzyl)oxy) | 0 |
| C-0450 | H | H | H | H | H | 3-((2-(trifluoromethylsulfonyl)benzyl)oxy) | 0 |
| C-0451 | H | H | H | H | H | 4-((2-(trifluoromethylsulfonyl)benzyl)oxy) | 0 |
| C-0452 | H | H | H | H | H | 2-((3-(trifluoromethylsulfonyl)benzyl)oxy) | 0 |
| C-0453 | H | H | H | H | H | 3-((3-(trifluoromethysulfonyl)benzyl)oxy) | 0 |
| C-0454 | H | H | H | H | H | 4-((3-(trifluoromethylsulfonyl)benzyl)oxy) | 0 |
| C-0455 | H | H | H | H | H | 2-((4-(trifluoromethylsulfonyl)benzyl)oxy) | 0 |
| C-0456 | H | H | H | H | H | 3-((4-(trifluoromethylsulfonyl)benzyl)oxy) | 0 |
| C-0457 | H | H | H | H | H | 4-((4-(trifluoromethylsulfonyl)benzyl)oxy) | 0 |
| C-0458 | H | H | H | H | H | 2-((2-aminobenzyl)oxy) | 0 |
| C-0459 | H | H | H | H | H | 3-((2-aminobenzyl)oxy) | 0 |
| C-0460 | H | H | H | H | H | 4-((2-aminobenzyl)oxy) | 0 |
| C-0461 | H | H | H | H | H | 2-((3-aminobenzyl)oxy) | 0 |
| C-0462 | H | H | H | H | H | 3-((3-aminobenzyl)oxy) | 0 |
| C-0463 | H | H | H | H | H | 4-((3-aminobenzyl)oxy) | 0 |
| C-0464 | H | H | H | H | H | 2-((4-aminobenzyl)oxy) | 0 |
| C-0465 | H | H | H | H | H | 3-((4-aminobenzyl)oxy) | 0 |
| C-0466 | H | H | H | H | H | 4-((4-aminobenzyl)oxy) | 0 |
| C-0467 | H | H | H | H | H | 2-((2-(methylamino)benzyl)oxy) | 0 |
| C-0468 | H | H | H | H | H | 3-((2-(methylamino)benzyl)oxy) | 0 |
| C-0469 | H | H | H | H | H | 4-((2-(methylamino)benzyl)oxy) | 0 |
| C-0470 | H | H | H | H | H | 2-((3-(methylamino)benzyl)oxy) | 0 |
| C-0471 | H | H | H | H | H | 3-((3-(methylamino)benzyl)oxy) | 0 |
| C-0472 | H | H | H | H | H | 4-((3-(methylamino)benzyl)oxy) | 0 |
| C-0473 | H | H | H | H | H | 2-((4-(methylamino)benzyl)oxy) | 0 |
| C-0474 | H | H | H | H | H | 3-((4-(methylamino)benzyl)oxy) | 0 |
| C-0475 | H | H | H | H | H | 4-((4-(methylamino)benzyl)oxy) | 0 |
| C-0476 | H | H | H | H | H | 2-((2-(dimethylamino)benzyl)oxy) | 0 |
| C-0477 | H | H | H | H | H | 3-((2-(dimethylamino)benzyl)oxy) | 0 |
| C-0478 | H | H | H | H | H | 4-((2-(dimethylamino)benzyl)oxy) | 0 |
| C-0479 | H | H | H | H | H | 2-((3-(dimethylamino)benzyl)oxy) | 0 |
| C-0480 | H | H | H | H | H | 3-((3-(dimethylamino)benzyl)oxy) | 0 |
| C-0481 | H | H | H | H | H | 4-((3-(dimethylamino)benzyl)oxy) | 0 |
| C-0482 | H | H | H | H | H | 2-((4-(dimethylamino)benzyl)oxy) | 0 |
| C-0483 | H | H | H | H | H | 3-((4-(dimethylamino)benzyl)oxy) | 0 |
| C-0484 | H | H | H | H | H | 4-((4-(dimethylamino)benzyl)oxy) | 0 |
| C-0485 | H | H | H | H | H | 2-((2-cyanobenzyl)oxy) | 0 |
| C-0486 | H | H | H | H | H | 3-((2-cyanobenzyl)oxy) | 0 |
| C-0487 | H | H | H | H | H | 4-((2-cyanobenzyl)oxy) | 0 |
| C-0488 | H | H | H | H | H | 2-((3-cyanobenzyl)oxy) | 0 |
| C-0489 | H | H | H | H | H | 3-((3-cyanobenzyl)oxy) | 0 |
| C-0490 | H | H | H | H | H | 4-((3-cyanobenzyl)oxy) | 0 |
| C-0491 | H | H | H | H | H | 2-((4-cyanobenzyl)oxy) | 0 |
| C-0492 | H | H | H | H | H | 3-((4-cyanobenzyl)oxy) | 0 |
| C-0493 | H | H | H | H | H | 4-((4-cyanobenzyl)oxy) | 0 |
| C-0494 | H | H | H | H | H | 2-((2-nitrobenzyl)oxy) | 0 |
| C-0495 | H | H | H | H | H | 3-((2-nitrobenzyl)oxy) | 0 |
| C-0496 | H | H | H | H | H | 4-((2-nitrobenzyl)oxy) | 0 |
| C-0497 | H | H | H | H | H | 2-((3-nitrobenzyl)oxy) | 0 |
| C-0498 | H | H | H | H | H | 3-((3-nitrobenzyl)oxy) | 0 |
| C-0499 | H | H | H | H | H | 4-((3-nitrobenzyl)oxy) | 0 |

TABLE 204

| compound | R¹ | R² | R³ | R⁴ | R⁵ | (R⁸)ₘ | p |
|---|---|---|---|---|---|---|---|
| C-0500 | H | H | H | H | H | 2-((4-nitrobenzyl)oxy) | 0 |
| C-0501 | H | H | H | H | H | 3-((4-nitrobenzyl)oxy) | 0 |
| C-0502 | H | H | H | H | H | 4-((4-nitrobenzyl)oxy) | 0 |
| C-0503 | H | H | H | H | H | 2-NH₂ | 0 |
| C-0504 | H | H | H | H | H | 3-NH₂ | 0 |
| C-0505 | H | H | H | H | H | 4-NH₂ | 0 |
| C-0506 | H | H | H | H | H | 2-NHMe | 0 |

TABLE 204-continued

| compound | R¹ | R² | R³ | R⁴ | R⁵ | (R⁸)ₘ | p |
|---|---|---|---|---|---|---|---|
| C-0507 | H | H | H | H | H | 3-NHMe | 0 |
| C-0508 | H | H | H | H | H | 4-NHMe | 0 |
| C-0509 | H | H | H | H | H | 2-NHEt | 0 |
| C-0510 | H | H | H | H | H | 3-NHEt | 0 |
| C-0511 | H | H | H | H | H | 4-NHEt | 0 |
| C-0512 | H | H | H | H | H | 2-N(Me)₂ | 0 |
| C-0513 | H | H | H | H | H | 3-N(Me)₂ | 0 |
| C-0514 | H | H | H | H | H | 4-N(Me)₂ | 0 |
| C-0515 | H | H | H | H | H | 2-N(Et)₂ | 0 |
| C-0516 | H | H | H | H | H | 3-N(Et)₂ | 0 |
| C-0517 | H | H | H | H | H | 4-N(Et)₂ | 0 |
| C-0518 | H | H | H | H | H | 2-CHO | 0 |
| C-0519 | H | H | H | H | H | 3-CHO | 0 |
| C-0520 | H | H | H | H | H | 4-CHO | 0 |
| C-0521 | H | H | H | H | H | 2-C(=O)OH | 0 |
| C-0522 | H | H | H | H | H | 3-C(=O)OH | 0 |
| C-0523 | H | H | H | H | H | 4-C(=O)OH | 0 |
| C-0524 | H | H | H | H | H | 2-(1,3-dioxolan-2-yl) | 0 |
| C-0525 | H | H | H | H | H | 3-(1,3-dioxolan-2-yl) | 0 |
| C-0526 | H | H | H | H | H | 4-(1,3-dioxolan-2-yl) | 0 |
| C-0527 | H | H | H | H | H | 2-(1,3-dioxan-2-yl) | 0 |
| C-0528 | H | H | H | H | H | 3-(1,3-dioxan-2-yl) | 0 |
| C-0529 | H | H | H | H | H | 4-(1,3-dioxan-2-yl) | 0 |
| C-0530 | H | H | H | H | H | 2-(1H-imidazol-2-yl) | 0 |
| C-0531 | H | H | H | H | H | 3-(1H-imidazol-2-yl) | 0 |
| C-0532 | H | H | H | H | H | 4-(1H-imidazol-2-yl) | 0 |
| C-0533 | H | H | H | H | H | 2-(thiazol-2-yl) | 0 |
| C-0534 | H | H | H | H | H | 3-(thiazol-2-yl) | 0 |
| C-0535 | H | H | H | H | H | 4-(thiazol-2-yl) | 0 |
| C-0536 | H | H | H | H | H | 2-(oxazol-2-yl) | 0 |
| C-0537 | H | H | H | H | H | 3-(oxazol-2-yl) | 0 |
| C-0538 | H | H | H | H | H | 4-(oxazo-2-yl) | 0 |
| C-0539 | H | H | H | H | H | 2-CH=NOH | 0 |
| C-0540 | H | H | H | H | H | 3-CH=NOH | 0 |
| C-0541 | H | H | H | H | H | 4-CH=NOH | 0 |
| C-0542 | H | H | H | H | H | 2-CH=NOMe | 0 |
| C-0543 | H | H | H | H | H | 3-CH=NOMe | 0 |
| C-0544 | H | H | H | H | H | 4-CH=NOMe | 0 |
| C-0545 | H | H | H | H | H | 2-(4,5-dihydro-3-isoxazolyl) | 0 |
| C-0546 | H | H | H | H | H | 3-(4,5-dihydro-3-isoxazolyl) | 0 |
| C-0547 | H | H | H | H | H | 4-(4,5-dihydro-3-isoxazolyl) | 0 |
| C-0548 | H | H | H | H | H | 2-CN | 0 |
| C-0549 | H | H | H | H | H | 3-CN | 0 |
| C-0550 | H | H | H | H | H | 4-CN | 0 |
| C-0551 | H | H | H | H | H | 2-NO₂ | 0 |
| C-0552 | H | H | H | H | H | 3-NO₂ | 0 |
| C-0553 | H | H | H | H | H | 4-NO₂ | 0 |
| C-0554 | H | H | H | H | H | 2,3-F₂ | 0 |
| C-0555 | H | H | H | H | H | 2,4-F₂ | 0 |

TABLE 205

| compound | R¹ | R² | R³ | R⁴ | R⁵ | (R⁸)ₘ | p |
|---|---|---|---|---|---|---|---|
| C-0556 | H | H | H | H | H | 2,5-F₂ | 0 |
| C-0557 | H | H | H | H | H | 2,6-F₂ | 0 |
| C-0558 | H | H | H | H | H | 3,4-F₂ | 0 |
| C-0559 | H | H | H | H | H | 3,5-F₂ | 0 |
| C-0560 | H | H | H | H | H | 2-F,3-Cl | 0 |
| C-0561 | H | H | H | H | H | 2-F,4-Cl | 0 |
| C-0562 | H | H | H | H | H | 2-F,5-Cl | 0 |
| C-0563 | H | H | H | H | H | 2-F,6-Cl | 0 |
| C-0564 | H | H | H | H | H | 3-F,2-Cl | 0 |
| C-0565 | H | H | H | H | H | 3-F,4-Cl | 0 |
| C-0566 | H | H | H | H | H | 3-F,5-Cl | 0 |
| C-0567 | H | H | H | H | H | 3-F,6-Cl | 0 |
| C-0568 | H | H | H | H | H | 4-F,2-Cl | 0 |
| C-0569 | H | H | H | H | H | 4-F,3-Cl | 0 |
| C-0570 | H | H | H | H | H | 2-F,3-Me | 0 |
| C-0571 | H | H | H | H | H | 2-F,4-Me | 0 |
| C-0572 | H | H | H | H | H | 2-F,5-Me | 0 |
| C-0573 | H | H | H | H | H | 2-F,6-Me | 0 |
| C-0574 | H | H | H | H | H | 3-F,2-Me | 0 |
| C-0575 | H | H | H | H | H | 3-F,4-Me | 0 |
| C-0576 | H | H | H | H | H | 3-F,5-Me | 0 |

TABLE 205-continued

| compound | R¹ | R² | R³ | R⁴ | R⁵ | (R⁸)ₘ | p |
|---|---|---|---|---|---|---|---|
| C-0577 | H | H | H | H | H | 3-F,6-Me | 0 |
| C-0578 | H | H | H | H | H | 4-F,2-Me | 0 |
| C-0579 | H | H | H | H | H | 4-F,3-Me | 0 |
| C-0580 | H | H | H | H | H | 2-F,3-CF₃ | 0 |
| C-0581 | H | H | H | H | H | 2-F,4-CF₃ | 0 |
| C-0582 | H | H | H | H | H | 2-F,5-CF₃ | 0 |
| C-0583 | H | H | H | H | H | 2-F,6-CF₃ | 0 |
| C-0584 | H | H | H | H | H | 3-F,2-CF₃ | 0 |
| C-0585 | H | H | H | H | H | 3-F,4-CF₃ | 0 |
| C-0586 | H | H | H | H | H | 3-F,5-CF₃ | 0 |
| C-0587 | H | H | H | H | H | 3-F,6-CF₃ | 0 |
| C-0588 | H | H | H | H | H | 4-F,2-CF₃ | 0 |
| C-0589 | H | H | H | H | H | 4-F,3-CF₃ | 0 |
| C-0590 | H | H | H | H | H | 2-F,3-OMe | 0 |
| C-0591 | H | H | H | H | H | 2-F,4-OMe | 0 |
| C-0592 | H | H | H | H | H | 2-F,5-OMe | 0 |
| C-0593 | H | H | H | H | H | 2-F,6-OMe | 0 |
| C-0594 | H | H | H | H | H | 3-F,2-OMe | 0 |
| C-0595 | H | H | H | H | H | 3-F,4-OMe | 0 |
| C-0596 | H | H | H | H | H | 3-F,5-OMe | 0 |
| C-0597 | H | H | H | H | H | 3-F,6-OMe | 0 |
| C-0598 | H | H | H | H | H | 4-F,2-OMe | 0 |
| C-0599 | H | H | H | H | H | 4-F,3-OMe | 0 |
| C-0600 | H | H | H | H | H | 2,3-Cl₂ | 0 |
| C-0601 | H | H | H | H | H | 2,4-Cl₂ | 0 |
| C-0602 | H | H | H | H | H | 2,5-Cl₂ | 0 |
| C-0603 | H | H | H | H | H | 2,6-Cl₂ | 0 |
| C-0604 | H | H | H | H | H | 3,4-Cl₂ | 0 |
| C-0605 | H | H | H | H | H | 3,5-Cl₂ | 0 |
| C-0606 | H | H | H | H | H | 2-Cl,3-Me | 0 |
| C-0607 | H | H | H | H | H | 2-Cl,4-Me | 0 |
| C-0608 | H | H | H | H | H | 2-Cl,5-Me | 0 |
| C-0609 | H | H | H | H | H | 2-Cl,6-Me | 0 |
| C-0610 | H | H | H | H | H | 3-Cl,2-Me | 0 |
| C-0611 | H | H | H | H | H | 3-Cl,4-Me | 0 |

TABLE 206

| compound | R¹ | R² | R³ | R⁴ | R⁵ | (R⁸)ₘ | p |
|---|---|---|---|---|---|---|---|
| C-0612 | H | H | H | H | H | 3-Cl,5-Me | 0 |
| C-0613 | H | H | H | H | H | 3-Cl,6-Me | 0 |
| C-0614 | H | H | H | H | H | 4-Cl,2-Me | 0 |
| C-0615 | H | H | H | H | H | 4-Cl,3-Me | 0 |
| C-0616 | H | H | H | H | H | 2-Cl,3-CF₃ | 0 |
| C-0617 | H | H | H | H | H | 2-Cl,4-CF₃ | 0 |
| C-0618 | H | H | H | H | H | 2-Cl,5-CF | 0 |
| C-0619 | H | H | H | H | H | 2-Cl,6-CF₃ | 0 |
| C-0620 | H | H | H | H | H | 3-Cl,2-CF₃ | 0 |
| C-0621 | H | H | H | H | H | 3-Cl,4-CF₃ | 0 |
| C-0622 | H | H | H | H | H | 3-Cl,5-CF₃ | 0 |
| C-0623 | H | H | H | H | H | 3-Cl,6-CF₃ | 0 |
| C-0624 | H | H | H | H | H | 4-Cl,2-CF₃ | 0 |
| C-0625 | H | H | H | H | H | 4-Cl,3-CF₃ | 0 |
| C-0626 | H | H | H | H | H | 2-Cl,3-OMe | 0 |
| C-0627 | H | H | H | H | H | 2-Cl,4-OMe | 0 |
| C-0628 | H | H | H | H | H | 2-Cl,5-OMe | 0 |
| C-0629 | H | H | H | H | H | 2-Cl,6-OMe | 0 |
| C-0630 | H | H | H | H | H | 3-Cl,2-OMe | 0 |
| C-0631 | H | H | H | H | H | 3-Cl,4-OMe | 0 |
| C-0632 | H | H | H | H | H | 3-Cl,5-OMe | 0 |
| C-0633 | H | H | H | H | H | 3-Cl,6-OMe | 0 |
| C-0634 | H | H | H | H | H | 4-Cl,2-OMe | 0 |
| C-0635 | H | H | H | H | H | 4-Cl,3-OMe | 0 |
| C-0636 | H | H | H | H | H | 2,3-Me₂ | 0 |
| C-0637 | H | H | H | H | H | 2,4-Me₂ | 0 |
| C-0638 | H | H | H | H | H | 2,5-Me₂ | 0 |
| C-0639 | H | H | H | H | H | 2,6-Me₂ | 0 |
| C-0640 | H | H | H | H | H | 3,4-Me₂ | 0 |
| C-0641 | H | H | H | H | H | 3,5-Me₂ | 0 |
| C-0642 | H | H | H | H | H | 2-Me,3-CF₃ | 0 |
| C-0643 | H | H | H | H | H | 2-Me,4-CF₃ | 0 |
| C-0644 | H | H | H | H | H | 2-Me,5-CF₃ | 0 |
| C-0645 | H | H | H | H | H | 2-Me,6-CF₃ | 0 |
| C-0646 | H | H | H | H | H | 3-Me,2-CF₃ | 0 |

TABLE 206-continued

| compound | R¹ | R² | R³ | R⁴ | R⁵ | (R⁸)ₘ | p |
|---|---|---|---|---|---|---|---|
| C-0647 | H | H | H | H | H | 3-Me,4-CF₃ | 0 |
| C-0648 | H | H | H | H | H | 3-Me,5-CF₃ | 0 |
| C-0649 | H | H | H | H | H | 3-Me,6-CF₃ | 0 |
| C-0650 | H | H | H | H | H | 4-Me,2-CF₃ | 0 |
| C-0651 | H | H | H | H | H | 4-Me,3-CF₃ | 0 |
| C-0652 | H | H | H | H | H | 2-Me,3-OMe | 0 |
| C-0653 | H | H | H | H | H | 2-Me,4-OMe | 0 |
| C-0654 | H | H | H | H | H | 2-Me,5-OMe | 0 |
| C-0655 | H | H | H | H | H | 2-Me,6-OMe | 0 |
| C-0656 | H | H | H | H | H | 3-Me,2-OMe | 0 |
| C-0657 | H | H | H | H | H | 3-Me,4-OMe | 0 |
| C-0658 | H | H | H | H | H | 3-Me,5-OMe | 0 |
| C-0659 | H | H | H | H | H | 3-Me,6-OMe | 0 |
| C-0660 | H | H | H | H | H | 4-Me,2-OMe | 0 |
| C-0661 | H | H | H | H | H | 4-Me,3-OMe | 0 |
| C-0662 | H | H | H | H | H | 2,3-OMe₂ | 0 |
| C-0663 | H | H | H | H | H | 2,4-OMe₂ | 0 |
| C-0664 | H | H | H | H | H | 2,5-OMe₂ | 0 |
| C-0665 | H | H | H | H | H | 2,6-OMe₂ | 0 |
| C-0666 | H | H | H | H | H | 3,4-OMe₂ | 0 |
| C-0667 | H | H | H | H | H | 3,5-OMe₂ | 0 |

TABLE 207

| compound | R¹ | R² | R³ | R⁴ | R⁵ | (R⁸)ₘ | p |
|---|---|---|---|---|---|---|---|
| C-0668 | H | H | H | H | H | 2-OMe,3-CF₃ | 0 |
| C-0669 | H | H | H | H | H | 2-OMe,4-CF₃ | 0 |
| C-0670 | H | H | H | H | H | 2-OMe,5-CF₃ | 0 |
| C-0671 | H | H | H | H | H | 2-OMe,6-CF₃ | 0 |
| C-0672 | H | H | H | H | H | 3-OMe,2-CF₃ | 0 |
| C-0673 | H | H | H | H | H | 3-OMe,4-CF₃ | 0 |
| C-0674 | H | H | H | H | H | 3-OMe,5-CF₃ | 0 |
| C-0675 | H | H | H | H | H | 3-OMe,6-CF₃ | 0 |
| C-0676 | H | H | H | H | H | 4-OMe,2-CF₃ | 0 |
| C-0677 | H | H | H | H | H | 4-OMe,3-CF₃ | 0 |
| C-0678 | H | H | H | H | H | 2-CHF₂,3-F | 0 |
| C-0679 | H | H | H | H | H | 2-CHF₂,4-F | 0 |
| C-0680 | H | H | H | H | H | 2-CHF₂,5-F | 0 |
| C-0681 | H | H | H | H | H | 2-CHF₂,6-F | 0 |
| C-0682 | H | H | H | H | H | 2-CHF₂,3-Me | 0 |
| C-0683 | H | H | H | H | H | 2-CHF₂,4-Me | 0 |
| C-0684 | H | H | H | H | H | 2-CHF₂,5-Me | 0 |
| C-0685 | H | H | H | H | H | 2-CHF₂,6-Me | 0 |
| C-0686 | H | H | H | H | H | 2-cyclopropyl,3-F | 0 |
| C-0687 | H | H | H | H | H | 2-cyclopropyl,4-F | 0 |
| C-0688 | H | H | H | H | H | 2-cyclopropyl,5-F | 0 |
| C-0689 | H | H | H | H | H | 2-cyclopropyl,6-F | 0 |
| C-0690 | H | H | H | H | H | 2-cyclopropyl,3-Me | 0 |
| C-0691 | H | H | H | H | H | 2-cyclopropyl,4-Me | 0 |
| C-0692 | H | H | H | H | H | 2-cyclopropyl,5-Me | 0 |
| C-0693 | H | H | H | H | H | 2-cyclopropyl,6-Me | 0 |
| C-0694 | H | H | H | H | H | 2-ethenyl,3-F | 0 |
| C-0695 | H | H | H | H | H | 2-ethenyl,4-F | 0 |
| C-0696 | H | H | H | H | H | 2-ethenyl,5-F | 0 |
| C-0697 | H | H | H | H | H | 2-ethenyl,6-F | 0 |
| C-0698 | H | H | H | H | H | 2-ethenyl,3-Me | 0 |
| C-0699 | H | H | H | H | H | 2-ethenyl,4-Me | 0 |
| C-0700 | H | H | H | H | H | 2-ethenyl,5-Me | 0 |
| C-0701 | H | H | H | H | H | 2-ethenyl,6-Me | 0 |
| C-0702 | H | H | H | H | H | 2-OEt,3-F | 0 |
| C-0703 | H | H | H | H | H | 2-OEt,4-F | 0 |
| C-0704 | H | H | H | H | H | 2-OEt,5-F | 0 |
| C-0705 | H | H | H | H | H | 2-OEt,6-F | 0 |
| C-0706 | H | H | H | H | H | 2-OEt,3-Cl | 0 |
| C-0707 | H | H | H | H | H | 2-OEt,4-Cl | 0 |
| C-0708 | H | H | H | H | H | 2-OEt,5-Cl | 0 |
| C-0709 | H | H | H | H | H | 2-OEt,6-Cl | 0 |
| C-0710 | H | H | H | H | H | 2-OEt,3-Me | 0 |
| C-0711 | H | H | H | H | H | 2-OEt,4-Me | 0 |
| C-0712 | H | H | H | H | H | 2-OEt,5-Me | 0 |
| C-0713 | H | H | H | H | H | 2-OEt,6-Me | 0 |
| C-0714 | H | H | H | H | H | 2-OPr,3-F | 0 |
| C-0715 | H | H | H | H | H | 2-OPr,4-F | 0 |
| C-0716 | H | H | H | H | H | 2-OPr,5-F | 0 |

TABLE 207-continued

| compound | R¹ | R² | R³ | R⁴ | R⁵ | (R⁸)ₘ | p |
|---|---|---|---|---|---|---|---|
| C-0717 | H | H | H | H | H | 2-OPr,6-F | 0 |
| C-0718 | H | H | H | H | H | 2-OPr,3-Me | 0 |
| C-0719 | H | H | H | H | H | 2-OPr,4-Me | 0 |
| C-0720 | H | H | H | H | H | 2-OPr,5-Me | 0 |
| C-0721 | H | H | H | H | H | 2-OPr,6-Me | 0 |
| C-0722 | H | H | H | H | H | 2-O(i-Pr),3-F | 0 |
| C-0723 | H | H | H | H | H | 2-O(i-Pr),4-F | 0 |

TABLE 208

| compound | R¹ | R² | R³ | R⁴ | R⁵ | (R⁸)ₘ | p |
|---|---|---|---|---|---|---|---|
| C-0724 | H | H | H | H | H | 2-O(i-Pr),5-F | 0 |
| C-0725 | H | H | H | H | H | 2-O(i-Pr),6-F | 0 |
| C-0726 | H | H | H | H | H | 2-O(i-Pr),3-Me | 0 |
| C-0727 | H | H | H | H | H | 2-O(i-Pr),4-Me | 0 |
| C-0728 | H | H | H | H | H | 2-O(i-Pr),5-Me | 0 |
| C-0729 | H | H | H | H | H | 2-O(i-Pr),6-Me | 0 |
| C-0730 | H | H | H | H | H | 2-OCF₃,3-F | 0 |
| C-0731 | H | H | H | H | H | 2-OCF₃,4-F | 0 |
| C-0732 | H | H | H | H | H | 2-OCF₃,5-F | 0 |
| C-0733 | H | H | H | H | H | 2-OCF₃,6-F | 0 |
| C-0734 | H | H | H | H | H | 2-OCF₃,3-Me | 0 |
| C-0735 | H | H | H | H | H | 2-OCF₃,4-Me | 0 |
| C-0736 | H | H | H | H | H | 2-OCF₃,5-Me | 0 |
| C-0737 | H | H | H | H | H | 2-OCF₃,6-Me | 0 |
| C-0738 | H | H | H | H | H | 2-OCHF₂,3-F | 0 |
| C-0739 | H | H | H | H | H | 2-OCHF₂,4-F | 0 |
| C-0740 | H | H | H | H | H | 2-OCHF₂,5-F | 0 |
| C-0741 | H | H | H | H | H | 2-OCHF₂,6-F | 0 |
| C-0742 | H | H | H | H | H | 2-OCHF₂,3-Me | 0 |
| C-0743 | H | H | H | H | H | 2-OCHF₂,4-Me | 0 |
| C-0744 | H | H | H | H | H | 2-OCHF₂,5-Me | 0 |
| C-0745 | H | H | H | H | H | 2-OCHF₂,6-Me | 0 |
| C-0746 | H | H | H | H | H | 2-(cyclopropyloxy),3-F | 0 |
| C-0747 | H | H | H | H | H | 2-(cyclopropyloxy),4-F | 0 |
| C-0748 | H | H | H | H | H | 2-(cyclopropyloxy),5-F | 0 |
| C-0749 | H | H | H | H | H | 2-(cyclopropyloxy),6-F | 0 |
| C-0750 | H | H | H | H | H | 2-(cyclopropyloxy),3-Me | 0 |
| C-0751 | H | H | H | H | H | 2-(cyclopropyloxy),4-Me | 0 |
| C-0752 | H | H | H | H | H | 2-(cyclopropyloxy),5-Me | 0 |
| C-0753 | H | H | H | H | H | 2-(cyclopropyloxy),6-Me | 0 |
| C-0754 | H | H | H | H | H | 2-(oxiran-2-yl),3-F | 0 |
| C-0755 | H | H | H | H | H | 2-(oxiran-2-yl),4-F | 0 |
| C-0756 | H | H | H | H | H | 2-(oxiran-2-yl),5-F | 0 |
| C-0757 | H | H | H | H | H | 2-(oxiran-2-yl),6-F | 0 |
| C-0758 | H | H | H | H | H | 2-(oxiran-2-yl),3-Me | 0 |
| C-0759 | H | H | H | H | H | 2-(oxiran-2-yl),4-Me | 0 |
| C-0760 | H | H | H | H | H | 2-(oxiran-2-yl),5-Me | 0 |
| C-0761 | H | H | H | H | H | 2-(oxiran-2-yl),6-Me | 0 |
| C-0762 | H | H | H | H | H | 2-(oxiran-2-ylmethyl),3-F | 0 |
| C-0763 | H | H | H | H | H | 2-(oxiran-2-ylmethyl),4-F | 0 |
| C-0764 | H | H | H | H | H | 2-(oxiran-2-ylmethyl),5-F | 0 |
| C-0765 | H | H | H | H | H | 2-(oxiran-2-ylmethyl),6-F | 0 |
| C-0766 | H | H | H | H | H | 2-(oxiran-2-ylmethyl),3-Me | 0 |
| C-0767 | H | H | H | H | H | 2-(oxiran-2-ylmethyl),4-Me | 0 |
| C-0768 | H | H | H | H | H | 2-(oxiran-2-ylmethyl),5-Me | 0 |
| C-0769 | H | H | H | H | H | 2-(oxiran-2-ylmethyl),6-Me | 0 |
| C-0770 | H | H | H | H | H | 2-SMe,3-F | 0 |
| C-0771 | H | H | H | H | H | 2-SMe,4-F | 0 |
| C-0772 | H | H | H | H | H | 2-SMe,5-F | 0 |
| C-0773 | H | H | H | H | H | 2-SMe,6-F | 0 |
| C-0774 | H | H | H | H | H | 2-SMe,3-Me | 0 |
| C-0775 | H | H | H | H | H | 2-SMe,4-Me | 0 |
| C-0776 | H | H | H | H | H | 2-SMe,5-Me | 0 |
| C-0777 | H | H | H | H | H | 2-SMe,6-Me | 0 |
| C-0778 | H | H | H | H | H | 2-SEt,3-F | 0 |
| C-0779 | H | H | H | H | H | 2-SEt,4-F | 0 |

TABLE 209

| compound | R¹ | R² | R³ | R⁴ | R⁵ | (R⁸)$_m$ | p |
|---|---|---|---|---|---|---|---|
| C-0780 | H | H | H | H | H | 2-SEt,5-F | 0 |
| C-0781 | H | H | H | H | H | 2-SEt,6-F | 0 |
| C-0782 | H | H | H | H | H | 2-SEt,3-Me | 0 |
| C-0783 | H | H | H | H | H | 2-SEt,4-Me | 0 |
| C-0784 | H | H | H | H | H | 2-SEt,5-Me | 0 |
| C-0785 | H | H | H | H | H | 2-SEt,6-Me | 0 |
| C-0786 | H | H | H | H | H | 2-S(=O)Me,3-F | 0 |
| C-0787 | H | H | H | H | H | 2-S(=O)Me,4-F | 0 |
| C-0788 | H | H | H | H | H | 2-S(=O)Me,5-F | 0 |
| C-0789 | H | H | H | H | H | 2-S(=O)Me,6-F | 0 |
| C-0790 | H | H | H | H | H | 3-S(=O)Me,2-F | 0 |
| C-0791 | H | H | H | H | H | 3-S(=O)Me,4-F | 0 |
| C-0792 | H | H | H | H | H | 3-S(=O)Me,5-F | 0 |
| C-0793 | H | H | H | H | H | 3-S(=O)Me,6-F | 0 |
| C-0794 | H | H | H | H | H | 2-S(=O)Me,3-Me | 0 |
| C-0795 | H | H | H | H | H | 2-S(=O)Me,4-Me | 0 |
| C-0796 | H | H | H | H | H | 2-S(=O)Me,5-Me | 0 |
| C-0797 | H | H | H | H | H | 2-S(=O)Me,6-Me | 0 |
| C-0798 | H | H | H | H | H | 3-S(=O)Me,2-Me | 0 |
| C-0799 | H | H | H | H | H | 3-S(=O)Me,4-Me | 0 |
| C-0800 | H | H | H | H | H | 3-S(=O)Me,5-Me | 0 |
| C-0801 | H | H | H | H | H | 3-S(=O)Me,6-Me | 0 |
| C-0802 | H | H | H | H | H | 2-S(=O)$_2$Me,3-F | 0 |
| C-0803 | H | H | H | H | H | 2-S(=O)$_2$Me,4-F | 0 |
| C-0804 | H | H | H | H | H | 2-S(=O)$_2$Me,5-F | 0 |
| C-0805 | H | H | H | H | H | 2-S(=O)$_2$Me,6-F | 0 |
| C-0806 | H | H | H | H | H | 2-S(=O)$_2$Me,3-Me | 0 |
| C-0807 | H | H | H | H | H | 2-S(=O)$_2$Me,4-Me | 0 |
| C-0808 | H | H | H | H | H | 2-S(=O)$_2$Me,5-Me | 0 |
| C-0809 | H | H | H | H | H | 2-S(=O)$_2$Me,6-Me | 0 |
| C-0810 | H | H | H | H | H | 2-SCF$_3$,3-F | 0 |
| C-0811 | H | H | H | H | H | 2-SCF$_3$,4-F | 0 |
| C-0812 | H | H | H | H | H | 2-SCF$_3$,5-F | 0 |
| C-0813 | H | H | H | H | H | 2-SCF$_3$,6-F | 0 |
| C-0814 | H | H | H | H | H | 2-SCF$_3$,3-Me | 0 |
| C-0815 | H | H | H | H | H | 2-SCF$_3$,4-Me | 0 |
| C-0816 | H | H | H | H | H | 2-SCF$_3$,5-Me | 0 |
| C-0817 | H | H | H | H | H | 2-SCF$_3$,6-Me | 0 |
| C-0818 | H | H | H | H | H | 2-S(=O)CF$_3$,3-F | 0 |
| C-0819 | H | H | H | H | H | 2-S(=O)CF$_3$,4-F | 0 |
| C-0820 | H | H | H | H | H | 2-S(=O)CF$_3$,5-F | 0 |
| C-0821 | H | H | H | H | H | 2-S(=O)CF$_3$,6-F | 0 |
| C-0822 | H | H | H | H | H | 2-S(=O)CF$_3$,3-Me | 0 |
| C-0823 | H | H | H | H | H | 2-S(=O)CF$_3$,4-Me | 0 |
| C-0824 | H | H | H | H | H | 2-S(=O)CF$_3$,5-Me | 0 |
| C-0825 | H | H | H | H | H | 2-S(=O)CF$_3$,6-Me | 0 |
| C-0826 | H | H | H | H | H | 2-S(=O)$_2$CF$_3$,3-F | 0 |
| C-0827 | H | H | H | H | H | 2-S(=O)$_2$CF$_3$,4-F | 0 |
| C-0828 | H | H | H | H | H | 2-S(=O)$_2$CF$_3$,5-F | 0 |
| C-0829 | H | H | H | H | H | 2-S(=O)$_2$CF$_3$,6-F | 0 |
| C-0830 | H | H | H | H | H | 2-S(=O)$_2$CF$_3$,3-Me | 0 |
| C-0831 | H | H | H | H | H | 2-S(=O)$_2$CF$_3$,4-Me | 0 |
| C-0832 | H | H | H | H | H | 2-S(=O)$_2$CF$_3$,5-Me | 0 |
| C-0833 | H | H | H | H | H | 2-S(=O)$_2$CF$_3$,6-Me | 0 |
| C-0834 | H | H | H | H | H | 2-(cyclopropylthio),3-F | 0 |
| C-0835 | H | H | H | H | H | 2-(cyclopropylthio),4-F | 0 |

TABLE 210

| compound | R¹ | R² | R³ | R⁴ | R⁵ | (R⁸)$_m$ | p |
|---|---|---|---|---|---|---|---|
| C-0836 | H | H | H | H | H | 2-(cyclopropylthio),5-F | 0 |
| C-0837 | H | H | H | H | H | 2-(cyclopropylthio),6-F | 0 |
| C-0838 | H | H | H | H | H | 2-(cyclopropylthio),3-Me | 0 |
| C-0839 | H | H | H | H | H | 2-(cyclopropylthio),4-Me | 0 |
| C-0840 | H | H | H | H | H | 2-(cyclopropylthio),5-Me | 0 |
| C-0841 | H | H | H | H | H | 2-(cyclopropylthio),6-Me | 0 |
| C-0842 | H | H | H | H | H | 2-C(=O)Me,3-F | 0 |
| C-0843 | H | H | H | H | H | 2-C(=O)Me,4-F | 0 |
| C-0844 | H | H | H | H | H | 2-C(=O)Me,5-F | 0 |
| C-0845 | H | H | H | H | H | 2-C(=O)Me,6-F | 0 |
| C-0846 | H | H | H | H | H | 2-C(=O)Me,3-Me | 0 |
| C-0847 | H | H | H | H | H | 2-C(=O)Me,4-Me | 0 |
| C-0848 | H | H | H | H | H | 2-C(=O)Me,5-Me | 0 |
| C-0849 | H | H | H | H | H | 2-C(=O)Me,6-Me | 0 |
| C-0850 | H | H | H | H | H | 3-C(=O)Me,2-F | 0 |
| C-0851 | H | H | H | H | H | 3-C(=O)Me,4-F | 0 |
| C-0852 | H | H | H | H | H | 3-C(=O)Me,5-F | 0 |
| C-0853 | H | H | H | H | H | 3-C(=O)Me,6-F | 0 |
| C-0854 | H | H | H | H | H | 3-C(=O)Me,2-Me | 0 |
| C-0855 | H | H | H | H | H | 3-C(=O)Me,4-Me | 0 |
| C-0856 | H | H | H | H | H | 3-C(=O)Me,5-Me | 0 |
| C-0857 | H | H | H | H | H | 3-C(=O)Me,6-Me | 0 |
| C-0858 | H | H | H | H | H | 2-C(=O)OMe,3-F | 0 |
| C-0859 | H | H | H | H | H | 2-C(=O)OMe,4-F | 0 |
| C-0860 | H | H | H | H | H | 2-C(=O)OMe,5-F | 0 |
| C-0861 | H | H | H | H | H | 2-C(=O)OMe,6-F | 0 |
| C-0862 | H | H | H | H | H | 2-C(=O)OMe,3-Me | 0 |
| C-0863 | H | H | H | H | H | 2-C(=O)OMe,4-Me | 0 |
| C-0864 | H | H | H | H | H | 2-C(=O)OMe,5-Me | 0 |
| C-0865 | H | H | H | H | H | 2-C(=O)OMe,6-Me | 0 |
| C-0866 | H | H | H | H | H | 2-C(=O)OEt,3-F | 0 |
| C-0867 | H | H | H | H | H | 2-C(=O)OEt,4-F | 0 |
| C-0868 | H | H | H | H | H | 2-C(=O)OEt,5-F | 0 |
| C-0869 | H | H | H | H | H | 2-C(=O)OEt,6-F | 0 |
| C-0870 | H | H | H | H | H | 2-C(=O)OEt,3-Me | 0 |
| C-0871 | H | H | H | H | H | 2-C(=O)OEt,4-Me | 0 |
| C-0872 | H | H | H | H | H | 2-C(=O)OEt,5-Me | 0 |
| C-0873 | H | H | H | H | H | 2-C(=O)OEt,6-Me | 0 |
| C-0874 | H | H | H | H | H | 2-C(=O)NH$_2$,3-F | 0 |
| C-0875 | H | H | H | H | H | 2-C(=O)NH$_2$,4-F | 0 |
| C-0876 | H | H | H | H | H | 2-C(=O)NH$_2$,5-F | 0 |
| C-0877 | H | H | H | H | H | 2-C(=O)NH$_2$,6-F | 0 |
| C-0878 | H | H | H | H | H | 2-C(=O)NH$_2$,3-Me | 0 |
| C-0879 | H | H | H | H | H | 2-C(=O)NH$_2$,4-Me | 0 |
| C-0880 | H | H | H | H | H | 2-C(=O)NH$_2$,5-Me | 0 |
| C-0881 | H | H | H | H | H | 2-C(=O)NH$_2$,6-Me | 0 |
| C-0882 | H | H | H | H | H | 2-C(=O)NHMe,3-F | 0 |
| C-0883 | H | H | H | H | H | 2-C(=O)NHMe,4-F | 0 |
| C-0884 | H | H | H | H | H | 2-C(=O)NHMe,5-F | 0 |
| C-0885 | H | H | H | H | H | 2-C(=O)NHMe,6-F | 0 |
| C-0886 | H | H | H | H | H | 2-C(=O)NHMe,3-Me | 0 |
| C-0887 | H | H | H | H | H | 2-C(=O)NHMe,4-Me | 0 |
| C-0888 | H | H | H | H | H | 2-C(=O)NHMe,5-Me | 0 |
| C-0889 | H | H | H | H | H | 2-C(=O)NHMe,6-Me | 0 |
| C-0890 | H | H | H | H | H | 2-C(=O)NMe$_2$,3-F | 0 |
| C-0891 | H | H | H | H | H | 2-C(=O)NMe$_2$,4-F | 0 |

TABLE 211

| compound | R¹ | R² | R³ | R⁴ | R⁵ | (R⁸)$_m$ | p |
|---|---|---|---|---|---|---|---|
| C-0892 | H | H | H | H | H | 2-C(=O)NMe$_2$,5-F | 0 |
| C-0893 | H | H | H | H | H | 2-C(=O)NMe$_2$,6-F | 0 |
| C-0894 | H | H | H | H | H | 2-C(=O)NMe$_2$,3-Me | 0 |
| C-0895 | H | H | H | H | H | 2-C(=O)NMe$_2$,4-Me | 0 |
| C-0896 | H | H | H | H | H | 2-C(=O)NMe$_2$,5-Me | 0 |
| C-0897 | H | H | H | H | H | 2-C(=O)NMe$_2$,6-Me | 0 |
| C-0898 | H | H | H | H | H | 2-CH$_2$OH,3-F | 0 |
| C-0899 | H | H | H | H | H | 2-CH$_2$OH,4-F | 0 |
| C-0900 | H | H | H | H | H | 2-CH$_2$OH,5-F | 0 |
| C-0901 | H | H | H | H | H | 2-CH$_2$OH,6-F | 0 |
| C-0902 | H | H | H | H | H | 2-CH$_2$OH,3-Me | 0 |
| C-0903 | H | H | H | H | H | 2-CH$_2$OH,4-Me | 0 |
| C-0904 | H | H | H | H | H | 2-CH$_2$OH,5-Me | 0 |
| C-0905 | H | H | H | H | H | 2-CH$_2$OH,6-Me | 0 |
| C-0906 | H | H | H | H | H | 2-CH$_2$OCH$_3$,3-F | 0 |
| C-0907 | H | H | H | H | H | 2-CH$_2$OCH$_3$,4-F | 0 |
| C-0908 | H | H | H | H | H | 2-CH$_2$OCH$_3$,5-F | 0 |
| C-0909 | H | H | H | H | H | 2-CH$_2$OCH$_3$,6-F | 0 |
| C-0910 | H | H | H | H | H | 2-CH$_2$OCH$_3$,3-Me | 0 |
| C-0911 | H | H | H | H | H | 2-CH$_2$OCH$_3$,4-Me | 0 |
| C-0912 | H | H | H | H | H | 2-CH$_2$OCH$_3$,5-Me | 0 |
| C-0913 | H | H | H | H | H | 2-CH$_2$OCH$_3$,6-Me | 0 |
| C-0914 | H | H | H | H | H | 2-CH$_2$OCH$_2$CH$_3$,3-F | 0 |
| C-0915 | H | H | H | H | H | 2-CH$_2$OCH$_2$CH$_3$,4-F | 0 |
| C-0916 | H | H | H | H | H | 2-CH$_2$OCH$_2$CH$_3$,5-F | 0 |
| C-0917 | H | H | H | H | H | 2-CH$_2$OCH$_2$CH$_3$,6-F | 0 |
| C-0918 | H | H | H | H | H | 2-CH$_2$OCH$_2$CH$_3$,3-Me | 0 |
| C-0919 | H | H | H | H | H | 2-CH$_2$OCH$_2$CH$_3$,4-Me | 0 |

TABLE 211-continued

| compound | R¹ | R² | R³ | R⁴ | R⁵ | (R⁸)$_m$ | p |
| --- | --- | --- | --- | --- | --- | --- | --- |
| C-0920 | H | H | H | H | H | 2-CH$_2$OCH$_2$CH$_3$,5-Me | 0 |
| C-0921 | H | H | H | H | H | 2-CH$_2$OCH$_2$CH$_3$,6-Me | 0 |
| C-0922 | H | H | H | H | H | 2-OC(=O)CH$_3$,3-F | 0 |
| C-0923 | H | H | H | H | H | 2-OC(=O)CH$_3$,4-F | 0 |
| C-0924 | H | H | H | H | H | 2-OC(=O)CH$_3$,5-F | 0 |
| C-0925 | H | H | H | H | H | 2-OC(=O)CH$_3$,6-F | 0 |
| C-0926 | H | H | H | H | H | 2-OC(=O)CH$_3$,3-Me | 0 |
| C-0927 | H | H | H | H | H | 2-OC(=O)CH$_3$,4-Me | 0 |
| C-0928 | H | H | H | H | H | 2-OC(=O)CH$_3$,5-Me | 0 |
| C-0929 | H | H | H | H | H | 2-OC(=O)CH$_3$,6-Me | 0 |
| C-0930 | H | H | H | H | H | 2-OS(=O)$_2$CH$_3$,3-F | 0 |
| C-0931 | H | H | H | H | H | 2-OS(=O)$_2$CH$_3$,4-F | 0 |
| C-0932 | H | H | H | H | H | 2-OS(=O)$_2$CH$_3$,5-F | 0 |
| C-0933 | H | H | H | H | H | 2-OS(=O)$_2$CH$_3$,6-F | 0 |
| C-0934 | H | H | H | H | H | 2-OS(=O)$_2$CH$_3$,3-Me | 0 |
| C-0935 | H | H | H | H | H | 2-OS(=O)$_2$CH$_3$,4-Me | 0 |
| C-0936 | H | H | H | H | H | 2-OS(=O)$_2$CH$_3$,5-Me | 0 |
| C-0937 | H | H | H | H | H | 2-OS(=O)$_2$CH$_3$,6-Me | 0 |
| C-0938 | H | H | H | H | H | 2-CH$_2$SCH$_3$,3-F | 0 |
| C-0939 | H | H | H | H | H | 2-CH$_2$SCH$_3$,4-F | 0 |
| C-0940 | H | H | H | H | H | 2-CH$_2$SCH$_3$,5-F | 0 |
| C-0941 | H | H | H | H | H | 2-CH$_2$SCH$_3$,6-F | 0 |
| C-0942 | H | H | H | H | H | 2-CH$_2$SCH$_3$,3-Me | 0 |
| C-0943 | H | H | H | H | H | 2-CH$_2$SCH$_3$,4-Me | 0 |
| C-0944 | H | H | H | H | H | 2-CH$_2$SCH$_3$,5-Me | 0 |
| C-0945 | H | H | H | H | H | 2-CH$_2$SCH$_3$,6-Me | 0 |
| C-0946 | H | H | H | H | H | 2-CH$_2$SCF$_3$,3-F | 0 |
| C-0947 | H | H | H | H | H | 2-CH$_2$SCF$_3$,4-F | 0 |

TABLE 212

| compound | R¹ | R² | R³ | R⁴ | R⁵ | (R⁸)$_m$ | p |
| --- | --- | --- | --- | --- | --- | --- | --- |
| C-0948 | H | H | H | H | H | 2-CH$_2$SCF$_3$,5-F | 0 |
| C-0949 | H | H | H | H | H | 2-CH$_2$SCF$_3$,6-F | 0 |
| C-0950 | H | H | H | H | H | 2-CH$_2$SCF$_3$,3-Me | 0 |
| C-0951 | H | H | H | H | H | 2-CH$_2$SCF$_3$,4-Me | 0 |
| C-0952 | H | H | H | H | H | 2-CH$_2$SCF$_3$,5-Me | 0 |
| C-0953 | H | H | H | H | H | 2-CH$_2$SCF$_3$,6-Me | 0 |
| C-0954 | H | H | H | H | H | 2-(benzyloxy),3-F | 0 |
| C-0955 | H | H | H | H | H | 2-(benzyloxy),4-F | 0 |
| C-0956 | H | H | H | H | H | 2-(benzyloxy),5-F | 0 |
| C-0957 | H | H | H | H | H | 2-(benzyloxy),6-F | 0 |
| C-0958 | H | H | H | H | H | 2-(benzyloxy),3-Me | 0 |
| C-0959 | H | H | H | H | H | 2-(benzyloxy),4-Me | 0 |
| C-0960 | H | H | H | H | H | 2-(benzyloxy),5-Me | 0 |
| C-0961 | H | H | H | H | H | 2-(benzyloxy),6-Me | 0 |
| C-0962 | H | H | H | H | H | 2-NH$_2$,3-F | 0 |
| C-0963 | H | H | H | H | H | 2-NH$_2$,4-F | 0 |
| C-0964 | H | H | H | H | H | 2-NH$_2$,5-F | 0 |
| C-0965 | H | H | H | H | H | 2-NH$_2$,6-F | 0 |
| C-0966 | H | H | H | H | H | 2-NH$_2$,3-Me | 0 |
| C-0967 | H | H | H | H | H | 2-NH$_2$,4-Me | 0 |
| C-0968 | H | H | H | H | H | 2-NH$_2$,5-Me | 0 |
| C-0969 | H | H | H | H | H | 2-NH$_2$,6-Me | 0 |
| C-0970 | H | H | H | H | H | 2-NHMe,3-F | 0 |
| C-0971 | H | H | H | H | H | 2-NHMe,4-F | 0 |
| C-0972 | H | H | H | H | H | 2-NHMe,5-F | 0 |
| C-0973 | H | H | H | H | H | 2-NHMe,6-F | 0 |
| C-0974 | H | H | H | H | H | 2-NHMe,3-Me | 0 |
| C-0975 | H | H | H | H | H | 2-NHMe,4-Me | 0 |
| C-0976 | H | H | H | H | H | 2-NHMe,5-Me | 0 |
| C-0977 | H | H | H | H | H | 2-NHMe,6-Me | 0 |
| C-0978 | H | H | H | H | H | 2-NHEt,3-F | 0 |
| C-0979 | H | H | H | H | H | 2-NHEt,4-F | 0 |
| C-0980 | H | H | H | H | H | 2-NHEt,5-F | 0 |
| C-0981 | H | H | H | H | H | 2-NHEt,6-F | 0 |
| C-0982 | H | H | H | H | H | 2-NHEt,3-Me | 0 |
| C-0983 | H | H | H | H | H | 2-NHEt,4-Me | 0 |
| C-0984 | H | H | H | H | H | 2-NHEt,5-Me | 0 |
| C-0985 | H | H | H | H | H | 2-NHEt,6-Me | 0 |
| C-0986 | H | H | H | H | H | 2-NMe$_2$,3-F | 0 |
| C-0987 | H | H | H | H | H | 2-NMe$_2$,4-F | 0 |
| C-0988 | H | H | H | H | H | 2-NMe$_2$,5-F | 0 |
| C-0989 | H | H | H | H | H | 2-NMe$_2$,6-F | 0 |

TABLE 212-continued

| compound | R¹ | R² | R³ | R⁴ | R⁵ | (R⁸)$_m$ | p |
| --- | --- | --- | --- | --- | --- | --- | --- |
| C-0990 | H | H | H | H | H | 2-NMe$_2$,3-Me | 0 |
| C-0991 | H | H | H | H | H | 2-NMe$_2$,4-Me | 0 |
| C-0992 | H | H | H | H | H | 2-NMe$_2$,5-Me | 0 |
| C-0993 | H | H | H | H | H | 2-NMe$_2$,6-Me | 0 |
| C-0994 | H | H | H | H | H | 2-NEt$_2$,3-F | 0 |
| C-0995 | H | H | H | H | H | 2-NEt$_2$,4-F | 0 |
| C-0996 | H | H | H | H | H | 2-NEt$_2$,5-F | 0 |
| C-0997 | H | H | H | H | H | 2-NEt$_2$,6-F | 0 |
| C-0998 | H | H | H | H | H | 2-NEt$_2$,3-Me | 0 |
| C-0999 | H | H | H | H | H | 2-NEt$_2$,4-Me | 0 |
| C-1000 | H | H | H | H | H | 2-NEt$_2$,5-Me | 0 |
| C-1001 | H | H | H | H | H | 2-NEt$_2$,6-Me | 0 |
| C-1002 | H | H | H | H | H | 2-CHO,3-F | 0 |
| C-1003 | H | H | H | H | H | 2-CHO,4-F | 0 |

TABLE 213

| compound | R¹ | R² | R³ | R⁴ | R⁵ | (R⁸)$_m$ | p |
| --- | --- | --- | --- | --- | --- | --- | --- |
| C-1004 | H | H | H | H | H | 2-CHO,5-F | 0 |
| C-1005 | H | H | H | H | H | 2-CHO,6-F | 0 |
| C-1006 | H | H | H | H | H | 2-CHO,3-Me | 0 |
| C-1007 | H | H | H | H | H | 2-CHO,4-Me | 0 |
| C-1008 | H | H | H | H | H | 2-CHO,5-Me | 0 |
| C-1009 | H | H | H | H | H | 2-CHO,6-Me | 0 |
| C-1010 | H | H | H | H | H | 2-C(=O)OH,3-F | 0 |
| C-1011 | H | H | H | H | H | 2-C(=O)OH,4-F | 0 |
| C-1012 | H | H | H | H | H | 2-C(=O)OH,5-F | 0 |
| C-1013 | H | H | H | H | H | 2-C(=O)OH,6-F | 0 |
| C-1014 | H | H | H | H | H | 2-C(=O)OH,3-Me | 0 |
| C-1015 | H | H | H | H | H | 2-C(=O)OH,4-Me | 0 |
| C-1016 | H | H | H | H | H | 2-C(=O)OH,5-Me | 0 |
| C-1017 | H | H | H | H | H | 2-C(=O)OH,6-Me | 0 |
| C-1018 | H | H | H | H | H | 2-(1,3-dioxolan-2-yl),3-F | 0 |
| C-1019 | H | H | H | H | H | 2-(1,3-dioxolan-2-yl),4-F | 0 |
| C-1020 | H | H | H | H | H | 2-(1,3-dioxolan-2-yl),5-F | 0 |
| C-1021 | H | H | H | H | H | 2-(1,3-dioxolan-2-yl),6-F | 0 |
| C-1022 | H | H | H | H | H | 2-(1,3-dioxolan-2-yl),3-Me | 0 |
| C-1023 | H | H | H | H | H | 2-(1,3-dioxolan-2-yl),4-Me | 0 |
| C-1024 | H | H | H | H | H | 2-(1,3-dioxolan-2-yl),5-Me | 0 |
| C-1025 | H | H | H | H | H | 2-(1,3-dioxolan-2-yl),6-Me | 0 |
| C-1026 | H | H | H | H | H | 2-(1,3-dioxan-2-yl),3-F | 0 |
| C-1027 | H | H | H | H | H | 2-(1,3-dioxan-2-yl),4-F | 0 |
| C-1028 | H | H | H | H | H | 2-(1,3-dioxan-2-yl),5-F | 0 |
| C-1029 | H | H | H | H | H | 2-(1,3-dioxan-2-yl),6-F | 0 |
| C-1030 | H | H | H | H | H | 2-(1,3-dioxan-2-yl),3-Me | 0 |
| C-1031 | H | H | H | H | H | 2-(1,3-dioxan-2-yl),4-Me | 0 |
| C-1032 | H | H | H | H | H | 2-(1,3-dioxan-2-yl),5-Me | 0 |
| C-1033 | H | H | H | H | H | 2-(1,3-dioxan-2-yl),6-Me | 0 |
| C-1034 | H | H | H | H | H | 2-(thiazol-2-yl),3-F | 0 |
| C-1035 | H | H | H | H | H | 2-(thiazol-2-yl),4-F | 0 |
| C-1036 | H | H | H | H | H | 2-(thiazol-2-yl),5-F | 0 |
| C-1037 | H | H | H | H | H | 2-(thiazol-2-yl),6-F | 0 |
| C-1038 | H | H | H | H | H | 2-(thiazol-2-yl),3-Me | 0 |
| C-1039 | H | H | H | H | H | 2-(thiazol-2-yl),4-Me | 0 |
| C-1040 | H | H | H | H | H | 2-(thiazol-2-yl),5-Me | 0 |
| C-1041 | H | H | H | H | H | 2-(thiazol-2-yl),6-Me | 0 |
| C-1042 | H | H | H | H | H | 2-(oxazol-2-yl),3-F | 0 |
| C-1043 | H | H | H | H | H | 2-(oxazol-2-yl),4-F | 0 |
| C-1044 | H | H | H | H | H | 2-(oxazol-2-yl),5-F | 0 |
| C-1045 | H | H | H | H | H | 2-(oxazol-2-yl),6-F | 0 |
| C-1046 | H | H | H | H | H | 2-(oxazol-2-yl),3-Me | 0 |
| C-1047 | H | H | H | H | H | 2-(oxazol-2-yl),4-Me | 0 |
| C-1048 | H | H | H | H | H | 2-(oxazol-2-yl),5-Me | 0 |
| C-1049 | H | H | H | H | H | 2-(oxazol-2-yl),6-Me | 0 |
| C-1050 | H | H | H | H | H | 2-CH=NOH,3-F | 0 |
| C-1051 | H | H | H | H | H | 2-CH=NOH,4-F | 0 |
| C-1052 | H | H | H | H | H | 2-CH=NOH,5-F | 0 |
| C-1053 | H | H | H | H | H | 2-CH=NOH,6-F | 0 |
| C-1054 | H | H | H | H | H | 2-CH=NOH,3-Me | 0 |
| C-1055 | H | H | H | H | H | 2-CH=NOH,4-Me | 0 |
| C-1056 | H | H | H | H | H | 2-CH=NOH,5-Me | 0 |

TABLE 213-continued

| compound | R¹ | R² | R³ | R⁴ | R⁵ | (R⁸)$_m$ | p |
|---|---|---|---|---|---|---|---|
| C-1057 | H | H | H | H | H | 2-CH=NOH,6-Me | 0 |
| C-1058 | H | H | H | H | H | 2-CH=NOMe,3-F | 0 |
| C-1059 | H | H | H | H | H | 2-CH=NOMe,4-F | 0 |

TABLE 214

| compound | R¹ | R² | R³ | R⁴ | R⁵ | (R⁸)$_m$ | p |
|---|---|---|---|---|---|---|---|
| C-1060 | H | H | H | H | H | 2-CH=NOMe,5-F | 0 |
| C-1061 | H | H | H | H | H | 2-CH=NOMe,6-F | 0 |
| C-1062 | H | H | H | H | H | 2-CH=NOMe,3-Me | 0 |
| C-1063 | H | H | H | H | H | 2-CH=NOMe,4-Me | 0 |
| C-1064 | H | H | H | H | H | 2-CH=NOMe,5-Me | 0 |
| C-1065 | H | H | H | H | H | 2-CH=NOMe,6-Me | 0 |
| C-1066 | H | H | H | H | H | 2-CN,3-F | 0 |
| C-1067 | H | H | H | H | H | 2-CN,4-F | 0 |
| C-1068 | H | H | H | H | H | 2-CN,5-F | 0 |
| C-1069 | H | H | H | H | H | 2-CN,6-F | 0 |
| C-1070 | H | H | H | H | H | 2-CN,3-Cl | 0 |
| C-1071 | H | H | H | H | H | 2-CN,4-Cl | 0 |
| C-1072 | H | H | H | H | H | 2-CN,5-Cl | 0 |
| C-1073 | H | H | H | H | H | 2-CN,6-Cl | 0 |
| C-1074 | H | H | H | H | H | 2-CN,3-Me | 0 |
| C-1075 | H | H | H | H | H | 2-CN,4-Me | 0 |
| C-1076 | H | H | H | H | H | 2-CN,5-Me | 0 |
| C-1077 | H | H | H | H | H | 2-CN,6-Me | 0 |
| C-1078 | H | H | H | H | H | 2-CN,3-OMe | 0 |
| C-1079 | H | H | H | H | H | 2-CN,4-OMe | 0 |
| C-1080 | H | H | H | H | H | 2-CN,5-OMe | 0 |
| C-1081 | H | H | H | H | H | 2-CN,6-OMe | 0 |
| C-1082 | H | H | H | H | H | 3-CN,2-F | 0 |
| C-1083 | H | H | H | H | H | 3-CN,4-F | 0 |
| C-1084 | H | H | H | H | H | 3-CN,5-F | 0 |
| C-1085 | H | H | H | H | H | 3-CN,6-F | 0 |
| C-1086 | H | H | H | H | H | 3-CN,2-Cl | 0 |
| C-1087 | H | H | H | H | H | 3-CN,4-Cl | 0 |
| C-1088 | H | H | H | H | H | 3-CN,5-Cl | 0 |
| C-1089 | H | H | H | H | H | 3-CN,6-Cl | 0 |
| C-1090 | H | H | H | H | H | 3-CN,2-Me | 0 |
| C-1091 | H | H | H | H | H | 3-CN,4-Me | 0 |
| C-1092 | H | H | H | H | H | 3-CN,5-Me | 0 |
| C-1093 | H | H | H | H | H | 3-CN,6-Me | 0 |
| C-1094 | H | H | H | H | H | 3-CN,2-OMe | 0 |
| C-1095 | H | H | H | H | H | 3-CN,4-OMe | 0 |
| C-1096 | H | H | H | H | H | 3-CN,5-OMe | 0 |
| C-1097 | H | H | H | H | H | 3-CN,6-OMe | 0 |
| C-1098 | H | H | H | H | H | 4-CN,2-F | 0 |
| C-1099 | H | H | H | H | H | 4-CN,3-F | 0 |
| C-1100 | H | H | H | H | H | 4-CN,2-Cl | 0 |
| C-1101 | H | H | H | H | H | 4-CN,3-Cl | 0 |
| C-1102 | H | H | H | H | H | 4-CN,2-Me | 0 |
| C-1103 | H | H | H | H | H | 4-CN,3-Me | 0 |
| C-1104 | H | H | H | H | H | 4-CN,2-OMe | 0 |
| C-1105 | H | H | H | H | H | 4-CN,3-OMe | 0 |
| C-1106 | H | H | H | H | H | 2-NO₂,3-F | 0 |
| C-1107 | H | H | H | H | H | 2-NO₂,4-F | 0 |
| C-1108 | H | H | H | H | H | 2-NO₂,5-F | 0 |
| C-1109 | H | H | H | H | H | 2-NO₂,6-F | 0 |
| C-1110 | H | H | H | H | H | 2-NO₂,3-Me | 0 |
| C-1111 | H | H | H | H | H | 2-NO₂,4-Me | 0 |
| C-1112 | H | H | H | H | H | 2-NO₂,5-Me | 0 |
| C-1113 | H | H | H | H | H | 2-NO₂,6-Me | 0 |
| C-1114 | H | H | H | H | H | 2-Me,3,4-F₂ | 0 |
| C-1115 | H | H | H | H | H | 2-Me,3,5-F₂ | 0 |

TABLE 215

| compound | R¹ | R² | R³ | R⁴ | R⁵ | (R⁸)$_m$ | p |
|---|---|---|---|---|---|---|---|
| C-1116 | H | H | H | H | H | 2-Me,3,6-F₂ | 0 |
| C-1117 | H | H | H | H | H | 2-Me,4,5-F₂ | 0 |
| C-1118 | H | H | H | H | H | 2-OMe,3,4-F₂ | 0 |
| C-1119 | H | H | H | H | H | 2-OMe,3,5-F₂ | 0 |
| C-1120 | H | H | H | H | H | 2-OMe,3,6-F₂ | 0 |
| C-1121 | H | H | H | H | H | 2-OMe,4,5-F₂ | 0 |
| C-1122 | H | H | H | H | H | 2-(CH₂)₃-3 | 0 |
| C-1123 | H | H | H | H | H | 2-(CH₂)₄-3 | 0 |
| C-1124 | H | H | H | H | H | 2-(OCH₂CH₂)-3 | 0 |
| C-1125 | H | H | H | H | H | 2-(OCH₂CH₂CH₂)-3 | 0 |
| C-1126 | H | H | H | H | H | 2-(CH₂CH₂O)-3 | 0 |
| C-1127 | H | H | H | H | H | 2-(CH₂CH₂CH₂O)-3 | 0 |
| C-1128 | H | H | H | H | H | 3-(CH₂)₃-4 | 0 |
| C-1129 | H | H | H | H | H | 3-(CH₂)₄-4 | 0 |
| C-1130 | H | H | H | H | H | 3-(OCH₂CH₂)-4 | 0 |
| C-1131 | H | H | H | H | H | 3-(OCH₂CH₂CH₂)-4 | 0 |
| C-1132 | H | H | H | H | H | 3-(CH₂CH₂O)-4 | 0 |
| C-1133 | H | H | H | H | H | 3-(CH₂CH₂CH₂O)-4 | 0 |
| C-1134 | H | H | H | H | H | 2-(OCH₂O)-3 | 0 |
| C-1135 | H | H | H | H | H | 3-(OCH₂O)-4 | 0 |
| C-1136 | H | H | H | H | H | 2-(OCH₂CH₂O)-3 | 0 |
| C-1137 | H | H | H | H | H | 3-(OCH₂CH₂O)-4 | 0 |
| C-1138 | H | H | H | H | H | 2-(OCF₂O)-3 | 0 |
| C-1139 | H | H | H | H | H | 3-(OCF₂O)-4 | 0 |
| C-1140 | H | H | H | H | H | 2-Me,6-Et | 0 |
| C-1141 | H | H | H | H | H | 2-CH₂OTBS | 0 |
| C-1142 | H | H | H | H | H | 2-cyclopropyl,3-OMe | 0 |
| C-1143 | H | H | H | H | H | 2-cyclopropyl,4-OMe | 0 |
| C-1144 | H | H | H | H | H | 2-cyclopropyl,5-OMe | 0 |
| C-1145 | H | H | H | H | H | 2-cyclopropyl,6-OMe | 0 |
| C-1146 | H | H | H | H | H | 2-Me,3-OMe,6-Me | 0 |
| C-1147 | H | H | H | H | H | 2-Me,4-OMe,6-Me | 0 |
| C-1148 | H | H | H | H | H | 2-OMe,3-Me,6-Me | 0 |
| C-1149 | H | H | H | H | H | 2-OMe,5-Me,6-Me | 0 |
| C-1150 | H | H | H | H | H | 2-OMe,3-F,6-Me | 0 |
| C-1151 | H | H | H | H | H | 2-OMe,5-F,6-Me | 0 |
| C-1152 | H | H | H | H | H | 2-OMe,5-Me,6-F | 0 |
| C-1153 | H | H | H | H | H | 2-Cl,3-Me,6-F | 0 |
| C-1154 | H | H | H | H | H | 2-Cl,5-Me,6-F | 0 |
| C-1155 | H | H | H | H | H | 2-Cl,3-OMe,6-F | 0 |
| C-1156 | H | H | H | H | H | 2-Cl,5-OMe,6-F | 0 |
| C-1157 | H | H | H | H | H | 2-Me,5-Et | 0 |
| C-1158 | H | H | H | H | H | 2,6-Et₂ | 0 |
| C-1159 | H | H | H | H | H | 2-Et,6-F | 0 |
| C-1160 | H | H | H | H | H | 2-CH₂OCH₃,6-Cl | 0 |
| C-1161 | H | H | H | H | H | 2-CH₂OCH₂CH₃,6-Cl | 0 |
| C-1162 | H | H | H | H | H | 2-OMe,5-CH=NOMe | 0 |
| C-1163 | H | H | H | H | H | 2-CH₂NMe₂ | 0 |
| C-1164 | H | H | H | H | H | 2-CH₂OCH₃,6-CF₃ | 0 |
| C-1165 | H | H | F | H | H | 2-Me | 0 |

TABLE 216

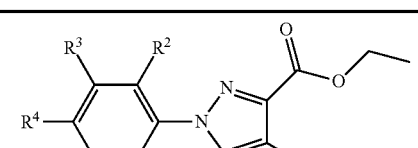

| compound | R¹ | R² | R³ | R⁴ | R⁵ | (R⁸)$_n$ | p |
|---|---|---|---|---|---|---|---|
| C-5001 | H | H | H | H | H | H | 1 |
| C-5002 | H | H | H | H | H | 2-F | 1 |
| C-5003 | H | H | H | H | H | 3-F | 1 |
| C-5004 | H | H | H | H | H | 4-F | 1 |
| C-5005 | H | H | H | H | H | 2-Cl | 1 |
| C-5006 | H | H | H | H | H | 3-Cl | 1 |
| C-5007 | H | H | H | H | H | 4-Cl | 1 |
| C-5008 | H | H | H | H | H | 2-Br | 1 |
| C-5009 | H | H | H | H | H | 3-Br | 1 |
| C-5010 | H | H | H | H | H | 4-Br | 1 |
| C-5011 | H | H | H | H | H | 2-I | 1 |
| C-5012 | H | H | H | H | H | 3-I | 1 |
| C-5013 | H | H | H | H | H | 4-I | 1 |

TABLE 216-continued

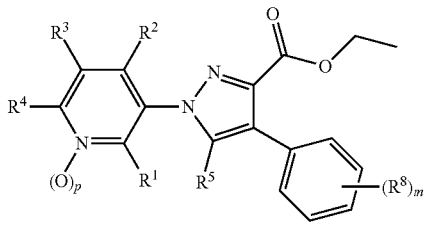

| compound | R¹ | R² | R³ | R⁴ | R⁵ | (R⁸)$_n$ | p |
|---|---|---|---|---|---|---|---|
| C-5014 | H | H | H | H | H | 2-OH | 1 |
| C-5015 | H | H | H | H | H | 3-OH | 1 |
| C-5016 | H | H | H | H | H | 4-OH | 1 |
| C-5017 | H | H | H | H | H | 2-SH | 1 |
| C-5018 | H | H | H | H | H | 3-SH | 1 |
| C-5019 | H | H | H | H | H | 4-SH | 1 |
| C-5020 | H | H | H | H | H | 2-Me | 1 |
| C-5021 | H | H | H | H | H | 3-Me | 1 |
| C-5022 | H | H | H | H | H | 4-Me | 1 |
| C-5023 | H | H | H | H | H | 2-Et | 1 |
| C-5024 | H | H | H | H | H | 3-Et | 1 |
| C-5025 | H | H | H | H | H | 4-Et | 1 |
| C-5026 | H | H | H | H | H | 2-Pr | 1 |
| C-5027 | H | H | H | H | H | 3-Pr | 1 |
| C-5028 | H | H | H | H | H | 4-Pr | 1 |
| C-5029 | H | H | H | H | H | 2-i-Pr | 1 |
| C-5030 | H | H | H | H | H | 3-i-Pr | 1 |
| C-5031 | H | H | H | H | H | 4-i-Pr | 1 |
| C-5032 | H | H | H | H | H | 2-Bu | 1 |
| C-5033 | H | H | H | H | H | 3-Bu | 1 |
| C-5034 | H | H | H | H | H | 4-Bu | 1 |
| C-5035 | H | H | H | H | H | 2-s-Bu | 1 |
| C-5036 | H | H | H | H | H | 3-s-Bu | 1 |
| C-5037 | H | H | H | H | H | 4-s-Bu | 1 |
| C-5038 | H | H | H | H | H | 2-i-Bu | 1 |
| C-5039 | H | H | H | H | H | 3-i-Bu | 1 |
| C-5040 | H | H | H | H | H | 4-i-Bu | 1 |
| C-5041 | H | H | H | H | H | 2-t-Bu | 1 |
| C-5042 | H | H | H | H | H | 3-t-Bu | 1 |
| C-5043 | H | H | H | H | H | 4-t-Bu | 1 |
| C-5044 | H | H | H | H | H | 2-CF₃ | 1 |
| C-5045 | H | H | H | H | H | 3-CF₃ | 1 |
| C-5046 | H | H | H | H | H | 4-CF₃ | 1 |
| C-5047 | H | H | H | H | H | 2-CHF₂ | 1 |
| C-5048 | H | H | H | H | H | 3-CHF₂ | 1 |
| C-5049 | H | H | H | H | H | 4-CHF₂ | 1 |
| C-5050 | H | H | H | H | H | 2-CH₂F | 1 |
| C-5051 | H | H | H | H | H | 3-CH₂F | 1 |
| C-5052 | H | H | H | H | H | 4-CH₂F | 1 |

TABLE 217

| compound | R¹ | R² | R³ | R⁴ | R⁵ | (R⁸)$_m$ | p |
|---|---|---|---|---|---|---|---|
| C-5053 | H | H | H | H | H | 2-CF₂Cl | 1 |
| C-5054 | H | H | H | H | H | 3-CF₂Cl | 1 |
| C-5055 | H | H | H | H | H | 4-CF₂Cl | 1 |
| C-5056 | H | H | H | H | H | 2-CF(CF₃)₂ | 1 |
| C-5057 | H | H | H | H | H | 3-CF(CF₃)₂ | 1 |
| C-5058 | H | H | H | H | H | 4-CF(CF₃)₂ | 1 |
| C-5059 | H | H | H | H | H | 2-cyclopropyl | 1 |
| C-5060 | H | H | H | H | H | 3-cyclopropyl | 1 |
| C-5061 | H | H | H | H | H | 4-cyclopropyl | 1 |
| C-5062 | H | H | H | H | H | 2-cyclobutyl | 1 |
| C-5063 | H | H | H | H | H | 3-cyclobutyl | 1 |
| C-5064 | H | H | H | H | H | 4-cyclobutyl | 1 |
| C-5065 | H | H | H | H | H | 2-cyclopentyl | 1 |
| C-5066 | H | H | H | H | H | 3-cyclopentyl | 1 |
| C-5067 | H | H | H | H | H | 4-cyclopentyl | 1 |
| C-5068 | H | H | H | H | H | 2-(cyclopropylmethyl) | 1 |
| C-5069 | H | H | H | H | H | 3-(cyclopropylmethyl) | 1 |
| C-5070 | H | H | H | H | H | 4-(cyclopropylmethyl) | 1 |
| C-5071 | H | H | H | H | H | 2-(cyclobutylmethyl) | 1 |
| C-5072 | H | H | H | H | H | 3-(cyclobutylmethyl) | 1 |

TABLE 217-continued

| compound | R¹ | R² | R³ | R⁴ | R⁵ | (R⁸)$_m$ | p |
|---|---|---|---|---|---|---|---|
| C-5073 | H | H | H | H | H | 4-(cyclobutylmethyl) | 1 |
| C-5074 | H | H | H | H | H | 2-(cyclopentylmethyl) | 1 |
| C-5075 | H | H | H | H | H | 3-(cyclopentylmethyl) | 1 |
| C-5076 | H | H | H | H | H | 4-(cyclopentylmethyl) | 1 |
| C-5077 | H | H | H | H | H | 2-(cyclopropylethyl) | 1 |
| C-5078 | H | H | H | H | H | 3-(cyclopropylethyl) | 1 |
| C-5079 | H | H | H | H | H | 4-(cyclopropylethyl) | 1 |
| C-5080 | H | H | H | H | H | 2-(2,2-difluorocyclopropyl) | 1 |
| C-5081 | H | H | H | H | H | 3-(2,2-difluorocyclopropyl) | 1 |
| C-5082 | H | H | H | H | H | 4-(2,2-difluorocyclopropyl) | 1 |
| C-5083 | H | H | H | H | H | 2-(2,2-dichlorocyclopropyl) | 1 |
| C-5084 | H | H | H | H | H | 3-(2,2-dichlorocyclopropyl) | 1 |
| C-5085 | H | H | H | H | H | 4-(2,2-dichlorocyclopropyl) | 1 |
| C-5086 | H | H | H | H | H | 2-ethenyl | 1 |
| C-5087 | H | H | H | H | H | 3-ethenyl | 1 |
| C-5088 | H | H | H | H | H | 4-ethenyl | 1 |
| C-5089 | H | H | H | H | H | 2-allyl | 1 |
| C-5090 | H | H | H | H | H | 3-allyl | 1 |
| C-5091 | H | H | H | H | H | 4-allyl | 1 |
| C-5092 | H | H | H | H | H | 2-(prop-1-en-1-yl) | 1 |
| C-5093 | H | H | H | H | H | 3-(prop-1-en-1-yl) | 1 |
| C-5094 | H | H | H | H | H | 4-(prop-1-en-1-yl) | 1 |
| C-5095 | H | H | H | H | H | 2-(trifluoroethenyl) | 1 |
| C-5096 | H | H | H | H | H | 3-(trifluoroethenyl) | 1 |
| C-5097 | H | H | H | H | H | 4-(trifluoroethenyl) | 1 |
| C-5098 | H | H | H | H | H | 2-(2,2-dichloroethenyl) | 1 |
| C-5099 | H | H | H | H | H | 3-(2,2-dichloroethenyl) | 1 |
| C-5100 | H | H | H | H | H | 4-(2,2-dichloroethenyl) | 1 |
| C-5101 | H | H | H | H | H | 2-ethynyl | 1 |
| C-5102 | H | H | H | H | H | 3-ethynyl | 1 |
| C-5103 | H | H | H | H | H | 4-ethynyl | 1 |
| C-5104 | H | H | H | H | H | 2-(1-propyn-1-yl) | 1 |
| C-5105 | H | H | H | H | H | 3-(1-propyn-1-yl) | 1 |
| C-5106 | H | H | H | H | H | 4-(1-propyn-1-yl) | 1 |
| C-5107 | H | H | H | H | H | 2-(2-propyn-1-yl) | 1 |
| C-5108 | H | H | H | H | H | 3-(2-propyn-1-yl) | 1 |
| C-5109 | H | H | H | H | H | 4-(2-propyn-1-yl) | 1 |

TABLE 218

| compound | R¹ | R² | R³ | R⁴ | R⁵ | (R⁸)$_m$ | p |
|---|---|---|---|---|---|---|---|
| C-5110 | H | H | H | H | H | 2-(2-cyclopropylethynyl) | 1 |
| C-5111 | H | H | H | H | H | 3-(2-cyclopropylethynyl) | 1 |
| C-5112 | H | H | H | H | H | 4-(2-cyclopropylethynyl) | 1 |
| C-5113 | H | H | H | H | H | 2-(2-chloroethynyl) | 1 |
| C-5114 | H | H | H | H | H | 3-(2-chloroethynyl) | 1 |
| C-5115 | H | H | H | H | H | 4-(2-chloroethynyl) | 1 |
| C-5116 | H | H | H | H | H | 2-(2-bromoethynyl) | 1 |
| C-5117 | H | H | H | H | H | 3-(2-bromoethynyl) | 1 |
| C-5118 | H | H | H | H | H | 4-(2-bromoethynyl) | 1 |
| C-5119 | H | H | H | H | H | 2-OMe | 1 |
| C-5120 | H | H | H | H | H | 3-OMe | 1 |
| C-5121 | H | H | H | H | H | 4-OMe | 1 |
| C-5122 | H | H | H | H | H | 2-OEt | 1 |
| C-5123 | H | H | H | H | H | 3-OEt | 1 |
| C-5124 | H | H | H | H | H | 4-OEt | 1 |
| C-5125 | H | H | H | H | H | 2-OPr | 1 |
| C-5126 | H | H | H | H | H | 3-OPr | 1 |
| C-5127 | H | H | H | H | H | 4-OPr | 1 |
| C-5128 | H | H | H | H | H | 2-O(i-Pr) | 1 |
| C-5129 | H | H | H | H | H | 3-O(i-Pr) | 1 |
| C-5130 | H | H | H | H | H | 4-O(i-Pr) | 1 |
| C-5131 | H | H | H | H | H | 2-OBu | 1 |
| C-5132 | H | H | H | H | H | 3-OBu | 1 |
| C-5133 | H | H | H | H | H | 4-OBu | 1 |
| C-5134 | H | H | H | H | H | 2-O(s-Bu) | 1 |
| C-5135 | H | H | H | H | H | 3-O(s-Bu) | 1 |
| C-5136 | H | H | H | H | H | 4-O(s-Bu) | 1 |
| C-5137 | H | H | H | H | H | 2-O(i-Bu) | 1 |
| C-5138 | H | H | H | H | H | 3-O(i-Bu) | 1 |
| C-5139 | H | H | H | H | H | 4-O(i-Bu) | 1 |
| C-5140 | H | H | H | H | H | 2-O(t-Bu) | 1 |
| C-5141 | H | H | H | H | H | 3-O(t-Bu) | 1 |
| C-5142 | H | H | H | H | H | 4-O(t-Bu) | 1 |

TABLE 218-continued

| compound | R¹ | R² | R³ | R⁴ | R⁵ | $(R^8)_m$ | p |
|---|---|---|---|---|---|---|---|
| C-5143 | H | H | H | H | H | 2-OCF$_3$ | 1 |
| C-5144 | H | H | H | H | H | 3-OCF$_3$ | 1 |
| C-5145 | H | H | H | H | H | 4-OCF$_3$ | 1 |
| C-5146 | H | H | H | H | H | 2-OCHF$_2$ | 1 |
| C-5147 | H | H | H | H | H | 3-OCHF$_2$ | 1 |
| C-5148 | H | H | H | H | H | 4-OCHF$_2$ | 1 |
| C-5149 | H | H | H | H | H | 2-OCH$_2$CF$_3$ | 1 |
| C-5150 | H | H | H | H | H | 3-OCH$_2$CF$_3$ | 1 |
| C-5151 | H | H | H | H | H | 4-OCH$_2$CF$_3$ | 1 |
| C-5152 | H | H | H | H | H | 2-(cyclopropyloxy) | 1 |
| C-5153 | H | H | H | H | H | 3-(cyclopropyloxy) | 1 |
| C-5154 | H | H | H | H | H | 4-(cyclopropyloxy) | 1 |
| C-5155 | H | H | H | H | H | 2-(cyclobutyloxy) | 1 |
| C-5156 | H | H | H | H | H | 3-(cyclobutyloxy) | 1 |
| C-5157 | H | H | H | H | H | 4-(cyclobutyloxy) | 1 |
| C-5158 | H | H | H | H | H | 2-(cyclopentyloxy) | 1 |
| C-5159 | H | H | H | H | H | 3-(cyclopentyloxy) | 1 |
| C-5160 | H | H | H | H | H | 4-(cyclopentyloxy) | 1 |
| C-5161 | H | H | H | H | H | 2-((2,2-dichlorocyclopropyl)oxy) | 1 |
| C-5162 | H | H | H | H | H | 3-((2,2-dichlorocyclopropyl)oxy) | 1 |
| C-5163 | H | H | H | H | H | 4-((2,2-dichlorocyclopropyl)oxy) | 1 |
| C-5164 | H | H | H | H | H | 2-(cyclopropylmethoxy) | 1 |
| C-5165 | H | H | H | H | H | 3-(cyclopropylmethoxy) | 1 |
| C-5166 | H | H | H | H | H | 4-(cyclopropylmethoxy) | 1 |

TABLE 219

| compound | R¹ | R² | R³ | R⁴ | R⁵ | $(R^8)_m$ | p |
|---|---|---|---|---|---|---|---|
| C-5167 | H | H | H | H | H | 2-((2,2-difluorocyclopropyl)methoxy) | 1 |
| C-5168 | H | H | H | H | H | 3-((2,2-difluorocyclopropyl)methoxy) | 1 |
| C-5169 | H | H | H | H | H | 4-((2,2-difluorocyclopropyl)methoxy) | 1 |
| C-5170 | H | H | H | H | H | 2-(oxiran-2-yl) | 1 |
| C-5171 | H | H | H | H | H | 3-(oxiran-2-yl) | 1 |
| C-5172 | H | H | H | H | H | 4-(oxiran-2-yl) | 1 |
| C-5173 | H | H | H | H | H | 2-(oxiran-2-ylmethyl) | 1 |
| C-5174 | H | H | H | H | H | 3-(oxiran-2-ylmethyl) | 1 |
| C-5175 | H | H | H | H | H | 4-(oxiran-2-ylmethyl) | 1 |
| C-5176 | H | H | H | H | H | 2-SMe | 1 |
| C-5177 | H | H | H | H | H | 3-SMe | 1 |
| C-5178 | H | H | H | H | H | 4-SMe | 1 |
| C-5179 | H | H | H | H | H | 2-SEt | 1 |
| C-5180 | H | H | H | H | H | 3-SEt | 1 |
| C-5181 | H | H | H | H | H | 4-SEt | 1 |
| C-5182 | H | H | H | H | H | 2-S(=O)Me | 1 |
| C-5183 | H | H | H | H | H | 3-S(=O)Me | 1 |
| C-5184 | H | H | H | H | H | 4-S(=O)Me | 1 |
| C-5185 | H | H | H | H | H | 2-S(=O)$_2$Me | 1 |
| C-5186 | H | H | H | H | H | 3-S(=O)$_2$Me | 1 |
| C-5187 | H | H | H | H | H | 4-S(=O)$_2$Me | 1 |
| C-5188 | H | H | H | H | H | 2-SCF$_3$ | 1 |
| C-5189 | H | H | H | H | H | 3-SCF$_3$ | 1 |
| C-5190 | H | H | H | H | H | 4-SCF$_3$ | 1 |
| C-5191 | H | H | H | H | H | 2-S(=O)CF$_3$ | 1 |
| C-5192 | H | H | H | H | H | 3-S(=O)CF$_3$ | 1 |
| C-5193 | H | H | H | H | H | 4-S(=O)CF$_3$ | 1 |
| C-5194 | H | H | H | H | H | 2-S(=O)$_2$CF$_3$ | 1 |
| C-5195 | H | H | H | H | H | 3-S(=O)$_2$CF$_3$ | 1 |
| C-5196 | H | H | H | H | H | 4-S(=O)$_2$CF$_3$ | 1 |
| C-5197 | H | H | H | H | H | 2-SCF(CF$_3$)$_2$ | 1 |
| C-5198 | H | H | H | H | H | 3-SCF(CF$_3$)$_2$ | 1 |
| C-5199 | H | H | H | H | H | 4-SCF(CF$_3$)$_2$ | 1 |
| C-5200 | H | H | H | H | H | 2-(cyclopropylthio) | 1 |
| C-5201 | H | H | H | H | H | 3-(cyclopropylthio) | 1 |
| C-5202 | H | H | H | H | H | 4-(cyclopropylthio) | 1 |
| C-5203 | H | H | H | H | H | 2-(cyclopropylsulfinyl) | 1 |
| C-5204 | H | H | H | H | H | 3-(cyclopropylsulfinyl) | 1 |
| C-5205 | H | H | H | H | H | 4-(cyclopropylsulfinyl) | 1 |
| C-5206 | H | H | H | H | H | 2-(cyclopropylsulfonyl) | 1 |
| C-5207 | H | H | H | H | H | 3-(cyclopropylsulfonyl) | 1 |
| C-5208 | H | H | H | H | H | 4-(cyclopropylsulfonyl) | 1 |
| C-5209 | H | H | H | H | H | 2-((cyclopropylmethyl)thio) | 1 |
| C-5210 | H | H | H | H | H | 3-((cyclopropylmethyl)thio) | 1 |
| C-5211 | H | H | H | H | H | 4-((cyclopropylmethyl)thio) | 1 |
| C-5212 | H | H | H | H | H | 2-((cyclopropylmethyl)sulfinyl) | 1 |
| C-5213 | H | H | H | H | H | 3-((cyclopropylmethyl)sulfinyl) | 1 |
| C-5214 | H | H | H | H | H | 4-((cyclopropylmethyl)sulfinyl) | 1 |
| C-5215 | H | H | H | H | H | 2-((cyclopropylmethyl)sulfonyl) | 1 |
| C-5216 | H | H | H | H | H | 3-((cyclopropylmethyl)sulfonyl) | 1 |
| C-5217 | H | H | H | H | H | 4-((cyclopropylmethyl)sulfonyl) | 1 |
| C-5218 | H | H | H | H | H | 2-(((2,2-difluorocyclopropyl)methyl)thio) | 1 |
| C-5219 | H | H | H | H | H | 3-(((2,2-difluorocyclopropyl)methyl)thio) | 1 |
| C-5220 | H | H | H | H | H | 4-(((2,2-difluorocyclopropyl)methyl)thio) | 1 |
| C-5221 | H | H | H | H | H | 2-(((2,2-difluorocyclopropyl)methyl)sulfinyl) | 1 |
| C-5222 | H | H | H | H | H | 3-(((2,2-difluorocyclopropyl)methyl)sulfinyl) | 1 |
| C-5223 | H | H | H | H | H | 4-(((2,2-difluorocyclopropyl)methyl)sulfinyl) | 1 |

TABLE 220

| compound | R¹ | R² | R³ | R⁴ | R⁵ | $(R^8)_m$ | p |
|---|---|---|---|---|---|---|---|
| C-5224 | H | H | H | H | H | 2-(((2,2-difluorocyclopropyl)methyl)sulfonyl) | 1 |
| C-5225 | H | H | H | H | H | 3-(((2,2-difluorocyclopropyl)methyl)sulfonyl) | 1 |
| C-5226 | H | H | H | H | H | 4-(((2,2-difluorocyclopropyl)methyl)sulfonyl) | 1 |
| C-5227 | H | H | H | H | H | 2-C(=O)Me | 1 |
| C-5228 | H | H | H | H | H | 3-C(=O)Me | 1 |
| C-5229 | H | H | H | H | H | 4-C(=O)Me | 1 |
| C-5230 | H | H | H | H | H | 2-C(=O)Et | 1 |
| C-5231 | H | H | H | H | H | 3-C(=O)Et | 1 |
| C-5232 | H | H | H | H | H | 4-C(=O)Et | 1 |
| C-5233 | H | H | H | H | H | 2-C(=O)CF$_3$ | 1 |
| C-5234 | H | H | H | H | H | 3-C(=O)CF$_3$ | 1 |
| C-5235 | H | H | H | H | H | 4-C(=O)CF$_3$ | 1 |
| C-5236 | H | H | H | H | H | 2-C(=O)OMe | 1 |
| C-5237 | H | H | H | H | H | 3-C(=O)OMe | 1 |
| C-5238 | H | H | H | H | H | 4-C(=O)OMe | 1 |
| C-5239 | H | H | H | H | H | 2-C(=O)OEt | 1 |
| C-5240 | H | H | H | H | H | 3-C(=O)OEt | 1 |
| C-5241 | H | H | H | H | H | 4-C(=O)OEt | 1 |
| C-5242 | H | H | H | H | H | 2-C(=O)NH$_2$ | 1 |
| C-5243 | H | H | H | H | H | 3-C(=O)NH$_2$ | 1 |
| C-5244 | H | H | H | H | H | 4-C(=O)NH$_2$ | 1 |
| C-5245 | H | H | H | H | H | 2-C(=O)NHMe | 1 |
| C-5246 | H | H | H | H | H | 3-C(=O)NHMe | 1 |
| C-5247 | H | H | H | H | H | 4-C(=O)NHMe | 1 |
| C-5248 | H | H | H | H | H | 2-C(=O)NMe$_2$ | 1 |
| C-5249 | H | H | H | H | H | 3-C(=O)NMe$_2$ | 1 |
| C-5250 | H | H | H | H | H | 4-C(=O)NMe$_2$ | 1 |
| C-5251 | H | H | H | H | H | 2-CH$_2$C(=O)CH$_3$ | 1 |
| C-5252 | H | H | H | H | H | 3-CH$_2$C(=O)CH$_3$ | 1 |
| C-5253 | H | H | H | H | H | 4-CH$_2$C(=O)CH$_3$ | 1 |
| C-5254 | H | H | H | H | H | 2-CH$_2$C(=O)CF$_3$ | 1 |
| C-5255 | H | H | H | H | H | 3-CH$_2$C(=O)CF$_3$ | 1 |
| C-5256 | H | H | H | H | H | 4-CH$_2$C(=O)CF$_3$ | 1 |
| C-5257 | H | H | H | H | H | 2-CH$_2$C(=O)OCH$_3$ | 1 |
| C-5258 | H | H | H | H | H | 3-CH$_2$C(=O)OCH$_3$ | 1 |
| C-5259 | H | H | H | H | H | 4-CH$_2$C(=O)OCH$_3$ | 1 |
| C-5260 | H | H | H | H | H | 2-CH$_2$OH | 1 |
| C-5261 | H | H | H | H | H | 3-CH$_2$OH | 1 |
| C-5262 | H | H | H | H | H | 4-CH$_2$OH | 1 |
| C-5263 | H | H | H | H | H | 2-CH$_2$OCH$_3$ | 1 |
| C-5264 | H | H | H | H | H | 3-CH$_2$OCH$_3$ | 1 |
| C-5265 | H | H | H | H | H | 4-CH$_2$OCH$_3$ | 1 |
| C-5266 | H | H | H | H | H | 2-CH$_2$OCH$_2$CH$_3$ | 1 |
| C-5267 | H | H | H | H | H | 3-CH$_2$OCH$_2$CH$_3$ | 1 |
| C-5268 | H | H | H | H | H | 4-CH$_2$OCH$_2$CH$_3$ | 1 |
| C-5269 | H | H | H | H | H | 2-CH(CH$_3$)OCH$_3$ | 1 |
| C-5270 | H | H | H | H | H | 3-CH(CH$_3$)OCH$_3$ | 1 |

TABLE 220-continued

| compound | R¹ | R² | R³ | R⁴ | R⁵ | (R⁸)ₘ | p |
|---|---|---|---|---|---|---|---|
| C-5271 | H | H | H | H | H | 4-CH(CH₃)OCH₃ | 1 |
| C-5272 | H | H | H | H | H | 2-CH₂CH₂OCH₃ | 1 |
| C-5273 | H | H | H | H | H | 3-CH₂CH₂OCH₃ | 1 |
| C-5274 | H | H | H | H | H | 4-CH₂CH₂OCH₃ | 1 |
| C-5275 | H | H | H | H | H | 2-CH₂OCF₃ | 1 |
| C-5276 | H | H | H | H | H | 3-CH₂OCF₃ | 1 |
| C-5277 | H | H | H | H | H | 4-CH₂OCF₃ | 1 |
| C-5278 | H | H | H | H | H | 2-CF₂OCH₃ | 1 |
| C-5279 | H | H | H | H | H | 3-CF₂OCH₃ | 1 |
| C-5280 | H | H | H | H | H | 4-CF₂OCH₃ | 1 |

TABLE 221

| compound | R¹ | R² | R³ | R⁴ | R⁵ | (R⁸)ₘ | p |
|---|---|---|---|---|---|---|---|
| C-5281 | H | H | H | H | H | 2-CF₂CF₂OCF₃ | 1 |
| C-5282 | H | H | H | H | H | 3-CF₂CF₂OCF₃ | 1 |
| C-5283 | H | H | H | H | H | 4-CF₂CF₂OCF₃ | 1 |
| C-5284 | H | H | H | H | H | 2-OC(=O)CH₃ | 1 |
| C-5285 | H | H | H | H | H | 3-OC(=O)CH₃ | 1 |
| C-5286 | H | H | H | H | H | 4-OC(=O)CH₃ | 1 |
| C-5287 | H | H | H | H | H | 2-OC(=O)CF₃ | 1 |
| C-5288 | H | H | H | H | H | 3-OC(=O)CF₃ | 1 |
| C-5289 | H | H | H | H | H | 4-OC(=O)CF₃ | 1 |
| C-5290 | H | H | H | H | H | 2-OC(=O)NH₂ | 1 |
| C-5291 | H | H | H | H | H | 3-OC(=O)NH₂ | 1 |
| C-5292 | H | H | H | H | H | 4-OC(=O)NH₂ | 1 |
| C-5293 | H | H | H | H | H | 2-OC(=O)NHCH₃ | 1 |
| C-5294 | H | H | H | H | H | 3-OC(=O)NHCH₃ | 1 |
| C-5295 | H | H | H | H | H | 4-OC(=O)NHCH₃ | 1 |
| C-5296 | H | H | H | H | H | 2-OC(=O)N(CH₃)₂ | 1 |
| C-5297 | H | H | H | H | H | 3-OC(=O)N(CH₃)₂ | 1 |
| C-5298 | H | H | H | H | H | 4-OC(=O)N(CH₃)₂ | 1 |
| C-5299 | H | H | H | H | H | 2-CH₂OC(=O)NH₂ | 1 |
| C-5300 | H | H | H | H | H | 3-CH₂OC(=O)NH₂ | 1 |
| C-5301 | H | H | H | H | H | 4-CH₂OC(=O)NH₂ | 1 |
| C-5302 | H | H | H | H | H | 2-CH₂OC(=O)NHCH₃ | 1 |
| C-5303 | H | H | H | H | H | 3-CH₂OC(=O)NHCH₃ | 1 |
| C-5304 | H | H | H | H | H | 4-CH₂OC(=O)NHCH₃ | 1 |
| C-5305 | H | H | H | H | H | 2-CH₂OC(=O)N(CH₃)₂ | 1 |
| C-5306 | H | H | H | H | H | 3-CH₂OC(=O)N(CH₃)₂ | 1 |
| C-5307 | H | H | H | H | H | 4-CH₂OC(=O)N(CH₃)₂ | 1 |
| C-5308 | H | H | H | H | H | 2-OC(=O)OCH₃ | 1 |
| C-5309 | H | H | H | H | H | 3-OC(=O)OCH₃ | 1 |
| C-5310 | H | H | H | H | H | 4-OC(=O)OCH₃ | 1 |
| C-5311 | H | H | H | H | H | 2-CH₂OC(=O)OCH₃ | 1 |
| C-5312 | H | H | H | H | H | 3-CH₂OC(=O)OCH₃ | 1 |
| C-5313 | H | H | H | H | H | 4-CH₂OC(=O)OCH₃ | 1 |
| C-5314 | H | H | H | H | H | 2-CH₂OC(=O)CH₃ | 1 |
| C-5315 | H | H | H | H | H | 3-CH₂OC(=O)CH₃ | 1 |
| C-5316 | H | H | H | H | H | 4-CH₂OC(=O)CH₃ | 1 |
| C-5317 | H | H | H | H | H | 2-OS(=O)₂CH₃ | 1 |
| C-5318 | H | H | H | H | H | 3-OS(=O)₂CH₃ | 1 |
| C-5319 | H | H | H | H | H | 4-OS(=O)₂CH₃ | 1 |
| C-5320 | H | H | H | H | H | 2-CH₂SCH₃ | 1 |
| C-5321 | H | H | H | H | H | 3-CH₂SCH₃ | 1 |
| C-5322 | H | H | H | H | H | 4-CH₂SCH₃ | 1 |
| C-5323 | H | H | H | H | H | 2-CH₂S(=O)CH₃ | 1 |
| C-5324 | H | H | H | H | H | 3-CH₂S(=O)CH₃ | 1 |
| C-5325 | H | H | H | H | H | 4-CH₂S(=O)CH₃ | 1 |
| C-5326 | H | H | H | H | H | 2-CH₂S(=O)₂CH₃ | 1 |
| C-5327 | H | H | H | H | H | 3-CH₂S(=O)₂CH₃ | 1 |
| C-5328 | H | H | H | H | H | 4-CH₂S(=O)₂CH₃ | 1 |
| C-5329 | H | H | H | H | H | 2-CH₂SCF₃ | 1 |
| C-5330 | H | H | H | H | H | 3-CH₂SCF₃ | 1 |
| C-5331 | H | H | H | H | H | 4-CH₂SCF₃ | 1 |
| C-5332 | H | H | H | H | H | 2-CH₂S(=O)CF₃ | 1 |
| C-5333 | H | H | H | H | H | 3-CH₂S(=O)CF₃ | 1 |
| C-5334 | H | H | H | H | H | 4-CH₂S(=O)CF₃ | 1 |
| C-5335 | H | H | H | H | H | 2-CH₂S(=O)₂CF₃ | 1 |
| C-5336 | H | H | H | H | H | 3-CH₂S(=O)₂CF₃ | 1 |
| C-5337 | H | H | H | H | H | 4-CH₂S(=O)₂CF₃ | 1 |

TABLE 222

| compound | R¹ | R² | R³ | R⁴ | R⁵ | (R⁸)ₘ | p |
|---|---|---|---|---|---|---|---|
| C-5338 | H | H | H | H | H | 2-phenyl | 1 |
| C-5339 | H | H | H | H | H | 3-phenyl | 1 |
| C-5340 | H | H | H | H | H | 4-phenyl | 1 |
| C-5341 | H | H | H | H | H | 2-(phenyloxy) | 1 |
| C-5342 | H | H | H | H | H | 3-(phenyloxy) | 1 |
| C-5343 | H | H | H | H | H | 4-(phenyloxy) | 1 |
| C-5344 | H | H | H | H | H | 2-benzyl | 1 |
| C-5345 | H | H | H | H | H | 3-benzyl | 1 |
| C-5346 | H | H | H | H | H | 4-benzyl | 1 |
| C-5347 | H | H | H | H | H | 2-(benzyloxy) | 1 |
| C-5348 | H | H | H | H | H | 3-(benzyloxy) | 1 |
| C-5349 | H | H | H | H | H | 4-(benzyloxy) | 1 |
| C-5350 | H | H | H | H | H | 2-((2-fluorobenzyl)oxy) | 1 |
| C-5351 | H | H | H | H | H | 3-((2-fluorobenzyl)oxy) | 1 |
| C-5352 | H | H | H | H | H | 4-((2-fluorobenzyl)oxy) | 1 |
| C-5353 | H | H | H | H | H | 2-((3-fluorobenzyl)oxy) | 1 |
| C-5354 | H | H | H | H | H | 3-((3-fluorobenzyl)oxy) | 1 |
| C-5355 | H | H | H | H | H | 4-((3-fluorobenzyl)oxy) | 1 |
| C-5356 | H | H | H | H | H | 2-((4-fluorobenzyl)oxy) | 1 |
| C-5357 | H | H | H | H | H | 3-((4-fluorobenzyl)oxy) | 1 |
| C-5358 | H | H | H | H | H | 4-((4-fluorobenzyl)oxy) | 1 |
| C-5359 | H | H | H | H | H | 2-((2-chlorobenzyl)oxy) | 1 |
| C-5360 | H | H | H | H | H | 3-((2-chlorobenzyl)oxy) | 1 |
| C-5361 | H | H | H | H | H | 4-((2-chlorobenzyl)oxy) | 1 |
| C-5362 | H | H | H | H | H | 2-((3-chlorobenzyl)oxy) | 1 |
| C-5363 | H | H | H | H | H | 3-((3-chlorobenzyl)oxy) | 1 |
| C-5364 | H | H | H | H | H | 4-((3-chlorobenzyl)oxy) | 1 |
| C-5365 | H | H | H | H | H | 2-((4-chlorobenzyl)oxy) | 1 |
| C-5366 | H | H | H | H | H | 3-((4-chlorobenzyl)oxy) | 1 |
| C-5367 | H | H | H | H | H | 4-((4-chlorobenzyl)oxy) | 1 |
| C-5368 | H | H | H | H | H | 2-((2-methylbenzyl)oxy) | 1 |
| C-5369 | H | H | H | H | H | 3-((2-methylbenzyl)oxy) | 1 |
| C-5370 | H | H | H | H | H | 4-((2-methylbenzyl)oxy) | 1 |
| C-5371 | H | H | H | H | H | 2-((3-methylbenzyl)oxy) | 1 |
| C-5372 | H | H | H | H | H | 3-((3-methylbenzyl)oxy) | 1 |
| C-5373 | H | H | H | H | H | 4-((3-methylbenzyl)oxy) | 1 |
| C-5374 | H | H | H | H | H | 2-((4-methylbenzyl)oxy) | 1 |
| C-5375 | H | H | H | H | H | 3-((4-methylbenzyl)oxy) | 1 |
| C-5376 | H | H | H | H | H | 4-((4-methylbenzyl)oxy) | 1 |
| C-5377 | H | H | H | H | H | 2-((2-(trifluoromethyl)benzyl)oxy) | 1 |
| C-5378 | H | H | H | H | H | 3-((2-(trifluoromethyl)benzyl)oxy) | 1 |
| C-5379 | H | H | H | H | H | 4-((2-(trifluoromethyl)benzyl)oxy) | 1 |
| C-5380 | H | H | H | H | H | 2-((3-(trifluoromethyl)benzyl)oxy) | 1 |
| C-5381 | H | H | H | H | H | 3-((3-(trifluoromethyl)benzyl)oxy) | 1 |
| C-5382 | H | H | H | H | H | 4-((3-(trifluoromethyl)benzyl)oxy) | 1 |
| C-5383 | H | H | H | H | H | 2-((4-(trifluoromethyl)benzyl)oxy) | 1 |
| C-5384 | H | H | H | H | H | 3-((4-(trifluoromethyl)benzyl)oxy) | 1 |
| C-5385 | H | H | H | H | H | 4-((4-(trifluoromethyl)benzyl)oxy) | 1 |
| C-5386 | H | H | H | H | H | 2-((2-methoxybenzyl)oxy) | 1 |
| C-5387 | H | H | H | H | H | 3-((2-methoxybenzyl)oxy) | 1 |
| C-5388 | H | H | H | H | H | 4-((2-methoxybenzyl)oxy) | 1 |
| C-5389 | H | H | H | H | H | 2-((3-methoxybenzyl)oxy) | 1 |
| C-5390 | H | H | H | H | H | 3-((3-methoxybenzyl)oxy) | 1 |
| C-5391 | H | H | H | H | H | 4-((3-methoxybenzyl)oxy) | 1 |
| C-5392 | H | H | H | H | H | 2-((4-methoxybenzyl)oxy) | 1 |
| C-5393 | H | H | H | H | H | 3-((4-methoxybenzyl)oxy) | 1 |
| C-5394 | H | H | H | H | H | 4-((4-methoxybenzyl)oxy) | 1 |

TABLE 223

| compound | R$^1$ | R$^2$ | R$^3$ | R$^4$ | R$^5$ | (R$^8$)$_m$ | p |
|---|---|---|---|---|---|---|---|
| C-5395 | H | H | H | H | H | 2-((2-(trifluoromethoxy)benzyl)oxy) | 1 |
| C-5396 | H | H | H | H | H | 3-((2-(trifluoromethoxy)benzyl)oxy) | 1 |
| C-5397 | H | H | H | H | H | 4-((2-(trifluoromethoxy)benzyl)oxy) | 1 |
| C-5398 | H | H | H | H | H | 2-((3-(trifluoromethoxy)benzyl)oxy) | 1 |
| C-5399 | H | H | H | H | H | 3-((3-(trifluoromethoxy)benzyl)oxy) | 1 |
| C-5400 | H | H | H | H | H | 4-((3-(trifluoromethoxy)benzyl)oxy) | 1 |
| C-5401 | H | H | H | H | H | 2-((4-(trifluoromethoxy)benzyl)oxy) | 1 |
| C-5402 | H | H | H | H | H | 3-((4-(trifluoromethoxy)benzyl)oxy) | 1 |
| C-5403 | H | H | H | H | H | 4-((4-(trifluoromethoxy)benzyl)oxy) | 1 |
| C-5404 | H | H | H | H | H | 2-((2-(methylthio)benzyl)oxy) | 1 |
| C-5405 | H | H | H | H | H | 3-((2-(methylthio)benzyl)oxy) | 1 |
| C-5406 | H | H | H | H | H | 4-((2-(methylthio)benzyl)oxy) | 1 |
| C-5407 | H | H | H | H | H | 2-((3-(methylthio)benzyl)oxy) | 1 |
| C-5408 | H | H | H | H | H | 3-((3-(methylthio)benzyl)oxy) | 1 |
| C-5409 | H | H | H | H | H | 4-((3-(methylthio)benzyl)oxy) | 1 |
| C-5410 | H | H | H | H | H | 2-((4-(methylthio)benzyl)oxy) | 1 |
| C-5411 | H | H | H | H | H | 3-((4-(methylthio)benzyl)oxy) | 1 |
| C-5412 | H | H | H | H | H | 4-((4-(methylthio)benzyl)oxy) | 1 |
| C-5413 | H | H | H | H | H | 2-((2-(methylsulfinyl)benzyl)oxy) | 1 |
| C-5414 | H | H | H | H | H | 3-((2-(methylsulfinyl)benzyl)oxy) | 1 |
| C-5415 | H | H | H | H | H | 4-((2-(methylsulfinyl)benzyl)oxy) | 1 |
| C-5416 | H | H | H | H | H | 2-((3-(methylsulfinyl)benzyl)oxy) | 1 |
| C-5417 | H | H | H | H | H | 3-((3-(methylsulfinyl)benzyl)oxy) | 1 |
| C-5418 | H | H | H | H | H | 4-((3-(methylsulfinyl)benzyl)oxy) | 1 |
| C-5419 | H | H | H | H | H | 2-((4-(methylsulfinyl)benzyl)oxy) | 1 |
| C-5420 | H | H | H | H | H | 3-((4-(methylsulfinyl)benzyl)oxy) | 1 |
| C-5421 | H | H | H | H | H | 4-((4-(methylsulfinyl)benzyl)oxy) | 1 |
| C-5422 | H | H | H | H | H | 2-((2-(methylsulfonyl)benzyl)oxy) | 1 |
| C-5423 | H | H | H | H | H | 3-((2-(methylsulfonyl)benzyl)oxy) | 1 |
| C-5424 | H | H | H | H | H | 4-((2-(methylsulfonyl)benzyl)oxy) | 1 |
| C-5425 | H | H | H | H | H | 2-((3-(methylsulfonyl)benzyl)oxy) | 1 |
| C-5426 | H | H | H | H | H | 3-((3-(methylsulfonyl)benzyl)oxy) | 1 |
| C-5427 | H | H | H | H | H | 4-((3-(methylsulfonyl)benzyl)oxy) | 1 |
| C-5428 | H | H | H | H | H | 2-((4-(methylsulfonyl)benzyl)oxy) | 1 |
| C-5429 | H | H | H | H | H | 3-((4-(methylsulfonyl)benzyl)oxy) | 1 |
| C-5430 | H | H | H | H | H | 4-((4-(methylsulfonyl)benzyl)oxy) | 1 |
| C-5431 | H | H | H | H | H | 2-((2-(trifluoromethylthio)benzyl)oxy) | 1 |
| C-5432 | H | H | H | H | H | 3-((2-(trifluoromethylthio)benzyl)oxy) | 1 |
| C-5433 | H | H | H | H | H | 4-((2-(trifluoromethylthio)benzyl)oxy) | 1 |
| C-5434 | H | H | H | H | H | 2-((3-(trifluoromethylthio)benzyl)oxy) | 1 |
| C-5435 | H | H | H | H | H | 3-((3-(trifluoromethylthio)benzyl)oxy) | 1 |
| C-5436 | H | H | H | H | H | 4-((3-(trifluoromethylthio)benzyl)oxy) | 1 |
| C-5437 | H | H | H | H | H | 2-((4-(trifluoromethylthio)benzyl)oxy) | 1 |
| C-5438 | H | H | H | H | H | 3-((4-(trifluoromethylthio)benzyl)oxy) | 1 |
| C-5439 | H | H | H | H | H | 4-((4-(trifluoromethylthio)benzyl)oxy) | 1 |
| C-5440 | H | H | H | H | H | 2-((2-(trifluoromethylsulfinyl)benzyl)oxy) | 1 |
| C-5441 | H | H | H | H | H | 3-((2-(trifluoromethylsulfinyl)benzyl)oxy) | 1 |
| C-5442 | H | H | H | H | H | 4-((2-(trifluoromethylsulfinyl)benzyl)oxy) | 1 |
| C-5443 | H | H | H | H | H | 2-((3-(trifluoromethylsulfinyl)benzyl)oxy) | 1 |
| C-5444 | H | H | H | H | H | 3-((3-(trifluoromethylsulfinyl)benzyl)oxy) | 1 |
| C-5445 | H | H | H | H | H | 4-((3-(trifluoromethylsulfinyl)benzyl)oxy) | 1 |
| C-5446 | H | H | H | H | H | 2-((4-(trifluoromethylsulfinyl)benzyl)oxy) | 1 |
| C-5447 | H | H | H | H | H | 3-((4-(trifluoromethylsulfinyl)benzyl)oxy) | 1 |
| C-5448 | H | H | H | H | H | 4-((4-(trifluoromethylsulfinyl)benzyl)oxy) | 1 |
| C-5449 | H | H | H | H | H | 2-((2-(trifluoromethylsulfonyl)benzyl)oxy) | 1 |
| C-5450 | H | H | H | H | H | 3-((2-(trifluoromethylsulfonyl)benzyl)oxy) | 1 |
| C-5451 | H | H | H | H | H | 4-((2-(trifluoromethylsulfonyl)benzyl)oxy) | 1 |

TABLE 224

| compound | R$^1$ | R$^2$ | R$^3$ | R$^4$ | R$^5$ | (R$^8$)$_m$ | p |
|---|---|---|---|---|---|---|---|
| C-5452 | H | H | H | H | H | 2-((3-(trifluoromethylsulfonyl)benzyl)oxy) | 1 |
| C-5453 | H | H | H | H | H | 3-((3-(trifluoromethylsulfonyl)benzyl)oxy) | 1 |
| C-5454 | H | H | H | H | H | 4-((3-(trifluoromethylsulfonyl)benzyl)oxy) | 1 |
| C-5455 | H | H | H | H | H | 2-((4-(trifluoromethylsulfonyl)benzyl)oxy) | 1 |
| C-5456 | H | H | H | H | H | 3-((4-(trifluoromethylsulfonyl)benzyl)oxy) | 1 |
| C-5457 | H | H | H | H | H | 4-((4-(trifluoromethylsulfonyl)benzyl)oxy) | 1 |
| C-5458 | H | H | H | H | H | 2-((2-aminobenzyl)oxy) | 1 |
| C-5459 | H | H | H | H | H | 3-((2-aminobenzyl)oxy) | 1 |
| C-5460 | H | H | H | H | H | 4-((2-aminobenzyl)oxy) | 1 |
| C-5461 | H | H | H | H | H | 2-((3-aminobenzyl)oxy) | 1 |
| C-5462 | H | H | H | H | H | 3-((3-aminobenzyl)oxy) | 1 |
| C-5463 | H | H | H | H | H | 4-((3-aminobenzyl)oxy) | 1 |
| C-5464 | H | H | H | H | H | 2-((4-aminobenzyl)oxy) | 1 |

TABLE 224-continued

| compound | R¹ | R² | R³ | R⁴ | R⁵ | (R⁸)ₘ | p |
|---|---|---|---|---|---|---|---|
| C-5465 | H | H | H | H | H | 3-((4-aminobenzyl)oxy) | 1 |
| C-5466 | H | H | H | H | H | 4-((4-aminobenzyl)oxy) | 1 |
| C-5467 | H | H | H | H | H | 2-((2-(methylamino)benzyl)oxy) | 1 |
| C-5468 | H | H | H | H | H | 3-((2-(methylamino)benzyl)oxy) | 1 |
| C-5469 | H | H | H | H | H | 4-((2-(methylamino)benzyl)oxy) | 1 |
| C-5470 | H | H | H | H | H | 2-((3-(methylamino)benzyl)oxy) | 1 |
| C-5471 | H | H | H | H | H | 3-((3-(methylamino)benzyl)oxy) | 1 |
| C-5472 | H | H | H | H | H | 4-((3-(methylamino)benzyl)oxy) | 1 |
| C-5473 | H | H | H | H | H | 2-((4-(methylamino)benzyl)oxy) | 1 |
| C-5474 | H | H | H | H | H | 3-((4-(methylamino)benzyl)oxy) | 1 |
| C-5475 | H | H | H | H | H | 4-((4-(methylamino)benzyl)oxy) | 1 |
| C-5476 | H | H | H | H | H | 2-((2-(dimethylamino)benzyl)oxy) | 1 |
| C-5477 | H | H | H | H | H | 3-((2-(dimethylamino)benzyl)oxy) | 1 |
| C-5478 | H | H | H | H | H | 4-((2-(dimethylamino)benzyl)oxy) | 1 |
| C-5479 | H | H | H | H | H | 2-((3-(dimethylamino)benzyl)oxy) | 1 |
| C-5480 | H | H | H | H | H | 3-((3-(dimethylamino)benzyl)oxy) | 1 |
| C-5481 | H | H | H | H | H | 4-((3-(dimethylamino)benzyl)oxy) | 1 |
| C-5482 | H | H | H | H | H | 2-((4-(dimethylamino)benzyl)oxy) | 1 |
| C-5483 | H | H | H | H | H | 3-((4-(dimethylamino)benzyl)oxy) | 1 |
| C-5484 | H | H | H | H | H | 4-((4-(dimethylamino)benzyl)oxy) | 1 |
| C-5485 | H | H | H | H | H | 2-((2-cyanobenzyl)oxy) | 1 |
| C-5486 | H | H | H | H | H | 3-((2-cyanobenzyl)oxy) | 1 |
| C-5487 | H | H | H | H | H | 4-((2-cyanobenzyl)oxy) | 1 |
| C-5488 | H | H | H | H | H | 2-((3-cyanobenzyl)oxy) | 1 |
| C-5489 | H | H | H | H | H | 3-((3-cyanobenzyl)oxy) | 1 |
| C-5490 | H | H | H | H | H | 4-((3-cyanobenzyl)oxy) | 1 |
| C-5491 | H | H | H | H | H | 2-((4-cyanobenzyl)oxy) | 1 |
| C-5492 | H | H | H | H | H | 3-((4-cyanobenzyl)oxy) | 1 |
| C-5493 | H | H | H | H | H | 4-((4-cyanobenzyl)oxy) | 1 |
| C-5494 | H | H | H | H | H | 2-((2-nitrobenzyl)oxy) | 1 |
| C-5495 | H | H | H | H | H | 3-((2-nitrobenzyl)oxy) | 1 |
| C-5496 | H | H | H | H | H | 4-((2-nitrobenzyl)oxy) | 1 |
| C-5497 | H | H | H | H | H | 2-((3-nitrobenzyl)oxy) | 1 |
| C-5498 | H | H | H | H | H | 3-((3-nitrobenzyl)oxy) | 1 |
| C-5499 | H | H | H | H | H | 4-((3-nitrobenzyl)oxy) | 1 |
| C-5500 | H | H | H | H | H | 2-((4-nitrobenzyl)oxy) | 1 |
| C-5501 | H | H | H | H | H | 3-((4-nitrobenzyl)oxy) | 1 |
| C-5502 | H | H | H | H | H | 4-((4-nitrobenzyl)oxy) | 1 |
| C-5503 | H | H | H | H | H | 2-NH₂ | 1 |
| C-5504 | H | H | H | H | H | 3-NH₂ | 1 |
| C-5505 | H | H | H | H | H | 4-NH₂ | 1 |
| C-5506 | H | H | H | H | H | 2-NHMe | 1 |
| C-5507 | H | H | H | H | H | 3-NHMe | 1 |
| C-5508 | H | H | H | H | H | 4-NHMe | 1 |

TABLE 225

| compound | R¹ | R² | R³ | R⁴ | R⁵ | (R⁸)ₘ | p |
|---|---|---|---|---|---|---|---|
| C-5509 | H | H | H | H | H | 2-NHEt | 1 |
| C-5510 | H | H | H | H | H | 3-NHEt | 1 |
| C-5511 | H | H | H | H | H | 4-NHEt | 1 |
| C-5512 | H | H | H | H | H | 2-N(Me)₂ | 1 |
| C-5513 | H | H | H | H | H | 3-N(Me)₂ | 1 |
| C-5514 | H | H | H | H | H | 4-N(Me)₂ | 1 |
| C-5515 | H | H | H | H | H | 2-N(Et)₂ | 1 |
| C-5516 | H | H | H | H | H | 3-N(Et)₂ | 1 |
| C-5517 | H | H | H | H | H | 4-N(Et)₂ | 1 |
| C-5518 | H | H | H | H | H | 2-CHO | 1 |
| C-5519 | H | H | H | H | H | 3-CHO | 1 |
| C-5520 | H | H | H | H | H | 4-CHO | 1 |
| C-5521 | H | H | H | H | H | 2-C(=O)OH | 1 |
| C-5522 | H | H | H | H | H | 3-C(=O)OH | 1 |
| C-5523 | H | H | H | H | H | 4-C(=O)OH | 1 |
| C-5524 | H | H | H | H | H | 2-(1,3-dioxolan-2-yl) | 1 |
| C-5525 | H | H | H | H | H | 3-(1,3-dioxolan-2-yl) | 1 |
| C-5526 | H | H | H | H | H | 4-(1,3-dioxolan-2-yl) | 1 |
| C-5527 | H | H | H | H | H | 2-(1,3-dioxan-2-yl) | 1 |
| C-5528 | H | H | H | H | H | 3-(1,3-dioxan-2-yl) | 1 |
| C-5529 | H | H | H | H | H | 4-(1,3-dioxan-2-yl) | 1 |
| C-5530 | H | H | H | H | H | 2-(1H-imidazol-2-yl) | 1 |
| C-5531 | H | H | H | H | H | 3-(1H-imidazol-2-yl) | 1 |
| C-5532 | H | H | H | H | H | 4-(1H-imidazol-2-yl) | 1 |
| C-5533 | H | H | H | H | H | 2-(thiazol-2-yl) | 1 |
| C-5534 | H | H | H | H | H | 3-(thiazol-2-yl) | 1 |
| C-5535 | H | H | H | H | H | 4-(thiazol-2-yl) | 1 |
| C-5536 | H | H | H | H | H | 2-(oxazol-2-yl) | 1 |
| C-5537 | H | H | H | H | H | 3-(oxazol-2-yl) | 1 |
| C-5538 | H | H | H | H | H | 4-(oxazol-2-yl) | 1 |
| C-5539 | H | H | H | H | H | 2-CH=NOH | 1 |
| C-5540 | H | H | H | H | H | 3-CH=NOH | 1 |
| C-5541 | H | H | H | H | H | 4-CH=NOH | 1 |
| C-5542 | H | H | H | H | H | 2-CH=NOMe | 1 |
| C-5543 | H | H | H | H | H | 3-CH=NOMe | 1 |
| C-5544 | H | H | H | H | H | 4-CH=NOMe | 1 |
| C-5545 | H | H | H | H | H | 2-(4,5-dihydro-3-isoxazolyl) | 1 |
| C-5546 | H | H | H | H | H | 3-(4,5-dihydro-3-isoxazolyl) | 1 |
| C-5547 | H | H | H | H | H | 4-(4,5-dihydro-3-isoxazolyl) | 1 |
| C-5548 | H | H | H | H | H | 2-CN | 1 |
| C-5549 | H | H | H | H | H | 3-CN | 1 |
| C-5550 | H | H | H | H | H | 4-CN | 1 |
| C-5551 | H | H | H | H | H | 2-NO₂ | 1 |
| C-5552 | H | H | H | H | H | 3-NO₂ | 1 |
| C-5553 | H | H | H | H | H | 4-NO₂ | 1 |
| C-5554 | H | H | H | H | H | 2,3-F₂ | 1 |
| C-5555 | H | H | H | H | H | 2,4-F₂ | 1 |
| C-5556 | H | H | H | H | H | 2,5-F₂ | 1 |
| C-5557 | H | H | H | H | H | 2,6-F₂ | 1 |
| C-5558 | H | H | H | H | H | 3,4-F₂ | 1 |
| C-5559 | H | H | H | H | H | 3,5-F₂ | 1 |
| C-5560 | H | H | H | H | H | 2-F,3-Cl | 1 |

TABLE 225-continued

| compound | R¹ | R² | R³ | R⁴ | R⁵ | $(R^8)_m$ | p |
|---|---|---|---|---|---|---|---|
| C-5561 | H | H | H | H | H | 2-F,4-Cl | 1 |
| C-5562 | H | H | H | H | H | 2-F,5-Cl | 1 |
| C-5563 | H | H | H | H | H | 2-F,6-Cl | 1 |
| C-5564 | H | H | H | H | H | 3-F,2-Cl | 1 |
| C-5565 | H | H | H | H | H | 3-F,4-Cl | 1 |

TABLE 226

| compound | R¹ | R² | R³ | R⁴ | R⁵ | $(R^8)_m$ | p |
|---|---|---|---|---|---|---|---|
| C-5566 | H | H | H | H | H | 3-F,5-Cl | 1 |
| C-5567 | H | H | H | H | H | 3-F,6-Cl | 1 |
| C-5568 | H | H | H | H | H | 4-F,2-Cl | 1 |
| C-5569 | H | H | H | H | H | 4-F,3-Cl | 1 |
| C-5570 | H | H | H | H | H | 2-F,3-Me | 1 |
| C-5571 | H | H | H | H | H | 2-F,4-Me | 1 |
| C-5572 | H | H | H | H | H | 2-F,5-Me | 1 |
| C-5573 | H | H | H | H | H | 2-F,6-Me | 1 |
| C-5574 | H | H | H | H | H | 3-F,2-Me | 1 |
| C-5575 | H | H | H | H | H | 3-F,4-Me | 1 |
| C-5576 | H | H | H | H | H | 3-F,5-Me | 1 |
| C-5577 | H | H | H | H | H | 3-F,6-Me | 1 |
| C-5578 | H | H | H | H | H | 4-F,2-Me | 1 |
| C-5579 | H | H | H | H | H | 4-F,3-Me | 1 |
| C-5580 | H | H | H | H | H | 2-F,3-CF₃ | 1 |
| C-5581 | H | H | H | H | H | 2-F,4-CF₃ | 1 |
| C-5582 | H | H | H | H | H | 2-F,5-CF₃ | 1 |
| C-5583 | H | H | H | H | H | 2-F,6-CF₃ | 1 |
| C-5584 | H | H | H | H | H | 3-F,2-CF₃ | 1 |
| C-5585 | H | H | H | H | H | 3-F,4-CF₃ | 1 |
| C-5586 | H | H | H | H | H | 3-F,5-CF₃ | 1 |
| C-5587 | H | H | H | H | H | 3-F,6-CF₃ | 1 |
| C-5588 | H | H | H | H | H | 4-F,2-CF₃ | 1 |
| C-5589 | H | H | H | H | H | 4-F,3-CF₃ | 1 |
| C-5590 | H | H | H | H | H | 2-F,3-OMe | 1 |
| C-5591 | H | H | H | H | H | 2-F,4-OMe | 1 |
| C-5592 | H | H | H | H | H | 2-F,5-OMe | 1 |
| C-5593 | H | H | H | H | H | 2-F,6-OMe | 1 |
| C-5594 | H | H | H | H | H | 3-F,2-OMe | 1 |
| C-5595 | H | H | H | H | H | 3-F,4-OMe | 1 |
| C-5596 | H | H | H | H | H | 3-F,5-OMe | 1 |
| C-5597 | H | H | H | H | H | 3-F,6-OMe | 1 |
| C-5598 | H | H | H | H | H | 4-F,2-OMe | 1 |
| C-5599 | H | H | H | H | H | 4-F,3-OMe | 1 |
| C-5600 | H | H | H | H | H | 2,3-Cl₂ | 1 |
| C-5601 | H | H | H | H | H | 2,4-Cl₂ | 1 |
| C-5602 | H | H | H | H | H | 2,5-Cl₂ | 1 |
| C-5603 | H | H | H | H | H | 2,6-Cl₂ | 1 |
| C-5604 | H | H | H | H | H | 3,4-Cl₂ | 1 |
| C-5605 | H | H | H | H | H | 3,5-Cl₂ | 1 |
| C-5606 | H | H | H | H | H | 2-Cl,3-Me | 1 |
| C-5607 | H | H | H | H | H | 2-Cl,4-Me | 1 |
| C-5608 | H | H | H | H | H | 2-Cl,5-Me | 1 |
| C-5609 | H | H | H | H | H | 2-Cl,6-Me | 1 |
| C-5610 | H | H | H | H | H | 3-Cl,2-Me | 1 |
| C-5611 | H | H | H | H | H | 3-Cl,4-Me | 1 |
| C-5612 | H | H | H | H | H | 3-Cl,5 Me | 1 |
| C-5613 | H | H | H | H | H | 3-Cl,6 Me | 1 |
| C-5614 | H | H | H | H | H | 4-Cl,2 Me | 1 |
| C-5615 | H | H | H | H | H | 4-Cl,3-Me | 1 |
| C-5616 | H | H | H | H | H | 2-Cl,3-CF₃ | 1 |
| C-5617 | H | H | H | H | H | 2-Cl,4-CF₃ | 1 |
| C-5618 | H | H | H | H | H | 2-Cl,5-CF₃ | 1 |
| C-5619 | H | H | H | H | H | 2-Cl,6-CF₃ | 1 |
| C-5620 | H | H | H | H | H | 3-Cl,2-CF₃ | 1 |
| C-5621 | H | H | H | H | H | 3-Cl,4-CF₃ | 1 |
| C-5622 | H | H | H | H | H | 3-Cl,5-CF₃ | 1 |

TABLE 227

| compound | R¹ | R² | R³ | R⁴ | R⁵ | $(R^8)_m$ | p |
|---|---|---|---|---|---|---|---|
| C-5623 | H | H | H | H | H | 3-Cl,6-CF₃ | 1 |
| C-5624 | H | H | H | H | H | 4-Cl,2-CF₃ | 1 |
| C-5625 | H | H | H | H | H | 4-Cl,3-CF₃ | 1 |
| C-5626 | H | H | H | H | H | 2-Cl,3-OMe | 1 |
| C-5627 | H | H | H | H | H | 2-Cl,4-OMe | 1 |
| C-5628 | H | H | H | H | H | 2-Cl,5-OMe | 1 |
| C-5629 | H | H | H | H | H | 2-Cl,6-OMe | 1 |
| C-5630 | H | H | H | H | H | 3-Cl,2-OMe | 1 |
| C-5631 | H | H | H | H | H | 3-Cl,4-OMe | 1 |
| C-5632 | H | H | H | H | H | 3-Cl,5-OMe | 1 |
| C-5633 | H | H | H | H | H | 3-Cl,6-OMe | 1 |
| C-5634 | H | H | H | H | H | 4-Cl,2-OMe | 1 |
| C-5635 | H | H | H | H | H | 4-Cl,3-OMe | 1 |
| C-5636 | H | H | H | H | H | 2,3-Me₂ | 1 |
| C-5637 | H | H | H | H | H | 2,4-Me₂ | 1 |
| C-5638 | H | H | H | H | H | 2,5-Me₂ | 1 |
| C-5639 | H | H | H | H | H | 2,6-Me₂ | 1 |
| C-5640 | H | H | H | H | H | 3,4-Me₂ | 1 |
| C-5641 | H | H | H | H | H | 3,5-Me₂ | 1 |
| C-5642 | H | H | H | H | H | 2-Me,3-CF₃ | 1 |
| C-5643 | H | H | H | H | H | 2-Me,4-CF₃ | 1 |
| C-5644 | H | H | H | H | H | 2-Me,5-CF₃ | 1 |
| C-5645 | H | H | H | H | H | 2-Me,6-CF₃ | 1 |
| C-5646 | H | H | H | H | H | 3-Me,2-CF₃ | 1 |
| C-5647 | H | H | H | H | H | 3-Me,4-CF₃ | 1 |
| C-5648 | H | H | H | H | H | 3-Me,5-CF₃ | 1 |
| C-5649 | H | H | H | H | H | 3-Me,6-CF₃ | 1 |
| C-5650 | H | H | H | H | H | 4-Me,2-CF₃ | 1 |
| C-5651 | H | H | H | H | P | 4-Me,3-CF₃ | 1 |
| C-5652 | H | H | H | H | H | 2-Me,3-OMe | 1 |
| C-5653 | H | H | H | H | H | 2-Me,4-OMe | 1 |
| C-5654 | H | H | H | H | H | 2-Me,5-OMe | 1 |
| C-5655 | H | H | H | H | H | 2-Me,6-OMe | 1 |
| C-5656 | H | H | H | H | H | 3-Me,2-OMe | 1 |
| C-5657 | H | H | H | H | H | 3-Me,4-OMe | 1 |
| C-5658 | H | H | H | H | H | 3-Me,5-OMe | 1 |
| C-5659 | H | H | H | H | H | 3-Me,6-OMe | 1 |
| C-5660 | H | H | H | H | H | 4-Me,2-OMe | 1 |
| C-5661 | H | H | H | H | H | 4-Me,3-OMe | 1 |
| C-5662 | H | H | H | H | H | 2,3-OMe₂ | 1 |
| C-5663 | H | H | H | H | H | 2,4-OMe₂ | 1 |
| C-5664 | H | H | H | H | H | 2,5-OMe₂ | 1 |
| C-5665 | H | H | H | H | H | 2,6-OMe₂ | 1 |
| C-5666 | H | H | H | H | H | 3,4-OMe₂ | 1 |
| C-5667 | H | H | H | H | H | 3,5-OMe₂ | 1 |
| C-5668 | H | H | H | H | H | 2-OMe,3-CF₃ | 1 |
| C-5669 | H | H | H | H | H | 2-OMe,4-CF₃ | 1 |
| C-5670 | H | H | H | H | H | 2-OMe,5-CF₃ | 1 |
| C-5671 | H | H | H | H | H | 2-OMe,6-CF₃ | 1 |
| C-5672 | H | H | H | H | H | 3-OMe,2-CF₃ | 1 |
| C-5673 | H | H | H | H | H | 3-OMe,4-CF₃ | 1 |
| C-5674 | H | H | H | H | H | 3-OMe,5-CF₃ | 1 |
| C-5675 | H | H | H | H | H | 3-OMe,6-CF₃ | 1 |
| C-5676 | H | H | H | H | H | 4-OMe,2-CF₃ | 1 |
| C-5677 | H | H | H | H | H | 4-OMe,3-CF₃ | 1 |
| C-5678 | H | H | H | H | H | 2-CHF₂,3-F | 1 |
| C-5679 | H | H | H | H | H | 2-CHF₂,4-F | 1 |

TABLE 228

| compound | R¹ | R² | R³ | R⁴ | R⁵ | $(R^8)_m$ | p |
|---|---|---|---|---|---|---|---|
| C-5680 | H | H | H | H | H | 2-CHF₂,5-F | 1 |
| C-5681 | H | H | H | H | H | 2-CHF₂,6-F | 1 |
| C-5682 | H | H | H | H | H | 2-CHF₂,3-Me | 1 |
| C-5683 | H | H | H | H | H | 2-CHF₂,4-Me | 1 |
| C-5684 | H | H | H | H | H | 2-CHF₂,5-Me | 1 |
| C-5685 | H | H | H | H | H | 2-CHF₂,6-Me | 1 |
| C-5686 | H | H | H | H | H | 2-cyclopropyl,3-F | 1 |
| C-5687 | H | H | H | H | H | 2-cyclopropyl,4-F | 1 |
| C-5688 | H | H | H | H | H | 2-cyclopropyl,5-F | 1 |
| C-5689 | H | H | H | H | H | 2-cyclopropyl,6-F | 1 |
| C-5690 | H | H | H | H | H | 2-cyclopropyl,3-Me | 1 |
| C-5691 | H | H | H | H | H | 2-cyclopropyl,4-Me | 1 |
| C-5692 | H | H | H | H | H | 2-cyclopropyl,5-Me | 1 |
| C-5693 | H | H | H | H | H | 2-cyclopropyl,6-Me | 1 |

TABLE 228-continued

| compound | R¹ | R² | R³ | R⁴ | R⁵ | (R⁸)ₘ | p |
|---|---|---|---|---|---|---|---|
| C-5694 | H | H | H | H | H | 2-ethenyl,3-F | 1 |
| C-5695 | H | H | H | H | H | 2-ethenyl,4-F | 1 |
| C-5696 | H | H | H | H | H | 2-ethenyl,5-F | 1 |
| C-5697 | H | H | H | H | H | 2-ethenyl,6-F | 1 |
| C-5698 | H | H | H | H | H | 2-ethenyl,3-Me | 1 |
| C-5699 | H | H | H | H | H | 2-ethenyl,4-Me | 1 |
| C-5700 | H | H | H | H | H | 2-ethenyl,5-Me | 1 |
| C-5701 | H | H | H | H | H | 2-ethenyl,6-Me | 1 |
| C-5702 | H | H | H | H | H | 2-OEt,3-F | 1 |
| C-5703 | H | H | H | H | H | 2-OEt,4-F | 1 |
| C-5704 | H | H | H | H | H | 2-OEt,5-F | 1 |
| C-5705 | H | H | H | H | H | 2-OEt,6-F | 1 |
| C-5706 | H | H | H | H | H | 2-OEt,3-Cl | 1 |
| C-5707 | H | H | H | H | H | 2-OEt,4-Cl | 1 |
| C-5708 | H | H | H | H | H | 2-OEt,5-Cl | 1 |
| C-5709 | H | H | H | H | H | 2-OEt,6-Cl | 1 |
| C-5710 | H | H | H | H | H | 2-OEt,3-Me | 1 |
| C-5711 | H | H | H | H | H | 2-OEt,4-Me | 1 |
| C-5712 | H | H | H | H | H | 2-OEt,5-Me | 1 |
| C-5713 | H | H | H | H | H | 2-OEt,6-Me | 1 |
| C-5714 | H | H | H | H | H | 2-OPr,3-F | 1 |
| C-5715 | H | H | H | H | H | 2-OPr,4-F | 1 |
| C-5716 | H | H | H | H | H | 2-OPr,5-F | 1 |
| C-5717 | H | H | H | H | H | 2-OPr,6-F | 1 |
| C-5718 | H | H | H | H | H | 2-OPr,3-Me | 1 |
| C-5719 | H | H | H | H | H | 2-OPr,4-Me | 1 |
| C-5720 | H | H | H | H | H | 2-OPr,5-Me | 1 |
| C-5721 | H | H | H | H | H | 2-OPr,6-Me | 1 |
| C-5722 | H | H | H | H | H | 2-O(i-Pr),3-F | 1 |
| C-5723 | H | H | H | H | H | 2-O(i-Pr),4-F | 1 |
| C-5724 | H | H | H | H | H | 2-O(i-Pr),5-F | 1 |
| C-5725 | H | H | H | H | H | 2-O(i-Pr),6-F | 1 |
| C-5726 | H | H | H | H | H | 2-O(i-Pr),3-Me | 1 |
| C-5727 | H | H | H | H | H | 2-O(i-Pr),4-Me | 1 |
| C-5728 | H | H | H | H | H | 2-O(i-Pr),5-Me | 1 |
| C-5729 | H | H | H | H | H | 2-O(i-Pr),6-Me | 1 |
| C-5730 | H | H | H | H | H | 2-OCF₃,3-F | 1 |
| C-5731 | H | H | H | H | H | 2-OCF₃,4-F | 1 |
| C-5732 | H | H | H | H | H | 2-OCF₃,5-F | 1 |
| C-5733 | H | H | H | H | H | 2-OCF₃,6-F | 1 |
| C-5734 | H | H | H | H | H | 2-OCF₃,3-Me | 1 |
| C-5735 | H | H | H | H | H | 2-OCF₃,4-Me | 1 |
| C-5736 | H | H | H | H | H | 2-OCF₃,5-Me | 1 |

TABLE 229

| compound | R¹ | R² | R³ | R⁴ | R⁵ | (R⁸)ₘ | p |
|---|---|---|---|---|---|---|---|
| C-5737 | H | H | H | H | H | 2-OCF₃,6-Me | 1 |
| C-5738 | H | H | H | H | H | 2-OCHF₂,3-F | 1 |
| C-5739 | H | H | H | H | H | 2-OCHF₂,4-F | 1 |
| C-5740 | H | H | H | H | H | 2-OCHF₂,5-F | 1 |
| C-5741 | H | H | H | H | H | 2-OCHF₂,6-F | 1 |
| C-5742 | H | H | H | H | H | 2-OCHF₂,3-Me | 1 |
| C-5743 | H | H | H | H | H | 2-OCHF₂,4-Me | 1 |
| C-5744 | H | H | H | H | H | 2-OCHF₂,5-Me | 1 |
| C-5745 | H | H | H | H | H | 2-OCHF₂,6-Me | 1 |
| C-5746 | H | H | H | H | H | 2-(cyclopropyloxy),3-F | 1 |
| C-5747 | H | H | H | H | H | 2-(cyclopropyloxy),4-F | 1 |
| C-5748 | H | H | H | H | H | 2-(cyclopropyloxy),5-F | 1 |
| C-5749 | H | H | H | H | H | 2-(cyclopropyloxy),6-F | 1 |
| C-5750 | H | H | H | H | H | 2-(cyclopropyloxy),3-Me | 1 |
| C-5751 | H | H | H | H | H | 2-(cyclopropyloxy),4-Me | 1 |
| C-5752 | H | H | H | H | H | 2-(cyclopropyloxy),5-Me | 1 |
| C-5753 | H | H | H | H | H | 2-(cyclopropyloxy),6-Me | 1 |
| C-5754 | H | H | H | H | H | 2-(oxiran-2-yl),3-F | 1 |
| C-5755 | H | H | H | H | H | 2-(oxiran-2-yl),4-F | 1 |
| C-5756 | H | H | H | H | H | 2-(oxiran-2-yl),5-F | 1 |
| C-5757 | H | H | H | H | H | 2-(oxiran-2-yl),6-F | 1 |
| C-5758 | H | H | H | H | H | 2-(oxiran-2-yl),3-Me | 1 |
| C-5759 | H | H | H | H | H | 2-(oxiran-2-yl),4-Me | 1 |
| C-5760 | H | H | H | H | H | 2-(oxiran-2-yl),5-Me | 1 |
| C-5761 | H | H | H | H | H | 2-(oxiran-2-yl),6-Me | 1 |
| C-5762 | H | H | H | H | H | 2-(oxiran-2-ylmethyl),3-F | 1 |
| C-5763 | H | H | H | H | H | 2-(oxiran-2-ylmethyl),4-F | 1 |

TABLE 229-continued

| compound | R¹ | R² | R³ | R⁴ | R⁵ | (R⁸)ₘ | p |
|---|---|---|---|---|---|---|---|
| C-5764 | H | H | H | H | H | 2-(oxiran-2-ylmethyl),5-F | 1 |
| C-5765 | H | H | H | H | H | 2-(oxiran-2-ylmethyl),6-F | 1 |
| C-5766 | H | H | H | H | H | 2-(oxiran-2-ylmethyl),3-Me | 1 |
| C-5767 | H | H | H | H | H | 2-(oxiran-2-ylmethyl),4-Me | 1 |
| C-5768 | H | H | H | H | H | 2-(oxiran-2-ylmethyl),5-Me | 1 |
| C-5769 | H | H | H | H | H | 2-(oxiran-2-ylmethyl),6-Me | 1 |
| C-5770 | H | H | H | H | H | 2-SMe,3-F | 1 |
| C-5771 | H | H | H | H | H | 2-SMe,4-F | 1 |
| C-5772 | H | H | H | H | H | 2-SMe,5-F | 1 |
| C-5773 | H | H | H | H | H | 2-SMe,6-F | 1 |
| C-5774 | H | H | H | H | H | 2-SMe,3-Me | 1 |
| C-5775 | H | H | H | H | H | 2-SMe,4-Me | 1 |
| C-5776 | H | H | H | H | H | 2-SMe,5-Me | 1 |
| C-5777 | H | H | H | H | H | 2-SMe,6-Me | 1 |
| C-5778 | H | H | H | H | H | 2-SEt,3-F | 1 |
| C-5779 | H | H | H | H | H | 2-SEt,4-F | 1 |
| C-5780 | H | H | H | H | H | 2-SEt,5-F | 1 |
| C-5781 | H | H | H | H | H | 2-SEt,6-F | 1 |
| C-5782 | H | H | H | H | H | 2-SEt,3-Me | 1 |
| C-5783 | H | H | H | H | H | 2-SEt,4-Me | 1 |
| C-5784 | H | H | H | H | H | 2-SEt,5-Me | 1 |
| C-5785 | H | H | H | H | H | 2-SEt,6-Me | 1 |
| C-5786 | H | H | H | H | H | 2-S(=O)Me,3-F | 1 |
| C-5787 | H | H | H | H | H | 2-S(=O)Me,4-F | 1 |
| C-5788 | H | H | H | H | H | 2-S(=O)Me,5-F | 1 |
| C-5789 | H | H | H | H | H | 2-S(=O)Me,6-F | 1 |
| C-5790 | H | H | H | H | H | 3-S(=O)Me,2-F | 1 |
| C-5791 | H | H | H | H | H | 3-S(=O)Me,4-F | 1 |
| C-5792 | H | H | H | H | H | 3-S(=O)Me,5-F | 1 |
| C-5793 | H | H | H | H | H | 3-S(=O)Me,6-F | 1 |

TABLE 230

| compound | R¹ | R² | R³ | R⁴ | R⁵ | (R⁸)ₘ | p |
|---|---|---|---|---|---|---|---|
| C-5794 | H | H | H | H | H | 2-S(=O)Me,3-Me | 1 |
| C-5795 | H | H | H | H | H | 2-S(=O)Me,4-Me | 1 |
| C-5796 | H | H | H | H | H | 2-S(=O)Me,5-Me | 1 |
| C-5797 | H | H | H | H | H | 2-S(=O)Me,6-Me | 1 |
| C-5798 | H | H | H | H | H | 3-S(=O)Me,2-Me | 1 |
| C-5799 | H | H | H | H | H | 3-S(=O)Me,4-Me | 1 |
| C-5800 | H | H | H | H | H | 3-S(=O)Me,5-Me | 1 |
| C-5801 | H | H | H | H | H | 3-S(=O)Me,6-Me | 1 |
| C-5802 | H | H | H | H | H | 2-S(=O)₂Me,3-F | 1 |
| C-5803 | H | H | H | H | H | 2-S(=O)₂Me,4-F | 1 |
| C-5804 | H | H | H | H | H | 2-S(=O)₂Me,5-F | 1 |
| C-5805 | H | H | H | H | H | 2-S(=O)₂Me,6-F | 1 |
| C-5806 | H | H | H | H | H | 2-S(=O)₂Me,3-Me | 1 |
| C-5807 | H | H | H | H | H | 2-S(=O)₂Me,4-Me | 1 |
| C-5808 | H | H | H | H | H | 2-S(=O)₂Me,5-Me | 1 |
| C-5809 | H | H | H | H | H | 2-S(=O)₂Me,6-Me | 1 |
| C-5810 | H | H | H | H | H | 2-SCF₃,3-F | 1 |
| C-5811 | H | H | H | H | H | 2-SCF₃,4-F | 1 |
| C-5812 | H | H | H | H | H | 2-SCF₃,5-F | 1 |
| C-5813 | H | H | H | H | H | 2-SCF₃,6-F | 1 |
| C-5814 | H | H | H | H | H | 2-SCF₃,3-Me | 1 |
| C-5815 | H | H | H | H | H | 2-SCF₃,4-Me | 1 |
| C-5816 | H | H | H | H | H | 2-SCF₃,5-Me | 1 |
| C-5817 | H | H | H | H | H | 2-SCF₃,6-Me | 1 |
| C-5818 | H | H | H | H | H | 2-S(=O)CF₃,3-F | 1 |
| C-5819 | H | H | H | H | H | 2-S(=O)CF₃,4-F | 1 |
| C-5820 | H | H | H | H | H | 2-S(=O)CF₃,5-F | 1 |
| C-5821 | H | H | H | H | H | 2-S(=O)CF₃,6-F | 1 |
| C-5822 | H | H | H | H | H | 2-S(=O)CF₃,3-Me | 1 |
| C-5823 | H | H | H | H | H | 2-S(=O)CF₃,3-Me | 1 |
| C-5824 | H | H | H | H | H | 2-S(=O)CF₃,3-Me | 1 |
| C-5825 | H | H | H | H | H | 2-S(=O)CF₃,3-Me | 1 |
| C-5826 | H | H | H | H | H | 2-S(=O)₂CF₃,3-F | 1 |
| C-5827 | H | H | H | H | H | 2-S(=O)₂CF₃,4-F | 1 |
| C-5828 | H | H | H | H | H | 2-S(=O)₂CF₃,5-F | 1 |
| C-5829 | H | H | H | H | H | 2-S(=O)₂CF₃,6-F | 1 |
| C-5830 | H | H | H | H | H | 2-S(=O)₂CF₃,3-Me | 1 |
| C-5831 | H | H | H | H | H | 2-S(=O)₂CF₃,4-Me | 1 |
| C-5832 | H | H | H | H | H | 2-S(=O)₂CF₃,5-Me | 1 |
| C-5833 | H | H | H | H | H | 2-S(=O)₂CF₃,6-Me | 1 |

TABLE 230-continued

| compound | R¹ | R² | R³ | R⁴ | R⁵ | (R⁸)$_m$ | p |
|---|---|---|---|---|---|---|---|
| C-5834 | H | H | H | H | H | 2-(cyclopropylthio),3-F | 1 |
| C-5835 | H | H | H | H | H | 2-(cyclopropylthio),4-F | 1 |
| C-5836 | H | H | H | H | H | 2-(cyclopropylthio),5-F | 1 |
| C-5837 | H | H | H | H | H | 2-(cyclopropylthio),6-F | 1 |
| C-5838 | H | H | H | H | H | 2-(cyclopropylthio),3-Me | 1 |
| C-5839 | H | H | H | H | H | 2-(cyclopropylthio),4-Me | 1 |
| C-5840 | H | H | H | H | H | 2-(cyclopropylthio),5-Me | 1 |
| C-5841 | H | H | H | H | H | 2-(cyclopropylthio),6-Me | 1 |
| C-5842 | H | H | H | H | H | 2-C(=O)Me,3-F | 1 |
| C-5843 | H | H | H | H | H | 2-C(=O)Me,4-F | 1 |
| C-5844 | H | H | H | H | H | 2-C(=O)Me,5-F | 1 |
| C-5845 | H | H | H | H | H | 2-C(=O)Me,6-F | 1 |
| C-5846 | H | H | H | H | H | 2-C(=O)Me,3-Me | 1 |
| C-5847 | H | H | H | H | H | 2-C(=O)Me,4-Me | 1 |
| C-5848 | H | H | H | H | H | 2-C(=O)Me,5-Me | 1 |
| C-5849 | H | H | H | H | H | 2-C(=O)Me,6-Me | 1 |
| C-5850 | H | H | H | H | H | 3-C(=O)Me,2-F | 1 |

TABLE 231

| compound | R¹ | R² | R³ | R⁴ | R⁵ | (R⁸)$_m$ | p |
|---|---|---|---|---|---|---|---|
| C-5851 | H | H | H | H | H | 3-C(=O)Me,4-F | 1 |
| C-5852 | H | H | H | H | H | 3-C(=O)Me,5-F | 1 |
| C-5853 | H | H | H | H | H | 3-C(=O)Me,6-F | 1 |
| C-5854 | H | H | H | H | H | 3-C(=O)Me,2-Me | 1 |
| C-5855 | H | H | H | H | H | 3-C(=O)Me,4-Me | 1 |
| C-5856 | H | H | H | H | H | 3-C(=O)Me,5-Me | 1 |
| C-5857 | H | H | H | H | H | 3-C(=O)Me,6-Me | 1 |
| C-5858 | H | H | H | H | H | 2-C(=O)OMe,3-F | 1 |
| C-5859 | H | H | H | H | H | 2-C(=O)OMe,4-F | 1 |
| C-5860 | H | H | H | H | H | 2-C(=O)OMe,5-F | 1 |
| C-5861 | H | H | H | H | H | 2-C(=O)OMe,6-F | 1 |
| C-5862 | H | H | H | H | H | 2-C(=O)OMe,3-Me | 1 |
| C-5863 | H | H | H | H | H | 2-C(=O)OMe,4-Me | 1 |
| C-5864 | H | H | H | H | H | 2-C(=O)OMe,5-Me | 1 |
| C-5865 | H | H | H | H | H | 2-C(=O)OMe,6-Me | 1 |
| C-5866 | H | H | H | H | H | 2-C(=O)OEt,3-F | 1 |
| C-5867 | H | H | H | H | H | 2-C(=O)OEt,4-F | 1 |
| C-5868 | H | H | H | H | H | 2-C(=O)OEt,5-F | 1 |
| C-5869 | H | H | H | H | H | 2-C(=O)OEt,6-F | 1 |
| C-5870 | H | H | H | H | H | 2-C(=O)OEt,3-Me | 1 |
| C-5871 | H | H | H | H | H | 2-C(=O)OEt,4-Me | 1 |
| C-5872 | H | H | H | H | H | 2-C(=O)OEt,5-Me | 1 |
| C-5873 | H | H | H | H | H | 2-C(=O)OEt,6-Me | 1 |
| C-5874 | H | H | H | H | H | 2-C(=O)NH$_2$,3-F | 1 |
| C-5875 | H | H | H | H | H | 2-C(=O)NH$_2$,4-F | 1 |
| C-5876 | H | H | H | H | H | 2-C(=O)NH$_2$,5-F | 1 |
| C-5877 | H | H | H | H | H | 2-C(=O)NH$_2$,6-F | 1 |
| C-5878 | H | H | H | H | H | 2-C(=O)NH$_2$,3-Me | 1 |
| C-5879 | H | H | H | H | H | 2-C(=O)NH$_2$,4-Me | 1 |
| C-5880 | H | H | H | H | H | 2-C(=O)NH$_2$,5-Me | 1 |
| C-5881 | H | H | H | H | H | 2-C(=O)NH$_2$,6-Me | 1 |
| C-5882 | H | H | H | H | H | 2-C(=O)NHMe,3-F | 1 |
| C-5883 | H | H | H | H | H | 2-C(=O)NHMe,4-F | 1 |
| C-5884 | H | H | H | H | H | 2-C(=O)NHMe,5-F | 1 |
| C-5885 | H | H | H | H | H | 2-C(=O)NHMe,6-F | 1 |
| C-5886 | H | H | H | H | H | 2-C(=O)NHMe,3-Me | 1 |
| C-5887 | H | H | H | H | H | 2-C(=O)NHMe,4-Me | 1 |
| C-5888 | H | H | H | H | H | 2-C(=O)NHMe,5-Me | 1 |
| C-5889 | H | H | H | H | H | 2-C(=O)NHMe,6-Me | 1 |
| C-5890 | H | H | H | H | H | 2-C(=O)NMe$_2$,3-F | 1 |
| C-5891 | H | H | H | H | H | 2-C(=O)NMe$_2$,4-F | 1 |
| C-5892 | H | H | H | H | H | 2-C(=O)NMe$_2$,5-F | 1 |
| C-5893 | H | H | H | H | H | 2-C(=O)NMe$_2$,6-F | 1 |
| C-5894 | H | H | H | H | H | 2-C(=O)NMe$_2$,3-Me | 1 |
| C-5895 | H | H | H | H | H | 2-C(=O)NMe$_2$,4-Me | 1 |
| C-5896 | H | H | H | H | H | 2-C(=O)NMe$_2$,5-Me | 1 |
| C-5897 | H | H | H | H | H | 2-C(=O)NMe$_2$,6-Me | 1 |
| C-5898 | H | H | H | H | H | 2-CH$_2$OH,3-F | 1 |
| C-5899 | H | H | H | H | H | 2-CH$_2$OH,4-F | 1 |
| C-5900 | H | H | H | H | H | 2-CH$_2$OH,5-F | 1 |
| C-5901 | H | H | H | H | H | 2-CH$_2$OH,6-F | 1 |
| C-5902 | H | H | H | H | H | 2-CH$_2$OH,3-Me | 1 |
| C-5903 | H | H | H | H | H | 2-CH$_2$OH,4-Me | 1 |

TABLE 231-continued

| compound | R¹ | R² | R³ | R⁴ | R⁵ | (R⁸)$_m$ | p |
|---|---|---|---|---|---|---|---|
| C-5904 | H | H | H | H | H | 2-CH$_2$OH,5-Me | 1 |
| C-5905 | H | H | H | H | H | 2-CH$_2$OH,6-Me | 1 |
| C-5906 | H | H | H | H | H | 2-CH$_2$OCH$_3$,3-F | 1 |
| C-5907 | H | H | H | H | H | 2-CH$_2$OCH$_3$,4-F | 1 |

TABLE 232

| compound | R¹ | R² | R³ | R⁴ | R⁵ | (R⁸)$_m$ | p |
|---|---|---|---|---|---|---|---|
| C-5908 | H | H | H | H | H | 2-CH$_2$OCH$_3$,5-F | 1 |
| C-5909 | H | H | H | H | H | 2-CH$_2$OCH$_3$,6-F | 1 |
| C-5910 | H | H | H | H | H | 2-CH$_2$OCH$_3$,3-Me | 1 |
| C-5911 | H | H | H | H | H | 2-CH$_2$OCH$_3$,4-Me | 1 |
| C-5912 | H | H | H | H | H | 2-CH$_2$OCH$_3$,5-Me | 1 |
| C-5913 | H | H | H | H | H | 2-CH$_2$OCH$_3$,6-Me | 1 |
| C-5914 | H | H | H | H | H | 2-CH$_2$OCH$_2$CH$_3$,3-F | 1 |
| C-5915 | H | H | H | H | H | 2-CH$_2$OCH$_2$CH$_3$,4-F | 1 |
| C-5916 | H | H | H | H | H | 2-CH$_2$OCH$_2$CH$_3$,5-F | 1 |
| C-5917 | H | H | H | H | H | 2-CH$_2$OCH$_2$CH$_3$,6-F | 1 |
| C-5918 | H | H | H | H | H | 2-CH$_2$OCH$_2$CH$_3$,3-Me | 1 |
| C-5919 | H | H | H | H | H | 2-CH$_2$OCH$_2$CH$_3$,4-Me | 1 |
| C-5920 | H | H | H | H | H | 2-CH$_2$OCH$_2$CH$_3$,5-Me | 1 |
| C-5921 | H | H | H | H | H | 2-CH$_2$OCH$_2$CH$_3$,6-Me | 1 |
| C-5922 | H | H | H | H | H | 2-OC(=O)CH$_3$,3-F | 1 |
| C-5923 | H | H | H | H | H | 2-OC(=O)CH$_3$,4-F | 1 |
| C-5924 | H | H | H | H | H | 2-OC(=O)CH$_3$,5-F | 1 |
| C-5925 | H | H | H | H | H | 2-OC(=O)CH$_3$,6-F | 1 |
| C-5926 | H | H | H | H | H | 2-OC(=O)CH$_3$,3-Me | 1 |
| C-5927 | H | H | H | H | H | 2-OC(=O)CH$_3$,4-Me | 1 |
| C-5928 | H | H | H | H | H | 2-OC(=O)CH$_3$,5-Me | 1 |
| C-5929 | H | H | H | H | H | 2-OC(=O)CH$_3$,6-Me | 1 |
| C-5930 | H | H | H | H | H | 2-OS(=O)$_2$CH$_3$,3-F | 1 |
| C-5931 | H | H | H | H | H | 2-OS(=O)$_2$CH$_3$,4-F | 1 |
| C-5932 | H | H | H | H | H | 2-OS(=O)$_2$CH$_3$,5-F | 1 |
| C-5933 | H | H | H | H | H | 2-OS(=O)$_2$CH$_3$,6-F | 1 |
| C-5934 | H | H | H | H | H | 2-OS(=O)$_2$CH$_3$,3-Me | 1 |
| C-5935 | H | H | H | H | H | 2-OS(=O)$_2$CH$_3$,4-Me | 1 |
| C-5936 | H | H | H | H | H | 2-OS(=O)$_2$CH$_3$,5-Me | 1 |
| C-5937 | H | H | H | H | H | 2-OS(=O)$_2$CH$_3$,6-Me | 1 |
| C-5938 | H | H | H | H | H | 2-CH$_2$SCH$_3$,3-F | 1 |
| C-5939 | H | H | H | H | H | 2-CH$_2$SCH$_3$,4-F | 1 |
| C-5940 | H | H | H | H | H | 2-CH$_2$SCH$_3$,5-F | 1 |
| C-5941 | H | H | H | H | H | 2-CH$_2$SCH$_3$,6-F | 1 |
| C-5942 | H | H | H | H | H | 2-CH$_2$SCH$_3$,3-Me | 1 |
| C-5943 | H | H | H | H | H | 2-CH$_2$SCH$_3$,4-Me | 1 |
| C-5944 | H | H | H | H | H | 2-CH$_2$SCH$_3$,5-Me | 1 |
| C-5945 | H | H | H | H | H | 2-CH$_2$SCH$_3$,6-Me | 1 |
| C-5946 | H | H | H | H | H | 2-CH$_2$SCF$_3$,3-F | 1 |
| C-5947 | H | H | H | H | H | 2-CH$_2$SCF$_3$,4-F | 1 |
| C-5948 | H | H | H | H | H | 2-CH$_2$SCF$_3$,5-F | 1 |
| C-5949 | H | H | H | H | H | 2-CH$_2$SCF$_3$,6-F | 1 |
| C-5950 | H | H | H | H | H | 2-CH$_2$SCF$_3$,3-Me | 1 |
| C-5951 | H | H | H | H | H | 2-CH$_2$SCF$_3$,4-Me | 1 |
| C-5952 | H | H | H | H | H | 2-CH$_2$SCF$_3$,5-Me | 1 |
| C-5953 | H | H | H | H | H | 2-CH$_2$SCF$_3$,6-Me | 1 |
| C-5954 | H | H | H | H | H | 2-(benzyloxy),3-F | 1 |
| C-5955 | H | H | H | H | H | 2-(benzyloxy),4-F | 1 |
| C-5956 | H | H | H | H | H | 2-(benzyloxy),5-F | 1 |
| C-5957 | H | H | H | H | H | 2-(benzyloxy),6-F | 1 |
| C-5958 | H | H | H | H | H | 2-(benzyloxy),3-Me | 1 |
| C-5959 | H | H | H | H | H | 2-(benzyloxy),4-Me | 1 |
| C-5960 | H | H | H | H | H | 2-(benzyloxy),5-Me | 1 |
| C-5961 | H | H | H | H | H | 2-(benzyloxy),6-Me | 1 |
| C-5962 | H | H | H | H | H | 2-NH$_2$,3-F | 1 |
| C-5963 | H | H | H | H | H | 2-NH$_2$,4-F | 1 |
| C-5964 | H | H | H | H | H | 2-NH$_2$,5-F | 1 |

TABLE 233

| compound | R¹ | R² | R³ | R⁴ | R⁵ | (R⁸)$_m$ | p |
|---|---|---|---|---|---|---|---|
| C-5965 | H | H | H | H | H | 2-NH$_2$,6-F | 1 |
| C-5966 | H | H | H | H | H | 2-NH$_2$,3-Me | 1 |

TABLE 233-continued

| compound | R¹ | R² | R³ | R⁴ | R⁵ | (R⁸)ₘ | p |
|---|---|---|---|---|---|---|---|
| C-5967 | H | H | H | H | H | 2-NH₂,4-Me | 1 |
| C-5968 | H | H | H | H | H | 2-NH₂,5-Me | 1 |
| C-5969 | H | H | H | H | H | 2-NH₂,6-Me | 1 |
| C-5970 | H | H | H | H | H | 2-NHMe,3-F | 1 |
| C-5971 | H | H | H | H | H | 2-NHMe,4-F | 1 |
| C-5972 | H | H | H | H | H | 2-NHMe,5-F | 1 |
| C-5973 | H | H | H | H | H | 2-NHMe,6-F | 1 |
| C-5974 | H | H | H | H | H | 2-NHMe,3-Me | 1 |
| C-5975 | H | H | H | H | H | 2-NHMe,4-Me | 1 |
| C-5976 | H | H | H | H | H | 2-NHMe,5-Me | 1 |
| C-5977 | H | H | H | H | H | 2-NHMe,6-Me | 1 |
| C-5978 | H | H | H | H | H | 2-NHEt,3-F | 1 |
| C-5979 | H | H | H | H | H | 2-NHEt,4-F | 1 |
| C-5980 | H | H | H | H | H | 2-NHEt,5-F | 1 |
| C-5981 | H | H | H | H | H | 2-NHEt,6-F | 1 |
| C-5982 | H | H | H | H | H | 2-NHEt,3-Me | 1 |
| C-5983 | H | H | H | H | H | 2-NHEt,4-Me | 1 |
| C-5984 | H | H | H | H | H | 2-NHEt,5-Me | 1 |
| C-5985 | H | H | H | H | H | 2-NHEt,6-Me | 1 |
| C-5986 | H | H | H | H | H | 2-NMe₂,3-F | 1 |
| C-5987 | H | H | H | H | H | 2-NMe₂,4-F | 1 |
| C-5988 | H | H | H | H | H | 2-NMe₂,5-F | 1 |
| C-5989 | H | H | H | H | H | 2-NMe₂,6-F | 1 |
| C-5990 | H | H | H | H | H | 2-NMe₂,3-Me | 1 |
| C-5991 | H | H | H | H | H | 2-NMe₂,4-Me | 1 |
| C-5992 | H | H | H | H | H | 2-NMe₂,5-Me | 1 |
| C-5993 | H | H | H | H | H | 2-NMe₂,6-Me | 1 |
| C-5994 | H | H | H | H | H | 2-NEt₂,3-F | 1 |
| C-5995 | H | H | H | H | H | 2-NEt₂,4-F | 1 |
| C-5996 | H | H | H | H | H | 2-NEt₂,5-F | 1 |
| C-5997 | H | H | H | H | H | 2-NEt₂,6-F | 1 |
| C-5998 | H | H | H | H | H | 2-NEt₂,3-Me | 1 |
| C-5999 | H | H | H | H | H | 2-NEt₂,4-Me | 1 |
| C-6000 | H | H | H | H | H | 2-NEt₂,5-Me | 1 |
| C-6001 | H | H | H | H | H | 2-NEt₂,6-Me | 1 |
| C-6002 | H | H | H | H | H | 2-CHO,3-F | 1 |
| C-6003 | H | H | H | H | H | 2-CHO,4-F | 1 |
| C-6004 | H | H | H | H | H | 2-CHO,5-F | 1 |
| C-6005 | H | H | H | H | H | 2-CHO,6-F | 1 |
| C-6006 | H | H | H | H | H | 2-CHO,3-Me | 1 |
| C-6007 | H | H | H | H | H | 2-CHO,4-Me | 1 |
| C-6008 | H | H | H | H | H | 2-CHO,5-Me | 1 |
| C-6009 | H | H | H | H | H | 2-CHO,6-Me | 1 |
| C-6010 | H | H | H | H | H | 2-C(=O)OH,3-F | 1 |
| C-6011 | H | H | H | H | H | 2-C(=O)OH,4-F | 1 |
| C-6012 | H | H | H | H | H | 2-C(=O)OH,5-F | 1 |
| C-6013 | H | H | H | H | H | 2-C(=O)OH,6-F | 1 |
| C-6014 | H | H | H | H | H | 2-C(=O)OH,3-Me | 1 |
| C-6015 | H | H | H | H | H | 2-C(=O)OH,4-Me | 1 |
| C-6016 | H | H | H | H | H | 2-C(=O)OH,5-Me | 1 |
| C-6017 | H | H | H | H | H | 2-C(=O)OH,6-Me | 1 |
| C-6018 | H | H | H | H | H | 2-(1,3-dioxolan-2-yl),3-F | 1 |
| C-6019 | H | H | H | H | H | 2-(1,3-dioxolan-2-yl),4-F | 1 |
| C-6020 | H | H | H | H | H | 2-(1,3-dioxolan-2-yl),5-F | 1 |
| C-6021 | H | H | H | H | H | 2-(1,3-dioxolan-2-yl),6-F | 1 |

TABLE 234

| compound | R¹ | R² | R³ | R⁴ | R⁵ | (R⁸)ₘ | p |
|---|---|---|---|---|---|---|---|
| C-6022 | H | H | H | H | H | 2-(1,3-dioxolan-2-yl),3-Me | 1 |
| C-6023 | H | H | H | H | H | 2-(1,3-dioxolan-2-yl),4-Me | 1 |
| C-6024 | H | H | H | H | H | 2-(1,3-dioxolan-2-yl),5-Me | 1 |
| C-6025 | H | H | H | H | H | 2-(1,3-dioxolan-2-yl),6-Me | 1 |
| C-6026 | H | H | H | H | H | 2-(1,3-dioxan-2-yl),3-F | 1 |
| C-6027 | H | H | H | H | H | 2-(1,3-dioxan-2-yl),4-F | 1 |
| C-6028 | H | H | H | H | H | 2-(1,3-dioxan-2-yl),5-F | 1 |
| C-6029 | H | H | H | H | H | 2-(1,3-dioxan-2-yl),6-F | 1 |
| C-6030 | H | H | H | H | H | 2-(1,3-dioxan-2-yl),3-Me | 1 |
| C-6031 | H | H | H | H | H | 2-(1,3-dioxan-2-yl),4-Me | 1 |
| C-6032 | H | H | H | H | H | 2-(1,3-dioxan-2-yl),5-Me | 1 |
| C-6033 | H | H | H | H | H | 2-(1,3-dioxan-2-yl),6-Me | 1 |
| C-6034 | H | H | H | H | H | 2-(thiazol-2-yl),3-F | 1 |
| C-6035 | H | H | H | H | H | 2-(thiazol-2-yl),4-F | 1 |
| C-6036 | H | H | H | H | H | 2-(thiazol-2-yl),5-F | 1 |

TABLE 234-continued

| compound | R¹ | R² | R³ | R⁴ | R⁵ | (R⁸)ₘ | p |
|---|---|---|---|---|---|---|---|
| C-6037 | H | H | H | H | H | 2-(thiazol-2-yl),6-F | 1 |
| C-6038 | H | H | H | H | H | 2-(thiazol-2-yl),3-Me | 1 |
| C-6039 | H | H | H | H | H | 2-(thiazol-2-yl),4-Me | 1 |
| C-6040 | H | H | H | H | H | 2-(thiazol-2-yl),5-Me | 1 |
| C-6041 | H | H | H | H | H | 2-(thiazol-2-yl),6-Me | 1 |
| C-6042 | H | H | H | H | H | 2-(oxazol-2-yl),3-F | 1 |
| C-6043 | H | H | H | H | H | 2-(oxazol-2-yl),4-F | 1 |
| C-6044 | H | H | H | H | H | 2-(oxazol-2-yl),5-F | 1 |
| C-6045 | H | H | H | H | H | 2-(oxazol-2-yl),6-F | 1 |
| C-6046 | H | H | H | H | H | 2-(oxazol-2-yl),3-Me | 1 |
| C-6047 | H | H | H | H | H | 2-(oxazol-2-yl),4-Me | 1 |
| C-6048 | H | H | H | H | H | 2-(oxazol-2-yl),5-Me | 1 |
| C-6049 | H | H | H | H | H | 2-(oxazol-2-yl),6-Me | 1 |
| C-6050 | H | H | H | H | H | 2-CH=NOH,3-F | 1 |
| C-6051 | H | H | H | H | H | 2-CH=NOH,4-F | 1 |
| C-6052 | H | H | H | H | H | 2-CH=NOH,5-F | 1 |
| C-6053 | H | H | H | H | H | 2-CH=NOH,6-F | 1 |
| C-6054 | H | H | H | H | H | 2-CH=NOH,3-Me | 1 |
| C-6055 | H | H | H | H | H | 2-CH=NOH,4-Me | 1 |
| C-6056 | H | H | H | H | H | 2-CH=NOH,5-Me | 1 |
| C-6057 | H | H | H | H | H | 2-CH=NOH,6-Me | 1 |
| C-6058 | H | H | H | H | H | 2-CH=NOMe,3-F | 1 |
| C-6059 | H | H | H | H | H | 2-CH=NOMe,4-F | 1 |
| C-6060 | H | H | H | H | H | 2-CH=NOMe,5-F | 1 |
| C-6061 | H | H | H | H | H | 2-CH=NOMe,6-F | 1 |
| C-6062 | H | H | H | H | H | 2-CH=NOMe,3-Me | 1 |
| C-6063 | H | H | H | H | H | 2-CH=NOMe,4-Me | 1 |
| C-6064 | H | H | H | H | H | 2-CH=NOMe,5-Me | 1 |
| C-6065 | H | H | H | H | H | 2-CH=NOMe,6-Me | 1 |
| C-6066 | H | H | H | H | H | 2-CN,3-F | 1 |
| C-6067 | H | H | H | H | H | 2-CN,4-F | 1 |
| C-6068 | H | H | H | H | H | 2-CN,5-F | 1 |
| C-6069 | H | H | H | H | H | 2-CN,6-F | 1 |
| C-6070 | H | H | H | H | H | 2-CN,3-Cl | 1 |
| C-6071 | H | H | H | H | H | 2-CN,4-Cl | 1 |
| C-6072 | H | H | H | H | H | 2-CN,5-Cl | 1 |
| C-6073 | H | H | H | H | H | 2-CN,6-Cl | 1 |
| C-6074 | H | H | H | H | H | 2-CN,3-Me | 1 |
| C-6075 | H | H | H | H | H | 2-CN,4-Me | 1 |
| C-6076 | H | H | H | H | H | 2-CN,5-Me | 1 |
| C-6077 | H | H | H | H | H | 2-CN,6-Me | 1 |
| C-6078 | H | H | H | H | H | 2-CN,3-OMe | 1 |

TABLE 235

| compound | R¹ | R² | R³ | R⁴ | R⁵ | (R⁸)ₘ | p |
|---|---|---|---|---|---|---|---|
| C-6079 | H | H | H | H | H | 2-CN,4-OMe | 1 |
| C-6080 | H | H | H | H | H | 2-CN,5-OMe | 1 |
| C-6081 | H | H | H | H | H | 2-CN,6-OMe | 1 |
| C-6082 | H | H | H | H | H | 3-CN,2-F | 1 |
| C-6083 | H | H | H | H | H | 3-CN,4-F | 1 |
| C-6084 | H | H | H | H | H | 3-CN,5-F | 1 |
| C-6085 | H | H | H | H | H | 3-CN,6-F | 1 |
| C-6086 | H | H | H | H | H | 3-CN,2-Cl | 1 |
| C-6087 | H | H | H | H | H | 3-CN,4-Cl | 1 |
| C-6088 | H | H | H | H | H | 3-CN,5-Cl | 1 |
| C-6089 | H | H | H | H | H | 3-CN,6-Cl | 1 |
| C-6090 | H | H | H | H | H | 3-CN,2-Me | 1 |
| C-6091 | H | H | H | H | H | 3-CN,4-Me | 1 |
| C-6092 | H | H | H | H | H | 3-CN,5-Me | 1 |
| C-6093 | H | H | H | H | H | 3-CN,6-Me | 1 |
| C-6094 | H | H | H | H | H | 3-CN,2-OMe | 1 |
| C-6095 | H | H | H | H | H | 3-CN,4-OMe | 1 |
| C-6096 | H | H | H | H | H | 3-CN,5-OMe | 1 |
| C-6097 | H | H | H | H | H | 3-CN,6-OMe | 1 |
| C-6098 | H | H | H | H | H | 4-CN,2-F | 1 |
| C-6099 | H | H | H | H | H | 4-CN,3-F | 1 |
| C-6100 | H | H | H | H | H | 4-CN,2-Cl | 1 |
| C-6101 | H | H | H | H | H | 4-CN,3-Cl | 1 |
| C-6102 | H | H | H | H | H | 4-CN,2-Me | 1 |
| C-6103 | H | H | H | H | H | 4-CN,3-Me | 1 |
| C-6104 | H | H | H | H | H | 4-CN,2-OMe | 1 |
| C-6105 | H | H | H | H | H | 4-CN,3-OMe | 1 |
| C-6106 | H | H | H | H | H | 2-NO₂,3-F | 1 |

TABLE 235-continued

| compound | R¹ | R² | R³ | R⁴ | R⁵ | (R⁸)ₘ | p |
|---|---|---|---|---|---|---|---|
| C-6107 | H | H | H | H | H | 2-NO₂,4-F | 1 |
| C-6108 | H | H | H | H | H | 2-NO₂,5-F | 1 |
| C-6109 | H | H | H | H | H | 2-NO₂,6-F | 1 |
| C-6110 | H | H | H | H | H | 2-NO₂,3-Me | 1 |
| C-6111 | H | H | H | H | H | 2-NO₂,4-Me | 1 |
| C-6112 | H | H | H | H | H | 2-NO₂,5-Me | 1 |
| C-6113 | H | H | H | H | H | 2-NO₂,6-Me | 1 |
| C-6114 | H | H | H | H | H | 2-Me,3,4-F₂ | 1 |
| C-6115 | H | H | H | H | H | 2-Me,3,5-F₂ | 1 |
| C-6116 | H | H | H | H | H | 2-Me,3,6-F₂ | 1 |
| C-6117 | H | H | H | H | H | 2-Me,4,5-F₂ | 1 |
| C-6118 | H | H | H | H | H | 2-OMe,3,4-F₂ | 1 |
| C-6119 | H | H | H | H | H | 2-OMe,3,5-F₂ | 1 |
| C-6120 | H | H | H | H | H | 2-OMe,3,6-F₂ | 1 |
| C-6121 | H | H | H | H | H | 2-OMe,4,5-F₂ | 1 |
| C-6122 | H | H | H | H | H | 2-(CH₂)₃-3 | 1 |
| C-6123 | H | H | H | H | H | 2-(CH₂)₄-3 | 1 |
| C-6124 | H | H | H | H | H | 2-(OCH₂CH₂)-3 | 1 |
| C-6125 | H | H | H | H | H | 2-(OCH₂CH₂CH₂)-3 | 1 |
| C-6126 | H | H | H | H | H | 2-(CH₂CH₂O)-3 | 1 |
| C-6127 | H | H | H | H | H | 2-(CH₂CH₂CH₂O)-3 | 1 |
| C-6128 | H | H | H | H | H | 3-(CH₂)₃-4 | 1 |
| C-6129 | H | H | H | H | H | 3-(CH₂)₄-4 | 1 |
| C-6130 | H | H | H | H | H | 3-(OCH₂CH₂)-4 | 1 |
| C-6131 | H | H | H | H | H | 3-(OCH₂CH₂CH₂)-4 | 1 |
| C-6132 | H | H | H | H | H | 3-(CH₂CH₂O)-4 | 1 |
| C-6133 | H | H | H | H | H | 3-(CH₂CH₂CH₂O)-4 | 1 |
| C-6134 | H | H | H | H | H | 2-(OCH₂O)-3 | 1 |
| C-6135 | H | H | H | H | H | 3-(OCH₂O)-4 | 1 |

TABLE 236

| compound | R¹ | R² | R³ | R⁴ | R⁵ | (R⁸)ₘ | p |
|---|---|---|---|---|---|---|---|
| C-6136 | H | H | H | H | H | 2-(OCH₂CH₂O)-3 | 1 |
| C-6137 | H | H | H | H | H | 3-(OCH₂CH₂O)-4 | 1 |
| C-6138 | H | H | H | H | H | 2-(OCF₂O)-3 | 1 |
| C-6139 | H | H | H | H | H | 3-(OCF₂O)-4 | 1 |
| C-6140 | H | H | H | H | H | 2-Me,6-Et | 1 |
| C-6141 | H | H | H | H | H | 2-Me,4,5-F₂ | 1 |
| C-6142 | H | H | H | H | H | 2-cyclopropyl,6-OMe | 1 |
| C-6143 | H | H | H | H | H | 2-Me,5-Et | 1 |
| C-6144 | H | H | H | H | H | 2,6-Et₂ | 1 |
| C-6145 | H | H | H | H | H | 2-Et,6-F | 1 |
| C-6146 | H | H | H | H | H | 2-CH₂OCH₃,6-Cl | 1 |
| C-6147 | H | H | H | H | H | 2-CH₂OCH₂CH₃,6-Cl | 1 |
| C-6148 | H | H | H | H | H | 2-CH₂NMe₂ | 1 |

TABLE 237

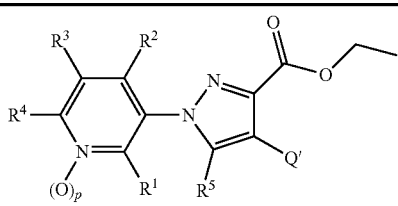

| compound | R¹ | R² | R³ | R⁴ | R⁵ | Q' | p |
|---|---|---|---|---|---|---|---|
| D-0001 | H | H | H | H | H | Cl | 0 |
| D-0002 | H | H | H | H | H | Br | 0 |
| D-0003 | H | H | H | H | H | I | 0 |
| D-0004 | H | H | H | H | H | OS(=O)₂Me | 0 |
| D-0005 | H | H | H | H | H | OS(=O)₂CF₃ | 0 |
| D-0006 | H | H | H | H | H | OS(=O)₂CF₂CF₃ | 0 |
| D-0007 | H | H | H | H | H | OS(=O)₂CF₂CF₂CF₃ | 0 |
| D-0008 | H | H | H | H | H | OS(=O)₂CF₂CF₂CF₂CF₃ | 0 |
| D-0009 | H | H | H | H | H | OS(=O)₂(4-MePh) | 0 |
| D-0010 | H | H | H | H | H | OS(=O)₂N(Me)₂ | 0 |
| D-0011 | H | H | H | H | H | OS(=O)₂N(Et)₂ | 0 |

TABLE 237-continued

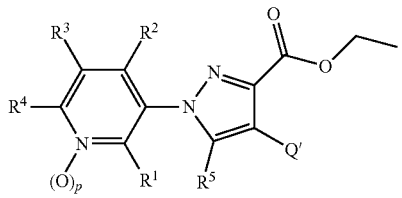

| compound | R¹ | R² | R³ | R⁴ | R⁵ | Q' | p |
|---|---|---|---|---|---|---|---|
| D-0012 | H | H | H | H | H | naphthalen-1-yl | 0 |
| D-0013 | H | H | H | H | H | 2-F-naphthalen-1-yl | 0 |
| D-0014 | H | H | H | H | H | 2-Me-naphthalen-1-yl | 0 |
| D-0015 | H | H | H | H | H | 2-CF₃-naphthalen-1-yl | 0 |
| D-0016 | H | H | H | H | H | 2-OMe-naphthalen-1-yl | 0 |
| D-0017 | H | H | H | H | H | naphthalen-2-yl | 0 |
| D-0018 | H | H | H | H | H | 1-F-naphthalen-2-yl | 0 |
| D-0019 | H | H | H | H | H | 1-Me-naphthalen-2-yl | 0 |
| D-0020 | H | H | H | H | H | 1-CF₃-naphthalen-2-yl | 0 |
| D-0021 | H | H | H | H | H | 1-OMe-naphthalen-2-yl | 0 |
| D-0022 | H | H | H | H | H | 3-F-naphthalen-2-yl | 0 |
| D-0023 | H | H | H | H | H | 3-Me-naphthalen-2-yl | 0 |
| D-0024 | H | H | H | H | H | 3-CF₃-naphthalen-2-yl | 0 |
| D-0025 | H | H | H | H | H | 3-OMe-naphthalen-2-yl | 0 |
| D-0026 | H | H | H | H | H | pyridin-2-yl | 0 |
| D-0027 | H | H | H | H | H | 3-F-pyridin-2-yl | 0 |
| D-0028 | H | H | H | H | H | 4-F-pyridin-2-yl | 0 |
| D-0029 | H | H | H | H | H | 5-F-pyridin-2-yl | 0 |
| D-0030 | H | H | H | H | H | 6-F-pyridin-2-yl | 0 |
| D-0031 | H | H | H | H | H | 3-Cl-pyridin-2-yl | 0 |
| D-0032 | H | H | H | H | H | 4-Cl-pyridin-2-yl | 0 |
| D-0033 | H | H | H | H | H | 5-Cl-pyridin-2-yl | 0 |
| D-0034 | H | H | H | H | H | 6-Cl-pyridin-2-yl | 0 |
| D-0035 | H | H | H | H | H | 3-Me-pyridin-2-yl | 0 |
| D-0036 | H | H | H | H | H | 4-Me-pyridin-2-yl | 0 |
| D-0037 | H | H | H | H | H | 5-Me-pyridin-2-yl | 0 |
| D-0038 | H | H | H | H | H | 6-Me-pyridin-2-yl | 0 |
| D-0039 | H | H | H | H | H | 3-CF₃-pyridin-2-yl | 0 |
| D-0040 | H | H | H | H | H | 4-CF₃-pyridin-2-yl | 0 |
| D-0041 | H | H | H | H | H | 5-CF₃-pyridin-2-yl | 0 |
| D-0042 | H | H | H | H | H | 6-CF₃-pyridin-2-yl | 0 |
| D-0043 | H | H | H | H | H | 3-OMe-pyridin-2-yl | 0 |
| D-0044 | H | H | H | H | H | 4-OMe-pyridin-2-yl | 0 |
| D-0045 | H | H | H | H | H | 5-OMe-pyridin-2-yl | 0 |
| D-0046 | H | H | H | H | H | 6-OMe-pyridin-2-yl | 0 |
| D-0047 | H | H | H | H | H | 3,4-F₂-pyridin-2-yl | 0 |
| D-0048 | H | H | H | H | H | 3,5-F₂-pyridin-2-yl | 0 |
| D-0049 | H | H | H | H | H | 3,6-F₂-pyridin-2-yl | 0 |
| D-0050 | H | H | H | H | H | 3,4-Cl₂-pyridin-2-yl | 0 |
| D-0051 | H | H | H | H | H | 3,5-Cl₂-pyridin-2-yl | 0 |
| D-0052 | H | H | H | H | H | 3,6-Cl₂-pyridin-2-yl | 0 |

TABLE 238

| compound | R¹ | R² | R³ | R⁴ | R⁵ | Q' | p |
|---|---|---|---|---|---|---|---|
| D-0053 | H | H | H | H | H | 3-F-4-Cl-pyridin-2-yl | 0 |
| D-0054 | H | H | H | H | H | 3-F-5-Cl-pyridin-2-yl | 0 |
| D-0055 | H | H | H | H | H | 3-F-6-Cl-pyridin-2-yl | 0 |
| D-0056 | H | H | H | H | H | 3-F-4-Me-pyridin-2-yl | 0 |
| D-0057 | H | H | H | H | H | 3-F-5-Me-pyridin-2-yl | 0 |
| D-0058 | H | H | H | H | H | 3-F-6-Me-pyridin-2-yl | 0 |
| D-0059 | H | H | H | H | H | 3-F-4-OMe-pyridin-2-yl | 0 |
| D-0060 | H | H | H | H | H | 3-F-5-OMe-pyridin-2-yl | 0 |
| D-0061 | H | H | H | H | H | 3-F-6-OMe-pyridin-2-yl | 0 |
| D-0062 | H | H | H | H | H | 3-Cl-4-F-pyridin-2-yl | 0 |
| D-0063 | H | H | H | H | H | 3-Cl-5-F-pyridin-2-yl | 0 |
| D-0064 | H | H | H | H | H | 3-Cl-6-F-pyridin-2-yl | 0 |
| D-0065 | H | H | H | H | H | 3-Cl-4-Me-pyridin-2-yl | 0 |
| D-0066 | H | H | H | H | H | 3-Cl-5-Me-pyridin-2-yl | 0 |
| D-0067 | H | H | H | H | H | 3-Cl-6-Me-pyridin-2-yl | 0 |
| D-0068 | H | H | H | H | H | 3-Me-4-F-pyridin-2-yl | 0 |
| D-0069 | H | H | H | H | H | 3-Me-5-F-pyridin-2-yl | 0 |
| D-0070 | H | H | H | H | H | 3-Me-6-F-pyridin-2-yl | 0 |
| D-0071 | H | H | H | H | H | 3-Me-4-Cl-pyridin-2-yl | 0 |

TABLE 238-continued

| compound | R¹ | R² | R³ | R⁴ | R⁵ | Q' | p |
|---|---|---|---|---|---|---|---|
| D-0072 | H | H | H | H | H | 3-Me-5-Cl-pyridin-2-yl | 0 |
| D-0073 | H | H | H | H | H | 3-Me-6-Cl-pyridin-2-yl | 0 |
| D-0074 | H | H | H | H | H | 3,4-(Me)$_2$-pyridin-2-yl | 0 |
| D-0075 | H | H | H | H | H | 3,5-(Me)$_2$-pyridin-2-yl | 0 |
| D-0076 | H | H | H | H | H | 3,6-(Me)$_2$-pyridin-2-yl | 0 |
| D-0077 | H | H | H | H | H | 3-Me-4-OMe-pyridin-2-yl | 0 |
| D-0078 | H | H | H | H | H | 3-Me-5-OMe-pyridin-2-yl | 0 |
| D-0079 | H | H | H | H | H | 3-Me-6-OMe-pyridin-2-yl | 0 |
| D-0080 | H | H | H | H | H | 3-CF$_3$-4-F-pyridin-2-yl | 0 |
| D-0081 | H | H | H | H | H | 3-CF$_3$-5-F-pyridin-2-yl | 0 |
| D-0082 | H | H | H | H | H | 3-CF$_3$-6-F-pyridin-2-yl | 0 |
| D-0083 | H | H | H | H | H | 3-CF$_3$-4-Me-pyridin-2-yl | 0 |
| D-0084 | H | H | H | H | H | 3-CF$_3$-5-Me-pyridin-2-yl | 0 |
| D-0085 | H | H | H | H | H | 3-CF$_3$-6-Me-pyridin-2-yl | 0 |
| D-0086 | H | H | H | H | H | 3-OMe-4-F-pyridin-2-yl | 0 |
| D-0087 | H | H | H | H | H | 3-OMe-5-F-pyridin-2-yl | 0 |
| D-0088 | H | H | H | H | H | 3-OMe-6-F-pyridin-2-yl | 0 |
| D-0089 | H | H | H | H | H | 3-OMe-4-Cl-pyridin-2-yl | 0 |
| D-0090 | H | H | H | H | H | 3-OMe-5-Cl-pyridin-2-yl | 0 |
| D-0091 | H | H | H | H | H | 3-OMe-6-Cl-pyridin-2-yl | 0 |
| D-0092 | H | H | H | H | H | 3-OMe-4-Me-pyridin-2-yl | 0 |
| D-0093 | H | H | H | H | H | 3-OMe-5-Me-pyridin-2-yl | 0 |
| D-0094 | H | H | H | H | H | 3-OMe-6-Me-pyridin-2-yl | 0 |
| D-0095 | H | H | H | H | H | 3,4-(OMe)$_2$-pyridin-2-yl | 0 |
| D-0096 | H | H | H | H | H | 3,5-(OMe)$_2$-pyridin-2-yl | 0 |
| D-0097 | H | H | H | H | H | 3,6-(OMe)$_2$-pyridin-2-yl | 0 |
| D-0098 | H | H | H | H | H | pyridin-3-yl | 0 |
| D-0099 | H | H | H | H | H | 2-F-pyridin-3-yl | 0 |
| D-0100 | H | H | H | H | H | 4-F-pyridin-3-yl | 0 |
| D-0101 | H | H | H | H | H | 5-F-pyridin-3-yl | 0 |
| D-0102 | H | H | H | H | H | 6-F-pyridin-3-yl | 0 |
| D-0103 | H | H | H | H | H | 2-Cl-pyridin-3-yl | 0 |
| D-0104 | H | H | H | H | H | 4-Cl-pyridin-3-yl | 0 |
| D-0105 | H | H | H | H | H | 5-Cl-pyridin-3-yl | 0 |
| D-0106 | H | H | H | H | H | 6-Cl-pyridin-3-yl | 0 |
| D-0107 | H | H | H | H | H | 2-Me-pyridin-3-yl | 0 |
| D-0108 | H | H | H | H | H | 4-Me-pyridin-3-yl | 0 |
| D-0109 | H | H | H | H | H | 5-Me-pyridin-3-yl | 0 |

TABLE 239

| compound | R¹ | R² | R³ | R⁴ | R⁵ | Q' | p |
|---|---|---|---|---|---|---|---|
| D-0110 | H | H | H | H | H | 6-Me-pyridin-3-yl | 0 |
| D-0111 | H | H | H | H | H | 2-CF$_3$-pyridin-3-yl | 0 |
| D-0112 | H | H | H | H | H | 4-CF$_3$-pyridin-3-yl | 0 |
| D-0113 | H | H | H | H | H | 5-CF$_3$-pyridin-3-yl | 0 |
| D-0114 | H | H | H | H | H | 6-CF$_3$-pyridin-3-yl | 0 |
| D-0115 | H | H | H | H | H | 2-OMe-pyridin-3-yl | 0 |
| D-0116 | H | H | H | H | H | 4-OMe-pyridin-3-yl | 0 |
| D-0117 | H | H | H | H | H | 5-OMe-pyridin-3-yl | 0 |
| D-0118 | H | H | H | H | H | 6-OMe-pyridin-3-yl | 0 |
| D-0119 | H | H | H | H | H | 2,4-F$_2$-pyridin-3-yl | 0 |
| D-0120 | H | H | H | H | H | 2,5-F$_2$-pyridin-3-yl | 0 |
| D-0121 | H | H | H | H | H | 2,6-F$_2$-pyridin-3-yl | 0 |
| D-0122 | H | H | H | H | H | 4,5-F$_2$-pyridin-3-yl | 0 |
| D-0123 | H | H | H | H | H | 4,6-F$_2$-pyridin-3-yl | 0 |
| D-0124 | H | H | H | H | H | 2,4-Cl$_2$-pyridin-3-yl | 0 |
| D-0125 | H | H | H | H | H | 2,5-Cl$_2$-pyridin-3-yl | 0 |
| D-0126 | H | H | H | H | H | 2,6-Cl$_2$-pyridin-3-yl | 0 |
| D-0127 | H | H | H | H | H | 4,5-Cl$_2$-pyridin-3-yl | 0 |
| D-0128 | H | H | H | H | H | 4,6-Cl$_2$-pyridin-3-yl | 0 |
| D-0129 | H | H | H | H | H | 2-F-4-Cl-pyridin-3-yl | 0 |
| D-0130 | H | H | H | H | H | 2-F-5-Cl-pyridin-3-yl | 0 |
| D-0131 | H | H | H | H | H | 2-F-6-Cl-pyridin-3-yl | 0 |
| D-0132 | H | H | H | H | H | 4-F-2-Cl-pyridin-3-yl | 0 |
| D-0133 | H | H | H | H | H | 4-F-5-Cl-pyridin-3-yl | 0 |
| D-0134 | H | H | H | H | H | 4-F-6-Cl-pyridin-3-yl | 0 |
| D-0135 | H | H | H | H | H | 2-F-4-Me-pyridin-3-yl | 0 |
| D-0136 | H | H | H | H | H | 2-F-5-Me-pyridin-3-yl | 0 |
| D-0137 | H | H | H | H | H | 2-F-6-Me-pyridin-3-yl | 0 |
| D-0138 | H | H | H | H | H | 4-F-2-Me-pyridin-3-yl | 0 |
| D-0139 | H | H | H | H | H | 4-F-5-Me-pyridin-3-yl | 0 |
| D-0140 | H | H | H | H | H | 4-F-6-Me-pyridin-3-yl | 0 |
| D-0141 | H | H | H | H | H | 2-F-4-OMe-pyridin-3-yl | 0 |

TABLE 239-continued

| compound | R¹ | R² | R³ | R⁴ | R⁵ | Q' | p |
|---|---|---|---|---|---|---|---|
| D-0142 | H | H | H | H | H | 2-F-5-OMe-pyridin-3-yl | 0 |
| D-0143 | H | H | H | H | H | 2-F-6-OMe-pyridin-3-yl | 0 |
| D-0144 | H | H | H | H | H | 4-F-2-OMe-pyridin-3-yl | 0 |
| D-0145 | H | H | H | H | H | 4-F-5-OMe-pyridin-3-yl | 0 |
| D-0146 | H | H | H | H | H | 4-F-6-OMe-pyridin-3-yl | 0 |
| D-0147 | H | H | H | H | H | 2-Cl-5-F-pyridin-3-yl | 0 |
| D-0148 | H | H | H | H | H | 2-Cl-6-F-pyridin-3-yl | 0 |
| D-0149 | H | H | H | H | H | 4-Cl-5-F-pyridin-3-yl | 0 |
| D-0150 | H | H | H | H | H | 4-Cl-6-F-pyridin-3-yl | 0 |
| D-0151 | H | H | H | H | H | 2-Cl-4-Me-pyridin-3-yl | 0 |
| D-0152 | H | H | H | H | H | 2-Cl-5-Me-pyridin-3-yl | 0 |
| D-0153 | H | H | H | H | H | 2-Cl-6-Me-pyridin-3-yl | 0 |
| D-0154 | H | H | H | H | H | 4-Cl-2-Me-pyridin-3-yl | 0 |
| D-0155 | H | H | H | H | H | 4-Cl-5-Me-pyridin-3-yl | 0 |
| D-0156 | H | H | H | H | H | 4-Cl-6-Me-pyridin-3-yl | 0 |
| D-0157 | H | H | H | H | H | 2-Me-5-F-pyridin-3-yl | 0 |
| D-0158 | H | H | H | H | H | 2-Me-6-F-pyridin-3-yl | 0 |
| D-0159 | H | H | H | H | H | 4-Me-5-F-pyridin-3-yl | 0 |
| D-0160 | H | H | H | H | H | 4-Me-6-F-pyridin-3-yl | 0 |
| D-0161 | H | H | H | H | H | 2-Me-5-Cl-pyridin-3-yl | 0 |
| D-0162 | H | H | H | H | H | 2-Me-6-Cl-pyridin-3-yl | 0 |
| D-0163 | H | H | H | H | H | 4-Me-5-Cl-pyridin-3-yl | 0 |
| D-0164 | H | H | H | H | H | 4-Me-6-Cl-pyridin-3-yl | 0 |
| D-0165 | H | H | H | H | H | 2,4-(Me)$_2$-pyridin-3-yl | 0 |
| D-0166 | H | H | H | H | H | 2,5-(Me)$_2$-pyridin-3-yl | 0 |

TABLE 240

| compound | R¹ | R² | R³ | R⁴ | R⁵ | Q' | p |
|---|---|---|---|---|---|---|---|
| D-0167 | H | H | H | H | H | 2,6-(Me)$_2$-pyridin-3-yl | 0 |
| D-0168 | H | H | H | H | H | 4,5-(Me)$_2$-pyridin-3-yl | 0 |
| D-0169 | H | H | H | H | H | 4,6-(Me)$_2$-pyridin-3-yl | 0 |
| D-0170 | H | H | H | H | H | 2-Me-4-OMe-pyridin-3-yl | 0 |
| D-0171 | H | H | H | H | H | 2-Me-5-OMe-pyridin-3-yl | 0 |
| D-0172 | H | H | H | H | H | 2-Me-6-OMe-pyridin-3-yl | 0 |
| D-0173 | H | H | H | H | H | 4-Me-2-OMe-pyridin-3-yl | 0 |
| D-0174 | H | H | H | H | H | 4-Me-5-OMe-pyridin-3-yl | 0 |
| D-0175 | H | H | H | H | H | 4-Me-6-OMe-pyridin-3-yl | 0 |
| D-0176 | H | H | H | H | H | 2-CF$_3$-4-F-pyridin-3-yl | 0 |
| D-0177 | H | H | H | H | H | 2-CF$_3$-5-F-pyridin-3-yl | 0 |
| D-0178 | H | H | H | H | H | 2-CF$_3$-6-F-pyridin-3-yl | 0 |
| D-0179 | H | H | H | H | H | 4-CF$_3$-2-F-pyridin-3-yl | 0 |
| D-0180 | H | H | H | H | H | 4-CF$_3$-5-F-pyridin-3-yl | 0 |
| D-0181 | H | H | H | H | H | 4-CF$_3$-6-F-pyridin-3-yl | 0 |
| D-0182 | H | H | H | H | H | 2-CF$_3$-4-Me-pyridin-3-yl | 0 |
| D-0183 | H | H | H | H | H | 2-CF$_3$-5-Me-pyridin-3-yl | 0 |
| D-0184 | H | H | H | H | H | 2-CF$_3$-6-Me-pyridin-3-yl | 0 |
| D-0185 | H | H | H | H | H | 4-CF$_3$-2-Me-pyridin-3-yl | 0 |
| D-0186 | H | H | H | H | H | 4-CF$_3$-5-Me-pyridin-3-yl | 0 |
| D-0187 | H | H | H | H | H | 4-CF$_3$-6-Me-pyridin-3-yl | 0 |
| D-0188 | H | H | H | H | H | 2-OMe-5-F-pyridin-3-yl | 0 |
| D-0189 | H | H | H | H | H | 2-OMe-6-F-pyridin-3-yl | 0 |
| D-0190 | H | H | H | H | H | 4-OMe-5-F-pyridin-3-yl | 0 |
| D-0191 | H | H | H | H | H | 4-OMe-6-F-pyridin-3-yl | 0 |
| D-0192 | H | H | H | H | H | 2-OMe-4-Cl-pyridin-3-yl | 0 |
| D-0193 | H | H | H | H | H | 2-OMe-5-Cl-pyridin-3-yl | 0 |
| D-0194 | H | H | H | H | H | 2-OMe-6-Cl-pyridin-3-yl | 0 |
| D-0195 | H | H | H | H | H | 4-OMe-2-Cl-pyridin-3-yl | 0 |
| D-0196 | H | H | H | H | H | 4-OMe-5-Cl-pyridin-3-yl | 0 |
| D-0197 | H | H | H | H | H | 4-OMe-6-Cl-pyridin-3-yl | 0 |
| D-0198 | H | H | H | H | H | 2-OMe-5-Me-pyridin-3-yl | 0 |
| D-0199 | H | H | H | H | H | 2-OMe-6-Me-pyridin-3-yl | 0 |
| D-0200 | H | H | H | H | H | 4-OMe-5-Me-pyridin-3-yl | 0 |
| D-0201 | H | H | H | H | H | 4-OMe-6-Me-pyridin-3-yl | 0 |
| D-0202 | H | H | H | H | H | 2,4-(OMe)$_2$-pyridin-3-yl | 0 |
| D-0203 | H | H | H | H | H | 2,5-(OMe)$_2$-pyridin-3-yl | 0 |
| D-0204 | H | H | H | H | H | 2,6-(OMe)$_2$-pyridin-3-yl | 0 |
| D-0205 | H | H | H | H | H | 4,5-(OMe)$_2$-pyridin-3-yl | 0 |
| D-0206 | H | H | H | H | H | 4,6-(OMe)$_2$-pyridin-3-yl | 0 |
| D-0207 | H | H | H | H | H | pyridin-4-yl | 0 |
| D-0208 | H | H | H | H | H | 2-F-pyridin-4-yl | 0 |
| D-0209 | H | H | H | H | H | 3-F-pyridin-4-yl | 0 |
| D-0210 | H | H | H | H | H | 2-Cl-pyridin-4-yl | 0 |
| D-0211 | H | H | H | H | H | 3-Cl-pyridin-4-yl | 0 |

TABLE 240-continued

| compound | R¹ | R² | R³ | R⁴ | R⁵ | Q' | p |
|---|---|---|---|---|---|---|---|
| D-0212 | H | H | H | H | H | 2-Me-pyridin-4-yl | 0 |
| D-0213 | H | H | H | H | H | 3-Me-pyridin-4-yl | 0 |
| D-0214 | H | H | H | H | H | 2-CF₃-pyridin-4-yl | 0 |
| D-0215 | H | H | H | H | H | 3-CF₃-pyridin-4-yl | 0 |
| D-0216 | H | H | H | H | H | 2-OMe-pyridin-4-yl | 0 |
| D-0217 | H | H | H | H | H | 3-OMe-pyridin-4-yl | 0 |
| D-0218 | H | H | H | H | H | 2,3-F₂-pyridin-4-yl | 0 |
| D-0219 | H | H | H | H | H | 2,5-F₂-pyridin-4-yl | 0 |
| D-0220 | H | H | H | H | H | 2,6-F₂-pyridin-4-yl | 0 |
| D-0221 | H | H | H | H | H | 3,5-F₂-pyridin-4-yl | 0 |
| D-0222 | H | H | H | H | H | 2,3-Cl₂-pyridin-4-yl | 0 |
| D-0223 | H | H | H | H | H | 2,5-Cl₂-pyridin-4-yl | 0 |

TABLE 241

| compound | R¹ | R² | R³ | R⁴ | R⁵ | Q' | p |
|---|---|---|---|---|---|---|---|
| D-0224 | H | H | H | H | H | 2,6-Cl₂-pyridin-4-yl | 0 |
| D-0225 | H | H | H | H | H | 3,5-Cl₂-pyridin-4-yl | 0 |
| D-0226 | H | H | H | H | H | 3-F-2-Cl-pyridin-4-yl | 0 |
| D-0227 | H | H | H | H | H | 3-F-5-Cl-pyridin-4-yl | 0 |
| D-0228 | H | H | H | H | H | 3-F-6-Cl-pyridin-4-yl | 0 |
| D-0229 | H | H | H | H | H | 3-F-2-Me-pyridin-4-yl | 0 |
| D-0230 | H | H | H | H | H | 3-F-5-Me-pyridin-4-yl | 0 |
| D-0231 | H | H | H | H | H | 3-F-6-Me-pyridin-4-yl | 0 |
| D-0232 | H | H | H | H | H | 3-F-2-OMe-pyridin-4-yl | 0 |
| D-0233 | H | H | H | H | H | 3-F-5-OMe-pyridin-4-yl | 0 |
| D-0234 | H | H | H | H | H | 3-F-6-OMe-pyridin-4-yl | 0 |
| D-0235 | H | H | H | H | H | 3-Cl-2-F-pyridin-4-yl | 0 |
| D-0236 | H | H | H | H | H | 3-Cl-6-F-pyridin-4-yl | 0 |
| D-0237 | H | H | H | H | H | 3-Cl-2-Me-pyridin-4-yl | 0 |
| D-0238 | H | H | H | H | H | 3-Cl-5-Me-pyridin-4-yl | 0 |
| D-0239 | H | H | H | H | H | 3-Cl-6-Me-pyridin-4-yl | 0 |
| D-0240 | H | H | H | H | H | 3-Me-2-F-pyridin-4-yl | 0 |
| D-0241 | H | H | H | H | H | 3-Me-6-F-pyridin-4-yl | 0 |
| D-0242 | H | H | H | H | H | 3-Me-2-Cl-pyridin-4-yl | 0 |
| D-0243 | H | H | H | H | H | 3-Me-6-Cl-pyridin-4-yl | 0 |
| D-0244 | H | H | H | H | H | 2,3-(Me)₂-pyridin-4-yl | 0 |
| D-0245 | H | H | H | H | H | 3,5-(Me)₂-pyridin-4-yl | 0 |
| D-0246 | H | H | H | H | H | 3,6-(Me)₂-pyridin-4-yl | 0 |
| D-0247 | H | H | H | H | H | 3-Me-2-OMe-pyridin-4-yl | 0 |
| D-0248 | H | H | H | H | H | 3-Me-5-OMe-pyridin-4-yl | 0 |
| D-0249 | H | H | H | H | H | 3-Me-6-OMe-pyridin-4-yl | 0 |
| D-0250 | H | H | H | H | H | 3-CF₃-2-F-pyridin-4-yl | 0 |
| D-0251 | H | H | H | H | H | 3-CF₃-5-F-pyridin-4-yl | 0 |
| D-0252 | H | H | H | H | H | 3-CF₃-6-F-pyridin-4-yl | 0 |
| D-0253 | H | H | H | H | H | 3-CF₃-2-Me-pyridin-4-yl | 0 |
| D-0254 | H | H | H | H | H | 3-CF₃-5-Me-pyridin-4-yl | 0 |
| D-0255 | H | H | H | H | H | 3-CF₃-6-Me-pyridin-4-yl | 0 |
| D-0256 | H | H | H | H | H | 3-OMe-2-F-pyridin-4-yl | 0 |
| D-0257 | H | H | H | H | H | 3-OMe-6-F-pyridin-4-yl | 0 |
| D-0258 | H | H | H | H | H | 3-OMe-2-Cl-pyridin-4-yl | 0 |
| D-0259 | H | H | H | H | H | 3-OMe-5-Cl-pyridin-4-yl | 0 |
| D-0260 | H | H | H | H | H | 3-OMe-6-Cl-pyridin-4-yl | 0 |
| D-0261 | H | H | H | H | H | 3-OMe-2-Me-pyridin-4-yl | 0 |
| D-0262 | H | H | H | H | H | 3-OMe-6-Me-pyridin-4-yl | 0 |
| D-0263 | H | H | H | H | H | 2,3-(OMe)₂-pyridin-4-yl | 0 |
| D-0264 | H | H | H | H | H | 3,5-(OMe)₂-pyridin-4-yl | 0 |
| D-0265 | H | H | H | H | H | 3,6-(OMe)₂-pyridin-4-yl | 0 |
| D-0266 | H | H | H | H | H | pyrimidin-2-yl | 0 |
| D-0267 | H | H | H | H | H | pyrimidin-4-yl | 0 |
| D-0268 | H | H | H | H | H | 5-F-pyrimidin-4-yl | 0 |
| D-0269 | H | H | H | H | H | 5-Me-pyrimidin-4-yl | 0 |
| D-0270 | H | H | H | H | H | 5-CF₃-pyrimidin-4-yl | 0 |
| D-0271 | H | H | H | H | H | 5-OMe-pyrimidin-4-yl | 0 |
| D-0272 | H | H | H | H | H | pyrimidin-5-yl | 0 |
| D-0273 | H | H | H | H | H | 4-F-pyrimidin-5-yl | 0 |
| D-0274 | H | H | H | H | H | 4-Cl-pyrimidin-5-yl | 0 |
| D-0275 | H | H | H | H | H | 4-Me-pyrimidin-5-yl | 0 |
| D-0276 | H | H | H | H | H | 4-CF₃-pyrimidin-5-yl | 0 |
| D-0277 | H | H | H | H | H | 4-OMe-pyrimidin-5-yl | 0 |
| D-0278 | H | H | H | H | H | pyridazin-3-yl | 0 |
| D-0279 | H | H | H | H | H | 4-F-pyridazin-3-yl | 0 |
| D-0280 | H | H | H | H | H | 4-Cl-pyridazin-3-yl | 0 |

TABLE 242

| compound | R¹ | R² | R³ | R⁴ | R⁵ | Q' | p |
|---|---|---|---|---|---|---|---|
| D-0281 | H | H | H | H | H | 4-Me-pyridazin-3-yl | 0 |
| D-0282 | H | H | H | H | H | 4-CF₃-pyridazin-3-yl | 0 |
| D-0283 | H | H | H | H | H | 4-OMe-pyridazin-3-yl | 0 |
| D-0284 | H | H | H | H | H | pyridazin-4-yl | 0 |
| D-0285 | H | H | H | H | H | 3-F-pyridazin-4-yl | 0 |
| D-0286 | H | H | H | H | H | 3-Cl-pyridazin-4-yl | 0 |
| D-0287 | H | H | H | H | H | 3-Me-pyridazin-4-yl | 0 |
| D-0288 | H | H | H | H | H | 3-CF₃-pyridazin-4-yl | 0 |
| D-0289 | H | H | H | H | H | 3-OMe-pyridazin-4-yl | 0 |
| D-0290 | H | H | H | H | H | 5-F-pyridazin-4-yl | 0 |
| D-0291 | H | H | H | H | H | 5-Cl-pyridazin-4-yl | 0 |
| D-0292 | H | H | H | H | H | 5-Me-pyridazin-4-yl | 0 |
| D-0293 | H | H | H | H | H | 5-CF₃-pyridazin-4-yl | 0 |
| D-0294 | H | H | H | H | H | 5-OMe-pyridazin-4-yl | 0 |
| D-0295 | H | H | H | H | H | thiophen-2-yl | 0 |
| D-0296 | H | H | H | H | H | 3-F-thiophen-2-yl | 0 |
| D-0297 | H | H | H | H | H | 3-Cl-thiophen-2-yl | 0 |
| D-0298 | H | H | H | H | H | 3-Me-thiophen-2-yl | 0 |
| D-0299 | H | H | H | H | H | 3-CF₃-thiophen-2-yl | 0 |
| D-0300 | H | H | H | H | H | 3-OMe-thiophen-2-yl | 0 |
| D-0301 | H | H | H | H | H | thiophen-3-yl | 0 |
| D-0302 | H | H | H | H | H | 2-F-thiophen-3-yl | 0 |
| D-0303 | H | H | H | H | H | 2-Cl-thiophen-3-yl | 0 |
| D-0304 | H | H | H | H | H | 2-Me-thiophen-3-yl | 0 |
| D-0305 | H | H | H | H | H | 2-CF₃-thiophen-3-yl | 0 |
| D-0306 | H | H | H | H | H | 2-OMe-thiophen-3-yl | 0 |
| D-0307 | H | H | H | H | H | 4-F-thiophen-3-yl | 0 |
| D-0308 | H | H | H | H | H | 4-Cl-thiophen-3-yl | 0 |
| D-0309 | H | H | H | H | H | 4-Me-thiophen-3-yl | 0 |
| D-0310 | H | H | H | H | H | 4-CF₃-thiophen-3-yl | 0 |
| D-0311 | H | H | H | H | H | 4-OMe-thiophen-3-yl | 0 |
| D-0312 | H | H | H | H | H | thiazol-2-yl | 0 |
| D-0313 | H | H | H | H | H | thiazol-4-yl | 0 |
| D-0314 | H | H | H | H | H | 5-F-thiazol-4-yl | 0 |
| D-0315 | H | H | H | H | H | 5-Me-thiazol-4-yl | 0 |
| D-0316 | H | H | H | H | H | 5-CF₃-thiazol-4-yl | 0 |
| D-0317 | H | H | H | H | H | 5-OMe-thiazol-4-yl | 0 |
| D-0318 | H | H | H | H | H | thiazol-5-yl | 0 |
| D-0319 | H | H | H | H | H | 4-F-thiazol-5-yl | 0 |
| D-0320 | H | H | H | H | H | 4-Me-thiazol-5-yl | 0 |
| D-0321 | H | H | H | H | H | 4-CF₃-thiazol-5-yl | 0 |
| D-0322 | H | H | H | H | H | 4-OMe-thiazol-5-yl | 0 |
| D-0323 | H | H | H | H | H | 1H-pyrrol-1-yl | 0 |
| D-0324 | H | H | H | H | H | 2-F-1H-pyrrol-1-yl | 0 |
| D-0325 | H | H | H | H | H | 2-Me-1H-pyrrol-1-yl | 0 |
| D-0326 | H | H | H | H | H | 2-CF₃-1H-pyrrol-1-yl | 0 |
| D-0327 | H | H | H | H | H | 2-OMe-1H-pyrrol-1-yl | 0 |
| D-0328 | H | H | H | H | H | 1H-pyrrol-2-yl | 0 |
| D-0329 | H | H | H | H | H | 1-Me-1H-pyrrol-2-yl | 0 |
| D-0330 | H | H | H | H | H | 3-F-1H-pyrrol-2-yl | 0 |
| D-0331 | H | H | H | H | H | 3-Me-1H-pyrrol-2-yl | 0 |
| D-0332 | H | H | H | H | H | 3-CF₃-1H-pyrrol-2-yl | 0 |
| D-0333 | H | H | H | H | H | 3-OMe-1H-pyrrol-2-yl | 0 |
| D-0334 | H | H | H | H | H | 1-Me-3-F-1H-pyrrol-2-yl | 0 |
| D-0335 | H | H | H | H | H | 1,3-(Me)₂-1H-pyrrol-2-yl | 0 |
| D-0336 | H | H | H | H | H | 1-Me-3-CF₃-1H-pyrrol-2-yl | 0 |
| D-0337 | H | H | H | H | H | 1-Me-3-OMe-1H-pyrrol-2-yl | 0 |

TABLE 243

| compound | R¹ | R² | R³ | R⁴ | R⁵ | Q' | p |
|---|---|---|---|---|---|---|---|
| D-0338 | H | H | H | H | H | 1H-pyrrol-3-yl | 0 |
| D-0339 | H | H | H | H | H | 1-Me-1H-pyrrol-3-yl | 0 |
| D-0340 | H | H | H | H | H | 2-F-1H-pyrrol-3-yl | 0 |
| D-0341 | H | H | H | H | H | 2-Me-1H-pyrrol-3-yl | 0 |
| D-0342 | H | H | H | H | H | 2-CF₃-1H-pyrrol-3-yl | 0 |
| D-0343 | H | H | H | H | H | 2-OMe-1H-pyrrol-3-yl | 0 |
| D-0344 | H | H | H | H | H | 1-Me-2-F-1H-pyrrol-3-yl | 0 |
| D-0345 | H | H | H | H | H | 1,2-(Me)₂-1H-pyrrol-3-yl | 0 |
| D-0346 | H | H | H | H | H | 1-Me-2-CF₃-1H-pyrrol-3-yl | 0 |
| D-0347 | H | H | H | H | H | 1-Me-2-OMe-1H-pyrrol-3-yl | 0 |
| D-0348 | H | H | H | H | H | 4-F-1H-pyrrol-3-yl | 0 |
| D-0349 | H | H | H | H | H | 4-Me-1H-pyrrol-3-yl | 0 |
| D-0350 | H | H | H | H | H | 4-CF₃-1H-pyrrol-3-yl | 0 |

TABLE 243-continued

| compound | R¹ | R² | R³ | R⁴ | R⁵ | Q' | p |
|---|---|---|---|---|---|---|---|
| D-0351 | H | H | H | H | H | 4-OMe-1H-pyrrol-3-yl | 0 |
| D-0352 | H | H | H | H | H | 1-Me-4-F-1H-pyrrol-3-yl | 0 |
| D-0353 | H | H | H | H | H | 1,4-(Me)₂-1H-pyrrol-3-yl | 0 |
| D-0354 | H | H | H | H | H | 1-Me-4-CF₃-1H-pyrrol-3-yl | 0 |
| D-0355 | H | H | H | H | H | 1-Me-4-OMe-1H-pyrrol-3-yl | 0 |
| D-0356 | H | H | H | H | H | 1H-pyrazol-1-yl | 0 |
| D-0357 | H | H | H | H | H | 5-F-1H-pyrazol-1-yl | 0 |
| D-0358 | H | H | H | H | H | 5-Cl-1H-pyrazol-1-yl | 0 |
| D-0359 | H | H | H | H | H | 5-Me-1H-pyrazol-1-yl | 0 |
| D-0360 | H | H | H | H | H | 5-CF₃-1H-pyrazol-1-yl | 0 |
| D-0361 | H | H | H | H | H | 5-OMe-1H-pyrazol-1-yl | 0 |
| D-0362 | H | H | H | H | H | 1H-pyrazol-3-yl | 0 |
| D-0363 | H | H | H | H | H | 1-Me-1H-pyrazol-3-yl | 0 |
| D-0364 | H | H | H | H | H | 4-F-1H-pyrazol-3-yl | 0 |
| D-0365 | H | H | H | H | H | 4-Cl-1H-pyrazol-3-yl | 0 |
| D-0366 | H | H | H | H | H | 4-Me-1H-pyrazol-3-yl | 0 |
| D-0367 | H | H | H | H | H | 4-CF₃-1H-pyrazol-3-yl | 0 |
| D-0368 | H | H | H | H | H | 4-OMe-1H-pyrazol-3-yl | 0 |
| D-0369 | H | H | H | H | H | 1-Me-4-F-1H-pyrazol-3-yl | 0 |
| D-0370 | H | H | H | H | H | 1-Me-4-Cl-1H-pyrazol-3-yl | 0 |
| D-0371 | H | H | H | H | H | 1,4-(Me)₂-1H-pyrazol-3-yl | 0 |
| D-0372 | H | H | H | H | H | 1-Me-4-CF₃-1H-pyrazol-3-yl | 0 |
| D-0373 | H | H | H | H | H | 1-Me-4-OMe-1H-pyrazol-3-yl | 0 |
| D-0374 | H | H | H | H | H | 1H-pyrazol-4-yl | 0 |
| D-0375 | H | H | H | H | H | 1-Me-1H-pyrazol-4-yl | 0 |
| D-0376 | H | H | H | H | H | 3-F-1H-pyrazol-4-yl | 0 |
| D-0377 | H | H | H | H | H | 3-Cl-1H-pyrazol-4-yl | 0 |
| D-0378 | H | H | H | H | H | 3-Me-1H-pyrazol-4-yl | 0 |
| D-0379 | H | H | H | H | H | 3-CF₃-17-pyrazol-4-yl | 0 |
| D-0380 | H | H | H | H | H | 3-OMe-1H-pyrazol-4-yl | 0 |
| D-0381 | H | H | H | H | H | 1-Me-3-F-1H-pyrazol-4-yl | 0 |
| D-0382 | H | H | H | H | H | 1-Me-3-Cl-1H-pyrazol-4-yl | 0 |
| D-0383 | H | H | H | H | H | 1,3-(Me)₂-1H-pyrazol-4-yl | 0 |
| D-0384 | H | H | H | H | H | 1-Me-3-CF₃-1H-pyrazol-4-yl | 0 |
| D-0385 | H | H | H | H | H | 1-Me-3-OMe-1H-pyrazol-4-yl | 0 |
| D-0386 | H | H | H | H | H | 5-F-1H-pyrazol-4-yl | 0 |
| D-0387 | H | H | H | H | H | 5-Cl-1H-pyrazol-4-yl | 0 |
| D-0388 | H | H | H | H | H | 5-Me-1H-pyrazol-4-yl | 0 |
| D-0389 | H | H | H | H | H | 5-CF₃-1H-pyrazol-4-yl | 0 |
| D-0390 | H | H | H | H | H | 5-OMe-1H-pyrazol-4-yl | 0 |
| D-0391 | H | H | H | H | H | 1-Me-5-F-1H-pyrazol-4-yl | 0 |
| D-0392 | H | H | H | H | H | 1-Me-5-Cl-1H-pyrazol-4-yl | 0 |
| D-0393 | H | H | H | H | H | 1,5-(Me)₂-1H-pyrazol-4-yl | 0 |
| D-0394 | H | H | H | H | H | 1-Me-5-CF₃-1H-pyrazol-4-yl | 0 |

TABLE 244

| compound | R¹ | R² | R³ | R⁴ | R⁵ | Q' | p |
|---|---|---|---|---|---|---|---|
| D-0395 | H | H | H | H | H | 1-Me-5-OMe-1H-pyrazol-4-yl | 0 |
| D-0396 | H | H | H | H | H | 1H-pyrazol-5-yl | 0 |
| D-0397 | H | H | H | H | H | 1-Me-1H-pyrazol-5-yl | 0 |
| D-0398 | H | H | H | H | H | 4-F-1H-pyrazol-5-yl | 0 |
| D-0399 | H | H | H | H | H | 4-Cl-1H-pyrazol-5-yl | 0 |
| D-0400 | H | H | H | H | H | 4-Me-1H-pyrazol-5-yl | 0 |
| D-0401 | H | H | H | H | H | 4-CF₃-1H-pyrazol-5-yl | 0 |
| D-0402 | H | H | H | H | H | 4-OMe-1H-pyrazol-5-yl | 0 |
| D-0403 | H | H | H | H | H | 1-Me-4-F-1H-pyrazol-5-yl | 0 |
| D-0404 | H | H | H | H | H | 1-Me-4-Cl-1H-pyrazol-5-yl | 0 |
| D-0405 | H | H | H | H | H | 1,4-(Me)₂-1H-pyrazol-5-yl | 0 |
| D-0406 | H | H | H | H | H | 1-Me-4-CF₃-1H-pyrazol-5-yl | 0 |
| D-0407 | H | H | H | H | H | 1-Me-4-OMe-1H-pyrazol-5-yl | 0 |
| D-0408 | H | H | H | H | H | furan-2-yl | 0 |
| D-0409 | H | H | H | H | H | 3-F-furan-2-yl | 0 |
| D-0410 | H | H | H | H | H | 3-Me-furan-2-yl | 0 |
| D-0411 | H | H | H | H | H | 3-CF₃-furan-2-yl | 0 |
| D-0412 | H | H | H | H | H | 3-OMe-furan-2-yl | 0 |
| D-0413 | H | H | H | H | H | furan-3-yl | 0 |
| D-0414 | H | H | H | H | H | 2-F-furan-3-yl | 0 |
| D-0415 | H | H | H | H | H | 2-Me-furan-3-yl | 0 |
| D-0416 | H | H | H | H | H | 2-CF₃-furan-3-yl | 0 |
| D-0417 | H | H | H | H | H | 2-OMe-furan-3-yl | 0 |
| D-0418 | H | H | H | H | H | 4-F-furan-3-yl | 0 |
| D-0419 | H | H | H | H | H | 4-Me-furan-3-yl | 0 |
| D-0420 | H | H | H | H | H | 4-CF₃-furan-3-yl | 0 |

TABLE 244-continued

| compound | R¹ | R² | R³ | R⁴ | R⁵ | Q' | p |
|---|---|---|---|---|---|---|---|
| D-0421 | H | H | H | H | H | 4-OMe-furan-3-yl | 0 |
| D-0422 | H | H | H | H | H | isoxazol-3-yl | 0 |
| D-0423 | H | H | H | H | H | 4-F-isoxazol-3-yl | 0 |
| D-0424 | H | H | H | H | H | 4-Me-isoxazol-3-yl | 0 |
| D-0425 | H | H | H | H | H | 4-CF₃-isoxazol-3-yl | 0 |
| D-0426 | H | H | H | H | H | 4-OMe-isoxazol-3-yl | 0 |
| D-0427 | H | H | H | H | H | isoxazol-4-yl | 0 |
| D-0428 | H | H | H | H | H | 5-F-isoxazol-4-yl | 0 |
| D-0429 | H | H | H | H | H | 5-Me-isoxazol-4-yl | 0 |
| D-0430 | H | H | H | H | H | 5-CF₃-isoxazol-4-yl | 0 |
| D-0431 | H | H | H | H | H | 5-OMe-isoxazol-4-yl | 0 |
| D-0432 | H | H | H | H | H | isoxazol-5-yl | 0 |
| D-0433 | H | H | H | H | H | 4-F-isoxazol-5-yl | 0 |
| D-0434 | H | H | H | H | H | 4-Me-isoxazol-5-yl | 0 |
| D-0435 | H | H | H | H | H | 4-CF₃-isoxazol-5-yl | 0 |
| D-0436 | H | H | H | H | H | 4-OMe-isoxazol-5-yl | 0 |
| D-0437 | H | H | H | H | H | 1H-1,2,3-triazol-1-yl | 0 |
| D-0438 | H | H | H | H | H | 5-F-1H-1,2,3-triazol-1-yl | 0 |
| D-0439 | H | H | H | H | H | 5-Me-1H-1,2,3-triazol-1-yl | 0 |
| D-0440 | H | H | H | H | H | 5-CF₃-1H-1,2,3-triazol-1-yl | 0 |
| D-0441 | H | H | H | H | H | 5-OMe-1H-1,2,3-triazol-1-yl | 0 |
| D-0442 | H | H | H | H | H | 1H-1,2,3-triazol-4-yl | 0 |
| D-0443 | H | H | H | H | H | 5-F-1H-1,2,3-triazol-4-yl | 0 |
| D-0444 | H | H | H | H | H | 5-Me-1H-1,2,3-triazol-4-yl | 0 |
| D-0445 | H | H | H | H | H | 5-CF₃-1H-1,2,3-triazol-4-yl | 0 |
| D-0446 | H | H | H | H | H | 5-OMe-1H-1,2,3-triazol-4-yl | 0 |
| D-0447 | H | H | H | H | H | 1H-1,2,3-triazol-5-yl | 0 |
| D-0448 | H | H | H | H | H | 4-F-1H-1,2,3-triazol-5-yl | 0 |
| D-0449 | H | H | H | H | H | 4-Me-1H-1,2,3-triazol-5-yl | 0 |
| D-0450 | H | H | H | H | H | 4-CF₃-1H-1,2,3-triazol-5-yl | 0 |
| D-0451 | H | H | H | H | H | 4-OMe-1H-1,2,3-triazol-5-yl | 0 |

TABLE 245

| compound | R¹ | R² | R³ | R⁴ | R⁵ | Q' | p |
|---|---|---|---|---|---|---|---|
| D-0452 | H | H | H | H | H | 1H-1,2,4-triazol-1-yl | 0 |
| D-0453 | H | H | H | H | H | 5-Me-1H-1,2,4-triazol-1-yl | 0 |
| D-0454 | H | H | H | H | H | 5-F-1H-1,2,4-triazol-1-yl | 0 |
| D-0455 | H | H | H | H | H | 5-CF₃-1H-1,2,4-triazol-1-yl | 0 |
| D-0456 | H | H | H | H | H | 5-OMe-1H-1,2,4-triazol-1-yl | 0 |
| D-0457 | H | H | H | H | H | 1H-1,2,4-triazol-3-yl | 0 |
| D-0458 | H | H | H | H | H | 1-Me-1H-1,2,4-triazol-3-yl | 0 |
| D-0459 | H | H | H | H | H | 1H-1,2,4-triazol-5-yl | 0 |
| D-0460 | H | H | H | H | H | 1-Me-1H-1,2,4-triazol-5-yl | 0 |
| D-0461 | H | H | H | H | H | 3,5-(Me)₂-isoxazol-4-yl | 0 |
| D-0462 | H | H | H | H | H | 3,5-(Et)₂-isoxazol-4-yl | 0 |
| D-0463 | H | H | H | H | H | quinolin-4-yl | 0 |
| D-0464 | H | H | H | H | H | isoquinolin-4-yl | 0 |
| D-0465 | H | H | H | H | H | 3,6-(OMe)₂-pyridazin-4-yl | 0 |
| D-0466 | H | H | H | H | H | 2,4-(OMe)₂-pyrimidin-5-yl | 0 |
| D-0467 | H | H | H | H | Cl | OS(=O)₂CF₃ | 0 |

TABLE 246

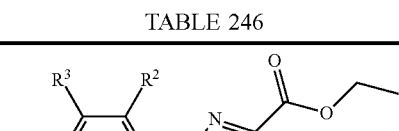

| compound | R¹ | R² | R³ | R⁴ | R⁵ | Q' | p |
|---|---|---|---|---|---|---|---|
| D-5001 | H | H | H | H | H | Cl | 1 |
| D-5002 | H | H | H | H | H | Br | 1 |
| D-5003 | H | H | H | H | H | I | 1 |
| D-5004 | H | H | H | H | H | OS(=O)₂Me | 1 |
| D-5005 | H | H | H | H | H | OS(=O)₂CF₃ | 1 |
| D-5006 | H | H | H | H | H | OS(=O)₂CF₂CF₃ | 1 |

TABLE 246-continued

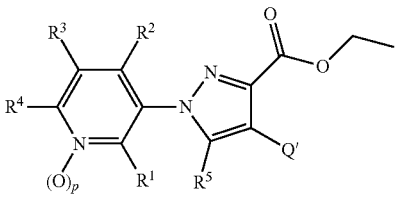

| compound | R¹ | R² | R³ | R⁴ | R⁵ | Q' | p |
|---|---|---|---|---|---|---|---|
| D-5007 | H | H | H | H | H | OS(=O)₂CF₂CF₂CF₃ | 1 |
| D-5008 | H | H | H | H | H | OS(=O)₂CF₂CF₂CF₂CF₃ | 1 |
| D-5009 | H | H | H | H | H | OS(=O)₂(4-MePh) | 1 |
| D-5010 | H | H | H | H | H | OS(=O)₂N(Me)₂ | 1 |
| D-5011 | H | H | H | H | H | OS(=O)₂N(Et)₂ | 1 |
| D-5012 | H | H | H | H | H | naphthalen-1-yl | 1 |
| D-5013 | H | H | H | H | H | 2-F-naphthalen-1-yl | 1 |
| D-5014 | H | H | H | H | H | 2-Me-naphthalen-1-yl | 1 |
| D-5015 | H | H | H | H | H | 2-CF₃-naphthalen-1-yl | 1 |
| D-5016 | H | H | H | H | H | 2-OMe-naphthalen-1-yl | 1 |
| D-5017 | H | H | H | H | H | naphthalen-2-yl | 1 |
| D-5018 | H | H | H | H | H | 1-F-naphthalen-2-yl | 1 |
| D-5019 | H | H | H | H | H | 1-Me-naphthalen-2-yl | 1 |
| D-5020 | H | H | H | H | H | 1-CF₃-naphthalen-2-yl | 1 |
| D-5021 | H | H | H | H | H | 1-OMe-naphthalen-2-yl | 1 |
| D-5022 | H | H | H | H | H | 3-F-naphthalen-2-yl | 1 |
| D-5023 | H | H | H | H | H | 3-Me-naphthalen-2-yl | 1 |
| D-5024 | H | H | H | H | H | 3-CF₃-naphthalen-2-yl | 1 |
| D-5025 | H | H | H | H | H | 3-OMe-naphthalen-2-yl | 1 |
| D-5026 | H | H | H | H | H | pyridin-2-yl | 1 |
| D-5027 | H | H | H | H | H | 3-F-pyridin-2-yl | 1 |
| D-5028 | H | H | H | H | H | 4-F-pyridin-2-yl | 1 |
| D-5029 | H | H | H | H | H | 5-F-pyridin-2-yl | 1 |
| D-5030 | H | H | H | H | H | 6-F-pyridin-2-yl | 1 |
| D-5031 | H | H | H | H | H | 3-Cl-pyridin-2-yl | 1 |
| D-5032 | H | H | H | H | H | 4-Cl-pyridin-2-yl | 1 |
| D-5033 | H | H | H | H | H | 5-Cl-pyridin-2-yl | 1 |
| D-5034 | H | H | H | H | H | 6-Cl-pyridin-2-yl | 1 |
| D-5035 | H | H | H | H | H | 3-Me-pyridin-2-yl | 1 |
| D-5036 | H | H | H | H | H | 4-Me-pyridin-2-yl | 1 |
| D-5037 | H | H | H | H | H | 5-Me-pyridin-2-yl | 1 |
| D-5038 | H | H | H | H | H | 6-Me-pyridin-2-yl | 1 |
| D-5039 | H | H | H | H | H | 3-CF₃-pyridin-2-yl | 1 |
| D-5040 | H | H | H | H | H | 4-CF₃-pyridin-2-yl | 1 |
| D-5041 | H | H | H | H | H | 5-CF₃-pyridin-2-yl | 1 |
| D-5042 | H | H | H | H | H | 6-CF₃-pyridin-2-yl | 1 |
| D-5043 | H | H | H | H | H | 3-OMe-pyridin-2-yl | 1 |
| D-5044 | H | H | H | H | H | 4-OMe-pyridn-2-yl | 1 |
| D-5045 | H | H | H | H | H | 5-OMe-pyridin-2-yl | 1 |
| D-5046 | H | H | H | H | H | 6-OMe-pyridin-2-yl | 1 |
| D-5047 | H | H | H | H | H | 3,4-F₂-pyridin-2-yl | 1 |
| D-5048 | H | H | H | H | H | 3,5-F₂-pyridin-2-yl | 1 |
| D-5049 | H | H | H | H | H | 3,6-F₂-pyridin-2-yl | 1 |
| D-5050 | H | H | H | H | H | 3,4-Cl₂-pyridin-2-yl | 1 |
| D-5051 | H | H | H | H | H | 3,5-Cl₂-pyridin-2-yl | 1 |
| D-5052 | H | H | H | H | H | 3,6-Cl₂-pyridin-2-yl | 1 |

TABLE 247

| compound | R¹ | R² | R³ | R⁴ | R⁵ | Q' | p |
|---|---|---|---|---|---|---|---|
| D-5053 | H | H | H | H | H | 3-F-4-Cl-pyridin-2-yl | 1 |
| D-5054 | H | H | H | H | H | 3-F-5-Cl-pyridin-2-yl | 1 |
| D-5055 | H | H | H | H | H | 3-F-6-Cl-pyridin-2-yl | 1 |
| D-5056 | H | H | H | H | H | 3-F-4-Me-pyridin-2-yl | 1 |
| D-5057 | H | H | H | H | H | 3-F-5-Me-pyridin-2-yl | 1 |
| D-5058 | H | H | H | H | H | 3-F-6-Me-pyridin-2-yl | 1 |
| D-5059 | H | H | H | H | H | 3-F-4-OMe-pyridin-2-yl | 1 |
| D-5060 | H | H | H | H | H | 3-F-5-OMe-pyridin-2-yl | 1 |
| D-5061 | H | H | H | H | H | 3-F-6-OMe-pyridin-2-yl | 1 |
| D-5062 | H | H | H | H | H | 3-Cl-4-F-pyridin-2-yl | 1 |
| D-5063 | H | H | H | H | H | 3-Cl-5-F-pyridin-2-yl | 1 |
| D-5064 | H | H | H | H | H | 3-Cl-6-F-pyridin-2-yl | 1 |
| D-5065 | H | H | H | H | H | 3-Cl-4-Me-pyridin-2-yl | 1 |
| D-5066 | H | H | H | H | H | 3-Cl-5-Me-pyridin-2-yl | 1 |

TABLE 247-continued

| compound | R¹ | R² | R³ | R⁴ | R⁵ | Q' | p |
|---|---|---|---|---|---|---|---|
| D-5067 | H | H | H | H | H | 3-Cl-6-Me-pyridin-2-yl | 1 |
| D-5068 | H | H | H | H | H | 3-Me-4-F-pyridin-2-yl | 1 |
| D-5069 | H | H | H | H | H | 3-Me-5-F-pyridin-2-yl | 1 |
| D-5070 | H | H | H | H | H | 3-Me-6-F-pyridin-2-yl | 1 |
| D-5071 | H | H | H | H | H | 3-Me-4-Cl-pyridin-2-yl | 1 |
| D-5072 | H | H | H | H | H | 3-Me-5-Cl-pyridin-2-yl | 1 |
| D-5073 | H | H | H | H | H | 3-Me-6-Cl-pyridin-2-yl | 1 |
| D-5074 | H | H | H | H | H | 3,4-(Me)₂-pyridin-2-yl | 1 |
| D-5075 | H | H | H | H | H | 3,5-(Me)₂-pyridin-2-yl | 1 |
| D-5076 | H | H | H | H | H | 3,6-(Me)₂-pyridin-2-yl | 1 |
| D-5077 | H | H | H | H | H | 3-Me-4-OMe-pyridin-2-yl | 1 |
| D-5078 | H | H | H | H | H | 3-Me-5-OMe-pyridin-2-yl | 1 |
| D-5079 | H | H | H | H | H | 3-Me-6-OMe-pyridin-2-yl | 1 |
| D-5080 | H | H | H | H | H | 3-CF₃-4-F-pyridin-2-yl | 1 |
| D-5081 | H | H | H | H | H | 3-CF₃-5-F-pyridin-2-yl | 1 |
| D-5082 | H | H | H | H | H | 3-CF₃-6-F-pyridin-2-yl | 1 |
| D-5083 | H | H | H | H | H | 3-CF₃-4-Me-pyridin-2-yl | 1 |
| D-5084 | H | H | H | H | H | 3-CF₃-5-Me-pyridin-2-yl | 1 |
| D-5085 | H | H | H | H | H | 3-CF₃-6-Me-pyridin-2-yl | 1 |
| D-5086 | H | H | H | H | H | 3-OMe-4-F-pyridin-2-yl | 1 |
| D-5087 | H | H | H | H | H | 3-OMe-5-F-pyridin-2-yl | 1 |
| D-5088 | H | H | H | H | H | 3-OMe-6-F-pyridin-2-yl | 1 |
| D-5089 | H | H | H | H | H | 3-OMe-4-Cl-pyridin-2-yl | 1 |
| D-5090 | H | H | H | H | H | 3-OMe-5-Cl-pyridin-2-yl | 1 |
| D-5091 | H | H | H | H | H | 3-OMe-6-Cl-pyridin-2-yl | 1 |
| D-5092 | H | H | H | H | H | 3-OMe-4-Me-pyridin-2-yl | 1 |
| D-5093 | H | H | H | H | H | 3-OMe-5-Me-pyridin-2-yl | 1 |
| D-5094 | H | H | H | H | H | 3-OMe-6-Me-pyridin-2-yl | 1 |
| D-5095 | H | H | H | H | H | 3,4-(OMe)₂-pyridin-2-yl | 1 |
| D-5096 | H | H | H | H | H | 3,5-(OMe)₂-pyridin-2-yl | 1 |
| D-5097 | H | H | H | H | H | 3,6-(OMe)₂-pyridin-2-yl | 1 |
| D-5098 | H | H | H | H | H | pyridin-3-yl | 1 |
| D-5099 | H | H | H | H | H | 2-F-pyridin-3-yl | 1 |
| D-5100 | H | H | H | H | H | 4-F-pyridin-3-yl | 1 |
| D-5101 | H | H | H | H | H | 5-F-pyridin-3-yl | 1 |
| D-5102 | H | H | H | H | H | 6-F-pyridin-3-yl | 1 |
| D-5103 | H | H | H | H | H | 2-Cl-pyridin-3-yl | 1 |
| D-5104 | H | H | H | H | H | 4-Cl-pyridin-3-yl | 1 |
| D-5105 | H | H | H | H | H | 5-Cl-pyridin-3-yl | 1 |
| D-5106 | H | H | H | H | H | 6-Cl-pyridin-3-yl | 1 |
| D-5107 | H | H | H | H | H | 2-Me-pyridin-3-yl | 1 |
| D-5108 | H | H | H | H | H | 4-Me-pyridin-3-yl | 1 |
| D-5109 | H | H | H | H | H | 5-Me-pyridin-3-yl | 1 |

TABLE 248

| compound | R¹ | R² | R³ | R⁴ | R⁵ | Q' | p |
|---|---|---|---|---|---|---|---|
| D-5110 | H | H | H | H | H | 6-Me-pyridin-3-yl | 1 |
| D-5111 | H | H | H | H | H | 2-CF₃-pyridin-3-yl | 1 |
| D-5112 | H | H | H | H | H | 4-CF₃-pyridin-3-yl | 1 |
| D-5113 | H | H | H | H | H | 5-CF₃-pyridin-3-yl | 1 |
| D-5114 | H | H | H | H | H | 6-CF₃-pyridin-3-yl | 1 |
| D-5115 | H | H | H | H | H | 2-OMe-pyridin-3-yl | 1 |
| D-5116 | H | H | H | H | H | 4-OMe-pyridin-3-yl | 1 |
| D-5117 | H | H | H | H | H | 5-OMe-pyridin-3-yl | 1 |
| D-5118 | H | H | H | H | H | 6-OMe-pyridin-3-yl | 1 |
| D-5119 | H | H | H | H | H | 2,4-F₂-pyridin-3-yl | 1 |
| D-5120 | H | H | H | H | H | 2,5-F₂-pyridin-3-yl | 1 |
| D-5121 | H | H | H | H | H | 2,6-F₂-pyridin-3-yl | 1 |
| D-5122 | H | H | H | H | H | 4,5-F₂-pyridin-3-yl | 1 |
| D-5123 | H | H | H | H | H | 4,6-F₂-pyridin-3-yl | 1 |
| D-5124 | H | H | H | H | H | 2,4-Cl₂-pyridin-3-yl | 1 |
| D-5125 | H | H | H | H | H | 2,5-Cl₂-pyridin-3-yl | 1 |
| D-5126 | H | H | H | H | H | 2,6-Cl₂-pyridin-3-yl | 1 |
| D-5127 | H | H | H | H | H | 4,5-Cl₂-pyridin-3-yl | 1 |
| D-5128 | H | H | H | H | H | 4,6-Cl₂-pyridin-3-yl | 1 |
| D-5129 | H | H | H | H | H | 2-F-4-Cl-pyridin-3-yl | 1 |
| D-5130 | H | H | H | H | H | 2-F-5-Cl-pyridin-3-yl | 1 |
| D-5131 | H | H | H | H | H | 2-F-6-Cl-pyridin-3-yl | 1 |
| D-5132 | H | H | H | H | H | 4-F-2-Cl-pyridin-3-yl | 1 |
| D-5133 | H | H | H | H | H | 4-F-5-Cl-pyridin-3-yl | 1 |
| D-5134 | H | H | H | H | H | 4-F-6-Cl-pyridin-3-yl | 1 |
| D-5135 | H | H | H | H | H | 2-F-4-Me-pyridin-3-yl | 1 |
| D-5136 | H | H | H | H | H | 2-F-5-Me-pyridin-3-yl | 1 |

TABLE 248-continued

| compound | R¹ | R² | R³ | R⁴ | R⁵ | Q' | p |
|---|---|---|---|---|---|---|---|
| D-5137 | H | H | H | H | H | 2-F-6-Me-pyridin-3-yl | 1 |
| D-5138 | H | H | H | H | H | 4-F-2-Me-pyridin-3-yl | 1 |
| D-5139 | H | H | H | H | H | 4-F-5-Me-pyridin-3-yl | 1 |
| D-5140 | H | H | H | H | H | 4-F-6-Me-pyridin-3-yl | 1 |
| D-5141 | H | H | H | H | H | 2-F-4-OMe-pyridin-3-yl | 1 |
| D-5142 | H | H | H | H | H | 2-F-5-OMe-pyridin-3-yl | 1 |
| D-5143 | H | H | H | H | H | 2-F-6-OMe-pyridin-3-yl | 1 |
| D-5144 | H | H | H | H | H | 4-F-2-OMe-pyridin-3-yl | 1 |
| D-5145 | H | H | H | H | H | 4-F-5-OMe-pyridin-3-yl | 1 |
| D-5146 | H | H | H | H | H | 4-F-6-OMe-pyridin-3-yl | 1 |
| D-5147 | H | H | H | H | H | 2-Cl-5-F-pyridin-3-yl | 1 |
| D-5148 | H | H | H | H | H | 2-Cl-6-F-pyridin-3-yl | 1 |
| D-5149 | H | H | H | H | H | 4-Cl-5-F-pyridin-3-yl | 1 |
| D-5150 | H | H | H | H | H | 4-Cl-6-F-pyridin-3-yl | 1 |
| D-5151 | H | H | H | H | H | 2-Cl-4-Me-pyridin-3-yl | 1 |
| D-5152 | H | H | H | H | H | 2-Cl-5-Me-pyridin-3-yl | 1 |
| D-5153 | H | H | H | H | H | 2-Cl-6-Me-pyridin-3-yl | 1 |
| D-5154 | H | H | H | H | H | 4-Cl-2-Me-pyridin-3-yl | 1 |
| D-5155 | H | H | H | H | H | 4-Cl-5-Me-pyridin-3-yl | 1 |
| D-5156 | H | H | H | H | H | 4-Cl-6-Me-pyridin-3-yl | 1 |
| D-5157 | H | H | H | H | H | 2-Me-5-F-pyridin-3-yl | 1 |
| D-5158 | H | H | H | H | H | 2-Me-6-F-pyridin-3-yl | 1 |
| D-5159 | H | H | H | H | H | 4-Me-5-F-pyridin-3-yl | 1 |
| D-5160 | H | H | H | H | H | 4-Me-6-F-pyridin-3-yl | 1 |
| D-5161 | H | H | H | H | H | 2-Me-5-Cl-pyridin-3-yl | 1 |
| D-5162 | H | H | H | H | H | 2-Me-6-Cl-pyridin-3-yl | 1 |
| D-5163 | H | H | H | H | H | 4-Me-5-Cl-pyridin-3-yl | 1 |
| D-5164 | H | H | H | H | H | 4-Me-6-Cl-pyridin-3-yl | 1 |
| D-5165 | H | H | H | H | H | 2,4-(Me)₂-pyridin-3-yl | 1 |
| D-5166 | H | H | H | H | H | 2,5-(Me)₂-pyridin-3-yl | 1 |

TABLE 249

| compound | R¹ | R² | R³ | R⁴ | R⁵ | Q' | p |
|---|---|---|---|---|---|---|---|
| D-5167 | H | H | H | H | H | 2,6-(Me)₂-pyridin-3-yl | 1 |
| D-5168 | H | H | H | H | H | 4,5-(Me)₂-pyridin-3-yl | 1 |
| D-5169 | H | H | H | H | H | 4,6-(Me)₂-pyridin-3-yl | 1 |
| D-5170 | H | H | H | H | H | 2-Me-4-OMe-pyridin-3-yl | 1 |
| D-5171 | H | H | H | H | H | 2-Me-5-OMe-pyridin-3-yl | 1 |
| D-5172 | H | H | H | H | H | 2-Me-6-OMe-pyridin-3-yl | 1 |
| D-5173 | H | H | H | H | H | 4-Me-2-OMe-pyridin-3-yl | 1 |
| D-5174 | H | H | H | H | H | 4-Me-5-OMe-pyridin-3-yl | 1 |
| D-5175 | H | H | H | H | H | 4-Me-6-OMe-pyridin-3-yl | 1 |
| D-5176 | H | H | H | H | H | 2-CF₃-4-F-pyridin-3-yl | 1 |
| D-5177 | H | H | H | H | H | 2-CF₃-5-F-pyridin-3-yl | 1 |
| D-5178 | H | H | H | H | H | 2-CF₃-6-F-pyridin-3-yl | 1 |
| D-5179 | H | H | H | H | H | 4-CF₃-2-F-pyridin-3-yl | 1 |
| D-5180 | H | H | H | H | H | 4-CF₃-5-F-pyridin-3-yl | 1 |
| D-5181 | H | H | H | H | H | 4-CF₃-6-F-pyridin-3-yl | 1 |
| D-5182 | H | H | H | H | H | 2-CF₃-4-Me-pyridin-3-yl | 1 |
| D-5183 | H | H | H | H | H | 2-CF₃-5-Me-pyridin-3-yl | 1 |
| D-5184 | H | H | H | H | H | 2-CF₃-6-Me-pyridin-3-yl | 1 |
| D-5185 | H | H | H | H | H | 4-CF₃-2-Me-pyridin-3-yl | 1 |
| D-5186 | H | H | H | H | H | 4-CF₃-5-Me-pyridin-3-yl | 1 |
| D-5187 | H | H | H | H | H | 4-CF₃-6-Me-pyridin-3-yl | 1 |
| D-5188 | H | H | H | H | H | 2-OMe-5-F-pyridin-3-yl | 1 |
| D-5189 | H | H | H | H | H | 2-OMe-6-F-pyridin-3-yl | 1 |
| D-5190 | H | H | H | H | H | 4-OMe-5-F-pyridin-3-yl | 1 |
| D-5191 | H | H | H | H | H | 4-OMe-6-F-pyridin-3-yl | 1 |
| D-5192 | H | H | H | H | H | 2-OMe-4-Cl-pyridin-3-yl | 1 |
| D-5193 | H | H | H | H | H | 2-OMe-5-Cl-pyridin-3-yl | 1 |
| D-5194 | H | H | H | H | H | 2-OMe-6-Cl-pyridin-3-yl | 1 |
| D-5195 | H | H | H | H | H | 4-OMe-2-Cl-pyridin-3-yl | 1 |
| D-5196 | H | H | H | H | H | 4-OMe-5-Cl-pyridin-3-yl | 1 |
| D-5197 | H | H | H | H | H | 4-OMe-6-Cl-pyridin-3-yl | 1 |
| D-5198 | H | H | H | H | H | 2-OMe-5-Me-pyridin-3-yl | 1 |
| D-5199 | H | H | H | H | H | 2-OMe-6-Me-pyridin-3-yl | 1 |
| D-5200 | H | H | H | H | H | 4-OMe-5-Me-pyridin-3-yl | 1 |
| D-5201 | H | H | H | H | H | 4-OMe-6-Me-pyridin-3-yl | 1 |
| D-5202 | H | H | H | H | H | 2,4-(OMe)₂-pyridin-3-yl | 1 |
| D-5203 | H | H | H | H | H | 2,5-(OMe)₂-pyridin-3-yl | 1 |
| D-5204 | H | H | H | H | H | 2,6-(OMe)₂-pyridin-3-yl | 1 |
| D-5205 | H | H | H | H | H | 4,5-(OMe)₂-pyridin-3-yl | 1 |
| D-5206 | H | H | H | H | H | 4,6-(OMe)₂-pyridin-3-yl | 1 |

TABLE 249-continued

| compound | R¹ | R² | R³ | R⁴ | R⁵ | Q' | p |
|---|---|---|---|---|---|---|---|
| D-5207 | H | H | H | H | H | pyridin-4-yl | 1 |
| D-5208 | H | H | H | H | H | 2-F-pyridin-4-yl | 1 |
| D-5209 | H | H | H | H | H | 3-F-pyridin-4-yl | 1 |
| D-5210 | H | H | H | H | H | 2-Cl-pyridin-4-yl | 1 |
| D-5211 | H | H | H | H | H | 3-Cl-pyridin-4-yl | 1 |
| D-5212 | H | H | H | H | H | 2-Me-pyridin-4-yl | 1 |
| D-5213 | H | H | H | H | H | 3-Me-pyridin-4-yl | 1 |
| D-5214 | H | H | H | H | H | 2-CF₃-pyridin-4-yl | 1 |
| D-5215 | H | H | H | H | H | 3-CF₃-pyridin-4-yl | 1 |
| D-5216 | H | H | H | H | H | 2-OMe-pyridin-4-yl | 1 |
| D-5217 | H | H | H | H | H | 3-OMe-pyridin-4-yl | 1 |
| D-5218 | H | H | H | H | H | 2,3-F₂-pyridin-4-yl | 1 |
| D-5219 | H | H | H | H | H | 2,5-F₂-pyridin-4-yl | 1 |
| D-5220 | H | H | H | H | H | 2,6-F₂-pyridin-4-yl | 1 |
| D-5221 | H | H | H | H | H | 3,5-F₂-pyridin-4-yl | 1 |
| D-5222 | H | H | H | H | H | 2,3-Cl₂-pyridin-4-yl | 1 |
| D-5223 | H | H | H | H | H | 2,5-Cl₂-pyridin-4-yl | 1 |

TABLE 250

| compound | R¹ | R² | R³ | R⁴ | R⁵ | Q' | p |
|---|---|---|---|---|---|---|---|
| D-5224 | H | H | H | H | H | 2,6-Cl₂-pyridin-4-yl | 1 |
| D-5225 | H | H | H | H | H | 3,5-Cl₂-pyridin-4-yl | 1 |
| D-5226 | H | H | H | H | H | 3-F-2-Cl-pyridin-4-yl | 1 |
| D-5227 | H | H | H | H | H | 3-F-5-Cl-pyridin-4-yl | 1 |
| D-5228 | H | H | H | H | H | 3-F-6-Cl-pyridin-4-yl | 1 |
| D-5229 | H | H | H | H | H | 3-F-2-Me-pyridin-4-yl | 1 |
| D-5230 | H | H | H | H | H | 3-F-5-Me-pyridin-4-yl | 1 |
| D-5231 | H | H | H | H | H | 3-F-6-Me-pyridin-4-yl | 1 |
| D-5232 | H | H | H | H | H | 3-F-2-OMe-pyridin-4-yl | 1 |
| D-5233 | H | H | H | H | H | 3-F-5-OMe-pyridin-4-yl | 1 |
| D-5234 | H | H | H | H | H | 3-F-6-OMe-pyridin-4-yl | 1 |
| D-5235 | H | H | H | H | H | 3-Cl-2-F-pyridin-4-yl | 1 |
| D-5236 | H | H | H | H | H | 3-Cl-6-F-pyridin-4-yl | 1 |
| D-5237 | H | H | H | H | H | 3-Cl-2-Me-pyridin-4-yl | 1 |
| D-5238 | H | H | H | H | H | 3-Cl-5-Me-pyridin-4-yl | 1 |
| D-5239 | H | H | H | H | H | 3-Cl-6-Me-pyridin-4-yl | 1 |
| D-5240 | H | H | H | H | H | 3-Me-2-F-pyridin-4-yl | 1 |
| D-5241 | H | H | H | H | H | 3-Me-6-F-pyridin-4-yl | 1 |
| D-5242 | H | H | H | H | H | 3-Me-2-Cl-pyridin-4-yl | 1 |
| D-5243 | H | H | H | H | H | 3-Me-6-Cl-pyridin-4-yl | 1 |
| D-5244 | H | H | H | H | H | 2,3-(Me)₂-pyridin-4-yl | 1 |
| D-5245 | H | H | H | H | H | 3,5-(Me)₂-pyridin-4-yl | 1 |
| D-5246 | H | H | H | H | H | 3,6-(Me)₂-pyridin-4-yl | 1 |
| D-5247 | H | H | H | H | H | 3-Me-2-OMe-pyridin-4-yl | 1 |
| D-5248 | H | H | H | H | H | 3-Me-5-OMe-pyridin-4-yl | 1 |
| D-5249 | H | H | H | H | H | 3-Me-6-OMe-pyridin-4-yl | 1 |
| D-5250 | H | H | H | H | H | 3-CF₃-2-F-pyridin-4-yl | 1 |
| D-5251 | H | H | H | H | H | 3-CF₃-5-F-pyridin-4-yl | 1 |
| D-5252 | H | H | H | H | H | 3-CF₃-6-F-pyridin-4-yl | 1 |
| D-5253 | H | H | H | H | H | 3-CF₃-2-Me-pyridin-4-yl | 1 |
| D-5254 | H | H | H | H | H | 3-CF₃-5-Me-pyridin-4-yl | 1 |
| D-5255 | H | H | H | H | H | 3-CF₃-6-Me-pyridin-4-yl | 1 |
| D-5256 | H | H | H | H | H | 3-OMe-2-F-pyridin-4-yl | 1 |
| D-5257 | H | H | H | H | H | 3-OMe-6-F-pyridin-4-yl | 1 |
| D-5258 | H | H | H | H | H | 3-OMe-2-Cl-pyridin-4-yl | 1 |
| D-5259 | H | H | H | H | H | 3-OMe-5-Cl-pyridin-4-yl | 1 |
| D-5260 | H | H | H | H | H | 3-OMe-6-Cl-pyridin-4-yl | 1 |
| D-5261 | H | H | H | H | H | 3-OMe-2-Me-pyridin-4-yl | 1 |
| D-5262 | H | H | H | H | H | 3-OMe-6-Me-pyridin-4-yl | 1 |
| D-5263 | H | H | H | H | H | 2,3-(OMe)₂-pyridin-4-yl | 1 |
| D-5264 | H | H | H | H | H | 3,5-(OMe)₂-pyridin-4-yl | 1 |
| D-5265 | H | H | H | H | H | 3,6-(OMe)₂-pyridin-4-yl | 1 |
| D-5266 | H | H | H | H | H | pyrimidin-2-yl | 1 |
| D-5267 | H | H | H | H | H | pyrimidin-4-yl | 1 |
| D-5268 | H | H | H | H | H | 5-F-pyrimidin-4-yl | 1 |
| D-5269 | H | H | H | H | H | 5-Me-pyrimidin-4-yl | 1 |
| D-5270 | H | H | H | H | H | 5-CF₃-pyrimidin-4-yl | 1 |
| D-5271 | H | H | H | H | H | 5-OMe-pyrimidin-4-yl | 1 |
| D-5272 | H | H | H | H | H | pyrimidin-5-yl | 1 |
| D-5273 | H | H | H | H | H | 4-F-pyrimidin-5-yl | 1 |
| D-5274 | H | H | H | H | H | 4-Cl-pyrimidin-5-yl | 1 |
| D-5275 | H | H | H | H | H | 4-Me-pyrimidin-5-yl | 1 |
| D-5276 | H | H | H | H | H | 4-CF₃-pyrimidin-5-yl | 1 |

TABLE 250-continued

| compound | R¹ | R² | R³ | R⁴ | R⁵ | Q' | p |
|---|---|---|---|---|---|---|---|
| D-5277 | H | H | H | H | H | 4-OMe-pyrimidin-5-yl | 1 |
| D-5278 | H | H | H | H | H | pyridazin-3-yl | 1 |
| D-5279 | H | H | H | H | H | 4-F-pyridazin-3-yl | 1 |
| D-5280 | H | H | H | H | H | 4-Cl-pyridazin-3-yl | 1 |

TABLE 251

| compound | R¹ | R² | R³ | R⁴ | R⁵ | Q' | p |
|---|---|---|---|---|---|---|---|
| D-5281 | H | H | H | H | H | 4-Me-pyridazin-3-yl | 1 |
| D-5282 | H | H | H | H | H | 4-CF₃-pyridazin-3-yl | 1 |
| D-5283 | H | H | H | H | H | 4-OMe-pyridazin-3-yl | 1 |
| D-5284 | H | H | H | H | H | pyridazin-4-yl | 1 |
| D-5285 | H | H | H | H | H | 3-F-pyridazin-4-yl | 1 |
| D-5286 | H | H | H | H | H | 3-Cl-pyridazin-4-yl | 1 |
| D-5287 | H | H | H | H | H | 3-Me-pyridazin-4-yl | 1 |
| D-5288 | H | H | H | H | H | 3-CF₃-pyridazn-4-yl | 1 |
| D-5289 | H | H | H | H | H | 3-OMe-pyridazin-4-yl | 1 |
| D-5290 | H | H | H | H | H | 5-F-pyridazin-4-yl | 1 |
| D-5291 | H | H | H | H | H | 5-Cl-pyridazin-4-yl | 1 |
| D-5292 | H | H | H | H | H | 5-Me-pyridazin-4-yl | 1 |
| D-5293 | H | H | H | H | H | 5-CF₃-pyridazin-4-yl | 1 |
| D-5294 | H | H | H | H | H | 5-OMe-pyridazin-4-yl | 1 |
| D-5295 | H | H | H | H | H | thiophen-2-yl | 1 |
| D-5296 | H | H | H | H | H | 3-F-thiophen-2-yl | 1 |
| D-5297 | H | H | H | H | H | 3-Cl-thiophen-2-yl | 1 |
| D-5298 | H | H | H | H | H | 3-Me-thiophen-2-yl | 1 |
| D-5299 | H | H | H | H | H | 3-CF₃-thiophen-2-yl | 1 |
| D-5300 | H | H | H | H | H | 3-OMe-thiophen-2-yl | 1 |
| D-5301 | H | H | H | H | H | thiophen-3-yl | 1 |
| D-5302 | H | H | H | H | H | 2F-thiophen-3-yl | 1 |
| D-5303 | H | H | H | H | H | 2-Cl-thiophen-3-yl | 1 |
| D-5304 | H | H | H | H | H | 2-Me-thiophen-3-yl | 1 |
| D-5305 | H | H | H | H | H | 2-CF₃-thiophen-3-y | 1 |
| D-5306 | H | H | H | H | H | 2-OMe-thiophen-3-yl | 1 |
| D-5307 | H | H | H | H | H | 4-F-thiophen-3-yl | 1 |
| D-5308 | H | H | H | H | H | 4-Cl-thiophen-3-yl | 1 |
| D-5309 | H | H | H | H | H | 4-Me-thiophen-3-yl | 1 |
| D-5310 | H | H | H | H | H | 4-CF₃-thiophen-3-yl | 1 |
| D-5311 | H | H | H | H | H | 4-OMe-thiophen-3-yl | 1 |
| D-5312 | H | H | H | H | H | thiazol-2-yl | 1 |
| D-5313 | H | H | H | H | H | thiazol-4-yl | 1 |
| D-5314 | H | H | H | H | H | 5-F-thiazol-4-yl | 1 |
| D-5315 | H | H | H | H | H | 5-Me-thiazol-4-yl | 1 |
| D-5316 | H | H | H | H | H | 5-CF₃-thiazol-4-yl | 1 |
| D-5317 | H | H | H | H | H | 5-OMe-thiazol-4-yl | 1 |
| D-5318 | H | H | H | H | H | thiazol-5-yl | 1 |
| D-5319 | H | H | H | H | H | 4-F-thiazol-5-yl | 1 |
| D-5320 | H | H | H | H | H | 4-Me-thiazol-5-yl | 1 |
| D-5321 | H | H | H | H | H | 4-CF₃-thiazol-5-yl | 1 |
| D-5322 | H | H | H | H | H | 4-OMe-thiazol-5-yl | 1 |
| D-5323 | H | H | H | H | H | 1H-pyrrol-1-yl | 1 |
| D-5324 | H | H | H | H | H | 2-F-1H-pyrrol-1-yl | 1 |
| D-5325 | H | H | H | H | H | 2-Me-1H-pyrrol-1-yl | 1 |
| D-5326 | H | H | H | H | H | 2-CF₃-1H-pyrrol-1-yl | 1 |
| D-5327 | H | H | H | H | H | 2-OMe-1H-pyrrol-1-yl | 1 |
| D-5328 | H | H | H | H | H | 1H-pyrrol-2-yl | 1 |
| D-5329 | H | H | H | H | H | 1-Me-1H-pyrrol-2-yl | 1 |
| D-5330 | H | H | H | H | H | 3-F-1H-pyrrol-2-yl | 1 |
| D-5331 | H | H | H | H | H | 3-Me-1H-pyrrol-2-yl | 1 |
| D-5332 | H | H | H | H | H | 3-CF₃-1H-pyrrol-2-yl | 1 |
| D-5333 | H | H | H | H | H | 3-OMe-1H-pyrrol-2-yl | 1 |
| D-5334 | H | H | H | H | H | 1-Me-3-F-1H-pyrrol-2-yl | 1 |
| D-5335 | H | H | H | H | H | 1,3-(Me)₂-1H-pyrrol-2-yl | 1 |
| D-5336 | H | H | H | H | H | 1-Me-3-CF₃-1H-pyrrol-2-yl | 1 |
| D-5337 | H | H | H | H | H | 1-Me-3-OMe-1H-pyrrol-2-yl | 1 |

TABLE 252

| compound | R¹ | R² | R³ | R⁴ | R⁵ | Q' | p |
|---|---|---|---|---|---|---|---|
| D-5338 | H | H | H | H | H | 1H-pyrrol-3-yl | 1 |
| D-5339 | H | H | H | H | H | 1-Me-1H-pyrrol-3-yl | 1 |
| D-5340 | H | H | H | H | H | 2-F-1H-pyrrol-3-yl | 1 |
| D-5341 | H | H | H | H | H | 2-Me-1H-pyrrol-3-yl | 1 |
| D-5342 | H | H | H | H | H | 2-CF₃-1H-pyrrol-3-yl | 1 |
| D-5343 | H | H | H | H | H | 2-OMe-1H-pyrrol-3-yl | 1 |
| D-5344 | H | H | H | H | H | 1-Me-2-F-1H-pyrrol-3-yl | 1 |
| D-5345 | H | H | H | H | H | 1,2-(Me)₂-1H-pyrrol-3-yl | 1 |
| D-5346 | H | H | H | H | H | 1-Me-2-CF₃-1H-pyrrol-3-yl | 1 |
| D-5347 | H | H | H | H | H | 1-Me-2-OMe-1H-pyrrol-3-yl | 1 |
| D-5348 | H | H | H | H | H | 4-F-1H-pyrrol-3-yl | 1 |
| D-5349 | H | H | H | H | H | 4-Me-1H-pyrrol-3-yl | 1 |
| D-5350 | H | H | H | H | H | 4-CF₃-1H-pyrrol-3-yl | 1 |
| D-5351 | H | H | H | H | H | 4-OMe-1H-pyrrol-3-yl | 1 |
| D-5352 | H | H | H | H | H | 1-Me-4-F-1H-pyrrol-3-yl | 1 |
| D-5353 | H | H | H | H | H | 1,4-(Me)₂-1H-pyrrol-3-yl | 1 |
| D-5354 | H | H | H | H | H | 1-Me-4-CF₃-1H-pyrrol-3-yl | 1 |
| D-5355 | H | H | H | H | H | 1-Me-4-OMe-1H-pyrrol-3-yl | 1 |
| D-5356 | H | H | H | H | H | 1H-pyrazol-1-yl | 1 |
| D-5357 | H | H | H | H | H | 5-F-1H-pyrazol-yl | 1 |
| D-5358 | H | H | H | H | H | 5-Cl-1H-pyrazol-1-yl | 1 |
| D-5359 | H | H | H | H | H | 5-Me-1H-pyrazol-1-yl | 1 |
| D-5360 | H | H | H | H | H | 5-CF₃-1H-pyrazol-1-yl | 1 |
| D-5361 | H | H | H | H | H | 5-OMe-1H-pyrazol-1-yl | 1 |
| D-5362 | H | H | H | H | H | 1H-pyrazol-3-yl | 1 |
| D-5363 | H | H | H | H | H | 1-Me-1H-pyrazol-3-yl | 1 |
| D-5364 | H | H | H | H | H | 4-F-1H-pyrazol-3-yl | 1 |
| D-5365 | H | H | H | H | H | 4-Cl-1H-pyrazol-3-yl | 1 |
| D-5366 | H | H | H | H | H | 4-Me-1H-pyrazol-3-yl | 1 |
| D-5367 | H | H | H | H | H | 4-CF₃-1H-pyrazol-3-y | 1 |
| D-5368 | H | H | H | H | H | 4-OMe-1H-pyrazol-3-yl | 1 |
| D-5369 | H | H | H | H | H | 1-Me-4-F-1H-pyrazol-3-yl | 1 |
| D-5370 | H | H | H | H | H | 1-Me-4-Cl-1H-pyrazol-3-yl | 1 |
| D-5371 | H | H | H | H | H | 1,4-(Me)₂-17-pyrazol-3-yl | 1 |
| D-5372 | H | H | H | H | H | 1-Me-4-CF₃-1H-pyrazol-3-yl | 1 |
| D-5373 | H | H | H | H | H | 1-Me-4-OMe-1H-pyrazol-3-yl | 1 |
| D-5374 | H | H | H | H | H | 1H-pyrazol-4-yl | 1 |
| D-5375 | H | H | H | H | H | 1-Me-1H-pyrazol-4-yl | 1 |
| D-5376 | H | H | H | H | H | 3-F-1H-pyrazol-4-yl | 1 |
| D-5377 | H | H | H | H | H | 3-Cl-1H-pyrazol-4-yl | 1 |
| D-5378 | H | H | H | H | H | 3-Me-1H-pyrazol-4-yl | 1 |
| D-5379 | H | H | H | H | H | 3-CF₃-1H-pyrazol-4-y | 1 |
| D-5380 | H | H | H | H | H | 3-OMe-1H-pyrazol-4-yl | 1 |
| D-5381 | H | H | H | H | H | 1-Me-3-F-1H-pyrazol-4-yl | 1 |
| D-5382 | H | H | H | H | H | 1-Me-3-Cl-1H-pyrazol-4-yl | 1 |
| D-5383 | H | H | H | H | H | 1,3-(Me)₂-1H-pyrazol-4-yl | 1 |
| D-5384 | H | H | H | H | H | 1-Me-3-CF₃-1H-pyrazol-4-yl | 1 |
| D-5385 | H | H | H | H | H | 1-Me-3-OMe-1H-pyrazol-4-yl | 1 |
| D-5386 | H | H | H | H | H | 5-F-1H-pyrazol-4-yl | 1 |
| D-5387 | H | H | H | H | H | 5-Cl-1H-pyrazol-4-yl | 1 |
| D-5388 | H | H | H | H | H | 5-Me-1H-pyrazol-4-yl | 1 |
| D-5389 | H | H | H | H | H | 5-CF₃-1H-pyrazol-4-yl | 1 |
| D-5390 | H | H | H | H | H | 5-OMe-1H-pyrazol-4-yl | 1 |
| D-5391 | H | H | H | H | H | 1-Me-5-F-1H-pyrazol-4-yl | 1 |
| D-5392 | H | H | H | H | H | 1-Me-5-Cl-1H-pyrazol-4-yl | 1 |
| D-5393 | H | H | H | H | H | 1,5-(Me)₂-1H-pyrazol-4-yl | 1 |
| D-5394 | H | H | H | H | H | 1-Me-5-CF₃-1H-pyrazol-4-yl | 1 |

TABLE 253

| compound | R¹ | R² | R³ | R⁴ | R⁵ | Q' | p |
|---|---|---|---|---|---|---|---|
| D-5395 | H | H | H | H | H | 1-Me-5-OMe-1H-pyrazol-4-yl | 1 |
| D-5396 | H | H | H | H | H | 1H-pyrazol-5-yl | 1 |
| D-5397 | H | H | H | H | H | 1-Me-1H-pyrazol-5-yl | 1 |
| D-5398 | H | H | H | H | H | 4-F-1H-pyrazol-5-yl | 1 |
| D-5399 | H | H | H | H | H | 4-Cl-1H-pyrazol-5-yl | 1 |
| D-5400 | H | H | H | H | H | 4-Me-1H-pyrazol-5-yl | 1 |
| D-5401 | H | H | H | H | H | 4-CF₃-1H-pyrazol-5-yl | 1 |
| D-5402 | H | H | H | H | H | 4-OMe-1H-pyrazol-5-yl | 1 |
| D-5403 | H | H | H | H | H | 1-Me-4-F-1H-pyrazol-5-yl | 1 |
| D-5404 | H | H | H | H | H | 1-Me-4-Cl-1H-pyrazol-5-yl | 1 |
| D-5405 | H | H | H | H | H | 1,4-(Me)₂-1H-pyrazol-5-yl | 1 |
| D-5406 | H | H | H | H | H | 1-Me-4-CF₃-1H-pyrazol-5-yl | 1 |
| D-5407 | H | H | H | H | H | 1-Me-4-OMe-1H-pyrazol-5-yl | 1 |
| D-5408 | H | H | H | H | H | furan-2-yl | 1 |
| D-5409 | H | H | H | H | H | 3-F-furan-2-yl | 1 |

TABLE 253-continued

| compound | R¹ | R² | R³ | R⁴ | R⁵ | Q' | p |
|---|---|---|---|---|---|---|---|
| D-5410 | H | H | H | H | H | 3-Me-furan-2-yl | 1 |
| D-5411 | H | H | H | H | H | 3-CF₃-furan-2-yl | 1 |
| D-5412 | H | H | H | H | H | 3-OMe-furan-2-yl | 1 |
| D-5413 | H | H | H | H | H | furan-3-yl | 1 |
| D-5414 | H | H | H | H | H | 2-F-furan-3-yl | 1 |
| D-5415 | H | H | H | H | H | 2-Me-furan-3-yl | 1 |
| D-5416 | H | H | H | H | H | 2-CF3-furan-3-yl | 1 |
| D-5417 | H | H | H | H | H | 2-OMe-furan-3-yl | 1 |
| D-5418 | H | H | H | H | H | 4-F-furan-3-yl | 1 |
| D-5419 | H | H | H | H | H | 4-Me-furan-3-yl | 1 |
| D-5420 | H | H | H | H | H | 4-CF₃-furan-3-yl | 1 |
| D-5421 | H | H | H | H | H | 4-OMe-furan-3-yl | 1 |
| D-5422 | H | H | H | H | H | isoxazol-3-yl | 1 |
| D-5423 | H | H | H | H | H | 4-F-isoxazol3-yl | 1 |
| D-5424 | H | H | H | H | H | 4-Me-isoxazol-3-yl | 1 |
| D-5425 | H | H | H | H | H | 4-CF₃-isoxazol-3-yl | 1 |
| D-5426 | H | H | H | H | H | 4-OMe-isoxazol-3-yl | 1 |
| D-5427 | H | H | H | H | H | isoxazol-4-yl | 1 |
| D-5428 | H | H | H | H | H | 5-F-isoxazol-4-yl | 1 |
| D-5429 | H | H | H | H | H | 5-Me-isoxazol-4-yl | 1 |
| D-5430 | H | H | H | H | H | 5-CF₃-isoxazol-4-yl | 1 |
| D-5431 | H | H | H | H | H | 5-OMe-isoxazol-4-yl | 1 |
| D-5432 | H | H | H | H | H | isoxazo-5-yl | 1 |
| D-5433 | H | H | H | H | H | 4-F-isoxazol-5-yl | 1 |
| D-5434 | H | H | H | H | H | 4-Me-isoxazol-5-yl | 1 |
| D-5435 | H | H | H | H | H | 4-CF₃-isoxazol-5-yl | 1 |
| D-5436 | H | H | H | H | H | 4-OMe-isoxazol-5-yl | 1 |
| D-5437 | H | H | H | H | H | 1H-1,2,3-triazol-1-yl | 1 |
| D-5438 | H | H | H | H | H | 5-F-1H-1,2,3-triazol-1-yl | 1 |
| D-5439 | H | H | H | H | H | 5-Me-1H-1,2,3-triazol-1-yl | 1 |
| D-5440 | H | H | H | H | H | 5-CF₃-1H-1,2,3-triazol-1-yl | 1 |
| D-5441 | H | H | H | H | H | 5-OMe-1H-1,2,3-triazol-1-yl | 1 |
| D-5442 | H | H | H | H | H | 1H-1,2,3-triazol-4-yl | 1 |
| D-5443 | H | H | H | H | H | 5-F-1H-1,2,3-triazol-4-yl | 1 |
| D-5444 | H | H | H | H | H | 5-Me-1H-1,2,3-triazol-4-yl | 1 |
| D-5445 | H | H | H | H | H | 5-CF₃-1H-1,2,3-triazol-4-yl | 1 |
| D-5446 | H | H | H | H | H | 5-OMe-1H-1,2,3-triazol-4-yl | 1 |
| D-5447 | H | H | H | H | H | 1H-1,2,3-triazol-5-yl | 1 |
| D-5448 | H | H | H | H | H | 4-F-1H-1,2,3-triazol-5-yl | 1 |
| D-5449 | H | H | H | H | H | 4-Me-1H-1,2,3-triazol-5-yl | 1 |
| D-5450 | H | H | H | H | H | 4-CF₃-1H-1,2,3-triazol-5-yl | 1 |
| D-5451 | H | H | H | H | H | 4-OMe-1H-1,2,3-triazol-5-yl | 1 |

TABLE 254

| compound | R¹ | R² | R³ | R⁴ | R⁵ | Q' | p |
|---|---|---|---|---|---|---|---|
| D-5452 | H | H | H | H | H | 1H-1,2,4-triazol-1-yl | 1 |
| D-5453 | H | H | H | H | H | 5-Me-1H-1,2,4-triazol-1-yl | 1 |
| D-5454 | H | H | H | H | H | 5-F-1H-1,2,4-triazol-1-yl | 1 |
| D-5455 | H | H | H | H | H | 5-CF₃-1H-1,2,4-triazol-1-yl | 1 |
| D-5456 | H | H | H | H | H | 5-OMe-1H-1,2,4-triazol-1-yl | 1 |
| D-5457 | H | H | H | H | H | 1H-1,2,4-triazol-3-yl | 1 |
| D-5458 | H | H | H | H | H | 1-Me-1H-1,2,4-triazol-3-yl | 1 |
| D-5459 | H | H | H | H | H | 1H-1,2,4-triazol-5-yl | 1 |
| D-5460 | H | H | H | H | H | 1-Me-1H-1,2,4-triazol-5-yl | 1 |
| D-5461 | H | H | H | H | H | 3,5-(Me)₂-isoxazol-4-yl | 1 |
| D-5462 | H | H | H | H | H | 3,5-(Et)₂-isoxazol-4-yl | 1 |
| D-5463 | H | H | H | H | H | 1,3,5-(Me)₃-1H-pyrazol-4-yl | 1 |
| D-5464 | H | H | H | H | H | quinolin-4-yl | 1 |
| D-5465 | H | H | H | H | H | isoquinolin-4-yl | 1 |
| D-5466 | H | H | H | H | H | 3,6-(OMe)₂-pyridazin-4-yl | 1 |
| D-5467 | H | H | H | H | H | 2,4-(OMe)₂-pyrmidin-5-yl | 1 |

TABLE 255

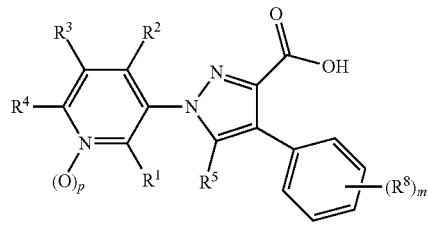

| compound | R¹ | R² | R³ | R⁴ | R⁵ | (R⁸)ₙ | p |
|---|---|---|---|---|---|---|---|
| E-0001 | H | H | H | H | H | H | 0 |
| E-0002 | H | H | H | H | H | 2-F | 0 |
| E-0003 | H | H | H | H | H | 3-F | 0 |
| E-0004 | H | H | H | H | H | 4-F | 0 |
| E-0005 | H | H | H | H | H | 2-Cl | 0 |
| E-0006 | H | H | H | H | H | 3-Cl | 0 |
| E-0007 | H | H | H | H | H | 4-Cl | 0 |
| E-0008 | H | H | H | H | H | 2-Br | 0 |
| E-0009 | H | H | H | H | H | 3-Br | 0 |
| E-0010 | H | H | H | H | H | 4-Br | 0 |
| E-0011 | H | H | H | H | H | 2-I | 0 |
| E-0012 | H | H | H | H | H | 3-I | 0 |
| E-0013 | H | H | H | H | H | 4-I | 0 |
| E-0014 | H | H | H | H | H | 2-OH | 0 |
| E-0015 | H | H | H | H | H | 3-OH | 0 |
| E-0016 | H | H | H | H | H | 4-OH | 0 |
| E-0017 | H | H | H | H | H | 2-SH | 0 |
| E-0018 | H | H | H | H | H | 3-SH | 0 |
| E-0019 | H | H | H | H | H | 4-SH | 0 |
| E-0020 | H | H | H | H | H | 2-Me | 0 |
| E-0021 | H | H | H | H | H | 3-Me | 0 |
| E-0022 | H | H | H | H | H | 4-Me | 0 |
| E-0023 | H | H | H | H | H | 2-Et | 0 |
| E-0024 | H | H | H | H | H | 3-Et | 0 |
| E-0025 | H | H | H | H | H | 4-Et | 0 |
| E-0026 | H | H | H | H | H | 2-Pr | 0 |
| E-0027 | H | H | H | H | H | 3-Pr | 0 |
| E-0028 | H | H | H | H | H | 4-Pr | 0 |
| E-0029 | H | H | H | H | H | 2-i-Pr | 0 |
| E-0030 | H | H | H | H | H | 3-i-Pr | 0 |
| E-0031 | H | H | H | H | H | 4-i-Pr | 0 |
| E-0032 | H | H | H | H | H | 2-Bu | 0 |
| E-0033 | H | H | H | H | H | 3-Bu | 0 |
| E-0034 | H | H | H | H | H | 4-Bu | 0 |
| E-0035 | H | H | H | H | H | 2-s-Bu | 0 |
| E-0036 | H | H | H | H | H | 3-s-Bu | 0 |
| E-0037 | H | H | H | H | H | 4-s-Bu | 0 |
| E-0038 | H | H | H | H | H | 2-i-Bu | 0 |
| E-0039 | H | H | H | H | H | 3-i-Bu | 0 |
| E-0040 | H | H | H | H | H | 4-i-Bu | 0 |
| E-0041 | H | H | H | H | H | 2-t-Bu | 0 |
| E-0042 | H | H | H | H | H | 3-t-Bu | 0 |
| E-0043 | H | H | H | H | H | 4-t-Bu | 0 |
| E-0044 | H | H | H | H | H | 2-CF₃ | 0 |
| E-0045 | H | H | H | H | H | 3-CF₃ | 0 |
| E-0046 | H | H | H | H | H | 4-CF₃ | 0 |
| E-0047 | H | H | H | H | H | 2-CHF₂ | 0 |
| E-0048 | H | H | H | H | H | 3-CHF₂ | 0 |
| E-0049 | H | H | H | H | H | 4-CHF₂ | 0 |
| E-0050 | H | H | H | H | H | 2-CH₂F | 0 |
| E-0051 | H | H | H | H | H | 3-CH₂F | 0 |
| E-0052 | H | H | H | H | H | 4-CH₂F | 0 |

TABLE 256

| compound | R¹ | R² | R³ | R⁴ | R⁵ | (R⁸)ₘ | p |
|---|---|---|---|---|---|---|---|
| E-0053 | H | H | H | H | H | 2-CF₂Cl | 0 |
| E-0054 | H | H | H | H | H | 3-CF₂Cl | 0 |
| E-0055 | H | H | H | H | H | 4-CF₂Cl | 0 |
| E-0056 | H | H | H | H | H | 2-CF(CF₃)₂ | 0 |
| E-0057 | H | H | H | H | H | 3-CF(CF₃)₂ | 0 |
| E-0058 | H | H | H | H | H | 4-CF(CF₃)₂ | 0 |
| E-0059 | H | H | H | H | H | 2-cyclopropyl | 0 |

TABLE 256-continued

| compound | R¹ | R² | R³ | R⁴ | R⁵ | (R⁸)ₘ | p |
|---|---|---|---|---|---|---|---|
| E-0060 | H | H | H | H | H | 3-cyclopropyl | 0 |
| E-0061 | H | H | H | H | H | 4-cyclopropyl | 0 |
| E-0062 | H | H | H | H | H | 2-cyclobutyl | 0 |
| E-0063 | H | H | H | H | H | 3-cyclobutyl | 0 |
| E-0064 | H | H | H | H | H | 4-cyclobutyl | 0 |
| E-0065 | H | H | H | H | H | 2-cyclopentyl | 0 |
| E-0066 | H | H | H | H | H | 3-cyclopentyl | 0 |
| E-0067 | H | H | H | H | H | 4-cyclopentyl | 0 |
| E-0068 | H | H | H | H | H | 2-(cyclopropylmethyl) | 0 |
| E-0069 | H | H | H | H | H | 3-(cyclopropylmethyl) | 0 |
| E-0070 | H | H | H | H | H | 4-(cyclopropylmethyl) | 0 |
| E-0071 | H | H | H | H | H | 2-(cyclobutylmethyl) | 0 |
| E-0072 | H | H | H | H | H | 3-(cyclobutylmethyl) | 0 |
| E-0073 | H | H | H | H | H | 4-(cyclobutylmethyl) | 0 |
| E-0074 | H | H | H | H | H | 2-(cyclopentylmethyl) | 0 |
| E-0075 | H | H | H | H | H | 3-(cyclopentylmethyl) | 0 |
| E-0076 | H | H | H | H | H | 4-(cyclopentylmethyl) | 0 |
| E-0077 | H | H | H | H | H | 2-(cyclopropylethyl) | 0 |
| E-0078 | H | H | H | H | H | 3-(cyclopropylethyl) | 0 |
| E-0079 | H | H | H | H | H | 4-(cyclopropylethyl) | 0 |
| E-0080 | H | H | H | H | H | 2-(2,2-difluorocyclopropyl) | 0 |
| E-0081 | H | H | H | H | H | 3-(2,2-difluorocyclopropyl) | 0 |
| E-0082 | H | H | H | H | H | 4-(2,2-difluorocyclopropyl) | 0 |
| E-0083 | H | H | H | H | H | 2-(2,2-dichlorocyclopropyl) | 0 |
| E-0084 | H | H | H | H | H | 3-(2,2-dichlorocyclopropyl) | 0 |
| E-0085 | H | H | H | H | H | 4-(2,2-dichlorocyclopropyl) | 0 |
| E-0086 | H | H | H | H | H | 2-ethenyl | 0 |
| E-0087 | H | H | H | H | H | 3-ethenyl | 0 |
| E-0088 | H | H | H | H | H | 4-ethenyl | 0 |
| E-0089 | H | H | H | H | H | 2-allyl | 0 |
| E-0090 | H | H | H | H | H | 3-allyl | 0 |
| E-0091 | H | H | H | H | H | 4-allyl | 0 |
| E-0092 | H | H | H | H | H | 2-(prop-1-en-1-yl) | 0 |
| E-0093 | H | H | H | H | H | 3-(prop-1-en-1-yl) | 0 |
| E-0094 | H | H | H | H | H | 4-(prop-1-en-1-yl) | 0 |
| E-0095 | H | H | H | H | H | 2-(trifluoroethenyl) | 0 |
| E-0096 | H | H | H | H | H | 3-(trifluoroethenyl) | 0 |
| E-0097 | H | H | H | H | H | 4-(trifluoroethenyl) | 0 |
| E-0098 | H | H | H | H | H | 2-(2,2-dichloroethenyl) | 0 |
| E-0099 | H | H | H | H | H | 3-(2,2-dichloroethenyl) | 0 |
| E-0100 | H | H | H | H | H | 4-(2,2-dichloroethenyl) | 0 |
| E-0101 | H | H | H | H | H | 2-ethynyl | 0 |
| E-0102 | H | H | H | H | H | 3-ethynyl | 0 |
| E-0103 | H | H | H | H | H | 4-ethynyl | 0 |
| E-0104 | H | H | H | H | H | 2-(1-propyn-1-yl) | 0 |
| E-0105 | H | H | H | H | H | 3-(1-propyn-1-yl) | 0 |
| E-0106 | H | H | H | H | H | 4-(1-propyn-1-yl) | 0 |
| E-0107 | H | H | H | H | H | 2-(2-propyn-1-yl) | 0 |
| E-0108 | H | H | H | H | H | 3-(2-propyn-1-yl) | 0 |
| E-0109 | H | H | H | H | H | 4-(2-propyn-1-yl) | 0 |

TABLE 257

| compound | R¹ | R² | R³ | R⁴ | R⁵ | (R⁸)ₘ | p |
|---|---|---|---|---|---|---|---|
| E-0110 | H | H | H | H | H | 2-(2-cyclopropylethynyl) | 0 |
| E-0111 | H | H | H | H | H | 3-(2-cyclopropylethynyl) | 0 |
| E-0112 | H | H | H | H | H | 4-(2-cyclopropylethynyl) | 0 |
| E-0113 | H | H | H | H | H | 2-(2-chloroethynyl) | 0 |
| E-0114 | H | H | H | H | H | 3-(2-chloroethynyl) | 0 |
| E-0115 | H | H | H | H | H | 4-(2-chloroethynyl) | 0 |
| E-0116 | H | H | H | H | H | 2-(2-bromoethynyl) | 0 |
| E-0117 | H | H | H | H | H | 3-(2-bromoethynyl) | 0 |
| E-0118 | H | H | H | H | H | 4-(2-bromoethynyl) | 0 |
| E-0119 | H | H | H | H | H | 2-OMe | 0 |
| E-0120 | H | H | H | H | H | 3-OMe | 0 |
| E-0121 | H | H | H | H | H | 4-OMe | 0 |
| E-0122 | H | H | H | H | H | 2-OEt | 0 |
| E-0123 | H | H | H | H | H | 3-OEt | 0 |
| E-0124 | H | H | H | H | H | 4-OEt | 0 |
| E-0125 | H | H | H | H | H | 2-OPr | 0 |
| E-0126 | H | H | H | H | H | 3-OPr | 0 |
| E-0127 | H | H | H | H | H | 4-OPr | 0 |
| E-0128 | H | H | H | H | H | 2-O(i-Pr) | 0 |
| E-0129 | H | H | H | H | H | 3-O(i-Pr) | 0 |
| E-0130 | H | H | H | H | H | 4-O(i-Pr) | 0 |
| E-0131 | H | H | H | H | H | 2-OBu | 0 |
| E-0132 | H | H | H | H | H | 3-OBu | 0 |
| E-0133 | H | H | H | H | H | 4-OBu | 0 |
| E-0134 | H | H | H | H | H | 2-O(s-Bu) | 0 |
| E-0135 | H | H | H | H | H | 3-O(s-Bu) | 0 |
| E-0136 | H | H | H | H | H | 4-O(s-Bu) | 0 |
| E-0137 | H | H | H | H | H | 2-O(i-Bu) | 0 |
| E-0138 | H | H | H | H | H | 3-O(i-Bu) | 0 |
| E-0139 | H | H | H | H | H | 4-O(i-Bu) | 0 |
| E-0140 | H | H | H | H | H | 2-O(t-Bu) | 0 |
| E-0141 | H | H | H | H | H | 3-O(t-Bu) | 0 |
| E-0142 | H | H | H | H | H | 4-O(t-Bu) | 0 |
| E-0143 | H | H | H | H | H | 2-OCF$_3$ | 0 |
| E-0144 | H | H | H | H | H | 3-OCF$_3$ | 0 |
| E-0145 | H | H | H | H | H | 4-OCF$_3$ | 0 |
| E-0146 | H | H | H | H | H | 2-OCHF$_2$ | 0 |
| E-0147 | H | H | H | H | H | 3-OCHF$_2$ | 0 |
| E-0148 | H | H | H | H | H | 4-OCHF$_2$ | 0 |
| E-0149 | H | H | H | H | H | 2-OCH$_2$CF$_3$ | 0 |
| E-0150 | H | H | H | H | H | 3-OCH$_2$CF$_3$ | 0 |
| E-0151 | H | H | H | H | H | 4-OCH$_2$CF$_3$ | 0 |
| E-0152 | H | H | H | H | H | 2-(cyclopropyloxy) | 0 |
| E-0153 | H | H | H | H | H | 3-(cyclopropyloxy) | 0 |
| E-0154 | H | H | H | H | H | 4-(cyclopropyloxy) | 0 |
| E-0155 | H | H | H | H | H | 2-(cyclobutyloxy) | 0 |
| E-0156 | H | H | H | H | H | 3-(cyclobutyloxy) | 0 |
| E-0157 | H | H | H | H | H | 4-(cyclobutyloxy) | 0 |
| E-0158 | H | H | H | H | H | 2-(cyclopentyloxy) | 0 |
| E-0159 | H | H | H | H | H | 3-(cyclopentyloxy) | 0 |
| E-0160 | H | H | H | H | H | 4-(cyclopentyloxy) | 0 |
| E-0161 | H | H | H | H | H | 2-((2,2-dichlorocyclopropyl)oxy) | 0 |
| E-0162 | H | H | H | H | H | 3-((2,2-dichlorocyclopropyl)oxy) | 0 |
| E-0163 | H | H | H | H | H | 4-((2,2-dichlorocyclopropyl)oxy) | 0 |
| E-0164 | H | H | H | H | H | 2-(cyclopropylmethoxy) | 0 |
| E-0165 | H | H | H | H | H | 3-(cyclopropylmethoxy) | 0 |
| E-0166 | H | H | H | H | H | 4-(cyclopropylmethoxy) | 0 |

TABLE 258

| compound | R¹ | R² | R³ | R⁴ | R⁵ | (R⁸)ₘ | p |
|---|---|---|---|---|---|---|---|
| E-0167 | H | H | H | H | H | 2-((2,2-difluorocyclopropyl)methoxy) | 0 |
| E-0168 | H | H | H | H | H | 3-((2,2-difluorocyclopropyl)methoxy) | 0 |
| E-0169 | H | H | H | H | H | 4-((2,2-difluorocyclopropyl)methoxy) | 0 |
| E-0170 | H | H | H | H | H | 2-(oxiran-2-yl) | 0 |
| E-0171 | H | H | H | H | H | 3-(oxiran-2-yl) | 0 |
| E-0172 | H | H | H | H | H | 4-(oxiran-2-yl) | 0 |
| E-0173 | H | H | H | H | H | 2-(oxiran-2-ylmethyl) | 0 |
| E-0174 | H | H | H | H | H | 3-(oxiran-2-ylmethyl) | 0 |
| E-0175 | H | H | H | H | H | 4-(oxiran-2-ylmethyl) | 0 |
| E-0176 | H | H | H | H | H | 2-SMe | 0 |
| E-0177 | H | H | H | H | H | 3-SMe | 0 |
| E-0178 | H | H | H | H | H | 4-SMe | 0 |
| E-0179 | H | H | H | H | H | 2-SEt | 0 |

TABLE 258-continued

| compound | R¹ | R² | R³ | R⁴ | R⁵ | (R⁸)ₘ | p |
|---|---|---|---|---|---|---|---|
| E-0180 | H | H | H | H | H | 3-SEt | 0 |
| E-0181 | H | H | H | H | H | 4-SEt | 0 |
| E-0182 | H | H | H | H | H | 2-S(=O)Me | 0 |
| E-0183 | H | H | H | H | H | 3-S(=O)Me | 0 |
| E-0184 | H | H | H | H | H | 4-S(=O)Me | 0 |
| E-0185 | H | H | H | H | H | 2-S(=O)₂Me | 0 |
| E-0186 | H | H | H | H | H | 3-S(=O)₂Me | 0 |
| E-0187 | H | H | H | H | H | 4-S(=O)₂Me | 0 |
| E-0188 | H | H | H | H | H | 2-SCF₃ | 0 |
| E-0189 | H | H | H | H | H | 3-SCF₃ | 0 |
| E-0190 | H | H | H | H | H | 4-SCF₃ | 0 |
| E-0191 | H | H | H | H | H | 2-S(=O)CF₃ | 0 |
| E-0192 | H | H | H | H | H | 3-S(=O)CF₃ | 0 |
| E-0193 | H | H | H | H | H | 4-S(=O)CF₃ | 0 |
| E-0194 | H | H | H | H | H | 2-S(=O)₂CF₃ | 0 |
| E-0195 | H | H | H | H | H | 3-S(=O)₂CF₃ | 0 |
| E-0196 | H | H | H | H | H | 4-S(=O)₂CF₃ | 0 |
| E-0197 | H | H | H | H | H | 2-SCF(CF₃)₂ | 0 |
| E-0198 | H | H | H | H | H | 3-SCF(CF₃)₂ | 0 |
| E-0199 | H | H | H | H | H | 4-SCF(CF₃)₂ | 0 |
| E-0200 | H | H | H | H | H | 2-(cyclopropylthio) | 0 |
| E-0201 | H | H | H | H | H | 3-(cyclopropylthio) | 0 |
| E-0202 | H | H | H | H | H | 4-(cyclopropylthio) | 0 |
| E-0203 | H | H | H | H | H | 2-(cyclopropylsulfinyl) | 0 |
| E-0204 | H | H | H | H | H | 3-(cyclopropylsulfinyl) | 0 |
| E-0205 | H | H | H | H | H | 4-(cyclopropylsulfinyl) | 0 |
| E-0206 | H | H | H | H | H | 2-(cyclopropylsulfonyl) | 0 |
| E-0207 | H | H | H | H | H | 3-(cyclopropylsulfonyl) | 0 |
| E-0208 | H | H | H | H | H | 4-(cyclopropylsulfonyl) | 0 |
| E-0209 | H | H | H | H | H | 2-((cyclopropylmethyl)thio) | 0 |
| E-0210 | H | H | H | H | H | 3-((cyclopropylmethyl)thio) | 0 |
| E-0211 | H | H | H | H | H | 4-((cyclopropylmethyl)thio) | 0 |
| E-0212 | H | H | H | H | H | 2-((cyclopropylmethyl)sulfinyl) | 0 |
| E-0213 | H | H | H | H | H | 3-((cyclopropylmethyl)sulfinyl) | 0 |
| E-0214 | H | H | H | H | H | 4-((cyclopropylmethyl)sulfinyl) | 0 |
| E-0215 | H | H | H | H | H | 2-((cyclopropylmethyl)sulfonyl) | 0 |
| E-0216 | H | H | H | H | H | 3-((cyclopropylmethyl)sulfonyl) | 0 |
| E-0217 | H | H | H | H | H | 4-((cyclopropylmethyl)sulfonyl) | 0 |
| E-0218 | H | H | H | H | H | 2-(((2,2-difluorocyclopropyl)methyl)thio) | 0 |
| E-0219 | H | H | H | H | H | 3-(((2,2-difluorocyclopropyl)methyl)thio) | 0 |
| E-0220 | H | H | H | H | H | 4-(((2,2-difluorocyclopropyl)methyl)thio) | 0 |
| E-0221 | H | H | H | H | H | 2-(((2,2-difluorocyclopropyl)methyl)sulfinyl) | 0 |
| E-0222 | H | H | H | H | H | 3-(((2,2-difluorocyclopropyl)methyl)sulfinyl) | 0 |
| E-0223 | H | H | H | H | H | 4-(((2,2-difluorocyclopropyl)methyl)sulfinyl) | 0 |

TABLE 259

| compound | R¹ | R² | R³ | R⁴ | R⁵ | (R⁸)ₘ | p |
|---|---|---|---|---|---|---|---|
| E-0224 | H | H | H | H | H | 2-(((2,2-difluorocyclopropyl)methyl)sulfonyl) | 0 |
| E-0225 | H | H | H | H | H | 3-(((2,2-difluorocyclopropyl)methyl)sulfonyl) | 0 |
| E-0226 | H | H | H | H | H | 4-(((2,2-difluorocyclopropyl)methyl)sulfonyl) | 0 |
| E-0227 | H | H | H | H | H | 2-C(=O)Me | 0 |
| E-0228 | H | H | H | H | H | 3-C(=O)Me | 0 |
| E-0229 | H | H | H | H | H | 4-C(=O)Me | 0 |
| E-0230 | H | H | H | H | H | 2-C(=O)Et | 0 |
| E-0231 | H | H | H | H | H | 3-C(=O)Et | 0 |
| E-0232 | H | H | H | H | H | 4-C(=O)Et | 0 |
| E-0233 | H | H | H | H | H | 2-C(=O)CF₃ | 0 |
| E-0234 | H | H | H | H | H | 3-C(=O)CF₃ | 0 |
| E-0235 | H | H | H | H | H | 4-C(=O)CF₃ | 0 |
| E-0236 | H | H | H | H | H | 2-C(=O)OMe | 0 |
| E-0237 | H | H | H | H | H | 3-C(=O)OMe | 0 |
| E-0238 | H | H | H | H | H | 4-C(=O)OMe | 0 |
| E-0239 | H | H | H | H | H | 2-C(=O)OEt | 0 |
| E-0240 | H | H | H | H | H | 3-C(=O)OEt | 0 |
| E-0241 | H | H | H | H | H | 4-C(=O)OEt | 0 |
| E-0242 | H | H | H | H | H | 2-C(=O)NH₂ | 0 |
| E-0243 | H | H | H | H | H | 3-C(=O)NH₂ | 0 |
| E-0244 | H | H | H | H | H | 4-C(=O)NH₂ | 0 |
| E-0245 | H | H | H | H | H | 2-C(=O)NHMe | 0 |
| E-0246 | H | H | H | H | H | 3-C(=O)NHMe | 0 |
| E-0247 | H | H | H | H | H | 4-C(=O)NHMe | 0 |
| E-0248 | H | H | H | H | H | 2-C(=O)NMe₂ | 0 |
| E-0249 | H | H | H | H | H | 3-C(=O)NMe₂ | 0 |

TABLE 259-continued

| compound | R¹ | R² | R³ | R⁴ | R⁵ | (R⁸)$_m$ | p |
|---|---|---|---|---|---|---|---|
| E-0250 | H | H | H | H | H | 4-C(=O)NMe$_2$ | 0 |
| E-0251 | H | H | H | H | H | 2-CH$_2$C(=O)CH$_3$ | 0 |
| E-0252 | H | H | H | H | H | 3-CH$_2$C(=O)CH$_3$ | 0 |
| E-0253 | H | H | H | H | H | 4-CH$_2$C(=O)CH$_3$ | 0 |
| E-0254 | H | H | H | H | H | 2-CH$_2$C(=O)CF$_3$ | 0 |
| E-0255 | H | H | H | H | H | 3-CH$_2$C(=O)CF$_3$ | 0 |
| E-0256 | H | H | H | H | H | 4-CH$_2$C(=O)CF$_3$ | 0 |
| E-0257 | H | H | H | H | H | 2-CH$_2$C(=O)OCH$_3$ | 0 |
| E-0258 | H | H | H | H | H | 3-CH$_2$C(=O)OCH$_3$ | 0 |
| E-0259 | H | H | H | H | H | 4-CH$_2$C(=O)OCH$_3$ | 0 |
| E-0260 | H | H | H | H | H | 2-CH$_2$OH | 0 |
| E-0261 | H | H | H | H | H | 3-CH$_2$OH | 0 |
| E-0262 | H | H | H | H | H | 4-CH$_2$OH | 0 |
| E-0263 | H | H | H | H | H | 2-CH$_2$OCH$_3$ | 0 |
| E-0264 | H | H | H | H | H | 3-CH$_2$OCH$_3$ | 0 |
| E-0265 | H | H | H | H | H | 4-CH$_2$OCH$_3$ | 0 |
| E-0266 | H | H | H | H | H | 2-CH$_2$OCH$_2$CH$_3$ | 0 |
| E-0267 | H | H | H | H | H | 3-CH$_2$OCH$_2$CH$_3$ | 0 |
| E-0268 | H | H | H | H | H | 4-CH$_2$OCH$_2$CH$_3$ | 0 |
| E-0269 | H | H | H | H | H | 2-CH(CH$_3$)OCH$_3$ | 0 |
| E-0270 | H | H | H | H | H | 3-CH(CH$_3$)OCH$_3$ | 0 |
| E-0271 | H | H | H | H | H | 4-CH(CH$_3$)OCH$_3$ | 0 |
| E-0272 | H | H | H | H | H | 2-CH$_2$CH$_2$OCH$_3$ | 0 |
| E-0273 | H | H | H | H | H | 3-CH$_2$CH$_2$OCH$_3$ | 0 |
| E-0274 | H | H | H | H | H | 4-CH$_2$CH$_2$OCH$_3$ | 0 |
| E-0275 | H | H | H | H | H | 2-CH$_2$OCF$_3$ | 0 |
| E-0276 | H | H | H | H | H | 3-CH$_2$OCF$_3$ | 0 |
| E-0277 | H | H | H | H | H | 4-CH$_2$OCF$_3$ | 0 |
| E-0278 | H | H | H | H | H | 2-CF$_2$OCH$_3$ | 0 |
| E-0279 | H | H | H | H | H | 3-CF$_2$OCH$_3$ | 0 |
| E-0280 | H | H | H | H | H | 4-CF$_2$OCH$_3$ | 0 |

TABLE 260

| compound | R¹ | R² | R³ | R⁴ | R⁵ | (R⁸)$_m$ | p |
|---|---|---|---|---|---|---|---|
| E-0281 | H | H | H | H | H | 2-CF$_2$CF$_2$OCF$_3$ | 0 |
| E-0282 | H | H | H | H | H | 3-CF$_2$CF$_2$OCF$_3$ | 0 |
| E-0283 | H | H | H | H | H | 4-CF$_2$CF$_2$OCF$_3$ | 0 |
| E-0284 | H | H | H | H | H | 2-OC(=O)CH$_3$ | 0 |
| E-0285 | H | H | H | H | H | 3-OC(=O)CH$_3$ | 0 |
| E-0286 | H | H | H | H | H | 4-OC(=O)CH$_3$ | 0 |
| E-0287 | H | H | H | H | H | 2-OC(=O)CF$_3$ | 0 |
| E-0288 | H | H | H | H | H | 3-OC(=O)CF$_3$ | 0 |
| E-0289 | H | H | H | H | H | 4-OC(=O)CF$_3$ | 0 |
| E-0290 | H | H | H | H | H | 2-OC(=O)NH$_2$ | 0 |
| E-0291 | H | H | H | H | H | 3-OC(=O)NH$_2$ | 0 |
| E-0292 | H | H | H | H | H | 4-OC(=O)NH$_2$ | 0 |
| E-0293 | H | H | H | H | H | 2-OC(=O)NHCH$_3$ | 0 |
| E-0294 | H | H | H | H | H | 3-OC(=O)NHCH$_3$ | 0 |
| E-0295 | H | H | H | H | H | 4-OC(=O)NHCH$_3$ | 0 |
| E-0296 | H | H | H | H | H | 2-OC(=O)N(CH$_3$)$_2$ | 0 |
| E-0297 | H | H | H | H | H | 3-OC(=O)N(CH$_3$)$_2$ | 0 |
| E-0298 | H | H | H | H | H | 4-OC(=O)N(CH$_3$)$_2$ | 0 |
| E-0299 | H | H | H | H | H | 2-CH$_2$OC(=O)NH$_2$ | 0 |
| E-0300 | H | H | H | H | H | 3-CH$_2$OC(=O)NH$_2$ | 0 |
| E-0301 | H | H | H | H | H | 4-CH$_2$OC(=O)NH$_2$ | 0 |
| E-0302 | H | H | H | H | H | 2-CH$_2$OC(=O)NHCH$_3$ | 0 |
| E-0303 | H | H | H | H | H | 3-CH$_2$OC(=O)NHCH$_3$ | 0 |
| E-0304 | H | H | H | H | H | 4-CH$_2$OC(=O)NHCH$_3$ | 0 |
| E-0305 | H | H | H | H | H | 2-CH$_2$OC(=O)N(CH$_3$)$_2$ | 0 |
| E-0306 | H | H | H | H | H | 3-CH$_2$OC(=O)N(CH$_3$)$_2$ | 0 |
| E-0307 | H | H | H | H | H | 4-CH$_2$OC(=O)N(CH$_3$)$_2$ | 0 |
| E-0308 | H | H | H | H | H | 2-OC(=O)OCH$_3$ | 0 |
| E-0309 | H | H | H | H | H | 3-OC(=O)OCH$_3$ | 0 |
| E-0310 | H | H | H | H | H | 4-OC(=O)OCH$_3$ | 0 |
| E-0311 | H | H | H | H | H | 2-CH$_2$OC(=O)OCH$_3$ | 0 |
| E-0312 | H | H | H | H | H | 3-CH$_2$OC(=O)OCH$_3$ | 0 |
| E-0313 | H | H | H | H | H | 4-CH$_2$OC(=O)OCH$_3$ | 0 |
| E-0314 | H | H | H | H | H | 2-CH$_2$OC(=O)CH$_3$ | 0 |
| E-0315 | H | H | H | H | H | 3-CH$_2$OC(=O)CH$_3$ | 0 |
| E-0316 | H | H | H | H | H | 4-CH$_2$OC(=O)CH$_3$ | 0 |
| E-0317 | H | H | H | H | H | 2-OS(=O)$_2$CH$_3$ | 0 |
| E-0318 | H | H | H | H | H | 3-OS(=O)$_2$CH$_3$ | 0 |
| E-0319 | H | H | H | H | H | 4-OS(=O)$_2$CH$_3$ | 0 |
| E-0320 | H | H | H | H | H | 2-CH$_2$SCH$_3$ | 0 |
| E-0321 | H | H | H | H | H | 3-CH$_2$SCH$_3$ | 0 |
| E-0322 | H | H | H | H | H | 4-CH$_2$SCH$_3$ | 0 |
| E-0323 | H | H | H | H | H | 2-CH$_2$S(=O)CH$_3$ | 0 |
| E-0324 | H | H | H | H | H | 3-CH$_2$S(=O)CH$_3$ | 0 |
| E-0325 | H | H | H | H | H | 4-CH$_2$S(=O)CH$_3$ | 0 |
| E-0326 | H | H | H | H | H | 2-CH$_2$S(=O)$_2$CH$_3$ | 0 |
| E-0327 | H | H | H | H | H | 3-CH$_2$S(=O)$_2$CH$_3$ | 0 |
| E-0328 | H | H | H | H | H | 4-CH$_2$S(=O)$_2$CH$_3$ | 0 |
| E-0329 | H | H | H | H | H | 2-CH$_2$SCF$_3$ | 0 |
| E-0330 | H | H | H | H | H | 3-CH$_2$SCF$_3$ | 0 |
| E-0331 | H | H | H | H | H | 4-CH$_2$SCF$_3$ | 0 |
| E-0332 | H | H | H | H | H | 2-CH$_2$S(=O)CF$_3$ | 0 |
| E-0333 | H | H | H | H | H | 3-CH$_2$S(=O)CF$_3$ | 0 |
| E-0334 | H | H | H | H | H | 4-CH$_2$S(=O)CF$_3$ | 0 |
| E-0335 | H | H | H | H | H | 2-CH$_2$S(=O)$_2$CF$_3$ | 0 |
| E-0336 | H | H | H | H | H | 3-CH$_2$S(=O)$_2$CF$_3$ | 0 |
| E-0337 | H | H | H | H | H | 4-CH$_2$S(=O)$_2$CF$_3$ | 0 |

TABLE 261

| compound | R¹ | R² | R³ | R⁴ | R⁵ | (R⁸)$_m$ | p |
|---|---|---|---|---|---|---|---|
| E-0338 | H | H | H | H | H | 2-phenyl | 0 |
| E-0339 | H | H | H | H | H | 3-phenyl | 0 |
| E-0340 | H | H | H | H | H | 4-phenyl | 0 |
| E-0341 | H | H | H | H | H | 2-(phenyloxy) | 0 |
| E-0342 | H | H | H | H | H | 3-(phenyloxy) | 0 |
| E-0343 | H | H | H | H | H | 4-(phenyloxy) | 0 |
| E-0344 | H | H | H | H | H | 2-benzyl | 0 |
| E-0345 | H | H | H | H | H | 3-benzyl | 0 |
| E-0346 | H | H | H | H | H | 4-benzyl | 0 |
| E-0347 | H | H | H | H | H | 2-(benzyloxy) | 0 |
| E-0348 | H | H | H | H | H | 3-(benzyloxy) | 0 |
| E-0349 | H | H | H | H | H | 4-(benzyloxy) | 0 |
| E-0350 | H | H | H | H | H | 2-((2-fluorobenzyl)oxy) | 0 |
| E-0351 | H | H | H | H | H | 3-((2-fluorobenzyl)oxy) | 0 |

TABLE 261-continued

| compound | R¹ | R² | R³ | R⁴ | R⁵ | (R⁸)ₘ | p |
|---|---|---|---|---|---|---|---|
| E-0352 | H | H | H | H | H | 4-((2-fluorobenzyl)oxy) | 0 |
| E-0353 | H | H | H | H | H | 2-((3-fluorobenzyl)oxy) | 0 |
| E-0354 | H | H | H | H | H | 3-((3-fluorobenzyl)oxy) | 0 |
| E-0355 | H | H | H | H | H | 4-((3-fluorobenzyl)oxy) | 0 |
| E-0356 | H | H | H | H | H | 2-((4-fluorobenzyl)oxy) | 0 |
| E-0357 | H | H | H | H | H | 3-((4-fluorobenzyl)oxy) | 0 |
| E-0358 | H | H | H | H | H | 4-((4-fluorobenzyl)oxy) | 0 |
| E-0359 | H | H | H | H | H | 2-((2-chlorobenzyl)oxy) | 0 |
| E-0360 | H | H | H | H | H | 3-((2-chlorobenzyl)oxy) | 0 |
| E-0361 | H | H | H | H | H | 4-((2-chlorobenzyl)oxy) | 0 |
| E-0362 | H | H | H | H | H | 2-((3-chlorobenzyl)oxy) | 0 |
| E-0363 | H | H | H | H | H | 3-((3-chlorobenzyl)oxy) | 0 |
| E-0364 | H | H | H | H | H | 4-((3-chlorobenzyl)oxy) | 0 |
| E-0365 | H | H | H | H | H | 2-((4-chlorobenzyl)oxy) | 0 |
| E-0366 | H | H | H | H | H | 3-((4-chlorobenzyl)oxy) | 0 |
| E-0367 | H | H | H | H | H | 4-((4-chlorobenzyl)oxy) | 0 |
| E-0368 | H | H | H | H | H | 2-((2-methybenzyl)oxy) | 0 |
| E-0369 | H | H | H | H | H | 3-((2-methybenzyl)oxy) | 0 |
| E-0370 | H | H | H | H | H | 4-((2-methybenzyl)oxy) | 0 |
| E-0371 | H | H | H | H | H | 2-((3-methybenzyl)oxy) | 0 |
| E-0372 | H | H | H | H | H | 3-((3-methybenzyl)oxy) | 0 |
| E-0373 | H | H | H | H | H | 4-((3-methybenzyl)oxy) | 0 |
| E-0374 | H | H | H | H | H | 2-((4-methybenzyl)oxy) | 0 |
| E-0375 | H | H | H | H | H | 3-((4-methybenzyl)oxy) | 0 |
| E-0376 | H | H | H | H | H | 4-((4-methybenzyl)oxy) | 0 |
| E-0377 | H | H | H | H | H | 2-((2-(trifluoromethyl)benzyl)oxy) | 0 |
| E-0378 | H | H | H | H | H | 3-((2-(trifluoromethyl)benzyl)oxy) | 0 |
| E-0379 | H | H | H | H | H | 4-((2-(trifluoromethyl)benzyl)oxy) | 0 |
| E-0380 | H | H | H | H | H | 2-((3-(trifluoromethyl)benzyl)oxy) | 0 |
| E-0381 | H | H | H | H | H | 3-((3-(trifluoromethyl)benzyl)oxy) | 0 |
| E-0382 | H | H | H | H | H | 4-((3-(trifluoromethyl)benzyl)oxy) | 0 |
| E-0383 | H | H | H | H | H | 2-((4-(trifluoromethyl)benzyl)oxy) | 0 |
| E-0384 | H | H | H | H | H | 3-((4-(trifluoromethyl)benzyl)oxy) | 0 |
| E-0385 | H | H | H | H | H | 4-((4-(trifluoromethyl)benzyl)oxy) | 0 |
| E-0386 | H | H | H | H | H | 2-((2-methoxybenzyl)oxy) | 0 |
| E-0387 | H | H | H | H | H | 3-((2-methoxybenzyl)oxy) | 0 |
| E-0388 | H | H | H | H | H | 4-((2-methoxybenzyl)oxy) | 0 |
| E-0389 | H | H | H | H | H | 2-((3-methoxybenzyl)oxy) | 0 |
| E-0390 | H | H | H | H | H | 3-((3-methoxybenzyl)oxy) | 0 |
| E-0391 | H | H | H | H | H | 4-((3-methoxybenzyl)oxy) | 0 |
| E-0392 | H | H | H | H | H | 2-((4-methoxybenzyl)oxy) | 0 |
| E-0393 | H | H | H | H | H | 3-((4-methoxybenzyl)oxy) | 0 |
| E-0394 | H | H | H | H | H | 4-((4-methoxybenzyl)oxy) | 0 |

TABLE 262

| compound | R¹ | R² | R³ | R⁴ | R⁵ | (R⁸)ₘ | p |
|---|---|---|---|---|---|---|---|
| E-0395 | H | H | H | H | H | 2-((2-(trifluoromethoxy)benzyl)oxy) | 0 |
| E-0396 | H | H | H | H | H | 3-((2-(trifluoromethoxy)benzyl)oxy) | 0 |
| E-0397 | H | H | H | H | H | 4-((2-(trifluoromethoxy)benzyl)oxy) | 0 |
| E-0398 | H | H | H | H | H | 2-((3-(trifluoromethoxy)benzyl)oxy) | 0 |
| E-0399 | H | H | H | H | H | 3-((3-(trifluoromethoxy)benzyl)oxy) | 0 |
| E-0400 | H | H | H | H | H | 4-((3-(trifluoromethoxy)benzyl)oxy) | 0 |
| E-0401 | H | H | H | H | H | 2-((4-(trifluoromethoxy)benzyl)oxy) | 0 |
| E-0402 | H | H | H | H | H | 3-((4-(trifluoromethoxy)benzyl)oxy) | 0 |
| E-0403 | H | H | H | H | H | 4-((4-(trifluoromethoxy)benzyl)oxy) | 0 |
| E-0404 | H | H | H | H | H | 2-((2-(methylthio)benzyl)oxy) | 0 |
| E-0405 | H | H | H | H | H | 3-((2-(methylthio)benzyl)oxy) | 0 |
| E-0406 | H | H | H | H | H | 4-((2-(methylthio)benzyl)oxy) | 0 |
| E-0407 | H | H | H | H | H | 2-((3-(methylthio)benzyl)oxy) | 0 |
| E-0408 | H | H | H | H | H | 3-((3-(methylthio)benzyl)oxy) | 0 |
| E-0409 | H | H | H | H | H | 4-((3-(methylthio)benzyl)oxy) | 0 |
| E-0410 | H | H | H | H | H | 2-((4-(methylthio)benzyl)oxy) | 0 |
| E-0411 | H | H | H | H | H | 3-((4-(methylthio)benzyl)oxy) | 0 |
| E-0412 | H | H | H | H | H | 4-((4-(methylthio)benzyl)oxy) | 0 |
| E-0413 | H | H | H | H | H | 2-((2-(methylsulfinyl)benzyl)oxy) | 0 |
| E-0414 | H | H | H | H | H | 3-((2-(methylsulfiny)benzyl)oxy) | 0 |
| E-0415 | H | H | H | H | H | 4-((2-(methylsuffiny)benzyl)oxy) | 0 |
| E-0416 | H | H | H | H | H | 2-((3-(methylsulfinyl)benzyl)oxy) | 0 |
| E-0417 | H | H | H | H | H | 3-((3-(methylsuffinyl)benzyl)oxy) | 0 |
| E-0418 | H | H | H | H | H | 4-((3-(methylsulfinyl)benzyl)oxy) | 0 |
| E-0419 | H | H | H | H | H | 2-((4-(methylsulfinyl)benzyl)oxy) | 0 |
| E-0420 | H | H | H | H | H | 3-((4-(methylsuffinyl)benzyl)oxy) | 0 |
| E-0421 | H | H | H | H | H | 4-((4-(methylsulfinyl)benzyl)oxy) | 0 |
| E-0422 | H | H | H | H | H | 2-((2-(methylsulfonyl)benzyl)oxy) | 0 |
| E-0423 | H | H | H | H | H | 3-((2-(methylsulfonyl)benzyl)oxy) | 0 |
| E-0424 | H | H | H | H | H | 4-((2-(methylsulfonyl)benzyl)oxy) | 0 |
| E-0425 | H | H | H | H | H | 2-((3-(methylsulfonyl)benzyl)oxy) | 0 |
| E-0426 | H | H | H | H | H | 3-((3-(methylsulfonyl)benzyl)oxy) | 0 |
| E-0427 | H | H | H | H | H | 4-((3-(methylsulfonyl)benzyl)oxy) | 0 |
| E-0428 | H | H | H | H | H | 2-((4-(methylsulfonyl)benzyl)oxy) | 0 |
| E-0429 | H | H | H | H | H | 3-((4-(methylsuffinyl)benzyl)oxy) | 0 |
| E-0430 | H | H | H | H | H | 4-((4-(methylsulfonyl)benzyl)oxy) | 0 |
| E-0431 | H | H | H | H | H | 2-((2-(trifluoromethylthio)benzyl)oxy) | 0 |
| E-0432 | H | H | H | H | H | 3-((2-(trifluoromethylthio)benzyl)oxy) | 0 |
| E-0433 | H | H | H | H | H | 4-((2-(trifluoromethylthio)benzyl)oxy) | 0 |
| E-0434 | H | H | H | H | H | 2-((3-(trifluoromethylthio)benzyl)oxy) | 0 |
| E-0435 | H | H | H | H | H | 3-((3-(trifluoromethylthio)benzyl)oxy) | 0 |
| E-0436 | H | H | H | H | H | 4-((3-(trifluoromethylthio)benzyl)oxy) | 0 |
| E-0437 | H | H | H | H | H | 2-((4-(trifluoromethylthio)benzyl)oxy) | 0 |
| E-0438 | H | H | H | H | H | 3-((4-(trifluoromethylthio)benzyl)oxy) | 0 |
| E-0439 | H | H | H | H | H | 4-((4-(trifluoromethylthio)benzyl)oxy) | 0 |
| E-0440 | H | H | H | H | H | 2-((2-(trifluoromethylsulfinyl)benzyl)oxy) | 0 |
| E-0441 | H | H | H | H | H | 3-((2-(trifluoromethylsulfinyl)benzyl)oxy) | 0 |
| E-0442 | H | H | H | H | H | 4-((2-(trifluoromethylsulfinyl)benzyl)oxy) | 0 |
| E-0443 | H | H | H | H | H | 2-((3-(trifluoromethylsulfinyl)benzyl)oxy) | 0 |

TABLE 262-continued

| compound | R¹ | R² | R³ | R⁴ | R⁵ | (R⁸)ₘ | p |
|---|---|---|---|---|---|---|---|
| E-0444 | H | H | H | H | H | 3-((3-(trifuoromethylsulfinyl)benzyl)oxy) | 0 |
| E-0445 | H | H | H | H | H | 4-((3-(trifuoromethylsulfinyl)benzyl)oxy) | 0 |
| E-0446 | H | H | H | H | H | 2-((4-(trifuoromethylsulfinyl)benzyl)oxy) | 0 |
| E-0447 | H | H | H | H | H | 3-((4-(trifuoromethylsulfinyl)benzyl)oxy) | 0 |
| E-0448 | H | H | H | H | H | 4-((4-(trifuoromethylsulfinyl)benzyl)oxy) | 0 |
| E-0449 | H | H | H | H | H | 2-((2-(trifuoromethylsulfinyl)benzyl)oxy) | 0 |
| E-0450 | H | H | H | H | H | 3-((2-(trifuoromethylsulfinyl)benzyl)oxy) | 0 |
| E-0451 | H | H | H | H | H | 4-((2-(trifuoromethylsulfinyl)benzyl)oxy) | 0 |

TABLE 263

| compound | R¹ | R² | R³ | R⁴ | R⁵ | (R⁸)ₘ | p |
|---|---|---|---|---|---|---|---|
| E-0452 | H | H | H | H | H | 2-((3-(trifuoromethylsulfonyl)benzyl)oxy) | 0 |
| E-0453 | H | H | H | H | H | 3-((3-(trifuoromethylsulfonyl)benzyl)oxy) | 0 |
| E-0454 | H | H | H | H | H | 4-((3-(trifuoromethylsulfonyl)benzyl)oxy) | 0 |
| E-0455 | H | H | H | H | H | 2-((4-(trifuoromethylsulfonyl)benzyl)oxy) | 0 |
| E-0456 | H | H | H | H | H | 3-((4-(trifuoromethylsulfonyl)benzyl)oxy) | 0 |
| E-0457 | H | H | H | H | H | 4 -((4-(trifuoromethylsulfonyl)benzyl)oxy) | 0 |
| E-0458 | H | H | H | H | H | 2-((2-aminobenzyl)oxy) | 0 |
| E-0459 | H | H | H | H | H | 3-((2-aminobenzyl)oxy) | 0 |
| E-0460 | H | H | H | H | H | 4-((2-aminobenzyl)oxy) | 0 |
| E-0461 | H | H | H | H | H | 2-((3-aminobenzyl)oxy) | 0 |
| E-0462 | H | H | H | H | H | 3-((3-aminobenzyl)oxy) | 0 |
| E-0463 | H | H | H | H | H | 4-((3-aminobenzyl)oxy) | 0 |
| E-0464 | H | H | H | H | H | 2-((4-aminobenzyl)oxy) | 0 |
| E-0465 | H | H | H | H | H | 3-((4-aminobenzyl)oxy) | 0 |
| E-0466 | H | H | H | H | H | 4-((4-aminobenzyl)oxy) | 0 |
| E-0467 | H | H | H | H | H | 2-((2-(methylamino)benzyl)oxy) | 0 |
| E-0468 | H | H | H | H | H | 3-((2-(methylamino)benzyl)oxy) | 0 |
| E-0469 | H | H | H | H | H | 4-((2-(methylamino)benzyl)oxy) | 0 |
| E-0470 | H | H | H | H | H | 2-((3-(methylamino)benzyl)oxy) | 0 |
| E-0471 | H | H | H | H | H | 3-((3-(methylamino)benzyl)oxy) | 0 |
| E-0472 | H | H | H | H | H | 4-((3-(methylamino)benzyl)oxy) | 0 |
| E-0473 | H | H | H | H | H | 2-((4-(methylamino)benzyl)oxy) | 0 |
| E-0474 | H | H | H | H | H | 3-((4-(methylamino)benzyl)oxy) | 0 |
| E-0475 | H | H | H | H | H | 4-((4-(methylamino)benzyl)oxy) | 0 |
| E-0476 | H | H | H | H | H | 2-((2-(dimethylamino)benzyl)oxy) | 0 |
| E-0477 | H | H | H | H | H | 3-((2-(dimethylamino)benzyl)oxy) | 0 |
| E-0478 | H | H | H | H | H | 4-((2-(dimethylamino)benzyl)oxy) | 0 |
| E-0479 | H | H | H | H | H | 2-((3-(dimethylamino)benzyl)oxy) | 0 |
| E-0480 | H | H | H | H | H | 3-((3-(dimethylamino)benzyl)oxy) | 0 |
| E-0481 | H | H | H | H | H | 4-((3-(dimethylamino)benzyl)oxy) | 0 |
| E-0482 | H | H | H | H | H | 2-((4-(dimethylamino)benzyl)oxy) | 0 |
| E-0483 | H | H | H | H | H | 3-((4-(dimethylamino)benzyl)oxy) | 0 |
| E-0484 | H | H | H | H | H | 4-((4-(dimethylamino)benzyl)oxy) | 0 |
| E-0485 | H | H | H | H | H | 2-((2-cyanobenzyl)oxy) | 0 |
| E-0486 | H | H | H | H | H | 3-((2-cyanobenzyl)oxy) | 0 |
| E-0487 | H | H | H | H | H | 4-((2-cyanobenzyl)oxy) | 0 |
| E-0488 | H | H | H | H | H | 2-((3-cyanobenzyl)oxy) | 0 |
| E-0489 | H | H | H | H | H | 3-((3-cyanobenzyl)oxy) | 0 |
| E-0490 | H | H | H | H | H | 4-((3-cyanobenzyl)oxy) | 0 |
| E-0491 | H | H | H | H | H | 2-((4-cyanobenzyl)oxy) | 0 |
| E-0492 | H | H | H | H | H | 3-((4-cyanobenzyl)oxy) | 0 |
| E-0493 | H | H | H | H | H | 4-((4-cyanobenzyl)oxy) | 0 |
| E-0494 | H | H | H | H | H | 2-((2-nitrobenzyl)oxy) | 0 |
| E-0495 | H | H | H | H | H | 3-((2-nitrobenzyl)oxy) | 0 |
| E-0496 | H | H | H | H | H | 4-((2-nitrobenzyl)oxy) | 0 |
| E-0497 | H | H | H | H | H | 2-((3-nitrobenzyl)oxy) | 0 |
| E-0498 | H | H | H | H | H | 3-((3-nitrobenzyl)oxy) | 0 |
| E-0499 | H | H | H | H | H | 4-((3-nitrobenzyl)oxy) | 0 |
| E-0500 | H | H | H | H | H | 2-((4-nitrobenzyl)oxy) | 0 |
| E-0501 | H | H | H | H | H | 3-((4-nitrobenzyl)oxy) | 0 |
| E-0502 | H | H | H | H | H | 4-((4-nitrobenzyl)oxy) | 0 |
| E-0503 | H | H | H | H | H | 2-NH₂ | 0 |
| E-0504 | H | H | H | H | H | 3-NH₂ | 0 |
| E-0505 | H | H | H | H | H | 4-NH₂ | 0 |
| E-0506 | H | H | H | H | H | 2-NHMe | 0 |
| E-0507 | H | H | H | H | H | 3-NHMe | 0 |
| E-0508 | H | H | H | H | H | 4-NHMe | 0 |

TABLE 264

| compound | R$^1$ | R$^2$ | R$^3$ | R$^4$ | R$^5$ | (R$^8$)$_m$ | p |
|---|---|---|---|---|---|---|---|
| E-0509 | H | H | H | H | H | 2-NHEt | 0 |
| E-0510 | H | H | H | H | H | 3-NHEt | 0 |
| E-0511 | H | H | H | H | H | 4-NHEt | 0 |
| E-0512 | H | H | H | H | H | 2-N(Me)$_2$ | 0 |
| E-0513 | H | H | H | H | H | 3-N(Me)$_2$ | 0 |
| E-0514 | H | H | H | H | H | 4-N(Me)$_2$ | 0 |
| E-0515 | H | H | H | H | H | 2-N(Et)$_2$ | 0 |
| E-0516 | H | H | H | H | H | 3-N(Et)$_2$ | 0 |
| E-0517 | H | H | H | H | H | 4-N(Et)$_2$ | 0 |
| E-0518 | H | H | H | H | H | 2-CHO | 0 |
| E-0519 | H | H | H | H | H | 3-CHO | 0 |
| E-0520 | H | H | H | H | H | 4-CHO | 0 |
| E-0521 | H | H | H | H | H | 2-C(=O)OH | 0 |
| E-0522 | H | H | H | H | H | 3-C(=O)OH | 0 |
| E-0523 | H | H | H | H | H | 4-C(=O)OH | 0 |
| E-0524 | H | H | H | H | H | 2-(1,3-dioxolan-2-yl) | 0 |
| E-0525 | H | H | H | H | H | 3-(1,3-dioxolan-2-yl) | 0 |
| E-0526 | H | H | H | H | H | 4-(1,3-dioxolan-2-yl) | 0 |
| E-0527 | H | H | H | H | H | 2-(1,3-dioxolan-2-yl) | 0 |
| E-0528 | H | H | H | H | H | 3-(1,3-dioxolan-2-yl) | 0 |
| E-0529 | H | H | H | H | H | 4-(1,3-dioxolan-2-yl) | 0 |
| E-0530 | H | H | H | H | H | 2-(1H-imidazol-2-yl) | 0 |
| E-0531 | H | H | H | H | H | 3-(1H-imidazol-2-yl) | 0 |
| E-0532 | H | H | H | H | H | 4-(1H-imidazol-2-yl) | 0 |
| E-0533 | H | H | H | H | H | 2-(thiazol-2-yl) | 0 |
| E-0534 | H | H | H | H | H | 3-(thiazol-2-yl) | 0 |
| E-0535 | H | H | H | H | H | 4-(thiazol-2-yl) | 0 |
| E-0536 | H | H | H | H | H | 2-(oxazol-2-yl) | 0 |
| E-0537 | H | H | H | H | H | 3-(oxazol-2-yl) | 0 |
| E-0538 | H | H | H | H | H | 4-(oxazol-2-yl) | 0 |
| E-0539 | H | H | H | H | H | 2-CH=NOH | 0 |
| E-0540 | H | H | H | H | H | 3-CH=NOH | 0 |
| E-0541 | H | H | H | H | H | 4-CH=NOH | 0 |
| E-0542 | H | H | H | H | H | 2-CH=NOMe | 0 |
| E-0543 | H | H | H | H | H | 3-CH=NOMe | 0 |
| E-0544 | H | H | H | H | H | 4-CH=NOMe | 0 |
| E-0545 | H | H | H | H | H | 2-(4,5-d hydro-3-isoxazolyl) | 0 |
| E-0546 | H | H | H | H | H | 3-(4,5-d hydro-3-isoxazolyl) | 0 |
| E-0547 | H | H | H | H | H | 4-(4,5-d hydro-3-isoxazolyl) | 0 |
| E-0548 | H | H | H | H | H | 2-CN | 0 |
| E-0549 | H | H | H | H | H | 3-CN | 0 |
| E-0550 | H | H | H | H | H | 4-CN | 0 |
| E-0551 | H | H | H | H | H | 2-NO$_2$ | 0 |
| E-0552 | H | H | H | H | H | 3-NO$_2$ | 0 |
| E-0553 | H | H | H | H | H | 4-NO$_2$ | 0 |
| E-0554 | H | H | H | H | H | 2,3-F$_2$ | 0 |
| E-0555 | H | H | H | H | H | 2,4-F$_2$ | 0 |
| E-0556 | H | H | H | H | H | 2,5-F$_2$ | 0 |
| E-0557 | H | H | H | H | H | 2,6-F$_2$ | 0 |
| E-0558 | H | H | H | H | H | 3,4-F$_2$ | 0 |
| E-0559 | H | H | H | H | H | 3,5-F$_2$ | 0 |
| E-0560 | H | H | H | H | H | 2-F,3-Cl | 0 |
| E-0561 | H | H | H | H | H | 2-F,4-Cl | 0 |
| E-0562 | H | H | H | H | H | 2-F,5-Cl | 0 |
| E-0563 | H | H | H | H | H | 2-F,6-Cl | 0 |
| E-0564 | H | H | H | H | H | 3-F,2-Cl | 0 |
| E-0565 | H | H | H | H | H | 3-F,4-Cl | 0 |

TABLE 265

| compound | R$^1$ | R$^2$ | R$^3$ | R$^4$ | R$^5$ | (R$^8$)$_m$ | p |
|---|---|---|---|---|---|---|---|
| E-0566 | H | H | H | H | H | 3-F,5-Cl | 0 |
| E-0567 | H | H | H | H | H | 3-F,6-Cl | 0 |
| E-0568 | H | H | H | H | H | 4-F,2-Cl | 0 |
| E-0569 | H | H | H | H | H | 4-F,3-Cl | 0 |
| E-0570 | H | H | H | H | H | 2-F,3-Me | 0 |
| E-0571 | H | H | H | H | H | 2-F,4-Me | 0 |
| E-0572 | H | H | H | H | H | 2-F,5-Me | 0 |
| E-0573 | H | H | H | H | H | 2-F,6-Me | 0 |
| E-0574 | H | H | H | H | H | 3-F,2-Me | 0 |
| E-0575 | H | H | H | H | H | 3-F,4-Me | 0 |
| E-0576 | H | H | H | H | H | 3-F,5-Me | 0 |
| E-0577 | H | H | H | H | H | 3-F,6-Me | 0 |
| E-0578 | H | H | H | H | H | 4-F,2-Me | 0 |
| E-0579 | H | H | H | H | H | 4-F,3-Me | 0 |
| E-0580 | H | H | H | H | H | 2-F,3-CF$_3$ | 0 |
| E-0581 | H | H | H | H | H | 2-F,4-CF$_3$ | 0 |
| E-0582 | H | H | H | H | H | 2-F,5-CF$_3$ | 0 |
| E-0583 | H | H | H | H | H | 2-F,6-CF$_3$ | 0 |
| E-0584 | H | H | H | H | H | 3-F,2-CF$_3$ | 0 |
| E-0585 | H | H | H | H | H | 3-F,4-CF$_3$ | 0 |
| E-0586 | H | H | H | H | H | 3-F,5-CF$_3$ | 0 |
| E-0587 | H | H | H | H | H | 3-F,6-CF$_3$ | 0 |
| E-0588 | H | H | H | H | H | 4-F,2-CF$_3$ | 0 |
| E-0589 | H | H | H | H | H | 4-F,3-CF$_3$ | 0 |
| E-0590 | H | H | H | H | H | 2-F,3-OMe | 0 |
| E-0591 | H | H | H | H | H | 2-F,4-OMe | 0 |
| E-0592 | H | H | H | H | H | 2-F,5-OMe | 0 |
| E-0593 | H | H | H | H | H | 2-F,6-OMe | 0 |
| E-0594 | H | H | H | H | H | 3-F,2-OMe | 0 |
| E-0595 | H | H | H | H | H | 3-F,4-OMe | 0 |
| E-0596 | H | H | H | H | H | 3-F,5-OMe | 0 |
| E-0597 | H | H | H | H | H | 3-F,6-OMe | 0 |
| E-0598 | H | H | H | H | H | 4-F,2-OMe | 0 |
| E-0599 | H | H | H | H | H | 4-F,3-OMe | 0 |
| E-0600 | H | H | H | H | H | 2,3-Cl$_2$ | 0 |
| E-0601 | H | H | H | H | H | 2,4-Cl$_2$ | 0 |
| E-0602 | H | H | H | H | H | 2,5-Cl$_2$ | 0 |
| E-0603 | H | H | H | H | H | 2,6-Cl$_2$ | 0 |
| E-0604 | H | H | H | H | H | 3,4-Cl$_2$ | 0 |
| E-0605 | H | H | H | H | H | 3,5-Cl$_2$ | 0 |
| E-0606 | H | H | H | H | H | 2-Cl,3-Me | 0 |
| E-0607 | H | H | H | H | H | 2-Cl,4-Me | 0 |
| E-0608 | H | H | H | H | H | 2-Cl,5-Me | 0 |
| E-0609 | H | H | H | H | H | 2-Cl,6-Me | 0 |
| E-0610 | H | H | H | H | H | 3-Cl,2-Me | 0 |
| E-0611 | H | H | H | H | H | 3-Cl,4-Me | 0 |
| E-0612 | H | H | H | H | H | 3-Cl,5-Me | 0 |
| E-0613 | H | H | H | H | H | 3-Cl,6-Me | 0 |
| E-0614 | H | H | H | H | H | 4-Cl,2-Me | 0 |
| E-0615 | H | H | H | H | H | 4-Cl,3-Me | 0 |
| E-0616 | H | H | H | H | H | 2-Cl,3-CF$_3$ | 0 |
| E-0617 | H | H | H | H | H | 2-Cl,4-CF$_3$ | 0 |
| E-0618 | H | H | H | H | H | 2-Cl,5-CF$_3$ | 0 |
| E-0619 | H | H | H | H | H | 2-Cl,6-CF$_3$ | 0 |
| E-0620 | H | H | H | H | H | 3-Cl,2-CF$_3$ | 0 |
| E-0621 | H | H | H | H | H | 3-Cl,4-CF$_3$ | 0 |
| E-0622 | H | H | H | H | H | 3-Cl,5-CF$_3$ | 0 |

TABLE 266

| compound | R$^1$ | R$^2$ | R$^3$ | R$^4$ | R$^5$ | (R$^8$)$_m$ | p |
|---|---|---|---|---|---|---|---|
| E-0623 | H | H | H | H | H | 3-Cl,6-CF$_3$ | 0 |
| E-0624 | H | H | H | H | H | 4-Cl,2-CF$_3$ | 0 |
| E-0625 | H | H | H | H | H | 4-Cl,3-CF$_3$ | 0 |
| E-0626 | H | H | H | H | H | 2-Cl,3-OMe | 0 |
| E-0627 | H | H | H | H | H | 2-Cl,4-OMe | 0 |
| E-0628 | H | H | H | H | H | 2-Cl,5-OMe | 0 |
| E-0629 | H | H | H | H | H | 2-Cl,6-OMe | 0 |
| E-0630 | H | H | H | H | H | 3-Cl,2-OMe | 0 |
| E-0631 | H | H | H | H | H | 3-Cl,4-OMe | 0 |
| E-0632 | H | H | H | H | H | 3-Cl,5-OMe | 0 |
| E-0633 | H | H | H | H | H | 3-Cl,6-OMe | 0 |
| E-0634 | H | H | H | H | H | 4-Cl,2-OMe | 0 |
| E-0635 | H | H | H | H | H | 4-Cl,3-OMe | 0 |
| E-0636 | H | H | H | H | H | 2,3-Me$_2$ | 0 |
| E-0637 | H | H | H | H | H | 2,4-Me$_2$ | 0 |
| E-0638 | H | H | H | H | H | 2,5-Me$_2$ | 0 |
| E-0639 | H | H | H | H | H | 2,6-Me$_2$ | 0 |
| E-0640 | H | H | H | H | H | 3,4-Me$_2$ | 0 |
| E-0641 | H | H | H | H | H | 3,5-Me$_2$ | 0 |
| E-0642 | H | H | H | H | H | 2-Me,3-CF$_3$ | 0 |
| E-0643 | H | H | H | H | H | 2-Me,4-CF$_3$ | 0 |
| E-0644 | H | H | H | H | H | 2-Me,5-CF$_3$ | 0 |
| E-0645 | H | H | H | H | H | 2-Me,6-CF$_3$ | 0 |
| E-0646 | H | H | H | H | H | 3-Me,2-CF$_3$ | 0 |
| E-0647 | H | H | H | H | H | 3-Me,4-CF$_3$ | 0 |
| E-0648 | H | H | H | H | H | 3-Me,5-CF$_3$ | 0 |

TABLE 266-continued

| compound | R¹ | R² | R³ | R⁴ | R⁵ | (R⁸)ₘ | p |
|---|---|---|---|---|---|---|---|
| E-0649 | H | H | H | H | H | 3-Me,6-CF₃ | 0 |
| E-0650 | H | H | H | H | H | 4-Me,2-CF₃ | 0 |
| E-0651 | H | H | H | H | H | 4-Me,3-CF₃ | 0 |
| E-0652 | H | H | H | H | H | 2-Me,3-OMe | 0 |
| E-0653 | H | H | H | H | H | 2-Me,4-OMe | 0 |
| E-0654 | H | H | H | H | H | 2-Me,5-OMe | 0 |
| E-0655 | H | H | H | H | H | 2-Me,6-OMe | 0 |
| E-0656 | H | H | H | H | H | 3-Me,2-OMe | 0 |
| E-0657 | H | H | H | H | H | 3-Me,4-OMe | 0 |
| E-0658 | H | H | H | H | H | 3-Me,5-OMe | 0 |
| E-0659 | H | H | H | H | H | 3-Me,6-OMe | 0 |
| E-0660 | H | H | H | H | H | 4-Me,2-OMe | 0 |
| E-0661 | H | H | H | H | H | 4-Me,3-OMe | 0 |
| E-0662 | H | H | H | H | H | 2,3-OMe₂ | 0 |
| E-0663 | H | H | H | H | H | 2,4-OMe₂ | 0 |
| E-0664 | H | H | H | H | H | 2,5-OMe₂ | 0 |
| E-0665 | H | H | H | H | H | 2,6-OMe₂ | 0 |
| E-0666 | H | H | H | H | H | 3,4-OMe₂ | 0 |
| E-0667 | H | H | H | H | H | 3,5-OMe₂ | 0 |
| E-0668 | H | H | H | H | H | 2-OMe,3-CF₃ | 0 |
| E-0669 | H | H | H | H | H | 2-OMe,4-CF₃ | 0 |
| E-0670 | H | H | H | H | H | 2-OMe,5-CF₃ | 0 |
| E-0671 | H | H | H | H | H | 2-OMe,6-CF₃ | 0 |
| E-0672 | H | H | H | H | H | 3-OMe,2-CF₃ | 0 |
| E-0673 | H | H | H | H | H | 3-OMe,4-CF₃ | 0 |
| E-0674 | H | H | H | H | H | 3-OMe,5-CF₃ | 0 |
| E-0675 | H | H | H | H | H | 3-OMe,6-CF₃ | 0 |
| E-0676 | H | H | H | H | H | 4-OMe,2-CF₃ | 0 |
| E-0677 | H | H | H | H | H | 4-OMe,3-CF₃ | 0 |
| E-0678 | H | H | H | H | H | 2-CHF₂,3-F | 0 |
| E-0679 | H | H | H | H | H | 2-CHF₂,4-F | 0 |

TABLE 267

| compound | R¹ | R² | R³ | R⁴ | R⁵ | (R⁸)ₘ | p |
|---|---|---|---|---|---|---|---|
| E-0680 | H | H | H | H | H | 2-CHF₂,5-F | 0 |
| E-0681 | H | H | H | H | H | 2-CHF₂,6-F | 0 |
| E-0682 | H | H | H | H | H | 2-CHF₂,3-Me | 0 |
| E-0683 | H | H | H | H | H | 2-CHF₂,4-Me | 0 |
| E-0684 | H | H | H | H | H | 2-CHF₂,5-Me | 0 |
| E-0685 | H | H | H | H | H | 2-CHF₂,6-Me | 0 |
| E-0686 | H | H | H | H | H | 2-cyclopropyl,3-F | 0 |
| E-0687 | H | H | H | H | H | 2-cyclopropyl,4-F | 0 |
| E-0688 | H | H | H | H | H | 2-cyclopropyl,5-F | 0 |
| E-0689 | H | H | H | H | H | 2-cyclopropyl,6-F | 0 |
| E-0690 | H | H | H | H | H | 2-cyclopropyl,3-Me | 0 |
| E-0691 | H | H | H | H | H | 2-cyclopropyl,4-Me | 0 |
| E-0692 | H | H | H | H | H | 2-cyclopropyl,5-Me | 0 |
| E-0693 | H | H | H | H | H | 2-cyclopropyl,6-Me | 0 |
| E-0694 | H | H | H | H | H | 2-ethenyl,3-F | 0 |
| E-0695 | H | H | H | H | H | 2-ethenyl,4-F | 0 |
| E-0696 | H | H | H | H | H | 2-ethenyl,5-F | 0 |
| E-0697 | H | H | H | H | H | 2-ethenyl,6-F | 0 |
| E-0698 | H | H | H | H | H | 2-ethenyl,3-Me | 0 |
| E-0699 | H | H | H | H | H | 2-ethenyl,4-Me | 0 |
| E-0700 | H | H | H | H | H | 2-ethenyl,5-Me | 0 |
| E-0701 | H | H | H | H | H | 2-ethenyl,6-Me | 0 |
| E-0702 | H | H | H | H | H | 2-OEt,3-F | 0 |
| E-0703 | H | H | H | H | H | 2-OEt,4-F | 0 |
| E-0704 | H | H | H | H | H | 2-OEt,5-F | 0 |
| E-0705 | H | H | H | H | H | 2-OEt,6-F | 0 |
| E-0706 | H | H | H | H | H | 2-OEt,3-Cl | 0 |
| E-0707 | H | H | H | H | H | 2-OEt,4-Cl | 0 |
| E-0708 | H | H | H | H | H | 2-OEt,5-Cl | 0 |
| E-0709 | H | H | H | H | H | 2-OEt,6-Cl | 0 |
| E-0710 | H | H | H | H | H | 2-OEt,3-Me | 0 |
| E-0711 | H | H | H | H | H | 2-OEt,4-Me | 0 |
| E-0712 | H | H | H | H | H | 2-OEt,5-Me | 0 |
| E-0713 | H | H | H | H | H | 2-OEt,6-Me | 0 |
| E-0714 | H | H | H | H | H | 2-OPr,3-F | 0 |
| E-0715 | H | H | H | H | H | 2-OPr,4-F | 0 |
| E-0716 | H | H | H | H | H | 2-OPr,5-F | 0 |
| E-0717 | H | H | H | H | H | 2-OPr,6-F | 0 |
| E-0718 | H | H | H | H | H | 2-OPr,3-Me | 0 |

TABLE 267-continued

| compound | R¹ | R² | R³ | R⁴ | R⁵ | (R⁸)ₘ | p |
|---|---|---|---|---|---|---|---|
| E-0719 | H | H | H | H | H | 2-OPr,4-Me | 0 |
| E-0720 | H | H | H | H | H | 2-OPr,5-Me | 0 |
| E-0721 | H | H | H | H | H | 2-OPr,6-Me | 0 |
| E-0722 | H | H | H | H | H | 2-O(i-Pr),3-F | 0 |
| E-0723 | H | H | H | H | H | 2-O(i-Pr),4-F | 0 |
| E-0724 | H | H | H | H | H | 2-O(i-Pr),5-F | 0 |
| E-0725 | H | H | H | H | H | 2-O(i-Pr),6-F | 0 |
| E-0726 | H | H | H | H | H | 2-O(i-Pr),3-Me | 0 |
| E-0727 | H | H | H | H | H | 2-O(i-Pr),4-Me | 0 |
| E-0728 | H | H | H | H | H | 2-O(i-Pr),5-Me | 0 |
| E-0729 | H | H | H | H | H | 2-O(i-Pr),6-Me | 0 |
| E-0730 | H | H | H | H | H | 2-OCF₃,3-F | 0 |
| E-0731 | H | H | H | H | H | 2-OCF₃,4-F | 0 |
| E-0732 | H | H | H | H | H | 2-OCF₃,5-F | 0 |
| E-0733 | H | H | H | H | H | 2-OCF₃,6-F | 0 |
| E-0734 | H | H | H | H | H | 2-OCF₃,3-Me | 0 |
| E-0735 | H | H | H | H | H | 2-OCF₃,4-Me | 0 |
| E-0736 | H | H | H | H | H | 2-OCF₃,5-Me | 0 |

TABLE 268

| compound | R¹ | R² | R³ | R⁴ | R⁵ | (R⁸)ₘ | p |
|---|---|---|---|---|---|---|---|
| E-0737 | H | H | H | H | H | 2-OCF₃,6-Me | 0 |
| E-0738 | H | H | H | H | H | 2-OCHF₂,3-F | 0 |
| E-0739 | H | H | H | H | H | 2-OCHF₂,4-F | 0 |
| E-0740 | H | H | H | H | H | 2-OCHF₂,5-F | 0 |
| E-0741 | H | H | H | H | H | 2-OCHF₂,6-F | 0 |
| E-0742 | H | H | H | H | H | 2-OCHF₂,3-Me | 0 |
| E-0743 | H | H | H | H | H | 2-OCHF₂,4-Me | 0 |
| E-0744 | H | H | H | H | H | 2-OCHF₂,5-Me | 0 |
| E-0745 | H | H | H | H | H | 2-OCHF₂,6-Me | 0 |
| E-0746 | H | H | H | H | H | 2-(cyclopropyloxy),3-F | 0 |
| E-0747 | H | H | H | H | H | 2-(cyclopropyloxy),4-F | 0 |
| E-0748 | H | H | H | H | H | 2-(cyclopropyloxy),5-F | 0 |
| E-0749 | H | H | H | H | H | 2-(cyclopropyloxy),6-F | 0 |
| E-0750 | H | H | H | H | H | 2-(cyclopropyloxy),3-Me | 0 |
| E-0751 | H | H | H | H | H | 2-(cyclopropyloxy),4-Me | 0 |
| E-0752 | H | H | H | H | H | 2-(cyclopropyloxy),5-Me | 0 |
| E-0753 | H | H | H | H | H | 2-(cyclopropyloxy),6-Me | 0 |
| E-0754 | H | H | H | H | H | 2-(oxiran-2-yl),3-F | 0 |
| E-0755 | H | H | H | H | H | 2-(oxiran-2-yl),4-F | 0 |
| E-0756 | H | H | H | H | H | 2-(oxiran-2-yl),5-F | 0 |
| E-0757 | H | H | H | H | H | 2-(oxiran-2-yl),6-F | 0 |
| E-0758 | H | H | H | H | H | 2-(oxiran-2-yl),3-Me | 0 |
| E-0759 | H | H | H | H | H | 2-(oxiran-2-yl),4-Me | 0 |
| E-0760 | H | H | H | H | H | 2-(oxiran-2-yl),5-Me | 0 |
| E-0761 | H | H | H | H | H | 2-(oxiran-2-yl),6-Me | 0 |
| E-0762 | H | H | H | H | H | 2-(oxiran-2-ylmethyl),3-F | 0 |
| E-0763 | H | H | H | H | H | 2-(oxiran-2-ylmethyl),4-F | 0 |
| E-0764 | H | H | H | H | H | 2-(oxiran-2-ylmethyl),5-F | 0 |
| E-0765 | H | H | H | H | H | 2-(oxiran-2-ylmethyl),6-F | 0 |
| E-0766 | H | H | H | H | H | 2-(oxiran-2-ylmethyl),3-Me | 0 |
| E-0767 | H | H | H | H | H | 2-(oxiran-2-ylmethyl),4-Me | 0 |
| E-0768 | H | H | H | H | H | 2-(oxiran-2-ylmethyl),5-Me | 0 |
| E-0769 | H | H | H | H | H | 2-(oxiran-2-ylmethyl),6-Me | 0 |
| E-0770 | H | H | H | H | H | 2-SMe,3-F | 0 |
| E-0771 | H | H | H | H | H | 2-SMe,4-F | 0 |
| E-0772 | H | H | H | H | H | 2-SMe,5-F | 0 |
| E-0773 | H | H | H | H | H | 2-SMe,6-F | 0 |
| E-0774 | H | H | H | H | H | 2-SMe,3-Me | 0 |
| E-0775 | H | H | H | H | H | 2-SMe,4-Me | 0 |
| E-0776 | H | H | H | H | H | 2-SMe,5-Me | 0 |
| E-0777 | H | H | H | H | H | 2-SMe,6-Me | 0 |
| E-0778 | H | H | H | H | H | 2-SEt,3-F | 0 |
| E-0779 | H | H | H | H | H | 2-SEt,4-F | 0 |
| E-0780 | H | H | H | H | H | 2-SEt,5-F | 0 |
| E-0781 | H | H | H | H | H | 2-SEt,6-F | 0 |
| E-0782 | H | H | H | H | H | 2-SEt,3-Me | 0 |
| E-0783 | H | H | H | H | H | 2-SEt,4-Me | 0 |
| E-0784 | H | H | H | H | H | 2-SEt,5-Me | 0 |
| E-0785 | H | H | H | H | H | 2-SEt,6-Me | 0 |
| E-0786 | H | H | H | H | H | 2-S(=O)Me,3-F | 0 |
| E-0787 | H | H | H | H | H | 2-S(=O)Me,4-F | 0 |
| E-0788 | H | H | H | H | H | 2-S(=O)Me,5-F | 0 |

TABLE 268-continued

| compound | R¹ | R² | R³ | R⁴ | R⁵ | (R⁸)$_m$ | p |
|---|---|---|---|---|---|---|---|
| E-0789 | H | H | H | H | H | 2-S(=O)Me,6-F | 0 |
| E-0790 | H | H | H | H | H | 3-S(=O)Me,2-F | 0 |
| E-0791 | H | H | H | H | H | 3-S(=O)Me,4-F | 0 |
| E-0792 | H | H | H | H | H | 3-S(=O)Me,5-F | 0 |
| E-0793 | H | H | H | H | H | 3-S(=O)Me,6-F | 0 |

TABLE 269

| compound | R¹ | R² | R³ | R⁴ | R⁵ | (R⁸)$_m$ | p |
|---|---|---|---|---|---|---|---|
| E-0794 | H | H | H | H | H | 2-S(=O)Me,3-Me | 0 |
| E-0795 | H | H | H | H | H | 2-S(=O)Me,4-Me | 0 |
| E-0796 | H | H | H | H | H | 2-S(=O)Me,5-Me | 0 |
| E-0797 | H | H | H | H | H | 2-S(=O)Me,6-Me | 0 |
| E-0798 | H | H | H | H | H | 3-S(=O)Me,2-Me | 0 |
| E-0799 | H | H | H | H | H | 3-S(=O)Me,4-Me | 0 |
| E-0800 | H | H | H | H | H | 3-S(=O)Me,5-Me | 0 |
| E-0801 | H | H | H | H | H | 3-S(=O)Me,6-Me | 0 |
| E-0802 | H | H | H | H | H | 2-S(=O)$_2$Me,3-F | 0 |
| E-0803 | H | H | H | H | H | 2-S(=O)$_2$Me,4-F | 0 |
| E-0804 | H | H | H | H | H | 2-S(=O)$_2$Me,5-F | 0 |
| E-0805 | H | H | H | H | H | 2-S(=O)$_2$Me,6-F | 0 |
| E-0806 | H | H | H | H | H | 2-S(=O)$_2$Me,3-Me | 0 |
| E-0807 | H | H | H | H | H | 2-S(=O)$_2$Me,4-Me | 0 |
| E-0808 | H | H | H | H | H | 2-S(=O)$_2$Me,5-Me | 0 |
| E-0809 | H | H | H | H | H | 2-S(=O)$_2$Me,6-Me | 0 |
| E-0810 | H | H | H | H | H | 2-SCF$_3$,3-F | 0 |
| E-0811 | H | H | H | H | H | 2-SCF$_3$,4-F | 0 |
| E-0812 | H | H | H | H | H | 2-SCF$_3$,5-F | 0 |
| E-0813 | H | H | H | H | H | 2-SCF$_3$,6-F | 0 |
| E-0814 | H | H | H | H | H | 2-SCF$_3$,3-Me | 0 |
| E-0815 | H | H | H | H | H | 2-SCF$_3$,4-Me | 0 |
| E-0816 | H | H | H | H | H | 2-SCF$_3$,5-Me | 0 |
| E-0817 | H | H | H | H | H | 2-SCF$_3$,6-Me | 0 |
| E-0818 | H | H | H | H | H | 2-S(=O)CF$_3$,3-F | 0 |
| E-0819 | H | H | H | H | H | 2-S(=O)CF$_3$,4-F | 0 |
| E-0820 | H | H | H | H | H | 2-S(=O)CF$_3$,5-F | 0 |
| E-0821 | H | H | H | H | H | 2-S(=O)CF$_3$,6-F | 0 |
| E-0822 | H | H | H | H | H | 2-S(=O)CF$_3$,3-Me | 0 |
| E-0823 | H | H | H | H | H | 2-S(=O)CF$_3$,4-Me | 0 |
| E-0824 | H | H | H | H | H | 2-S(=O)CF$_3$,5-Me | 0 |
| E-0825 | H | H | H | H | H | 2-S(=O)CF$_3$,6-Me | 0 |
| E-0826 | H | H | H | H | H | 2-S(=O)CF$_3$,3-F | 0 |
| E-0827 | H | H | H | H | H | 2-S(=O)CF$_3$,4-F | 0 |
| E-0828 | H | H | H | H | H | 2-S(=O)CF$_3$,5-F | 0 |
| E-0829 | H | H | H | H | H | 2-S(=O)CF$_3$,6-F | 0 |
| E-0830 | H | H | H | H | H | 2-S(=O)$_2$CF$_3$,3-Me | 0 |
| E-0831 | H | H | H | H | H | 2-S(=O)$_2$CF$_3$,4-Me | 0 |
| E-0832 | H | H | H | H | H | 2-S(=O)$_2$CF$_3$,5-Me | 0 |
| E-0833 | H | H | H | H | H | 2-S(=O)$_2$CF$_3$,6-Me | 0 |
| E-0834 | H | H | H | H | H | 2-(cyclopropylthio),3-F | 0 |
| E-0835 | H | H | H | H | H | 2-(cyclopropylthio),4-F | 0 |
| E-0836 | H | H | H | H | H | 2-(cyclopropylthio),5-F | 0 |
| E-0837 | H | H | H | H | H | 2-(cyclopropylthio),6-F | 0 |
| E-0838 | H | H | H | H | H | 2-(cyclopropylthio),3-Me | 0 |
| E-0839 | H | H | H | H | H | 2-(cyclopropylthio),4-Me | 0 |
| E-0840 | H | H | H | H | H | 2-(cyclopropylthio),5-Me | 0 |
| E-0841 | H | H | H | H | H | 2-(cyclopropylthio),6-Me | 0 |
| E-0842 | H | H | H | H | H | 2-C(=O)Me,3-F | 0 |
| E-0843 | H | H | H | H | H | 2-C(=O)Me,4-F | 0 |
| E-0844 | H | H | H | H | H | 2-C(=O)Me,5-F | 0 |
| E-0845 | H | H | H | H | H | 2-C(=O)Me,6-F | 0 |
| E-0846 | H | H | H | H | H | 2-C(=O)Me,3-Me | 0 |
| E-0847 | H | H | H | H | H | 2-C(=O)Me,4-Me | 0 |
| E-0848 | H | H | H | H | H | 2-C(=O)Me,5-Me | 0 |
| E-0849 | H | H | H | H | H | 2-C(=O)Me,6-Me | 0 |
| E-0850 | H | H | H | H | H | 3-C(=O)Me,2-F | 0 |

TABLE 270

| compound | R¹ | R² | R³ | R⁴ | R⁵ | (R⁸)$_m$ | p |
|---|---|---|---|---|---|---|---|
| E-0851 | H | H | H | H | H | 3-C(=O)Me,4-F | 0 |
| E-0852 | H | H | H | H | H | 3-C(=O)Me,5-F | 0 |
| E-0853 | H | H | H | H | H | 3-C(=O)Me,6-F | 0 |
| E-0854 | H | H | H | H | H | 3-C(=O)Me,2-Me | 0 |
| E-0855 | H | H | H | H | H | 3-C(=O)Me,4-Me | 0 |
| E-0856 | H | H | H | H | H | 3-C(=O)Me,5-Me | 0 |
| E-0857 | H | H | H | H | H | 3-C(=O)Me,6-Me | 0 |
| E-0858 | H | H | H | H | H | 2-C(=O)OMe,3-F | 0 |
| E-0859 | H | H | H | H | H | 2-C(=O)OMe,4-F | 0 |
| E-0860 | H | H | H | H | H | 2-C(=O)OMe,5-F | 0 |
| E-0861 | H | H | H | H | H | 2-C(=O)OMe,6-F | 0 |
| E-0862 | H | H | H | H | H | 2-C(=O)OMe,3-Me | 0 |
| E-0863 | H | H | H | H | H | 2-C(=O)OMe,4-Me | 0 |
| E-0864 | H | H | H | H | H | 2-C(=O)OMe,5-Me | 0 |
| E-0865 | H | H | H | H | H | 2-C(=O)OMe,6-Me | 0 |
| E-0866 | H | H | H | H | H | 2-C(=O)OEt,3-F | 0 |
| E-0867 | H | H | H | H | H | 2-C(=O)OEt,4-F | 0 |
| E-0868 | H | H | H | H | H | 2-C(=O)OEt,5-F | 0 |
| E-0869 | H | H | H | H | H | 2-C(=O)OEt,6-F | 0 |
| E-0870 | H | H | H | H | H | 2-C(=O)OEt,3-Me | 0 |
| E-0871 | H | H | H | H | H | 2-C(=O)OEt,4-Me | 0 |
| E-0872 | H | H | H | H | H | 2-C(=O)OEt,5-Me | 0 |
| E-0873 | H | H | H | H | H | 2-C(=O)OEt,6-Me | 0 |
| E-0874 | H | H | H | H | H | 2-C(=O)NH$_2$,3-F | 0 |
| E-0875 | H | H | H | H | H | 2-C(=O)NH$_2$,4-F | 0 |
| E-0876 | H | H | H | H | H | 2-C(=O)NH$_2$,5-F | 0 |
| E-0877 | H | H | H | H | H | 2-C(=O)NH$_2$,6-F | 0 |
| E-0878 | H | H | H | H | H | 2-C(=O)NH$_2$,3-Me | 0 |
| E-0879 | H | H | H | H | H | 2-C(=O)NH$_2$,4-Me | 0 |
| E-0880 | H | H | H | H | H | 2-C(=O)NH$_2$,5-Me | 0 |
| E-0881 | H | H | H | H | H | 2-C(=O)NH$_2$,6-Me | 0 |
| E-0882 | H | H | H | H | H | 2-C(=O)NHMe,3-F | 0 |
| E-0883 | H | H | H | H | H | 2-C(=O)NHMe,4-F | 0 |
| E-0884 | H | H | H | H | H | 2-C(=O)NHMe,5-F | 0 |
| E-0885 | H | H | H | H | H | 2-C(=O)NHMe,6-F | 0 |
| E-0886 | H | H | H | H | H | 2-C(=O)NHMe,3-Me | 0 |
| E-0887 | H | H | H | H | H | 2-C(=O)NHMe,4-Me | 0 |
| E-0888 | H | H | H | H | H | 2-C(=O)NHMe,5-Me | 0 |
| E-0889 | H | H | H | H | H | 2-C(=O)NHMe,6-Me | 0 |
| E-0890 | H | H | H | H | H | 2-C(=O)NHMe$_2$,3-F | 0 |
| E-0891 | H | H | H | H | H | 2-C(=O)NHMe$_2$,4-F | 0 |
| E-0892 | H | H | H | H | H | 2-C(=O)NHMe$_2$,5-F | 0 |
| E-0893 | H | H | H | H | H | 2-C(=O)NHMe$_2$,6-F | 0 |
| E-0894 | H | H | H | H | H | 2-C(=O)NHMe$_2$,3-Me | 0 |
| E-0895 | H | H | H | H | H | 2-C(=O)NHMe$_2$,4-Me | 0 |
| E-0896 | H | H | H | H | H | 2-C(=O)NHMe$_2$,5-Me | 0 |
| E-0897 | H | H | H | H | H | 2-C(=O)NHMe$_2$,6-Me | 0 |
| E-0898 | H | H | H | H | H | 2-CH$_2$OH,3-F | 0 |
| E-0899 | H | H | H | H | H | 2-CH$_2$OH,4-F | 0 |
| E-0900 | H | H | H | H | H | 2-CH$_2$OH,5-F | 0 |
| E-0901 | H | H | H | H | H | 2-CH$_2$OH,6-F | 0 |
| E-0902 | H | H | H | H | H | 2-CH$_2$OH,3-Me | 0 |
| E-0903 | H | H | H | H | H | 2-CH$_2$OH,4-Me | 0 |
| E-0904 | H | H | H | H | H | 2-CH$_2$OH,5-Me | 0 |
| E-0905 | H | H | H | H | H | 2-CH$_2$OH,6-Me | 0 |
| E-0906 | H | H | H | H | H | 2-CH$_2$OCH$_3$,3-F | 0 |
| E-0907 | H | H | H | H | H | 2-CH$_2$OCH$_3$,4-F | 0 |

TABLE 271

| compound | R¹ | R² | R³ | R⁴ | R⁵ | (R⁸)$_m$ | p |
|---|---|---|---|---|---|---|---|
| E-0908 | H | H | H | H | H | 2-CH$_2$OCH$_3$,5-F | 0 |
| E-0909 | H | H | H | H | H | 2-CH$_2$OCH$_3$,6-F | 0 |
| E-0910 | H | H | H | H | H | 2-CH$_2$OCH$_3$,3-Me | 0 |
| E-0911 | H | H | H | H | H | 2-CH$_2$OCH$_3$,4-Me | 0 |
| E-0912 | H | H | H | H | H | 2-CH$_2$OCH$_3$,5-Me | 0 |
| E-0913 | H | H | H | H | H | 2-CH$_2$OCH$_3$,6-Me | 0 |
| E-0914 | H | H | H | H | H | 2-CH$_2$OCH$_2$CH$_3$,3-F | 0 |
| E-0915 | H | H | H | H | H | 2-CH$_2$OCH$_2$CH$_3$,4-F | 0 |
| E-0916 | H | H | H | H | H | 2-CH$_2$OCH$_2$CH$_3$,5-F | 0 |
| E-0917 | H | H | H | H | H | 2-CH$_2$OCH$_2$CH$_3$,6-F | 0 |
| E-0918 | H | H | H | H | H | 2-CH$_2$OCH$_2$CH$_3$,3-Me | 0 |
| E-0919 | H | H | H | H | H | 2-CH$_2$OCH$_2$CH$_3$,4-Me | 0 |
| E-0920 | H | H | H | H | H | 2-CH$_2$OCH$_2$CH$_3$,5-Me | 0 |

TABLE 271-continued

| compound | R¹ | R² | R³ | R⁴ | R⁵ | (R⁸)ₘ | p |
|---|---|---|---|---|---|---|---|
| E-0921 | H | H | H | H | H | 2-CH₂OCH₂CH₃,6-Me | 0 |
| E-0922 | H | H | H | H | H | 2-OC(=O)CH₃,3-F | 0 |
| E-0923 | H | H | H | H | H | 2-OC(=O)CH₃,4-F | 0 |
| E-0924 | H | H | H | H | H | 2-OC(=O)CH₃,5-F | 0 |
| E-0925 | H | H | H | H | H | 2-OC(=O)CH₃,6-F | 0 |
| E-0926 | H | H | H | H | H | 2-OC(=O)CH₃,3-Me | 0 |
| E-0927 | H | H | H | H | H | 2-OC(=O)CH₃,4-Me | 0 |
| E-0928 | H | H | H | H | H | 2-OC(=O)CH₃,5-Me | 0 |
| E-0929 | H | H | H | H | H | 2-OC(=O)CH₃,6-Me | 0 |
| E-0930 | H | H | H | H | H | 2-OS(=O)₂CH₃,3-F | 0 |
| E-0931 | H | H | H | H | H | 2-OS(=O)₂CH₃,4-F | 0 |
| E-0932 | H | H | H | H | H | 2-OS(=O)₂CH₃,5-F | 0 |
| E-0933 | H | H | H | H | H | 2-OS(=O)₂CH₃,6-F | 0 |
| E-0934 | H | H | H | H | H | 2-OS(=O)₂CH₃,3-Me | 0 |
| E-0935 | H | H | H | H | H | 2-OS(=O)₂CH₃,4-Me | 0 |
| E-0936 | H | H | H | H | H | 2-OS(=O)₂CH₃,5-Me | 0 |
| E-0937 | H | H | H | H | H | 2-OS(=O)₂CH₃,6-Me | 0 |
| E-0938 | H | H | H | H | H | 2-CH₂SCH₃,3-F | 0 |
| E-0939 | H | H | H | H | H | 2-CH₂SCH₃,4-F | 0 |
| E-0940 | H | H | H | H | H | 2-CH₂SCH₃,5-F | 0 |
| E-0941 | H | H | H | H | H | 2-CH₂SCH₃,6 F | 0 |
| E-0942 | H | H | H | H | H | 2-CH₂SCH₃,3-Me | 0 |
| E-0943 | H | H | H | H | H | 2-CH₂SCH₃,4-Me | 0 |
| E-0944 | H | H | H | H | H | 2-CH₂SCH₃,5-Me | 0 |
| E-0945 | H | H | H | H | H | 2-CH₂SCH₃,6-Me | 0 |
| E-0946 | H | H | H | H | H | 2-CH₂SCF₃,3-F | 0 |
| E-0947 | H | H | H | H | H | 2-CH₂SCF₃,4-F | 0 |
| E-0948 | H | H | H | H | H | 2-CH₂SCF₃,5-F | 0 |
| E-0949 | H | H | H | H | H | 2-CH₂SCF₃,6-F | 0 |
| E-0950 | H | H | H | H | H | 2-CH₂SCF₃,3-Me | 0 |
| E-0951 | H | H | H | H | H | 2-CH₂SCF₃,4-Me | 0 |
| E-0952 | H | H | H | H | H | 2-CH₂SCF₃,5-Me | 0 |
| E-0953 | H | H | H | H | H | 2-CH₂SCF₃,6-Me | 0 |
| E-0954 | H | H | H | H | H | 2-(benzyloxy),3-F | 0 |
| E-0955 | H | H | H | H | H | 2-(benzyloxy),4-F | 0 |
| E-0956 | H | H | H | H | H | 2-(benzyloxy),5-F | 0 |
| E-0957 | H | H | H | H | H | 2-(benzyloxy),6-F | 0 |
| E-0958 | H | H | H | H | H | 2-(benzyloxy),3-Me | 0 |
| E-0959 | H | H | H | H | H | 2-(benzyloxy),4-Me | 0 |
| E-0960 | H | H | H | H | H | 2-(benzyloxy),5-Me | 0 |
| E-0961 | H | H | H | H | H | 2-(benzyloxy),6-Me | 0 |
| E-0962 | H | H | H | H | H | 2-NH₂,3-F | 0 |
| E-0963 | H | H | H | H | H | 2-NH₂,4-F | 0 |
| E-0964 | H | H | H | H | H | 2-NH₂,5-F | 0 |

TABLE 272

| compound | R¹ | R² | R³ | R⁴ | R⁵ | (R⁸)ₘ | p |
|---|---|---|---|---|---|---|---|
| E-0965 | H | H | H | H | H | 2-NH₂,6-F | 0 |
| E-0966 | H | H | H | H | H | 2-NH₂,3-Me | 0 |
| E-0967 | H | H | H | H | H | 2-NH₂,4-Me | 0 |
| E-0968 | H | H | H | H | H | 2-NH₂,5-Me | 0 |
| E-0969 | H | H | H | H | H | 2-NH₂,6-Me | 0 |
| E-0970 | H | H | H | H | H | 2-NHMe,3F | 0 |
| E-0971 | H | H | H | H | H | 2-NHMe,4-F | 0 |
| E-0972 | H | H | H | H | H | 2-NHMe,5-F | 0 |
| E-0973 | H | H | H | H | H | 2-NHMe,6-F | 0 |
| E-0974 | H | H | H | H | H | 2-NHMe,3-Me | 0 |
| E-0975 | H | H | H | H | H | 2-NHMe,4-Me | 0 |
| E-0976 | H | H | H | H | H | 2-NHMe,5-Me | 0 |
| E-0977 | H | H | H | H | H | 2-NHMe,6-Me | 0 |
| E-0978 | H | H | H | H | H | 2-NHEt,3-F | 0 |
| E-0979 | H | H | H | H | H | 2-NHEt,4-F | 0 |
| E-0980 | H | H | H | H | H | 2-NHEt,5-F | 0 |
| E-0981 | H | H | H | H | H | 2-NHEt,6-F | 0 |
| E-0982 | H | H | H | H | H | 2-NHEt,3-Me | 0 |
| E-0983 | H | H | H | H | H | 2-NHEt,4-Me | 0 |
| E-0984 | H | H | H | H | H | 2-NHEt,5-Me | 0 |
| E-0985 | H | H | H | H | H | 2-NHEt,6-Me | 0 |
| E-0986 | H | H | H | H | H | 2-NMe₂,3-F | 0 |
| E-0987 | H | H | H | H | H | 2-NMe₂,4-F | 0 |
| E-0988 | H | H | H | H | H | 2-NMe₂,5-F | 0 |
| E-0989 | H | H | H | H | H | 2-NMe₂,6-F | 0 |
| E-0990 | H | H | H | H | H | 2-NMe₂,3-Me | 0 |
| E-0991 | H | H | H | H | H | 2-NMe₂,4-Me | 0 |
| E-0992 | H | H | H | H | H | 2-NMe₂,5-Me | 0 |
| E-0993 | H | H | H | H | H | 2-NMe₂,6-Me | 0 |
| E-0994 | H | H | H | H | H | 2-NEt₂,3-F | 0 |
| E-0995 | H | H | H | H | H | 2-NEt₂,4-F | 0 |
| E-0996 | H | H | H | H | H | 2-NEt₂,5-F | 0 |
| E-0997 | H | H | H | H | H | 2-NEt₂,6-F | 0 |
| E-0998 | H | H | H | H | H | 2-NEt₂,3-Me | 0 |
| E-0999 | H | H | H | H | H | 2-NEt₂,4-Me | 0 |
| E-1000 | H | H | H | H | H | 2-NEt₂,5-Me | 0 |
| E-1001 | H | H | H | H | H | 2-NEt₂,6-Me | 0 |
| E-1002 | H | H | H | H | H | 2-CHO,3-F | 0 |
| E-1003 | H | H | H | H | H | 2-CHO,4-F | 0 |
| E-1004 | H | H | H | H | H | 2-CHO,5-F | 0 |
| E-1005 | H | H | H | H | H | 2-CHO,6-F | 0 |
| E-1006 | H | H | H | H | H | 2-CHO,3-Me | 0 |
| E-1007 | H | H | H | H | H | 2-CHO,4-Me | 0 |
| E-1008 | H | H | H | H | H | 2-CHO,5-Me | 0 |
| E-1009 | H | H | H | H | H | 2-CHO,6-Me | 0 |
| E-1010 | H | H | H | H | H | 2-C(=O)OH,3-F | 0 |
| E-1011 | H | H | H | H | H | 2-C(=O)OH,4-F | 0 |
| E-1012 | H | H | H | H | H | 2-C(=O)OH,5-F | 0 |
| E-1013 | H | H | H | H | H | 2-C(=O)OH,6-F | 0 |
| E-1014 | H | H | H | H | H | 2-C(=O)OH,3-Me | 0 |
| E-1015 | H | H | H | H | H | 2-C(=O)OH,4-Me | 0 |
| E-1016 | H | H | H | H | H | 2-C(=O)OH,5-Me | 0 |
| E-1017 | H | H | H | H | H | 2-C(=O)OH,6-Me | 0 |
| E-1018 | H | H | H | H | H | 2-(1,3-dioxolan-2-yl),3-F | 0 |
| E-1019 | H | H | H | H | H | 2-(1,3-dioxolan-2-yl),4-F | 0 |
| E-1020 | H | H | H | H | H | 2-(1,3-dioxolan-2-yl),5-F | 0 |
| E-1021 | H | H | H | H | H | 2-(1,3-dioxolan-2-yl),6-F | 0 |

TABLE 273

| compound | R¹ | R² | R³ | R⁴ | R⁵ | (R⁸)ₘ | p |
|---|---|---|---|---|---|---|---|
| E-1022 | H | H | H | H | H | 2-(1,3-dioxolan-2-yl),3-Me | 0 |
| E-1023 | H | H | H | H | H | 2-(1,3-dioxolan-2-yl),4-Me | 0 |
| E-1024 | H | H | H | H | H | 2-(1,3-dioxolan-2-yl),5-Me | 0 |
| E-1025 | H | H | H | H | H | 2-(1,3-dioxolan-2-yl),6-Me | 0 |
| E-1026 | H | H | H | H | H | 2-(1,3-dioxolan-2-yl),3-F | 0 |
| E-1027 | H | H | H | H | H | 2-(1,3-dioxolan-2-yl),4-Me | 0 |
| E-1028 | H | H | H | H | H | 2-(1,3-dioxolan-2-yl),5 F | 0 |
| E-1029 | H | H | H | H | H | 2-(1,3-dioxolan-2-yl),6-F | 0 |
| E-1030 | H | H | H | H | H | 2-(1,3-dioxolan-2-yl),3-Me | 0 |
| E-1031 | H | H | H | H | H | 2-(1,3-dioxolan-2-yl),4-Me | 0 |
| E-1032 | H | H | H | H | H | 2-(1,3-dioxolan-2-yl),5-Me | 0 |
| E-1033 | H | H | H | H | H | 2-(1,3-dioxolan-2-yl),6-Me | 0 |
| E-1034 | H | H | H | H | H | 2-(thiazol-2-yl),3-F | 0 |
| E-1035 | H | H | H | H | H | 2-(thiazol-2-yl),4-F | 0 |
| E-1036 | H | H | H | H | H | 2-(thiazol-2-yl),5-F | 0 |
| E-1037 | H | H | H | H | H | 2-(thiazol-2-yl),6-F | 0 |
| E-1038 | H | H | H | H | H | 2-(thiazol-2-yl),3-Me | 0 |
| E-1039 | H | H | H | H | H | 2-(thiazol-2-yl),4-Me | 0 |
| E-1040 | H | H | H | H | H | 2-(thiazol-2-yl),5-Me | 0 |
| E-1041 | H | H | H | H | H | 2-(thiazol-2-yl),6-Me | 0 |
| E-1042 | H | H | H | H | H | 2-(oxazol-2-yl),3-F | 0 |
| E-1043 | H | H | H | H | H | 2-(oxazol-2-yl),4-F | 0 |
| E-1044 | H | H | H | H | H | 2-(oxazol-2-yl),5-F | 0 |
| E-1045 | H | H | H | H | H | 2-(oxazol-2-yl),6-F | 0 |
| E-1046 | H | H | H | H | H | 2-(oxazol-2-yl),3-Me | 0 |
| E-1047 | H | H | H | H | H | 2-(oxazol-2-yl),4-Me | 0 |
| E-1048 | H | H | H | H | H | 2-(oxazol-2-yl),5-Me | 0 |
| E-1049 | H | H | H | H | H | 2-(oxazol-2-yl),6-Me | 0 |
| E-1050 | H | H | H | H | H | 2-CH=NOH,3-F | 0 |
| E-1051 | H | H | H | H | H | 2-CH=NOH,4-F | 0 |
| E-1052 | H | H | H | H | H | 2-CH=NOH,5-F | 0 |
| E-1053 | H | H | H | H | H | 2-CH=NOH,6-F | 0 |
| E-1054 | H | H | H | H | H | 2-CH=NOH,3-Me | 0 |
| E-1055 | H | H | H | H | H | 2-CH=NOH,4-Me | 0 |
| E-1056 | H | H | H | H | H | 2-CH=NOH,5-Me | 0 |
| E-1057 | H | H | H | H | H | 2-CH=NOH,6-Me | 0 |
| E-1058 | H | H | H | H | H | 2-CH=NOMe,3-F | 0 |
| E-1059 | H | H | H | H | H | 2-CH=NOMe,4-F | 0 |
| E-1060 | H | H | H | H | H | 2-CH=NOMe,5-F | 0 |

TABLE 273-continued

| compound | R¹ | R² | R³ | R⁴ | R⁵ | (R⁸)ₘ | p |
|---|---|---|---|---|---|---|---|
| E-1061 | H | H | H | H | H | 2-CH=NOMe,6-F | 0 |
| E-1062 | H | H | H | H | H | 2-CH=NOMe,3-Me | 0 |
| E-1063 | H | H | H | H | H | 2-CH=NOMe,4-Me | 0 |
| E-1064 | H | H | H | H | H | 2-CH=NOMe,5-Me | 0 |
| E-1065 | H | H | H | H | H | 2-CH=NOMe,6-Me | 0 |
| E-1066 | H | H | H | H | H | 2-CN,3-F | 0 |
| E-1067 | H | H | H | H | H | 2-CN,4-F | 0 |
| E-1068 | H | H | H | H | H | 2-CN,5-F | 0 |
| E-1069 | H | H | H | H | H | 2-CN,6-F | 0 |
| E-1070 | H | H | H | H | H | 2-CN,3-Cl | 0 |
| E-1071 | H | H | H | H | H | 2-CN,4-Cl | 0 |
| E-1072 | H | H | H | H | H | 2-CN,5-Cl | 0 |
| E-1073 | H | H | H | H | H | 2-CN,6-C | 0 |
| E-1074 | H | H | H | H | H | 2-CN,3-Me | 0 |
| E-1075 | H | H | H | H | H | 2-CN,4-Me | 0 |
| E-1076 | H | H | H | H | H | 2-CN,5-Me | 0 |
| E-1077 | H | H | H | H | H | 2-CN,6-Me | 0 |
| E-1078 | H | H | H | H | H | 2-CN,3-OMe | 0 |

TABLE 274

| compound | R¹ | R² | R³ | R⁴ | R⁵ | (R⁸)ₘ | p |
|---|---|---|---|---|---|---|---|
| E-1079 | H | H | H | H | H | 2-CN,4-OMe | 0 |
| E-1080 | H | H | H | H | H | 2-CN,5-OMe | 0 |
| E-1081 | H | H | H | H | H | 2-CN,6-OMe | 0 |
| E-1082 | H | H | H | H | H | 3-CN,2-F | 0 |
| E-1083 | H | H | H | H | H | 3-CN,4-F | 0 |
| E-1084 | H | H | H | H | H | 3-CN,5-F | 0 |
| E-1085 | H | H | H | H | H | 3-CN,6-F | 0 |
| E-1086 | H | H | H | H | H | 3-CN,2-Cl | 0 |
| E-1087 | H | H | H | H | H | 3-CN,4-Cl | 0 |
| E-1088 | H | H | H | H | H | 3-CN,5-Cl | 0 |
| E-1089 | H | H | H | H | H | 3-CN,6-Cl | 0 |
| E-1090 | H | H | H | H | H | 3-CN,2-Me | 0 |
| E-1091 | H | H | H | H | H | 3-CN,4-Me | 0 |
| E-1092 | H | H | H | H | H | 3-CN,5 Me | 0 |
| E-1093 | H | H | H | H | H | 3-CN,6-Me | 0 |
| E-1094 | H | H | H | H | H | 3-CN,2-OMe | 0 |
| E-1095 | H | H | H | H | H | 3-CN,4-OMe | 0 |
| E-1096 | H | H | H | H | H | 3-CN,5-OMe | 0 |
| E-1097 | H | H | H | H | H | 3-CN,6-OMe | 0 |
| E-1098 | H | H | H | H | H | 4-CN,2-F | 0 |
| E-1099 | H | H | H | H | H | 4-CN,3-F | 0 |
| E-1100 | H | H | H | H | H | 4-CN,2-Cl | 0 |
| E-1101 | H | H | H | H | H | 4-CN,3-Cl | 0 |
| E-1102 | H | H | H | H | H | 4-CN,2-Me | 0 |
| E-1103 | H | H | H | H | H | 4-CN,3-Me | 0 |
| E-1104 | H | H | H | H | H | 4-CN,2-OMe | 0 |
| E-1105 | H | H | H | H | H | 4-CN,3-OMe | 0 |
| E-1106 | H | H | H | H | H | 2-NO₂,3-F | 0 |
| E-1107 | H | H | H | H | H | 2-NO₂,4-F | 0 |
| E-1108 | H | H | H | H | H | 2-NO₂,5-F | 0 |
| E-1109 | H | H | H | H | H | 2-NO₂,6-F | 0 |
| E-1110 | H | H | H | H | H | 2-NO₂,3-Me | 0 |
| E-1111 | H | H | H | H | H | 2-NO₂,4-Me | 0 |
| E-1112 | H | H | H | H | H | 2-NO₂,5-Me | 0 |
| E-1113 | H | H | H | H | H | 2-NO₂,6-Me | 0 |
| E-1114 | H | H | H | H | H | 2-Me,3,4-F₂ | 0 |
| E-1115 | H | H | H | H | H | 2-Me,3,5-F₂ | 0 |
| E-1116 | H | H | H | H | H | 2-Me,3,6-F₂ | 0 |
| E-1117 | H | H | H | H | H | 2-Me,4,5-F₂ | 0 |
| E-1118 | H | H | H | H | H | 2-OMe,3,4-F₂ | 0 |
| E-1119 | H | H | H | H | H | 2-OMe,3,5-F₂ | 0 |
| E-1120 | H | H | H | H | H | 2-OMe,3,6-F₂ | 0 |
| E-1121 | H | H | H | H | H | 2-OMe,4,5-F₂ | 0 |
| E-1122 | H | H | H | H | H | 2-(CH₂)₃-3 | 0 |
| E-1123 | H | H | H | H | H | 2-(CH₂)₄-3 | 0 |
| E-1124 | H | H | H | H | H | 2-(OCH₂CH₂)-3 | 0 |
| E-1125 | H | H | H | H | H | 2-(OCH₂CH₂)-3 | 0 |
| E-1126 | H | H | H | H | H | 2-(CH₂CH₂O)-3 | 0 |
| E-1127 | H | H | H | H | H | 2-(CH₂CH₂CH₂O)-3 | 0 |
| E-1128 | H | H | H | H | H | 3-(CH₂)₃-4 | 0 |
| E-1129 | H | H | H | H | H | 3-(CH₂)₄-4 | 0 |
| E-1130 | H | H | H | H | H | 3-(OCH₂CH₂)-4 | 0 |

TABLE 274-continued

| compound | R¹ | R² | R³ | R⁴ | R⁵ | (R⁸)ₘ | p |
|---|---|---|---|---|---|---|---|
| E-1131 | H | H | H | H | H | 3-(OCH₂CH₂CH₂)-4 | 0 |
| E-1132 | H | H | H | H | H | 3-(CH₂CH₂O)-4 | 0 |
| E-1133 | H | H | H | H | H | 3-(CH₂CH₂CH₂O)-4 | 0 |
| E-1134 | H | H | H | H | H | 2-(OCH₂O)-3 | 0 |
| E-1135 | H | H | H | H | H | 3-OCH₂O)-4 | 0 |

TABLE 275

| compound | R¹ | R² | R³ | R⁴ | R⁵ | (R⁸)ₘ | p |
|---|---|---|---|---|---|---|---|
| E-1136 | H | H | H | H | H | 2-(OCH₂CH₂O)-3 | 0 |
| E-1137 | H | H | H | H | H | 3-(OCH₂CH₂O)-4 | 0 |
| E-1138 | H | H | H | H | H | 2-(OCF₂O)-3 | 0 |
| E-1139 | H | H | H | H | H | 3-(OCF₂O)-4 | 0 |
| E-1140 | H | H | H | H | H | 2-Me,6-Et | 0 |
| E-1141 | H | H | H | H | H | 2-CH₂OTBS | 0 |
| E-1142 | H | H | H | H | H | 2-cyclopropyl,3-OMe | 0 |
| E-1143 | H | H | H | H | H | 2-cyclopropyl,4-OMe | 0 |
| E-1144 | H | H | H | H | H | 2-cyclopropyl,5-OMe | 0 |
| E-1145 | H | H | H | H | H | 2-cyclopropyl,6-OMe | 0 |
| E-1146 | H | H | H | H | H | 2-Me,3-OMe,6 Me | 0 |
| E-1147 | H | H | H | H | H | 2-Me,4-OMe,6-Me | 0 |
| E-1148 | H | H | H | H | H | 2-OMe,3-Me,6-Me | 0 |
| E-1149 | H | H | H | H | H | 2-OMe,5-Me,6-Me | 0 |
| E-1150 | H | H | H | H | H | 2-OMe,3-F,6-Me | 0 |
| E-1151 | H | H | H | H | H | 2-OMe,5-F,6-Me | 0 |
| E-1152 | H | H | H | H | H | 2-OMe,5-Me,6-F | 0 |
| E-1153 | H | H | H | H | H | 2-Cl,3-Me,6-F | 0 |
| E-1154 | H | H | H | H | H | 2-Cl,5-Me,6-F | 0 |
| E-1155 | H | H | H | H | H | 2-Cl,3-OMe,6-F | 0 |
| E-1156 | H | H | H | H | H | 2-Cl,5-OMe,6-F | 0 |
| E-1157 | H | H | H | H | H | 2-Me,5-Et | 0 |
| E-1158 | H | H | H | H | H | 2,6-Et₂ | 0 |
| E-1159 | H | H | H | H | H | 2-Et,6-F | 0 |
| E-1160 | H | H | H | H | H | 2-CH₂OCH₃,6-Cl | 0 |
| E-1161 | H | H | H | H | H | 2-CH₂OCH₂CH₃,6-Cl | 0 |
| E-1162 | H | H | H | H | H | 2-OMe,5-CH=NOMe | 0 |
| E-1163 | H | H | H | H | H | 2-CH₂NMe₂ | 0 |
| E-1164 | H | H | H | H | H | 2-CH₂OCH₃,6-CF₃ | 0 |
| E-1165 | H | H | F | H | H | 2-Me | 0 |

TABLE 276

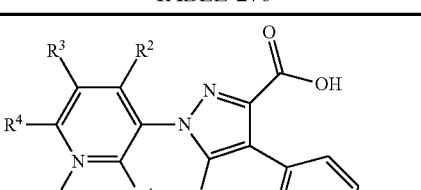

| compound | R¹ | R² | R³ | R⁴ | R⁵ | (R⁸)ₙ | p |
|---|---|---|---|---|---|---|---|
| E-5001 | H | H | H | H | H | H | 1 |
| E-5002 | H | H | H | H | H | 2-F | 1 |
| E-5003 | H | H | H | H | H | 3-F | 1 |
| E-5004 | H | H | H | H | H | 4-F | 1 |
| E-5005 | H | H | H | H | H | 2-Cl | 1 |
| E-5006 | H | H | H | H | H | 3-Cl | 1 |
| E-5007 | H | H | H | H | H | 4-Cl | 1 |
| E-5008 | H | H | H | H | H | 2-Br | 1 |
| E-5009 | H | H | H | H | H | 3-Br | 1 |
| E-5010 | H | H | H | H | H | 4-Br | 1 |
| E-5011 | H | H | H | H | H | 2-I | 1 |
| E-5012 | H | H | H | H | H | 3-I | 1 |
| E-5013 | H | H | H | H | H | 4-I | 1 |
| E-5014 | H | H | H | H | H | 2-OH | 1 |
| E-5015 | H | H | H | H | H | 3-OH | 1 |
| E-5016 | H | H | H | H | H | 4-OH | 1 |
| E-5017 | H | H | H | H | H | 2-SH | 1 |

TABLE 276-continued

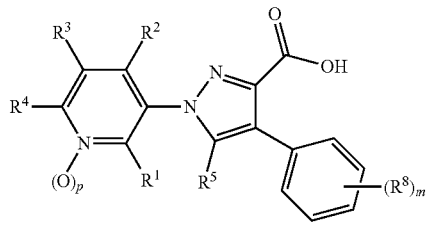

| compound | R¹ | R² | R³ | R⁴ | R⁵ | (R⁸)$_m$ | p |
|---|---|---|---|---|---|---|---|
| E-5018 | H | H | H | H | H | 3-SH | 1 |
| E-5019 | H | H | H | H | H | 4-SH | 1 |
| E-5020 | H | H | H | H | H | 2-Me | 1 |
| E-5021 | H | H | H | H | H | 3-Me | 1 |
| E-5022 | H | H | H | H | H | 4-Me | 1 |
| E-5023 | H | H | H | H | H | 2-Et | 1 |
| E-5024 | H | H | H | H | H | 3-Et | 1 |
| E-5025 | H | H | H | H | H | 4-Et | 1 |
| E-5026 | H | H | H | H | H | 2-Pr | 1 |
| E-5027 | H | H | H | H | H | 3-Pr | 1 |
| E-5028 | H | H | H | H | H | 4-Pr | 1 |
| E-5029 | H | H | H | H | H | 2-i-Pr | 1 |
| E-5030 | H | H | H | H | H | 3-i-Pr | 1 |
| E-5031 | H | H | H | H | H | 4-i-Pr | 1 |
| E-5032 | H | H | H | H | H | 2-Bu | 1 |
| E-5033 | H | H | H | H | H | 3-Bu | 1 |
| E-5034 | H | H | H | H | H | 4-Bu | 1 |
| E-5035 | H | H | H | H | H | 2-s-Bu | 1 |
| E-5036 | H | H | H | H | H | 3-s-Bu | 1 |
| E-5037 | H | H | H | H | H | 4-s-Bu | 1 |
| E-5038 | H | H | H | H | H | 2-i-Bu | 1 |
| E-5039 | H | H | H | H | H | 3-i-Bu | 1 |
| E-5040 | H | H | H | H | H | 4-i-Bu | 1 |
| E-5041 | H | H | H | H | H | 2-t-Bu | 1 |
| E-5042 | H | H | H | H | H | 3-t-Bu | 1 |
| E-5043 | H | H | H | H | H | 4-t-Bu | 1 |
| E-5044 | H | H | H | H | H | 2-CF₃ | 1 |
| E-5045 | H | H | H | H | H | 3-CF₃ | 1 |
| E-5046 | H | H | H | H | H | 4-CF₃ | 1 |
| E-5047 | H | H | H | H | H | 2-CHF₂ | 1 |
| E-5048 | H | H | H | H | H | 3-CHF₂ | 1 |
| E-5049 | H | H | H | H | H | 4-CHF₂ | 1 |
| E-5050 | H | H | H | H | H | 2-CH₂F | 1 |
| E-5051 | H | H | H | H | H | 3-CH₂F | 1 |
| E-5052 | H | H | H | H | H | 4-CH₂F | 1 |

TABLE 277

| compound | R¹ | R² | R³ | R⁴ | R⁵ | (R⁸)$_m$ | p |
|---|---|---|---|---|---|---|---|
| E-5053 | H | H | H | H | H | 2-CF₂Cl | 1 |
| E-5054 | H | H | H | H | H | 3-CF₂Cl | 1 |
| E-5055 | H | H | H | H | H | 4-CF₂Cl | 1 |
| E-5056 | H | H | H | H | H | 2-CF(CF₃)₂ | 1 |
| E-5057 | H | H | H | H | H | 3-CF(CF₃)₂ | 1 |
| E-5058 | H | H | H | H | H | 4-CF(CF₃)₂ | 1 |
| E-5059 | H | H | H | H | H | 2-cyclopropyl | 1 |
| E-5060 | H | H | H | H | H | 3-cyclopropyl | 1 |
| E-5061 | H | H | H | H | H | 4-cyclopropyl | 1 |
| E-5062 | H | H | H | H | H | 2-cyclobutyl | 1 |
| E-5063 | H | H | H | H | H | 3-cyclobutyl | 1 |
| E-5064 | H | H | H | H | H | 4-cyclobutyl | 1 |
| E-5065 | H | H | H | H | H | 2-cyclopentyl | 1 |
| E-5066 | H | H | H | H | H | 3-cyclopentyl | 1 |
| E-5067 | H | H | H | H | H | 4-cyclopentyl | 1 |
| E-5068 | H | H | H | H | H | 2-(cyclopropylmethyl) | 1 |
| E-5069 | H | H | H | H | H | 3-(cyclopropylmethyl) | 1 |
| E-5070 | H | H | H | H | H | 4-(cyclopropylmethyl) | 1 |
| E-5071 | H | H | H | H | H | 2-(cyclobutylmethyl) | 1 |
| E-5072 | H | H | H | H | H | 3-(cyclobutylmethyl) | 1 |
| E-5073 | H | H | H | H | H | 4-(cyclobutylmethyl) | 1 |
| E-5074 | H | H | H | H | H | 2-(cyclopentylmethyl) | 1 |
| E-5075 | H | H | H | H | H | 3-(cyclopentylmethyl) | 1 |
| E-5076 | H | H | H | H | H | 4-(cyclopentylmethyl) | 1 |

TABLE 277-continued

| compound | R¹ | R² | R³ | R⁴ | R⁵ | (R⁸)$_m$ | p |
|---|---|---|---|---|---|---|---|
| E-5077 | H | H | H | H | H | 2-(cyclopropylethyl) | 1 |
| E-5078 | H | H | H | H | H | 3-(cyclopropylethyl) | 1 |
| E-5079 | H | H | H | H | H | 4-(cyclopropylethyl) | 1 |
| E-5080 | H | H | H | H | H | 2-(2,2-difluorocyclopropyl) | 1 |
| E-5081 | H | H | H | H | H | 3-(2,2-difluorocyclopropyl) | 1 |
| E-5082 | H | H | H | H | H | 4-(2,2-difluorocyclopropyl) | 1 |
| E-5083 | H | H | H | H | H | 2-(2,2-dichlorocyclopropyl) | 1 |
| E-5084 | H | H | H | H | H | 3-(2,2-dichlorocyclopropyl) | 1 |
| E-5085 | H | H | H | H | H | 4-(2,2-dichlorocyclopropyl) | 1 |
| E-5086 | H | H | H | H | H | 2-ethenyl | 1 |
| E-5087 | H | H | H | H | H | 3-ethenyl | 1 |
| E-5088 | H | H | H | H | H | 4-ethenyl | 1 |
| E-5089 | H | H | H | H | H | 2-allyl | 1 |
| E-5090 | H | H | H | H | H | 3-allyl | 1 |
| E-5091 | H | H | H | H | H | 4-allyl | 1 |
| E-5092 | H | H | H | H | H | 2-(prop-1-en-1-yl) | 1 |
| E-5093 | H | H | H | H | H | 3-(prop-1-en-1-yl) | 1 |
| E-5094 | H | H | H | H | H | 4-(prop-1-en-1-yl) | 1 |
| E-5095 | H | H | H | H | H | 2-(trifluoroethenyl) | 1 |
| E-5096 | H | H | H | H | H | 3-(trifluoroethenyl) | 1 |
| E-5097 | H | H | H | H | H | 4-(trifluoroethenyl) | 1 |
| E-5098 | H | H | H | H | H | 2-(2,2-dichloroethenyl) | 1 |
| E-5099 | H | H | H | H | H | 3-(2,2-dichloroethenyl) | 1 |
| E-5100 | H | H | H | H | H | 4-(2,2-dichloroethenyl) | 1 |
| E-5101 | H | H | H | H | H | 2-ethynyl | 1 |
| E-5102 | H | H | H | H | H | 3-ethynyl | 1 |
| E-5103 | H | H | H | H | H | 4-ethynyl | 1 |
| E-5104 | H | H | H | H | H | 2-(1-propyn-1-yl) | 1 |
| E-5105 | H | H | H | H | H | 3-(1-propyn-1-yl) | 1 |
| E-5106 | H | H | H | H | H | 4-(1-propyn-1-yl) | 1 |
| E-5107 | H | H | H | H | H | 2-(2-propyn-1-yl) | 1 |
| E-5108 | H | H | H | H | H | 3-(2-propyn-1-yl) | 1 |
| E-5109 | H | H | H | H | H | 4-(2-propyn-1-yl) | 1 |

TABLE 278

| compound | R¹ | R² | R³ | R⁴ | R⁵ | (R⁸)$_m$ | p |
|---|---|---|---|---|---|---|---|
| E-5110 | H | H | H | H | H | 2-(2-cyclopropylethynyl) | 1 |
| E-5111 | H | H | H | H | H | 3-(2-cyclopropylethynyl) | 1 |
| E-5112 | H | H | H | H | H | 4-(2-cyclopropylethynyl) | 1 |
| E-5113 | H | H | H | H | H | 2-(2-chloroethynyl) | 1 |
| E-5114 | H | H | H | H | H | 3-(2-chloroethynyl) | 1 |
| E-5115 | H | H | H | H | H | 4-(2-chloroethynyl) | 1 |
| E-5116 | H | H | H | H | H | 2-(2-bromoethynyl) | 1 |
| E-5117 | H | H | H | H | H | 3-(2-bromoethynyl) | 1 |
| E-5118 | H | H | H | H | H | 4-(2-bromoethynyl) | 1 |
| E-5119 | H | H | H | H | H | 2-OMe | 1 |
| E-5120 | H | H | H | H | H | 3-OMe | 1 |
| E-5121 | H | H | H | H | H | 4-OMe | 1 |
| E-5122 | H | H | H | H | H | 2-OEt | 1 |
| E-5123 | H | H | H | H | H | 3-OEt | 1 |
| E-5124 | H | H | H | H | H | 4-OEt | 1 |
| E-5125 | H | H | H | H | H | 2-OPr | 1 |
| E-5126 | H | H | H | H | H | 3-OPr | 1 |
| E-5127 | H | H | H | H | H | 4-OPr | 1 |
| E-5128 | H | H | H | H | H | 2-O(i-Pr) | 1 |
| E-5129 | H | H | H | H | H | 3-O(i-Pr) | 1 |
| E-5130 | H | H | H | H | H | 4-O(i-Pr) | 1 |
| E-5131 | H | H | H | H | H | 2-OBu | 1 |
| E-5132 | H | H | H | H | H | 3-OBu | 1 |
| E-5133 | H | H | H | H | H | 4-OBu | 1 |
| E-5134 | H | H | H | H | H | 2-O(s-Bu) | 1 |
| E-5135 | H | H | H | H | H | 3-O(s-Bu) | 1 |
| E-5136 | H | H | H | H | H | 4-O(s-Bu) | 1 |
| E-5137 | H | H | H | H | H | 2-O(i-Bu) | 1 |
| E-5138 | H | H | H | H | H | 3-O(i-Bu) | 1 |
| E-5139 | H | H | H | H | H | 4-O(i-Bu) | 1 |
| E-5140 | H | H | H | H | H | 2-O(t-Bu) | 1 |
| E-5141 | H | H | H | H | H | 3-O(t-Bu) | 1 |
| E-5142 | H | H | H | H | H | 4-O(t-Bu) | 1 |
| E-5143 | H | H | H | H | H | 2-OCF₃ | 1 |
| E-5144 | H | H | H | H | H | 3-OCF₃ | 1 |
| E-5145 | H | H | H | H | H | 4-OCF₃ | 1 |
| E-5146 | H | H | H | H | H | 2-OCHF₂ | 1 |

TABLE 278-continued

| compound | R¹ | R² | R³ | R⁴ | R⁵ | (R⁸)ₘ | p |
|---|---|---|---|---|---|---|---|
| E-5147 | H | H | H | H | H | 3-OCHF₂ | 1 |
| E-5148 | H | H | H | H | H | 4-OCHF₂ | 1 |
| E-5149 | H | H | H | H | H | 2-OCH₂CF₃ | 1 |
| E-5150 | H | H | H | H | H | 3-OCH₂CF₃ | 1 |
| E-5151 | H | H | H | H | H | 4-OCH₂CF₃ | 1 |
| E-5152 | H | H | H | H | H | 2-(cyclopropyloxy) | 1 |
| E-5153 | H | H | H | H | H | 3-(cyclopropyloxy) | 1 |
| E-5154 | H | H | H | H | H | 4-(cyclopropyloxy) | 1 |
| E-5155 | H | H | H | H | H | 2-(cyclobutyloxy) | 1 |
| E-5156 | H | H | H | H | H | 3-(cyclobutyloxy) | 1 |
| E-5157 | H | H | H | H | H | 4-(cyclobutyloxy) | 1 |
| E-5158 | H | H | H | H | H | 2-(cyclopentyloxy) | 1 |
| E-5159 | H | H | H | H | H | 3-(cyclopentyloxy) | 1 |
| E-5160 | H | H | H | H | H | 4-(cyclopentyloxy) | 1 |
| E-5161 | H | H | H | H | H | 2-((2,2-dichlorocyclopropyl)oxy) | 1 |
| E-5162 | H | H | H | H | H | 3-((2,2-dichlorocyclopropyl)oxy) | 1 |
| E-5163 | H | H | H | H | H | 4-((2,2-dichlorocyclopropyl)oxy) | 1 |
| E-5164 | H | H | H | H | H | 2-(cyclopropylmethoxy) | 1 |
| E-5165 | H | H | H | H | H | 3-(cyclopropylmethoxy) | 1 |
| E-5166 | H | H | H | H | H | 4-(cyclopropylmethoxy) | 1 |

TABLE 279

| compound | R¹ | R² | R³ | R⁴ | R⁵ | (R⁸)ₘ | p |
|---|---|---|---|---|---|---|---|
| E-5167 | H | H | H | H | H | 2-((2,2-difluorocyclopropyl)methoxy) | 1 |
| E-5168 | H | H | H | H | H | 3-((2,2-difluorocyclopropyl)methoxy) | 1 |
| E-5169 | H | H | H | H | H | 4-((2,2-difluorocyclopropyl)methoxy) | 1 |
| E-5170 | H | H | H | H | H | 2-(oxiran-2-yl) | 1 |
| E-5171 | H | H | H | H | H | 3-(oxiran-2-yl) | 1 |
| E-5172 | H | H | H | H | H | 4-(oxiran-2-yl) | 1 |
| E-5173 | H | H | H | H | H | 2-(oxiran-2-ylmethyl) | 1 |
| E-5174 | H | H | H | H | H | 3-(oxiran-2-ylmethyl) | 1 |
| E-5175 | H | H | H | H | H | 4-(oxiran-2-ylmethyl) | 1 |
| E-5176 | H | H | H | H | H | 2-SMe | 1 |
| E-5177 | H | H | H | H | H | 3-SMe | 1 |
| E-5178 | H | H | H | H | H | 4-SMe | 1 |
| E-5179 | H | H | H | H | H | 2-SEt | 1 |
| E-5180 | H | H | H | H | H | 3-SEt | 1 |
| E-5181 | H | H | H | H | H | 4-SEt | 1 |
| E-5182 | H | H | H | H | H | 2-S(=O)Me | 1 |
| E-5183 | H | H | H | H | H | 3-S(=O)Me | 1 |
| E-5184 | H | H | H | H | H | 4-S(=O)Me | 1 |
| E-5185 | H | H | H | H | H | 2-S(=O)₂Me | 1 |
| E-5186 | H | H | H | H | H | 3-S(=O)₂Me | 1 |
| E-5187 | H | H | H | H | H | 4-S(=O)₂Me | 1 |
| E-5188 | H | H | H | H | H | 2-SCF₃ | 1 |
| E-5189 | H | H | H | H | H | 3-SCF₃ | 1 |
| E-5190 | H | H | H | H | H | 4-SCF₃ | 1 |
| E-5191 | H | H | H | H | H | 2-S(=O)CF₃ | 1 |
| E-5192 | H | H | H | H | H | 3-S(=O)CF₃ | 1 |
| E-5193 | H | H | H | H | H | 4-S(=O)CF₃ | 1 |
| E-5194 | H | H | H | H | H | 2-S(=O)₂CF₃ | 1 |
| E-5195 | H | H | H | H | H | 3-S(=O)₂CF₃ | 1 |
| E-5196 | H | H | H | H | H | 4-S(=O)₂CF₃ | 1 |
| E-5197 | H | H | H | H | H | 2-SCF(CF₃)₂ | 1 |
| E-5198 | H | H | H | H | H | 3-SCF(CF₃)₂ | 1 |
| E-5199 | H | H | H | H | H | 4-SCF(CF₃)₂ | 1 |
| E-5200 | H | H | H | H | H | 2-(cyclopropylthio) | 1 |
| E-5201 | H | H | H | H | H | 3-(cyclopropylthio) | 1 |
| E-5202 | H | H | H | H | H | 4-(cyclopropylthio) | 1 |
| E-5203 | H | H | H | H | H | 2-(cyclopropylsulfinyl) | 1 |
| E-5204 | H | H | H | H | H | 3-(cyclopropylsulfinyl) | 1 |
| E-5205 | H | H | H | H | H | 4-(cyclopropylsulfinyl) | 1 |
| E-5206 | H | H | H | H | H | 2-(cyclopropylsulfonyl) | 1 |
| E-5207 | H | H | H | H | H | 3-(cyclopropylsulfonyl) | 1 |
| E-5208 | H | H | H | H | H | 4-(cyclopropylsulfonyl) | 1 |
| E-5209 | H | H | H | H | H | 2-((cyclopropylmethyl)thio) | 1 |
| E-5210 | H | H | H | H | H | 3-((cyclopropylmethyl)thio) | 1 |
| E-5211 | H | H | H | H | H | 4-((cyclopropylmethyl)thio) | 1 |
| E-5212 | H | H | H | H | H | 2-((cyclopropylmethyl)sulfinyl) | 1 |
| E-5213 | H | H | H | H | H | 3-((cyclopropylmethyl)sulfinyl) | 1 |
| E-5214 | H | H | H | H | H | 4-((cyclopropylmethyl)sulfinyl) | 1 |
| E-5215 | H | H | H | H | H | 2-((cyclopropylmethyl)sulfonyl) | 1 |

TABLE 279-continued

| compound | R¹ | R² | R³ | R⁴ | R⁵ | (R⁸)ₘ | p |
|---|---|---|---|---|---|---|---|
| E-5216 | H | H | H | H | H | 3-((cyclopropylmethyl)sulfonyl) | 1 |
| E-5217 | H | H | H | H | H | 4-((cyclopropylmethyl)sulfonyl) | 1 |
| E-5218 | H | H | H | H | H | 2-(((2,2-difluorocyclopropyl)methyl)thio) | 1 |
| E-5219 | H | H | H | H | H | 3-(((2,2-difluorocyclopropyl)methyl)thio) | 1 |
| E-5220 | H | H | H | H | H | 4-(((2,2-difluorocyclopropyl)methyl)thio) | 1 |
| E-5221 | H | H | H | H | H | 2-(((2,2-difluorocyclopropyl)methyl)sulfinyl) | 1 |
| E-5222 | H | H | H | H | H | 3-(((2,2-difluorocyclopropyl)methyl)sulfinyl) | 1 |
| E-5223 | H | H | H | H | H | 4-(((2,2-difluorocyclopropyl)methyl)sulfinyl) | 1 |

TABLE 280

| compound | R¹ | R² | R³ | R⁴ | R⁵ | (R⁸)ₘ | p |
|---|---|---|---|---|---|---|---|
| E-5224 | H | H | H | H | H | 2-(((2,2-difluorocyclopropyl)methyl)sulfonyl) | 1 |
| E-5225 | H | H | H | H | H | 3-(((2,2-difluorocyclopropyl)methyl)sulfonyl) | 1 |
| E-5226 | H | H | H | H | H | 4-(((2,2-difluorocyclopropyl)methyl)sulfonyl) | 1 |
| E-5227 | H | H | H | H | H | 2-C(=O)Me | 1 |
| E-5228 | H | H | H | H | H | 3-C(=O)Me | 1 |
| E-5229 | H | H | H | H | H | 4-C(=O)Me | 1 |
| E-5230 | H | H | H | H | H | 2-C(=O)Et | 1 |
| E-5231 | H | H | H | H | H | 3-C(=O)Et | 1 |
| E-5232 | H | H | H | H | H | 4-C(=O)Et | 1 |
| E-5233 | H | H | H | H | H | 2-C(=O)CF₃ | 1 |
| E-5234 | H | H | H | H | H | 3-C(=O)CF₃ | 1 |
| E-5235 | H | H | H | H | H | 4-C(=O)CF₃ | 1 |
| E-5236 | H | H | H | H | H | 2-C(=O)OMe | 1 |
| E-5237 | H | H | H | H | H | 3-C(=O)OMe | 1 |
| E-5238 | H | H | H | H | H | 4-C(=O)OMe | 1 |
| E-5239 | H | H | H | H | H | 2-C(=O)OEt | 1 |
| E-5240 | H | H | H | H | H | 3-C(=O)OEt | 1 |
| E-5241 | H | H | H | H | H | 4-C(=O)OEt | 1 |
| E-5242 | H | H | H | H | H | 2-C(=O)NH₂ | 1 |
| E-5243 | H | H | H | H | H | 3-C(=O)NH₂ | 1 |
| E-5244 | H | H | H | H | H | 4-C(=O)NH₂ | 1 |
| E-5245 | H | H | H | H | H | 2-C(=O)NHMe | 1 |
| E-5246 | H | H | H | H | H | 3-C(=O)NHMe | 1 |
| E-5247 | H | H | H | H | H | 4-C(=O)NHMe | 1 |
| E-5248 | H | H | H | H | H | 2-C(=O)NMe₂ | 1 |
| E-5249 | H | H | H | H | H | 3-C(=O)NMe₂ | 1 |
| E-5250 | H | H | H | H | H | 4-C(=O)NMe₂ | 1 |
| E-5251 | H | H | H | H | H | 2-CH₂C(=O)CH₃ | 1 |
| E-5252 | H | H | H | H | H | 3-CH₂C(=O)CH₃ | 1 |
| E-5253 | H | H | H | H | H | 4-CH₂C(=O)CH₃ | 1 |
| E-5254 | H | H | H | H | H | 2-CH₂C(=O)CF₃ | 1 |
| E-5255 | H | H | H | H | H | 3-CH₂C(=O)CF₃ | 1 |
| E-5256 | H | H | H | H | H | 4-CH₂C(=O)CF₃ | 1 |
| E-5257 | H | H | H | H | H | 2-CH₂C(=O)OCH₃ | 1 |
| E-5258 | H | H | H | H | H | 3-CH₂C(=O)OCH₃ | 1 |
| E-5259 | H | H | H | H | H | 4-CH₂C(=O)OCH₃ | 1 |
| E-5260 | H | H | H | H | H | 2-CH₂OH | 1 |
| E-5261 | H | H | H | H | H | 3-CH₂OH | 1 |
| E-5262 | H | H | H | H | H | 4-CH₂OH | 1 |
| E-5263 | H | H | H | H | H | 2-CH₂OCH₃ | 1 |
| E-5264 | H | H | H | H | H | 3-CH₂OCH₃ | 1 |
| E-5265 | H | H | H | H | H | 4-CH₂OCH₃ | 1 |
| E-5266 | H | H | H | H | H | 2-CH₂OCH₂CH₃ | 1 |
| E-5267 | H | H | H | H | H | 3-CH₂OCH₂CH₃ | 1 |
| E-5268 | H | H | H | H | H | 4-CH₂OCH₂CH₃ | 1 |
| E-5269 | H | H | H | H | H | 2-CH(CH₃)OCH₃ | 1 |
| E-5270 | H | H | H | H | H | 3-CH(CH₃)OCH₃ | 1 |
| E-5271 | H | H | H | H | H | 4-CH(CH₃)OCH₃ | 1 |
| E-5272 | H | H | H | H | H | 2-CH₂CH₂OCH₃ | 1 |
| E-5273 | H | H | H | H | H | 3-CH₂CH₂OCH₃ | 1 |
| E-5274 | H | H | H | H | H | 4-CH₂CH₂OCH₃ | 1 |

TABLE 280-continued

| compound | R¹ | R² | R³ | R⁴ | R⁵ | (R⁸)ₘ | p |
|---|---|---|---|---|---|---|---|
| E-5275 | H | H | H | H | H | 2-CH$_2$OCF$_3$ | 1 |
| E-5276 | H | H | H | H | H | 3-CH$_2$OCF$_3$ | 1 |
| E-5277 | H | H | H | H | H | 4-CH$_2$OCF$_3$ | 1 |
| E-5278 | H | H | H | H | H | 2-CF$_2$OCH$_3$ | 1 |
| E-5279 | H | H | H | H | H | 3-CF$_2$OCH$_3$ | 1 |
| E-5280 | H | H | H | H | H | 4-CF$_2$OCH$_3$ | 1 |

TABLE 281

| compound | R¹ | R² | R³ | R⁴ | R⁵ | (R⁸)ₘ | p |
|---|---|---|---|---|---|---|---|
| E-5281 | H | H | H | H | H | 2-CF$_2$CF$_2$OCF$_3$ | 1 |
| E-5282 | H | H | H | H | H | 3-CF$_2$CF$_2$OCF$_3$ | 1 |
| E-5283 | H | H | H | H | H | 4-CF$_2$CF$_2$OCF$_3$ | 1 |
| E-5284 | H | H | H | H | H | 2-OC(=O)CH$_3$ | 1 |
| E-5285 | H | H | H | H | H | 3-OC(=O)CH$_3$ | 1 |
| E-5286 | H | H | H | H | H | 4-OC(=O)CH$_3$ | 1 |
| E-5287 | H | H | H | H | H | 2-OC(=O)CF$_3$ | 1 |
| E-5288 | H | H | H | H | H | 3-OC(=O)CF$_3$ | 1 |
| E-5289 | H | H | H | H | H | 4-OC(=O)CF$_3$ | 1 |
| E-5290 | H | H | H | H | H | 2-OC(=O)NH$_2$ | 1 |
| E-5291 | H | H | H | H | H | 3-OC(=O)NH$_2$ | 1 |
| E-5292 | H | H | H | H | H | 4-OC(=O)NH$_2$ | 1 |
| E-5293 | H | H | H | H | H | 2-OC(=O)NHCH$_3$ | 1 |
| E-5294 | H | H | H | H | H | 3-OC(=O)NHCH$_3$ | 1 |
| E-5295 | H | H | H | H | H | 4-OC(=O)NHCH$_3$ | 1 |
| E-5296 | H | H | H | H | H | 2-OC(=O)N(CH$_3$)$_2$ | 1 |
| E-5297 | H | H | H | H | H | 3-OC(=O)N(CH$_3$)$_2$ | 1 |
| E-5298 | H | H | H | H | H | 4-OC(=O)N(CH$_3$)$_2$ | 1 |
| E-5299 | H | H | H | H | H | 2-CH$_2$OC(=O)NH$_2$ | 1 |
| E-5300 | H | H | H | H | H | 3-CH$_2$OC(=O)NH$_2$ | 1 |
| E-5301 | H | H | H | H | H | 4-CH$_2$OC(=O)NH$_2$ | 1 |
| E-5302 | H | H | H | H | H | 2-CH$_2$OC(=O)NHCH$_3$ | 1 |
| E-5303 | H | H | H | H | H | 3-CH$_2$OC(=O)NHCH$_3$ | 1 |
| E-5304 | H | H | H | H | H | 4-CH$_2$OC(=O)NHCH$_3$ | 1 |
| E-5305 | H | H | H | H | H | 2-CH$_2$OC(=O)N(CH$_3$)$_2$ | 1 |
| E-5306 | H | H | H | H | H | 3-CH$_2$OC(=O)N(CH$_3$)$_2$ | 1 |
| E-5307 | H | H | H | H | H | 4-CH$_2$OC(=O)N(CH$_3$)$_2$ | 1 |
| E-5308 | H | H | H | H | H | 2-OC(=O)OCH$_3$ | 1 |
| E-5309 | H | H | H | H | H | 3-OC(=O)OCH$_3$ | 1 |
| E-5310 | H | H | H | H | H | 4-OC(=O)OCH$_3$ | 1 |
| E-5311 | H | H | H | H | H | 2-CH$_2$OC(=O)OCH$_3$ | 1 |
| E-5312 | H | H | H | H | H | 3-CH$_2$OC(=O)OCH$_3$ | 1 |
| E-5313 | H | H | H | H | H | 4-CH$_2$OC(=O)OCH$_3$ | 1 |
| E-5314 | H | H | H | H | H | 2-CH$_2$OC(=O)CH$_3$ | 1 |
| E-5315 | H | H | H | H | H | 3-CH$_2$OC(=O)CH$_3$ | 1 |
| E-5316 | H | H | H | H | H | 4-CH$_2$OC(=O)CH$_3$ | 1 |
| E-5317 | H | H | H | H | H | 2-OS(=O)$_2$CH$_3$ | 1 |
| E-5318 | H | H | H | H | H | 3-OS(=O)$_2$CH$_3$ | 1 |
| E-5319 | H | H | H | H | H | 4-OS(=O)$_2$CH$_3$ | 1 |
| E-5320 | H | H | H | H | H | 2-CH$_2$SCH$_3$ | 1 |
| E-5321 | H | H | H | H | H | 3-CH$_2$SCH$_3$ | 1 |
| E-5322 | H | H | H | H | H | 4-CH$_2$SCH$_3$ | 1 |
| E-5323 | H | H | H | H | H | 2-CH$_2$S(=O)CH$_3$ | 1 |
| E-5324 | H | H | H | H | H | 3-CH$_2$S(=O)CH$_3$ | 1 |
| E-5325 | H | H | H | H | H | 4-CH$_2$S(=O)CH$_3$ | 1 |
| E-5326 | H | H | H | H | H | 2-CH$_2$S(=O)$_2$CH$_3$ | 1 |
| E-5327 | H | H | H | H | H | 3-CH$_2$S(=O)$_2$CH$_3$ | 1 |
| E-5328 | H | H | H | H | H | 4-CH$_2$S(=O)$_2$CH$_3$ | 1 |
| E-5329 | H | H | H | H | H | 2-CH$_2$SCF$_3$ | 1 |
| E-5330 | H | H | H | H | H | 3-CH$_2$SCF$_3$ | 1 |
| E-5331 | H | H | H | H | H | 4-CH$_2$SCF$_3$ | 1 |
| E-5332 | H | H | H | H | H | 2-CH$_2$S(=O)CF$_3$ | 1 |
| E-5333 | H | H | H | H | H | 3-CH$_2$S(=O)CF$_3$ | 1 |
| E-5334 | H | H | H | H | H | 4-CH$_2$S(=O)CF$_3$ | 1 |
| E-5335 | H | H | H | H | H | 2-CH$_2$S(=O)$_2$CF$_3$ | 1 |
| E-5336 | H | H | H | H | H | 3-CH$_2$S(=O)$_2$CF$_3$ | 1 |
| E-5337 | H | H | H | H | H | 4-CH$_2$S(=O)$_2$CF$_3$ | 1 |

TABLE 282

| compound | R¹ | R² | R³ | R⁴ | R⁵ | (R⁸)ₘ | p |
|---|---|---|---|---|---|---|---|
| E-5338 | H | H | H | H | H | 2-phenyl | 1 |
| E-5339 | H | H | H | H | H | 3-phenyl | 1 |
| E-5340 | H | H | H | H | H | 4-phenyl | 1 |
| E-5341 | H | H | H | H | H | 2-(phenyloxy) | 1 |
| E-5342 | H | H | H | H | H | 3-(phenyloxy) | 1 |
| E-5343 | H | H | H | H | H | 4-(phenyloxy) | 1 |
| E-5344 | H | H | H | H | H | 2-benzyl | 1 |
| E-5345 | H | H | H | H | H | 3-benzyl | 1 |
| E-5346 | H | H | H | H | H | 4-benzyl | 1 |
| E-5347 | H | H | H | H | H | 2-(benzyloxy) | 1 |
| E-5348 | H | H | H | H | H | 3-(benzyloxy) | 1 |
| E-5349 | H | H | H | H | H | 4-(benzyloxy) | 1 |
| E-5350 | H | H | H | H | H | 2-((2-fluorobenzyl)oxy) | 1 |
| E-5351 | H | H | H | H | H | 3-((2-fluorobenzyl)oxy) | 1 |
| E-5352 | H | H | H | H | H | 4-((2-fluorobenzyl)oxy) | 1 |
| E-5353 | H | H | H | H | H | 2-((3-fluorobenzyl)oxy) | 1 |
| E-5354 | H | H | H | H | H | 3-((3-fluorobenzyl)oxy) | 1 |
| E-5355 | H | H | H | H | H | 4-((3-fluorobenzyl)oxy) | 1 |
| E-5356 | H | H | H | H | H | 2-((4-fluorobenzyl)oxy) | 1 |
| E-5357 | H | H | H | H | H | 3-((4-fluorobenzyl)oxy) | 1 |
| E-5358 | H | H | H | H | H | 4-((4-fluorobenzyl)oxy) | 1 |
| E-5359 | H | H | H | H | H | 2-((2-chlorobenzyl)oxy) | 1 |
| E-5360 | H | H | H | H | H | 3-((2-chlorobenzyl)oxy) | 1 |
| E-5361 | H | H | H | H | H | 4-((2-chlorobenzyl)oxy) | 1 |
| E-5362 | H | H | H | H | H | 2-((3-chlorobenzyl)oxy) | 1 |
| E-5363 | H | H | H | H | H | 3-((3-chlorobenzyl)oxy) | 1 |
| E-5364 | H | H | H | H | H | 4-((3-chlorobenzyl)oxy) | 1 |
| E-5365 | H | H | H | H | H | 2-((4-chlorobenzyl)oxy) | 1 |
| E-5366 | H | H | H | H | H | 3-((4-chlorobenzyl)oxy) | 1 |
| E-5367 | H | H | H | H | H | 4-((4-chlorobenzyl)oxy) | 1 |
| E-5368 | H | H | H | H | H | 2-((2-methylbenzyl)oxy) | 1 |
| E-5369 | H | H | H | H | H | 3-((2-methylbenzyl)oxy) | 1 |
| E-5370 | H | H | H | H | H | 4-((2-methylbenzyl)oxy) | 1 |
| E-5371 | H | H | H | H | H | 2-((3-methylbenzyl)oxy) | 1 |
| E-5372 | H | H | H | H | H | 3-((3-methylbenzyl)oxy) | 1 |
| E-5373 | H | H | H | H | H | 4-((3-methylbenzyl)oxy) | 1 |
| E-5374 | H | H | H | H | H | 2-((4-methylbenzyl)oxy) | 1 |
| E-5375 | H | H | H | H | H | 3-((4-methylbenzyl)oxy) | 1 |
| E-5376 | H | H | H | H | H | 4-((4-methylbenzyl)oxy) | 1 |
| E-5377 | H | H | H | H | H | 2-((2-(trifluoromethyl)benzyl)oxy) | 1 |
| E-5378 | H | H | H | H | H | 3-((2-(trifluoromethyl)benzyl)oxy) | 1 |
| E-5379 | H | H | H | H | H | 4-((2-(trifluoromethyl)benzyl)oxy) | 1 |
| E-5380 | H | H | H | H | H | 2-((3-(trifluoromethyl)benzyl)oxy) | 1 |
| E-5381 | H | H | H | H | H | 3-((3-(trifluoromethyl)benzyl)oxy) | 1 |
| E-5382 | H | H | H | H | H | 4-((3-(trifluoromethyl)benzyl)oxy) | 1 |
| E-5383 | H | H | H | H | H | 2-((4-(trifluoromethyl)benzyl)oxy) | 1 |
| E-5384 | H | H | H | H | H | 3-((4-(trifluoromethyl)benzyl)oxy) | 1 |
| E-5385 | H | H | H | H | H | 4-((4-(trifluoromethyl)benzyl)oxy) | 1 |
| E-5386 | H | H | H | H | H | 2-((2-methoxybenzyl)oxy) | 1 |
| E-5387 | H | H | H | H | H | 3-((2-methoxybenzyl)oxy) | 1 |
| E-5388 | H | H | H | H | H | 4-((2-methoxybenzyl)oxy) | 1 |
| E-5389 | H | H | H | H | H | 2-((3-methoxybenzyl)oxy) | 1 |
| E-5390 | H | H | H | H | H | 3-((3-methoxybenzyl)oxy) | 1 |
| E-5391 | H | H | H | H | H | 4-((3-methoxybenzyl)oxy) | 1 |
| E-5392 | H | H | H | H | H | 2-((4-methoxybenzyl)oxy) | 1 |
| E-5393 | H | H | H | H | H | 3-((4-methoxybenzyl)oxy) | 1 |
| E-5394 | H | H | H | H | H | 4-((4-methoxybenzyl)oxy) | 1 |

TABLE 283

| compound | R¹ | R² | R³ | R⁴ | R⁵ | (R⁸)ₘ | p |
|---|---|---|---|---|---|---|---|
| E-5395 | H | H | H | H | H | 2-((2-(trifluoromethoxy)benzyl)oxy) | 1 |
| E-5396 | H | H | H | H | H | 3-((2-(trifluoromethoxy)benzyl)oxy) | 1 |
| E-5397 | H | H | H | H | H | 4-((2-(trifluoromethoxy)benzyl)oxy) | 1 |
| E-5398 | H | H | H | H | H | 2-((3-(trifluoromethoxy)benzyl)oxy) | 1 |
| E-5399 | H | H | H | H | H | 3-((3-(trifluoromethoxy)benzyl)oxy) | 1 |
| E-5400 | H | H | H | H | H | 4-((3-(trifluoromethoxy)benzyl)oxy) | 1 |
| E-5401 | H | H | H | H | H | 2-((4-(trifluoromethoxy)benzyl)oxy) | 1 |
| E-5402 | H | H | H | H | H | 3-((4-(trifluoromethoxy)benzyl)oxy) | 1 |
| E-5403 | H | H | H | H | H | 4-((4-(trifluoromethoxy)benzyl)oxy) | 1 |
| E-5404 | H | H | H | H | H | 2-((2-(methylthio)benzyl)oxy) | 1 |
| E-5405 | H | H | H | H | H | 3-((2-(methylthio)benzyl)oxy) | 1 |
| E-5406 | H | H | H | H | H | 4-((2-(methylthio)benzyl)oxy) | 1 |

TABLE 283-continued

| compound | R¹ | R² | R³ | R⁴ | R⁵ | (R⁸)ₘ | p |
|---|---|---|---|---|---|---|---|
| E-5407 | H | H | H | H | H | 2-((3-(methylthio)benzyl)oxy) | 1 |
| E-5408 | H | H | H | H | H | 3-((3-(methylthio)benzyl)oxy) | 1 |
| E-5409 | H | H | H | H | H | 4-((3-(methylthio)benzyl)oxy) | 1 |
| E-5410 | H | H | H | H | H | 2-((4-(methylthio)benzyl)oxy) | 1 |
| E-5411 | H | H | H | H | H | 3-((4-(methylthio)benzyl)oxy) | 1 |
| E-5412 | H | H | H | H | H | 4-((4-(methylthio)benzyl)oxy) | 1 |
| E-5413 | H | H | H | H | H | 2-((2-(methylsulfinyl)benzyl)oxy) | 1 |
| E-5414 | H | H | H | H | H | 3-((2-(methylsulfinyl)benzyl)oxy) | 1 |
| E-5415 | H | H | H | H | H | 4-((2-(methylsulfinyl)benzyl)oxy) | 1 |
| E-5416 | H | H | H | H | H | 2-((3-(methylsulfinyl)benzyl)oxy) | 1 |
| E-5417 | H | H | H | H | H | 3-((3-(methylsulfinyl)benzyl)oxy) | 1 |
| E-5418 | H | H | H | H | H | 4-((3-(methylsulfinyl)benzyl)oxy) | 1 |
| E-5419 | H | H | H | H | H | 2-((4-(methylsulfinyl)benzyl)oxy) | 1 |
| E-5420 | H | H | H | H | H | 3-((4-(methylsulfinyl)benzyl)oxy) | 1 |
| E-5421 | H | H | H | H | H | 4-((4-(methylsulfinyl)benzyl)oxy) | 1 |
| E-5422 | H | H | H | H | H | 2-((2-(methylsulfonyl)benzyl)oxy) | 1 |
| E-5423 | H | H | H | H | H | 3-((2-(methylsulfonyl)benzyl)oxy) | 1 |
| E-5424 | H | H | H | H | H | 4-((2-(methylsulfonyl)benzyl)oxy) | 1 |
| E-5425 | H | H | H | H | H | 2-((3-(methylsulfonyl)benzyl)oxy) | 1 |
| E-5426 | H | H | H | H | H | 3-((3-(methylsulfonyl)benzyl)oxy) | 1 |
| E-5427 | H | H | H | H | H | 4-((3-(methylsulfonyl)benzyl)oxy) | 1 |
| E-5428 | H | H | H | H | H | 2-((4-(methylsulfonyl)benzyl)oxy) | 1 |
| E-5429 | H | H | H | H | H | 3-((4-(methylsulfonyl)benzyl)oxy) | 1 |
| E-5430 | H | H | H | H | H | 4-((4-(methylsulfonyl)benzyl)oxy) | 1 |
| E-5431 | H | H | H | H | H | 2-((2-(trifluoromethylthio)benzyl)oxy) | 1 |
| E-5432 | H | H | H | H | H | 3-((2-(trifluoromethylthio)benzyl)oxy) | 1 |
| E-5433 | H | H | H | H | H | 4-((2-(trifluoromethylthio)benzyl)oxy) | 1 |
| E-5434 | H | H | H | H | H | 2-((3-(trifluoromethylthio)benzyl)oxy) | 1 |
| E-5435 | H | H | H | H | H | 3-((3-(trifluoromethylthio)benzyl)oxy) | 1 |
| E-5436 | H | H | H | H | H | 4-((3-(trifluoromethylthio)benzyl)oxy) | 1 |
| E-5437 | H | H | H | H | H | 2-((4-(trifluoromethylthio)benzyl)oxy) | 1 |
| E-5438 | H | H | H | H | H | 3-((4-(trifluoromethylthio)benzyl)oxy) | 1 |
| E-5439 | H | H | H | H | H | 4-((4-(trifluoromethylthio)benzyl)oxy) | 1 |
| E-5440 | H | H | H | H | H | 2-((2-(trifluoromethylsulfinyl)benzyl)oxy) | 1 |
| E-5441 | H | H | H | H | H | 3-((2-(trifluoromethylsulfinyl)benzyl)oxy) | 1 |
| E-5442 | H | H | H | H | H | 4-((2-(trifluoromethylsulfinyl)benzyl)oxy) | 1 |
| E-5443 | H | H | H | H | H | 2-((3-(trifluoromethylsulfinyl)benzyl)oxy) | 1 |
| E-5444 | H | H | H | H | H | 3-((3-(trifluoromethylsulfinyl)benzyl)oxy) | 1 |
| E-5445 | H | H | H | H | H | 4-((3-(trifluoromethylsulfinyl)benzyl)oxy) | 1 |
| E-5446 | H | H | H | H | H | 2-((4-(trifluoromethylsulfinyl)benzyl)oxy) | 1 |
| E-5447 | H | H | H | H | H | 3-((4-(trifluoromethylsulfinyl)benzyl)oxy) | 1 |
| E-5448 | H | H | H | H | H | 4-((4-(trifluoromethylsulfinyl)benzyl)oxy) | 1 |
| E-5449 | H | H | H | H | H | 2-((2-(trifluoromethylsulfonyl)benzyl)oxy) | 1 |
| E-5450 | H | H | H | H | H | 3-((2-(trifluoromethylsulfonyl)benzyl)oxy) | 1 |
| E-5451 | H | H | H | H | H | 4-((2-(trifluoromethylsulfonyl)benzyl)oxy) | 1 |

TABLE 284

| compound | R¹ | R² | R³ | R⁴ | R⁵ | (R⁸)ₘ | p |
|---|---|---|---|---|---|---|---|
| E-5452 | H | H | H | H | H | 2-((3-(trifluoromethylsulfonyl)benzyl)oxy) | 1 |
| E-5453 | H | H | H | H | H | 3-((3-(trifluoromethylsulfonyl)benzyl)oxy) | 1 |
| E-5454 | H | H | H | H | H | 4-((3-(trifluoromethylsulfonyl)benzyl)oxy) | 1 |
| E-5455 | H | H | H | H | H | 2-((4-(trifluoromethylsulfonyl)benzyl)oxy) | 1 |
| E-5456 | H | H | H | H | H | 3-((4-(trifluoromethylsulfonyl)benzyl)oxy) | 1 |
| E-5457 | H | H | H | H | H | 4-((4-(trifluoromethylsulfonyl)benzyl)oxy) | 1 |
| E-5458 | H | H | H | H | H | 2-((2-aminobenzyl)oxy) | 1 |
| E-5459 | H | H | H | H | H | 3-((2-aminobenzyl)oxy) | 1 |
| E-5460 | H | H | H | H | H | 4-((2-aminobenzyl)oxy) | 1 |
| E-5461 | H | H | H | H | H | 2-((3-aminobenzyl)oxy) | 1 |
| E-5462 | H | H | H | H | H | 3-((3-aminobenzyl)oxy) | 1 |
| E-5463 | H | H | H | H | H | 4-((3-aminobenzyl)oxy) | 1 |
| E-5464 | H | H | H | H | H | 2-((4-aminobenzyl)oxy) | 1 |
| E-5465 | H | H | H | H | H | 3-((4-aminobenzyl)oxy) | 1 |
| E-5466 | H | H | H | H | H | 4-((4-aminobenzyl)oxy) | 1 |
| E-5467 | H | H | H | H | H | 2-((2-(methylamino)benzyl)oxy) | 1 |
| E-5468 | H | H | H | H | H | 3-((2-(methylamino)benzyl)oxy) | 1 |
| E-5469 | H | H | H | H | H | 4-((2-(methylamino)benzyl)oxy) | 1 |
| E-5470 | H | H | H | H | H | 2-((3-(methylamino)benzyl)oxy) | 1 |
| E-5471 | H | H | H | H | H | 3-((3-(methylamino)benzyl)oxy) | 1 |
| E-5472 | H | H | H | H | H | 4-((3-(methylamino)benzyl)oxy) | 1 |
| E-5473 | H | H | H | H | H | 2-((4-(methylamino)benzyl)oxy) | 1 |
| E-5474 | H | H | H | H | H | 3-((4-(methylamino)benzyl)oxy) | 1 |
| E-5475 | H | H | H | H | H | 4-((4-(methylamino)benzyl)oxy) | 1 |
| E-5476 | H | H | H | H | H | 2-((2-(dimethylamino)benzyl)oxy) | 1 |
| E-5477 | H | H | H | H | H | 3-((2-(dimethylamino)benzyl)oxy) | 1 |
| E-5478 | H | H | H | H | H | 4-((2-(dimethylamino)benzyl)oxy) | 1 |
| E-5479 | H | H | H | H | H | 2-((3-(dimethylamino)benzyl)oxy) | 1 |
| E-5480 | H | H | H | H | H | 3-((3-(dimethylamino)benzyl)oxy) | 1 |
| E-5481 | H | H | H | H | H | 4-((3-(dimethylamino)benzyl)oxy) | 1 |
| E-5482 | H | H | H | H | H | 2-((4-(dimethylamino)benzyl)oxy) | 1 |
| E-5483 | H | H | H | H | H | 3-((4-(dimethylamino)benzyl)oxy) | 1 |
| E-5484 | H | H | H | H | H | 4-((4-(dimethylamino)benzyl)oxy) | 1 |
| E-5485 | H | H | H | H | H | 2-((2-cyanobenzyl)oxy) | 1 |
| E-5486 | H | H | H | H | H | 3-((2-cyanobenzyl)oxy) | 1 |
| E-5487 | H | H | H | H | H | 4-((2-cyanobenzyl)oxy) | 1 |
| E-5488 | H | H | H | H | H | 2-((3-cyanobenzyl)oxy) | 1 |
| E-5489 | H | H | H | H | H | 3-((3-cyanobenzyl)oxy) | 1 |
| E-5490 | H | H | H | H | H | 4-((3-cyanobenzyl)oxy) | 1 |
| E-5491 | H | H | H | H | H | 2-((4-cyanobenzyl)oxy) | 1 |
| E-5492 | H | H | H | H | H | 3-((4-cyanobenzyl)oxy) | 1 |
| E-5493 | H | H | H | H | H | 4-((4-cyanobenzyl)oxy) | 1 |
| E-5494 | H | H | H | H | H | 2-((2-nitrobenzyl)oxy) | 1 |
| E-5495 | H | H | H | H | H | 3-((2-nitrobenzyl)oxy) | 1 |
| E-5496 | H | H | H | H | H | 4-((2-nitrobenzyl)oxy) | 1 |
| E-5497 | H | H | H | H | H | 2-((3-nitrobenzyl)oxy) | 1 |
| E-5498 | H | H | H | H | H | 3-((3-nitrobenzyl)oxy) | 1 |
| E-5499 | H | H | H | H | H | 4-((3-nitrobenzyl)oxy) | 1 |
| E-5500 | H | H | H | H | H | 2-((4-nitrobenzyl)oxy) | 1 |
| E-5501 | H | H | H | H | H | 3-((4-nitrobenzyl)oxy) | 1 |
| E-5502 | H | H | H | H | H | 4-((4-nitrobenzyl)oxy) | 1 |
| E-5503 | H | H | H | H | H | 2-NH₂ | 1 |
| E-5504 | H | H | H | H | H | 3-NH₂ | 1 |
| E-5505 | H | H | H | H | H | 4-NH₂ | 1 |
| E-5506 | H | H | H | H | H | 2-NHMe | 1 |
| E-5507 | H | H | H | H | H | 3-NHMe | 1 |
| E-5508 | H | H | H | H | H | 4-NHMe | 1 |

TABLE 285

| compound | R¹ | R² | R³ | R⁴ | R⁵ | (R⁸)ₘ | p |
|---|---|---|---|---|---|---|---|
| E-5509 | H | H | H | H | H | 2-NHEt | 1 |
| E-5510 | H | H | H | H | H | 3-NHEt | 1 |
| E-5511 | H | H | H | H | H | 4-NHEt | 1 |
| E-5512 | H | H | H | H | H | 2-N(Me)₂ | 1 |
| E-5513 | H | H | H | H | H | 3-N(Me)₂ | 1 |
| E-5514 | H | H | H | H | H | 4-N(Me)₂ | 1 |
| E-5515 | H | H | H | H | H | 2-N(Et)₂ | 1 |
| E-5516 | H | H | H | H | H | 3-N(Et)₂ | 1 |
| E-5517 | H | H | H | H | H | 4-N(Et)₂ | 1 |
| E-5518 | H | H | H | H | H | 2-CHO | 1 |
| E-5519 | H | H | H | H | H | 3-CHO | 1 |
| E-5520 | H | H | H | H | H | 4-CHO | 1 |
| E-5521 | H | H | H | H | H | 2-C(=O)OH | 1 |
| E-5522 | H | H | H | H | H | 3-C(=O)OH | 1 |
| E-5523 | H | H | H | H | H | 4-C(=O)OH | 1 |
| E-5524 | H | H | H | H | H | 2-(1,3-dioxolan-2-yl) | 1 |

TABLE 285-continued

| compound | R¹ | R² | R³ | R⁴ | R⁵ | (R⁸)$_m$ | p |
|---|---|---|---|---|---|---|---|
| E-5525 | H | H | H | H | H | 3-(1,3-dioxolan-2-yl) | 1 |
| E-5526 | H | H | H | H | H | 4-(1,3-dioxolan-2-yl) | 1 |
| E-5527 | H | H | H | H | H | 2-(1,3-dioxan-2-yl) | 1 |
| E-5528 | H | H | H | H | H | 3-(1,3-dioxan-2-yl) | 1 |
| E-5529 | H | H | H | H | H | 4-(1,3-dioxan-2-yl) | 1 |
| E-5530 | H | H | H | H | H | 2-(1H-imidazol-2-yl) | 1 |
| E-5531 | H | H | H | H | H | 3-(1H-imidazol-2-yl) | 1 |
| E-5532 | H | H | H | H | H | 4-(1H-imidazol-2-yl) | 1 |
| E-5533 | H | H | H | H | H | 2-(thiazol-2-yl) | 1 |
| E-5534 | H | H | H | H | H | 3-(thiazol-2-yl) | 1 |
| E-5535 | H | H | H | H | H | 4-(thiazol-2-yl) | 1 |
| E-5536 | H | H | H | H | H | 2-(oxazol-2-yl) | 1 |
| E-5537 | H | H | H | H | H | 3-(oxazol-2-yl) | 1 |
| E-5538 | H | H | H | H | H | 4-(oxazol-2-yl) | 1 |
| E-5539 | H | H | H | H | H | 2-CH=NOH | 1 |
| E-5540 | H | H | H | H | H | 3-CH=NOH | 1 |
| E-5541 | H | H | H | H | H | 4-CH=NOH | 1 |
| E-5542 | H | H | H | H | H | 2-CH=NOMe | 1 |
| E-5543 | H | H | H | H | H | 3-CH=NOMe | 1 |
| E-5544 | H | H | H | H | H | 4-CH=NOMe | 1 |
| E-5545 | H | H | H | H | H | 2-(4,5-dihydro-3-isoxazolyl) | 1 |
| E-5546 | H | H | H | H | H | 3-(4,5-dihydro-3-isoxazolyl) | 1 |
| E-5547 | H | H | H | H | H | 4-(4,5-dihydro-3-isoxazolyl) | 1 |
| E-5548 | H | H | H | H | H | 2-CN | 1 |
| E-5549 | H | H | H | H | H | 3-CN | 1 |
| E-5550 | H | H | H | H | H | 4-CN | 1 |
| E-5551 | H | H | H | H | H | 2-NO₂ | 1 |
| E-5552 | H | H | H | H | H | 3-NO₂ | 1 |
| E-5553 | H | H | H | H | H | 4-NO₂ | 1 |
| E-5554 | H | H | H | H | H | 2,3-F₂ | 1 |
| E-5555 | H | H | H | H | H | 2,4-F₂ | 1 |
| E-5556 | H | H | H | H | H | 2,5-F₂ | 1 |
| E-5557 | H | H | H | H | H | 2,6-F₂ | 1 |
| E-5558 | H | H | H | H | H | 3,4-F₂ | 1 |
| E-5559 | H | H | H | H | H | 3,5-F₂ | 1 |
| E-5560 | H | H | H | H | H | 2-F,3-Cl | 1 |
| E-5561 | H | H | H | H | H | 2-F,4-Cl | 1 |
| E-5562 | H | H | H | H | H | 2-F,5-Cl | 1 |
| E-5563 | H | H | H | H | H | 2-F,6-Cl | 1 |
| E-5564 | H | H | H | H | H | 3-F,2-Cl | 1 |
| E-5565 | H | H | H | H | H | 3-F,4-Cl | 1 |

TABLE 286

| compound | R¹ | R² | R³ | R⁴ | R⁵ | (R⁸)$_m$ | p |
|---|---|---|---|---|---|---|---|
| E-5566 | H | H | H | H | H | 3-F,5-Cl | 1 |
| E-5567 | H | H | H | H | H | 3-F,6-Cl | 1 |
| E-5568 | H | H | H | H | H | 4-F,2-Cl | 1 |
| E-5569 | H | H | H | H | H | 4-F,3-Cl | 1 |
| E-5570 | H | H | H | H | H | 2-F,3-Me | 1 |
| E-5571 | H | H | H | H | H | 2-F,4-Me | 1 |
| E-5572 | H | H | H | H | H | 2-F,5-Me | 1 |
| E-5573 | H | H | H | H | H | 2-F,6-Me | 1 |
| E-5574 | H | H | H | H | H | 3-F,2-Me | 1 |
| E-5575 | H | H | H | H | H | 3-F,4-Me | 1 |
| E-5576 | H | H | H | H | H | 3-F,5-Me | 1 |
| E-5577 | H | H | H | H | H | 3-F,6-Me | 1 |
| E-5578 | H | H | H | H | H | 4-F,2-Me | 1 |
| E-5579 | H | H | H | H | H | 4-F,3-Me | 1 |
| E-5580 | H | H | H | H | H | 2-F,3-CF₃ | 1 |
| E-5581 | H | H | H | H | H | 2-F,4-CF₃ | 1 |
| E-5582 | H | H | H | H | H | 2-F,5-CF₃ | 1 |
| E-5583 | H | H | H | H | H | 2-F,6-CF₃ | 1 |
| E-5584 | H | H | H | H | H | 3-F,2-CF₃ | 1 |
| E-5585 | H | H | H | H | H | 3-F,4-CF₃ | 1 |
| E-5586 | H | H | H | H | H | 3-F,5-CF₃ | 1 |
| E-5587 | H | H | H | H | H | 3-F,6-CF₃ | 1 |
| E-5588 | H | H | H | H | H | 4-F,2-CF₃ | 1 |
| E-5589 | H | H | H | H | H | 4-F,3-CF₃ | 1 |
| E-5590 | H | H | H | H | H | 2-F,3-OMe | 1 |
| E-5591 | H | H | H | H | H | 2-F,4-OMe | 1 |
| E-5592 | H | H | H | H | H | 2-F,5-OMe | 1 |
| E-5593 | H | H | H | H | H | 2-F,6-OMe | 1 |
| E-5594 | H | H | H | H | H | 3-F,2-OMe | 1 |

TABLE 286-continued

| compound | R¹ | R² | R³ | R⁴ | R⁵ | (R⁸)$_m$ | p |
|---|---|---|---|---|---|---|---|
| E-5595 | H | H | H | H | H | 3-F,4-OMe | 1 |
| E-5596 | H | H | H | H | H | 3-F,5-OMe | 1 |
| E-5597 | H | H | H | H | H | 3-F,6-OMe | 1 |
| E-5598 | H | H | H | H | H | 4-F,2-OMe | 1 |
| E-5599 | H | H | H | H | H | 4-F,3-OMe | 1 |
| E-5600 | H | H | H | H | H | 2,3-Cl₂ | 1 |
| E-5601 | H | H | H | H | H | 2,4-Cl₂ | 1 |
| E-5602 | H | H | H | H | H | 2,5-Cl₂ | 1 |
| E-5603 | H | H | H | H | H | 2,6-Cl₂ | 1 |
| E-5604 | H | H | H | H | H | 3,4-Cl₂ | 1 |
| E-5605 | H | H | H | H | H | 3,5-Cl₂ | 1 |
| E-5606 | H | H | H | H | H | 2-Cl,3-Me | 1 |
| E-5607 | H | H | H | H | H | 2-Cl,4-Me | 1 |
| E-5608 | H | H | H | H | H | 2-Cl,5-Me | 1 |
| E-5609 | H | H | H | H | H | 2-Cl,6-Me | 1 |
| E-5610 | H | H | H | H | H | 3-Cl,2-Me | 1 |
| E-5611 | H | H | H | H | H | 3-Cl,4-Me | 1 |
| E-5612 | H | H | H | H | H | 3-Cl,5-Me | 1 |
| E-5613 | H | H | H | H | H | 3-Cl,6-Me | 1 |
| E-5614 | H | H | H | H | H | 4-Cl,2-Me | 1 |
| E-5615 | H | H | H | H | H | 4-Cl,3-Me | 1 |
| E-5616 | H | H | H | H | H | 2-Cl,3-CF₃ | 1 |
| E-5617 | H | H | H | H | H | 2-Cl,4-CF₃ | 1 |
| E-5618 | H | H | H | H | H | 2-Cl,5-CF₃ | 1 |
| E-5619 | H | H | H | H | H | 2-Cl,6-CF₃ | 1 |
| E-5620 | H | H | H | H | H | 3-Cl,2-CF₃ | 1 |
| E-5621 | H | H | H | H | H | 3-Cl,4-CF₃ | 1 |
| E-5622 | H | H | H | H | H | 3-Cl,5-CF₃ | 1 |

TABLE 287

| compound | R¹ | R² | R³ | R⁴ | R⁵ | (R⁸)$_m$ | p |
|---|---|---|---|---|---|---|---|
| E-5623 | H | H | H | H | H | 3-Cl,6-CF₃ | 1 |
| E-5624 | H | H | H | H | H | 4-Cl,2-CF₃ | 1 |
| E-5625 | H | H | H | H | H | 4-Cl,3-CF₃ | 1 |
| E-5626 | H | H | H | H | H | 2-Cl,3-OMe | 1 |
| E-5627 | H | H | H | H | H | 2-Cl,4-OMe | 1 |
| E-5628 | H | H | H | H | H | 2-Cl,5-OMe | 1 |
| E-5629 | H | H | H | H | H | 2-Cl,6-OMe | 1 |
| E-5630 | H | H | H | H | H | 3-Cl,2-OMe | 1 |
| E-5631 | H | H | H | H | H | 3-Cl,4-OMe | 1 |
| E-5632 | H | H | H | H | H | 3-Cl,5-OMe | 1 |
| E-5633 | H | H | H | H | H | 3-Cl,6-OMe | 1 |
| E-5634 | H | H | H | H | H | 4-Cl,2-OMe | 1 |
| E-5635 | H | H | H | H | H | 4-Cl,3-OMe | 1 |
| E-5636 | H | H | H | H | H | 2,3-Me₂ | 1 |
| E-5637 | H | H | H | H | H | 2,4-Me₂ | 1 |
| E-5638 | H | H | H | H | H | 2,5-Me₂ | 1 |
| E-5639 | H | H | H | H | H | 2,6-Me₂ | 1 |
| E-5640 | H | H | H | H | H | 3,4-Me₂ | 1 |
| E-5641 | H | H | H | H | H | 3,5-Me₂ | 1 |
| E-5642 | H | H | H | H | H | 2-Me,3-CF₃ | 1 |
| E-5643 | H | H | H | H | H | 2-Me,4-CF₃ | 1 |
| E-5644 | H | H | H | H | H | 2-Me,5-CF₃ | 1 |
| E-5645 | H | H | H | H | H | 2-Me,6-CF₃ | 1 |
| E-5646 | H | H | H | H | H | 3-Me,2-CF₃ | 1 |
| E-5647 | H | H | H | H | H | 3-Me,4-CF₃ | 1 |
| E-5648 | H | H | H | H | H | 3-Me,5-CF₃ | 1 |
| E-5649 | H | H | H | H | H | 3-Me,6-CF₃ | 1 |
| E-5650 | H | H | H | H | H | 4-Me,2-CF₃ | 1 |
| E-5651 | H | H | H | H | H | 4-Me,3-CF₃ | 1 |
| E-5652 | H | H | H | H | H | 2-Me,3-OMe | 1 |
| E-5653 | H | H | H | H | H | 2-Me,4-OMe | 1 |
| E-5654 | H | H | H | H | H | 2-Me,5-OMe | 1 |
| E-5655 | H | H | H | H | H | 2-Me,6-OMe | 1 |
| E-5656 | H | H | H | H | H | 3-Me,2-OMe | 1 |
| E-5657 | H | H | H | H | H | 3-Me,4-OMe | 1 |
| E-5658 | H | H | H | H | H | 3-Me,5-OMe | 1 |
| E-5659 | H | H | H | H | H | 3-Me,6-OMe | 1 |
| E-5660 | H | H | H | H | H | 4-Me,2-OMe | 1 |
| E-5661 | H | H | H | H | H | 4-Me,3-OMe | 1 |
| E-5662 | H | H | H | H | H | 2,3-OMe₂ | 1 |
| E-5663 | H | H | H | H | H | 2,4-OMe₂ | 1 |
| E-5664 | H | H | H | H | H | 2,5-OMe₂ | 1 |

TABLE 287-continued

| compound | R¹ | R² | R³ | R⁴ | R⁵ | (R⁸)$_m$ | p |
|---|---|---|---|---|---|---|---|
| E-5665 | H | H | H | H | H | 2,6-OMe₂ | 1 |
| E-5666 | H | H | H | H | H | 3,4-OMe₂ | 1 |
| E-5667 | H | H | H | H | H | 3,5-OMe₂ | 1 |
| E-5668 | H | H | H | H | H | 2-OMe,3-CF₃ | 1 |
| E-5669 | H | H | H | H | H | 2-OMe,4-CF₃ | 1 |
| E-5670 | H | H | H | H | H | 2-OMe,5-CF₃ | 1 |
| E-5671 | H | H | H | H | H | 2-OMe,6-CF₃ | 1 |
| E-5672 | H | H | H | H | H | 3-OMe,2-CF₃ | 1 |
| E-5673 | H | H | H | H | H | 3-OMe,4-CF₃ | 1 |
| E-5674 | H | H | H | H | H | 3-OMe,5-CF₃ | 1 |
| E-5675 | H | H | H | H | H | 3-OMe,6-CF₃ | 1 |
| E-5676 | H | H | H | H | H | 4-OMe,2-CF₃ | 1 |
| E-5677 | H | H | H | H | H | 4-OMe,3-CF₃ | 1 |
| E-5678 | H | H | H | H | H | 2-CHF₂,3-F | 1 |
| E-5679 | H | H | H | H | H | 2-CHF₂,4-F | 1 |

TABLE 288

| compound | R¹ | R² | R³ | R⁴ | R⁵ | (R⁸)$_m$ | p |
|---|---|---|---|---|---|---|---|
| E-5680 | H | H | H | H | H | 2-CHF₂,5-F | 1 |
| E-5681 | H | H | H | H | H | 2-CHF₂,6-F | 1 |
| E-5682 | H | H | H | H | H | 2-CHF₂,3-Me | 1 |
| E-5683 | H | H | H | H | H | 2-CHF₂,4-Me | 1 |
| E-5684 | H | H | H | H | H | 2-CHF₂,5-Me | 1 |
| E-5685 | H | H | H | H | H | 2-CHF₂,6-Me | 1 |
| E-5686 | H | H | H | H | H | 2-cyclopropyl,3-F | 1 |
| E-5687 | H | H | H | H | H | 2-cyclopropyl,4-F | 1 |
| E-5688 | H | H | H | H | H | 2-cyclopropyl,5-F | 1 |
| E-5689 | H | H | H | H | H | 2-cyclopropyl,6-F | 1 |
| E-5690 | H | H | H | H | H | 2-cyclopropyl,3-Me | 1 |
| E-5691 | H | H | H | H | H | 2-cyclopropyl,4-Me | 1 |
| E-5692 | H | H | H | H | H | 2-cyclopropyl,5-Me | 1 |
| E-5693 | H | H | H | H | H | 2-cyclopropyl,6-Me | 1 |
| E-5694 | H | H | H | H | H | 2-ethenyl,3-F | 1 |
| E-5695 | H | H | H | H | H | 2-ethenyl,4-F | 1 |
| E-5696 | H | H | H | H | H | 2-ethenyl,5-F | 1 |
| E-5697 | H | H | H | H | H | 2-ethenyl,6-F | 1 |
| E-5698 | H | H | H | H | H | 2-ethenyl,3-Me | 1 |
| E-5699 | H | H | H | H | H | 2-ethenyl,4-Me | 1 |
| E-5700 | H | H | H | H | H | 2-ethenyl,5-Me | 1 |
| E-5701 | H | H | H | H | H | 2-ethenyl,6-Me | 1 |
| E-5702 | H | H | H | H | H | 2-OEt,3-F | 1 |
| E-5703 | H | H | H | H | H | 2-OEt,4-F | 1 |
| E-5704 | H | H | H | H | H | 2-OEt,5-F | 1 |
| E-5705 | H | H | H | H | H | 2-OEt,6-F | 1 |
| E-5706 | H | H | H | H | H | 2-OEt,3-Cl | 1 |
| E-5707 | H | H | H | H | H | 2-OEt,4-Cl | 1 |
| E-5708 | H | H | H | H | H | 2-OEt,5-Cl | 1 |
| E-5709 | H | H | H | H | H | 2-OEt,6-Cl | 1 |
| E-5710 | H | H | H | H | H | 2-OEt,3-Me | 1 |
| E-5711 | H | H | H | H | H | 2-OEt,4-Me | 1 |
| E-5712 | H | H | H | H | H | 2-OEt,5-Me | 1 |
| E-5713 | H | H | H | H | H | 2-OEt,6-Me | 1 |
| E-5714 | H | H | H | H | H | 2-OPr,3-F | 1 |
| E-5715 | H | H | H | H | H | 2-OPr,4-F | 1 |
| E-5716 | H | H | H | H | H | 2-OPr,5-F | 1 |
| E-5717 | H | H | H | H | H | 2-OPr,6-F | 1 |
| E-5718 | H | H | H | H | H | 2-OPr,3-Me | 1 |
| E-5719 | H | H | H | H | H | 2-OPr,4-Me | 1 |
| E-5720 | H | H | H | H | H | 2-OPr,5-Me | 1 |
| E-5721 | H | H | H | H | H | 2-OPr,6-Me | 1 |
| E-5722 | H | H | H | H | H | 2-O(i-Pr),3-F | 1 |
| E-5723 | H | H | H | H | H | 2-O(i-Pr),4-F | 1 |
| E-5724 | H | H | H | H | H | 2-O(i-Pr),5-F | 1 |
| E-5725 | H | H | H | H | H | 2-O(i-Pr),6-F | 1 |
| E-5726 | H | H | H | H | H | 2-O(i-Pr),3-Me | 1 |
| E-5727 | H | H | H | H | H | 2-O(i-Pr),4-Me | 1 |
| E-5728 | H | H | H | H | H | 2-O(i-Pr),5-Me | 1 |
| E-5729 | H | H | H | H | H | 2-O(i-Pr),6-Me | 1 |
| E-5730 | H | H | H | H | H | 2-OCF₃,3-F | 1 |
| E-5731 | H | H | H | H | H | 2-OCF₃,4-F | 1 |
| E-5732 | H | H | H | H | H | 2-OCF₃,5-F | 1 |
| E-5733 | H | H | H | H | H | 2-OCF₃,6-F | 1 |
| E-5734 | H | H | H | H | H | 2-OCF₃,3-Me | 1 |

TABLE 288-continued

| compound | R¹ | R² | R³ | R⁴ | R⁵ | (R⁸)$_m$ | p |
|---|---|---|---|---|---|---|---|
| E-5735 | H | H | H | H | H | 2-OCF₃,4-Me | 1 |
| E-5736 | H | H | H | H | H | 2-OCF₃,5-Me | 1 |

TABLE 289

| compound | R¹ | R² | R³ | R⁴ | R⁵ | (R⁸)$_m$ | p |
|---|---|---|---|---|---|---|---|
| E-5737 | H | H | H | H | H | 2-OCF₃,6-Me | 1 |
| E-5738 | H | H | H | H | H | 2-OCHF₂,3-F | 1 |
| E-5739 | H | H | H | H | H | 2-OCHF₂,4-F | 1 |
| E-5740 | H | H | H | H | H | 2-OCHF₂,5-F | 1 |
| E-5741 | H | H | H | H | H | 2-OCHF₂,6-F | 1 |
| E-5742 | H | H | H | H | H | 2-OCHF₂,3-Me | 1 |
| E-5743 | H | H | H | H | H | 2-OCHF₂,4-Me | 1 |
| E-5744 | H | H | H | H | H | 2-OCHF₂,5-Me | 1 |
| E-5745 | H | H | H | H | H | 2-OCHF₂,6-Me | 1 |
| E-5746 | H | H | H | H | H | 2-(cyclopropyloxy),3-F | 1 |
| E-5747 | H | H | H | H | H | 2-(cyclopropyloxy),4-F | 1 |
| E-5748 | H | H | H | H | H | 2-(cyclopropyloxy),5-F | 1 |
| E-5749 | H | H | H | H | H | 2-(cyclopropyloxy),6-F | 1 |
| E-5750 | H | H | H | H | H | 2-(cyclopropyloxy),3-Me | 1 |
| E-5751 | H | H | H | H | H | 2-(cyclopropyloxy),4-Me | 1 |
| E-5752 | H | H | H | H | H | 2-(cyclopropyloxy),5-Me | 1 |
| E-5753 | H | H | H | H | H | 2-(cyclopropyloxy),6-Me | 1 |
| E-5754 | H | H | H | H | H | 2-(oxiran-2-yl),3-F | 1 |
| E-5755 | H | H | H | H | H | 2-(oxiran-2-yl),4-F | 1 |
| E-5756 | H | H | H | H | H | 2-(oxiran-2-yl),5-F | 1 |
| E-5757 | H | H | H | H | H | 2-(oxiran-2-yl),6-F | 1 |
| E-5758 | H | H | H | H | H | 2-(oxiran-2-yl),3-Me | 1 |
| E-5759 | H | H | H | H | H | 2-(oxiran-2-yl),4-Me | 1 |
| E-5760 | H | H | H | H | H | 2-(oxiran-2-yl),5-Me | 1 |
| E-5761 | H | H | H | H | H | 2-(oxiran-2-yl),6-Me | 1 |
| E-5762 | H | H | H | H | H | 2-(oxiran-2-ylmethyl),3-F | 1 |
| E-5763 | H | H | H | H | H | 2-(oxiran-2-ylmethyl),4-F | 1 |
| E-5764 | H | H | H | H | H | 2-(oxiran-2-ylmethyl),5-F | 1 |
| E-5765 | H | H | H | H | H | 2-(oxiran-2-ylmethyl),6-F | 1 |
| E-5766 | H | H | H | H | H | 2-(oxiran-2-ylmethyl),3-Me | 1 |
| E-5767 | H | H | H | H | H | 2-(oxiran-2-ylmethyl),4-Me | 1 |
| E-5768 | H | H | H | H | H | 2-(oxiran-2-ylmethyl),5-Me | 1 |
| E-5769 | H | H | H | H | H | 2-(oxiran-2-ylmethyl),6-Me | 1 |
| E-5770 | H | H | H | H | H | 2-SMe,3-F | 1 |
| E-5771 | H | H | H | H | H | 2-SMe,4-F | 1 |
| E-5772 | H | H | H | H | H | 2-SMe,5-F | 1 |
| E-5773 | H | H | H | H | H | 2-SMe,6-F | 1 |
| E-5774 | H | H | H | H | H | 2-SMe,3-Me | 1 |
| E-5775 | H | H | H | H | H | 2-SMe,4-Me | 1 |
| E-5776 | H | H | H | H | H | 2-SMe,5-Me | 1 |
| E-5777 | H | H | H | H | H | 2-SMe,6-Me | 1 |
| E-5778 | H | H | H | H | H | 2-SEt,3-F | 1 |
| E-5779 | H | H | H | H | H | 2-SEt,4-F | 1 |
| E-5780 | H | H | H | H | H | 2-SEt,5-F | 1 |
| E-5781 | H | H | H | H | H | 2-SEt,6-F | 1 |
| E-5782 | H | H | H | H | H | 2-SEt,3-Me | 1 |
| E-5783 | H | H | H | H | H | 2-SEt,4-Me | 1 |
| E-5784 | H | H | H | H | H | 2-SEt,5-Me | 1 |
| E-5785 | H | H | H | H | H | 2-SEt,6-Me | 1 |
| E-5786 | H | H | H | H | H | 2-S(=O)Me,3-F | 1 |
| E-5787 | H | H | H | H | H | 2-S(=O)Me,4-F | 1 |
| E-5788 | H | H | H | H | H | 2-S(=O)Me,5-F | 1 |
| E-5789 | H | H | H | H | H | 2-S(=O)Me,6-F | 1 |
| E-5790 | H | H | H | H | H | 3-S(=O)Me,2-F | 1 |
| E-5791 | H | H | H | H | H | 3-S(=O)Me,4-F | 1 |
| E-5792 | H | H | H | H | H | 3-S(=O)Me,5-F | 1 |
| E-5793 | H | H | H | H | H | 3-S(=O)Me,6-F | 1 |

TABLE 290

| compound | R¹ | R² | R³ | R⁴ | R⁵ | (R⁸)$_m$ | p |
|---|---|---|---|---|---|---|---|
| E-5794 | H | H | H | H | H | 2-S(=O)Me,3-Me | 1 |
| E-5795 | H | H | H | H | H | 2-S(=O)Me,4-Me | 1 |
| E-5796 | H | H | H | H | H | 2-S(=O)Me,5-Me | 1 |
| E-5797 | H | H | H | H | H | 2-S(=O)Me,6-Me | 1 |

TABLE 290-continued

| compound | R¹ | R² | R³ | R⁴ | R⁵ | (R⁸)ₘ | p |
|---|---|---|---|---|---|---|---|
| E-5798 | H | H | H | H | H | 2-S(=O)Me,2-Me | 1 |
| E-5799 | H | H | H | H | H | 3-S(=O)Me,4-Me | 1 |
| E-5800 | H | H | H | H | H | 3-S(=O)Me,5-Me | 1 |
| E-5801 | H | H | H | H | H | 3-S(=O)Me,6-Me | 1 |
| E-5802 | H | H | H | H | H | 2-S(=O)₂Me,3-F | 1 |
| E-5803 | H | H | H | H | H | 2-S(=O)₂Me,4-F | 1 |
| E-5804 | H | H | H | H | H | 2-S(=O)₂Me,5-F | 1 |
| E-5805 | H | H | H | H | H | 2-S(=O)₂Me,6-F | 1 |
| E-5806 | H | H | H | H | H | 2-S(=O)₂Me,3-Me | 1 |
| E-5807 | H | H | H | H | H | 2-S(=O)₂Me,4-Me | 1 |
| E-5808 | H | H | H | H | H | 2-S(=O)₂Me,5-Me | 1 |
| E-5809 | H | H | H | H | H | 2-S(=O)₂Me,6-Me | 1 |
| E-5810 | H | H | H | H | H | 2-SCF₃,3-F | 1 |
| E-5811 | H | H | H | H | H | 2-SCF₃,4-F | 1 |
| E-5812 | H | H | H | H | H | 2-SCF₃,5-F | 1 |
| E-5813 | H | H | H | H | H | 2-SCF₃,6-F | 1 |
| E-5814 | H | H | H | H | H | 2-SCF₃,3-Me | 1 |
| E-5815 | H | H | H | H | H | 2-SCF₃,4-Me | 1 |
| E-5816 | H | H | H | H | H | 2-SCF₃,5-Me | 1 |
| E-5817 | H | H | H | H | H | 2-SCF₃,6-Me | 1 |
| E-5818 | H | H | H | H | H | 2-S(=O)CF₃,3-F | 1 |
| E-5819 | H | H | H | H | H | 2-S(=O)CF₃,4-F | 1 |
| E-5820 | H | H | H | H | H | 2-S(=O)CF₃,5-F | 1 |
| E-5821 | H | H | H | H | H | 2-S(=O)CF₃,6-F | 1 |
| E-5822 | H | H | H | H | H | 2-S(=O)CF₃,3-Me | 1 |
| E-5823 | H | H | H | H | H | 2-S(=O)CF₃,4-Me | 1 |
| E-5824 | H | H | H | H | H | 2-S(=O)CF₃,5-Me | 1 |
| E-5825 | H | H | H | H | H | 2-S(=O)CF₃,6-Me | 1 |
| E-5826 | H | H | H | H | H | 2-S(=O)₂CF₃,3-F | 1 |
| E-5827 | H | H | H | H | H | 2-S(=O)₂CF₃,4-F | 1 |
| E-5828 | H | H | H | H | H | 2-S(=O)₂CF₃,5-F | 1 |
| E-5829 | H | H | H | H | H | 2-S(=O)₂CF₃,6-F | 1 |
| E-5830 | H | H | H | H | H | 2-S(=O)₂CF₃,3-Me | 1 |
| E-5831 | H | H | H | H | H | 2-S(=O)₂CF₃,4-Me | 1 |
| E-5832 | H | H | H | H | H | 2-S(=O)₂CF₃,5-Me | 1 |
| E-5833 | H | H | H | H | H | 2-S(=O)₂CF₃,6-Me | 1 |
| E-5834 | H | H | H | H | H | 2-(cyclopropylthio),3-F | 1 |
| E-5835 | H | H | H | H | H | 2-(cyclopropylthio),4-F | 1 |
| E-5836 | H | H | H | H | H | 2-(cyclopropylthio),5-F | 1 |
| E-5837 | H | H | H | H | H | 2-(cyclopropylthio),6-F | 1 |
| E-5838 | H | H | H | H | H | 2-(cyclopropylthio),3-Me | 1 |
| E-5839 | H | H | H | H | H | 2-(cyclopropylthio),4-Me | 1 |
| E-5840 | H | H | H | H | H | 2-(cyclopropylthio),5-Me | 1 |
| E-5841 | H | H | H | H | H | 2-(cyclopropylthio),6-Me | 1 |
| E-5842 | H | H | H | H | H | 2-C(=O)Me,3-F | 1 |
| E-5843 | H | H | H | H | H | 2-C(=O)Me,4-F | 1 |
| E-5844 | H | H | H | H | H | 2-C(=O)Me,5-F | 1 |
| E-5845 | H | H | H | H | H | 2-C(=O)Me,6-F | 1 |
| E-5846 | H | H | H | H | H | 2-C(=O)Me,3-Me | 1 |
| E-5847 | H | H | H | H | H | 2-C(=O)Me,4-Me | 1 |
| E-5848 | H | H | H | H | H | 2-C(=O)Me,5-Me | 1 |
| E-5849 | H | H | H | H | H | 2-C(=O)Me,6-Me | 1 |
| E-5850 | H | H | H | H | H | 3-C(=O)Me,2-F | 1 |

TABLE 291

| compound | R¹ | R² | R³ | R⁴ | R⁵ | (R⁸)ₘ | p |
|---|---|---|---|---|---|---|---|
| E-5851 | H | H | H | H | H | 3-C(=O)Me,4-F | 1 |
| E-5852 | H | H | H | H | H | 3-C(=O)Me,5-F | 1 |
| E-5853 | H | H | H | H | H | 3-C(=O)Me,6-F | 1 |
| E-5854 | H | H | H | H | H | 3-C(=O)Me,2-Me | 1 |
| E-5855 | H | H | H | H | H | 3-C(=O)Me,4-Me | 1 |
| E-5856 | H | H | H | H | H | 3-C(=O)Me,5-Me | 1 |
| E-5857 | H | H | H | H | H | 3-C(=O)Me,6-Me | 1 |
| E-5858 | H | H | H | H | H | 2-C(=O)OMe,3-F | 1 |
| E-5859 | H | H | H | H | H | 2-C(=O)OMe,4-F | 1 |
| E-5860 | H | H | H | H | H | 2-C(=O)OMe,5-F | 1 |
| E-5861 | H | H | H | H | H | 2-C(=O)OMe,6-F | 1 |
| E-5862 | H | H | H | H | H | 2-C(=O)OMe,3-Me | 1 |
| E-5863 | H | H | H | H | H | 2-C(=O)OMe,4-Me | 1 |
| E-5864 | H | H | H | H | H | 2-C(=O)OMe,5-Me | 1 |
| E-5865 | H | H | H | H | H | 2-C(=O)OMe,6-Me | 1 |
| E-5866 | H | H | H | H | H | 2-C(=O)OEt,3-F | 1 |
| E-5867 | H | H | H | H | H | 2-C(=O)OEt,4-F | 1 |

TABLE 291-continued

| compound | R¹ | R² | R³ | R⁴ | R⁵ | (R⁸)ₘ | p |
|---|---|---|---|---|---|---|---|
| E-5868 | H | H | H | H | H | 2-C(=O)OEt,5-F | 1 |
| E-5869 | H | H | H | H | H | 2-C(=O)OEt,6-F | 1 |
| E-5870 | H | H | H | H | H | 2-C(=O)OEt,3-Me | 1 |
| E-5871 | H | H | H | H | H | 2-C(=O)OEt,4-Me | 1 |
| E-5872 | H | H | H | H | H | 2-C(=O)OEt,5-Me | 1 |
| E-5873 | H | H | H | H | H | 2-C(=O)OEt,6-Me | 1 |
| E-5874 | H | H | H | H | H | 2-C(=O)NH₂,3-F | 1 |
| E-5875 | H | H | H | H | H | 2-C(=O)NH₂,4-F | 1 |
| E-5876 | H | H | H | H | H | 2-C(=O)NH₂,5-F | 1 |
| E-5877 | H | H | H | H | H | 2-C(=O)NH₂,6-F | 1 |
| E-5878 | H | H | H | H | H | 2-C(=O)NH₂,3-Me | 1 |
| E-5879 | H | H | H | H | H | 2-C(=O)NH₂,4-Me | 1 |
| E-5880 | H | H | H | H | H | 2-C(=O)NH₂,5-Me | 1 |
| E-5881 | H | H | H | H | H | 2-C(=O)NH₂,6-Me | 1 |
| E-5882 | H | H | H | H | H | 2-C(=O)NHMe,3-F | 1 |
| E-5883 | H | H | H | H | H | 2-C(=O)NHMe,4-F | 1 |
| E-5884 | H | H | H | H | H | 2-C(=O)NHMe,5-F | 1 |
| E-5885 | H | H | H | H | H | 2-C(=O)NHMe,6-F | 1 |
| E-5886 | H | H | H | H | H | 2-C(=O)NHMe,3-Me | 1 |
| E-5887 | H | H | H | H | H | 2-C(=O)NHMe,4-Me | 1 |
| E-5888 | H | H | H | H | H | 2-C(=O)NHMe,5-Me | 1 |
| E-5889 | H | H | H | H | H | 2-C(=O)NHMe,6-Me | 1 |
| E-5890 | H | H | H | H | H | 2-C(=O)NMe₂,3-F | 1 |
| E-5891 | H | H | H | H | H | 2-C(=O)NMe₂,4-F | 1 |
| E-5892 | H | H | H | H | H | 2-C(=O)NMe₂,5-F | 1 |
| E-5893 | H | H | H | H | H | 2-C(=O)NMe₂,6-F | 1 |
| E-5894 | H | H | H | H | H | 2-C(=O)NMe₂,3-Me | 1 |
| E-5895 | H | H | H | H | H | 2-C(=O)NMe₂,4-Me | 1 |
| E-5896 | H | H | H | H | H | 2-C(=O)NMe₂,5-Me | 1 |
| E-5897 | H | H | H | H | H | 2-C(=O)NMe₂,6-Me | 1 |
| E-5898 | H | H | H | H | H | 2-CH₂OH,3-F | 1 |
| E-5899 | H | H | H | H | H | 2-CH₂OH,4-F | 1 |
| E-5900 | H | H | H | H | H | 2-CH₂OH,5-F | 1 |
| E-5901 | H | H | H | H | H | 2-CH₂OH,6-F | 1 |
| E-5902 | H | H | H | H | H | 2-CH₂OH,3-Me | 1 |
| E-5903 | H | H | H | H | H | 2-CH₂OH,4-Me | 1 |
| E-5904 | H | H | H | H | H | 2-CH₂OH,5-Me | 1 |
| E-5905 | H | H | H | H | H | 2-CH₂OH,6-Me | 1 |
| E-5906 | H | H | H | H | H | 2-CH₂OCH₃,3-F | 1 |
| E-5907 | H | H | H | H | H | 2-CH₂OCH₃,4-F | 1 |

TABLE 292

| compound | R¹ | R² | R³ | R⁴ | R⁵ | (R⁸)ₘ | p |
|---|---|---|---|---|---|---|---|
| E-5908 | H | H | H | H | H | 2-CH₂OCH₃,5-F | 1 |
| E-5909 | H | H | H | H | H | 2-CH₂OCH₃,6-F | 1 |
| E-5910 | H | H | H | H | H | 2-CH₂OCH₃,3-Me | 1 |
| E-5911 | H | H | H | H | H | 2-CH₂OCH₃,4-Me | 1 |
| E-5912 | H | H | H | H | H | 2-CH₂OCH₃,5-Me | 1 |
| E-5913 | H | H | H | H | H | 2-CH₂OCH₃,6-Me | 1 |
| E-5914 | H | H | H | H | H | 2-CH₂OCH₂CH₃,3-F | 1 |
| E-5915 | H | H | H | H | H | 2-CH₂OCH₂CH₃,4-F | 1 |
| E-5916 | H | H | H | H | H | 2-CH₂OCH₂CH₃,5-F | 1 |
| E-5917 | H | H | H | H | H | 2-CH₂OCH₂CH₃,6-F | 1 |
| E-5918 | H | H | H | H | H | 2-CH₂OCH₂CH₃,3-Me | 1 |
| E-5919 | H | H | H | H | H | 2-CH₂OCH₂CH₃,4-Me | 1 |
| E-5920 | H | H | H | H | H | 2-CH₂OCH₂CH₃,5-Me | 1 |
| E-5921 | H | H | H | H | H | 2-CH₂OCH₂CH₃,6-Me | 1 |
| E-5922 | H | H | H | H | H | 2-OC(=O)CH₃,3-F | 1 |
| E-5923 | H | H | H | H | H | 2-OC(=O)CH₃,4-F | 1 |
| E-5924 | H | H | H | H | H | 2-OC(=O)CH₃,5-F | 1 |
| E-5925 | H | H | H | H | H | 2-OC(=O)CH₃,6-F | 1 |
| E-5926 | H | H | H | H | H | 2-OC(=O)CH₃,3-Me | 1 |
| E-5927 | H | H | H | H | H | 2-OC(=O)CH₃,4-Me | 1 |
| E-5928 | H | H | H | H | H | 2-OC(=O)CH₃,5-Me | 1 |
| E-5929 | H | H | H | H | H | 2-OC(=O)CH₃,6-Me | 1 |
| E-5930 | H | H | H | H | H | 2-OS(=O)₂CH₃,3-F | 1 |
| E-5931 | H | H | H | H | H | 2-OS(=O)₂CH₃,4-F | 1 |
| E-5932 | H | H | H | H | H | 2-OS(=O)₂CH₃,5-F | 1 |
| E-5933 | H | H | H | H | H | 2-OS(=O)₂CH₃,6-F | 1 |
| E-5934 | H | H | H | H | H | 2-OS(=O)₂CH₃,3-Me | 1 |
| E-5935 | H | H | H | H | H | 2-OS(=O)₂CH₃,4-Me | 1 |
| E-5936 | H | H | H | H | H | 2-OS(=O)₂CH₃,5-Me | 1 |
| E-5937 | H | H | H | H | H | 2-OS(=O)₂CH₃,6-Me | 1 |

TABLE 292-continued

| compound | R¹ | R² | R³ | R⁴ | R⁵ | (R⁸)ₘ | p |
|---|---|---|---|---|---|---|---|
| E-5938 | H | H | H | H | H | 2-CH₂SCH₃,3-F | 1 |
| E-5939 | H | H | H | H | H | 2-CH₂SCH₃,4-F | 1 |
| E-5940 | H | H | H | H | H | 2-CH₂SCH₃,5-F | 1 |
| E-5941 | H | H | H | H | H | 2-CH₂SCH₃,6-F | 1 |
| E-5942 | H | H | H | H | H | 2-CH₂SCH₃,3-Me | 1 |
| E-5943 | H | H | H | H | H | 2-CH₂SCH₃,4-Me | 1 |
| E-5944 | H | H | H | H | H | 2-CH₂SCH₃,5-Me | 1 |
| E-5945 | H | H | H | H | H | 2-CH₂SCH₃,6-Me | 1 |
| E-5946 | H | H | H | H | H | 2-CH₂SCF₃,3-F | 1 |
| E-5947 | H | H | H | H | H | 2-CH₂SCF₃,4-F | 1 |
| E-5948 | H | H | H | H | H | 2-CH₂SCF₃,5-F | 1 |
| E-5949 | H | H | H | H | H | 2-CH₂SCF₃,6-F | 1 |
| E-5950 | H | H | H | H | H | 2-CH₂SCF₃,3-Me | 1 |
| E-5951 | H | H | H | H | H | 2-CH₂SCF₃,4-Me | 1 |
| E-5952 | H | H | H | H | H | 2-CH₂SCF₃,5-Me | 1 |
| E-5953 | H | H | H | H | H | 2-CH₂SCF₃,6-Me | 1 |
| E-5954 | H | H | H | H | H | 2-(benzyloxy),3-F | 1 |
| E-5955 | H | H | H | H | H | 2-(benzyloxy),4-F | 1 |
| E-5956 | H | H | H | H | H | 2-(benzyloxy),5-F | 1 |
| E-5957 | H | H | H | H | H | 2-(benzyloxy),6-F | 1 |
| E-5958 | H | H | H | H | H | 2-(benzyloxy),3-Me | 1 |
| E-5959 | H | H | H | H | H | 2-(benzyloxy),4-Me | 1 |
| E-5960 | H | H | H | H | H | 2-(benzyloxy),5-Me | 1 |
| E-5961 | H | H | H | H | H | 2-(benzyloxy),6-Me | 1 |
| E-5962 | H | H | H | H | H | 2-NH₂,3-F | 1 |
| E-5963 | H | H | H | H | H | 2-NH₂,4-F | 1 |
| E-5964 | H | H | H | H | H | 2-NH₂,5-F | 1 |

TABLE 293

| compound | R¹ | R² | R³ | R⁴ | R⁵ | (R⁸)ₘ | p |
|---|---|---|---|---|---|---|---|
| E-5965 | H | H | H | H | H | 2-NH₂,6-F | 1 |
| E-5966 | H | H | H | H | H | 2-NH₂,3-Me | 1 |
| E-5967 | H | H | H | H | H | 2-NH₂,4-Me | 1 |
| E-5968 | H | H | H | H | H | 2-NH₂,5-Me | 1 |
| E-5969 | H | H | H | H | H | 2-NH₂,6-Me | 1 |
| E-5970 | H | H | H | H | H | 2-NHMe,3-F | 1 |
| E-5971 | H | H | H | H | H | 2-NHMe,4-F | 1 |
| E-5972 | H | H | H | H | H | 2-NHMe,5-F | 1 |
| E-5973 | H | H | H | H | H | 2-NHMe,6-F | 1 |
| E-5974 | H | H | H | H | H | 2-NHMe,3-Me | 1 |
| E-5975 | H | H | H | H | H | 2-NHMe,4-Me | 1 |
| E-5976 | H | H | H | H | H | 2-NHMe,5-Me | 1 |
| E-5977 | H | H | H | H | H | 2-NHMe,6-Me | 1 |
| E-5978 | H | H | H | H | H | 2-NHEt,3-F | 1 |
| E-5979 | H | H | H | H | H | 2-NHEt,4-F | 1 |
| E-5980 | H | H | H | H | H | 2-NHEt,5-F | 1 |
| E-5981 | H | H | H | H | H | 2-NHEt,6-F | 1 |
| E-5982 | H | H | H | H | H | 2-NHEt,3-Me | 1 |
| E-5983 | H | H | H | H | H | 2-NHEt,4-Me | 1 |
| E-5984 | H | H | H | H | H | 2-NHEt,5-Me | 1 |
| E-5985 | H | H | H | H | H | 2-NHEt,6-Me | 1 |
| E-5986 | H | H | H | H | H | 2-NMe₂,3-F | 1 |
| E-5987 | H | H | H | H | H | 2-NMe₂,4-F | 1 |
| E-5988 | H | H | H | H | H | 2-NMe₂,5-F | 1 |
| E-5989 | H | H | H | H | H | 2-NMe₂,6-F | 1 |
| E-5990 | H | H | H | H | H | 2-NMe₂,3-Me | 1 |
| E-5991 | H | H | H | H | H | 2-NMe₂,4-Me | 1 |
| E-5992 | H | H | H | H | H | 2-NMe₂,5-Me | 1 |
| E-5993 | H | H | H | H | H | 2-NMe₂,6-Me | 1 |
| E-5994 | H | H | H | H | H | 2-NEt₂,3-F | 1 |
| E-5995 | H | H | H | H | H | 2-NEt₂,4-F | 1 |
| E-5996 | H | H | H | H | H | 2-NEt₂,5-F | 1 |
| E-5997 | H | H | H | H | H | 2-NEt₂,6-F | 1 |
| E-5998 | H | H | H | H | H | 2-NEt₂,3-Me | 1 |
| E-5999 | H | H | H | H | H | 2-NEt₂,4-Me | 1 |
| E-6000 | H | H | H | H | H | 2-NEt₂,5-Me | 1 |
| E-6001 | H | H | H | H | H | 2-NEt₂,6-Me | 1 |
| E-6002 | H | H | H | H | H | 2-CHO,3-F | 1 |
| E-6003 | H | H | H | H | H | 2-CHO,4-F | 1 |
| E-6004 | H | H | H | H | H | 2-CHO,5-F | 1 |
| E-6005 | H | H | H | H | H | 2-CHO,6-F | 1 |
| E-6006 | H | H | H | H | H | 2-CHO,3-Me | 1 |
| E-6007 | H | H | H | H | H | 2-CHO,4-Me | 1 |
| E-6008 | H | H | H | H | H | 2-CHO,5-Me | 1 |
| E-6009 | H | H | H | H | H | 2-CHO,6-Me | 1 |
| E-6010 | H | H | H | H | H | 2-C(=O)OH,3-F | 1 |
| E-6011 | H | H | H | H | H | 2-C(=O)OH,4-F | 1 |
| E-6012 | H | H | H | H | H | 2-C(=O)OH,5-F | 1 |
| E-6013 | H | H | H | H | H | 2-C(=O)OH,6-F | 1 |
| E-6014 | H | H | H | H | H | 2-C(=O)OH,3-Me | 1 |
| E-6015 | H | H | H | H | H | 2-C(=O)OH,4-Me | 1 |
| E-6016 | H | H | H | H | H | 2-C(=O)OH,5-Me | 1 |
| E-6017 | H | H | H | H | H | 2-C(=O)OH,6-Me | 1 |
| E-6018 | H | H | H | H | H | 2-(1,3-dioxolan-2-yl),3-F | 1 |
| E-6019 | H | H | H | H | H | 2-(1,3-dioxolan-2-yl),4-F | 1 |
| E-6020 | H | H | H | H | H | 2-(1,3-dioxolan-2-yl),5-F | 1 |
| E-6021 | H | H | H | H | H | 2-(1,3-dioxolan-2-yl),6-F | 1 |

TABLE 294

| compound | R¹ | R² | R³ | R⁴ | R⁵ | (R⁸)ₘ | p |
|---|---|---|---|---|---|---|---|
| E-6022 | H | H | H | H | H | 2-(1,3-dioxolan-2-yl),3-Me | 1 |
| E-6023 | H | H | H | H | H | 2-(1,3-dioxolan-2-yl),4-Me | 1 |
| E-6024 | H | H | H | H | H | 2-(1,3-dioxolan-2-yl),5-Me | 1 |
| E-6025 | H | H | H | H | H | 2-(1,3-dioxolan-2-yl),6-Me | 1 |
| E-6026 | H | H | H | H | H | 2-(1,3-dioxan-2-yl),3-F | 1 |
| E-6027 | H | H | H | H | H | 2-(1,3-dioxan-2-yl),4-F | 1 |
| E-6028 | H | H | H | H | H | 2-(1,3-dioxan-2-yl),5-F | 1 |
| E-6029 | H | H | H | H | H | 2-(1,3-dioxan-2-yl),6-F | 1 |
| E-6030 | H | H | H | H | H | 2-(1,3-dioxan-2-yl),3-Me | 1 |
| E-6031 | H | H | H | H | H | 2-(1,3-dioxan-2-yl),4-Me | 1 |
| E-6032 | H | H | H | H | H | 2-(1,3-dioxan-2-yl),5-Me | 1 |
| E-6033 | H | H | H | H | H | 2-(1,3-dioxan-2-yl),6-Me | 1 |
| E-6034 | H | H | H | H | H | 2-(thiazol-2-yl),3-F | 1 |
| E-6035 | H | H | H | H | H | 2-(thiazol-2-yl),4-F | 1 |
| E-6036 | H | H | H | H | H | 2-(thiazol-2-yl),5-F | 1 |
| E-6037 | H | H | H | H | H | 2-(thiazol-2-yl),6-F | 1 |
| E-6038 | H | H | H | H | H | 2-(thiazol-2-yl),3-Me | 1 |
| E-6039 | H | H | H | H | H | 2-(thiazol-2-yl),4-Me | 1 |
| E-6040 | H | H | H | H | H | 2-(thiazol-2-yl),5-Me | 1 |
| E-6041 | H | H | H | H | H | 2-(thiazol-2-yl),6-Me | 1 |
| E-6042 | H | H | H | H | H | 2-(oxazol-2-yl),3-F | 1 |
| E-6043 | H | H | H | H | H | 2-(oxazol-2-yl),4-F | 1 |
| E-6044 | H | H | H | H | H | 2-(oxazol-2-yl),5-F | 1 |
| E-6045 | H | H | H | H | H | 2-(oxazol-2-yl),6-F | 1 |
| E-6046 | H | H | H | H | H | 2-(oxazol-2-yl),3-Me | 1 |
| E-6047 | H | H | H | H | H | 2-(oxazol-2-yl),4-Me | 1 |
| E-6048 | H | H | H | H | H | 2-(oxazol-2-yl),5-Me | 1 |
| E-6049 | H | H | H | H | H | 2-(oxazol-2-yl),6-Me | 1 |
| E-6050 | H | H | H | H | H | 2-CH=NOH,3-F | 1 |
| E-6051 | H | H | H | H | H | 2-CH=NOH,4-F | 1 |
| E-6052 | H | H | H | H | H | 2-CH=NOH,5-F | 1 |
| E-6053 | H | H | H | H | H | 2-CH=NOH,6-F | 1 |
| E-6054 | H | H | H | H | H | 2-CH=NOH,3-Me | 1 |
| E-6055 | H | H | H | H | H | 2-CH=NOH,4-Me | 1 |
| E-6056 | H | H | H | H | H | 2-CH=NOH,5-Me | 1 |
| E-6057 | H | H | H | H | H | 2-CH=NOH,6-Me | 1 |
| E-6058 | H | H | H | H | H | 2-CH=NOMe,3-F | 1 |
| E-6059 | H | H | H | H | H | 2-CH=NOMe,4-F | 1 |
| E-6060 | H | H | H | H | H | 2-CH=NOMe,5-F | 1 |
| E-6061 | H | H | H | H | H | 2-CH=NOMe,6-F | 1 |
| E-6062 | H | H | H | H | H | 2-CH=NOMe,3-Me | 1 |
| E-6063 | H | H | H | H | H | 2-CH=NOMe,4-Me | 1 |
| E-6064 | H | H | H | H | H | 2-CH=NOMe,5-Me | 1 |
| E-6065 | H | H | H | H | H | 2-CH=NOMe,6-Me | 1 |
| E-6066 | H | H | H | H | H | 2-CN,3-F | 1 |
| E-6067 | H | H | H | H | H | 2-CN,4-F | 1 |
| E-6068 | H | H | H | H | H | 2-CN,5-F | 1 |
| E-6069 | H | H | H | H | H | 2-CN,6-F | 1 |
| E-6070 | H | H | H | H | H | 2-CN,3-Cl | 1 |
| E-6071 | H | H | H | H | H | 2-CN,4-Cl | 1 |
| E-6072 | H | H | H | H | H | 2-CN,5-Cl | 1 |
| E-6073 | H | H | H | H | H | 2-CN,6-Cl | 1 |
| E-6074 | H | H | H | H | H | 2-CN,3-Me | 1 |

TABLE 294-continued

| compound | R¹ | R² | R³ | R⁴ | R⁵ | (R⁸)ₘ | p |
|---|---|---|---|---|---|---|---|
| E-6075 | H | H | H | H | H | 2-CN,4-Me | 1 |
| E-6076 | H | H | H | H | H | 2-CN,5-Me | 1 |
| E-6077 | H | H | H | H | H | 2-CN,6-Me | 1 |
| E-6078 | H | H | H | H | H | 2-CN,3-OMe | 1 |

TABLE 295

| compound | R¹ | R² | R³ | R⁴ | R⁵ | (R⁸)ₘ | p |
|---|---|---|---|---|---|---|---|
| E-6079 | H | H | H | H | H | 2-CN,4-OMe | 1 |
| E-6080 | H | H | H | H | H | 2-CN,5-OMe | 1 |
| E-6081 | H | H | H | H | H | 2-CN,6-OMe | 1 |
| E-6082 | H | H | H | H | H | 3-CN,2-F | 1 |
| E-6083 | H | H | H | H | H | 3-CN,4-F | 1 |
| E-6084 | H | H | H | H | H | 3-CN,5-F | 1 |
| E-6085 | H | H | H | H | H | 3-CN,6-F | 1 |
| E-6086 | H | H | H | H | H | 3-CN,2-Cl | 1 |
| E-6087 | H | H | H | H | H | 3-CN,4-Cl | 1 |
| E-6088 | H | H | H | H | H | 3-CN,5-Cl | 1 |
| E-6089 | H | H | H | H | H | 3-CN,6-Cl | 1 |
| E-6090 | H | H | H | H | H | 3-CN,2-Me | 1 |
| E-6091 | H | H | H | H | H | 3-CN,4-Me | 1 |
| E-6092 | H | H | H | H | H | 3-CN,5-Me | 1 |
| E-6093 | H | H | H | H | H | 3-CN,6-Me | 1 |
| E-6094 | H | H | H | H | H | 3-CN,2-OMe | 1 |
| E-6095 | H | H | H | H | H | 3-CN,4-OMe | 1 |
| E-6096 | H | H | H | H | H | 3-CN,5-OMe | 1 |
| E-6097 | H | H | H | H | H | 3-CN,6-OMe | 1 |
| E-6098 | H | H | H | H | H | 4-CN,2-F | 1 |
| E-6099 | H | H | H | H | H | 4-CN,3-F | 1 |
| E-6100 | H | H | H | H | H | 4-CN,2-Cl | 1 |
| E-6101 | H | H | H | H | H | 4-CN,3-Cl | 1 |
| E-6102 | H | H | H | H | H | 4-CN,2-Me | 1 |
| E-6103 | H | H | H | H | H | 4-CN,3-Me | 1 |
| E-6104 | H | H | H | H | H | 4-CN,2-OMe | 1 |
| E-6105 | H | H | H | H | H | 4-CN,3-OMe | 1 |
| E-6106 | H | H | H | H | H | 2-NO₂,3-F | 1 |
| E-6107 | H | H | H | H | H | 2-NO₂,4-F | 1 |
| E-6108 | H | H | H | H | H | 2-NO₂,5-F | 1 |
| E-6109 | H | H | H | H | H | 2-NO₂,6-F | 1 |
| E-6110 | H | H | H | H | H | 2-NO₂,3-Me | 1 |
| E-6111 | H | H | H | H | H | 2-NO₂,4-Me | 1 |
| E-6112 | H | H | H | H | H | 2-NO₂,5-Me | 1 |
| E-6113 | H | H | H | H | H | 2-NO₂,6-Me | 1 |
| E-6114 | H | H | H | H | H | 2-Me,3,4-F₂ | 1 |
| E-6115 | H | H | H | H | H | 2-Me,3,5-F₂ | 1 |
| E-6116 | H | H | H | H | H | 2-Me,3,6-F₂ | 1 |
| E-6117 | H | H | H | H | H | 2-Me,4,5-F₂ | 1 |
| E-6118 | H | H | H | H | H | 2-OMe,3,4-F₂ | 1 |
| E-6119 | H | H | H | H | H | 2-OMe,3,5-F₂ | 1 |
| E-6120 | H | H | H | H | H | 2-OMe,3,6-F₂ | 1 |
| E-6121 | H | H | H | H | H | 2-OMe,4,5-F₂ | 1 |
| E-6122 | H | H | H | H | H | 2-(CH₂)₃-3 | 1 |
| E-6123 | H | H | H | H | H | 2-(CH₂)₄-3 | 1 |
| E-6124 | H | H | H | H | H | 2-(OCH₂CH₂)-3 | 1 |
| E-6125 | H | H | H | H | H | 2-(OCH₂CH₂CH₂)-3 | 1 |
| E-6126 | H | H | H | H | H | 2-(CH₂CH₂O)-3 | 1 |
| E-6127 | H | H | H | H | H | 2-(CH₂CH₂CH₂O)-3 | 1 |
| E-6128 | H | H | H | H | H | 3-(CH₂)₃-4 | 1 |
| E-6129 | H | H | H | H | H | 3-(CH₂)₄-4 | 1 |
| E-6130 | H | H | H | H | H | 3-(OCH₂CH₂)-4 | 1 |
| E-6131 | H | H | H | H | H | 3-(OCH₂CH₂CH₂)-4 | 1 |
| E-6132 | H | H | H | H | H | 3-(CH₂CH₂O)-4 | 1 |
| E-6133 | H | H | H | H | H | 3-(CH₂CH₂CH₂O)-4 | 1 |
| E-6134 | H | H | H | H | H | 2-(OCH₂O)-3 | 1 |
| E-6135 | H | H | H | H | H | 3-(OCH₂O)-4 | 1 |

TABLE 296

| compound | R¹ | R² | R³ | R⁴ | R⁵ | (R⁸)ₘ | p |
|---|---|---|---|---|---|---|---|
| E-6136 | H | H | H | H | H | 2-(OCH₂CH₂O)-3 | 1 |
| E-6137 | H | H | H | H | H | 3-(OCH₂CH₂O)-4 | 1 |
| E-6138 | H | H | H | H | H | 2-(OCF₂O)-3 | 1 |
| E-6139 | H | H | H | H | H | 3-(OCF₂O)-4 | 1 |
| E-6140 | H | H | H | H | H | 2-Me,6-Et | 1 |
| E-6141 | H | H | H | H | H | 2-Me,4,5-F₂ | 1 |
| E-6142 | H | H | H | H | H | 2-cyclopropyl,6-OMe | 1 |
| E-6143 | H | H | H | H | H | 2-Me,5-Et | 1 |
| E-6144 | H | H | H | H | H | 2,6-Et₂ | 1 |
| E-6145 | H | H | H | H | H | 2-Et,6-F | 1 |
| E-6146 | H | H | H | H | H | 2-CH₂OCH₃,6-Cl | 1 |
| E-6147 | H | H | H | H | H | 2-CH₂OCH₂CH₃,6-Cl | 1 |
| E-6148 | H | H | H | H | H | 2-CH₂NMe₂ | 1 |

TABLE 297

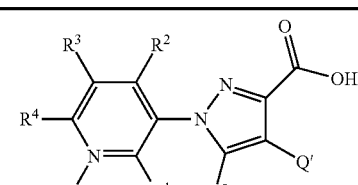

| compound | R¹ | R² | R³ | R⁴ | R⁵ | Q' | p |
|---|---|---|---|---|---|---|---|
| F-0001 | H | H | H | H | H | Cl | 0 |
| F-0002 | H | H | H | H | H | Br | 0 |
| F-0003 | H | H | H | H | H | I | 0 |
| F-0004 | H | H | H | H | H | OS(=O)₂Me | 0 |
| F-0005 | H | H | H | H | H | OS(=O)₂CF₃ | 0 |
| F-0006 | H | H | H | H | H | OS(=O)₂CF₂CF₃ | 0 |
| F-0007 | H | H | H | H | H | OS(=O)₂CF₂CF₂CF₃ | 0 |
| F-0008 | H | H | H | H | H | OS(=O)₂CF₂CF₂CF₂CF₃ | 0 |
| F-0009 | H | H | H | H | H | OS(=O)₂(4-MePh) | 0 |
| F-0010 | H | H | H | H | H | OS(=O)₂N(Me)₂ | 0 |
| F-0011 | H | H | H | H | H | OS(=O)₂N(Et)₂ | 0 |
| F-0012 | H | H | H | H | H | naphthalen-1-yl | 0 |
| F-0013 | H | H | H | H | H | 2-F-naphthalen-1-yl | 0 |
| F-0014 | H | H | H | H | H | 2-Me-naphthalen-1-yl | 0 |
| F-0015 | H | H | H | H | H | 2-CF₃-naphthalen-1-yl | 0 |
| F-0016 | H | H | H | H | H | 2-OMe-naphthalen-1-yl | 0 |
| F-0017 | H | H | H | H | H | naphthalen-2-yl | 0 |
| F-0018 | H | H | H | H | H | 1-F-naphthalen-2-yl | 0 |
| F-0019 | H | H | H | H | H | 1-Me-naphthalen-2-yl | 0 |
| F-0020 | H | H | H | H | H | 1-CF₃-naphthalen-2-yl | 0 |
| F-0021 | H | H | H | H | H | 1-OMe-naphthalen-2-yl | 0 |
| F-0022 | H | H | H | H | H | 3-F-naphthalen-2-yl | 0 |
| F-0023 | H | H | H | H | H | 3-Me-naphthalen-2-yl | 0 |
| F-0024 | H | H | H | H | H | 3-CF₃-naphthalen-2-yl | 0 |
| F-0025 | H | H | H | H | H | 3-OMe-naphthalen-2-yl | 0 |
| F-0026 | H | H | H | H | H | pyridin-2-yl | 0 |
| F-0027 | H | H | H | H | H | 3-F-pyridin-2-yl | 0 |
| F-0028 | H | H | H | H | H | 4-F-pyridin-2-yl | 0 |
| F-0029 | H | H | H | H | H | 5-F-pyridin-2-yl | 0 |
| F-0030 | H | H | H | H | H | 6-F-pyridin-2-yl | 0 |
| F-0031 | H | H | H | H | H | 3-Cl-pyridin-2-yl | 0 |
| F-0032 | H | H | H | H | H | 4-Cl-pyridin-2-yl | 0 |
| F-0033 | H | H | H | H | H | 5-Cl-pyridin-2-yl | 0 |
| F-0034 | H | H | H | H | H | 6-Cl-pyridin-2-yl | 0 |
| F-0035 | H | H | H | H | H | 3-Me-pyridin-2-yl | 0 |
| F-0036 | H | H | H | H | H | 4-Me-pyridin-2-yl | 0 |
| F-0037 | H | H | H | H | H | 5-Me-pyridin-2-yl | 0 |
| F-0038 | H | H | H | H | H | 6-Me-pyridin-2-yl | 0 |
| F-0039 | H | H | H | H | H | 3-CF₃-pyridin-2-yl | 0 |
| F-0040 | H | H | H | H | H | 4-CF₃-pyridin-2-yl | 0 |
| F-0041 | H | H | H | H | H | 5-CF₃-pyridin-2-yl | 0 |
| F-0042 | H | H | H | H | H | 6-CF₃-pyridin-2-yl | 0 |
| F-0043 | H | H | H | H | H | 3-OMe-pyridin-2-yl | 0 |
| F-0044 | H | H | H | H | H | 4-OMe-pyridin-2-yl | 0 |
| F-0045 | H | H | H | H | H | 5-OMe-pyridin-2-yl | 0 |
| F-0046 | H | H | H | H | H | 6-OMe-pyridin-2-yl | 0 |
| F-0047 | H | H | H | H | H | 3,4-F₂-pyridin-2-yl | 0 |
| F-0048 | H | H | H | H | H | 3,5-F₂-pyridin-2-yl | 0 |
| F-0049 | H | H | H | H | H | 3,6-F₂-pyridin-2-yl | 0 |

TABLE 297-continued

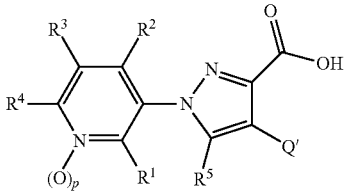

| compound | R¹ | R² | R³ | R⁴ | R⁵ | Q' | p |
|---|---|---|---|---|---|---|---|
| F-0050 | H | H | H | H | H | 3,4-Cl₂-pyridin-2-yl | 0 |
| F-0051 | H | H | H | H | H | 3,5-Cl₂-pyridin-2-yl | 0 |
| F-0052 | H | H | H | H | H | 3,6-Cl₂-pyridin-2-yl | 0 |

TABLE 298

| compound | R¹ | R² | R³ | R⁴ | R⁵ | Q' | p |
|---|---|---|---|---|---|---|---|
| F-0053 | H | H | H | H | H | 3-F-4-Cl-pyridin-2-yl | 0 |
| F-0054 | H | H | H | H | H | 3-F-5-Cl-pyridin-2-yl | 0 |
| F-0055 | H | H | H | H | H | 3-F-6-Cl-pyridin-2-yl | 0 |
| F-0056 | H | H | H | H | H | 3-F-4-Me-pyridin-2-yl | 0 |
| F-0057 | H | H | H | H | H | 3-F-5-Me-pyridin-2-yl | 0 |
| F-0058 | H | H | H | H | H | 3-F-6-Me-pyridin-2-yl | 0 |
| F-0059 | H | H | H | H | H | 3-F-4-OMe-pyridin-2-yl | 0 |
| F-0060 | H | H | H | H | H | 3-F-5-OMe-pyridin-2-yl | 0 |
| F-0061 | H | H | H | H | H | 3-F-6-OMe-pyridin-2-yl | 0 |
| F-0062 | H | H | H | H | H | 3-Cl-4-F-pyridin-2-yl | 0 |
| F-0063 | H | H | H | H | H | 3-Cl-5-F-pyridin-2-yl | 0 |
| F-0064 | H | H | H | H | H | 3-Cl-6-F-pyridin-2-yl | 0 |
| F-0065 | H | H | H | H | H | 3-Cl-4-Me-pyridin-2-yl | 0 |
| F-0066 | H | H | H | H | H | 3-Cl-5-Me-pyridin-2-yl | 0 |
| F-0067 | H | H | H | H | H | 3-Cl-6-Me-pyridin-2-yl | 0 |
| F-0068 | H | H | H | H | H | 3-Me-4-F-pyridin-2-yl | 0 |
| F-0069 | H | H | H | H | H | 3-Me-5-F-pyridin-2-yl | 0 |
| F-0070 | H | H | H | H | H | 3-Me-6-F-pyridin-2-yl | 0 |
| F-0071 | H | H | H | H | H | 3-Me-4-Cl-pyridin-2-yl | 0 |
| F-0072 | H | H | H | H | H | 3-Me-5-Cl-pyridin-2-yl | 0 |
| F-0073 | H | H | H | H | H | 3-Me-6-Cl-pyridin-2-yl | 0 |
| F-0074 | H | H | H | H | H | 3,4-(Me)₂-pyridin-2-yl | 0 |
| F-0075 | H | H | H | H | H | 3,5-(Me)₂-pyridin-2-yl | 0 |
| F-0076 | H | H | H | H | H | 3,6-(Me)₂-pyridin-2-yl | 0 |
| F-0077 | H | H | H | H | H | 3-Me-4-OMe-pyridin-2-yl | 0 |
| F-0078 | H | H | H | H | H | 3-Me-5-OMe-pyridin-2-yl | 0 |
| F-0079 | H | H | H | H | H | 3-Me-6-OMe-pyridin-2-yl | 0 |
| F-0080 | H | H | H | H | H | 3-CF₃-4-F-pyridin-2-yl | 0 |
| F-0081 | H | H | H | H | H | 3-CF₃-5-F-pyridin-2-yl | 0 |
| F-0082 | H | H | H | H | H | 3-CF₃-6-F-pyridin-2-yl | 0 |
| F-0083 | H | H | H | H | H | 3-CF₃-4-Me-pyridin-2-yl | 0 |
| F-0084 | H | H | H | H | H | 3-CF₃-5-Me-pyridin-2-yl | 0 |
| F-0085 | H | H | H | H | H | 3-CF₃-6-Me-pyridin-2-yl | 0 |
| F-0086 | H | H | H | H | H | 3-OMe-4-F-pyridin-2-yl | 0 |
| F-0087 | H | H | H | H | H | 3-OMe-5-F-pyridin-2-yl | 0 |
| F-0088 | H | H | H | H | H | 3-OMe-6-F-pyridin-2-yl | 0 |
| F-0089 | H | H | H | H | H | 3-OMe-4-Cl-pyridin-2-yl | 0 |
| F-0090 | H | H | H | H | H | 3-OMe-5-Cl-pyridin-2-yl | 0 |
| F-0091 | H | H | H | H | H | 3-OMe-6-Cl-pyridin-2-yl | 0 |
| F-0092 | H | H | H | H | H | 3-OMe-4-Me-pyridin-2-yl | 0 |
| F-0093 | H | H | H | H | H | 3-OMe-5-Me-pyridin-2-yl | 0 |
| F-0094 | H | H | H | H | H | 3-OMe-6-Me-pyridin-2-yl | 0 |
| F-0095 | H | H | H | H | H | 3,4-(OMe)₂-pyridin-2-yl | 0 |
| F-0096 | H | H | H | H | H | 3,5-(OMe)₂-pyridin-2-yl | 0 |
| F-0097 | H | H | H | H | H | 3,6-(OMe)₂-pyridin-2-yl | 0 |
| F-0098 | H | H | H | H | H | pyridin-3-yl | 0 |
| F-0099 | H | H | H | H | H | 2-F-pyridin-3-yl | 0 |
| F-0100 | H | H | H | H | H | 4-F-pyridin-3-yl | 0 |
| F-0101 | H | H | H | H | H | 5-F-pyridin-3-yl | 0 |
| F-0102 | H | H | H | H | H | 6-F-pyridin-3-yl | 0 |
| F-0103 | H | H | H | H | H | 2-Cl-pyridin-3-yl | 0 |
| F-0104 | H | H | H | H | H | 4-Cl-pyridin-3-yl | 0 |
| F-0105 | H | H | H | H | H | 5-Cl-pyridin-3-yl | 0 |
| F-0106 | H | H | H | H | H | 6-Cl-pyridin-3-yl | 0 |
| F-0107 | H | H | H | H | H | 2-Me-pyridin-3-yl | 0 |
| F-0108 | H | H | H | H | H | 4-Me-pyridin-3-yl | 0 |
| F-0109 | H | H | H | H | H | 5-Me-pyridin-3-yl | 0 |

TABLE 299

| compound | R¹ | R² | R³ | R⁴ | R⁵ | Q' | p |
|---|---|---|---|---|---|---|---|
| F-0110 | H | H | H | H | H | 6-Me-pyridin-3-yl | 0 |
| F-0111 | H | H | H | H | H | 2-CF₃-pyridin-3-yl | 0 |
| F-0112 | H | H | H | H | H | 4-CF₃-pyridin-3-yl | 0 |
| F-0113 | H | H | H | H | H | 5-CF₃-pyridin-3-yl | 0 |
| F-0114 | H | H | H | H | H | 6-CF₃-pyridin-3-yl | 0 |
| F-0115 | H | H | H | H | H | 2-OMe-pyridin-3-yl | 0 |
| F-0116 | H | H | H | H | H | 4-OMe-pyridin-3-yl | 0 |
| F-0117 | H | H | H | H | H | 5-OMe-pyridin-3-yl | 0 |
| F-0118 | H | H | H | H | H | 6-OMe-pyridin-3-yl | 0 |
| F-0119 | H | H | H | H | H | 2,4-F₂-pyridin-3-yl | 0 |
| F-0120 | H | H | H | H | H | 2,5-F₂-pyridin-3-yl | 0 |
| F-0121 | H | H | H | H | H | 2,6-F₂-pyridin-3-yl | 0 |
| F-0122 | H | H | H | H | H | 4,5-F₂-pyridin-3-yl | 0 |
| F-0123 | H | H | H | H | H | 4,6-F₂-pyridin-3-yl | 0 |
| F-0124 | H | H | H | H | H | 2,4-Cl₂-pyridin-3-yl | 0 |
| F-0125 | H | H | H | H | H | 2,5-Cl₂-pyridin-3-yl | 0 |
| F-0126 | H | H | H | H | H | 2,6-Cl₂-pyridin-3-yl | 0 |
| F-0127 | H | H | H | H | H | 4,5-Cl₂-pyridin-3-yl | 0 |
| F-0128 | H | H | H | H | H | 4,6-Cl₂-pyridin-3-yl | 0 |
| F-0129 | H | H | H | H | H | 2-F-4-Cl-pyridin-3-yl | 0 |
| F-0130 | H | H | H | H | H | 2-F-5-Cl-pyridin-3-yl | 0 |
| F-0131 | H | H | H | H | H | 2-F-6-Cl-pyridin-3-yl | 0 |
| F-0132 | H | H | H | H | H | 4-F-2-Cl-pyridin-3-yl | 0 |
| F-0133 | H | H | H | H | H | 4-F-5-Cl-pyridin-3-yl | 0 |
| F-0134 | H | H | H | H | H | 4-F-6-Cl-pyridin-3-yl | 0 |
| F-0135 | H | H | H | H | H | 2-F-4-Me-pyridin-3-yl | 0 |
| F-0136 | H | H | H | H | H | 2-F-5-Me-pyridin-3-yl | 0 |
| F-0137 | H | H | H | H | H | 2-F-6-Me-pyridin-3-yl | 0 |
| F-0138 | H | H | H | H | H | 4-F-2-Me-pyridin-3-yl | 0 |
| F-0139 | H | H | H | H | H | 4-F-5-Me-pyridin-3-yl | 0 |
| F-0140 | H | H | H | H | H | 4-F-6-Me-pyridin-3-yl | 0 |
| F-0141 | H | H | H | H | H | 2-F-4-OMe-pyridin-3-yl | 0 |
| F-0142 | H | H | H | H | H | 2-F-5-OMe-pyridin-3-yl | 0 |
| F-0143 | H | H | H | H | H | 2-F-6-OMe-pyridin-3-yl | 0 |
| F-0144 | H | H | H | H | H | 4-F-2-OMe-pyridin-3-yl | 0 |
| F-0145 | H | H | H | H | H | 4-F-5-OMe-pyridin-3-yl | 0 |
| F-0146 | H | H | H | H | H | 4-F-6-OMe-pyridin-3-yl | 0 |
| F-0147 | H | H | H | H | H | 2-Cl-5-F-pyridin-3-yl | 0 |
| F-0148 | H | H | H | H | H | 2-Cl-6-F-pyridin-3-yl | 0 |
| F-0149 | H | H | H | H | H | 4-Cl-5-F-pyridin-3-yl | 0 |
| F-0150 | H | H | H | H | H | 4-Cl-6-F-pyridin-3-yl | 0 |
| F-0151 | H | H | H | H | H | 2-Cl-4-Me-pyridin-3-yl | 0 |
| F-0152 | H | H | H | H | H | 2-Cl-5-Me-pyridin-3-yl | 0 |
| F-0153 | H | H | H | H | H | 2-Cl-6-Me-pyridin-3-yl | 0 |
| F-0154 | H | H | H | H | H | 4-Cl-2-Me-pyridin-3-yl | 0 |
| F-0155 | H | H | H | H | H | 4-Cl-5-Me-pyridin-3-yl | 0 |
| F-0156 | H | H | H | H | H | 4-Cl-6-Me-pyridin-3-yl | 0 |
| F-0157 | H | H | H | H | H | 2-Me-5-F-pyridin-3-yl | 0 |
| F-0158 | H | H | H | H | H | 2-Me-6-F-pyridin-3-yl | 0 |
| F-0159 | H | H | H | H | H | 4-Me-5-F-pyridin-3-yl | 0 |
| F-0160 | H | H | H | H | H | 4-Me-6-F-pyridin-3-yl | 0 |
| F-0161 | H | H | H | H | H | 2-Me-5-Cl-pyridin-3-yl | 0 |
| F-0162 | H | H | H | H | H | 2-Me-6-Cl-pyridin-3-yl | 0 |
| F-0163 | H | H | H | H | H | 4-Me-5-Cl-pyridin-3-yl | 0 |
| F-0164 | H | H | H | H | H | 4-Me-6-Cl-pyridin-3-yl | 0 |
| F-0165 | H | H | H | H | H | 2,4-(Me)₂-pyridin-3-yl | 0 |
| F-0166 | H | H | H | H | H | 2,5-(Me)₂-pyridin-3-yl | 0 |

TABLE 300

| compound | R¹ | R² | R³ | R⁴ | R⁵ | Q' | p |
|---|---|---|---|---|---|---|---|
| F-0167 | H | H | H | H | H | 2,6-(Me)₂-pyridin-3-yl | 0 |
| F-0168 | H | H | H | H | H | 4,5-(Me)₂-pyridin-3-yl | 0 |
| F-0169 | H | H | H | H | H | 4,6-(Me)₂-pyridin-3-yl | 0 |

TABLE 300-continued

| compound | R¹ | R² | R³ | R⁴ | R⁵ | Q' | p |
|---|---|---|---|---|---|---|---|
| F-0170 | H | H | H | H | H | 2-Me-4-OMe-pyridin-3-yl | 0 |
| F-0171 | H | H | H | H | H | 2-Me-5-OMe-pyridin-3-yl | 0 |
| F-0172 | H | H | H | H | H | 2-Me-6-OMe-pyridin-3-yl | 0 |
| F-0173 | H | H | H | H | H | 4-Me-2-OMe-pyridin-3-yl | 0 |
| F-0174 | H | H | H | H | H | 4-Me-5-OMe-pyridin-3-yl | 0 |
| F-0175 | H | H | H | H | H | 4-Me-6-OMe-pyridin-3-yl | 0 |
| F-0176 | H | H | H | H | H | 2-CF₃-4-F-pyridin-3-yl | 0 |
| F-0177 | H | H | H | H | H | 2-CF₃-5-F-pyridin-3-yl | 0 |
| F-0178 | H | H | H | H | H | 2-CF₃-6-F-pyridin-3-yl | 0 |
| F-0179 | H | H | H | H | H | 4-CF₃-2-F-pyridin-3-yl | 0 |
| F-0180 | H | H | H | H | H | 4-CF₃-5-F-pyridin-3-yl | 0 |
| F-0181 | H | H | H | H | H | 4-CF₃-6-F-pyridin-3-yl | 0 |
| F-0182 | H | H | H | H | H | 2-CF₃-4-Me-pyridin-3-yl | 0 |
| F-0183 | H | H | H | H | H | 2-CF₃-5-Me-pyridin-3-yl | 0 |
| F-0184 | H | H | H | H | H | 2-CF₃-6-Me-pyridin-3-yl | 0 |
| F-0185 | H | H | H | H | H | 4-CF₃-2-Me-pyridin-3-yl | 0 |
| F-0186 | H | H | H | H | H | 4-CF₃-5-Me-pyridin-3-yl | 0 |
| F-0187 | H | H | H | H | H | 4-CF₃-6-Me-pyridin-3-yl | 0 |
| F-0188 | H | H | H | H | H | 2-OMe-5-F-pyridin-3-yl | 0 |
| F-0189 | H | H | H | H | H | 2-OMe-6-F-pyridin-3-yl | 0 |
| F-0190 | H | H | H | H | H | 4-OMe-5-F-pyridin-3-yl | 0 |
| F-0191 | H | H | H | H | H | 4-OMe-6-F-pyridin-3-yl | 0 |
| F-0192 | H | H | H | H | H | 2-OMe-4-Cl-pyridin-3-yl | 0 |
| F-0193 | H | H | H | H | H | 2-OMe-5-Cl-pyridin-3-yl | 0 |
| F-0194 | H | H | H | H | H | 2-OMe-6-Cl-pyridin-3-yl | 0 |
| F-0195 | H | H | H | H | H | 4-OMe-2-Cl-pyridin-3-yl | 0 |
| F-0196 | H | H | H | H | H | 4-OMe-5-Cl-pyridin-3-yl | 0 |
| F-0197 | H | H | H | H | H | 4-OMe-6-Cl-pyridin-3-yl | 0 |
| F-0198 | H | H | H | H | H | 2-OMe-5-Me-pyridin-3-yl | 0 |
| F-0199 | H | H | H | H | H | 2-OMe-6-Me-pyridin-3-yl | 0 |
| F-0200 | H | H | H | H | H | 4-OMe-5-Me-pyridin-3-yl | 0 |
| F-0201 | H | H | H | H | H | 4-OMe-6-Me-pyridin-3-yl | 0 |
| F-0202 | H | H | H | H | H | 2,4-(OMe)₂-pyridin-3-yl | 0 |
| F-0203 | H | H | H | H | H | 2,5-(OMe)₂-pyridin-3-yl | 0 |
| F-0204 | H | H | H | H | H | 2,6-(OMe)₂-pyridin-3-yl | 0 |
| F-0205 | H | H | H | H | H | 4,5-(OMe)₂-pyridin-3-yl | 0 |
| F-0206 | H | H | H | H | H | 4,6-(OMe)₂-pyridin-3-yl | 0 |
| F-0207 | H | H | H | H | H | pyridin-4-yl | 0 |
| F-0208 | H | H | H | H | H | 2-F-pyridin-4-yl | 0 |
| F-0209 | H | H | H | H | H | 3-F-pyridin-4-yl | 0 |
| F-0210 | H | H | H | H | H | 2-Cl-pyridin-4-yl | 0 |
| F-0211 | H | H | H | H | H | 3-Cl-pyridin-4-yl | 0 |
| F-0212 | H | H | H | H | H | 2-Me-pyridin-4-yl | 0 |
| F-0213 | H | H | H | H | H | 3-Me-pyridin-4-yl | 0 |
| F-0214 | H | H | H | H | H | 2-CF₃-pyridin-4-yl | 0 |
| F-0215 | H | H | H | H | H | 3-CF₃-pyridin-4-yl | 0 |
| F-0216 | H | H | H | H | H | 2-OMe-pyridin-4-yl | 0 |
| F-0217 | H | H | H | H | H | 3-OMe-pyridin-4-yl | 0 |
| F-0218 | H | H | H | H | H | 2,3-F₂-pyridin-4-yl | 0 |
| F-0219 | H | H | H | H | H | 2,5-F₂-pyridin-4-yl | 0 |
| F-0220 | H | H | H | H | H | 2,6-F₂-pyridin-4-yl | 0 |
| F-0221 | H | H | H | H | H | 3,5-F₂-pyridin-4-yl | 0 |
| F-0222 | H | H | H | H | H | 2,3-Cl₂-pyridin-4-yl | 0 |
| F-0223 | H | H | H | H | H | 2,5-Cl₂-pyridin-4-yl | 0 |

TABLE 301

| compound | R¹ | R² | R³ | R⁴ | R⁵ | Q' | p |
|---|---|---|---|---|---|---|---|
| F-0224 | H | H | H | H | H | 2,6-Cl₂-pyridin-4-yl | 0 |
| F-0225 | H | H | H | H | H | 3,5-Cl₂-pyridin-4-yl | 0 |
| F-0226 | H | H | H | H | H | 3-F-2-Cl-pyridin-4-yl | 0 |
| F-0227 | H | H | H | H | H | 3-F-5-Cl-pyridin-4-yl | 0 |
| F-0228 | H | H | H | H | H | 3-F-6-Cl-pyridin-4-yl | 0 |
| F-0229 | H | H | H | H | H | 3-F-2-Me-pyridin-4-yl | 0 |
| F-0230 | H | H | H | H | H | 3-F-5-Me-pyridin-4-yl | 0 |
| F-0231 | H | H | H | H | H | 3-F-6-Me-pyridin-4-yl | 0 |
| F-0232 | H | H | H | H | H | 3-F-2-OMe-pyridin-4-yl | 0 |
| F-0233 | H | H | H | H | H | 3-F-5-OMe-pyridin-4-yl | 0 |
| F-0234 | H | H | H | H | H | 3-F-6-OMe-pyridin-4-yl | 0 |
| F-0235 | H | H | H | H | H | 3-Cl-2-F-pyridin-4-yl | 0 |
| F-0236 | H | H | H | H | H | 3-Cl-6-F-pyridin-4-yl | 0 |
| F-0237 | H | H | H | H | H | 3-Cl-2-Me-pyridin-4-yl | 0 |
| F-0238 | H | H | H | H | H | 3-Cl-5-Me-pyridin-4-yl | 0 |
| F-0239 | H | H | H | H | H | 3-Cl-6-Me-pyridin-4-yl | 0 |

TABLE 301-continued

| compound | R¹ | R² | R³ | R⁴ | R⁵ | Q' | p |
|---|---|---|---|---|---|---|---|
| F-0240 | H | H | H | H | H | 3-Me-2-F-pyridin-4-yl | 0 |
| F-0241 | H | H | H | H | H | 3-Me-6-F-pyridin-4-yl | 0 |
| F-0242 | H | H | H | H | H | 3-Me-2-Cl-pyridin-4-yl | 0 |
| F-0243 | H | H | H | H | H | 3-Me-6-Cl-pyridin-4-yl | 0 |
| F-0244 | H | H | H | H | H | 2,3-(Me)₂-pyridin-4-yl | 0 |
| F-0245 | H | H | H | H | H | 3,5-(Me)₂-pyridin-4-yl | 0 |
| F-0246 | H | H | H | H | H | 3,6-(Me)₂-pyridin-4-yl | 0 |
| F-0247 | H | H | H | H | H | 3-Me-2-OMe-pyridin-4-yl | 0 |
| F-0248 | H | H | H | H | H | 3-Me-5-OMe-pyridin-4-yl | 0 |
| F-0249 | H | H | H | H | H | 3-Me-6-OMe-pyridin-4-yl | 0 |
| F-0250 | H | H | H | H | H | 3-CF₃-2-F-pyridin-4-yl | 0 |
| F-0251 | H | H | H | H | H | 3-CF₃-5-F-pyridin-4-yl | 0 |
| F-0252 | H | H | H | H | H | 3-CF₃-6-F-pyridin-4-yl | 0 |
| F-0253 | H | H | H | H | H | 3-CF₃-2-Me-pyridin-4-yl | 0 |
| F-0254 | H | H | H | H | H | 3-CF₃-5-Me-pyridin-4-yl | 0 |
| F-0255 | H | H | H | H | H | 3-CF₃-6-Me-pyridin-4-yl | 0 |
| F-0256 | H | H | H | H | H | 3-OMe-2-F-pyridin-4-yl | 0 |
| F-0257 | H | H | H | H | H | 3-OMe-6-F-pyridin-4-yl | 0 |
| F-0258 | H | H | H | H | H | 3-OMe-2-Cl-pyridin-4-yl | 0 |
| F-0259 | H | H | H | H | H | 3-OMe-5-Cl-pyridin-4-yl | 0 |
| F-0260 | H | H | H | H | H | 3-OMe-6-Cl-pyridin-4-yl | 0 |
| F-0261 | H | H | H | H | H | 3-OMe-2-Me-pyridin-4-yl | 0 |
| F-0262 | H | H | H | H | H | 3-OMe-6-Me-pyridin-4-yl | 0 |
| F-0263 | H | H | H | H | H | 2,3-(OMe)₂-pyridin-4-yl | 0 |
| F-0264 | H | H | H | H | H | 3,5-(OMe)₂-pyridin-4-yl | 0 |
| F-0265 | H | H | H | H | H | 3,6-(OMe)₂-pyridin-4-yl | 0 |
| F-0266 | H | H | H | H | H | pyrimidin-2-yl | 0 |
| F-0267 | H | H | H | H | H | pyrimidin-4-yl | 0 |
| F-0268 | H | H | H | H | H | 5-F-pyrimidin-4-yl | 0 |
| F-0269 | H | H | H | H | H | 5-Me-pyrimidin-4-yl | 0 |
| F-0270 | H | H | H | H | H | 5-CF₃-pyrimidin-4-yl | 0 |
| F-0271 | H | H | H | H | H | 5-OMe-pyrimidin-4-yl | 0 |
| F-0272 | H | H | H | H | H | pyrimidin-5-yl | 0 |
| F-0273 | H | H | H | H | H | 4-F-pyrimidin-5-yl | 0 |
| F-0274 | H | H | H | H | H | 4-Cl-pyrimidin-5-yl | 0 |
| F-0275 | H | H | H | H | H | 4-Me-pyrimidin-5-yl | 0 |
| F-0276 | H | H | H | H | H | 4-CF₃-pyrimidin-5-yl | 0 |
| F-0277 | H | H | H | H | H | 4-OMe-pyrimidin-5-yl | 0 |
| F-0278 | H | H | H | H | H | pyridazin-3-yl | 0 |
| F-0279 | H | H | H | H | H | 4-F-pyridazin-3-yl | 0 |
| F-0280 | H | H | H | H | H | 4-Cl-pyridazin-3-yl | 0 |

TABLE 302

| compound | R¹ | R² | R³ | R⁴ | R⁵ | Q' | p |
|---|---|---|---|---|---|---|---|
| F-0281 | H | H | H | H | H | 4-Me-pyridazin-3-yl | 0 |
| F-0282 | H | H | H | H | H | 4-CF₃-pyridazin-3-yl | 0 |
| F-0283 | H | H | H | H | H | 4-OMe-pyridazin-3-yl | 0 |
| F-0284 | H | H | H | H | H | pyridazin-4-yl | 0 |
| F-0285 | H | H | H | H | H | 3-F-pyridazin-4-yl | 0 |
| F-0286 | H | H | H | H | H | 3-Cl-pyridazin-4-yl | 0 |
| F-0287 | H | H | H | H | H | 3-Me-pyridazin-4-yl | 0 |
| F-0288 | H | H | H | H | H | 3-CF₃-pyridazin-4-yl | 0 |
| F-0289 | H | H | H | H | H | 3-OMe-pyridazin-4-yl | 0 |
| F-0290 | H | H | H | H | H | 5-F-pyridazin-4-yl | 0 |
| F-0291 | H | H | H | H | H | 5-Cl-pyridazin-4-yl | 0 |
| F-0292 | H | H | H | H | H | 5-Me-pyridazin-4-yl | 0 |
| F-0293 | H | H | H | H | H | 5-CF₃-pyridazin-4-yl | 0 |
| F-0294 | H | H | H | H | H | 5-OMe-pyridazin-4-yl | 0 |
| F-0295 | H | H | H | H | H | thiophen-2-yl | 0 |
| F-0296 | H | H | H | H | H | 3-F-thiophen-2-yl | 0 |
| F-0297 | H | H | H | H | H | 3-Cl-thiophen-2-yl | 0 |
| F-0298 | H | H | H | H | H | 3-Me-thiophen-2-yl | 0 |
| F-0299 | H | H | H | H | H | 3-CF₃-thiophen-2-yl | 0 |
| F-0300 | H | H | H | H | H | 3-OMe-thiophen-2-yl | 0 |
| F-0301 | H | H | H | H | H | thiophen-3-yl | 0 |
| F-0302 | H | H | H | H | H | 2-F-thiophen-3-yl | 0 |
| F-0303 | H | H | H | H | H | 2-Cl-thiophen-3-yl | 0 |
| F-0304 | H | H | H | H | H | 2-Me-thiophen-3-yl | 0 |
| F-0305 | H | H | H | H | H | 2-CF₃-thiophen-3-yl | 0 |
| F-0306 | H | H | H | H | H | 2-OMe-thiophen-3-yl | 0 |
| F-0307 | H | H | H | H | H | 4-F-thiophen-3-yl | 0 |
| F-0308 | H | H | H | H | H | 4-Cl-thiophen-3-yl | 0 |
| F-0309 | H | H | H | H | H | 4-Me-thiophen-3-yl | 0 |

TABLE 302-continued

| compound | R¹ | R² | R³ | R⁴ | R⁵ | Q' | p |
|---|---|---|---|---|---|---|---|
| F-0310 | H | H | H | H | H | 4-CF$_3$-thiophen-3-yl | 0 |
| F-0311 | H | H | H | H | H | 4-OMe-thiophen-3-yl | 0 |
| F-0312 | H | H | H | H | H | thiazol-2-yl | 0 |
| F-0313 | H | H | H | H | H | thiazol-4-yl | 0 |
| F-0314 | H | H | H | H | H | 5-F-thiazol-4-yl | 0 |
| F-0315 | H | H | H | H | H | 5-Me-thiazol-4-yl | 0 |
| F-0316 | H | H | H | H | H | 5-CF$_3$-thiazol-4-yl | 0 |
| F-0317 | H | H | H | H | H | 5-OMe-thiazol-4-yl | 0 |
| F-0318 | H | H | H | H | H | thiazol-5-yl | 0 |
| F-0319 | H | H | H | H | H | 4-F-thiazol-5-yl | 0 |
| F-0320 | H | H | H | H | H | 4-Me-thiazol-5-yl | 0 |
| F-0321 | H | H | H | H | H | 4-CF$_3$-thiazol-5-y | 0 |
| F-0322 | H | H | H | H | H | 4-OMe-thiazol-5-yl | 0 |
| F-0323 | H | H | H | H | H | 1H-pyrrol-1-yl | 0 |
| F-0324 | H | H | H | H | H | 2-F-1H-pyrrol-1-yl | 0 |
| F-0325 | H | H | H | H | H | 2-Me-1H-pyrrol-1-yl | 0 |
| F-0326 | H | H | H | H | H | 2-CF$_3$-1H-pyrrol-1-yl | 0 |
| F-0327 | H | H | H | H | H | 2-OMe-1H-pyrrol-1-yl | 0 |
| F-0328 | H | H | H | H | H | 1H-pyrrol-2-yl | 0 |
| F-0329 | H | H | H | H | H | 1-Me-1H-pyrrol-2-yl | 0 |
| F-0330 | H | H | H | H | H | 3-F-1H-pyrrol-2-yl | 0 |
| F-0331 | H | H | H | H | H | 3-Me-1H-pyrrol-2-yl | 0 |
| F-0332 | H | H | H | H | H | 3-CF$_3$-1H-pyrrol-2-yl | 0 |
| F-0333 | H | H | H | H | H | 3-OMe-1H-pyrrol-2-yl | 0 |
| F-0334 | H | H | H | H | H | 1-Me-3-F-1H-pyrrol-2-yl | 0 |
| F-0335 | H | H | H | H | H | 1,3-(Me)$_2$-1H-pyrrol-2-yl | 0 |
| F-0336 | H | H | H | H | H | 1-Me-3-CF$_3$-1H-pyrrol-2-yl | 0 |
| F-0337 | H | H | H | H | H | 1-Me-3-OMe-1H-pyrrol-2-yl | 0 |

TABLE 303

| compound | R¹ | R² | R³ | R⁴ | R⁵ | Q' | p |
|---|---|---|---|---|---|---|---|
| F-0338 | H | H | H | H | H | 1H-pyrrol-3-yl | 0 |
| F-0339 | H | H | H | H | H | 1-Me-1H-pyrrol-3-yl | 0 |
| F-0340 | H | H | H | H | H | 2-F-1H-pyrrol-3-yl | 0 |
| F-0341 | H | H | H | H | H | 2-Me-1H-pyrrol-3-yl | 0 |
| F-0342 | H | H | H | H | H | 2-CF$_3$-1H-pyrrol-3-yl | 0 |
| F-0343 | H | H | H | H | H | 2-OMe-1H-pyrrol-3-yl | 0 |
| F-0344 | H | H | H | H | H | 1-Me-2-F-1H-pyrrol-3-yl | 0 |
| F-0345 | H | H | H | H | H | 1,2-(Me)$_2$-1H-pyrrol-3-yl | 0 |
| F-0346 | H | H | H | H | H | 1-Me-2-CF$_3$-1H-pyrrol-3-yl | 0 |
| F-0347 | H | H | H | H | H | 1-Me-2-OMe-1H-pyrrol-3-yl | 0 |
| F-0348 | H | H | H | H | H | 4-F-1H-pyrrol-3-yl | 0 |
| F-0349 | H | H | H | H | H | 4-Me-1H-pyrrol-3-yl | 0 |
| F-0350 | H | H | H | H | H | 4-CF$_3$-1H-pyrrol-3-yl | 0 |
| F-0351 | H | H | H | H | H | 4-OMe-1H-pyrrol-3-yl | 0 |
| F-0352 | H | H | H | H | H | 1-Me-4-F-1H-pyrrol-3-yl | 0 |
| F-0353 | H | H | H | H | H | 1,4-(Me)$_2$-1H-pyrrol-3-yl | 0 |
| F-0354 | H | H | H | H | H | 1-Me-4-CF$_3$-1H-pyrrol-3-yl | 0 |
| F-0355 | H | H | H | H | H | 1-Me-4-OMe-1H-pyrrol-3-yl | 0 |
| F-0356 | H | H | H | H | H | 1H-pyrazol-1-yl | 0 |
| F-0357 | H | H | H | H | H | 5-F-1H-pyrazol-1-yl | 0 |
| F-0358 | H | H | H | H | H | 5-Cl-1H-pyrazol-1-yl | 0 |
| F-0359 | H | H | H | H | H | 5-Me-1H-pyrazol-1-yl | 0 |
| F-0360 | H | H | H | H | H | 5-CF$_3$-1H-pyrazol-1-yl | 0 |
| F-0361 | H | H | H | H | H | 5-OMe-1H-pyrazol-1-yl | 0 |
| F-0362 | H | H | H | H | H | 1H-pyrazol-3-yl | 0 |
| F-0363 | H | H | H | H | H | 1-Me-1H-pyrazol-3-yl | 0 |
| F-0364 | H | H | H | H | H | 4-F-1H-pyrazol-3-yl | 0 |
| F-0365 | H | H | H | H | H | 4-Cl-1H-pyrazol-3-yl | 0 |
| F-0366 | H | H | H | H | H | 4-Me-1H-pyrazol-3-yl | 0 |
| F-0367 | H | H | H | H | H | 4-CF$_3$-1H-pyrazol-3-yl | 0 |
| F-0368 | H | H | H | H | H | 4-OMe-1H-pyrazol-3-yl | 0 |
| F-0369 | H | H | H | H | H | 1-Me-4-F-1H-pyrazol-3-yl | 0 |
| F-0370 | H | H | H | H | H | 1-Me-4-Cl-1H-pyrazol-3-yl | 0 |
| F-0371 | H | H | H | H | H | 1,4-(Me)$_2$-1H-pyrazol-3-yl | 0 |
| F-0372 | H | H | H | H | H | 1-Me-4-CF$_3$-1H-pyrazol-3-yl | 0 |
| F-0373 | H | H | H | H | H | 1-Me-4-OMe-1H-pyrazol-3-yl | 0 |
| F-0374 | H | H | H | H | H | 1H-pyrazol-4-yl | 0 |
| F-0375 | H | H | H | H | H | 1-Me-1H-pyrazol-4-yl | 0 |
| F-0376 | H | H | H | H | H | 3-F-1H-pyrazol-4-yl | 0 |
| F-0377 | H | H | H | H | H | 3-Cl-1H-pyrazol-4-yl | 0 |
| F-0378 | H | H | H | H | H | 3-Me-1H-pyrazol-4-yl | 0 |
| F-0379 | H | H | H | H | H | 3-CF$_3$-1H-pyrazol-4-yl | 0 |

TABLE 303-continued

| compound | R¹ | R² | R³ | R⁴ | R⁵ | Q' | p |
|---|---|---|---|---|---|---|---|
| F-0380 | H | H | H | H | H | 3-OMe-1H-pyrazol-4-yl | 0 |
| F-0381 | H | H | H | H | H | 1-Me-3-F-1H-pyrazol-4-yl | 0 |
| F-0382 | H | H | H | H | H | 1-Me-3-Cl-1H-pyrazol-4-yl | 0 |
| F-0383 | H | H | H | H | H | 1,3-(Me)$_2$-1H-pyrazol-4-yl | 0 |
| F-0384 | H | H | H | H | H | 1-Me-3-CF$_3$-1H-pyrazol-4-yl | 0 |
| F-0385 | H | H | H | H | H | 1-Me-3-OMe-1H-pyrazol-4-yl | 0 |
| F-0386 | H | H | H | H | H | 5-F-1H-pyrazol-4-yl | 0 |
| F-0387 | H | H | H | H | H | 5-Cl-1H-pyrazol-4-yl | 0 |
| F-0388 | H | H | H | H | H | 5-Me-1H-pyrazol-4-yl | 0 |
| F-0389 | H | H | H | H | H | 5-CF$_3$-1H-pyrazol-4-yl | 0 |
| F-0390 | H | H | H | H | H | 5-OMe-1H-pyrazol-4-yl | 0 |
| F-0391 | H | H | H | H | H | 1-Me-5-F-1H-pyrazol-4-yl | 0 |
| F-0392 | H | H | H | H | H | 1-Me-5-Cl-1H-pyrazol-4-yl | 0 |
| F-0393 | H | H | H | H | H | 1,5-(Me)$_2$-1H-pyrazol-4-yl | 0 |
| F-0394 | H | H | H | H | H | 1-Me-5-CF$_3$-1H-pyrazol-4-yl | 0 |

TABLE 304

| compound | R¹ | R² | R³ | R⁴ | R⁵ | Q' | p |
|---|---|---|---|---|---|---|---|
| F-0395 | H | H | H | H | H | 1-Me-5-OMe-1H-pyrazol-4-yl | 0 |
| F-0396 | H | H | H | H | H | 1H-pyrazol-5-yl | 0 |
| F-0397 | H | H | H | H | H | 1-Me-1H-pyrazol-5-yl | 0 |
| F-0398 | H | H | H | H | H | 4-F-1H-pyrazol-5-yl | 0 |
| F-0399 | H | H | H | H | H | 4-Cl-1H-pyrazol-5-yl | 0 |
| F-0400 | H | H | H | H | H | 4-Me-1H-pyrazol-5-yl | 0 |
| F-0401 | H | H | H | H | H | 4-CF$_3$-1H-pyrazol-5-yl | 0 |
| F-0402 | H | H | H | H | H | 4-OMe-1H-pyrazol-5-yl | 0 |
| F-0403 | H | H | H | H | H | 1-Me-4-F-1H-pyrazol-5-yl | 0 |
| F-0404 | H | H | H | H | H | 1-Me-4-Cl-1H-pyrazol-5-yl | 0 |
| F-0405 | H | H | H | H | H | 1,4-(Me)$_2$-1H-pyrazol-5-yl | 0 |
| F-0406 | H | H | H | H | H | 1-Me-4-CF$_3$-1H-pyrazol-5-yl | 0 |
| F-0407 | H | H | H | H | H | 1-Me-4-OMe-1H-pyrazol-5-yl | 0 |
| F-0408 | H | H | H | H | H | furan-2-yl | 0 |
| F-0409 | H | H | H | H | H | 3-F-furan-2-yl | 0 |
| F-0410 | H | H | H | H | H | 3-Me-furan-2-yl | 0 |
| F-0411 | H | H | H | H | H | 3-CF$_3$-furan-2-yl | 0 |
| F-0412 | H | H | H | H | H | 3-OMe-furan-2-yl | 0 |
| F-0413 | H | H | H | H | H | furan-3-yl | 0 |
| F-0414 | H | H | H | H | H | 2-F-furan-3-yl | 0 |
| F-0415 | H | H | H | H | H | 2-Me-furan-3-yl | 0 |
| F-0416 | H | H | H | H | H | 2-CF$_3$-furan-3-yl | 0 |
| F-0417 | H | H | H | H | H | 2-OMe-furan-3-yl | 0 |
| F-0418 | H | H | H | H | H | 4-F-furan-3-yl | 0 |
| F-0419 | H | H | H | H | H | 4-Me-furan-3-yl | 0 |
| F-0420 | H | H | H | H | H | 4-CF3-furan-3-yl | 0 |
| F-0421 | H | H | H | H | H | 4-OMe-furan-3-yl | 0 |
| F-0422 | H | H | H | H | H | isoxazol-3-yl | 0 |
| F-0423 | H | H | H | H | H | 4-F-isoxazol-3-yl | 0 |
| F-0424 | H | H | H | H | H | 4-Me-isoxazol-3-yl | 0 |
| F-0425 | H | H | H | H | H | 4-CF$_3$-isoxazol-3-yl | 0 |
| F-0426 | H | H | H | H | H | 4-OMe-isoxazol-3-yl | 0 |
| F-0427 | H | H | H | H | H | isoxazol-4-yl | 0 |
| F-0428 | H | H | H | H | H | 5-F-isoxazol-4-yl | 0 |
| F-0429 | H | H | H | H | H | 5-Me-isoxazol-4-yl | 0 |
| F-0430 | H | H | H | H | H | 5-CF$_3$-isoxazol-4-yl | 0 |
| F-0431 | H | H | H | H | H | 5-OMe-isoxazol-4-yl | 0 |
| F-0432 | H | H | H | H | H | isoxazol-5-yl | 0 |
| F-0433 | H | H | H | H | H | 4-F-isoxazol-5-yl | 0 |
| F-0434 | H | H | H | H | H | 4-Me-isoxazol-5-yl | 0 |
| F-0435 | H | H | H | H | H | 4-CF$_3$-isoxazol-5-yl | 0 |
| F-0436 | H | H | H | H | H | 4-OMe-isoxazol-5-yl | 0 |
| F-0437 | H | H | H | H | H | 1H-1,2,3-triazol-1-yl | 0 |
| F-0438 | H | H | H | H | H | 5-F-1H-1,2,3-triazol-1-yl | 0 |
| F-0439 | H | H | H | H | H | 5-Me-1H-1,2,3-triazol-1-yl | 0 |
| F-0440 | H | H | H | H | H | 5-CF$_3$-1H-1,2,3-triazol-1-yl | 0 |
| F-0441 | H | H | H | H | H | 5-OMe-1H-1,2,3-triazol-1-yl | 0 |
| F-0442 | H | H | H | H | H | 1H-1,2,3-triazol-4-yl | 0 |
| F-0443 | H | H | H | H | H | 5-F-1H-1,2,3-triazol-4-yl | 0 |
| F-0444 | H | H | H | H | H | 5-Me-1H-1,2,3-triazol-4-yl | 0 |
| F-0445 | H | H | H | H | H | 5-CF$_3$-1H-1,2,3-triazol-4-yl | 0 |
| F-0446 | H | H | H | H | H | 5-OMe-1H-1,2,3-triazol-4-yl | 0 |
| F-0447 | H | H | H | H | H | 1H-1,2,3-triazol-5-yl | 0 |
| F-0448 | H | H | H | H | H | 4-F-1H-1,2,3-triazol-5-yl | 0 |
| F-0449 | H | H | H | H | H | 4-Me-1H-1,2,3-triazol-5-yl | 0 |

TABLE 304-continued

| compound | R¹ | R² | R³ | R⁴ | R⁵ | Q' | p |
|---|---|---|---|---|---|---|---|
| F-0450 | H | H | H | H | H | 4-CF$_3$-1H-1,2,3-triazol-5-yl | 0 |
| F-0451 | H | H | H | H | H | 4-OMe-1H-1,2,3-triazol-5-yl | 0 |

TABLE 305

| compound | R¹ | R² | R³ | R⁴ | R⁵ | Q' | p |
|---|---|---|---|---|---|---|---|
| F-0452 | H | H | H | H | H | 1H-1,2,4-triazol-1-yl | 0 |
| F-0453 | H | H | H | H | H | 5-Me-1H-1,2,4-triazol-1-yl | 0 |
| F-0454 | H | H | H | H | H | 5-F-1H-1,2,4-triazol-1-yl | 0 |
| F-0455 | H | H | H | H | H | 5-CF$_3$-1H-1,2,4-triazol-1-y | 0 |
| F-0456 | H | H | H | H | H | 5-OMe-1H-1,2,4-triazol-1-yl | 0 |
| F-0457 | H | H | H | H | H | 1H-1,2,4-triazol-3-yl | 0 |
| F-0458 | H | H | H | H | H | 1-Me-1H-1,2,4-triazol-3-yl | 0 |
| F-0459 | H | H | H | H | H | 1H-1,2,4-triazol-5-yl | 0 |
| F-0460 | H | H | H | H | H | 1-Me-1H-1,2,4-triazol-5-yl | 0 |
| F-0461 | H | H | H | H | H | 3,5-(Me)$_2$-isoxazol-4-yl | 0 |
| F-0462 | H | H | H | H | H | 3,5-(Et)$_2$-isoxazol-4-yl | 0 |
| F-0463 | H | H | H | H | H | quinolin-4-yl | 0 |
| F-0464 | H | H | H | H | H | isoquinolin-4-yl | 0 |
| F-0465 | H | H | H | H | H | 3,6-(OMe)$_2$-pyridazin-4-yl | 0 |
| F-0466 | H | H | H | H | H | 2,4-(OMe)$_2$-pyrimidin-5-yl | 0 |

TABLE 306

| compound | R¹ | R² | R³ | R⁴ | R⁵ | Q' | p |
|---|---|---|---|---|---|---|---|
| F-5001 | H | H | H | H | H | Cl | 1 |
| F-5002 | H | H | H | H | H | Br | 1 |
| F-5003 | H | H | H | H | H | I | 1 |
| F-5004 | H | H | H | H | H | OS(=O)$_2$Me | 1 |
| F-5005 | H | H | H | H | H | OS(=O)$_2$CF$_3$ | 1 |
| F-5006 | H | H | H | H | H | OS(=O)$_2$CF$_2$CF$_3$ | 1 |
| F-5007 | H | H | H | H | H | OS(=O)$_2$CF$_2$CF$_2$CF$_3$ | 1 |
| F-5008 | H | H | H | H | H | OS(=O)$_2$CF$_2$CF$_2$CF$_2$CF$_3$ | 1 |
| F-5009 | H | H | H | H | H | OS(=O)$_2$(4-MePh) | 1 |
| F-5010 | H | H | H | H | H | OS(=O)$_2$N(Me)$_2$ | 1 |
| F-5011 | H | H | H | H | H | OS(=O)$_2$N(Et)$_2$ | 1 |
| F-5012 | H | H | H | H | H | naphthalen-1-yl | 1 |
| F-5013 | H | H | H | H | H | 2-F-naphthalen-1-yl | 1 |
| F-5014 | H | H | H | H | H | 2-Me-naphthalen-1-yl | 1 |
| F-5015 | H | H | H | H | H | 2-CF$_3$-naphthalen-1-yl | 1 |
| F-5016 | H | H | H | H | H | 2-OMe-naphthalen-1-yl | 1 |
| F-5017 | H | H | H | H | H | naphthalen-2-yl | 1 |
| F-5018 | H | H | H | H | H | 1-F-naphthalen-2-yl | 1 |
| F-5019 | H | H | H | H | H | 1-Me-naphthalen-2-yl | 1 |
| F-5020 | H | H | H | H | H | 1-CF$_3$-naphthalen-2-yl | 1 |
| F-5021 | H | H | H | H | H | 1-OMe-naphthalen-2-yl | 1 |
| F-5022 | H | H | H | H | H | 3-F-naphthalen-2-yl | 1 |
| F-5023 | H | H | H | H | H | 3-Me-naphthalen-2-yl | 1 |
| F-5024 | H | H | H | H | H | 3-CF$_3$-naphthalen-2-yl | 1 |
| F-5025 | H | H | H | H | H | 3-OMe-naphthalen-2-yl | 1 |
| F-5026 | H | H | H | H | H | pyridin-2-yl | 1 |
| F-5027 | H | H | H | H | H | 3-F-pyridin-2-yl | 1 |
| F-5028 | H | H | H | H | H | 4-F-pyridin-2-yl | 1 |
| F-5029 | H | H | H | H | H | 5-F-pyridin-2-yl | 1 |
| F-5030 | H | H | H | H | H | 6-F-pyridin-2-yl | 1 |
| F-5031 | H | H | H | H | H | 3-Cl-pyridin-2-yl | 1 |
| F-5032 | H | H | H | H | H | 4-Cl-pyridin-2-yl | 1 |
| F-5033 | H | H | H | H | H | 5-Cl-pyridin-2-yl | 1 |
| F-5034 | H | H | H | H | H | 6-Cl-pyridin-2-yl | 1 |
| F-5035 | H | H | H | H | H | 3-Me-pyridin-2-yl | 1 |
| F-5036 | H | H | H | H | H | 4-Me-pyridin-2-yl | 1 |

TABLE 306-continued

| compound | R¹ | R² | R³ | R⁴ | R⁵ | Q' | p |
|---|---|---|---|---|---|---|---|
| F-5037 | H | H | H | H | H | 5-Me-pyridin-2-yl | 1 |
| F-5038 | H | H | H | H | H | 6-Me-pyridin-2-yl | 1 |
| F-5039 | H | H | H | H | H | 3-CF$_3$-pyridin-2-yl | 1 |
| F-5040 | H | H | H | H | H | 4-CF$_3$-pyridin-2-yl | 1 |
| F-5041 | H | H | H | H | H | 5-CF$_3$-pyridin-2-yl | 1 |
| F-5042 | H | H | H | H | H | 6-CF$_3$-pyridin-2-yl | 1 |
| F-5043 | H | H | H | H | H | 3-OMe-pyridin-2-yl | 1 |
| F-5044 | H | H | H | H | H | 4-OMe-pyridin-2-yl | 1 |
| F-5045 | H | H | H | H | H | 5-OMe-pyridin-2-yl | 1 |
| F-5046 | H | H | H | H | H | 6-OMe-pyridin-2-yl | 1 |
| F-5047 | H | H | H | H | H | 3,4-F$_2$-pyridin-2-yl | 1 |
| F-5048 | H | H | H | H | H | 3,5-F$_2$-pyridin-2-yl | 1 |
| F-5049 | H | H | H | H | H | 3,6-F$_2$-pyridin-2-yl | 1 |
| F-5050 | H | H | H | H | H | 3,4-Cl$_2$-pyridin-2-yl | 1 |
| F-5051 | H | H | H | H | H | 3,5-Cl$_2$-pyridin-2-yl | 1 |
| F-5052 | H | H | H | H | H | 3,6-Cl$_2$-pyridin-2-yl | 1 |

TABLE 307

| compound | R¹ | R² | R³ | R⁴ | R⁵ | Q' | p |
|---|---|---|---|---|---|---|---|
| F-5053 | H | H | H | H | H | 3-F-4-Cl-pyridin-2-yl | 1 |
| F-5054 | H | H | H | H | H | 3-F-5-Cl-pyridin-2-yl | 1 |
| F-5055 | H | H | H | H | H | 3-F-6-Cl-pyridin-2-yl | 1 |
| F-5056 | H | H | H | H | H | 3-F-4-Me-pyridin-2-yl | 1 |
| F-5057 | H | H | H | H | H | 3-F-5-Me-pyridin-2-yl | 1 |
| F-5058 | H | H | H | H | H | 3-F-6-Me-pyridin-2-yl | 1 |
| F-5059 | H | H | H | H | H | 3-F-4-OMe-pyridin-2-yl | 1 |
| F-5060 | H | H | H | H | H | 3-F-5-OMe-pyridin-2-yl | 1 |
| F-5061 | H | H | H | H | H | 3-F-6-OMe-pyridin-2-yl | 1 |
| F-5062 | H | H | H | H | H | 3-Cl-4-F-pyridin-2-yl | 1 |
| F-5063 | H | H | H | H | H | 3-Cl-5-F-pyridin-2-yl | 1 |
| F-5064 | H | H | H | H | H | 3-Cl-6-F-pyridin-2-yl | 1 |
| F-5065 | H | H | H | H | H | 3-Cl-4-Me-pyridin-2-yl | 1 |
| F-5066 | H | H | H | H | H | 3-Cl-5-Me-pyridin-2-yl | 1 |
| F-5067 | H | H | H | H | H | 3-Cl-6-Me-pyridin-2-yl | 1 |
| F-5068 | H | H | H | H | H | 3-Me-4-F-pyridin-2-yl | 1 |
| F-5069 | H | H | H | H | H | 3-Me-5-F-pyridin-2-yl | 1 |
| F-5070 | H | H | H | H | H | 3-Me-6-F-pyridin-2-yl | 1 |
| F-5071 | H | H | H | H | H | 3-Me-4-Cl-pyridin-2-yl | 1 |
| F-5072 | H | H | H | H | H | 3-Me-5-Cl-pyridin-2-yl | 1 |
| F-5073 | H | H | H | H | H | 3-Me-6-Cl-pyridin-2-yl | 1 |
| F-5074 | H | H | H | H | H | 3,4-(Me)$_2$-pyridin-2-yl | 1 |
| F-5075 | H | H | H | H | H | 3,5-(Me)$_2$-pyridin-2-yl | 1 |
| F-5076 | H | H | H | H | H | 3,6-(Me)$_2$-pyridin-2-yl | 1 |
| F-5077 | H | H | H | H | H | 3-Me-4-OMe-pyridin-2-yl | 1 |
| F-5078 | H | H | H | H | H | 3-Me-5-OMe-pyridin-2-yl | 1 |
| F-5079 | H | H | H | H | H | 3-Me-6-OMe-pyridin-2-yl | 1 |
| F-5080 | H | H | H | H | H | 3-CF$_3$-4-F-pyridin-2-yl | 1 |
| F-5081 | H | H | H | H | H | 3-CF$_3$-5-F-pyridin-2-yl | 1 |
| F-5082 | H | H | H | H | H | 3-CF$_3$-6-F-pyridin-2-yl | 1 |
| F-5083 | H | H | H | H | H | 3-CF$_3$-4-Me-pyridin-2-yl | 1 |
| F-5084 | H | H | H | H | H | 3-CF$_3$-5-Me-pyridin-2-yl | 1 |
| F-5085 | H | H | H | H | H | 3-CF$_3$-6-Me-pyridin-2-yl | 1 |
| F-5086 | H | H | H | H | H | 3-OMe-4-F-pyridin-2-yl | 1 |
| F-5087 | H | H | H | H | H | 3-OMe-5-F-pyridin-2-yl | 1 |
| F-5088 | H | H | H | H | H | 3-OMe-6-F-pyridin-2-yl | 1 |
| F-5089 | H | H | H | H | H | 3-OMe-4-Cl-pyridin-2-yl | 1 |
| F-5090 | H | H | H | H | H | 3-OMe-5-Cl-pyridin-2-yl | 1 |
| F-5091 | H | H | H | H | H | 3-OMe-6-Cl-pyridin-2-yl | 1 |
| F-5092 | H | H | H | H | H | 3-OMe-4-Me-pyridin-2-yl | 1 |
| F-5093 | H | H | H | H | H | 3-OMe-5-Me-pyridin-2-yl | 1 |
| F-5094 | H | H | H | H | H | 3-OMe-6-Me-pyridin-2-yl | 1 |
| F-5095 | H | H | H | H | H | 3,4-(OMe)$_2$-pyridin-2-yl | 1 |
| F-5096 | H | H | H | H | H | 3,5-(OMe)$_2$-pyridin-2-yl | 1 |

TABLE 307-continued

| compound | R¹ | R² | R³ | R⁴ | R⁵ | Q' | p |
|---|---|---|---|---|---|---|---|
| F-5097 | H | H | H | H | H | 3,6-(OMe)$_2$-pyridin-2-yl | 1 |
| F-5098 | H | H | H | H | H | pyridin-3-yl | 1 |
| F-5099 | H | H | H | H | H | 2-F-pyridin-3-yl | 1 |
| F-5100 | H | H | H | H | H | 4-F-pyridin-3-yl | 1 |
| F-5101 | H | H | H | H | H | 5-F-pyridin-3-yl | 1 |
| F-5102 | H | H | H | H | H | 6-F-pyridin-3-yl | 1 |
| F-5103 | H | H | H | H | H | 2-Cl-pyridin-3-yl | 1 |
| F-5104 | H | H | H | H | H | 4-Cl-pyridin-3-yl | 1 |
| F-5105 | H | H | H | H | H | 5-Cl-pyridin-3-yl | 1 |
| F-5106 | H | H | H | H | H | 6-Cl-pyridin-3-yl | 1 |
| F-5107 | H | H | H | H | H | 2-Me-pyridin-3-yl | 1 |
| F-5108 | H | H | H | H | H | 4-Me-pyridin-3-yl | 1 |
| F-5109 | H | H | H | H | H | 5-Me-pyridin-3-yl | 1 |

TABLE 308

| compound | R¹ | R² | R³ | R⁴ | R⁵ | Q' | p |
|---|---|---|---|---|---|---|---|
| F-5110 | H | H | H | H | H | 6-Me-pyridin-3-yl | 1 |
| F-5111 | H | H | H | H | H | 2-CF$_3$-pyridin-3-yl | 1 |
| F-5112 | H | H | H | H | H | 4-CF$_3$-pyridin-3-yl | 1 |
| F-5113 | H | H | H | H | H | 5-CF$_3$-pyridin-3-yl | 1 |
| F-5114 | H | H | H | H | H | 6-CF$_3$-pyridin-3-yl | 1 |
| F-5115 | H | H | H | H | H | 2-OMe-pyridin-3-yl | 1 |
| F-5116 | H | H | H | H | H | 4-OMe-pyridin-3-yl | 1 |
| F-5117 | H | H | H | H | H | 5-OMe-pyridin-3-yl | 1 |
| F-5118 | H | H | H | H | H | 6-OMe-pyridin-3-yl | 1 |
| F-5119 | H | H | H | H | H | 2,4-F$_2$-pyridin-3-yl | 1 |
| F-5120 | H | H | H | H | H | 2,5-F$_2$-pyridin-3-yl | 1 |
| F-5121 | H | H | H | H | H | 2,6-F$_2$-pyridin-3-yl | 1 |
| F-5122 | H | H | H | H | H | 4,5-F$_2$-pyridin-3-yl | 1 |
| F-5123 | H | H | H | H | H | 4,6-F$_2$-pyridin-3-yl | 1 |
| F-5124 | H | H | H | H | H | 2,4-Cl$_2$-pyridin-3-yl | 1 |
| F-5125 | H | H | H | H | H | 2,5-Cl$_2$-pyridin-3-yl | 1 |
| F-5126 | H | H | H | H | H | 2,6-Cl$_2$-pyridin-3-yl | 1 |
| F-5127 | H | H | H | H | H | 4,5-Cl$_2$-pyridin-3-yl | 1 |
| F-5128 | H | H | H | H | H | 4,6-Cl$_2$-pyridin-3-yl | 1 |
| F-5129 | H | H | H | H | H | 2-F-4-Cl-pyridin-3-yl | 1 |
| F-5130 | H | H | H | H | H | 2-F-5-Cl-pyridin-3-yl | 1 |
| F-5131 | H | H | H | H | H | 2-F-6-Cl-pyridin-3-yl | 1 |
| F-5132 | H | H | H | H | H | 4-F-2-Cl-pyridin-3-yl | 1 |
| F-5133 | H | H | H | H | H | 4-F-5-Cl-pyridin-3-yl | 1 |
| F-5134 | H | H | H | H | H | 4-F-6-Cl-pyridin-3-yl | 1 |
| F-5135 | H | H | H | H | H | 2-F-4-Me-pyridin-3-yl | 1 |
| F-5136 | H | H | H | H | H | 2-F-5-Me-pyridin-3-yl | 1 |
| F-5137 | H | H | H | H | H | 2-F-6-Me-pyridin-3-yl | 1 |
| F-5138 | H | H | H | H | H | 4-F-2-Me-pyridin-3-yl | 1 |
| F-5139 | H | H | H | H | H | 4-F-5-Me-pyridin-3-yl | 1 |
| F-5140 | H | H | H | H | H | 4-F-6-Me-pyridin-3-yl | 1 |
| F-5141 | H | H | H | H | H | 2-F-4-OMe-pyridin-3-yl | 1 |
| F-5142 | H | H | H | H | H | 2-F-5-OMe-pyridin-3-yl | 1 |
| F-5143 | H | H | H | H | H | 2-F-6-OMe-pyridin-3-yl | 1 |
| F-5144 | H | H | H | H | H | 4-F-2-OMe-pyridin-3-yl | 1 |
| F-5145 | H | H | H | H | H | 4-F-5-OMe-pyridin-3-yl | 1 |
| F-5146 | H | H | H | H | H | 4-F-6-OMe-pyridin-3-yl | 1 |
| F-5147 | H | H | H | H | H | 2-Cl-5-F-pyridin-3-yl | 1 |
| F-5148 | H | H | H | H | H | 2-Cl-6-F-pyridin-3-yl | 1 |
| F-5149 | H | H | H | H | H | 4-Cl-5F-pyridin-3-yl | 1 |
| F-5150 | H | H | H | H | H | 4-Cl-6-F-pyridin-3-yl | 1 |
| F-5151 | H | H | H | H | H | 2-Cl-4-Me-pyridin-3-yl | 1 |
| F-5152 | H | H | H | H | H | 2-Cl-5-Me-pyridin-3-yl | 1 |
| F-5153 | H | H | H | H | H | 2-Cl-6-Me-pyridin-3-yl | 1 |
| F-5154 | H | H | H | H | H | 4-Cl-2-Me-pyridin-3-yl | 1 |
| F-5155 | H | H | H | H | H | 4-Cl-5-Me-pyridin-3-yl | 1 |
| F-5156 | H | H | H | H | H | 4-Cl-6-Me-pyridin-3-yl | 1 |
| F-5157 | H | H | H | H | H | 2-Me-5-F-pyridin-3-yl | 1 |
| F-5158 | H | H | H | H | H | 2-Me-6-F-pyridin-3-yl | 1 |
| F-5159 | H | H | H | H | H | 4-Me-5-F-pyridin-3-yl | 1 |
| F-5160 | H | H | H | H | H | 4-Me-6-F-pyridin-3-yl | 1 |
| F-5161 | H | H | H | H | H | 2-Me-5-Cl-pyridin-3-yl | 1 |
| F-5162 | H | H | H | H | H | 2-Me-6-Cl-pyridin-3-yl | 1 |
| F-5163 | H | H | H | H | H | 4-Me-5-Cl-pyridin-3-yl | 1 |

TABLE 308-continued

| compound | R¹ | R² | R³ | R⁴ | R⁵ | Q' | p |
|---|---|---|---|---|---|---|---|
| F-5164 | H | H | H | H | H | 4-Me-6-Cl-pyridin-3-yl | 1 |
| F-5165 | H | H | H | H | H | 2,4-(Me)$_2$-pyridin-3-yl | 1 |
| F-5166 | H | H | H | H | H | 2,5-(Me)$_2$-pyridin-3-yl | 1 |

TABLE 309

| compound | R¹ | R² | R³ | R⁴ | R⁵ | Q' | p |
|---|---|---|---|---|---|---|---|
| F-5167 | H | H | H | H | H | 2,6-(Me)$_2$-pyridin-3-yl | 1 |
| F-5168 | H | H | H | H | H | 4,5-(Me)$_2$-pyridin-3-yl | 1 |
| F-5169 | H | H | H | H | H | 4,6-(Me)$_2$-pyridin-3-yl | 1 |
| F-5170 | H | H | H | H | H | 2-Me-4-OMe-pyridin-3-yl | 1 |
| F-5171 | H | H | H | H | H | 2-Me-5-OMe-pyridin-3-yl | 1 |
| F-5172 | H | H | H | H | H | 2-Me-6-OMe-pyridin-3-yl | 1 |
| F-5173 | H | H | H | H | H | 4-Me-2-OMe-pyridin-3-yl | 1 |
| F-5174 | H | H | H | H | H | 4-Me-5-OMe-pyridin-3-yl | 1 |
| F-5175 | H | H | H | H | H | 4-Me-6-OMe-pyridin-3-yl | 1 |
| F-5176 | H | H | H | H | H | 2-CF$_3$-4-F-pyridin-3-yl | 1 |
| F-5177 | H | H | H | H | H | 2-CF$_3$-5-F-pyridin-3-yl | 1 |
| F-5178 | H | H | H | H | H | 2-CF$_3$-6-F-pyridin-3-yl | 1 |
| F-5179 | H | H | H | H | H | 4-CF$_3$-2-Fpyridin-3-yl | 1 |
| F-5180 | H | H | H | H | H | 4-CF$_3$-5-F-pyridin-3-yl | 1 |
| F-5181 | H | H | H | H | H | 4-CF$_3$-6-F-pyridin-3-yl | 1 |
| F-5182 | H | H | H | H | H | 2-CF$_3$-4-Me-pyridin-3-yl | 1 |
| F-5183 | H | H | H | H | H | 2-CF$_3$-5-Me-pyridin-3-yl | 1 |
| F-5184 | H | H | H | H | H | 2-CF$_3$-6-Me-pyridin-3-yl | 1 |
| F-5185 | H | H | H | H | H | 4-CF$_3$-2-Me-pyridin-3-yl | 1 |
| F-5186 | H | H | H | H | H | 4-CF$_3$-5-Me-pyridin-3-yl | 1 |
| F-5187 | H | H | H | H | H | 4-CF$_3$-6Me-pyridin-3-yl | 1 |
| F-5188 | H | H | H | H | H | 2-OMe-5-F-pyridin-3-yl | 1 |
| F-5189 | H | H | H | H | H | 2-OMe-6-F-pyridin-3-yl | 1 |
| F-5190 | H | H | H | H | H | 4-OMe-5-F-pyridin-3-yl | 1 |
| F-5191 | H | H | H | H | H | 4-OMe-6-F-pyridin-3-yl | 1 |
| F-5192 | H | H | H | H | H | 2-OMe-4-Cl-pyridin-3-yl | 1 |
| F-5193 | H | H | H | H | H | 2-OMe-5-Cl-pyridin-3-yl | 1 |
| F-5194 | H | H | H | H | H | 2-OMe-6-Cl-pyridin-3-yl | 1 |
| F-5195 | H | H | H | H | H | 4-OMe-2-Cl-pyridin-3-yl | 1 |
| F-5196 | H | H | H | H | H | 4-OMe-5-Cl-pyridin-3-yl | 1 |
| F-5197 | H | H | H | H | H | 4-OMe-6-Cl-pyridin-3-yl | 1 |
| F-5198 | H | H | H | H | H | 2-OMe-5-Me-pyridin-3-yl | 1 |
| F-5199 | H | H | H | H | H | 2-OMe-6-Me-pyridin-3-yl | 1 |
| F-5200 | H | H | H | H | H | 4-OMe-5-Me-pyridin-3-yl | 1 |
| F-5201 | H | H | H | H | H | 4-OMe-6-Me-pyridin-3-yl | 1 |
| F-5202 | H | H | H | H | H | 2,4-(OMe)$_2$-pyridin-3-yl | 1 |
| F-5203 | H | H | H | H | H | 2,5-(OMe)$_2$-pyridin-3-yl | 1 |
| F-5204 | H | H | H | H | H | 2,6-(OMe)$_2$-pyridin-3-yl | 1 |
| F-5205 | H | H | H | H | H | 4,5-(OMe)$_2$-pyridin-3-yl | 1 |
| F-5206 | H | H | H | H | H | 4,6-(OMe)$_2$-pyridin-3-yl | 1 |
| F-5207 | H | H | H | H | H | pyridin-4-yl | 1 |
| F-5208 | H | H | H | H | H | 2-F-pyridin-4-yl | 1 |
| F-5209 | H | H | H | H | H | 3-F-pyridin-4-yl | 1 |
| F-5210 | H | H | H | H | H | 2-Cl-pyridin-4-yl | 1 |
| F-5211 | H | H | H | H | H | 3-Cl-pyridin-4-yl | 1 |
| F-5212 | H | H | H | H | H | 2-Me-pyridin-4-yl | 1 |
| F-5213 | H | H | H | H | H | 3-Me-pyridn-4-yl | 1 |
| F-5214 | H | H | H | H | H | 2-CF$_3$-pyridin-4-yl | 1 |
| F-5215 | H | H | H | H | H | 3-CF$_3$-pyridin-4-yl | 1 |
| F-5216 | H | H | H | H | H | 2-OMe-pyridin-4-yl | 1 |
| F-5217 | H | H | H | H | H | 3-OMe-pyridin-4-yl | 1 |
| F-5218 | H | H | H | H | H | 2,3-F$_2$-pyridin-4-yl | 1 |
| F-5219 | H | H | H | H | H | 2,5-F$_2$-pyridin-4-yl | 1 |
| F-5220 | H | H | H | H | H | 2,6-F$_2$-pyridin-4-yl | 1 |
| F-5221 | H | H | H | H | H | 3,5-F$_2$-pyridin-4-yl | 1 |
| F-5222 | H | H | H | H | H | 2,3-Cl$_2$-pyridin-4-yl | 1 |
| F-5223 | H | H | H | H | H | 2,5-Cl$_2$-pyridin-4-yl | 1 |

TABLE 310

| compound | R¹ | R² | R³ | R⁴ | R⁵ | Q' | p |
|---|---|---|---|---|---|---|---|
| F-5224 | H | H | H | H | H | 2,6-Cl$_2$-pyridin-4-yl | 1 |
| F-5225 | H | H | H | H | H | 3,5-Cl$_2$-pyridin-4-yl | 1 |
| F-5226 | H | H | H | H | H | 3-F-2-Cl-pyridin-4-yl | 1 |

TABLE 310-continued

| compound | R¹ | R² | R³ | R⁴ | R⁵ | Q' | p |
|---|---|---|---|---|---|---|---|
| F-5227 | H | H | H | H | H | 3-F-5-Cl-pyridin-4-yl | 1 |
| F-5228 | H | H | H | H | H | 3-F-6-Cl-pyridin-4-yl | 1 |
| F-5229 | H | H | H | H | H | 3-F-2-Me-pyridin-4-yl | 1 |
| F-5230 | H | H | H | H | H | 3-F-5-Me-pyridin-4-yl | 1 |
| F-5231 | H | H | H | H | H | 3-F-6-Me-pyridin-4-yl | 1 |
| F-5232 | H | H | H | H | H | 3-F-2-OMe-pyridin-4-yl | 1 |
| F-5233 | H | H | H | H | H | 3-F-5-OMe-pyridin-4-yl | 1 |
| F-5234 | H | H | H | H | H | 3-F-6-OMe-pyridin-4-yl | 1 |
| F-5235 | H | H | H | H | H | 3-Cl-2-F-pyridin-4-yl | 1 |
| F-5236 | H | H | H | H | H | 3-Cl-6-F-pyridin-4-yl | 1 |
| F-5237 | H | H | H | H | H | 3-Cl-2-Me-pyridin-4-y | 1 |
| F-5238 | H | H | H | H | H | 3-Cl-5-Me-pyridin-4-yl | 1 |
| F-5239 | H | H | H | H | H | 3-Cl-6-Me-pyridin-4-yl | 1 |
| F-5240 | H | H | H | H | H | 3-Me-2-F-pyridin-4-yl | 1 |
| F-5241 | H | H | H | H | H | 3-Me-6-F-pyridin-4-yl | 1 |
| F-5242 | H | H | H | H | H | 3-Me-2-Cl-pyridin-4-yl | 1 |
| F-5243 | H | H | H | H | H | 3-Me-6-Cl-pyridin-4-yl | 1 |
| F-5244 | H | H | H | H | H | 2,3-(Me)₂-pyridin-4-yl | 1 |
| F-5245 | H | H | H | H | H | 3,5-(Me)₂-pyridin-4-yl | 1 |
| F-5246 | H | H | H | H | H | 3,6-(Me)₂-pyridin-4-yl | 1 |
| F-5247 | H | H | H | H | H | 3-Me-2-OMe-pyridin-4-yl | 1 |
| F-5248 | H | H | H | H | H | 3-Me-5-OMe-pyridin-4-yl | 1 |
| F-5249 | H | H | H | H | H | 3-Me-6-OMe-pyridin-4-yl | 1 |
| F-5250 | H | H | H | H | H | 3-CF₃-2-F-pyridin-4-yl | 1 |
| F-5251 | H | H | H | H | H | 3-CF₃-5-F-pyridin-4-yl | 1 |
| F-5252 | H | H | H | H | H | 3-CF₃-6-F-pyridin-4-yl | 1 |
| F-5253 | H | H | H | H | H | 3-CF₃-2-Me-pyridin-4-yl | 1 |
| F-5254 | H | H | H | H | H | 3-CF₃-5-Me-pyridin-4-yl | 1 |
| F-5255 | H | H | H | H | H | 3-CF₃-6-Me-pyridin-4-yl | 1 |
| F-5256 | H | H | H | H | H | 3-OMe-2-F-pyridin-4-yl | 1 |
| F-5257 | H | H | H | H | H | 3-OMe-6-F-pyridin-4-yl | 1 |
| F-5258 | H | H | H | H | H | 3-OMe-2-Cl-pyridin-4-yl | 1 |
| F-5259 | H | H | H | H | H | 3-OMe-5-Cl-pyridin-4-yl | 1 |
| F-5260 | H | H | H | H | H | 3-OMe-6-Cl-pyridin-4-yl | 1 |
| F-5261 | H | H | H | H | H | 3-OMe-2-Me-pyridin-4-yl | 1 |
| F-5262 | H | H | H | H | H | 3-OMe-6-Me-pyridin-4-yl | 1 |
| F-5263 | H | H | H | H | H | 2,3-(OMe)₂-pyridin-4-yl | 1 |
| F-5264 | H | H | H | H | H | 3,5-(OMe)₂-pyridin-4-yl | 1 |
| F-5265 | H | H | H | H | H | 3,6-(OMe)₂-pyridin-4-yl | 1 |
| F-5266 | H | H | H | H | H | pyrimidin-2-yl | 1 |
| F-5267 | H | H | H | H | H | pyrimidin-4-yl | 1 |
| F-5268 | H | H | H | H | H | 5-F-pyrimidin-4-yl | 1 |
| F-5269 | H | H | H | H | H | 5-Me-pyrimidin-4-yl | 1 |
| F-5270 | H | H | H | H | H | 5-CF₃-pyrimidin-4-yl | 1 |
| F-5271 | H | H | H | H | H | 5-OMe-pyrimidin-4-yl | 1 |
| F-5272 | H | H | H | H | H | pyrimidin-5-yl | 1 |
| F-5273 | H | H | H | H | H | 4-F-pyrimidin-5-yl | 1 |
| F-5274 | H | H | H | H | H | 4-Cl-pyrimidin-5-yl | 1 |
| F-5275 | H | H | H | H | H | 4-Me-pyrimidin-5-yl | 1 |
| F-5276 | H | H | H | H | H | 4-CF₃-pyrimidin-5-yl | 1 |
| F-5277 | H | H | H | H | H | 4-OMe-pyrimidin-5-yl | 1 |
| F-5278 | H | H | H | H | H | pyridazin-3-yl | 1 |
| F-5279 | H | H | H | H | H | 4-F-pyridazin-3-yl | 1 |
| F-5280 | H | H | H | H | H | 4-Cl-pyridazin-3-yl | 1 |

TABLE 311

| compound | R¹ | R² | R³ | R⁴ | R⁵ | Q' | p |
|---|---|---|---|---|---|---|---|
| F-5281 | H | H | H | H | H | 4-Me-pyridazin-3-yl | 1 |
| F-5282 | H | H | H | H | H | 4-CF₃-pyridazin-3-yl | 1 |
| F-5283 | H | H | H | H | H | 4-OMe-pyridazin-3-yl | 1 |
| F-5284 | H | H | H | H | H | pyridazin-4-yl | 1 |
| F-5285 | H | H | H | H | H | 3-F-pyridazin-4-yl | 1 |
| F-5286 | H | H | H | H | H | 3-Cl-pyridazin-4-yl | 1 |
| F-5287 | H | H | H | H | H | 3-Me-pyridazin-4-yl | 1 |
| F-5288 | H | H | H | H | H | 3-CF₃-pyridazin-4-yl | 1 |
| F-5289 | H | H | H | H | H | 3-OMe-pyridazin-4-yl | 1 |
| F-5290 | H | H | H | H | H | 5-F-pyridazin-4-yl | 1 |
| F-5291 | H | H | H | H | H | 5-Cl-pyridazin-4-yl | 1 |
| F-5292 | H | H | H | H | H | 5-Me-pyridazin-4-yl | 1 |
| F-5293 | H | H | H | H | H | 5-CF₃-pyridazin-4-y | 1 |
| F-5294 | H | H | H | H | H | 5-OMe-pyridazin-4-yl | 1 |
| F-5295 | H | H | H | H | H | thiophen-2-yl | 1 |
| F-5296 | H | H | H | H | H | 3-F-thiophen-2-yl | 1 |

TABLE 311-continued

| compound | R¹ | R² | R³ | R⁴ | R⁵ | Q' | p |
|---|---|---|---|---|---|---|---|
| F-5297 | H | H | H | H | H | 3-Cl-thiophen-2-yl | 1 |
| F-5298 | H | H | H | H | H | 3-Me-thiophen-2-yl | 1 |
| F-5299 | H | H | H | H | H | 3-CF₃-thiophen-2-yl | 1 |
| F-5300 | H | H | H | H | H | 3-OMe-thiophen-2-yl | 1 |
| F-5301 | H | H | H | H | H | thiophen-3-yl | 1 |
| F-5302 | H | H | H | H | H | 2-F-thiophen-3-yl | 1 |
| F-5303 | H | H | H | H | H | 2-Cl-thiophen-3-yl | 1 |
| F-5304 | H | H | H | H | H | 2-Me-thiophen-3-yl | 1 |
| F-5305 | H | H | H | H | H | 2-CF₃-thiophen-3-yl | 1 |
| F-5306 | H | H | H | H | H | 2-OMe-thiophen-3-yl | 1 |
| F-5307 | H | H | H | H | H | 4-F-thiophen-3-yl | 1 |
| F-5308 | H | H | H | H | H | 4-Cl-thiophen-3-yl | 1 |
| F-5309 | H | H | H | H | H | 4-Me-thiophen-3-yl | 1 |
| F-5310 | H | H | H | H | H | 4-CF₃-thiophen-3-yl | 1 |
| F-5311 | H | H | H | H | H | 4-OMe-thiophen-3-yl | 1 |
| F-5312 | H | H | H | H | H | thiazol-2-yl | 1 |
| F-5313 | H | H | H | H | H | thiazol-4-yl | 1 |
| F-5314 | H | H | H | H | H | 5-F-thiazol-4-yl | 1 |
| F-5315 | H | H | H | H | H | 5-Me-thiazol-4-yl | 1 |
| F-5316 | H | H | H | H | H | 5-CF₃-thiazol-4-yl | 1 |
| F-5317 | H | H | H | H | H | 5-OMe-thiazol-4-yl | 1 |
| F-5318 | H | H | H | H | H | thiazol-5-yl | 1 |
| F-5319 | H | H | H | H | H | 4-F-thiazol-5-yl | 1 |
| F-5320 | H | H | H | H | H | 4-Me-thiazol-5-yl | 1 |
| F-5321 | H | H | H | H | H | 4-CF₃-thiazol-5-yl | 1 |
| F-5322 | H | H | H | H | H | 4-OMe-thiazol-5-yl | 1 |
| F-5323 | H | H | H | H | H | 1H-pyrrol-1-yl | 1 |
| F-5324 | H | H | H | H | H | 2-F-1H-pyrrol-1-yl | 1 |
| F-5325 | H | H | H | H | H | 2-Me-1H-pyrrol-1-yl | 1 |
| F-5326 | H | H | H | H | H | 2-CF₃-1H-pyrrol-1-yl | 1 |
| F-5327 | H | H | H | H | H | 2-OMe-1H-pyrrol-1-yl | 1 |
| F-5328 | H | H | H | H | H | 1H-pyrrol-2-yl | 1 |
| F-5329 | H | H | H | H | H | 1-Me-1H-pyrrol-2-yl | 1 |
| F-5330 | H | H | H | H | H | 3-F-1H-pyrrol-2-yl | 1 |
| F-5331 | H | H | H | H | H | 3-Me-1H-pyrrol-2-yl | 1 |
| F-5332 | H | H | H | H | H | 3-CF₃-1H-pyrrol-2-yl | 1 |
| F-5333 | H | H | H | H | H | 3-OMe-1H-pyrrol-2-yl | 1 |
| F-5334 | H | H | H | H | H | 1-Me-3-F-1H-pyrrol-2-yl | 1 |
| F-5335 | H | H | H | H | H | 1,3-(Me)₂-1H-pyrro-2-yl | 1 |
| F-5336 | H | H | H | H | H | 1-Me-3-CF₃-1H-pyrrol-2-yl | 1 |
| F-5337 | H | H | H | H | H | 1-Me-3-OMe-1H-pyrrol-2-yl | 1 |

TABLE 312

| compound | R¹ | R² | R³ | R⁴ | R⁵ | Q' | p |
|---|---|---|---|---|---|---|---|
| F-5338 | H | H | H | H | H | 1H-pyrrol-3-yl | 1 |
| F-5339 | H | H | H | H | H | 1-Me-1H-pyrrol-3-yl | 1 |
| F-5340 | H | H | H | H | H | 2-F-1H-pyrrol-3-yl | 1 |
| F-5341 | H | H | H | H | H | 2-Me-1H-pyrrol-3-yl | 1 |
| F-5342 | H | H | H | H | H | 2-CF₃-1H-pyrrol-3-yl | 1 |
| F-5343 | H | H | H | H | H | 2-OMe-1H-pyrrol-3-yl | 1 |
| F-5344 | H | H | H | H | H | 1-Me-2-F-1H-pyrrol-3-yl | 1 |
| F-5345 | H | H | H | H | H | 1,2-(Me)₂-1H-pyrrol-3-yl | 1 |
| F-5346 | H | H | H | H | H | 1-Me-2-CF₃-1H-pyrrol-3-yl | 1 |
| F-5347 | H | H | H | H | H | 1-Me-2-OMe-1H-pyrrol-3-yl | 1 |
| F-5348 | H | H | H | H | H | 4-F-1H-pyrrol-3-yl | 1 |
| F-5349 | H | H | H | H | H | 4-Me-1H-pyrrol-3-yl | 1 |
| F-5350 | H | H | H | H | H | 4-CF₃-1H-pyrrol-3-yl | 1 |
| F-5351 | H | H | H | H | H | 4-OMe-1H-pyrrol-3-yl | 1 |
| F-5352 | H | H | H | H | H | 1-Me-4-F-1H-pyrrol-3-yl | 1 |
| F-5353 | H | H | H | H | H | 1,4-(Me)₂-1H-pyrrol-3-yl | 1 |
| F-5354 | H | H | H | H | H | 1-Me-4-CF₃-1H-pyrrol-3-yl | 1 |
| F-5355 | H | H | H | H | H | 1-Me-4-OMe-1H-pyrrol-3-yl | 1 |
| F-5356 | H | H | H | H | H | 1H-pyrazol-1-yl | 1 |
| F-5357 | H | H | H | H | H | 5-F-1H-pyrazol-1-yl | 1 |
| F-5358 | H | H | H | H | H | 5-Cl-1H-pyrazol-1-yl | 1 |
| F-5359 | H | H | H | H | H | 5-Me-1H-pyrazol-1-yl | 1 |
| F-5360 | H | H | H | H | H | 5-CF₃-1H-pyrazol-1-yl | 1 |
| F-5361 | H | H | H | H | H | 5-OMe-1H-pyrazol-1-yl | 1 |
| F-5362 | H | H | H | H | H | 1H-pyrazol-3-yl | 1 |
| F-5363 | H | H | H | H | H | 1-Me-1H-pyrazol-3-yl | 1 |
| F-5364 | H | H | H | H | H | 4-F-1H-pyrazol-3-yl | 1 |
| F-5365 | H | H | H | H | H | 4-Cl-1H-pyrazol-3-yl | 1 |
| F-5366 | H | H | H | H | H | 4-Me-1H-pyrazol-3-yl | 1 |

TABLE 312-continued

| compound | $R^1$ | $R^2$ | $R^3$ | $R^4$ | $R^5$ | Q' | p |
|---|---|---|---|---|---|---|---|
| F-5367 | H | H | H | H | H | 4-CF$_3$-1H-pyrazol-3-yl | 1 |
| F-5368 | H | H | H | H | H | 4-OMe-1H-pyrazol-3-yl | 1 |
| F-5369 | H | H | H | H | H | 1-Me-4-F-1H-pyrazol-3-yl | 1 |
| F-5370 | H | H | H | H | H | 1-Me-4-Cl-1H-pyrazol-3-yl | 1 |
| F-5371 | H | H | H | H | H | 1,4-(Me)$_2$-1H-pyrazol-3-yl | 1 |
| F-5372 | H | H | H | H | H | 1-Me-4-CF$_3$-1H-pyrazol-3-yl | 1 |
| F-5373 | H | H | H | H | H | 1-Me-4-OMe-1H-pyrazol-3-yl | 1 |
| F-5374 | H | H | H | H | H | 1H-pyrazol-4-yl | 1 |
| F-5375 | H | H | H | H | H | 1-Me-1H-pyrazol-4-yl | 1 |
| F-5376 | H | H | H | H | H | 3-F-1H-pyrazol-4-yl | 1 |
| F-5377 | H | H | H | H | H | 3-Cl-1H-pyrazol-4-yl | 1 |
| F-5378 | H | H | H | H | H | 3-Me-1H-pyrazol4-yl | 1 |
| F-5379 | H | H | H | H | H | 3-CF$_3$-1H-pyrazol-4-yl | 1 |
| F-5380 | H | H | H | H | H | 3-OMe-1H-pyrazol-4-yl | 1 |
| F-5381 | H | H | H | H | H | 1-Me-3-F-1H-pyrazol-4-yl | 1 |
| F-5382 | H | H | H | H | H | 1-Me-3-Cl-1H-pyrazol-4-yl | 1 |
| F-5383 | H | H | H | H | H | 1,3-(Me)$_2$-1H-pyrazol-4-yl | 1 |
| F-5384 | H | H | H | H | H | 1-Me-3-CF$_3$-1H-pyrazol-4-yl | 1 |
| F-5385 | H | H | H | H | H | 1-Me-3-OMe-1H-pyrazol-4-yl | 1 |
| F-5386 | H | H | H | H | H | 5-F-1H-pyrazol-4-yl | 1 |
| F-5387 | H | H | H | H | H | 5-Cl-1H-pyrazol-4-yl | 1 |
| F-5388 | H | H | H | H | H | 5-Me-1H-pyrazol-4-yl | 1 |
| F-5389 | H | H | H | H | H | 5-CF$_3$-1H-pyrazol-4-yl | 1 |
| F-5390 | H | H | H | H | H | 5-OMe-1H-pyrazol-4-yl | 1 |
| F-5391 | H | H | H | H | H | 1-Me-5-F-1H-pyrazol-4-yl | 1 |
| F-5392 | H | H | H | H | H | 1-Me-5-Cl-1H-pyrazol-4-yl | 1 |
| F-5393 | H | H | H | H | H | 1,5-(Me)$_2$-1H-pyrazol-4-yl | 1 |
| F-5394 | H | H | H | H | H | 1-Me-5-CF$_3$-1H-pyrazol4-yl | 1 |

TABLE 313

| compound | $R^1$ | $R^2$ | $R^3$ | $R^4$ | $R^5$ | Q' | p |
|---|---|---|---|---|---|---|---|
| F-5395 | H | H | H | H | H | 1-Me-5-OMe-1H-pyrazol-4-yl | 1 |
| F-5396 | H | H | H | H | H | 1H-pyrazol-5-yl | 1 |
| F-5397 | H | H | H | H | H | 1-Me-1H-pyrazol-5-yl | 1 |
| F-5398 | H | H | H | H | H | 4-F-1H-pyrazol-5-yl | 1 |
| F-5399 | H | H | H | H | H | 4-Cl-1H-pyrazol-5-yl | 1 |
| F-5400 | H | H | H | H | H | 4-Me-1H-pyrazol-5-yl | 1 |
| F-5401 | H | H | H | H | H | 4-CF$_3$-1H-pyrazol5-yl | 1 |
| F-5402 | H | H | H | H | H | 4-OMe-1H-pyrazol-5-yl | 1 |
| F-5403 | H | H | H | H | H | 1-Me-4-F-1H-pyrazol-5-yl | 1 |
| F-5404 | H | H | H | H | H | 1-Me-4-Cl-1H-pyrazol-5-yl | 1 |
| F-5405 | H | H | H | H | H | 1,4-(Me)$_2$-1H-pyrazol-5-yl | 1 |
| F-5406 | H | H | H | H | H | 1-Me-4-CF$_3$-1H-pyrazol-5-yl | 1 |
| F-5407 | H | H | H | H | H | 1-Me-4-OMe-1H-pyrazol-5-yl | 1 |
| F-5408 | H | H | H | H | H | furan-2-yl | 1 |
| F-5409 | H | H | H | H | H | 3-F-furan-2-yl | 1 |
| F-5410 | H | H | H | H | H | 3-Me-furan-2-yl | 1 |
| F-5411 | H | H | H | H | H | 3-CF$_3$-furan-2-yl | 1 |
| F-5412 | H | H | H | H | H | 3-OMe-furan-2-yl | 1 |
| F-5413 | H | H | H | H | H | furan-3-yl | 1 |
| F-5414 | H | H | H | H | H | 2-F-furan-3-yl | 1 |
| F-5415 | H | H | H | H | H | 2-Me-furan-3-yl | 1 |
| F-5416 | H | H | H | H | H | 2-CF$_3$-furan-3-yl | 1 |
| F-5417 | H | H | H | H | H | 2-OMe-furan-3-yl | 1 |
| F-5418 | H | H | H | H | H | 4-F-furan-3-yl | 1 |
| F-5419 | H | H | H | H | H | 4-Me-furan-3-yl | 1 |
| F-5420 | H | H | H | H | H | 4-CF$_3$-furan-3-yl | 1 |
| F-5421 | H | H | H | H | H | 4-OMe-furan-3-yl | 1 |
| F-5422 | H | H | H | H | H | isoxazol-3-yl | 1 |
| F-5423 | H | H | H | H | H | 4-F-isoxazol-3-yl | 1 |
| F-5424 | H | H | H | H | H | 4-Me-isoxazol-3-yl | 1 |
| F-5425 | H | H | H | H | H | 4-CF$_3$-isoxazol-3-yl | 1 |
| F-5426 | H | H | H | H | H | 4-OMe-isoxazol-3-yl | 1 |
| F-5427 | H | H | H | H | H | isoxazol-4-yl | 1 |
| F-5428 | H | H | H | H | H | 5-F-isoxazol-4-yl | 1 |
| F-5429 | H | H | H | H | H | 5-Me-isoxazol-4-yl | 1 |
| F-5430 | H | H | H | H | H | 5-CF$_3$-isoxazol-4-yl | 1 |
| F-5431 | H | H | H | H | H | 5-OMe-isoxazol-4-yl | 1 |
| F-5432 | H | H | H | H | H | isoxazol-5-yl | 1 |
| F-5433 | H | H | H | H | H | 4-F-isoxazol-5-yl | 1 |
| F-5434 | H | H | H | H | H | 4-Me-isoxazol-5-yl | 1 |
| F-5435 | H | H | H | H | H | 4-CF$_3$-isoxazol-5-yl | 1 |
| F-5436 | H | H | H | H | H | 4-OMe-isoxazol-5-yl | 1 |

TABLE 313-continued

| compound | $R^1$ | $R^2$ | $R^3$ | $R^4$ | $R^5$ | Q' | p |
|---|---|---|---|---|---|---|---|
| F-5437 | H | H | H | H | H | 1H-1,2,3-triazol-1-yl | 1 |
| F-5438 | H | H | H | H | H | 5-F-1H-1,2,3-triazol-1-yl | 1 |
| F-5439 | H | H | H | H | H | 5-Me-1H-1,2,3-triazol-1-yl | 1 |
| F-5440 | H | H | H | H | H | 5-CF$_3$-1H-1,2,3-triazol-1-yl | 1 |
| F-5441 | H | H | H | H | H | 5-OMe-1H-1,2,3-triazol-1-yl | 1 |
| F-5442 | H | H | H | H | H | 1H-1,2,3-triazol-4-yl | 1 |
| F-5443 | H | H | H | H | H | 5-F-1H-1,2,3-triazol-4-yl | 1 |
| F-5444 | H | H | H | H | H | 5-Me-1H-1,2,3-triazol-4-yl | 1 |
| F-5445 | H | H | H | H | H | 5-CF$_3$-1H-1,2,3-triazol-4-yl | 1 |
| F-5446 | H | H | H | H | H | 5-OMe-1H-1,2,3-triazol-4-yl | 1 |
| F-5447 | H | H | H | H | H | 1H-1,2,3-triazol-5-yl | 1 |
| F-5448 | H | H | H | H | H | 4-F-1H-1,2,3-triazol-5-yl | 1 |
| F-5449 | H | H | H | H | H | 4-Me-1H-1,2,3-triazol-5-yl | 1 |
| F-5450 | H | H | H | H | H | 4-CF$_3$-1H-1,2,3-triazol-5-yl | 1 |
| F-5451 | H | H | H | H | H | 4-OMe-1H-1,2,3-triazol-5-yl | 1 |

TABLE 314

| compound | $R^1$ | $R^2$ | $R^3$ | $R^4$ | $R^5$ | Q' | p |
|---|---|---|---|---|---|---|---|
| F-5452 | H | H | H | H | H | 1H-1,2,4-triazol-1-yl | 1 |
| F-5453 | H | H | H | H | H | 5-Me-1H-1,2,4-triazol-1-yl | 1 |
| F-5454 | H | H | H | H | H | 5-F-1H-1,2,4-triazol-1-yl | 1 |
| F-5455 | H | H | H | H | H | 5-CF$_3$-1H-1,2,4-triazol-1-yl | 1 |
| F-5456 | H | H | H | H | H | 5-OMe-1H-1,2,4-triazol-1-yl | 1 |
| F-5457 | H | H | H | H | H | 1H-1,2,4-triazol-3-yl | 1 |
| F-5458 | H | H | H | H | H | 1-Me-1H-1,2,4-triazol-3-yl | 1 |
| F-5459 | H | H | H | H | H | 1H-1,2,4-triazol-5-yl | 1 |
| F-5460 | H | H | H | H | H | 1-Me-1H-1,2,4-triazol-5-yl | 1 |
| F-5461 | H | H | H | H | H | 3,5-(Me)$_2$-isoxazol-4-y | 1 |
| F-5462 | H | H | H | H | H | 3,5-(Et)$_2$-isoxazol-4-yl | 1 |
| F-5463 | H | H | H | H | H | 1,3,5-(Me)$_3$-1H-pyrazol-4-yl | 1 |
| F-5464 | H | H | H | H | H | quinolin-4-yl | 1 |
| F-5465 | H | H | H | H | H | isoquinolin-4-yl | 1 |
| F-5466 | H | H | H | H | H | 3,6-(OMe)$_2$-pyridazin-4-y | 1 |
| F-5467 | H | H | H | H | H | 2,4-(OMe)$_2$-pyrmidin-5-yl | 1 |

On the other hand, the present compound represented by general formula [I] or [II] can be produced in accordance with, but not limited to, the production methods shown below. Hereinafter, for example, "compound represented by general formula [I]" is synonymous to "compound represented by formula [I]" and "compound [I]".

<Production Method 1>

A compound represented by general formula [VI] among the present compounds can be produced, for example, in accordance with the following method.

[Chemical formula 3]

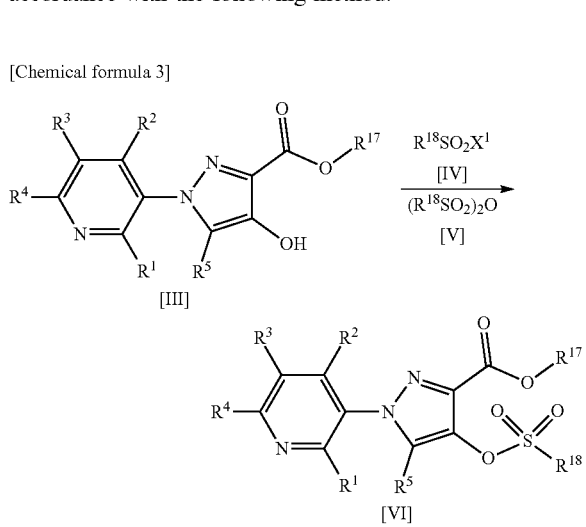

(wherein, $R^{17}$ represents a $C_1$-$C_6$ alkyl group, $R^{18}$ represents a $C_1$-$C_6$ alkyl group, $C_1$-$C_6$ haloalkyl group, di($C_1$-$C_6$ alkyl)amino group, or a phenyl group that is unsubstituted or substituted with $(R^9)_m$, $X^1$ represents a halogen atom, and $R^1$, $R^2$, $R^3$, $R^4$, $R^5$, and $R^9$ are as defined above.)

That is, the compound represented by general formula [VI] can be produced by reacting compound [III] and compound [IV] or compound [V] in an appropriate solvent in the presence of an appropriate base.

The compound represented by general formula [III] used in the present reaction can be produced by a method described in WO 2012/028332 A, WO 2014/114649 A, WO 2016/027790 A, WO 2016/166250 A, or U.S. Pat. No. 5,055,482, or produced in accordance with such a method.

The use amount of compound [IV] or compound [V] used in the present reaction may be appropriately selected from the range of 1 to 5 mol, and is preferably 1.0 to 2.0 mol, relative to 1 mol of compound [III].

Examples of the solvent that can be used in the present reaction include halogenated hydrocarbons such as dichloromethane, chloroform, 1,2-dichloroethane, or carbon tetrachloride; ethers such as diethylether, tetrahydrofuran, or 1,4-dioxane, 1,2-dimethoxyethane, or methyl tert-butyl ether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; aliphatic hydrocarbons such as pentane, hexane, cyclohexane, or heptane; nitriles such as acetonitrile, or propionitrile; pyridines such as pyridine, or picoline; tertiary amines such as triethylamine, or tributylamine; water, or mixed solvents thereof. The use amount of the solvent is 0.1 to 300 liters, preferably 0.3 to 50 liters relative to 1 mol of compound [III].

Examples of the base that can be used in the present reaction include inorganic bases such as hydroxides of alkali metal (e.g. sodium hydroxide or potassium hydroxide); hydroxides of alkali earth metal (e.g. calcium hydroxide or magnesium hydroxide); carbonates of alkali metal (e.g. sodium carbonate or potassium carbonate); bicarbonates of alkali metal (e.g. sodium hydrogen carbonate or potassium hydrogen carbonate); metal hydrides (e.g. sodium hydride or potassium hydride); metal salts of alcohol (e.g. sodium methoxide, sodium ethoxide, or potassium tert-butoxide); or organic bases such as triethylamine, N,N-dimethylaniline, pyridine, 4-N,N-dimethylaminepyridine, 1,8-diazacyclo[5.4.0]-7-undecene, and so on. The use amount of the base may be appropriately selected from the range of 1.0 to 5.0 mol, and is preferably 1.0 to 3.5 mol, relative to 1 mol of compound [III]. The organic bases such as triethylamine or pyridine can also be used as the solvent.

The reaction temperature of the present reaction may be selected from any range of temperature typically from −70° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, water is added to the reaction mixture, and then extraction with an organic solvent is conducted, and then concentration or the like operation is conducted, and thus compound [VI] can be isolated. The isolated compound [VI] can be further purified by column chromatography, recrystallization, or the like as necessary.

<Production Method 2>

A compound represented by general formula [VIII] among the present compounds can be produced, for example, in accordance with the following method.

[Chemical formula 4]

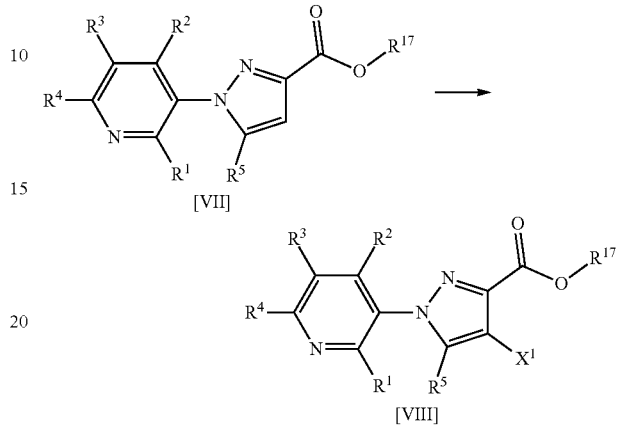

(wherein, $R^1$, $R^2$, $R^3$, $R^4$, $R^5$, $R^{17}$, and $X^1$ are as defined above.)

That is, the compound represented by general formula [VIII] can be produced by reacting compound [VII] and a halogenating agent in an appropriate solvent in the presence or absence of an appropriate acid, in the presence or absence of an appropriate oxidizing agent.

The compound represented by general formula [VII] used in the present reaction can be produced by a method described in WO 2008/019357 A or WO 2008/157740 A, or produced in accordance with such a method.

Examples of the halogenating agent used in the present reaction include fluorine, chlorine, bromine, iodine, N-chlorosuccinimide, N-bromosuccinimide, N-iodosuccinimide, sulfuryl chloride, iodine monochloride, tert-butyl hypochlorite, N-fluoro-N'-(chloromethyl)-triethylenediaminebis(tetrafluoroborate), 1-fluoro-2,6-dichloropyridinium tetrafluoroborate, or 1,3-dibromo-5,5-dimethylhydantoin. The use amount of the halogenating agent may be appropriately selected from the range of 1.0 to 10 mol, and is preferably 1.0 to 3.0 mol, relative to 1 mol of compound [VII].

Examples of the oxidizing agent that can be used in the present reaction include ammonium hexanitratocerate (IV), hydrogen peroxide, or iodobenzene diacetate. The use amount of the oxidizing agent may be appropriately selected from the range of 0 to 10 mol, and is preferably 0 to 3.0 mol, relative to 1 mol of compound [VII].

Examples of the solvent that can be used in the present reaction include inorganic acids such as sulfuric acid; ethers such as diethylether, tetrahydrofuran, 1,4-dioxane, 1,2-dimethoxyethane, or methyl tert-butyl ether; aromatic hydrocarbons such as benzene, toluene, xylene, or chlorobenzene; halogenated hydrocarbons such as dichloromethane, chloroform, 1,2-dichloroethane, or carbon tetrachloride; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; nitriles such as acetonitrile or propionitrile; carboxylic acids such as acetic acid or trifluoroacetic acid; pyridines such as pyridine or picoline; ketones such as acetone or methyl ethyl ketone; water, or mixed solvents thereof. The use amount of the solvent is 0.1 to 100 liters, preferably 0.3 to 10 liters relative to 1 mol of compound [VII].

Examples of the acid that can be used in the present reaction include inorganic acids such as sulfuric acid; or carboxylic acids such as acetic acid or trifluoro acetic acid. The use amount of the acid may be appropriately selected from the range of 1.0 to 10 mol, and is preferably 0 to 3.0 mol, relative to 1 mol of compound [VII]. The acid may be used as the solvent.

The reaction temperature of the present reaction may be selected from any range of temperature from −60° C. to a reflux temperature in a reaction system, and is preferably in the range of −20° C. to 100° C.

The reaction time of the present reaction is typically 10 minutes to 24 hours although it differs depending on the reaction temperature, the reaction substrate, the reaction amount, and the like.

After end of the reaction, water is added to the reaction mixture, and then extraction with an organic solvent is conducted, and then concentration or the like operation is conducted, and thus compound [VIII] can be isolated. The isolated compound [VIII] can be further purified by column chromatography, recrystallization, or the like as necessary.

<Production Method 3>

A compound represented by general formula [XII] among the compounds of the present invention can be produced, for example, in accordance with the following method.

[Chemical formula 5]

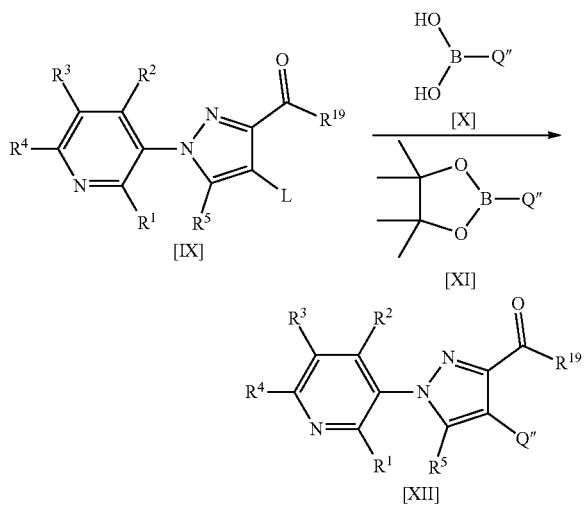

(wherein, L represents a halogen atom, $C_1$-$C_6$ alkylsulfonyloxy group, $C_1$-$C_6$ haloalkylsulfonyloxy group, di($C_1$-$C_6$ alkyl)sulfamoyloxy group, or a phenylsulfonyloxy group that is unsubstituted or substituted with ($R^9$)$_m$, Q" represents a $C_6$-$C_{10}$ aryl group that is unsubstituted or substituted with ($R^8$)$_m$ or a heteroaryl group that is unsubstituted or substituted with ($R^8$)$_m$, $R^{19}$ represents a group $OR^{16}$ or a group $NR^6R^7$, and m, $R^1$, $R^2$, $R^3$, $R^4$, $R^5$, $R^6$, $R^7$, $R^8$, $R^9$, and $R^{16}$ are as defined above.)

Some of [X] or [XI] used herein are known compounds, part of which are commercially available. The remainder can be easily synthesized according to the method described in literature, for example, in the methods described in Chemical Review, 1995, vol. 95, p. 2457; Journal of Organic Chemistry, 1995, vol. 60, p. 7508; Journal of Organic Chemistry 1997, vol. 62, p. 6458 and so on.

That is, the compound represented by general formula [XII] can be produced by reacting compound [IX] and compound [X] or compound [XI] in an appropriate solvent in the presence of an appropriate catalyst and an appropriate base.

The use amount of compound [X] or compound [XI] used in the present reaction may be appropriately selected from the range of 1.0 to 10 mol, and is preferably 1.0 to 3.0 mol, relative to 1 mol of compound [IX].

Examples of the solvent that can be used in the present reaction include ethers such as diethylether, tetrahydrofuran, 1,4-dioxane, 1,2-dimethoxyethane, or methyl tert-butylether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; aliphatic hydrocarbons such as pentane, hexane, cyclohexane, or heptane; water, or mixed solvents thereof. The use amount of the solvent is 0.1 to 300 liters, preferably 0.3 to 50 liters relative to 1 mol of compound [IX].

Examples of the catalyst that can be used in the present reaction include palladium catalysts such as palladium-carbon, palladium chloride, palladium acetate, tris(dibenzylideneacetone)dipalladium, bis(dibenzylideneacetone)dipalladium, bis(triphenylphosphine)palladium dichloride, tetrakis(triphenylphosphine)palladium, [1,1'-bis(diphenylphosphino)ferrocene]palladium dichloride, or [1,2-bis(diphenylphosphino)ethane]palladium dichloride; or copper catalysts such as metal copper, copper (I) acetate, coper (II) acetate, copper (I) oxide, copper(II) oxide, copper (I) chloride, or copper (I) iodide.

Besides the above, a palladium catalyst prepared from a palladium catalyst and a ligand may be used. Examples of the palladium catalyst include palladium acetate, tris(dibenzylidene acetone)dipalladium, and bis(dibenzylidene acetone)palladium. Examples of the ligand include triphenylphosphine, tri(tert-butyl)phosphine, tricyclohexylphosphine, SPhos, Xantphos, and BINAP.

The use amount of the catalyst may be appropriately selected from the range of 0.001 to 1.0 mol, and is preferably 0.01 to 0.5 mol, relative to 1 mol of compound [IX].

Examples of the base that can be used in the present reaction include organic bases such as pyridine, diisopropylethylamine, or triethylamine; hydroxides of alkali metal such as sodium hydroxide or potassium hydroxide; carbonates of alkali metal such as sodium carbonate, potassium carbonate, or cesium carbonate; bicarbonates of alkali metal such as sodium hydrogen carbonate or potassium hydrogen carbonate; metal salts of alcohol such as sodium methoxide, sodium ethoxide, or potassium tert-butoxide; tripotassium phosphate, potassium fluoride, or cesium fluoride. The use amount of the base may be appropriately selected from the range of 0.1 to 10 mol, and is preferably 1.0 to 5.0 mol, relative to 1 mol of compound [IX].

The reaction temperature of the present reaction may be selected from any range of temperature typically from −30° C. to a reflux temperature in a reaction system, and is preferably in the range of 0° C. to 150° C.

The reaction time of the present reaction is typically 1 minute to 72 hours although it differs depending on the reaction temperature, the reaction substrate, the reaction amount, and the like.

After end of the reaction, water is added to the reaction mixture, and then the precipitated solid is filtered off or extracted with an organic solvent, followed by concentration or the like operation, and thus compound [XII] can be isolated. The isolated compound [XII] can be further purified by column chromatography, recrystallization, or the like as necessary.

<Production Method 4>

A compound represented by general formula [XIV] among the present compounds can be produced, for example, in accordance with the following method.

[Chemical formula 6]

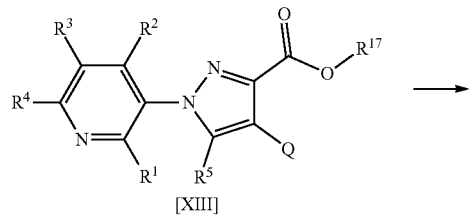

[XIII]

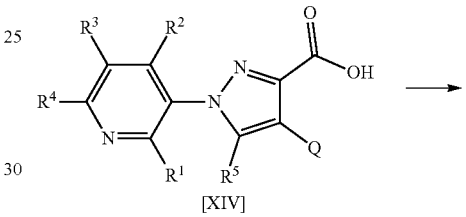

[XIV]

(wherein, Q, R¹, R², R³, R⁴, R⁵, and R¹⁷ are as defined above.)

That is, the compound represented by general formula [XIV] can be produced by hydrolysis of compound [XIII] in an appropriate solvent in the presence of an appropriate base or appropriate acid.

Examples of the base that can be used in the present reaction include inorganic bases such as hydroxides of alkali metal (e.g. sodium hydroxide, potassium hydroxide, lithium hydroxide, or barium hydroxide); carbonates of alkali metal (e.g. sodium carbonate or potassium carbonate); bicarbonates of alkali metal (e.g. sodium hydrogen carbonate or potassium hydrogen carbonate). The use amount of the base may be appropriately selected from the range of 0.1 to 50 mol, and is preferably 0.5 to 20 mol, relative to 1 mol of compound [XIII].

Examples of the acid that can be used in the present reaction include inorganic acids such as hydrochloric acid, hydrobromic acid, or sulfuric acid; or carboxylic acids such as acetic acid or trifluoro acetic acid. The use amount of the acid may be appropriately selected from the range of 1 to 1000 mol, and is preferably 1 to 100 mol, relative to 1 mol of compound [XIII].

Examples of the solvent that can be used in the present reaction include ethers such as diethyl ether, tetrahydrofuran, 1,4-dioxane, 1,2-dimethoxyethane, or methyl tert-butyl ether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; nitriles such as acetonitrile or propionitrile; ketones such as acetone or methylethylketone; water; or mixed solvents thereof. The use amount of the solvent is 0.1 to 500 liters, preferably 0.3 to 30 liters relative to 1 mol of compound [XIII].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 72 hours although it differs depending on the reaction temperature, the reaction substrate, the reaction amount, and the like.

After end of the reaction, the reaction mixture water is neutralized by adding water, and then the precipitated solid is filtered off or extracted with an organic solvent, followed by concentration or the like operation, and thus compound [XIV] can be isolated. The isolated compound [XIV] can be further purified by column chromatography, recrystallization, or the like as necessary.

<Production Method 5>

A compound represented by general formula [XVII] among the present compounds can also be produced, for example, in accordance with the following method.

[Chemical formula 7]

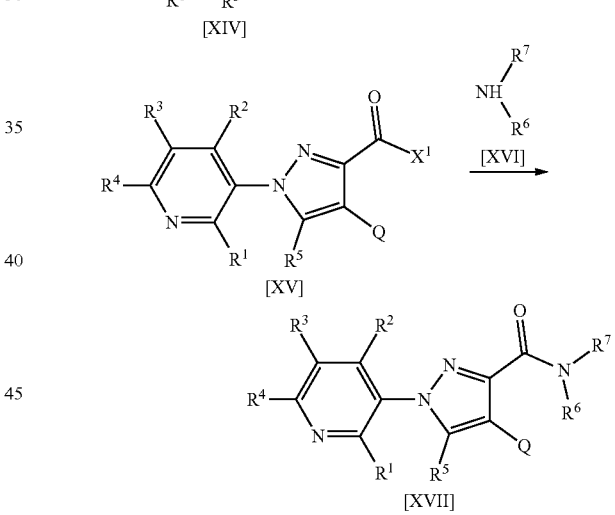

[XVII]

(wherein, Q, R¹, R², R³, R⁴, R⁵, R⁶, R⁷, and X¹ are as defined above.)

That is, the compound represented by general formula [XVII] can be produced by (step 1) making compound [XIV] into compound [XV] by using an acid halogenating agent in an appropriate solvent in the presence or absence of an appropriate catalyst, and then (step 2) reacting with compound [XVI] or a salt thereof in an appropriate solvent in the presence or absence of an appropriate base.

(Step 1)

Examples of the acid halogenating agent that can be used in the present reaction include thionyl chloride, oxalyl chloride, or phosphoryl chloride. The use amount of the acid halogenating agent may be appropriately selected from the range of 0.1 to 30 mol, and is preferably 0.5 to 10 mol, relative to 1 mol of compound [XIV].

Examples of the catalyst that can be used in the present reaction include N,N-dimethylformamide. The use amount of the catalyst may be appropriately selected from the range of 0.01 to 1.0 mol, and is preferably 0.01 to 0.1 mol, relative to 1 mol of compound [XIV].

Examples of the solvent that can be used in the present reaction include ethers such as diethylether, tetrahydrofuran, 1,4-dioxane, 1,2-dimethoxyethane, or methyl tert-butyl ether; aromatic hydrocarbons such as benzene, toluene, xylene, or chlorobenzene; halogenated hydrocarbons such as dichloromethane, chloroform, 1,2-dichloroethane, or carbon tetrachloride; nitriles such as acetonitrile or propionitrile; esters such as ethyl acetate, or ethyl propionate; aliphatic hydrocarbons such as pentane, hexane, cyclohexane, or heptane; or mixed solvents thereof. The use amount of the solvent is 0.1 to 100 liters, preferably 0.3 to 10 liters relative to 1 mol of compound [XIV].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [XV] can be isolated by conducting concentration or the like operation.

(Step 2)

The use amount of compound [XVI] used in the present reaction may be appropriately selected from the range of typically 1 to 500 mol, and is preferably 1.0 to 300 mol, relative to 1 mol of compound [XV].

Examples of the solvent that can be used in the present reaction include ethers such as diethylether, tetrahydrofuran, 1,4-dioxane, 1,2-dimethoxyethane, or methyl tert-butyl ether; aromatic hydrocarbons such as benzene, toluene, xylene, or chlorobenzene; halogenated hydrocarbons such as dichloromethane, chloroform, 1,2-dichloroethane, or carbon tetrachloride; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; nitriles such as acetonitrile or propionitrile; esters such as ethyl acetate or ethyl propionate; aliphatic hydrocarbons such as pentane, hexane, cyclohexane, or heptane; pyridines such as pyridine or picoline; water, or mixed solvents thereof. The use amount of the solvent is 0.1 to 500 liters, preferably 0.2 to 50 liters relative to 1 mol of compound [XV].

Examples of the base that can be used in the present reaction include inorganic bases such as hydroxides of alkali metal (e.g. sodium hydroxide or potassium hydroxide); hydroxides of alkali earth metal (e.g. calcium hydroxide or magnesium hydroxide); carbonates of alkali metal (e.g. sodium carbonate or potassium carbonate); bicarbonates of alkali metal (e.g. sodium hydrogen carbonate or potassium hydrogen carbonate): metal hydrides (e.g. sodium hydride or potassium hydride); metal salts of alcohol (e.g. sodium methoxide, sodium ethoxide, or potassium tert-butoxide); or organic bases such as triethylamine, N,N-dimethylaniline, pyridine, 4-N,N-dimethylaminepyridine, 1,8-diazacyclo[5.4.0]-7-undecene, and so on. The use amount of the base may be appropriately selected from the range of 0 to 5 mol, and is preferably 0 to 1.2 mol, relative to 1 mol of compound [XV].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, water is added to the reaction mixture, and then the precipitated solid is filtered off or extracted with an organic solvent, followed by concentration or the like operation, and thus compound [XVII] can be isolated. The isolated compound [XVII] can be further purified by column chromatography, recrystallization, or the like as necessary.

<Production Method 6>

A compound represented by general formula [XVII] among the present compounds can also be produced, for example, in accordance with the following method.

[Chemical formula 8]

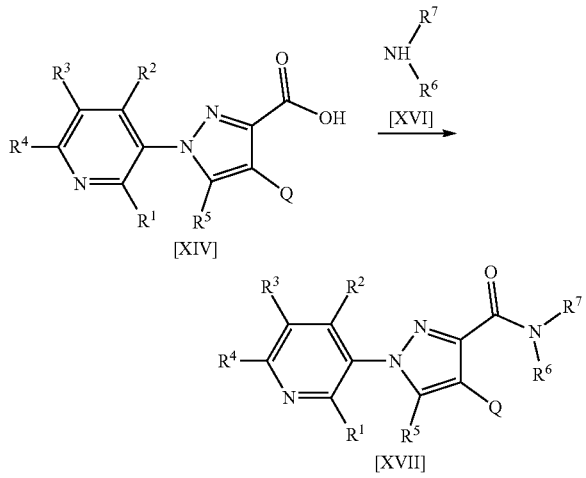

(wherein, Q, $R^1$, $R^2$, $R^3$, $R^4$, $R^5$, $R^6$, and $R^7$ are as defined above.)

That is, the compound represented by general formula [XVII] can be produced by reacting compound [XIV] and compound [XVI] or a salt thereof in an appropriate solvent in the presence or absence of an appropriate condensing agent and an appropriate base.

The use amount of compound [XVI] or a salt thereof used in the present reaction may be appropriately selected from the range of 1 to 10 mol, and is preferably 1.0 to 3.0 mol, relative to 1 mol of compound [XIV].

Examples of the condensing agent that can be used in the present reaction include 1-ethyl-3-(3-dimethylaminopropyl)carbodiimide hydrochloride, a mixture of 1-ethyl-3-(3-dimethylaminopropyl)carbodiimide hydrochloride and 1-hydroxybenzotriazole, 1-ethyl-3-(3-dimethylaminopropyl)carbodiimide, a mixture of 1-ethyl-3-(3-dimethylaminopropyl)carbodiimide and 1-hydroxybenzotriazole, N,N'-dicyclohexylcarbodiimide, N,N'-diisopropylcarbodiimide, N,N'-carbonyldiimidazole, 4-(4,6-dimethoxy-1,3,5-triazine-2-yl)-4-methylmorpholinium chloride, 1H-benzotriazole-1-yloxytris(dimethylamino)phosphonium hexafluorophosphate, {{[(1-cyano-2-ethoxy-2-oxoethylidene)amino]oxy}-4-morpholinomethylene}dimethylammonium hexafluorophosphate, or O-(7-azabenzotriazole-1-yl)-N,N,N',N'-tetramethyluronium hexafluorophosphate. The use amount of the condensing agent may be appropriately selected from the range of 1.0 to 10 mol, and is preferably 1.0 to 6.0 mol, relative to 1 mol of compound [XIV].

When a base is used in the present reaction, examples of the base that can be used include organic bases such as triethylamine, 4-methylmorpholine, diisopropylethylamine, 1,8-diazabicyclo[5.4.0]-7-undecene, pyridine, or 2,6-lutidine. The use amount of the base may be appropriately selected from the range of 0 to 10 mol, and is preferably 0.1 to 6.0 mol, relative to 1 mol of compound [XIV].

Examples of the solvent that can be used in the present reaction include halogenated hydrocarbons such as dichloromethane, chloroform, or 1,2-dichloroethane, or carbon tetrachloride; aliphatic hydrocarbons such as pentane, hexane, cyclohexane, or heptane; esters such as ethyl acetate, or ethyl propionate; nitriles such as acetonitrile or propionitrile; aprotic polar solvents such as N,N-dimethylformamide, N,N-dimethylacetamide, N-methyl-2-pyrrolidone, dimethyl sulfoxide, or sulfolane; ethers such as diethylether, tetrahydrofuran, 1,4-dioxane, 1,2-dimethoxyethane, or methyl tert-butyl ether; or mixed solvents thereof. The use amount of the solvent is 0.1 to 100 liters, preferably 0.3 to 50 liters relative to 1 mol of compound [XIV].

The present reaction can be conducted in the presence of a catalyst as necessary, and examples of the catalyst include 4-(N,N-dimethyl)aminopyridine. The use amount of the catalyst may be appropriately selected from the range of 0.001 to 10 mol, and is preferably 0.01 to 0.3 mol, relative to 1 mol of compound [XIV].

The reaction temperature of the present reaction may be selected from any range of temperature from −20° C. to a reflux temperature in a reaction system, and is preferably in the range of 0° C. to 80° C.

The reaction time of the present reaction is typically 1 minute to 48 hours although it differs depending on the reaction temperature, the reaction substrate, the reaction amount, and the like.

After end of the reaction, water is added to the reaction mixture, and then the precipitated solid is filtered off or extracted with an organic solvent, followed by concentration or the like operation, and thus compound [XVII] can be isolated. The isolated compound [XVII] can be further purified by column chromatography, recrystallization, or the like as necessary.

<Production Method 7>

A compound represented by general formula [XVII] among the present compounds can be produced, for example, in accordance with the following method.

[Chemical formula 9]

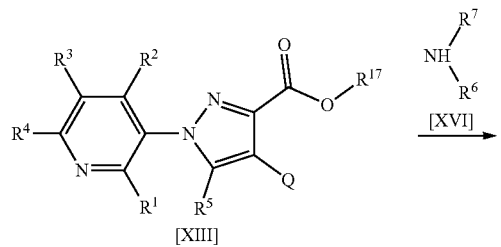

[XIII]

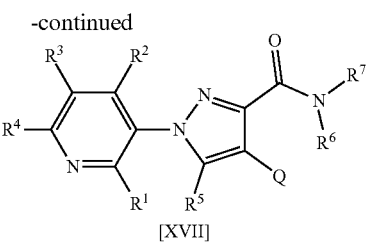

[XVII]

(wherein, Q, $R^1$, $R^2$, $R^3$, $R^4$, $R^5$, $R^6$, $R^7$, and $R^{17}$ are as defined above.)

That is, the compound represented by general formula [XVII] can be produced by reacting the compound represented by general formula [XIII] and the compound represented by general formula [XVI] in an appropriate solvent in the presence or absence of an appropriate base.

The use amount of compound [XVI] used in the present reaction may be appropriately selected from the range of typically 1.0 to 500 mol, and is preferably 1.0 to 300 mol, relative to 1 mol of compound [XIII].

Examples of the solvent that can be used in the present reaction include ethers such as diethylether, tetrahydrofuran, 1,4-dioxane, 1,2-dimethoxyethane, or methyl tert-butyl ether; aromatic hydrocarbons such as benzene, toluene, xylene, or chlorobenzene; halogenated hydrocarbons such as dichloromethane, chloroform, 1,2-dichloroethane, or carbon tetrachloride; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; nitriles such as acetonitrile or propionitrile; esters such as ethyl acetate or ethyl propionate; aliphatic hydrocarbons such as pentane, hexane, cyclohexane, or heptane; pyridines such as pyridine or picoline; water, or mixed solvents thereof. The use amount of the solvent is 0.1 to 500 liters, preferably 0.2 to 50 liters relative to 1 mol of compound [XIII].

Examples of the base that can be used in the present reaction include inorganic bases such as hydroxides of alkali metal (e.g. sodium hydroxide or potassium hydroxide); hydroxides of alkali earth metal (e.g. calcium hydroxide or magnesium hydroxide); carbonates of alkali metal (e.g. sodium carbonate or potassium carbonate); bicarbonates of alkali metal (e.g. sodium hydrogen carbonate or potassium hydrogen carbonate): metal hydrides (e.g. sodium hydride or potassium hydride); metal salts of alcohol (e.g. sodium methoxide, sodium ethoxide, or potassium tert-butoxide); or organic bases such as triethylamine, N,N-dimethylaniline, pyridine, 4-N,N-dimethylaminepyridine, 1,8-diazacyclo [5.4.0]-7-undecene, and so on. The use amount of the base may be appropriately selected from the range of 0 to 5.0 mol, and is preferably 0 to 1.2 mol, relative to 1 mol of compound [XIII].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 1 week although it differs depending on the reaction temperature, the reaction substrate, the reaction amount, and the like.

After end of the reaction, water is added to the reaction mixture, and then extraction with an organic solvent is conducted, and then concentration or the like operation is conducted, and thus compound [XVII] can be isolated. The isolated compound [XVII] can be further purified by column chromatography, recrystallization, or the like as necessary.

<Production Method 8>

A compound represented by general formula [XIX] among the present compounds can be produced, for example, in accordance with the following method.

[Chemical formula 10]

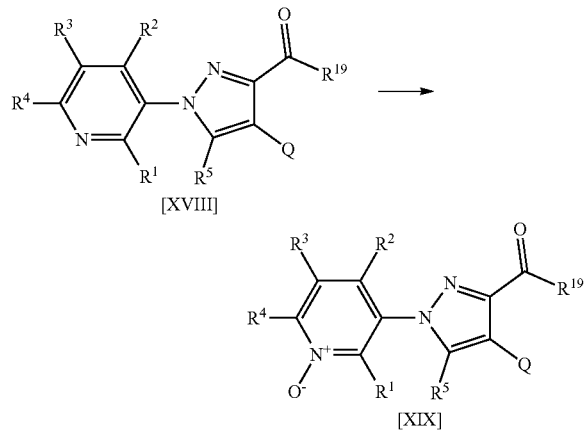

(wherein, Q, $R^1$, $R^2$, $R^3$, $R^4$, $R^5$, and $R^{19}$ are as defined above.)

That is, the compound represented by general formula [XIX] can be produced by reacting compound [XVIII] and an appropriate oxidizing agent in an appropriate solvent in the presence or absence of a catalyst.

Examples of the solvent that can be used in the present reaction include halogenated hydrocarbons such as dichloromethane, chloroform, 1,2-dichloroethane, carbon tetrachloride; ethers such as diethylether, tetrahydrofuran, 1,4-dioxane, 1,2-dimethoxyethane, or methyl tert-butyl ether; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; ketones such as acetone or methyl ethyl ketone; nitriles such as acetonitrile or propionitrile; acetic acid, water, or mixtures thereof. The use amount of the solvent is 0.1 to 500 liters, preferably 0.3 to 200 liters relative to 1 mol of compound [XVIII].

Examples of the oxidizing agent that can be used in the present reaction include organic peroxides such as m-chloroperbenzoic acid, performic acid, or peracetic acid; and inorganic peroxides such as hydrogen peroxide, potassium permanganate, OXONE (registered tradename available from E. I. du Pont de Nemours and Company, product containing potassium peroxymonosulfate), or sodium periodate. The use amount of the oxidizing agent is 0.5 to 3.0 mol, relative to 1 mol of compound [XVIII].

Examples of the catalyst that can be used in the present reaction include sodium tungstate. The use amount of the catalyst is 0.01 to 0.5 mol, relative to 1 mol of compound [XVIII].

The reaction temperature of the present reaction may be selected from any range of temperature typically from −30° C. to a reflux temperature in a reaction system, and is preferably in the range of −10° C. to 100° C.

The reaction time of the present reaction is typically 10 minutes to 48 hours although it differs depending on the reaction temperature, the reaction substrate, the reaction amount, and the like.

After end of the reaction, water is added to the reaction mixture, and then extraction with an organic solvent is conducted, and then concentration or the like operation is conducted, and thus compound [XIX] can be isolated. Alternatively, compound [XIX] can also be isolated by concentrating the solvent of the reaction mixture. The isolated compound [XIX] can be further purified by column chromatography, recrystallization, or the like as necessary.

<Production Method 9>

A compound represented by general formula [XX] among the present compounds can be produced, for example, in accordance with the following method.

[Chemical formula 11]

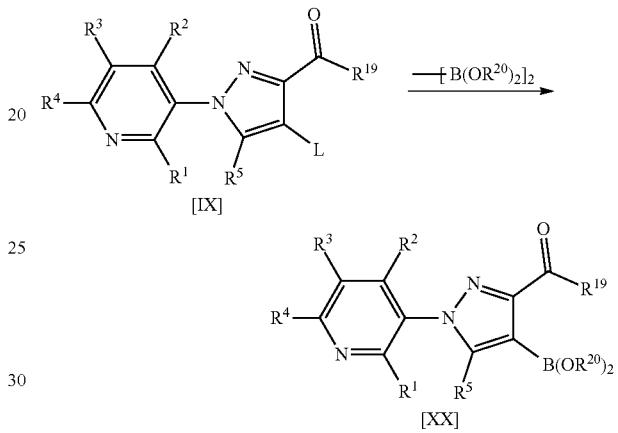

(wherein, $R^{20}$s, which may be the same or different, each represent a hydrogen atom or $C_1$-$C_6$ alkyl, or two $R^{20}$s may together form —$CH_2CH_2$— or —$C(CH_3)_2$$C(CH_3)_2$—, and L, $R^1$, $R^2$, $R^3$, $R^4$, $R^5$ and $R^{19}$ are as defined above.)

That is, the compound represented by general formula [XX] can be produced by reacting compound [IX] and compound —$[B(OR^{20})_2]_2$ in an appropriate solvent in the presence of an appropriate catalyst and an appropriate base.

The use amount of compound —$[B(OR^{20})_2]_2$ used in the present reaction may be appropriately selected from the range of 1 to 10 mol, and is preferably 1.0 to 3.0 mol, relative to 1 mol of compound [IX].

Examples of the solvent that can be used in the present reaction include ethers such as diethyl ether, tetrahydrofuran, 1,4-dioxane, 1,2-dimethoxyethane, or methyl tert-butyl ether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; aliphatic hydrocarbons such as pentane, hexane, cyclohexane, or heptane; water, or mixed solvents thereof. The use amount of the solvent is 0.1 to 300 liters, preferably 0.3 to 50 liters relative to 1 mol of compound [IX].

Examples of the catalyst that can be used in the present reaction include palladium catalysts such as palladium-carbon, palladium chloride, palladium acetate, tris(dibenzylideneacetone)dipalladium, bis(dibenzylideneacetone) palladium, bis(triphenylphosphine)palladium dichloride, tetrakis(triphenylphosphine)palladium, [1,1'-bis(diphenylphosphino)ferrocene]palladium dichloride, or [1,2-bis(diphenylphosphino)ethane]palladium dichloride; or copper catalysts such as metal copper, copper (I) acetate, coper (II)

acetate, copper (I) oxide, copper (II) oxide, copper (I) chloride, or copper (I) iodide.

Besides the above, a palladium catalyst prepared from a palladium catalyst and a ligand may be used. Examples of the palladium catalyst include palladium acetate, tris(dibenzylidene acetone)dipalladium, and bis(dibenzylidene acetone)palladium. Examples of the ligand include triphenylphosphine, tri(tert-butyl)phosphine, tricyclohexylphosphine, SPhos, Xantphos, and BINAP.

The use amount of the catalyst may be appropriately selected from the range of 0.001 to 1.0 mol, and is preferably 0.01 to 0.5 mol, relative to 1 mol of compound [IX].

Examples of the base that can be used in the present reaction include organic bases such as pyridine, diisopropylethylamine, or triethylamine; carbonates of alkali metal such as sodium carbonate, potassium carbonate, or cesium carbonate; bicarbonates of alkali metal such as sodium hydrogen carbonate or potassium hydrogen carbonate; metal salts of alcohol such as sodium methoxide, sodium ethoxide, or potassium tert-butoxide; potassium phosphate, potassium fluoride, cesium fluoride, or potassium acetate. The use amount of the base may be appropriately selected from the range of 0.1 to 10 mol, and is preferably 1.0 to 5.0 mol, relative to 1 mol of compound [IX].

The reaction temperature of the present reaction may be selected from any range of temperature typically from 25° C. to a reflux temperature in a reaction system, and is preferably in the range of 30° C. to 150° C.

The reaction time of the present reaction is typically 1 minute to 72 hours although it differs depending on the reaction temperature, the reaction substrate, the reaction amount, and the like.

After end of the reaction, water is added to the reaction mixture, and then the precipitated solid is filtered off or extracted with an organic solvent, followed by concentration or the like operation, and thus compound [XX] can be isolated. The isolated compound [XX] can be further purified by column chromatography, recrystallization, or the like as necessary.

<Production Method 10>

A compound represented by general formula [XII] among the present compounds can be produced, for example, in accordance with the following method.

[Chemical formula 12]

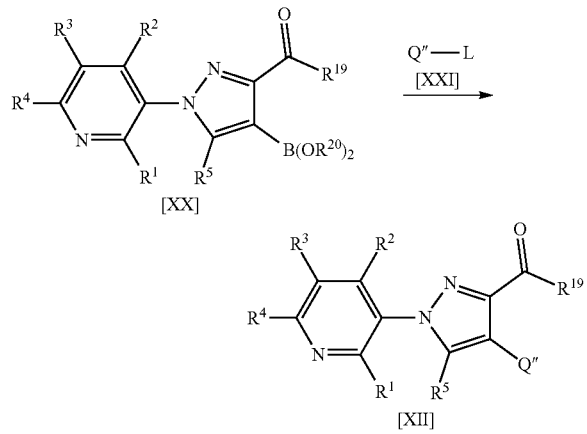

(wherein, Q", L, R$^1$, R$^2$, R$^3$, R$^4$, R$^5$, R$^{19}$ and R$^{20}$ are as defined above.)

That is, the compound represented by general formula [XII] can be produced by reacting compound [XX] and compound [XX] in an appropriate solvent in the presence of an appropriate catalyst and an appropriate base.

The use amount of compound [XX] used in the present reaction may be appropriately selected from the range of 0.3 to 10 mol, and is preferably 0.4 to 3.0 mol, relative to 1 mol of compound [XX].

Examples of the solvent that can be used in the present reaction include ethers such as diethyl ether, tetrahydrofuran, 1,4-dioxane, 1,2-dimethoxyethane, or methyltert-butyl ether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; aliphatic hydrocarbons such as pentane, hexane, cyclohexane, or heptane; water, or mixed solvents thereof. The use amount of the solvent is 0.1 to 300 liters, preferably 0.3 to 50 liters relative to 1 mol of compound [XX].

Examples of the catalyst that can be used in the present reaction include palladium catalysts such as palladium-carbon, palladium chloride, palladium acetate, tris(dibenzylideneacetone)dipalladium, bis(dibenzylideneacetone)palladium, bis(triphenylphosphine)palladium dichloride, tetrakis(triphenylphosphine)palladium, [1,1'-bis(diphenylphosphino)ferrocene]palladium dichloride, or [1,2-bis(diphenylphosphino)ethane]palladium dichloride; or copper catalysts such as metal copper, copper (I) acetate, coper (II) acetate, copper (I) oxide, copper (II) oxide, copper (I) chloride, or copper (I) iodide.

Besides the above, a palladium catalyst prepared from a palladium catalyst and a ligand may be used. Examples of the palladium catalyst include palladium acetate, tris(dibenzylidene acetone)dipalladium, and bis(dibenzylidene acetone)palladium. Examples of the ligand include triphenylphosphine, tri(tert-butyl)phosphine, tricyclohexylphosphine, SPhos, Xantphos, and BINAP.

The use amount of the catalyst may be appropriately selected from the range of 0.001 to 1.0 mol, and is preferably 0.01 to 0.5 mol, relative to 1 mol of compound [XX].

Examples of the base that can be used in the present reaction include organic bases such as pyridine, diisopropylethylamine, or triethylamine; hydroxides of alkali metal such as sodium hydroxide or potassium hydroxide; carbonates of alkali metal such as sodium carbonate, potassium carbonate, or cesium carbonate; bicarbonates of alkali metal such as sodium hydrogen carbonate or potassium hydrogen carbonate; metal salts of alcohol such as sodium methoxide, sodium ethoxide, or potassium tert-butoxide; potassium phosphate, potassium fluoride, or cesium fluoride. The use amount of the base may be appropriately selected from the range of 0.1 to 10 mol, and is preferably 1.0 to 5.0 mol, relative to 1 mol of compound [XX].

The reaction temperature of the present reaction may be selected from any range of temperature typically from −30° C. to a reflux temperature in a reaction system, and is preferably in the range of 0° C. to 150° C.

The reaction time of the present reaction is typically 1 minute to 72 hours although it differs depending on the reaction temperature, the reaction substrate, the reaction amount, and the like.

After end of the reaction, water is added to the reaction mixture, and then the precipitated solid is filtered off or extracted with an organic solvent, followed by concentration or the like operation, and thus compound [XII] can be isolated. The isolated compound [XII] can be further purified by column chromatography, recrystallization, or the like as necessary.

<Production Method 11>

A compound represented by general formula [XXII] among the present compounds can be produced, for example, by using a compound represented by general formula [XVII] in accordance with the following method.

[Chemical formula 13]

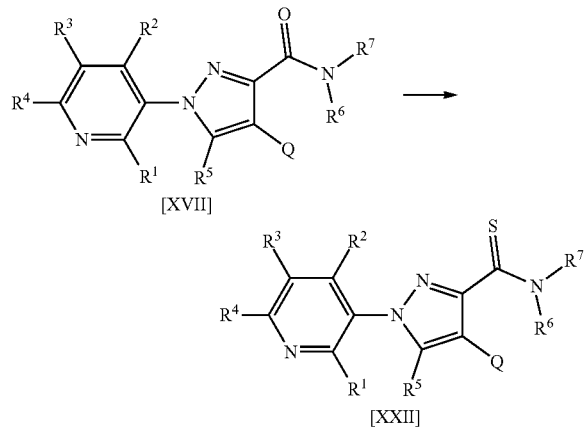

[XVII]

[XXII]

(wherein, $R^1$, $R^2$, $R^3$, $R^4$, $R^5$, $R^6$, $R^7$ and Q are as defined above.)

That is, the compound represented by general formula [XXII] can be produced by reacting compound [XVII] with an appropriate sulphidizing agent.

Examples of the solvent that can be used in the present reaction include ethers such as diethyl ether, tetrahydrofuran, 1,4-dioxane, 1,2-dimethoxyethane, or methyltert-butyl ether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; halogenated hydrocarbons such as dichloromethane, chloroform, 1,2-dichloroethane, or carbon tetrachloride; aliphatic hydrocarbons such as pentane, hexane, cyclohexane, or heptane; water, or mixed solvents thereof. The use amount of the solvent is 0.1 to 300 liters, preferably 0.3 to 50 liters relative to 1 mol of compound [XVII].

Examples of the sulphidizing agent that can be used in the present reaction include phosphorus pentasulfide, or Lawesson's reagent. The use amount of the sulphidizing agent may be appropriately selected from the range of 0.5 to 30 mol, and is preferably 0.5 to 5 mol, relative to 1 mol of compound [XVII].

The reaction temperature of the present reaction may be selected from any range of temperature typically from −70° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, water is added to the reaction mixture, and then extraction with an organic solvent is conducted, and then concentration or the like operation is conducted, and thus compound [XXII] can be isolated. Alternatively, compound [XXII] can also be isolated by concentrating the solvent of the reaction mixture. The isolated compound [XXII] can be further purified by column chromatography, recrystallization, or the like as necessary.

<Production Method 12>

A compound represented by general formula [XXVI] among the present compounds can be produced, for example, by using a compound represented by general formula [XXIII] in accordance with the following method.

[Chemical formula 14]

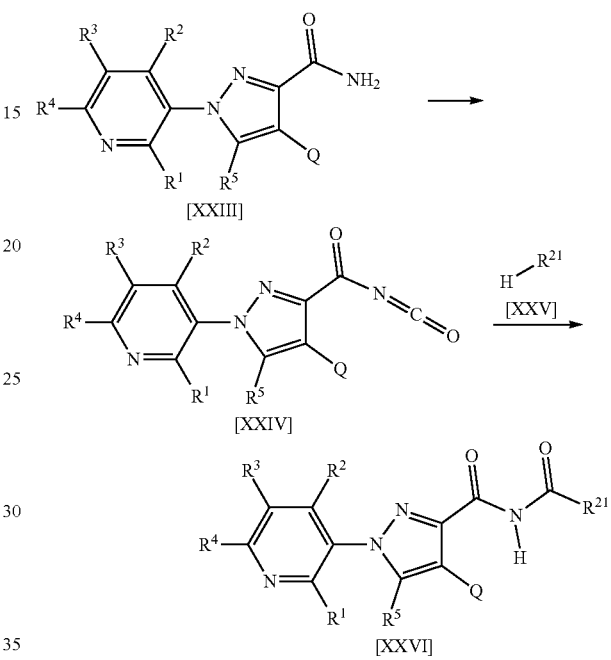

[XXIII]

[XXIV]

[XXVI]

(wherein, $R^{21}$ represents a $C_1$-$C_6$ alkoxy group, amino group, mono($C_1$-$C_6$ alkyl)amino group, di($C_1$-$C_6$ alkyl) amino group, $C_1$-$C_6$ alkylthio group, or $C_1$-$C_6$ alkoxy $C_1$-$C_6$ alkoxy group, and $R^1$, $R^2$, $R^3$, $R^4$, $R^5$ and Q are as defined above.)

That is, the compound represented by general formula [XXVI] can be produced by (step 1) making compound [XXIII] into compound [XXIV] by using oxalyl chloride in an appropriate solvent or in the absence of a solvent, and then (step 2) reacting with compound [XXV] or a salt thereof in an appropriate solvent or in the absence of a solvent.

(Step 1)

The use amount of oxalyl chloride may be appropriately selected from the range of 1.0 to 1000 mol, and is preferably 1.0 to 300 mol, relative to 1 mol of compound [XXIII].

Examples of the solvent that can be used in the present reaction include ethers such as diethyl ether, tetrahydrofuran, methyltert-butyl ether, or 1,4-dioxane; aromatic hydrocarbons such as benzene, toluene, xylene, or chlorobenzene; halogenated hydrocarbons such as dichloromethane, chloroform, 1,2-dichloroethane, or carbon tetrachloride; aprotic polar solvents such as N,N-dimethylformamide, N,N-dimethylacetamide, N-methyl-2-pyrrolidone, dimethyl sulfoxide, or sulfolane; nitriles such as acetonitrile or propionitrile; esters such as ethyl acetate or ethyl propionate, or mixed solvents thereof. The use amount of the solvent is 0.1 to 500 liters, preferably 0.2 to 50 liters relative to 1 mol of compound [XXIII].

The reaction temperature of the present reaction may be selected from any range of temperature typically from 0° C. to a reflux temperature in a reaction system, and is preferably in the range of 20° C. to 90° C.

The reaction time of the present reaction is typically 1 minute to 6 hours although it differs depending on the reaction temperature, the reaction substrate, the reaction amount, and the like.

After end of the reaction, compound [XXIV] can be isolated by conducting concentration or the like operation.
(Step 2)

The use amount of compound [XXV] used in the present reaction may be appropriately selected from the range of typically 1.0 to 500 mol, and is preferably 1.0 to 300 mol, relative to 1 mol of compound [XXIV].

Examples of the solvent that can be used in the present reaction include ethers such as diethyl ether, tetrahydrofuran, 1,4-dioxane, 1,2-dimethoxyethane, or methyl tert-butyl ether; halogenated hydrocarbons such as dichloromethane, chloroform, 1,2-dichloroethane, or carbon tetrachloride; aprotic polar solvents such as N,N-dimethylformamide, N,N-dimethylacetamide, N-methyl-2-pyrrolidone, dimethyl sulfoxide, or sulfolane; nitriles such as acetonitrile or propionitrile; esters such as ethyl acetate or ethyl propionate, or mixed solvents thereof. The use amount of the solvent is 0.1 to 500 liters, preferably 0.2 to 50 liters relative to 1 mol of compound [XXIV].

The reaction temperature of the present reaction may be selected from any range of temperature typically from −30° C. to a reflux temperature in a reaction system, and is preferably in the range of −10° C. to 100° C.

The reaction time of the present reaction is typically 5 minutes to 24 hours although it differs depending on the reaction temperature, the reaction substrate, the reaction amount, and the like.

After end of the reaction, water is added to the reaction mixture, and then the precipitated solid is filtered off or extracted with an organic solvent, followed by concentration or the like operation, and thus compound [XXVI] can be isolated. The isolated compound [XXVI] can be further purified by column chromatography, recrystallization, or the like as necessary.

<Production Method 13>

A compound represented by general formula [XVII] among the present compounds can be produced, for example, by using a compound represented by general formula [XXVII] in accordance with the following method.

[Chemical formula 15]

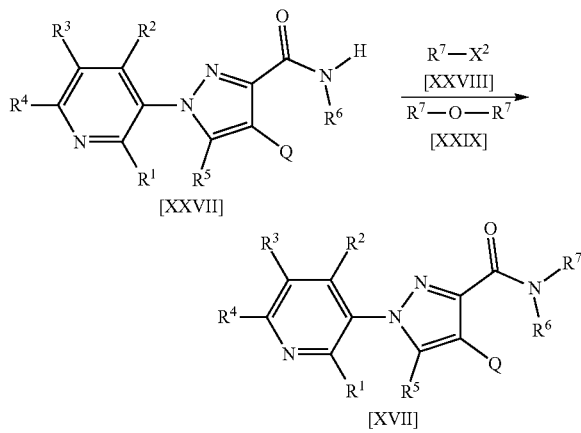

(wherein, $X^2$ represents a halogen atom, $C_1$-$C_6$ alkylsulfonyloxy group, trifluoromethanesulfonyloxy group, nonafluorobutylsulfonyloxy group, phenylsulfonyloxy group, 4-toluenesulfonyloxy group, $C_1$-$C_6$ alkylsulfonyl group, phenylsulfonyl group or 4-toluenesulfonyl group, and $R^1$, $R^2$, $R^3$, $R^4$, $R^5$, $R^6$, $R^7$ and Q are as defined above.)

That is, the compound represented by general formula [XVII] can be produced by reacting compound [XXVII] and compound [XXVIII] or compound [XXIX] in an appropriate solvent in the presence or absence of an appropriate base.

The use amount of compound [XXVIII] or compound [XXIX] used in the present reaction may be appropriately selected from the range of 1.0 to 10 mol, and is preferably 1.0 to 5.0 mol, relative to 1 mol of compound [XXVII].

Examples of the solvent that can be used in the present reaction include ethers such as diethyl ether, tetrahydrofuran, 1,4-dioxane, 1,2-dimethoxyethane, or methyl tert-butyl ether; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; nitriles such as acetonitrile or propionitrile; aliphatic hydrocarbons such as pentane, hexane, cyclohexane, or heptane; pyridines such as pyridine or picoline; water, or mixed solvents thereof. The use amount of the solvent is 0.1 to 300 liters, preferably 0.3 to 50 liters relative to 1 mol of compound [XXVII].

Examples of the base that can be used in the present reaction include inorganic bases such as hydroxides of alkali metal (e.g. sodium hydroxide or potassium hydroxide); hydroxides of alkali earth metal (e.g. calcium hydroxide or magnesium hydroxide); carbonates of alkali metal (e.g. sodium carbonate or potassium carbonate); bicarbonates of alkali metal (e.g. sodium hydrogen carbonate or potassium hydrogen carbonate); metal hydrides (e.g. sodium hydride or potassium hydride); metal salts of alcohol (e.g. sodium methoxide, sodium ethoxide, or potassium tert-butoxide); or organic bases such as triethylamine, N,N-dimethylaniline, pyridine, 4-N,N-dimethylaminepyridine, 1,8-diazacyclo[5.4.0]-7-undecene, and so on. The use amount of the base may be appropriately selected from the range of 1.0 to 10 mol, and is preferably 1.0 to 6.0 mol, relative to 1 mol of compound [XXVII]. The organic bases such as triethylamine or pyridine can also be used as the solvent.

The present reaction can be conducted in the presence of a catalyst as necessary, and examples of the catalyst include pyridine, 4-(N,N-dimethyl)aminopyridine, or 4-pyrrolidinopyridine. The use amount of the catalyst may be appropriately selected from the range of 0.001 to 1.0 mol, and is preferably 0.01 to 0.1 mol, relative to 1 mol of compound [XXVII].

The reaction temperature of the present reaction may be selected from any range of temperature from −70° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, water is added to the reaction mixture, and then extraction with an organic solvent is conducted, and then concentration or the like operation is conducted, and thus compound [XVII] can be isolated. The isolated compound [XVII] can be further purified by column chromatography, recrystallization, or the like as necessary.

An agrochemical composition of the present invention contains the pyrazole derivative or an agriculturally acceptable salt thereof represented by general formula [I] or [II] of the present invention, as an active ingredient.

The agrochemical composition can contain an additive component (carrier) that is typically used in an agrochemical formulation, as necessary.

The present pest control agent contains the pyrazole derivative or an agriculturally acceptable salt thereof represented by general formula [I] or [II] of the present invention, as an active ingredient. The present pest control agent is representatively an insecticide and a miticide.

The present pest control agent can contain an additive component (carrier) that is typically used in an agrochemical formulation, as necessary.

Examples of the additive component include a carrier such as a solid carrier or a liquid carrier, a surfactant, a binder or a tackifier, a thickener, a coloring agent, a spreader, a sticker, an antifreezing agent, an anticaking agent, a disintegrating agent, and a stabilizing agent, and besides the above, an antiseptic, a plant piece, or the like may be added to the additive component as necessary. These additive components may be used singly or in combination of two or more kinds.

Hereinafter, the aforementioned additive components are described.

Examples of the solid carrier include mineral carriers such as pyrophyllite clay, kaolin clay, silica clay, talc, diatomite, zeolite, bentonite, Japanese acid clay, activated clay, attapulgus clay, vermiculite, pearlite, pumice, white carbon (synthetic silicic acid, synthetic silicate, or the like), or titanium dioxide; vegetal carriers such as woody powder, corn haulm, walnut shell, fruit stone, chaff, sawdust, bran, soybean meal, powdered cellulose, starch, dextrin, or saccgarudes; inorganic salt carriers such as calcium carbonate, ammonium sulfate, sodium sulfate, or potassium chloride; and polymeric carriers such as polyethylene, polypropylene, polyvinyl chloride, polyvinyl acetate, ethylene-vinyl acetate copolymer, or urea-aldehyde resin.

Examples of the liquid carrier include monohydric alcohols such as methanol, ethanol, propanol, 2-propanol, butanol, or cyclohexanol; polyhydric alcohols such as ethylene glycol, diethylene glycol, propylene glycol, hexylene glycol, polyethylene glycol, polypropylene glycol, or glycerin; polyhydric alcohol derivatives such as propylene glycol ether; ketones such as acetone, methylethyl ketone, methylisobutyl ketone, diisobutyl ketone, cyclohexanone, or isophoron; ethers such as ethyl ether, 1,4-dioxane, Cellosolve, dipropyl ether, or tetrahydrofuran; aliphatic hydrocarbons such as normal paraffin, naphthene, isoparaffin, kerosene, or mineral oil; aromatic hydrocarbons such as toluene, $C_9$-$C_{10}$ alkylbenzene, xylene, solvent naphtha, alkyl naphthalene, or high boiling point aromatic hydrocarbons; halogenated hydrocarbons such as 1,2-dichloroethane, chloroform, or carbon tetrachloride; esters such as ethyl acetate, diisopropyl phthalate, dibutyl phthalate, dioctyl phthalate, or dimethyl adipate; lactones such as γ-butyrolactone; amides such as N,N-dimethylformamide, N,N-diethylformamide, N,N-dimethylacetamide, or N-methyl-2-pyrrolidone; nitriles such as acetonitrile; sulfur compounds such as dimethyl sulfoxide; vegetable oils such as soybean oil, rapeseed oil, cottonseed oil, coconut oil, or castor oil; and water.

Although not particularly limited, the surfactant preferably gelates or shows swelling property in water, and examples of the surfactant include noionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether formalin condensate, polyoxyethylene polyoxypropylene block polymer, alkylpolyoxyethylene polypropylene block polymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether silicone, ester silicone, fluorine surfactant, polyoxyethylene castor oil, or polyoxyethylene hardened castor oil; anionic surfactants such as alkyl sulfates, polyoxyethylene alkyl ether sulfates, polyoxyethylene alkyl phenyl ether sulfates, polyoxyethylene styryl phenyl ether sulfate, alkyl benzenesulfonates, lignin sulfonate, alkyl sulfosuccinates, naphthalene sulfonate, alkylnaphthalene sulfonates, salts of formalin condensate of naphthalene sulfonate, salts of formalin condensate of alkylnaphthalene sulfonate, fatty acid salts, polycarboxylates, N-methyl-fatty acid Sarcosinates, resinates, polyoxyethylene alkyl ether phosphates, or polyoxyethylene alkyl pheny ether phosphates; cationic surfactants such as alkyl amine salts such as lauryl amine hydrochloride, stearyl amine hydrochloride, oleyl amine hydrochloride, stearyl amine acetate, stearyl aminopropylamine acetate, alkyl trimethyl ammonium chlorides, or alkyl dimethylbenzarconium chloride; and amphoteric surfactants including a betaine type such as dialkyl diaminoethyl betaine, or alkyl dimethylbenzyl betaine, and an amino acid type such as dialkylaminoethyl glycin, or alkyl dimethylbenzyl glycin.

Examples of the binder or the tackifier include carboxymethylcelullose or a salt thereof, dextrin, soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6000 to 20000, polyethylene oxide having an average molecular weight of 100000 to 5000000, and naturally-occurring phospholipid (for example, Cephalin, lecithin, or the like).

Examples of the thickener include water-soluble polymers such as xanthan gum, guar gum, carboxymethylcelullose, polyvinylpyrrolidone, carboxyvinyl polymer, acrylic polymer, starch derivatives, or polysaccharides; and inorganic fine powder such as high purity bentonite or white carbon.

Examples of the coloring agent include inorganic pigments such as iron oxide, titanium oxide, or Prussian blue; and organic dyes such as an alizarin dye, an azo dye, or a metal phthalocyanine dye.

Examples of the spreader include a silicone surfactant, cellulose powder, dextrin, processed starch, a polyaminocarboxylic acid chelete compound, a cross-linked polyvinylpyrrolidone, malic acid and styrenes, methacrylic acid copolymer, a half ester of a polymer of polyhydric alcohol and dicarboxylic acid anhydride, and a water-soluble salt of polystyrene sulfonic acid.

Examples of the sticker include various surfactants such as sodium dialkyl sulfosuccinate, polyoxyethylene alkyl ether, polyoxyethylene alkylphenyl ether, or polyoxyethylene fatty acid ester; paraffin, terpene, polyamide resin, polyacrylate, polyoxyethylene, wax, polyvinylalkyl ether, an alkylphenol formalin condensate, and a synthetic resin emulsion.

Examples of the antifreezing agent include polyhydric alcohols such as ethylene glycol, diethylene glycol, propylene glycol, or glycerin.

Examples of the anticaking agent include polysaccharides such as starch, alginic acid, mannose, or galactose; polyvinylpyrrolidone, white carbon, ester gum, and petroleum resin.

Examples of the disintegrating agent include sodium tripolyphosphate, sodium hexametaphosphate, a stearic metal salt, cellulose powder, dextrin, copolymer of methacrylic ester, polynylpyrrolidone, polyaminocarboxylic chelate compound, styrene sulfonate-isobutylene-maleic anhydride copolymer, and starch-polyacrylonitrile graft copolymer.

Examples of the stabilizing agent include a desiccant such as zeolite, calcined lime, or magnesium oxide; an antioxidant based on phenol, amine, sulfur, phosphoric acid, or the like; an ultraviolet absorber based on salicylic acid, benzophenone, or the like.

In the present pest control agent, when the additive component is contained, the content thereof is selected typically in a range of 5 to 95%, preferably in the range of 20 to 90% on the mass basis in the case of a carrier such as a solid carrier or a liquid carrier, selected typically in a range of 0.1% to 30%, preferably in a range of 0.5 to 10% in the case of a surfactant, and selected typically in a range of 0.1 to 30%, preferably in a range of 0.5 to 10% in the case of other additive.

The present pest control agent is used while it is prepared into any formulation including dusts, dusts and granules, granules, water-dispersible powders, water-soluble powders, water-dispersible granules, tablets, Jumbos, emulsifiable concentrates, oils, solutions, flowable concentrates, emulsions, microemulsions, suspoemulsions, ultra-low volume dusting powders, microcapsules, smoking agents, aerosols, baiting agents, and pastes.

In actual use of the formulation, the formulation can be used per se or after dilution with a diluent such as water in a predetermined concentration. Application of various formulations containing the present compound, and dilution products thereof can be conducted by a method ordinarily used, such as dispersion (e.g., spraying, misting, atomizing, powder dispersion, granule dispersion, on-water-surface dispersion, or inbox dispersion), in-soil application (e.g., mixing or drenching), on-surface application (e.g., coating, dust coating, or covering), seed treatment (e.g., smearing or dressing treatment), immersion, poison bait, smoking, and the like. It is also possible to mix the above-mentioned active ingredient with a livestock feed in order to prevent the infestation and growth of pests, particularly harmful insects in the excreta of the livestock.

A method for controlling a pest of the present invention can be conducted by using an active ingredient amount of the pyrazole derivative represented by general formula [I] or [II] of the present invention or an agriculturally acceptable salt thereof in the above-mentioned application method described above.

The mixing proportion (% by mass) of the active ingredient in the present pest control agent is appropriately selected as needed. For example, the mixing proportion may be appropriately selected in the following ranges: 0.01 to 20%, preferably to 10% for dusts, dusts and granules, microgranules, or the like; 0.1 to 30%, preferably to 20% for granules or the like; 1 to 70%, preferably 5 to 50% for water-dispersible powders, water-dispersible granules, or the like; 1 to 95%, preferably 10 to 80% for water-soluble powders, solutions, or the like; 5 to 90%, preferably 10 to 80% for emulsifiable concentrates or the like; 1 to 50%, preferably 5 to 30% for oils or the like; 5 to 60%, preferably 10 to 50% for flowable concentrates or the like; 5 to 70%, preferably 10 to 60% for emulsions, microemulsions, suspoemulsions, or the like; 1 to 80%, preferably 5 to 50% for tablets, baiting agents, pastes, or the like; 0.1 to 50%, preferably 1 to 30% for smoking agents or the like; and 0.05 to 20%, preferably 0.1 to 10% for aerosols or the like.

The formulation is sprayed after dilution in an appropriate concentration, or applied directly.

When present pest control agent is used after dilution with a diluent, the concentration of the active ingredient is generally 0.1 to 5000 ppm. When the formulation is used per se, the application amount thereof per unit area is 0.1 to 5000 g per 1 ha in terms of the active ingredient compound; however, the application amount is not restricted thereto.

It goes without saying that the present pest control agent is sufficiently effective when the present compound is used alone as an active ingredient. However, the present pest control agent may be mixed or used in combination, as necessary, with other fertilizers and agricultural chemicals such as insecticide, miticide, nematicide, synergist, fungicide, antiviral agent, attractant, herbicide, plant growth-controlling agent, and the like. In this case, a more excellent effect can be exhibited.

Below are shown examples of known insecticides, miticides, nematicides, and synergist compounds, which may be mixed or used in combination.

Insecticide Active Ingredients:

acrinathrin, azadirachtin, azamethiphos, acynonapyr, azinphos-ethyl, azinphos-methyl, acequinocyl, acetamiprid, acetoprole, acephate, azocyclotin, abamectin, afidopyropen, afoxolaner, amidoflumet, amitraz, alanycarb, aldicarb, aldoxycarb, allethrin [including d-cis-trans-form, and d-trans-form], isazophos, isamidofos, isocarbophos, isoxathion, isocycloseram, isofenphos-methyl, isoprocarb, epsilon-metofluthrin, epsilon-momfluorothrin, ivermectin, imicyafos, imidacloprid, imiprothrin, indoxacarb, esfenvalerate, ethiofencarb, ethion, ethiprole, ethylene dibromide, etoxazole, etofenprox, ethoprophos, etrimfos, emamectin, emamectin benzoate, endosulfan, empenthrin, oxazosulfyl, oxamyl, oxydemeton-methyl, oxydeprofos, omethoate, cadusafos, kappa-tefluthrin, kappa-bifenthrin, karanjin, cartap, carbaryl, carbosulfan, carbofuran, gamma-BHC, xylylcarb, quinalphos, kinoprene, chinomethionat, coumaphos, cryolite, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, chloroprallethrin, cyazypyr, cyanophos, diafenthiuron, diamidafos, cyantraniliprole, dienochlor, cyenopyrafen, dioxabenzofos, diofenolan, cyclaniliprole, cycloxaprid, dicrotophos, dichlofenthion, cycloprothrin, dichlorvos, dicloromezotiaz, dicofol, dicyclanil, disulfoton, dinotefuran, dinobuton, cyhalodiamide, cyhalothrin [including gamma-form, and lambda-form], cyphenothrin [including (1R)-trans-form], cyfluthrin) [including beta-form], diflubenzuron, cyflumetofen, diflovidazin, cyhexatin, cypermethrin [including alpha-form, beta-form, theta-form, and zeta-form], dimpropyridaz, dimethyl-2,2,2-trichloro-1-hydroxy-ethyl phosphate (DEP), dimethylvinphos, dimethoate, dimefluthrin, silafluofen, cyromazine, spinetoram, spinosad, spirodiclofen, spirotetramat, spiropidion, spiromesifen, sulcofuron-sodium, sulfluramid, sulfoxaflor, sulfotep, diazinon, thiacloprid, thiamethoxam, tioxazafen, thiodicarb, thiocyclam, thiosultap, thionazin, thiofanox, thiometon, tyclopyrazoflor, tetrachlorantraniliprole, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, triflumezopyrim, trimethacarb, tolfenpyrad, naled, nicotine, nitenpyram, nemadectin, novaluron, noviflumuron, *Verticillium lecanii*, hydroprene, *Bacillus sphaericus*, *Bacillus subtillis*, *Bacillus thuringiensis*, insect toxin produced by *Bacillus thuringiensis*, *Bacillus thuringiensis* subsp. *aizawai, Bacillus thuringiensis* subsp. *israelensis, Bacillus thuringiensis* subsp. *kurstaki, Bacillus thuringiensis* subsp. *tenebrionis, Bacillus popilliae*, Pasteuriapenetrans spore, vamidothion, parathion, parathion-methyl, halfenprox, halofenozide, bioallethrin, bioallethrin S-cyclopentenyl, bioresmethrin, bis-(2-chloro-1-methylethyl)ether (DCIP), bistrifluron, hydramethylnon, bifenazate, bifenthrin, pyflubumide, piperonyl butoxide, pymetrozine, pyraclofos, pyrafluprole, pyridaphenthion, pyridaben, pyridalyl, pyrifluquinazon, pyriprole, pyriproxyfen, pirimicarb, pyrimidifen, pyriminostrobin, pirimiphos-methyl, pyrethrine, famphur, fipronil, fenazaquin, fenamiphos, fenitrothion, fenoxycarb, fenothiocarb, phenothrin [including (1R)-trans-form], fenobucarb, fenthion, phenthoate, fenvalerate, fenpyroximate, fenbutatin oxide, fenpropathrin, fonofos, sulfuryl fluoride, butocarboxim, butoxycarboxim, buprofezin, furathiocarb, prallethrin, fluacrypyrim, fluazaindolizine, fluazuron, fluensulfone, fluopyram, sodium fluoroacetate, fluxametamide, flucycloxuron, flucythrinate, flusulfamide, fluthrin, fluvalinate [including tau-form], flupyradifurone, flupyrazofos, flupyrimin, flufiprole, flufenerim, flufenoxystrobin, flufenoxuron, fluhexafon, flubendiamide, flumethrin, fluralaner, flurimfen, prothiofos, protrifenbute, flonicamid, propaphos, propargite, profenofos, broflanilide, profluthrin, propetamphos, propoxur, flometoquin, bromopropylate, hexythiazox, hexaflumuron, *Pacilimyces tenuipes, Paecilomyces fumosoroceus*, heptafluthrin, heptenophos, permethrin, benclothiaz, benzpyrimoxan, bensultap, benzoximate, bendiocarb, benfuracarb, *Beauveria tenella, Beauveria bassiana, Beauveria brongniartii*, phoxim, phosalone, fosthiazate, fosthietan, phosphamidon, phosmet, polynactins, formetanate, phorate, machine oil, malathion, milbemectin, mecarbam, mesulfenfos, methomyl, metaldehyde, metaflumizone, methamidophos, metham, methiocarb, methidathion, methyl isothiocyanate, methyl bromide, methoxychlor, methoxyfenozide, methothrin, metofluthrin, methoprene, metolcarb, mevinphos, meperfluthrin, Monacrosporium phymatophagum, monocrotophos, momfluorothrin, litlure-A, litlure-B, aluminium phosphide, zinc phosphide, phosphine, lufenuron, rescalure, resmethrin, lepimectin, rotenone, nuclear polyhedrosis virus silkworm-embedded form, fenbutatin oxide, calcium cyanide, organotins, nicotine-sulfate, (Z)-11-tetradecenyl=acetate, (Z)-11-hexadecenal, (Z)-11-hexadecenyl=acetate, (Z)-9,12-tetradecadienyl=acetate, (Z)-9-tetradecene-1-ol, (Z,E)-9,11-tetradecadienyl=acetate, (Z,E)-9,12-tetradecadienyl=acetate, 1,1,1-trichloro-2,2-bis(4-chlorophenyl)ethane (DDT), 1,3-dichloropropene(1,3-dichloropropene), 2,4-dichloro-5-{2-[4-(trifluoromethyl)phenyl]ethoxy}phenyl 2,2,2-trifluoroethyl sulfoxide (Chemical name, CAS registry number: 1472050-04-6), 2,4-dichloro-5-12-[4-(trifluoromethyl)phenyl]ethoxylphenyl 2,2,2-trifluoroethyl sulfoxide (Chemical name, CAS registry number: 1472052-11-1), 2,4-dimethyl-5-[6-(trifluoromethylthio)hexyloxy]phenyl-2,2,2-trifluoroethyl sulfoxide (Chemical name, CAS registry number: 1472050-34-2), 2-{2-fluoro-4-methyl-5-[(2,2,2-trifluoroethyl)sulfinyl]phenoxy}-5-(trifluoromethyl)pyridine (Chemical name, CAS registry number: 1448758-62-0), 3-chloro-2-{2-fluoro-4-methyl-5-[(2,2,2-trifluoroethyl)sulfinyl] phenoxy}-5-(trifluoromethyl)pyridine (Chemical name, CAS registry number: 1448761-28-1), 4,6-dinitro-o-cresol (DNOC), 4-fluoro-2-methyl-5-(5,5-dimethylhexyloxy]phenyl-2,2,2-trifluoroethyl sulfoxide (Chemical name, CAS registry number: 1472047-71-4), Bt protein (Cry1Ab, Cry1Ac, Cry1Fa, Cry2Ab, mCry3A, Cry3Ab, Cry3Bb, Cry34/35Ab1), CL900167 (code number), NA-85 (code number), NI-30 (code number), O,O-diethyl-O-[4-(dimethylsulfamoyl)phenyl]-phosphorothioate (DSP), O-ethyl-O-4-(nitrophenyl)phenylphosphonothioate (EPN), RU15525 (code number), XMC(XMC), Z-13-icosen-10-one, ZXI8901 (code number).

Next, examples of known bactericides or disease controller compounds that can be mixed or used in combination are shown below.

Bactericide active Ingredients:

azaconazole, acibenzolar-S-methyl, azoxystrobin, anilazine, amisulbrom, aminopyrifen, ametoctradin, aldimorph, isotianil, isopyrazam, isofetamid, isoflucypram, isoprothiolane, ipconazole, ipflufenoquin, ipfentrifluconazole, iprodione, iprovalicarb, iprobenfos, imazalil, iminoctadine-albesilate, iminoctadine-triacetate, imibenconazole, inpyrfluxam, imprimatin A, imprimatin B, edifenphos, etaconazole, ethaboxam, ethirimol, ethoxyquin, etridiazole, enestroburin, enoxastrobin, epoxiconazole, organic oils, oxadixyl, oxazinylazole, oxathiapiprolin, oxycarboxin, oxine-copper, oxytetracycline, oxpoconazole-fumarate, oxolinic acid, copper dioctanoate, octhilinone, ofurace, orysastrobin, o-phenylphenol, kasugamycin, captafol, carpropamid, carbendazim, carboxin, carvone, quinoxyfen, quinofumelin, chinomethionat, captan, quinconazole, quintozene, guazatine, cufraneb, coumethoxystrobin, coumoxystrobin, kresoxim-methyl, clozylacon, chlozolinate, chlorothalonil, chloroneb, cyazofamid, diethofencarb, diclocymet, dichlofluanid, dichlobentiazox, diclomezine, dicloran, dichlorophen, dithianon, diniconazole, diniconazole-M, zineb, dinocap, dipymetitrone, diphenylamine, difenoconazole, cyflufenamid, diflumetorim, cyproconazole, cyprodinil, simeconazole, dimethirimol, dimethyl disulfide, dimethomorph, cymoxanil, dimoxystrobin, *Pseudomonas rhodesiae* HAI-0804, ziram, silthiofam, streptomycin, spiroxamine, sedaxane, zoxamide, solatenol, dazomet, *Talaromyces flavus*, tiadinil, thiabendazole, thiram, thiophanate, thiophanate-methyl, thifluzamide, thiram, tecnazene, tecloftalam, tetraconazole, debacarb, tebuconazole, tebufloquin, terbinafine, dodine, dodemorph, triadimenol, triadimefon, triazoxide, trichlamide, triclopyricarb, *Trichoderma atroviride*, tricyclazole, triticonazole, tridemorph, triflumizole, trifloxystrobin, triforine, tolylfluanid, tolclofos-methyl, tolnifanide, tolprocarb, nabam, natamycin, naftifine, nitrapyrin, nitrothal-isopropyl, nuarimol, copper nonyl phenol sulphonate, *Bacillus subtilis*)(strain: QST 713, validamycin, valifenalate, picarbutrazox, bixafen, picoxystrobin, pydiflumetofen, bitertanol, binapacryl, hinokitiol, biphenyl, piperalin, hymexazol, pyraoxystrobin, pyraclostrobin, pyraziflumid, pyrazophos, pyrapropoyne, pyrametostrobin, pyriofenone, pyrisoxazole, pyridachlometyl, pyrifenox, pyributicarb, pyribencarb, pyrimethanil, pyroquilon, vinclozolin, ferbam, famoxadone, phenazine oxide, fenamidone, fenaminstrobin, fenarimol, fenoxanil, ferimzone, fenpiclonil, fenpicoxamid, fenpyrazamine, fenbuconazole, fenfuram, fenpropidin, fenpropimorph, fenhexamid, folpet, phthalide, bupirimate, fuberidazole, blasticidin-S, furametpyr, furalaxyl, furancarboxylic acid, fluazinam, fluindapyr, fluoxastrobin, fluoxapiprolin, fluopicolide, fluopimomide, fluopyram, fluoroimide, fluxapyroxad, fluquinconazole, furconazole, furconazole-cis, fludioxonil, flusilazole, flusulfamide, flutianil, flutolanil, flutriafol, flufenoxystrobin, flumetover, flumorph, proquinazid, prochloraz, procymidone, prothiocarb, prothioconazole, bronopol, propamocarb-hydrochloride, propiconazole, propineb, probenazole, bromuconazole, flometoquin, florylpicoxamid, hexaconazole, benalaxyl, benalaxyl-M, benodanil, benomyl, pefurazoate, penconazole, pencycuron, benzovindiflupyr, benthiazole, benthiavalicarb-isopropyl, penthiopyrad, penflufen, boscalid, fosetyl (aluminium, calcium, sodium), polyoxin, polycarbamate, Bordeaux mixture, mancopper, mancozeb, mandipropamid, mandestrobin, maneb, myclobutanil, mineral oils, mildiomycin, methasulfocarb, metam, metalaxyl, metalaxyl-M, metiram, metyltetraprole, metconazole, metominostrobin, metrafenone, mepanipyrim, mefentrifluconazole, meptyldinocap, mepronil, iodocarb, laminarin, *Rhizobium vitis*, phosphorous acid and salts, copper oxychloride, silver, cuprous oxide, copper hydroxide, potassium bicarbonate, sodium bicarbonate, sulfur, oxyquinoline sulfate, copper sulfate, (3,4-dichloroisothiazole-5-yl)methyl 4-(tert-butyl)benzoic ester (Chemical name, CAS registry number: 1231214-23-5), BAF-045 (code number), BAG-010 (code number), UK-2A (code number), dodecylbenzenesulfonic acid bisethylenediamine copper [II] salt (DBEDC), MIF-1002 (code number), NF-180 (code number), triphenyltin acetate (TPTA), triphenyltin chloride (TPTC), triphenyltin hydroxide (TPTH), avirulent *Erwinia carotovora*.

Next, examples of known herbicides or plant growth regulator compounds that can be mixed or used in combination are shown below.

Herbicide active Ingredients:
ioxynil, aclonifen, acrolein, azafenidin, acifluorfen (including a salt with sodium or the like), azimsulfuron, asulam, acetochlor, atrazine, anilofos, amicarbazone, amidosulfuron, amitrole, aminocyclopyrachlor, aminopyralid, amiprofos-methyl, ametryn, alachlor, alloxydim, ancymidol, isouron, isoxachlortole, isoxaflutole, isoxaben, isodecylalkoholethoxylate, isoproturon, ipfencarbazone, imazaquin, imazapic (including a salt with amine or the like), imazapyr (including a salt of isopropylamine or the like), imazamethabenz-methyl, imazamox, imazethapyr, imazosulfuron, indaziflam, indanofan, eglinazine-ethyl, esprocarb, ethametsulfuron-methyl, ethalfluralin, ethidimuron, ethoxysulfuron, ethoxyfen-ethyl, ethofumesate, etobenzanid, endothal-disodium, oxadiazon, oxadiargyl, oxaziclomefone, oxasulfuron, oxyfluorfen, oryzalin, orthosulfamuron, orbencarb, oleic acid, cafenstrole, carfentrazone-ethyl, karbutilate, carbetamide, quizalofop, quizalofop-ethyl, quizalofop-P-ethyl, quizalofop-P-tefuryl, quinoclamine, quinclorac, quinmerac, cumyluron, clacyfos, glyphosate (including a salt of sodium, potassium, amine, propylamine, isopropylamine, dimethylamine, trimesium, or the like), glufosinate (including a salt of amine, sodium, or the like), glufosinate-P, glufosinate-P-sodium, clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorphthalim, chlorflurenol-methyl, chlorpropham, chlorbromuron, chloroxuron, chlorotoluron, ketospiradox (including a salt of sodium, calcium, ammonia, or the like), saflufenacil, sarmentine, cyanazine, cyanamide, diuron, diethatyl-ethyl, dicamba (including a salt of amine, diethylamine, isopropylamine, diglycolamine, sodium, lithium, or the like), cycloate, cycloxydim, diclosulam, cyclosulfamuron, cyclopyranil, cyclopyrimorate, dichlobenil, diclofop-P-methyl, diclofop-methyl, dichlorprop, dichlorprop-P, diquat, dithiopyr, siduron, dinitramine, cinidon-ethyl, cinosulfuron, dinoseb, dinoterb, cyhalofop-butyl, diphenamid, difenzoquat, diflufenican, diflufenzopyr, simazine, dimethachlor, dimethametryn, dimethenamid, dimethenamid-P, simetryn, dimepiperate, dimefuron, cinmethylin, swep, sulcotrione, sulfentrazone, sulfosate, sulfosulfuron, sulfometuron-methyl, sethoxydim, terbacil, daimuron, thaxtomin A, dalapon, thiazopyr, tiafenacil, thiencarbazone (including sodium salt, methyl ester, or the like), tiocarbazil, thiobencarb, thidiazimin, thidiazuron, thifensulfuron-methyl, desmedipham, desmetryne, tetflupyrolimet, thenylchlor, tebutam, tebuthiuron, tepraloxydim, tefuryltrione, terbuthylazine, terbutryn, terbumeton, tembotrione, topramezone, tralkoxydim, triaziflam, triasulfuron, triafamone, tri-allate, trietazine, triclopyr, triclopyr-butotyl, tritosulfuron, trifludimoxazin, triflusulfuron-methyl, trifluralin, trifloxysulfuron-sodium, tribenuron-methyl, tolpyralate, naptalam (including a salt with sodium or the like), naproanilide, napropamide, napropamide-M, nicosulfuron, neburon, norflurazon, vernolate, paraquat dichloride, halauxifen-benzyl, halauxifen-methyl, haloxyfop, haloxyfop-P, haloxyfop-etotyl, halosafen, halosulfuron-methyl, bixlozone, picloram, picolinafen, bicyclopyrone, bispyribac-sodium, pinoxaden, bifenox, piperophos, pyraclonil, pyrasulfotole, pyrazoxyfen, pyrazosulfuron-ethyl, pyrazolynate, bilanafos, pyraflufen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, phenisopham, fenuron, fenoxasulfone, fenoxaprop (including methyl, ethyl, isopropylester), fenoxaprop-P (including methyl, ethyl, isopropyl ester), fenquinotrione, fenthiaprop-ethyl, fentrazamide, phenmedipham, foramsulfuron, butachlor, butafenacil, butamifos, butylate, butenachlor, butralin, butroxydim, flazasulfuron, flamprop (including methyl, ethyl, isopropyl ester), flamprop-M (including methyl, ethyl, isopropyl ester), primisulfuron-methyl, fluazifop-butyl, fluazifop-P-butyl, fluazolate, fluometuron, fluoroglycofen-ethyl, flucarbazone-sodium, fluchloralin, flucetosulfuron, fluthiacet-methyl, flupyrsulfuron-methyl (including a salt of sodium, calcium, ammonia, or the like), flufenacet, flufenpyr-ethyl, flupropanate, flupoxame, flumioxazin, flumiclorac-pentyl, flumetsulam, fluridone, flurtamone, fluroxypyr (including an ester such as butomethyl or meptyl, a salt of sodium, calcium, ammonia, or the like), flurochloridone, pretilachlor, procarbazone-sodium, prodiamine, prosulfuron, prosulfocarb, propaquizafop, propachlor, propazine, propanil, propyzamide, propisochlor, propyrisulfuron, propham, profluazol, prohexadione-calcium, propoxycarbazone, propoxycarbazone-sodium, profoxydim, bromacil, brompyrazon, prometryn, prometon, bromoxynil (including an ester of butyric acid, octanoic acid, heptanoic acid, or the like), bromofenoxim, bromobutide, florasulam, florpyrauxifen, florpyrauxifen-benzyl, hexazinone, pethoxamid, benazolin, penoxsulam, heptamaloxyloglucan, beflubutamid, beflubutamid-M, pebulate, pelargonic acid, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, foramsulfuron, forchlorfenuron, mecoprop (including a salt of sodium, potassium, isopropylamine, triethanolamine, dimethylamine, or the like), mecoprop-P-potassium, mesosulfuron (including an ester of methyl or the like), mesotrione, metazachlor, metazosulfuron, methabenzthiazuron, metamitron, metamifop, metam, disodium methanearsonate (DSMA), methiozolin, methyldymuron, metoxuron, metosulam, metsulfuron-methyl, metobromuron, metobenzuron, metolachlor, metribuzin, mepiquat chloride, mefenacet, monosulfuron (including methyl, ethyl, isopropylester), monolinuron, molinate, iodosulfuron, iodosulfulon-methyl-sodium, iofensulfuron, iofensulfuron-sodium, lactofen, lancotrione, linuron, rimsulfuron, lenacil, 2,2,2-trichloroacetic acid (TCA) (including a salt of sodium, calcium, ammonia, or the like), 2,3,6-trichlorobenzoic acid (2,3,6-TBA), 2,4,5-trichlorophenoxyacetic acid (2,4,5-T), 2,4-dichlorophenoxyacetic acid (2,4-D) (including a salt of amine, diethylamine, triethanolamine, isopropylamine, sodium, lithium, or the like), 2-amino-3-chloro-1,4-naphthoquinone (ACN), 2-methyl-4-chlorophenoxyacetic acid (MCPA) (including a sodium salt, ethyl ester, or the like), 2-methyl-4-chlorophenoxyacetic acid (MCPB) (including a sodium salt, ethyl ester, or the like), 4-(2,4-dichlorophenoxy)butyric acid (2,4-DB), 4,6-dinitro-O-cresol (DNOC) (including a salt of amine, sodium, or the like), AE-F-150944 (code number), IR-6396 (code number), MCPA-thioethyl, SYP-298 (code number), SYP-300 (code number), S-ethyldipropylthiocarbamate (EPTC), S-metolachlor, S-9750 (code number), MSMA, HW-02 (code number).

Plant Growth Regulators:

1-naphthylacetamide, 1-methylcyclopropene, 2,6-diisopropylnaphthalene, 4-oxo-4-(2-phenylethyl)aminobutyric acid (Chemical name, CAS registry number: 1083-55-2), 4-chlorophenoxyacetic acid (4-CPA), n-decanol, aviglycine, ancymidol, abscisic acid, inabenfide, indole acetic acid, indole butyric acid, uniconazole, uniconazole-P, Ecolyst, ethychlozate, ethephon, epocholeone, oxine-sulfate, carvone, calcium formate, cloxyfonac, cloxyfonac-potassium, cloprop, chlormequat, choline, cytokinins, cyclanilide, dikegulac, gibberellin acid, dimethipin, sintofen, daminozide, thidiazuron, triacontanol, trinexapac-ethyl, paclobutrazol, paraffin, flumetralin, flurprimidol, flurenol, prohydrojasmon, prohexadione-calcium, heptamaloxyloglucan, benzylaminopurine, forchlorfenuron, maleic hydrazide, mepiquat chloride, mefluidide, calcium peroxide.

Next, examples of known phytotoxicity alleviating compounds that can be mixed or used in combination are shown below.

Isoxadifen, isoxadifen-ethyl, oxabetrinil, cloquintcetmexyl, dietholate, cyometrinil, dichlormid, dicyclonone, cyprosulfamide, 1,8-Naphthalic Anhydride, fenchlorazole-O-ethyl, fenclorim, furilazole, fluxofenim, flurazole, benoxacor, mephenate, mefenpyr, mefenpyr-ethyl, mefenpyr-diethyl, lower alkyl-substituted benzoic acid, 2,2-dichloro-N-(1,3-dioxane-2-ylmethyl)-N-(2-propenyl)acetamide (PPG-1292), 2-dichloromethyl-2-methyl-1,3-dioxane (MG-191), 3-dichloroacetyl-2,2,5-trimethyl-1,3-oxazolidine (R-29148), 4-dichloroacetyl-1-oxa-4-azaspiro[4.5]decane (AD-67), MON4660 (code number), metcamifen, N1,N2-diallyl-N2-dichloroacetyl glycineamide (DKA-24), TI-35 (code number).

The present pest control agent configured as described above exhibits excellent controlling effect on Orthoptera pests, Thysanoptera pests, Hemiptera pests, Coleoptera pests, Diptera pests, Lepidoptera pests, Hymenoptera pests, Collembola pests, Thysanura pests, Blattodea pests, Isoptera pests, Psocoptera pests, Mallophage pests, Anoplura pests, plant parasitic Acari, plant parasitic nematoda, plant parasitic mollusks, and other pests such as harmful animals, uncomfortable animals, sanitary insects, and parasites. As such pests, the following organism species can be exemplified.

Examples of the Orthopteran pests include *Ruspolia lineosa* or the like of Tettigoniidae, *Teleogryllus emma*, *Truljalia hibinonis*, or the like of Gryllidae, *Gryllotalpa orientalis* or the like of Gryllotalpidae, *Oxya hyla* intricate, *Locusta migratoria*, *Melanoplus sanguinipes*, *Melanoplus differentialis*, *Melanoplus femurrubrum*, or the like of Acrididae, *Atractomorpha lata* of Pyrgomorphidae, *Euscyrtus japonicus* of Eneopteridae, and *Xya japonicus* or the like of Tridactylidae.

Examples of the Thysanoptera pests include *Frankliniella intonsa*, *Frankliniella occidentalis*, *Scirtothrips dorsalis*, *Thrips palmi*, *Thrips tabaci*, *Thrips setosus*, *Heliothrips haemorrhoidalis*, *Stenchaetothrips biformis*, or the like of Thripidae, and *Ponticulothrips diospyrosi*, *Liothrips wasabiae*, *Haplothrips aculeatus*, or the like of Phlaeothripidaes.

Examples of the Hemipteran pests include *Mogannia minuta* or the like of Cicadidae, *Aphrophora intermedia* or the like of Aphrophoridae, *Machaerotypus sibiricus* or the like of Membracidae, *Arboridia apicalis*, *Empoasca onukii*, *Nephotettix cincticeps*, *Nephotettix malayanus*, *Nephotettix virescens*, *Nephotettix nigropictus*, *Recilia dorsalis*, Okura Leafhopper (*Amrasca biguttula*), Mango Leafhopper (*Idioscopus nitidulus*, *Idioscopus clypealis*, *Amritodus atkinsoni*), *Recilia dorsalis*, *Empoasca fabae*, or the like of Cicadellidae, *Pentastiridius apicalis* or the like of Cixiidae, *Laodelphax striatellus*, *Nilaparvata lugens*, *Sogatella furcifera*, or the like of Delphacidae, *Nisia nervosa* or the like of Meenoplidae, *Kamendaka saccharivora* or the like of Derbidae, *Achilus flammeus* or the like of Cixidia, *Orosanga japonicus* or the like of Ricaniidae, *Mimophantia maritima* or the like of Flatidae, *Cacopsylla pyrisuga*, *Diaphorina citri*, or the like of Psyllidae, *Calophya mangiferae* or the like of Calophyidae, *Daktulosphaira vitifoliae* or the like of Phylloxeridae, *Adelges laricis*, *Adelges tsugae*, or the like of Adelgidae, *Acyrthosiphon pisum*, *Aphis gossypii*, *Aphis spiraecola*, *Lipaphis erysimi*, *Brevicoryne brassicae*, *Myzuspersicae*, *Schizaphis graminum*, *Rhopalosiphum padi*, *Toxoptera aurautii*, *Aulacorthum solani*, *Macrosiphum euphorbiae*, *Nasonovia ribisnigri*, *Sitobion avenae*, *Aphis glycines*, or the like of Aphydidae, *Aleurocanthus camelliae*,

*Aleurocanthus spiniferus, Bemisia tabaci, Bemisia argentifolii, Trialeurodes vaporariorum*, or the like of Aleyrodidae, *Drosicha corpulenta, Icerya purchasi*, or the like of Margarodidae, *Dysmicoccus brevipes, Planococcus citri, Pseudococcus comstocki*, or the like of Pseudococcidae, *Ceroplastes ceriferus, Ceroplastes rubens*, or the like of Coccidae, *Aclerda takahashii* or the like of Aclerdidae, *Aonidiella aurantii, Diaspidiotus perniciosus, Pseudaulacaspis pentagoa, Unaspis yanonensis*, or the like of Diaspididae, *Lygus lineolaris, Trigonotylus caelestialium, Apolygus lucorum, Nesidiocoris tenuis, Halticus bractatus*, or the like of Miridae, *Stephanitis pyrioides, Stephanitis nashi*, or the like of Tingidae, *Eurydema rugosum, Eysarcoris lewisi, Eysarcoris aeneus, Lagynotomus elongatus, Nezara viridula, Plautia crossota, Nezara antennata, Eushistus heros*, or the like of Pentatomidae, *Megacopta cribraria* or the like of Plataspidae, *Urochela luteovoria* or the like of Urostylididae, *Cavelerius saccharivorus* or the like of Lygaeidae, *Malcus japonicus* or the like of Malcidae, *Dysdercus cingulatus* or the like of Pyrrhocoridae, *Leptocorisa acuta, Leptocorisa chinensis*, or the like of Alydidae, *Anacanthocoris striicornis* or the like of Coreidae, *Rhopalus maculatus* or the like of Rhopalidae, and *Cimex lectularis* or the like of Cimicidae.

Examples of the Coleoptera pests include *Anomara cuprea, Anomara rufocuprea, Popillia japonica, Oxycetonia jucunda, Anomala geniculata, Oryctes rhinoceros, Heptophylla picea*, or the like of Scarabaeidae, *Agriotes ogurae, Agriotes lineatus, Agriotes obscurus, Melanotus okinawensis, Melanotus fortnumi*, or the like of Elateridae, *Anthrenus verbasci* or the like of Dermestidae, *Heterobostrychus hamatipennis* or the like of Bostrychidae, *Stegobium paniceum* or the like of Anobiidae, *Pitinus clavipes* or the like of Ptinidae, *Tenebroides mauritanicus* or the like of Trogossitidae, *Necrobia rufipes* of Cleridae, *Carpophilus hemipterus, Meligethes aeneus*, or the like of Nitidulidae, *Ahasverus advena* or the like of Silvanidae, *Cryptolestes ferrugineus* or the like of Laemophloeidae, *Epilachna varivestis, Henosepilachna vigintioctopunctata* or the like of Coccinellidae, *Tenebrio molitor, Tribolium castaneum*, or the like of Tenebrionidae, *Epicauta gorhami* or the like of Meloidae, *Anoplophora glabripennis, Xylotrechus pyrrhoderus, Monochamus alternatus, Dectes texanus*, or the like of Cerambycidae, *Callosobruchus chinensis* or the like of Bruchidae, *Leptinotarsa decemlineata, Diabrotica virgifera virgifera, Diabrotica barberi, Diabrotica undecimpunctata howardi, Aulacophora femoralis, Phaedon brassicae, Cassida nebulosa, Oulema oryzae, Epilachna varivestis, Phyllotreta striolata, Demotina fasciculata, Psylliodes chrysocephala, Cerotoma trifurcate, Colaspis brunnea, Colaspis crinnicornis, Odontota horni, Chaetocnema pulicaria*, or the like of Chrysomelidae, *Cylas formicarius* or the like of Brentidae, *Hypera postica, Listroderes costirostris, Euscepes postfasciatus, Curculio sikkimensis*, or the like of Curculionidae, *Echinocnemus bipunctatus, Lissorhoptrus oryzophilus, Oryzophagus oryzae*, or the like of Erirhinidae, *Sitophilus zeamais, Sphenophrus venatus*, or the like of Dryophthoridae, *Tomicus piniperda* or the like of Scolytidae, *Crossotarsus niponicus* or the like of Platypodidae, and *Lyctus brunneus* or the like of Lyctidae.

Examples of the Diptera pests include *Tipula aino* or the like of Tipulidae, *Plecia nearctica* or the like of Bibionidae, *Exechia shiitakevora* or the like of Mycetophidae, *Pnyxiascabiei, Bradysia agrestis*, or the like of Sciaridae, *Asphondylia yushimai, Mayetiola destructor, Dasineura oxycoccana*, or the like of Cecidomyiidae, *Aedes aegypti, Culex pipiens pallens*, or the like of Culicidae, *Simulium takahashii* or the like of Simuliidae, *Chironomus oryzae* or the like of Chironomidae, *Chrysops suavis, Tabanus trigonus*, or the like of Tabanidae, *Eumerus strigatus* or the like of Syrphidae, *Bactrocera dorsalis, Euphranta japonica, Ceratitis capitata*, or the like of Tephritidae, *Liriomyza trifolii, Liriomyza sativae, Agromyza oryzae, Liriomyza bryoniae, Chromatomyia horticola, Liriomyza chinensis, Liriomyza trifolii*, or the like of Agromyzidae, *Meromyza nigriventris* or the like of Chloropidae, *Drosophila suzukii, Drosophila melanogaster*, or the like of Drosophilidae, *Hydrellia griseola* or the like of Ephydridae, *Hippobosca equina* or the like of Hippoboscidae, *Parallelpmma sasakawae* or the like of Scatophagidae, *Delia antiqua, Delia platura*, or the like of Anthomyiidae, *Fannia canicularis* or the like of Fanniidae, *Musca domestica, Stomoxys calcitrans* or the like of Muscidae, *Sarcophaga peregrina* or the like of Sarcophagidae, *Gasterophilus intestinalis* or the like of Gasterophilidae, *Hypoderma lineatum* or the like of Hypodermatidae, and *Oestrus ovis* or the like of Oestridae.

Examples of the Lepidoptera pests include *Endoclita excrescens* or the like of Hepialidae, *Antispila ampelopsia* or the like of Heliozelidae, *Zeuzera leuconotum, Cossus insularis*, or the like of Cossidae, *Archips fuscocupreanus, Adoxophyes orana fasciata, Grapholita molesta, Homona magnanima, Leguminivora glycinivorella, Cydia pomonella, Lobesia botrana*, or the like of Tortricidae, *Eupoecilia ambiguella* or the like of Cochylidae, *Bambalina* sp., *Eumeta minuscula*, or the like of Psychidae, *Nemapogon granella, Tinea translucens*, or the like of Tineidae, *Bucculatrix pyrivorella* or the like of Bucculatricidae, *Lyonetia clerkella, Lyonetiaprunifoliella malinella*, or the like of Lyonetiidae, *Caloptilia theivora, Phyllonorycter ringoniella*, or the like of Gracilariidae, *Phyllocnistis citrella* or the like of Phyllocnistidae, *Acrolepiopsis sapporensis* or the like of Acrolepiidae, *Plutella xylostella* of Plutellidae, *Yponomeuta orientalis*, or the like of Yponomeutidae, *Argyresthia conjugella* or the like of Argyresthidae, *Nokona regalis, Synanthedin hector* or the like of Sesidae, *Phthorimaea operculella, Sitotroga cerealella, Pectinophora gossypiella, Tuta absoluta*, or the like of Gelechiidae, *Carposina sasakii* or the like of Carposinidae, *Illiberis pruni* or the like of Zygaenidae, *Monema flavescens* or the like of Limacodidae, *Ancylolomia japonica, Chilo suppressalis, Cnaphalocrocis medinalis, Ostrinia furnacalis, Hellulla undalis, Conogethes punctiferlis, Diaphania indica, Parapediasia teterrella, Ostrinia nubilalis*, or the like of Crambidae, *Diatraea saccharalis, Cadra cautella, Galleria mellonella*, or the like of Pyralidae, *Nippoptilia vitis* or the like of Pterophoridae, *Papilio xuthus* or the like of Papilionidae, *Pieris rapae* or the like of Pieridae, *Parnara guttata* or the like of Hesperiidae, *Ascotis selenaria* or the like of Geometridae, *Dendrolimus spectabilis, Malacosoma neustrium testaceum*, or the like of Lasiocampidae, *Agrius convolvuli* or the like of Sphingidae, *Ama pseudoconspersa, Orygia recens approximans, Lymantria dispar*, or the like of Lymantriidae, *Hyphantria cunea* or the like of Arctiidae, and *Agrotis ipsilon, Agrotis segetum, Autographa nigrisigna, Helicoverpa armigera, Helicoverpa zea, Heliothis virescens, Spodoptera exigua, Spodoptera litura, Chrysodeix includens, Spodoptera frugiperda, Nephelodes minians*, or the like of Noctuidae.

Examples of the Hymenoptera pests include *Arge pagana* or the like of Argidae, *Apethymus kuri, Athalia rosae ruficomis*, or the like of Tenthredinidae, *Dryocosmus kuriphilus*, or the like of Cynipidae, *Vespa simillima xanthoptera* or the like of Vespidae, *Solenopsis invicta, Linepithema humile,* or the like of Formicidae, and *Megachile nipponica* or the like of Megachilidae.

Examples of the Collembola pests include *Bourletiellahortensis* or the like of Sminthuridae.

Examples of the Thysanura pests include *Lepisma saccharina, Ctenolepisma villosa,* or the like of Lepismatidae.

Examples of the Blattodea pests include *Periplaneta americana* of Blattidae, and *Blattella germanica* or the like of Blattellidae.

Examples of the Isoptera pests include *Incisitermes minor* or the like of Kalotermitidae, *Coptotermes formosanus* or the like of Rhinotermitidae, and *Odontotermes formosanus* or the like of Termitidae.

Examples of the Psocoptera pests include *Trogium pulsatorium* or the like of Trogiidae, and *Liposcelis corrodens* or the like of Liposcelididae.

Examples of the Dermaptera pests include *Labodura riparia* or the like of Labiduridae.

Examples of the Mallophaga pests include *Lipeurus caponis* or the like of Menoponidae, and *Damalinia bovis* or the like of Trichodectidae.

Examples of the Anoplura pests include *Haematopinus suis* or the like of Haematopinidae, *Pediculus humanus* or the like of Pediculine, *Linognathus setosus* or the like of Linognathidae, and *Pthirus pubis* or the like of Pthiridae Examples of the Acari pests include *Penthaleus major* or the like of Eupodidae, *Phytonemus pallidus, Polyphagotarsonemus latus,* or the like of Tarsonemidae, one species of *Siteroptes* sp. or the like of Pyemotidae, *Brevipalpus lewisi* or the like of Tenuipalpidae, *Tuckerella pavoniformis* or the like of Tuckerellidae, Eotetranychusboreus, *Panonychus citri, Panonychus ulmi, Tetranychus urticae, Tetranychus kanzawai,* or the like of Tetranychidae, *Trisetacus pini* or the like of Nalepellidae, *Aculops pelekassi, Epitrimerus pyri, Phyllocoptruta oleivora, Aculops lycopersici,* or the like of Eriophyidae, *Diptacus crenatae* or the like of Diptilomiopida, *Aleuroglyphus ovatus, Tyrophagus putrescentiae,* or *Rhizoglyphus robini* of Acaridae, *Varroa jacobsoni* or the like of Varroidae, *Dermanyssus gallinae* or the like of Dermanyssidae, *Ornithonyssus sylvialum* or the like of Macronyssidae, *Boophilus microplus, Rhipicephalus sanguineus, Haemaphysalis longicornis,* or the like of Ixodidae, and *Sarcoptes scabiei* or the like of Sarcoptidae.

Examples of the plant parasitic nematoda, include *Xiphinema index* or the like of Longidoridae, Paratrichodorus minor or the like of Trichodoridae, one species of Rhabditidae (*Rhabditella* sp.) or the like, one species of Tylenchidae (*Aglenchus* sp.) or the like, one species of Tylodoridae (*Cephalenchus* sp.) or the like, *Nothotylenchus acris, Ditylenchus destructor,* or the like of Anguinidae, *Rotylenchulus reniformis, Helicotylenchus dihystera,* or the like of Hoplolaimidae, *Paratylenchus curvitatus* or the like of Paratylenchidae, *Meloidogyne incognita, Meloidogyne hapla, Meloidogyne javanica, Meloidogyne arenaria, Melidogyne chitwoodi, Meloidogyne fallax* or the like of Meloidogynidae, *Globodera rostochiensis, Globodera pallida, Heterodera glycines* or the like of Heteroderidae, *Tylenchorhynchus claytoni* or the like of Telotylenchidae, one species of Psilenchidae (*Psilenchus* sp.) or the like, one species of Criconematidae (*Criconemoides* sp.) or the like, *Tylenchulus semipenetrans* or the like of Tylenchulidae, *Sphaeronema camelliae* or the like of Sphaeronematidae, *Sphaeronema camelliae, Radopholus citrophilus, Radopholus similis, Nacobbus aberrans, Pratylenchus penetrans, Pratylenchus coffeae, Platylechus zeae, Platylenchus brachyurus* or the like of Pratylenchidae, *Iotonchium ungulatum* or the like of Iotonchiidae, *Aphelenchus avenae* or the like of Aphelenchidae, *Aphelenchoides besseyi, Aphelenchoides fragariae,* or the like of Aphelenchoididae, and *Bursaphelenchus xylophilus* or the like ofPalasitaphelenchidae.

Examples of the plant parasitic mollusks include *Pomacea canaliculata* or the like of Pilidae, *Leavicaulis alte* or the like of Veronicellidae, *Achatina fulica* or the like of Achatinidae, *Meghimatium bilineatum* or the like of Philomycidae, Succinealauta or the like of Succineidae, *Discus pauper* or the like of Didcidae, *Zonitoides yessoensis* or the like of Zonitidae, *Limax flavus, Lehmannia valentiana, Deroceras reticulatum,* or the like of Limacidae, *Parakaliella harimensis* or the like of Helicarionidae, and *Acusta despecta sieboldiana, Bradybaena similaris,* or the like of Bradybaenidae.

Examples of pests such as harmful animals, uncomfortable animals, sanitary insects, livestock insects, and parasites include *Procambarus clarkii* or the like of Decapoda Astacidae, *Porcellio scaber* or the like of Isopoda Porcellionidae, Chilopoda pests such as Scutigeromorpha Sutigeridae, *Scolopendra subspinipes,* or the like, Diplopoda pests such as *Oxidus gracilis, Theridiidae hasseltii* or the like of Araneae *Latrodectus hasseltii, Chiracanthium japonicum,* or the like of Clubionidae, *Androctonus crassicauda* or the like of Scorpiones, roundworm endoparasites such as *Ascaris lumbricoides* or the like, *Syphacia* sp. or the like, and *Wuchereria bancrofti* or the like, and flatworm endoparasites such as Distomum sp., *Paragonimus westermanii, Metagonimus yokokawai, Schistosoma japonicum, Taenia solium, Taeniarhynchus saginatus, Echinococcus* sp., or *Diphyllobothrium latum.*

The present pest control agent exhibits a controlling effect also on the pests and the like exemplified above that have acquired the resistance to existing pest control agents. Furthermore, the present pest control agent can be applied to plants that have acquired characteristics such as pest tolerance, disease tolerance, herbicide tolerance, or the like by gene recombination, artificial mating, or the like.

The "plant provided with tolerance by a breeding method or a gene recombination technique" in the present invention includes plants provided with tolerance by new plant breeding techniques (NBTs) established by combining molecular biological techniques with existing mating techniques, as well as those provided with tolerance by classical mating, or by gene recombinant techniques. The new plant breeding techniques (NBTs) are described in the publication "Atarashii syokubutu ikusyu wo rikaishiyo" (Kokusai bunken sha, written by Ryo OSAWA, and Hiroshi EZURA), the review "Genome Editing Tools in Plants" (Genes 2017, 8, 399, written by Tapan Kumar Mohanta, Tufail Bashir, Abeer Hashem, Elsayed Fathi Abd Allah and Hanhong Bae), and so on.

Next, the production methods, formulation methods and applications of the present compound will be described in detail by way of Examples. However, the present invention is in no way restricted by these Examples. The melting point which is a physical property value of the present compound was determined by a MP-500V micro melting point measuring apparatus available from Yanaco. The refractive index was determined by using an Abbe refractometer available from ATAGO CO., LTD. $^1$H NMR spectrum was determined by using JNM-LA400 (400 MHz), JNM-LA300 (300 MHz) or JNM-ECS300 (300 MHz) available from JEOL Ltd. and tetramethylsilane (TMS) as the internal standard.

Methods for producing production intermediates of the present compound are also described.

EXAMPLES

Example 1

Production of 1-(pyridine-3-yl)-4-[2-(trifluoromethyl)phenyl]-1H-pyrazole-3-carboxamide (Present Compound Number: A-0044)

1) Ethyl 4-{[(nonafluorobutyl)sulfonyl]oxy}-1-(pyridine-3-yl)-1H-pyrazole-3-carboxylate (Present Compound Number: D-0008)

Ethyl 4-hydroxy-1-(pyridine-3-yl)-1H-pyrazole-3-carboxylate (15.0 g, 64.3 mmol) synthesized by the method described in Reference examples 1 and 2 of WO 2016/027790 A, triethylamine (13.0 g, 128.5 mmol), and nonafluorobutanesulfonic acid fluoride (27.2 g, 90.0 mmol) were sequentially added into dichloromethane (300 mL) under ice-cooling, and stirred overnight at room temperature. The reaction solution was poured into saturated brine, and extracted with dichloromethane. The obtained organic layer was dried over anhydrous magnesium sulfate, and then the solvent was distilled off under reduced pressure. The residue was washed with diisopropyl ether to give ethyl 4-{[(nonafluorobutyl)sulfonyl]oxy}-1-(pyridine-3-yl)-1H-pyrazole-3-carboxylate (29.0 g, yield: 88%).

Melting point: 103-104° C.

$^1$H-NMR data (400 MHz, CDCl$_3$/TMS δ (ppm)): 1.44 (3H, t), 4.50 (2H, q), 7.48 (1H, dd), 8.08 (1H, s), 8.15 (1H, dd), 8.70 (1H, d), 8.99 (1H, d)

2) Ethyl 1-(pyridine-3-yl)-4-(2-(trifluoromethyl)phenyl)-1H-pyrazole-3-carboxylate (Present Compound Number: C-0044)

Ethyl 4-{[(nonafluorobutyl)sulfonyl]oxy}-1-(pyridine-3-yl)-1H-pyrazole-3-carboxylate (4.0 g, 7.8 mmol), 2-(trifluoromethyl)phenylboronic acid (2.4 g, 12.6 mmol), sodium carbonate (2.7 g, 25.5 mmol), and tetrakis(triphenylphosphine) palladium (0.45 g, 0.39 mmol) were added to a mixed solvent of tetrahydrofuran (30 mL) and water (6 mL), and refluxed under heating for 5 hours in a nitrogen atmosphere. After end of the reaction, the reaction solution was poured into saturated brine, and extracted with ethyl acetate. The obtained organic layer was dried over anhydrous magnesium sulfate, and then the solvent was distilled off under reduced pressure. The residue was purified by silica gel column chromatography, to give ethyl 1-(pyridine-3-yl)-4-[2-(trifluoromethyl)phenyl]-1H-pyrazole-3-carboxylate (2.6 g, yield: 93%).

Melting point: 131-134° C.

$^1$H-NMR data (400 MHz, CDCl$_3$/TMS δ (ppm)): 1.13 (3H, t), 4.24 (2H, q), 7.30-7.70 (4H, m), 7.77 (1H, d), 7.98 (1H, s), 8.21 (1H, ddd), 8.65 (1H, dd), 9.04 (1H, d)

3) 1-(pyridine-3-yl)-4-[2-(trifluoromethyl)phenyl]-1H-pyrazole-3-carboxamide (Present Compound Number: A-0044)

Ethyl 1-(pyridine-3-yl)-4-[2-(trifluoromethyl)phenyl]-1H-pyrazole-3-carboxylate (2.5 g, 6.9 mmol) was dissolved in ethanol (30 mL), and sodium hydroxide (0.84 g, 21.0 mmol) and water (5.0 mL) were added at room temperature, and further, the resultant solution was heated to 40° C. with an oil bath and stirred for 1 hour. The solvent of the reaction solution was distilled off under reduced pressure, and 6 N hydrochloric acid was added to the residue, and the precipitated solid was filtered off, and dried to give crude 1-(pyridine-3-yl)-4-[2-(trifluoromethyl)phenyl]-1H-pyrazole-3-carboxylic acid. The obtained 1-(pyridine-3-yl)-4-[2-(trifluoromethyl)phenyl]-1H-pyrazole-3-carboxylic acid was dissolved in dichloromethane (50 mL), and oxalyl chloride (5.9 g, 46.5 mmol) and N,N-dimethylformamide (catalytic amount) were added, and allowed to react at room temperature for 1 hour. The solvent was distilled off under reduced pressure, and the residue was dissolved in tetrahydrofuran (10 mL). The solution was then added to a mixed solution of tetrahydrofuran (20 mL) and aqueous ammonia (content: 28%, 10 mL) at 0° C., and then stirred at room temperature for 1 hour. The solvent of the reaction solution was distilled off under reduced pressure. The residue was washed sequentially with water and 2-propanol, and the obtained crude product was recrystallized in chloroform to give 1-(pyridine-3-yl)-4-[2-(trifluoromethyl)phenyl]-1H-pyrazole-3-carboxamide (1.1 g, yield: 48%).

Melting point: 178-181° C.

$^1$H-NMR data (400 MHz, CDCl$_3$/TMS δ (ppm)): 5.34 (1H, brs), 6.79 (1H, brs), 7.44-7.61 (4H, m), 7.75 (1H, d), 7.96 (1H, s), 8.09 (1H, dd), 8.64 (1H, d), 9.04 (1H, d)

Example 2

Production of 4-(4-methylpyridine-3-yl)-1-(pyridine-3-yl)-1H-pyrazole-3-carboxamide (Present Compound Number: B-100)

1) Ethyl 4-(4-methylpyridine-3-yl)-1-(pyridine-3-yl)-1H-pyrazole-3-carboxylate (Present Compound Number: D-0108)

Ethyl 4-{[(nonafluorobutyl)sulfonyl]oxy}-1-(pyridine-3-yl)-1H-pyrazole-3-carboxylate (3.4 g, 6.6 mmol), 4-(methylpyridine-3-yl)boronic acid (1.0 g, 7.3 mmol), sodium carbonate (1.6 g, 15.1 mmol), and tetrakis(triphenylphosphine) palladium (0.38 g, 0.33 mmol) were added to a mixed solvent of 1,2-dimethoxyethane (30 mL) and water (6 mL), and refluxed under heating for 9 hours in a nitrogen atmosphere. After end of the reaction, the reaction solution was poured into saturated brine, and extracted with ethyl acetate. The obtained organic layer was dried over anhydrous magnesium sulfate, and then the solvent was distilled off under reduced pressure. The residue was purified by silica gel column chromatography, to give ethyl 4-(4-methylpyridine-3-yl)-1-(pyridine-3-yl)-1H-pyrazole-3-carboxylate (1.3 g, yield: 64%).

Melting point: 120-123° C.

$^1$H-NMR data (300 MHz, CDCl$_3$/TMS δ (ppm)): 1.20 (3H, t), 2.24 (3H, s), 4.28 (2H, q), 7.21 (1H, d), 7.47 (1H, dd), 7.96 (1H, s), 8.21 (1H, ddd), 8.41 (1H, s), 8.48 (1H, dd), 8.65 (1H, dd), 9.05 (1H, d)

2) 4-(4-methylpyridine-3-yl)-1-(pyridine-3-yl)-1H-pyrazole-3-carboxylic acid (Present Compound Number: F-0108)

Ethyl 4-(4-methylpyridine-3-yl)-1-(pyridine-3-yl)-1H-pyrazole-3-carboxylate (1.2 g, 3.9 mmol) was dissolved in ethanol (15 mL), and sodium hydroxide (0.47 g, 11.8 mmol) and water (3.0 mL) were added at room temperature, and stirred for 1 hour. The solvent of the reaction solution was distilled off under reduced pressure, and 6 N hydrochloric acid was added to the residue, and the precipitated solid was filtered off, and washed with water and hexane, and dried to give 4-(4-methylpyridine-3-yl)-1-(pyridine-3-yl)-1H-pyrazole-3-carboxylic acid (0.8 g, yield: 73%).
Melting point: 277-280° C.
$^1$H-NMR data (300 MHz, DMSO-$d_6$/TMS δ (ppm)): 2.05 (3H, s), 7.29 (1H, d), 7.58 (1H, dd), 8.30 (1H, dd), 8.34 (1H, s), 8.39 (1H, d), 8.59 (1H, d), 8.80 (1H, s), 9.15 (1H, d)

3) 4-(4-methylpyridine-3-yl)-1-(pyridine-3-yl)-1H-pyrazole-3-carboxamide (Present Compound Number: B-0100)

4-(4-methylpyridine-3-yl)-1-(pyridine-3-yl)-1H-pyrazole-3-carboxylic acid (0.20 g, 0.71 mmol) was dissolved in N,N-dimethylformamide (5.0 mL), and ammonium chloride (0.076 g, 1.4 mmol), 1-hydroxybenzotriazole (0.12 g, 0.89 mmol), 1-ethyl-3-(3-dimethylaminopropyl)carbodiimide hydrochloride (0.20 g, 1.0 mol), and triethylamine (0.15 g, 1.5 mmol) were added, and the mixture was allowed to react at room temperature for 2 hours. The reaction solution was poured into a saturated aqueous solution of sodium hydrogen carbonate, and the solid was filtered off, and washed sequentially with water and n-hexane, to give 4-(4-methylpyridine-3-yl)-1-(pyridine-3-yl)-1H-pyrazole-3-carboxamide (0.16 g, yield: 80%).
Melting point: 264-267° C.
$^1$H-NMR data (400 MHz, DMSO-$d_6$/TMS δ (ppm)): 2.22 (3H, s) 7.30 (1H, d), 7.43 (1H, brs), 7.62 (1H, dd), 7.87 (1H, brs), 8.37 (1H, s), 8.38-8.45 (2H, m), 8.61 (1H, d), 8.80 (1H, s), 9.28 (1H, d)

Example 3

Production of 4-(4-chloro-2-methoxyphenyl)-1-(pyridine-3-yl)-1H-pyrazole-3-carboxamide (Present Compound Number: A-0634)

1) Ethyl 4-(4-chloro-2-methoxyphenyl)-1-(pyridine-3-yl)-1H-pyrazole-3-carboxylate (Present Compound Number: C-0634)

Ethyl 4-{[(nonafluorobutyl)sulfonyl]oxy}-1-(pyridine-3-yl)-1H-pyrazole-3-carboxylate (0.42 g, 0.82 mmol), 4-chloro-2-methoxyphenylboronic acid (0.20 g, 1.1 mmol), sodium carbonate (0.19 g, 1.8 mmol), and tetrakis(triphenylphosphine) palladium (0.050 g, mmol) were added to a mixed solvent of tetrahydrofuran (5.0 mL) and water (0.50 mL), and refluxed under heating for 3 hours in a nitrogen atmosphere. After end of the reaction, the reaction solution was poured into saturated brine, and extracted with ethyl acetate. The obtained organic layer was dried over anhydrous magnesium sulfate, and then the solvent was distilled off under reduced pressure. The residue was purified by silica gel column chromatography, to give ethyl 4-(4-chloro-2-methoxyphenyl)-1-(pyridine-3-yl)-1H-pyrazole-3-carboxylate (0.25 g, yield: 86%).
Melting point: 133-134° C.
$^1$H-NMR data (300 MHz, CDCl$_3$/TMS δ (ppm)): 1.27 (3H, t), 3.78 (3H, s), 4.32 (2H, q), 6.94 (1H, d), 7.00 (1H, dd), 7.26 (1H, d), 7.44 (1H, dd), 7.99 (1H, s), 8.17 (1H, ddd), 8.61 (1H, dd), 9.02 (1H, d)

2) 4-(4-chloro-2-methoxyphenyl)-1-(pyridine-3-yl)-1H-pyrazole-3-carboxamide (Present Compound Number: A-0634)

Ethyl 4-(4-chloro-2-methoxyphenyl)-1-(pyridine-3-yl)-1H-pyrazole-3-carboxylate (0.15 g, 0.42 mmol) was dissolved in a 7 M ammonia solution in methanol (20 mL), and stirred at room temperature for 2 days. Further, a 7 M ammonia solution in methanol (30 mL) was added to the reaction solution, and stirred at room temperature for 3 days. The solvent of the reaction solution was distilled off under reduced pressure, and the residue was purified by silica gel column chromatography to give 4-(4-chloro-2-methoxyphenyl)-1-(pyridine-3-yl)-1H-pyrazole-3-carboxamide (0.12 g, yield: 87%).
Melting point: 192-194° C.
$^1$H-NMR data (300 MHz, CDCl$_3$/TMS δ (ppm)): 3.81 (3H, s), 5.44 (1H, brs), 6.77 (1H, brs), 6.94 (1H, d), 6.99 (1H, dd), 7.40 (1H, d), 7.42-7.48 (1H, m), 8.05 (1H, s), 8.05-8.11 (1H, m), 8.57-8.67 (1H, m), 8.98-9.09 (1H, m)

Example 4

Production of ethyl 4-iodo-1-(pyridine-3-yl)-1H-pyrazole-3-carboxylate (Present Compound Number: D-0003)

Ethyl 1-(pyridine-3-yl)-1H-pyrazole-3-carboxylate (0.92 g, 4.2 mmol) was dissolved in acetonitrile (10 mL), and iodine (1.1 g, 4.3 mmol) and ammonium hexanitratocerate (IV) (2.4 g, 4.3 mmol) were added, and refluxed under heating for 10 hours. After end of the reaction, a saturated aqueous solution of sodium thiosulfate was added to the reaction solution, and extracted with ethyl acetate. The obtained organic layer was dried over anhydrous magnesium sulfate, and then the solvent was distilled off under reduced pressure, and the residue was purified by silica gel column chromatography to give ethyl 4-iodo-1-(pyridine-3-yl)-1H-pyrazole-3-carboxylate (0.75 g, yield: 52%).
Melting point 128-130° C.
$^1$H-NMR data (300 MHz, CDCl$_3$/TMS δ (ppm)): 1.44 (3H, t), 4.47 (2H, q), 7.45 (1H, dd), 8.07 (1H, s), 8.10 (1H, ddd), 8.64 (1H, dd), 8.97 (1H, d)

Example 5

Production of 3-[3-carbamoyl-4-(2-methylphenyl)-1H-pyrazole-1-yl]pyridine-1-oxide (Present Compound Number: A-8862)

In chloroform (50 mL), 1-(pyridine-3-yl)-4-(2-methylphenyl)-1H-pyrazole-3-carboxamide (present compound number: A-0020; 0.30 g, 1.1 mmol) was dissolved, and m-chloroperbenzoic acid (content: 77%, 0.48 g, 2.1 mmol) was added, and refluxed under heating for 2 hours. After end of the reaction, the solvent was distilled off under reduced pressure, and the residue was purified by silica gel column chromatography to give 3-[3-carbamoyl-4-(2-methylphenyl)-1H-pyrazole-1-yl]pyridine-1-oxide (0.31 g, yield: 98%).
$^1$H-NMR data (400 MHz, CDCl$_3$/TMS δ (ppm)): 2.24 (3H, s), 5.39 (1H, brs), 6.63 (1H, brs), 7.23-7.34 (4H, m), 7.40 (1H, dd), 7.62 (1H, d), 7.84 (1H, s), 8.19 (1H, d), 8.81 (1H, s)

Example 6

Production of 4-(3-methylpyridine-2-yl)-1-(pyridine-3-yl)-1H-pyrazole-3-carboxamide (Present Compound Number: B-0027)

1) Ethyl 4-(3-methylpyridine-2-yl)-1-(pyridine-3-yl)-1H-pyrazole-3-carboxylate (Present Compound Number: D-0035)

Ethyl 4-{[(nonafluorobutyl)sulfonyl]oxy}-1-(pyridine-3-yl)-1H-pyrazole-3-carboxylate (3.1 g, 6.0 mmol), bis(pinacolato)diboron (2.3 g, 9.1 mmol), potassium acetate (1.8 g, 18.3 mmol), and [1,1'-bis(diphenylphosphino)ferrocene]palladium dichloride dichloromethane adduct (0.49 g, 0.60 mmol) were dissolved in N,N-dimethylformamide (60 mL), and heated to 90° C. and stirred for 4 hours in a nitrogen atmosphere by using an oil bath. After end of the reaction, the reaction solution was poured into saturated brine, and extracted with ethyl acetate. The obtained organic layer was dried over anhydrous magnesium sulfate, and then the solvent was distilled off under reduced pressure. Further, silica gel column chromatography was conducted to give crude (3-(ethoxycarbonyl)-1-(pyridine-3-yl)-1H-pyrazole-4-yl)boronic acid. The obtained (3-(ethoxycarbonyl)-1-(pyridine-3-yl)-1H-pyrazole-4-yl)boronic acid was dissolved in a mixed solvent of tetrahydrofuran (15 mL) and water (3 mL), and 2-bromo-3-methylpyridine (0.44 g, 2.6 mmol), sodium carbonate (0.53 g, 5.0 mmol), and tetrakis (triphenylphosphine)palladium (0.25 g, 0.22 mmol) were added, and refluxed under heating for 1 hour in a nitrogen atmosphere. After end of the reaction, the reaction solution was poured into saturated brine, and extracted with ethyl acetate. The obtained organic layer was dried over anhydrous magnesium sulfate, and then the solvent was distilled off under reduced pressure. The residue was purified by silica gel column chromatography, to give ethyl 4-(3-methylpyridine-2-yl)-1-(pyridine-3-yl)-1H-pyrazole-3-carboxylate (0.74 g, yield; 40%).

Melting point: 97-100° C.

$^1$H-NMR data (400 MHz, DMSO/TMS δ (ppm)): 0.86 (3H, t), 2.25 (3H, s), 4.19 (2H, q), 7.31 (1H, dd), 7.64 (1H, dd), 7.71 (1H, d), 8.30-8.39 (1H, m), 8.40 (1H, d), 8.64 (1H, d), 8.90 (1H, s), 9.19 (1H, d)

2) 4-(3-methylpyridine-2-yl)-1-(pyridine-3-yl)-1H-pyrazole-3-carboxamide (Present Compound Number: B-0027)

Ethyl 4-(3-methylpyridine-2-yl)-1-(pyridine-3-yl)-1H-pyrazole-3-carboxylate (0.69 g, 2.2 mmol) was dissolved in ethanol (15 mL), and sodium hydroxide (0.27 g, 6.8 mmol) and water (3.0 mL) were added at room temperature, and stirred for 2 hours. The solvent of the reaction solution was distilled off under reduced pressure, and the residue was dissolved in water, and 2N hydrochloric acid was added to adjust the pH to 4 to 7. Further, water was distilled off under reduced pressure to give crude 4-(3-methylpyridine-2-yl)-1-(pyridine-3-yl)-1H-pyrazole-3-carboxylic acid. The obtained 4-(3-methylpyridine-2-yl)-1-(pyridine-3-yl)-1H-pyrazole-3-carboxylic acid was dissolved in N,N-dimethylformamide (10 mL), and ammonium chloride (0.24 g, 4.5 mmol), 1-hydroxybenzotriazole (0.36 g, 2.7 mmol), 1-ethyl-3-(3-dimethylaminopropyl)carbodiimide hydrochloride (0.64 g, 3.3 mol) and triethylamine (1.1 g, 10.9 mmol) were added, and allowed to react at room temperature for 2 hours. The reaction solution was poured into a saturated aqueous solution of sodium hydrogen carbonate, and extracted with ethyl acetate. The obtained organic layer was dried over anhydrous magnesium sulfate, and then the solvent was distilled off under reduced pressure. Ethyl acetate and hexane were added to the residue, and the precipitated solid was washed with ethyl acetate and hexane, to give 4-(3-methylpyridine-2-yl)-1-(pyridine-3-yl)-1H-pyrazole-3-carboxamide (0.11 g, yield; 18%).

Melting point: 145-148° C.

$^1$H-NMR data (400 MHz, DMSO/TMS δ (ppm)): 2.22 (3H, s), 7.28 (1H, dd), 7.40 (1H, s), 7.60 (1H, dd), 7.67 (1H, d), 7.90 (1H, s), 8.35-8.43 (2H, m), 8.60 (1H, d), 8.80 (1H, s), 9.27 (1H, d)

Example 7

Production of ethyl 1-(pyridine-3-yl)-4-(2-methylphenyl)-1H-pyrazole-3-carbonyl carbamate (Present Compound Number: A-5414)

In oxalyl chloride (15 g, 118 mmol), 1-(pyridine-3-yl)-4-(2-methylphenyl)-1H-pyrazole-3-carboxamide (present compound number: A-0020; 0.50 g, 1.8 mmol) was dissolved, and the resultant solution was refluxed under heating for 10 minutes. Oxalyl chloride was distilled off under reduced pressure, and the residue was dissolved in ethanol (7.9 g, 171 mmol), and stirred at room temperature for 10 minutes. After end of the reaction, the reaction solution was poured into a saturated aqueous solution of sodium hydrogen carbonate, and extracted with ethyl acetate. The obtained organic layer was dried over anhydrous magnesium sulfate, and then the solvent was distilled off under reduced pressure. The residue was purified by silica gel column chromatography, to give ethyl 1-(pyridine-3-yl)-4-(2-methylphenyl)-1H-pyrazole-3-carbonyl carbamate (0.18 g, yield: 29%).

$^1$H-NMR data (300 MHz, CDCl$_3$/TMS δ (ppm)): 1.40 (3H, t), 2.22 (3H, s), 4.41 (2H, q), 7.13-7.37 (4H, m), 7.51 (1H, dd), 7.97 (1H, s), 8.14 (1H, dd), 8.68 (1H, d), 9.07 (1H, d), 10.75 (1H, s)

Example 8

Production of N-(2-methoxyacetyl)-1-(pyridine-3-yl)-4-(2-methylphenyl)-1H-pyrazole-3-carboxamide (Present Compound Number: A-4808)

In toluene (5 mL), 1-(pyridine-3-yl)-4-(2-methylphenyl)-1H-pyrazole-3-carboxamide (present compound number: A-0020; 0.20 g, 0.72 mmol) was dissolved, and 2-methoxyacetyl chloride (0.17 g, 1.6 mmol) was added and refluxed under heating for 2 hours. The reaction solution was poured into water and extraction with ethyl acetate was conducted. The obtained organic layer was dried over anhydrous magnesium sulfate, and then the solvent was distilled off under reduced pressure. The residue was purified by silica gel column chromatography, to give N-(2-methoxyacetyl)-1-(pyridine-3-yl)-4-(2-methylphenyl)-1H-pyrazole-3-carboxamide (0.080 g, yield: 32%).

$^1$H-NMR data (300 MHz, CDCl$_3$/TMS δ (ppm)): 2.24 (3H, s), 3.50 (3H, s), 4.42 (2H, s), 7.23-7.37 (4H, m), 7.52 (1H, dd), 8.00 (1H, s), 8.14 (1H, dd), 8.69 (1H, d), 9.06 (1H, d), 9.89 (1H, s)

Example 9

Production of 1-(pyridine-3-yl)-4-(2-methylphenyl)-1H-pyrazole-3-carbothioamide (Present Compound Number: A-8646)

In 1,4-dioxane (10 mL), 1-(pyridine-3-yl)-4-(2-methylphenyl)-1H-pyrazole-3-carboxamide (present compound number: A-0020; 0.70 g, 2.5 mmol) was dissolved, and Lawesson's reagent (1.2 g, 3.0 mmol) was added and stirred at 80° C. for 40 minutes. After end of the reaction, the solvent was distilled off under reduced pressure, and the residue was purified by silica gel column chromatography, to give 1-(pyridine-3-yl)-4-(2-methylphenyl)-1H-pyrazole-3-carbothioamide (0.66 g, yield: 89%).

$^1$H-NMR data (400 MHz, CDCl$_3$/TMS δ (ppm)): 2.24 (3H, s), 7.22-7.38 (5H, m), 7.47 (1H, dd), 7.90 (1H, s), 8.00 (1H, s), 8.12 (1H, dd), 8.64 (1H, d), 9.06 (1H, d)

Physical property values, including those in the above-described examples, of the present compound [I] synthesized in accordance with the above-described examples are shown in the following Table 315 to Table 323, and physical property values of the present compound [II] are similarly shown in the following Table 324 to Table 334. The compound numbers and the signs in Tables are as defined above.

TABLE 315

| compound | physical property value | |
|---|---|---|
| A-0001 | melting point (° C.) | 161-163 |
| A-0002 | melting point (° C.) | 183-185 |
| A-0003 | melting point (° C.) | 204-207 |
| A-0004 | melting point (° C.) | 203-206 |
| A-0005 | melting point (° C.) | 164-166 |
| A-0006 | melting point (° C.) | 169-172 |
| A-0007 | melting point (° C.) | 203-206 |
| A-0008 | melting point (° C.) | 171-174 |
| A-0014 | melting point (° C.) | 171-174 |
| A-0020 | melting point (° C.) | 181-184 |
| A-0021 | melting point (° C.) | 170-173 |
| A-0022 | melting point (° C.) | 177-179 |
| A-0023 | melting point (° C.) | 166-168 |
| A-0025 | melting point (° C.) | 170-173 |
| A-0029 | melting point (° C.) | 192-194 |
| A-0041 | melting point (° C.) | 188-190 |
| A-0044 | melting point (° C.) | 178-181 |
| A-0045 | melting point (° C.) | 179-181 |
| A-0046 | melting point (° C.) | 205-208 |
| A-0047 | melting point (° C.) | 202-205 |
| A-0059 | melting point (° C.) | 140-143 |
| A-0086 | melting point (° C.) | 145-147 |
| A-0101 | melting point (° C.) | 162-165 |
| A-0103 | melting point (° C.) | 205-208 |
| A-0119 | melting point (° C.) | 177-179 |
| A-0120 | melting point (° C.) | 123-126 |
| A-0121 | melting point (° C.) | 168-171 |
| A-0122 | melting point (° C.) | 205-207 |
| A-0123 | melting point (° C.) | 170-173 |
| A-0124 | melting point (° C.) | 190-193 |
| A-0125 | melting point (° C.) | 169-170 |
| A-0128 | melting point (° C.) | 190-193 |
| A-0134 | melting point (° C.) | 129-132 |
| A-0137 | melting point (° C.) | 147-149 |
| A-0143 | melting point (° C.) | 154-157 |
| A-0144 | melting point (° C.) | 160-162 |
| A-0145 | melting point (° C.) | 182-183 |
| A-0146 | melting point (° C.) | 163-166 |
| A-0147 | melting point (° C.) | 150-153 |
| A-0148 | melting point (° C.) | 190-192 |
| A-0152 | melting point (° C.) | 193-196 |

TABLE 316

| compound | physical property value | |
|---|---|---|
| A-0176 | melting point (° C.) | 126-128 |
| A-0177 | melting point (° C.) | 138-141 |
| A-0179 | melting point (° C.) | 127-130 |
| A-0183 | melting point (° C.) | 183-185 |
| A-0185 | melting point (° C.) | 201-202 |
| A-0186 | melting point (° C.) | 186-188 |
| A-0188 | melting point (° C.) | 204-206 |
| A-0189 | melting point (° C.) | 167-170 |
| A-0192 | melting point (° C.) | 250-253 |
| A-0198 | melting point (° C.) | 157-160 |
| A-0227 | melting point (° C.) | 200-202 |
| A-0239 | melting point (° C.) | 226-229 |

TABLE 316-continued

| compound | physical property value | |
|---|---|---|
| A-0242 | melting point (° C.) | 297-300 |
| A-0260 | melting point (° C.) | 155-157 |
| A-0263 | melting point (° C.) | 180-182 |
| A-0266 | melting point (° C.) | 147-150 |
| A-0269 | melting point (° C.) | 200-203 |
| A-0320 | melting point (° C.) | 196-199 |
| A-0329 | melting point (° C.) | 173-175 |
| A-0338 | melting point (° C.) | 185-188 |
| A-0340 | melting point (° C.) | 218-221 |
| A-0347 | melting point (° C.) | 190-193 |
| A-0512 | melting point (° C.) | 163-166 |
| A-0521 | melting point (° C.) | 245-248 |
| A-0524 | melting point (° C.) | 237-240 |
| A-0542 | melting point (° C.) | 243-245 |
| A-0548 | melting point (° C.) | 195-198 |
| A-0549 | melting point (° C.) | 263-266 |
| A-0550 | melting point (° C.) | 197-200 |
| A-0551 | melting point (° C.) | 239-242 |
| A-0553 | melting point (° C.) | 297-300 |
| A-0555 | melting point (° C.) | 202-205 |
| A-0557 | melting point (° C.) | 199-202 |
| A-0561 | melting point (° C.) | 239-242 |
| A-0563 | melting point (° C.) | 176-178 |
| A-0571 | melting point (° C.) | 170-173 |
| A-0573 | melting point (° C.) | 177-178 |
| A-0574 | melting point (° C.) | 170-173 |
| A-0577 | melting point (° C.) | 147-150 |
| A-0578 | melting point (° C.) | 195-198 |
| A-0582 | melting point (° C.) | 170-173 |

TABLE 317

| compound | physical property value | |
|---|---|---|
| A-0583 | melting point (° C.) | 186-188 |
| A-0587 | melting point (° C.) | 203-206 |
| A-0588 | melting point (° C.) | 213-216 |
| A-0591 | melting point (° C.) | 196-199 |
| A-0593 | melting point (° C.) | 127-130 |
| A-0594 | melting point (° C.) | 90-93 |
| A-0597 | melting point (° C.) | 170-173 |
| A-0598 | melting point (° C.) | 202-203 |
| A-0600 | melting point (° C.) | 214-216 |
| A-0603 | melting point (° C.) | 216-219 |
| A-0608 | melting point (° C.) | 167-170 |
| A-0609 | melting point (° C.) | 215-218 |
| A-0613 | melting point (° C.) | 167-170 |
| A-0614 | melting point (° C.) | 197-198 |
| A-0618 | melting point (° C.) | 195-198 |
| A-0624 | melting point (° C.) | 209-212 |
| A-0629 | melting point (° C.) | 203-206 |
| A-0633 | melting point (° C.) | 200-203 |
| A-0634 | melting point (° C.) | 192-194 |
| A-0636 | melting point (° C.) | 163-166 |
| A-0637 | melting point (° C.) | 179-182 |
| A-0638 | melting point (° C.) | 113-116 |
| A-0639 | melting point (° C.) | 220-223 |
| A-0644 | melting point (° C.) | 171-174 |
| A-0645 | melting point (° C.) | 194-196 |
| A-0649 | melting point (° C.) | 156-159 |
| A-0652 | melting point (° C.) | 175-178 |
| A-0653 | melting point (° C.) | 213-216 |
| A-0654 | melting point (° C.) | 145-148 |
| A-0655 | melting point (° C.) | 154-157 |
| A-0656 | melting point (° C.) | 144-147 |
| A-0659 | melting point (° C.) | 141-144 |
| A-0660 | melting point (° C.) | 210-213 |
| A-0663 | melting point (° C.) | 213-216 |
| A-0664 | melting point (° C.) | 143-146 |
| A-0665 | melting point (° C.) | 253-256 |
| A-0670 | melting point (° C.) | 192-195 |
| A-0671 | melting point (° C.) | 206-209 |

TABLE 317-continued

| compound | physical property value | |
|---|---|---|
| A-0688 | melting point (° C.) | 144-147 |
| A-0689 | melting point (° C.) | 161-163 |
| A-0691 | melting point (° C.) | 165-168 |

TABLE 318

| compound | physical property value | |
|---|---|---|
| A-0692 | melting point (° C.) | 150-153 |
| A-0693 | melting point (° C.) | 165-166 |
| A-0697 | melting point (° C.) | 160-163 |
| A-0701 | melting point (° C.) | 171-173 |
| A-0705 | melting point (° C.) | 156-159 |
| A-0709 | melting point (° C.) | 150-153 |
| A-0712 | melting point (° C.) | 173-175 |
| A-0713 | melting point (° C.) | 113-115 |
| A-0733 | melting point (° C.) | 183-186 |
| A-0875 | melting point (° C.) | 220-223 |
| A-0906 | melting point (° C.) | 177-180 |
| A-0907 | melting point (° C.) | 188-190 |
| A-0908 | melting point (° C.) | 194-197 |
| A-0909 | melting point (° C.) | 137-140 |
| A-0910 | melting point (° C.) | 186-189 |
| A-0911 | melting point (° C.) | 230-233 |
| A-0912 | melting point (° C.) | 196-198 |
| A-0913 | melting point (° C.) | 160-162 |
| A-1067 | melting point (° C.) | 225-227 |
| A-1076 | melting point (° C.) | 145-148 |
| A-1077 | melting point (° C.) | 198-201 |
| A-1097 | melting point (° C.) | 233-236 |
| A-1102 | melting point (° C.) | 256-258 |
| A-1117 | melting point (° C.) | 209-211 |
| A-1134 | melting point (° C.) | 205-208 |
| A-1136 | melting point (° C.) | 222-225 |
| A-1140 | melting point (° C.) | 180-183 |
| A-1141 | melting point (° C.) | 131-134 |
| A-1145 | melting point (° C.) | 155-157 |
| A-1146 | melting point (° C.) | 183-184 |
| A-1147 | melting point (° C.) | 193-196 |
| A-1148 | melting point (° C.) | 166-167 |
| A-1151 | melting point (° C.) | 206-208 |
| A-1152 | melting point (° C.) | 127-130 |
| A-1153 | melting point (° C.) | 173-175 |
| A-1154 | melting point (° C.) | 172-174 |
| A-1155 | melting point (° C.) | 133-136 |
| A-1156 | melting point (° C.) | 156-159 |
| A-1157 | melting point (° C.) | 171-174 |
| A-1158 | melting point (° C.) | 180-183 |
| A-1159 | melting point (° C.) | 169-171 |

TABLE 319

| compound | physical property value | |
|---|---|---|
| A-1160 | melting point (° C.) | 184-187 |
| A-1161 | melting point (° C.) | 140-143 |
| A-1162 | melting point (° C.) | 85-88 |
| A-1163 | melting point (° C.) | 167-170 |
| A-1164 | melting point (° C.) | 167-170 |
| A-1165 | melting point (° C.) | 200-203 |
| A-1166 | melting point (° C.) | 130-133 |
| A-1980 | melting point (° C.) | 90-93 |
| A-2182 | melting point (° C.) | 136-139 |
| A-2384 | refractive index ($n_D^{20}$) | 1.5741 |
| A-2586 | melting point (° C.) | 157-160 |
| A-2600 | melting point (° C.) | 139-141 |
| A-2788 | melting point (° C.) | 110-113 |
| A-2990 | melting point (° C.) | 157-160 |
| A-3192 | melting point (° C.) | 153-156 |
| A-3596 | melting point (° C.) | 90-93 |
| A-3798 | melting point (° C.) | 159-161 |
| A-3812 | melting point (° C.) | 103-106 |
| A-4000 | melting point (° C.) | 172-174 |

TABLE 319-continued

| compound | physical property value | |
|---|---|---|
| A-4202 | refractive index ($n_D^{20}$) | 1.5991 |
| A-4404 | melting point (° C.) | 140-143 |
| A-4606 | melting point (° C.) | 166-168 |
| A-5616 | melting point (° C.) | 97-100 |
| A-6020 | refractive index ($n_D^{20}$) | 1.6006 |
| A-6222 | melting point (° C.) | 132-134 |
| A-6424 | melting point (° C.) | 200-203 |
| A-6626 | melting point (° C.) | 217-219 |
| A-7030 | refractive index ($n_D^{20}$) | 1.5688 |
| A-7232 | melting point (° C.) | 204-206 |
| A-7434 | melting point (° C.) | 136-139 |
| A-7636 | melting point (° C.) | 117-120 |
| A-7838 | melting point (° C.) | 150-152 |
| A-8040 | melting point (° C.) | 129-132 |
| A-8242 | melting point (° C.) | 120-123 |
| A-8444 | melting point (° C.) | 75-78 |
| A-8646 | melting point (° C.) | 134-135 |
| A-8862 | melting point (° C.) | 147-150 |
| A-9435 | melting point (° C.) | 236-239 |
| A-9480 | melting point (° C.) | 176-179 |
| A-9993 | refractive index ($n_D^{20}$) | 1.6292 |
| A-9994 | melting point (° C.) | 72-75 |

TABLE 320

| compound | physical property value | |
|---|---|---|
| hydrochloride of A-0593 | melting point (° C.) | 147-150 |

TABLE 321

| compound | physical property value ($^1$H-NMR data, in CDCl$_3$ TMS δ(ppm)) | |
|---|---|---|
| A-0044 | 400 MHz | 5.34 (1H, brs), 6.79 (1H, brs), 7.44-7.61 (4H, m), 7.75 (1H, d), 7.96 (1H, s), 8.09 (1H, dd), 8.64 (1H, d), 9.04 (1H, d) |
| A-0182 | 300 MHz | 2.66 (3H, s), 5.42 (1H, s), 6.90 (1H, s), 7.34 (1H, dd), 7.45-7.57 (2H, m), 7.64 (1H, dt), 8.02 (1H, s), 8.04-8.12 (2H, m), 8.66 (1H, dd), 9.07 (1H, d) |
| A-0634 | 300 Mhz | 3.81 (3H, s), 5.44 (1H, brs), 6.77 (1H, brs), 6.94 (1H, d), 6.99 (1H, dd), 7.40 (1H, d), 7.42-7.48 (1H, m), 8.05 (1H, s), 8.05-8.11 (1H, m), 8.57-8.67 (1H, m), 8.98-9.09 (1H, m) |

TABLE 322

| compound | physical property value | |
|---|---|---|
| B-0001 | melting point (° C.) | 194-197 |
| B-0002 | melting point (° C.) | 193-196 |
| B-0003 | melting point (° C.) | 210-213 |
| B-0004 | melting point (° C.) | 214-217 |
| B-0009 | melting point (° C.) | 175-178 |
| B-0018 | melting point (° C.) | 245-248 |
| B-0027 | melting point (° C.) | 145-148 |
| B-0090 | melting point (° C.) | 254-257 |
| B-0091 | melting point (° C.) | 262-264 |
| B-0095 | melting point (° C.) | 241-243 |
| B-0099 | melting point (° C.) | 188-191 |
| B-0100 | melting point (° C.) | 264-267 |
| B-0107 | melting point (° C.) | 235-237 |
| B-0165 | melting point (° C.) | 217-220 |
| B-0199 | melting point (° C.) | 244-247 |
| B-0205 | melting point (° C.) | 224-227 |
| B-0287 | melting point (° C.) | 178-180 |
| B-0290 | melting point (° C.) | 137-140 |
| B-0293 | melting point (° C.) | 185-188 |
| B-0296 | melting point (° C.) | 140-143 |
| B-0301 | melting point (° C.) | 166-168 |
| B-0367 | melting point (° C.) | 233-236 |

TABLE 322-continued

| compound | physical property | value |
|---|---|---|
| B-0389 | melting point (° C.) | 242-245 |
| B-0453 | melting point (° C.) | 201-204 |
| B-0454 | melting point (° C.) | 180-183 |
| B-0455 | melting point (° C.) | 167-170 |
| B-0456 | melting point (° C.) | 197-200 |
| B-0457 | melting point (° C.) | 230-233 |
| B-0458 | melting point (° C.) | 270-273 |
| B-0459 | melting point (° C.) | 253-255 |

TABLE 323

| compound | physical property value ($^1$H-NMR data, in DMSO-d6 TMS δ(ppm)) |
|---|---|
| B-0100 | 400 MHz 2.22 (3H, s), 7.30 (1H, d), 7.43 (1H, brs), 7.62 (1H, dd), 7.87 (1H, brs), 8.37 (1H, s), 8.38-8.45 (2H, m), 8.61 (1H, d), 8.80 (1H, s), 9.28 (1H, d) |

TABLE 324

| compound | physical property | value |
|---|---|---|
| C-0001 | melting point (° C.) | 57-59 |
| C-0003 | melting point (° C.) | 110-112 |
| C-0004 | melting point (° C.) | 134-136 |
| C-0005 | melting point (° C.) | 113-115 |
| C-0006 | melting point (° C.) | 101-103 |
| C-0007 | melting point (° C.) | 114-116 |
| C-0008 | melting point (° C.) | 131-133 |
| C-0020 | refractive index ($n_D^{20}$) | 1.6018 |
| C-0021 | refractive index ($n_D^{20}$) | 1.6099 |
| C-0022 | melting point (° C.) | 113-116 |
| C-0023 | melting point (° C.) | 108-110 |
| C-0025 | refractive index ($n_D^{20}$) | 1.6062 |
| C-0029 | melting point (° C.) | 92-95 |
| C-0041 | melting point (° C.) | 119-122 |
| C-0044 | melting point (° C.) | 131-134 |
| C-0045 | melting point (° C.) | 100-101 |
| C-0046 | melting point (° C.) | 124-126 |
| C-0047 | melting point (° C.) | 108-109 |
| C-0086 | melting point (° C.) | 90-93 |
| C-0119 | refractive index ($n_D^{20}$) | 1.5782 |
| C-0120 | melting point (° C.) | 110-112 |
| C-0121 | melting point (° C.) | 97-100 |
| C-0122 | refractive index ($n_D^{20}$) | 1.5981 |
| C-0124 | melting point (° C.) | 87-90 |
| C-0125 | refractive index ($n_D^{20}$) | 1.5982 |
| C-0128 | refractive index ($n_D^{20}$) | 1.5890 |
| C-0134 | refractive index ($n_D^{20}$) | 1.5873 |
| C-0137 | refractive index ($n_D^{20}$) | 1.5901 |
| C-0143 | melting point (° C.) | 78-80 |
| C-0144 | melting point (° C.) | 62-63 |
| C-0145 | melting point (° C.) | 92-94 |
| C-0147 | melting point (° C.) | 93-94 |
| C-0152 | refractive index ($n_D^{20}$) | 1.5951 |
| C-0176 | melting point (° C.) | 87-89 |
| C-0179 | melting point (° C.) | 88-89 |
| C-0182 | melting point (° C.) | 160-163 |
| C-0183 | melting point (° C.) | 137-139 |
| C-0186 | melting point (° C.) | 190-193 |
| C-0198 | melting point (° C.) | 111-112 |
| C-0227 | melting point (° C.) | 105-108 |
| C-0239 | melting point (° C.) | 110-113 |

TABLE 325

| compound | physical property | value |
|---|---|---|
| C-0263 | refractive index ($n_D^{20}$) | 1.5818 |
| C-0266 | refractive index ($n_D^{20}$) | 1.5869 |
| C-0269 | melting point (° C.) | 87-90 |

TABLE 325-continued

| compound | physical property | value |
|---|---|---|
| C-0320 | melting point (° C.) | 90-92 |
| C-0329 | melting point (° C.) | 96-98 |
| C-0338 | melting point (° C.) | 117-119 |
| C-0340 | melting point (° C.) | 113-116 |
| C-0512 | refractive index ($n_D^{20}$) | 1.6076 |
| C-0518 | melting point (° C.) | 134-136 |
| C-0520 | melting point (° C.) | 140-143 |
| C-0549 | melting point (° C.) | 191-194 |
| C-0550 | melting point (° C.) | 170-173 |
| C-0553 | melting point (° C.) | 144-147 |
| C-0555 | melting point (° C.) | 103-104 |
| C-0557 | melting point (° C.) | 99-100 |
| C-0561 | melting point (° C.) | 96-98 |
| C-0563 | melting point (° C.) | 97-100 |
| C-0571 | melting point (° C.) | 109-111 |
| C-0573 | melting point (° C.) | 95-97 |
| C-0574 | melting point (° C.) | 46-49 |
| C-0577 | melting point (° C.) | 116-118 |
| C-0578 | melting point (° C.) | 116-118 |
| C-0587 | melting point (° C.) | 153-155 |
| C-0588 | melting point (° C.) | 127-129 |
| C-0591 | melting point (° C.) | 150-153 |
| C-0593 | melting point (° C.) | 118-120 |
| C-0594 | refractive index ($n_D^{20}$) | 1.5904 |
| C-0597 | melting point (° C.) | 142-144 |
| C-0598 | melting point (° C.) | 92-93 |
| C-0600 | melting point (° C.) | 123-126 |
| C-0608 | refractive index ($n_D^{20}$) | 1.5777 |
| C-0613 | melting point (° C.) | 111-113 |
| C-0614 | refractive index ($n_D^{20}$) | 1.6008 |
| C-0624 | melting point (° C.) | 93-96 |
| C-0629 | refractive index ($n_D^{20}$) | 1.5092 |
| C-0633 | melting point (° C.) | 151-154 |
| C-0634 | melting point (° C.) | 133-134 |
| C-0636 | melting point (° C.) | 89-91 |
| C-0637 | melting point (° C.) | 75-77 |
| C-0638 | refractive index ($n_D^{20}$) | 1.6013 |
| C-0639 | refractive index ($n_D^{20}$) | 1.5971 |

TABLE 326

| compound | physical property | value |
|---|---|---|
| C-0644 | melting point (° C.) | 137-140 |
| C-0652 | melting point (° C.) | 87-90 |
| C-0653 | refractive index ($n_D^{20}$) | 1.6039 |
| C-0655 | refractive index ($n_D^{20}$) | 1.5994 |
| C-0656 | melting point (° C.) | 85-88 |
| C-0659 | melting point (° C.) | 124-127 |
| C-0660 | melting point (° C.) | 110-113 |
| C-0663 | refractive index ($n_D^{20}$) | 1.6038 |
| C-0664 | refractive index ($n_D^{20}$) | 1.6066 |
| C-0670 | refractive index ($n_D^{20}$) | 1.5635 |
| C-0692 | refractive index ($n_D^{20}$) | 1.5928 |
| C-0697 | refractive index ($n_D^{20}$) | 1.5911 |
| C-0705 | refractive index ($n_D^{20}$) | 1.5889 |
| C-0712 | melting point (° C.) | 131-133 |
| C-0906 | melting point (° C.) | 92-94 |
| C-0907 | refractive index ($n_D^{20}$) | 1.5875 |
| C-0908 | melting point (° C.) | 92-95 |
| C-0910 | refractive index ($n_D^{20}$) | 1.5816 |
| C-0911 | refractive index ($n_D^{20}$) | 1.5919 |
| C-0912 | refractive index ($n_D^{20}$) | 1.5881 |
| C-1067 | melting point (° C.) | 146-148 |
| C-1097 | melting point (° C.) | 173-175 |
| C-1102 | melting point (° C.) | 93-96 |
| C-1117 | melting point (° C.) | 119-120 |
| C-1136 | melting point (° C.) | 120-123 |
| C-1140 | refractive index ($n_D^{20}$) | 1.5821 |
| C-1141 | melting point (° C.) | 95-97 |
| C-1145 | melting point (° C.) | 80-83 |
| C-1148 | melting point (° C.) | 98-100 |
| C-1152 | melting point (° C.) | 150-153 |
| C-1155 | melting point (° C.) | 130-133 |
| C-1156 | melting point (° C.) | 145-148 |

TABLE 326-continued

| compound | physical property value | |
|---|---|---|
| C-1162 | melting point (° C.) | 92-95 |
| C-1163 | refractive index ($n_D^{20}$) | 1.5996 |
| C-1165 | melting point (° C.) | 84-87 |

TABLE 327

| compound | physical property value | |
|---|---|---|
| D-0002 | melting point (° C.) | 207-210 |
| D-0003 | melting point (° C.) | 128-130 |
| D-0004 | melting point (° C.) | 114-117 |
| D-0005 | melting point (° C.) | 96-98 |
| D-0008 | melting point (° C.) | 103-104 |
| D-0012 | melting point (° C.) | 109-111 |
| D-0035 | melting point (° C.) | 97-100 |
| D-0098 | melting point (° C.) | 156-159 |
| D-0099 | melting point (° C.) | 163-166 |
| D-0103 | melting point (° C.) | 126-129 |
| D-0107 | melting point (° C.) | 95-98 |
| D-0108 | melting point (° C.) | 120-123 |
| D-0115 | melting point (° C.) | 87-90 |
| D-0207 | melting point (° C.) | 145-148 |
| D-0213 | melting point (° C.) | 123-126 |
| D-0295 | melting point (° C.) | 100-102 |
| D-0301 | melting point (° C.) | 97-100 |
| D-0309 | melting point (° C.) | 96-98 |
| D-0375 | melting point (° C.) | 182-185 |
| D-0464 | melting point (° C.) | 120-123 |
| D-0466 | melting point (° C.) | 146-149 |

TABLE 328

| compound | physical property value | |
|---|---|---|
| E-0002 | melting point (° C.) | 190-193 |
| E-0003 | melting point (° C.) | 235-237 |
| E-0004 | melting point (° C.) | 220-223 |
| E-0005 | melting point (° C.) | 204-207 |
| E-0006 | melting point (° C.) | 224-227 |
| E-0007 | melting point (° C.) | 228-231 |
| E-0008 | melting point (° C.) | 225-227 |
| E-0020 | melting point (° C.) | 200-203 |
| E-0021 | melting point (° C.) | 153-156 |
| E-0022 | melting point (° C.) | 235-238 |
| E-0023 | melting point (° C.) | 200-203 |
| E-0025 | melting point (° C.) | 243-246 |
| E-0029 | melting point (° C.) | 182-185 |
| E-0041 | melting point (° C.) | 219-222 |
| E-0044 | melting point (° C.) | 193-196 |
| E-0046 | melting point (° C.) | 237-240 |
| E-0047 | melting point (° C.) | 220-223 |
| E-0086 | melting point (° C.) | 195-198 |
| E-0119 | melting point (° C.) | 171-174 |
| E-0120 | melting point (° C.) | 185-188 |
| E-0121 | melting point (° C.) | 242-245 |
| E-0122 | melting point (° C.) | 219-222 |
| E-0123 | melting point (° C.) | 172-175 |
| E-0124 | melting point (° C.) | 263-263 |
| E-0125 | melting point (° C.) | 222-225 |
| E-0128 | melting point (° C.) | 217-220 |
| E-0134 | melting point (° C.) | 203-206 |
| E-0137 | melting point (° C.) | 210-213 |
| E-0147 | melting point (° C.) | 210-212 |
| E-0148 | melting point (° C.) | 223-226 |
| E-0152 | melting point (° C.) | 233-236 |
| E-0176 | melting point (° C.) | 211-214 |
| E-0177 | melting point (° C.) | 176-178 |
| E-0179 | melting point (° C.) | 211-214 |
| E-0227 | melting point (° C.) | 225-228 |
| E-0263 | melting point (° C.) | 212-214 |
| E-0266 | melting point (° C.) | 202-205 |
| E-0269 | melting point (° C.) | 183-186 |
| E-0320 | melting point (° C.) | 221-224 |

TABLE 328-continued

| compound | physical property value | |
|---|---|---|
| E-0329 | melting point (° C.) | 183-186 |
| E-0338 | melting point (° C.) | 240-243 |

TABLE 329

| compound | physical property value | |
|---|---|---|
| E-0340 | melting point (° C.) | 223-226 |
| E-0518 | melting point (° C.) | 260-263 |
| E-0520 | melting point (° C.) | 247-250 |
| E-0521 | melting point (° C.) | 155-158 |
| E-0542 | melting point (° C.) | 203-206 |
| E-0549 | melting point (° C.) | 204-207 |
| E-0553 | melting point (° C.) | 275-277 |
| E-0555 | melting point (° C.) | 239-241 |
| E-0557 | melting point (° C.) | 221-224 |
| E-0561 | melting point (° C.) | 238-240 |
| E-0563 | melting point (° C.) | 200-203 |
| E-0571 | melting point (° C.) | 246-248 |
| E-0573 | melting point (° C.) | 234-236 |
| E-0574 | melting point (° C.) | 197-200 |
| E-0577 | melting point (° C.) | 240-241 |
| E-0578 | melting point (° C.) | 199-201 |
| E-0587 | melting point (° C.) | 231-234 |
| E-0588 | melting point (° C.) | 245-248 |
| E-0591 | melting point (° C.) | 217-220 |
| E-0593 | melting point (° C.) | 224-226 |
| E-0594 | melting point (° C.) | 223-225 |
| E-0597 | melting point (° C.) | 239-241 |
| E-0598 | melting point (° C.) | 248-250 |
| E-0600 | melting point (° C.) | 219-221 |
| E-0608 | melting point (° C.) | 247-250 |
| E-0609 | melting point (° C.) | 217-220 |
| E-0613 | melting point (° C.) | 251-254 |
| E-0614 | melting point (° C.) | 236-239 |
| E-0618 | melting point (° C.) | 250-253 |
| E-0624 | melting point (° C.) | 234-237 |
| E-0629 | melting point (° C.) | 197-200 |
| E-0633 | melting point (° C.) | 235-238 |
| E-0636 | melting point (° C.) | 199-201 |
| E-0638 | melting point (° C.) | 232-234 |
| E-0639 | melting point (° C.) | 220-223 |
| E-0644 | melting point (° C.) | 197-200 |
| E-0652 | melting point (° C.) | 227-230 |
| E-0653 | melting point (° C.) | 221-224 |
| E-0655 | melting point (° C.) | 221-224 |
| E-0656 | melting point (° C.) | 264-267 |
| E-0659 | melting point (° C.) | 233-236 |

TABLE 330

| compound | physical property value | |
|---|---|---|
| E-0660 | melting point (° C.) | 208-211 |
| E-0663 | melting point (° C.) | 240-243 |
| E-0664 | melting point (° C.) | 237-240 |
| E-0665 | melting point (° C.) | 267-270 |
| E-0670 | melting point (° C.) | 220-223 |
| E-0688 | melting point (° C.) | 203-206 |
| E-0689 | melting point (° C.) | 228-231 |
| E-0691 | melting point (° C.) | 211-213 |
| E-0692 | melting point (° C.) | 230-233 |
| E-0693 | melting point (° C.) | 219-222 |
| E-0697 | melting point (° C.) | 192-195 |
| E-0701 | melting point (° C.) | 180-183 |
| E-0705 | melting point (° C.) | 251-253 |
| E-0712 | melting point (° C.) | 257-260 |
| E-0733 | melting point (° C.) | 210-213 |
| E-0906 | melting point (° C.) | 203-205 |
| E-0907 | melting point (° C.) | 215-218 |
| E-0908 | melting point (° C.) | 226-229 |
| E-0910 | melting point (° C.) | 190-193 |
| E-0911 | melting point (° C.) | 223-226 |

TABLE 330-continued

| compound | physical property value | |
|---|---|---|
| E-0912 | melting point (° C.) | 198-201 |
| E-0913 | melting point (° C.) | 155-157 |
| E-1067 | melting point (° C.) | 240-243 |
| E-1076 | melting point (° C.) | 264-267 |
| E-1077 | melting point (° C.) | 253-256 |
| E-1102 | melting point (° C.) | 260-263 |
| E-1117 | melting point (° C.) | 233-236 |
| E-1136 | melting point (° C.) | 246-248 |
| E-1140 | melting point (° C.) | 237-240 |
| E-1148 | melting point (° C.) | 198-200 |
| E-1152 | melting point (° C.) | 233-236 |
| E-1153 | melting point (° C.) | 217-220 |
| E-1155 | melting point (° C.) | 241-244 |
| E-1156 | melting point (° C.) | 232-235 |
| E-1160 | melting point (° C.) | 165-168 |
| E-1163 | melting point (° C.) | 240-243 |
| E-1165 | melting point (° C.) | 165-168 |

TABLE 331

| compound | physical property value | |
|---|---|---|
| F-0003 | melting point (° C.) | 261-264 |
| F-0008 | melting point (° C.) | 237-240 |
| F-0012 | melting point (° C.) | 240-243 |
| F-0017 | melting point (° C.) | 243-246 |
| F-0099 | melting point (° C.) | 292-295 |
| F-0108 | melting point (° C.) | 277-280 |
| F-0115 | melting point (° C.) | 213-216 |
| F-0207 | melting point (° C.) | 260-263 |
| F-0213 | melting point (° C.) | 264-267 |
| F-0295 | melting point (° C.) | 245-248 |
| F-0301 | melting point (° C.) | 201-204 |
| F-0309 | melting point (° C.) | 172-174 |
| F-0375 | melting point (° C.) | 267-270 |
| F-0461 | melting point (° C.) | 242-245 |
| F-0462 | melting point (° C.) | 200-202 |
| F-0463 | melting point (° C.) | 263-266 |
| F-0464 | melting point (° C.) | 294-297 |
| F-0466 | melting point (° C.) | 227-230 |

TABLE 332

| compound | physical property value ($^1$H-NMR data, in CDCl$_3$ TMS δ(ppm)) | |
|---|---|---|
| C-0002 | 300 MHz | 1.29 (3H, t), 4.37 (2H, q), 7.11-7.29 (2H, m), 7.32-7.51 (3H, m), 8.08 (1H, s), 8.20 (1H, ddd), 8.65 (1H, dd), 9.04 (1H, d) |
| C-0044 | 400 MHz | 1.13 (3H, t), 4.24 (2H, q), 7.30-7.70 (4H, m), 7.77 (1H, d), 7.98 (1H, s), 8.21 (1H, ddd), 8.65 (1H, dd), 9.04 (1H, d) |
| C-0123 | 300 MHz | 1.33 (3H, t), 1.43 (3H, t), 4.38 (2H, q), 4.70 (2H, q), 6.86-6.92 (1H, m), 7.03-7.09 (2H, m), 7.28 (1H, dd), 7.44 (1H, dd), 8.00 (1H, s), 8.16 (1H, dd), 8.62 (1H, d), 9.03 (1H, d) |
| C-0177 | 400 MHz | 1.32 (3H, t), 2.52 (3H, s), 4.39 (2H, q), 7.24-7.37 (3H, m), 7.41 (1H, s), 7.42-7.50 (1H, m), 8.04 (1H, s), 8.16-8.21 (1H, m), 8.63 (1H, d), 9.08 (1H, s) |
| C-0185 | 400 MHz | 1.22 (3H, t), 2.62 (3H, s), 4.28 (2H, q), 7.42 (1H, d), 7.47 (1H, dd), 7.59-7.70 (2H, m), 8.14-8.26 (3H, m), 8.67 (1H, d), 9.09 (1H, d) |
| C-0189 | 400 MHz | 1.32 (3H, t), 4.38 (2H, q), 7.26-7.35 (1H, m), 7.41-7.62 (3H, m), 7.67 (1H, d), 8.04 (1H, s), 8.20 (1H, dd), 8.65 (1H, d), 9.05 (1H, d) |
| C-0634 | 300 MHz | 1.27 (3H, t), 3.78 (3H, s), 4.32 (2H, q), 6.94 (1H, d), 7.00 (1H, dd), 7.26 (1H, d), 7.44 (1H, dd), 7.99 (1H, s), 8.17 (1H, ddd), 8.61 (1H, d), 9.02 (1H, d) |
| C-0665 | 300 MHz | 1.21 (3H, t), 3.76 (6H, s), 4.29 (2H, q), 6.62 (2H, d), 7.30 (1H, d), 7.43 (1H, dd), 8.03 (1H, s), 8.18 (1H, dd), 8.80 (1H, d), 9.19 (1H, d) |

TABLE 332-continued

| compound | physical property value ($^1$H-NMR data, in CDCl$_3$ TMS δ(ppm)) | |
|---|---|---|
| C-0689 | 300 MHz | 0.63-0.72 (2H, m), 0.78-0.90 (2H, m), 1.15 (3H, t), 1.66-1.78 (1H, m), 4.27 (2H, q), 6.72 (1H, d), 6.95 (1H, t), 7.25 (1H, dd), 7.47 (1H, dd), 8.03 (1H, s), 8.22 (1H, ddd), 8.63 (1H, dd), 9.05 (1H, d) |
| C-1077 | 300 MHz | 1.21 (3H, t), 2.23 (3H, s), 4.30 (2H, q), 7.30-7.68 (4H, m), 8.05 (1H, s), 8.23 (1H, dd), 8.67 (1H, d), 9.07 (1H, d) |
| C-1134 | 300 MHz | 1.35 (3H, t), 4.40 (2H, q), 6.00 (2H, s), 6.80-6.93 (2H, m), 7.09 (1H, d), 7.47 (1H, dd), 8.12-8.23 (2H, m), 8.63 (1H, d), 9.04 (1H, s) |

TABLE 333

| compound | physical property value ($^1$H-NMR data, in CDCl$_3$ TMS δ(ppm)) | |
|---|---|---|
| C-1153 | 400 MHz | 1.21 (3H, t), 2.41 (3H, s), 4.30 (2H, q), 7.01 (1H, t), 7.16-7.30 (1H, m), 7.48 (1H, dd), 8.03 (1H, s), 8.22 (1H, d), 8.63 (1H, d), 9.06 (1H, s) |
| C-1160 | 400 MHz | 1.15 (3H, t), 3.28 (3H, s), 4.21 (2H, s), 4.25 (2H, q), 7.35 (1H, t), 7.39-8.01 (3H, m), 8.01 (1H, s), 8.23 (1H, d), 8.65 (1H, d), 9.07 (1H, s) |
| D-0017 | 300 MHz | 1.31 (3H, t), 4.39 (2H, q), 7.42-7.56 (3H, m), 7.64 (1H, d), 7.82-7.92 (3H, m), 7.98 (1H, s), 8.11 (1H, s), 8.22 (1H, d), 8.65 (1H, d), 9.09 (1H, s) |
| D-0108 | 300 MHz | 1.20 (3H, t), 2.24 (3H, s), 4.28 (2H, q), 7.21 (1H, d), 7.47 (1H, dd), 7.96 (1H, s), 8.21 (1H, ddd), 8.41 (1H, s), 8.48 (1H, dd), 8.65 (1H, dd), 9.05 (1H, d) |
| D-0461 | 400 MHz | 1.33 (3H, t), 2.18 (3H, s), 2.30 (3H, s), 4.38 (2H, q), 7.50 (1H, dd), 7.93 (1H, s), 8.19 (1H, dd), 8.67 (1H, d), 9.04 (1H, d) |
| D-0462 | 400 MHz | 1.10-1.31 (9H, m), 2.55 (2H, q), 2.63 (2H, q), 4.32 (2H, q), 7.48 (1H, dd), 7.91 (1H, s), 8.18 (1H, dd), 8.63 (1H, d), 9.03 (1H, d) |
| D-0463 | 300 MHz | 0.87 (3H, t), 4.10 (2H, q), 7.39 (1H, d), 7.45-7.57 (2H, m), 7.70-7.80 (2H, m), 8.12 (1H, s), 8.18 (1H, dd), 8.25 (1H, d), 8.67 (1H, d), 8.96 (1H, d), 9.09 (1H, d) |

TABLE 334

| compound | physical property value ($^1$H-NMR data, in CDCl$_3$ TMS δ(ppm)) | |
|---|---|---|
| F-0103 | 300 MHz | 7.48 (1H, dd), 7.60 (1H, dd), 7.90 (1H, dd), 8.29 (1H, ddd), 8.40 (1H, dd), 8.60 (1H, dd), 8.89 (1H, s), 9.14 (1H, d) |
| F-0108 | 300 MHz | 2.05 (3H, s), 7.29 (1H, d), 7.58 (1H, dd), 8.30 (1H, dd), 8.34 (1H, s), 8.39 (1H, d), 8.59 (1H, d), 8.80 (1H, s), 9.15 (1H, d) |

Next, formulation examples of the pest control agent of the present invention using the pyrazole derivative of the present invention produced in the manner as described above, or an agriculturally acceptable salt thereof will be specifically described. It is to be noted that the compound, the kinds and the mixing ratios of additives are not limited to this, but may be changed in a wide range. In the following description, "part" means a part by mass.

(Formulation Example 1) Emulsifiable Concentrate

Compound described in Table 1 to Table 334 10 parts
Cyclohexanone 30 parts
Polyoxyethylene alkyl aryl ether 11 parts
Calcium alkylbenzene sulfonate 4 parts
Methylnaphthalene 45 parts
These ingredients were uniformly dissolved to give an emulsifiable concentrate.

(Formulation Example 2) Water-Dispersible Powder

Compound described in Table 1 to Table 334 10 parts
Sodium salt of naphthalene sulfonic acid formalin condensate 0.5 parts
Polyoxyethylene alkyl aryl ether 0.5 parts
Diatomaceous earth 24 parts
Clay 65 parts
These ingredients were uniformly mixed and ground to give a water-dispersible powder.

(Formulation Example 3) Dust

Compound described in Table 1 to Table 334 2 parts
Diatomaceous earth 5 parts
Clay 93 parts
These ingredients were uniformly mixed and ground to give a dust.

(Formulation Example 4) Granules

Compound described in Table 1 to Table 334 5 parts
Sodium salt of lauryl alcohol sulfate ester 2 parts
Sodium lignin sulfonate 5 parts
Carboxymethylcellulose 2 parts
Clay 86 parts
These ingredients were uniformly mixed and ground. To this mixture, water in an amount corresponding to 20 parts was added and kneaded, and processed into 14 to 32 mesh granules by using an extruding granulator, and then dried to give granules.

(Formulation Example 5) Flowable Concentrate

Compound described in Table 1 to Table 334 20 parts
Polyoxyethylene styrenated phenyl ether sulfate 4 parts
Ethylene glycol 7 parts
Silicone AF-118N (available from Asahi Kasei Corporation) 0.02 parts
Water 68.98 parts
These ingredients were mixed with a high-speed stirrer for 30 minutes, and then ground with a wet grinder to give a flowable concentrate.

(Formulation Example 6) Water-Dispersible Granule

Compound described in Table 1 to Table 334 10 parts
Sodium lignin sulfonate 5 parts
Polyoxyethylene alkyl aryl ether 1 part
Sodium polycarboxylate 3 parts
White carbon 5 parts
Pregelatinized starch 1 part
Calcium carbonate 65 parts
Water 10 parts These ingredients were mixed and kneaded and extrusion granulated. The obtained granules were dried by a fluidized-bed dryer, to give a water-dispersible granule.

Next, the effect exerted by the pest control agent of the present invention will be described by way of test examples.

(Test Example 1) *Plutella xylostella* Killing Test

The water-dispersible powder prepared in accordance with Formulation example 2 was diluted in water so that the concentration of the active ingredient was 500 ppm. A cabbage leaf was dipped in this liquid agent, and air-dried, and then put into a plastic cup. Ten second instar larvae of *Plutella xylostella* were released in the cup, and the cup was lidded. Then, the cup was placed in a thermostatic chamber at 25° C., and the number of dead insects was examined after 6 days, and the insect mortality was determined by the calculation formula of numerical formula 1. The test was conducted singly.

Insect mortality (%)=[1−(number of living insects)/(number of tested insects)]×100  [Numerical formula 1]

The compounds showing an insect mortality of 50% or more in this test are as follows.
A-0020, A-0023, A-0025, A-0029, A-0047, A-0059, A-0125, A-0134, A-0144, A-0147, A-0148, A-0152, A-0176, A-0182, A-0183, A-0185, A-0186, A-0192, A-0227, A-0260, A-0263, A-0266, A-0269, A-0329, A-338, A-0340, A-0524, A-0542, A-0551, A-0555, A-0557, A-0571, A-0573, A-0574, A-0577, A-0578, A-0587, A-0588, A-0593, A-0594, A-0597, A-0598, A-0600, A-0613, A-0614, A-0618, A-0624, A-0634, A-0636, A-0637, A-0638, A-0639, A-0645, A-0649, A-0654, A-0655, A-0659, A-0663, A-0670, A-0671, A-0688, A-0692, A-0693, A-0697, A-0701, A-0709, A-0875, A-0906, A-0907, A-0908, A-0909, A-0911, A-1067, A-1077, A-1097, A-1117, A-1136, A-1141, A-1145, A-1151, A-1155, A-1156, A-1162, A-1164, A-1980, A-2182, A-2384, A-2600, A-2990, A-3192, A-3812, A-4404, A-4606, A-5414, A-7030, A-7838, A-8646, A-9993, A-9994, B-0003, B-0018, B-0027, B-0090, B-0095, B-0099, B-0100, B-0107, B-0165, B-0199, B-0205, B-0290, B-0296, B-0367, B-0456, B-0457, B-0458, C-0001, C-0002, C-0008, C-0020, C-0021, C-0023, C-0047, C-0086, C-0134, C-0137, C-0144, C-0145, C-0152, C-0176, C-0179, C-0185, C-0186, C-0189, C-0198, C-0239, C-0263, C-0269, C-0329, C-0340, C-0520, C-0555, C-0557, C-0561, C-0563, C-0571, C-0573, C-0587, C-0588, C-0594, C-0597, C-0598, C-0600, C-0614, C-0624, C-0629, C-0634, C-0637, C-0638, C-0656, C-0663, C-0907, C-0910, C-1067, C-1097, C-1145, C-1153, C-1162, C-1165, D-0035, D-0098, D-0099, D-0103, D-0107, D-0108, D-0207, D-0309, D-0466, E-0002, E-0003, E-0006, E-0008, E-0020, E-0023, E-0041, E-0047, E-0086, E-0119, E-0125, E-0128, E-0134, E-0137, E-0176, E-0177, E-0179, E-0263, E-0329, E-0340, E-0518, E-0557, E-0561, E-0563, E-0571, E-0573, E-0587, E-0588, E-0593, E-0594, E-0597, E-0598, E-0600, E-0609, E-0613, E-0614, E-0618, E-0624, E-0633, E-0644, E-0652, E-0653, E-0663, E-0693, E-0733, E-0907, E-0908, E-1067, E-1076, E-1077, E-1117, E-1148, E-1152, F-0012, F-0108, F-0207, F-0295, F-0301, F-0309, F-0464, F-0466

(Test Example 2) *Helicoverpa armigera* Killing Test

The water-dispersible powder prepared in accordance with Formulation example 2 was diluted in water so that the concentration of the active ingredient was 500 ppm. A cabbage leaf was dipped in this liquid agent, and air-dried, and then put into a plastic cup. Five newly hatched larvae of *Helicoverpa armigera* were released in the cup, and the cup was lidded. Then, the cup was placed in a thermostatic chamber at 25° C., and the number of dead insects was examined after 6 days, and the insect mortality was determined by the calculation formula of numerical formula 1. The test was conducted in duplicate.

The compounds showing an insect mortality of 50% or more in this test are as follows.

A-0002, A-0008, A-0014, A-0020, A-0023, A-0029, A-0086, A-0103, A-0128, A-0137, A-0145, A-0148, A-0152, A-0179, A-0183, A-0188, A-0242, A-0263, A-0266, A-0329, A-0338, A-0340, A-0512, A-0524, A-0542, A-0551, A-0553, A-0555, A-0561, A-0574, A-0583, A-0587, A-0588, A-0591, A-0593, A-0594, A-0597, A-0608, A-0614, A-0633, A-0634, A-0638, A-0639, A-0644, A-0645, A-0653, A-0654, A-0655, A-0659, A-0660, A-0671, A-0688, A-0689, A-0691, A-0692, A-0693, A-0705, A-0709, A-0713, A-0906, A-0907, A-0908, A-0909, A-0910, A-0911, A-0912, A-0913, A-1076, A-1117, A-1140, A-1141, A-1145, A-1146, A-1148, A-1151, A-1153, A-1158, A-1162, A-1163, A-1164, A-1165, A-1166, A-2182, A-2384, A-2586, A-2600, A-2990, A-6020, A-7838, A-9480, A-9993, A-9994, B-0004, B-0027, B-0090, B-0091, B-0095, B-0099, B-0100, B-0165, B-0199, B-0287, B-0290, B-0367, B-0454, B-0455, B-0457, C-0004, C-0008, C-0021, C-0022, C-0041, C-0046, C-0086, C-0120, C-0125, C-0134, C-0137, C-0147, C-0179, C-0189, C-0227, C-0239, C-0263, C-0266, C-0269, C-0320, C-0329, C-0340, C-0512, C-0518, C-0553, C-0557, C-0561, C-0563, C-0573, C-0574, C-0577, C-0578, C-0587, C-0588, C-0594, C-0597, C-0598, C-0600, C-0608, C-0614, C-0633, C-0636, C-0637, C-0653, C-0656, C-0659, C-0660, C-0689, C-0692, C-0705, C-0906, C-0907, C-0908, C-0911, C-1117, C-1140, C-1141, C-1162, C-1163, C-1165, D-0003, D-0004, D-0012, D-0035, D-0099, D-0107, D-0108, D-0115, D-0207, D-0295, D-0301, D-0375, D-0464, E-0006, E-0008, E-0047, E-0086, E-0119, E-0121, E-0128, E-0148, E-0177, E-0263, E-0329, E-0521, E-0542, E-0561, E-0563, E-0571, E-0573, E-0587, E-0588, E-0594, E-0597, E-0600, E-0614, E-0633, E-0639, E-0644, E-0659, E-0660, E-0688, E-0692, E-0693, E-0705, E-0733, E-0906, E-0907, E-0908, E-0911, E-0912, E-1076, E-1117, E-1160, F-0003, F-0012, F-0017, F-0099, F-0108, F-0207, F-0301, F-0375, F-0461, F-0466

(Test Example 3) *Aphis gossypii* Killing Test

The water-dispersible powder prepared in accordance with Formulation example 2 was diluted in water so that the concentration of the active ingredient was 500 ppm. A nursery plant of cucumber preliminarily inoculated with nymphs of *Aphis gossypii* was dipped in this liquid agent, and air-dried. The nursery plant of cucumber after the treatment was placed in a thermostatic chamber at 25° C., and the number of live insects was counted after 3 days, and the insect mortality was determined by the calculation formula of numerical formula 1. The test was conducted singly.

The compounds showing an insect mortality of 50% or more in this test are as follows.

A-0001, A-0002, A-0004, A-0005, A-0006, A-0007, A-0008, A-0014, A-0020, A-0021, A-0022, A-0023, A-0025, A-0029, A-0044, A-0045, A-0046, A-0047, A-0059, A-0086, A-0101, A-0103, A-0119, A-0120, A-0121, A-0122, A-0123, A-0124, A-0143, A-0144, A-0145, A-0146, A-0147, A-0148, A-0152, A-0176, A-0177, A-0179, A-0182, A-0183, A-0185, A-0186, A-0189, A-0260, A-0263, A-0266, A-0269, A-0320, A-0340, A-0347, A-0512, A-0524, A-0550, A-0555, A-0557, A-0561, A-0563, A-0571, A-0573, A-0574, A-0577, A-0578, A-0582, A-0583, A-0591, A-0593, A-0594, A-0597, A-0598, A-0603, A-0609, A-0613, A-0614, A-0618, A-0634, A-0636, A-0637, A-0639, A-0644, A-0652, A-0653, A-0654, A-0655, A-0656, A-0659, A-0660, A-0663, A-0665, A-0670, A-0688, A-0689, A-0691, A-0692, A-0693, A-0697, A-0701, A-0705, A-0709, A-0712, A-0713, A-0875, A-0906, A-0907, A-0908, A-0909, A-0913, A-1067, A-1077, A-1102, A-1117, A-1134, A-1140, A-1141, A-1145, A-1146, A-1147, A-1152, A-1157, A-1158, A-1160, A-1161, A-1162, A-1163, A-1165, A-1166, A-2182, A-2586, A-2600, A-3596, A-3798, A-3812, A-4202, A-4404, A-4606, A-4808, A-5414, A-5616, A-6020, A-6022, A-7434, A-7636, A-7838, A-8040, A-8862, A-9993, A-9994, B-0001, B-0002, B-0003, B-0004, B-0009, B-0027, B-0091, B-0095, B-0099, B-0107, B-0290, B-0293, B-0301, B-0367, B-0389, B-0453, B-0455, C-0001, C-0002, C-0003, C-0006, C-0007, C-0020, C-0021, C-0025, C-0044, C-0045, C-0047, C-0119, C-0122, C-0125, C-0128, C-0134, C-0137, C-0145, C-0176, C-0177, C-0183, C-0186, C-0189, C-0227, C-0239, C-0320, C-0553, C-0557, C-0561, C-0574, C-0578, C-0594, C-0600, C-0637, C-0638, C-0639, C-0653, C-0655, C-0660, C-0697, C-0907, C-0910, C-0911, C-1077, C-1117, C-1141, C-1162, D-0002, D-0003, D-0005, D-0008, D-0012, D-0035, D-0103, D-0107, D-0108, D-0115, D-0207, D-0213, D-0301, D-0375, D-0463, D-0464, E-0023, E-0121, E-0124, E-0128, E-0269, E-0609, E-0656, E-0693, E-1067, F-0003

(Test Example 4) *Nilaparvata lugens* Killing Activity Test

The water-dispersible powder prepared in accordance with Formulation example 2 was diluted in water so that the concentration of the active ingredient was 500 ppm. Paddy was dipped in this liquid agent, and then put into a plastic cup. Ten second instar larvae of *Nilaparvata lugens* were released in the plastic cup, and the cup was lidded, and placed in a thermostatic chamber at 25° C. After 6 days, the number of live insects was counted, and the insect mortality was determined by the calculation formula of numerical formula 1. The test was conducted singly.

The compounds showing an insect mortality of 50% or more in this test are as follows.

A-0002, A-0003, A-0004, A-0005, A-0007, A-0008, A-0014, A-0020, A-0021, A-0022, A-0023, A-0025, A-0041, A-0045, A-0046, A-0047, A-0059, A-0086, A-0101, A-0119, A-0120, A-0121, A-0122, A-0123, A-0124, A-0125, A-0128, A-0134, A-0145, A-0146, A-0147, A-0148, A-0152, A-0176, A-0177, A-0179, A-0182, A-0183, A-0185, A-0186, A-0188, A-0189, A-0198, A-0227, A-0239, A-0242, A-0260, A-0263, A-0266, A-0269, A-0320, A-0329, A-0340, A-0347, A-0548, A-0550, A-0551, A-0555, A-0557, A-0561, A-0563, A-0571, A-0577, A-0578, A-0583, A-0587, A-0588, A-0591, A-0593, A-0594, A-0597, A-0598, A-0600, A-0603, A-0609, A-0613, A-0614, A-0618, A-0624, A-0629, A-0633, A-0634, A-0636, A-0637, A-0638, A-0639, A-0644, A-0645, A-0653, A-0654, A-0655, A-0656, A-0659, A-0660, A-0663, A-0664, A-0665, A-0670, A-0671, A-0688, A-0689, A-0692, A-0693, A-0697, A-0701, A-0705, A-0709, A-0712, A-0713, A-0733, A-0907, A-0910, A-1067, A-1076, A-1077, A-1097, A-1102, A-1117, A-1134, A-1136, A-1140, A-1145, A-1146, A-1147, A-1148, A-1151, A-1153, A-1154, A-1155, A-1156, A-1158, A-1159, A-1161, A-1162, A-1163, A-1164, A-1166, A-1980, A-2182, A-2384, A-2586, A-2600, A-2788, A-2990, A-3192, A-3596, A-3798, A-3812, A-4000, A-4202, A-4404, A-4808, A-5414, A-5616, A-6020, A-6222, A-6424, A-7030, A-7232, A-7434, A-7636, A-7838, A-8040, A-8242, A-8444, A-8646, A-8862, A-9435, A-9993, A-9994, B-0001, B-0004, B-0018, B-0027, B-0090,

B-0091, B-0095, B-0099, B-0100, B-0107, B-0165, B-0205, B-0287, B-0290, B-0296, B-0301, B-0389, B-0454, B-0455, B-0456, B-0457, B-0458, B-0459, C-0001, C-0002, C-0021, C-0022, C-0023, C-0025, C-0041, C-0044, C-0047, C-0086, C-0119, C-0120, C-0121, C-0123, C-0124, C-0125, C-0128, C-0134, C-0137, C-0145, C-0147, C-0152, C-0176, C-0177, C-0179, C-0185, C-0186, C-0189, C-0227, C-0239, C-0263, C-0269, C-0320, C-0340, C-0549, C-0557, C-0561, C-0571, C-0574, C-0577, C-0578, C-0587, C-0588, C-0591, C-0593, C-0594, C-0597, C-0598, C-0600, C-0614, C-0624, C-0633, C-0636, C-0637, C-0638, C-0639, C-0653, C-0665, C-0656, C-0660, C-0663, C-0665, C-0689, C-0692, C-0697, C-0705, C-0712, C-0912, C-1067, C-1077, C-1097, C-1102, C-1134, C-1140, C-1141, C-1145, C-1152, C-1153, C-1162, C-1163, C-1165, D-0005, D-0012, D-0017, D-0035, D-0098, D-0099, D-0103, D-0107, D-0213, D-0295, D-0375, D-0462, D-0463, D-0464, D-0466, E-0044, E-0086, E-0125, E-0134, E-0148, E-0152, E-0177, E-0179, E-0227, E-0266, E-0329, E-0521, E-0555, E-0578, E-0587, E-0588, E-0600, E-0614, E-0618, E-0629, E-0633, E-0660, E-0693, E-0908, E-1077, F-0003, F-0012, F-0099, F-0295, F-0462

The present invention provides a novel compound having excellent insecticide activity, and is useful in pesticide fields and agricultural fields, and has industrial applicability.

What is claimed is:

1. A pyrazole derivative represented by general formula [I] or an agriculturally acceptable salt thereof

[Chemical formula 1]

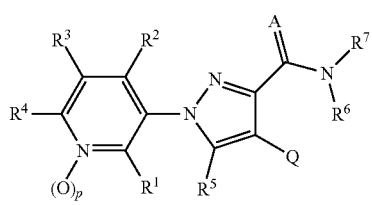

[I]

wherein, p represents an integer of 0, $R^1$, $R^2$, $R^3$, $R^4$, and $R^5$ each independently represent a hydrogen atom, A represents an oxygen atom, Q represents a $C_6$-$C_{10}$ aryl group that is substituted with $(R^8)_m$, $R^6$ and $R^7$ each independently represent a hydrogen atom, $R^8$ represents a hydrogen atom, halogen atom, hydroxy group, a $C_1$-$C_6$ alkyl group, $C_1$-$C_6$ haloalkyl group, $C_3$-$C_6$ cycloalkyl group, $C_2$-$C_6$ alkenyl group $C_2$-$C_6$ alkynyl group, $C_1$-$C_6$ haloalkoxy group, $C_3$-$C_6$ cycloalkoxy group, $C_1$-$C_6$ alkylthio group, $C_1$-$C_6$ alkylsulfinyl group, $C_1$-$C_6$ alkylsulfonyl group, $C_1$-$C_6$ haloalkylthio group, $C_1$-$C_6$ haloalkylsulfinyl group, $C_1$-$C_6$ alkylcarbonyl group, $C_1$-$C_6$ alkoxycarbonyl group, aminocarbonyl group, di($C_1$-$C_6$ alkyl)amino $C_1$-$C_6$-alkyl group, -hydroxy $C_1$-$C_6$ alkyl group, $C_1$-$C_6$ alkoxy $C_1$-$C_6$ alkyl group, $C_1$-$C_6$ alkylcarbonyloxy group, -di($C_1$-$C_6$ alkyl)aminocarbonyloxy group, $C_1$-$C_6$ alkylsulfonyloxy group, $C_1$-$C_6$ alkylthio $C_1$-$C_6$ alkyl group, $C_1$-$C_6$ haloalkylthio $C_1$-$C_6$ alkyl group, -phenyl group, benzyloxy group, amino group, mono($C_1$-$C_6$ alkyl)amino group, di($C_1$-$C_6$ alkyl)amino group, carboxy group, 1,3-dioxolane-2-yl group, -(methyloxyimino)methyl group, cyano group, or nitro group, and further, neighboring two $R^8$s may form, together with a carbon atom bound to each $R^8$, a 4 to 8-membered carbon ring, or a 4 to 8-membered hetero ring having 1 to 4 hetero atoms selected from an oxygen atom, m represents a number of chemically acceptable $R^8$s and is an integer of 0 to 7, $R^8$s may be the same or different from each other when m is 2 or more.

2. A agrochemical composition comprising the pyrazole derivative or an agriculturally acceptable salt thereof according to claim 1 as an active ingredient.

3. The agrochemical composition according to claim 2, wherein the agrochemical composition further comprises a surfactant.

4. A pest control agent comprising the pyrazole derivative or an agriculturally acceptable salt thereof according to claim 1 as an active ingredient.

5. The pest control agent according to claim 4 that is an insecticide.

6. The pest control agent according to claim 4 having a control effect on a pest in a dry field or a paddy field where a farming or gardening plant is cultured.

7. The pest control agent according to claim 6, wherein the farming or gardening plant is a plant provided with tolerance by a breeding method or a gene recombination technique.

* * * * *